(12) United States Patent
Ahn et al.

(10) Patent No.: US 12,421,249 B2
(45) Date of Patent: *Sep. 23, 2025

(54) INHIBITORS OF APOL1 AND METHODS OF USING SAME

(71) Applicant: Vertex Pharmaceuticals Incorporated, Boston, MA (US)

(72) Inventors: Jun Myun Ahn, Waltham, MA (US); Samantha Angle, Cambridge, MA (US); Michael Aaron Brodney, Newton, MA (US); Jingrong Cao, Newton, MA (US); John E. Cochran, Marshfield, MA (US); Jon H. Come, Cambridge, MA (US); Leslie A. Dakin, Framingham, MA (US); Elena Dolgikh, Boston, MA (US); Brad D. Maxwell, Holliston, MA (US); Suganthini S. Nanthakumar, Newton, MA (US); Hardwin O'Dowd, Cambridge, MA (US); Jessica Howard Olsen, Jamaica Plain, MA (US); Timothy J. Senter, Arlington, MA (US); Akira Joseph Shimizu, Framingham, MA (US); Steven David Stone, Quincy, MA (US); Haoxuan Wang, Somerville, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,559

(22) Filed: Nov. 8, 2023

(65) Prior Publication Data
US 2024/0368180 A1 Nov. 7, 2024

Related U.S. Application Data

(63) Continuation of application No. 17/446,135, filed on Aug. 26, 2021, now Pat. No. 11,866,446.

(60) Provisional application No. 63/070,705, filed on Aug. 26, 2020.

(51) Int. Cl.
*C07D 495/20* (2006.01)
*C07D 519/00* (2006.01)
(52) U.S. Cl.
CPC ......... *C07D 495/20* (2013.01); *C07D 519/00* (2013.01)
(58) Field of Classification Search
CPC .............................. C07D 495/20; C07D 519/00
USPC ...................................................... 514/230.5
See application file for complete search history.

(56) References Cited

U.S. PATENT DOCUMENTS

| 11,618,746 B2 | 4/2023 | Cao et al. |
| 11,801,234 B2 | 10/2023 | Mallalieu et al. |
| 11,807,635 B2 | 11/2023 | Li et al. |
| 11,866,446 B2 * | 1/2024 | Ahn ........................ A61P 13/12 |
| 2003/0124028 A1 | 7/2003 | Carlson et al. |
| 2008/0153861 A1 | 6/2008 | Bissantz et al. |
| 2010/0317661 A1 | 12/2010 | Wang et al. |
| 2021/0246121 A1 | 8/2021 | Lai et al. |
| 2022/0340523 A1 | 10/2022 | Dakin et al. |
| 2023/0011118 A1 | 1/2023 | Dakin et al. |
| 2023/0014907 A1 | 1/2023 | Dakin et al. |
| 2023/0119114 A1 | 4/2023 | Daniel et al. |
| 2023/0201201 A1 | 6/2023 | Skorecki et al. |
| 2023/0203000 A1 | 6/2023 | Dakin et al. |
| 2023/0250087 A1 | 8/2023 | Gagnon et al. |
| 2024/0059681 A1 | 2/2024 | Li et al. |
| 2024/0277661 A1 | 8/2024 | Mallalieu et al. |
| 2024/0368180 A1 | 11/2024 | Ahn et al. |
| 2025/0084094 A1 | 3/2025 | Senter et al. |

FOREIGN PATENT DOCUMENTS

| WO | WO 2005/021505 A1 | 3/2005 |
| WO | WO 2008/155132 A1 | 12/2008 |
| WO | WO 2011/060035 A1 | 11/2010 |

(Continued)

OTHER PUBLICATIONS

Brittain H. G. et al., (2001) "X-Ray Diffraction III: Pharmaceutical Applications of X-ray Powder Diffraction," Spectroscopy, 16(7), pp. 14-18.

(Continued)

*Primary Examiner* — Kahsay Habte
(74) *Attorney, Agent, or Firm* — Finnegan, Henderson, Farabow, Garrett & Dunner, LLP

(57) ABSTRACT

The disclosure provides at least one entity chosen from compounds of Formula I, a tautomer thereof, a deuterated derivative of that compound or tautomer, and a pharmaceutically acceptable salt of any of the foregoing, compositions comprising the same, and methods of using the same, including uses in treating APOL1-mediated diseases, including pancreatic cancer, focal segmental glomerulosclerosis (FSGS), and/or non-diabetic kidney disease (NDKD).

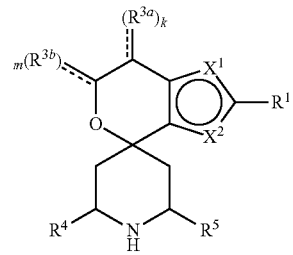

Formula I

23 Claims, 34 Drawing Sheets

(56) References Cited

FOREIGN PATENT DOCUMENTS

| WO | WO 2011/060217 A1 | 11/2010 |
|---|---|---|
| WO | WO 2016/078770 A1 | 5/2016 |
| WO | WO 2017/137334 A1 | 8/2017 |
| WO | WO 2020/131807 A1 | 6/2020 |
| WO | WO 2020/186220 A1 | 9/2020 |
| WO | WO 2021/216665 A1 | 4/2021 |
| WO | WO 2021/092115 A1 | 5/2021 |
| WO | WO 2021/127337 A1 | 6/2021 |
| WO | WO 2021/154997 A1 | 8/2021 |
| WO | WO 2021/158666 A1 | 8/2021 |
| WO | WO 2021/178768 A1 | 9/2021 |
| WO | WO 2021/224927 A1 | 9/2021 |
| WO | WO 2021/220178 A1 | 11/2021 |
| WO | WO 2021/252849 A1 | 12/2021 |
| WO | WO 2021/252859 A1 | 12/2021 |
| WO | WO 2021/252863 A1 | 12/2021 |
| WO | WO 2022/047031 A1 | 3/2022 |
| WO | WO 2023/028237 A1 | 3/2023 |
| WO | WO 2023/101981 A1 | 6/2023 |
| WO | WO 2023/154309 A1 | 8/2023 |
| WO | WO 2023/154310 A1 | 8/2023 |
| WO | WO 2023/154314 A1 | 8/2023 |
| WO | WO 2023/154344 A1 | 8/2023 |

OTHER PUBLICATIONS

Database Registry (2011), Aurora Fine Chemicals: "Spiro[isobenzofuran-1(3H),4'-piperidine]-3-carboxamide, N,N-dimethyl-1'-[(5-methyl-2-furanyl)methyl]-2,2,2-trifluoroacetate (1:1)", XP093038422, retrieved from STN Database accession No. 2649946-46-1 abstract.
Database Registry (2018), Aurora Fine Chemicals: "Spiro[isobenzofuran-1(3H),4'-piperidine]-3-carboxamide,N,N-climethyl-1'-(3-thienylmethyl)-", XP093038444, retrieved from STN Database accession No. 2184532-71-4 abstract.
Database Registry (2018), Aurora Fine Chemicals: "Spiro[isobenzofuran-1(3H),4'-piperidine]-3-carboxamide,N,N-climethyl-1'-[(1-methyl-1H-imidazol-2-yl) methyl]-", XP093038484, retrieved from Database accession No. 2182642-77-7.
Database Registry (2018), Aurora Fine Chemicals: "Spiro[isobenzofuran-1(3H),4'-piperidine]-3-carboxamide,N,N-dimethyl-1'-(2-thiazolylmethyl)-", XP093038443, retrieved from STN Database accession No. 2185335-69-5 abstract.
Database Registry (2018), Aurora Fine Chemicals: "Spiro[isobenzofuran-1(3H), 4'-piperidine]-3-carboxamide,N,N-dimethyl-1'-[(5-methyl-2-furanyl)methyl)-, 2,2,2-trifluoroacetate (1:1)", XP093038441, retrieved from STN Database accesion No. 2185363-22-6 abstract.
Database Registry (2021), "2'-Cyclopropyl-6,7-dihydro-6,6'-dimethyls piro[I,7-naphthyridine-8(5H),4'-piperidine]," XP093024335, retrieved from STN Database accession No. 2644543-73-5 abstract.
Database Registry (2021), "2'-Cyclopropyl-7,8-dihydro-6'-methylspiro [I,6-naphthyridine-5(6H),4'-piperidine]," XP093024331, retrieved from STN Database accession No. 2645191-67-7 abstract.
Database Registry (2021), Anonymous: "2'-Cyclopropyl-3,4-dihydro-3,6'-dimethyls piro[2,6-naphthyridine-1(2H), 4'piperidine]," XP093024352, retrieved from STN Database accession No. 2620609-98-3 abstract.
Database Registry (2021), Anonymous: "2'-Cyclopropyl-3,4-dihydro-6'-methylspiro [isoquinoline-1(2H), 4'-piperidin]-7-ol," XP093024340, retrieved from STN Database accession No. 2631256-91-0 abstract.
Database Registry (2021), Anonymous: "2'-Cyclopropyl-6,7-dihydro-6'-methylspiro [I,7-naphthyridine-8(5H),4' piperidine]-5-methanol," XP093024350, retrieved from STN Database accession No. 2617381-98-1 abstract.
Database Registry (2021), Anonymous: "2'-Cyclopropyl-6,7-dihydro-6'-methylspiro [I,7-naphthyridine-8(5H), 4' piperidine]-6-methanol," XP093024346, retrieved from STN Database accession No. 2626788-69-8 abstract.
Database Registry (2021), Anonymous: "2-Cyclopropyl-7',8'-dihydro-2',6-dimethyl spiro[piperidine-4,5' (3'H)-pyrido[4,3-d]py rimidin]-4' (6'H)-one", XP093024343, retrieved from STN Database accession No. 2631119-41-8 abstract.
Database Registry (2021), Anonymous: "Name not yet assigned", XP093024338, retrieved from STN Database accession No. 2642534-36-7 abstract.
Database Registry (2021), Anonymous: "Name not yet assigned", XP093024344, retrieved from STN Database accession No. 2630494-88-9 abstract.
Database Registry (2021), Anonymous: "rel-(2'R,6'R)-3,4-Dihydro-7-methoxy-2',6'-dimethylspiro[2,6-naphthyridine1(2H),4'-p iperidine]," XP093024348, retrieved from STN Database accession No. 2625380-27-8 abstract.
Dummer, P.D. et al. (2015), "APOL1 kidney disease risk variants—an evolving landscape," Semin Nephrol. 35(3):222-236. HHS Public Access Author Manuscript; available in PMC May 1, 2016 (25 pages).
International Search Report and Written Opinion for International Application No. PCT/US2021/047754, mailed Oct. 25, 2021 (13 pages).
Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.
Lennox, A. (2018) "Electrochemical Aminoxyl-Mediated-Cyanation of Secondary Piperidines for Pharmaceutical Building Block Diversification" J. Am. Chem. Soc. 140, 11227-11231.
Lin, J. et al. (2021), "Oncogene APOL1 promotes proliferation and inhibits apoptosis via activating NOTCH1 signaling pathway in pancreatic cancer," Cell Death and Disease 12:760 (11 pages).
Nitta, A. et al. (2012) "Pyrrolidinyl phenylurea derivatives as novel CCR3 antagonists," Bioorg. Med. Chem. Lett. 22(2012), 6876-6881.
Pedregal, A. et al. (2012) "Development of LC-MS/MS-Based Receptor Occupancy Tracers and Positron Emission Tomography Radioligands for the Nociceptin/Orphanin FQ (NOP) Receptor," J. Med. Chem. 55, 4955-4967.
Takai, K. et al., (2014) "Discovery of N-substituted 7-azaindoline derivatives as potent, orally available M1 and M4 muscarinic acetylcholine receptors selective agonist," Bioorg. Med. Chem. Lett. 24(2014), 3189-3193.
The United States Pharmacopeia, Jan. 1, 1995, 23rd Revision, USP 23/NF 18, General Chapter on X-ray diffraction, pp. 1843-1844.
Vajgel, G. et al. (2020), "A single APOL1 nephropathy variant increases risk of advanced lupus nephritis in Brazilians," J Rheumatol. 47(8):1209-1217. HHS Public Access Author Manuscript; available in PMC Aug. 1, 2021 (18 pages).
*Vertex Announces Positive Results From Phase 2 Study of VX-147 in APOL1-Mediated Focal Segmental Glomerulosclerosis*, Vertex (Dec. 1, 2021), https://news.vrtx.com/press-release/vertex-announces-positive-results-phase-2-study-vx-147-apol1-mediated-focal-segmental (6 pages).
Wünsch, B. et al. (1992), "Synthese und ZNS-Aktivität spirocyclischer Pethidin- und Prodin-Analoga," Arch. Pharm. (Weinheim), 326:513-518.
Andres J., "Polymorphs in Pharmaceutical Products" USPTO, Dec. 9, 2009, https://www.njipla.org/event-831656.
Gardner, C.R. et al. (2004), "Application of high throughput technologies to drug substance and drug product development," Computers and Chemical Engineering 28(2004), 943-953.
Strachan, C.J. et al., (2007) "Raman spectroscopy for quantitative analysis of pharmaceutical solids," Journal of Pharmacy and Pharmacology, 59(2), 179-192.
U.S. Appl. No. 18/836,539, filed Aug. 7, 2024, by Angle et. al.
U.S. Appl. No. 18/836,407, filed Aug. 7, 2024, by Senter et. al.
U.S. Appl. No. 18/836,681, filed Aug. 7, 2024, by Senter et. al.

* cited by examiner

INHIBITORS OF APOL1 AND METHODS OF USING SAME

This application is a continuation of U.S. application Ser. No. 17/446,135, filed on Aug. 26, 2021, which claims the benefit of priority of U.S. Provisional Patent Application No. 63/070,705, filed Aug. 26, 2020, the contents of which are incorporated by reference herein in their entirety.

This disclosure provides compounds that may inhibit apolipoprotein L1 (APOL1) and methods of using those compounds to treat APOL1-mediated diseases, such as, e.g., pancreatic cancer, focal segmental glomerulosclerosis (FSGS), and/or non-diabetic kidney disease (NDKD). In some embodiments, the FSGS and/or NDKD is associated with at least one of the 2 common APOL1 genetic variants (G1: S342G:I384M and G2: N388del:Y389del). In some embodiments, the pancreatic cancer is associated with elevated levels of APOL1 (such as, e.g., elevated levels of APOL1 in pancreatic cancer tissues).

FSGS is a rare kidney disease with an estimated global incidence of 0.2 to 1.1/100,000/year. FSGS is a disease of the podocyte (glomerular visceral epithelial cells) responsible for proteinuria and progressive decline in kidney function. NDKD is a kidney disease involving damage to the podocyte or glomerular vascular bed that is not attributable to diabetes. NDKD is a disease characterized by hypertension and progressive decline in kidney function. Human genetics support a causal role for the G1 and G2 APOL1 variants in inducing kidney disease. Individuals with 2 APOL1 alleles are at increased risk of developing end-stage kidney disease (ESKD), including primary (idiopathic) FSGS, human immunodeficiency virus (HIV)-associated FSGS, NDKD, arterionephrosclerosis, lupus nephritis, microalbuminuria, and chronic kidney disease. See, P. Dummer et al., *Semin Nephrol.* 35(3): 222-236 (2015).

FSGS and NDKD can be divided into different subgroups based on the underlying etiology. One homogeneous subgroup of FSGS is characterized by the presence of independent common sequence variants in the apolipoprotein L1 (APOL1) gene termed G1 and G2, which are referred to as the "APOL1 risk alleles." G1 encodes a correlated pair of non-synonymous amino acid changes (S342G and I384M), G2 encodes a 2 amino acid deletion (N388del:Y389del) near the C terminus of the protein, and G0 is the ancestral (low risk) allele. A distinct phenotype of NDKD is found in patients with APOL1 genetic risk variants as well. In both APOL1-mediated FSGS and NDKD, higher levels of proteinuria and a more accelerated loss of kidney function occur in patients with two risk alleles compared to patients with the same disease who have no or just 1 APOL1 genetic risk variant. Alternatively in AMKD, higher levels of proteinuria and accelerated loss of kidney function can also occur in patients with one risk allele. See, G. Vajgel et al., J. Rheumatol., November 2019, jrheum.190684.

APOL1 is a 44 kDa protein that is only expressed in humans, gorillas, and baboons. The APOL1 gene is expressed in multiple organs in humans, including the liver and kidney. APOL1 is produced mainly by the liver and contains a signal peptide that allows for secretion into the bloodstream, where it circulates bound to a subset of high-density lipoproteins. APOL1 is responsible for protection against the invasive parasite, *Trypanosoma brucei brucei* (*T. b. brucei*). APOL1 is endocytosed by *T. b. brucei* and transported to lysosomes, where it inserts into the lysosomal membrane and forms pores that lead to parasite swelling and death.

While the ability to lyse *T. b. brucei* is shared by all 3 APOL1 variants (G0, G1, and G2), APOL1 G1 and G2 variants confer additional protection against parasite species that have evolved a serum resistant associated-protein (SRA) which inhibits APOL1 G0; APOL1 G1 and G2 variants confer additional protection against *trypanosoma* species that cause sleeping sickness. G1 and G2 variants evade inhibition by SRA; G1 confers additional protection against *T. b. gambiense* (which causes West African sleeping sickness) while G2 confers additional protection against *T. b. rhodesiense* (which causes East African sleeping sickness).

In the kidney, APOL1 is expressed in podocytes, endothelial cells (including glomerular endothelial cells), and some tubular cells. Podocyte-specific expression of APOL1 G1 or G2 (but not G0) in transgenic mice induces structural and functional changes, including albuminuria, decreased kidney function, podocyte abnormalities, and glomerulosclerosis. Consistent with these data, G1 and G2 variants of APOL1 play a causative role in inducing FSGS and accelerating its progression in humans. Individuals with APOL1 risk alleles (i.e., homozygous or compound heterozygous for the APOL1 G1 or APOL1 G2 alleles) have increased risk of developing FSGS and they are at risk for rapid decline in kidney function if they develop FSGS. Thus, inhibition of APOL1 could have a positive impact in individuals who harbor APOL1 risk alleles.

Although normal plasma concentrations of APOL1 are relatively high and can vary at least 20-fold in humans, circulating APOL1 is not causally associated with kidney disease. However, APOL1 in the kidney is thought to be responsible for the development of kidney diseases, including FSGS and NDKD. Under certain circumstances, APOL1 protein synthesis can be increased by approximately 200-fold by pro-inflammatory cytokines such as interferons or tumor necrosis factor-α. In addition, several studies have shown that APOL1 protein can form pH-gated $Na^+/K^+$ pores in the cell membrane, resulting in a net efflux of intracellular $K^+$, ultimately resulting in activation of local and systemic inflammatory responses, cell swelling, and death.

The risk of ESKD is substantially higher in people of recent sub-Saharan African ancestry as compared to those of European ancestry. In the United States, ESKD is responsible for nearly as many lost years of life in women as from breast cancer and more lost years of life in men than from colorectal cancer.

FSGS and NDKD are caused by damage to podocytes, which are part of the glomerular filtration barrier, resulting in proteinuria. Patients with proteinuria are at a higher risk of developing end-stage kidney disease (ESKD) and developing proteinuria-related complications, such as infections or thromboembolic events. There is no standardized treatment regimen nor approved drugs for FSGS or NDKD. Currently, FSGS and NDKD are managed with symptomatic treatment (including blood pressure control using blockers of the renin angiotensin system), and patients with FSGS and heavy proteinuria may be offered high dose steroids. Current therapeutic options for NDKD are anchored on blood pressure control and blockade of the renin angiotensin system.

Corticosteroids, alone or in combination with other immunosuppressants, induce remission in a minority of patients (e.g., remission of proteinuria in a minority of patients) and are associated with numerous side effects. However, remission is frequently indurable even in patients initially responsive to corticosteroid and/or immunosuppressant treatment. As a result, patients, in particular individuals of recent sub-Saharan African ancestry with 2 APOL1 risk alleles, experience rapid disease progression leading to end-stage renal disease (ESRD). Thus, there is an unmet medical need for treatment for FSGS and NDKD. Illustratively, in view of evidence that APOL1 plays a causative role in inducing and accelerating the progression of kidney disease, inhibition of APOL1 should have a positive impact on patients with APOL1 mediated kidney disease, particularly those who carry two APOL1 risk alleles (i.e., are homozygous or compound heterozygous for the G1 or G2 alleles).

Additionally, APOL1 is an aberrantly expressed gene in multiple cancers (Lin et al., *Cell Death and Disease* (2021), 12:760). Recently, APOL1 was found to be abnormally elevated in human pancreatic cancer tissues compared with adjacent tissues and was associated with poor prognosis in pancreatic cancer patients. In in vivo and in vitro experiments, knockdown of APOL1 significantly inhibited cancer cell proliferation and promoted the apoptosis of pancreatic cancer cells.

One aspect of the disclosure provides at least one compound selected from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing, which can be employed in the treatment of diseases mediated by APOL1, such as FSGS and NDKD. For example, the at least one compound is a compound represented by Formula I:

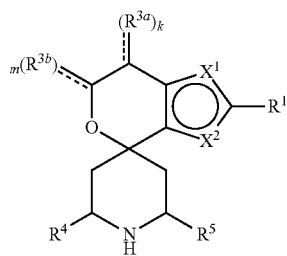

wherein $X^1$, $X^2$, $R^1$, $R^{3a}$, $R^{3b}$, $R^4$, $R^5$, k, and m are as defined in an embodiment disclosed herein.

In some embodiments, at least one compound of the disclosure is a compound represented by the following structural formula:

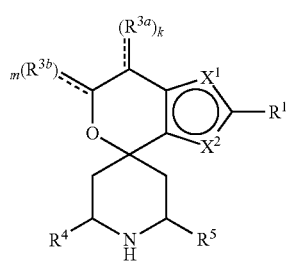

Formula I a tautomer thereof, a deuterated derivative of that compound or tautomer, or a
pharmaceutically acceptable salt of any of the foregoing, wherein:
$X^1$ is selected from S and $-CR^{2a}$ and $X^2$ is selected from S and $-CR^{2b}$, wherein:
one of $X^1$ and $X^2$ is S;
when $X^1$ is S, then $X^2$ is $-CR^{2b}$; and
when $X^2$ is S, then $X^1$ is $-CR^{2a}$;
$R^1$ is selected from hydrogen, halogen, $-OH$, cyano, $C_1$-$C_6$ alkyl, $C_1$-$C_6$ alkoxy, $C_3$-$C_6$ cycloalkyl, and phenyl, wherein:
the $C_1$-$C_6$ alkyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl)$_2$, and $C_1$-$C_4$ alkoxy;
the $C_1$-$C_6$ alkoxy of $R^1$ is optionally substituted with 1 to 3 groups independently selected from halogen;
the $C_3$-$C_6$ cycloalkyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl)$_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl)$_2$; and
the phenyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl)$_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl)$_2$;
$R^{2a}$ is selected from hydrogen, halogen, cyano, $-OH$, $=O$, and $C_1$-$C_6$ alkyl, wherein:
the $C_1$-$C_6$ alkyl of $R^{2a}$ is optionally substituted with 1 to 3 groups independently selected from halogen, cyano, $-OH$, and $C_1$-$C_4$ alkoxy;
$R^{2b}$ is selected from hydrogen, halogen, cyano, $-OH$, $=O$, and $C_1$-$C_6$ alkyl;
$R^{3a}$ is selected from halogen, cyano, $-OH$, $C_1$-$C_6$ alkyl, and $=O$; wherein:
the $C_1$-$C_6$ alkyl of $R^{3a}$ is optionally substituted with 1 to 3 groups independently selected from halogen, cyano, and $-OH$;
$R^3$ is selected from $C_1$-$C_2$ alkyl and $=O$; wherein:
the $C_1$-$C_2$ alkyl of $R^3$ is optionally substituted with 1 to 3 groups independently selected from halogen, cyano, and $-OH$;
$=====$, for each occurrence, is a single bond when $R^{3a}$ is selected from halogen, cyano, $-OH$, $C_1$-$C_6$ alkyl or when $R^3$ is selected from $C_1$-$C_2$ alkyl; or alternatively $=====$, for each occurrence, is a double bond when $R^{3a}$ is $=O$ or when $R^3$ is $=O$;
$R^4$ is selected from $C_1$-$C_6$ alkyl, $-C(=O)O(C_1$-$C_4$ alkyl), $C_2$-$C_6$ alkynyl, and

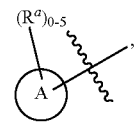

wherein:
the $C_1$-$C_6$ alkyl of $R^4$ is optionally substituted with 1 to 3 groups independently selected from halogen, cyano, $-OH$, $-NH_2$, $-NH(C_1$-$C_4$ alkyl), $-N(C_1$-$C_4$ alkyl)$_2$, $C_1$-$C_4$ alkoxy, $-C(=O)NH_2$, —C(=O)NH($C_1$-$C_4$ alkyl), —C(=O)N($C_1$-$C_4$ alkyl)$_2$, $C_3$-$C_6$ cycloalkyl, 5 to 10-membered heterocyclyl, phenyl, and 5 to 10-membered heteroaryl;

Ring A is selected from $C_3$-$C_{12}$ carbocyclyl, 3 to 12-membered heterocyclyl, $C_6$ and $C_{10}$ aryl, and 5 to 10-membered heteroaryl, wherein Ring A is optionally substituted with 1, 2, 3, 4, or 5 $R^a$ groups; wherein:

$R^a$, for each occurrence, is independently selected from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R, —OC(=O)OR$^k$, —OC(=O)NR$^h$R$^i$, —[O(CH$_2$)$_q$]$_r$O($C_1$-$C_6$ alkyl), —S(=O)$_p$R$^k$, —S(=O)$_p$NR$^h$R$^i$, —C(=O)OR$^k$, $C_3$-$C_{12}$ carbocyclyl, 3- to 12-membered heterocyclyl, $C_6$ and $C_{10}$ aryl, and 5- to 10-membered heteroaryl; wherein:

the $C_1$-$C_6$ alkyl, $C_1$-$C_6$ alkoxy, and the $C_2$-$C_6$ alkenyl of $R^a$ are each optionally substituted with 1 to 3 groups independently selected from $C_6$ to $C_{10}$ aryl (optionally substituted with 1 to 3 $R^m$ groups), 5- to 10-membered heterocyclyl (optionally substituted with 1 to 3 $R^m$ groups), 5- to 10-membered heteroaryl (optionally substituted with 1 to 3 $R^m$ groups), cyano, —C(=O)R$^k$, —C(=O)OR$^k$, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —S(=O)$_p$R$^k$, —S(=O)$_p$NR$^h$R$^i$, and $C_3$-$C_6$ carbocyclyl (optionally substituted with 1 to 3 $R^m$ groups);

the $C_3$-$C_{12}$ carbocyclyl, the 3 to 12-membered heterocyclyl, the $C_6$ and $C_{10}$ aryl, and the 5 to 10-membered heteroaryl of $R^a$ are each optionally substituted with 1 to 3 groups independently selected from halogen, cyano, $C_1$-$C_4$ alkyl, —NR$^h$R$^i$, and —OR; wherein:

$R^h$, $R^i$, and $R^j$, for each occurrence, are each independently selected from hydrogen, $C_1$-$C_4$ alkyl, $C_6$-$C_{10}$ aryl, and $C_3$-$C_6$ cycloalkyl; wherein:

the $C_1$-$C_4$ alkyl of any one of $R^h$, $R^i$, and $R^j$ is optionally substituted with 1 to 3 groups independently selected from halogen, cyano, and —OH;

$R^k$, for each occurrence, are each independently selected from hydrogen, $C_1$-$C_4$ alkyl, 5- to 10-membered heterocyclyl, and $C_3$-$C_6$ carbocyclyl; wherein:

the $C_1$-$C_4$ alkyl of any one of $R^k$ is optionally substituted with 1 to 3 groups independently selected from halogen, cyano, and —OH;

$R^m$, for each occurrence, is independently selected from halogen, cyano, oxo, $C_1$-$C_6$ alkyl, $C_1$-$C_6$ alkoxy, —S(=O)$_p$R$^k$, and —OR$^k$; wherein:

the $C_1$-$C_6$ alkyl of $R^m$ is optionally substituted with 1 to 3 groups independently selected from halogen, cyano, and —OH;

$R^5$ is selected from $C_1$-$C_6$ alkyl, —C(=O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl; wherein:

the $C_1$-$C_6$ alkyl of $R^5$ is optionally substituted with 1 to 3 groups independently selected from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), and —C(=O)N($C_1$-$C_4$ alkyl)$_2$;

the $C_3$-$C_{12}$ carbocyclyl, the 3 to 12-membered heterocyclyl, the $C_6$ and $C_{10}$ aryl, and the 5 to 10-membered heteroaryl of $R^5$ are each optionally substituted with 1 to 3 groups independently selected from halogen, cyano, —OH, —NH$_2$, —NH($C_1$-$C_4$ alkyl) (optionally substituted with —OH), —N($C_1$-$C_4$ alkyl)$_2$, $C_1$-$C_5$ alkyl (optionally substituted with —OH), $C_1$-$C_4$ alkoxy, —C(=O)NH$_2$, —C(=O)NH($C_1$-$C_4$ alkyl), —NHC(=O)($C_1$-$C_4$ alkyl), —C(=O)($C_1$-$C_4$ alkoxy), and —C(=O)N($C_1$-$C_4$ alkyl)$_2$;

k is an integer selected from 0, 1, and 2, wherein:
when $R^{3a}$ is selected from halogen, cyano, —OH, and $C_1$-$C_6$ alkyl, k is 1 or 2; and
when $R^{3a}$ is =O, k is 1;

m is an integer selected from 0, 1, and 2, wherein:
when $R^{3A}$ is selected from $C_1$-$C_2$ alkyl, m is 1 or 2; and
when $R^{3b}$ is =O, m is 1;

p is an integer selected from 1 and 2; and q and r are each an integer selected from 1, 2, 3, and 4.

In some embodiments, $R^4$ is selected from $C_1$-$C_6$ alkyl and

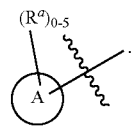

In some embodiments, $R^5$ is selected from $C_1$-$C_6$ alkyl, —C(=O)O($C_1$-$C_4$ alkyl), $C_3$-$C_{12}$ carbocyclyl, 3 to 12-membered heterocyclyl, $C_6$ and $C_{10}$ aryl, and 5 to 10-membered heteroaryl, wherein:

the $C_1$-$C_6$ alkyl of $R^5$ is optionally substituted with 1 to 3 groups selected from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), and —C(=O)N($C_1$-$C_4$ alkyl)$_2$;

the $C_3$-$C_{12}$ carbocyclyl, the 3 to 12-membered heterocyclyl, the $C_6$ and $C_{10}$ aryl, and the 5- to 10-membered heteroaryl of $R^5$ are each optionally substituted with 1 to 3 groups selected from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$.

In some embodiments, at least one compound of the disclosure (e.g., at least one compound of Formula I) is a compound represented by the following structural formula:

Formula I₀

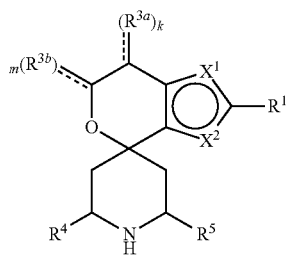

a tautomer thereof, a deuterated derivative of that compound or tautomer, or a
pharmaceutically acceptable salt of any of the foregoing, wherein:
  $X^1$ and $X^2$ are each selected from S and —$CR^2$, wherein:
    one of $X^1$ and $X^2$ is S;
    when $X^1$ is S, then $X^2$ is —$CR^{2b}$; and
    when $X^2$ is S, then $X^1$ is —$CR^{2a}$;
  $R^1$ is selected from halogen, cyano, $C_1$-$C_6$ alkyl, $C_1$-$C_6$ alkoxy, $C_3$-$C_6$ cycloalkyl, and phenyl; wherein:
    the $C_1$-$C_6$ alkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, and $C_1$-$C_4$ alkoxy;
    the $C_1$-$C_6$ alkoxy of $R^1$ is optionally substituted with 1 to 3 groups independently selected from halogen;
    the $C_3$-$C_6$ cycloalkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$; and
    the phenyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$;
  $R^{2a}$ is selected from hydrogen, halogen, cyano, —OH, =O, and $C_1$-$C_6$ alkyl; wherein:
    the $C_1$-$C_6$ alkyl of $R^{2a}$ is optionally substituted with 1 to 3 groups independently selected from halogen, cyano, —OH, and $C_1$-$C_4$ alkoxy;
  $R^{2b}$ is selected from hydrogen, halogen, cyano, —OH, =O, and $C_1$-$C_6$ alkyl;
  $R^{3a}$ is selected from halogen, cyano, —OH, $C_1$-$C_6$ alkyl, and =O; wherein:
    the $C_1$-$C_6$ alkyl of $R^{3a}$ is optionally substituted with 1 to 3 groups independently selected from halogen, cyano, and —OH;
  $R^3$ is selected from $C_1$-$C_2$ alkyl and =O; wherein:
    the $C_1$-$C_2$ alkyl of $R^3$ is optionally substituted with 1 to 3 groups independently selected from halogen, cyano, and —OH;
  ═════, for each occurrence, is a single bond when $R^{3a}$ is selected from halogen, cyano, —OH, $C_1$-$C_6$ alkyl or when $R^3$ is selected from $C_1$-$C_2$ alkyl; or alternatively ═════, for each occurrence, is a double bond when $R^{3a}$ is =O or when $R^3$ is =O;

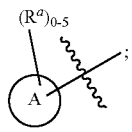

$R^4$ is selected from $C_1$-$C_6$ alkyl and; wherein:
    the $C_1$-$C_6$ alkyl of $R^4$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH($C_1$-$C_4$ alkyl), —C(=O)N($C_1$-$C_4$ alkyl)$_2$, $C_3$-$C_6$ cycloalkyl, 5 to 10-membered heterocyclyl, phenyl, and 5 to 10-membered heteroaryl;
  Ring A is selected from $C_3$-$C_{12}$ carbocyclyl, 3 to 12-membered heterocyclyl, $C_6$ and $C_{10}$ aryl, and 5 to 10-membered heteroaryl, wherein Ring A is optionally substituted with 1, 2, 3, 4, or 5 $R^a$ groups; wherein:
    $R^a$, for each occurrence, is independently selected from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^hC$(=O)$R^k$, —$NR^hC$(=O)$OR^k$, —$NR^hC$(=O)$NR^iR^j$, —$NR^hS$(=O)$_pR^k$, —$OR^k$, —OC(=O)R, —OC(=O)$OR^k$, —OC(=O)$NR^hR^i$, —[O(CH$_2$)$_q$]$_rO(C_1$-$C_6$ alkyl), —S(=O)$_pR^k$, —S(=O)$_pNR^hR^i$, $C_3$-$C_{12}$ carbocyclyl, 3 to 12-membered heterocyclyl, $C_6$ and $C_{10}$ aryl, and 5 to 10-membered heteroaryl; wherein:
      the $C_1$-$C_6$ alkyl and the $C_2$-$C_6$ alkenyl of $R^a$ are each optionally substituted with 1 to 3 groups independently selected from cyano, —C(=O)$R^k$, —C(=O)$OR^k$, —C(=O)$NR^hR^i$, —$NR^hR^i$, —$NR^hC$(=O)$R^k$, —$NR^hC$(=O)$OR^k$, —$NR^hC$(=O)$NR^iR^j$, —$NR^hS$(=O)$_pR^k$, —$OR^k$, —OC(=O)$R^k$, —OC(=O)$OR^k$, —OC(=O)$NR^hR^i$, —S(=O)$_pR^k$, —S(=O)$_pNR^hR^i$, and $C_3$-$C_6$ cycloalkyl;
      the $C_3$-$C_{12}$ carbocyclyl, the 3 to 12-membered heterocyclyl, the $C_6$ and $C_{10}$ aryl, and the 5 to 10-membered heteroaryl of $R^a$ are each optionally substituted with 1 to 3 groups selected from halogen, cyano, $C_1$-$C_4$ alkyl, —$NR^hR^i$, and —$OR^k$; wherein:
        $R^h$, $R^i$, and $R^j$, for each occurrence, are each independently selected from hydrogen, $C_1$-$C_4$ alkyl, and $C_3$-$C_6$ cycloalkyl; wherein:
          the $C_1$-$C_4$ alkyl of any one of $R^h$, $R^i$, and $R^j$ is optionally substituted with 1 to 3 groups selected from halogen, cyano, and —OH;
        $R^k$, for each occurrence, are each independently selected from hydrogen, $C_1$-$C_4$ alkyl, and $C_3$-$C_6$ cycloalkyl; wherein:
          the $C_1$-$C_4$ alkyl of any one of $R^k$ is optionally substituted with 1 to 3 groups selected from halogen, cyano, and —OH;
  $R^5$ is selected from $C_1$-$C_6$ alkyl, —C(=O)O($C_1$-$C_4$ alkyl), $C_3$-$C_{12}$ carbocyclyl, 3 to 12-membered heterocyclyl, $C_6$ and $C_{10}$ aryl, and 5 to 10-membered heteroaryl; wherein:
    the $C_1$-$C_6$ alkyl of $R^5$ is optionally substituted with 1 to 3 groups selected from halogen, cyano, —OH, —NH$_2$, —NH(C$_1$-C$_4$ alkyl), —N(C$_1$-C$_4$ alkyl)$_2$, C$_1$-C$_4$ alkoxy, —C(=O)NH$_2$, —C(=O)NH(C$_1$-C$_4$ alkyl), and —C(=O)N(C$_1$-C$_4$ alkyl)$_2$;

the C$_3$-C$_{12}$ carbocyclyl, the 3 to 12-membered heterocyclyl, the C$_6$ and C$_{10}$ aryl, and the 5 to 10-membered heteroaryl of R$^5$ are each optionally substituted with 1 to 3 groups selected from halogen, cyano, —OH, —NH$_2$, —NH(C$_1$-C$_4$ alkyl), —N(C$_1$-C$_4$ alkyl)$_2$, C$_1$-C$_4$ alkyl, C$_1$-C$_4$ alkoxy, —C(=O)NH$_2$, —C(=O)NH(C$_1$-C$_4$ alkyl), and —C(=O)N(C$_1$-C$_4$ alkyl)$_2$;

k is an integer selected from 0, 1, and 2 when R$^{3a}$ is selected from halogen, cyano, —OH, C$_1$-C$_6$ alkyl; or alternatively k is an integer selected from 0 and 1 when R$^{3a}$ is =O;

m is an integer selected from 0, 1, and 2 when R$^{3A}$ is selected from C$_1$-C$_2$ alkyl; and when R$^{3b}$ is =O, m is an integer selected from 0 and 1;

p is an integer selected from 1 and 2; and q and r are each an integer selected from 1, 2, 3, and 4.

In one aspect of the disclosure, the compounds of Formula I are chosen from Compounds 1 to 391 (e.g., from Compounds 1 to 220), such that the at least one entity is chosen from Compounds 1 to 391 (e.g., from Compounds 1 to 220), pharmaceutically acceptable salts of any of those compounds, solvates of any of the foregoing, and deuterated derivatives of any of the foregoing.

In some embodiments, the disclosure provides pharmaceutical compositions comprising at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing. In some embodiments, the pharmaceutical compositions may comprise at least one compound chosen from Compounds 1 to 391 (e.g., from Compounds 1 to 220), pharmaceutically acceptable salts of any of those compounds, solvates of any of the foregoing, and deuterated derivatives of any of the foregoing. These compositions may further include at least one additional active pharmaceutical ingredient and/or at least one carrier.

Another aspect of the disclosure provides methods of treating an APOL1-mediated disease (e.g., an APOL1-mediated kidney disease) comprising administering to a subject in need thereof, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing or a pharmaceutical composition comprising the at least one entity. In some embodiments, the methods comprise administering at least one entity chosen from Compounds 1 to 391 (e.g., from Compounds 1 to 220), a tautomer thereof, a deuterated derivative of that compound or tautomer, or a pharmaceutically acceptable salt of any of the foregoing.

Another aspect of the disclosure provides methods of treating an APOL1-mediated cancer (such as, e.g., pancreatic cancer) comprising administering to a subject in need thereof, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing or a pharmaceutical composition comprising the at least one entity. In some embodiments, the methods comprise administering at least one entity chosen from Compounds 1 to 391 (e.g., from Compounds 1 to 220), a tautomer thereof, a deuterated derivative of that compound or tautomer, or a pharmaceutically acceptable salt of any of the foregoing.

Another aspect of the disclosure provides methods of treating FSGS and/or NDKD comprising administering to a subject in need thereof, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing or a pharmaceutical composition comprising the at least one entity. In some embodiments, the methods comprise administering at least one entity chosen from Compounds 1 to 391 (e.g., from Compounds 1 to 220), a tautomer thereof, a deuterated derivative of that compound or tautomer, or a pharmaceutically acceptable salt of any of the foregoing.

In some embodiments, the methods of treatment include administration of at least one additional active agent to the subject in need thereof, either in the same pharmaceutical composition as the at least one entity chosen from compounds of Formulae I, IIa, IIb, IIIa, IIIb, IVa, IVb, Va, Vb, I', Ia', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing, or as separate compositions. In some embodiments, the methods comprise administering at least one entity chosen from Compounds 1 to 391 (e.g., from Compounds 1 to 220), a tautomer thereof, a deuterated derivative of that compound or tautomer, or a pharmaceutically acceptable salt of any of the foregoing with at least one additional active agent either in the same pharmaceutical composition or in a separate composition.

Also provided are methods of inhibiting APOL1, comprising administering to a subject in need thereof, at least one entity chosen from compounds of Formulae I, IIa, IIb, IIIa, IIIb, IVa, IVb, V, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', I'', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing or a pharmaceutical composition comprising the at least one entity. In some embodiments, the methods of inhibiting APOL1 comprise administering at least one entity chosen from Compounds 1 to 391 (e.g., from Compounds 1 to 220), a tautomer thereof, a deuterated derivative of that compound or tautomer, or a pharmaceutically acceptable salt of any of the foregoing or a pharmaceutical composition comprising the at least one entity.

DETAILED DESCRIPTION

Definitions

Figure 1:
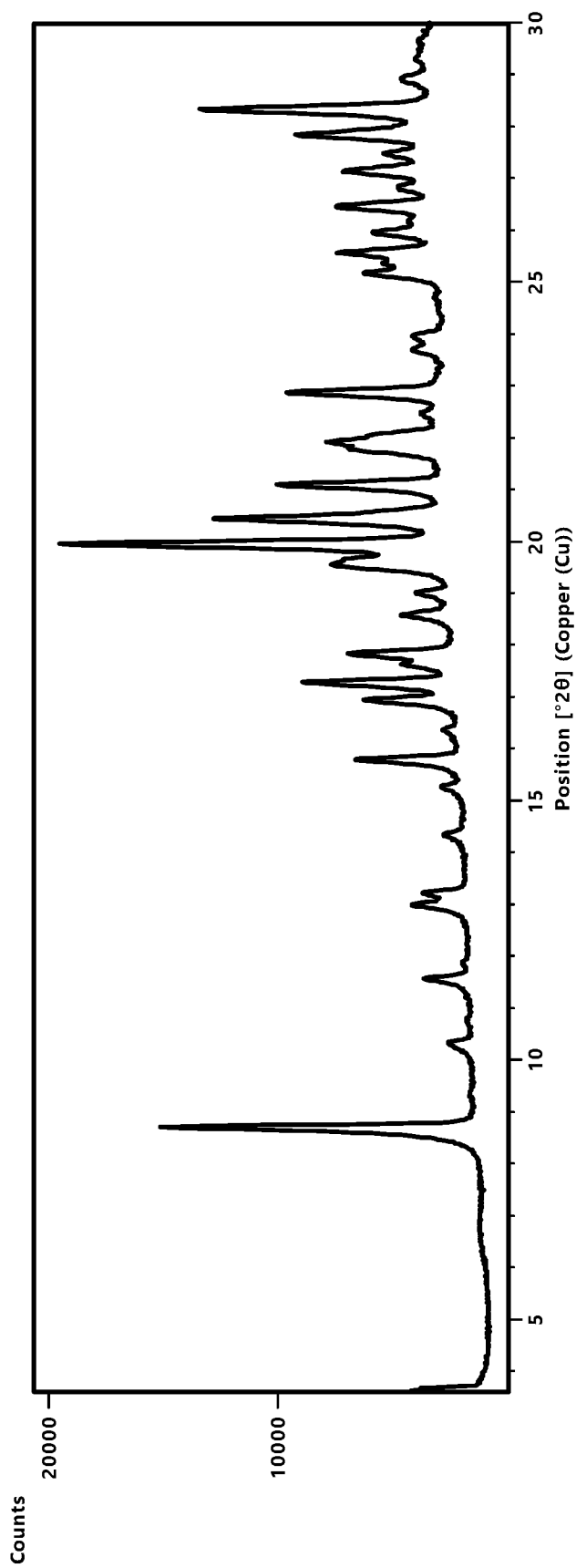
FIG. 1 depicts an XRPD diffractogram of Compound 181 Phosphate Salt Hydrate at 25±2° C. and 40% RH.

The terms "selected from" and "chosen from" are used interchangeably herein.

The term "APOL1," as used herein, means apolipoprotein L1 protein and the term "APOL1" means apolipoprotein L1 gene.

The term "APOL1 mediated disease" refers to a disease or condition associated with aberrant APOL1 (e.g., certain APOL1 genetic variants; elevated levels of APOL1). In some embodiments, an APOL1 mediated disease is an APOL1 mediated kidney disease. In some embodiments, an APOL1 mediated disease is associated with patients having two APOL1 risk alleles, e.g., patients who are homozygous or compound heterozygous for the G1 or G2 alleles. In some embodiments, an APOL1 mediated disease is associated with patients having one APOL1 risk allele.

The term "APOL1 mediated kidney disease" refers to a disease or condition that impairs kidney function and can be attributed to APOL1. In some embodiments, APOL1 mediated kidney disease is associated with patients having two APOL1 risk alleles, e.g., patients who are homozygous or compound heterozygous for the G1 or G2 alleles. In some embodiments, the APOL1 mediated kidney disease is chosen from ESKD, NDKD, FSGS, HIV-associated nephropathy, arterionephrosclerosis, lupus nephritis, microalbuminuria, and chronic kidney disease. In some embodiments, the APOL1 mediated kidney disease is chronic kidney disease or proteinuria.

The term "FSGS," as used herein, means focal segmental glomerulosclerosis, which is a disease of the podocyte (glomerular visceral epithelial cells) responsible for proteinuria and progressive decline in kidney function, and associated with 2 common APOL1 genetic variants (G1: S342G: I384M and G2: N388del:Y389del).

The term "NDKD," as used herein, means non-diabetic kidney disease, which is characterized by severe hypertension and progressive decline in kidney function, and associated with 2 common APOL1 genetic variants (G1: S342G: I384M and G2: N388del:Y389del).

The terms "ESKD" and "ESRD" are used interchangeably herein to refer to end stage kidney disease or end stage renal disease. ESKD/ESRD is the last stage of kidney disease, i.e., kidney failure, and means that the kidneys have stopped working well enough for the patient to survive without dialysis or a kidney transplant. In some embodiments, ESKD/ESRD is associated with two APOL1 risk alleles.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms will also contain lesser amounts of isotopologues having hydrogen atoms at one or more of the designated deuterium positions in that structure. The relative amount of such isotopologues in a compound of this disclosure will depend upon a number of factors, including the isotopic purity of reagents used to make the compound and the efficiency of incorporation of isotopes in the various synthesis steps used to prepare the compound. However, as set forth above, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted," whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a reference compound only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$, are within the scope of this disclosure.

Unless otherwise indicated, structures depicted herein are also meant to include all isomeric forms of the structures, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer," as used herein, refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation, is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), or at least 6600 (99% deuterium incorporation).

The term "isotopic enrichment factor," as used herein, means the ratio between the isotopic abundance and the natural abundance of a specified isotope.

The term "alkyl" or "aliphatic," as used herein, means a straight-chain (i.e., linear or unbranched) or branched, substituted or unsubstituted hydrocarbon chain that is completely saturated. Unless otherwise specified, alkyl groups contain 1 to 20 alkyl carbon atoms. In some embodiments, alkyl groups contain 1 to 10 aliphatic carbon atoms. In some embodiments, alkyl groups contain 1 to 8 aliphatic carbon atoms. In some embodiments, alkyl groups contain 1 to 6 alkyl carbon atoms, and in some embodiments, alkyl groups contain 1 to 4 alkyl carbon atoms. In other embodiments, alkyl groups contain 1 to 3 alkyl carbon atoms, and in yet other embodiments, alkyl groups contain 1 to 2 alkyl carbon atoms. In some embodiments, alkyl groups are substituted. In some embodiments, alkyl groups are unsubstituted. In some embodiments, alkyl groups are linear or straight-chain or unbranched. In some embodiments, alkyl groups are branched.

The terms "cycloalkyl," or "cyclic alkyl," as used herein, refer to a monocyclic $C_{3-8}$ hydrocarbon or a spirocyclic, fused, or bridged bicyclic or tricyclic $C_5$-14 hydrocarbon that is completely saturated, wherein any individual ring in said bicyclic ring system has 3 to 7 members. In some embodiments, cycloalkyl groups are substituted. In some embodiments, cycloalkyl groups are unsubstituted. In some embodiments, the cycloalkyl is a $C_3$ to $C_{12}$ cycloalkyl. In some embodiments, the cycloalkyl is a $C_3$ to $C_8$ cycloalkyl. In some embodiments, the cycloalkyl is a $C_3$ to $C_6$ cycloalkyl. Non-limiting examples of monocyclic cycloalkyls include cyclopropyl, cyclobutyl, cyclopentanyl, and cyclohexyl.

The terms "carbocyclyl" or "cycloaliphatic," as used herein, encompass the terms "cycloalkyl" or "cyclic alkyl," and refer to a monocyclic $C_{3-8}$ hydrocarbon or a spirocyclic, fused, or bridged bicyclic or tricyclic $C_{8-14}$ hydrocarbon that is completely saturated, or is partially saturated as in it contains one or more units of unsaturation but is not aromatic, wherein any individual ring in said bicyclic ring system has 3 to 7 members. Bicyclic carbocyclyls include combinations of a monocyclic carbocyclic ring fused to a phenyl. In some embodiments, carbocyclyl groups are substituted. In some embodiments, carbocyclyl groups are unsubstituted. In some embodiments, the carbocyclyl is a $C_3$ to $C_{12}$ carbocyclyl. In some embodiments, the carbocyclyl is a $C_3$ to $C_{10}$ carbocyclyl. In some embodiments, the carbocyclyl is a $C_3$ to $C_8$ carbocyclyl.

The terms "heteroalkyl," or "heteroaliphatic," as used herein, refer to alkyl or aliphatic groups as defined above, wherein one or two carbon atoms are independently replaced by one or more of oxygen, sulfur, nitrogen, phosphorus, or silicon.

The term "alkenyl," as used herein, means a straight-chain (i.e., linear or unbranched), branched, substituted or unsubstituted hydrocarbon chain that contains one or more double bonds. In some embodiments, alkenyl groups are substituted. In some embodiments, alkenyl groups are unsubstituted. In some embodiments, alkenyl groups are straight-chain. In some embodiments, alkenyl groups are branched.

The term "heterocycle," "heterocyclyl," "heterocycloaliphatic," or "heterocyclic," as used herein, means non-aromatic (i.e., completely saturated or partially saturated as in it contains one or more units of unsaturation but is not aromatic), monocyclic, or spirocyclic, fused, or bridged bicyclic or tricyclic ring systems in which one or more ring members is an independently chosen heteroatom. Bicyclic heterocyclyls include the following combinations of monocyclic rings: a monocyclic heteroaryl fused to a monocyclic heterocyclyl; a monocyclic heterocyclyl fused to another monocyclic heterocyclyl; a monocyclic heterocyclyl fused to phenyl; a monocyclic heterocyclyl fused to a monocyclic carbocyclyl/cycloalkyl; and a monocyclic heteroaryl fused to a monocyclic carbocyclyl/cycloalkyl.

In some embodiments, the heterocycle comprises a ring atom substituted with one or more oxo groups (such as, e.g., a C=O group, a S=O group, or a $SO_2$ group).

In some embodiments, the "heterocycle," "heterocyclyl," "heterocycloaliphatic," or "heterocyclic" group has 3 to 14 ring members in which one or more ring members is a heteroatom independently chosen from oxygen, sulfur, nitrogen, and phosphorus. In some embodiments, each ring in a bicyclic or tricyclic ring system contains 3 to 7 ring members. In some embodiments, the heterocycle has at least one unsaturated carbon-carbon bond. In some embodiments, the heterocycle has at least one unsaturated carbon-nitrogen bond. In some embodiments, the heterocycle has one heteroatom independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has two heteroatoms that are each independently selected from nitrogen and oxygen. In some embodiments, the heterocycle has three heteroatoms that are each independently selected from nitrogen and oxygen. In some embodiments, heterocycles are substituted. In some embodiments, heterocycles are unsubstituted. In some embodiments, the heterocyclyl is a 3- to 12-membered heterocyclyl. In some embodiments, the heterocyclyl is a 3- to 10-membered heterocyclyl. In some embodiments, the heterocyclyl is a 3- to 8-membered heterocyclyl. In some embodiments, the heterocyclyl is a 5- to 10-membered heterocyclyl. In some embodiments, the heterocyclyl is a 5- to 8-membered heterocyclyl. In some embodiments, the heterocyclyl is a 5- or 6-membered heterocyclyl. Non-limiting examples of monocyclic heterocyclyls include piperidinyl, piperazinyl, tetrahydropyranyl, azetidinyl, tetrahydrothiophenyl 1,1-dioxide, etc.

The term "heteroatom" means one or more of oxygen, sulfur, nitrogen, phosphorus, or silicon (including, e.g., any oxidized form of nitrogen, sulfur, phosphorus, or silicon; the quaternized form of any basic nitrogen or; a substitutable nitrogen of a heterocyclic ring, for example, N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units or degrees of unsaturation. Unsaturation is the state in which not all of the available valence bonds in a compound are satisfied by substituents and thus the compound contains double or triple bonds.

The term "alkoxy" or "thioalkyl," as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. Non-limiting examples of alkoxy groups include methoxy, ethoxy, methylmethoxy, and the like. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl. In some embodiments, "alkoxy" and/or "thioalkyl" groups are substituted. In some embodiments, "alkoxy" and/or "thioalkyl" groups are unsubstituted.

The terms "haloalkyl," "haloalkenyl," and "haloalkoxy," as used herein, refer to a linear or branched alkyl, alkenyl, or alkoxy, respectively, which is substituted with one or more halogen atoms. Non-limiting examples of haloalkyl groups include —$CHF_2$, —$CH_2F$, —$CF_3$, —$CF_2$—, and perhaloalkyls, such as —$CF_2CF_3$. Non-limiting examples of haloalkoxy groups include —$OCHF_2$, —$OCH_2F$, —$OCF_3$, and —$OCF_2$.

The term "halogen" includes F, Cl, Br, and I, i.e., fluoro, chloro, bromo, and iodo, respectively.

The term "aminoalkyl" means an alkyl group which is substituted with or contains an amino group.

As used herein, an "amino" refers to a group which is a primary, secondary, or tertiary amine.

As used herein, a "carbonyl" group refers to C=O.

As used herein, a "cyano" or "nitrile" group refer to —C≡N.

As used herein, a "hydroxy" group refers to —OH.

As used herein, a "thiol" group refers to —SH.

As used herein, "tert" and "t-" each refer to tertiary.

As used herein, "aromatic groups" or "aromatic rings" refer to chemical groups that contain conjugated, planar ring systems with delocalized pi electron orbitals comprised of [4n+2]p orbital electrons, wherein n is an integer ranging from 0 to 6. Non-limiting examples of aromatic groups include aryl and heteroaryl groups.

The term "aryl" used alone, or as part of a larger moiety as in "arylalkyl," "arylalkoxy," or "aryloxyalkyl," refers to monocyclic or spirocyclic, fused, or bridged bicyclic or tricyclic ring systems having a total of five to fourteen ring members, wherein every ring in the system is an aromatic ring containing only carbon atoms and wherein each ring in a bicyclic or tricyclic ring system contains 3 to 7 ring members. Non-limiting examples of aryl groups include phenyl ($C_6$) and naphthyl ($C_{10}$) rings. In some embodiments, aryl groups are substituted. In some embodiments, aryl groups are unsubstituted.

The term "heteroaryl," used alone or as part of a larger moiety as in "heteroarylalkyl" or "heteroarylalkoxy," refers to monocyclic or spirocyclic, fused, or bridged bicyclic or tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. Bicyclic heteroaryls include the following combinations of monocyclic rings: a monocyclic heteroaryl fused to another monocyclic heteroaryl; and a monocyclic heteroaryl fused to a phenyl. In some embodiments, heteroaryl groups are substituted. In some embodiments, heteroaryl groups have one or more heteroatoms chosen from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted. In some embodiments, the heteroaryl is a 3- to 12-membered heteroaryl. In some embodiments, the heteroaryl is a 3- to 10-membered heteroaryl. In some embodiments, the heteroaryl is a 3- to 8-membered heteroaryl. In some embodiments, the heteroaryl is a 5- to 10-membered heteroaryl. In some embodiments, the heteroaryl is a 5- to 8-membered heteroaryl. In some embodiments, the heteroaryl is a 5- or 6-membered heteroaryl. Non-limiting examples of monocyclic heteroaryls are pyridinyl, pyrimidinyl, thiophenyl, thiazolyl, isoxazolyl, etc.

In some embodiments, the heteroaryl comprises a ring atom substituted with one or more oxo groups (such as, e.g., a C=O group, a S=O group, or a $SO_2$ group). Illustratively, a non-limiting example of a heteroaryl group is a benzo[d]oxazol-2(3H)-one group.

Non-limiting examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999) and $4^{th}$ Edition (John Wiley & Sons, New Jersey, 2014).

Non-limiting examples of suitable solvents that may be used in methods of this disclosure include, but are not limited to, water, methanol (MeOH), ethanol (EtOH), dichloromethane or "methylene chloride" ($CH_2C_2$), toluene, acetonitrile (MeCN), dimethylformamide (DMF), dimethyl sulfoxide (DMSO), methyl acetate (MeOAc), ethyl acetate (EtOAc), heptane, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in methods of this disclosure include, but are not limited to, 1,8-diazabicyclo[5.4.0]undec-7-ene (DBU), potassium tert-butoxide (KOtBu), potassium carbonate ($K_2CO_3$), N-methylmorpholine (NMN), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response, and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences*, 1977, 66, 1 to 19.

Acids commonly employed to form pharmaceutically acceptable salts include inorganic acids such as hydrogen bisulfide, hydrochloric acid, hydrobromic acid, hydroiodic acid, sulfuric acid, and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate, and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}$ alkyl$)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

The terms "patient" and "subject" are used interchangeably herein and refer to an animal, including a human.

The terms "effective dose" and "effective amount" are used interchangeably herein and refer to that amount of compound that produces the desired effect for which it is administered (e.g., improvement in symptoms of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates as used herein, include, but are not limited to, the following: complete or partial remission, lower risk of kidney failure (e.g., ESRD), and disease-related complications (e.g., edema, susceptibility to infections, or thromboembolic events). Improvements in or lessening the severity of any of these symptoms can be readily assessed according to methods and techniques known in the art or subsequently developed.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

The at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing may be administered once daily, twice daily, or three times daily, for example, for the treatment of FSGS. In some embodiments, the compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$) are chosen from Compounds 1 to 391 (e.g., from Compounds 1 to 220), a tautomer thereof, a deuterated derivative of that compound or tautomer, or a pharmaceutically acceptable salt of any of the foregoing. In some embodiments, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing is administered once daily. In some embodiments, at least one entity chosen from Compounds 1 to 391 (e.g., from Compounds 1 to 220), a tautomer thereof, a deuterated derivative of that compound or tautomer, or a pharmaceutically acceptable salt of any of the foregoing is administered once daily. In some embodiments, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing is administered twice daily. In some embodiments, at least one entity chosen from Compounds 1 to 391 (e.g., from Compounds 1 to 220), a tautomer thereof, a deuterated derivative of that compound or tautomer, or a pharmaceutically acceptable salt of any of the foregoing is administered twice daily. In some embodiments, at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing are administered three times daily. In some embodiments, at least one entity chosen from Compounds 1 to 391 (e.g., from Compounds 1 to 220), a tautomer thereof, a deuterated derivative of that compound or tautomer, or a pharmaceutically acceptable salt of any of the foregoing is administered three times daily.

In some embodiments, 2 mg to 1500 mg or 5 mg to 1000 mg of at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., from compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing are administered once daily, twice daily, or three times daily. In some embodiments, 2 mg to 1500 mg or 5 mg to 1000 mg of at least one entity chosen from Compounds 1 to 391 (e.g., from Compounds 1 to 220), a tautomer thereof, a deuterated derivative of that compound or tautomer, or a pharmaceutically acceptable salt of any of the foregoing is administered once daily, twice daily, or three times daily.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "1000 mg of at least one compound chosen from compounds of Formula I and pharmaceutically acceptable salts thereof" includes 1000 mg of a compound of Formula I and a concentration of a pharmaceutically acceptable salt of compounds of Formula I equivalent to 1000 mg of compounds of Formula I.

As used herein, the term "ambient conditions" means room temperature, open air condition, and uncontrolled humidity condition.

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), infrared radiation (IR), and/or thermogravimetric analysis (TGA). Accordingly, as used herein, the term "Form A of Compound [X]" or "Compound [X] Form A" refers to a unique crystalline form that can be identified and distinguished from other crystalline forms of Compound I by one or more characterization techniques including, for example, X-ray powder diffraction (XRPD), single crystal X-ray diffraction, SSNMR, differential scanning calorimetry (DSC), infrared radiation (IR), and/or thermogravimetric analysis (TGA).

As used herein, the term "SSNMR" refers to the analytical characterization method of solid state nuclear magnetic resonance. SSNMR spectra can be recorded at ambient conditions or at alternative conditions (e.g., at 275 K) on any magnetically active isotope present in the sample. The typical examples of active isotopes for small molecule active pharmaceutical ingredients include $^1$H, $^2$H, $^{13}$C, $^{19}$F, $^{31}$P, $^{15}$N, $^{14}$N, $^{35}$Cl, $^{11}$B, $^7$Li, $^{17}$O, $^{23}$Na, $^{79}$Br, and $^{195}$Pt.

As used herein, the term "XRPD" refers to the analytical characterization method of X-ray powder diffraction. XRPD patterns can be recorded under ambient conditions in transmission or reflection geometry using a diffractometer.

As used herein, the terms "X-ray powder diffractogram," "X-ray powder diffraction pattern," and "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) selected from . . . ."

A "signal" or "peak," as used herein, refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[ ] of . . . ," and/or "a signal at at least . . . two-theta value(s) selected from . . . ." refer to X-ray reflection positions as measured and observed in X-ray powder diffraction experiments (° 2θ).

The repeatability of the angular values is in the range of ±0.2°2θ, i.e., the angular value can be at the recited angular value +0.2 degrees two-theta, the angular value -0.2 degrees two-theta, or any value between those two end points (angular value +0.2 degrees two-theta and angular value -0.2 degrees two-theta).

As used herein, the terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, the term "DSC" refers to the analytical method of Differential Scanning Calorimetry.

As used herein, the term "TGA" refers to the analytical method of Thermo Gravimetric (or thermogravimetric) Analysis.

As used herein, a "crystalline hydrate" is a crystal form comprising either stoichiometric or nonstoichiometric water in the crystal lattice. In the case of nonstoichiometric hydrate, the amount of water present in a crystalline hydrate may vary as a function of at least the relative humidity ("RH"). The presence (or absence) of water or different amounts of water may lead to X-ray diffractogram peak position shifts, or the appearance or disappearance of peaks. The presence (or absence) of water or different amount of water may lead to peak shifts or even appearances of new peaks in proton, carbon, fluorine, phosphorus, nitrogen, chlorine (or other NMR active nuclei) solid state NMR spectra.

Compounds and Compositions

In some embodiments, at least one entity of the disclosure is a compound represented by the following structural formula:

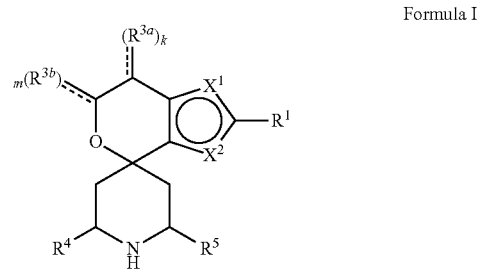

Formula I a tautomer thereof, a deuterated derivative of that compound or tautomer, or a
pharmaceutically acceptable salt of any of the foregoing, wherein:
  $X^1$ is selected from S and —$CR^{2a}$ and $X^2$ is selected from S and —$CR^{2b}$, wherein:
    one of $X^1$ and $X^2$ is S;
    when $X^1$ is S, then $X^2$ is —$CR^{2b}$; and
    when $X^2$ is S, then $X^1$ is —$CR^{2a}$;
  $R^1$ is selected from halogen, cyano, $C_1$-$C_6$ alkyl, $C_1$-$C_6$ alkoxy, $C_3$-$C_6$ cycloalkyl, and phenyl, wherein:
    the $C_1$-$C_6$ alkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, and $C_1$-$C_4$ alkoxy;
    the $C_1$-$C_6$ alkoxy of $R^1$ is optionally substituted with 1 to 3 groups independently selected from halogen;
    the $C_3$-$C_6$ cycloalkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$; and
    the phenyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH(C$_1$-C$_4$ alkyl), and —C(=O)N(C$_1$-C$_4$ alkyl)$_2$;

R$^{2a}$ is selected from hydrogen, halogen, cyano, —OH, =O, and C$_1$-C$_6$ alkyl, wherein:
the C$_1$-C$_6$ alkyl of R$^{2a}$ is optionally substituted with 1 to 3 groups independently selected from halogen, cyano, —OH, and C$_1$-C$_4$ alkoxy;

R$^{2b}$ is selected from hydrogen, halogen, cyano, —OH, =O, and C$_1$-C$_6$ alkyl;

R$^{3a}$ is selected from halogen, cyano, —OH, C$_1$-C$_6$ alkyl, and =O; wherein:
the C$_1$-C$_6$ alkyl of R$^{3a}$ is optionally substituted with 1 to 3 groups independently selected from halogen, cyano, and —OH;

R$^3$ is selected from C$_1$-C$_2$ alkyl and =O; wherein:
the C$_1$-C$_2$ alkyl of R$^3$ is optionally substituted with 1 to 3 groups independently selected from halogen, cyano, and —OH;

━━━━, for each occurrence, is a single bond when R$^{3a}$ is selected from halogen, cyano, —OH, C$_1$-C$_6$ alkyl or when R$^3$ is selected from C$_1$-C$_2$ alkyl; or alternatively ━━━━, for each occurrence, is a double bond when R$^{3a}$ is =O or when R$^3$ is =O;

R$^4$ is selected from C$_1$-C$_6$ alkyl, —C(=O)O(C$_1$-C$_4$ alkyl), C$_2$-C$_6$ alkynyl, and

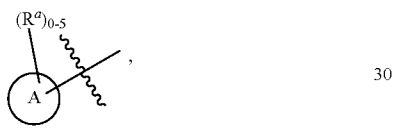

wherein:
the C$_1$-C$_6$ alkyl of R$^4$ is optionally substituted with 1 to 3 groups independently selected from halogen, cyano, —OH, —NH$_2$, —NH(C$_1$-C$_4$ alkyl), —N(C$_1$-C$_4$ alkyl)$_2$, C$_1$-C$_4$ alkoxy, —C(=O)NH$_2$, —C(=O)NH(C$_1$-C$_4$ alkyl), —C(=O)N(C$_1$-C$_4$ alkyl)$_2$, C$_3$-C$_6$ cycloalkyl, 5 to 10-membered heterocyclyl, phenyl, and 5 to 10-membered heteroaryl;

Ring A is selected from C$_3$-C$_{12}$ carbocyclyl, 3 to 12-membered heterocyclyl, C$_6$ and C$_{10}$ aryl, and 5 to 10-membered heteroaryl, wherein Ring A is optionally substituted with 1, 2, 3, 4, or 5 R$^a$ groups; wherein:
R$^a$, for each occurrence, is independently selected from halogen, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkenyl, C$_1$-C$_6$ haloalkoxy, —C(=O)NR$^h$R$^i$, —NR$^h$R$^i$, —NR$^h$C(=O)R$^i$, —NR$^h$C(=O)OR$^i$, —NR$^h$C(=O)NR$^i$R$^j$, —NR$^h$S(=O)$_p$R, —OR$^k$, —OC(=O)R, —OC(=O)OR$^k$, —OC(=O)NR$^h$R$^i$, —[O(CH$_2$)$_q$]$_r$O(C$_1$-C$_6$ alkyl), —S(=O)$_p$R$^k$, —S(=O)$_p$NR$^h$R$^i$, —C(=O)OR$^k$, C$_3$-C$_{12}$ carbocyclyl, 3- to 12-membered heterocyclyl, C$_6$ and C$_{10}$ aryl, and 5- to 10-membered heteroaryl; wherein:
the C$_1$-C$_6$ alkyl, C$_1$-C$_6$ alkoxy, and the C$_2$-C$_6$ alkenyl of R$^a$ are each optionally substituted with 1 to 3 groups independently selected from C$_6$ to C$_{10}$ aryl (optionally substituted with 1 to 3 R$^m$ groups), 5- to 10-membered heterocyclyl (optionally substituted with 1 to 3 R$^m$ groups), 5- to 10-membered heteroaryl (optionally substituted with 1 to 3 R$^m$ groups), cyano, —C(=O)R$^h$, —C(=O)OR$^k$, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —S(=O)$_p$R$^k$, —S(=O)$_p$NR$^h$R$^i$, and C$_3$-C$_6$ carbocyclyl (optionally substituted with 1 to 3 R$^m$ groups);

the C$_3$-C$_{12}$ carbocyclyl, the 3 to 12-membered heterocyclyl, the C$_6$ and C$_{10}$ aryl, and the 5 to 10-membered heteroaryl of R$^a$ are each optionally substituted with 1 to 3 groups independently selected from halogen, cyano, C$_1$-C$_4$ alkyl, —NR$^h$R$^i$, and —OR$^k$; wherein:
R$^h$, R$^i$, and R$^j$, for each occurrence, are each independently selected from hydrogen, C$_1$-C$_4$ alkyl, C$_6$-C$_{10}$ aryl, and C$_3$-C$_6$ cycloalkyl; wherein:
the C$_1$-C$_4$ alkyl of any one of R$^h$, R$^i$, and R$^j$ is optionally substituted with 1 to 3 groups independently selected from halogen, cyano, and —OH; R$^k$, for each occurrence, are each independently selected from hydrogen, C$_1$-C$_4$ alkyl, 5- to 10-membered heterocyclyl, and C$_3$-C$_6$ carbocyclyl; wherein:
the C$_1$-C$_4$ alkyl of any one of R$^k$ is optionally substituted with 1 to 3 groups independently selected from halogen, cyano, and —OH; R$^k$, for each occurrence, is independently selected from halogen, cyano, oxo, C$_1$-C$_6$ alkyl, C$_1$-C$_6$ alkoxy, —S(=O)$_p$R$^k$, and —OR$^k$; wherein:
the C$_1$-C$_6$ alkyl of R$^m$ is optionally substituted with 1 to 3 groups independently selected from halogen, cyano, and —OH;

R$^5$ is selected from C$_1$-C$_6$ alkyl, —C(=O)O(C$_1$-C$_4$ alkyl), C$_3$-C$_{12}$ carbocyclyl, 3- to 12-membered heterocyclyl, C$_6$ and C$_{10}$ aryl, and 5- to 10-membered heteroaryl; wherein:
the C$_1$-C$_6$ alkyl of R$^5$ is optionally substituted with 1 to 3 groups independently selected from halogen, cyano, —OH, —NH$_2$, —NH(C$_1$-C$_4$ alkyl), —N(C$_1$-C$_4$ alkyl)$_2$, C$_1$-C$_4$ alkoxy, —C(=O)NH$_2$, —C(=O)NH(C$_1$-C$_4$ alkyl), and —C(=O)N(C$_1$-C$_4$ alkyl)$_2$;

the C$_3$-C$_{12}$ carbocyclyl, the 3 to 12-membered heterocyclyl, the C$_6$ and C$_{10}$ aryl, and the 5 to 10-membered heteroaryl of R$^5$ are each optionally substituted with 1 to 3 groups independently selected from halogen, cyano, —OH, —NH$_2$, —NH(C$_1$-C$_4$ alkyl) (optionally substituted with —OH), —N(C$_1$-C$_4$ alkyl)$_2$, C$_1$-C$_5$ alkyl (optionally substituted with —OH), C$_1$-C$_4$ alkoxy, —C(=O)NH$_2$, —C(=O)NH(C$_1$-C$_4$ alkyl), —NHC(=O)(C$_1$-C$_4$ alkyl), —C(=O)(C$_1$-C$_4$ alkoxy), and —C(=O)N(C$_1$-C$_4$ alkyl)$_2$;

k is an integer selected from 0, 1, and 2, wherein:
when R$^{3a}$ is selected from halogen, cyano, —OH, and C$_1$-C$_6$ alkyl, k is 1 or 2; and
when R$^{3a}$ is =O, k is 1;

m is an integer selected from 0, 1, and 2, wherein:
when R$^{3b}$ is selected from C$_1$-C$_2$ alkyl, m is 1 or 2; and
when R$^{3b}$ is =O, m is 1;

p is an integer selected from 1 and 2; and q and r are each an integer selected from 1, 2, 3, and 4.

In certain embodiments, a compound of the disclosure is represented by one of the following structural formulae:

Formula IIa

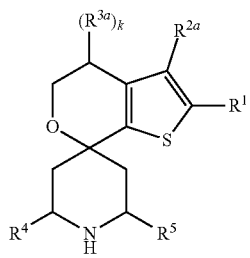

Formula IIb

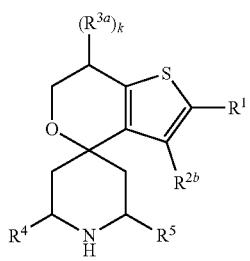

a tautomer thereof, a deuterated derivative of that compound or tautomer, or a pharmaceutically acceptable salt of any of the foregoing, wherein:

$R^{2a}$ is selected from hydrogen, halogen, cyano, and $C_1$-$C_4$ alkyl; wherein:

the $C_1$-$C_4$ alkyl of $R^{2a}$ is optionally substituted with 1 to 3 groups independently selected from halogen, —OH, and $C_1$-$C_2$ alkoxy;

$R^{2b}$ is selected from hydrogen, halogen, cyano, and $C_1$-$C_4$ alkyl; and k is an integer selected from 0, 1, and 2;

and all other variables not specifically defined herein are as defined in the foregoing embodiment.

In certain embodiments, in a compound, tautomer, deuterated derivative, or pharmaceutically acceptable salt of the disclosure, $R^4$ is selected from $C_1$-$C_4$ alkyl and

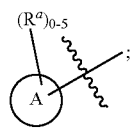

wherein:

the $C_1$-$C_4$ alkyl of $R^4$ is optionally substituted with 1 to 3 groups independently selected from halogen, cyano, —OH, —$NH_2$, —$NH(C_1$-$C_4$ alkyl), —$N(C_1$-$C_4$ alkyl)$_2$, $C_1$-$C_2$ alkoxy, $C_3$-$C_6$ cycloalkyl, 5- to 6-membered heterocyclyl, phenyl, and 5 to 6-membered heteroaryl; and all other variables not specifically defined herein are as defined in any one of the foregoing embodiments.

In certain embodiments, in a compound, tautomer, deuterated derivative, or pharmaceutically acceptable salt of the disclosure, $R^4$ is selected from $C_1$-$C_2$ alkyl and

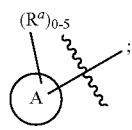

wherein:

the $C_1$-$C_2$ alkyl of $R^4$ is optionally substituted with 1 to 3 groups independently selected from halogen, cyano, —OH, and 5- to 6-membered heterocyclyl;

and all other variables not specifically defined herein are as defined in any one of the foregoing embodiments.

In certain embodiments, in a compound, tautomer, deuterated derivative, or pharmaceutically acceptable salt of the disclosure, $R^4$ is selected from —$CH_3$, —$CH_2OH$, and (tetrahydro-2H-pyran-4-yl)methyl; and all other variables not specifically defined herein are as defined in any one of the foregoing embodiments.

In certain embodiments, a compound of the disclosure is represented by one of the following structural formulae:

Formula IIIa

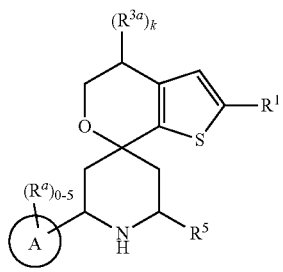

Formula IIIb

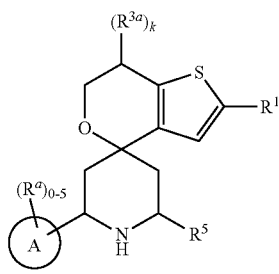

a tautomer thereof, a deuterated derivative of that compound or tautomer, or a pharmaceutically acceptable salt of any of the foregoing, wherein:

Ring A, for each occurrence, is selected from $C_3$-$C_6$ cycloalkyl, 5- to 10-membered heterocyclyl, phenyl, and 5- to 10-membered heteroaryl; each of which is optionally substituted with 1, 2, 3, 4, or 5 $R^a$ groups;

and all other variables not specifically defined herein are as defined in any one of the foregoing embodiments.

In certain embodiments, in a compound, tautomer, deuterated derivative, or pharmaceutically acceptable salt of the disclosure, Ring A is selected from cyclopropyl, 5- to 10-membered heterocyclyl, phenyl, and 5 to 9-membered heteroaryl; each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, Ring A is selected from cyclopropyl, 5- to 10-membered heterocyclyl containing 1 to 3 heteroatoms selected from N and O, phenyl, and 5 to 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, Ring A is selected from cyclopropyl, 5-membered heterocyclyl containing 1 to 3 heteroatoms selected from N and O, 6-membered heterocyclyl containing 1 to 3 heteroatoms selected from N and O, 9-membered heterocyclyl containing 1 to 3 heteroatoms selected from N and O, 10-membered heterocyclyl containing 1 to 3 heteroatoms selected from N and O, phenyl, 5-membered heteroaryl containing 1 to 3 heteroatoms selected from N and O, 6-membered heteroaryl containing 1 to 3 heteroatoms selected from N and O, and 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, Ring A is selected from

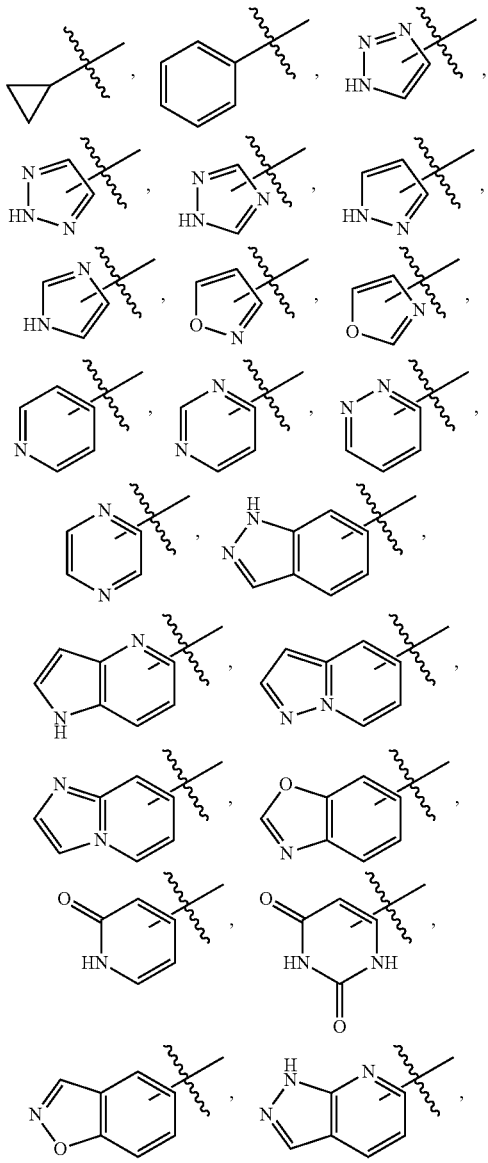

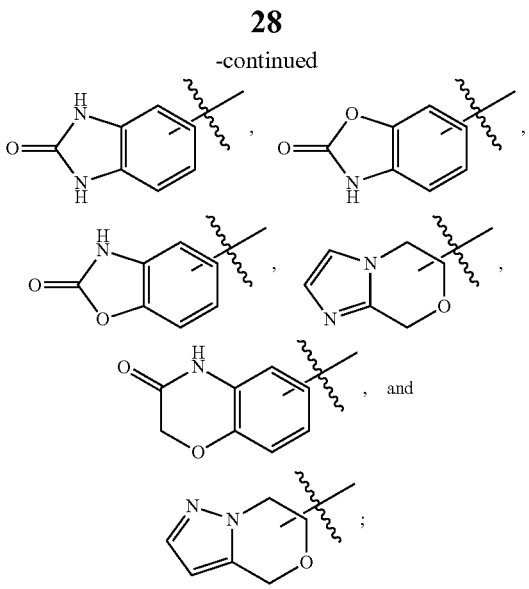

each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, Ring A is selected from

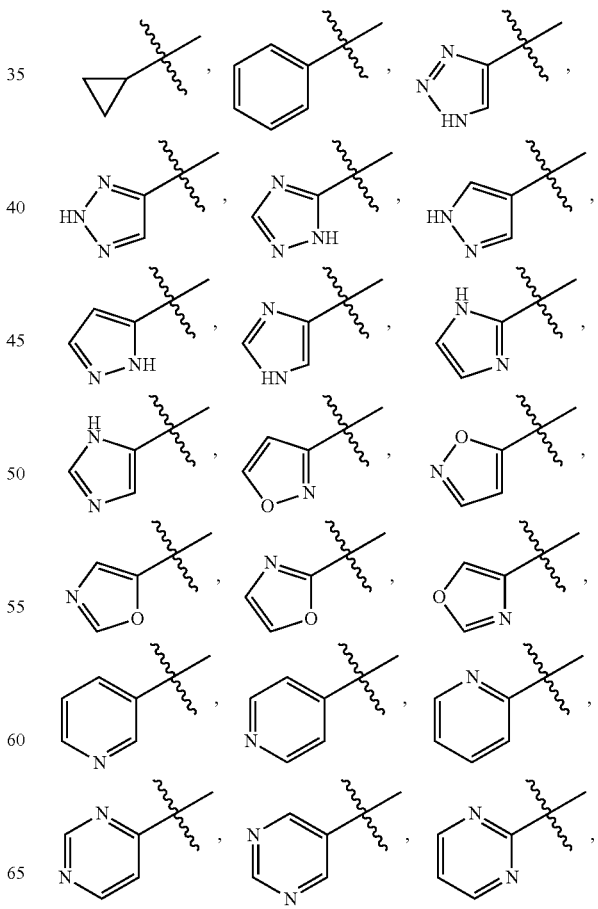

-continued

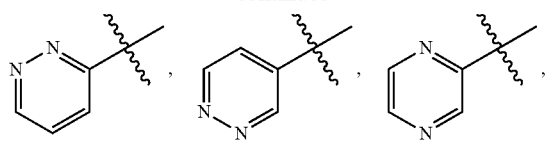
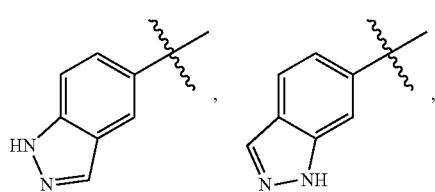
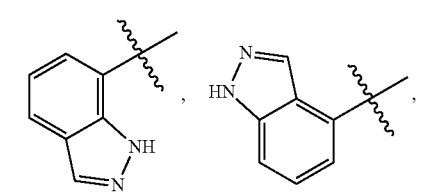
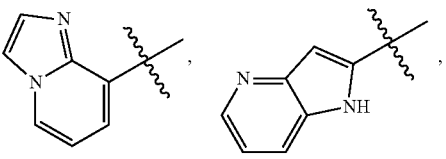
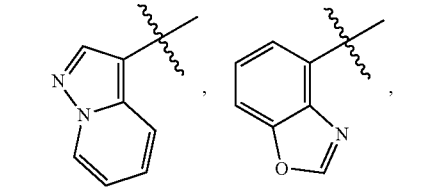
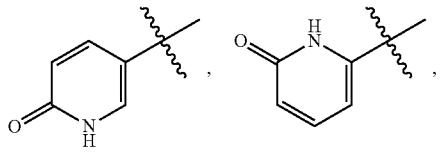

-continued

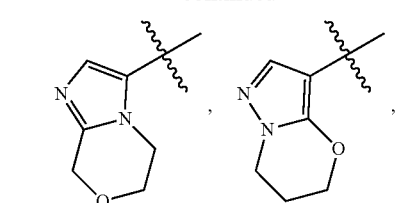
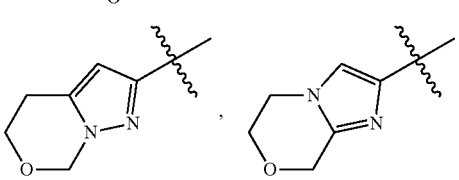
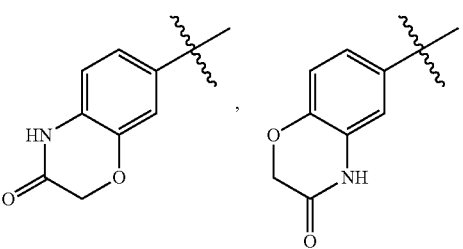
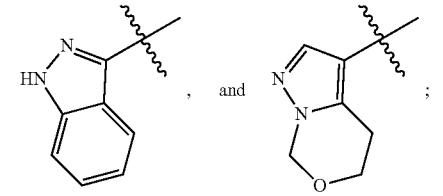

each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, $R^4$ is selected from —$CH_3$ and Ring A; wherein Ring A is selected from

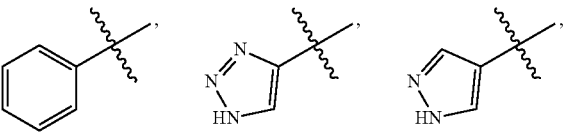
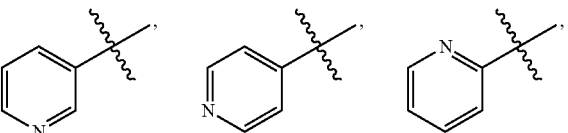
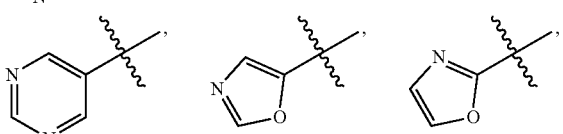
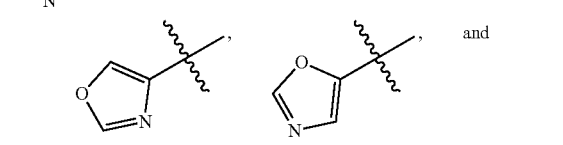

-continued

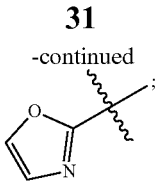

each of which is optionally substituted with 1, 2, 3, 4, or 5 $R^a$ groups; and all other variables not specifically defined herein are as defined in any one of the foregoing embodiments.

In certain embodiments, in a compound, tautomer, deuterated derivative, or pharmaceutically acceptable salt of the disclosure, $R^5$ is selected from $C_1$-$C_4$ alkyl, —C(═O)O($C_1$-$C_2$ alkyl), $C_3$-$C_6$ cycloalkyl, and 5 to 10-membered heterocyclyl; wherein:
- the $C_1$-$C_4$ alkyl of $R^5$ is optionally substituted with 1 to 3 groups independently selected from halogen, cyano, —OH, and $C_1$-$C_2$ alkoxy; and
- the $C_3$-$C_6$ cycloalkyl and the 5- to 10-membered heterocyclyl of $R^5$ are each optionally substituted with 1 to 3 groups independently selected from halogen, cyano, —OH, $C_1$-$C_2$ alkyl, and $C_1$-$C_2$ alkoxy;

and all other variables not specifically defined herein are as defined in any one of the foregoing embodiments.

In certain embodiments, in a compound, tautomer, deuterated derivative, or pharmaceutically acceptable salt of the disclosure, $R^5$ is selected from $C_1$-$C_2$ alkyl, —C(═O)O($C_1$-$C_2$ alkyl), cyclopropyl, cyclobutyl, and 5- to 6-membered heterocyclyl; wherein:
- the $C_1$-$C_2$ alkyl of $R^5$ is optionally substituted with 1 to 3 groups independently selected from F, Cl, Br, cyano, —OH, and $C_1$-$C_2$ alkoxy; and
- the cyclopropyl, the cyclobutyl, and the 5 to 6-membered heterocyclyl of $R^5$ are each optionally substituted with 1 to 3 groups independently selected from F, Cl, Br, cyano, —OH, $C_1$-$C_2$ alkyl, and $C_1$-$C_2$ alkoxy;

and all other variables not specifically defined herein are as defined in any one of the foregoing embodiments.

In certain embodiments, in a compound, tautomer, deuterated derivative, or pharmaceutically acceptable salt of the disclosure, $R^5$ is selected from —$CH_3$, —$CH_2CH_3$, —$CH_2OH$, —C(═O)$OCH_3$, —$CH_2OCH_3$, —CH($CH_3$)$_2$, cyclopropyl, difluorocyclopropyl, and tetrahydro-2H-pyranyl; and all other variables not specifically defined herein are as defined in any one of the foregoing embodiments.

In certain embodiments, a compound of the disclosure is represented by one of the following structural formulae:

Formula IVa

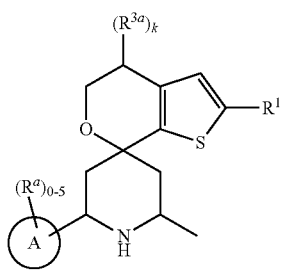

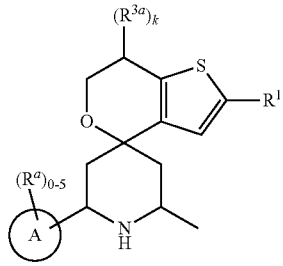

Formula IVb a tautomer thereof, a deuterated derivative of that compound or tautomer, or a pharmaceutically acceptable salt of any of the foregoing; and all other variables not specifically defined herein are as defined in any one of the foregoing embodiments.

In certain embodiments, in a compound, tautomer, deuterated derivative, or pharmaceutically acceptable salt of the disclosure, $R^1$ is selected from hydrogen, halogen, cyano, —OH, $C_1$-$C_4$ alkyl, $C_1$-$C_4$ alkoxy, and $C_3$-$C_6$ cycloalkyl; wherein:
- the $C_1$-$C_4$ alkyl of $R^1$ is optionally substituted with 1 to 3 groups independently selected from halogen, cyano, —OH, and $C_1$-$C_2$ alkoxy;
- the $C_1$-$C_4$ alkoxy of $R^1$ is optionally substituted with 1 to 3 independently selected halogen groups; and
- the $C_3$-$C_6$ cycloalkyl of $R^1$ is optionally substituted with 1 to 3 groups independently selected from halogen, cyano, —OH, and $C_1$-$C_2$ alkoxy;

and all other variables not specifically defined herein are as defined in any one of the foregoing embodiments.

In certain embodiments, in a compound, tautomer, deuterated derivative, or pharmaceutically acceptable salt of the disclosure, $R^1$ is selected from F, Cl, Br, $C_1$-$C_4$ alkyl, and $C_3$-$C_6$ cycloalkyl; wherein:
- the $C_1$-$C_4$ alkyl of $R^1$ is optionally substituted with 1 to 3 groups independently selected from halogen and —OH; and
- the $C_3$-$C_6$ cycloalkyl of $R^1$ is optionally substituted with 1 to 3 groups independently selected from halogen, and —OH;

and all other variables not specifically defined herein are as defined in any one of the foregoing embodiments.

In certain embodiments, in a compound, tautomer, deuterated derivative, or pharmaceutically acceptable salt of the disclosure, $R^1$ is selected from F, Cl, Br, $C_1$-$C_4$ alkyl, and $C_3$-$C_6$ cycloalkyl; wherein:
- the $C_1$-$C_4$ alkyl of $R^1$ is optionally substituted with 1 to 3 groups independently selected from halogen and —OH; and
- the $C_3$-$C_6$ cycloalkyl of $R^1$ is optionally substituted with 1 to 3 groups independently selected from halogen and —OH;

and all other variables not specifically defined herein are as defined in any one of the foregoing embodiments.

In certain embodiments, in a compound, tautomer, deuterated derivative, or pharmaceutically acceptable salt of the disclosure, $R^1$ is selected from $C_1$, Br, —$CH_3$, —$CF_3$, —$CH_2CH_3$, —CH($CH_3$)$_2$, —$CH_2CHF_2$, —$CH_2CH(CH_3)_2$, difluorocyclobutyl, and cyclohexyl; and all other variables not specifically defined herein are as defined in any one of the foregoing embodiments.

In certain embodiments, in a compound, tautomer, deuterated derivative, or pharmaceutically acceptable salt of the disclosure, $R^1$ is $C_1$; and all other variables not specifically defined herein are as defined in any one of the foregoing embodiments.

In certain embodiments, in a compound, tautomer, deuterated derivative, or pharmaceutically acceptable salt of the disclosure, $R^{3a}$ is selected from halogen, —OH, and $C_1$-$C_4$ alkyl; wherein:
the $C_1$-$C_4$ alkyl of $R^{3a}$ is optionally substituted with 1 to 3 groups independently selected from halogen and —OH;
and all other variables not specifically defined herein are as defined in any one of the foregoing embodiments.

In certain embodiments, in a compound, tautomer, deuterated derivative, or pharmaceutically acceptable salt of the disclosure, $R^{3a}$ is selected from F, Cl, Br, —OH, and $C_1$-$C_2$ alkyl; wherein:
the $C_1$-$C_2$ alkyl of $R^{3a}$ is optionally substituted with 1 to 3 groups independently selected from F, Cl, and —OH;
and all other variables not specifically defined herein are as defined in any one of the foregoing embodiments.

In certain embodiments, in a compound, tautomer, deuterated derivative, or pharmaceutically acceptable salt of the disclosure, $R^{3a}$ is selected from F, —OH, —CH$_3$, —CHF$_2$, and —CH$_2$OH; and all other variables not specifically defined herein are as defined in any one of the foregoing embodiments.

In certain embodiments, a compound of the disclosure is represented by one of the following structural formulae:

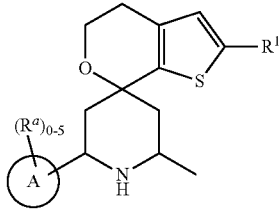

Formula Va

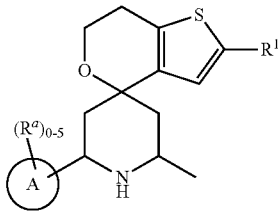

Formula Vb a tautomer thereof, a deuterated derivative of that compound or tautomer, or a pharmaceutically acceptable salt of any of the foregoing; and all other variables not specifically defined herein are as defined in any one of the foregoing embodiments.

In certain embodiments, in a compound, tautomer, deuterated derivative, or pharmaceutically acceptable salt of the disclosure, $R^a$, for each occurrence, is independently selected from halogen, cyano, $C_1$-$C_6$ alkyl, $C_1$-$C_4$ alkoxy, $C_1$-$C_6$ haloalkyl, $C_1$-$C_6$ haloalkoxy, —C(=O)NR$^h$R$^i$, —NR$^h$R$^i$, —NR$^h$C(=O)R$^k$, —OR$^k$, —[O(CH$_2$)$_q$]$_r$O(C$_1$-C$_6$ alkyl), —S(=O)$_2$R$^k$, —S(=O)$_2$NR$^h$R$^i$, $C_3$-$C_6$ cycloalkyl, 5 to 10-membered heterocyclyl, phenyl, and 5 to 8-membered heteroaryl; wherein:
the $C_1$-$C_6$ alkyl of $R^a$ is optionally substituted with 1 to 3 groups independently selected from cyano, —C(=O)NR$^h$R$^i$, —NR$^h$R$^i$, —NR$^h$C(=O)R$^k$, —NR$^h$C(=O) OR$^k$, —NR$^h$C(=O)NR$^i$R$^j$, —NR$^h$S(=O)$_p$R$^k$, —OR$^k$, —S(=O)$_2$R$^k$, —S(=O)$_p$NR$^h$R$^i$, and $C_3$-$C_6$ cycloalkyl;
the $C_3$-$C_6$ cycloalkyl, the 5 to 10-membered heterocyclyl, the phenyl, and the 5 to 8-membered heteroaryl of $R^a$ are each optionally substituted with 1 to 3 groups independently selected from halogen, $C_1$-$C_2$ alkyl, and —OR$^k$; wherein:
R$^h$, R$^i$, and R$^j$, for each occurrence, are each independently selected from hydrogen, $C_1$-$C_2$ alkyl, cyclopropyl, and cyclobutyl; wherein:
the $C_1$-$C_2$ alkyl of any one of R$^h$, R$^i$, and R$^j$ is optionally substituted with 1 to 3 groups independently selected from halogen and —OH;
R$^k$, for each occurrence, is each independently selected from hydrogen and $C_1$-$C_4$ alkyl; wherein:
the $C_1$-$C_4$ alkyl of R$^k$ is optionally substituted with 1 to 3 groups independently selected from halogen and —OH; and
q and r are each an integer selected from 1, 2, and 3;
and all other variables not specifically defined herein are as defined in any one of the foregoing embodiments.

In certain embodiments, in a compound, tautomer, deuterated derivative, or pharmaceutically acceptable salt of the disclosure, $R^a$, for each occurrence, is independently selected from halogen, cyano, $C_1$-$C_6$ alkyl, $C_1$-$C_4$ alkoxy, $C_1$-$C_4$ haloalkyl, $C_1$-$C_4$ haloalkoxy, —C(=O)NR$^h$R$^i$, —NR$^h$R$^i$, —NR$^h$C(=O)R, —OR$^k$, —[O(CH$_2$)$_q$]$_r$O(C$_1$-C$_4$ alkyl), —S(=O)$_2$R$^k$, —S(=O)$_2$NR$^h$R$^i$, cyclopropyl, cyclobutyl, 5 to 6-membered heterocyclyl, phenyl, and 5- to 6-membered heteroaryl; wherein:
the $C_1$-$C_6$ alkyl of $R^a$ is optionally substituted with 1 to 3 groups independently selected from cyano, —C(=O)NR$^h$R$^i$, —NR$^h$R$^i$, —OR$^k$, cyclopropyl, and cyclobutyl;
the cyclopropyl, the cyclobutyl, the 5- to 6-membered heterocyclyl, the phenyl, and the 5 to 6-membered heteroaryl of $R^a$ are each optionally substituted with 1 to 3 groups independently selected from halogen, —CH$_3$, —OH, and —OCH$_3$; wherein:
R$^h$ and R$^1$, for each occurrence, are each independently selected from hydrogen, —CH$_3$, cyclopropyl, and cyclobutyl; wherein:
the —CH$_3$ of any one of R$^h$ and R$^i$ is optionally substituted with 1 to 3 groups independently selected from F, Cl, and —OH;
R$^k$, for each occurrence, is each independently selected from hydrogen and —CH$_3$; wherein:
the —CH$_3$ of R$^k$ is optionally substituted with 1 to 3 groups independently selected from halogen and —OH;
and all other variables not specifically defined herein are as defined in any one of the foregoing embodiments.

In certain embodiments, in a compound, tautomer, deuterated derivative, or pharmaceutically acceptable salt of the disclosure, $R^a$, for each occurrence, is independently selected from F, Cl, Br, cyano, $C_1$-$C_6$ alkyl, $C_1$-$C_2$ alkoxy, $C_1$-$C_2$ haloalkyl, —C(=O)NR$^h$R$^i$, —NR$^h$R$^i$, —NR$^h$C(=O) R$^k$, —OR$^k$, —[O(CH$_2$)$_q$]$_r$O(C$_1$-C$_2$ alkyl), —S(=O)$_2$R$^k$, —S(=O)$_2$NR$^h$R$^i$, cyclopropyl, cyclobutyl, 5-membered heterocyclyl, phenyl, and 6-membered heteroaryl; wherein:
the $C_1$-$C_6$ alkyl of $R^a$ is optionally substituted with 1 to 3 groups independently selected from cyano, —C(=O)NR$^h$R$^i$, —OR$^k$, and cyclopropyl;
the cyclopropyl, the cyclobutyl, the 5 to 6-membered heterocyclyl, the phenyl, and the 5 to 6-membered heteroaryl of $R^a$ are each optionally substituted with 1 to 3 groups independently selected from halogen, —CH$_3$, —OH, and —OCH$_3$; wherein:

$R^h$ and $R^i$, for each occurrence, are each independently selected from hydrogen, —$CH_3$, and cyclopropyl; wherein:

the —$CH_3$ of any one of $R^h$ and Riis optionally substituted with 1 to 3 groups independently selected from F, Cl, and —OH;

$R^k$, for each occurrence, is each independently selected from hydrogen and —$CH_3$; and q and r are each an integer selected from 1 and 2;

and all other variables not specifically defined herein are as defined in any one of the foregoing embodiments.

In certain embodiments, in a compound, tautomer, deuterated derivative, or pharmaceutically acceptable salt of the disclosure, $R^a$, for each occurrence, is independently selected from F, cyano, —OH, —$CH_3$, —$CF_3$, —$CH(CH_3)_2$, —$(CH_2)_2OH$, —$(CH_2)_2OCH_3$, —$CH_2CH(OH)C_2H_5$, —$CH_2C(CH_3)(CH_2OH)_2$, —$OCH_3$, —$OCH_2CH_3$, —[O$(CH_2)_2]_2OCH_3$, —$CH_2C(=O)NHCH_3$, —$(CH_2)_2SO_2CH_3$, —$CH_2C(=O)N(CH_3)_2$, —$CH_2$(cyclopropyl), —$C(=O)NH_2$, —$C(=O)NH$(cyclopropyl), —$NH_2$, —$NHCH_3$, —$N(CH_3)_2$, —$NHC(CH_3)_2CH_2OH$, —$NHC(=O)CH_3$, —$SO_2CH_3$, —$SO_2NH_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide; and all other variables not specifically defined herein are as defined in any one of the foregoing embodiments.

In certain embodiments, a compound of the disclosure is represented by one of the following structural formulae:

Formula I'

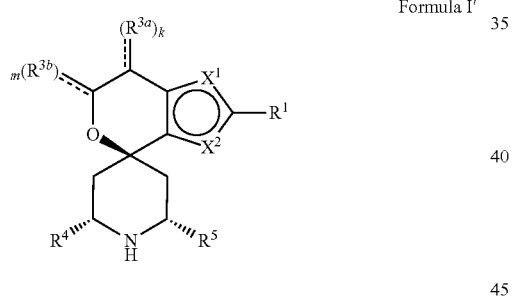

Formula IIa'

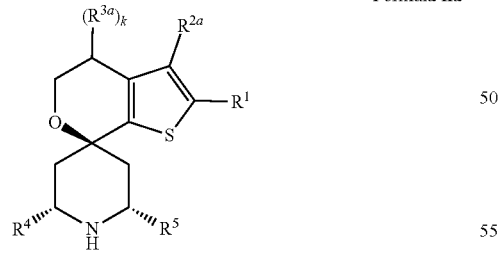

Formula IIb'


Formula IIIa'

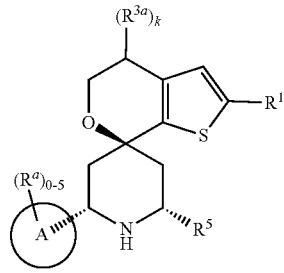

Formula IIIb'

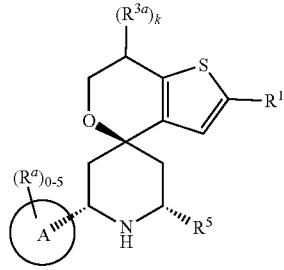

Formula IVa'

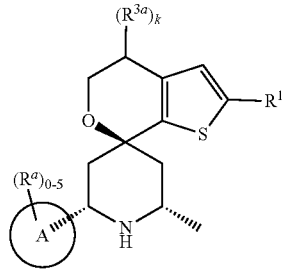

Formula IVb'

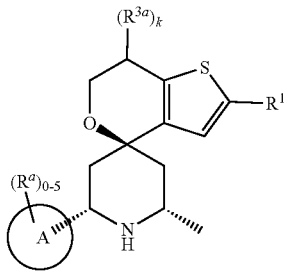

Formula Va'

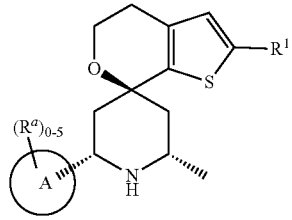

Formula Vb'

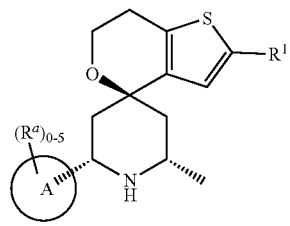

a tautomer thereof, a deuterated derivative of that compound or tautomer, or a pharmaceutically acceptable salt of any of the foregoing; and all other variables not specifically defined herein are as defined in any one of the foregoing embodiments.

In certain embodiments, a compound of the disclosure is represented by one of the following structural formulae:

Formula IIa″

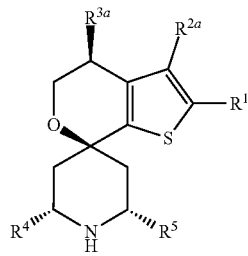

Formula IIb″

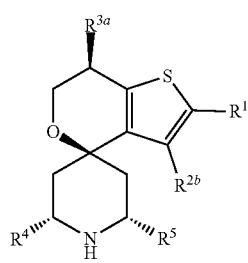

Formula IIIa″

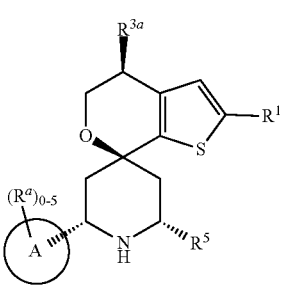

Formula IIIb″

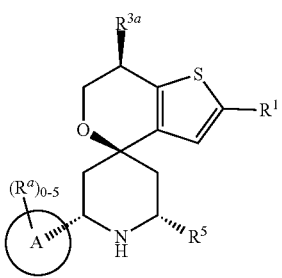

Formula IVa″

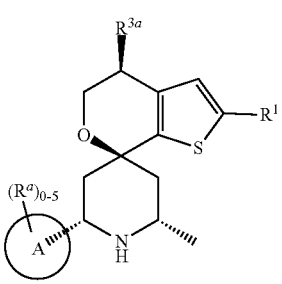

Formula IVb″

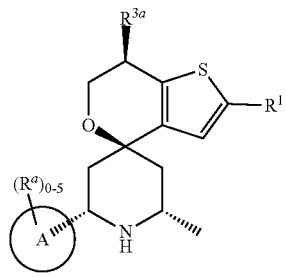

a tautomer thereof, a deuterated derivative of that compound or tautomer, or a pharmaceutically acceptable salt of any of the foregoing; and all other variables not specifically defined herein are as defined in any one of the foregoing embodiments.

In certain embodiments, a compound of the disclosure is represented by one of the following structural formulae:

Formula IIa‴

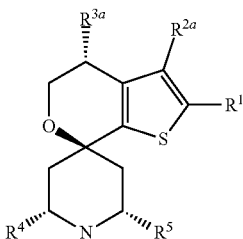

Formula IIb‴

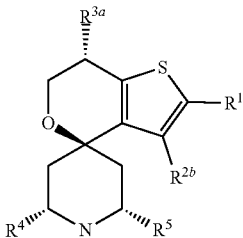

Formula IIIa‴

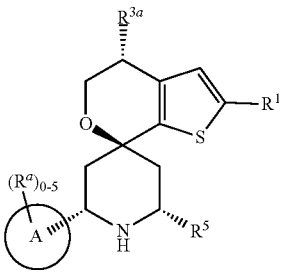

Formula IIIb‴

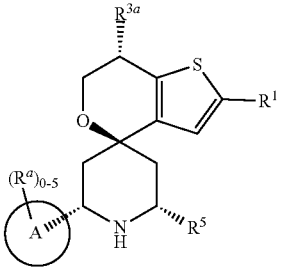

Formula IVa'''

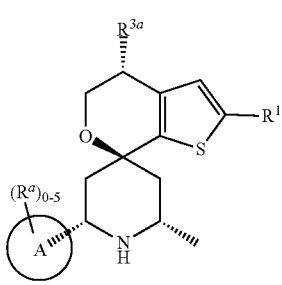

Formula IVb'''

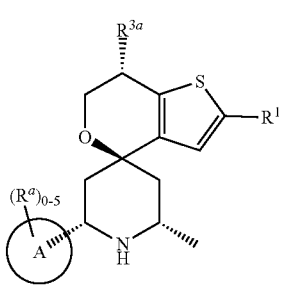

a tautomer thereof, a deuterated derivative of that compound or tautomer, or a pharmaceutically acceptable salt of any of the foregoing; and all other variables not specifically defined herein are as defined in any one of the foregoing embodiments.

In certain embodiments, the at least one compound of the disclosure is chosen from Compounds 1 to 220 depicted in Table I, a tautomer thereof, a deuterated derivative of that compound or tautomer, or a pharmaceutically acceptable salt of any of the foregoing. A wavy line in a compound in Table I (i.e., ⌇) depicts a bond between two atoms and indicates a position of mixed stereochemistry for a collection of molecules, such as a racemic mixture, cis/trans isomers, or (E)/(Z) isomers. An asterisk adjacent to an atom

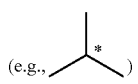

in a compound in Table I, indicates a chiral position in the molecule.

In certain embodiments, the at least one compound of the disclosure is chosen from Compounds 221 to 391 depicted in Table II, a tautomer thereof, a deuterated derivative of that compound or tautomer, or a pharmaceutically acceptable salt of any of the foregoing. A wavy line in a compound in Table II (i.e., ⌇) depicts a bond between two atoms and indicates a position of mixed stereochemistry for a collection of molecules, such as a racemic mixture, cis/trans isomers, or (E)/(Z) isomers. An asterisk adjacent to an atom

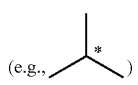

in a compound in Table II, indicates a chiral position in the molecule.

In certain embodiments, the at least one compound of the disclosure is chosen from Compounds 1 to 391 depicted in Table I or II, a tautomer thereof, a deuterated derivative of that compound or tautomer, or a pharmaceutically acceptable salt of any of the foregoing.

In certain embodiments, the at least one compound of the disclosure is chosen from compounds depicted in Table III, a tautomer thereof, a deuterated derivative of that compound or tautomer, or a pharmaceutically acceptable salt of any of the foregoing. A wavy line in a compound in Table III (i.e., ⌇) depicts a bond between two atoms and indicates a position of mixed stereochemistry for a collection of molecules, such as a racemic mixture, cis/trans isomers, or (E)/(Z) isomers. An asterisk adjacent to an atom

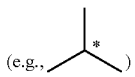

in a compound in Table III, indicates a chiral position in the molecule.

TABLE I

Compounds 1 to 220

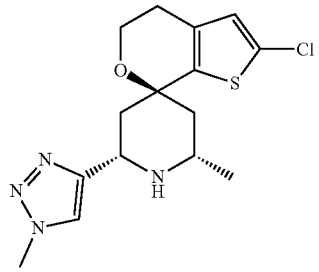 [SMILES: C[C@H]1C[C@@]2(C[C@@H](c3cn(C)nn3)N1)OCCc1cc(Cl)sc12]

1

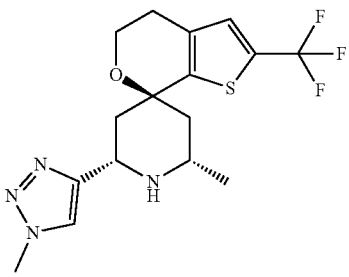 [SMILES: C[C@H]1C[C@@]2(C[C@@H](c3cn(C)nn3)N1)OCCc1cc(C(F)(F)F)sc12]

2

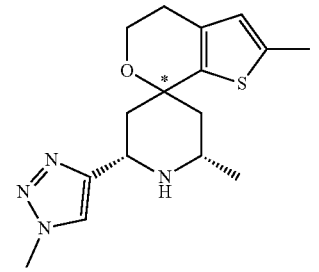 [SMILES: Cc1cc2c(s1)C1(C[C@@H](c3cn(C)nn3)N[C@@H](C)C1)OCC2]

3

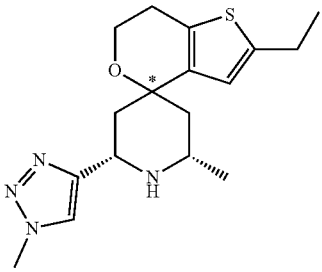 [SMILES: CCc1cc2c(s1)CCOC21C[C@@H](c2cn(C)nn2)N[C@@H](C)C1]

4

TABLE I-continued
Compounds 1 to 220
| | |
|---|---|
| 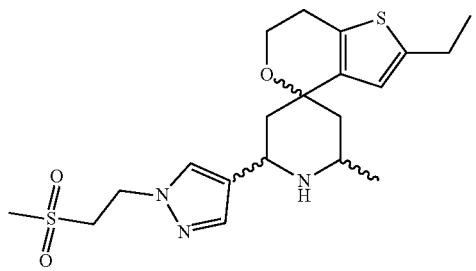 [SMILES: CCc1cc2c(s1)CCOC21CC(C)NC(c2cnn(CCS(C)(=O)=O)c2)C1] | 5 |
| 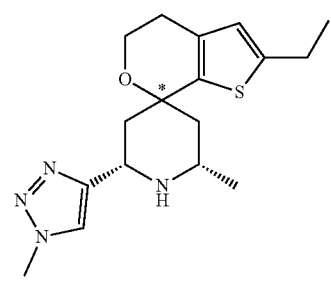 [SMILES: CCc1cc2c(s1)C1(C[C@@H](c3cn(C)nn3)N[C@@H](C)C1)OCC2] | 6 |
| 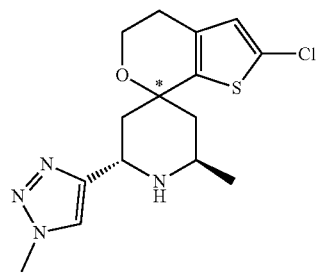 [SMILES: C[C@@H]1CC2(C[C@@H](c3cn(C)nn3)N1)OCCc1cc(Cl)sc12] | 7 |
| 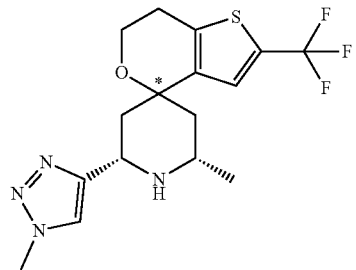 [SMILES: C[C@H]1CC2(C[C@@H](c3cn(C)nn3)N1)OCCc1sc(C(F)(F)F)cc12] | 8 |
| 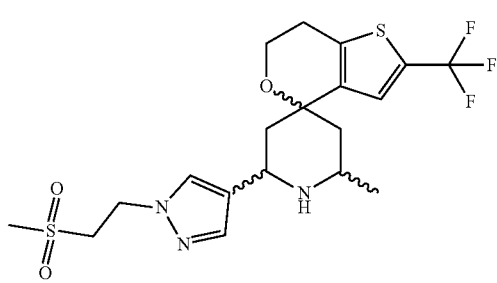 [SMILES: CC1CC2(CC(c3cnn(CCS(C)(=O)=O)c3)N1)OCCc1sc(C(F)(F)F)cc12] | 9 |
| 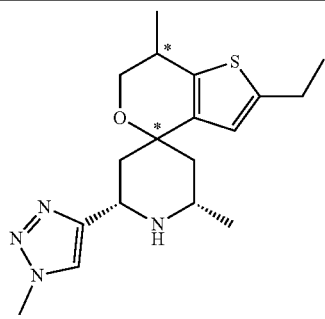 | 10 |
| 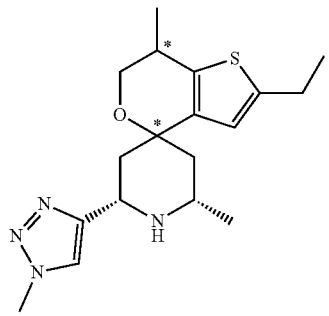 [SMILES: CCc1cc2c(s1)C(C)COC21C[C@@H](c2cn(C)nn2)N[C@@H](C)C1] | 11 |
| 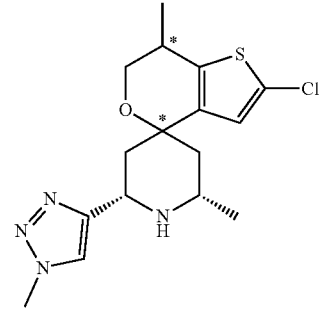 [SMILES: CC1COC2(C[C@@H](c3cn(C)nn3)N[C@@H](C)C2)c2cc(Cl)sc21] | 12 |
| 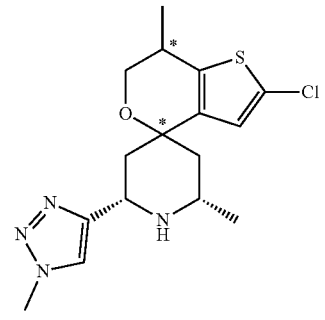 [SMILES: CC1COC2(C[C@@H](c3cn(C)nn3)N[C@@H](C)C2)c2cc(Cl)sc21] | 13 |
| 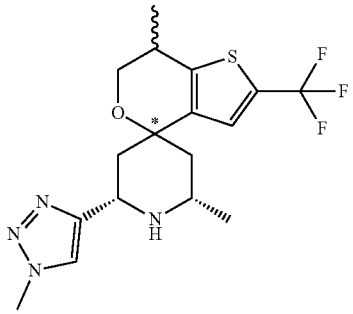 [SMILES: CC1COC2(C[C@@H](c3cn(C)nn3)N[C@@H](C)C2)c2cc(C(F)(F)F)sc21] | 14 |

TABLE I-continued
Compounds 1 to 220
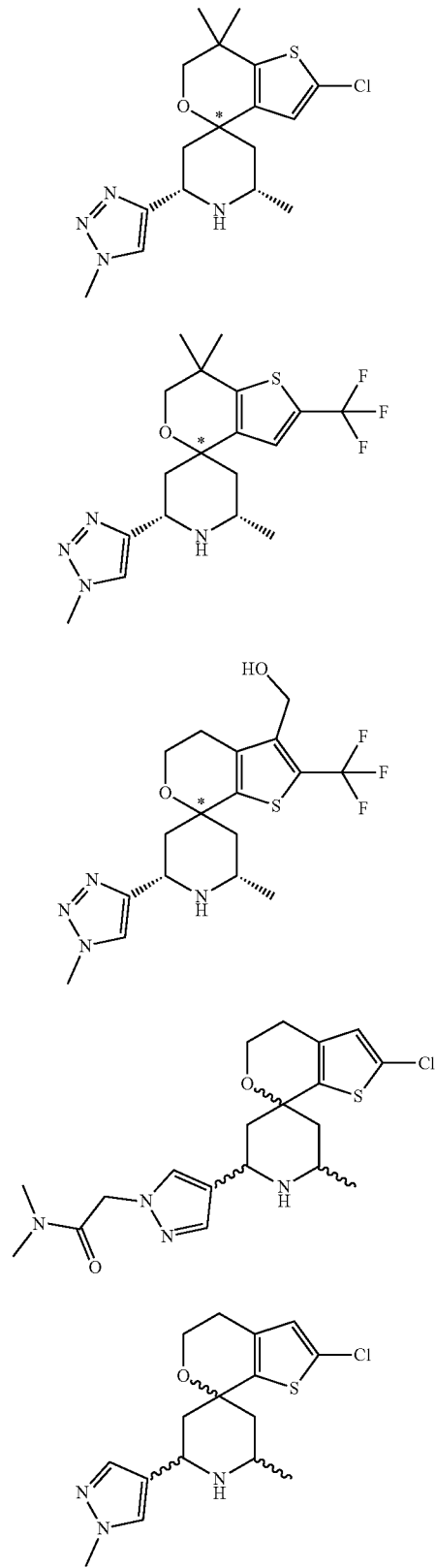
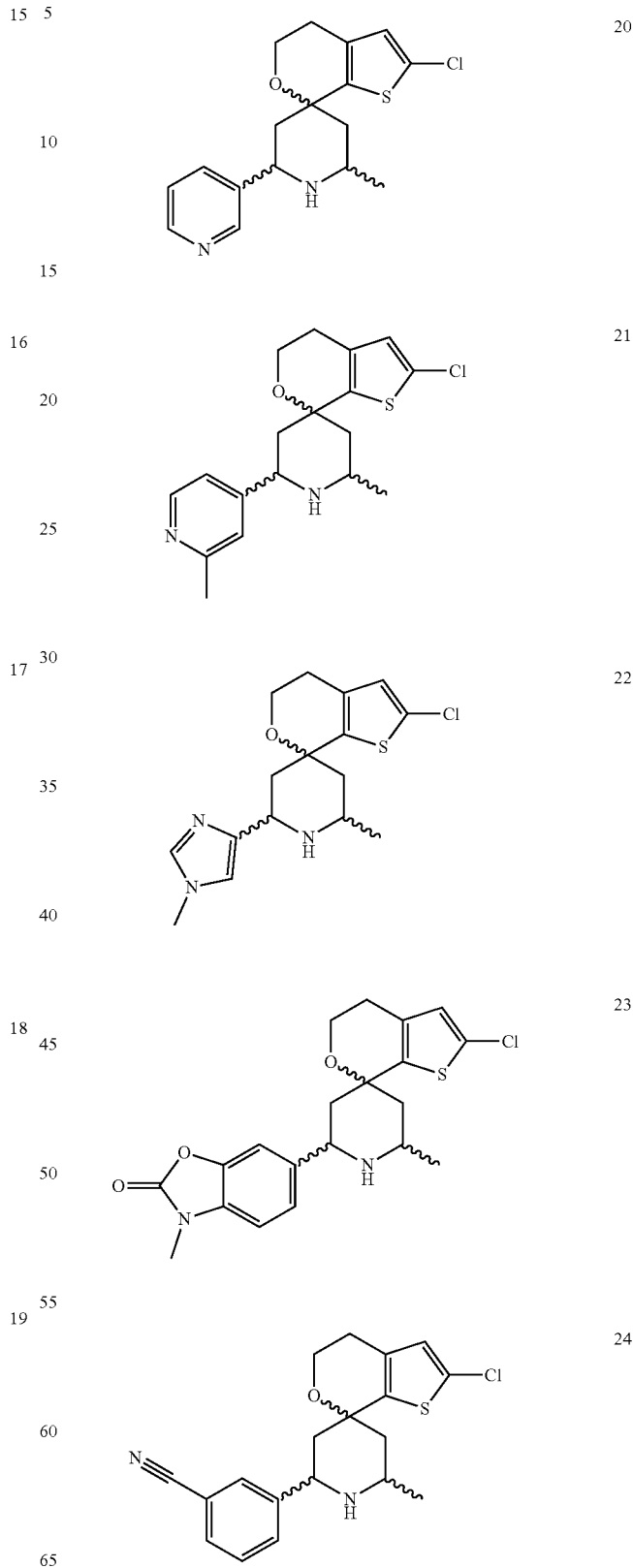

TABLE I-continued
Compounds 1 to 220
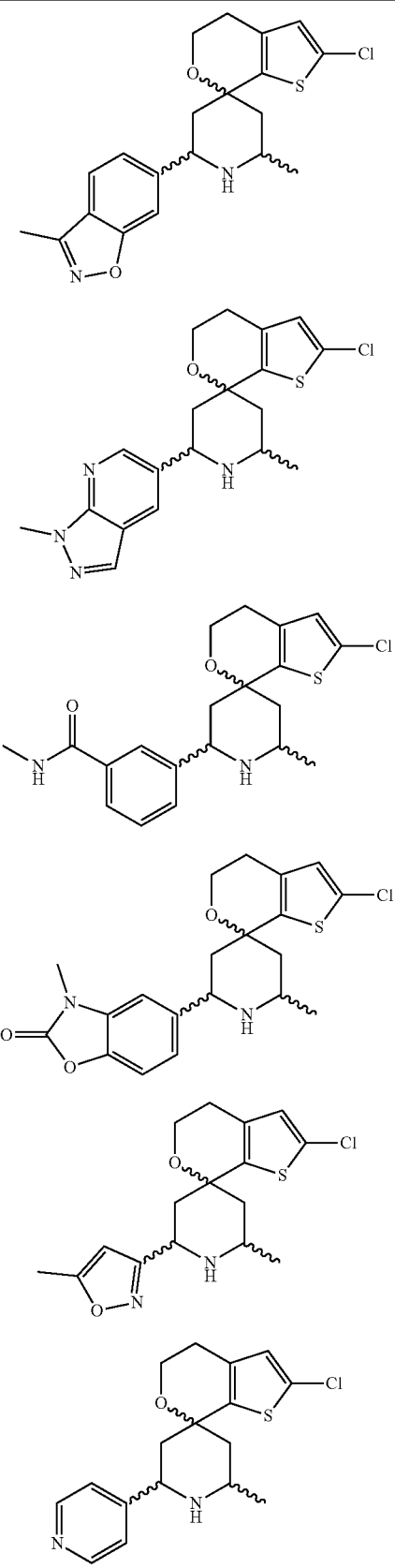
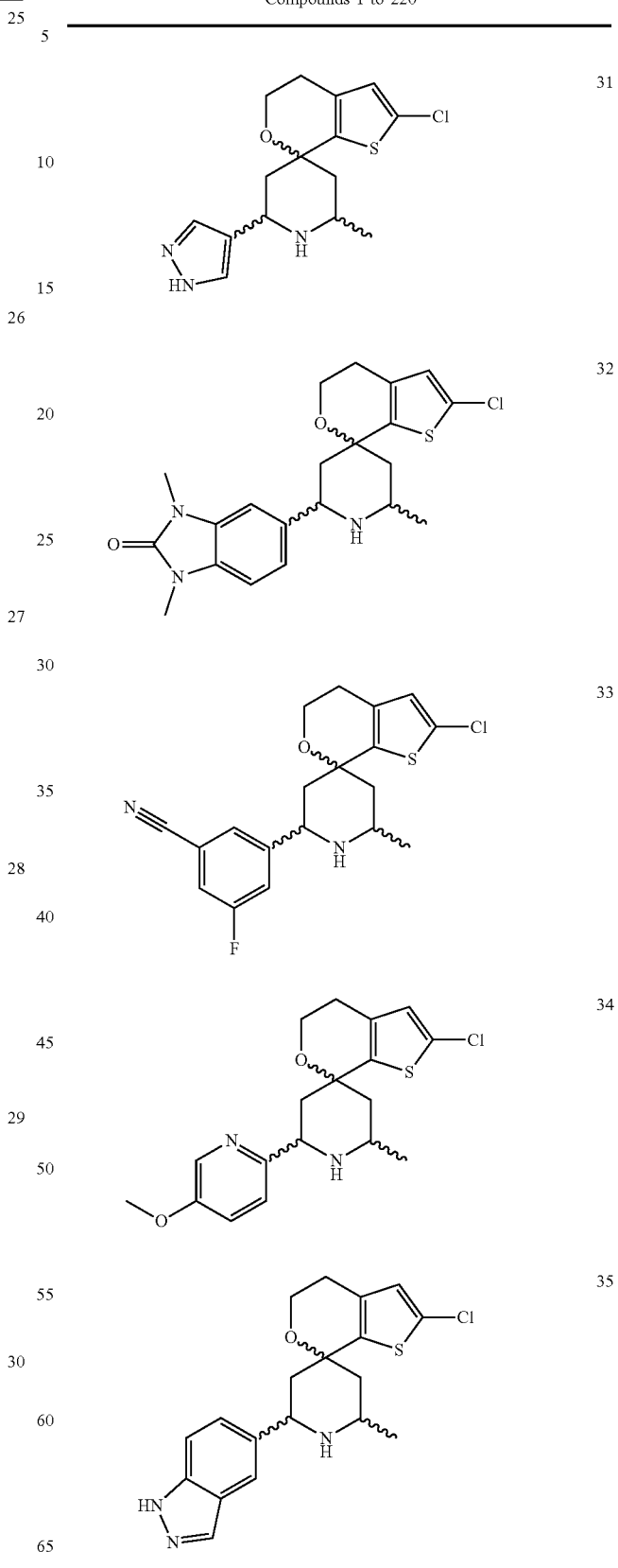

TABLE I-continued

Compounds 1 to 220

TABLE I-continued
Compounds 1 to 220
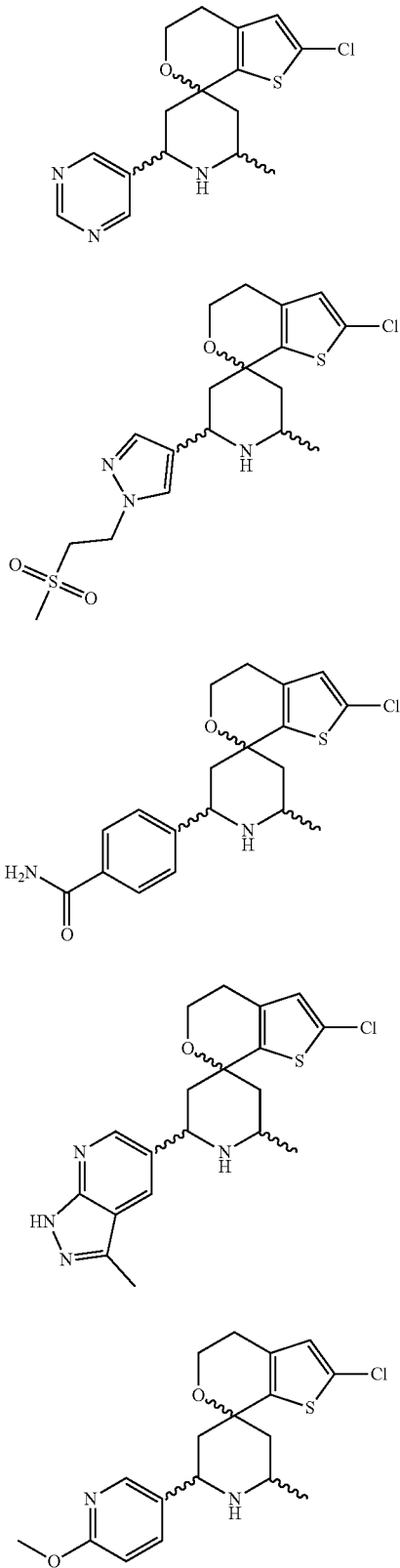
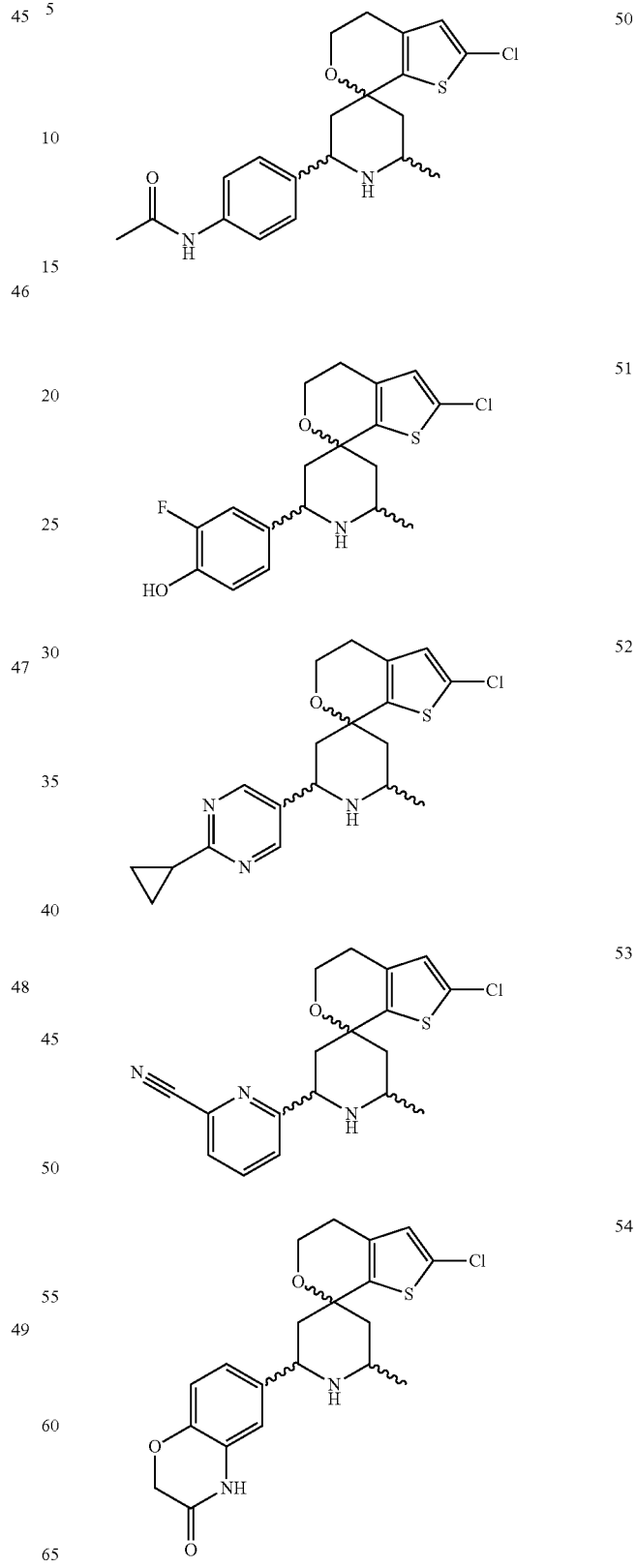

TABLE I-continued
Compounds 1 to 220
55 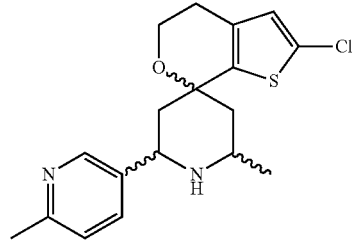 [SMILES: Cc1ccc(C2CC3(CC(C)N2)OCCc2cc(Cl)sc23)cn1]
56 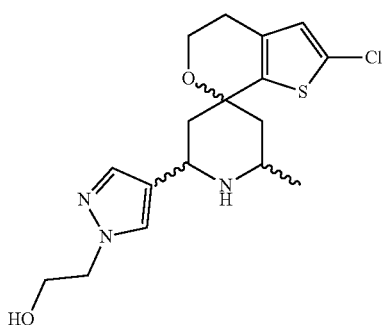 [SMILES: CC1CC2(CC(c3cnn(CCO)c3)N1)OCCc1cc(Cl)sc12]
57 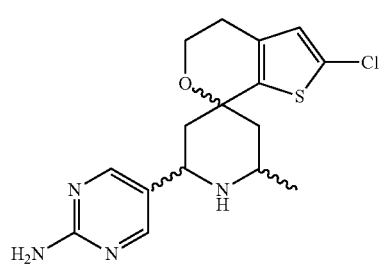 [SMILES: CC1CC2(CC(c3cnc(N)nc3)N1)OCCc1cc(Cl)sc12]
58 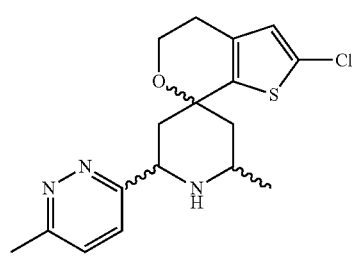 [SMILES: Cc1ccc(C2CC3(CC(C)N2)OCCc2cc(Cl)sc23)nn1]
59 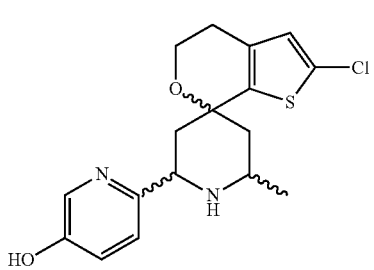 [SMILES: CC1CC2(CC(c3ccc(O)cn3)N1)OCCc1cc(Cl)sc12]
60 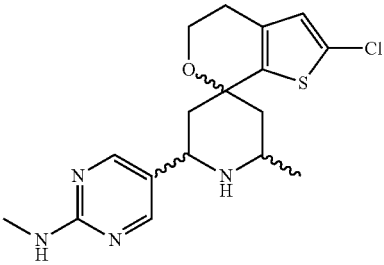 [SMILES: CNc1ncc(C2CC3(CC(C)N2)OCCc2cc(Cl)sc23)cn1]
61 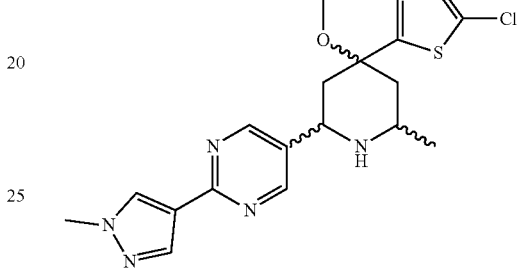
62 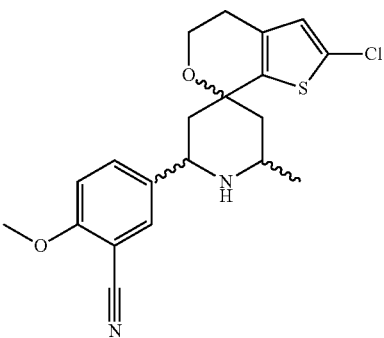 [SMILES: COc1ccc(C2CC3(CC(C)N2)OCCc2cc(Cl)sc23)cc1C#N]
63 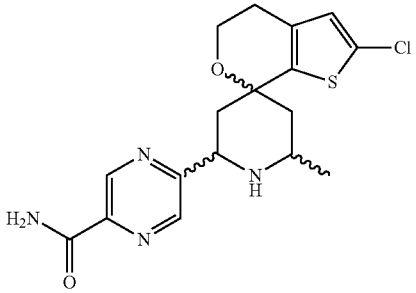 [SMILES: CC1CC2(CC(c3cnc(C(N)=O)cn3)N1)OCCc1cc(Cl)sc12]
64 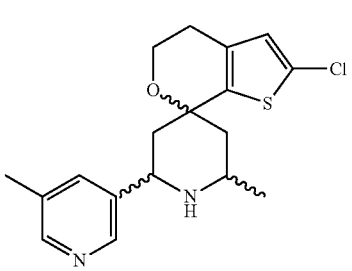 [SMILES: Cc1cncc(C2CC3(CC(C)N2)OCCc2cc(Cl)sc23)c1]

TABLE I-continued
Compounds 1 to 220
| | |
|---|---|
| 65 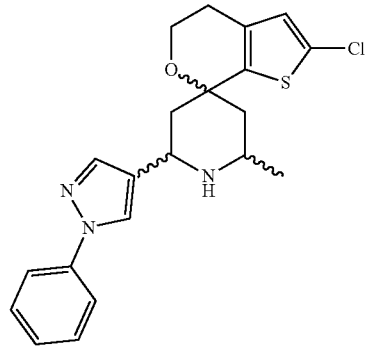 [SMILES: CC1CC2(CC(c3cnn(-c4ccccc4)c3)N1)OCCc1cc(Cl)sc12] | 70 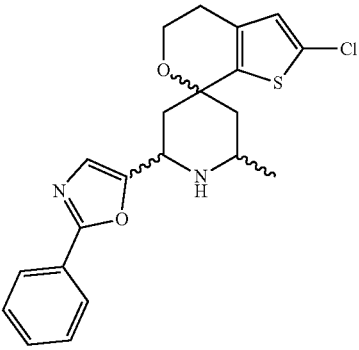 |
| 66 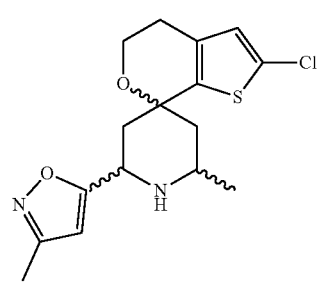 [SMILES: Cc1cc(C2CC3(CC(C)N2)OCCc2cc(Cl)sc23)on1] | 71 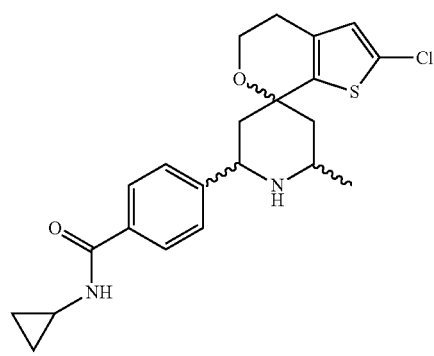 |
| 67 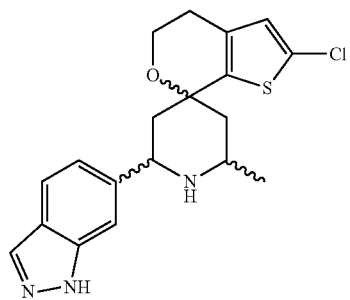 [SMILES: CC1CC2(CC(c3ccc4cn[nH]c4c3)N1)OCCc1cc(Cl)sc12] | 72 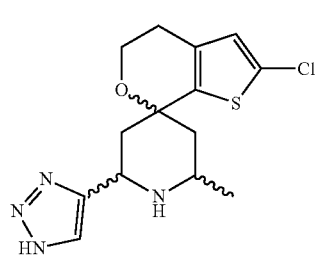 |
| 68 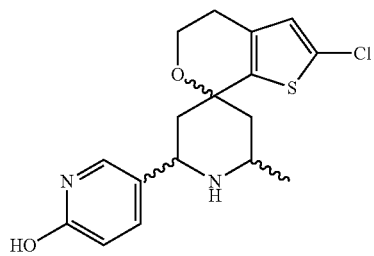 [SMILES: CC1CC2(CC(c3ccc(O)nc3)N1)OCCc1cc(Cl)sc12] | 73 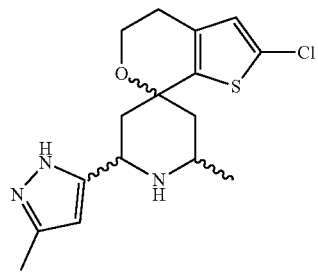 |
| 69 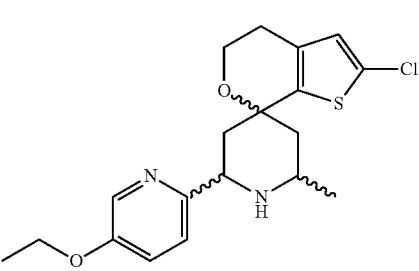 [SMILES: CCOc1ccc(C2CC3(CC(C)N2)OCCc2cc(Cl)sc23)nc1] | 74 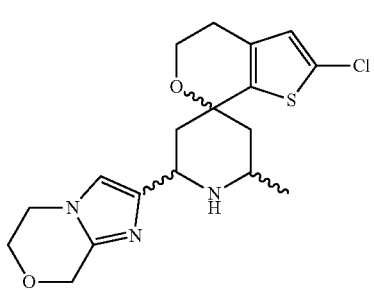 [SMILES: CC1CC2(CC(c3cn4c(n3)COCC4)N1)OCCc1cc(Cl)sc12] |

TABLE I-continued
Compounds 1 to 220
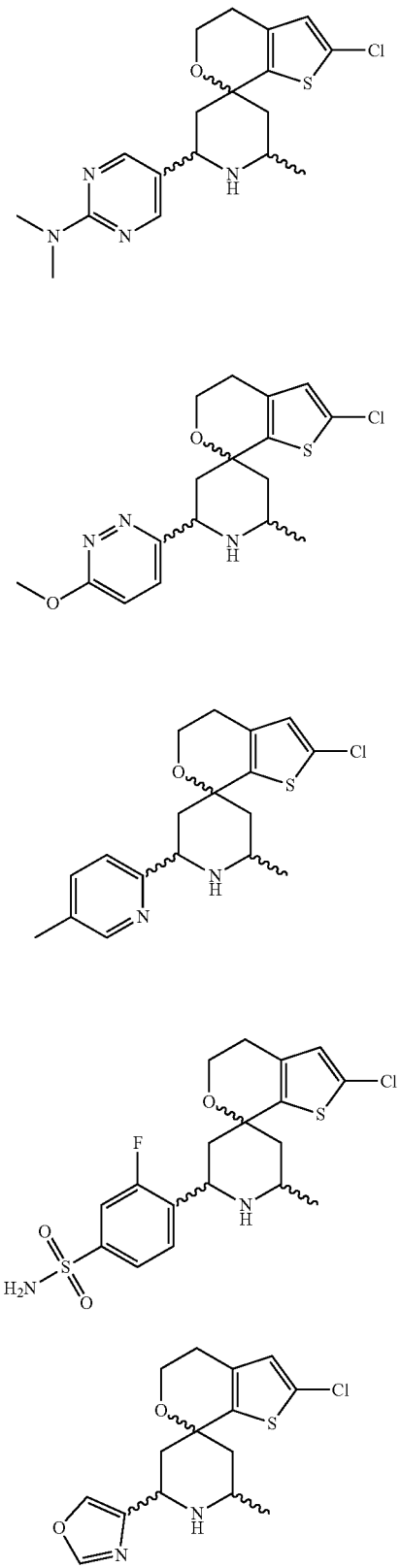
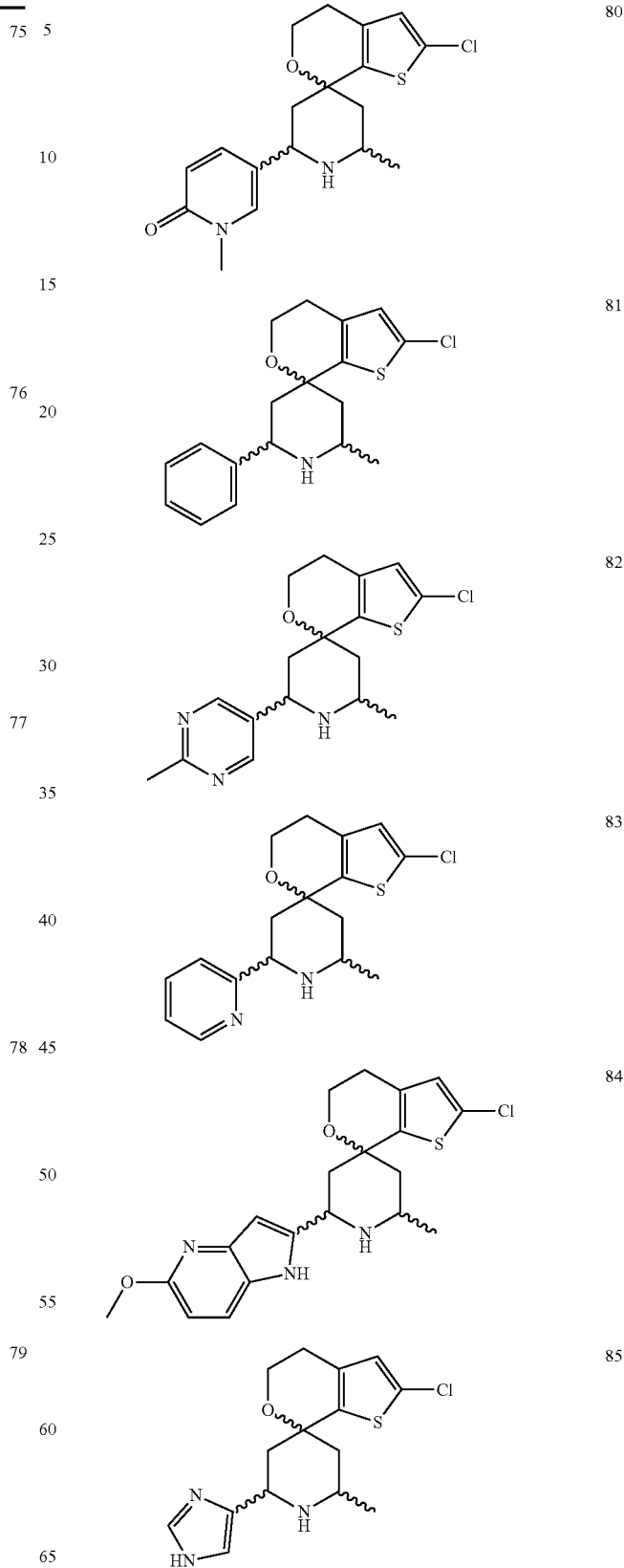

TABLE I-continued
Compounds 1 to 220
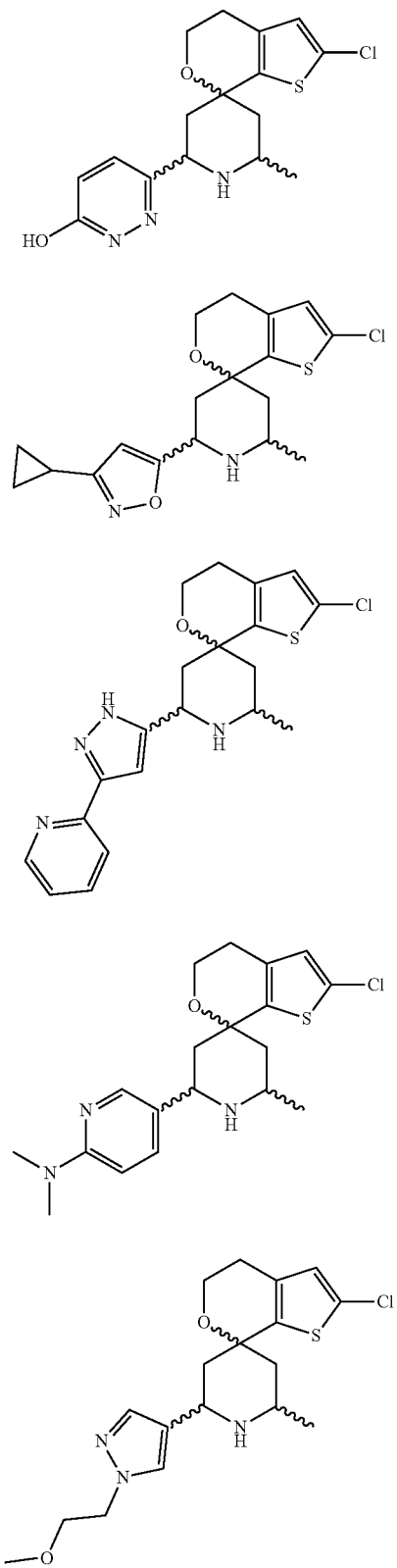
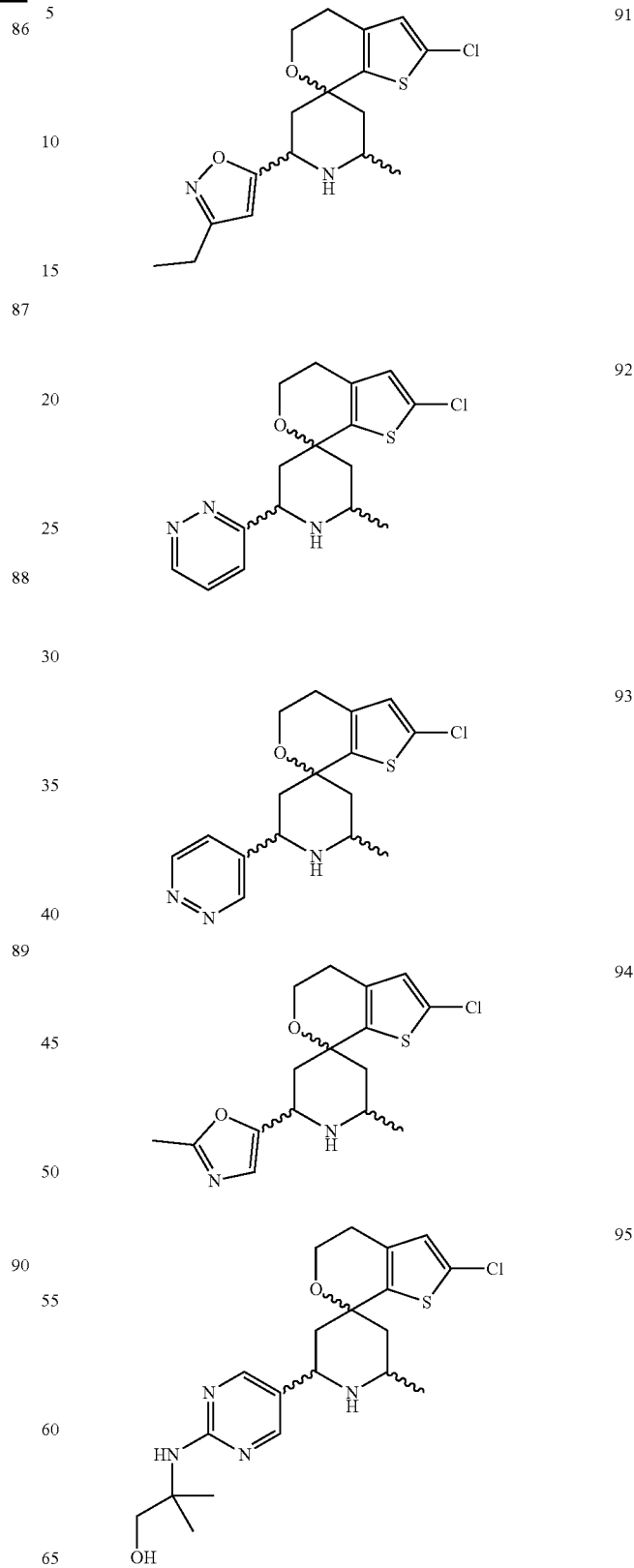

TABLE I-continued
Compounds 1 to 220
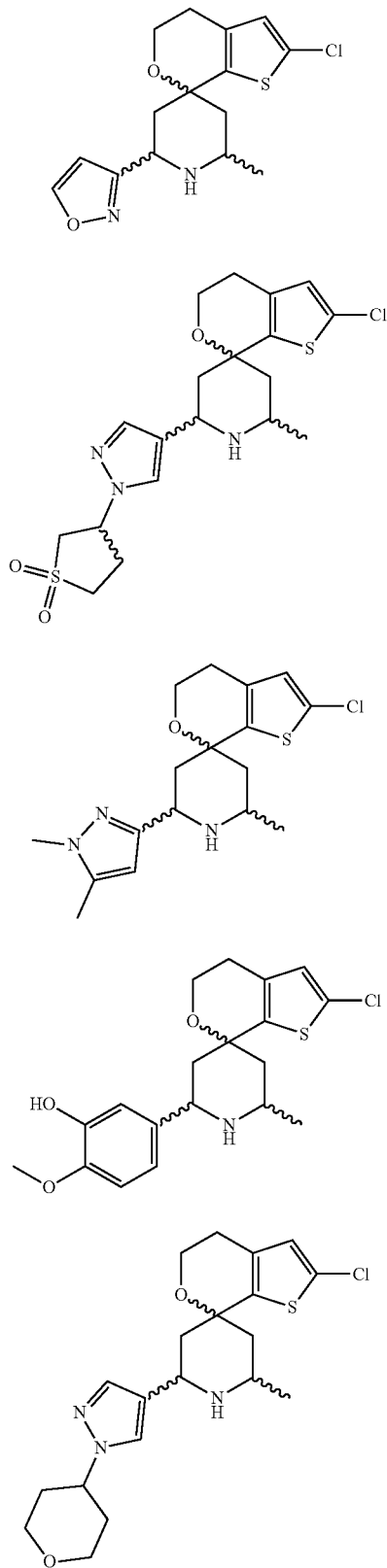
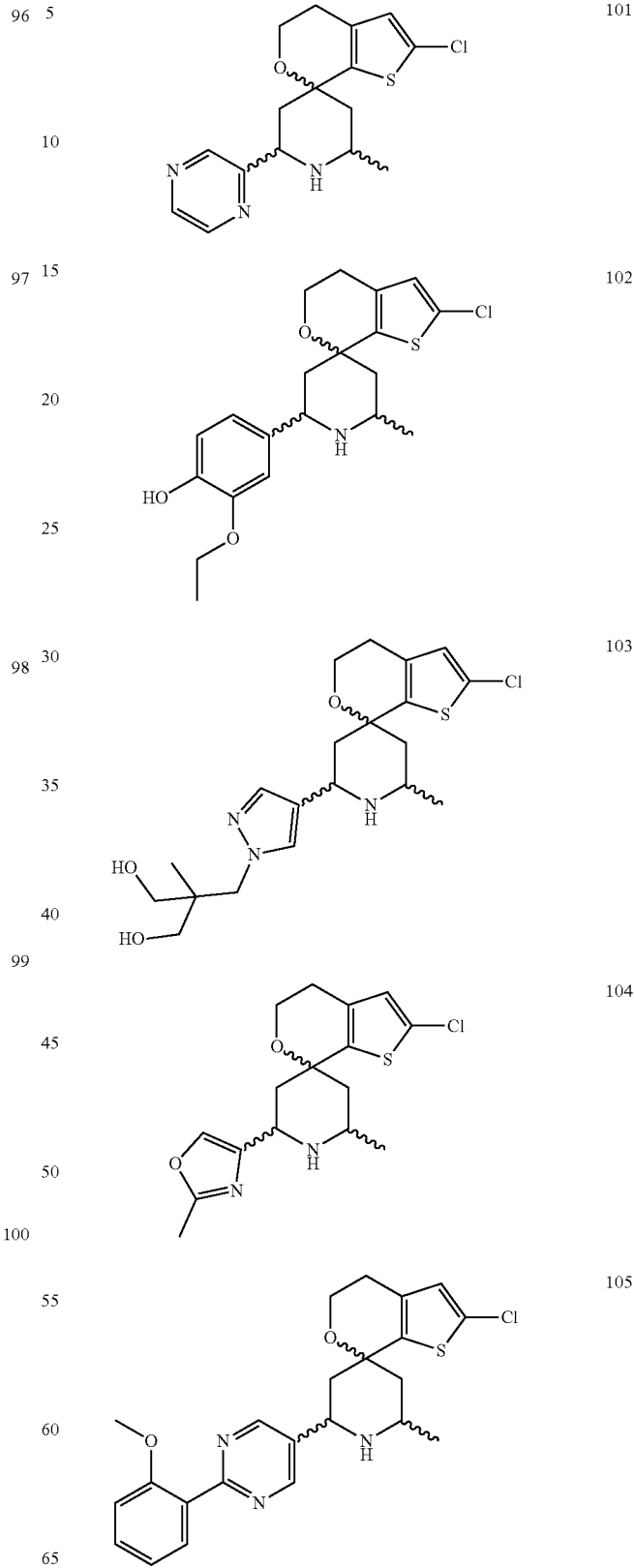

TABLE I-continued
Compounds 1 to 220
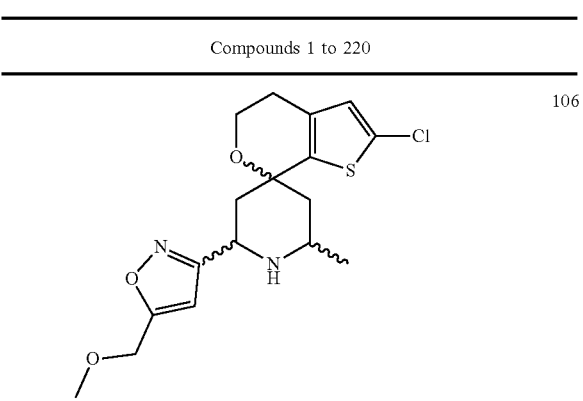
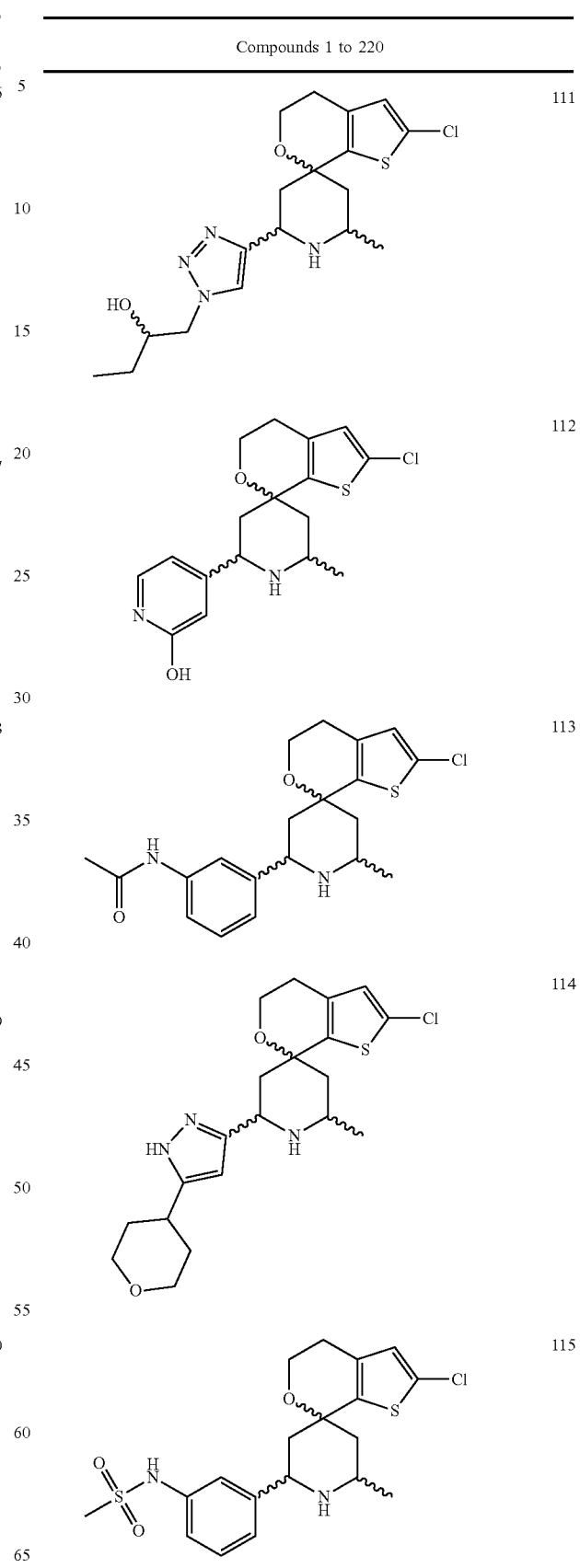

TABLE I-continued
Compounds 1 to 220
| | |
|---|---|
| 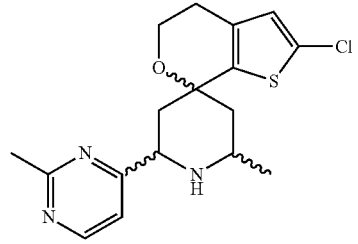 [SMILES: Cc1nccc(C2CC3(CC(C)N2)OCCc2cc(Cl)sc23)n1] | 116 |
| 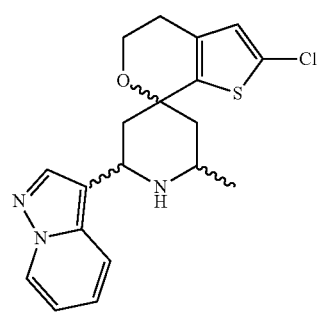 [SMILES: CC1CC2(CC(c3cnn4ccccc34)N1)OCCc1cc(Cl)sc12] | 117 |
| 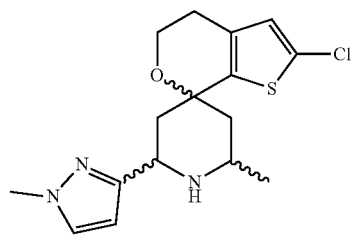 [SMILES: CC1CC2(CC(c3ccn(C)n3)N1)OCCc1cc(Cl)sc12] | 118 |
| 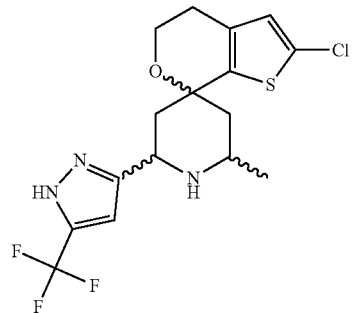 [SMILES: CC1CC2(CC(c3cc(C(F)(F)F)[nH]n3)N1)OCCc1cc(Cl)sc12] | 119 |
| 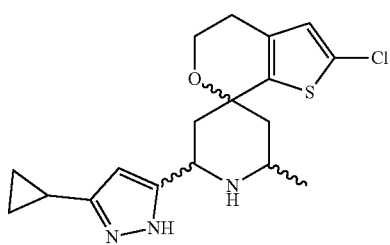 [SMILES: CC1CC2(CC(c3cc(C4CC4)n[nH]3)N1)OCCc1cc(Cl)sc12] | 120 |
| 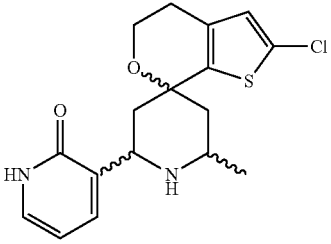 [SMILES: CC1CC2(CC(c3ccc[nH]c3=O)N1)OCCc1cc(Cl)sc12] | 121 |
| 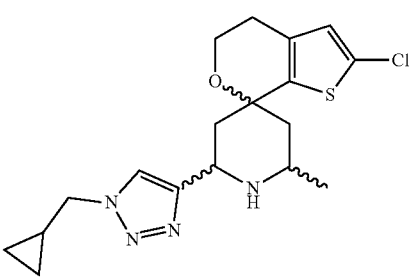 [SMILES: CC1CC2(CC(c3cn(CC4CC4)nn3)N1)OCCc1cc(Cl)sc12] | 122 |
| 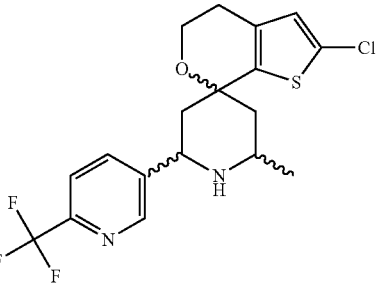 | 123 |
| 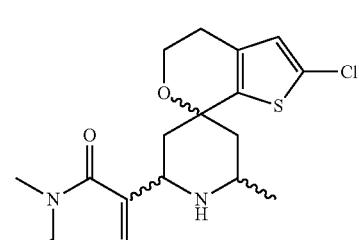 | 124 |
| 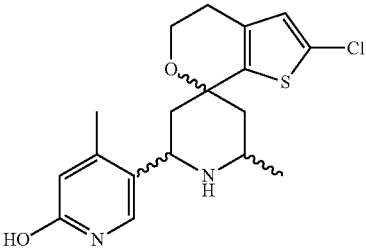 [SMILES: Cc1cc(O)ncc1C1CC2(CC(C)N1)OCCc1cc(Cl)sc12] | 125 |

TABLE I-continued
Compounds 1 to 220
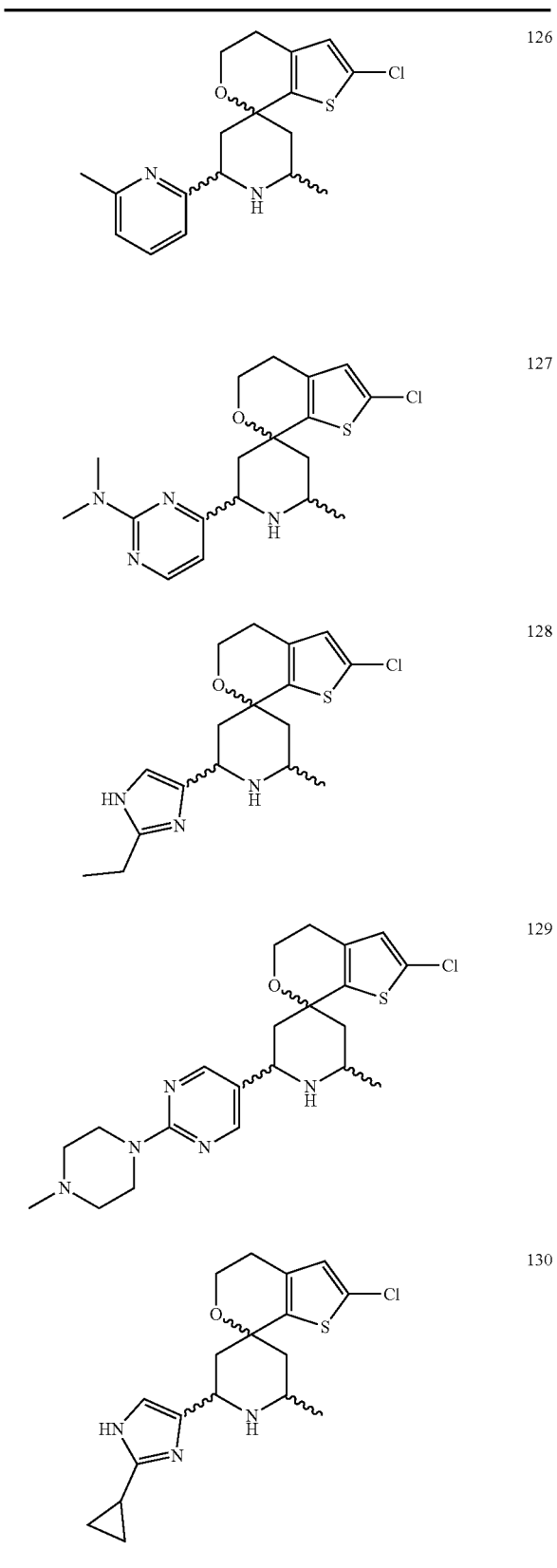
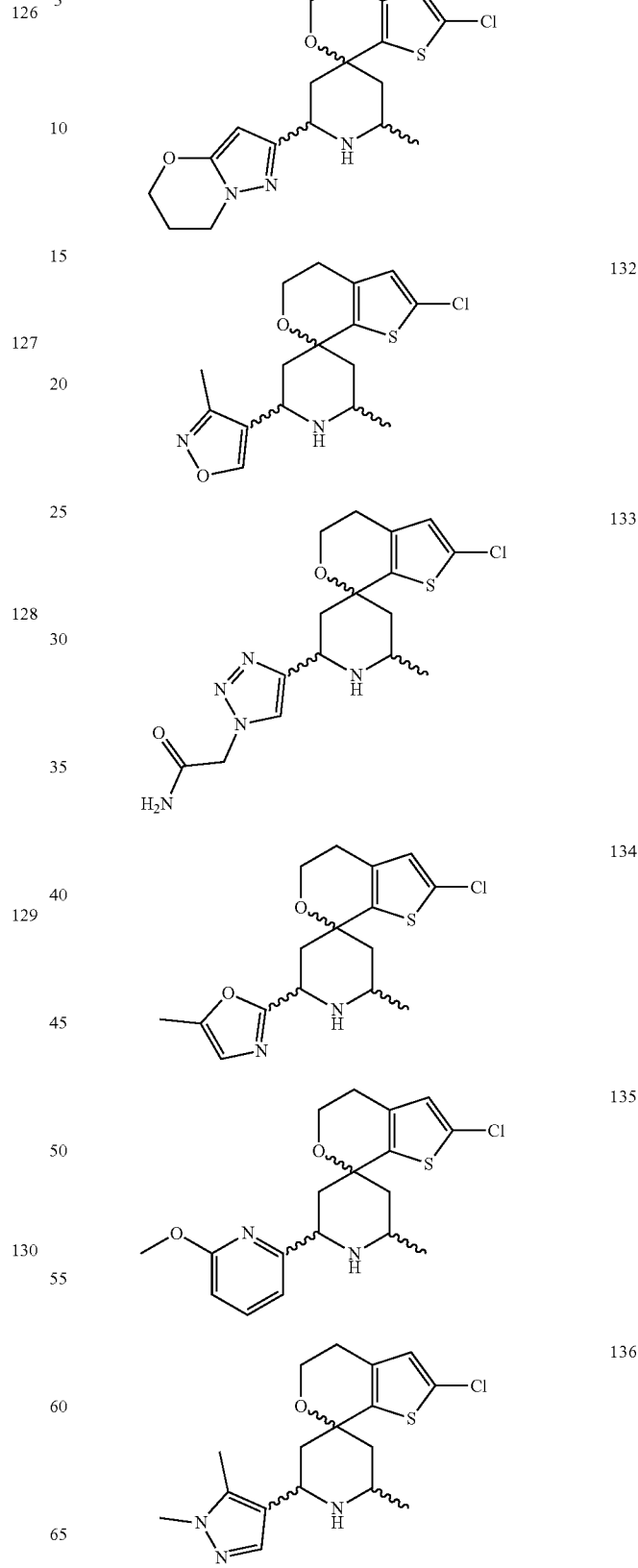

TABLE I-continued
Compounds 1 to 220
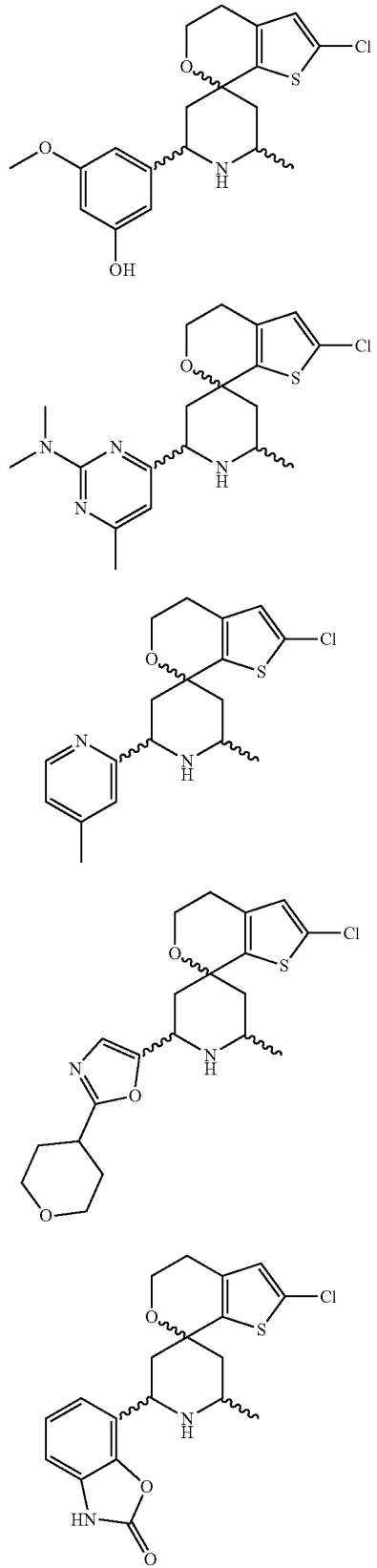
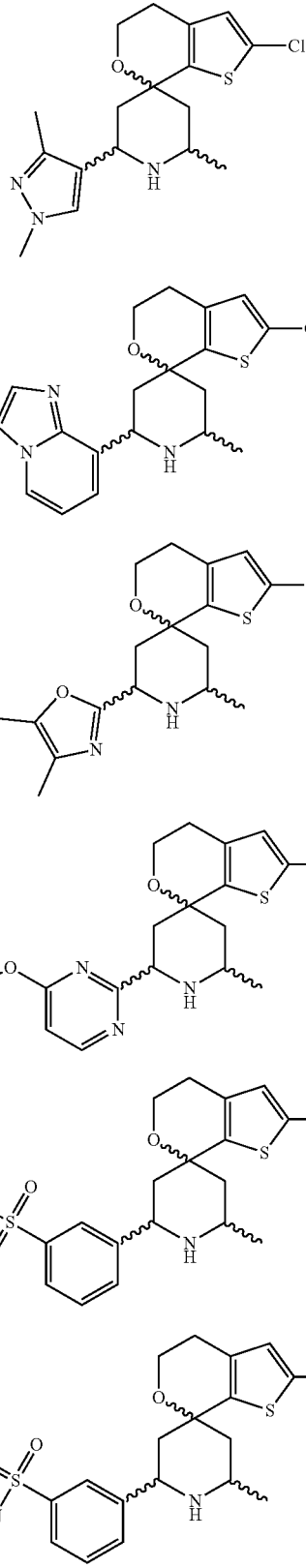

TABLE I-continued
Compounds 1 to 220
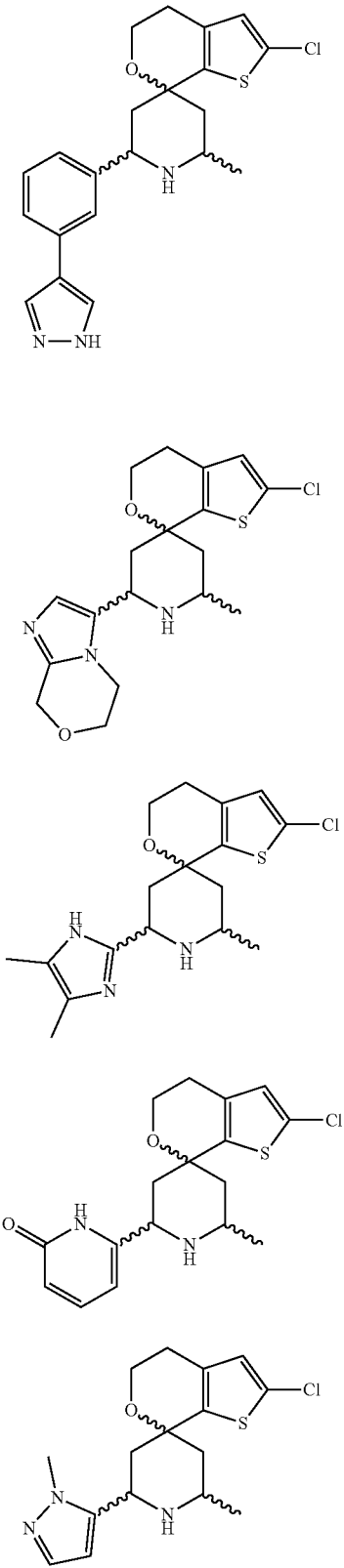
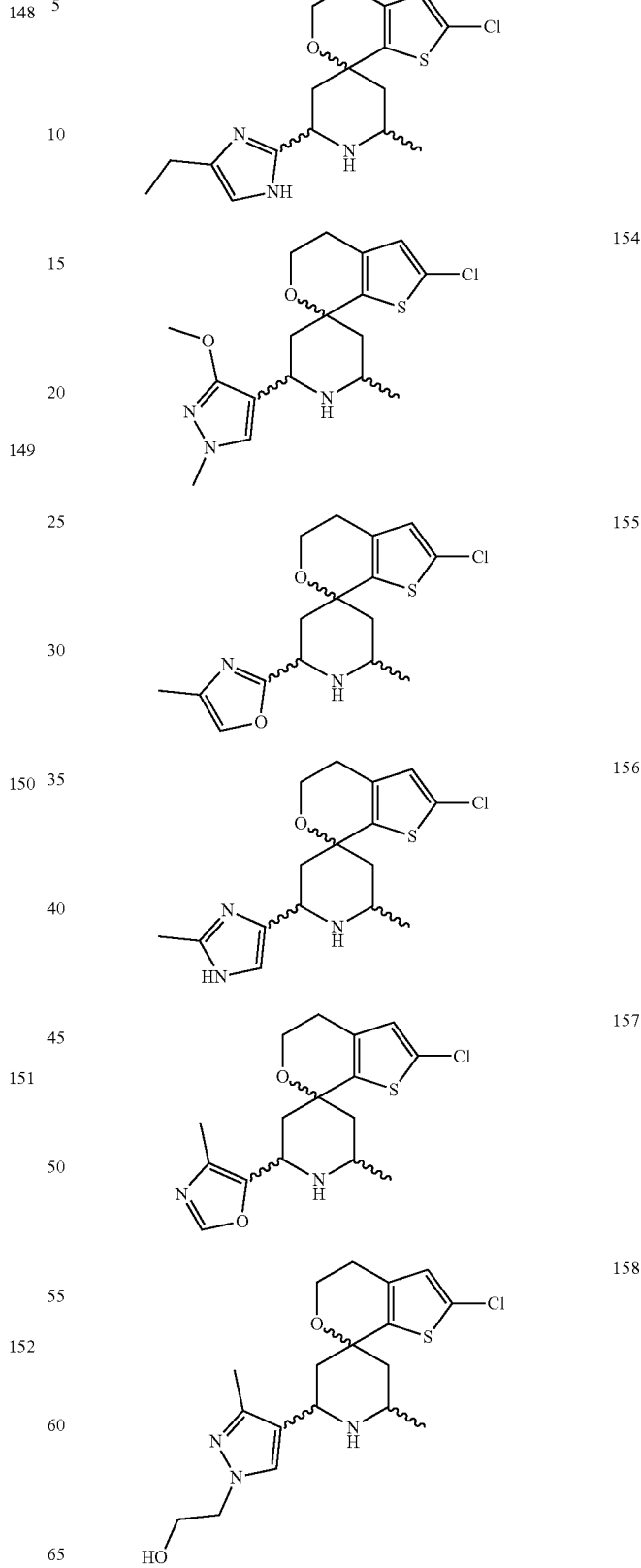

TABLE I-continued
Compounds 1 to 220
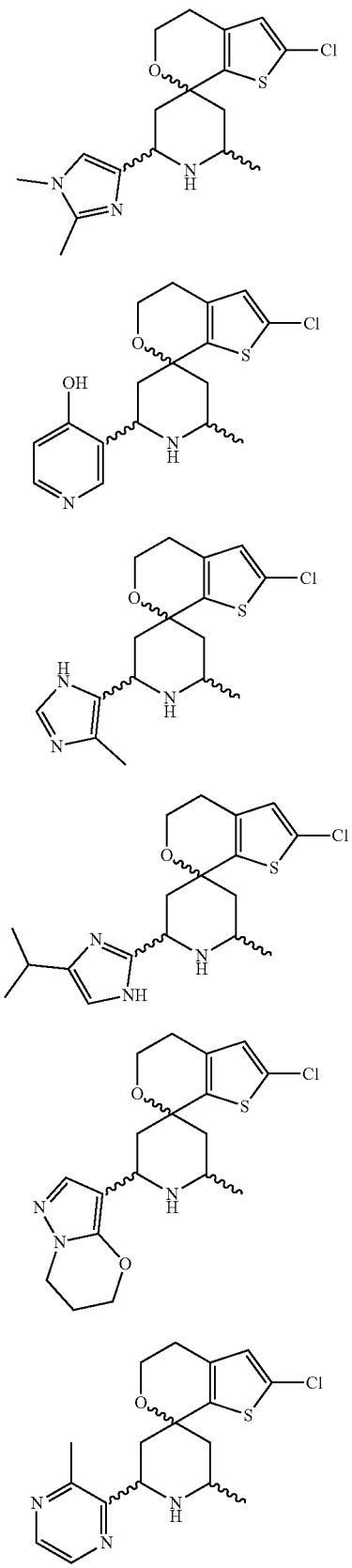
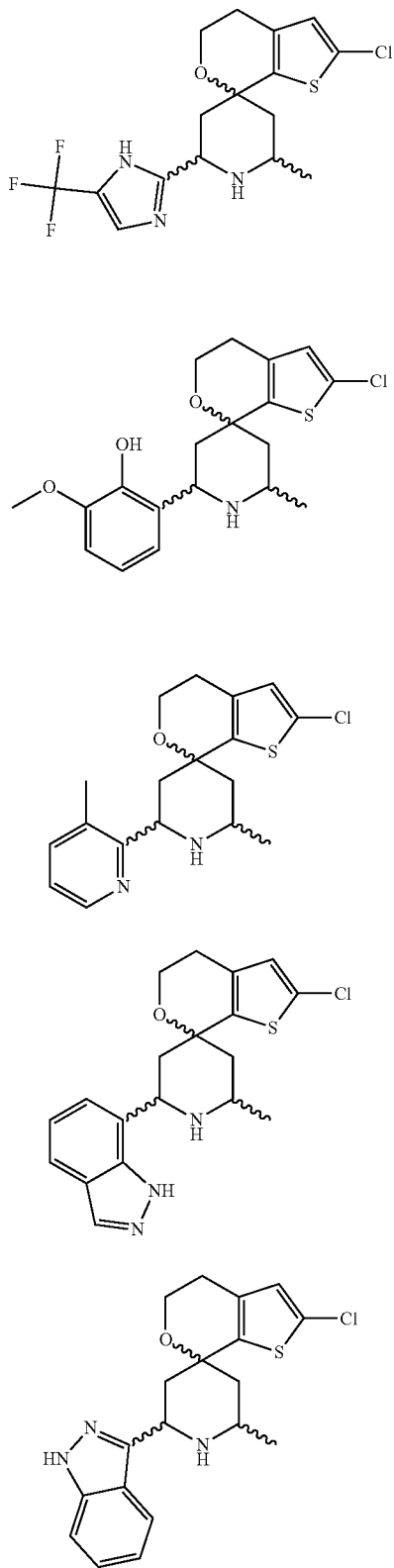

TABLE I-continued
Compounds 1 to 220
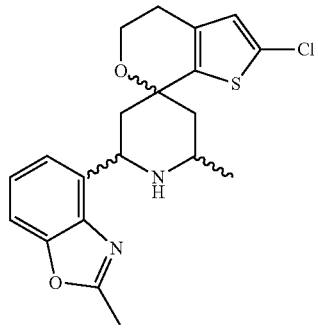 [SMILES: Cc1nc2c(C3CC4(CC(C)N3)OCCc3cc(Cl)sc34)cccc2o1] 170
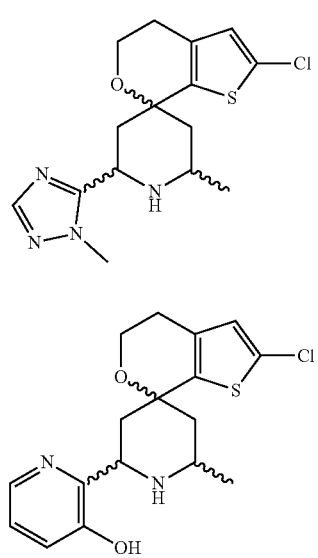 171
172
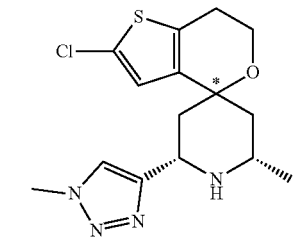 173
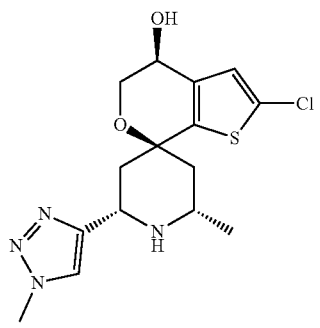 [SMILES: C[C@H]1C[C@@]2(C[C@@H](c3cn(C)nn3)N1)OC[C@@H](O)c1cc(Cl)sc12] 174
TABLE I-continued
Compounds 1 to 220
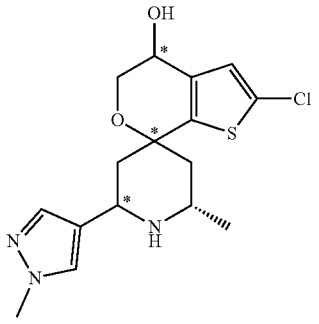 [SMILES: C[C@H]1CC2(CC(c3cnn(C)c3)N1)OCC(O)c1cc(Cl)sc12] 175
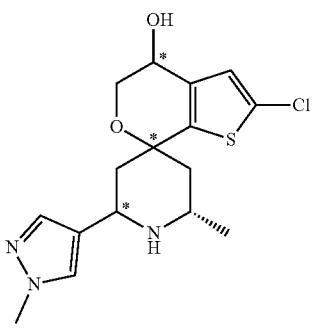 [SMILES: C[C@H]1CC2(CC(c3cnn(C)c3)N1)OCC(O)c1cc(Cl)sc12] 176
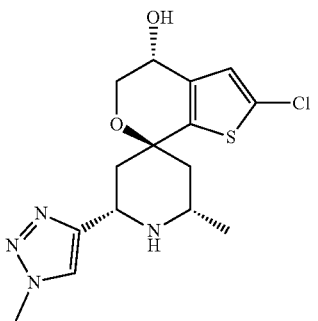 [SMILES: C[C@H]1C[C@@]2(C[C@@H](c3cn(C)nn3)N1)OC[C@H](O)c1cc(Cl)sc12] 177
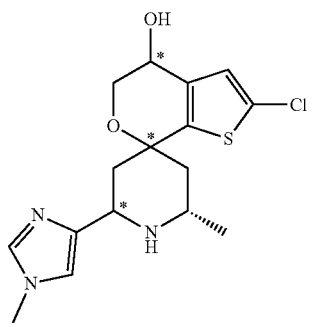 [SMILES: C[C@H]1CC2(CC(c3cn(C)cn3)N1)OCC(O)c1cc(Cl)sc12] 178

TABLE I-continued
Compounds 1 to 220
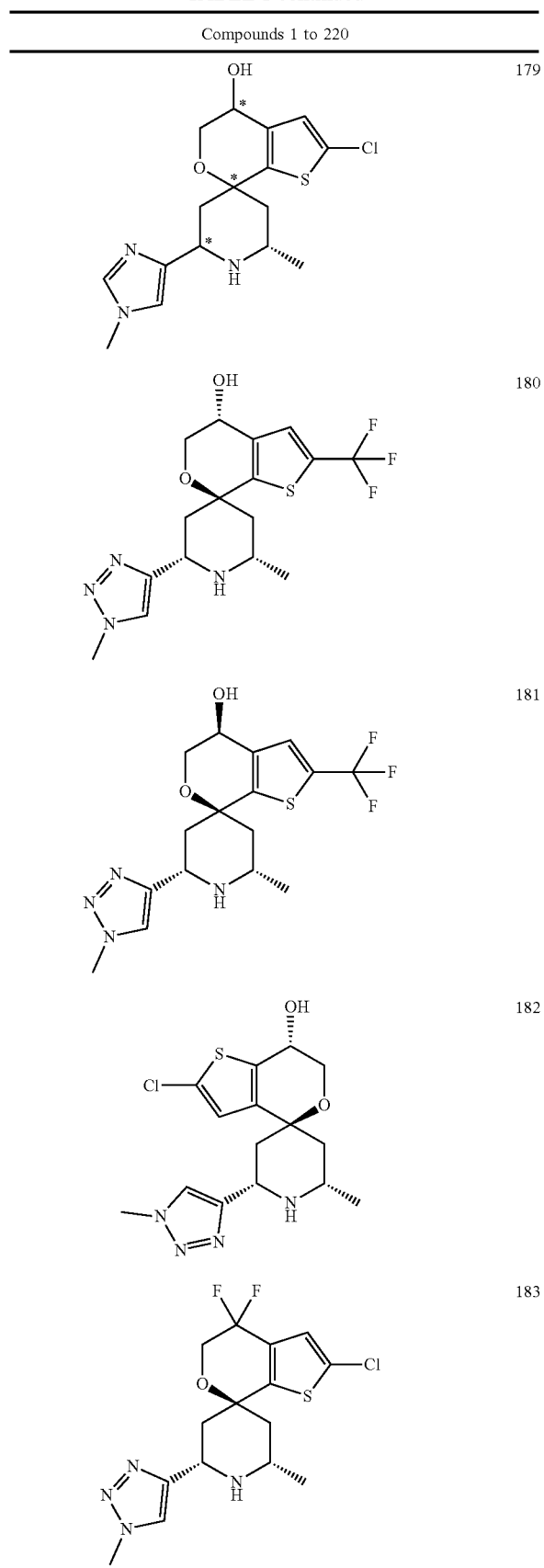
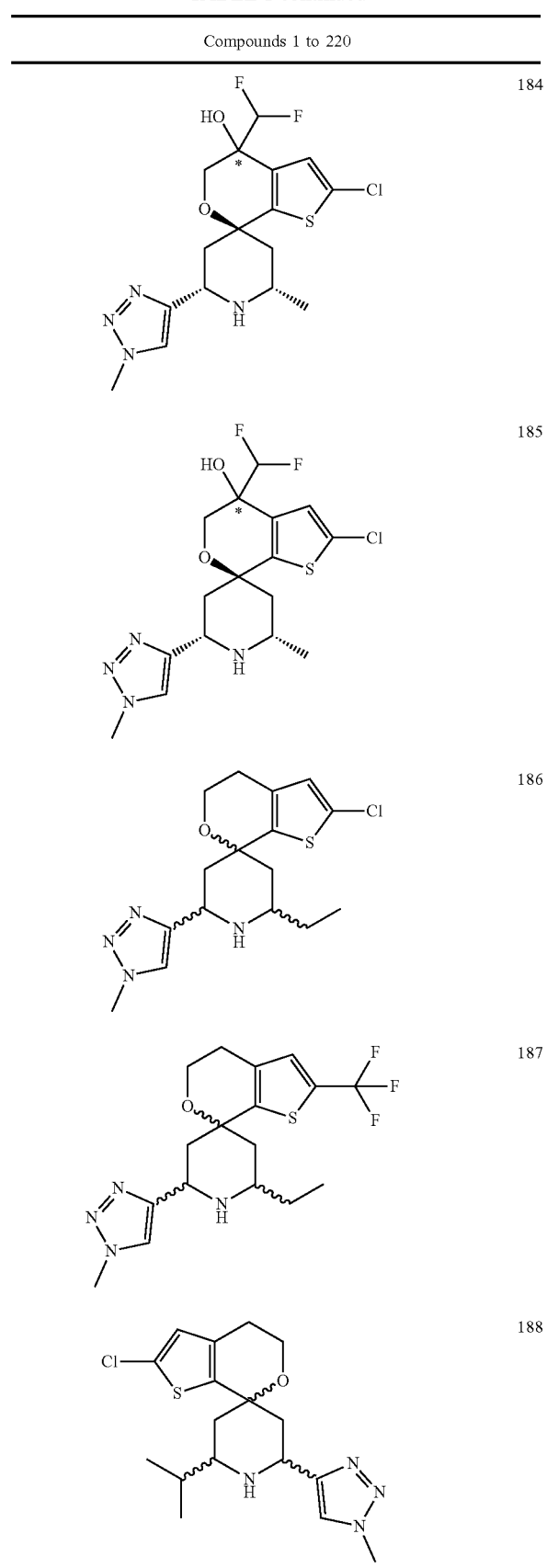

TABLE I-continued
Compounds 1 to 220
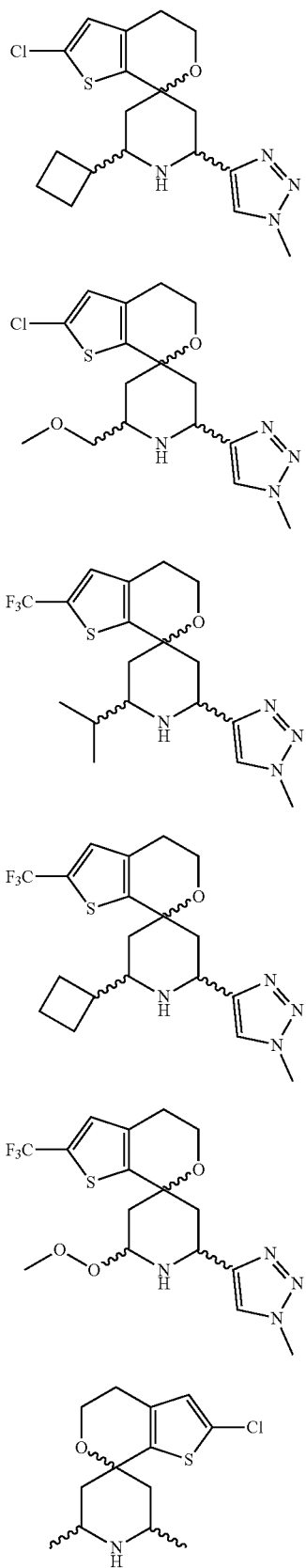
189
190
191
192
193
194
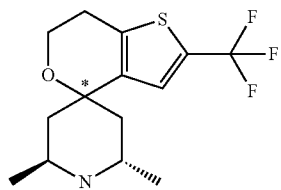 195
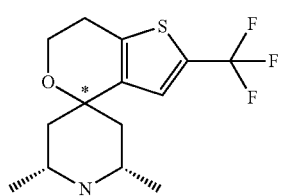 196
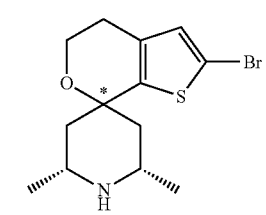 197
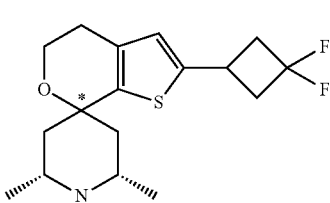 198
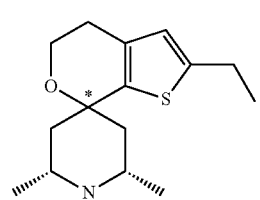 199
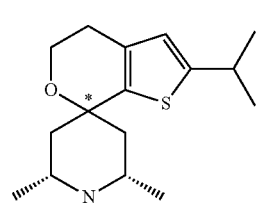 200
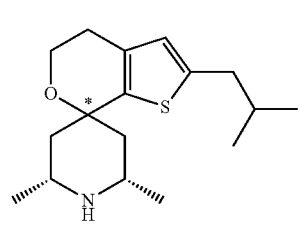 [SMILES: CC(C)Cc1cc2c(s1)C1(C[C@@H](C)N[C@@H](C)C1)OCC2] 201

TABLE I-continued
Compounds 1 to 220
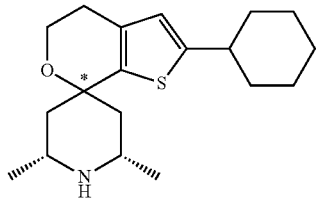 [SMILES: C[C@@H]1CC2(C[C@H](C)N1)OCCc1cc(C3CCCCC3)sc12]
202
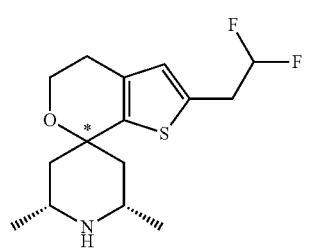
203
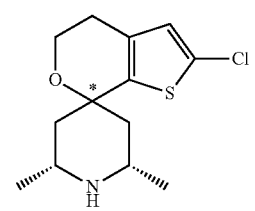 [SMILES: C[C@@H]1CC2(C[C@H](C)N1)OCCc1cc(Cl)sc12]
204
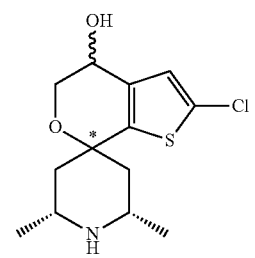 [SMILES: C[C@@H]1CC2(C[C@H](C)N1)OCC(O)c1cc(Cl)sc12]
205
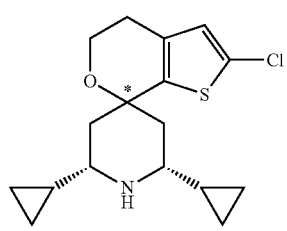 [SMILES: Clc1cc2c(s1)C1(C[C@@H](C3CC3)N[C@@H](C3CC3)C1)OCC2]
206
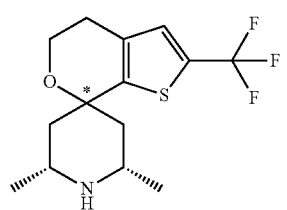 [SMILES: C[C@@H]1CC2(C[C@H](C)N1)OCCc1cc(C(F)(F)F)sc12]
207
TABLE I-continued
Compounds 1 to 220
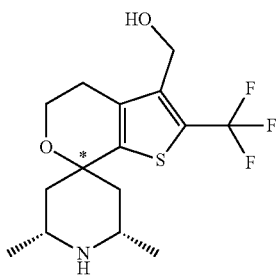 [SMILES: C[C@@H]1CC2(C[C@H](C)N1)OCCc1c2sc(C(F)(F)F)c1CO]
208
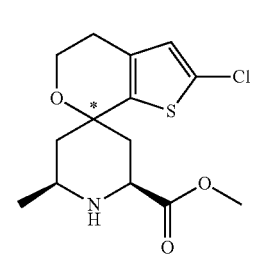
209
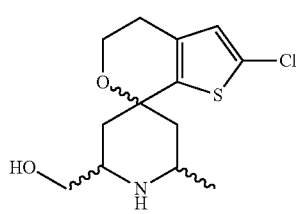 [SMILES: CC1CC2(CC(CO)N1)OCCc1cc(Cl)sc12]
210
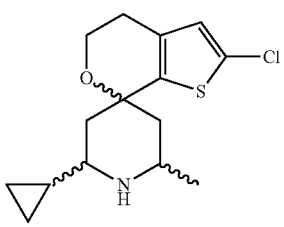 [SMILES: CC1CC2(CC(C3CC3)N1)OCCc1cc(Cl)sc12]
211
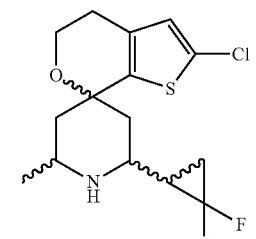
212
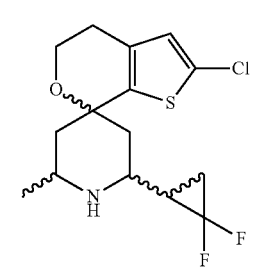
213

TABLE I-continued
Compounds 1 to 220
| | |
|---|---|
| 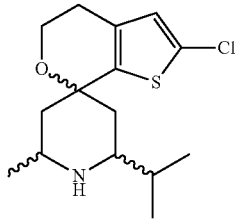 [SMILES: CC1CC2(CC(C(C)C)N1)OCCc1cc(Cl)sc12] | 214 |
| 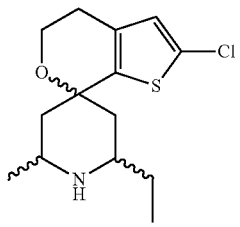 [SMILES: CCC1CC2(CC(C)N1)OCCc1cc(Cl)sc12] | 215 |
| 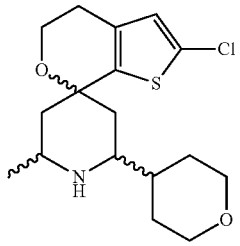 [SMILES: CC1CC2(CC(C3CCOCC3)N1)OCCc1cc(Cl)sc12] | 216 |
| 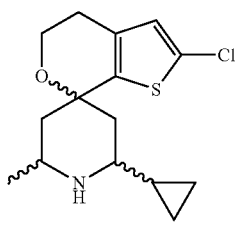 | 217 |
| 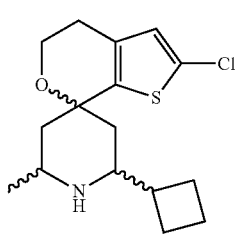 | 218 |
| 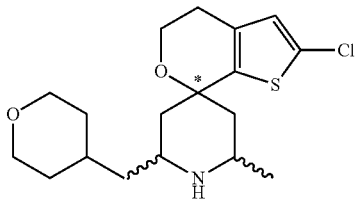 [SMILES: CC1CC2(CC(CC3CCOCC3)N1)OCCc1cc(Cl)sc12] | 219 |
| 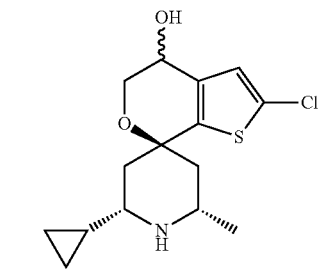 | 220 |
TABLE II
Compounds 221 to 391
| | |
|---|---|
| 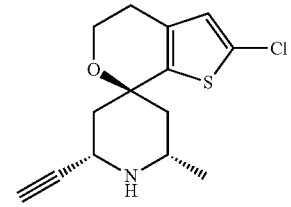 [SMILES: C#C[C@@H]1C[C@]2(C[C@H](C)N1)OCCc1cc(Cl)sc12] | 221 |
| 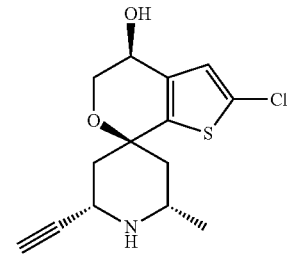 [SMILES: C#C[C@@H]1C[C@]2(C[C@H](C)N1)OC[C@@H](O)c1cc(Cl)sc12] | 222 |
| 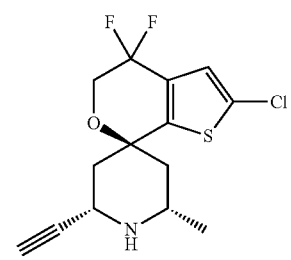 [SMILES: C#C[C@@H]1C[C@]2(C[C@H](C)N1)OCC(F)(F)c1cc(Cl)sc12] | 223 |

TABLE II-continued
Compounds 221 to 391
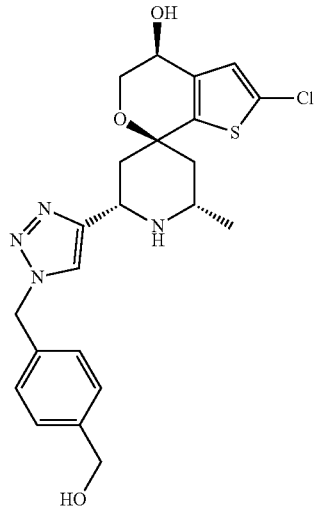 [SMILES: C[C@H]1C[C@@]2(C[C@@H](c3cn(Cc4ccc(CO)cc4)nn3)N1)OC[C@@H](O)c1cc(Cl)sc12] 224
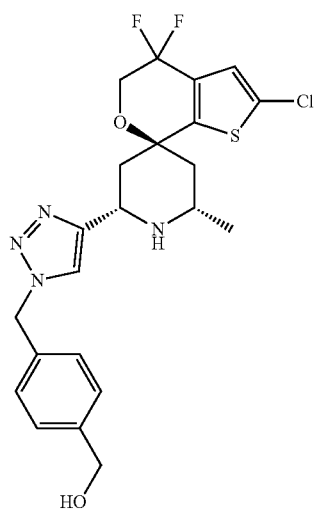 [SMILES: C[C@H]1C[C@@]2(C[C@@H](c3cn(Cc4ccc(CO)cc4)nn3)N1)OCC(F)(F)c1cc(Cl)sc12] 225
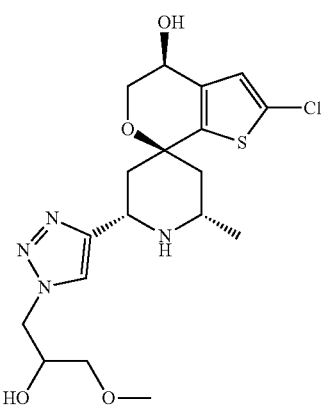 [SMILES: COCC(O)Cn1cc([C@@H]2C[C@]3(C[C@H](C)N2)OC[C@@H](O)c2cc(Cl)sc23)nn1] 226
TABLE II-continued
Compounds 221 to 391
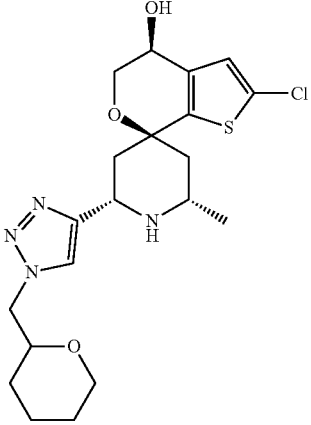 [SMILES: C[C@H]1C[C@@]2(C[C@@H](c3cn(CC4CCCCO4)nn3)N1)OC[C@@H](O)c1cc(Cl)sc12] 227
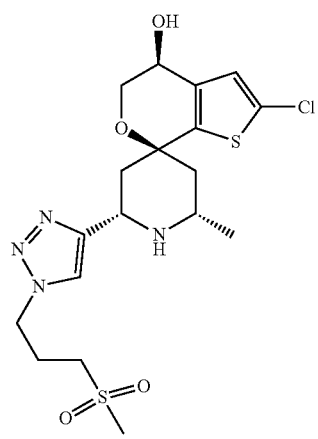 [SMILES: C[C@H]1C[C@@]2(C[C@@H](c3cn(CCCS(C)(=O)=O)nn3)N1)OC[C@@H](O)c1cc(Cl)sc12] 228
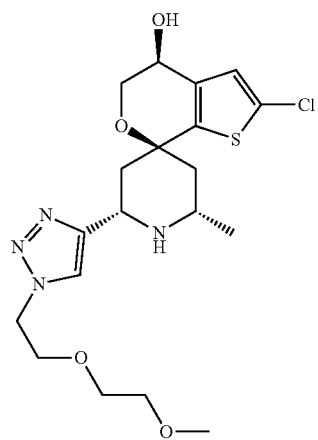 [SMILES: COCCOCCn1cc([C@@H]2C[C@]3(C[C@H](C)N2)OC[C@@H](O)c2cc(Cl)sc23)nn1] 229

TABLE II-continued
Compounds 221 to 391
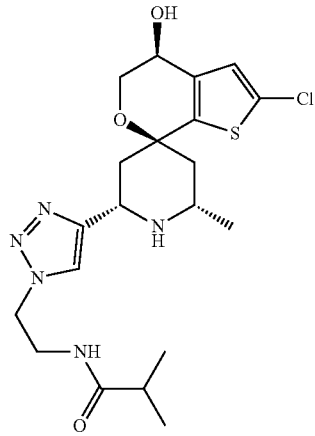 [SMILES: CC(C)C(=O)NCCn1cc([C@@H]2C[C@]3(C[C@H](C)N2)OC[C@@H](O)c2cc(Cl)sc23)nn1]
230
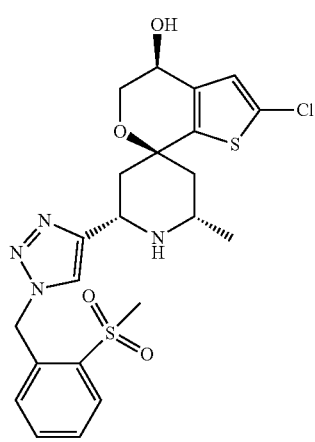 [SMILES: C[C@H]1C[C@@]2(C[C@@H](c3cn(Cc4ccccc4S(C)(=O)=O)nn3)N1)OC[C@@H](O)c1cc(Cl)sc12]
231
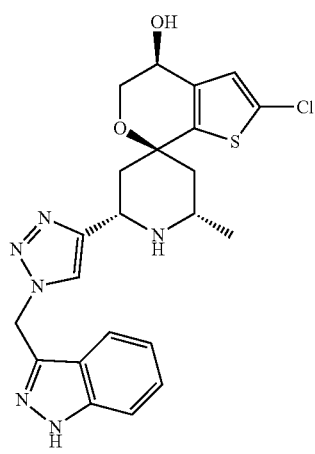 [SMILES: C[C@H]1C[C@@]2(C[C@@H](c3cn(Cc4n[nH]c5ccccc45)nn3)N1)OC[C@@H](O)c1cc(Cl)sc12]
232
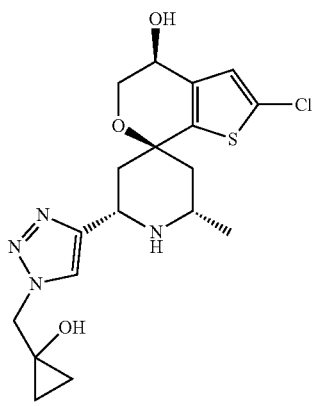 [SMILES: C[C@H]1C[C@@]2(C[C@@H](c3cn(CC4(O)CC4)nn3)N1)OC[C@@H](O)c1cc(Cl)sc12]
233
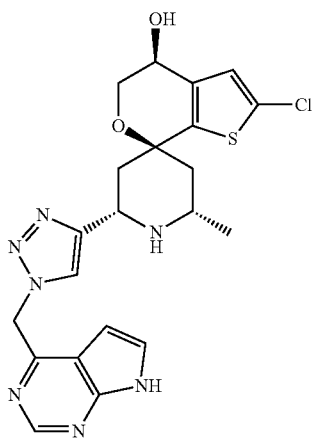 [SMILES: C[C@H]1C[C@@]2(C[C@@H](c3cn(Cc4ncnc5[nH]ccc45)nn3)N1)OC[C@@H](O)c1cc(Cl)sc12]
234
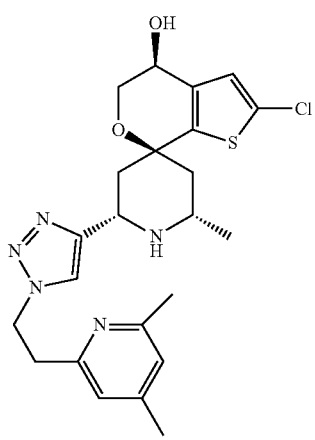 [SMILES: Cc1cc(C)nc(CCn2cc([C@@H]3C[C@]4(C[C@H](C)N3)OC[C@@H](O)c3cc(Cl)sc34)nn2)c1]
235

TABLE II-continued
Compounds 221 to 391
| | |
|---|---|
| 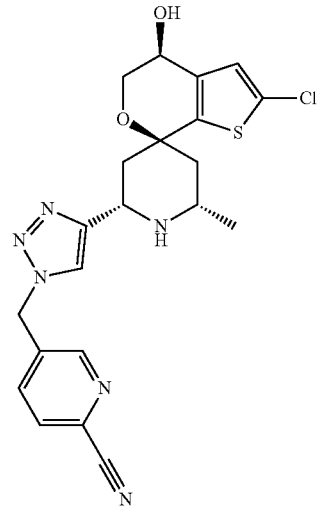 236 | 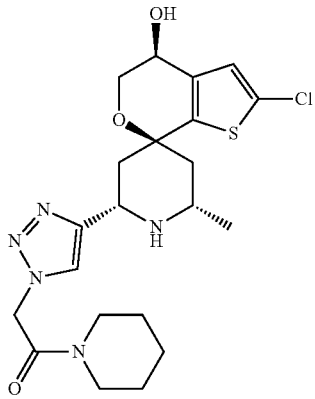 239 |
| 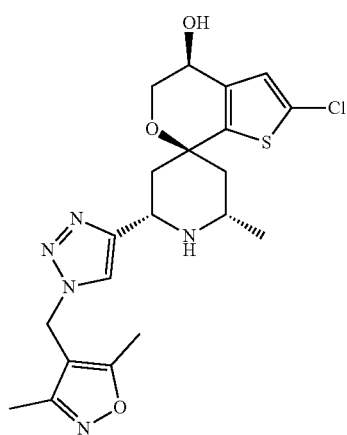 [SMILES: Cc1noc(C)c1Cn1cc([C@@H]2C[C@]3(C[C@H](C)N2)OC[C@@H](O)c2cc(Cl)sc23)nn1] 237 | 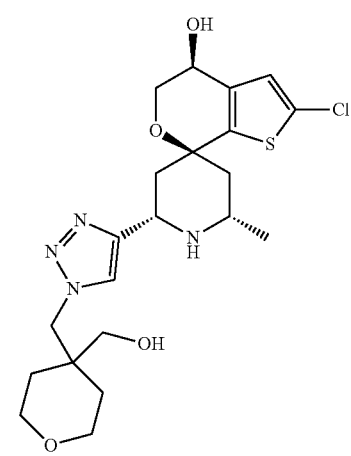 240 |
| 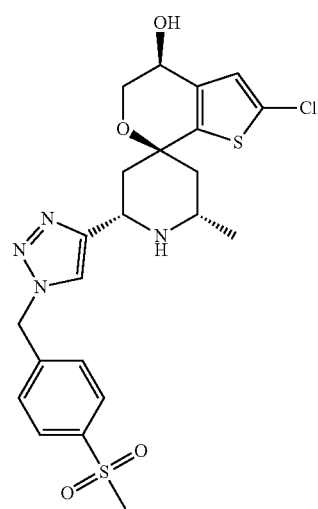 [SMILES: C[C@H]1C[C@@]2(C[C@@H](c3cn(Cc4ccc(S(C)(=O)=O)cc4)nn3)N1)OC[C@@H](O)c1cc(Cl)sc12] 238 | 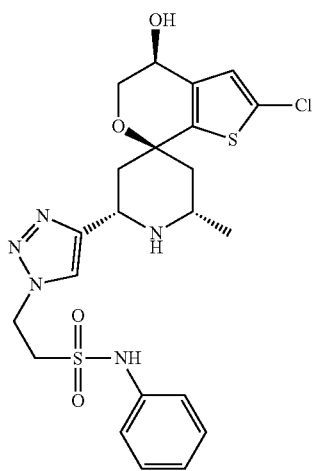 [SMILES: C[C@H]1C[C@@]2(C[C@@H](c3cn(CCS(=O)(=O)Nc4ccccc4)nn3)N1)OC[C@@H](O)c1cc(Cl)sc12] 241 |

TABLE II-continued
Compounds 221 to 391
| | |
|---|---|
| 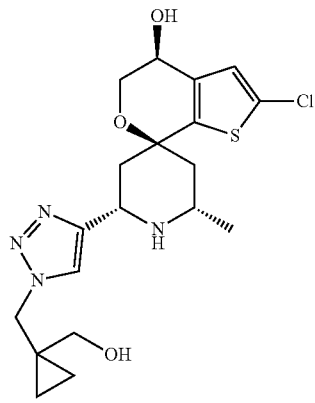 [SMILES: C[C@H]1C[C@@]2(C[C@@H](c3cn(CC4(CO)CC4)nn3)N1)OC[C@@H](O)c1cc(Cl)sc12] 242 | 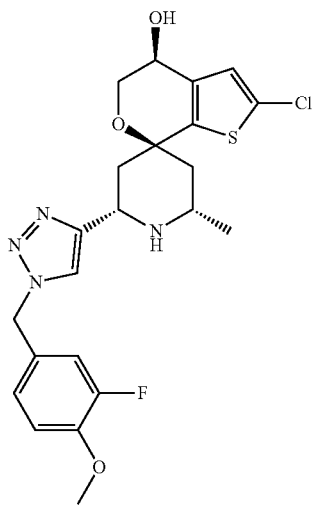 245 |
| 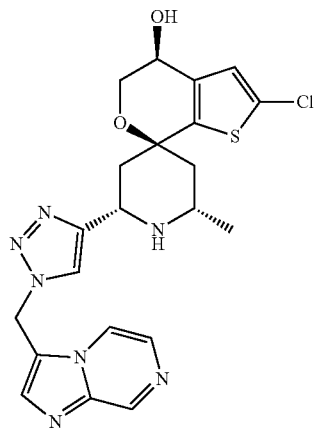 [SMILES: C[C@H]1C[C@@]2(C[C@@H](c3cn(Cc4cnc5cnccn45)nn3)N1)OC[C@@H](O)c1cc(Cl)sc12] 243 | 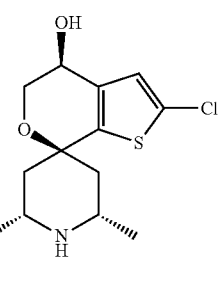 246 |
| 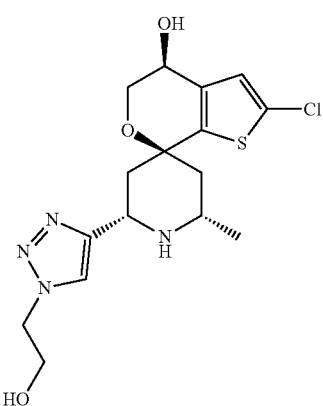 244 | 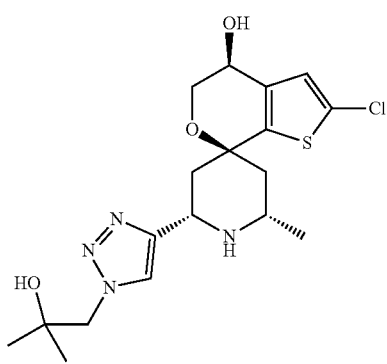 [SMILES: C[C@H]1C[C@@]2(C[C@@H](c3cn(CC(C)(C)O)nn3)N1)OC[C@@H](O)c1cc(Cl)sc12] 247 |

TABLE II-continued
Compounds 221 to 391
| | |
|---|---|
| 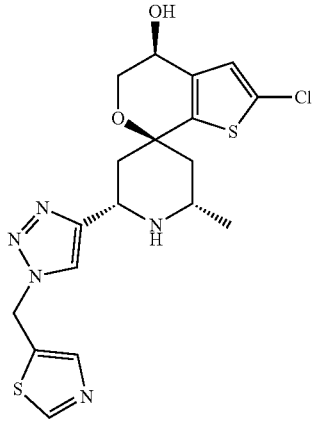 | 248 |
| 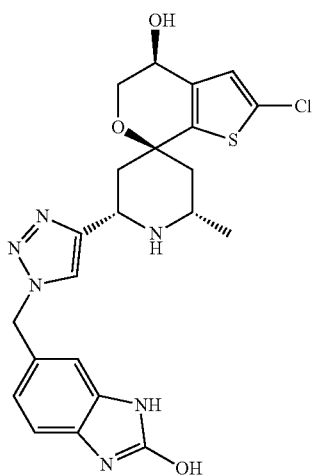 [SMILES: C[C@H]1C[C@@]2(C[C@@H](c3cn(Cc4ccc5nc(O)[nH]c5c4)nn3)N1)OC[C@@H](O)c1cc(Cl)sc12] | 249 |
| 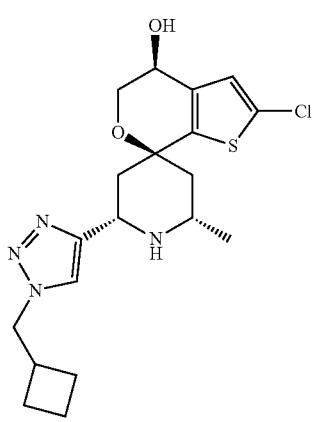 [SMILES: C[C@H]1C[C@@]2(C[C@@H](c3cn(CC4CCC4)nn3)N1)OC[C@@H](O)c1cc(Cl)sc12] | 250 |
| 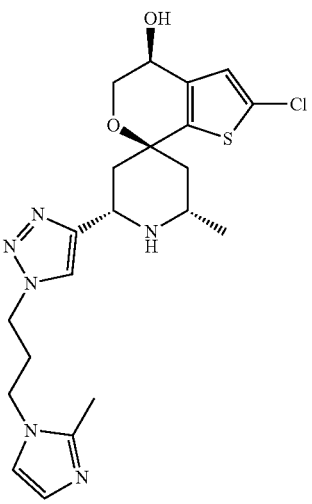 [SMILES: Cc1nccn1CCCn1cc([C@@H]2C[C@]3(C[C@H](C)N2)OC[C@@H](O)c2cc(Cl)sc23)nn1] | 251 |
| 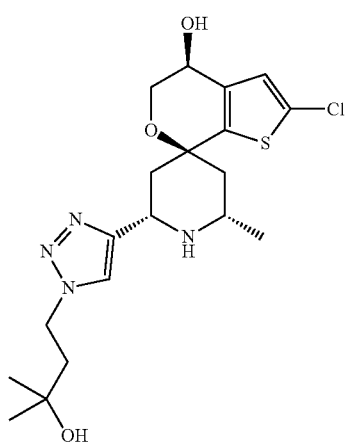 [SMILES: C[C@H]1C[C@@]2(C[C@@H](c3cn(CCC(C)(C)O)nn3)N1)OC[C@@H](O)c1cc(Cl)sc12] | 252 |
| 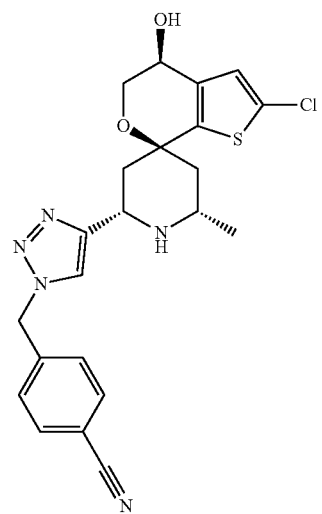 [SMILES: C[C@H]1C[C@@]2(C[C@@H](c3cn(Cc4ccc(C#N)cc4)nn3)N1)OC[C@@H](O)c1cc(Cl)sc12] | 253 |

TABLE II-continued
Compounds 221 to 391
| | |
|---|---|
| 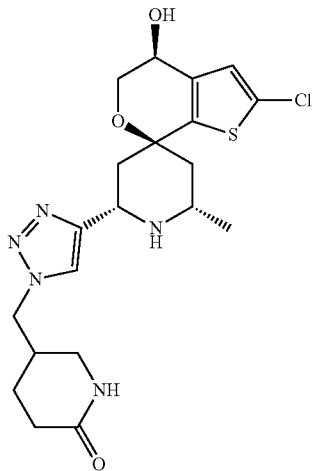 [SMILES: C[C@H]1C[C@@]2(C[C@@H](c3cn(CC4CCC(=O)NC4)nn3)N1)OC[C@@H](O)c1cc(Cl)sc12] | 254 |
| 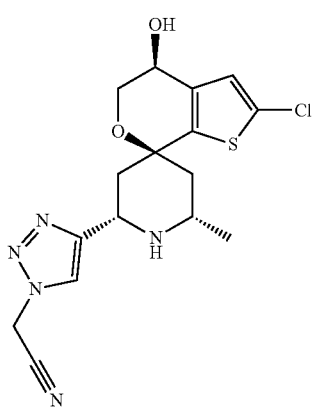 [SMILES: C[C@H]1C[C@@]2(C[C@@H](c3cn(CC#N)nn3)N1)OC[C@@H](O)c1cc(Cl)sc12] | 255 |
| 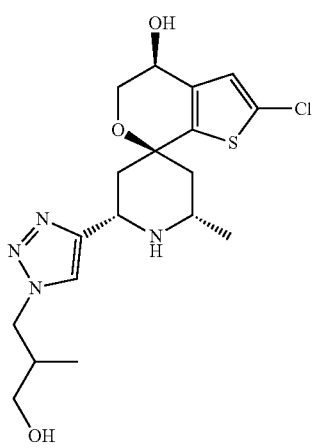 [SMILES: CC(CO)Cn1cc([C@@H]2C[C@]3(C[C@H](C)N2)OC[C@@H](O)c2cc(Cl)sc23)nn1] | 256 |
| 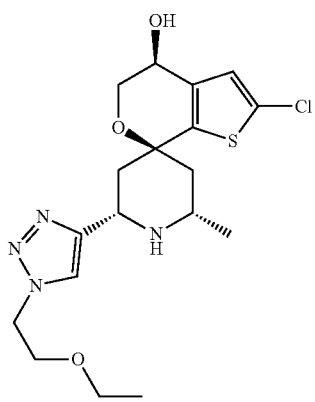 [SMILES: CCOCCn1cc([C@@H]2C[C@]3(C[C@H](C)N2)OC[C@@H](O)c2cc(Cl)sc23)nn1] | 257 |
| 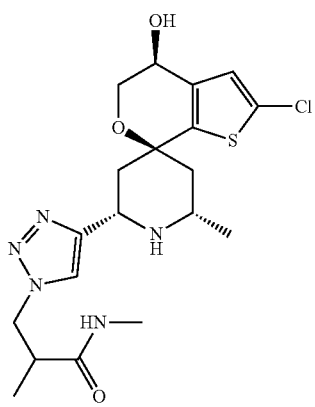 [SMILES: CNC(=O)C(C)Cn1cc([C@@H]2C[C@]3(C[C@H](C)N2)OC[C@@H](O)c2cc(Cl)sc23)nn1] | 258 |
| 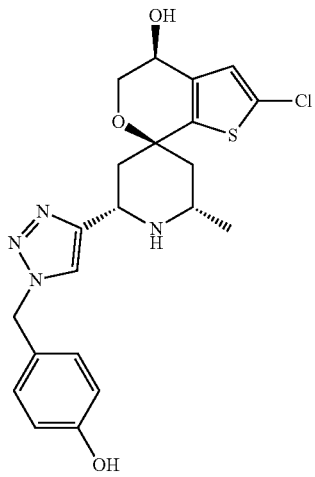 [SMILES: C[C@H]1C[C@@]2(C[C@@H](c3cn(Cc4ccc(O)cc4)nn3)N1)OC[C@@H](O)c1cc(Cl)sc12] | 259 |

TABLE II-continued
Compounds 221 to 391
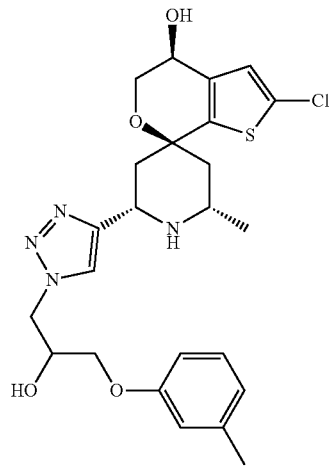 [SMILES: Cc1cccc(OCC(O)Cn2cc([C@@H]3C[C@]4(C[C@H](C)N3)OC[C@@H](O)c3cc(Cl)sc34)nn2)c1]
260
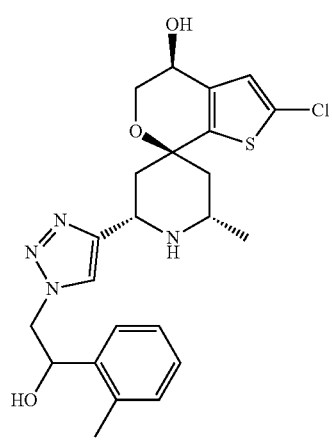 [SMILES: Cc1ccccc1C(O)Cn1cc([C@@H]2C[C@]3(C[C@H](C)N2)OC[C@@H](O)c2cc(Cl)sc23)nn1]
261
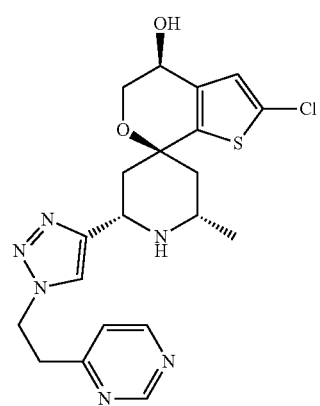 [SMILES: C[C@H]1C[C@@]2(C[C@@H](c3cn(CCc4ccncn4)nn3)N1)OC[C@@H](O)c1cc(Cl)sc12]
262
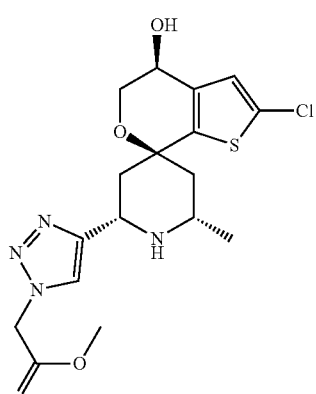
263
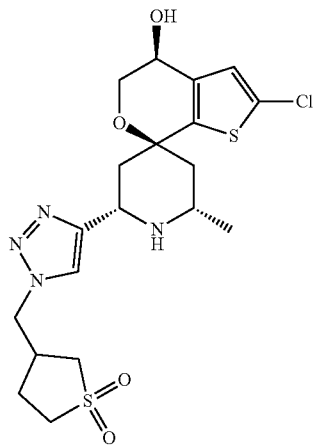 [SMILES: C[C@H]1C[C@@]2(C[C@@H](c3cn(CC4CCS(=O)(=O)C4)nn3)N1)OC[C@@H](O)c1cc(Cl)sc12]
264
265

TABLE II-continued
Compounds 221 to 391
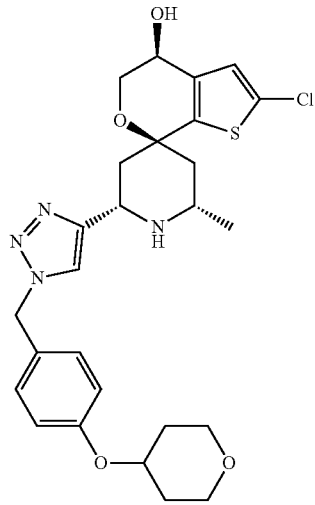 [SMILES: C[C@H]1C[C@@]2(C[C@@H](c3cn(Cc4ccc(OC5CCOCC5)cc4)nn3)N1)OC[C@@H](O)c1cc(Cl)sc12] 266
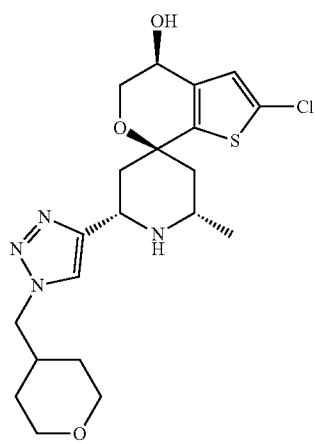 [SMILES: C[C@H]1C[C@@]2(C[C@@H](c3cn(CC4CCOCC4)nn3)N1)OC[C@@H](O)c1cc(Cl)sc12] 267
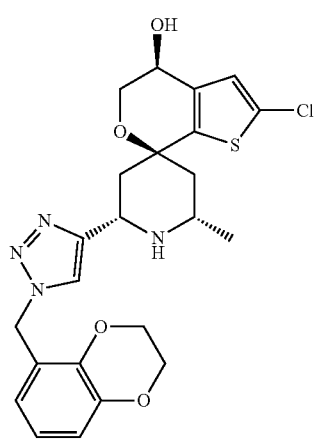 [SMILES: C[C@H]1C[C@@]2(C[C@@H](c3cn(Cc4cccc5c4OCCO5)nn3)N1)OC[C@@H](O)c1cc(Cl)sc12] 268
TABLE II-continued
Compounds 221 to 391
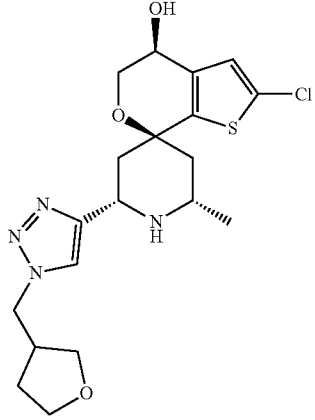 269
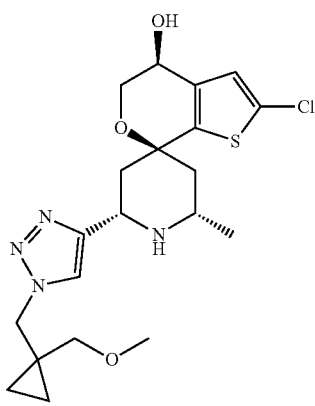 [SMILES: COCC1(Cn2cc([C@@H]3C[C@]4(C[C@H](C)N3)OC[C@@H](O)c3cc(Cl)sc34)nn2)CC1] 270
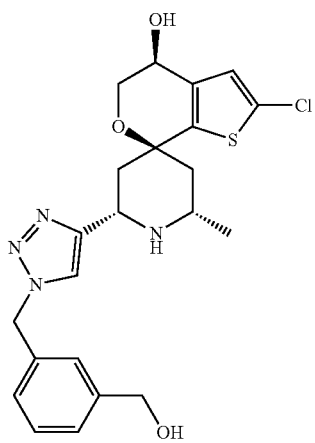 [SMILES: C[C@H]1C[C@@]2(C[C@@H](c3cn(Cc4cccc(CO)c4)nn3)N1)OC[C@@H](O)c1cc(Cl)sc12] 271

TABLE II-continued
Compounds 221 to 391
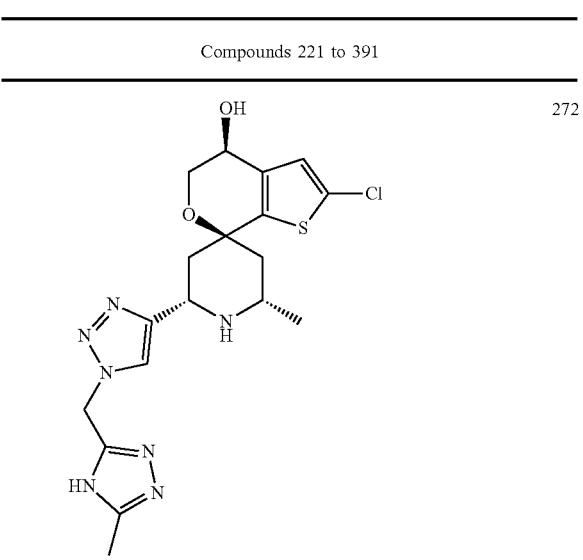
272
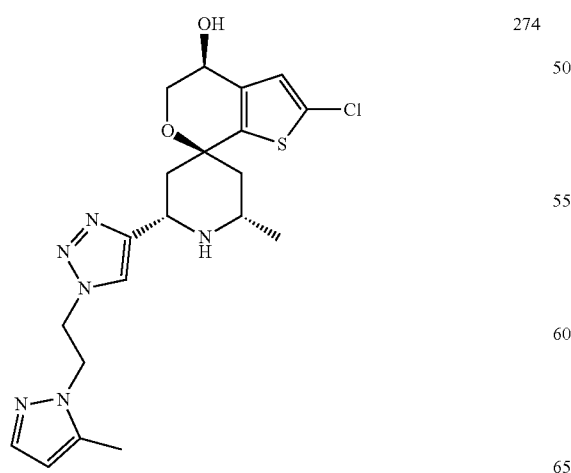
273
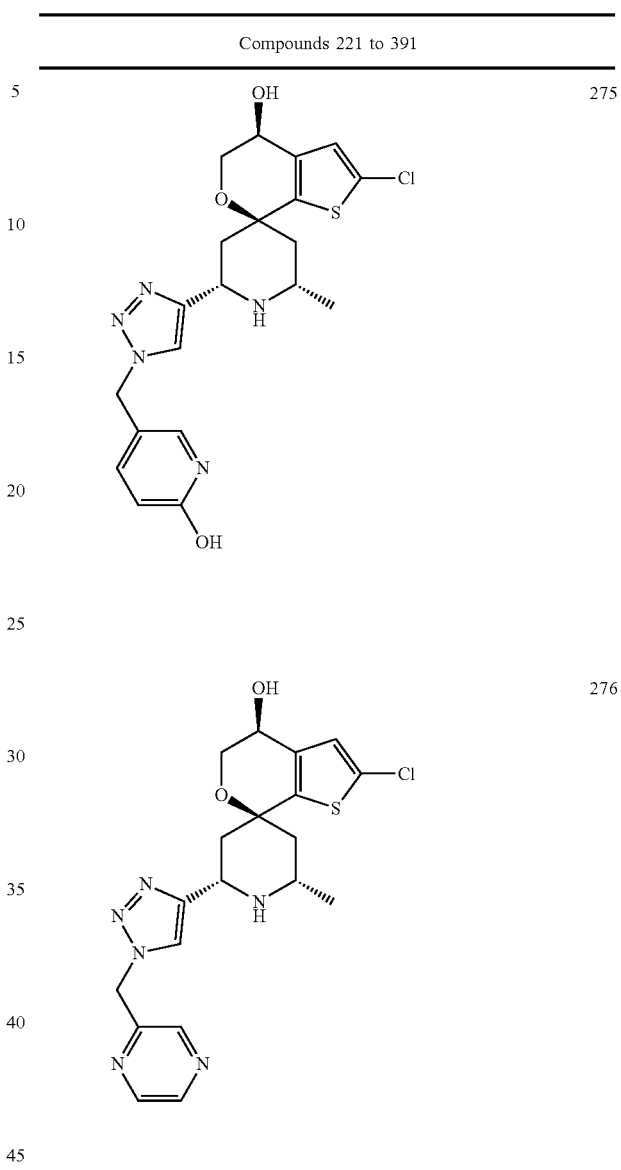
274
275
276
277

TABLE II-continued
Compounds 221 to 391
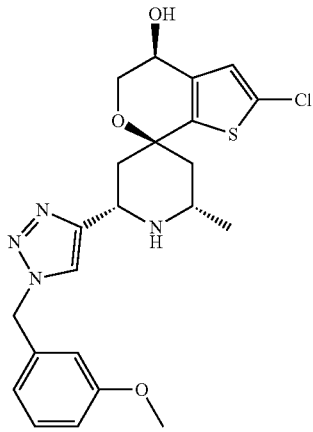 [SMILES: COc1cccc(Cn2cc([C@@H]3C[C@]4(C[C@H](C)N3)OC[C@@H](O)c3cc(Cl)sc34)nn2)c1]
278
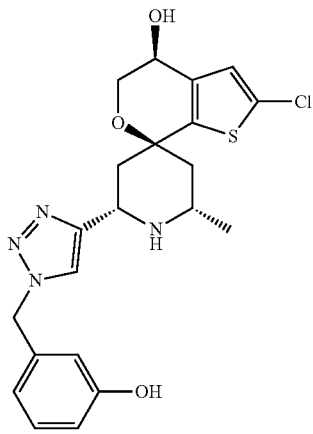 [SMILES: C[C@H]1C[C@@]2(C[C@@H](c3cn(Cc4cccc(O)c4)nn3)N1)OC[C@@H](O)c1cc(Cl)sc12]
279
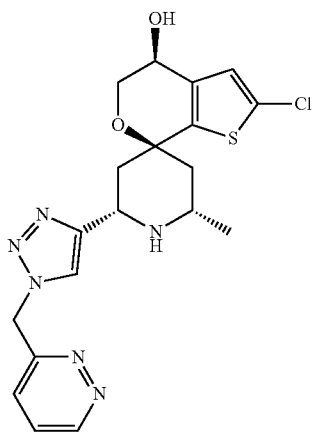
280
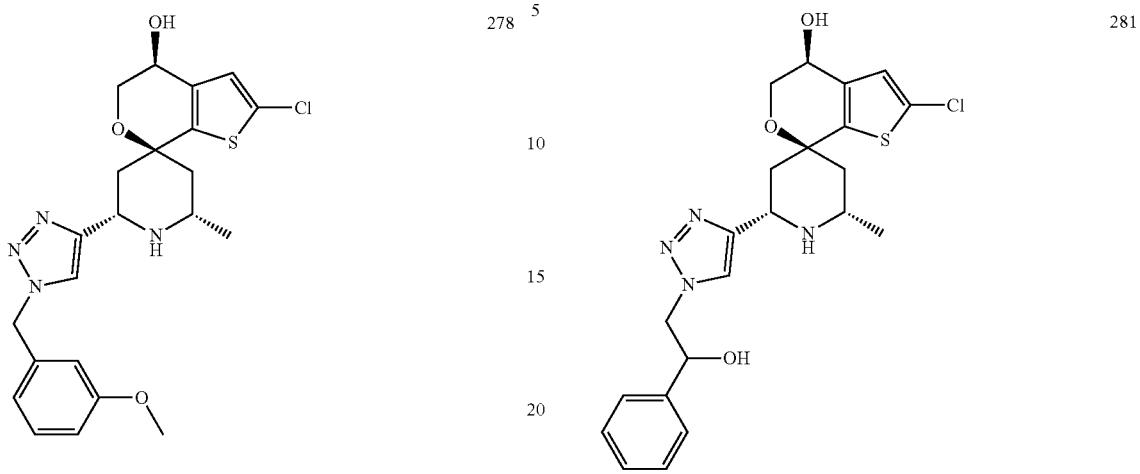
281
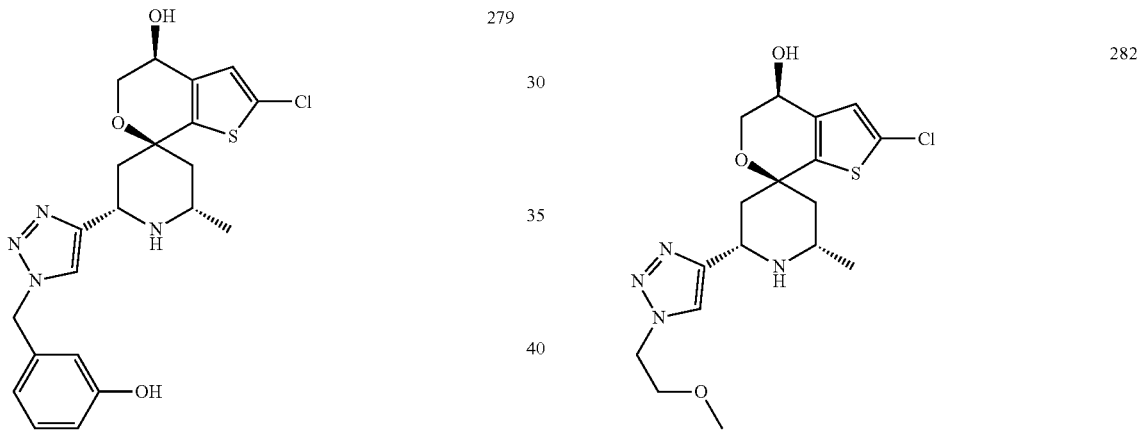
282
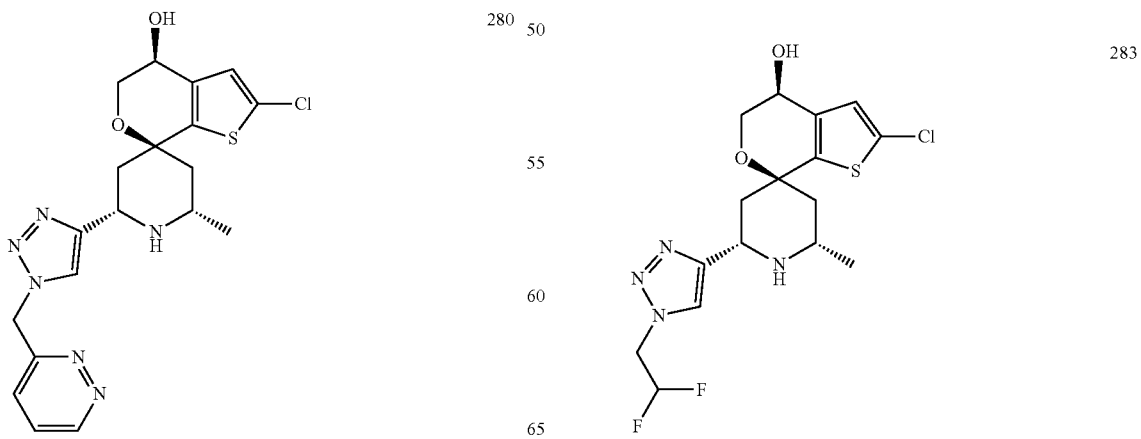
283

TABLE II-continued
Compounds 221 to 391
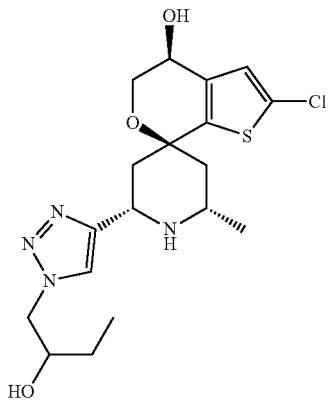 [SMILES: CCC(O)Cn1cc([C@@H]2C[C@]3(C[C@H](C)N2)OC[C@@H](O)c2cc(Cl)sc23)nn1]
284
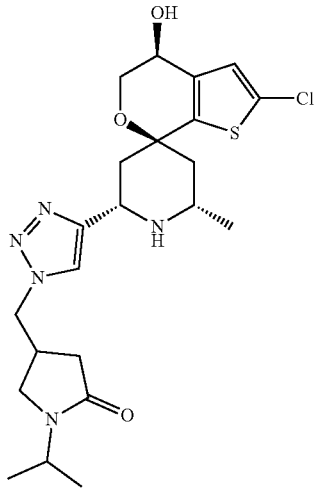
287
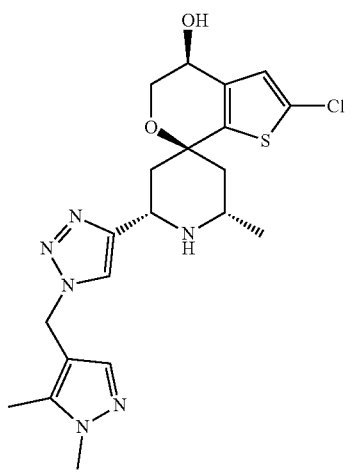 [SMILES: Cc1c(Cn2cc([C@@H]3C[C@]4(C[C@H](C)N3)OC[C@@H](O)c3cc(Cl)sc34)nn2)cnn1C]
285
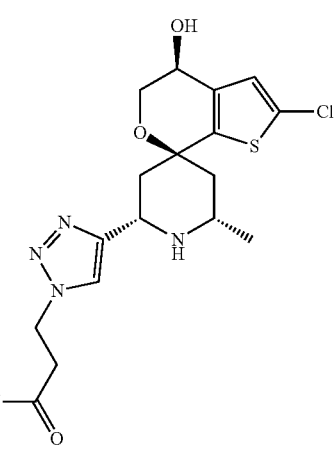
288
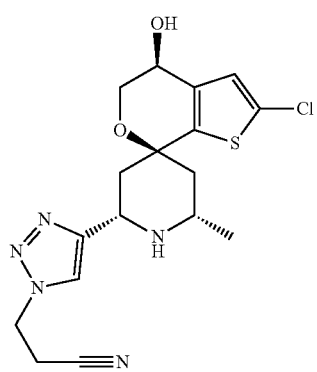 [SMILES: C[C@H]1C[C@@]2(C[C@@H](c3cn(CCC#N)nn3)N1)OC[C@@H](O)c1cc(Cl)sc12]
286
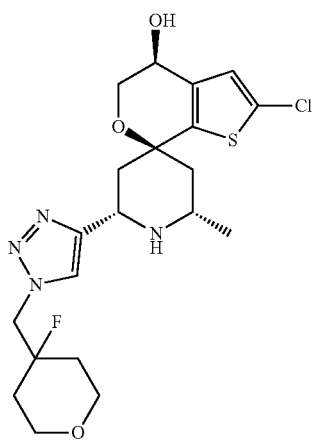 [SMILES: C[C@H]1C[C@@]2(C[C@@H](c3cn(CC4(F)CCOCC4)nn3)N1)OC[C@@H](O)c1cc(Cl)sc12]
289

TABLE II-continued
Compounds 221 to 391
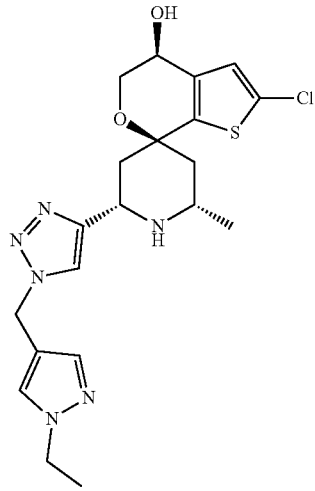 [SMILES: CCn1cc(Cn2cc([C@@H]3C[C@]4(C[C@H](C)N3)OC[C@@H](O)c3cc(Cl)sc34)nn2)cn1] 290
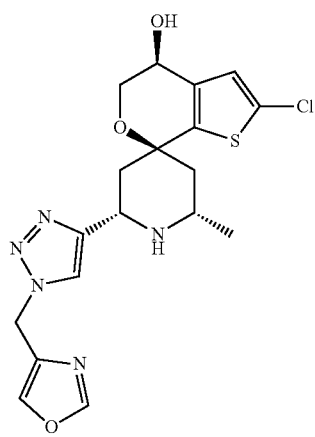 [SMILES: C[C@H]1C[C@@]2(C[C@@H](c3cn(Cc4cocn4)nn3)N1)OC[C@@H](O)c1cc(Cl)sc12] 291
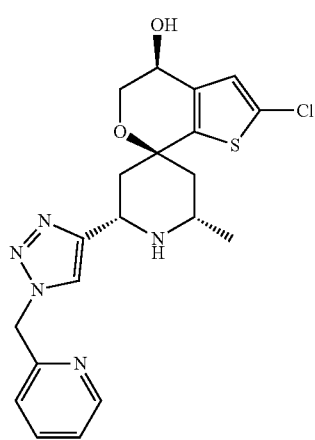 [SMILES: C[C@H]1C[C@@]2(C[C@@H](c3cn(Cc4ccccn4)nn3)N1)OC[C@@H](O)c1cc(Cl)sc12] 292
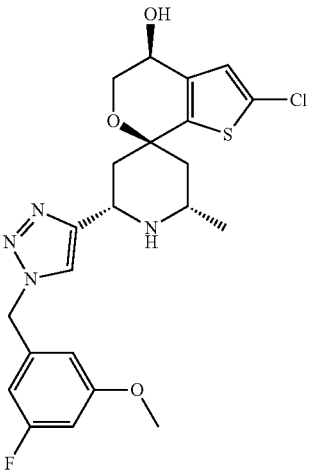 [SMILES: COc1cc(F)cc(Cn2cc([C@@H]3C[C@]4(C[C@H](C)N3)OC[C@@H](O)c3cc(Cl)sc34)nn2)c1] 293
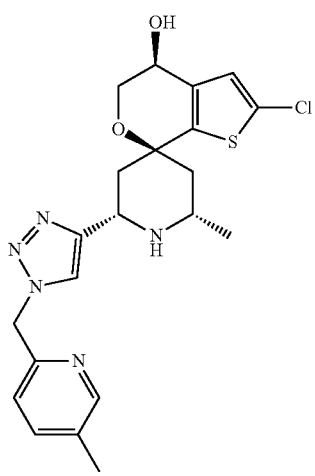 [SMILES: Cc1ccc(Cn2cc([C@@H]3C[C@]4(C[C@H](C)N3)OC[C@@H](O)c3cc(Cl)sc34)nn2)nc1] 294
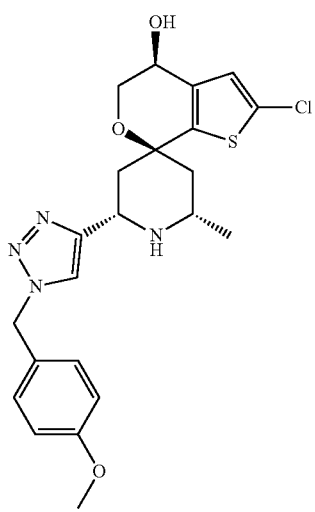 [SMILES: COc1ccc(Cn2cc([C@@H]3C[C@]4(C[C@H](C)N3)OC[C@@H](O)c3cc(Cl)sc34)nn2)cc1] 295

TABLE II-continued
Compounds 221 to 391
| | |
|---|---|
| 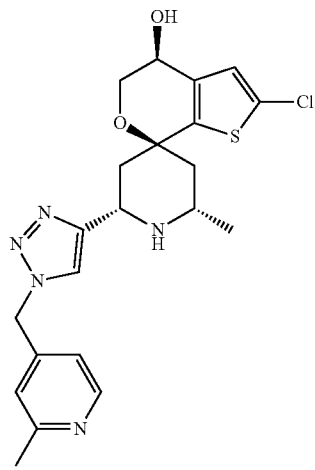 [SMILES: Cc1cc(Cn2cc([C@@H]3C[C@]4(C[C@H](C)N3)OC[C@@H](O)c3cc(Cl)sc34)nn2)ccn1] | 296 |
| 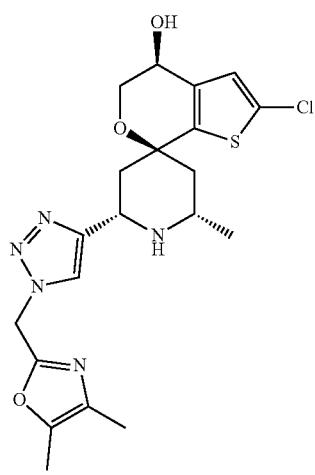 [SMILES: Cc1nc(Cn2cc([C@@H]3C[C@]4(C[C@H](C)N3)OC[C@@H](O)c3cc(Cl)sc34)nn2)oc1C] | 297 |
| 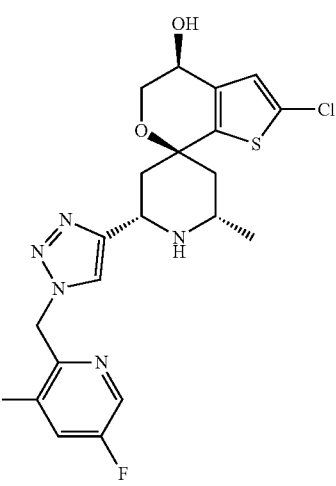 | 298 |
| 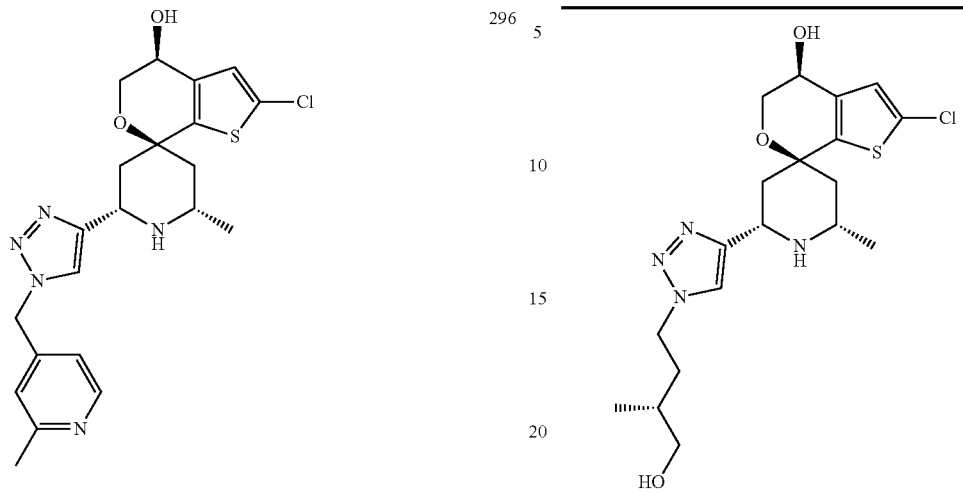 | 299 |
| 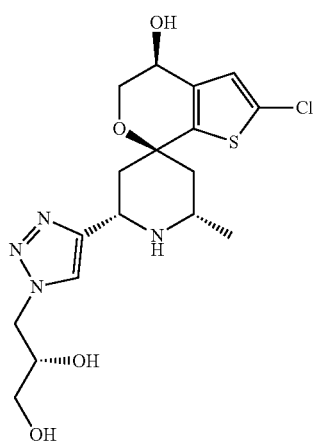 [SMILES: C[C@H]1C[C@@]2(C[C@@H](c3cn(C[C@H](O)CO)nn3)N1)OC[C@@H](O)c1cc(Cl)sc12] | 300 |
| 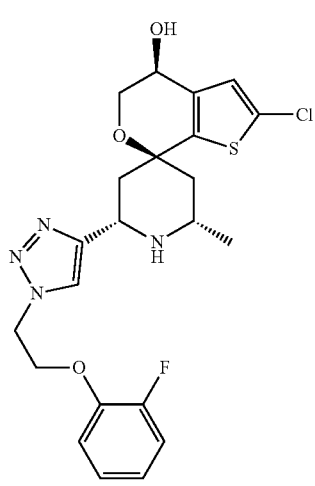 [SMILES: C[C@H]1C[C@@]2(C[C@@H](c3cn(CCOc4ccccc4F)nn3)N1)OC[C@@H](O)c1cc(Cl)sc12] | 301 |

TABLE II-continued
Compounds 221 to 391
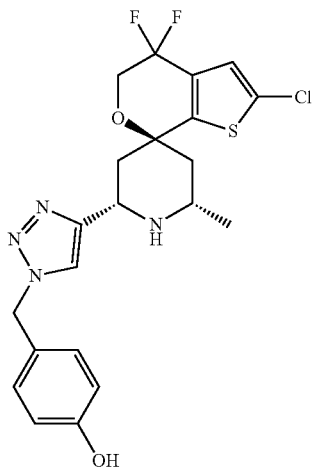 [SMILES: C[C@H]1C[C@@]2(C[C@@H](c3cn(Cc4ccc(O)cc4)nn3)N1)OCC(F)(F)c1cc(Cl)sc12]
302
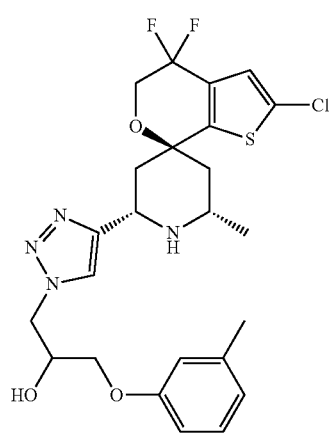 [SMILES: Cc1cccc(OCC(O)Cn2cc([C@@H]3C[C@]4(C[C@H](C)N3)OCC(F)(F)c3cc(Cl)sc34)nn2)c1]
303
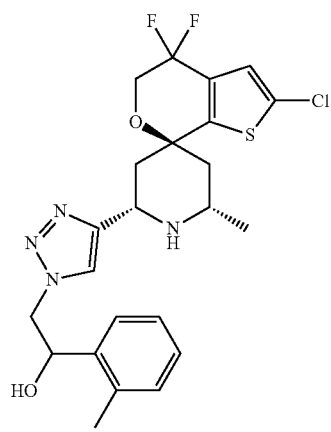 [SMILES: Cc1ccccc1C(O)Cn1cc([C@@H]2C[C@]3(C[C@H](C)N2)OCC(F)(F)c2cc(Cl)sc23)nn1]
304
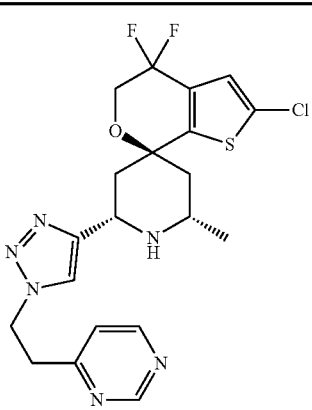
305
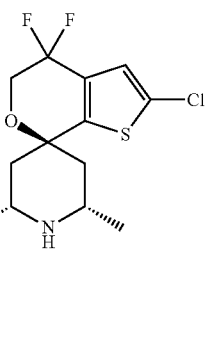
306
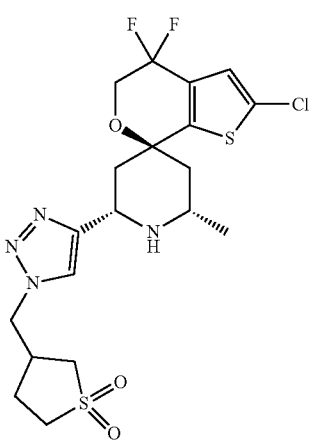 [SMILES: C[C@H]1C[C@@]2(C[C@@H](c3cn(CC4CCS(=O)(=O)C4)nn3)N1)OCC(F)(F)c1cc(Cl)sc12]
307

TABLE II-continued
Compounds 221 to 391
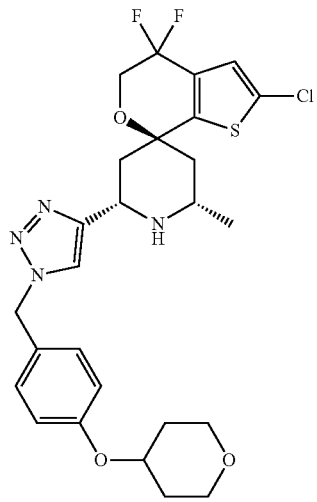 [SMILES: C[C@H]1C[C@@]2(C[C@@H](c3cn(Cc4ccc(OC5CCOCC5)cc4)nn3)N1)OCC(F)(F)c1cc(Cl)sc12]
308
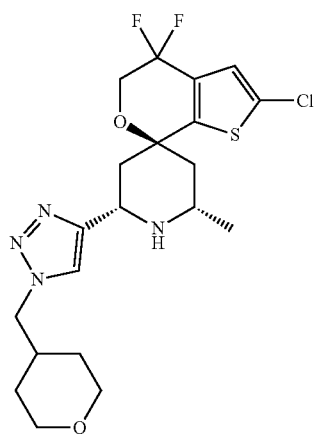 [SMILES: C[C@H]1C[C@@]2(C[C@@H](c3cn(CC4CCOCC4)nn3)N1)OCC(F)(F)c1cc(Cl)sc12]
309
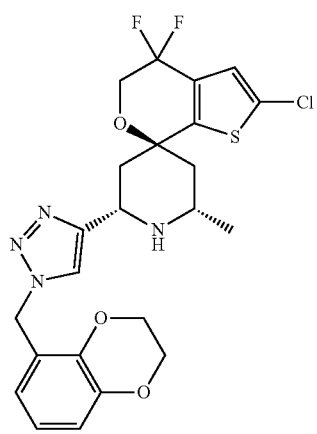 [SMILES: C[C@H]1C[C@@]2(C[C@@H](c3cn(Cc4cccc5c4OCCO5)nn3)N1)OCC(F)(F)c1cc(Cl)sc12]
310
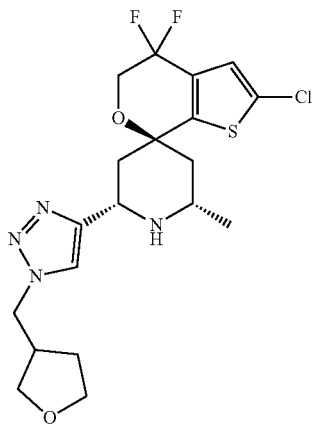 [SMILES: C[C@H]1C[C@@]2(C[C@@H](c3cn(CC4CCOC4)nn3)N1)OCC(F)(F)c1cc(Cl)sc12]
311
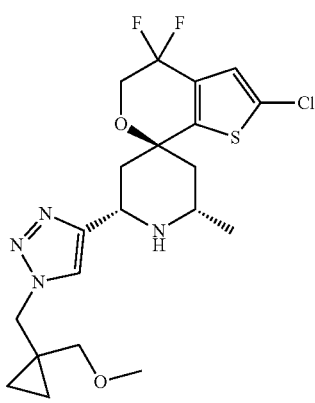 [SMILES: COCC1(Cn2cc([C@@H]3C[C@]4(C[C@H](C)N3)OCC(F)(F)c3cc(Cl)sc34)nn2)CC1]
312
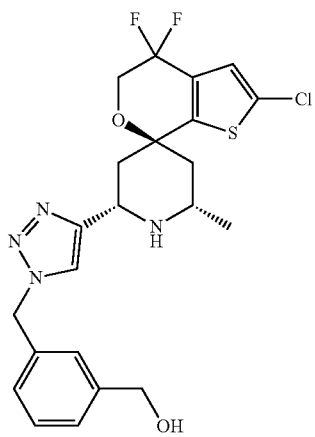 [SMILES: C[C@H]1C[C@@]2(C[C@@H](c3cn(Cc4cccc(CO)c4)nn3)N1)OCC(F)(F)c1cc(Cl)sc12]
313

TABLE II-continued
Compounds 221 to 391
314
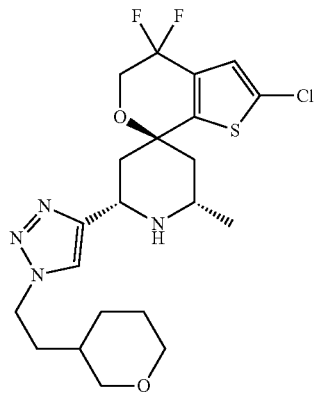 [SMILES: C[C@H]1C[C@@]2(C[C@@H](c3cn(CCC4CCCOC4)nn3)N1)OCC(F)(F)c1cc(Cl)sc12]
315
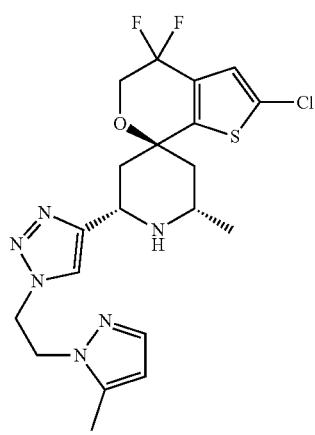 [SMILES: Cc1ccnn1CCn1cc([C@@H]2C[C@]3(C[C@H](C)N2)OCC(F)(F)c2cc(Cl)sc23)nn1]
316
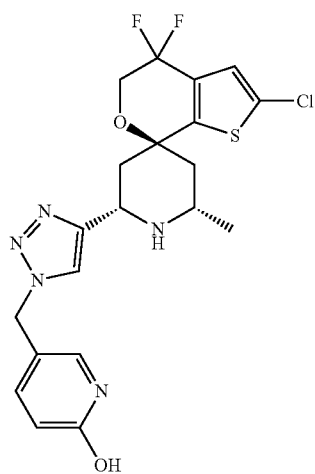
317
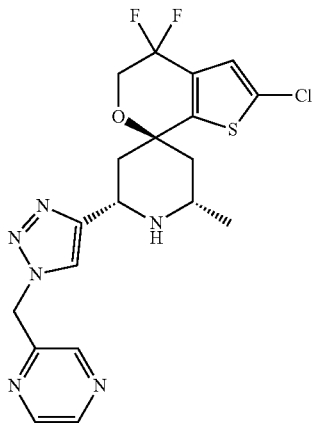 [SMILES: C[C@H]1C[C@@]2(C[C@@H](c3cn(Cc4cnccn4)nn3)N1)OCC(F)(F)c1cc(Cl)sc12]
318
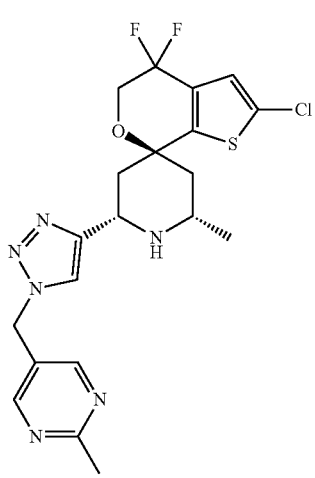 [SMILES: Cc1ncc(Cn2cc([C@@H]3C[C@]4(C[C@H](C)N3)OCC(F)(F)c3cc(Cl)sc34)nn2)cn1]
319
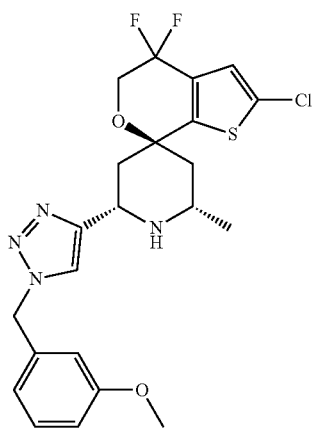 [SMILES: COc1cccc(Cn2cc([C@@H]3C[C@]4(C[C@H](C)N3)OCC(F)(F)c3cc(Cl)sc34)nn2)c1]

TABLE II-continued
Compounds 221 to 391
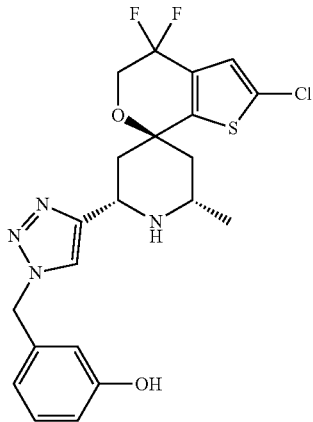 [SMILES: C[C@H]1C[C@@]2(C[C@@H](c3cn(Cc4cccc(O)c4)nn3)N1)OCC(F)(F)c1cc(Cl)sc12]
320
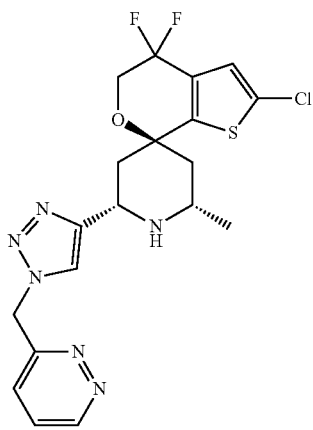 [SMILES: C[C@H]1C[C@@]2(C[C@@H](c3cn(Cc4cccnn4)nn3)N1)OCC(F)(F)c1cc(Cl)sc12]
321
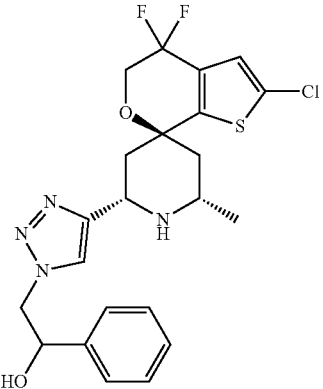 [SMILES: C[C@H]1C[C@@]2(C[C@@H](c3cn(CC(O)c4ccccc4)nn3)N1)OCC(F)(F)c1cc(Cl)sc12]
322
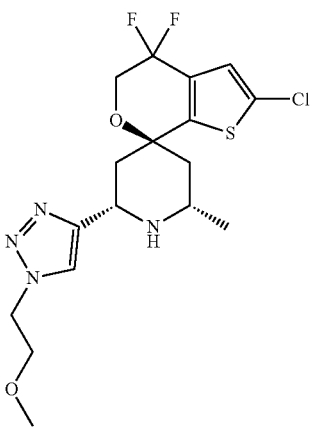 [SMILES: COCCn1cc([C@@H]2C[C@]3(C[C@H](C)N2)OCC(F)(F)c2cc(Cl)sc23)nn1]
323
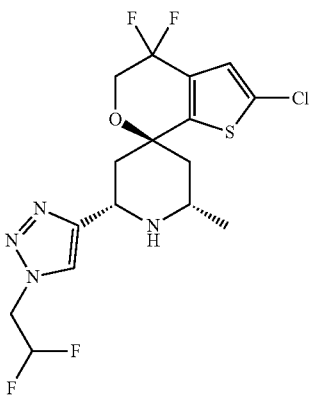 [SMILES: C[C@H]1C[C@@]2(C[C@@H](c3cn(CC(F)F)nn3)N1)OCC(F)(F)c1cc(Cl)sc12]
324
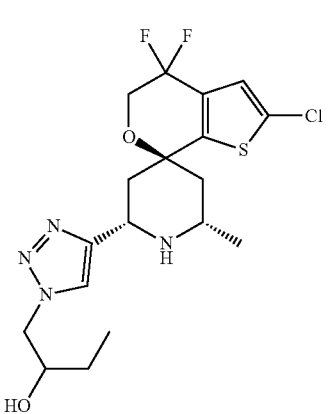 [SMILES: CCC(O)Cn1cc([C@@H]2C[C@]3(C[C@H](C)N2)OCC(F)(F)c2cc(Cl)sc23)nn1]
325

TABLE II-continued
Compounds 221 to 391
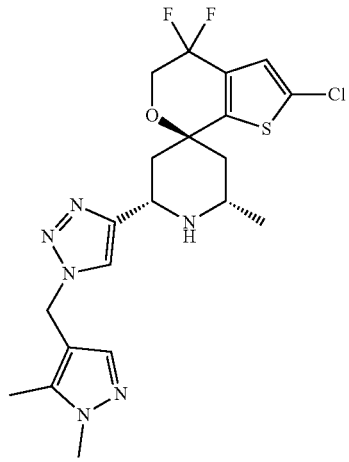 [SMILES: Cc1c(Cn2cc([C@@H]3C[C@]4(C[C@H](C)N3)OCC(F)(F)c3cc(Cl)sc34)nn2)cnn1C] 326
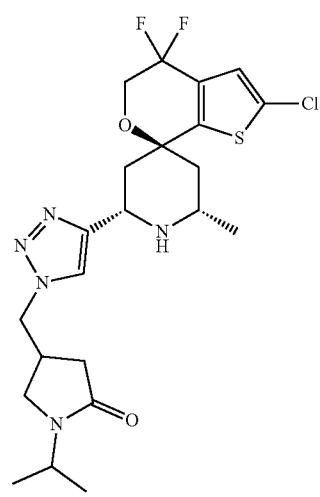 [SMILES: CC(C)N1CC(Cn2cc([C@@H]3C[C@]4(C[C@H](C)N3)OCC(F)(F)c3cc(Cl)sc34)nn2)CC1=O] 327
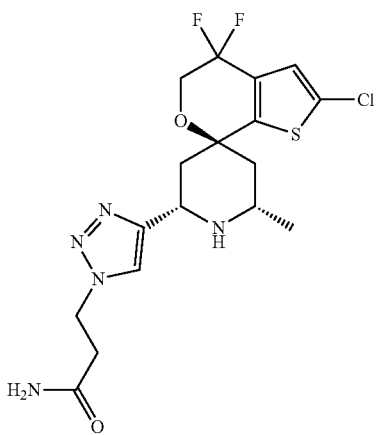 [SMILES: C[C@H]1C[C@@]2(C[C@@H](c3cn(CCC(N)=O)nn3)N1)OCC(F)(F)c1cc(Cl)sc12] 328
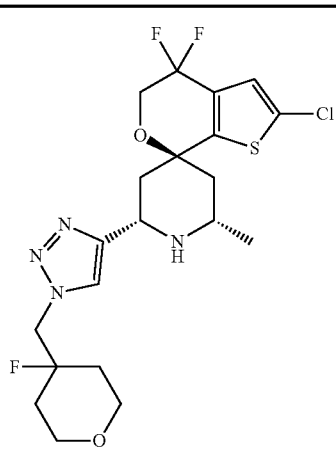 329
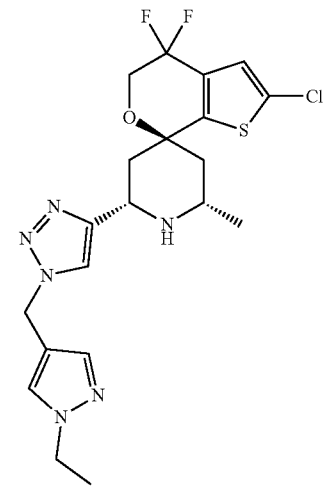 [SMILES: CCn1cc(Cn2cc([C@@H]3C[C@]4(C[C@H](C)N3)OCC(F)(F)c3cc(Cl)sc34)nn2)cn1] 330
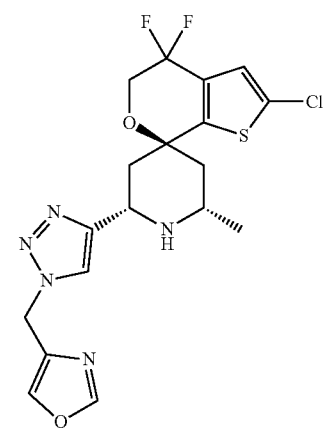 [SMILES: C[C@H]1C[C@@]2(C[C@@H](c3cn(Cc4cocn4)nn3)N1)OCC(F)(F)c1cc(Cl)sc12] 331

TABLE II-continued
Compounds 221 to 391
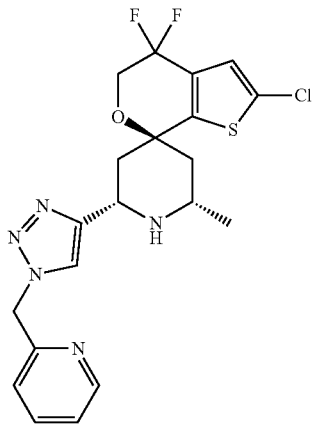 332
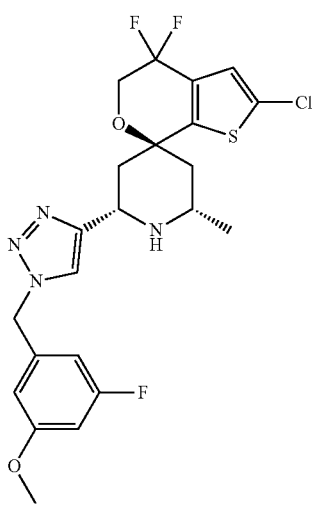 [SMILES: COc1cc(F)cc(Cn2cc([C@@H]3C[C@]4(C[C@H](C)N3)OCC(F)(F)c3cc(Cl)sc34)nn2)c1] 333
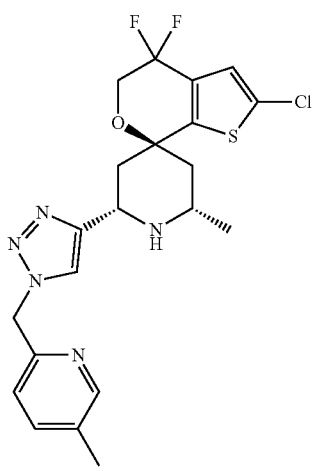 [SMILES: Cc1ccc(Cn2cc([C@@H]3C[C@]4(C[C@H](C)N3)OCC(F)(F)c3cc(Cl)sc34)nn2)nc1] 334
TABLE II-continued
Compounds 221 to 391
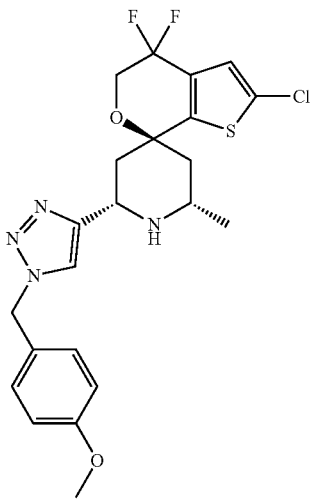 335
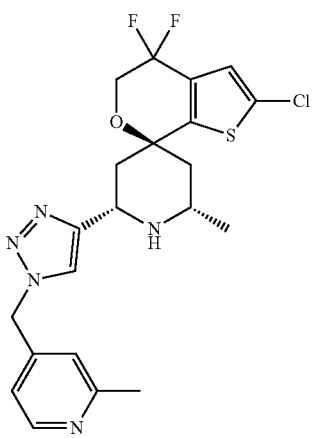 [SMILES: Cc1cc(Cn2cc([C@@H]3C[C@]4(C[C@H](C)N3)OCC(F)(F)c3cc(Cl)sc34)nn2)ccn1] 336
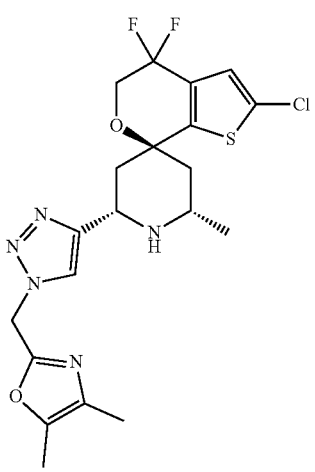 [SMILES: Cc1nc(Cn2cc([C@@H]3C[C@]4(C[C@H](C)N3)OCC(F)(F)c3cc(Cl)sc34)nn2)oc1C] 337

TABLE II-continued
Compounds 221 to 391
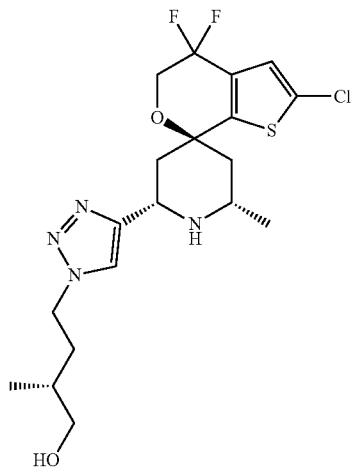 [SMILES: C[C@@H](CO)CCn1cc([C@@H]2C[C@]3(C[C@H](C)N2)OCC(F)(F)c2cc(Cl)sc23)nn1]
338
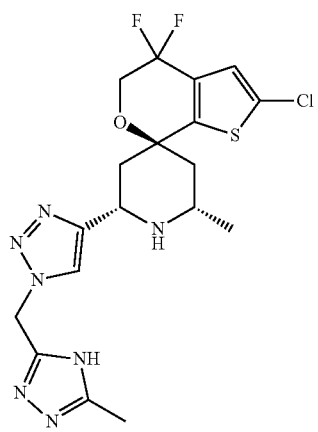 [SMILES: Cc1nnc(Cn2cc([C@@H]3C[C@]4(C[C@H](C)N3)OCC(F)(F)c3cc(Cl)sc34)nn2)[nH]1]
339
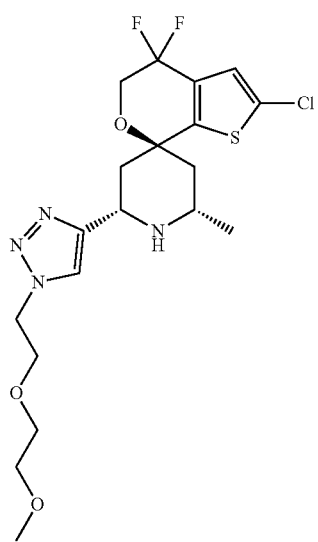 [SMILES: COCCOCCn1cc([C@@H]2C[C@]3(C[C@H](C)N2)OCC(F)(F)c2cc(Cl)sc23)nn1]
340
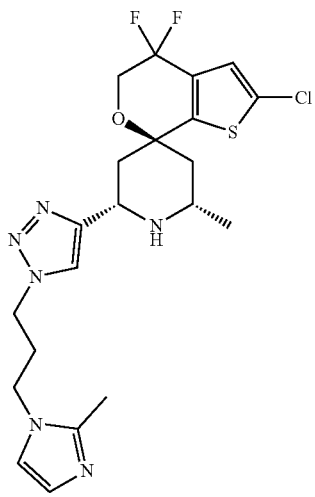 [SMILES: Cc1nccn1CCCn1cc([C@@H]2C[C@]3(C[C@H](C)N2)OCC(F)(F)c2cc(Cl)sc23)nn1]
341
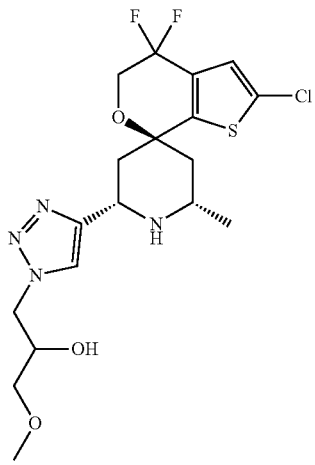 [SMILES: COCC(O)Cn1cc([C@@H]2C[C@]3(C[C@H](C)N2)OCC(F)(F)c2cc(Cl)sc23)nn1]
342
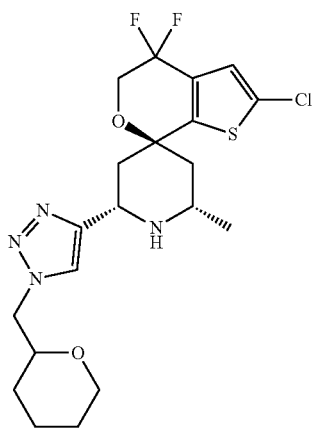 [SMILES: C[C@H]1C[C@@]2(C[C@@H](c3cn(CC4CCCCO4)nn3)N1)OCC(F)(F)c1cc(Cl)sc12]
343

TABLE II-continued
Compounds 221 to 391
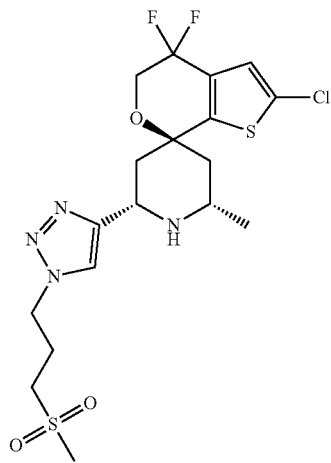 [SMILES: C[C@H]1C[C@@]2(C[C@@H](c3cn(CCCS(C)(=O)=O)nn3)N1)OCC(F)(F)c1cc(Cl)sc12]
344
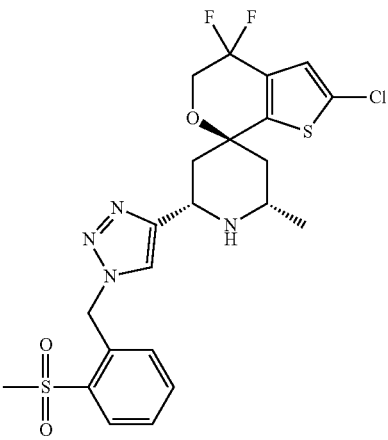
347
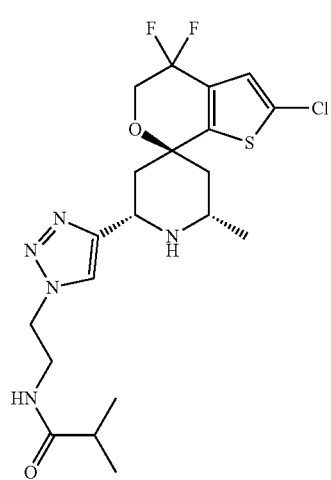 [SMILES: CC(C)C(=O)NCCn1cc([C@@H]2C[C@]3(C[C@H](C)N2)OCC(F)(F)c2cc(Cl)sc23)nn1]
345
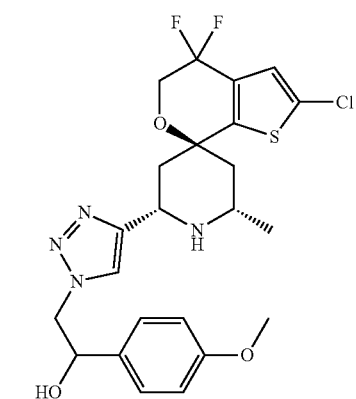
348
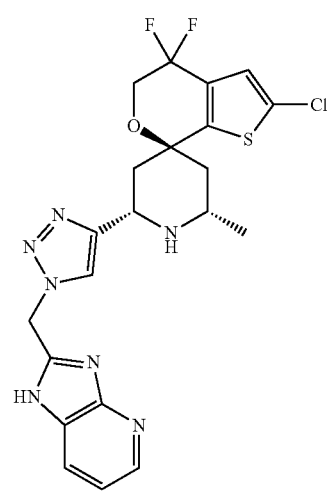 [SMILES: C[C@H]1C[C@@]2(C[C@@H](c3cn(Cc4nc5ncccc5[nH]4)nn3)N1)OCC(F)(F)c1cc(Cl)sc12]
346
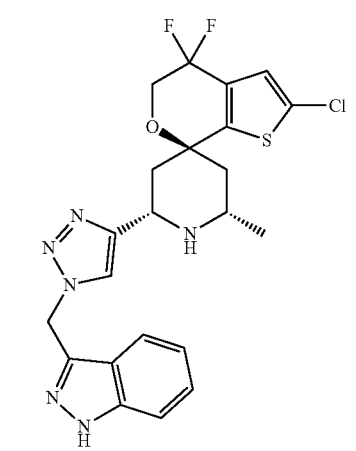 [SMILES: C[C@H]1C[C@@]2(C[C@@H](c3cn(Cc4n[nH]c5ccccc45)nn3)N1)OCC(F)(F)c1cc(Cl)sc12]
349

TABLE II-continued
Compounds 221 to 391
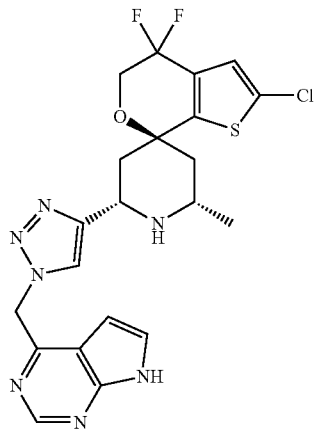 [SMILES: C[C@H]1C[C@@]2(C[C@@H](c3cn(Cc4ncnc5[nH]ccc45)nn3)N1)OCC(F)(F)c1cc(Cl)sc12] 350
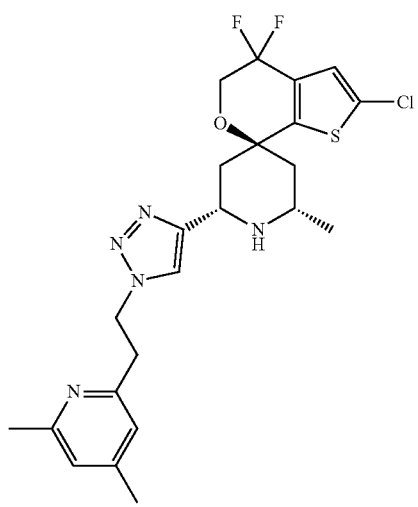 [SMILES: Cc1cc(C)nc(CCn2cc([C@@H]3C[C@]4(C[C@H](C)N3)OCC(F)(F)c3cc(Cl)sc34)nn2)c1] 351
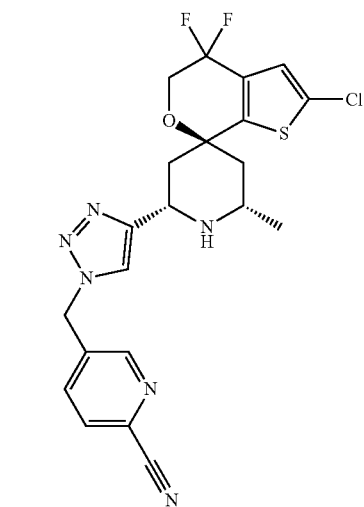 [SMILES: C[C@H]1C[C@@]2(C[C@@H](c3cn(Cc4ccc(C#N)nc4)nn3)N1)OCC(F)(F)c1cc(Cl)sc12] 352
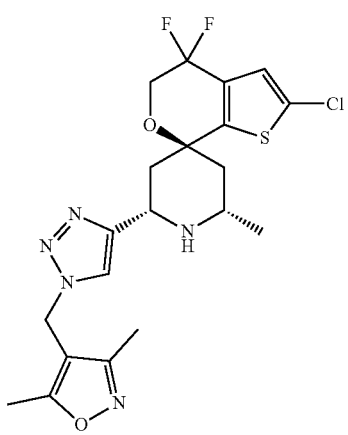 [SMILES: Cc1noc(C)c1Cn1cc([C@@H]2C[C@]3(C[C@H](C)N2)OCC(F)(F)c2cc(Cl)sc23)nn1] 353
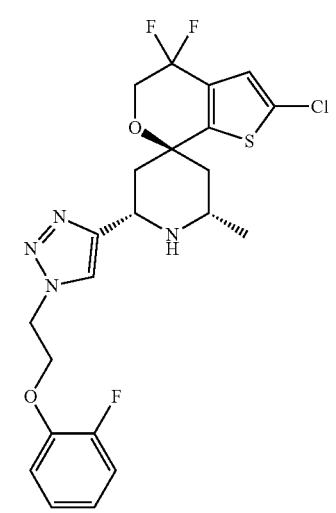 [SMILES: C[C@H]1C[C@@]2(C[C@@H](c3cn(CCOc4ccccc4F)nn3)N1)OCC(F)(F)c1cc(Cl)sc12] 354
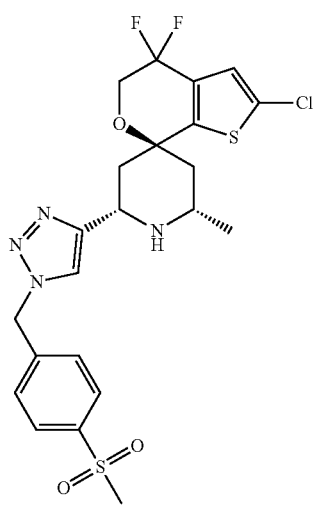 [SMILES: C[C@H]1C[C@@]2(C[C@@H](c3cn(Cc4ccc(S(C)(=O)=O)cc4)nn3)N1)OCC(F)(F)c1cc(Cl)sc12] 355

TABLE II-continued
Compounds 221 to 391
| 356 | 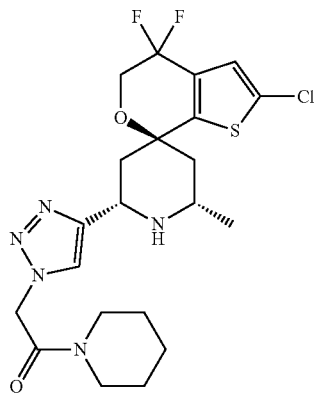 [SMILES: C[C@H]1C[C@@]2(C[C@@H](c3cn(CC(=O)N4CCCCC4)nn3)N1)OCC(F)(F)c1cc(Cl)sc12] |
| 357 | 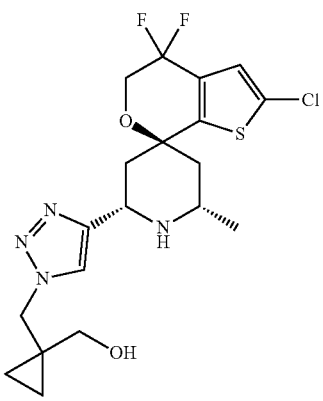 [SMILES: C[C@H]1C[C@@]2(C[C@@H](c3cn(CC4(CO)CC4)nn3)N1)OCC(F)(F)c1cc(Cl)sc12] |
| 358 | 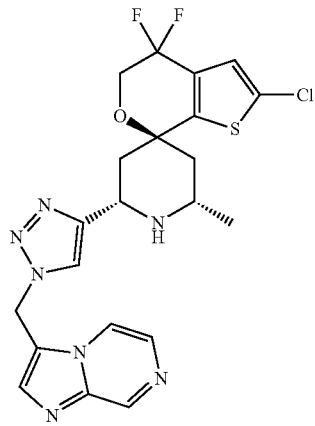 [SMILES: C[C@H]1C[C@@]2(C[C@@H](c3cn(Cc4cnc5cnccn45)nn3)N1)OCC(F)(F)c1cc(Cl)sc12] |
| 359 | 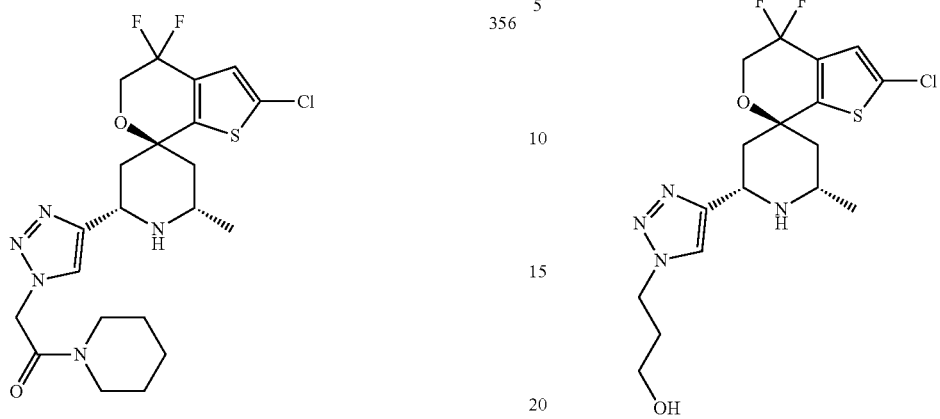 |
| 360 | 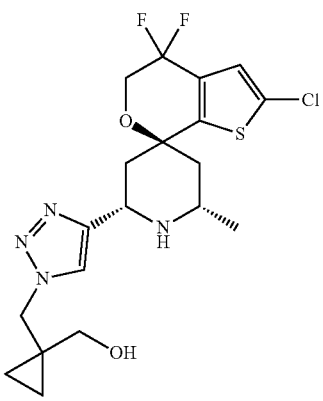 [SMILES: C[C@H]1C[C@@]2(C[C@@H](c3cn(CC4(CO)CC4)nn3)N1)OCC(F)(F)c1cc(Cl)sc12] |
| 361 | 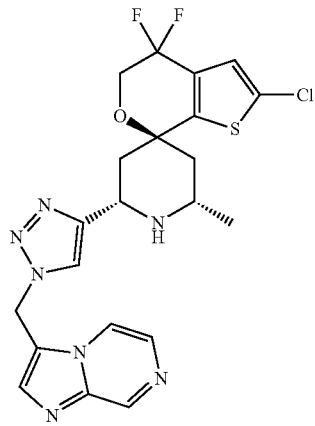 [SMILES: C[C@H]1C[C@@]2(C[C@@H](c3cn(Cc4cnc5cnccn45)nn3)N1)OCC(F)(F)c1cc(Cl)sc12] |

TABLE II-continued
Compounds 221 to 391
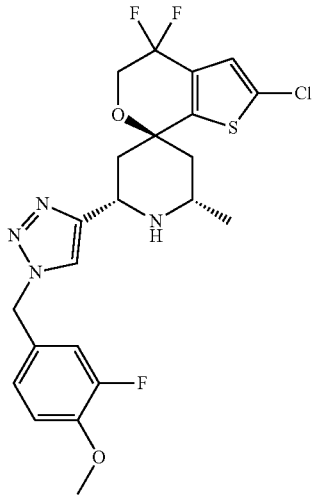 [SMILES: COc1ccc(Cn2cc([C@@H]3C[C@]4(C[C@H](C)N3)OCC(F)(F)c3cc(Cl)sc34)nn2)cc1F]
362
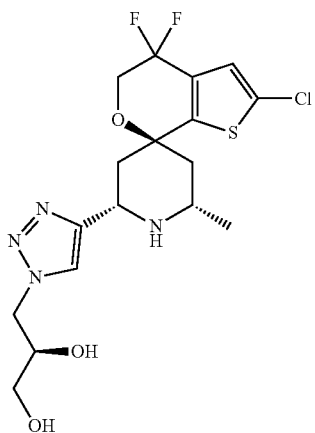 [SMILES: C[C@H]1C[C@@]2(C[C@@H](c3cn(C[C@@H](O)CO)nn3)N1)OCC(F)(F)c1cc(Cl)sc12]
363
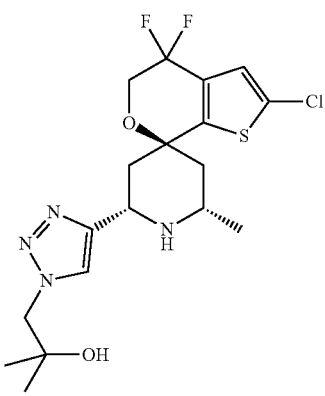 [SMILES: C[C@H]1C[C@@]2(C[C@@H](c3cn(CC(C)(C)O)nn3)N1)OCC(F)(F)c1cc(Cl)sc12]
364
TABLE II-continued
Compounds 221 to 391
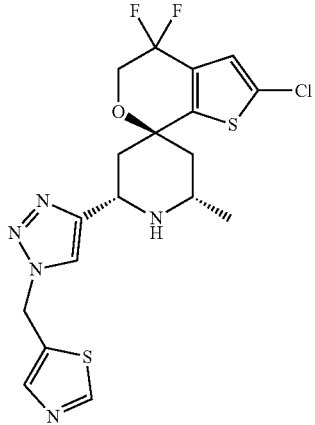 [SMILES: C[C@H]1C[C@@]2(C[C@@H](c3cn(Cc4cncs4)nn3)N1)OCC(F)(F)c1cc(Cl)sc12]
365
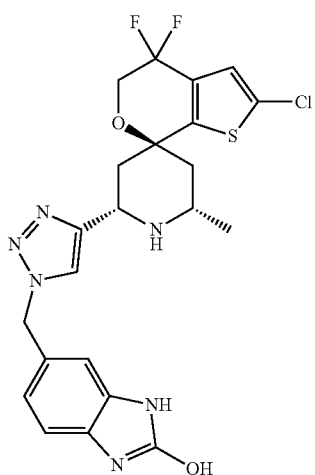 [SMILES: C[C@H]1C[C@@]2(C[C@@H](c3cn(Cc4ccc5nc(O)[nH]c5c4)nn3)N1)OCC(F)(F)c1cc(Cl)sc12]
366
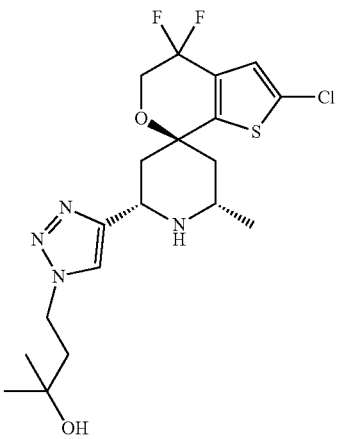 [SMILES: C[C@H]1C[C@@]2(C[C@@H](c3cn(CCC(C)(C)O)nn3)N1)OCC(F)(F)c1cc(Cl)sc12]
367

TABLE II-continued
Compounds 221 to 391
| | |
|---|---|
| 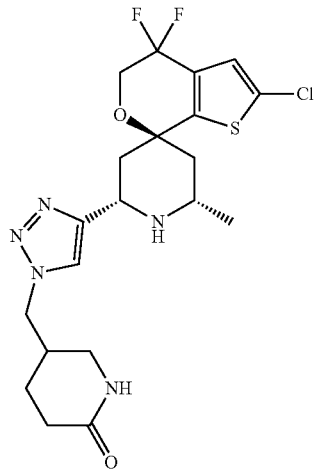 [SMILES: C[C@H]1C[C@@]2(C[C@@H](c3cn(CC4CCC(=O)NC4)nn3)N1)OCC(F)(F)c1cc(Cl)sc12] | 368 |
| 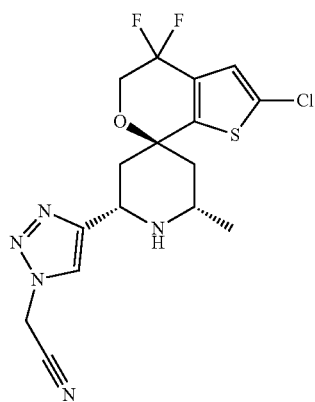 [SMILES: C[C@H]1C[C@@]2(C[C@@H](c3cn(CC#N)nn3)N1)OCC(F)(F)c1cc(Cl)sc12] | 369 |
| 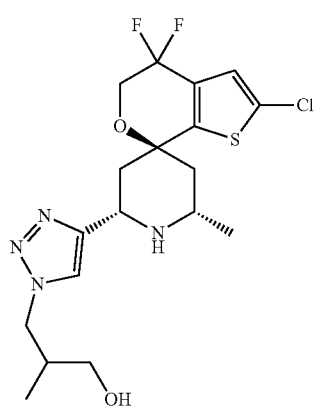 [SMILES: CC(CO)Cn1cc([C@@H]2C[C@]3(C[C@H](C)N2)OCC(F)(F)c2cc(Cl)sc23)nn1] | 370 |
| 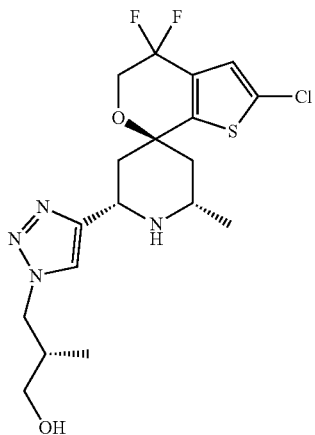 [SMILES: C[C@H](CO)Cn1cc([C@@H]2C[C@]3(C[C@H](C)N2)OCC(F)(F)c2cc(Cl)sc23)nn1] | 371 |
| 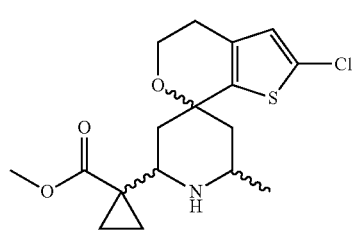 [SMILES: COC(=O)C1(C2CC3(CC(C)N2)OCCc2cc(Cl)sc23)CC1] | 372 |
| 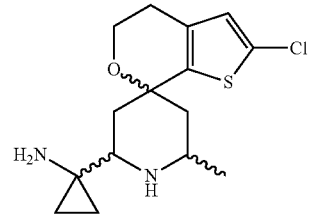 [SMILES: CC1CC2(CC(C3(N)CC3)N1)OCCc1cc(Cl)sc12] | 373 |
| 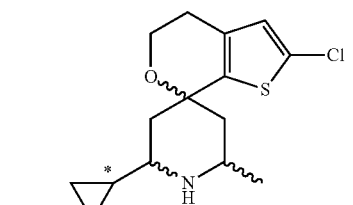 | 374 |
| 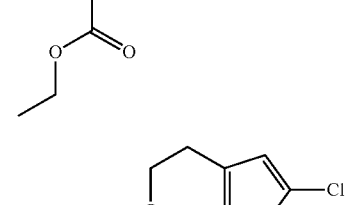 | 375 |

TABLE II-continued
Compounds 221 to 391
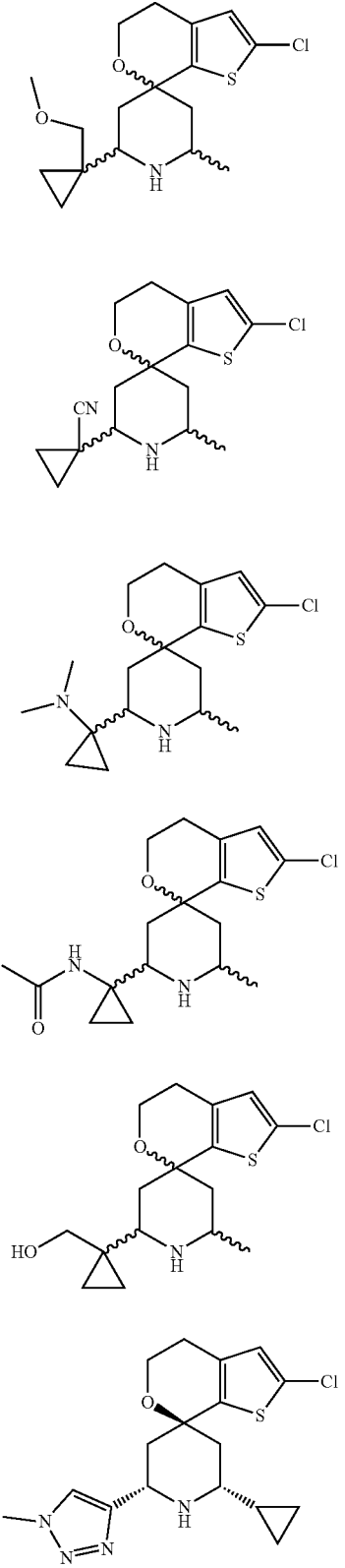
376
377
378
379
380
381
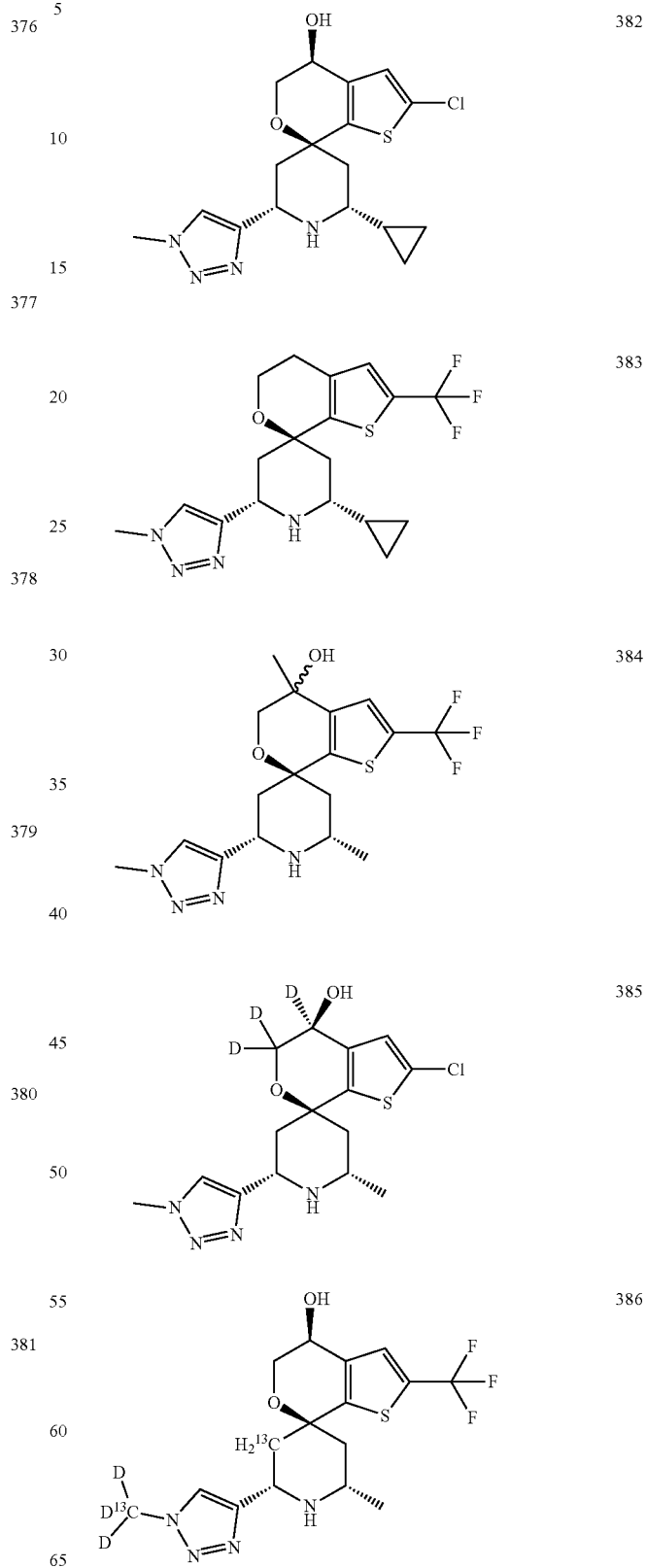
382
383
384
385
386

TABLE II-continued
Compounds 221 to 391
| | |
|---|---|
| 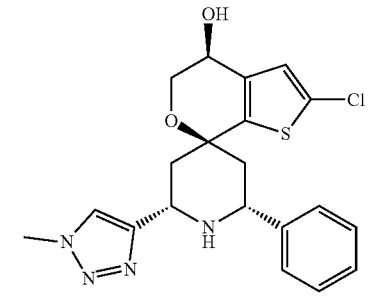 [SMILES: Cn1cc([C@@H]2C[C@]3(C[C@H](c4ccccc4)N2)OC[C@@H](O)c2cc(Cl)sc23)nn1] | 387 |
| 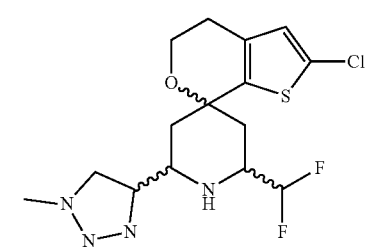 [SMILES: CN1CC(C2CC3(CC(C(F)F)N2)OCCc2cc(Cl)sc23)NN1] | 388 |
| 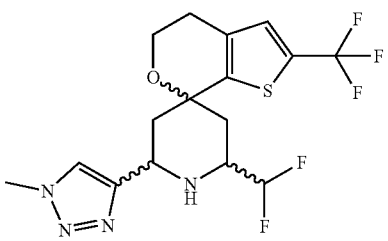 [SMILES: Cn1cc(C2CC3(CC(C(F)F)N2)OCCc2cc(C(F)(F)F)sc23)nn1] | 389 |
| 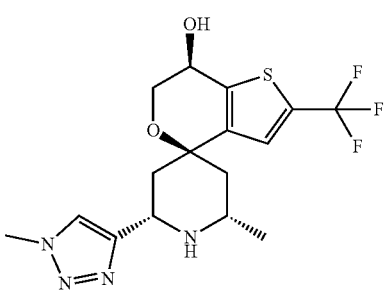 [SMILES: C[C@H]1C[C@@]2(C[C@@H](c3cn(C)nn3)N1)OC[C@@H](O)c1sc(C(F)(F)F)cc12] | 390 |
| 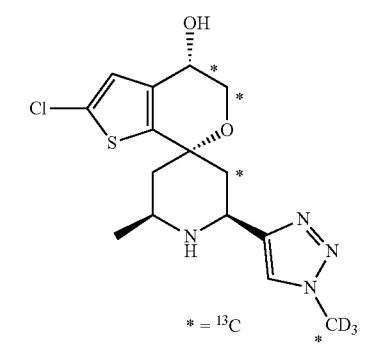 [SMILES: [2H]C([2H])([2H])n1cc([C@@H]2C[C@]3(C[C@H](C)N2)OC[C@@H](O)c2cc(Cl)sc23)nn1] * = $^{13}C$ | 391 |
TABLE III
Inferred Stereochemistry of Certain Compounds of Table I and Table II
| | |
|---|---|
| 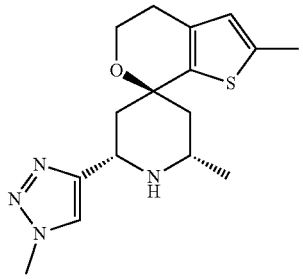 [SMILES: Cc1cc2c(s1)[C@]1(C[C@@H](c3cn(C)nn3)N[C@@H](C)C1)OCC2] | 3 |
| 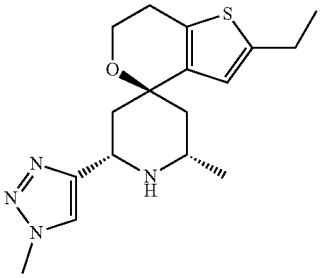 [SMILES: CCc1cc2c(s1)CCO[C@@]21C[C@@H](c2cn(C)nn2)N[C@@H](C)C1] | 4 |
| 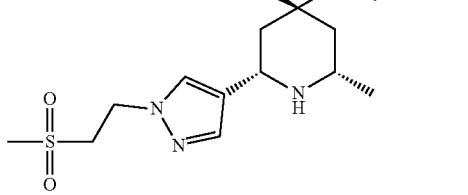 | 5 |
| 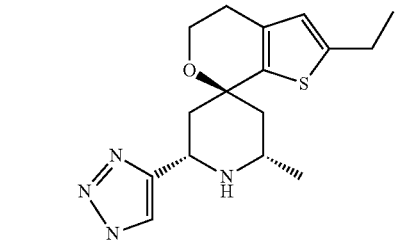 | 6 |
| 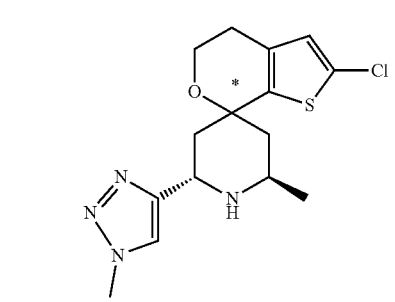 | 7 |

TABLE III-continued
Inferred Stereochemistry of Certain Compounds of Table I and Table II
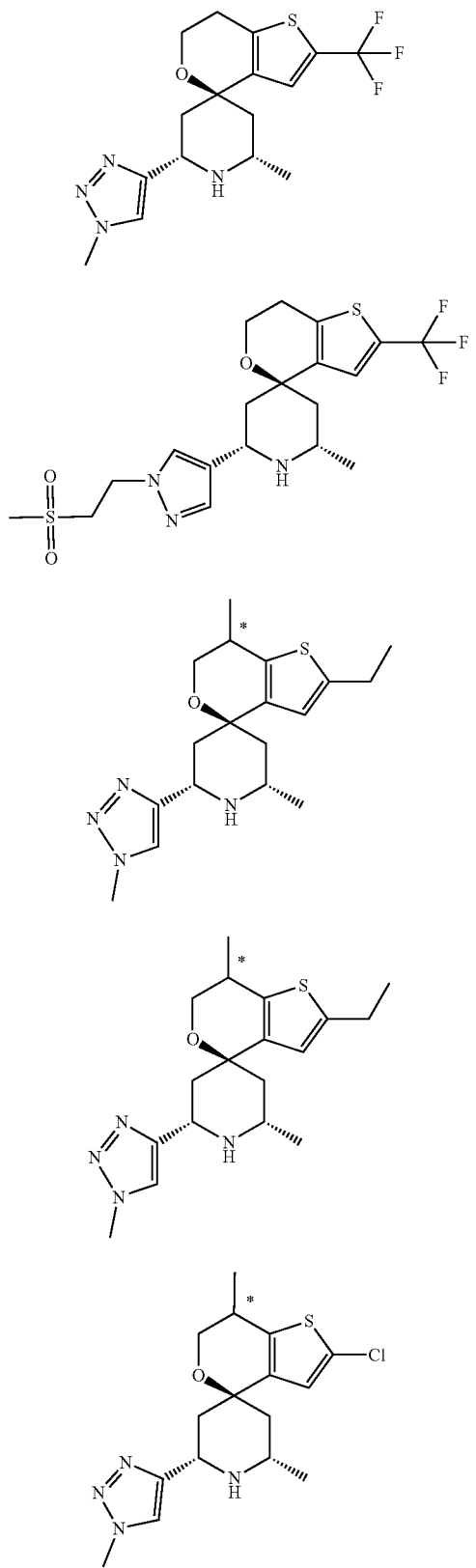
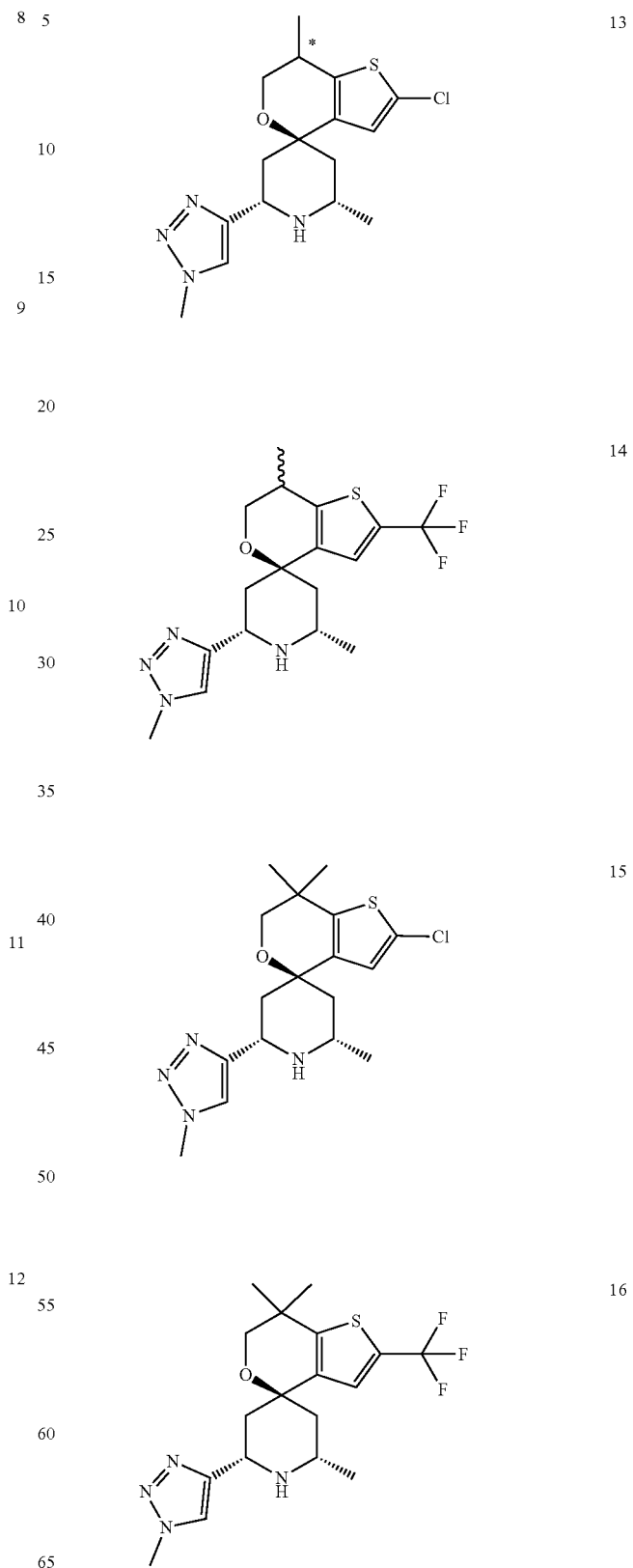

TABLE III-continued
Inferred Stereochemistry of Certain Compounds of Table I and Table II
17
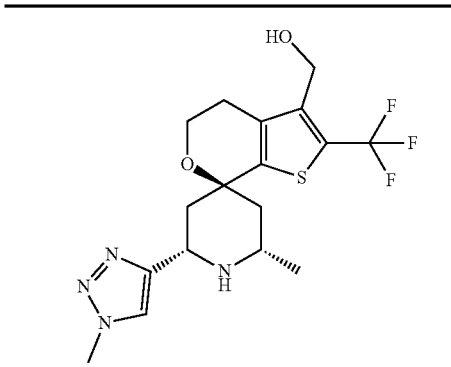
18
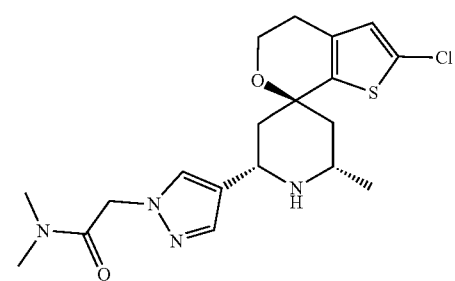
19
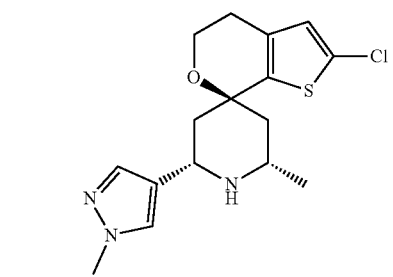
20*
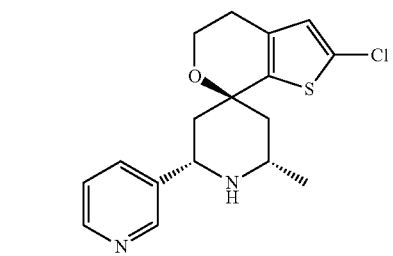 [SMILES: C[C@H]1C[C@@]2(C[C@@H](c3cccnc3)N1)OCCc1cc(Cl)sc12]
21
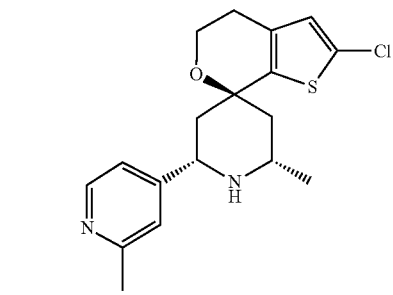 [SMILES: Cc1cc([C@@H]2CC[C@]3(C[C@H](C)N2)OCCc2cc(Cl)sc23)ccn1]
22
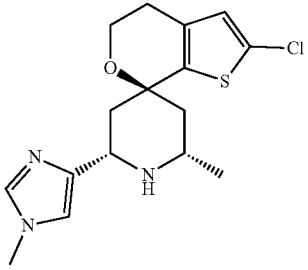
23
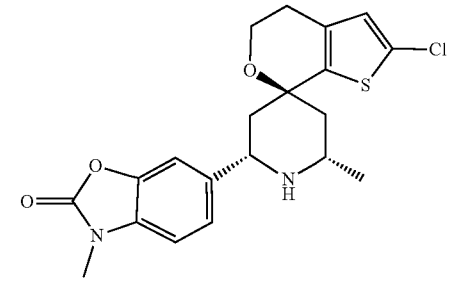 [SMILES: C[C@@H]1CN[C@H](c2ccc3c(c2)COC(=O)N3C)C[C@]2(C1)OCCc1cc(Cl)sc12]
24
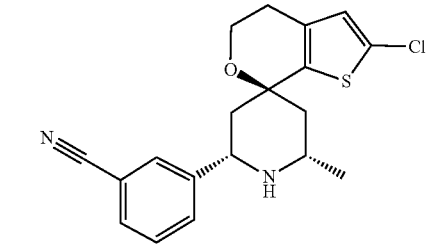 [SMILES: C[C@H]1C[C@@]2(CC[C@@H](c3cccc(C#N)c3)N1)OCCc1cc(Cl)sc12]
25
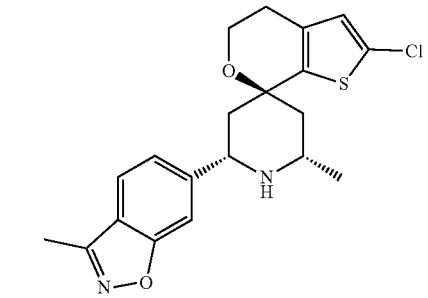 [SMILES: Cc1noc2cc([C@@H]3C[C@]4(C[C@H](C)N3)OCCc3cc(Cl)sc34)ccc12]
26
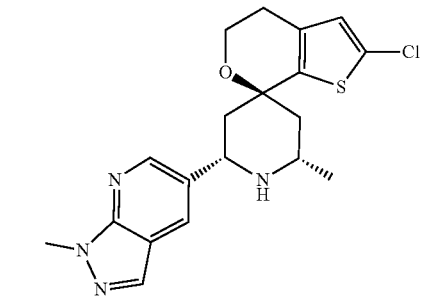 [SMILES: C[C@H]1C[C@@]2(C[C@@H](c3cnc4c(cnn4C)c3)N1)OCCc1cc(Cl)sc12]

TABLE III-continued
Inferred Stereochemistry of Certain Compounds of Table I and Table II
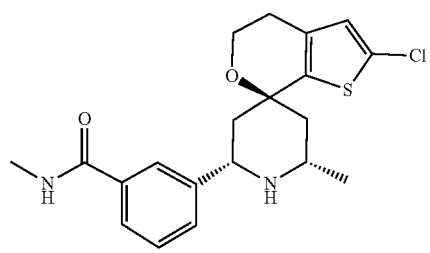 [SMILES: CNC(=O)c1cccc([C@@H]2CC[C@]3(C[C@H](C)N2)OCCc2cc(Cl)sc23)c1]
27
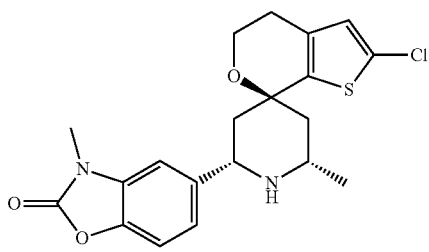 [SMILES: C[C@H]1C[C@@]2(C[C@@H](c3ccc4oc(=O)n(C)c4c3)N1)OCCc1cc(Cl)sc12]
28
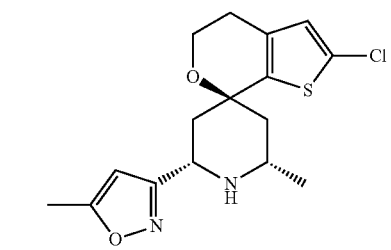 [SMILES: Cc1cc([C@@H]2C[C@]3(C[C@H](C)N2)OCCc2cc(Cl)sc23)no1]
29
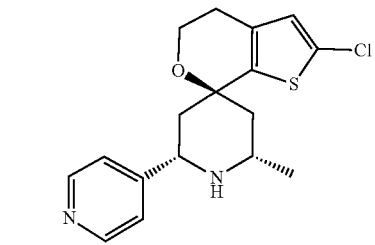 [SMILES: C[C@H]1C[C@@]2(CC[C@@H](c3ccncc3)N1)OCCc1cc(Cl)sc12]
30[1]
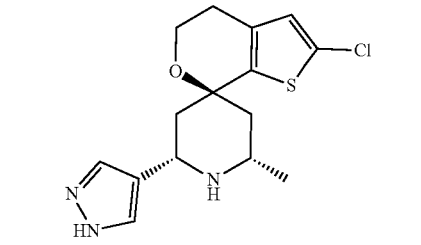 [SMILES: C[C@H]1C[C@@]2(C[C@@H](c3cn[nH]c3)N1)OCCC1=C2SCC(Cl)=C1]
31*
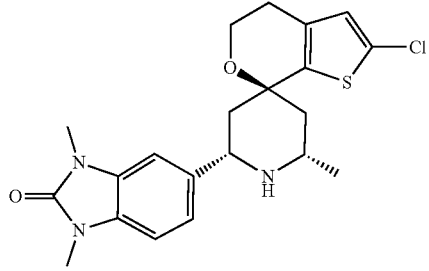 [SMILES: C[C@H]1C[C@@]2(C[C@@H](c3ccc4c(c3)n(C)c(=O)n4C)N1)OCCc1cc(Cl)sc12]
32*
TABLE III-continued
Inferred Stereochemistry of Certain Compounds of Table I and Table II
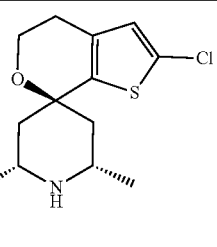
33
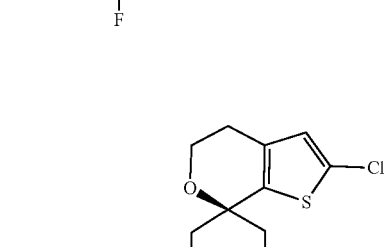
34
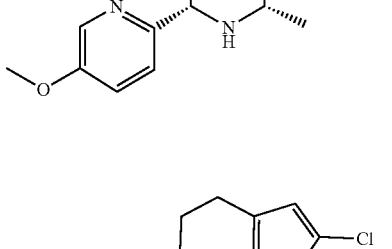
35
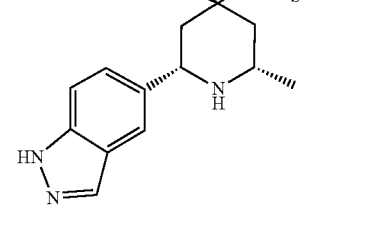
36
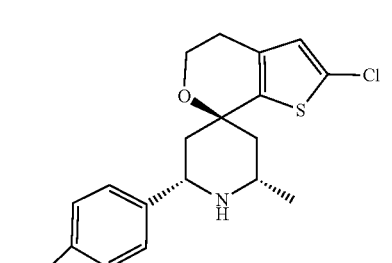

TABLE III-continued
Inferred Stereochemistry of Certain Compounds of Table I and Table II
| | |
|---|---|
| 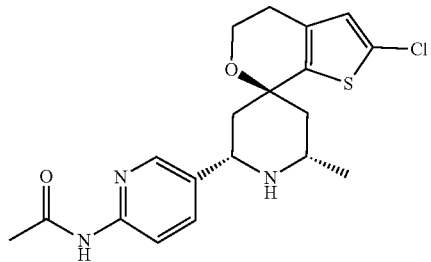 [SMILES: CC(=O)Nc1ccc([C@@H]2CC[C@]3(C[C@H](C)N2)OCCc2cc(Cl)sc23)cn1] | 37 |
| 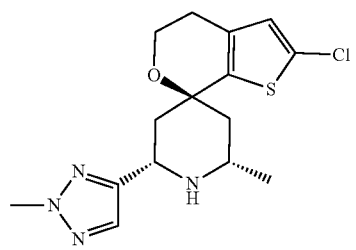 [SMILES: C[C@H]1C[C@@]2(CC[C@@H](c3cnn(C)n3)N1)OCCc1cc(Cl)sc12] | 38 |
| 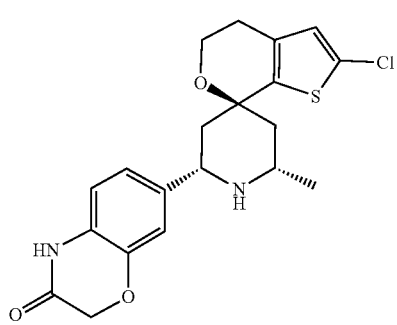 [SMILES: C[C@H]1C[C@@]2(CC[C@@H](c3ccc4c(c3)OCC(=O)N4)N1)OCCc1cc(Cl)sc12] | 39 |
| 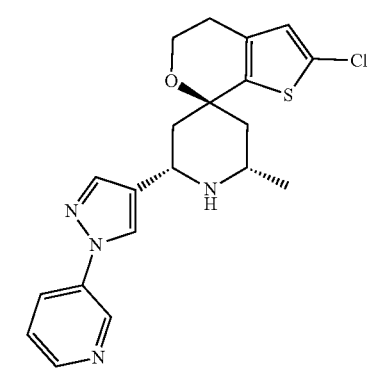 [SMILES: C[C@H]1C[C@@]2(CC[C@@H](c3cnn(-c4cccnc4)c3)N1)OCCc1cc(Cl)sc12] | 40 |
| 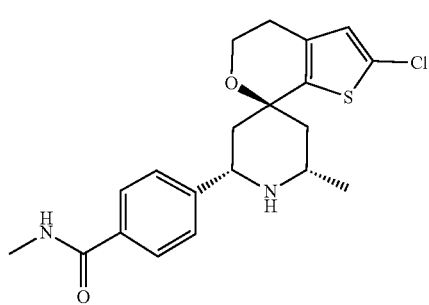 [SMILES: CNC(=O)c1ccc([C@@H]2CC[C@]3(C[C@H](C)N2)OCCc2cc(Cl)sc23)cc1] | 41 |
| 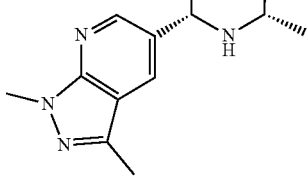 | 42 |
| 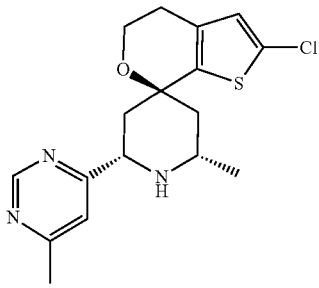 [SMILES: Cc1cc([C@@H]2CC[C@]3(C[C@H](C)N2)OCCc2cc(Cl)sc23)ncn1] | 43 |
| 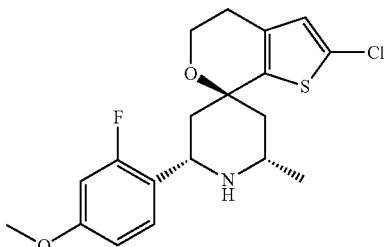 | 44 |
| 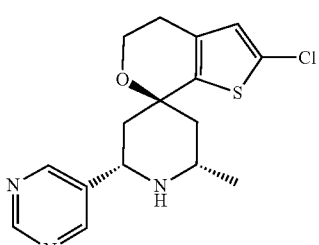 | 45 |
| 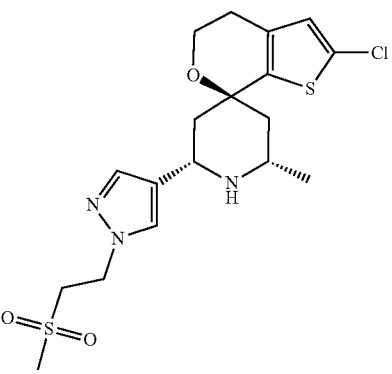 [SMILES: C[C@H]1C[C@@]2(CC[C@@H](c3cnn(CCS(C)(=O)=O)c3)N1)OCCc1cc(Cl)sc12] | 46 |

TABLE III-continued
Inferred Stereochemistry of Certain Compounds of Table I and Table II
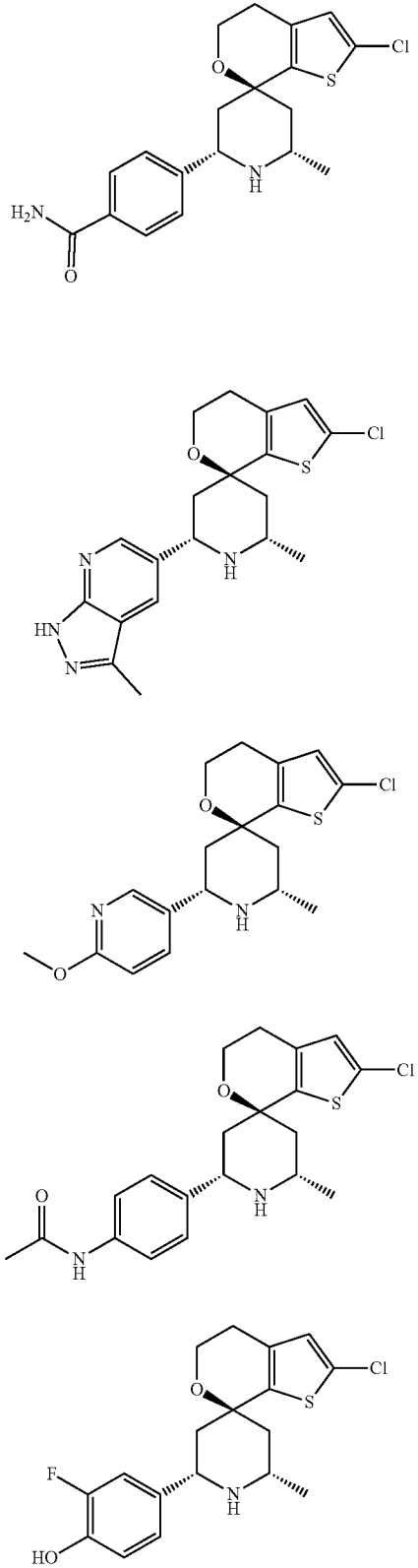
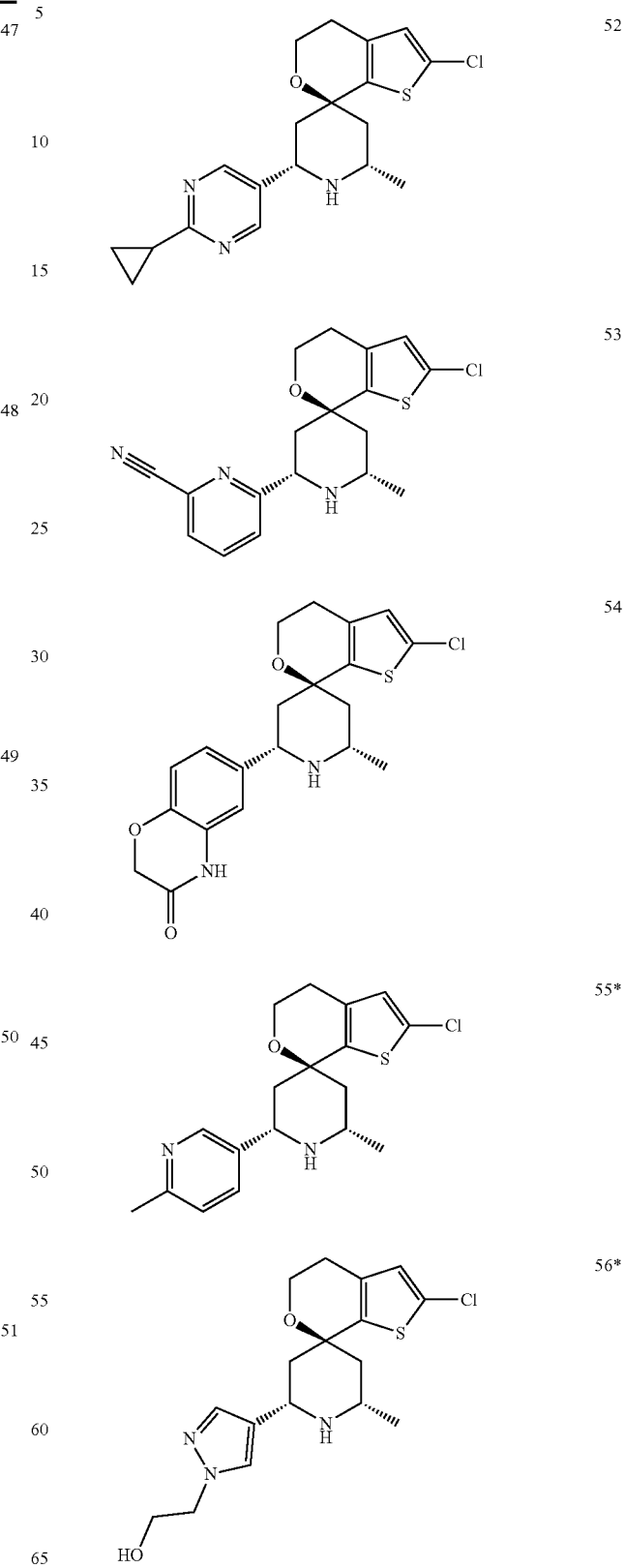

TABLE III-continued
Inferred Stereochemistry of Certain Compounds of Table I and Table II
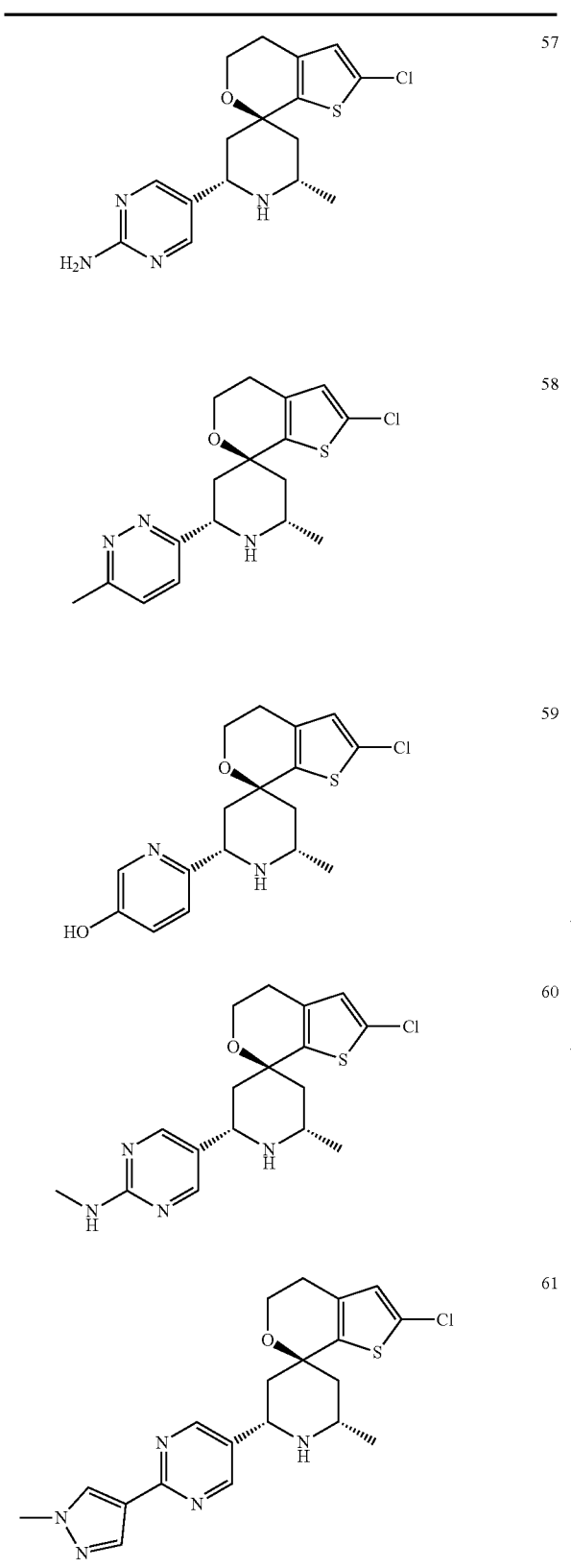
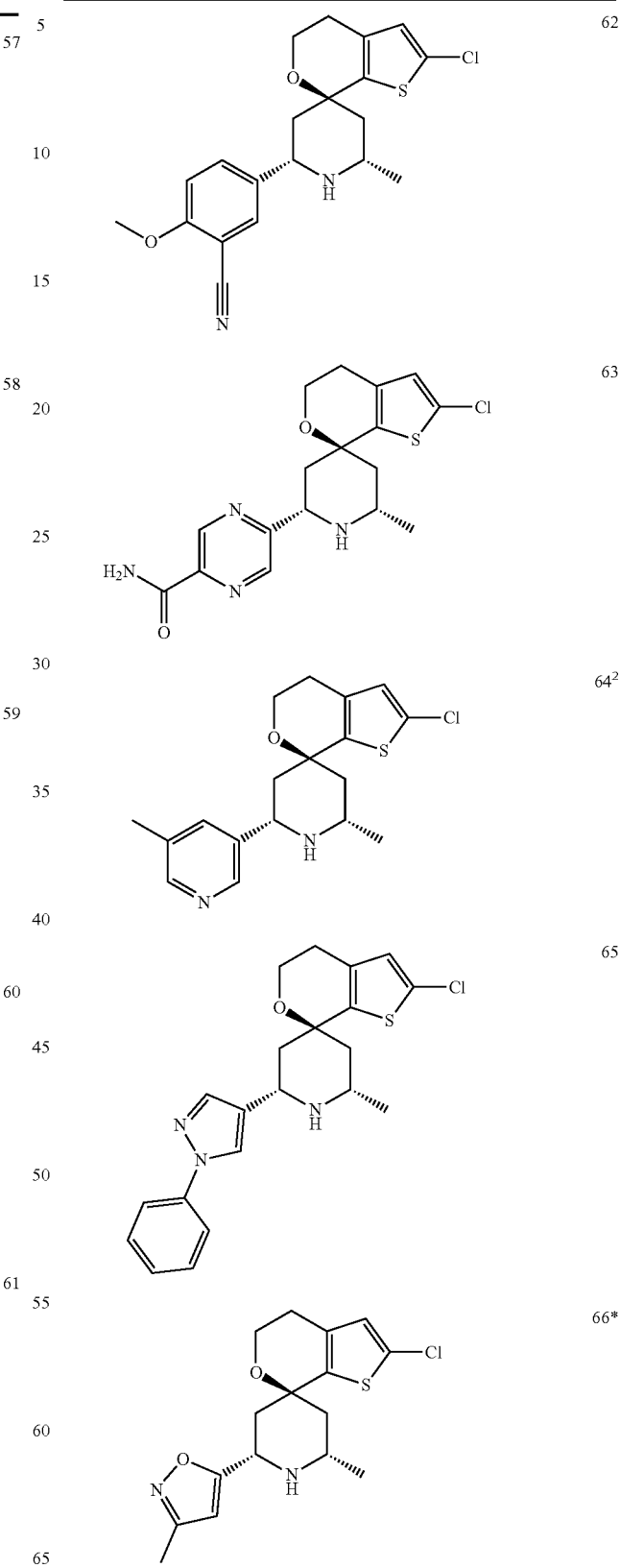

TABLE III-continued
Inferred Stereochemistry of Certain Compounds of Table I and Table II
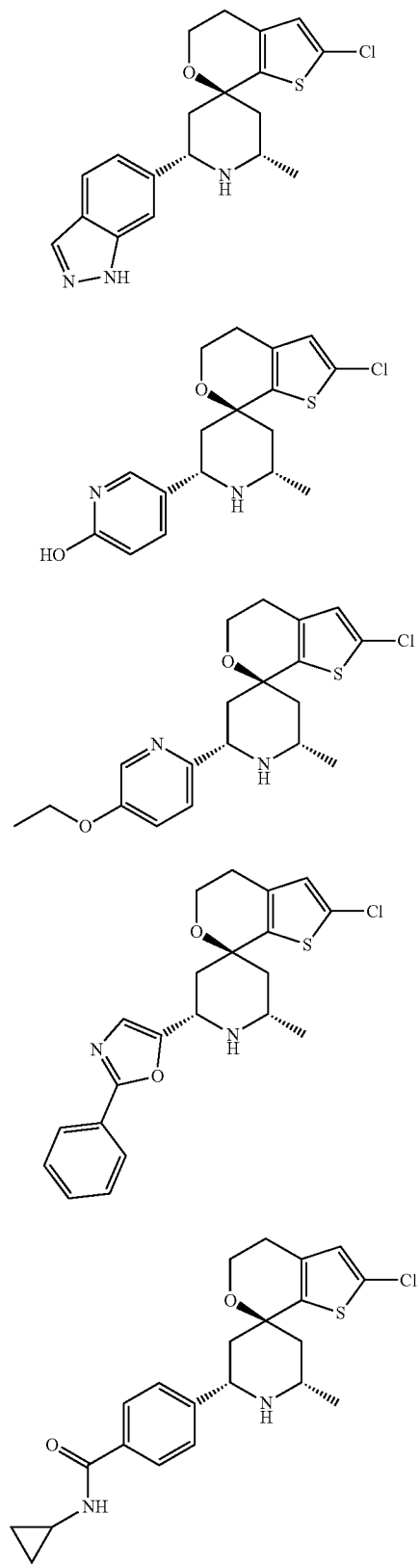
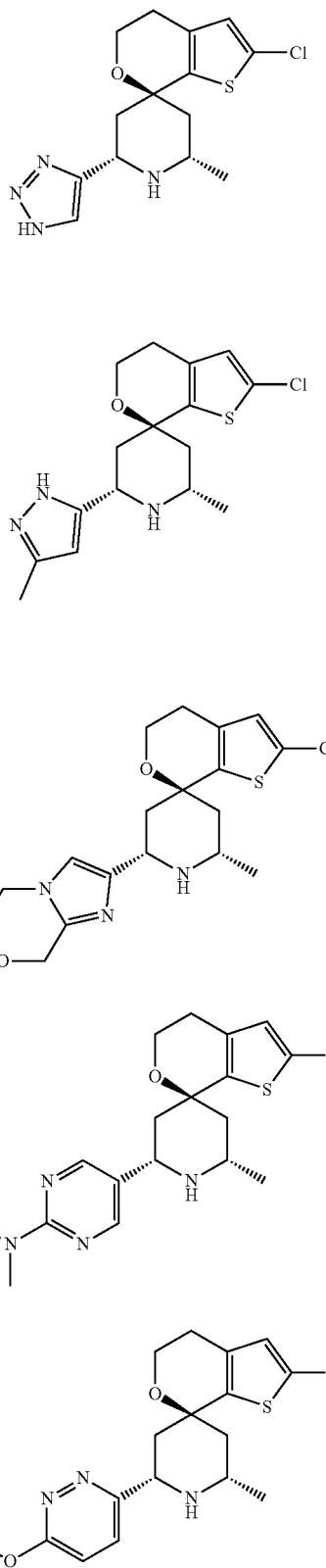

TABLE III-continued
Inferred Stereochemistry of Certain Compounds of Table I and Table II
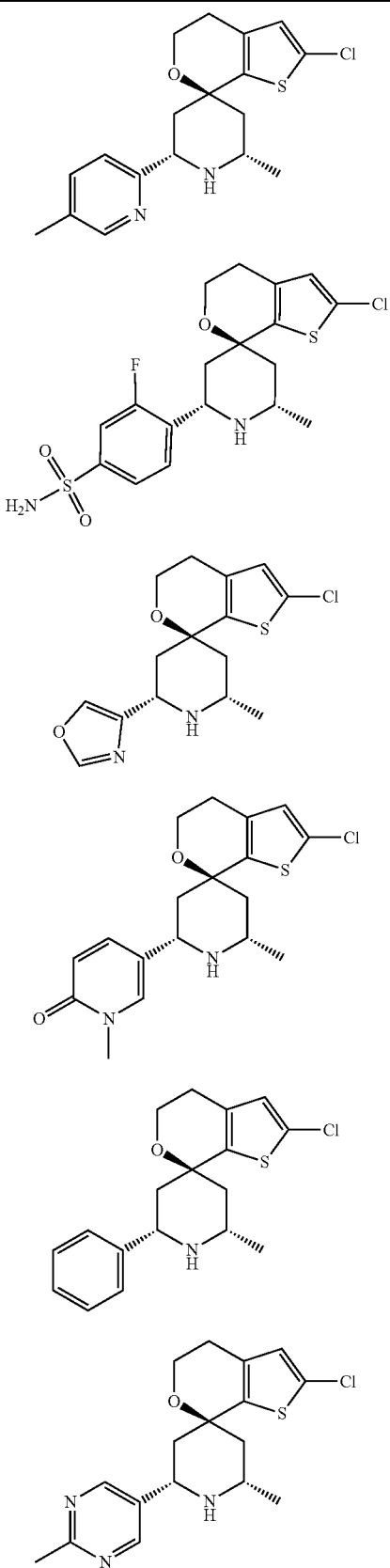
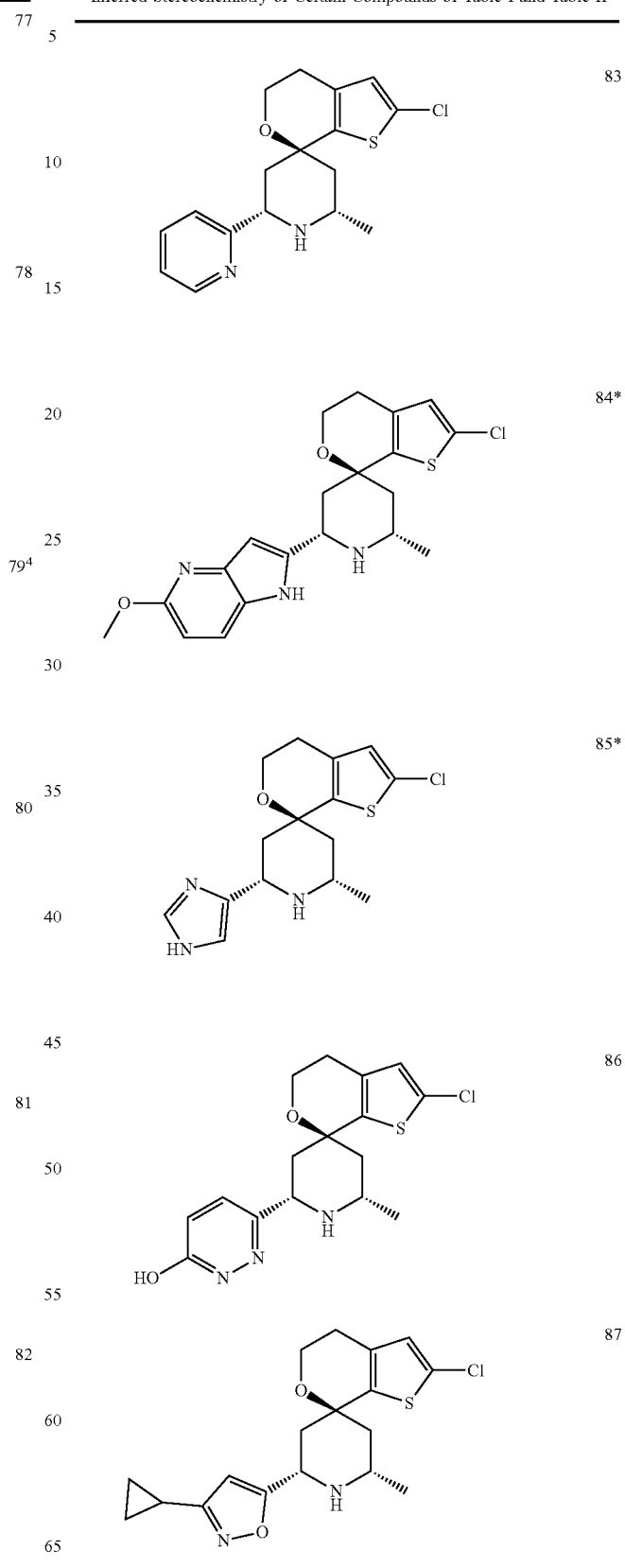

TABLE III-continued
Inferred Stereochemistry of Certain Compounds of Table I and Table II
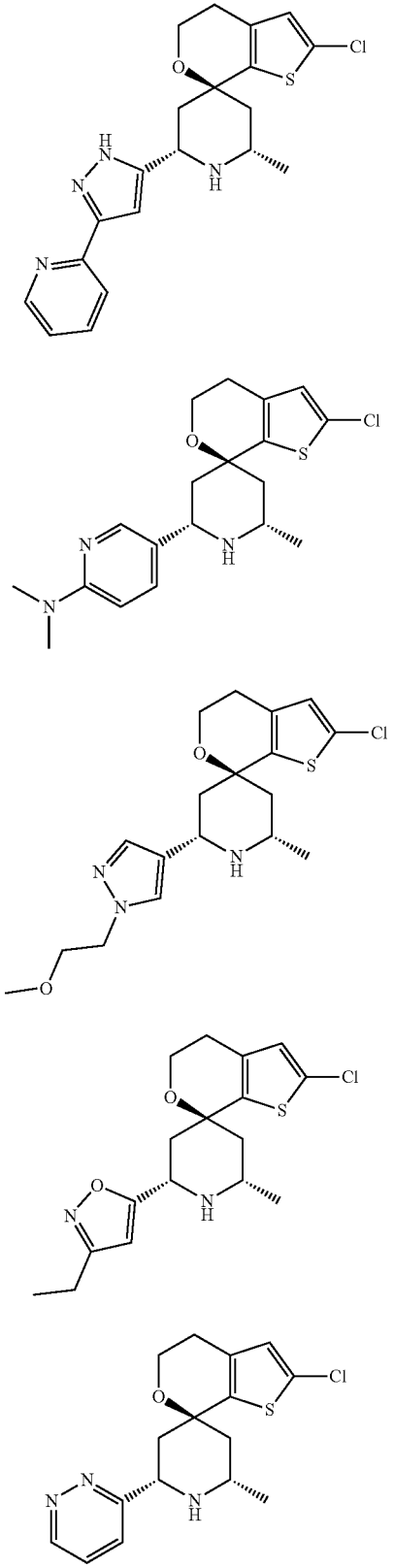
88
89
90
91[5]
92[6]
TABLE III-continued
Inferred Stereochemistry of Certain Compounds of Table I and Table II
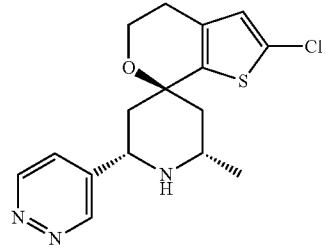 [SMILES: C[C@H]1C[C@@]2(C[C@@H](c3ccnnc3)N1)OCCc1cc(Cl)sc12]
93
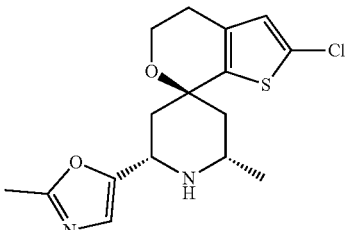
94
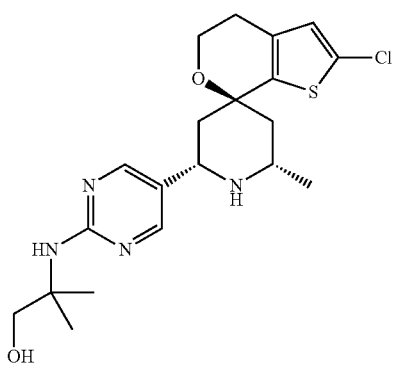 [SMILES: C[C@H]1C[C@@]2(C[C@@H](c3cnc(NC(C)(C)CO)nc3)N1)OCCc1cc(Cl)sc12]
95*
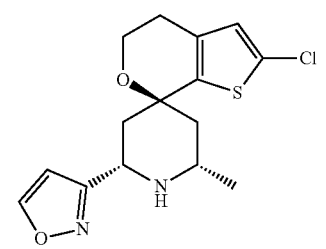 [SMILES: C[C@H]1C[C@@]2(C[C@@H](c3ccon3)N1)OCCc1cc(Cl)sc12]
96
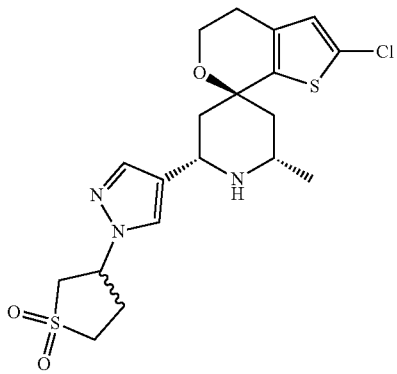 [SMILES: C[C@H]1C[C@@]2(C[C@@H](c3cnn(C4CCS(=O)(=O)C4)c3)N1)OCCc1cc(Cl)sc12]
97

TABLE III-continued
Inferred Stereochemistry of Certain Compounds of Table I and Table II
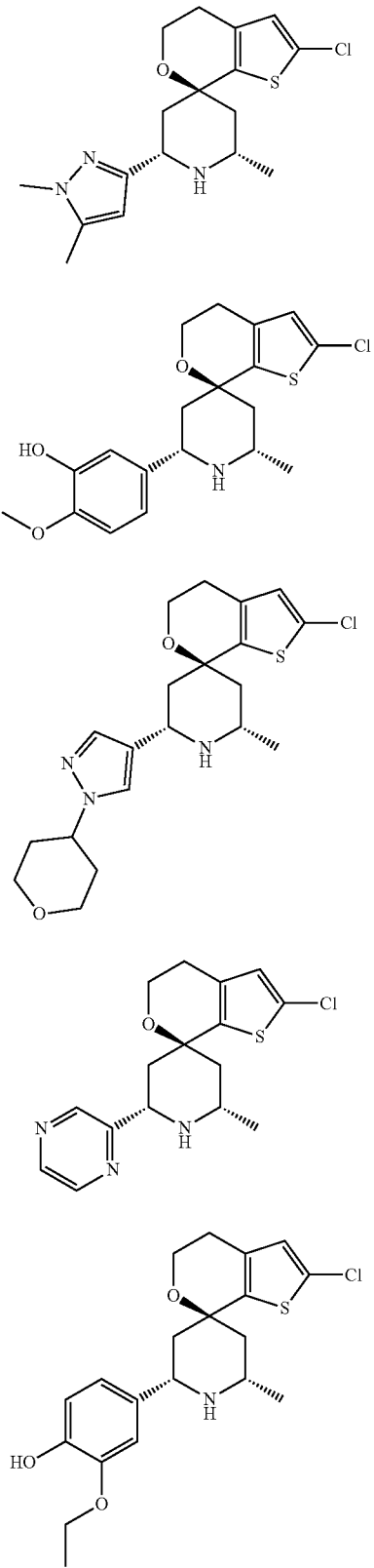
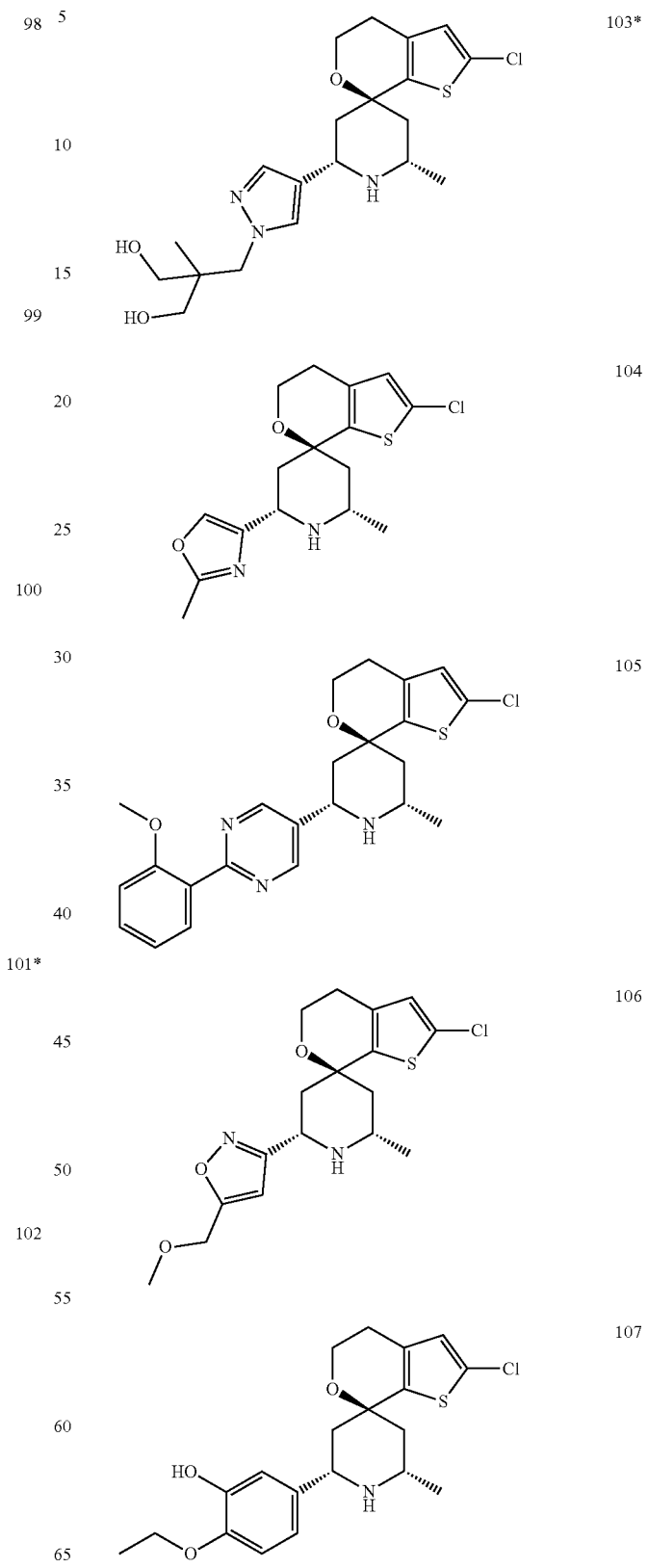

TABLE III-continued
Inferred Stereochemistry of Certain Compounds of Table I and Table II
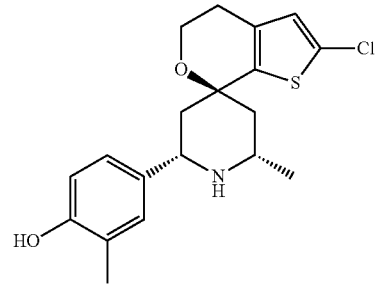 [SMILES: Cc1cc([C@@H]2C[C@]3(C[C@H](C)N2)OCCc2cc(Cl)sc23)ccc1O]
108
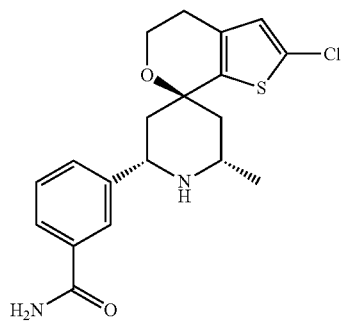 [SMILES: C[C@H]1C[C@@]2(C[C@@H](c3cccc(C(N)=O)c3)N1)OCCc1cc(Cl)sc12]
109
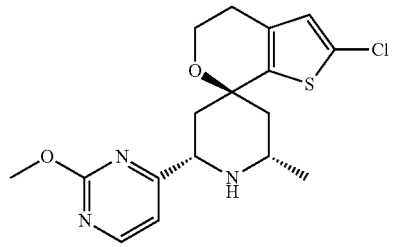 [SMILES: COc1nccc([C@@H]2C[C@]3(C[C@H](C)N2)OCCc2cc(Cl)sc23)n1]
110
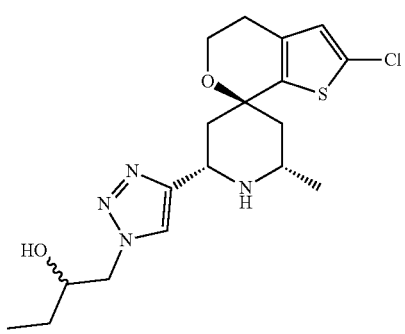 [SMILES: CCC(O)Cn1cc([C@@H]2C[C@]3(C[C@H](C)N2)OCCc2cc(Cl)sc23)nn1]
111
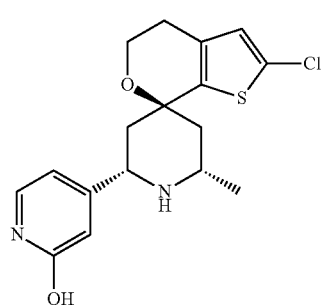 [SMILES: C[C@H]1C[C@@]2(C[C@@H](c3ccnc(O)c3)N1)OCCc1cc(Cl)sc12]
112
TABLE III-continued
Inferred Stereochemistry of Certain Compounds of Table I and Table II
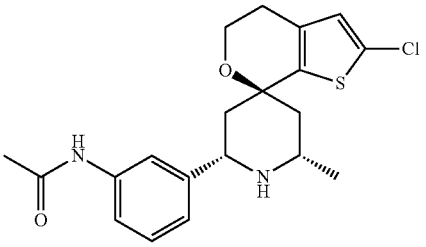 [SMILES: CC(=O)Nc1cccc([C@@H]2C[C@]3(C[C@H](C)N2)OCCc2cc(Cl)sc23)c1]
113
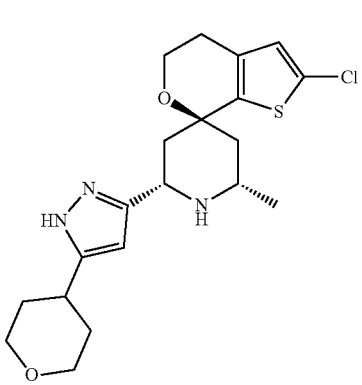 [SMILES: C[C@H]1C[C@@]2(C[C@@H](c3cc(C4CCOCC4)[nH]n3)N1)OCCc1cc(Cl)sc12]
114
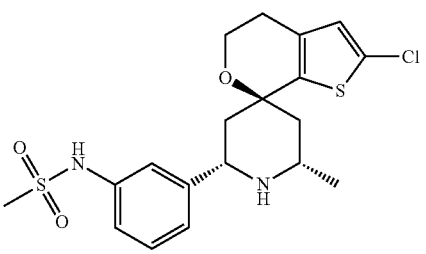 [SMILES: C[C@H]1C[C@@]2(C[C@@H](c3cccc(NS(C)(=O)=O)c3)N1)OCCc1cc(Cl)sc12]
115
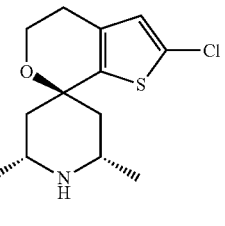
116*
117

TABLE III-continued
Inferred Stereochemistry of Certain Compounds of Table I and Table II
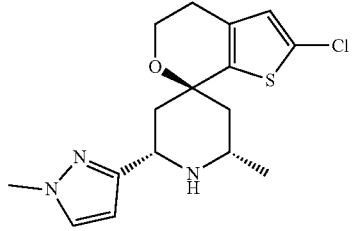 [SMILES: C[C@H]1C[C@@]2(C[C@@H](c3ccn(C)n3)N1)OCCc1cc(Cl)sc12]
118
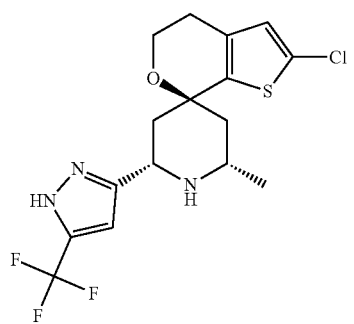 [SMILES: C[C@H]1C[C@@]2(C[C@@H](c3cc(C(F)(F)F)[nH]n3)N1)OCCc1cc(Cl)sc12]
119
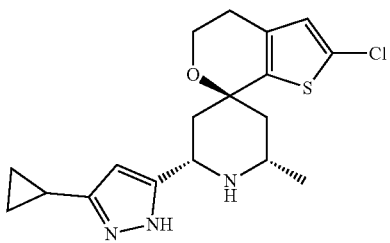 [SMILES: C[C@H]1C[C@@]2(C[C@@H](c3cc(C4CC4)n[nH]3)N1)OCCc1cc(Cl)sc12]
120
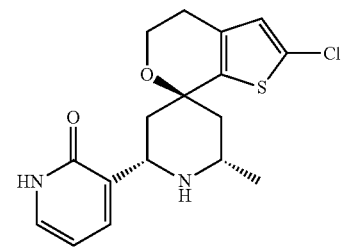 [SMILES: C[C@H]1C[C@@]2(C[C@@H](c3ccc[nH]c3=O)N1)OCCc1cc(Cl)sc12]
121
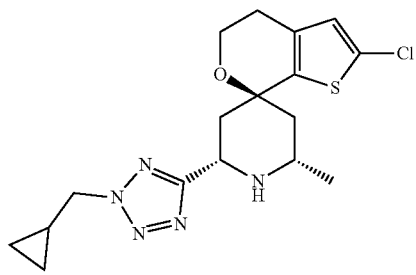 [SMILES: C[C@H]1C[C@@]2(C[C@@H](c3nnn(CC4CC4)n3)N1)OCCc1cc(Cl)sc12]
122
TABLE III-continued
Inferred Stereochemistry of Certain Compounds of Table I and Table II
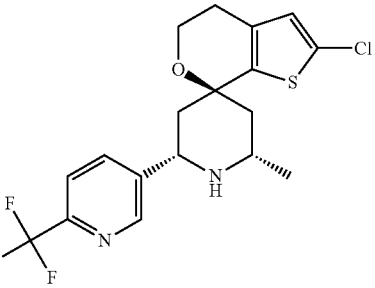
123
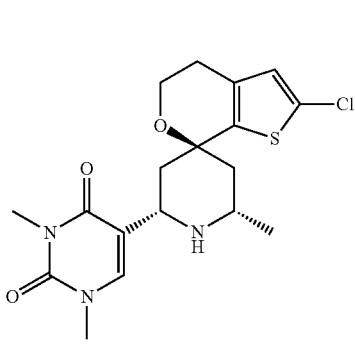 [SMILES: C[C@H]1C[C@@]2(C[C@@H](c3cn(C)c(=O)n(C)c3=O)N1)OCCc1cc(Cl)sc12]
124
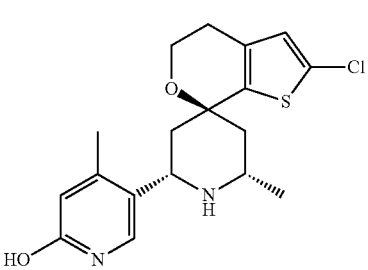 [SMILES: Cc1cc(O)ncc1[C@@H]1C[C@]2(C[C@H](C)N1)OCCc1cc(Cl)sc12]
125
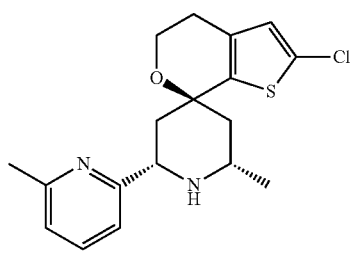 [SMILES: Cc1cccc([C@@H]2C[C@]3(C[C@H](C)N2)OCCc2cc(Cl)sc23)n1]
126*
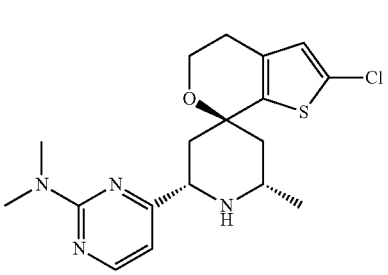 [SMILES: C[C@H]1C[C@@]2(C[C@@H](c3ccnc(N(C)C)n3)N1)OCCc1cc(Cl)sc12]
127

TABLE III-continued
Inferred Stereochemistry of Certain Compounds of Table I and Table II
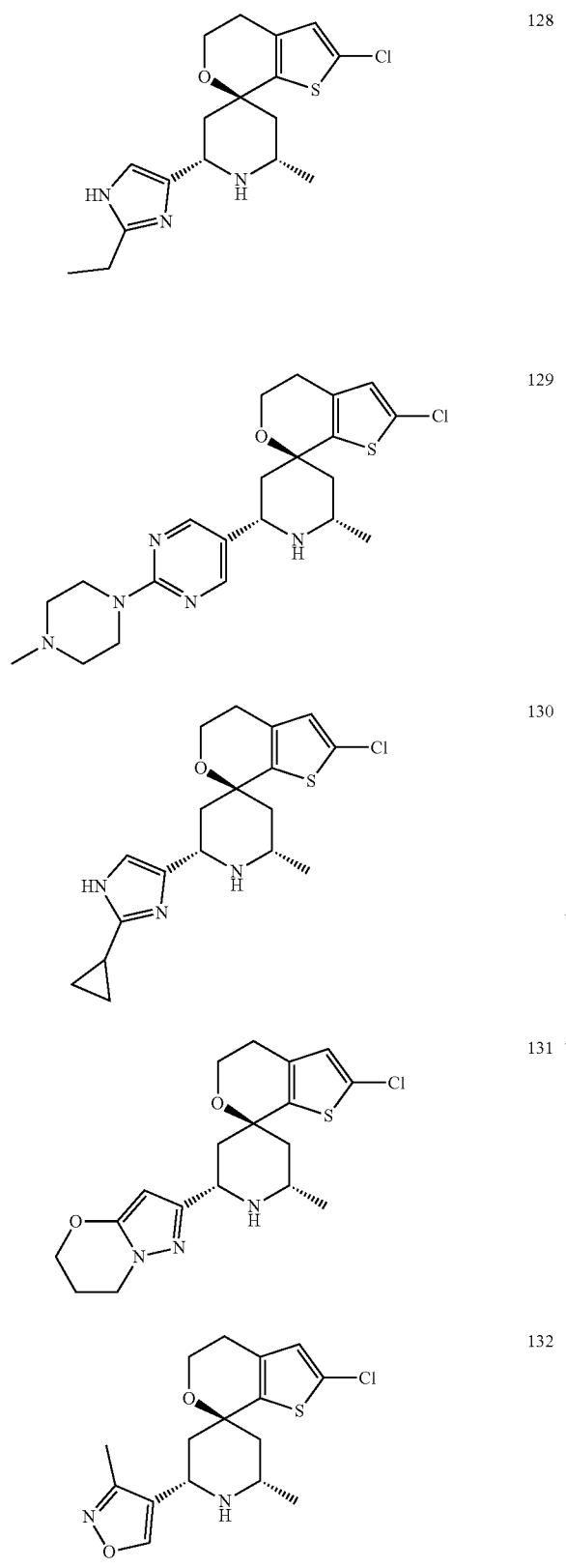
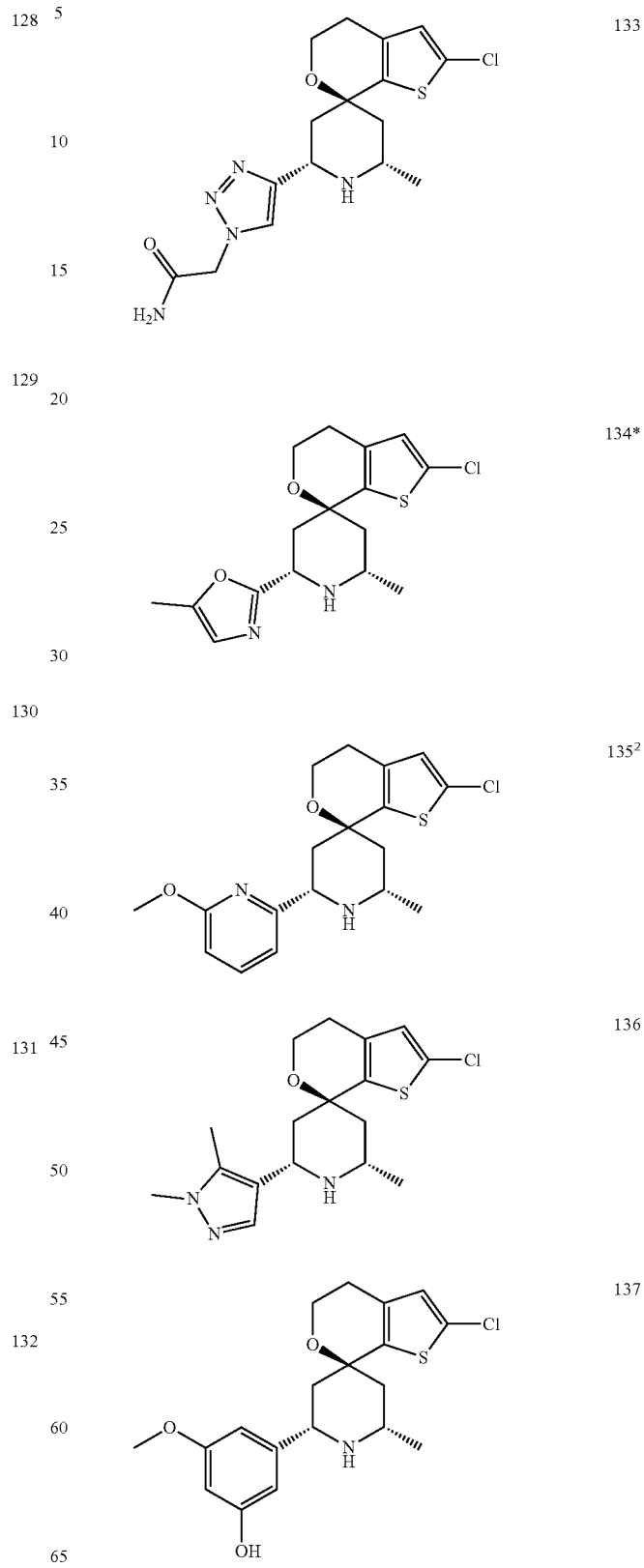

TABLE III-continued
Inferred Stereochemistry of Certain Compounds of Table I and Table II
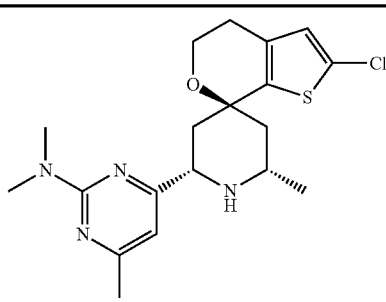 138
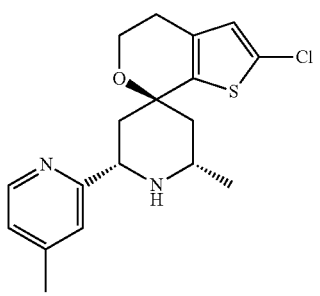 139
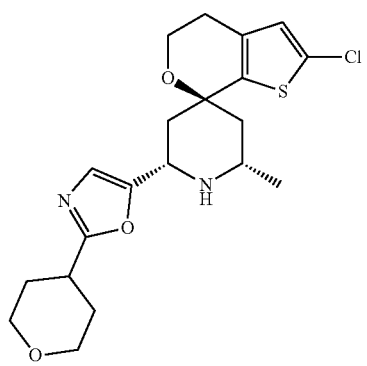 [SMILES: C[C@H]1C[C@@]2(C[C@@H](c3cnc(C4CCOCC4)o3)N1)OCCc1cc(Cl)sc12] 140
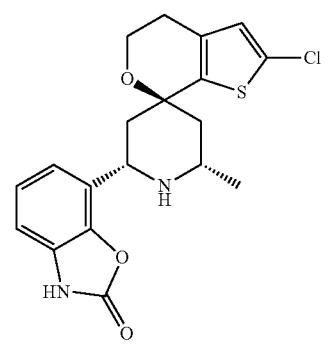 [SMILES: C[C@H]1C[C@@]2(C[C@@H](c3cccc4[nH]c(=O)oc34)N1)OCCc1cc(Cl)sc12] 141
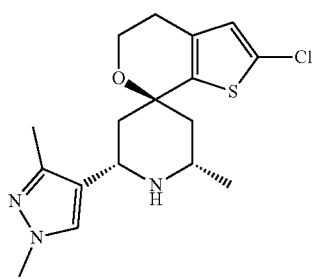 [SMILES: Cc1nn(C)cc1[C@@H]1C[C@]2(C[C@H](C)N1)OCCc1cc(Cl)sc12] 142
TABLE III-continued
Inferred Stereochemistry of Certain Compounds of Table I and Table II
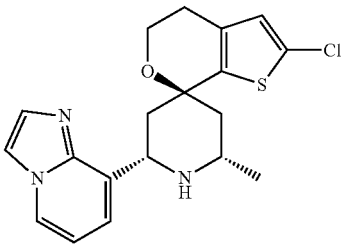 [SMILES: C[C@H]1C[C@@]2(C[C@@H](c3cccn4ccnc34)N1)OCCc1cc(Cl)sc12] 143*
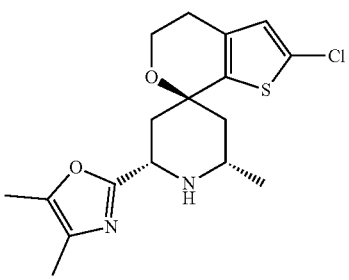 [SMILES: Cc1nc([C@@H]2C[C@]3(C[C@H](C)N2)OCCc2cc(Cl)sc23)oc1C] 144
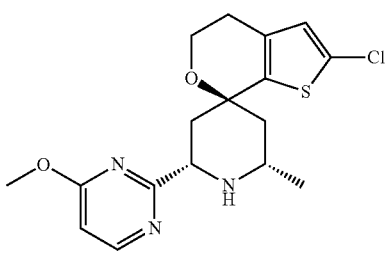 145[1]
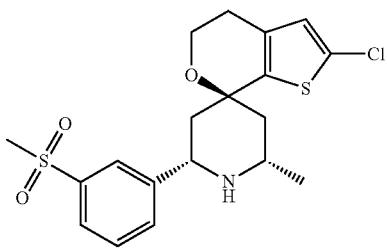 [SMILES: C[C@H]1C[C@@]2(C[C@@H](c3cccc(S(C)(=O)=O)c3)N1)OCCc1cc(Cl)sc12] 146
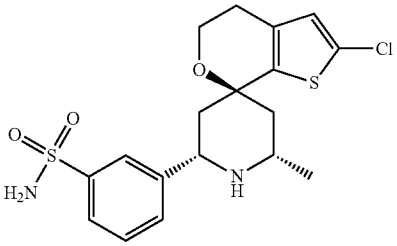 [SMILES: C[C@H]1C[C@@]2(C[C@@H](c3cccc(S(N)(=O)=O)c3)N1)OCCc1cc(Cl)sc12] 147

TABLE III-continued
Inferred Stereochemistry of Certain Compounds of Table I and Table II
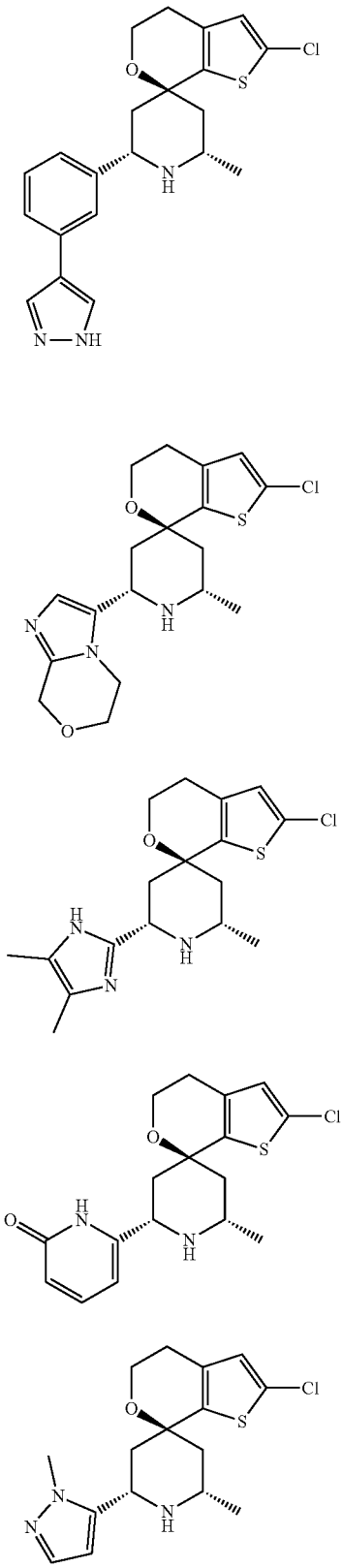
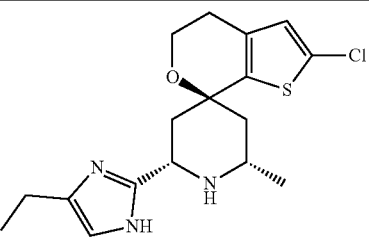
153
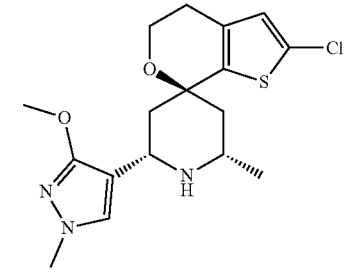 [SMILES: COc1nn(C)cc1[C@@H]1C[C@]2(C[C@H](C)N1)OCCc1cc(Cl)sc12]
154
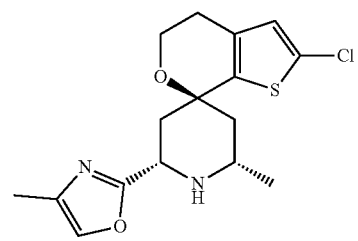 [SMILES: Cc1coc([C@@H]2C[C@]3(C[C@H](C)N2)OCCc2cc(Cl)sc23)n1]
155*
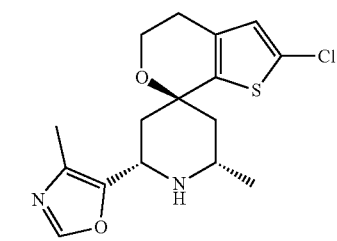 [SMILES: Cc1ncoc1[C@@H]1C[C@]2(C[C@H](C)N1)OCCc1cc(Cl)sc12]
156*
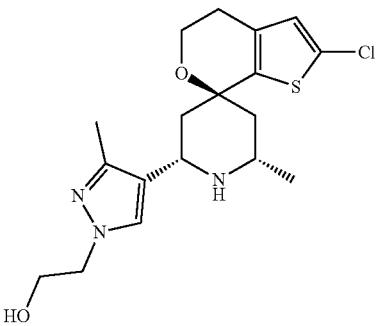 [SMILES: Cc1nn(CCO)cc1[C@@H]1C[C@]2(C[C@H](C)N1)OCCc1cc(Cl)sc12]
157
158*

TABLE III-continued
Inferred Stereochemistry of Certain Compounds of Table I and Table II
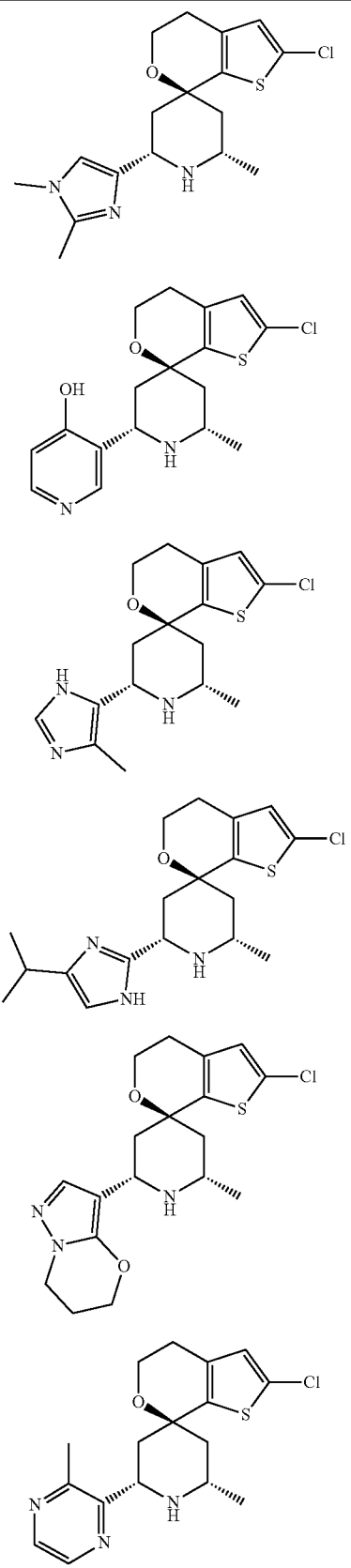
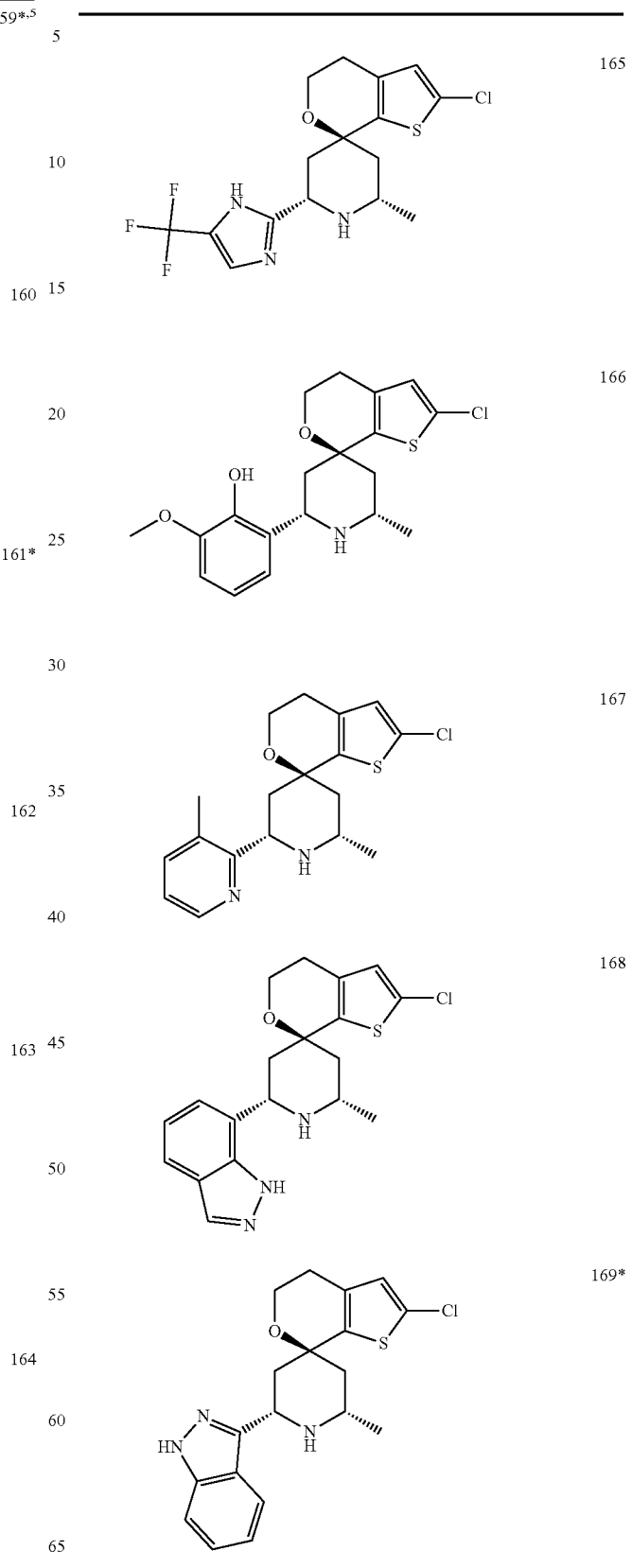

TABLE III-continued
Inferred Stereochemistry of Certain Compounds of Table I and Table II
170[7]
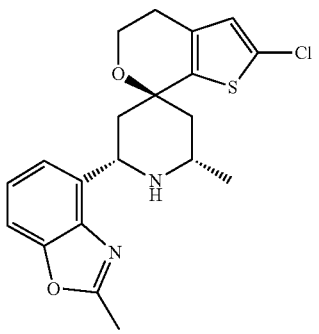 [SMILES: Cc1nc2c([C@@H]3C[C@]4(C[C@H](C)N3)OCCc3cc(Cl)sc34)cccc2o1]
171*
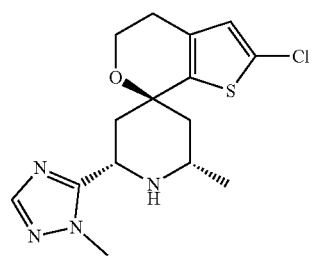 [SMILES: C[C@H]1C[C@@]2(C[C@@H](c3ncnn3C)N1)OCCc1cc(Cl)sc12]
172
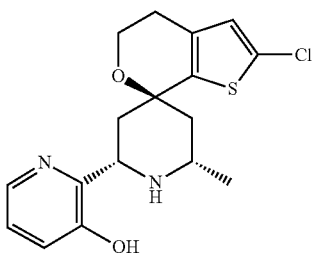
173
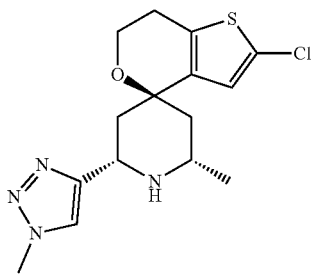 [SMILES: C[C@H]1C[C@@]2(C[C@@H](c3cn(C)nn3)N1)OCCc1sc(Cl)cc12]
175
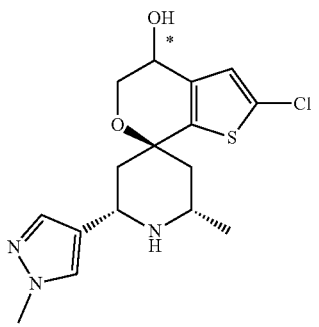
176
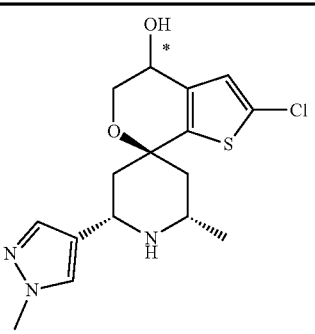
178
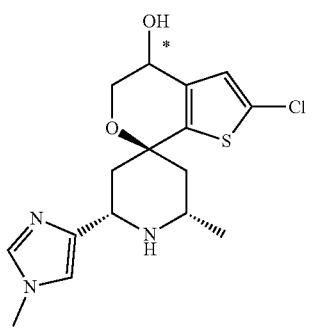
179
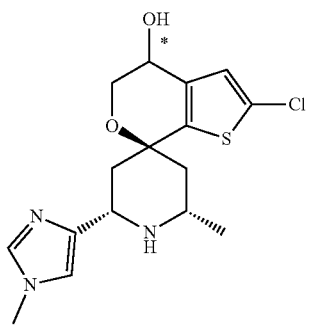
196
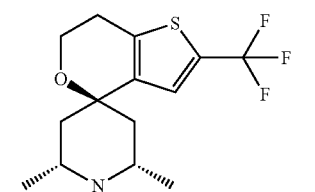
197
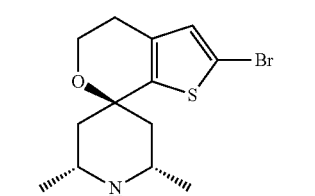
198
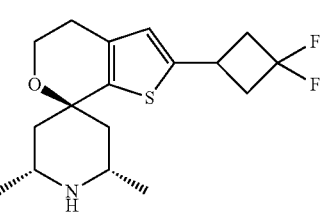

TABLE III-continued
Inferred Stereochemistry of Certain Compounds of Table I and Table II
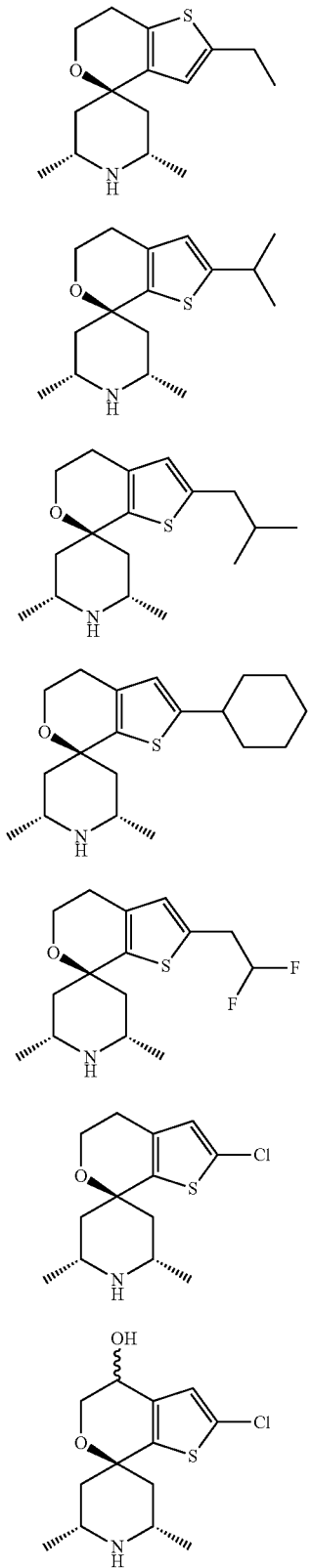
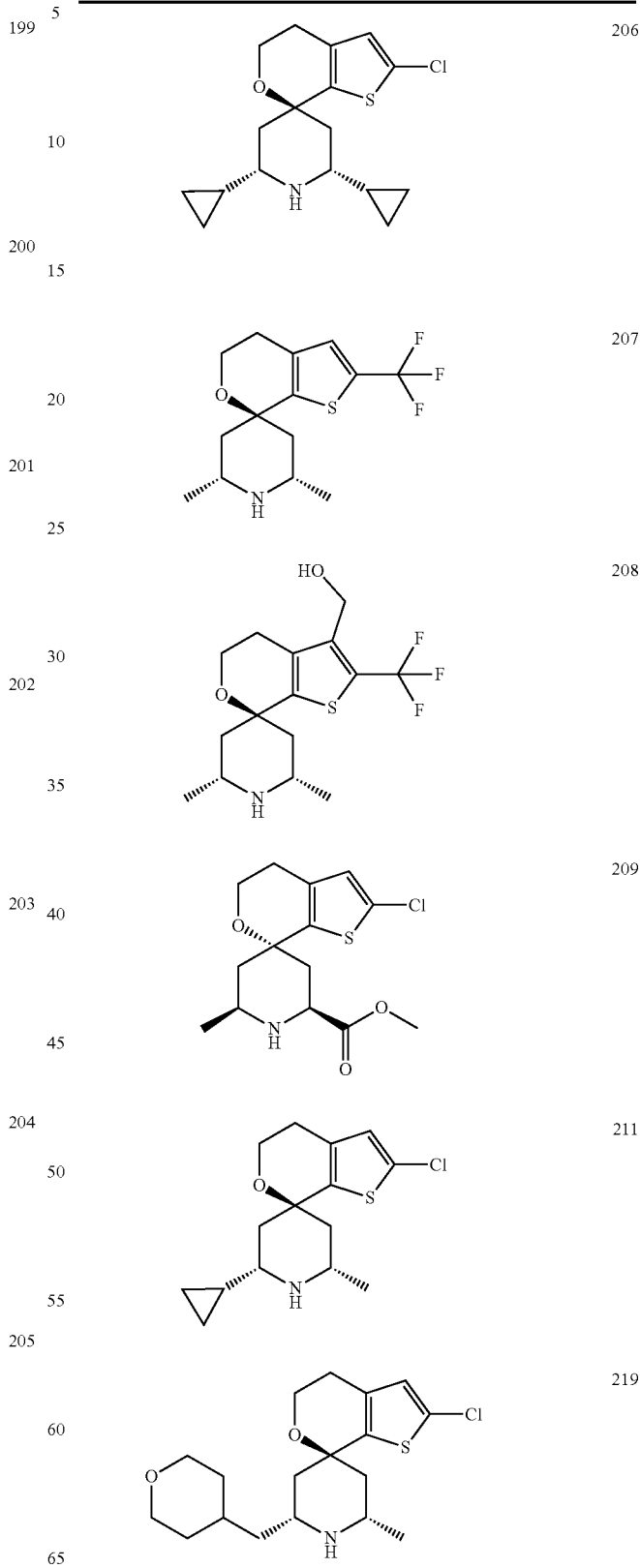

TABLE III-continued

Inferred Stereochemistry of Certain Compounds of Table I and Table II

220

372

373

374

375

376

377

378

379

380

*Racemic starting material was used, stereochemistry depicted is relative as a mixture of 2 enantiomers
[1] 3:2 mixture
[2] 4.5:1 mixture
[3] 2:1 mixture
[4] 3:1 mixture
[5] 5:1 mixture
[6] 3.5:1 mixture
[7] 2:1 mixture Some embodiments of the disclosure include derivatives of Compounds 1 to 391 (e.g., of Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., compounds of Formulae $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$), a tautomer thereof, a deuterated derivative of that compound or tautomer, or a pharmaceutically acceptable salt of any of the foregoing. In some embodiments, the derivatives are silicon derivatives in which at least one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_0$, $IIa_0$, $IIb_0$, $IIIa_0$, $IIIb_0$, $IVa_0$, $IVb_0$, $Va_0$, $Vb_0$, $I'_0$, $IIa'_0$, $IIb'_0$, $IIIa'_0$, $IIIb'_0$, $IVa'_0$, $IVb'_0$, $Va'_0$, and $Vb'_0$ (e.g., compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by silicon. In some embodiments, the derivatives are boron derivatives, in which at least one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by boron. In other embodiments, the derivatives are phosphorus derivatives, in which at least one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by phosphorus.

In some embodiments, the derivative is a silicon derivative in which one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by silicon or a silicon derivative (e.g., $-Si(CH_3)_2-$ or $-Si(OH)_2-$). The carbon replaced by silicon may be a non-aromatic carbon. In other embodiments, a fluorine has been replaced by silicon derivative (e.g., $-Si(CH_3)_3$). In some embodiments, the silicon derivatives of the disclosure may include one or more hydrogen atoms replaced by deuterium. In some embodiments, a silicon derivative of compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, may have silicon incorporated into a heterocycle ring.

In some embodiments, the derivative is a boron derivative in which one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by boron or a boron derivative.

In some embodiments, the derivative is a phosphorus derivative in which one carbon atom in a compound chosen from Compounds 1 to 391 (e.g., from Compounds 1 to 220) or compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$), a tautomer thereof, a deuterated derivative of that compound or tautomer, or a pharmaceutically acceptable salt of any of the foregoing, has been replaced by phosphorus or a phosphorus derivative.

Another aspect of the disclosure provides pharmaceutical compositions comprising at least one compound according to any one formula chosen from Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$) and Compounds 1 to 391 (e.g., from Compounds 1 to 220), a tautomer thereof, a deuterated derivative of that compound or tautomer, or a pharmaceutically acceptable salt of any of the foregoing. In some embodiments, the pharmaceutical composition comprising at least one compound chosen from Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$ (e.g., from compounds of Formulae $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$) and Compounds 1 to 391 (e.g., from Compounds 1 to 220), a tautomer thereof, a deuterated derivative of that compound or tautomer, or a pharmaceutically acceptable salt of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, and lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising at least one compound chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., from compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing can be administered as a separate composition concurrently with, prior to, or subsequent to, a composition comprising at least one other active therapeutic agent. In some embodiments, a pharmaceutical composition comprising at least one compound chosen from Compounds 1 to 391 (e.g., from Compounds 1 to 220), a tautomer thereof, a deuterated derivative of that compound or tautomer, or a pharmaceutically acceptable salt of any of the foregoing can be administered as a separate composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as, e.g., human serum albumin), buffer substances (such as, e.g., phosphates, glycine, sorbic acid, and potassium sorbate), partial glyceride mixtures of saturated vegetable fatty acids, water, salts, and electrolytes (such as, e.g., protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as, e.g., lactose, glucose, and sucrose), starches (such as, e.g., corn starch and potato starch), cellulose and its derivatives (such as, e.g., sodium carboxymethyl cellulose, ethyl cellulose, and cellulose acetate), powdered tragacanth, malt, gelatin, talc, excipients (such as, e.g., cocoa butter and suppository waxes), oils (such as, e.g., peanut oil, cottonseed oil, safflower oil, sesame oil, olive oil, corn oil, and soybean oil), glycols (such as, e.g., propylene glycol and polyethylene glycol), esters (such as, e.g., ethyl oleate and ethyl laurate), agar, buffering agents (such as, e.g., magnesium hydroxide and aluminum hydroxide), alginic acid, pyrogen-free water, isotonic saline, Ringer's solution, ethyl alcohol, phosphate buffer solutions, non-toxic compatible lubricants (such as, e.g., sodium lauryl sulfate and magnesium stearate), coloring agents, releasing agents, coating agents, sweetening agents, flavoring agents, perfuming agents, preservatives, and antioxidants.

In some embodiments of the disclosure, the compounds and the pharmaceutical compositions described herein are used to treat FSGS and/or NDKD. In some embodiments, FSGS is mediated by APOL1. In some embodiments, NDKD is mediated by APOL1.

In some embodiments, the methods of the disclosure comprise administering to a patient in need thereof at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing. In some embodiments, the compound of Formula I is chosen from Compounds 1 to 391 (e.g., from Compounds 1 to 220), a tautomer thereof, a deuterated derivative of that compound or tautomer, or a pharmaceutically acceptable salt of any of the foregoing. In some embodiments, said patient in need thereof possesses APOL1 genetic variants, i.e., G1: S342G:I384M and G2: N388del:Y389del.

Another aspect of the disclosure provides methods of inhibiting APOL1 activity comprising contacting said APOL1 with at least one entity chosen from compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IVa'', IVb'', IIa''', IIb''', IIIa''', IIIb''', IVa''', IVb''', I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$ (e.g., compounds of Formulae I$_0$, IIa$_0$, IIb$_0$, IIIa$_0$, IIIb$_0$, IVa$_0$, IVb$_0$, Va$_0$, Vb$_0$, I'$_0$, IIa'$_0$, IIb'$_0$, IIIa'$_0$, IIIb'$_0$, IVa'$_0$, IVb'$_0$, Va'$_0$, and Vb'$_0$), a tautomer thereof, a deuterated derivative of that compound or tautomer, or a pharmaceutically acceptable salt of any of the foregoing. In some embodiments, the methods of inhibiting APOL1 activity comprise contacting said APOL1 with at least one entity chosen from Compounds 1 to 391 (e.g., from Compounds 1 to 220), a tautomer thereof, a deuterated derivative of that compound or tautomer, or a pharmaceutically acceptable salt of any of the foregoing.

Non-Limiting Exemplary Embodiments 1

Without limitation, some embodiments of the present disclosure include:

1. A compound represented by the following structural formula:

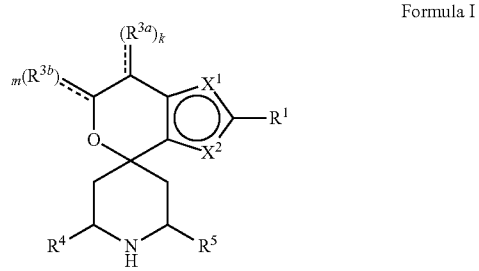

Formula I a tautomer thereof, a deuterate derivative of that compound or tautomer, or a pharmaceutically acceptable salt of any of the foregoing, wherein:

$X^1$ is selected from S and —$CR^{2a}$ and $X^2$ is selected from S and —$CR^{2b}$, wherein:
one of X and $X^2$ is S;
when $X^1$ is S, then $X^2$ is —$CR^{2b}$; and
when $X^2$ is S, then $X^1$ is —$CR^{2a}$;

$R^1$ is selected from hydrogen, halogen, cyano, —OH, $C_1$-$C_6$ alkyl, $C_1$-$C_6$ alkoxy, $C_3$-$C_6$ cycloalkyl, and phenyl, wherein:
the $C_1$-$C_6$ alkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, and $C_1$-$C_4$ alkoxy;
the $C_1$-$C_6$ alkoxy of $R^1$ is optionally substituted with 1 to 3 groups independently selected from halogen;
the $C_3$-$C_6$ cycloalkyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$; and
the phenyl of $R^1$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$;

$R^{2a}$ is selected from hydrogen, halogen, cyano, —OH, =O, and $C_1$-$C_6$ alkyl, wherein:
the $C_1$-$C_6$ alkyl of $R^{2a}$ is optionally substituted with 1 to 3 groups independently selected from halogen, cyano, —OH, and $C_1$-$C_4$ alkoxy;

$R^{2b}$ is selected from hydrogen, halogen, cyano, —OH, =O, and $C_1$-$C_6$ alkyl;

$R^{3a}$ is selected from halogen, cyano, —OH, $C_1$-$C_6$ alkyl, and =O; wherein:
the $C_1$-$C_6$ alkyl of $R^{3a}$ is optionally substituted with 1 to 3 groups independently selected from halogen, cyano, and —OH;

$R^3$ is selected from $C_1$-$C_2$ alkyl and =O; wherein:
the $C_1$-$C_2$ alkyl of $R^3$ is optionally substituted with 1 to 3 groups independently selected from halogen, cyano, and —OH;

═════, for each occurrence, is a single bond when $R^{3a}$ is selected from halogen, cyano, —OH, $C_1$-$C_6$ alkyl or when $R^3$ is selected from $C_1$-$C_2$ alkyl; or alternatively ═════, for each occurrence, is a double bond when $R^{3a}$ is =O or when $R^3$ is =O;

$R^4$ is selected from $C_1$-$C_6$ alkyl, —C(=O)O($C_1$-$C_4$ alkyl), $C_2$-$C_6$ alkynyl, and

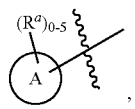

, wherein:
the $C_1$-$C_6$ alkyl of $R^4$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH($C_1$-$C_4$ alkyl), —C(=O)N($C_1$-$C_4$ alkyl)$_2$, $C_3$-$C_6$ cycloalkyl, 5- to 10-membered heterocyclyl, phenyl, and 5- to 10-membered heteroaryl;

Ring A is selected from $C_3$-$C_{12}$ carbocyclyl, 3- to 12-membered heterocyclyl, $C_6$ and $C_{10}$ aryl, and 5- to 10-membered heteroaryl, wherein Ring A is optionally substituted with 1, 2, 3, 4, or 5 $R^a$ groups; wherein:

$R^a$, for each occurrence, is independently selected from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^hC(=O)R^k$, —$NR^hC(=O)OR^k$, —$NR^hC(=O)NR^iR^j$, —$NR^hS(=O)_pR^k$, —$OR^k$, —OC(=O)R, —OC(=O)$OR^k$, —OC(=O)$NR^hR^i$, —[O($CH_2$)$_q$]$_r$O($C_1$-$C_6$ alkyl), —S(=O)$_pR^k$, —S(=O)$_pNR^hR^i$, —C(=O)$OR^k$, $C_3$-$C_{12}$ carbocyclyl, 3- to 12-membered heterocyclyl, $C_6$ and $C_{10}$ aryl, and 5- to 10-membered heteroaryl; wherein:
the $C_1$-$C_6$ alkyl, $C_1$-$C_6$ alkoxy, and the $C_2$-$C_6$ alkenyl of $R^a$ are each optionally substituted with 1 to 3 groups independently selected from $C_6$ to $C_{10}$ aryl (optionally substituted with 1 to 3 $R^m$ groups), 5- to 10-membered heterocyclyl (optionally substituted with 1 to 3 $R^m$ groups), 5- to 10-membered heteroaryl (optionally substituted with 1 to 3 $R^m$ groups), cyano, —C(=O)$R^k$, —C(=O)$OR^k$, —C(=O)$NR^hR^i$, —$NR^hR^i$, —$NR^hC(=O)R^k$, —$NR^hC(=O)OR^k$, —$NR^hC(=O)NR^iR^j$, —$NR^hS(=O)_pR^k$, —$OR^k$, —OC(=O)$R^k$, —OC(=O)$OR^k$, —OC(=O)$NR^hR^i$, —S(=O)$_pR^k$, —S(=O)$_pNR^hR^i$, and $C_3$-$C_6$ carbocyclyl (optionally substituted with 1 to 3 $R^m$ groups);
the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently selected from halogen, cyano, $C_1$-$C_4$ alkyl, —$NR^hR^i$, and —$OR^k$; wherein:

$R^h$, $R^i$, and $R^j$, for each occurrence, are each independently selected from hydrogen, $C_1$-$C_4$ alkyl, $C_6$-$C_{10}$ aryl, and $C_3$-$C_6$ cycloalkyl; wherein:
the $C_1$-$C_4$ alkyl of any one of $R^h$, $R^i$, and $R^j$ is optionally substituted with 1 to 3 groups independently selected from halogen, cyano, and —OH;

$R^k$, for each occurrence, are each independently selected from hydrogen, $C_1$-$C_4$ alkyl, 5- to 10-membered heterocyclyl, and $C_3$-$C_6$ carbocyclyl; wherein:
the $C_1$-$C_4$ alkyl of any one of $R^k$ is optionally substituted with 1 to 3 groups independently selected from halogen, cyano, and —OH;

$R^m$, for each occurrence, is independently selected from halogen, cyano, oxo, $C_1$-$C_6$ alkyl, $C_1$-$C_6$ alkoxy, —S(=O)$_pR^k$, and —$OR^k$; wherein:
the $C_1$-$C_6$ alkyl of $R^m$ is optionally substituted with 1 to 3 groups independently selected from halogen, cyano, and —OH;

$R^5$ is selected from $C_1$-$C_6$ alkyl, —C(=O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl; wherein:
the $C_1$-$C_6$ alkyl of $R^5$ is optionally substituted with 1 to 3 groups independently selected from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH($C_1$-$C_4$ alkyl), and —C(=O)N($C_1$-$C_4$ alkyl)$_2$;
the $C_3$-$C_{12}$ carbocyclyl, the 3 to 12-membered heterocyclyl, the $C_6$ and $C_{10}$ aryl, and the 5 to 10-membered heteroaryl of $R^5$ are each optionally substituted with 1 to 3 groups independently selected from halogen, cyano, —OH, —NH$_2$, —NH(C$_1$-C$_4$ alkyl) (optionally substituted with —OH), —N(C$_1$-C$_4$ alkyl)$_2$, C$_1$-C$_5$ alkyl (optionally substituted with —OH), C$_1$-C$_4$ alkoxy, —C(=O)NH$_2$, —C(=O)NH(C$_1$-C$_4$ alkyl), —NHC(=O)(C$_1$-C$_4$ alkyl), —C(=O)(C$_1$-C$_4$ alkoxy), and —C(=O)N(C$_1$-C$_4$ alkyl)$_2$;

k is an integer selected from 0, 1, and 2, wherein:
when R$^{3a}$ is selected from halogen, cyano, —OH, and C$_1$-C$_6$ alkyl, k is 1 or 2; and
when R$^{3a}$ is =O, k is 1;
m is an integer selected from 0, 1, and 2, wherein:
when R$^{3b}$ is selected from C$_1$-C$_2$ alkyl, m is 1 or 2; and
when R$^{3b}$ is =O, m is 1;
p is an integer selected from 1 and 2; and
q and r are each an integer selected from 1, 2, 3, and 4.

2. The compound, tautomer, deuterated derivative, or pharmaceutically acceptable salt according to Embodiment 1, wherein the compound is represented by one of the following structural formulae:

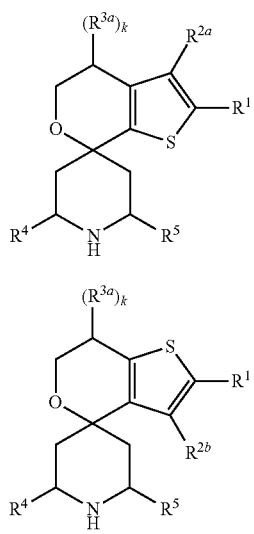

Formula IIa

Formula IIb or is a tautomer thereof, a deuterated derivative of that compound or tautomer, or a
pharmaceutically acceptable salt of any of the foregoing, wherein:
R$^{2a}$ is selected from hydrogen, halogen, cyano, and C$_1$-C$_4$ alkyl; wherein:
the C$_1$-C$_4$ alkyl of R$^{2a}$ is optionally substituted with 1 to 3 groups independently selected from halogen, —OH, and C$_1$-C$_2$ alkoxy;
R$^{2b}$ is selected from hydrogen, halogen, cyano, and C$_1$-C$_4$ alkyl; and
k is an integer selected from 0, 1, and 2; and all other variables not specifically defined herein are as defined in Embodiment 1.

3. The compound, tautomer, deuterated derivative, or pharmaceutically acceptable salt according to Embodiment 1 or Embodiment 2, wherein R$^4$ is selected from C$_1$-C$_4$ alkyl and

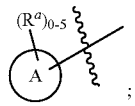

wherein:
the C$_1$-C$_4$ alkyl of R$^4$ is optionally substituted with 1 to 3 groups independently selected from halogen, cyano, —OH, —NH$_2$, —NH(C$_1$-C$_4$ alkyl), —N(C$_1$-C$_4$ alkyl)$_2$, C$_1$-C$_2$ alkoxy, C$_3$-C$_6$ cycloalkyl, 5- to 6-membered heterocyclyl, phenyl, and 5- to 6-membered heteroaryl; and all other variables not specifically defined herein are as defined in Embodiment 1 or Embodiment 2.

4. The compound, tautomer, deuterated derivative, or pharmaceutically acceptable salt according to any one of Embodiments 1 to 3, wherein R$^4$ is selected from C$_1$-C$_2$ alkyl and

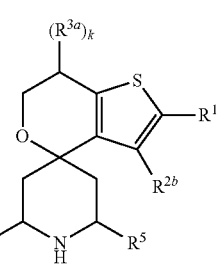

wherein:
the C$_1$-C$_2$ alkyl of R$^4$ is optionally substituted with 1 to 3 groups independently selected from halogen, cyano, —OH, and 5- to 6-membered heterocyclyl; and all other variables not specifically defined herein are as defined in any one of Embodiments 1 to 3.

5. The compound, tautomer, deuterated derivative, or pharmaceutically acceptable salt according to any one of Embodiments 1 to 4, wherein R$^4$ is selected from —CH$_3$, —CH$_2$OH, and (tetrahydro-2H-pyran-4-yl)methyl; and all other variables not specifically defined herein are as defined in any one of Embodiments 1 to 4.

6. The compound according to any one of Embodiments 1 to 4, wherein the compound is represented by one of the following structural formulae:

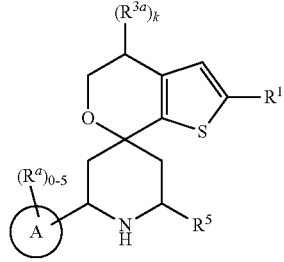

Formula IIIa

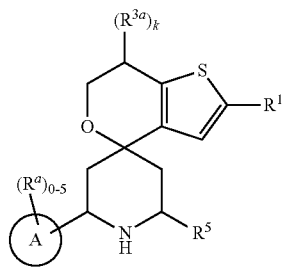

Formula IIIb a tautomer thereof, a deuterated derivative of that compound or tautomer, or a
pharmaceutically acceptable salt of any of the foregoing, wherein:
Ring A, for each occurrence, is selected from C$_3$-C$_6$ cycloalkyl, 5- to 10-membered heterocyclyl, phenyl, and 5- to 10-membered heteroaryl; each of which is optionally substituted with 1, 2, 3, 4, or 5 $R^a$ groups; and all other variables not specifically defined herein are as defined in any one of Embodiments 1 to 5.

7. The compound, tautomer, deuterated derivative, or pharmaceutically acceptable salt according to any one of Embodiments 1 to 4 and 6, wherein Ring A is selected from cyclopropyl, 5- to 10-membered heterocyclyl, phenyl, and 5- to 9-membered heteroaryl; each of which is optionally substituted with 1, 2, 3, 4, or 5 $R^a$ groups; and all other variables not specifically defined herein are as defined in any one of Embodiments 1 to 6.

8. The compound, tautomer, deuterated derivative, or pharmaceutically acceptable salt according to any one of Embodiments 1 to 4, 6, and 7, wherein Ring A is selected from cyclopropyl, 5 to 10-membered heterocyclyl containing 1 to 3 heteroatoms selected from N and O, phenyl, and 5 to 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of Embodiments 1 to 7.

9. The compound, tautomer, deuterated derivative, or pharmaceutically acceptable salt according to any one of Embodiments 1 to 4 and 6 to 8, wherein Ring A is selected from cyclopropyl, 5-membered heterocyclyl containing 1 to 3 heteroatoms selected from N and O, 6-membered heterocyclyl containing 1 to 3 heteroatoms selected from N and O, 9-membered heterocyclyl containing 1 to 3 heteroatoms selected from N and O, 10-membered heterocyclyl containing 1 to 3 heteroatoms selected from N and O, phenyl, 5-membered heteroaryl containing 1 to 3 heteroatoms selected from N and O, 6-membered heteroaryl containing 1 to 3 heteroatoms selected from N and O, and 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of Embodiments 1 to 8.

10. The compound, tautomer, deuterated derivative, or pharmaceutically acceptable salt according to any one of Embodiments 1 to 4 and 6 to 9, wherein Ring A is selected from

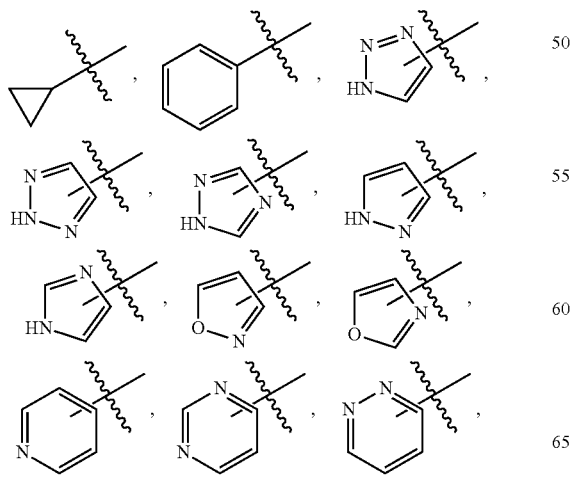

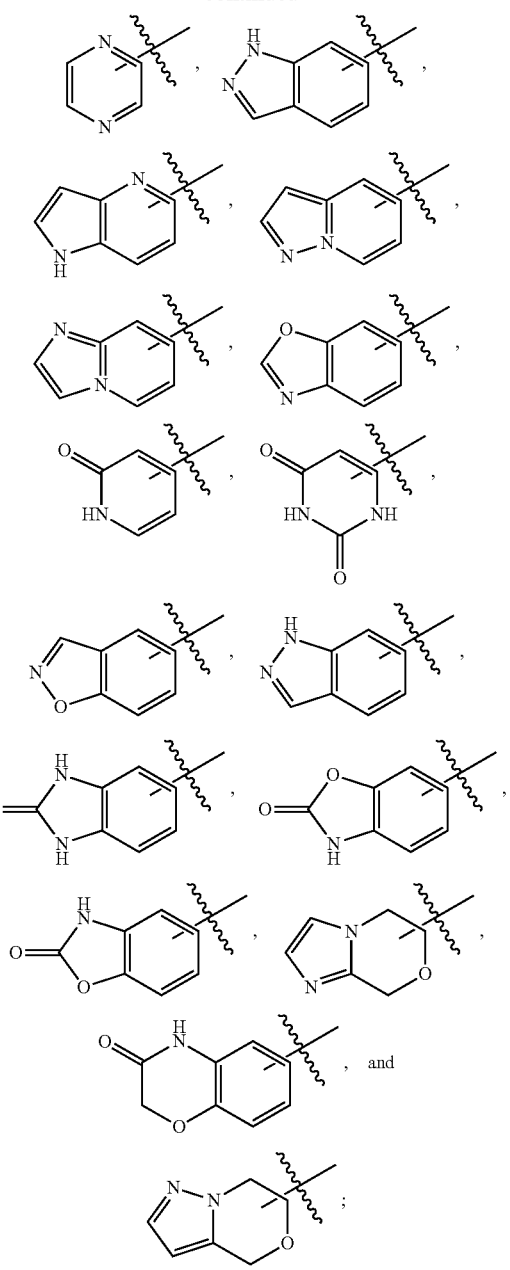

, and

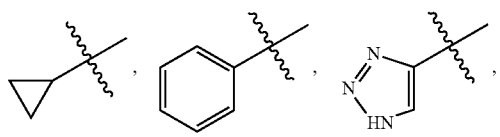

;

each of which is optionally substituted with 1, 2, 3, 4, or 5 $R^a$ groups; and all other variables not specifically defined herein are as defined in any one of Embodiments 1 to 9.

11. The compound, tautomer, deuterated derivative, or pharmaceutically acceptable salt according to any one of Embodiments 1 to 4 and 6 to 10, wherein Ring A is selected from

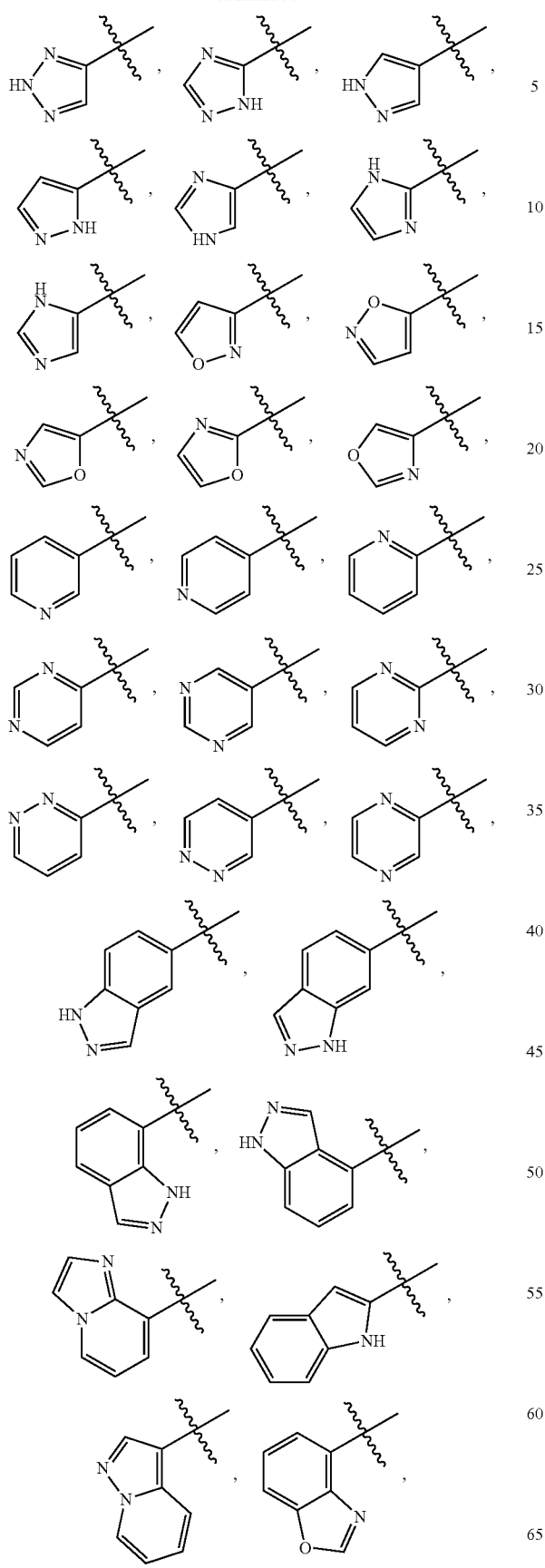
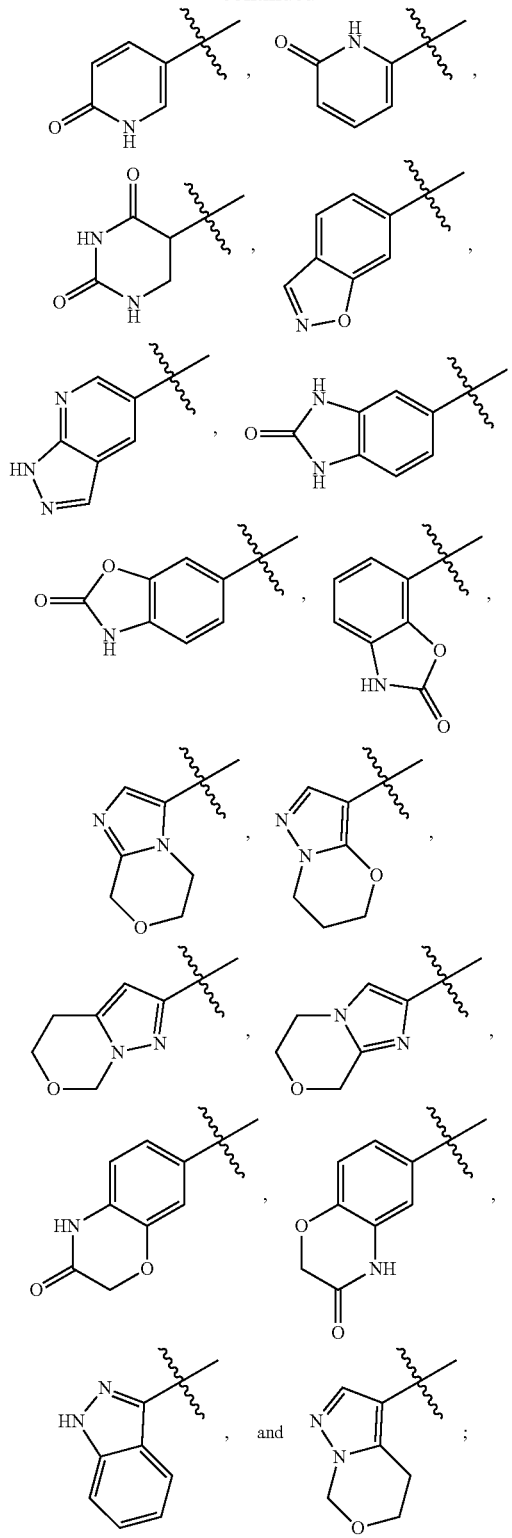
each of which is optionally substituted with 1, 2, 3, 4, or 5 $R^a$ groups; and all other variables not specifically defined herein are as defined in any one of Embodiments 1 to 4 and 6 to 10.
12. The compound, tautomer, deuterated derivative, or pharmaceutically acceptable salt according to any one of Embodiments 1 to 4 and 6 to 11, wherein R⁴ is selected from —CH₃ and Ring A; wherein Ring A is selected from

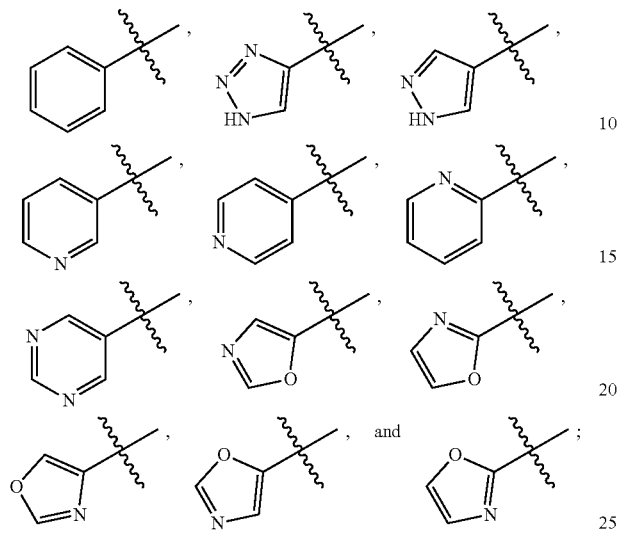

each of which is optionally substituted with 1, 2, 3, 4, or 5 R$^a$ groups; and all other variables not specifically defined herein are as defined in any one of Embodiments 1 to 4 and 6 to 11.

13. The compound, tautomer, deuterated derivative, or pharmaceutically acceptable salt according to any one of Embodiments 1 to 12, wherein R⁵ is selected from $C_1$-$C_4$ alkyl, —C(=O)O($C_1$-$C_2$ alkyl), $C_3$-$C_6$ cycloalkyl, and 5 to 10-membered heterocyclyl; wherein:
the $C_1$-$C_4$ alkyl of R⁵ is optionally substituted with 1 to 3 groups independently selected from halogen, cyano, —OH, and $C_1$-$C_2$ alkoxy; and
the $C_3$-$C_6$ cycloalkyl and the 5- to 10-membered heterocyclyl of R⁵ are each optionally substituted with 1 to 3 groups independently selected from halogen, cyano, —OH, $C_1$-$C_2$ alkyl, and $C_1$-$C_2$ alkoxy;
and all other variables not specifically defined herein are as defined in any one of Embodiments 1 to 12.

14. The compound, tautomer, deuterated derivative, or pharmaceutically acceptable salt according to any one of Embodiments 1 to 13, wherein R⁵ is selected from $C_1$-$C_2$ alkyl, —C(=O)O($C_1$-$C_2$ alkyl), cyclopropyl, cyclobutyl, and 5- to 6-membered heterocyclyl; wherein:
the $C_1$-$C_2$ alkyl of R⁵ is optionally substituted with 1 to 3 groups independently selected from F, Cl, Br, cyano, —OH, and $C_1$-$C_2$ alkoxy; and
the cyclopropyl, the cyclobutyl, and the 5- to 6-membered heterocyclyl of R⁵ are each optionally substituted with 1 to 3 groups independently selected from F, Cl, Br, cyano, —OH, $C_1$-$C_2$ alkyl, and $C_1$-$C_2$ alkoxy;
and all other variables not specifically defined herein are as defined in any one of Embodiments 1 to 13.

15. The compound, tautomer, deuterated derivative, or pharmaceutically acceptable salt according to any one of Embodiments 1 to 14, wherein R⁵ is selected from —CH₃, —CH₂CH₃, —CH₂OH, —C(=O)OCH₃, —CH₂OCH₃, —CH(CH₃)₂, cyclopropyl, difluorocyclopropyl, and tetrahydro-2H-pyranyl; and all other variables not specifically defined herein are as defined in any one of Embodiments 1 to 14.

16. The compound according to any one of Embodiments 1 to 4 and 6 to 15, wherein the compound is represented by one of the following structural formulae:

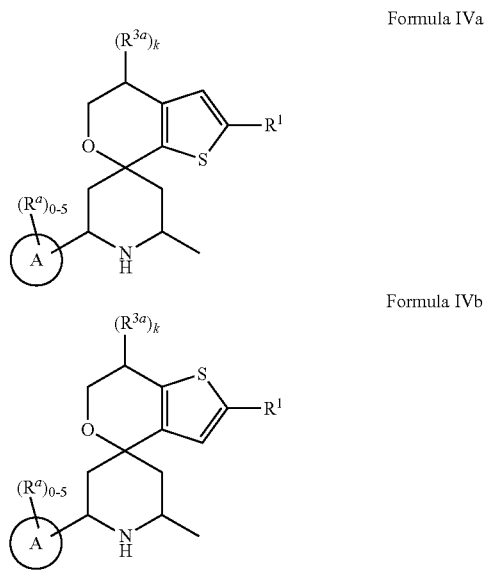

Formula IVa

Formula IVb a tautomer thereof, a deuterated derivative of that compound or tautomer, or a pharmaceutically acceptable salt of any of the foregoing; and all other variables not specifically defined herein are as defined in any one of Embodiments 1 to 4 and 6 to 15.

17. The compound, tautomer, deuterated derivative, or pharmaceutically acceptable salt according to any one of Embodiments 1 to 16, wherein R¹ is selected from hydrogen, halogen, cyano, —OH, $C_1$-$C_4$ alkyl, $C_1$-$C_4$ alkoxy, and $C_3$-$C_6$ cycloalkyl; wherein:
the $C_1$-$C_4$ alkyl of R¹ is optionally substituted with 1 to 3 groups independently selected from halogen, cyano, —OH, and $C_1$-$C_2$ alkoxy;
the $C_1$-$C_4$ alkoxy of R¹ is optionally substituted with 1 to 3 independently selected from halogen groups; and
the $C_3$-$C_6$ cycloalkyl of R¹ is optionally substituted with 1 to 3 groups independently selected from halogen, cyano, —OH, and $C_1$-$C_2$ alkoxy;
and all other variables not specifically defined herein are as defined in any one of Embodiments 1 to 16.

18. The compound, tautomer, deuterated derivative, or pharmaceutically acceptable salt according to any one of Embodiments 1 to 17, wherein R¹ is selected from F, Cl, Br, $C_1$-$C_4$ alkyl, and $C_3$-$C_6$ cycloalkyl; wherein:
the $C_1$-$C_4$ alkyl of R¹ is optionally substituted with 1 to 3 groups independently selected from halogen and —OH; and
the $C_3$-$C_6$ cycloalkyl of R¹ is optionally substituted with 1 to 3 groups independently selected from halogen and —OH;
and all other variables not specifically defined herein are as defined in any one of Embodiments 1 to 17.

19. The compound, tautomer, deuterated derivative, or pharmaceutically acceptable salt according to any one of Embodiments 1 to 18, wherein R¹ is selected from F, Cl, Br, $C_1$-$C_4$ alkyl, and $C_3$-$C_6$ cycloalkyl; wherein:

the $C_1$-$C_4$ alkyl of $R^1$ is optionally substituted with 1 to 3 groups independently selected from halogen and —OH;

and all other variables not specifically defined herein are as defined in any one of Embodiments 1 to 18.

20. The compound, tautomer, deuterated derivative, or pharmaceutically acceptable salt according to any one of Embodiments 1 to 18, wherein $R^1$ is selected from $C_1$, Br, —$CH_3$, —$CF_3$, —$CH_2CH_3$, —$CH(CH_3)_2$, —$CH_2CHF_2$, —$CH_2CH(CH_3)_2$, difluorocyclobutyl, and cyclohexyl.

21. The compound, tautomer, deuterated derivative, or pharmaceutically acceptable salt according to any one of Embodiments 1 to 20, wherein $R^1$ is $C_1$; and all other variables not specifically defined herein are as defined in any one of Embodiments 1 to 20.

22. The compound, tautomer, deuterated derivative, or pharmaceutically acceptable salt according to any one of Embodiments 1 to 21, wherein $R^{3a}$ is selected from halogen, —OH, and $C_1$-$C_4$ alkyl; wherein:

the $C_1$-$C_4$ alkyl of $R^{3a}$ is optionally substituted with 1 to 3 groups independently selected from halogen and —OH;

and all other variables not specifically defined herein are as defined in any one of Embodiments 1 to 21.

23. The compound, tautomer, deuterated derivative, or pharmaceutically acceptable salt according to any one of Embodiments 1 to 22, wherein $R^{3a}$ is selected from F, Cl, Br, —OH, and $C_1$-$C_2$ alkyl; wherein:

the $C_1$-$C_2$ alkyl of $R^{3a}$ is optionally substituted with 1 to 3 groups independently selected from F, Cl, and —OH;

and all other variables not specifically defined herein are as defined in any one of Embodiments 1 to 22.

24. The compound, tautomer, deuterated derivative, or pharmaceutically acceptable salt according to any one of Embodiments 1 to 23, wherein $R^{3a}$ is selected from F, —OH, —$CH_3$, —$CHF_2$, and $CH_2OH$; and all other variables not specifically defined herein are as defined in any one of Embodiments 1 to 23.

25. The compound according to any one of Embodiments 1 to 4 and 6 to 24, wherein the compound is represented by one of the following structural formulae:

Formula Va

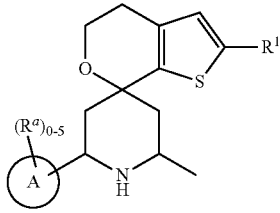

Formula Vb

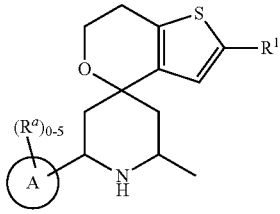

a tautomer thereof, a deuterated derivative of that compound or tautomer, or a pharmaceutically acceptable salt of any of the foregoing; and all other variables not specifically defined herein are as defined in any one of Embodiments 1 to 4 and 6 to 24.

26. The compound, tautomer, deuterated derivative, or pharmaceutically acceptable salt according to any one of Embodiments 1 to 4 and 6 to 25, wherein $R^a$, for each occurrence, is independently selected from halogen, cyano, $C_1$-$C_6$ alkyl, $C_1$-$C_4$ alkoxy, $C_1$-$C_6$ haloalkyl, $C_1$-$C_6$ haloalkoxy, —C(=O)$NR^hR^i$, —$NR^hR^i$, —$NR^hC$(=O)$R^1$, —$OR^k$, —[O($CH_2$)$_q$]$_r$O($C_1$-$C_6$ alkyl), —S(=O)$_2R^k$, —S(=O)$_2NR^hR^i$, $C_3$-$C_6$ cycloalkyl, 5 to 10-membered heterocyclyl, phenyl, and 5- to 8-membered heteroaryl; wherein:

the $C_1$-$C_6$ alkyl of $R^a$ is optionally substituted with 1 to 3 groups independently selected from cyano, —C(=O)$NR^hR^i$, —$NR^hR^i$, —$NR^hC$(=O)$R^h$, —$NR^hC$(=O)$OR^k$, —$NR^hC$(=O)$NR^iR^j$, —$NR^hS$(=O)$_pR^k$, —$OR^k$, —S(=O)$_2R^k$, —S(=O)$_pNR^hR^i$, and $C_3$-$C_6$ cycloalkyl;

the $C_3$-$C_6$ cycloalkyl, the 5 to 10-membered heterocyclyl, the phenyl, and the 5- to 8-membered heteroaryl of $R^a$ are each optionally substituted with 1 to 3 groups independently selected from halogen, $C_1$-$C_2$ alkyl, and —$OR^k$; wherein:

$R^h$, $R^i$, and $R^j$, for each occurrence, are each independently selected from hydrogen, $C_1$-$C_2$ alkyl, cyclopropyl, and cyclobutyl; wherein:

the $C_1$-$C_2$ alkyl of any one of $R^h$, $R^i$, and $R^j$ is optionally substituted with 1 to 3 groups independently selected from halogen and —OH;

$R^k$, for each occurrence, is each independently selected from hydrogen and $C_1$-$C_4$ alkyl; wherein:

the $C_1$-$C_4$ alkyl of $R^k$ is optionally substituted with 1 to 3 groups independently selected from halogen and —OH; and q and r are each an integer selected from 1, 2, and 3;

and all other variables not specifically defined herein are as defined in any one of Embodiments 1 to 4 and 6 to 25.

27. The compound, tautomer, deuterated derivative, or pharmaceutically acceptable salt according to any one of Embodiments 1 to 4 and 6 to 26, wherein $R^a$, for each occurrence, is independently selected from halogen, cyano, $C_1$-$C_6$ alkyl, $C_1$-$C_4$ alkoxy, $C_1$-$C_4$ haloalkyl, $C_1$-$C_4$ haloalkoxy, —C(=O)$NR^hR^i$, —$NR^hR^i$, —$NR^hC$(=O)$R^k$, —$OR^k$, —[O($CH_2$)$_q$]$_r$O($C_1$-$C_4$ alkyl), —S(=O)$_2R^k$, —S(=O)$_2NR^hR^i$, cyclopropyl, cyclobutyl, 5- to 6-membered heterocyclyl, phenyl, and 5- to 6-membered heteroaryl; wherein:

the $C_1$-$C_6$ alkyl of $R^a$ is optionally substituted with 1 to 3 groups independently selected from cyano, —C(=O)$NR^hR^i$, —$NR^hR^i$, —$OR^k$, cyclopropyl, and cyclobutyl;

the cyclopropyl, the cyclobutyl, the 5- to 6-membered heterocyclyl, the phenyl, and the 5 to 6-membered heteroaryl of $R^a$ are each optionally substituted with 1 to 3 groups independently selected from halogen, —$CH_3$, —OH, and —$OCH_3$; wherein:

$R^h$ and $R^i$, for each occurrence, are each independently selected from hydrogen, —$CH_3$, cyclopropyl, and cyclobutyl; wherein:

the —$CH_3$ of any one of $R^h$ and $R^i$ is optionally substituted with 1 to 3 groups independently selected from F, Cl, and —OH;

$R^k$, for each occurrence, is each independently selected from hydrogen and —$CH_3$; wherein:

the —CH₃ of Rᵏ is optionally substituted with 1 to 3 groups independently selected from halogen and —OH;
and all other variables not specifically defined herein are as defined in any one of Embodiments 1 to 4 and 6 to 26.

28. The compound, tautomer, deuterated derivative, or pharmaceutically acceptable salt according to any one of Embodiments 1 to 4 and 6 to 27, wherein Rᵃ, for each occurrence, is independently selected from F, Cl, Br, cyano, $C_1$-$C_6$ alkyl, $C_1$-$C_2$ alkoxy, $C_1$-$C_2$ haloalkyl, —C(=O)NRʰRⁱ, —NRʰRⁱ, —NRʰC(=O)Rᵏ, —ORᵏ, —[O(CH₂)q]rO($C_1$-$C_2$ alkyl), —S(=O)₂Rᵏ, —S(=O)₂NRʰRⁱ, cyclopropyl, cyclobutyl, 5-membered heterocyclyl, phenyl, and 6-membered heteroaryl; wherein:
   the $C_1$-$C_6$ alkyl of Rᵃ is optionally substituted with 1 to 3 groups independently selected from cyano, —C(=O)NRʰRⁱ, —ORᵏ, and cyclopropyl;
   the cyclopropyl, the cyclobutyl, the 5- to 6-membered heterocyclyl, the phenyl, and the 5- to 6-membered heteroaryl of Rᵃ are each optionally substituted with 1 to 3 groups independently selected from halogen, —CH₃, —OH, and —OCH₃; wherein:
   Rʰ and Rⁱ, for each occurrence, are each independently selected from hydrogen, —CH₃, and cyclopropyl; wherein:
   the —CH₃ of any one of Rʰ and Riis optionally substituted with 1 to 3 groups independently selected from F, Cl, and —OH;
   Rᵏ, for each occurrence, is each independently selected from hydrogen and —CH₃; and
   q and r are each an integer selected from 1 and 2;
and all other variables not specifically defined herein are as defined in any one of Embodiments 1 to 4 and 6 to 27.

29. The compound, tautomer, deuterated derivative, or pharmaceutically acceptable salt according to any one of Embodiments 1 to 4 and 6 to 28, wherein Rᵃ, for each occurrence, is independently selected from F, cyano, —OH, —CH₃, —CF₃, —CH(CH₃)₂, —(CH₂)₂OH, —(CH₂)₂OCH₃, —CH₂CH(OH)C₂H5, —CH₂C(CH₃)(CH₂OH)₂, —OCH₃, —OCH₂CH₃, —[O(CH₂)₂]₂OCH₃, —CH₂C(=O)NHCH₃, —(CH₂)₂SO₂CH₃, —CH₂C(=O)N(CH₃)₂, —CH₂(cyclopropyl), —C(=O)NH₂, —C(=O)NH(cyclopropyl), —NH₂, —NHCH₃, —N(CH₃)₂, —NHC(CH₃)₂CH₂OH, —NHC(=O)CH₃, —SO₂CH₃, —SO₂NH₂, cyclopropyl, 2-methoxyphenyl, N-methylpiperazinyl, tetrahydro-2H-pyranyl, methylpyrazolyl, pyridinyl, and tetrahydrothiophenyl 1,1-dioxide; and all other variables not specifically defined herein are as defined in any one of Embodiments 1 to 4 and 6 to 28.

30. The compound according to Embodiment 1, wherein the compound is represented by one of the following structural formulae:

Formula I'

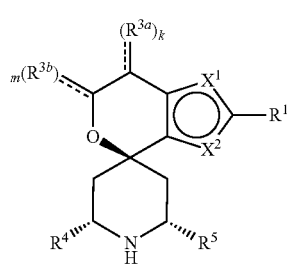

Formula IIa'

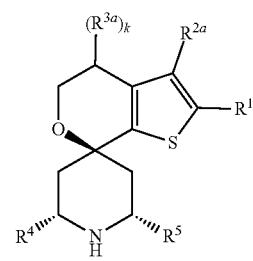

Formula IIb'

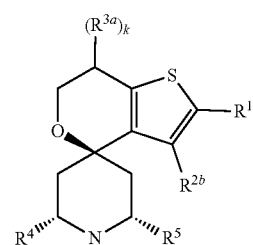

Formula IIIa'

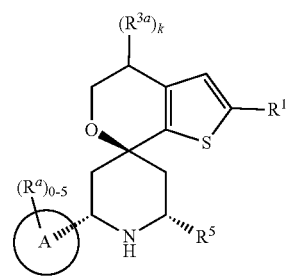

Formula IIIb'

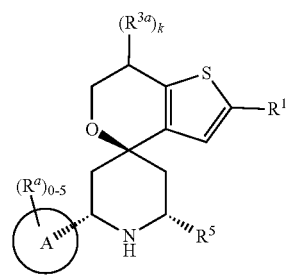

Formula IVa'

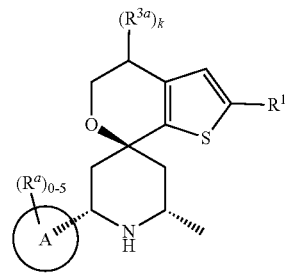

Formula IVb'

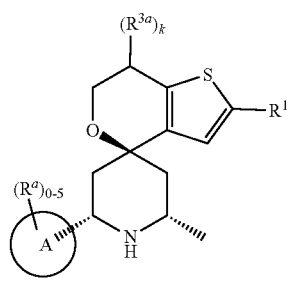

-continued

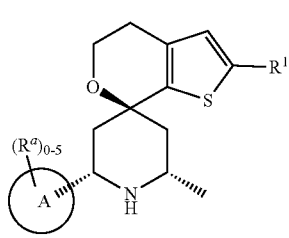
Formula Va′

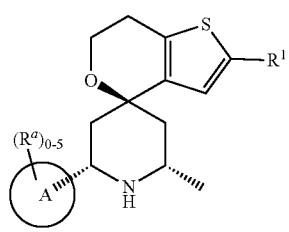
Formula Vb′ a tautomer thereof, a deuterated derivative of that compound or tautomer, or a pharmaceutically acceptable salt of any of the foregoing; and all other variables not specifically defined herein are as defined in any one of the foregoing embodiments.

31. A compound selected from the compounds of Table I, tautomers thereof, deuterated derivative of those compounds and tautomers, and pharmaceutically acceptable salts of any of the foregoing.

32. A compound selected from the compounds of Table II, tautomers thereof, deuterated derivative of those compounds and tautomers, and pharmaceutically acceptable salts of any of the foregoing.

33. A compound selected from the compounds of Table III, tautomers thereof, deuterated derivative of those compounds and tautomers, and pharmaceutically acceptable salts of any of the foregoing.

34. A pharmaceutical composition comprising at least one compound, tautomer, deuterated derivative, or pharmaceutically acceptable salt according to any one of Embodiments 1 to 33 and a pharmaceutically acceptable carrier.

35. A method of treating focal segmental glomerulosclerosis and/or non-diabetic kidney disease comprising administering to a patient in need thereof at least one compound according to any one of Embodiments 1 to 33 or a pharmaceutical composition according to Embodiment 34.

36. Use of at least one compound, tautomer, deuterated derivative, or pharmaceutically acceptable salt according to any one of Embodiments 1 to 33 or a pharmaceutical composition according to Embodiment 34 for the manufacture of a medicament for treating focal segmental glomerulosclerosis and/or non-diabetic kidney disease.

37. At least one compound, tautomer, deuterated derivative, or pharmaceutically acceptable salt according to any one of Embodiments 1 to 33 or a pharmaceutical composition according to Embodiment 34 for use in treating focal segmental glomerulosclerosis and/or non-diabetic kidney disease.

38. A method of inhibiting APOL1 activity comprising contacting said APOL1 with at least one compound, tautomer, deuterated derivative, or pharmaceutically acceptable salt according to any one of Embodiments 1 to 33 or a pharmaceutical composition according to Embodiment 34.

39. Use of at least one compound, tautomer, deuterated derivative, or pharmaceutically acceptable salt according to any one of Embodiments 1 to 33 or a pharmaceutical composition according to Embodiment 34 for the manufacture of a medicament for inhibiting APOL1 activity.

40. At least one compound, tautomer, deuterated derivative, or pharmaceutically acceptable salt according to any one of Embodiments 1 to 33 or a pharmaceutical composition according to Embodiment 34 for use in inhibiting APOL1 activity.

41. A method of treating an APOL1-mediated disease (e.g., an APOL1-mediated kidney disease) comprising administering to a patient in need thereof at least one compound according to any one of Embodiments 1 to 33 or a pharmaceutical composition according to Embodiment 34.

42. The method according to Embodiment 41, wherein the APOL1-mediated disease is cancer.

43. The method according to Embodiment 41 or Embodiment 42, wherein the APOL1-mediated disease is pancreatic cancer.

44. Use of at least one compound, tautomer, deuterated derivative, or pharmaceutically acceptable salt according to any one of Embodiments 1 to 33 or a pharmaceutical composition according to Embodiment 34 for the manufacture of a medicament for treating an APOL1-mediated disease (e.g., an APOL1-mediated kidney disease).

45. The use according to Embodiment 44, wherein the APOL1-mediated disease is cancer.

46. The use according to Embodiment 44 or Embodiment 45, wherein the APOL1-mediated disease is pancreatic cancer.

47. At least one compound, tautomer, deuterated derivative, or pharmaceutically acceptable salt according to any one of Embodiments 1 to 33 or a pharmaceutical composition according to Embodiment 34 for use in treating an APOL1-mediated disease (e.g., an APOL1-mediated kidney disease).

48. The at least one compound, tautomer, deuterated derivative, or pharmaceutically acceptable salt for use or the pharmaceutical composition for use according to Embodiment 47, wherein the APOL1-mediated disease is cancer.

49. The at least one compound, tautomer, deuterated derivative, or pharmaceutically acceptable salt for use or the pharmaceutical composition for use according to Embodiment 47 or Embodiment 48, wherein the APOL1-mediated disease is pancreatic cancer.

50. A method of inhibiting APOL1 activity comprising contacting said APOL1 with at least one compound, tautomer, deuterated derivative, or pharmaceutically acceptable salt according to any one of Embodiments 1 to 33 or a pharmaceutical composition according to Embodiment 34.

51. Use of at least one compound, tautomer, deuterated derivative, or pharmaceutically acceptable salt according to any one of Embodiments 1 to 33 or a pharmaceutical composition according to Embodiment 34 for the manufacture of a medicament for inhibiting APOL1 activity.

52. At least one compound, tautomer, deuterated derivative, or pharmaceutically acceptable salt according to any one of Embodiments 1 to 33 or a pharmaceutical composition according to Embodiment 34 for use in inhibiting APOL1 activity.

53. A silicon derivative of the at least one compound, tautomer, deuterated derivative, or pharmaceutically acceptable salt according to any one of Embodiments 1 to 33.
54. A pharmaceutical composition comprising a silicon derivative of Embodiment 53.
55. A method of treating focal segmental glomerulosclerosis and/or non-diabetic kidney disease comprising administering to a patient in need thereof a silicon derivative according to Embodiment 53 or a pharmaceutical composition according to Embodiment 54.
56. Use of the silicon derivative according to Embodiment 53 or a pharmaceutical composition according to Embodiment 54 for the manufacture of a medicament for treating focal segmental glomerulosclerosis and/or non-diabetic kidney disease.
57. The silicon derivative according to Embodiment 53 or a pharmaceutical composition according to Embodiment 54 for use in treating focal segmental glomerulosclerosis and/or non-diabetic kidney disease.
58. A method of treating an APOL1-mediated disease (e.g., an APOL1-mediated kidney disease) comprising administering to a patient in need thereof a silicon derivative according to Embodiment 53 or a pharmaceutical composition according to Embodiment 54.
59. The method according to Embodiment 58, wherein the APOL1-mediated disease is cancer.
60. The method according to Embodiment 58 or Embodiment 59, wherein the APOL1-mediated disease is pancreatic cancer.
61. Use of the silicon derivative according to Embodiment 53 or a pharmaceutical composition according to Embodiment 54 for the manufacture of a medicament for treating an APOL1-mediated disease (e.g., an APOL1-mediated kidney disease).
62. The use according to Embodiment 61, wherein the APOL1-mediated disease is cancer.
63. The use according to Embodiment 61 or Embodiment 62, wherein the APOL1-mediated disease is pancreatic cancer.
64. The silicon derivative according to Embodiment 53 or a pharmaceutical composition according to Embodiment 54 for use in treating an APOL1-mediated disease (e.g., an APOL1-mediated kidney disease).
65. The silicon derivative or pharmaceutical composition for use according to Embodiment 64, wherein the APOL1-mediated disease is cancer.
66. The silicon derivative or pharmaceutical composition for use according to Embodiment 64 or Embodiment 65, wherein the APOL1-mediated disease is pancreatic cancer.
67. A boron derivative of the at least one compound, tautomer, deuterated derivative, or pharmaceutically acceptable salt according to any one of Embodiments 1 to 33.
68. A pharmaceutical composition comprising a boron derivative of Embodiment 67.
69. A method of treating focal segmental glomerulosclerosis and/or non-diabetic kidney disease comprising administering to a patient in need thereof a boron derivative according to Embodiment 67 or a pharmaceutical composition according to Embodiment 68.
70. Use of the boron derivative according to Embodiment 67 or a pharmaceutical composition according to Embodiment 68 for the manufacture of a medicament for treating focal segmental glomerulosclerosis and/or non-diabetic kidney disease.
71. The boron derivative according to Embodiment 67 or a pharmaceutical composition according to Embodiment 68 for use in treating focal segmental glomerulosclerosis and/or non-diabetic kidney disease.
72. A method of treating an APOL1-mediated disease (e.g., an APOL1-mediated kidney disease) comprising administering to a patient in need thereof a boron derivative according to Embodiment 67 or a pharmaceutical composition according to Embodiment 68.
73. The method according to Embodiment 72, wherein the APOL1-mediated disease is cancer.
74. The method according to Embodiment 72 or Embodiment 73, wherein the APOL1-mediated disease is pancreatic cancer.
75. Use of the boron derivative according to Embodiment 67 or a pharmaceutical composition according to Embodiment 68 for the manufacture of a medicament for treating an APOL1-mediated disease (e.g., an APOL1-mediated kidney disease).
76. The use according to Embodiment 75, wherein the APOL1-mediated disease is cancer.
77. The use according to Embodiment 75 or Embodiment 76, wherein the APOL1-mediated disease is pancreatic cancer.
78. The boron derivative according to Embodiment 67 or a pharmaceutical composition according to Embodiment 68 for use in treating an APOL1-mediated disease (e.g., an APOL1-mediated kidney disease).
79. The boron derivative or pharmaceutical composition for use according to Embodiment 78, wherein the APOL1-mediated disease is cancer.
80. The boron derivative or pharmaceutical composition for use according to Embodiment 78 or Embodiment 79, wherein the APOL1-mediated disease is pancreatic cancer.
81. A phosphorus derivative of at least one compound, tautomer, deuterated derivative or pharmaceutically acceptable salt according to any one of Embodiments 1 to 33.
82. A pharmaceutical composition comprising a phosphorus derivative of Embodiment 81.
83. A method of treating focal segmental glomerulosclerosis and/or non-diabetic kidney disease comprising administering to a patient in need thereof a phosphorus derivative according to Embodiment 81 or a pharmaceutical composition according to Embodiment 82.
84. Use of the phosphorus derivative according to Embodiment 81 or a pharmaceutical composition according to Embodiment 82 for the manufacture of a medicament for treating focal segmental glomerulosclerosis and/or non-diabetic kidney disease.
85. The phosphorus derivative according to Embodiment 81 or a pharmaceutical composition according to Embodiment 82 for use in treating focal segmental glomerulosclerosis and/or non-diabetic kidney disease.
86. A method of treating an APOL1-mediated disease (e.g., an APOL1-mediated kidney disease) comprising administering to a patient in need thereof a phosphorus derivative according to Embodiment 81 or a pharmaceutical composition according to Embodiment 82.
87. The method according to Embodiment 86, wherein the APOL1-mediated disease is cancer.
88. The method according to Embodiment 86 or Embodiment 87, wherein the APOL1-mediated disease is pancreatic cancer.
89. Use of the phosphorus derivative according to Embodiment 81 or a pharmaceutical composition according to Embodiment 82 for the manufacture of a medicament for treating an APOL1-mediated disease (e.g., an APOL1-mediated kidney disease).

90. The use according to Embodiment 89, wherein the APOL1-mediated disease is cancer.

91. The use according to Embodiment 89 or Embodiment 90, wherein the APOL1-mediated disease is pancreatic cancer.

92. The phosphorus derivative according to Embodiment 81 or a pharmaceutical composition according to Embodiment 82 for use in treating an APOL1-mediated disease (e.g., an APOL1-mediated kidney disease).

93. The phosphorus derivative or pharmaceutical composition for use according to Embodiment 92, wherein the APOL1-mediated disease is cancer.

94. The phosphorus derivative or pharmaceutical composition for use according to Embodiment 92 or Embodiment 93, wherein the APOL1-mediated disease is pancreatic cancer.

95. A method of treating a patient; an entity (e.g., a compound, tautomer, deuterated derivative, pharmaceutically acceptable salt, silicon derivative, boron derivative, phosphorus derivative) or pharmaceutical composition for use in treating a patient; or use of an entity or pharmaceutical composition in treating a patient as described in any embodiment herein, wherein the patient has 2 APOL1 risk alleles.

96. A method of treating a patient; an entity (e.g., a compound, tautomer, deuterated derivative, pharmaceutically acceptable salt, silicon derivative, boron derivative, phosphorus derivative) or pharmaceutical composition for use in treating a patient; or use of an entity or pharmaceutical composition in treating a patient as described in any embodiment herein, wherein the patient has 1 APOL1 risk allele.

97. The compound according to Embodiment 1, wherein the compound is represented by one of the following structural formulae:

Formula IIa″
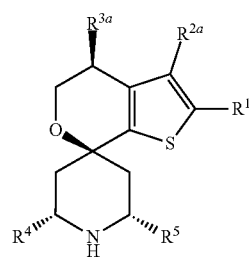

Formula IIb″
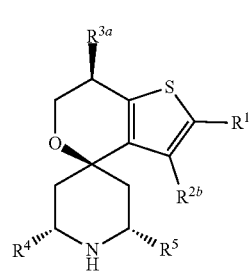

-continued

Formula IIIa″
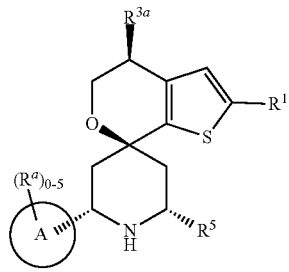

Formula IIIb″
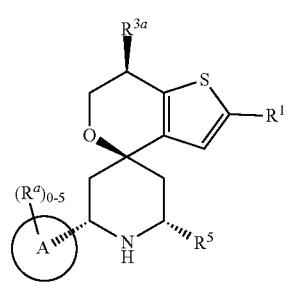

Formula IVa″
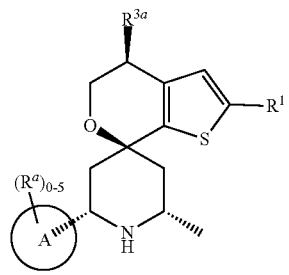

Formula IVb″
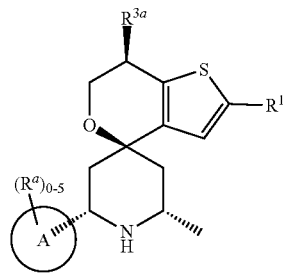

a tautomer thereof, a deuterated derivative of that compound or tautomer, or a pharmaceutically acceptable salt of any of the foregoing; and all other variables not specifically defined herein are as defined in any one of the foregoing embodiments.

98. The compound according to Embodiment 1, wherein the compound is represented by one of the following structural formulae:

Formula IIa''' 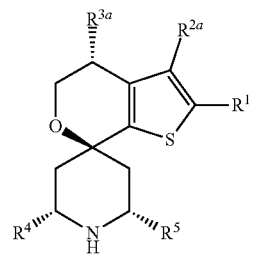

Formula IIb''' 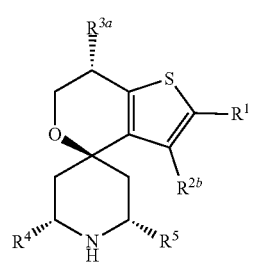

Formula IIIa''' 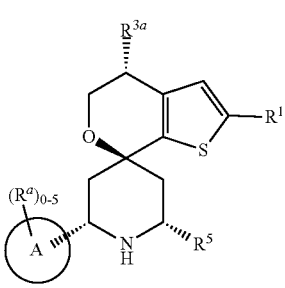

Formula IIIb''' 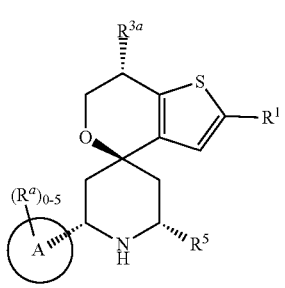

Formula IVa''' 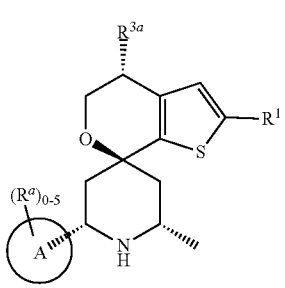

Formula IVb''' 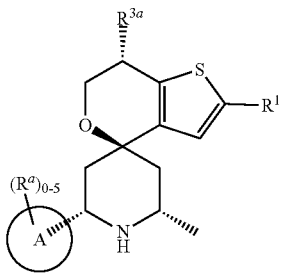

a tautomer thereof, a deuterated derivative of that compound or tautomer, or a pharmaceutically acceptable salt of any of the foregoing; and all other variables not specifically defined herein are as defined in any one of the foregoing embodiments.

99. A pharmaceutical composition comprising at least one compound, tautomer, deuterated derivative, or pharmaceutically acceptable salt according to Embodiment 97 or Embodiment 98 and a pharmaceutically acceptable carrier.

100. A method of treating focal segmental glomerulosclerosis and/or non-diabetic kidney disease comprising administering to a patient in need thereof at least one compound, tautomer, deuterated derivative, or pharmaceutically acceptable salt according to Embodiment 97 or Embodiment 98 or a pharmaceutical composition according to Embodiment 99.

101. Use of at least one compound, tautomer, deuterated derivative, or pharmaceutically acceptable salt according to according to Embodiment 97 or Embodiment 98 or a pharmaceutical composition according to Embodiment 99 for the manufacture of a medicament for treating focal segmental glomerulosclerosis and/or non-diabetic kidney disease.

102. At least one compound, tautomer, deuterated derivative, or pharmaceutically acceptable salt according to Embodiment 97 or Embodiment 98 or a pharmaceutical composition according to Embodiment 99 for use in treating focal segmental glomerulosclerosis and/or non-diabetic kidney disease.

103. A method of inhibiting APOL1 activity comprising contacting said APOL1 with at least one compound, tautomer, deuterated derivative, or pharmaceutically acceptable salt according to Embodiment 97 or Embodiment 98 or a pharmaceutical composition according to Embodiment 99.

104. Use of at least one compound, tautomer, deuterated derivative, or pharmaceutically acceptable salt according to Embodiment 97 or Embodiment 98 or a pharmaceutical composition according to Embodiment 99 for the manufacture of a medicament for inhibiting APOL1 activity.

105. At least one compound, tautomer, deuterated derivative, or pharmaceutically acceptable salt according to Embodiment 97 or Embodiment 98 or a pharmaceutical composition according to Embodiment 99 for use in inhibiting APOL1 activity.

106. A method of treating an APOL1-mediated disease (e.g., an APOL1-mediated kidney disease) comprising administering to a patient in need thereof at least one compound, tautomer, deuterated derivative, or pharmaceutically acceptable salt according to Embodiment 97 or Embodiment 98 or a pharmaceutical composition according to Embodiment 99.

107. The method according to Embodiment 106, wherein the APOL1-mediated disease is cancer.

108. The method according to Embodiment 106 or Embodiment 107, wherein the APOL1-mediated disease is pancreatic cancer.

109. Use of at least one compound, tautomer, deuterated derivative, or pharmaceutically acceptable salt according to Embodiment 97 or Embodiment 98 or a pharmaceutical composition according to Embodiment 99 for the manufacture of a medicament for treating an APOL1-mediated disease (e.g., an APOL1-mediated kidney disease).

110. The use according to Embodiment 109, wherein the APOL1-mediated disease is cancer.

111. The use according to Embodiment 109 or Embodiment 110, wherein the APOL1-mediated disease is pancreatic cancer.

112. At least one compound, tautomer, deuterated derivative, or pharmaceutically acceptable salt according to Embodiment 97 or Embodiment 98 or a pharmaceutical composition according to Embodiment 99 for use in treating an APOL1-mediated disease (e.g., an APOL1-mediated kidney disease).

113. The at least one compound, tautomer, deuterated derivative, or pharmaceutically acceptable salt for use or the pharmaceutical composition for use according to Embodiment 112, wherein the APOL1-mediated disease is cancer.

114. The at least one compound, tautomer, deuterated derivative, or pharmaceutically acceptable salt for use or the pharmaceutical composition for use according to Embodiment 112 or Embodiment 113, wherein the APOL1-mediated disease is pancreatic cancer.

115. A method of inhibiting APOL1 activity comprising contacting said APOL1 with at least one compound, tautomer, deuterated derivative, or pharmaceutically acceptable salt according to Embodiment 97 or Embodiment 98 or a pharmaceutical composition according to Embodiment 99.

116. Use of at least one compound, tautomer, deuterated derivative, or pharmaceutically acceptable salt according to Embodiment 97 or Embodiment 98 or a pharmaceutical composition according to Embodiment 99 for the manufacture of a medicament for inhibiting APOL1 activity.

117. At least one compound, tautomer, deuterated derivative, or pharmaceutically acceptable salt according to Embodiment 97 or Embodiment 98 or a pharmaceutical composition according to Embodiment 99 for use in inhibiting APOL1 activity.

Non-Limiting Exemplary Embodiments 2

Without limitation, some embodiments/clauses of the present disclosure include:

1. A compound represented by the following structural formula:

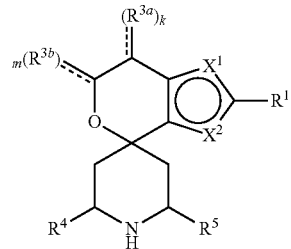

Formula $I_0$ a tautomer thereof, a deuterated derivative of that compound or tautomer, or a pharmaceutically acceptable salt of any of the foregoing, wherein:

$X^1$ and $X^2$ are each selected from S and $-CR^2$, wherein:

one of $X^1$ and $X^2$ is S;

when $X^1$ is S, then $X^2$ is $-CR^{2b}$; and when $X^2$ is S, then $X^1$ is $-CR^{2a}$;

$R^1$ is selected from halogen, cyano, $C_1$-$C_6$ alkyl, $C_1$-$C_6$ alkoxy, $C_3$-$C_6$ cycloalkyl, and phenyl; wherein:

the $C_1$-$C_6$ alkyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl$)_2$, and $C_1$-$C_4$ alkoxy;

the $C_1$-$C_6$ alkoxy of $R^1$ is optionally substituted with 1 to 3 groups independently selected from halogen;

the $C_3$-$C_6$ cycloalkyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl$)_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl$)_2$; and the phenyl of $R^1$ is optionally substituted with 1 to 3 groups independently selected from halogen, cyano, $-OH$, $-NH_2$, $-NH(C_1$-$C_4$ alkyl), $-N(C_1$-$C_4$ alkyl$)_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl$)_2$;

$R^{2a}$ is selected from hydrogen, halogen, cyano, $-OH$, $=O$, and $C_1$-$C_6$ alkyl; wherein:

the $C_1$-$C_6$ alkyl of $R^{2a}$ is optionally substituted with 1 to 3 groups independently selected from halogen, cyano, $-OH$, and $C_1$-$C_4$ alkoxy;

$R^{2b}$ is selected from hydrogen, halogen, cyano, $-OH$, $=O$, and $C_1$-$C_6$ alkyl;

$R^{3a}$ is selected from halogen, cyano, $-OH$, $C_1$-$C_6$ alkyl, and $=O$; wherein:

the $C_1$-$C_6$ alkyl of $R^{3a}$ is optionally substituted with 1 to 3 groups independently selected from halogen, cyano, and $-OH$;

$R^{3b}$ is selected from $C_1$-$C_2$ alkyl and $=O$; wherein:

the $C_1$-$C_2$ alkyl of $R^3$ is optionally substituted with 1 to 3 groups independently selected from halogen, cyano, and $-OH$;

$\text{-----}$, for each occurrence, is a single bond when $R^{3a}$ is selected from halogen, cyano, $-OH$, $C_1$-$C_6$ alkyl or when $R^3$ is selected from $C_1$-$C_2$ alkyl; or alternatively $\text{=====}$, for each occurrence, is a double bond when $R^{3a}$ is $=O$ or when $R^3$ is $=O$;

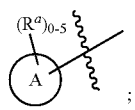

R⁴ is selected from $C_1$-$C_6$ alkyl and; wherein:
  the $C_1$-$C_6$ alkyl of R⁴ is optionally substituted with 1 to 3 groups independently selected from halogen, cyano, —OH, —NH₂, —NH($C_1$-$C_4$ alkyl), —N($C_1$-$C_4$ alkyl)₂, $C_1$-$C_4$ alkoxy, —C(=O)NH₂, —C(=O)NH($C_1$-$C_4$ alkyl), —C(=O)N($C_1$-$C_4$ alkyl)₂, $C_3$-$C_6$ cycloalkyl, 5 to 10-membered heterocyclyl, phenyl, and 5 to 10-membered heteroaryl;
  Ring A is selected from $C_3$-$C_{12}$ carbocyclyl, 3 to 12-membered heterocyclyl, $C_6$ and $C_{10}$ aryl, and 5 to 10-membered heteroaryl, wherein Ring A is optionally substituted with 1, 2, 3, 4, or 5 $R^a$ groups; wherein:
    $R^a$, for each occurrence, is independently selected from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^hC(=O)R^i$, —$NR^hC(=O)OR^i$, —$NR^hC(=O)NR^iR^j$, —$NR^hS(=O)_pR$, —$OR^k$, —OC(=O)R, —OC(=O)$OR^k$, —OC(=O)$NR^hR^i$, —[O(CH₂)$_q$]$_r$O($C_1$-$C_6$ alkyl), —S(=O)$_pR^k$, —S(=O)$_pNR^hR^i$, $C_3$-$C_{12}$ carbocyclyl, 3 to 12-membered heterocyclyl, $C_6$ and $C_{10}$ aryl, and 5 to 10-membered heteroaryl; wherein:
      the $C_1$-$C_6$ alkyl and the $C_2$-$C_6$ alkenyl of $R^a$ are optionally substituted with 1 to 3 groups independently selected from cyano, —C(=O)$R^k$, —C(=O)$OR^k$, —C(=O)$NR^hR^i$, —$NR^hR^i$, —$NR^hC(=O)R^k$, —$NR^hC(=O)OR^k$, —$NR^hC(=O)NR^iR^j$, —$NR^hS(=O)_pR^k$, —$OR^k$, —OC(=O)$R^k$, —OC(=O)$OR^k$, —OC(=O)$NR^hR^i$, —S(=O)$_pR^k$, —S(=O)$_pNR^hR^i$, and $C_3$-$C_6$ cycloalkyl;
      the $C_3$-$C_{12}$ carbocyclyl, the 3 to 12-membered heterocyclyl, the $C_6$ and $C_{10}$ aryl, and the 5 to 10-membered heteroaryl of $R^a$ are each optionally substituted with 1 to 3 groups selected from halogen, cyano, $C_1$-$C_4$ alkyl, —$NR^hR^i$, and —$OR^k$; wherein:
        $R^h$, $R^i$, and $R^j$, for each occurrence, are each independently selected from hydrogen, $C_1$-$C_4$ alkyl, and $C_3$-$C_6$ cycloalkyl; wherein:
          the $C_1$-$C_4$ alkyl of any one of $R^h$, $R^i$, and $R^j$ is optionally substituted with 1 to 3 groups independently selected from halogen, cyano, and —OH;
        $R^k$, for each occurrence, are each independently selected from hydrogen, $C_1$-$C_4$ alkyl, and $C_3$-$C_6$ cycloalkyl; wherein:
          the $C_1$-$C_4$ alkyl of any one of $R^k$ is optionally substituted with 1 to 3 groups independently selected from halogen, cyano, and —OH;
  R⁵ is selected from $C_1$-$C_6$ alkyl, —C(=O)O($C_1$-$C_4$ alkyl), $C_3$-$C_{12}$ carbocyclyl, 3 to 12-membered heterocyclyl, $C_6$ and $C_{10}$ aryl, and 5 to 10-membered heteroaryl; wherein:
    the $C_1$-$C_6$ alkyl of R⁵ is optionally substituted with 1 to 3 groups selected from halogen, cyano, —OH, —NH₂, —NH($C_1$-$C_4$ alkyl), —N($C_1$-$C_4$ alkyl)₂, $C_1$-$C_4$ alkoxy, —C(=O)NH₂, —C(=O)NH($C_1$-$C_4$ alkyl), and —C(=O)N($C_1$-$C_4$ alkyl)₂;
    the $C_3$-$C_{12}$ carbocyclyl, the 3 to 12-membered heterocyclyl, the $C_6$ and $C_{10}$ aryl, and the 5 to 10-membered heteroaryl of R⁵ are each optionally substituted with 1 to 3 groups selected from halogen, cyano, —OH, —NH₂, —NH($C_1$-$C_4$ alkyl), —N($C_1$-$C_4$ alkyl)₂, $C_1$-$C_4$ alkyl, $C_1$-$C_4$ alkoxy, —C(=O)NH₂, —C(=O)NH($C_1$-$C_4$ alkyl), and —C(=O)N($C_1$-$C_4$ alkyl)₂;
  k is an integer selected from 0, 1, and 2 when $R^{3a}$ is selected from halogen, cyano, —OH, $C_1$-$C_6$ alkyl; or alternatively k is an integer selected from 0 and 1 when $R^{3a}$ is =O;
  m is an integer selected from 0, 1, and 2 when $R^{3A}$ is selected from $C_1$-$C_2$ alkyl; and when $R^{3b}$ is =O, m is an integer selected from 0 and 1;
  p is an integer selected from 1 and 2; and
  q and r are each an integer selected from 1, 2, 3, and 4.

2. The compound, tautomer, deuterated derivative, or pharmaceutically acceptable salt according to Clause 1, wherein the compound is represented by one of the following structural formulae:

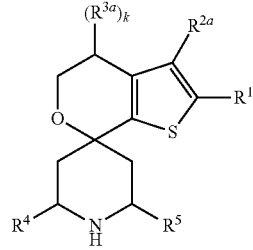

Formula IIa₀

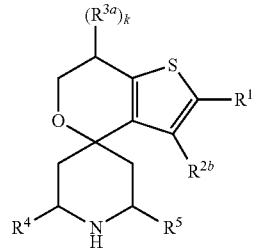

Formula IIb₀ or is a tautomer thereof, a deuterated derivative of that compound or tautomer, or a
pharmaceutically acceptable salt of any of the foregoing, wherein:
  $R^{2a}$ is selected from hydrogen, halogen, cyano, and $C_1$-$C_4$ alkyl; wherein:
    the $C_1$-$C_4$ alkyl of $R^{2a}$ is optionally substituted with 1 to 3 groups selected from halogen, —OH, and $C_1$-$C_2$ alkoxy;
  $R^{2b}$ is selected from hydrogen, halogen, cyano, and $C_1$-$C_4$ alkyl; and
  k is an integer selected from 0, 1, and 2;
and all other variables not specifically defined herein are as defined in Clause 1.

3. The compound, tautomer, deuterated derivative, or pharmaceutically acceptable salt according to Clause 1 or Clause 2, wherein R⁴ is selected from $C_1$-$C_4$ alkyl and

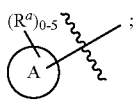

wherein:
the $C_1$-$C_4$ alkyl of $R^4$ is optionally substituted with 1 to 3 groups selected from halogen, cyano, —OH, —NH$_2$, —NH($C_1$-$C_4$ alkyl), —N($C_1$-$C_4$ alkyl)$_2$, $C_1$-$C_2$ alkoxy, $C_3$-$C_6$ cycloalkyl, 5 to 6-membered heterocyclyl, phenyl, and 5 to 6-membered heteroaryl;

and all other variables not specifically defined herein are as defined in Clause 1 or Clause 2.

4. The compound, tautomer, deuterated derivative, or pharmaceutically acceptable salt according to any one of Clauses 1 to 3, wherein $R^4$ is selected from $C_1$-$C_2$ alkyl and

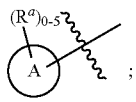

wherein:
the $C_1$-$C_2$ alkyl of $R^4$ is optionally substituted with 1 to 3 groups selected from halogen, cyano, —OH, and 5 to 6-membered heterocyclyl;

and all other variables not specifically defined herein are as defined in any one of Clauses 1 to 3.

5. The compound, tautomer, deuterated derivative, or pharmaceutically acceptable salt according to any one of Clauses 1 to 4, wherein $R^4$ is selected from —CH$_3$, —CH$_2$OH, and (tetrahydro-2H-pyran-4-yl)methyl; and all other variables not specifically defined herein are as defined in any one of Clauses 1 to 4.

6. The compound according to any one of Clauses 1 to 4, wherein the compound is represented by one of the following structural formulae:

Formula IIIa$_0$

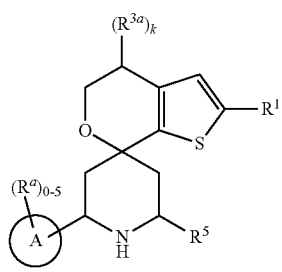

Formula IIIb$_0$

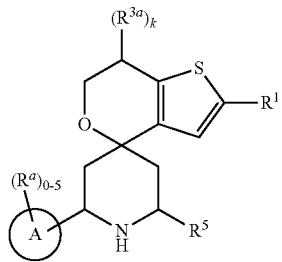

a tautomer thereof, a deuterated derivative of that compound or tautomer, or a
pharmaceutically acceptable salt of the foregoing, wherein:
Ring A, for each occurrence, is selected from $C_3$-$C_6$ cycloalkyl, 5 to 10-membered heterocyclyl, phenyl, and 5 to 10-membered heteroaryl; each of which is optionally substituted with 1, 2, 3, 4, or 5 $R^a$ groups;
and all other variables not specifically defined herein are as defined in any one of Clauses 1 to 5.

7. The compound, tautomer, deuterated derivative, or pharmaceutically acceptable salt according to any one of Clauses 1 to 4 and 6, wherein Ring A is selected from cyclopropyl, 5 to 10-membered heterocyclyl, phenyl, and 5 to 9-membered heteroaryl; each of which is optionally substituted with 1, 2, 3, 4, or 5 $R^a$ groups; and all other variables not specifically defined herein are as defined in any one of Clauses 1 to 6.

8. The compound, tautomer, deuterated derivative, or pharmaceutically acceptable salt according to any one of Clauses 1 to 4, 6, and 7, wherein Ring A is selected from cyclopropyl, 5 to 10-membered heterocyclyl containing 1 to 3 heteroatoms selected from N and O, phenyl, and 5 to 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of Clauses 1 to 7.

9. The compound, tautomer, deuterated derivative, or pharmaceutically acceptable salt according to any one of Clauses 1 to 4 and 6 to 8, wherein Ring A is selected from cyclopropyl, 5-membered heterocyclyl containing 1 to 3 heteroatoms selected from N and O, 6-membered heterocyclyl containing 1 to 3 heteroatoms selected from N and O, 9-membered heterocyclyl containing 1 to 3 heteroatoms selected from N and O, 10-membered heterocyclyl containing 1 to 3 heteroatoms selected from N and O, phenyl, 5-membered heteroaryl containing 1 to 3 heteroatoms selected from N and O, 6-membered heteroaryl containing 1 to 3 heteroatoms selected from N and O, and 9-membered heteroaryl containing 1 to 3 heteroatoms selected from N and O; each of which is optionally substituted with 1, 2, 3, 4, or 5 $R^a$ groups; and all other variables not specifically defined herein are as defined in any one of Clauses 1 to 8.

10. The compound, tautomer, deuterated derivative, or pharmaceutically acceptable salt according to any one of Clauses 1 to 4 and 6 to 9, wherein Ring A is selected from

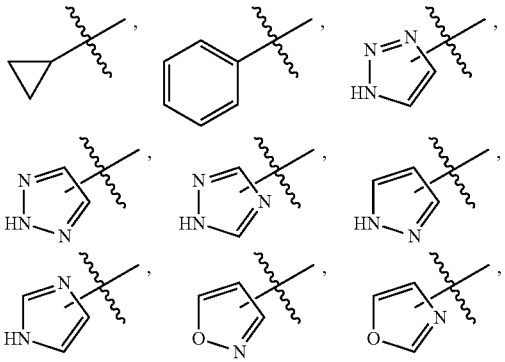

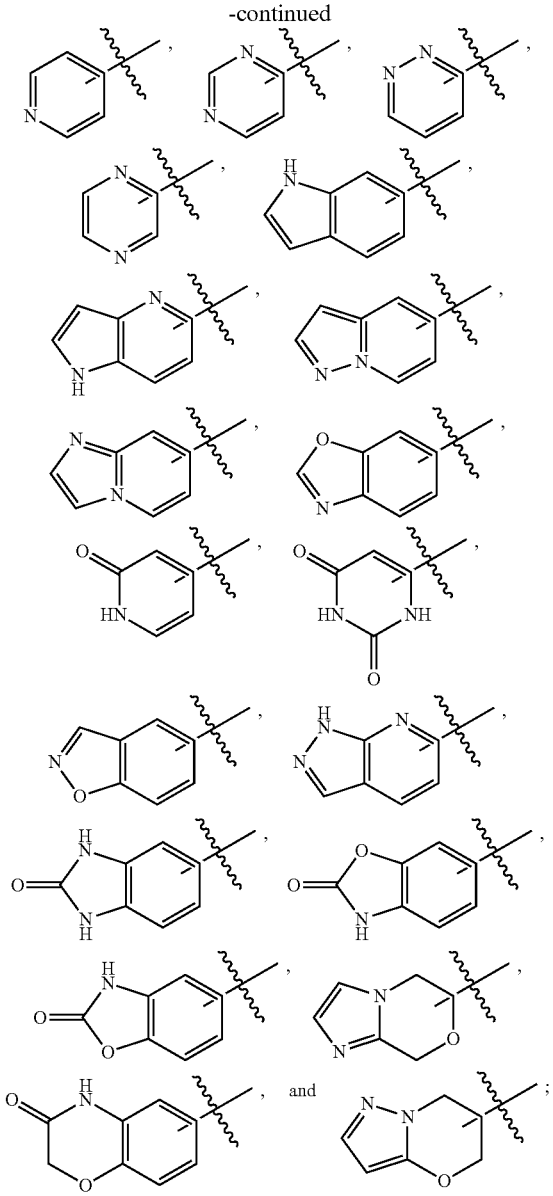
each of which is optionally substituted with 1, 2, 3, 4, or 5 $R^a$ groups; and all other variables not specifically defined herein are as defined in any one of Clauses 1 to 9.
11. The compound, tautomer, deuterated derivative, or pharmaceutically acceptable salt according to any one of Clauses 1 to 4 and 6 to 10, wherein Ring A is selected from
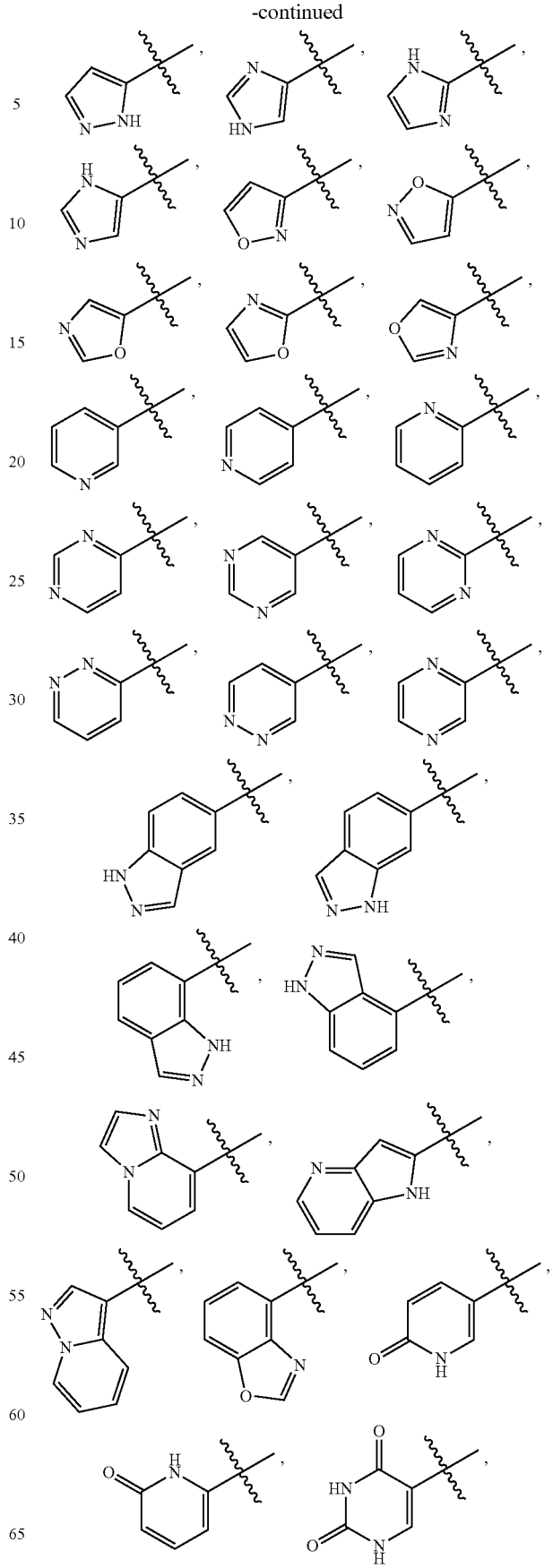

-continued

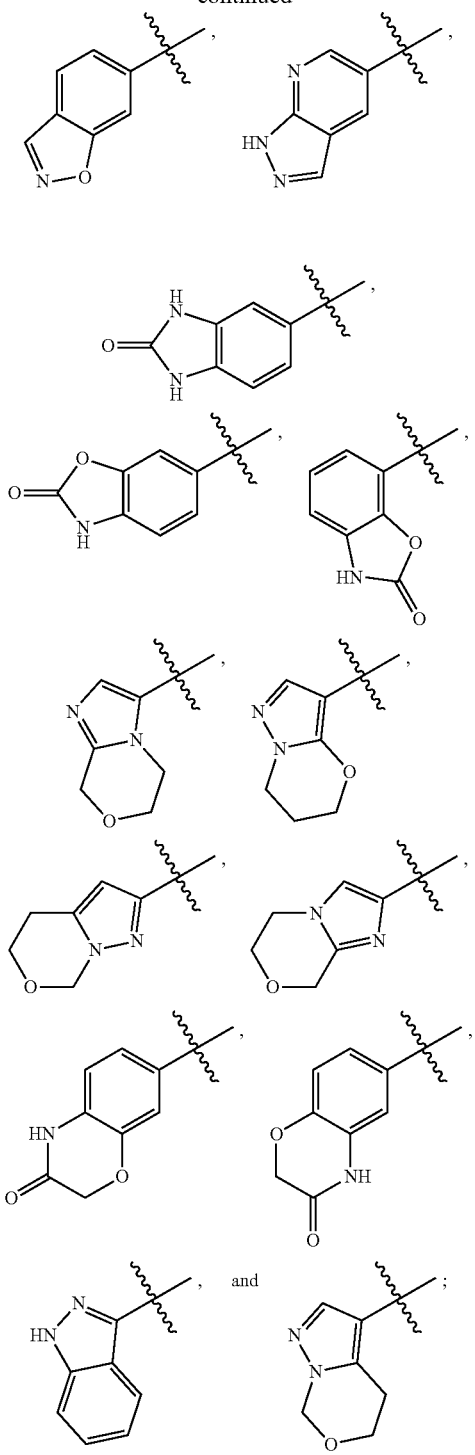

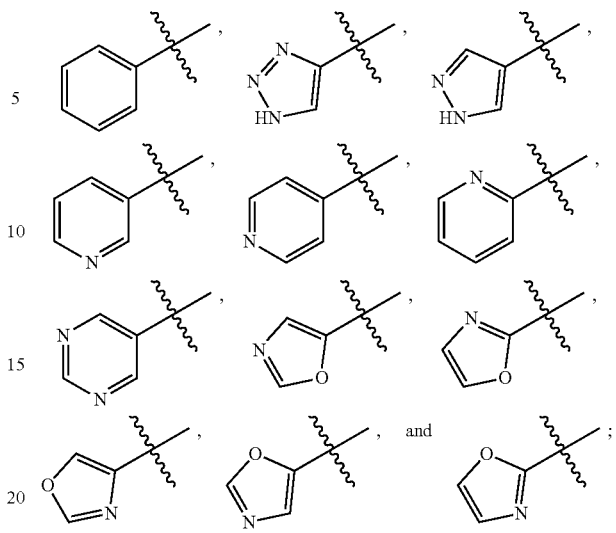

each of which is optionally substituted with 1, 2, 3, 4, or 5 $R^a$ groups; and all other variables not specifically defined herein are as defined in any one of Clauses 1 to 4 and 6 to 10.

12. The compound, tautomer, deuterated derivative, or pharmaceutically acceptable salt according to any one of Clauses 1 to 4 and 6 to 11, wherein $R^4$ is selected from —$CH_3$ and Ring A; wherein Ring A is selected from each of which is optionally substituted with 1, 2, 3, 4, or 5 $R^a$ groups; and all other variables not specifically defined herein are as defined in any one of Clauses 1 to 4 and 6 to 11.

13. The compound, tautomer, deuterated derivative, or pharmaceutically acceptable salt according to any one of Clauses 1 to 12, wherein $R^5$ is selected from $C_1$-$C_4$ alkyl, —C(=O)O($C_1$-$C_2$ alkyl), $C_3$-$C_6$ cycloalkyl, and 5 to 10-membered heterocyclyl; wherein:
the $C_1$-$C_4$ alkyl of $R^5$ is optionally substituted with 1 to 3 groups selected from halogen, cyano, —OH, and $C_1$-$C_2$ alkoxy; and
the $C_3$-$C_6$ cycloalkyl and the 5 to 10-membered heterocyclyl of $R^5$ are each optionally substituted with 1 to 3 groups selected from halogen, cyano, —OH, $C_1$-$C_2$ alkyl, and $C_1$-$C_2$ alkoxy;
and all other variables not specifically defined herein are as defined in any one of Clauses 1 to 12.

14. The compound, tautomer, deuterated derivative, or pharmaceutically acceptable salt according to any one of Clauses 1 to 13, wherein $R^5$ is selected from $C_1$-$C_2$ alkyl, C(=O)O($C_1$-$C_2$ alkyl), cyclopropyl, cyclobutyl, and 5 to 6-membered heterocyclyl; wherein:
the $C_1$-$C_2$ alkyl of $R^5$ is optionally substituted with 1 to 3 groups selected from F, Cl, Br, cyano, —OH, and $C_1$-$C_2$ alkoxy; and
the cyclopropyl, the cyclobutyl, and the 5 to 6-membered heterocyclyl of $R^5$ are each optionally substituted with 1 to 3 groups selected from F, Cl, Br, cyano, —OH, $C_1$-$C_2$ alkyl, and $C_1$-$C_2$ alkoxy;
and all other variables not specifically defined herein are as defined in any one of Clauses 1 to 13.

15. The compound, tautomer, deuterated derivative, or pharmaceutically acceptable salt according to any one of Clauses 1 to 14, wherein $R^5$ is selected from —$CH_3$, —$CH_2CH_3$, —$CH_2OH$, —C(=O)O$CH_3$, —$CH_2OCH_3$, —CH($CH_3$)$_2$, cyclopropyl, difluorocyclopropyl, and tetrahydro-2H-pyranyl; and all other variables not specifically defined herein are as defined in any one of Clauses 1 to 14.

16. The compound according to any one of Clauses 1 to 4 and 6 to 15, wherein the compound is represented by one of the following structural formulae:

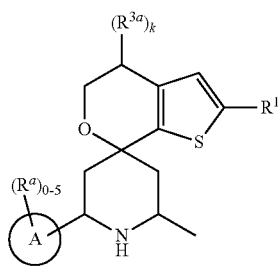

Formula IVa₀

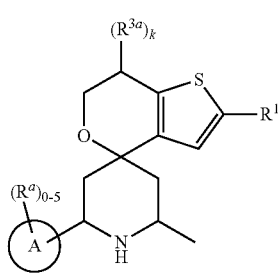

Formula IVb₀ a tautomer thereof, a deuterated derivative of that compound or tautomer, or a pharmaceutical y acceptable salt of the foregoing; and all other variables not specifically defined herein are as defined in any one of Clauses 1 to 4 and 6 to 15.

17. The compound, tautomer, deuterated derivative, or pharmaceutically acceptable salt according to any one of Clauses 1 to 16, wherein $R^1$ is selected from hydrogen, halogen, cyano, —OH, $C_1$-$C_4$ alkyl, $C_1$-$C_4$ alkoxy, and $C_3$-$C_6$ cycloalkyl; wherein:
the $C_1$-$C_4$ alkyl of $R^1$ is optionally substituted with 1 to 3 groups selected from halogen, cyano, —OH, and $C_1$-$C_2$ alkoxy;
the $C_1$-$C_4$ alkoxy of $R^1$ is optionally substituted with 1 to 3 groups of halogen; and
the $C_3$-$C_6$ cycloalkyl of $R^1$ is optionally substituted with 1 to 3 groups selected from halogen, cyano, —OH, and $C_1$-$C_2$ alkoxy;
and all other variables not specifically defined herein are as defined in any one of Clauses 1 to 16.

18. The compound, tautomer, deuterated derivative, or pharmaceutically acceptable salt according to any one of Clauses 1 to 17, wherein $R^1$ is selected from F, Cl, Br, $C_1$-$C_4$ alkyl, and $C_3$-$C_6$ cycloalkyl; wherein:
the $C_1$-$C_4$ alkyl of $R^1$ is optionally substituted with 1 to 3 groups selected from halogen and —OH; and
the $C_3$-$C_6$ cycloalkyl of $R^1$ is optionally substituted with 1 to 3 groups selected from halogen, and —OH;
and all other variables not specifically defined herein are as defined in any one of Clauses 1 to 17.

19. The compound, tautomer, deuterated derivative, or pharmaceutically acceptable salt according to any one of Clauses 1 to 18, wherein $R^1$ is selected from F, Cl, Br, $C_1$-$C_4$ alkyl, and $C_3$-$C_6$ cycloalkyl; wherein:
the $C_1$-$C_4$ alkyl of $R^1$ is optionally substituted with 1 to 3 groups selected from halogen and —OH;
and all other variables not specifically defined herein are as defined in any one of Clauses 1 to 18.

20. The compound, tautomer, deuterated derivative, or pharmaceutically acceptable salt according to any one of Clauses 1 to 18, wherein $R^1$ is selected from $C_1$, Br, —$CH_3$, —$CF_3$, —$CH_2CH_3$, —$CH(CH_3)_2$, —$CH_2CHF_2$, —$CH_2CH(CH_3)_2$, difluorocyclobutyl, and cyclohexyl.

21. The compound, tautomer, deuterated derivative, or pharmaceutically acceptable salt according to any one of Clauses 1 to 20, wherein $R^1$ is $C_1$; and all other variables not specifically defined herein are as defined in any one of Clauses 1 to 20.

22. The compound, tautomer, deuterated derivative, or pharmaceutically acceptable salt according to any one of Clauses 1 to 21, wherein $R^{3a}$ is selected from halogen, —OH, and $C_1$-$C_4$ alkyl; wherein:
the $C_1$-$C_4$ alkyl of $R^{3a}$ is optionally substituted with 1 to 3 groups selected from halogen and —OH;
and all other variables not specifically defined herein are as defined in any one of Clauses 1 to 21.

23. The compound, tautomer, deuterated derivative, or pharmaceutically acceptable salt according to any one of Clauses 1 to 22, wherein $R^{3a}$ is selected from F, Cl, Br, —OH, and $C_1$-$C_2$ alkyl; wherein:
the $C_1$-$C_2$ alkyl of $R^{3a}$ is optionally substituted with 1 to 3 groups selected from F, Cl, and —OH;
and all other variables not specifically defined herein are as defined in any one of Clauses 1 to 22.

24. The compound, tautomer, deuterated derivative, or pharmaceutically acceptable salt according to any one of Clauses 1 to 23, wherein $R^{3a}$ is selected from F, —OH, —$CH_3$, —$CHF_2$, and $CH_2OH$; and all other variables not specifically defined herein are as defined in any one of Clauses 1 to 23.

25. The compound according to any one of Clauses 1 to 4 and 6 to 24, wherein the compound is represented by one of the following structural formulae:

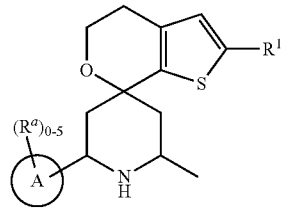

Formula Va₀

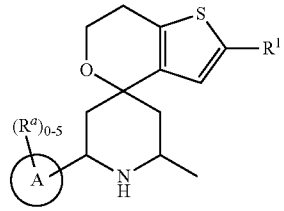

Formula Vb₀ a tautomer thereof, a deuterated derivative of that compound or tautomer, or a pharmaceutically acceptable salt of the foregoing; and all other variables not specifically defined herein are as defined in any one of Clauses 1 to 4 and 6 to 24.

26. The compound, tautomer, deuterated derivative, or pharmaceutically acceptable salt according to any one of Clauses 1 to 4 and 6 to 25, wherein $R^a$, for each occurrence, is independently selected from halogen, cyano, $C_1$-$C_6$ alkyl, $C_1$-$C_4$ alkoxy, $C_1$-$C_6$ haloalkyl, $C_1$-$C_6$ haloalkoxy, —C(=O)$NR^hR^i$, —$NR^hR^i$, —$NR^hC$(=O)$R^1$, —$OR^k$, —[O(CH$_2$)$_q$]$_r$O($C_1$-$C_6$ alkyl), —S(=O)$_2R^k$, —S(=O)$_2NR^hR^i$, $C_3$-$C_6$ cycloalkyl, 5 to 10-membered heterocyclyl, phenyl, and 5 to 8-membered heteroaryl; wherein:

the $C_1$-$C_6$ alkyl of $R^a$ is optionally substituted with 1 to 3 groups selected from cyano, —C(=O)NR$^h$R$^i$, —NR$^h$R$^i$, —NR$^h$C(=O)R$^h$, —NR$^h$C(=O)OR$^k$, —NR$^h$C(=O)NR$^i$R$^j$, —NR$^h$S(=O)$_p$R$^k$, —OR$^k$, —S(=O)$_2$R$^k$, —S(=O)$_p$NR$^h$R$^i$, and $C_3$-$C_6$ cycloalkyl;

the $C_3$-$C_6$ cycloalkyl, the 5 to 10-membered heterocyclyl, the phenyl, and the 5 to 8-membered heteroaryl of $R^a$ are each optionally substituted with 1 to 3 groups selected from halogen, $C_1$-$C_2$ alkyl, and —OR; wherein:

$R^h$, $R^i$, and $R^j$, for each occurrence, are each independently selected from hydrogen, $C_1$-$C_2$ alkyl, cyclopropyl, and cyclobutyl; wherein:

the $C_1$-$C_2$ alkyl of any one of $R^h$, $R^i$, and $R^j$ is optionally substituted with 1 to 3 groups selected from halogen and —OH;

$R^k$, for each occurrence, is each independently selected from hydrogen and $C_1$-$C_4$ alkyl; wherein:

the $C_1$-$C_4$ alkyl of $R^k$ is optionally substituted with 1 to 3 groups selected from halogen and —OH; and q and r are each an integer selected from 1, 2, and 3; and all other variables not specifically defined herein are as defined in any one of Clauses 1 to 4 and 6 to 25.

27. The compound, tautomer, deuterated derivative, or pharmaceutically acceptable salt according to any one of Clauses 1 to 4 and 6 to 26, wherein $R^a$, for each occurrence, is independently selected from halogen, cyano, $C_1$-$C_6$ alkyl, $C_1$-$C_4$ alkoxy, $C_1$-$C_4$ haloalkyl, $C_1$-$C_4$ haloalkoxy, —C(=O)NR$^h$R$^i$, —NR$^h$R$^i$, —NR$^h$C(=O)R, —OR$^k$, —[O(CH$_2$)$_q$]$_r$O(C$_1$-C$_4$ alkyl), —S(=O)$_2$R$^k$, —S(=O)$_2$NR$^h$R$^i$, cyclopropyl, cyclobutyl, 5 to 6-membered heterocyclyl, phenyl, and 5 to 6-membered heteroaryl; wherein:

the $C_1$-$C_6$ alkyl of $R^a$ is optionally substituted with 1 to 3 groups selected from cyano, —C(=O)NR$^h$R$^i$, —NR$^h$R$^i$, —OR$^h$, cyclopropyl, and cyclobutyl;

the cyclopropyl, the cyclobutyl, the 5 to 6-membered heterocyclyl, the phenyl, and the 5 to 6-membered heteroaryl of $R^a$ are each optionally substituted with 1 to 3 groups selected from halogen, —CH$_3$, —OH, and —OCH$_3$; wherein:

$R^h$ and $R^i$, for each occurrence, are each independently selected from hydrogen, —CH$_3$, cyclopropyl, and cyclobutyl; wherein:

the —CH$_3$ of any one of $R^h$ and $R^i$ is optionally substituted with 1 to 3 groups selected from F, Cl, and —OH;

$R^k$, for each occurrence, is each independently selected from hydrogen and —CH$_3$; wherein:

the —CH$_3$ of $R^k$ is optionally substituted with 1 to 3 groups selected from halogen and —OH; and all other variables not specifically defined herein are as defined in any one of Clauses 1 to 4 and 6 to 26.

28. The compound, tautomer, deuterated derivative, or pharmaceutically acceptable salt according to any one of Clauses 1 to 4 and 6 to 27, wherein $R^a$, for each occurrence, is independently selected from F, Cl, Br, cyano, $C_1$-$C_6$ alkyl, $C_1$-$C_2$ alkoxy, $C_1$-$C_2$ haloalkyl, —C(=O)NR$^h$R$^i$, —NR$^h$R$^i$, —NR$^h$C(=O)R$^k$, —OR$^k$, —[O(CH$_2$)$_q$]$_r$O(C$_1$-C$_2$ alkyl), —S(=O)$_2$R$^k$, —S(=O)$_2$NR$^h$R$^i$, cyclopropyl, cyclobutyl, 5-membered heterocyclyl, phenyl, and 6-membered heteroaryl; wherein:

the $C_1$-$C_6$ alkyl of $R^a$ is optionally substituted with 1 to 3 groups selected from cyano, —C(=O)NR$^h$R$^i$, —OR$^k$, and cyclopropyl;

the cyclopropyl, the cyclobutyl, the 5 to 6-membered heterocyclyl, the phenyl, and the 5 to 6-membered heteroaryl of $R^a$ are each optionally substituted with 1 to 3 groups selected from halogen, —CH$_3$, —OH, and —OCH$_3$; wherein:

$R^h$ and $R^i$, for each occurrence, are each independently selected from hydrogen, —CH$_3$, and cyclopropyl; wherein:

the —CH$_3$ of any one of $R^h$ and $R^i$ is optionally substituted with 1 to 3 groups selected from F, Cl, and —OH;

$R^k$, for each occurrence, is each independently selected from hydrogen and —CH$_3$; and q and r are each an integer selected from 1 and 2;

and all other variables not specifically defined herein are as defined in any one of Clauses 1 to 4 and 6 to 27.

29. The compound, tautomer, deuterated derivative, or pharmaceutically acceptable salt according to any one of Clauses 1 to 4 and 6 to 28, wherein $R^a$, for each occurrence, is independently selected from F, cyano, —OH, —CH$_3$, —CF$_3$, —CH(CH$_3$)$_2$, —(CH$_2$)$_2$OH, —(CH$_2$)$_2$OCH$_3$, —CH$_2$CH(OH)C$_2$H$_5$, —CH$_2$C(CH$_3$)(CH$_2$OH)$_2$, —OCH$_3$, —OCH$_2$CH$_3$, —[O(CH$_2$)$_2$]$_2$OCH$_3$, —CH$_2$C(=O)NHCH$_3$, —(CH$_2$)$_2$SO$_2$CH$_3$, —CH$_2$C(=O)N(CH$_3$)$_2$, —CH$_2$(cyclopropyl), —C(=O)NH$_2$, —C(=O)NH(cyclopropyl), —NH$_2$, —NHCH$_3$, —N(CH$_3$)$_2$, —NHC(CH$_3$)$_2$CH$_2$OH, —NHC(=O)CH$_3$, —SO$_2$CH$_3$, —SO$_2$NH$_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide; and all other variables not specifically defined herein are as defined in any one of Clauses 1 to 4 and 6 to 28.

30. The compound according to Clause 1, wherein the compound is represented by one of the following structural formulae:

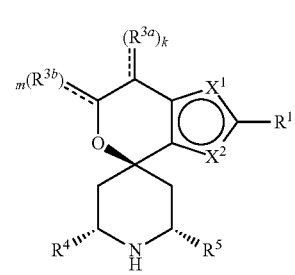

Formula I'$_0$

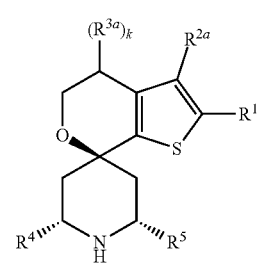

Formula IIa'$_0$

Formula IIb'₀
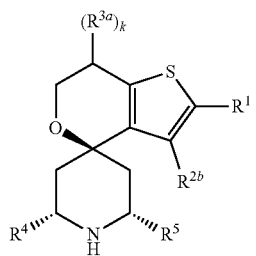

Formula IIIa'₀
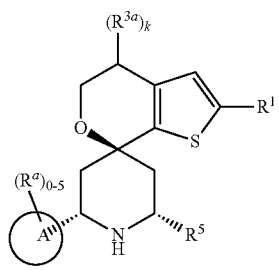

Formula IIIb'₀
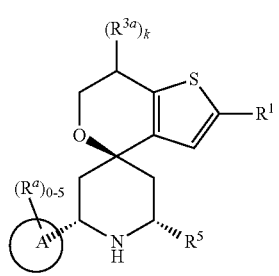

Formula IVa'₀
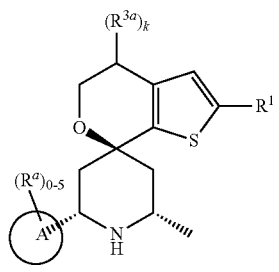

Formula IVb'₀
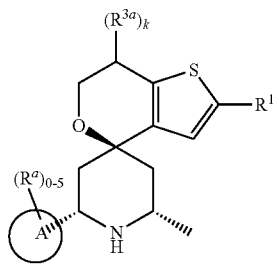

Formula Va'₀
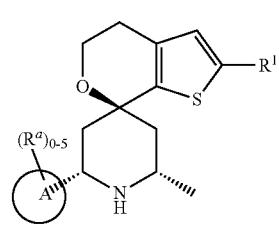

Formula Vb'₀
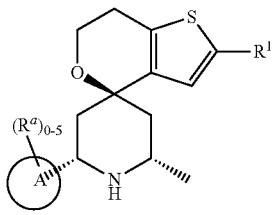

a tautomer thereof, a deuterated derivative of that compound or tautomer, or a pharmaceutically acceptable salt of the foregoing; and all other variables not specifically defined herein are as defined in any one of the foregoing Clauses.

31. A compound selected from the compounds of Table I, tautomers thereof, deuterated derivative of those compounds and tautomers, and pharmaceutically acceptable salts of any of the foregoing.

32. A pharmaceutical composition comprising at least one compound, tautomer, deuterated derivative or pharmaceutically acceptable salt according to any one of Clauses 1 to 31 and a pharmaceutically acceptable carrier.

33. A method of treating focal segmental glomerulosclerosis and/or non-diabetic kidney disease comprising administering to a patient in need thereof at least one compound according to any one of Clauses 1 to 31 or a pharmaceutical composition according to Clause 32.

34. Use of at least one compound, tautomer, deuterated derivative or pharmaceutically acceptable salt according to any one of Clauses 1 to 31 or a pharmaceutical composition according to Clause 32 for the manufacture of a medicament for treating focal segmental glomerulosclerosis and/or non-diabetic kidney disease.

35. At least one compound, tautomer, deuterated derivative or pharmaceutically acceptable salt according to any one of Clauses 1 to 31 or a pharmaceutical composition according to Clause 32 for use in treating focal segmental glomerulosclerosis and/or non-diabetic kidney disease.

36. A method of inhibiting APOL1 activity comprising contacting said APOL1 with at least one compound, tautomer, deuterated derivative or pharmaceutically acceptable salt according to any one of Clauses 1 to 31 or a pharmaceutical composition according to Clause 32.

37. Use of at least one compound, tautomer, deuterated derivative or pharmaceutically acceptable salt according to any one of Clauses 1 to 31 or a pharmaceutical composition according to Clause 32 for the manufacture of a medicament for inhibiting APOL1 activity.

38. At least one compound, tautomer, deuterated derivative or pharmaceutically acceptable salt according to any one of Clauses 1 to 31 or a pharmaceutical composition according to Clause 32 for use in inhibiting APOL1 activity.

39. A silicon derivative of the at least one compound, tautomer, deuterated derivative or pharmaceutically acceptable salt according to any one of Clauses 1 to 31.

40. A pharmaceutical composition comprising a silicon derivative of Clause 39.

41. A method of treating focal segmental glomerulosclerosis and/or non-diabetic kidney disease comprising administering to a patient in need thereof a silicon derivative according to Clause 39 or a pharmaceutical composition according to Clause 40.

42. Use of the silicon derivative according to Clause 39 or a pharmaceutical composition according to Clause 40 for the manufacture of a medicament for treating focal segmental glomerulosclerosis and/or non-diabetic kidney disease.

43. The silicon derivative according to Clause 39 or a pharmaceutical composition according to Clause 40 for use in treating focal segmental glomerulosclerosis and/or non-diabetic kidney disease.

44. A boron derivative of the at least one compound, tautomer, deuterated derivative or pharmaceutically acceptable salt according to any one of Clauses 1 to 31.

45. A pharmaceutical composition comprising a boron derivative of Clause 44.

46. A method of treating focal segmental glomerulosclerosis and/or non-diabetic kidney disease comprising administering to a patient in need thereof a boron derivative according to Clause 44 or a pharmaceutical composition according to Clause 45.

47. Use of the boron derivative according to Clause 44 or a pharmaceutical composition according to Clause 45 for the manufacture of a medicament for treating focal segmental glomerulosclerosis and/or non-diabetic kidney disease.

48. The boron derivative according to Clause 44 or a pharmaceutical composition according to Clause 45 for use in treating focal segmental glomerulosclerosis and/or non-diabetic kidney disease.

49. A phosphorus derivative of at least one compound, tautomer, deuterated derivative or pharmaceutically acceptable salt according to any one of Clauses 1 to 31.

50. A pharmaceutical composition comprising a phosphorus derivative of Clause 48.

51. A method of treating focal segmental glomerulosclerosis and/or non-diabetic kidney disease comprising administering to a patient in need thereof a phosphorus derivative according to Clause 48 or a pharmaceutical composition according to Clause 49.

52. Use of the phosphorus derivative according to Clause 48 or a pharmaceutical composition according to Clause 49 for the manufacture of a medicament for treating focal segmental glomerulosclerosis and/or non-diabetic kidney disease.

53. The phosphorus derivative according to Clause 48 or a pharmaceutical composition according to Clause 49 for use in treating focal segmental glomerulosclerosis and/or non-diabetic kidney disease.

EXAMPLES

In order that the disclosure described herein may be more fully understood, the following examples are set forth. It should be understood that these examples are for illustrative purposes only and are not to be construed as limiting this disclosure in any manner.

The compounds of the disclosure may be made according to standard chemical practices or as described herein. Throughout the following synthetic schemes and in the descriptions for preparing compounds of Formulae I, IIa, IIb, IIIa, IIIb, IVa, IVb, Va, Vb, I', IIa', IIb', IIIa', IIIb', IVa', IVb', Va', Vb', IIa'', IIb'', IIIa'', IIIb'', IVa'', IVb'', IIa''', IIb''', IIIa''', IIIb''', IVa''', IVb''', $I_O$, $IIa_O$, $IIb_O$, $IIIa_O$, $IIIb_O$, $IVa_O$, $IVb_O$, $Va_O$, $Vb_O$, $I'_O$, $IIa'_O$, $IIb'_O$, $IIIa'_O$, $IIIb'_O$, $IVa'_O$, $IVb'_O$, $Va'_O$, and $Vb'_O$, Compounds 1 to 391, a tautomer thereof, a deuterated derivative of that compound or tautomer, or a pharmaceutically acceptable salt of any of the foregoing, the following abbreviations are used:

Abbreviations

AIBN=azobisisobutyronitrile
ARP=assay ready plate
BBBPY=4,4'-Di-tert-butyl-2,2'-dipyridyl
$BF_3$=boron trifluoride
$BF_3 \cdot OEt_2$=boro trifluoride diethyl etherate
$Boc_2O$=di-tert-butyl dicarbonate
CBzCl=benzyl chloroformate
CDMT=2-chloro-4,6-dimethoxy-1,3,5-triazine
DAST=diethylaminosulfur trifluoride
DBU=1,8-diazabicyclo[5.4.0]undec-7-ene
DCM=dichloromethane
DIBAL-H=diisobutylaluminum hydride
DIPEA=N,N-Diisopropylethylamine or N-ethyl-N-isopropyl-propan-2-amine
DMAP=dimethylamino pyridine
DMA=dimethyl acetamide
DME=dimethoxyethane
DMEM=Dulbecco's modified Eagle's medium
DMF=dimethylformamide
DMPU=N,N'-dimethylpropyleneurea
DMSO=dimethyl sulfoxide
DPPA=diphenylphosphoryl azide
EtOAc=ethyl acetate
EtOH=ethanol
$Et_2O$=diethyl ether
FBS=fetal bovine serum
FLU=fluorescent values
HATU=[dimethylamino(triazolo[4,5-b]pyridin-3-yloxy)methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
$Ir[df(CF_3)ppy]_2(dtbbpy)PF_6$=phosphorus hexafluoride
LDA=lithium diisopropyl amide
LED=light emitting diode
MeCN=acetonitrile
MeI=methyl iodide
MeOH=methanol
MsOH=methanesulfonic acid
MTBE or TBME=Methyl tert-butyl ether
n-BuLi=n-butyllithium
NBS=n-bromosuccinimide
NMM=N-methyl morpholine
NMP=N-methyl pyrrolidine
PBS=phosphate-buffered saline
$Pd(dppf)_2Cl_2$=[1,1'-Bis(diphenylphosphino)ferrocene]dichloropalladium(II)
$PdCl_2(PPh_3)_2$=Bis(triphenylphosphine)palladium(II) dichloride
PP=polypropylene
PTSA=p-Toluenesulfonic acid monohydrate
T3P=2,4,6-Tripropyl-1,3,5,2,4,6-trioxatriphosphorinane-2,4,6-trioxide
TBAF=tetra-n-butylammonium fluoride
TBSCl=tert-butyldimethylsilyl chloride
TEA=triethylamine
Tet=tetracycline TFA or TFAA=trifluoroacetic acid
TfOH=triflic acid
THF=tetrahydrofuran
2-Me-THF=2-methyltetrahydrofuran
THP=tetrahydropyran
TMSCl=trimethylsilyl chloride
TMSS=Tris(trimethylsilyl)silane Example 1. Synthesis of Compounds All the specific and generic compounds, and the intermediates disclosed for making those compounds, are considered to be part of the disclosure disclosed herein.

Synthesis of Starting Materials

Preparations describe synthetic routes to intermediates used in the synthesis of Compounds 1 to 391.

General Schemes

In some embodiments, processes for preparing compounds of Formula I comprise the reactions described in Schemes 1-6.

Scheme 1 shows a process for the preparation of compounds of Formula I. $R^1$, $R^3$, $R^4$, $R^5$, $X^1$, $X^2$, m, and k are defined as above. An amino ketone of formula 1-1 may undergo reaction with an aldehyde of formula 1-2 to afford a piperidone of formula 1-3. In some embodiments, the reaction may occur in the presence of an amine catalyst such as L-proline, in the presence of a base such as triethyl amine, and magnesium sulfate reagent. Compounds of formula 1-3 may be prepared using any suitable method for the preparation of a piperidone. A compound of formula 1-3 may be prepared from a piperidone of formula 1-3 and an alcohol of formula 1-4 using any suitable conditions to perform a Pictet-Spengler reaction. For example, the reaction may be performed in the presence of an acid such as trifluoromethyl sulfonic acid and a solvent such as 1,4-dioxane. In an alternative embodiment, an acid such as methanesulfonic acid may be used. The reaction may be performed in a solvent such as dichloromethane in the presence of added heat (e.g., 40° C.).

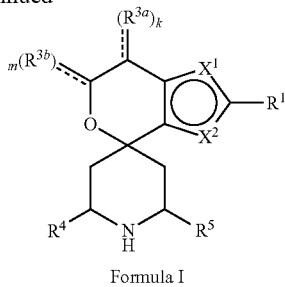

Formula I

Scheme 2 depicts processes for the preparation of compounds of formula 2-3. $PG^1$ is any suitable nitrogen protecting group. For example, in some embodiments, $PG^1$ is a trifluoroacetate group. A compound of formula 2-2 may be prepared from 2-1 using any suitable method for benzylic oxidation. For example, in some embodiments, the reaction is performed in the presence of oxygen gas under balloon pressure, N-hydroxypthalamide, and cobalt diacetate catalyst. In some embodiments, the reaction is performed in the presence of acetonitrile. The reaction may be performed in the presence of added heat (e.g., at 60° C.). Compounds of formula 2-3 may be prepared from a compound of formula 2-2 using any suitable method for the reduction of a ketone to an alcohol. For example, a Corey-Bakshi-Shibata catalyst (CBS catalyst) in the presence of a reducing agent such as borane may be used. In alternative embodiments, transition metal catalyzed transfer hydrogenation system may be used. In the presence of a chiral ligand, transition metal transfer hydrogenation reaction may result in an asymmetric reduction of the ketone.

Scheme 1

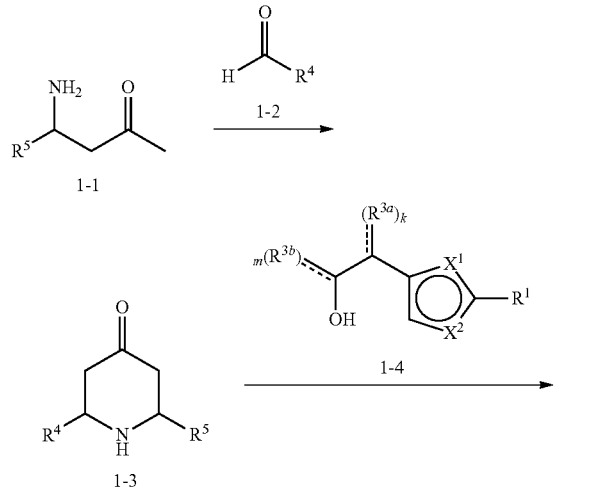

Scheme 2

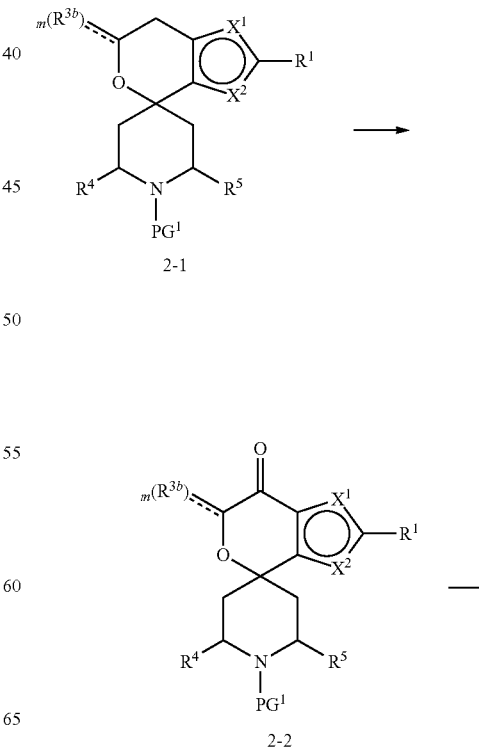

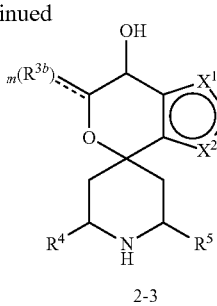

2-3

Scheme 3 shows processes for the preparation of compounds of formula 3-4. $PG^2$ is any suitable alcohol protecting group, for example, THP. A heterocyclic bromide of formula 3-1 may be coupled with a trifluoroboronate salt of formula 3-2 using any suitable method for the coupling of a halide with an alkyl boronate. For example, in some embodiments, the reaction may be performed in the presence of a catalyst system such as palladium (II) dicyclohexyl-[2-(2,6-diisopropoxyphenyl)phenyl]phosphane methanesulfonate N-methyl-2-phenyl-aniline and a base such as $Cs_2CO_3$. The reaction may be performed in the presence of added heat (e.g., 100° C.). In some embodiments, the reaction is performed in a solvent such as toluene. Any suitable method for the removal of an alcohol protecting group may be used to prepare a compound of formula 3-4. For example, where $PG^2$ is THP, an acid such as p-toluene sulfonic acid in a solvent such as methanol may be used. The reaction may be performed at room temperature.

Scheme 3

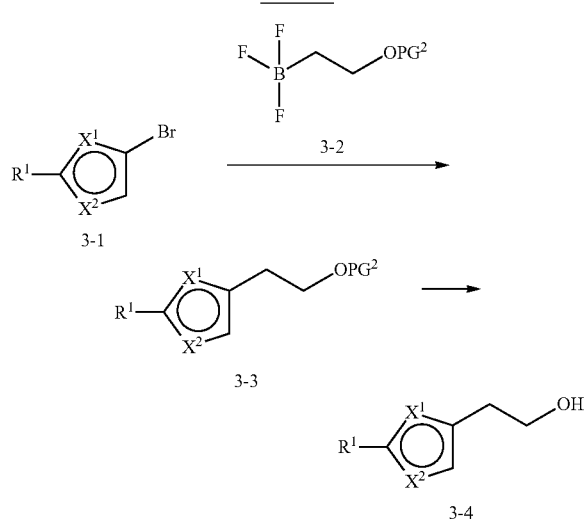

Scheme 4 shows processes for the preparation of alcohols of formula 4-5 from aryl halides of formula 3-1. Any suitable reagent for performing a lithium-halogen exchange on an heteroaryl bromide, such as treatment with n-butyl lithium, may be used to generate a heteroaryl organometallic reagent in situ. The reaction may be performed in a solvent such as THF or diethyl ether at low temperature (e.g., 0 to −78° C.). Addition of the organometallic reagent to an epoxide such as ethylene oxide in the presence of a Lewis acid such as trifluoroboron diethyl etherate affords alcohols of formula 4-2. In some embodiments, the lithium halogen exchange reaction may be performed under continuous flow conditions.

In an alternative process for the preparation of compounds of formula 4-2, an aldehyde of formula 4-3 may undergo a Wittig reaction with a reagent such as an ylide of formula 4-4 to afford an enol ether of formula 4-5. In some embodiments, the reaction is performed in the presence of a base such as potassium tert-butoxide in a solvent such as diethyl ether. In some embodiments, enol ethers of formula 4-5 may be converted to compounds of formula 4-6 by treatment with an acid such as HCl. In some embodiments, a compound of formula 4-2 may be prepared from a compound of formula 4-6 using any suitable reagent for reduction of an aldehyde to an alcohol, for example, sodium borohydride in methanol may be used.

Scheme 4

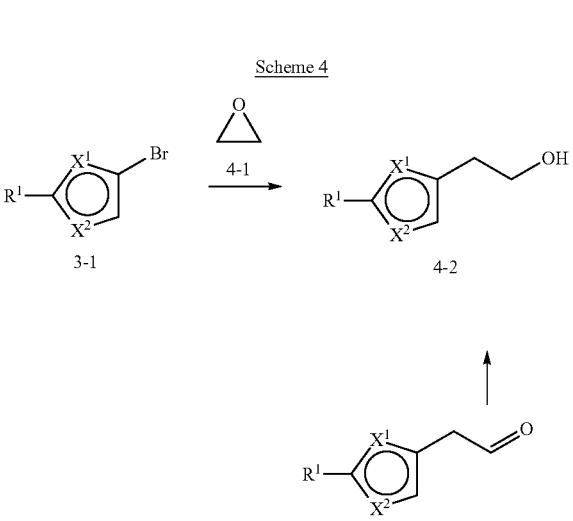

Scheme 5 shows processes for the preparation of compounds of formula 1-1. $PG^3$ is any suitable nitrogen protecting group. Compounds of formula 5-1 may be protected with any suitable nitrogen protecting group. For example, where $PG^3$ is a Boc group, any suitable reagents for addition of a Boc group onto an amine may be used. A compound of formula 5-3 (Weinreb amide) may be prepared from a compound of formula 5-2 and N-methyl N-methoxy amine using any suitable amide coupling reagent. For example, the reaction may be performed in a solvent such as dichloromethane in the presence of T3P and DIPEA. A compound of formula 5-5 may be prepared from a compound of formula 5-3 by addition of an organometallic reagent such as methyl magnesium iodide. The reaction may be performed in a solvent such as THF at low temperature (e.g., 0° C.). Compounds of formula 1-1 may be prepared from compounds of formula 5-5 using any suitable method for the removal of a nitrogen protecting group. For example, where $PG^3$ is Boc, a solution of HCl in 1,4-dioxane may be used.

Scheme 5

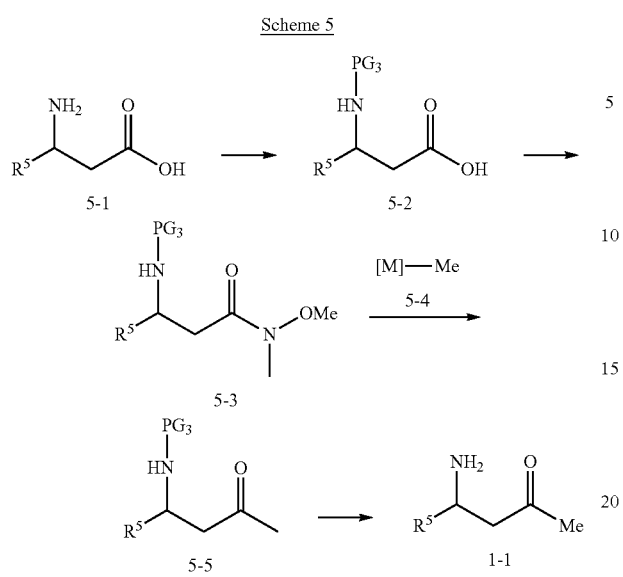

Scheme 6 shows an alternative process for the preparation of a compound of formula 1-3 from N-protected beta-amino acids of formula 6-1. $PG^4$ may be Boc or any suitable nitrogen protecting group. Compound 6-2 dimagnesium salt may be coupled to compounds of formula 6-1 using a reagent such as CDI in a solvent such as THF. Condensation of compounds of formula 6-3 with aldehydes of formula 6-4 affords compounds of formula 6-5. In some embodiments, the reaction may be performed by treatment of a compound of formula 6-3 with an acid such as TFA in a solvent such as dichloromethane, followed by the addition of aldehyde of formula 6-4. A compound of formula 1-3 may be prepared from a compound of formula 6-5 by treatment with an acid such as methanesulfonic acid in a solvent such as dichloromethane. The reaction may be performed in the presence of added heat (e.g., reflux conditions).

Scheme 6

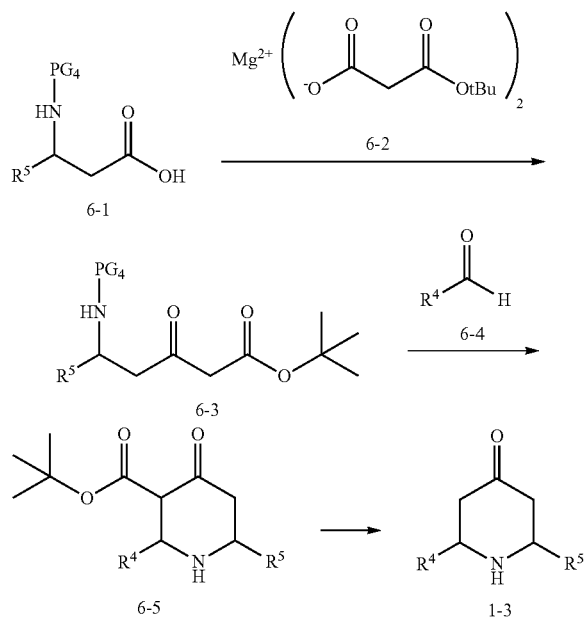

Preparation of S1
2-(3-thienyl)ethanol (S1)

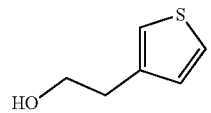

2-(3-thienyl)ethanol (S1) was obtained from commercial sources.

Preparation of S2
2-(5-chloro-3-thienyl)ethanol (S2)

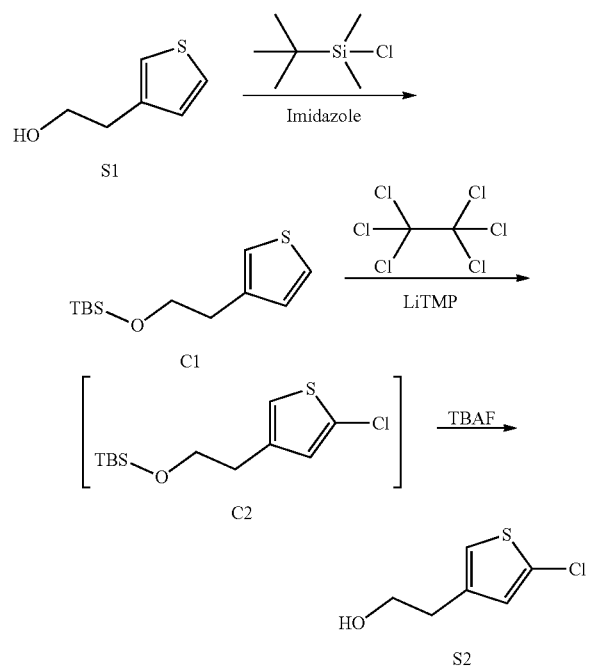

Step 1. Synthesis of tert-butyl-dimethyl-[2-(3-thienyl)ethoxy]silane (C1)

To a solution of 2-(3-thienyl)ethanol S1 (18 g, 140.4 mmol) in DMF (100 mL) was added imidazole (12 g, 176.3 mmol) and tert-butyl-chloro-dimethyl-silane (24 g, 159.2 mmol) sequentially. An exotherm was observed. The reaction mixture was stirred at room temperature for 3 hours. The reaction mixture was diluted with MTBE (500 mL) and washed with water (200 mL), 0.5 N HCl (200 mL), water (200 mL), and brine (200 mL). The organic layer was dried, filtered, and concentrated in vacuo. The organic layer was dissolved in heptane and passed through a silica gel plug; which was washed with 1-5% MTBE/Heptane. Solvent was removed to afford tert-butyl-dimethyl-[2-(3-thienyl)ethoxy] silane C1 (34 g, 99%). $^1$H NMR (400 MHz, Chloroform-d) δ 7.28-7.13 (m, 1H), 7.04-6.91 (m, 2H), 3.80 (t, J=6.9 Hz, 2H), 2.90-2.75 (m, 2H), 0.88 (s, 9H), −0.00 (s, 6H).

Step 2. Synthesis of tert-butyl-[2-(5-chloro-3-thienyl)ethoxy]-dimethyl-silane (C2)

To a solution of 2,2,6,6-tetramethylpiperidine (36 mL, 213.3 mmol) in tetrahydrofuran (200 mL) cooled to 0° C.

was added a solution of hexyllithium (92 mL of 2.3 M, 211.6 mmol). The reaction was stirred for 30 minutes at −78° C. A solution of tert-butyl-dimethyl-[2-(3-thienyl)ethoxy]silane C1 (34 g, 138.8 mmol) in THF (150 mL) was added to the reaction over 20 minutes. The reaction was stirred at −30° C. for 45 minutes. The reaction was cooled to −78° C. and 1,1,1,2,2,2-hexachloroethane (54 g, 228.1 mmol) was added portion-wise. The reaction was warmed to room temperature and stirred overnight. The reaction was quenched with saturated ammonium chloride (125 mL), diluted with water (100 mL), extracted with EtOAc (500 mL), and back extracted with EtOAc (100 mL). The combined organic layers were washed with 0.5 N HCl (200 mL), water (300 mL), and brine (200 mL). The organic layer was dried over sodium sulfate, filtered, and concentrated to afford the crude product tert-butyl-[2-(5-chloro-3-thienyl)ethoxy]-dimethyl-silane C2.

Step 3. Synthesis of 2-(5-chloro-3-thienyl)ethanol (S2)

To a solution of tert-butyl-[2-(5-chloro-3-thienyl)ethoxy]-dimethyl-silane C2 (12.5 g, 42.89 mmol) in 2-Me-THF (120 mL) was added TBAF (63 mL of 1 M in THF, 63.00 mmol). The reaction was stirred at room temperature overnight. The reaction was partitioned between EtOAc (400 mL) and water (400 mL). The layers were separated, and the organic layer was extracted with EtOAc (200 mL), dried over sodium sulfate, filtered, and concentrated in vacuo. Purification by silica gel chromatography (Gradient: 0-50% EtOAc in heptane) yielded the product 2-(5-chloro-3-thienyl)ethanol S2 (4.5 g, 58%). $^1$H NMR (300 MHz, Chloroform-d) δ 6.82 (d, J=0.9 Hz, 2H), 3.89-3.71 (m, 2H), 2.79 (t, J=6.4 Hz, 2H), 2.05 (s, 1H). LCMS m/z 162.91 [M+H]$^+$.

Preparation of S3

2-[5-(trifluoromethyl)-3-thienyl]ethanol (S3)

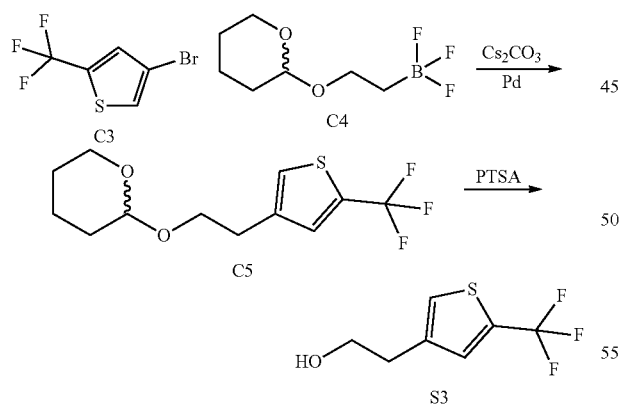

Step 1. Synthesis of 2-[2-[5-(trifluoromethyl)-3-thienyl]ethoxy]tetra hydropyrane (C5)

To a mixture of 4-bromo-2-(trifluoromethyl)thiophene C3 (9 g, 38.96 mmol), dicyclohexyl-[2-(2,6-diisopropoxyphenyl)phosphane; methanesulfonate; N-methyl-2-phenyl-aniline palladium (2+) (1.8 g, 2.117 mmol), and potassium trifluoro(2-tetrahydropyran-2-yloxyethyl)boranuide C4 (10 g, 42.36 mmol) was added toluene (75 mL) and water (25 mL). Nitrogen was passed over the top of the reaction before addition of Cs$_2$CO$_3$ (40 g, 122.8 mmol). A reflux condenser was added, and the reaction was heated at 100° C. for 48 hours. The reaction was diluted with EtOAc (150 mL) and water (100 mL). The two layers were separated and the aqueous layer was extracted with EtOAc (100 mL). The combined organics were washed with brine, dried over sodium sulfate, filtered, and concentrated in vacuo. Purification by silica gel chromatography (Gradient: 0-20% EtOAc in heptane) yielded the product 2-[2-[5-(trifluoromethyl)-3-thienyl]ethoxy]tetrahydropyran C5 (9 g, 82%). $^1$H NMR (300 MHz, Chloroform-d) δ 7.37 (t, J=1.3 Hz, 1H), 7.22 (d, J=1.5 Hz, 1H), 4.62 (dd, J=4.2, 2.8 Hz, 1H), 3.96 (dt, J=9.6, 6.7 Hz, 1H), 3.75 (ddd, J=11.3, 8.0, 3.4 Hz, 1H), 3.62 (dt, J=9.6, 6.5 Hz, 1H), 3.55-3.41 (m, 1H), 2.93 (t, J=6.6 Hz, 2H), 1.83 (ddd, J=14.2, 6.6, 3.4 Hz, 1H), 1.73 (td, J=9.0, 4.2 Hz, 1H), 1.66-1.50 (m, 4H).

Step 2. Synthesis of 2-[5-(trifluoromethyl)-3-thienyl]ethanol (S3)

To a stirred solution of 2-[2-[5-(trifluoromethyl)-3-thienyl]ethoxy]tetrahydropyran C5 (1.8 g, 6.100 mmol) in MeOH (25 mL) was added 4-methylbenzenesulfonic acid monohydrate (1.2 g, 6.309 mmol) at room temperature. The reaction mixture was stirred at room temperature for 1 hour. The reaction mixture was diluted with water (100 mL) and extracted with MTBE (2×100 mL). The combined organic layers were washed with dilute NaHCO$_3$ (10 mL NaHCO$_3$ and 10 mL water) and brine (10 mL), dried over sodium sulfate, filtered, and evaporated under vacuum to get crude compound. Purification by silica gel chromatography (Gradient: 0-30% EtOAc in heptane) yielded the product 2-[5-(trifluoromethyl)-3-thienyl]ethanol S3 (820 mg, 69%). $^1$H NMR (400 MHz, Chloroform-d) δ 7.35 (p, J=1.3 Hz, 1H), 7.23 (dt, J=1.7, 0.9 Hz, 1H), 3.85 (td, J=7.1, 6.5, 2.7 Hz, 2H), 2.87 (td, J=6.4, 0.8 Hz, 2H), 2.06 (d, J=4.3 Hz, 1H).

Alternative Preparation of S3

2-[5-(trifluoromethyl)-3-thienyl]ethanol (S3)

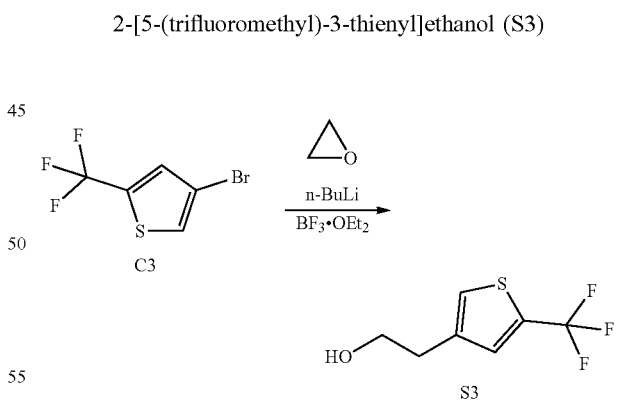

A solution of 4-bromo-2-(trifluoromethyl)thiophene C3 (50.13 g, 217.0 mmol) in Et$_2$O (500 mL) was cooled to −78° C. and nBuLi (91 mL of 2.48 M, 225.7 mmol) was added at a rate adapted to keep the temperature below −68° C. The reaction was stirred for 20 minutes and ethylene oxide (14 g, 317.8 mmol) was added at a rate to keep the temperature below −70° C. BF$_3$·OEt$_2$ (28 mL, 226.9 mmol) was added at a rate to keep the temperature below −68° C. The BF$_3$·OEt$_2$ addition was highly exothermic. The reaction was stirred for one hour at −78° C. and then poured into 500 mL of 1 N HCl and extracted with 500 mL of Et$_2$O. The extract was dried with MgSO$_4$, filtered, and evaporated in vacuo. Purification by column chromatography (1600 g: isocratic gradient:10% CH$_3$CN-DCM) afforded 2-[5-(trifluoromethyl)-3-thienyl]ethanol S3 (22.48 g, 53%). $^1$H NMR (300 MHz, Chloroform-d) δ 7.36 (t, J=1.3 Hz, 1H), 7.24 (d, J=1.5 Hz, 1H), 3.88 (q, J=6.0 Hz, 2H), 2.90 (t, J=6.3 Hz, 2H), 1.55 (t, J=5.4 Hz, 1H) ppm. 19F NMR (282 MHz, Chloroform-d) δ −55.36 ppm.

Preparation of S4

2-(5-ethyl-3-thienyl)ethanol (S4)

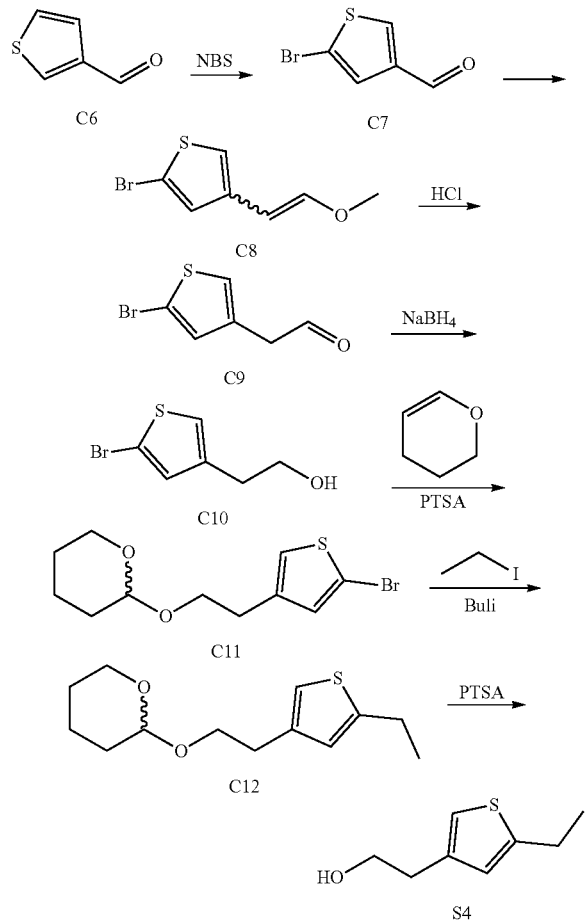

Step 1. Synthesis of 5-bromothiophene-3-carbaldehyde (C$_7$)

To a stirred solution of thiophene-3-carbaldehyde C6 (50 g, 40.717 mL, 0.4458 mol) in DMF (500 mL) was added NBS (119.02 g, 0.6687 mol) at 0° C. The reaction mixture was stirred at room temperature for 16 hours. The reaction mixture was quenched with ice cold water (600 mL) and extracted with EtOAc (2×600 mL). The combined organic layers were dried over Na$_2$SO$_4$, filtered, and concentrated. Purification by silica gel chromatography (Gradient: 0-2% EtOAc in petroleum ether) yielded the product 5-bromothiophene-3-carbaldehyde C7 (39.2 g, 44%). $^1$H NMR (400 MHz, Chloroform-d) δ 9.77 (s, 1H), 7.99 (d, J=1.2 Hz, 1H), 7.505 (d, J=1.6 Hz, 1H).

Step 2. Synthesis of 2-bromo-4-[(E)-2-methoxyvinyl]thiophene (C8)

To a stirred solution of (methoxymethyl)triphenylphosphonium chloride (115.1 g, 0.3358 mol) in diethyl ether (450.00 mL) at 0° C. was added potassium tert-butoxide (1 M in THF) (381 mL of 1 M, 0.3810 mol) dropwise. The reaction was stirred at 0° C. for 1 hour. A solution of 5-bromothiophene-3-carbaldehyde C7 (45 g, 0.2215 mol) in diethyl ether (90 mL) was added, and then the reaction mixture was stirred at room temperature for 30 minutes. The reaction mixture was quenched with NH$_4$Cl solution (900 mL) at 0° C. and extracted with EtOAc (2×700 mL). The combined organic layers were dried over Na$_2$SO$_4$, filtered, and concentrated. Purification by silica gel chromatography (Eluent: petroleum ether) afforded the product, 2-bromo-4-[(E)-2-methoxyvinyl]thiophene C8 (44.1 g, 82%). $^1$H NMR (400 MHz, Chloroform-d) δ 7.25 (d, J=2 Hz, 1H), 7.18 (d, J=0.8 Hz, 1H), 7.00 (d, J=1.8 Hz, 1H), 6.91 (d, J=12.8 Hz, 1H), 6.97 (d, J=1.2 Hz, 1H), 6.05 (d, J=6.8 Hz, 1H), 5.72 (d, J=12.8 Hz, 1H), 5.22 (d, J=6.4 Hz, 1H), 3.77 (d, J=2.8 Hz, 3H), 3.64 (d, J=5.2 Hz, 3H). NMR shows a 1:1 mixture of E and Z isomers.

Step 3. Synthesis of 2-(5-bromo-3-thienyl)acetaldehyde (C9)

To a stirred solution of 2-bromo-4-[(E)-2-methoxyvinyl]thiophene C8 (14.1 g, 0.0602 mol) in 1,4-Dioxane (141.00 mL) was added HCl (60.200 mL of 4 M in Dioxane, 0.2408 mol) at 0° C. The reaction mixture was stirred at room temperature for 30 minutes. The reaction mixture was quenched with saturated NaHCO$_3$ at 0° C. and extracted with EtOAc. The organic layer was dried over Na$_2$SO$_4$, filtered, and concentrated to afford 2-(5-bromo-3-thienyl)acetaldehyde C9 (13.1 g, 89%). $^1$H NMR (400 MHz, Chloroform-d) δ 9.72 (t, J=2.4 Hz, 1H), 7.04 (s, 1H), 6.94 (d, J=1.2 Hz, 1H), 3.66 (d, J=1.6 Hz, 2H).

Step 4. Synthesis of 2-(5-bromo-3-thienyl)ethanol (C10)

To a stirred solution of 2-(5-bromo-3-thienyl)acetaldehyde C9 (38.5 g, 0.1524 mol) in MeOH (390 mL) was added NaBH$_4$ (13.3 g, 0.3515 mol) at 0° C. The reaction was stirred for 1 hour. The reaction mixture was quenched with ice water (400 mL) and concentrated in vacuo to remove the MeOH. The crude residue was diluted with water (500 mL) and extracted with EtOAc (3×300 mL). The separated organic layers were dried over Na$_2$SO$_4$, filtered, and concentrated. Purification by column chromatography with neutral alumina (Eluent: 35% EtOAc in petroleum ether) afforded the product 2-(5-bromo-3-thienyl)ethanol C10 (30.2 g, 84%) as a pale yellow liquid. $^1$H NMR (300 MHz, DMSO-d$_6$) δ 7.20 (t, J=0.9 Hz, 1H), 7.10 (d, J=1.2 Hz, 1H), 4.64 (q, J=5.2 Hz, 1H), 3.59-3.55 (m, 2H), 2.67 (t, J=6.8 Hz, 2H).

Step 5. Synthesis of 2-[2-(5-bromo-3-thienyl)ethoxy]tetrahydropyran (C11)

To a stirred solution of 2-(5-bromo-3-thienyl)ethanol C10 (8 g, 0.0328 mol) in THF (80. mL) was added 3,4-dihydro-2H-pyran (3.7696 g, 3.8 mL, 0.0448 mol) and PTSA (259 mg, 0.0015 mol) at room temperature and then the reaction mixture was stirred at room temperature for 16 hours. The reaction mixture was quenched with saturated aqueous $K_2CO_3$ (300 mL) and extracted with EtOAc (2×600 mL). The organic layers were dried over $Na_2SO_4$, filtered, and concentrated. Purification by silica gel chromatography (Gradient: 0-5% EtOAc in petroleum ether) yielded the product 2-[2-(5-bromo-3-thienyl)ethoxy]tetra hydropyran C11 (10.1 g, 90%). $^1$H NMR (400 MHz, Chloroform-d) δ 6.95 (d, J=1.6 Hz, 1H), 6.92 (d, J=0.8, 1H), 4.59 (t, J=2.8 Hz, 1H), 3.94-3.74 (m, 2H), 3.60-3.46 (m, 2H), 2.85 (q, J=6.4 Hz, 2H), 1.80-1.61 (m, 6H). LCMS m/z 291.03 [M+H]$^+$.

Step 6. Synthesis of 2-[2-(5-ethyl-3-thienyl)ethoxy] tetrahydropyran (C12)

To a stirred solution of 2-[2-(5-bromotetrahydrothiophen-3-yl)ethoxy]tetrahydropyran C11 (25 g, 0.0719 mol) in THF (250.00 mL) was added n-BuLi (2.5 M in Hexane) (46.1 mL of 2.5 M, 0.1153 mol) at −76° C. The reaction was stirred for 1 hour. Ethyl iodide (24.832 g, 12.8 mL, 0.1592 mol) was added at −76° C. and then reaction temperature was slowly increased to room temperature, and was then stirred for 16 hours. The reaction mixture was quenched with $NH_4Cl$ solution (500 mL), and extracted with EtOAc (2×300 mL). The combined organic layers were dried over $Na_2SO_4$, filtered, and concentrated. Purification by silica gel chromatography (Gradient: 0-3% EtOAc in petroleum ether) yielded the product 2-[2-(5-ethyl-3-thienyl)ethoxy]tetrahydropyran C12 (13.2 g, 59%). LCMS m/z 241.21 [M+H]$^+$.

Step 7. Synthesis of 2-(5-ethyl-3-thienyl)ethanol (S4)

To a stirred solution of 2-[2-(5-ethyl-3-thienyl)ethoxy] tetrahydropyran C12 (4.4 g, 0.0142 mol) in MeOH (44 mL) was added PTSA (3.0 g, 0.0174 mol) at room temperature and the reaction was stirred for 2 hours. The reaction mixture was quenched with saturated $NaHCO_3$ solution (150 mL), extracted with EtOAc (2×150 mL), dried over $Na_2SO_4$, filtered, and concentrated. Purification by column chromatography with neutral alumina (Eluent: 10% EtOAc in petroleum ether) afforded the product 2-(5-ethyl-3-thienyl) ethanol S4 (1.1 g, 45%). $^1$H NMR (400 MHz, DMSO-$d_6$) δ 6.90 (d, J=1.2 Hz, 1H), 6.71 (d, J=1.2 Hz, 1H), 4.62-4.58 (m, 1H), 3.59-3.55 (m, 2H), 2.77-2.71 (m, 2H), 2.64 (t, J=7.2, 2H), 1.22-1.85 (m, 3H).

Preparation of S5

2-(5-ethyl-2-thienyl)ethanol (S5)

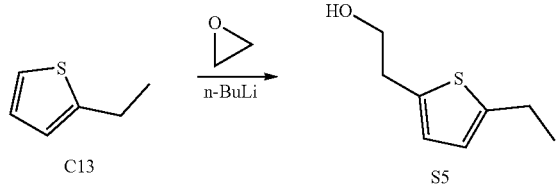

Step 1. Synthesis of 2-(5-ethyl-2-thienyl)ethanol (S5)

To a solution of 2-ethylthiophene C13 (54 g, 466.9 mmol) in anhydrous THF (1 L) at 0° C. was added n-BuLi in hexane (255 mL of 2.2 M, 561.0 mmol) over 45 minutes. A light yellow/orange solution resulted. The temperature range during the addition was 0-10° C. The mixture was stirred at room temperature for 30 minutes. After cooling to 0° C., a solution of ethylene-oxide (200 mL of 2.9 M, 580.0 mmol) was added over 30 minutes. The reaction was stirred at 0° C. for 2 hours and then was warmed to room temperature. The reaction mixture was quenched with water (700 mL) and saturated $NH_4Cl$ (200 mL) and the THF was evaporated. The product was extracted with EtOAc (1×400 mL; 2×150 mL). The combined organic layers were dried over anhydrous sodium sulfate, filtered, and concentrated in vacuo. The organic layer was passed through a silica gel plug washing with DCM (1000 mL), 80% EtOAc/Heptane (2×200 mL), and DCM (2×250 mL) to afford 2-(5-ethyl-2-thienyl)ethanol S5 (71.25 g, 93%). $^1$H NMR (300 MHz, Chloroform-d) δ 6.69 (dt, J=3.4, 0.9 Hz, 1H), 6.64 (dt, J=3.3, 1.0 Hz, 1H), 3.84 (t, J=6.3 Hz, 2H), 3.08-2.97 (m, 2H), 2.82 (qd, J=7.5, 1.0 Hz, 2H), 1.31 (t, J=7.5 Hz, 4H).

Preparation of S6

2-[5-(trifluoromethyl)-2-thienyl]ethanol (S6)

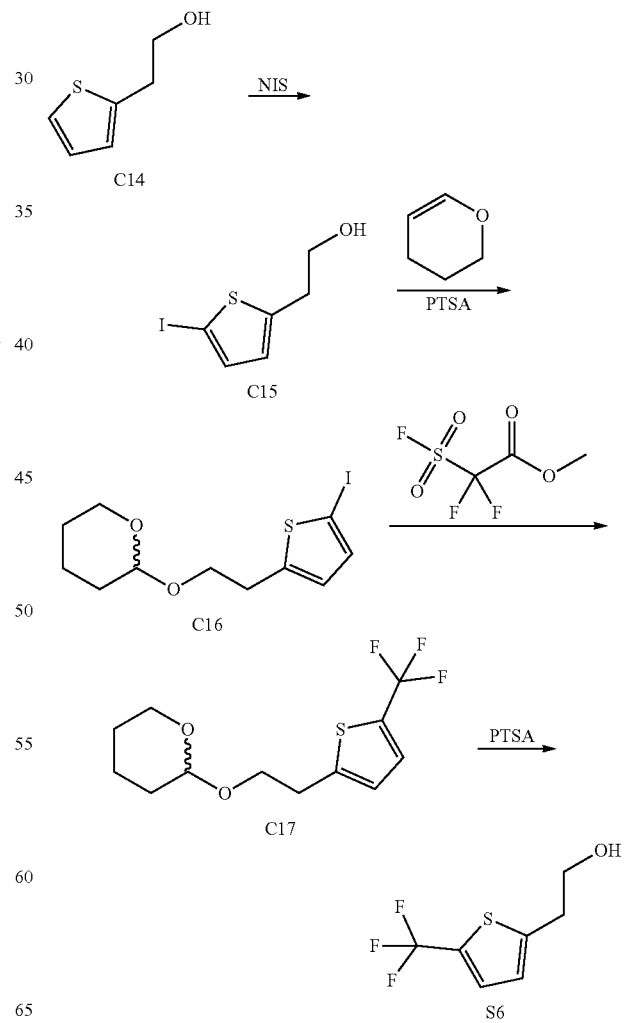

Step 1. Synthesis of 2-(5-iodo-2-thienyl)ethanol (C15)

To a stirred solution of NIS (104.83 g, 0.4680 mol) in DCM (1000 mL) was added 2-(2-thienyl)ethanol C14 (50 g, 0.3900 mol) at 0° C. The reaction was warmed to room temperature and stirred for 16 hours. The reaction mixture was diluted with DCM (500 mL), washed with saturated sodium thiosulphate, brine, dried over $Na_2SO_4$, and concentrated in vacuo. Purification by column chromatography (Eluent: 20% EtOAc in petroleum ether) afforded the product 2-(5-iodo-2-thienyl)ethanol C15 (62 g, 56%). $^1$H NMR (400 MHz, Chloroform-d) δ 7.08 (d, J=3.6 Hz, 1H), 6.57-6.56 (m, 1H), 3.82 (q, J=6 Hz, 2H), 3.05 (q, J=6.4 Hz, 2H). LCMS m/z 254.89 [M+H]$^+$.

Step 2. Synthesis of 2-[2-(5-iodo-2-thienyl)ethoxy]tetrahydropyran (C16)

To a stirred solution of 2-(5-iodo-2-thienyl)ethanol C15 (15 g, 0.0525 mol) and 3,4-dihydro-2H-pyran (6.6284 g, 0.0788 mol) in THF (60 mL) was added PTSA (1.3604 g, 1.2714 mL, 0.0079 mol) at room temperature. The reaction was stirred for 16 hours under argon balloon pressure. The reaction mixture was concentrated under reduced pressure. Purification by silica gel chromatography (Eluent: 5% EtOAc in petroleum ether) yielded the product 2-[2-(5-iodo-2 thienyl)ethoxy]tetrahydropyran C16 (12.8 g, 68%). $^1$H NMR (400 MHz, DMSO-$d_6$) δ 7.14 (d, J=3.6 Hz, 1H), 6.64 (d, J=3.6 Hz, 1H), 4.59 (t, J=3.6 Hz, 1H), 3.80-3.76 (m, 1H), 3.74-3.67 (m, 1H), 3.54-3.50 (m, 1H), 3.48-3.41 (m, 1H), 3.03 (t, J=6 Hz, 2H), 1.75-1.69 (m, 1H), 1.61-1.59 (m, 1H), 1.51-1.42 (m, 4H).

Step 3. Synthesis of 2-[2-[5-(trifluoromethyl)-2-thienyl]ethoxy]tetrahydropyran (C17)

To a stirred solution of 2-[2-(5-iodo-2-thienyl)ethoxy]tetrahydropyran C16 (10 g, 0.0219 mol) and methyl 2,2-difluoro-2-fluorosulfonyl-acetate (12.63 g, 0.0657 mol) in DMF (40 mL) was added copper(I) bromide dimethyl sulfide complex 99% (2.241 g, 0.0109 mol). The reaction was stirred at 100° C. for 16 hours. The reaction was warmed to room temperature, diluted with EtOAc (100 mL), filtered, and washed with EtOAc (50 mL). The filtrates were washed with chilled brine solution, dried over $Na_2SO_4$, and concentrated under reduced pressure. Purification by column chromatography with neutral alumina (Eluent: 5% EtOAc in petroleum ether) afforded the product 2-[2-[5-(trifluoromethyl)-2-thienyl]ethoxy]tetrahydro pyran C17 (2.9 g, 41%). $^1$H NMR (400 MHz, Chloroform-d) δ 7.25 (s, 1H), 6.82-6.81 (m, 1H), 4.63 (t, J=3.6 Hz, 1H), 4.00-3.95 (m, 1H), 3.78-3.75 (m, 1H), 3.64-3.58 (m, 1H), 3.51-3.48 (m, 1H), 3.12 (d, J=6.4 Hz, 2H), 1.90-1.80 (m, 1H), 1.73-1.64 (m, 1H), 1.65-1.51 (m, 4H). GCMS: 87.26%, m/z: 280 [M]$^+$.

Step 4. Synthesis of 2-[5-(trifluoromethyl)-2-thienyl]ethanol (S6)

To a stirred solution of 2-[2-[5-(trifluoromethyl)-2-thienyl]ethoxy]tetrahydropyran C17 (5.8 g, 0.0170 mol) in MeOH (100 mL) was added PTSA (2.93 g, 0.0170 mol) at room temperature. The reaction was stirred for 16 hours. The reaction mixture was concentrated under reduced pressure. Purification by column chromatography with neutral alumina (Eluent: 10% EtOAc in petroleum ether) afforded the product 2-[5-(trifluoromethyl)-2-thienyl]ethanol S6 (2.3 g, 61%). $^1$H NMR (400 MHz, DMSO-$d_6$) δ 7.52-7.51 (m, 1H), 6.99-6.98 (m, 1H), 4.92 (t, J=4.8 Hz, 1H), 3.65-3.61 (m, 2H), 2.98 (t, J=6 Hz, 2H). $^{19}$F NMR (376.22 MHz, DMSO-$d_6$) δ −53.53 (s, 3F). GCMS: 88.56% m/z: 196.0 [M]$^+$.

Preparation of S7

2-[5-(trifluoromethyl)-2-thienyl]propan-1-ol (S7)

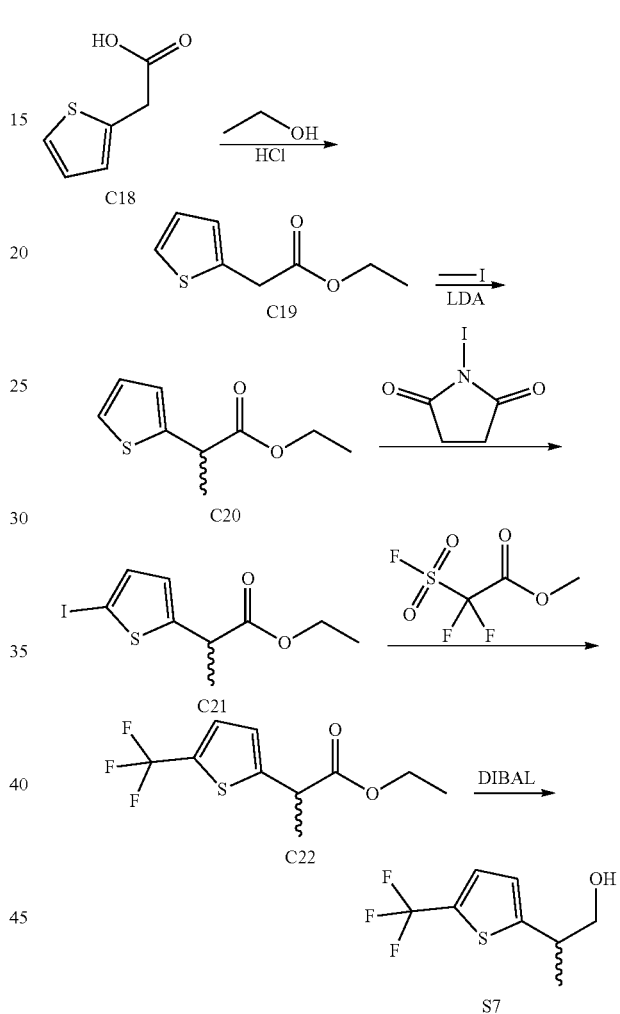

Step 1. Synthesis of ethyl 2-(2-thienyl)acetateethanol (C19)

To a stirred solution of 2-(2-thienyl)acetic acid C18 (100 g, 703.35 mmol) in ethanol (2000 mL) was added HCl (aqueous) (50 mL of 36% (w/v), 493.68 mmol) at room temperature. The reaction mixture was stirred for 12 hours at 70° C. The mixture was concentrated, and the resulting crude material was diluted with EtOAc (1000 mL), washed with 5% $Na_2CO_3$ aqueous solution (3×200 mL), and brine (200 mL). The organic layer was dried and concentrated to afford desired product, ethyl 2-(2-thienyl)acetate C19 (100 g, 82%). $^1$H NMR (Chloroform-d, 400 MHz) δ 7.22-7.21 (dd, J=1.2 Hz, J=3.6 Hz, 1H), 6.97-6.95 (m, 2H), 4.21-4.16 (q, J=7.2 Hz, 2H), 3.83 (s, 2H), 1.30-1.26 (t, J=7.2 Hz, 3H). LCMS m/z 171.26 [M+H]$^+$.

Step 2. Synthesis of ethyl 2-(2-thienyl)propanoate (C20)

To a solution of ethyl 2-(2-thienyl)acetate C19 (1.36 g, 7.99 mmol) in THF (20 mL) at −78° C. was added (diisopropylamino)lithium (8 mL of 1 M, 8.000 mmol). After 15 minutes, MeI (500 µL, 8.032 mmol) was added and the reaction was mixture stirred at −78° C. for 2 hours. The reaction was quenched with saturated $NH_4Cl$ (50 mL) and extracted with EtOAc. The organic layer was dried and concentrated to an oil. Purification by silica chromatography (Gradient: 0 to 25% EtOAc in heptane) afforded the product, ethyl 2-(2-thienyl)propanoate C20 (1.04 g, 71%). $^1$H NMR (300 MHz, Chloroform-d) δ 7.25-7.17 (m, 1H), 7.02-6.93 (m, 2H), 4.18 (d, J=7.2 Hz, 2H), 4.02 (q, J=7.1 Hz, 1H), 1.60 (d, J=7.2 Hz, 3H), 1.28 (t, J=7.1 Hz, 3H).

Step 3. Synthesis of ethyl 2-(5-iodo-2-thienyl)propanoate (C21)

To a stirred solution of ethyl 2-(2-thienyl)propanoate C20 (35 g, 143.99 mmol) in Acetic acid (350 mL) was added N-Iodosuccinimide (38.875 g, 172.79 mmol). The reaction mixture was stirred for one hour at 100° C. The mixture was concentrated and the resulting crude material was diluted with EtOAc (700 mL), washed with water (300 mL), saturated sodium bicarbonate solution (300 mL), saturated sodium thiosulfate solution (300 mL), and brine solution (250 mL) sequentially. The organic layer was dried over $Na_2SO_4$, filtered, and concentrated to afford crude product. Purification by silica gel chromatography (Eluent: 3% EtOAc in petroleum ether) yielded the product ethyl 2-(5-iodo-2-thienyl)propanoate C21 (30 g, 42%). $^1$H NMR (Chloroform-d, 400 MHz) δ 7.08 (d, J=4 Hz, 1H), 6.62 (d, J=4 Hz, 1H), 4.19-4.13 (m, 2H), 3.98-3.92 (m, 1H), 1.55-1.51 (m, 3H), 1.28-1.24 (m, 3H). LCMS m/z 309.9 [M+H]$^+$.

Step 4. Synthesis of ethyl 2-[5-(trifluoromethyl)-2-thienyl]propanoate (C22)

To a stirred solution of ethyl 2-(5-iodo-2-thienyl)propanoate C21 (5 g, 9.9629 mmol) and Methyl 2,2-difluoro-2-(fluorosulfonyl)acetate (9.57 g, 49.814 mmol) in DMF (50 mL) was added CuI (2.2768 g, 11.955 mmol) under nitrogen atmosphere. The reaction mixture was stirred for 12 hours at 100° C. The mixture was filtered through Celite® and the Celite® pad was washed with Diethyl Ether (2×100 mL). Filtrate was quenched with cold water (100 mL). The two layers were separated and the aqueous layer was extracted with diethyl ether (2×50 mL). The combined organic layers were washed with brine (30 mL), dried, and concentrated. Purification by silica gel chromatography (Eluent: 3% EtOAc in petroleum ether) yielded the product ethyl 2-[5-(trifluoromethyl)-2-thienyl]propanoate C22 (2 g, 58%). $^1$H NMR (Chloroform-d, 400 MHz) δ 7.29-7.26 (m, 1H), 6.92-6.90 (m, 1H), 4.21-4.15 (m, 2H), 3.99-3.96 (m, 1H), 1.57-1.53 (m, 3H), 1.23-1.27 (m, 3H). GCMS: m/z: 252.1 [M]$^+$

Step 5. Synthesis of 2-[5-(trifluoromethyl)-2-thienyl]propan-1-ol (S7)

To a stirred solution of ethyl 2-[5-(trifluoromethyl)-2-thienyl]propanoate C22 (12 g, 41.701 mmol) in THF (250 mL) was added DIBAL-H (35.584 mL of 25% (w/v), 62.5 mmol) dropwise at 0° C. The reaction mixture was stirred for 2 hours at 0° C. The mixture was slowly quenched with saturated $NH_4Cl$ solution (300 mL) at 0° C. and the suspension was filtered through Celite® and the Celite® pad was washed with EtOAc (2×200 mL). The filtrate was separated into layers. The aqueous layer was extracted with EtOAc (2×200 mL). The combined organic layers were washed with brine (200 mL), dried over $Na_2SO_4$, and concentrated. Purification by silica gel chromatography (Eluent: 3% EtOAc in petroleum ether) yielded crude product. The racemic compound, 2-[5-(trifluoromethyl)-2-thienyl]propan-1-ol (1.6 g, 7.3067 mmol) was separated from the dimethyl over alkylation byproduct using chiral SFC separation. Column: Daicel Chiralpak® AD-H, 30×250 mm; Mobile Phase: 10% Methanol/Hexane Mixture (7:3), 90% carbon dioxide. Flow: 90 g/minutes. 2-[5-(trifluoromethyl)-2-thienyl]propan-1-ol S7 (3.64 g). $^1$H NMR (400 MHz, Chloroform-d) δ 7.52 (m, 1H), 7.00 (m, 1H), 4.97 (t, J=5.6 Hz, 1H), 3.51 (t, J=6.0 Hz, 2H) 3.17 (m, 1H), 1.27 (d, J=6.8 Hz, 3H). GCMS: m/z: 210.0 [M]$^+$.

Preparation of S8

2-methyl-2-[5-(trifluoromethyl)-2-thienyl]propan-1-ol (S8)

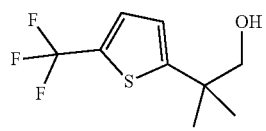

S8 was obtained during SFC purification of S7 as a side product due to over alkylation in step 2 described above.

Preparation of S9, S10, and S11

2-methyl-2-[5-(chloro)-2-thienyl]propan-1-ol (S9)

2-[5-(chloro)-2-thienyl]propan-1-ol (S10[ENANT-1], S11 [ENANT-2])

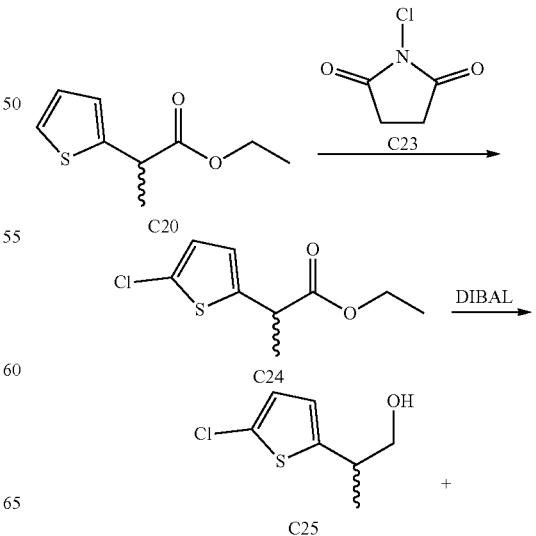

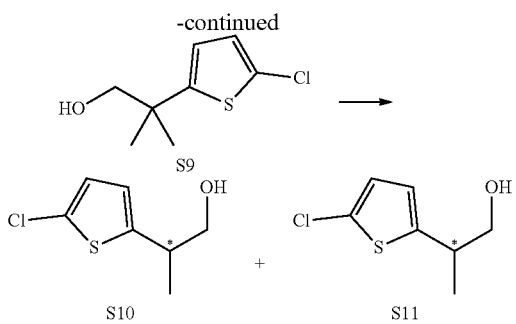

Step 1. Synthesis of ethyl 2-(5-chloro-2-thienyl)propanoate (C24)

To a stirred solution of ethyl 2-(2-thienyl)propanoate C20 (1 g, 4.1139 mmol) in acetic acid (10 mL) was added N-Chlorosuccinimide C23 (549.34 mg, 4.1139 mmol). The reaction mixture was stirred for 1 hour at 100° C. The mixture was concentrated and the resulting crude material was diluted with EtOAc (25 mL), washed with water (10 mL), saturated sodium bicarbonate solution (10 mL), saturated sodium thiosulfate solution (10 mL), and brine solution (10 mL). The organic layer was dried over $Na_2SO_4$, filtered, and concentrated to afford crude product. Purification by silica gel chromatography (Eluent: 3% EtOAc in petroleum ether) yielded the product ethyl 2-(5-chloro-2-thienyl)propanoate C24 (700 mg, 60%). $^1$H NMR (Chloroform-d, 400 MHz): δ=6.75-6.73 (m, 1H), 6.71-6.69 (m, 1H), 4.20-4.14 (m, 2H), 3.88-3.73 (q, J=6.4 Hz, 1H), 1.55-1.53 (t, J=2.8 Hz, 3H), 1.30-1.221 (m, 3H). GCMS: m/z: 218.0 $[M]^+$

Step 2. Synthesis of 2-(5-chloro-2-thienyl)-2-methyl-propan-1-ol and 2-(5-chloro-2-thienyl)propan-1-ol (S9) and (C25)

To a stirred solution of ethyl 2-(5-chloro-2-thienyl)propanoate C24 (25 g, 86.877 mmol) in THF (500 mL) was added DIBAL-H (74.135 mL of 25% (w/v), 130.32 mmol) dropwise at 0° C. The reaction mixture was stirred for 2 hours at 0° C. The mixture was slowly quenched with saturated $NH_4Cl$ solution (300 mL) at 0° C. and the suspension was filtered through Celite® and the Celite® pad was washed with EtOAc (2×200 mL). The filtrate was separated into two layers. The aqueous layer was extracted with EtOAc (2×200 mL). The combined organic layers were washed with brine (200 mL), dried over sodium sulfate, and concentrated. Purification by silica gel chromatography (Eluent: 3% EtOAc in petroleum ether) yielded S9 2-(5-chloro-2-thienyl)-2-methyl-propan-1-ol (410 mg, 2%). $^1$H NMR (Chloroform-d, 400 MHz) δ 6.76-6.75 (d, J=4 Hz, 1H), 6.67-6.65 (t, J=4 Hz, 1H), 3.54-3.52 (d, J=6.8 Hz, 2H), 1.47-1.43 (t, J=6.8 Hz, 1H), 1.34 (s, 6H). GCMS: m/z: 190.0 $[M]^+$; and 2-(5-chloro-2-thienyl)propan-1-ol C25 (12 g, 72%). $^1$H NMR (Chloroform-d, 400 MHz) δ 6.76-6.75 (d, J=3.6 Hz, 1H), 6.66-6.65 (dd, J=4.4 Hz, 1H), 3.71-3.61 (m, 2H), 3.15-3.10 (m, 1H), 1.57-1.52 (m, 1H), 1.34-1.31 (t, J=6 Hz, 3H). GCMS: m/z: 176.0 $[M]^+$. NOTE: the dimethyl compound (S9) was formed as a side product due to over alkylation during synthesis of C20.

Step 3. Synthesis of 2-(5-chloro-2-thienyl)propan-1-ol (S10) and (S11)

The racemic compound, 2-(5-chloro-2-thienyl)propan-1-ol C25 (12 g, 62.492 mmol) was separated into constituent enantiomers by chiral SFC separation. Column: Daicel Chiralpak® AD-H, 30×250 mm; Mobile Phase: 10% Methanol/Hexane Mixture (7:3), 90% carbon dioxide. Flow: 90 g/minutes. 2-(5-chloro-2-thienyl)propan-1-ol S10 (4 g, 35%). $^1$H NMR (Chloroform-d, 400 MHz) δ 6.76-6.75 (d, J=3.6 Hz, 1H), 6.66-6.65 (dd, J=3.6 Hz, 1H), 3.73-3.61 (m, 2H), 3.17-3.10 (m, 1H), 1.52-1.49 (t, J=5.2 Hz, 1H), 1.32-1.30 (d, J=6.8 Hz, 3H). GCMS: m/z: 176.0 $[M]^+$; and 2-(5-chloro-2-thienyl)propan-1-ol S11 (3.75 g, 34%). $^1$H NMR (Chloroform-d, 400 MHz) δ 6.76-6.75 (d, J=4 Hz, 1H), 6.66-6.65 (dd, J=3.6 Hz, 1H), 3.73-3.61 (m, 2H), 3.15-3.10 (q, J=6.8 Hz, 1H), 1.51-1.48 (t, J=5.6 Hz, 1H), 1.33-1.30 (d, J=7.2 Hz, 3H). GCMS: m/z: 176.0 $[M]^+$.

Preparation of S12 and S13

2-(5-ethyl-2-thienyl)propan-1-ol (S12 ENANT-1) and (S13 ENANT-2)

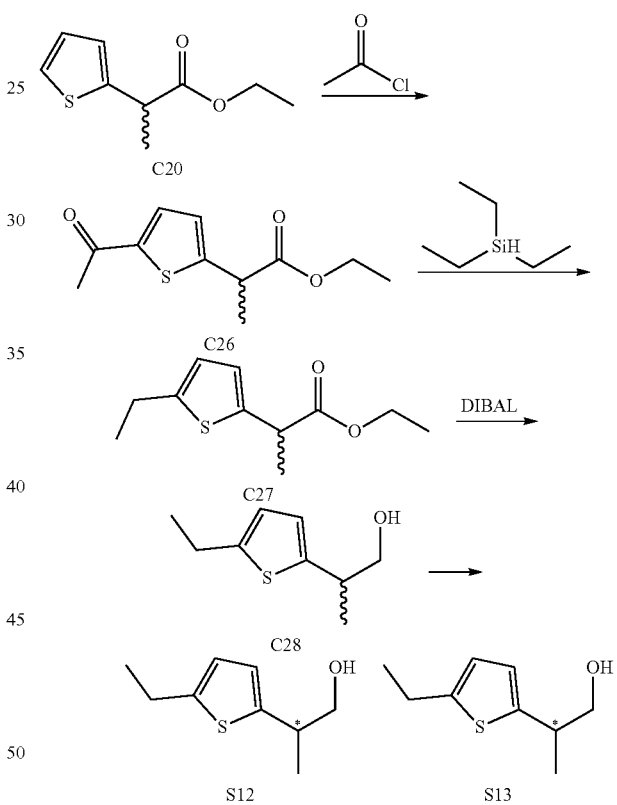

Step 1. Synthesis of ethyl 2-(5-acetyl-2-thienyl)propanoate (C26)

To a stirred solution of ethyl 2-(2-thienyl)propanoate C20 (80 g, 336.92 mmol) in DCM (1500 mL) was added Acetyl chloride (39.671 g, 35.934 mL, 505.38 mmol) dropwise at 0° C., followed by addition of $AlCl_3$ (67.388 g, 505.38 mmol) at 0° C. The reaction mixture was stirred for 2 hours at 0° C. The mixture was slowly quenched with ice water (1000 mL), the two layers were separated, and the aqueous layer was extracted with DCM (2×500 mL). The combined organic layers were washed with brine (500 mL), dried over sodium sulfate. Purification by silica gel chromatography (Gradient: 0-5% EtOAc in petroleum ether) yielded the product ethyl 2-(5-acetyl-2-thienyl)propanoate C26 (60 g, 73%). $^1$H NMR (Chloroform-d, 400 MHz) δ 7.56-7.54 (t, J=4.0 Hz, 1H), 6.99-6.98 (m, 1H), 4.20-4.14 (m, 2H), 4.01-3.96 (q, J=7.2 Hz, 1H), 2.52 (s, 3H), 1.60-1.56 (d, J=7.2 Hz, 3H), 1.28-1.23 (m, 3H). LCMS m/z 227.1 [M+H]$^+$.

Step 2. Synthesis of ethyl 2-(5-ethyl-2-thienyl)propanoate (C27)

To a stirred solution of ethyl 2-(5-acetyl-2-thienyl)propanoate C26 (60 g, 245.79 mmol) in TFA (400 mL) was added Triethyl-silane (42.870 g, 58.9 mL, 368.69 mmol) dropwise at 0° C. The reaction mixture was stirred for 4 hours at room temperature. The reaction was concentrated and quenched with ice water (500 mL) and extracted with EtOAc (3×500 mL). The combined organic layers were washed with brine (250 mL), dried over sodium sulfate, and concentrated to afford crude product. Purification by silica gel chromatography (Gradient: 0-3% EtOAc in petroleum ether) yielded the product ethyl 2-(5-ethyl-2-thienyl)propanoate C27 (50 g, 82%). $^1$H NMR (Chloroform-d, 400 MHz) δ 6.73-6.72 (dd, J=3.6 Hz, 1H), 6.62-6.60 (m, 1H), 4.18-4.13 (m, 2H), 3.93-3.88 (q, J=7.2 Hz, 1H), 2.82-2.78 (m, 2H), 1.55-1.53 (d, J=7.2 Hz, 3H) 1.30-1.23 (m, 6H). LCMS m/z 213.2 [M+H]$^+$.

Step 3. Synthesis of 2-(5-ethyl-2-thienyl)propan-1-ol (C28)

To a stirred solution of ethyl 2-(5-ethyl-2-thienyl)propanoate C27 (50 g, 200.18 mmol) in THF (1000 mL) was added DIBAL-H (25% in toluene) (227.75 mL of 25% (w/v), 400.36 mmol) dropwise at 0° C. The reaction mixture was stirred for 2 hours at 0° C. The mixture was slowly quenched with saturated NH$_4$Cl solution (500 mL) at 0° C. and extracted with EtOAc (2×500 mL). The combined organic layers were washed with brine (250 mL), dried over sodium sulfate, and concentrated. Purification by silica gel chromatography (Gradient: 0-5% EtOAc in Petroleum ether) yielded the product 2-(5-ethyl-2-thienyl)propan-1-ol C28 (31 g, 89%). $^1$H NMR (Chloroform-d, 400 MHz): δ 6.69-6.68 (d, J=3.6 Hz, 1H), 6.64-6.62 (m, 1H), 3.72-3.60 (m, 2H), 3.18-3.13 (q, J=6.8 Hz, 1H), 2.83-2.77 (m, 2H), 1.61-1.5 (m, 1H), 1.35-1.28 (m, 6H). LCMS m/z 171.02 [M+H]$^+$.

Step 4. Synthesis of 2-(5-ethyl-2-thienyl)propan-1-ol (S12) and (S13)

The racemic compound 2-(5-ethyl-2-thienyl)propan-1-ol C28 (31 g, 178.06 mmol) was separated into constituent enantiomers by chiral SFC separation. Column: Daicel Chiralpak @AD-H, 30×250 mm; Mobile Phase: 10% Methanol/Hexane Mixture (7:3), 85% carbon dioxide. 2-(5-ethyl-2-thienyl)propan-1-ol S12 (13.45 g, 43%). $^1$H NMR (Chloroform-d, 400 MHz): δ=6.69-6.68 (d, J=3.2 Hz, 1H), 6.63-6.62 (d, J=3.2 Hz, 1H), 3.73-3.61 (m, 2H), 3.19-3.14 (q, J=6.8 Hz, 1H), 2.83-2.78 (m, 2H), 1.54-1.47 (m, 1H), 1.35-1.27 (m, 6H). LCMS m/z 171.1 [M+H]$^+$; And 2-(5-ethyl-2-thienyl)propan-1-ol S13 (11.35 g, 37%). $^1$H NMR (Chloroform-d, 400 MHz): δ 6.68-6.67 (d, J=3.6 Hz, 1H), 6.63 (d, J=3.6 Hz, 1H), 3.73-3.61 (m, 2H), 3.20-3.12 (m, 1H), 2.83-2.77 (q, J=7.6 Hz, 2H), 1.54-1.45 (m, 1H), 1.33-1.27 (m, 6H). LCMS m/z 171.1 [M+H]$^+$.

Preparation of S14

2-(5-methyl-3-thienyl)ethanol (S14)

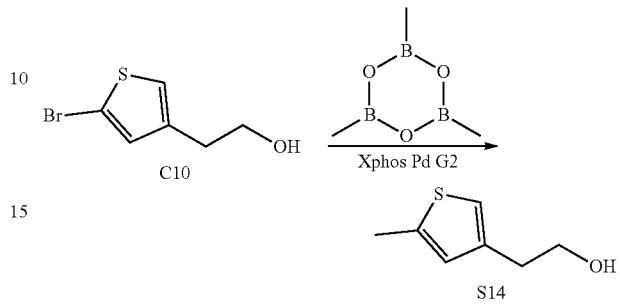

To a stirred solution of 2-(5-bromo-3-thienyl)ethanol C10 (2.5 g, 0.0098 mol) in 1,4-Dioxane (16.000 mL) was added K$_2$CO$_3$ (4.9 g, 0.036 mol) at room temperature in a sealed tube. The reaction mixture was degassed with argon gas for 10 minutes. Xphos Pd G2 (457 mg, 580.83 μmol) was added and again degassed for 5 minutes. Trimethylboroxine (50% solution in THF) (24.605 mL of 50% (w/v), 0.0980 mol) was added and heated to 80° C. for 16 hours. The reaction mixture was diluted with water (200 mL) and extracted with EtOAc (3×150 mL). The combined organic layers were dried over Na$_2$SO$_4$, filtered, and concentrated under reduced pressure. Purification by column chromatography (Eluent: 20% EtOAc in petroleum ether) afforded the product S14 2-(5-methyl-3-thienyl)ethanol (950 mg, 66%) as a yellow liquid. $^1$H NMR (400 MHz, DMSO-d$_6$) δ 6.87 (d, J=0.8 Hz, 1H), 6.68 (s, 1H), 4.59 (t, J=5.2 Hz, 1H), 3.58-3.53 (m, 2H), 2.63 (t, J=7.2 Hz, 2H), 2.38 (d, J=0.8 Hz, 3H).

Preparation of S15

2-(5-methyl-2-thienyl)ethanol (S15)

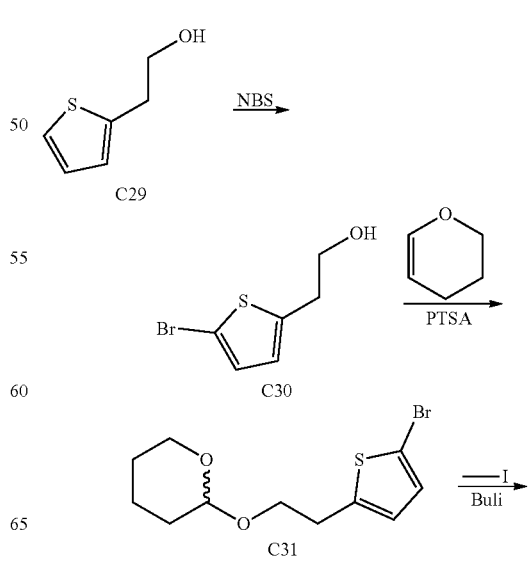

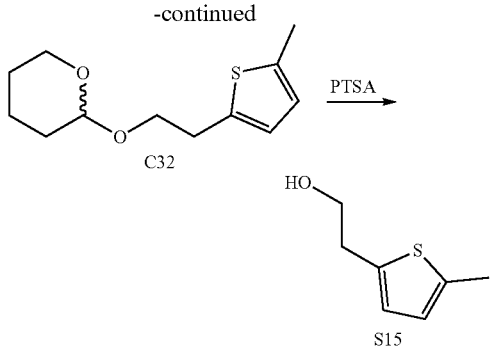

Step 1. Synthesis of 2-(5-bromo-2-thienyl)ethanol (C30)

A solution of 2-(2-thienyl)ethanol C29 (15 g, 0.1170 mol) in DMF (150.00 mL) was added dropwise to a solution of NBS (20.824 g, 0.1170 mol) in DMF at −10° C. The reaction was stirred at room temperature for 16 hours. The reaction mixture was quenched with water (300 mL) and extracted with EtOAc (3×200 mL). The combined organic layers were washed with 6% KOH solution, ice water (2×150 mL), and brine (150 mL). The organic layer was dried over sodium sulfate and concentrated. Purification by column chromatography (Eluent: 10% EtOAc in petroleum ether) afforded the product 2-(5-bromo-2-thienyl)ethanol C30 (20.5 g, 79%). $^1$H NMR (400 MHz, Chloroform-d) δ 6.89 (d, J=3.6 Hz, 1H), 6.64-6.28 (m, 1H), 3.82 (t, J=6.0 Hz, 2H), 2.99 (t, J=6.0 Hz, 2H).

Step 2. Synthesis of 2-[2-(5-bromo-2-thienyl)ethoxy]tetrahydropyran (C31)

To a stirred solution of 2-(5-bromo-2-thienyl)ethanol C30 (20 g, 0.0869 mol) and 3,4-dihydro-2H-pyran (10.969 g, 0.1304 mol) in THE (80 mL) was added with PTSA (603 mg, 0.5636 mL, 0.0035 mol) and reaction was stirred for 24 hour at room temperature. The reaction mixture was diluted with EtOAc, washed with saturated sodium bicarbonate solution (50 mL), water, and brine. The organic layer was separated, dried over sodium sulfate, and concentrated. Purification by silica gel chromatography (Gradient: 0-5% EtOAc in petroleum ether) yielded 2-[2-(5-bromo-2-thienyl)ethoxy]tetrahydropyran C31 (18.5 g, 64%). $^1$H NMR (400 MHz, Chloroform-d) δ 6.86 (d, J=3.6 Hz, 1H), 6.61-6.60 (m, 1H), 4.62 (t, J=3.6 Hz, 1H), 3.99-3.50 (m, 4H), 3.05-3.01 (m, 2H), 1.73-1.50 (m, 6H).

Step 3. Synthesis of 2-[2-(5-methyl-2-thienyl)ethoxy]tetrahydropyran (C32)

To a solution of 2-[2-(5-bromo-2-thienyl)ethoxy]tetrahydropyran C31 (19 g, 0.0555 mol) in THE (380.00 mL) was added n-BuLi (33.320 mL of 2.5 M, 0.0833 mol) dropwise at −78° C. The reaction was stirred for one hour at −78° C. Iodomethane (15.755 g, 6.9101 mL, 0.1110 mol) was added dropwise at −78° C. and the reaction mixture was allowed to stir at room temperature for 16 hours. The reaction mixture was quenched with saturated NH$_4$Cl solution and diluted with water. The aqueous layer was extracted with EtOAc (2×250 mL). Purification by silica gel chromatography (Eluent: 100% petroleum ether) yielded 2-[2-(5-methyl-2-thienyl)ethoxy]tetrahydropyran C32 (19 g, 130%). $^1$H NMR (400 MHz, Chloroform-d) δ 6.61 (d, J=3.2 Hz, 1H), 6.55-6.54 (m, 1H), 4.63 (m, 1H), 3.96-3.50 (m, 4H), 3.03 (t, J=2.8 Hz, 2H), 2.42 (s, 3H), 1.72-1.42 (m, 6H).

Step 4. Synthesis of 2-(5-methyl-2-thienyl)ethanol (S15)

To a solution of 2-[2-(5-methyl-2-thienyl)ethoxy]tetrahydropyran C32 (14 g, 0.0532 mol) in MeOH (280.00 mL) was added with PTSA (10.9 g, 10.187 mL, 0.0633 mol) at room temperature. The reaction was stirred for 24 hours. The reaction mixture was diluted with EtOAc (500 mL) and then washed with water (200 mL). The organic layer was washed with saturated aqueous sodium bicarbonate solution (2×100 mL). Aqueous layer was again extracted with EtOAc (2×100 mL). The combined organic layers were dried over Na$_2$SO$_4$. Purification by silica gel chromatography (Gradient: 0-15% EtOAc in petroleum ether) yielded 2-(5-methyl-2-thienyl)ethanol S15 (6.56 g, 82%). $^1$H NMR (400 MHz, DMSO-d$_6$) δ 6.61 (d, J=3.6 Hz, 1H), 6.58-6.57 (d, J=4.0 Hz, 1H), 4.73 (t, J=5.2 Hz, 1H), 3.58-3.53 (m, 2H), 2.82 (t, J=6.8 Hz, 2H), 2.36 (s, 3H).

Preparation of S16

[4-(2-hydroxyethyl)-2-(trifluoromethyl)-3-thienyl]methyl acetate (S16)

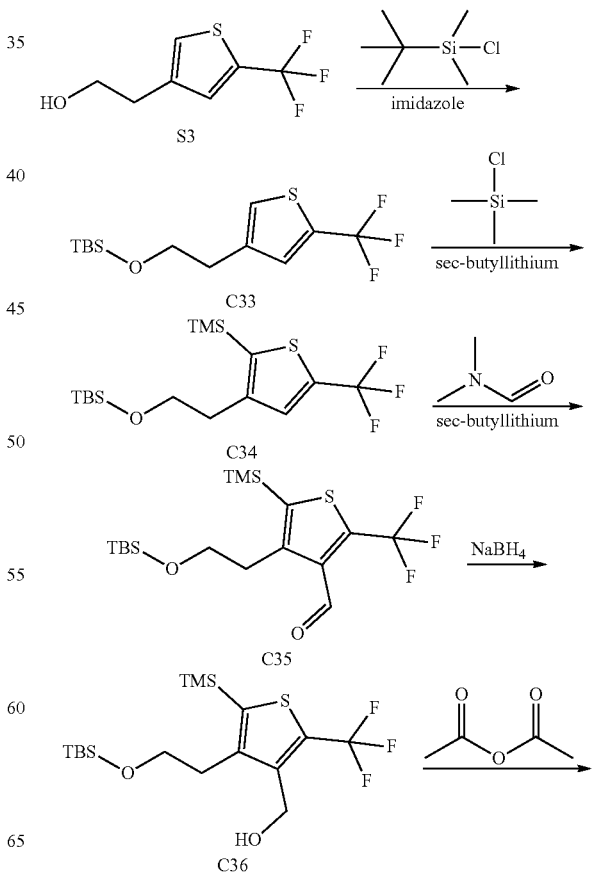

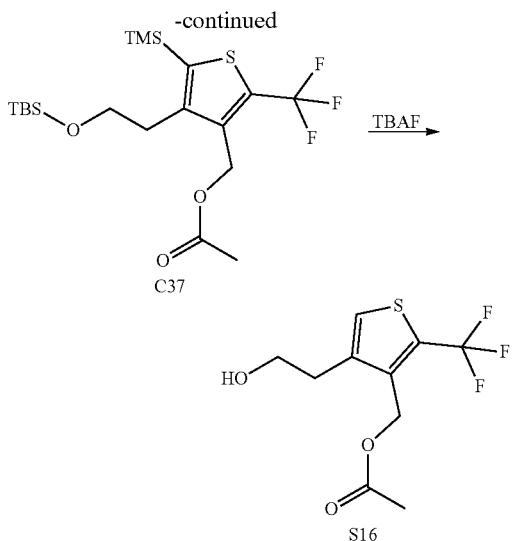

Step 1. Synthesis of tert-butyl-dimethyl-[2-[5-(trifluoromethyl)-3-thienyl]ethoxy]silane (C33)

To a mixture of 2-[5-(trifluoromethyl)-3-thienyl]ethanol S3 (500 mg, 2.498 mmol) in DCM (10 mL) was added imidazole (190 mg, 2.791 mmol) followed by TBSCl (420 mg, 2.787 mmol) which immediately precipitated a white solid. The solid was filtered and the organic layer was washed with 1 N HCl (10 mL), brine (10 mL), dried with MgSO$_4$, filtered, and concentrated. Purification by silica gel chromatography (Gradient: 0-30% EtOAc in heptane) yielded the product, tert-butyl-dimethyl-[2-[5-(trifluoromethyl)-3-thienyl]ethoxy]silane C33, assumed to be quantitative and carried forward without further purification.

Step 2. Synthesis of tert-butyl-dimethyl-[2-[5-(trifluoromethyl)-2-trimethylsilyl-3-thienyl]ethoxy]silane (C34)

A mixture of tert-butyl-dimethyl-[2-[5-(trifluoromethyl)-3-thienyl]ethoxy]silane C33 in THF (10 mL) was cooled to −78° C. and sec-butyllithium (2.3 mL of 1.4 M, 3.220 mmol) was added followed by TMSCl (3 mL of 1 M, 3.000 mmol). After 5 minutes, the yellow mixture was quenched with saturated aqueous ammonium chloride. The mixture was diluted with water (10 mL) and MTBE (10 mL). The organic layer was washed with brine, dried with MgSO$_4$, filtered, and concentrated. Purification by silica gel chromatography (Gradient: 0-10% EtOAc in heptane) yielded tert-butyl-dimethyl-[2-[5-(trifluoromethyl)-2-trimethylsilyl-3-thienyl]ethoxy]silane C34 (400 mg, 42%). $^1$H NMR (300 MHz, Chloroform-d) δ 7.41 (d, J=1.2 Hz, 1H), 3.80-3.75 (m, 2H), 2.87 (t, J=6.8 Hz, 2H), 0.87 (s, 9H), 0.36 (s, 9H), −0.00 (d, J=2.2 Hz, 6H).

Step 3. Synthesis of 4-[2-[tert-butyl(dimethyl)silyl]oxyethyl]-2-(trifluoromethyl)-5-trimethylsilyl-thiophene-3-carbaldehyde (C35)

To a mixture of tert-butyl-dimethyl-[2-[5-(trifluoromethyl)-2-trimethylsilyl-3-thienyl]ethoxy]silane C34 (400 mg, 1.024 mmol) in THF (10 mL) cooled to −78° C. was added sec-butyllithium (1.2 mL of 1.4 M, 1.680 mmol) followed by DMF (3 mL of 1 M, 3.000 mmol). After 5 minutes, the yellow mixture was quenched with saturated aqueous ammonium chloride. The mixture was diluted with EtOAc (20 mL) and water (20 mL) and separated. The organic layer was washed with brine (20 mL), dried with MgSO$_4$, filtered, and concentrated. Purification by silica gel chromatography (Eluent: 100% heptane) yielded the product, 4-[2-[tert-butyl(dimethyl)silyl]oxyethyl]-2-(trifluoromethyl)-5-trimethylsilyl-thiophene-3-carbaldehyde C35. The mixture was concentrated, diluted with heptane (5 mL) and washed with water (5 mL). The organic layer was passed over a phase separator, concentrated, and telescoped directly to the next step.

Step 4. Synthesis of [4-[2-[tert-butyl(dimethyl)silyl]oxyethyl]-2-(trifluoromethyl)-5-trimethylsilyl-3-thienyl]methanol (C36)

4-[2-[tert-butyl(dimethyl)silyl]oxyethyl]-2-(trifluoromethyl)-5-trimethylsilyl-thiophene-3-carbaldehyde C35 was diluted in MeOH (1 mL) and to the mixture was added NaBH$_4$ (7 mg, 0.1850 mmol). After 10 minutes the mixture was concentrated, and re-diluted in heptane (2 mL) and water (2 mL). The organic layer was separated and the aqueous layer was extracted with additional heptane. The organic layer was passed over a phase separator and concentrated. Purification by silica gel chromatography (Gradient: 0-10% EtOAc in heptane) yielded the product C36. $^1$H NMR (300 MHz, Chloroform-d) δ 4.65 (d, J=6.3 Hz, 2H), 4.00-3.72 (m, 2H), 3.34 (t, J=6.3 Hz, 1H), 2.97 (t, J=6.1 Hz, 2H), 0.82 (s, 10H), 0.36 (s, 9H).

Step 5. Synthesis of [4-[2-[tert-butyl(dimethyl)silyl]oxyethyl]-2-(trifluoromethyl)-5-trimethylsilyl-3-thienyl]methyl acetate (C37)

To [4-[2-[tert-butyl(dimethyl)silyl]oxyethyl]-2-(trifluoromethyl)-5-trimethylsilyl-3-thienyl]methanol C36 in DCM (4 mL) was added DMAP (2 mg, 0.016 mmol) and DIPEA (50 μL, 0.2871 mmol) followed by Ac2O (30 μL, 0.3180 mmol). The mixture was concentrated, diluted with heptane (5 mL) and washed with water (5 mL). The organic layer was passed over a phase separator and concentrated to yield the product which was telescoped directly in to the next step.

Step 6. Synthesis of [4-(2-hydroxyethyl)-2-(trifluoromethyl)-3-thienyl]methyl acetate (S16)

[4-[2-[tert-butyl(dimethyl)silyl]oxyethyl]-2-(trifluoromethyl)-5-trimethylsilyl-3-thienyl]methyl acetate C37 from step 5 was diluted with EtOAc (2 mL) and to the mixture was added a THF solution of TBAF (1 mL of 1 M, 1.000 mmol) and the mixture was stirred. The reaction was stirred for 48 hours. The mixture was diluted with additional EtOAc (3 mL), washed with water, passed over a phase separator, and concentrated. Purification by silica gel chromatography (Gradient: 0-60% EtOAc in heptane) yielded the product [4-(2-hydroxyethyl)-2-(trifluoromethyl)-3-thienyl]methyl acetate S16 (35 mg, 12%). $^1$H NMR (300 MHz, Chloroform-d) δ 7.26 (s, 1H), 5.14 (d, J=1.1 Hz, 2H), 3.86 (t, J=6.4 Hz, 2H), 2.97-2.74 (m, 2H), 2.07 (s, 3H), 1.80 (s, 1H). LCMS m/z 269.21 [M+H]$^+$.

Preparation of S17

1-methyltriazole-4-carbaldehyde (S17)

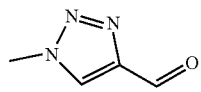

1-methyltriazole-4-carbaldehyde S17 was obtained from commercially available sources.

Preparation of S18

1-(2-methylsulfonylethyl)triazole-4-carbaldehyde (S18)

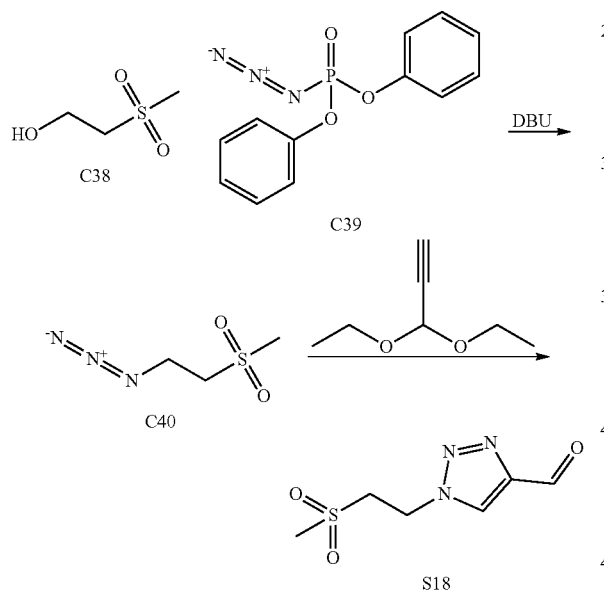

Step 1. Synthesis of 1-azido-2-methylsulfonyl-ethane (C40)

A solution of 2-methylsulfonylethanol C38 (5 g, 0.04 mol) and Diphenyl phosphoryl azide C39 (8.8614 g, 0.0322 mol) in Toluene (50 mL) was stirred at 0° C. for 10 minutes and DBU (5.5 g, 5.42 mL, 0.04 mol) was added dropwise at 0° C. over 10 minutes and the reaction was stirred at room temperature for 16 hours. The reaction mixture was quenched with water (25 mL) and EtOAc (100 mL) and stirred for 20 minutes. The organic layer was separated and aqueous layer was again extracted with EtOAc (2×100 mL). The organic layer was dried over $Na_2SO_4$ and concentrated. Purification by silica gel chromatography (Gradient: 0-100% ethyl acetate in petroleum ether) gave 1-azido-2-methylsulfonyl-ethane C40 (5.2 g, 86%). $^1$H NMR (400 MHz, DMSO-$d_6$) δ 3.77-3.73 (t, J=8.8 Hz, 2H), 3.44-3.42 (t, J=8.8 Hz, 2H), 3.03 (s, 3H).

Step 2. Synthesis of 1-(2-methylsulfonylethyl)triazole-4-carbaldehyde (S18)

A mixture of 3,3-diethoxyprop-1-yne (555 μL, 3.897 mmol), 1-azido-2-methylsulfonyl-ethane C40 (600 mg, 4.022 mmol), $CuSO_4$ (15 mg, 0.09398 mmol), 1-(1-benzyl-triazol-4-yl)-N,N-bis[(1-benzyltriazol-4-yl)methyl]methanamine (100 mg, 0.1885 mmol), and sodium ascorbate (700 mg, 3.974 mmol) in MeOH (12 mL)/water (3 mL) was heated to 60° C. for 2 hours. The reaction was cooled to room temperature, concentrated, and diluted in EtOAc (100 mL) and water (50 mL). The layers were split and the aqueous layer was extracted with EtOAc (50 mL). The layers were combined and dried, diluted in 1 N HCl (20 mL), and stirred overnight. At this time, the solution was concentrated to yield 1-(2-methylsulfonylethyl)triazole-4-carbaldehyde (Hydrochloride salt) S18 (553 mg, 59%). $^1$H NMR (400 MHz, Methanol-d4) δ 8.07 (s, 1H), 5.58-5.45 (m, 1H), 4.89-4.82 (m, 2H), 3.76-3.67 (m, 2H), 3.24 (s, 3H). LCMS m/z 204.47 $[M+H]^+$.

Preparation of S19

1-(2-methylsulfonylethyl)pyrazole-4-carbaldehyde (S19)

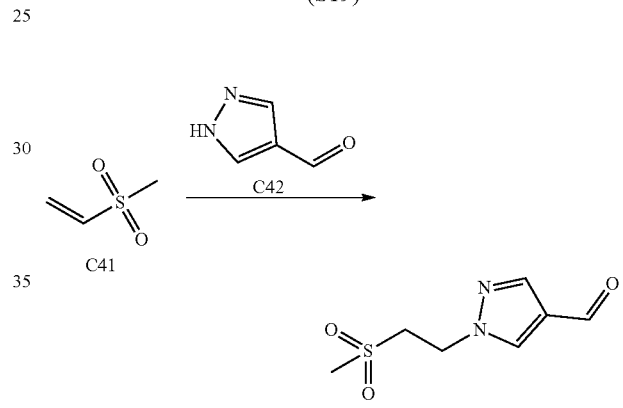

A solution of 1H-pyrazole-4-carbaldehyde C42 (10 g, 104.1 mmol) 11-methylsulfonylethylene C41 (10 mL, 114.2 mmol) and $K_2CO_3$ (25 g, 180.9 mmol) in THF (200 mL) was stirred at 60° C. After stirring overnight, the mixture was cooled to room temperature and concentrated to dryness. The product was suspended in diethyl ether (100 mL) to triturate the product and stirred for 2 hours. The product was filtered and dried overnight to yield 11-(2-methylsulfonylethyl)pyrazole-4-carbaldehyde S19 (20.28 g, 83%). $^1$H NMR (400 MHz, DMSO-d6) δ 9.80 (s, 1H), 8.54 (d, J=0.7 Hz, 1H), 8.05 (d, J=0.7 Hz, 1H), 4.64 (t, J=6.8 Hz, 2H), 3.80-3.67 (m, 2H), 2.96 (d, J=0.7 Hz, 3H). LCMS m/z 203.01 $[M+H]^+$.

Preparation of S20

1-[2-[tert-butyl(dimethyl)silyl]oxyethyl]pyrazole-4-carbaldehyde (S20)

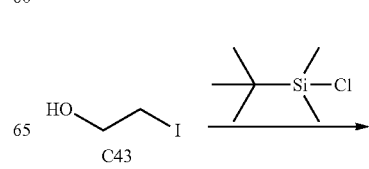

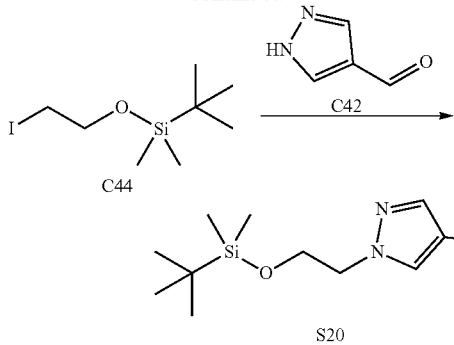

Step 1. Synthesis of tert-butyl-(2-iodoethoxy)-dimethyl-silane (C44)

To a stirred solution of 2-iodoethanol C43 (2 g, 0.0116 mol) and imidazole (1.58 g, 0.0232 mol) in DCM (40 mL) was added tert-butyl-chloro-dimethyl-silane (1.9 g, 0.0126 mol) at 0° C. The reaction was warmed to room temperature and stirred for 4 hours. The reaction mixture was diluted with DCM (100 mL), washed with sat NaHCO$_3$ and brine, dried over Na$_2$SO$_4$, and concentrated under reduced pressure to get tert-butyl-(2-iodoethoxy)-dimethyl-silane C44 (2.5 g, 68%). $^1$H NMR (400 MHz, Chloroform-d) δ 3.83 (t, J=6.8 Hz, 2H), 3.20 (t, J=6.8 Hz, 2H), 0.90 (s, 9H), 0.08 (s, 6H).

Step 2. Synthesis of 1-[2-[tert-butyl(dimethyl)silyl]oxyethyl]pyrazole-4-carbaldehyde (S20)

To a solution of 1H-pyrazole-4-carbaldehyde C42 (20 g, 208.1 mmol) and K$_2$CO$_3$ (115 g, 832.1 mmol) in MeCN (200 mL) was added tert-butyl-(2-iodoethoxy)-dimethyl-silane C44 (65 g, 227.1 mmol). The reaction was heated to 80° C. The reaction was stirred for 5 hours. The reaction was cooled to 50° C. and stirred for 16 hours. The reaction mixture was allowed to reach ambient temperature, filtered, and solids were washed with MeCN (200 mL). The solids were discarded and the filtrate was concentrated. The residue was partitioned between EtOAc (400 mL) and water (400 mL). The organic layer was separated, washed with water (400 mL) and brine (400 mL), dried over MgSO$_4$, filtered, and concentrated. Purification by silica gel chromatography (800 g column, 0-80% EtOAc in hexane) afforded the product. 1-[2-[tert-butyl(dimethyl)silyl]oxyethyl]pyrazole-4-carbaldehyde S20 (46 g, 87%) as a pale yellow oil. $^1$H NMR (300 MHz, Chloroform-d) δ 9.86 (s, 1H), 7.98 (s, 2H), 4.25 (dd, J=5.5, 4.5 Hz, 2H), 3.96 (dd, J=5.5, 4.5 Hz, 2H), 0.83 (s, 9H), −0.06 (s, 6H). LCMS m/z 255.14 [M+H]$^+$.

Preparation of S21

1-[3-[tert-butyl(dimethyl)silyl]oxy-2-[[tert-butyl(dimethyl)silyl]oxymethyl]-2-methyl-propyl]pyrazole-4-carbaldehyde (S21)

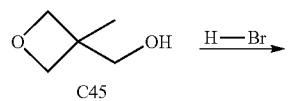

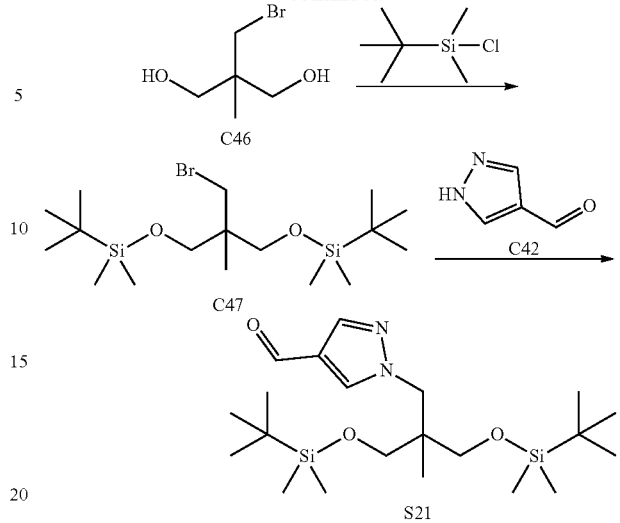

Step 1. Synthesis of 2-(bromomethyl)-2-methyl-propane-1,3-diol (C46)

To a mixture of (3-methyloxetan-3-yl)methanol C45 (10 mL, 100.3 mmol) in THF (70 mL) at 0° C. was added hydrogen bromide (14 mL of 48% (w/w), 123.7 mmol). After stirring for 24 hours, the mixture was concentrated to a minimum volume, diluted in DCM/MeOH and the excess HBr was quenched with saturated sodium bicarbonate. The layers were split and the organic layer was dried with Na$_2$SO$_4$, filtered, rinsed with methanol, and concentrated to yield 2-(bromomethyl)-2-methyl-propane-1,3-diol C46 (13.6682 g, 74%). $^1$H NMR (400 MHz, Methanol-d4) δ 3.47 (d, J=1.1 Hz, 6H), 0.96 (s, 3H).

Step 2. Synthesis of [2-(bromomethyl)-3-[tert-butyl(dimethyl)silyl]oxy-2-methyl-propoxy]-tert-butyl-dimethyl-silane (C47)

To a mixture of 2-(bromomethyl)-2-methyl-propane-1,3-diol C46 (10 g, 54.09 mmol) in DCM (200 mL) was added imidazole (7.7 g, 113.1 mmol) followed by TBSCl (17 g, 112.8 mmol). After 5 minutes, the mixture had precipitated a white crystalline solid. The mixture was filtered, rinsed with DCM, and concentrated. The mixture was diluted with heptane (25 mL) to further precipitate imidazole/imidazole HCl, filtered, and the solid was rinsed with additional heptane (10 mL). The mixture was concentrated, which precipitated additional solid. The mixture was diluted and concentrated twice more with heptane (50 mL) to afford [2-(bromomethyl)-3-[tert-butyl(dimethyl)silyl]oxy-2-methyl-propoxy]-tert-butyl-dimethyl-silane C47 (22.246 g, 100%)$^1$H NMR (400 MHz, Chloroform-d) δ 3.44 (s, 4H), 3.40 (s, 2H), 0.94 (s, 3H), 0.89 (s, 18H), 0.04 (d, J=1.2 Hz, 12H).

Step 3. Synthesis of 1-[3-[tert-butyl(dimethyl)silyl]oxy-2-[[tert-butyl(dimethyl)silyl]oxymethyl]-2-methyl-propyl]pyrazole-4-carbaldehyde (S21)

To a vial was added 1H-pyrazole-4-carbaldehyde C42 (2 g, 20.81 mmol), K$_2$CO$_3$ (4 g, 28.94 mmol), and [2-(bromomethyl)-3-[tert-butyl(dimethyl)silyl]oxy-2-methyl-propoxy]-tert-butyl-dimethyl-silane C47 (9.5 g, 23.08 mmol) in DMF (20 mL). The mixture was heated to 130° C. After 3 hours the mixture was cooled to room temperature, diluted with water (100 mL) and heptane (100 mL). The layers were mixed, and the aqueous layer was washed with heptane (2×100 mL). The combined organic layers were washed with water (100 mL), brine (100 mL) and the organic layer was dried over $Na_2SO_4$ and concentrated. Purification by silica gel chromatography (Gradient: 0-60% EtOAc:Heptane) yielded the product 1-[3-[tert-butyl(dimethyl)silyl]oxy-2-[[tert-butyl(dimethyl)silyl]oxymethyl]-2-methyl-propyl]pyrazole-4-carbaldehyde S21 (2.39 mg, 23%). $^1$H NMR (400 MHz, Chloroform-d) δ 9.85 (s, 1H), 7.98-7.91 (m, 2H), 4.12 (s, 2H), 3.43-3.29 (m, 4H), 0.91 (s, 18H), 0.84 (s, 3H), 0.05 (d, J=0.6 Hz, 12H). LCMS m/z 427.31 [M+H]$^+$.

Preparation of S22

2-[(2-hydroxy-1,1-dimethyl-ethyl)amino]pyrimidine-5-carbaldehyde (S22)

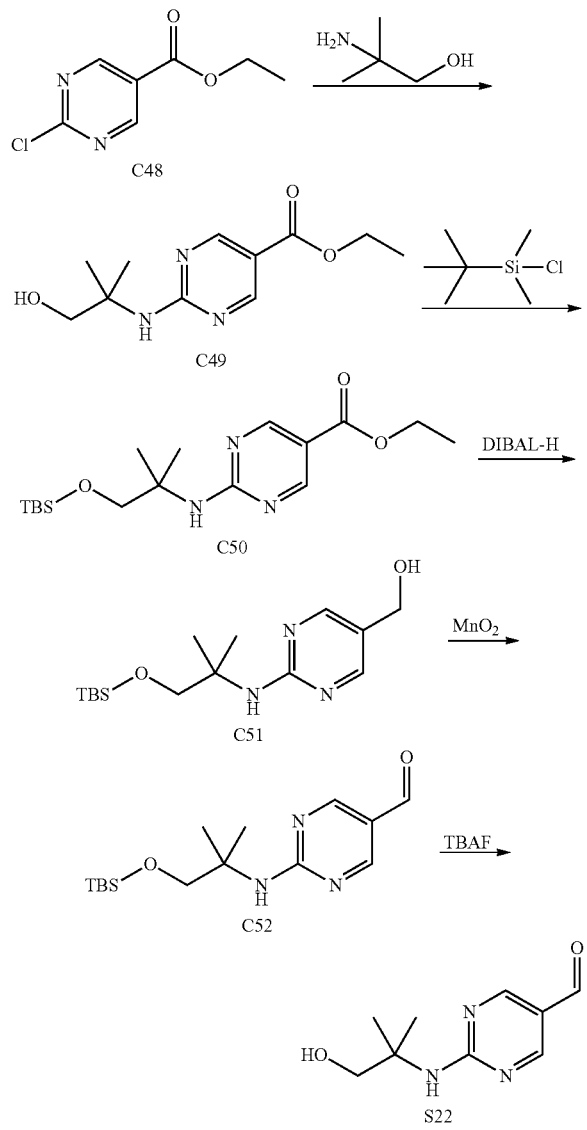

Step 1. Synthesis of ethyl 2-[(2-hydroxy-1,1-dimethyl-ethyl)amino]pyrimidine-5-carboxylate (C49)

To a stirred solution of ethyl 2-chloropyrimidine-5-carboxylate C48 (25 g, 0.1340 mol) in Ethanol (750 mL) was added 2-amino-2-methyl-propan-1-ol (14.333 g, 15.412 mL, 0.1608 mol) followed by DIPEA (34.637 g, 46.681 mL, 0.2680 mol) at room temperature. The reaction was stirred at 80° C. for 8 hours. The reaction was warmed to room temperature and concentrated under reduced pressure. Purification by silica gel chromatography (Eluent: 70% EtOAc in petroleum ether) afforded ethyl 2-[(2-hydroxy-1,1-dimethyl-ethyl)amino]pyrimidine-5-carboxylate C49 (18 g, 55%). $^1$H NMR (400 MHz, DMSO-$d_6$) δ 8.70 (s, 2H), 7.39 (s, 1H), 4.86 (t, J=6 Hz, 1H), 4.25 (q, J=6.8 Hz, 2H), 3.52 (d, J=6 Hz, 2H), 1.32 (s, 6H), 1.28 (t, J=6.8 Hz, 3H). LCMS m/z 240.27 [M+H]$^+$.

Step 2. Synthesis of ethyl 2-[[2-[tert-butyl(dimethyl)silyl]oxy-1,1-dimethyl-ethyl]amino]pyrimidine-5-carboxylate (C50)

To a stirred solution of ethyl 2-[(2-hydroxy-1,1-dimethyl-ethyl)amino]pyrimidine-5-carboxylate C49 (10 g, 0.0410 mol) and tert-butyl-chloro-dimethyl-silane (9.2694 g, 0.0615 mol) in DCM (500 mL) was added imidazole (8.3735 g, 0.1230 mol) followed by DMAP (1.0018 g, 0.0082 mol) at room temperature and stirred for 16 hours. The reaction was concentrated under reduced pressure. The crude material was diluted with water (500 mL) and pentane (500 mL). The organic layer was separated, washed with water, dried over $Na_2SO_4$, and concentrated under reduced pressure to afford ethyl 2-[[2-[tert-butyl(dimethyl)silyl]oxy-1,1-dimethyl-ethyl]amino]pyrimidine-5-carboxylate C50 (14.9 g, 100%). $^1$H NMR (400 MHz, DMSO-$d_6$) δ 8.70 (s, 2H), 7.46 (s, 1H), 4.25 (q, J=7.2 Hz, 2H), 3.77 (s, 2H), 1.30 (s, 6H), 1.28 (t, J=7.6 Hz, 3H), 0.82 (s, 9H), −0.06 (s, 6H). LCMS m/z 354.3 [M+H]$^+$.

Step 3. Synthesis of [2-[[2-[tert-butyl(dimethyl)silyl]oxy-1,1-dimethyl-ethyl]amino]pyrimidin-5-yl]methanol (C51)

To a stirred solution of ethyl 2-[[2-[tert-butyl(dimethyl)silyl]oxy-1,1-dimethyl-ethyl]amino]pyrimidine-5-carboxylate C50 (15 g, 0.0411 mol) in THF (600 mL), was added DIBAL-H (1 M in Toluene) (205.50 mL of 1 M, 0.2055 mol) at −78° C. slowly under nitrogen. The reaction was stirred for 30 minutes at −78° C. and then warmed to room temperature and stirred for 4 hours. The reaction mixture was quenched with sat $NH_4Cl$ (500 mL) at 0° C. and compound was extracted with EtOAc (2×500 mL). The organic layers were washed with 1 N HCl (100 mL), brine, dried over $Na_2SO_4$, and concentrated under reduced pressure. Purification by silica gel chromatography (Eluent: 50% EtOAc in petroleum ether) afforded [2-[[2-[tert-butyl(dimethyl)silyl]oxy-1,1-dimethyl-ethyl]amino]pyrimidin-5-yl]methanol C51 (6 g, 46%). $^1$H NMR (400 MHz, DMSO-$d_6$) δ 8.19 (s, 2H), 6.25 (s, 1H), 4.99 (t, J=5.6 Hz, 1H), 4.27 (d, J=5.6 Hz, 2H), 3.71 (s, 2H), 1.30 (s, 6H), 0.84 (s, 9H), −0.03 (s, 6H). LCMS m/z 312.23 [M+H]$^+$.

Step 4. Synthesis of 2-[[2-[tert-butyl(dimethyl)silyl]oxy-1,1-dimethyl-ethyl]amino]pyrimidine-5-carbaldehyde (C52)

To a stirred solution of [2-[[2-[tert-butyl(dimethyl)silyl]oxy-1,1-dimethyl-ethyl]amino]pyrimidin-5-yl]methanol C51 (120 mg, 271.55 μmol) in DCM (10 mL) was added MnO₂ (851.98 mg, 0.0098 mol) at room temperature and stirred for 6 hours. The reaction was filtered through Celite® and washed with DCM (10 mL). The filtrates were concentrated under reduced pressure to provide 2-[[2-[tert-butyl (dimethyl)silyl]oxy-1,1-dimethyl-ethyl]amino]pyrimidine-5-carbaldehyde C52 (90 mg, 99%). $^1$H NMR (400 MHz, DMSO-$d_6$) δ 9.71 (s, 1H), 8.71 (d, J=11.6 Hz, 2H), 7.72 (s, 1H), 3.78 (s, 2H), 1.34 (s, 6H), 0.84 (s, 9H), −0.05 (s, 6H). LCMS m/z 310.22 [M+H]$^+$.

Step 5. Synthesis of 2-[(2-hydroxy-1,1-dimethyl-ethyl)amino]pyrimidine-5-carbaldehyde (S22)

To a stirred solution of 2-[[2-[tert-butyl(dimethyl)silyl] oxy-1,1-dimethyl-ethyl]amino]pyrimidine-5-carbaldehyde C52 (2.9 g, 0.0087 mol) in THF (20 mL) was added TBAF (1 M in THF) (21.700 mL of 1 M, 0.0217 mol) at room temperature and stirred for 2 hours. The reaction was diluted with EtOAc (100 mL), washed with brine solution, dried over Na₂SO₄, and concentrated under reduced pressure. The crude compound was washed with pentane and dried to afford 2-[(2-hydroxy-1,1-dimethyl-ethyl)amino]pyrimidine-5-carbaldehyde S22 (1.47 g, 86%). $^1$H NMR (400 MHz, DMSO-$d_6$) δ 9.72 (s, 1H), 8.71 (d, J=13.2 Hz, 2H), 7.64 (s, 1H), 4.87 (t, J=6 Hz, 1H), 3.54 (d, J=6 Hz, 2H), 1.33 (s, 6H). LCMS m/z 196.35 [M+H]$^+$.

Preparation of S23

(3S)-3-aminobutanoic acid (S23)

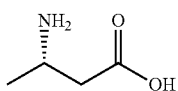

S23

(3S)-3-aminobutanoic acid (S23) was obtained from commercial sources.

Preparation of S24

4-aminopentan-2-one hydrochloride (S24)

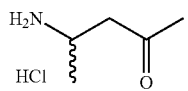

S24

4-aminopentan-2-one hydrochloride (S24) was obtained from commercial sources.

Preparation of S25

(4S)-4-aminopentan-2-one hydrochloride (S25)

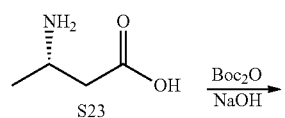

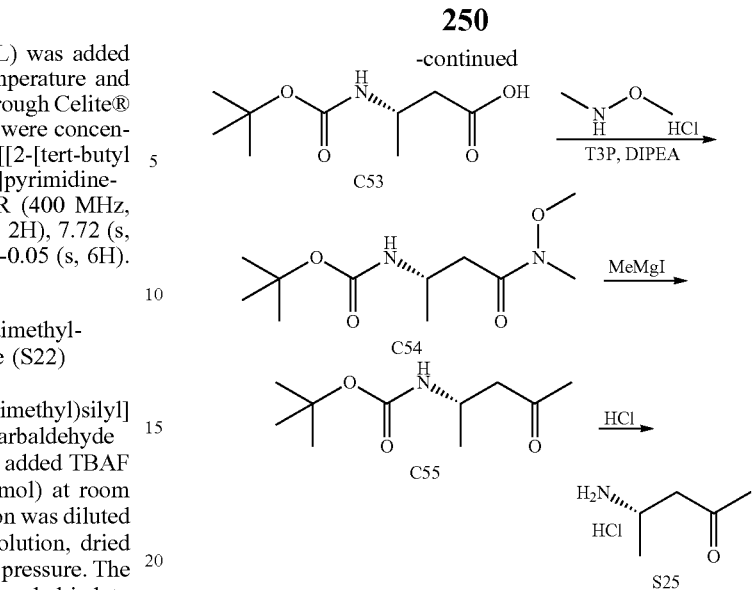

Step 1. Synthesis of (3S)-3-(tert-butoxycarbonylamino)butanoic acid (C53)

To a solution of (3S)-3-aminobutanoic acid S23 (100 g, 969.7 mmol) in dioxane (600 mL) was added aqueous NaOH solution (950 mL of 1 M, 950.0 mmol) over 15 minutes, followed by Boc₂O (300 g, 1.375 mol). The reaction mixture was stirred at room temperature for 12 hours. The reaction was partitioned with MTBE (1 L) and water (300 mL). The layers were separated, and the aqueous layer was extracted again with MTBE (500 mL). The aqueous layer was then acidified with 1 N HCl until pH=2 and extracted with DCM (3×600 mL). The combined organic layers were washed with brine, dried over MgSO4, filtered, and concentrated in vacuo to yield (3S)-3-(tert-butoxycarbonylamino)butanoic acid C53 (176 g, 89%) as a white solid. $^1$H NMR (300 MHz, Chloroform-d) δ 4.92 (s, 1H), 4.04 (s, 1H), 2.56 (dd, J=5.5, 2.9 Hz, 2H), 1.44 (s, 9H), 1.25 (d, J=6.8 Hz, 3H).

Step 2. Synthesis of tert-butyl N—[(S)-3-[methoxy (methyl)amino]-1-methyl-3-oxo-propyl]carbamate (C54)

To a solution of (3S)-3-(tert-butoxycarbonylamino)butanoic acid C53 (160 g, 787.3 mmol) in DCM (1.5 L) was added N-methoxymethanamine (Hydrochloride salt) (81 g, 830.4 mmol) followed by the addition of DIPEA (560 mL, 3.215 mol) over 10 minutes. The reaction mixture was cooled to 0° C. and T3P (600 g of 50% (w/w) in EtOAc, 942.9 mmol) was added over 45 minutes. After the addition, the cooling bath was removed and the reaction was stirred at room temperature for 1 hour. The reaction mixture was cooled to 10° C. and aqueous 1 N NaOH solution (700 mL) was added and the solution stirred for 15 minutes. The organic phase was separated, washed with aqueous saturated ammonium chloride solution (200 mL) and brine (200 mL), dried, filtered through a silica plug, and concentrated in vacuo to afford tert-butyl N-[(1S)-3-[methoxy(methyl) amino]-1-methyl-3-oxo-propyl]carbamate C54 (180 g, 93%) as a clear, colorless viscous oil. $^1$H NMR (300 MHz, Chloroform-d) δ 5.30 (s, 1H), 4.06 (ddd, J=14.3, 9.7, 6.0 Hz, 1H), 3.68 (s, 3H), 3.17 (s, 3H), 2.71 (dd, J=15.6, 5.2 Hz, 1H), 2.54 (dd, J=15.7, 5.7 Hz, 1H), 1.43 (s, 9H), 1.24 (d, J=6.8 Hz, 3H).

Step 3. Synthesis of tert-butyl N-[(1S)-1-methyl-3-oxo-butyl]carbamate (C55)

To a solution of tert-butyl N-[(1S)-3-[methoxy(methyl)amino]-1-methyl-3-oxo-propyl]carbamate C54 (220 g, 893.2 mmol) in THF (4 L) at 0° C. was added iodo(methyl)magnesium (900 mL of 3 M, 2.700 mol) over 40 minutes. The resulting reaction mixture was stirred at 0° C. for 4 hours. The reaction was quenched with saturated ammonium chloride solution (2 L), followed by MTBE (1 L) and water (2 L). The mixture was stirred for 30 minutes and the organic layer was separated. The aqueous phase was extracted with MTBE (1 L) and the combined organic layers were washed with saturated ammonium chloride solution (1 L), dried over MgSO₄, filtered, and concentrated in vacuo. Purification by silica gel chromatography (Gradient: 0-70% EtOAc in heptane) yielded the product tert-butyl N-[(1S)-1-methyl-3-oxo-butyl]carbamate C55 (115 g, 64%) as a white solid. ¹H NMR (300 MHz, Chloroform-d) δ 4.83 (s, 1H), 4.12-3.87 (m, 1H), 2.69 (dd, J=16.5, 5.2 Hz, 1H), 2.63-2.47 (m, 1H), 2.15 (d, J=2.3 Hz, 3H), 1.43 (d, J=2.4 Hz, 9H), 1.20 (dd, J=6.8, 2.4 Hz, 3H).

Step 4. Synthesis of (4S)-4-aminopentan-2-one (Hydrochloride salt) (S25)

To a solution of tert-butyl N-[(1S)-1-methyl-3-oxo-butyl]carbamate C55 (16.3 g, 80.18 mmol) in MeOH (30 mL) was added hydrogen chloride (50 mL of 4 M in dioxane, 200.0 mmol) over 3 minutes. The reaction was stirred at room temperature for 5 hours and then concentrated under reduced pressure. The residue was co-evaporated with EtOH (2×30 mL) and dried under vacuum to afford (4S)-4-aminopentan-2-one (Hydrochloride salt) S25 (12 g, 98%) as a pink viscous oil. ¹H NMR (300 MHz, Chloroform-d) δ 8.06 (s, 3H), 3.48 (d, J=6.8 Hz, 1H), 2.88 (dd, J=18.0, 5.8 Hz, 1H), 2.75 (dd, J=18.0, 7.2 Hz, 1H), 2.13 (s, 3H), 1.17 (d, J=6.6 Hz, 3H).

Preparation of S26 (Method A)

(2S,6S)-2-methyl-6-(1-methyltriazol-4-yl)piperidin-4-one (S26)

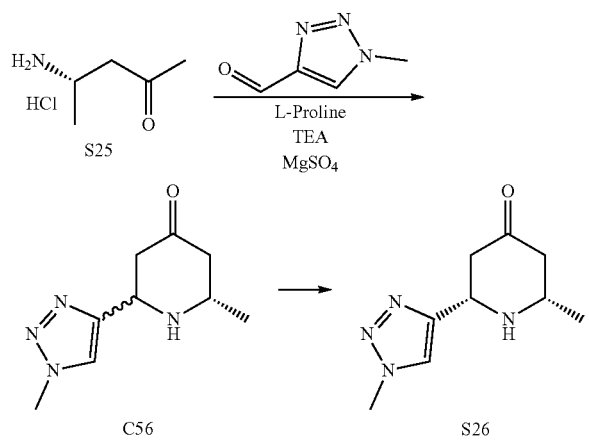

Step 1. Synthesis of (2S)-2-methyl-6-(1-methyltriazol-4-yl)piperidin-4-one (C56)

To a mixture of (4S)-4-aminopentan-2-one (Hydrochloride salt) S25 (12 g, 78.48 mmol) in EtOH (300 mL) was added 1-methyltriazole-4-carbaldehyde S17 (9 g, 81.01 mmol), L-Proline (2 g, 17.37 mmol), magnesium sulfate (12 g, 99.69 mmol), and TEA (13 mL, 93.27 mmol). The reaction mixture was stirred at room temperature overnight. The mixture was filtered and concentrated under reduced pressure. The crude residue was quenched with saturated sodium bicarbonate solution (150 mL) and extracted with DCM (3×100 mL). The combined organic layers were washed with brine (50 mL), dried over magnesium sulfate, filtered, and concentrated in vacuo. Purification by silica gel chromatography (Gradient: 0-60% of 20% MeOH/DCM in DCM) yielded the product (2S)-2-methyl-6-(1-methyltriazol-4-yl)piperidin-4-one C56 (6.7 g, 44%) as a 5:1 cis to trans ratio. Additionally, the e.r. at the stereocenter from S25 was eroded to ~85%.

NMR for the major (CIS) stereoisomer in C56: ¹H NMR (300 MHz, Chloroform-d) δ 7.47 (s, 1H), 4.26 (dd, J=10.3, 4.9 Hz, 1H), 4.11 (s, 3H), 3.17 (dqd, J=12.2, 6.2, 3.0 Hz, 1H), 2.73-2.56 (m, 2H), 2.47 (ddd, J=14.2, 3.0, 1.6 Hz, 1H), 2.21 (dd, J=14.2, 11.7 Hz, 2H), 1.28 (d, J=6.2 Hz, 3H).

NMR Rationalization of Stereoisomer Assignments in C56: Note that major component in C56 was assigned as the cis stereoisomer using NMR coupling constant data for the peak at 4.26 ppm (C5-methylene proton). The triazole at C6 is assumed to occupy an equatorial position in the lowest energy conformation. The coupling between the axial CH at C4 and one of the CH protons at C5 (J=10.3 Hz) indicates a 180° relationship as defined by the Karplus equation. The minor trans product was removed in the subsequent re-crystallization step to afford S26.

Step 2. Synthesis of (2S,6S)-2-methyl-6-(1-methyltriazol-4-yl)piperidin-4-one (S26)

A solution of (2S)-2-methyl-6-(1-methyltriazol-4-yl)piperidin-4-one C56 (6.7 g) as a 5:1 cis to trans ratio in MTBE (100 mL) was heated to reflux for 30 minutes. Ethanol was added slowly until all solids dissolved (20 mL). The solution was refluxed for 30 minutes and allowed to slowly cool overnight. A solid crystalized out which was diluted with MTBE (30 mL), filtered, and dried under vacuum to afford the (2S,6S)-2-methyl-6-(1-methyltriazol-4-yl)piperidin-4-one S26 (3.2 g, 48%) as a white solid with an enantiomeric ratio of ≥85% which was carried through to all further compounds which utilized S26 as a starting material unless otherwise noted (excluding examples which were subjected to SFC purification). ¹H NMR (300 MHz, Chloroform-d) δ 7.45 (s, 1H), 4.23 (dd, J=10.3, 4.9 Hz, 1H), 4.09 (s, 3H), 3.14 (ddp, J=12.2, 6.1, 3.1 Hz, 1H), 2.71-2.52 (m, 2H), 2.44 (ddd, J=14.1, 3.0, 1.5 Hz, 1H), 2.27-2.00 (m, 2H), 1.26 (d, J=6.2 Hz, 3H).

Alternative Preparation of S26 (Method B)

((2S,6S)-2-methyl-6-(1-methyltriazol-4-yl)piperidin-4-one (S26)

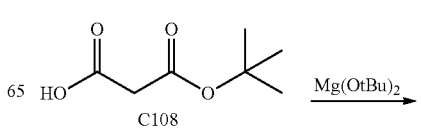

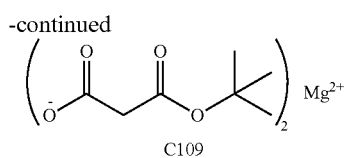

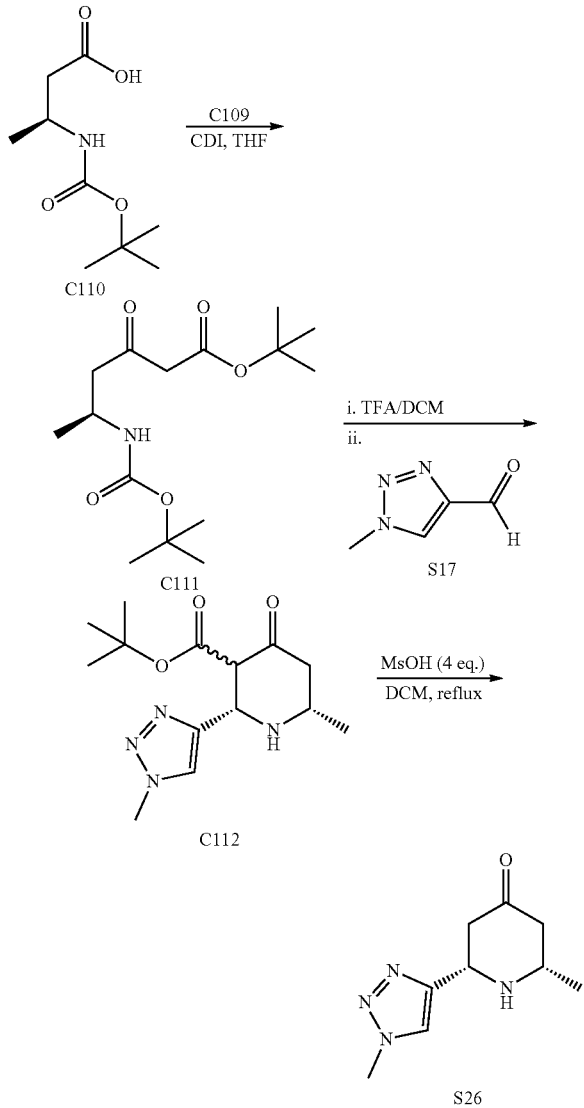

Step 1. Synthesis of bis[(3-tert-butoxy-3-oxo-propanoyl)oxy] magnesium(C109)

A solution of 3-tert-butoxy-3-oxo-propanoic acid C108 (321.51 g, 1.907 mol) in THF (2 L) was cooled to 5° C. in an ice-bath and Mg(OEt)$_2$ (111.33 g, 953.5 mmol) was added. The reaction was stirred for 30 minutes at 0° C., removed from the cooling bath and stirred at room temperature overnight. The reaction was filtered over a plug of Celite® and the plug was washed with additional THF. The clear, colorless filtrate was evaporated in vacuo to afford a mushy solid. The solid was triturated with 1 L of diethyl ether and filtered. The filter-cake was washed with Et$_2$O and dried in vacuo. The filtrate was evaporated in vacuo again and was then triturated with a small volume of Et$_2$O and filtered to afford a second crop of the product. The crops were combined and dried in vacuo to afford bis[(3-tert-butoxy-3-oxo-propanoyl)oxy]magnesium C109 (294.49 g, 90%) as a white solid. $^1$H NMR (300 MHz, Methanol-d4) δ 4.92 (s, 4H), 1.48 (s, 18H) ppm.

Step 2. Synthesis of tert-butyl (5S)-5-(tert-butoxy-carbonylamino)-3-oxo-hexanoate (C111)

To a solution of (3S)-3-(tert-butoxycarbonylamino)butanoic acid C110 (170.15 g, 837.2 mmol) in THF (1.5 L) was added CDI (149.8 g, 923.8 mmol). The milky suspension cleared over the next few minutes. Gas evolution was observed. The reaction was stirred for 3 hours at room temperature. Bis[(3-tert-butoxy-3-oxo-propanoyl)oxy]magnesium C109 (172.19 g, 502.6 mmol) was added. Another milky suspension was formed that cleared after stirring for 30 minutes. The reaction was stirred for 48 hours. The reaction was poured into 1.5 L of 1 N HCl and extracted with MTBE (1 L). The pH was confirmed to be approximately pH 3. The extract was washed with saturated aqueous NaHCO$_3$, separated, dried with MgSO$_4$, filtered, and evaporated in vacuo to afford tert-butyl (5S)-5-(tert-butoxycarbonylamino)-3-oxo-hexanoate C111 (248.5 g, 98.5%). $^1$H NMR (300 MHz, Chloroform-d) δ 4.90 (d, J=18.1 Hz, 1H), 4.04 (dt, J=13.8, 6.6 Hz, 1H), 3.47-3.22 (m, 2H), 2.76 (qd, J=17.0, 5.7 Hz, 2H), 1.48 (s, 9H), 1.44 (s, 9H), 1.23 (d, J=6.8 Hz, 3H) ppm.

Step 3. Synthesis of tert-butyl (2S,3R,6S)-6-methyl-2-(1-methyltriazol-4-yl)-4-oxo-piperidine-3-carboxylate (C112)

To a solution of tert-butyl (5S)-5-(tert-butoxycarbonylamino)-3-oxo-hexanoate C111 (248.5 g, 824.5 mmol) in DCM (1.5 L) was added TFA (240 mL, 3.115 mol) and the reaction was stirred overnight. The reaction was evaporated in vacuo at 25° C. The solid that remained was triturated with 500 mL of pentane and filtered. The filter-cake was washed with pentane and most of the solvent was pulled off of the filter-cake. The cake was transferred back to the reaction flask and dissolved in 1 L of DCM.

1-methyltriazole-4-carbaldehyde S17 (120.7 g, 1.086 mol) was added. The reaction was stirred at room temperature overnight. Brine (100 mL) was added and 6N NaOH was added until the aqueous layer remained alkaline when the funnel was shaken. The organic layer was isolated and the aqueous layer was extracted with DCM (1 L). The organic layers were combined, dried with MgSO$_4$, and filtered over a plug of silica gel. The plug was eluted with 10% MeOH in EtOAc. The filtrate was evaporated in vacuo to afford a solid that was triturated with MTBE (500 mL) and filtered. The filter-cake was washed with MTBE and dried in vacuo to give a crop of product. The mother liquor from the trituration was concentrated. The solid that precipitated was filtered to provide a second crop of the product. The crops were combined to give (2S,3R,6S)-6-methyl-2-(1-methyltriazol-4-yl)-4-oxo-piperidine-3-carboxylate C112 (105.45 g, 43%). $^1$H NMR (300 MHz, Chloroform-d) δ 7.48 (s, 1H), 4.52 (d, J=11.0 Hz, 1H), 4.09 (s, 3H), 3.61 (dd, J=11.0, 1.0 Hz, 1H), 3.21 (ddd, J=11.7, 6.1, 2.9 Hz, 1H), 2.55 (dd, J=13.7, 2.9 Hz, 1H), 2.37-2.13 (m, 1H), 1.98 (s, 1H), 1.39 (s, 9H), 1.29 (d, J=6.3 Hz, 3H) ppm.

Step 4. Synthesis of (2S,6S)-2-methyl-6-(1-methyltriazol-4-yl)piperidin-4-one (S26)

To a solution of tert-butyl (2S,3R,6S)-6-methyl-2-(1-methyltriazol-4-yl)-4-oxo-piperidine-3-carboxylate C112

(70.59 g, 239.8 mmol) in DCM (750 mL) was added MsOH (62 mL, 955.4 mmol) and the reaction was heated to reflux for 6 hours. The reaction was cooled and poured into a separatory funnel. Brine (approx. 100 mL) was added. 6N NaOH was added until the aqueous layer remained alkaline after shaking. The organic layer was separated and the aqueous was extracted with DCM (2×500 mL). The organic layers were combined, dried with $MgSO_4$, filtered, and evaporated in vacuo to afford (2S,6S)-2-methyl-6-(1-methyltriazol-4-yl)piperidin-4-one S26 (43.74 g, 94%). $^1$H NMR (300 MHz, Chloroform-d) δ 7.46 (s, 1H), 4.20 (dd, J=10.1, 5.1 Hz, 1H), 4.06 (s, 3H), 3.11 (dqd, J=12.3, 6.2, 3.0 Hz, 1H), 2.73-2.48 (m, 2H), 2.40 (ddd, J=14.1, 3.0, 1.5 Hz, 1H), 2.25-2.00 (m, 2H), 1.23 (d, J=6.2 Hz, 3H) ppm.

Preparation of S27-S29

Intermediates S27-S29 (see Table 1) were prepared in a single step from intermediate S25 using the appropriate aldehyde and the method described for intermediate S26 (Method A). Aldehydes were prepared by methods described above or obtained from commercial sources. As for intermediate S26 (prepared by method A), partial stereochemical erosion of the enantiomerically pure starting material (4S)-4-aminopentan-2-one (Hydrochloride salt) S25 was observed in step 1 leading to unseparated mixtures of stereoisomers being generated in Step 1. In each case, the cis-product was the major isomer. This mixture is represented by use of wavy bonds. Any modifications to methods are noted in Table 1 and accompanying footnotes.

TABLE 1

Method of preparation, structure and physicochemical data for intermediates S27-S29

| Product | Aldehyde Reagent | Method | $^1$H NMR |
|---|---|---|---|
| S27 | | Preparation of S26[1,2,3,4] | $^1$H NMR (300 MHz, Chloroform-d) δ 7.45 (s, 1H), 7.34 (s, 1H), 3.97 (dd, J = 11.5, 3.4 Hz, 1H), 3.87 (s, 3H), 3.07 (dqd, J = 12.3, 6.2, 2.9 Hz, 1H), 2.53 (ddd, J = 14.0, 3.4, 2.0 Hz, 1H), 2.47-2.35 (m, 2H), 2.14 (ddd, J = 14.1, 11.6, 1.1 Hz, 1H), 1.23 (d, J = 6.2 Hz, 3H). |
| S28 | | Preparation of S26[2,4,5] | $^1$H NMR (300 MHz, Chloroform-d) δ 7.40 (s, 1H), 6.78 (s, 1H), 4.02 (dd, J = 9.6, 5.5 Hz, 1H), 3.67 (s, 3H), 3.12 (dtt, J = 12.1, 6.1, 3.0 Hz, 1H), 2.66-2.58 (m, 2H), 2.47-2.38 (m, 1H), 2.17 (dd, J = 14.1, 11.6 Hz, 1H), 1.26 (d, J = 6.3 Hz, 3H). |
| S29 | S18 | Preparation of S26[2,4,5] | $^1$H NMR (300 MHz, Chloroform-d) δ 7.58 (s, 1H), 7.53 (s, 1H), 4.60 (t, J = 6.3 Hz, 2H), 4.00 (dd, J = 11.6, 3.3 Hz, 1H), 3.65 (t, J = 6.2 Hz, 2H), 3.10 (dqd, J = 12.1, 6.0, 2.9 Hz, 1H), 2.58-2.51 (m, 4H), 2.48-2.37 (m, 2H), 2.17 (dd, J = 14.1, 11.6 Hz, 1H), 1.26 (d, J = 6.1 Hz, 3H). |

TABLE 1-continued

Method of preparation, structure and physicochemical data for intermediates S27-S29

| Product | Aldehyde Reagent | Method | ¹H NMR |
|---|---|---|---|
| 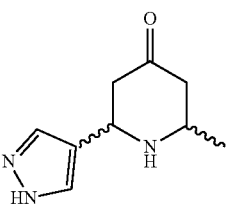<br>S30 | 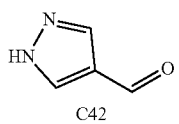<br>C42 | Preparation of S26[4,5] | ¹H NMR (300 MHz, Chloroform-d) δ 7.60 (s, 2H), 4.05 (dd, J = 11.6, 3.4 Hz, 1H), 3.10 (ddd, J = 11.8, 6.0, 2.9 Hz, 1H), 2.63-2.34 (m, 3H), 2.18 (dd, J = 14.0, 11.5 Hz, 1H), 1.26 (d, J = 6.2 Hz, 3H). |

[1]Reaction was stirred over the weekend (step 1)
[2]The crude residue was diluted with water and saturated sodium bicarbonate solution and extracted with DCM (5×) through a phase separator. (step 1)
[3]Purification by silica gel chromatography (Gradient: 0-50% of 20% MeOH/DCM in DCM) yielded the product. (step 1)
[4]The minor isomer was purged via chromatography and step 2 was not performed.
[5]Purification by silica gel chromatography (Gradient: 0-100% of 20% MeOH/DCM in DCM) yielded the product. (step 1)

Compound 1

(2'S,6'S, 7S)-2-chloro-2'-methyl-6'-(1-methyltriazol-4-yl)spiro[4,5-dihydrothieno[2,3-c]pyran-7,4'-piperidine] (1)

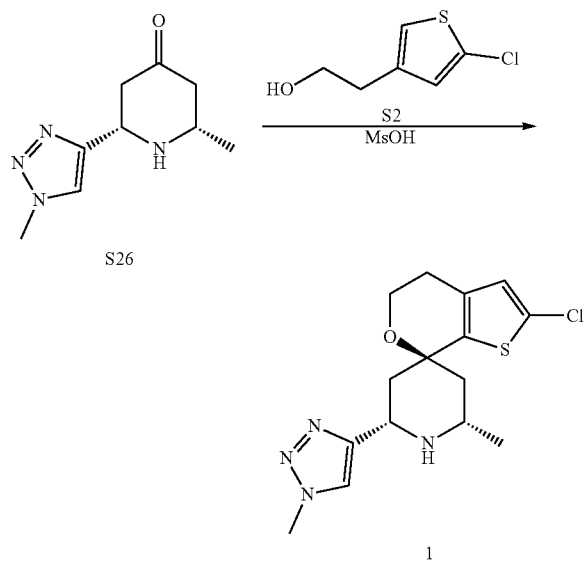

To a solution of (2S,6S)-2-methyl-6-(1-methyltriazol-4-yl)piperidin-4-one S26 (1380 mg, 7.11 mmol, S26 was prepared by Method A) in DCM (30 mL) was added 2-(5-chloro-3-thienyl)ethanol S2 (1100 µL, 8.894 mmol) followed by MsOH (3 mL, 46.23 mmol). The reaction was heated to reflux for 90 minutes at which time it was cooled to room temperature and quenched with 2 N NaOH until the pH reached 14. The mixture was diluted with DCM (20 mL) and the organic layer separated, washed with brine (30 mL), dried over MgSO₄, and concentrated in vacuo. Purification by silica gel chromatography (Gradient: 0-25% of 20% MeOH/DCM in DCM) yielded the product (2'S,6'S,7S)-2-chloro-2'-methyl-6'-(1-methyltriazol-4-yl)spiro[4,5-dihydrothieno[2,3-c]pyran-7,4'-piperidine] 1 (1162 mg, 48%) as a pale yellow oil in a >8:1 ratio. The minor isomer observed is inferred to be the enantiomer of compound 1, since S26 prepared by method A contains minor quantities of the other cis enantiomer. Note that relative stereochemistry in compound 1 was assigned through NOE NMR studies. ¹H NMR (400 MHz, Chloroform-d) δ 7.42 (s, 1H), 6.58 (s, 1H), 4.41 (dd, J=11.8, 2.6 Hz, 1H), 4.06 (s, 3H), 4.02-3.86 (m, 2H), 3.30 (ddt, J=12.7, 6.3, 3.2 Hz, 1H), 2.70-2.49 (m, 2H), 2.35 (dt, J=13.6, 2.6 Hz, 1H), 2.06 (dt, J=13.7, 2.5 Hz, 1H), 1.79 (dd, J=13.6, 11.8 Hz, 1H), 1.42 (dd, J=13.7, 11.3 Hz, 1H), 1.31-1.19 (m, 1H), 1.12 (d, J=6.4 Hz, 3H). LCMS m/z 339.0 [M+H]⁺.

Alternative Preparation of Compound 1 (HCl salt)

(2'S,6'S, 7S)-2-chloro-2'-methyl-6'-(1-methyltriazol-4-yl)spiro[4,5-dihydrothieno[2,3-c]pyran-7,4'-piperidine] hydrochloride salt (1)

(2S,6S)-2-methyl-6-(1-methyltriazol-4-yl)piperidin-4-one S26 (205 mg, 1.055 mmol) in DCM (5 mL) was added 2-(5-chloro-3-thienyl)ethanol S2 (150 µL, 1.213 mmol) followed by MsOH (300 µL, 4.623 mmol). The mixture was heated to reflux for 10 minutes at which time it was cooled to room temperature and quenched with 2 N NaOH until the pH reached 14. The mixture was diluted with DCM (5 mL) and the organic layer was separated and concentrated in vacuo. Purification by silica gel chromatography (Gradient: 0-25% of 20% MeOH/DCM in DCM) yielded product which was immediately dissolved in minimal DCM and treated with HCl (100 µL of 4 M in dioxane, 0.4000 mmol). The mixture was concentrated in vacuo and the residue was azeotroped with DCM (5 mL) and dried to yield (2'S,6'S, 7S)-2-chloro-2'-methyl-6'-(1-methyltriazol-4-yl)spiro[4,5-dihydrothieno[2,3-c]pyran-7,4'-piperidine] (Hydrochloride salt) 1 (171.6 mg, 43%) as a pale yellow solid. ¹H NMR (300 MHz, DMSO-d₆) δ 9.46 (s, 1H), 9.24 (d, J=8.3 Hz, 1H), 8.29 (s, 1H), 6.95 (s, 1H), 4.67 (t, J=11.1 Hz, 1H), 4.09 (s, 3H), 3.95 (t, J=5.4 Hz, 2H), 3.72 (s, 1H), 2.61 (t, J=5.3 Hz, 2H), 2.46-2.32 (m, 2H), 2.25 (d, J=15.1 Hz, 1H), 2.01-1.86 (m, 1H), 1.29 (d, J=6.5 Hz, 3H). LCMS m/z 339.0 [M+H]⁺

Compound 2

(2'S,6'S, 7S)-2'-methyl-6'-(1-methyltriazol-4-yl)-2-(trifluoromethyl)spiro[4,5-dihydrothieno[2,3-c]pyran-7,4'-piperidine] (2)

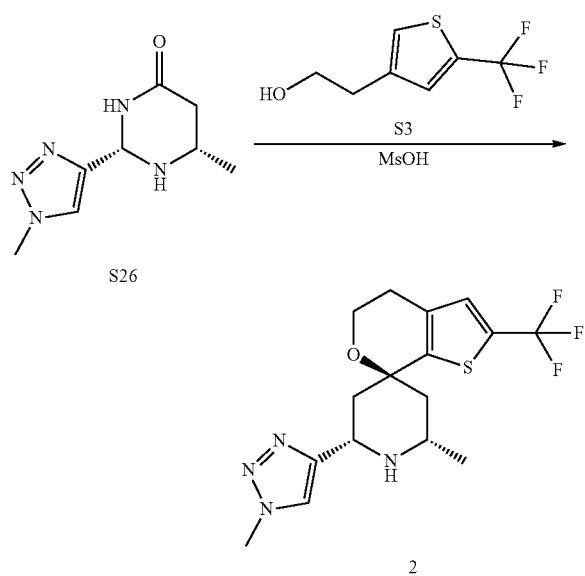

To a solution of (2S,6S)-2-methyl-6-(1-methyltriazol-4-yl)piperidin-4-one S26 (250 mg, 1.287 mmol) and 2-[5-(trifluoromethyl)-3-thienyl]ethanol S3 (350 mg, 1.748 mmol) in DCM (5 mL) was added MsOH (500 µL, 7.705 mmol) and the reaction was heated to 40° C. After 16 hours, additional MsOH (200 µL, 3.082 mmol) was added and the reaction was continued heating overnight. The mixture was diluted with water (4 mL) and DCM (5 mL) and quenched with aqueous NaOH (2 mL of 6 M, 12.00 mmol). The mixture was separated, extracted with DCM (2×5 mL), passed over a phase separator, and the organics concentrated in vacuo. Purification by silica gel chromatography (Gradient: 0-10% MeOH in DCM) yielded (2'S,6'S,7S)-2'-methyl-6'-(1-methyltriazol-4-yl)-2-(trifluoromethyl)spiro[4,5-dihydrothieno[2,3-c]pyran-7,4'-piperidine] 2 (445 mg, 93%) as a white solid. Note that relative stereochemistry in Compound 2 was assigned through NOE NMR studies. $^1$H NMR (300 MHz, Chloroform-d) δ 7.46 (s, 1H), 7.14 (s, 1H), 4.47 (d, J=11.6 Hz, 1H), 4.08 (d, J=3.3 Hz, 3H), 4.00 (s, 2H), 3.36 (s, 1H), 2.72 (d, J=5.6 Hz, 2H), 2.41 (d, J=14.2 Hz, 1H), 2.12 (d, J=13.7 Hz, 1H), 1.86 (t, J=12.7 Hz, 1H), 1.49 (d, J=12.8 Hz, 1H), 1.15 (d, J=6.3 Hz, 3H). LCMS m/z 373.07 [M+H]$^+$

Compounds 3-16

Compounds 3-16 (see Table 2) were prepared from a single Oxa-Pictet Spengler step with isolated piperidones (S26, S29, or C56) and the relevant thiophene ethanols as described for compounds 1 and 2. Thiophene ethanols and piperidone were prepared by methods described above or obtained from commercial sources. In examples where S26 was used, S26 was prepared by Method A, therefore the piperidone used may contain minor amounts of the other cis-isomer. Any modifications to methods are noted in Table 2 and accompanying footnotes.

TABLE 2

Method of preparation, structure and physicochemical data for Compounds 3-16.

| Product | Piperidone and Thiophene ethanol | Method | $^1$H NMR; LCMS m/z [M + H]$^+$ |
|---|---|---|---|
| Compound 3 | S26; S14 | Compound 1[1,2,3] | $^1$H NMR (300 MHz, Methanol-d$_4$) δ 8.03 (s, 1H), 6.51 (s, 1H), 4.92-4.85 (m, 1H), 4.12 (s, 3H), 3.99 (t, J = 5.4 Hz, 2H), 3.79 (s, 1H), 2.64 (t, J = 5.5 Hz, 2H), 2.50 (d, J = 15.1 Hz, 1H), 2.42 (d, J = 1.1 Hz, 3H), 2.37-2.27 (m, 2H), 1.88 (dd, J = 14.8, 12.3 Hz, 1H), 1.39 (d, J = 6.6 Hz, 3H). LCMS m/z 319.2 [M + H]$^+$ |
| Compound 4 | S26; S5 | Compound 1[2,3] | $^1$H NMR (400 MHz, DMSO-d$_6$) δ 9.36 (d, J = 23.7 Hz, 2H), 8.31 (s, 1H), 6.55 (s, 1H), 4.63 (t, J = 11.2 Hz, 1H), 4.08 (s, 3H), 3.93 (t, J = 5.3 Hz, 2H), 3.57 (s, 1H), 2.80-2.66 (m, 4H), 2.43 (d, J = 13.4 Hz, 1H), 2.20 (d, J = 14.1 Hz, 1H), 2.09-1.96 (m, 2H), 1.30 (d, J = 6.4 Hz, 3H), 1.21 (t, J = 7.5 Hz, 3H). LCMS m/z 333.2 [M + H]$^+$ |

TABLE 2-continued

Method of preparation, structure and physicochemical data for Compounds 3-16.

| Product | Piperidone and Thiophene ethanol | Method | ¹H NMR; LCMS m/z [M + H]⁺ |
| --- | --- | --- | --- |
| Compound 5 | S29; S5 | Compound 1[1,3,4,5] | ¹H NMR (300 MHz, DMSO-d$_6$) δ 9.24-8.96 (m, 2H), 8.06 (s, 1H), 7.79 (s, 1H), 6.57 (s, 1H), 4.54 (t, J = 6.8 Hz, 2H), 4.44 (t, J = 10.9 Hz, 1H), 3.91 (t, J = 5.3 Hz, 2H), 3.67 (t, J = 6.8 Hz, 2H), 3.51 (s, 1H), 2.85 (s, 3H), 2.81-2.67 (m, 4H), 2.41 (d, J = 13.8 Hz, 1H), 2.13-1.98 (m, 3H), 1.29 (d, J = 6.4 Hz, 3H), 1.22 (t, J = 7.5 Hz, 3H). LCMS m/z 424.18 [M + H]⁺ |
| Compound 6 | S26; S4 | Compound 1[2,3] | ¹H NMR (400 MHz, DMSO-d$_6$) δ 9.58-9.19 (m, 2H), 8.30 (s, 1H), 6.59 (s, 1H), 4.66 (q, J = 8.8 Hz, 1H), 4.09 (s, 3H), 3.92 (t, J = 5.4 Hz, 2H), 3.58 (s, 1H), 2.76 (q, J = 7.5 Hz, 2H), 2.59 (t, J = 5.4 Hz, 2H), 2.36 (d, J = 8.0 Hz, 2H), 2.20 (d, J = 13.3 Hz, 1H), 1.95 (dd, J = 14.4, 12.2 Hz, 1H), 1.30 (d, J = 6.4 Hz, 3H), 1.21 (t, J = 7.5 Hz, 3H). LCMS m/z 333.2 [M + H]⁺ |
| Compound 7 | S56; S2 | Compound 1[6,7,8,9] | ¹H NMR (300 MHz, Chloroform-d) δ 7.43 (s, 1H), 6.57 (s, 1H), 4.62 (dd, J = 11.6, 2.6 Hz, 1H), 4.06 (s, 3H), 3.94 (t, J = 5.5 Hz, 2H), 3.48 (s, 1H), 2.60 (td, J = 5.5, 2.6 Hz, 2H), 2.33 (dt, J = 13.5, 2.6 Hz, 1H), 2.08 (dt, J = 14.4, 2.2 Hz, 1H), 1.93 (dd, J = 14.5, 6.1 Hz, 1H), 1.84 (dd, J = 13.5, 11.7 Hz, 1H), 1.46 (d, J = 7.1 Hz, 3H). LCMS m/z 339.09 [M + H]⁺ |
| Compound 8 | S26; S6 | Compound 1[2,3] | ¹H NMR (400 MHz, DMSO-d$_6$) δ 9.41 (d, J = 26.0 Hz, 2H), 8.33 (s, 1H), 7.43 (s, 1H), 4.71-4.57 (m, 1H), 4.09 (s, 3H), 4.00 (t, J = 5.4 Hz, 2H), 3.59 (s, 1H), 2.91 (t, J = 5.3 Hz, 2H), 2.58 (d, J = 13.9 Hz, 1H), 2.28 (d, J = 14.3 Hz, 1H), 2.14 (dt, J = 25.5, 14.1 Hz, 2H), 1.31 (d, J = 6.5 Hz, 3H). LCMS m/z 373.16 [M + H]⁺ |

TABLE 2-continued

*Method of preparation, structure and physicochemical data for Compounds 3-16.*

| Product | Piperidone and Thiophene ethanol | Method | ¹H NMR; LCMS m/z [M + H]⁺ |
|---|---|---|---|
| Compound 9 | S29; S6 | Compound 1[1,3,4,5] | ¹H NMR (300 MHz, Methanol-d₄) δ 7.97 (s, 1H), 7.75 (s, 1H), 7.47 (s, 1H), 4.74-4.68 (m, 1H), 4.65 (t, J = 6.4 Hz, 2H), 4.04 (t, J = 5.4 Hz, 2H), 3.78 (s, 1H), 3.70 (t, J = 6.4 Hz, 2H), 2.93 (t, J = 5.5 Hz, 2H), 2.84 (s, 3H), 2.40-2.31 (m, 2H), 2.21 (d, J = 14.5 Hz, 1H), 2.02-1.88 (m, 1H), 1.39 (d, J = 6.6 Hz, 3H). LCMS m/z 464.1 [M + H]⁺ |
| Compound 10 | S26; S12 | Compound 1[2,3] | ¹H NMR (400 MHz, DMSO-d₆) δ 9.40 (s, 2H), 8.32 (s, 1H), 6.53 (s, 1H), 4.63 (s, 1H), 4.08 (s, 3H), 3.96 (dd, J = 11.4, 4.6 Hz, 1H), 3.64-3.48 (m, 2H), 2.94 (d, J = 10.9 Hz, 1H), 2.77 (q, J = 7.5 Hz, 2H), 2.39 (d, J = 13.2 Hz, 1H), 2.28 (d, J = 14.3 Hz, 1H), 2.10 (t, J = 13.2 Hz, 1H), 1.95 (d, J = 14.1 Hz, 1H), 1.30 (d, J = 6.5 Hz, 3H), 1.22 (t, J = 7.5 Hz, 3H), 1.15 (d, J = 6.8 Hz, 3H). LCMS m/z 347.24 [M + H]⁺ |
| Compound 11 | S26; S13 | Compound 1[2,3] | ¹H NMR (400 MHz, DMSO-d₆) δ 9.36 (d, J = 22.0 Hz, 2H), 8.31 (d, J = 1.9 Hz, 1H), 6.52 (s, 1H), 4.64 (t, J = 11.3 Hz, 1H), 4.08 (s, 3H), 3.96 (dd, J = 11.5, 4.6 Hz, 1H), 3.55 (s, 3H), 3.00-2.89 (m, 1H), 2.76 (q, J = 7.5 Hz, 2H), 2.12 (d, J = 15.6 Hz, 1H), 2.05-1.89 (m, 1H), 1.30 (d, J = 6.5 Hz, 3H), 1.22 (t, J = 7.5 Hz, 3H), 1.16 (t, J = 6.8 Hz, 3H). LCMS m/z 347.24 [M + H]⁺ |
| Compound 12 | S26; S10 | Compound 1[2,3] | ¹H NMR (400 MHz, DMSO-d₆) δ 9.46 (d, J = 26.5 Hz, 2H), 8.33 (s, 1H), 6.81 (s, 1H), 4.63 (t, J = 11.0 Hz, 1H), 4.08 (s, 3H), 3.99 (dd, J = 11.5, 4.5 Hz, 1H), 3.57 (dd, J = 11.5, 6.8 Hz, 2H), 2.98 (dd, J = 10.6, 5.5 Hz, 1H), 2.10 (dt, J = 40.8, 13.6 Hz, 3H), 1.30 (d, J = 6.4 Hz, 3H), 1.18 (d, J = 6.9 Hz, 3H). LCMS m/z 353.16 [M + H]⁺ |

TABLE 2-continued

*Method of preparation, structure and physicochemical data for Compounds 3-16.*

| Product | Piperidone and Thiophene ethanol | Method | 1H NMR; LCMS m/z [M + H]+ |
|---|---|---|---|
| Compound 13 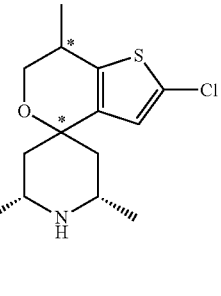 | S26; 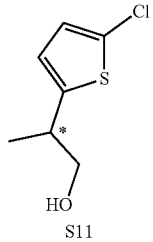 S11 | Compound 1[2,3] | 1H NMR (400 MHz, DMSO-d6) δ 9.43 (s, 2H), 8.32 (s, 1H), 6.82 (d, J = 1.6 Hz, 1H), 4.73-4.54 (m, 1H), 4.09 (s, 3H), 3.99 (dd, J = 11.6, 4.6 Hz, 1H), 3.57 (dd, J = 11.6, 6.8 Hz, 2H), 3.03-2.93 (m, 1H), 2.45-2.36 (m, 1H), 2.31 (d, J = 14.6 Hz, 1H), 2.07 (dt, J = 52.7, 14.0 Hz, 2H), 1.30 (d, J = 6.4 Hz, 3H), 1.17 (t, J = 6.9 Hz, 3H). [1] LCMS m/z 353.16 [M + H]+ |
| Compound 14 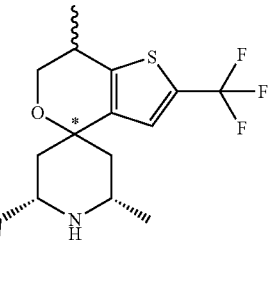 | S26; 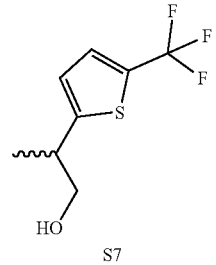 S7 | Compound 1[2,3] | 1H NMR (400 MHz, DMSO-d6) δ 9.41 (d, J = 25.4 Hz, 2H), 8.33 (s, 1H), 7.43 (s, 1H), 4.71-4.60 (m, 1H), 4.08 (s, 3H), 4.06-3.97 (m, 1H), 3.62 (dd, J = 11.7, 6.8 Hz, 2H), 3.14 (q, J = 6.5 Hz, 1H), 2.61 (d, J = 13.6 Hz, 1H), 2.40-1.96 (m, 3H), 1.31 (d, J = 6.4 Hz, 3H), 1.24 (t, J = 6.9 Hz, 3H). LCMS m/z 387.16 [M + H]+ |
| Compound 15 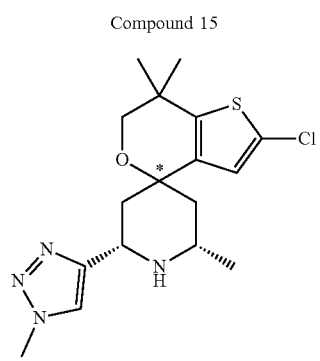 | S26; 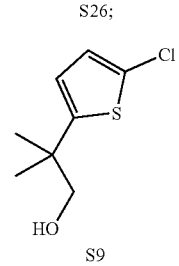 S9 | Compound 1[2,3] | 1H NMR (400 MHz, DMSO-d6) δ 9.49 (d, J = 53.8 Hz, 2H), 8.34 (s, 1H), 6.78 (s, 1H), 4.64 (t, J = 11.3 Hz, 1H), 4.09 (s, 3H), 3.65 (s, 2H), 3.59 (s, 1H), 2.48 (s, 1H), 2.25 (d, J = 14.2 Hz, 1H), 2.10 (d, J = 11.2 Hz, 2H), 1.31 (d, J = 6.5 Hz, 3H), 1.24 (d, J = 6.6 Hz, 6H). LCMS m/z 367.16 [M + H]+ |

TABLE 2-continued

Method of preparation, structure and physicochemical data for Compounds 3-16.

| Product | Piperidone and Thiophene ethanol | Method | ¹H NMR; LCMS m/z [M + H]⁺ |
|---|---|---|---|
| Compound 16<br>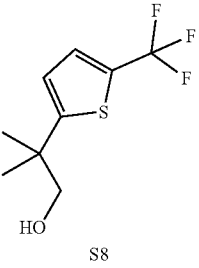 | S26;<br>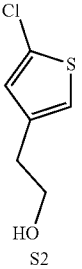\ S8 | Compound 1[2,3] | ¹H NMR (400 MHz, DMSO-d$_6$) δ 9.51 (d, J = 23.4 Hz, 2H), 8.35 (s, 1H), 7.39 (s, 1H), 4.67 (t, J = 11.1 Hz, 1H), 4.09 (s, 3H), 3.70 (s, 2H), 3.62 (s, 1H), 2.60 (d, J = 13.9 Hz, 1H), 2.37-2.27 (m, 1H), 2.27-2.06 (m, 2H), 1.31 (t, J = 6.5 Hz, 9H). LCMS m/z 401.16 [M + H]⁺ |
| S31<br>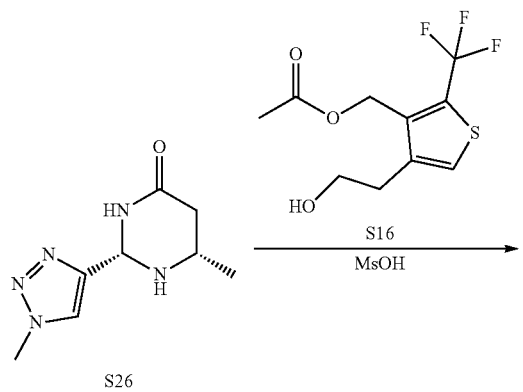 | S30;<br>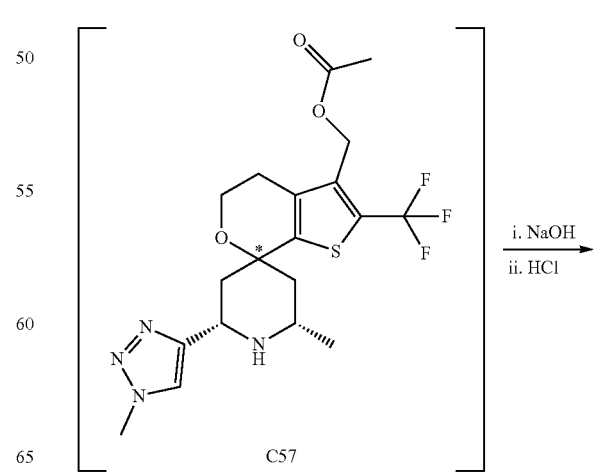\ S2 | Compound 1[8,10] | ¹H NMR (300 MHz, Chloroform-d) δ 7.57 (s, 2H), 6.58 (s, 1H), 4.22 (dd, J = 11.6, 2.5 Hz, 1H), 3.95 (t, J = 5.5 Hz, 2H), 3.38-3.13 (m, 1H), 2.61 (t, J = 5.4 Hz, 2H), 2.40-2.16 (m, 1H), 2.16-1.99 (m, 1H), 1.71 (dd, J = 13.6, 11.6 Hz, 1H), 1.41 (dd, J = 13.7, 11.3 Hz, 1H), 1.13 (d, J = 6.4 Hz, 3H). LCMS m/z 324.02 [M + 1]⁺ |

[1] The reaction was stirred for 30 minutes.
[2] After completion, the mixture was concentrated and diluted in MeOH. No further workup was done.
[3] Purification by reversed-phase HPLC (Method: C18 Waters Sunfire column (30 × 150 mm, 5 micron). Gradient: MeCN in H$_2$O with 5 mM HCl) yielded the product as the HCl salt.
[4] The organic layer was collected through a phase separator and dried under nitrogen.
[5] After purification, the product was brought up in 0.6 mL of water, frozen, and lyophilized overnight to afford.
[6] The reaction was stirred overnight.
[7] Once the reaction had gone to completion the organic layer was separated, dried over Na$_2$SO$_4$, filtered, and concentrated.
[8] Purification by silica gel chromatography (Gradient: 0-20% MeOH in DCM) yielded the product.
[9] Reaction was run with C56 which was enriched as a mixture of two isomers from purification of S26. Compound 7 was isolated as the minor product of the Pictet Spangler reaction as a single diastereomer. As described for Method A of S26, epimerization of the S25 stereocenter was observed, which provided this compound as a mixture of enantiomers.
[10] After 50 minutes, the reaction was quenched with saturated NaHCO$_3$ solution and extracted with DCM (6×). The combined organic layer was dried over Na$_2$SO$_4$, filtered, and concentrated.

Compound 17

[(2'S,6'S, 7S)-2'-methyl-6'-(1-methyltriazol-4-yl)-2-(trifluoromethyl)spiro[4,5-dihydrothieno[2,3-c]pyran-7,4'-piperidine]-3-yl]methanol (17)

269
-continued

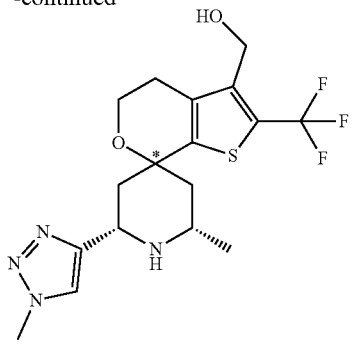

17

Step 1. Synthesis of [(2S,6S)-2'-methyl-6'-(1-methyltriazol-4-yl)-2-(trifluoromethyl)spiro[4,5-dihydrothieno[2,3-c]pyran-7,4'-piperidine]-3-yl]methyl acetate (C57)

To a mixture of (2S,6S)-2-methyl-6-(1-methyltriazol-4-yl)piperidin-4-one S26 (10 mg, 0.05148 mmol) and [4-(2-hydroxyethyl)-2-(trifluoromethyl)-3-thienyl]methyl acetate S16 (18 mg, 0.06710 mmol) in DCM (500 μL) was added MsOH (30 μL, 0.4623 mmol) and the mixture was heated to 40° C. After stirring for 4 hours, the reaction was quenched with saturated NaHCO$_3$ solution, the layers were separated and the mixture was concentrated to dryness to give crude C57.

Step 2. Synthesis of [(2S,6S)-2'-methyl-6'-(1-methyltriazol-4-yl)-2-(trifluoromethyl)spiro[4,5-dihydrothieno[2,3-c]pyran-7,4'-piperidine]-3-yl]methanol (17)

The crude material C57 was diluted with MeOH (2 mL) and to the mixture was added NaOH (20 μL of 6 M, 0.1200 mmol). The reaction was stirred for 5 minutes. The mixture was concentrated, re-diluted in DCM and washed with brine. The organic layer was passed over a phase separator, and concentrated. Silica gel chromatography (Gradient: 0-20% MeOH-DCM) yielded 17 as the parent.

17 (parent) from the deprotection was diluted with diethyl ether (1 mL) and HCl (13 μL of 4 M in dioxane, 0.05200 mmol) was added which immediately precipitated a white solid. The mixture was concentrated, and azeotroped three times with diethyl ether to yield [(2S,6S)-2'-methyl-6'-(1-methyltriazol-4-yl)-2-(trifluoromethyl)spiro[4,5-dihydrothieno[2,3-c]pyran-7,4'-piperidine]-3-yl]methanol 17 (Hydrochloride salt) (10.9 mg, 45%). $^1$H NMR (300 MHz, DMSO-d$_6$) δ 9.35 (d, J=9.8 Hz, 1H), 9.04 (s, 1H), 8.26 (s, 1H), 5.32 (s, 1H), 4.73 (s, 1H), 4.48 (s, 2H), 4.09 (s, 3H), 4.01 (s, 2H), 3.62 (s, 1H), 2.73 (s, 2H), 2.34 (s, 2H), 1.91 (d, J=13.5 Hz, 1H), 1.29 (d, J=6.5 Hz, 3H). LCMS m/z 403.13 [M+H]$^+$.

270

Compound 18

2-[4-[(2S,6S)-2-chloro-6'-methyl-spiro[4,5-dihydrothieno[2,3-c]pyran-7,4'-piperidine]-2'-yl]pyrazol-1-yl]-N,N-dimethyl-acetamide (18)

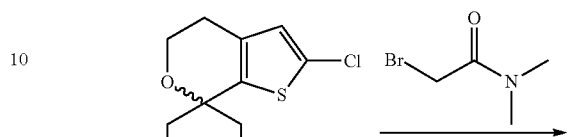

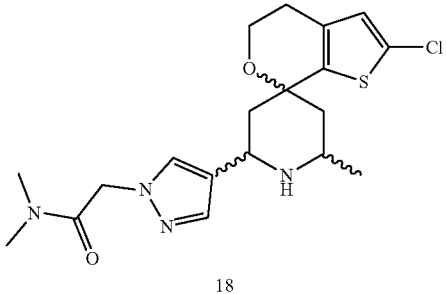

To a solution of (2S,6S)-2-chloro-2'-methyl-6'-(1H-pyrazol-4-yl)spiro[4,5-dihydrothieno[2,3-c]pyran-7,4'-piperidine] S31 (20 mg, 0.05865 mmol) in DMF (280 μL) was added Cs$_2$CO$_3$ (57 mg, 0.1749 mmol). 2-bromo-N,N-dimethyl-acetamide (7.6 μL, 0.07050 mmol) was added at room temperature. The reaction was stirred for 1 hour. The reaction was quenched with saturated NaHCO$_3$ solution and extracted with EtOAc (4×). The combined organic layer was dried over Na$_2$SO$_4$, filtered, and concentrated. Purification by reversed-phase HPLC (Method: C18 Waters Sunfire column (30×150 mm, 5 micron). Gradient: MeCN in H$_2$O) afforded 2-[4-[(2S,6S)-2-chloro-6'-methyl-spiro[4,5-dihydrothieno[2,3-c]pyran-7,4'-piperidine]-2'-yl]pyrazol-1-yl]-N,N-dimethyl-acetamide 18 (6.2 mg, 23%). $^1$H NMR (300 MHz, Chloroform-d) δ 7.50 (s, 2H), 6.57 (s, 1H), 4.92 (s, 2H), 4.17 (dd, J=11.6, 2.5 Hz, 1H), 3.93 (t, J=5.5 Hz, 2H), 3.25 (d, J=9.1 Hz, 1H), 3.06 (s, 3H), 2.97 (s, 3H), 2.60 (td, J=5.4, 1.8 Hz, 2H), 2.25 (d, J=13.6 Hz, 1H), 2.01 (s, 1H), 1.70 (d, J=12.5 Hz, 1H), 1.47-1.32 (m, 1H), 1.11 (d, J=6.4 Hz, 3H). LCMS m/z 409.19 [M+H]$^+$.

Compound 19

(2S)-2-chloro-2'-methyl-6'-(1-methylpyrazol-4-yl)spiro[4,5-dihydrothieno[2,3-c]pyran-7,4'-piperidine] (19)

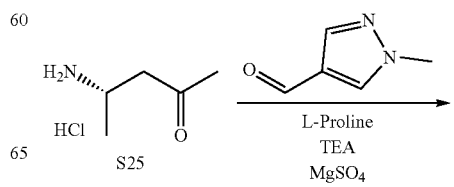

-continued

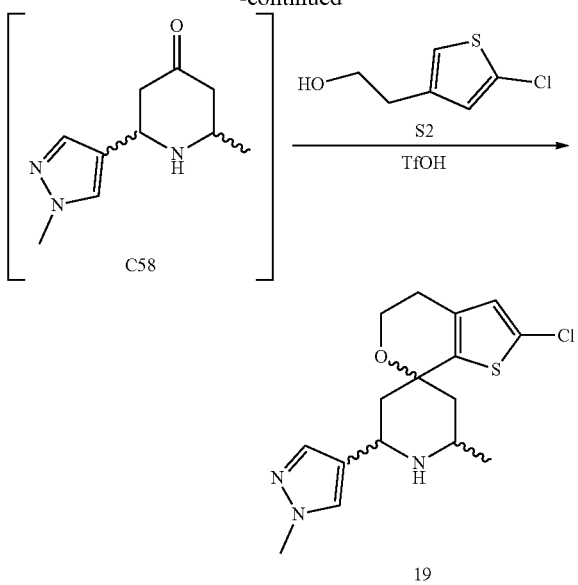

Compound 20

2-chloro-2'-methyl-6'-(3-pyridyl)spiro[4,5-dihydrothieno[2,3-c]pyran-7,4'-piperidine] (20)

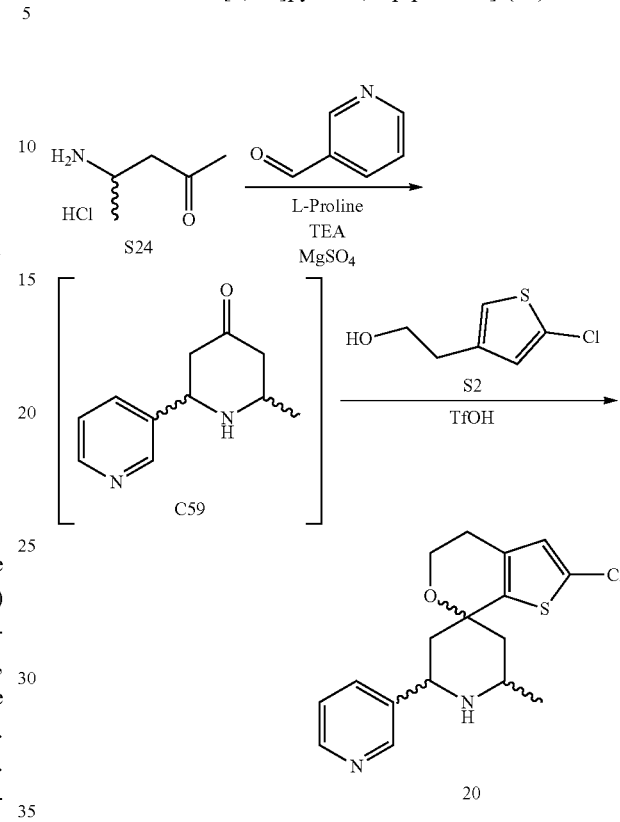

A solution of (4S)-4-aminopentan-2-one hydrochloride S25 (25 mg, 0.1817 mmol) and TEA (30 µL, 0.2152 mmol) in MeCN (1.000 mL) was added to 1-methylpyrazole-4-carbaldehyde (22.01 mg, 0.20 mmol), MgSO$_4$ (25 mg, 0.2077 mmol), and L-proline (5 mg, 0.043 mmol). The resulting mixture was stirred at room temperature overnight. The reaction mixture was evaporated via Genevac at 40° C. until dry to afford crude C58. To this, a solution of 2-(5-chloro-3-thienyl)ethanol S2 (25 µL, 0.2080 mmol) in dioxane (750.0 µL) was added, followed by a solution of TfOH (80 µL, 0.90 mmol) in dioxane (750.0 µL). The mixture was stirred at room temperature for 30 minutes. Additional triflic acid (50 µL, 0.5650 mmol) was added and stirring was continued for 10 minutes. The reaction was placed under a nitrogen stream until the volume was reduced by half. The remaining solution was quenched with NaOH (1.5 mL of 2 M, 3.000 mmol) and diluted with DCM (1.500 mL). The resulting biphasic mixture was stirred for several minutes and then passed through a phase separator. The organic layer was blown down with nitrogen. Purification by reversed-phase HPLC (Method: C18 Waters Sunfire column (30×150 mm, 5 micron). Gradient: MeCN in H$_2$O with 0.1% trifluoroacetic acid) afforded (2S)-2-chloro-2'-methyl-6'-(1-methylpyrazol-4-yl)spiro[4,5-dihydrothieno[2,3-c]pyran-7,4'-piperidine]19 as a trifluoroacetate salt (6.6 mg, 11%). Compound 19 was determined to be 88% e.r. by chiral SFC analysis (Method: AD-H column (4.6×100 mm). Gradient: 10% MeOH with 5 mM ammonia with 90% CO$_2$). $^1$H NMR (400 MHz, DMSO-d$_6$) δ 8.91 (d, J=10.8 Hz, 1H), 8.49 (d, J=11.3 Hz, 1H), 7.86 (s, 1H), 7.59 (s, 1H), 6.94 (s, 1H), 4.49 (t, J=11.2 Hz, 1H), 3.93 (t, J=5.5 Hz, 2H), 3.84 (s, 3H), 2.93 (td, J=13.9, 6.9 Hz, 1H), 2.60 (t, J=5.5 Hz, 2H), 2.35 (d, J=17.2 Hz, 1H), 2.21 (q, J=13.9 Hz, 2H), 1.84-1.73 (m, 1H), 1.24 (d, J=6.6 Hz, 3H). LCMS m/z 338.17 [M+H]$^+$ A solution of 4-aminopentan-2-one hydrochloride S24 (25 mg, 0.1817 mmol) in EtOH (1 mL) was added to pyridine-3-carbaldehyde (19.5 mg, 17.06 µL, 0.1817 mmol), MgSO$_4$ (25 mg, 0.2077 mmol), and L-proline (5 mg, 0.04343 mmol). TEA (30 µL, 0.2152 mmol) was added and the reaction was stirred at room temperature over 3 days. The reaction mixture was evaporated under a stream of nitrogen to afford crude C59. To this, a solution of 2-(5-chloro-3-thienyl)ethanol S2 (25 µL, 0.2075 mmol) in dioxane (750 µL) was added, followed by a freshly prepared solution of TfOH (100 µL, 1.130 mmol) in dioxane (750 µL). The mixture was stirred at room temperature for 30 minutes. The reaction was placed under a nitrogen stream until the volume was reduced by half. The remaining solution was quenched with NaOH (1.5 mL of 2 M, 3.000 mmol) and diluted with DCM (1.500 mL). The resulting biphasic mixture was stirred for several minutes and then passed through a phase separator. The organic layer was blown down with nitrogen. Purification by reversed-phase HPLC (Method: C18 Waters Sunfire column (30×150 mm, 5 micron). Gradient: MeCN in H$_2$O with 0.1% trifluoroacetic acid) afforded 2-chloro-2'-methyl-6'-(3-pyridyl)spiro[4,5-dihydrothieno[2,3-c]pyran-7,4'-piperidine]20 as a trifluoroacetate salt (34.4 mg, 56%). Compound 20 was determined to be 94% cis enantiomers and 6% trans enantiomers by chiral SFC analysis (Method: AD-H column (4.6×100 mm). Gradient: 10% MeOH with 5 mM ammonia with 90% CO$_2$). $^1$H NMR (300 MHz, Methanol-d4) δ 8.87 (d, J=2.3 Hz, 1H), 8.74 (dd, J=5.2, 1.5 Hz, 1H), 8.36-8.27 (m, 1H), 7.77 (dd, J=8.1, 5.2 Hz, 1H), 6.75 (s, 1H), 4.93-4.88 (m, 1H), 4.03 (t, J=5.5 Hz, 2H), 3.90 (dqd, J=13.4, 6.7, 3.1 Hz, 1H), 2.67 (t, J=5.6 Hz, 2H), 2.51 (dt, J=14.5, 2.9 Hz, 1H), 2.46-2.30 (m, 2H), 1.93 (dd, J=14.8, 12.2 Hz, 1H), 1.41 (d, J=6.6 Hz, 3H). LCMS m/z 335.14 [M+H]+.

Compound 21

(2S)-2-chloro-2'-methyl-6'-(2-methyl-4-pyridyl)spiro[4,5-dihydrothieno[2,3-c]pyran-7,4'-piperidine] (21)

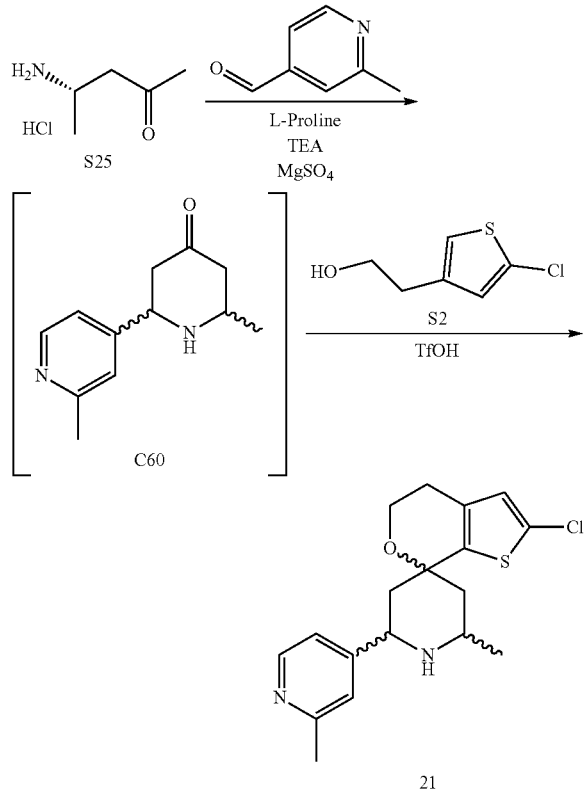

A solution of (4S)-4-aminopentan-2-one hydrochloride S25 (34.40 mg, 0.2500 mmol) in EtOH (1 mL) was added to 2-methylpyridine-4-carbaldehyde (30.28 mg, 0.2500 mmol), MgSO4 (45 mg, 0.3739 mmol), and L-proline (7 mg, 0.06080 mmol). TEA (40 µL, 0.2870 mmol) was added and the reaction was stirred at room temperature overnight. The reaction mixture was evaporated via Genevac between 35-40° C. to afford crude C60. To C60, a solution of 2-(5-chloro-3-thienyl)ethanol S2 (35 µL, 0.2905 mmol) in dioxane (1 mL) was added, followed by a freshly prepared solution of TfOH (130 µL, 1.469 mmol) in dioxane (1 mL). The mixture was stirred at room temperature for 30 minutes. The reaction mixtures were evaporated via Genevac at 40° C. The residue was quenched with NaOH (1.7 mL of 2 M, 3.400 mmol) and diluted with DCM (1.7 mL). The resulting biphasic mixture was stirred for several minutes and then passed through a phase separator. The organic layer was blown down with nitrogen. Purification by reversed-phase HPLC (Method: C18 Waters Sunfire column (30×150 mm, 5 micron). Gradient: MeCN in H2O with 0.1% trifluoroacetic acid) afforded (2S)-2-chloro-2'-methyl-6'-(2-methyl-4-pyridyl)spiro[4,5-dihydrothieno[2,3-c]pyran-7,4'-piperidine] 21 as a trifluoroacetate salt (19.3 mg, 21%). Compound 21 was determined to be 77% e.r. by chiral SFC analysis (Method: AD-H column (4.6×100 mm). Gradient: 10% MeOH with 5 mM ammonia with 90% CO2). $^1$H NMR (400 MHz, DMSO-$d_6$) δ 9.28 (s, 1H), 8.87 (s, 1H), 8.55 (d, J=5.3 Hz, 1H), 7.51 (s, 1H), 7.42 (d, J=5.3 Hz, 1H), 6.94 (s, 1H), 4.57 (t, J=11.5, 9.8 Hz, 1H), 3.97 (t, J=5.4 Hz, 2H), 3.6 (1H hidden under water peak), 3.17-2.84 (m, 1H), 2.61 (q, J=5.3 Hz, 2H), 2.52 (s, 3H), 2.43-2.13 (m, 3H), 1.90 (t, J=13.3 Hz, 1H), 1.29 (d, J=6.4 Hz, 3H). LCMS m/z 349.14 [M+H]+

Compounds 22-172

Compounds 22-172 (see Table 3) were prepared as trifluoroacetate salts in a two-step, one pot procedure following the methods described for compounds 19, 20, or 21. Intermediate S24 or S25, appropriate aldehyde, and thiophene ethanol S2 were used. Aldehydes were prepared by methods described above or obtained from commercial sources. Partial stereochemical erosion of the enantiomerically pure starting material (4S)-4-aminopentan-2-one (Hydrochloride salt) S25 was observed under step 1 reaction conditions, leading to unseparated mixtures of enantiomers of the 2,6-trans piperidines. This results from the mixture of cis-piperidinone intermediates (as previously described in Method A preparation of S26) and subsequent 2,6 trans piperidine final products, in which the 2 and 6 substituents are cis, and the 2 and 4 substituents are trans. Any modifications to methods are noted in Table 3 and accompanying footnotes.

TABLE 3

Method of preparation, structure and physicochemical data for compounds 22-172

| Product | Starting Material and Aldehyde | Method | $^1$H NMR; LCMS m/z [M + H]+ |
|---|---|---|---|
| Compound 22 | S25; | Compound 19[1] | $^1$H NMR (400 MHz, DMSO-$d_6$) δ 7.55 (s, 1H), 7.07 (s, 1H), 6.89 (s, 1H), 4.12 (dd, J = 11.9, 2.7 Hz, 1H), 3.90 (t, J = 5.5 Hz, 2H), 3.61 (s, 3H), 3.30-3.15 (m, 1H), 2.57 (t, J = 5.4 Hz, 2H), 2.22 (d, J = 13.9 Hz, 1H), 2.10-2.01 (m, 1H), 1.79 (t, J = 12.9 Hz, 1H), 1.46 (t, J = 12.6 Hz, 1H), 1.10 (d, J = 6.4 Hz, 3H). LCMS m/z 338.17 [M + H]+. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 23 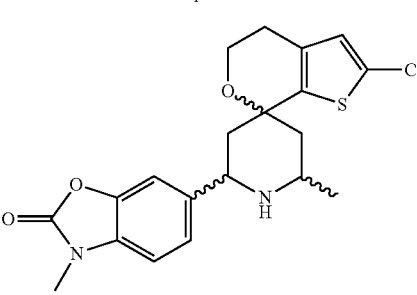 | S25; 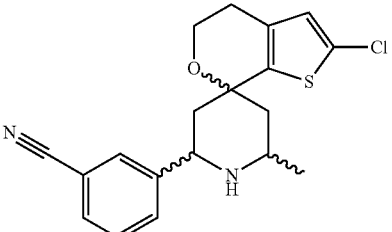 | Compound 20 | $^1$H NMR (300 MHz, DMSO-d$_6$) δ 9.02 (s, 1H), 8.42 (s, 1H), 7.60 (d, J = 1.5 Hz, 1H), 7.48-7.41 (m, 1H), 7.35 (d, J = 8.1 Hz, 1H), 6.94 (s, 1H), 4.61 (s, 1H), 3.96 (t, J = 5.4 Hz, 2H), 3.64 (s, 1H), 3.36 (s, 3H), 2.61 (t, J = 5.4 Hz, 2H), 2.34-2.23 (m, 3H), 1.87 (t, J = 13.3 Hz, 1H), 1.28 (d, J = 6.5 Hz, 3H). LCMS m/z 405.13 [M + H]$^+$. |
| Compound 24 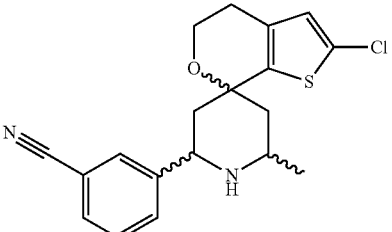 | S25; 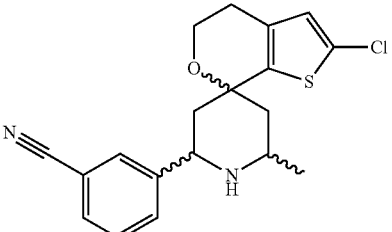 | Compound 21 | $^1$H NMR (400 MHz, DMSO-d$_6$) δ 9.12 (s, 1H), 8.68 (s, 1H), 8.10 (s, 1H), 7.94-7.89 (m, 2H), 7.68 (t, J = 7.8 Hz, 1H), 6.94 (s, 1H), 4.70-4.60 (m, 1H), 3.97 (t, J = 5.5 Hz, 2H), 3.65 (s, 1H), 2.61 (q, J = 5.0 Hz, 2H), 2.41-2.22 (m, 3H), 1.89 (t, J = 13.3 Hz, 1H), 1.28 (d, J = 6.5 Hz, 3H). LCMS m/z 359.12 [M + H]$^+$. |
| Compound 25 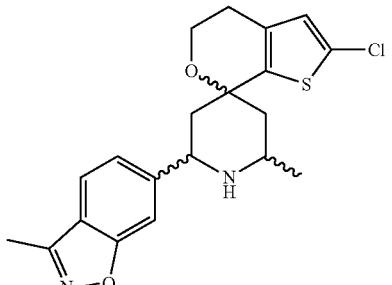 | S25; 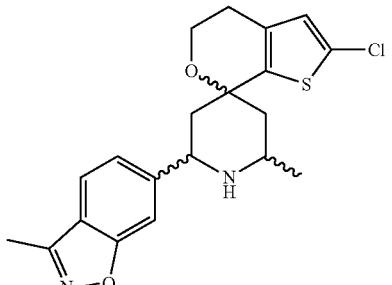 | Compound 21 | $^1$H NMR (400 MHz, DMSO-d$_6$) δ 9.25 (s, 1H), 8.75 (s, 1H), 8.00-7.94 (m, 2H), 7.60 (d, J = 8.3 Hz, 1H), 6.94 (s, 1H), 4.76 (t, J = 10.8 Hz, 1H), 3.99 (t, J = 5.5 Hz, 2H), 3.68 (s, 1H), 2.62 (d, J = 6.0 Hz, 2H), 2.57 (s, 3H), 2.42-2.26 (m, 3H), 1.93 (t, J = 13.3 Hz, 1H), 1.30 (d, J = 6.5 Hz, 3H). LCMS m/z 389.15 [M + H]$^+$. |
| Compound 26 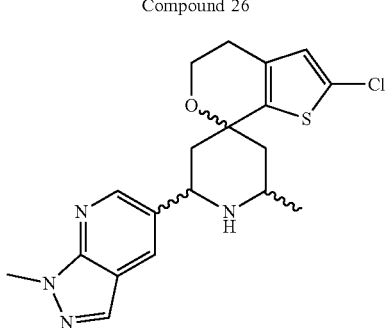 | S25; 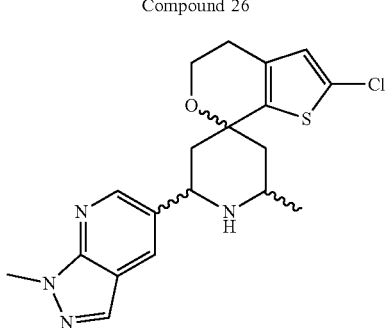 | Compound 21 | $^1$H NMR (300 MHz, Methanol-d$_4$) δ 8.72 (d, J = 2.2 Hz, 1H), 8.41 (d, J = 2.1 Hz, 1H), 8.16 (s, 1H), 6.77 (s, 1H), 4.96 (dd, J = 12.5, 2.8 Hz, 1H), 4.13 (s, 3H), 4.05 (t, J = 5.4 Hz, 2H), 3.92 (s, 1H), 2.68 (t, J = 5.7 Hz, 2H), 2.55 (dd, J = 14.3, 2.3 Hz, 1H), 2.43 (dtd, J = 12.7, 7.3, 6.3, 2.5 Hz, 2H), 1.89 (t, J = 13.6 Hz, 1H), 1.41 (d, J = 6.6 Hz, 3H). LCMS m/z 389.15 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 27  | S25;  | Compound 21 | $^1$H NMR (400 MHz, DMSO-d$_6$) δ 9.09 (d, J = 10.0 Hz, 1H), 8.66-8.50 (m, 2H), 8.05 (s, 1H), 7.87 (d, J = 7.8 Hz, 1H), 7.70 (d, J = 7.7 Hz, 1H), 7.55 (t, J = 7.7 Hz, 1H), 6.95 (s, 1H), 4.60 (t, J = 11.1 Hz, 1H), 3.97 (t, J = 5.4 Hz, 2H), 3.66 (s, 1H), 2.81 (d, J = 4.4 Hz, 3H), 2.65-2.58 (m, 2H), 2.31 (dd, J = 28.1, 14.2 Hz, 3H), 1.90 (t, J = 13.3 Hz, 1H), 1.28 (d, J = 6.5 Hz, 3H). LCMS m/z 391.13 [M + H]$^+$. |
| Compound 28 | S25; | Compound 21 | $^1$H NMR (400 MHz, DMSO-d$_6$) δ 9.16 (s, 1H), 8.68 (s, 1H), 7.56-7.27 (m, 3H), 6.94 (s, 1H), 4.59 (s, 1H), 3.96 (t, J = 5.4 Hz, 2H), 3.63 (s, 1H), 3.36 (s, 3H), 2.62 (d, J = 6.1 Hz, 2H), 2.28 (d, J = 15.6 Hz, 3H), 1.90 (t, J = 13.3 Hz, 1H), 1.28 (d, J = 6.4 Hz, 3H). LCMS m/z 405.13 [M + H]$^+$. |
| Compound 29 | S25; | Compound 19 | $^1$H NMR (400 MHz, DMSO-d$_6$) δ 9.55 (s, 1H), 9.07 (s, 1H), 6.95 (s, 1H), 6.49 (s, 1H), 4.77-4.66 (m, 1H), 4.01-3.93 (m, 3H), 2.62 (t, J = 5.5 Hz, 2H), 2.51 (d, J = 14.3 Hz, peak obscured by DMSO solvent, 1H), 2.45 (s, 3H), 2.27 (d, J = 14.3 Hz, 1H), 2.06 (t, J = 13.4 Hz, 1H), 1.83 (t, J = 13.3 Hz, 1H), 1.29 (d, J = 6.5 Hz, 3H). LCMS m/z 339.21 [M + H]$^+$. |
| Compound 30 | S25; | Compound 19[2] | LCMS m/z 335.19 [M + H]$^+$. |
| Compound 31 | S24; | Compound 19[1,3,4] | $^1$H NMR (300 MHz, Chloroform-d) δ 7.57 (s, 2H), 6.57 (s, 1H), 4.22 (dd, J = 11.7, 2.5 Hz, 1H), 3.94 (t, J = 5.5 Hz, 2H), 3.28 (dtd, J = 11.6, 6.1, 5.3, 3.6 Hz, 1H), 2.61 (t, J = 5.4 Hz, 2H), 2.24 (dt, J = 13.7, 2.6 Hz, 1H), 2.07 (dt, J = 13.8, 2.5 Hz, 1H), 1.74 (dd, J = 13.7, 11.7 Hz, 1H), 1.44 (dd, J = 13.8, 11.4 Hz, 1H), 1.14 (d, J = 6.4 Hz, 3H). LCMS m/z 324.02 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 32 | S24; | Compound 19[1,3,4] | ¹H NMR (300 MHz, Chloroform-d) δ 7.13 (d, J = 10.8 Hz, 2H), 6.88 (d, J = 7.9 Hz, 1H), 6.58 (s, 1H), 4.25 (d, J = 11.5 Hz, 1H), 3.97 (t, J = 5.4 Hz, 2H), 3.49-3.33 (m, 7H), 2.62 (t, J = 5.4 Hz, 2H), 2.15 (dd, J = 23.1, 13.7 Hz, 2H), 1.98-1.74 (m, 2H), 1.18 (d, J = 6.2 Hz, 3H). LCMS m/z 418.12 [M + H]⁺. |
| Compound 33 | S25; | Compound 20 | ¹H NMR (300 MHz, Methanol-d₄) δ 7.78 (d, J = 1.5 Hz, 1H), 7.74-7.66 (m, 2H), 6.76 (s, 1H), 4.81 (dd, J = 3.0 Hz, under water peak, 1H), 4.03 (t, J = 5.5 Hz, 2H), 3.87 (dtq, J = 12.8, 6.5, 2.9 Hz, 1H), 2.67 (t, J = 5.5 Hz, 2H), 2.51 (dt, J = 14.6, 2.8 Hz, 1H), 2.45-2.37 (m, 1H), 2.28-2.17 (m, 1H), 1.88 (dd, J = 14.8, 12.3 Hz, 1H), 1.41 (d, J = 6.6 Hz, 3H). LCMS m/z 377.14 [M + H]⁺. |
| Compound 34 | S25; | Compound 20 | ¹H NMR (400 MHz, DMSO-d₆) δ 9.28 (d, J = 10.5 Hz, 1H), 8.82 (d, J = 11.3 Hz, 1H), 8.37 (d, J = 2.8 Hz, 1H), 7.60-7.45 (m, 2H), 6.94 (s, 1H), 4.63 (t, J = 11.2 Hz, 1H), 3.98 (hept, J = 5.9, 5.4 Hz, 2H), 3.86 (s, 3H), 3.58 (s, 1H), 2.61 (t, J = 5.5 Hz, 2H), 2.46-2.18 (m, 2H), 1.98 (ddd, J = 65.1, 14.4, 12.3 Hz, 2H), 1.30 (d, J = 6.5 Hz, 3H). LCMS m/z 365.17 [M + H]⁺. |
| Compound 35 | S25; | Compound 20 | ¹H NMR (400 MHz, DMSO-d₆) δ 13.25 (s, 1H), 9.07 (d, J = 10.7 Hz, 1H), 8.55 (d, J = 11.5 Hz, 1H), 8.16 (s, 1H), 7.99 (s, 1H), 7.62 (d, J = 8.6 Hz, 1H), 7.54 (dd, J = 8.7, 1.6 Hz, 1H), 6.94 (s, 1H), 4.65 (q, J = 8.8 Hz, 1H), 3.97 (t, J = 5.5 Hz, 2H), 3.67 (s, 1H), 2.61 (q, J = 4.8 Hz, 2H), 2.32 (dd, J = 23.3, 11.3 Hz, 3H), 1.97-1.85 (m, 1H), 1.28 (d, J = 6.5 Hz, 3H). LCMS m/z 374.16 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 36 | S25; | Compound 21 | ¹H NMR (400 MHz, DMSO-d₆) δ 9.02 (d, J = 10.7 Hz, 1H), 8.49 (s, 1H), 7.49 (d, J = 8.5 Hz, 2H), 7.02 (d, J = 8.3 Hz, 2H), 6.93 (s, 1H), 4.53-4.43 (m, 1H), 4.11 (dd, J = 5.7, 3.6 Hz, 2H), 3.95 (t, J = 5.4 Hz, 2H), 3.76-3.69 (m, 2H), 3.67-3.60 (m, 1H), 3.58 (dd, J = 5.7, 3.7 Hz, 2H), 3.48-3.42 (m, 2H), 3.24 (s, 3H), 2.64-2.57 (m, 2H), 2.30-2.22 (m, 3H), 1.87 (t, J = 13.3 Hz, 1H), 1.27 (d, J = 6.5 Hz, 3H). LCMS m/z 365.17 [M + H]⁺. |
| Compound 37 | S25; | Compound 21 | ¹H NMR (300 MHz, DMSO-d₆) δ 10.65 (s, 1H), 8.94 (s, 1H), 8.52 (s, 1H), 8 48 (d, J = 2.4 Hz, 1H), 8.13 (d, J = 8.7 Hz, 1H), 7.96 (dd, J = 8.7, 2.5 Hz, 1H), 6.94 (s, 1H), 4.58 (s, 1H), 3.96 (t, J = 5.4 Hz, 2H), 3.64 (s, 1H), 2.61 (s, 2H), 2.34-2.21 (m, 3H), 2.10 (s, 3H), 1.92-1.80 (m, 1H), 1.27 (d, J = 6.5 Hz, 3H). LCMS m/z 392.13 [M + H]⁺. |
| Compound 38 | S25; | Compound 21 | ¹H NMR (400 MHz, DMSO-d₆) δ 9.37 (s, 1H), 8.94 (s, 1H), 7.92 (s, 1H), 6.95 (s, 1H), 4.72 (t, J = 11.4 Hz, 1H), 4.19 (s, 3H), 3.95 (t, J = 5.4 Hz, 2H), 3.67-3.55 (m, 1H), 2.61 (t, J = 5.4 Hz, 2H), 2.47-2.45 (m, 1H), 2.31-2.15 (m, 2H), 1.83 (dd, J = 14.5, 12.3 Hz, 1H), 1.27 (d, J = 6.4 Hz, 3H). LCMS m/z 339.16 [M + H]⁺. |
| Compound 39 | S25; | Compound 21 | ¹H NMR (400 MHz, DMSO-d₆) δ 10.86 (s, 1H), 9.03 (d, J = 10.1 Hz, 1H), 8.63-8.31 (m, 1H), 7.21 (d, J = 1.8 Hz, 1H), 7.16-7.10 (m, 1H), 6.93 (t, J = 4.1 Hz, 2H), 4.60 (s, 2H), 4.45 (q, J = 10.2, 9.6 Hz, 1H), 3.94 (t, J = 5.4 Hz, 2H), 3.60 (s, 1H), 2.59 (t, J = 5.3 Hz, 2H), 2.29-2.19 (m, 3H), 1.92-1.80 (m, 1H), 1.26 (d, J = 6.5 Hz, 3H). LCMS m/z 405.09 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 40 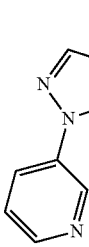 | S25; 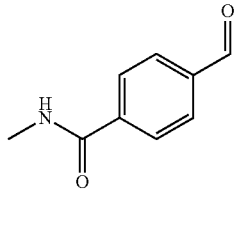 | Compound 21 | ¹H NMR (400 MHz, DMSO-$d_6$) δ 9.19-9.07 (m, 1H), 8.81 (s, 1H), 8.78-8.70 (m, 1H), 8.60-8.55 (m, 1H), 8.25-8.20 (m, 1H), 8.02 (s, 1H), 7.59 (dd, J = 8.4, 4.7 Hz, 1H), 6.96 (s, 1H), 4.61 (t, J = 11.2 Hz, 1H), 3.96 (t, J = 5.5 Hz, 2H), 3.62 (s, 2H), 2.62 (t, J = 5.2 Hz, 2H), 2.48-2.43 (m, 1H), 2.31 (dd, J = 27.8, 13.8 Hz, 2H), 1.84 (t, J = 13.3 Hz, 1H), 1.28 (d, J = 6.4 Hz, 3H). LCMS m/z 401.11 [M + H]⁺. |
| Compound 41 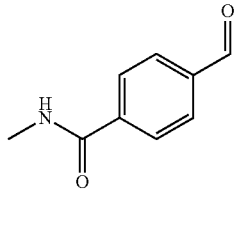 | S25; 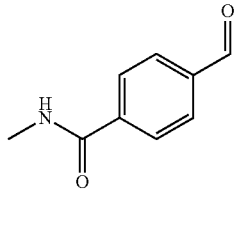 | Compound 21 | ¹H NMR (400 MHz, DMSO-$d_6$) δ 9.17 (s, 1H), 8.69 (s, 1H), 8.54 (d, J = 4.8 Hz, 1H), 7.91 (d, J = 8.0 Hz, 2H), 7.65 (d, J = 8.1 Hz, 2H), 6.94 (s, 1H), 4.61 (t, J = 11.2 Hz, 1H), 3.97 (t, J = 5.5 Hz, 2H), 3.65 (s, 1H), 2.79 (d, J = 4.4 Hz, 3H), 2.61 (s, 2H), 2.39-2.19 (m, 3H), 1.91 (t, J = 13.3 Hz, 1H), 1.29 (d, J = 6.4 Hz, 3H). LCMS m/z 391.13 [M + H]⁺. |
| Compound 42 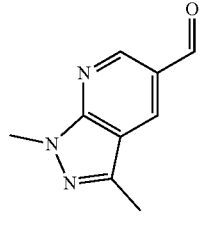 | S25; 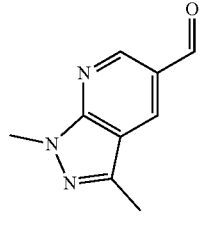 | Compound 21¹ | ¹H NMR (400 MHz, DMSO-$d_6$) δ 8.52 (d, J = 1.9 Hz, 1H), 8.21 (s, 1H), 6.86 (s, 1H), 4.21 (d, J = 11.4 Hz, 1H), 3.95 (s, 5H), 3.18 (s, 1H), 2.58 (t, J = 5.4 Hz, 2H), 2.49 (s, 3H), 2.11 (d, J = 13.2 Hz, 1H), 2.03 (d, J = 13.6 Hz, 1H), 1.67 (s, 1H), 1.35 (t, J = 13.1 Hz, 1H), 1.06 (d, J = 6.3 Hz, 3H). LCMS m/z 403.14 [M + H]⁺. |
| Compound 43 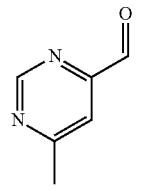 | S25; 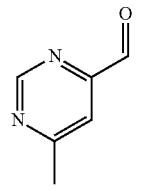 | Compound 21 | ¹H NMR (400 MHz, DMSO-$d_6$) δ 9.53 (s, 1H), 9.16 (d, J = 1.4 Hz, 1H), 9.04 (d, J = 10.5 Hz, 1H), 7.65 (s, 1H), 6.95 (s, 1H), 4.74-4.61 (m, 1H), 4.01 (m, 2H), 3.66-3.52 (m, 1H), 2.63 (t, J = 5.5 Hz, 2H), 2.57 (s, 1H), 2.50 (s, 3H), 2.25 (d, J = 14.4 Hz, 1H), 1.94 (dt, J = 30.8, 13.5 Hz, 2H), 1.33 (d, J = 6.4 Hz, 3H). LCMS m/z 350.14 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 44 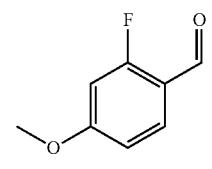 | S25; 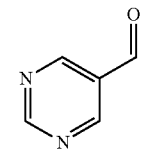 | Compound 21 | LCMS m/z 382.1 [M + H]$^+$. |
| Compound 45 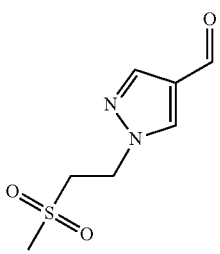 | S25; 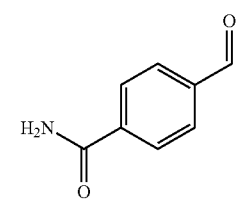 | Compound 19[11] | $^1$H NMR (400 MHz, DMSO-d$_6$) δ 9.24 (s, 1H), 9.16 (s, 1H), 9.01 (s, 2H), 8.88 (s, 1H), 6.95 (s, 1H), 4.71 (s, 1H), 3.97 (t, J = 5.5 Hz, 2H), 3.66 (s, 1H), 2.61 (t, J = 4.9 Hz, 2H), 2.41 (d, J = 11.7 Hz, 2H), 2.29 (d, J = 14.4 Hz, 1H), 1.93-1.84 (m, 1H), 1.29 (d, J = 6.7 Hz, 3H). LCMS m/z 336.18 [M + H]$^+$. |
| Compound 46 | S25; | Compound 19 | $^1$H NMR (400 MHz, DMSO-d$_6$) δ 8.95 (d, J = 10.6 Hz, 1H), 8.51 (d, J = 11.3 Hz, 1H), 8.00 (s, 1H), 7.69 (s, 1H), 6.95 (s, 1H), 4.54 (q, J = 9.0, 7.9 Hz, 3H), 3.93 (t, J = 5.5 Hz, 2H), 3.68 (t, J = 6.7 Hz, 2H), 3.57 (s, 1H), 2.86 (s, 3H), 2.64-2.56 (m, 2H), 2.38-2.31 (m, 1H), 2.27-2.14 (m, 2H), 1.83-1.70 (m, 1H), 1.25 (d, J = 6.5 Hz, 3H). LCMS m/z 430.1 [M + H]$^+$. |
| Compound 47 | S25; | Compound 20 | $^1$H NMR (300 MHz, Methanol-d$_4$) δ 7.99 (d, J = 8.4 Hz, 2H), 7.63 (d, J = 8.2 Hz, 2H), 6.76 (s, 1H), 4.77 (dd, J = 12.7, 2.8 Hz, 1H), 4.03 (t, J = 5.4 Hz, 2H), 3.89 (dt, J = 11.3, 7.8 Hz, 1H), 2.67 (t, J = 5.5 Hz, 2H), 2.52-2.37 (m, 2H), 2.31-2.18 (m, 1H), 1.89 (t, J = 13.5 Hz, 1H), 1.41 (d, J = 6.6 Hz, 3H). LCMS m/z 377.18 [M + H]$^+$. |

TABLE 3-continued

Method of preparation, structure and physicochemical data for compounds 22-172

| Product | Starting Material and Aldehyde | Method | $^{1}$H NMR; LCMS m/z [M + H]$^{+}$ |
|---|---|---|---|
| Compound 48 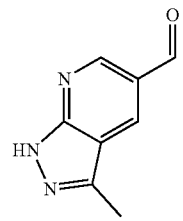 | S25; | Compound 20 | $^{1}$H NMR (400 MHz, DMSO-d$_{6}$) δ 13.37 (s, 1H), 9.07 (d, J = 10.7 Hz, 1H), 8.71 (s, 1H), 8.66 (d, J = 2.1 Hz, 1H), 8.47 (d, J = 2.1 Hz, 1H), 6.95 (s, 1H), 4.77 (t, J = 11.2 Hz, 1H), 3.98 (t, J = 5.4 Hz, 2H), 3.68 (s, 1H), 2.64-2.56 (m, 2H), 2.52 (s, 3H), 2.48-2.25 (m, 3H), 1.92 (t, J = 13.3 Hz, 1H), 1.28 (d, J = 6.5 Hz, 3H). LCMS m/z 389.19 [M + H]$^{+}$. |
| Compound 49 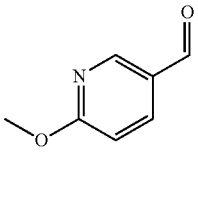 | S25; | Compound 20 | $^{1}$H NMR (300 MHz, Methanol-d$_{4}$) δ 8.30 (d, J = 2.6 Hz, 1H), 7.85 (dd, J = 8.7, 2.6 Hz, 1H), 6.90 (d, J = 8.7 Hz, 1H), 6.75 (s, 1H), 4.71 (dd, J = 12.5, 3.0 Hz, 1H), 4.02 (t, J = 5.5 Hz, 2H), 3.93 (s, 3H), 3.85 (dddd, J = 15.6, 9.1, 6.9, 3.3 Hz, 1H), 2.66 (t, J = 5.5 Hz, 2H), 2.48-2.22 (m, 3H), 1.87 (dd, J = 14.9, 12.3 Hz, 1H), 1.38 (d, J = 6.6 Hz, 3H). LCMS m/z 365.17 [M + H]$^{+}$. |
| Compound 50 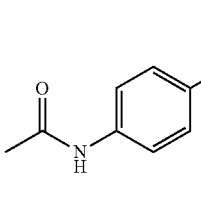 | S25; | Compound 20 | $^{1}$H NMR (400 MHz, DMSO-d$_{6}$) δ 10.09 (s, 1H), 9.04 (s, 1H), 8.55 (s, 1H), 7.64 (d, J = 8.4 Hz, 2H), 7.48 (d, J = 8.3 Hz, 2H), 6.94 (s, 1H), 4.53-4.42 (m, 1H), 3.96 (t, J = 5.1 Hz, 2H), 3.67-3.58 (m, 1H), 2.60 (t, 2H), 2.26 (d, J = 7.8 Hz, 3H), 2.05 (s, 3H), 1.88 (t, J = 13.4 Hz, 1H), 1.27 (d, J = 6.5 Hz, 3H). LCMS m/z 391.13 [M + H]$^{+}$. |
| Compound 51 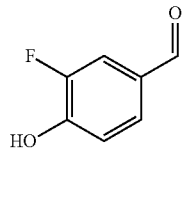 | S25; | Compound 21 | $^{1}$H NMR (400 MHz, DMSO-d$_{6}$) δ 10.25 (s, 1H), 9.00 (s, 1H), 8.51 (s, 1H), 7.41 (dd, J = 12.5, 2.1 Hz, 1H), 7.23-7.14 (m, 1H), 7.04-6.96 (m, 1H), 6.93 (s, 1H), 4.51-4.40 (m, 1H), 3.94 (t, J = 5.3 Hz, 2H), 3.65-3.56 (m, 1H), 2.60 (s, 2H), 2.24 (d, J = 10.4 Hz, 3H), 1.86 (t, J = 13.4 Hz, 1H), 1.26 (d, J = 6.5 Hz, 3H). LCMS m/z 368.11 [M + H]$^{+}$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 52 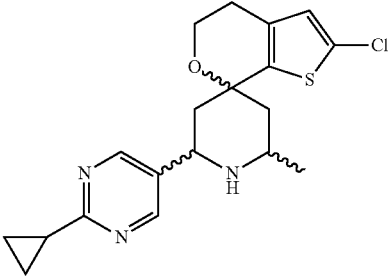 [SMILES: CC1CC2(CC(c3cnc(C4CC4)nc3)N1)OCCc1cc(Cl)sc12] | S25; 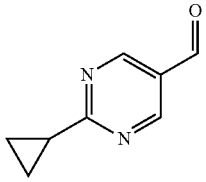 | Compound 21 | ¹H NMR (300 MHz, DMSO-$d_6$) δ 8.92 (s, 1H), 8.80 (d, J = 2.9 Hz, 2H), 8.63 (s, 1H), 6.95 (s, 1H), 4.62 (s, 1H), 3.96 (s, 2H), 3.64 (s, 1H), 2.61 (s, 2H), 2.40-2.20 (m, 4H), 1.86 (t, J = 13.6 Hz, 1H), 1.30-1.22 (m, 3H), 1.05 (ddt, J = 23.3, 5.6, 2.9 Hz, 4H). LCMS m/z 376.14 [M + H]⁺. |
| Compound 53 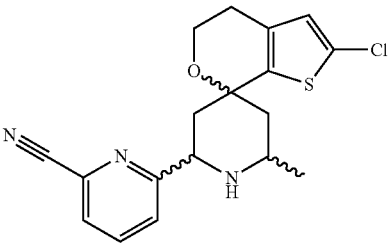 [SMILES: CC1CC2(CC(c3cccc(C#N)n3)N1)OCCc1cc(Cl)sc12] | S25; 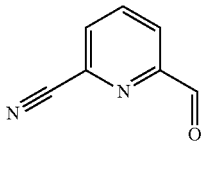 | Compound 21 | ¹H NMR (300 MHz, DMSO-$d_6$) δ 9.41 (d, J = 10.3 Hz, 1H), 9.07-8.83 (m, 1H), 8.26-8.10 (m, 2H), 7.96 (dd, J = 7.7, 1.4 Hz, 1H), 6.95 (s, 1H), 4.83 (t, J = 11.1 Hz, 1H), 4.01 (h, J = 6.3 Hz, 2H), 3.61 (s, 1H), 2.63 (t, J = 5.4 Hz, 2H), 2.58-2.54 (m, under DMSO, 1H), 2.27 (d, J = 14.0 Hz, 1H), 1.98 (dt, J = 27.4, 13.3 Hz, 2H), 1.33 (d, J = 6.5 Hz, 3H). LCMS m/z 360.12 [M + H]⁺. |
| Compound 54 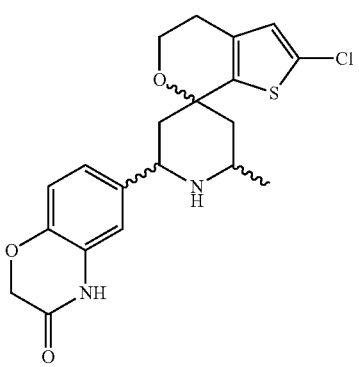 | S25; 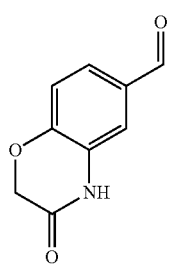 | Compound 21 | ¹H NMR (400 MHz, DMSO-$d_6$) δ 10.93 (s, 1H), 8.97 (s, 1H), 8.51 (s, 1H), 7.17-7.13 (m, 1H), 7.06-7.02 (m, 2H), 6.94 (s, 1H), 4.61 (s, 2H), 4.45 (t, J = 11.0 Hz, 1H), 3.95 (t, J = 5.5 Hz, 2H), 3.63 (s, 1H), 2.60 (t, 2H), 2.31-2.19 (m, 3H), 1.86 (t, J = 13.4 Hz, 1H), 1.25 (d, J = 6.5 Hz, 3H). LCMS m/z 365.17 [M + H]⁺. |
| Compound 55 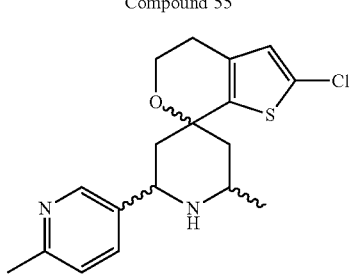 | S24; 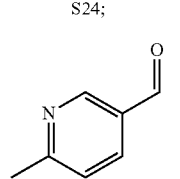 | Compound 19[1,3,4] | ¹H NMR (300 MHz, Chloroform-d) δ 8.49 (d, J = 2.3 Hz, 1H), 7.68 (dd, J = 8.0, 2.4 Hz, 1H), 7.13 (d, J = 8.0 Hz, 1H), 6.59 (s, 1H), 4.17 (dd, J = 11.6, 2.4 Hz, 1H), 3.98 (t, J = 5.5 Hz, 2H), 3.38-3.24 (m, 1H), 2.63 (t, J = 5.5 Hz, 2H), 2.55 (s, 3H), 2.18-2.05 (m, 2H), 1.71 (dd, J = 13.6, 11.6 Hz, 1H), 1.46 (dd, J = 13.7, 11.3 Hz, 1H), 1.14 (d, J = 6.3 Hz, 3H). LCMS 349.0 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 56  | S24;  | Compound 19[1,3,4,5] | ¹H NMR (300 MHz, Chloroform-d) δ 7.49 (s, 1H), 7.45 (s, 1H), 6.58 (s, 1H), 4.22-4.14 (m, 3H), 3.99-3.90 (m, 4H), 3.35-3.18 (m, 1H), 2.61 (t, J = 5.4 Hz, 2H), 2.22 (dt, J = 13.8, 2.6 Hz, 1H), 2.06 (dt, J = 13.8, 2.5 Hz, 1H), 1.73 (t, J = 12.7 Hz, 1H), 1.48-1.38 (m, 1H), 1.13 (d, J = 6.4 Hz, 3H). LCMS m/z 368.03 [M + H]⁺. |
| Compound 57  | S25;  | Compound 20 | ¹H NMR (400 MHz, DMSO-d₆) δ 8.86 (d, J = 10.7 Hz, 1H), 8.50 (s, 1H), 8.38 (s, 2H), 6.99-6.85 (m, 3H), 4.41 (t, J = 11.1 Hz, 1H), 3.93 (t, J = 5.6 Hz, 2H), 3.66-3.55 (m, 1H), 2.60 (q, J = 4.9 Hz, 2H), 2.41-2.16 (m, 3H), 1.88-1.76 (m, 1H), 1.25 (d, J = 6.5 Hz, 3H). LCMS m/z 351.17 [M + H]⁺. |
| Compound 58  | S25;  | Compound 21 | ¹H NMR (400 MHz, DMSO-d₆) δ 9.61 (s, 1H), 9.24 (d, J = 11.2 Hz, 1H), 7.81 (d, J = 8.8 Hz, 1H), 7.70 (d, J = 8.6 Hz, 1H), 6.95 (s, 1H), 4.86 (t, J = 11.1 Hz, 1H), 4.01 (tt, J = 11.9, 6.3 Hz, 2H), 3.62 (s, 1H), 2.67 (s, 3H), 2.62 (dd, J = 12.0, 6.1 Hz, 2H), 2.57 (m, 1H), 2.29 (d, J = 14.5 Hz, 1H), 2.12-2.02 (m, 1H), 1.99-1.90 (m, 1H), 1.34 (d, J = 6.5 Hz, 3H). LCMS m/z 350.14 [M + H]⁺. |
| Compound 59  | S25; | Compound 21 | ¹H NMR (400 MHz, DMSO-d₆) δ 10.35 (s, 1H), 9.23 (s, 1H), 8.77 (d, J = 11.9 Hz, 1H), 8.21 (d, J = 2.8 Hz, 1H), 7.41 (d, J = 8.5 Hz, 1H), 7.29-7.22 (m, 1H), 6.94 (s, 1H), 4.55 (t, J = 11.5 Hz, 1H), 3.98 (h, J = 6.2 Hz, 2H), 3.56 (s, 1H), 2.67-2.59 (m, 2H), 2.37 (d, J = 14.4 Hz, 1H), 2.24 (d, J = 14.3 Hz, 1H), 2.13-2.01 (m, 1H), 1.95-1.85 (m, 1H), 1.29 (d, J = 6.5 Hz, 3H). LCMS m/z 351.13 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 60 | S25; | Compound 21 | ¹H NMR (300 MHz, Methanol-d₄) δ 8.42 (s, 2H), 6.76 (s, 1H), 4.66-4.55 (m, 1H), 4.00 (t, J = 5.5 Hz, 2H), 3.81 (d, J = 10.5 Hz, 1H), 2.93 (s, 3H), 2.66 (t, J = 5.4 Hz, 2H), 2.49-2.20 (m, 3H), 1.89-1.75 (m, 1H), 1.37 (d, J = 6.6 Hz, 3H). LCMS m/z 365.13 [M + H]⁺. |
| Compound 61 | S25; | Compound 21 | ¹H NMR (400 MHz, DMSO-d₆) δ 9.10 (s, 1H), 8.91 (s, 3H), 8.44 (s, 1H), 8.06 (s, 1H), 6.95 (s, 1H), 4.65 (d, J = 8.9 Hz, 1H), 4.05-3.95 (m, 2H), 3.91 (s, 3H), 3.66 (s, 1H), 2.66-2.58 (m, 2H), 2.41 (d, J = 8.0 Hz, 2H), 2.28 (d, J = 14.2 Hz, 1H), 1.90 (t, J = 13.3 Hz, 1H), 1.28 (d, J = 6.5 Hz, 3H). LCMS m/z 416.1 [M + H]⁺. |
| Compound 62 | S25; | Compound 21[1,6] | ¹H NMR (400 MHz, DMSO-d₆) δ 7.74-7.64 (m, 2H), 7.17 (d, J = 8.8 Hz, 1H), 6.85 (s, 1H), 4.05-3.89 (m, 3H), 3.89 (s, 3H), 3.09 (s, 1H), 2.61-2.55 (m, 2H), 2.00 (dd, J = 23.1, 13.5 Hz, 2H), 1.47 (t, J = 12.4 Hz, 1H), 1.27 (t, J = 12.4 Hz, 1H), 1.03 (d, J = 6.3 Hz, 3H). LCMS m/z 389.15 [M + H]⁺. |
| Compound 63 | S25; | Compound 21 | ¹H NMR (400 MHz, DMSO-d₆) δ 9.55 (s, 1H), 9.25 (d, J = 1.5 Hz, 1H), 9.17 (s, 1H), 8.94 (d, J = 1.5 Hz, 1H), 8.38 (s, 1H), 7.95 (s, 1H), 6.95 (s, 1H), 4.97 (d, J = 12.0 Hz, 1H), 4.08-3.95 (m, 2H), 3.64 (s, 1H), 2.66-2.61 (m, 2H), 2.74-2.54 (m, 1H), 2.28 (d, J = 14.4 Hz, 1H), 2.16-2.05 (m, 1H), 1.94 (t, J = 13.3 Hz, 1H), 1.32 (d, J = 6.5 Hz, 3H). LCMS m/z 379.17 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 64 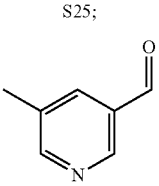 | S25; | Compound 19[7] | $^1$H NMR (400 MHz, DMSO-d$_6$) δ 9.10 (s, 1H), 8.69 (d, J = 10.8 Hz, 1H), 8.57 (d, J = 2.1 Hz, 1H), 8.49 (s, 1H), 7.89 (s, 1H), 6.94 (s, 1H), 4.61 (t, 1H), 3.97 (t, J = 5.5 Hz, 2H), 2.96-2.89 (m, 1H), 2.52 (d, under DMSO, 1H), 2.64-2.57 (m, 2H), 2.35 (s, 3H), 2.29 (d, J = 18.5 Hz, 2H), 1.94-1.84 (m, 1H), 1.28 (d, J = 6.3 Hz, 3H). LCMS m/z 349.19 [M + H]$^+$. |
| Compound 65 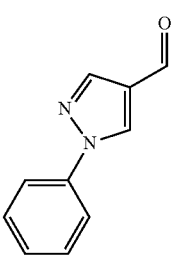 | S25; | Compound 19 | $^1$H NMR (400 MHz, DMSO-d$_6$) δ 8.97 (s, 1H), 8.70 (s, 1H), 8.61 (d, J = 12.6 Hz, 1H), 7.94 (s, 1H), 7.82 (d, J = 8.0 Hz, 2H), 7.53 (t, J = 7.8 Hz, 2H), 7.35 (t, J = 7.4 Hz, 1H), 6.96 (s, 1H), 4.60 (t, J = 11.1 Hz, 1H), 3.96 (t, J = 5.4 Hz, 2H), 3.61 (s, 1H), 2.61 (d, J = 6.2 Hz, 2H), 2.46 (d, under DMSO, 1H), 2.35-2.24 (m, 2H), 1.81 (t, J = 13.3 Hz, 1H), 1.28 (d, J = 6.5 Hz, 3H). LCMS m/z 400.16 [M + H]$^+$. |
| Compound 66 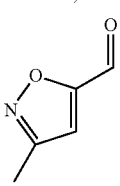 | S24; | Compound 19[8] | $^1$H NMR (300 MHz, Methanol-d$_6$) δ 6.76 (s, 1H), 6.51 (s, 1H), 4.98 (dd, J = 12.7, 3.1 Hz, 1H), 4.00 (t, J = 5.4 Hz, 2H), 3.83 (ddd, J = 12.3, 6.5, 2.9 Hz, 1H), 2.66 (t, J = 5.4 Hz, 2H), 2.60 (dt, J = 14.5, 2.8 Hz, 1H), 2.38 (dt, J = 14.8, 2.8 Hz, 1H), 2.31 (s, 3H), 2.23 (dd, J = 14.4, 12.6 Hz, 1H), 1.83 (dd, J = 14.7, 12.3 Hz, 1H), 1.39 (d, J = 6.6 Hz, 3H). LCMS m/z 339.16 [M + H]$^+$. |
| Compound 67 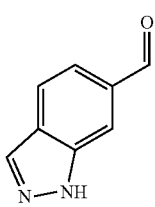 | S25; | Compound 20 | $^1$H NMR (400 MHz, DMSO-d$_6$) δ 13.33 (s, 1H), 9.15 (d, J = 9.1 Hz, 1H), 8.60 (d, J = 11.5 Hz, 1H), 8.12 (s, 1H), 7.85 (d, J = 8.4 Hz, 1H), 7.76 (s, 1H), 7.30 (dd, J = 8.4, 1.4 Hz, 1H), 6.94 (s, 1H), 4.69 (t, J = 10.8 Hz, 1H), 3.98 (t, J = 5.5 Hz, 2H), 3.69 (d, J = 11.0 Hz, 1H), 2.63-2.59 (m, 2H), 2.43-2.24 (m, 3H), 1.92 (dd, J = 14.5, 12.2 Hz, 1H), 1.29 (d, J = 6.5 Hz, 3H). LCMS m/z 374.16 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 68 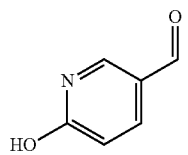 | S25; 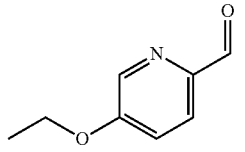 | Compound 21 | ¹H NMR (400 MHz, DMSO-$d_6$) δ 11.82 (s, 1H), 8.89 (s, 1H), 8.49 (s, 1H), 7.63 (d, J = 9.8 Hz, 2H), 6.93 (s, 1H), 6.39 (d, J = 9.3 Hz, 1H), 4.39 (q, J = 6.2 Hz, 1H), 3.93 (t, J = 5.4 Hz, 2H), 3.57 (q, J = 9.1, 6.8 Hz, 1H), 2.59 (t, 2H), 2.22 (d, J = 9.9 Hz, 3H), 1.81 (t, J = 13.3 Hz, 1H), 1.25 (d, J = 6.7 Hz, 3H). LCMS m/z 351.13 [M + H]⁺. |
| Compound 69 | S25; | Compound 21 | ¹H NMR (400 MHz, DMSO-$d_6$) δ 9.29 (d, J = 10.5 Hz, 1H), 8.82 (d, J = 11.1 Hz, 1H), 8.36 (d, J = 2.8 Hz, 1H), 7.57-7.45 (m, 2H), 6.94 (s, 1H), 4.62 (t, J = 11.2 Hz, 1H), 4.14 (q, J = 7.0 Hz, 2H), 3.98 (q, J = 5.8 Hz, 2H), 3.58 (s, 1H), 2.61 (t, J = 5.4 Hz, 2H), 2.40 (d, J = 14.5 Hz, 1H), 2.25 (d, J = 14.4 Hz, 1H), 2.12-2.01 (m, 1H), 1.98-1.81 (m, 1H), 1.35 (t, J = 6.9 Hz, 3H), 1.29 (d, J = 6.5 Hz, 3H). LCMS m/z 379.12 [M + H]⁺ |
| Compound 70 | S25; | Compound 21 | ¹H NMR (400 MHz, DMSO-$d_6$) δ 9.45 (s, 1H), 9.10 (s, 1H), 8.09-7.99 (m, 2H), 7.61-7.55 (m, 3H), 7.52 (s, 1H), 6.97 (s, 1H), 4.86 (s, 1H), 3.97 (t, J = 5.5 Hz, 2H), 3.68 (s, 1H), 2.61 (d, J = 14.1 Hz, 3H), 2.34 (t, J = 13.6 Hz, 1H), 2.27 (d, J = 14.5 Hz, 1H), 1.87 (t, J = 13.4 Hz, 1H), 1.29 (d, J = 6.5 Hz, 3H). LCMS m/z 401.11 [M + H]⁺ |
| Compound 71 | S25; | Compound 21 | ¹H NMR (400 MHz, DMSO-$d_6$) δ 9.19 (s, 1H), 8.71 (s, 1H), 8.52 (d, J = 4.3 Hz, 1H), 7.89 (d, J = 8.2 Hz, 2H), 7.63 (d, J = 8.2 Hz, 2H), 6.93 (s, 1H), 4.60 (t, J = 11.0 Hz, 1H), 3.97 (t, J = 5.5 Hz, 2H), 3.65 (s, 1H), 2.85 (dq, J = 7.5, 3.7 Hz, 1H), 2.61 (s, 2H), 2.28 (h, J = 13.5 Hz, 3H), 1.91 (t, J = 13.3 Hz, 1H), 1.29 (d, J = 6.5 Hz, 3H), 0.70 (h, J = 4.6 Hz, 2H), 0.58 (q, J = 3.8, 3.2 Hz, 2H). LCMS m/z 417.14 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 72 | S24; | Compound 19[1,3,4,9] | $^1$H NMR (300 MHz, Chloroform-d) δ 7.62 (s, 1H), 6.58 (s, 1H), 4.60 (dd, J = 12.1, 2.8 Hz, 1H), 3.94 (t, J = 5.5 Hz, 2H), 3.58-3.50 (m, 1H), 2.61 (d, J = 3.1 Hz, 2H), 2.44-2.32 (m, 1H), 2.20-2.01 (m, 2H), 1.70 (dd, J = 14.1, 11.7 Hz, 1H), 1.26 (d, J = 6.4 Hz, 3H). LCMS m/z 325.01 [M + H]$^+$. |
| Compound 73 | S24; | Compound 20 | $^1$H NMR (400 MHz, DMSO-$d_6$) δ 12.82 (s, 1H), 9.25 (d, J = 10.7 Hz, 1H), 8.72 (d, J = 11.3 Hz, 1H), 6.94 (s, 1H), 6.17 (s, 1H), 4.47 (t, J = 11.1 Hz, 1H), 3.94 (d, J = 5.7 Hz, 2H), 3.62-3.51 (m, obscured by water, 1H), 2.61 (t, J = 5.4 Hz, 2H), 2.41 (d, J = 14.5 Hz, 1H), 2.24 (s, 4H), 2.10 (t, J = 13.6 Hz, 1H), 1.86 1.77 (m, 1H), 1.27 (d, J = 6.4 Hz, 3H). LCMS m/z 338.17 [M + H]$^+$. |
| Compound 74 | S24; | Compound 20 | $^1$H NMR (400 MHz, DMSO-$d_6$) δ 9.11 (d, J = 10.8 Hz, 1H), 8.67 (s, 1H), 7.32 (s, 1H), 6.94 (s, 1H), 4.76 (d, J = 1.6 Hz, 2H), 4.45 (s, 1H), 4.01 (p, J = 4.7, 4.1 Hz, 4H), 3.93 (t, J = 5.5 Hz, 2H), 3.50 (s, 1H), 2.60 (t, J = 5.3 Hz, 2H), 2.39-2.13 (m, 3H), 1.80 (dd, J = 14.4, 12.2 Hz, 1H), 1.24 (d, J = 6.5 Hz, 3H). LCMS m/z 380.16 [M + H]$^+$. |
| Compound 75 | S25; | Compound 21 | $^1$H NMR (400 MHz, DMSO-$d_6$) δ 8.93 (s, 1H), 8.61 (s, 1H), 8.49 (s, 2H), 6.94 (s, 1H), 4.45 (t, J = 11.1 Hz, 1H), 3.94 (t, J = 5.5 Hz, 2H), 3.65-3.55 (m, 1H), 3.13 (s, 6H), 2.60 (t, J = 5.3 Hz, 2H), 2.41-2.31 (m, 1H), 2.26 (d, J = 13.8 Hz, 2H), 1.84 (t, J = 13.3 Hz, 1H), 1.25 (d, J = 6.4 Hz, 3H). LCMS m/z 379.17 [M + H]$^+$. |
| Compound 76 | S25; | Compound 21[10] | LCMS m/z 366.12 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 77 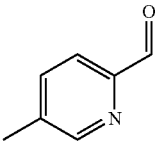 | S25; | Compound 19 | $^1$H NMR (400 MHz, DMSO-d$_6$) δ 9.30 (s, 1H), 8.87 (s, 1H), 8.53 (d, J = 2.1 Hz, 1H), 7.73 (d, J = 8.0 Hz, 1H), 7.49 (d, J = 8.0 Hz, 1H), 6.94 (s, 1H), 4.64 (t, 1H), 3.99 (h, J = 6.2 Hz, 2H), 3.65-3.56 (m, 1H), 2.62 (t, J = 5.4 Hz, 2H), 2.43 (d, J = 14.4 Hz, 1H), 2.34 (s, 3H), 2.26 (d, J = 14.5 Hz, 1H), 2.08-1.98 (m, 1H), 1.96-1.87 (m, 1H), 1.31 (d, J = 6.5 Hz, 3H). LCMS m/z 349.23 [M + H]$^+$. |
| Compound 78 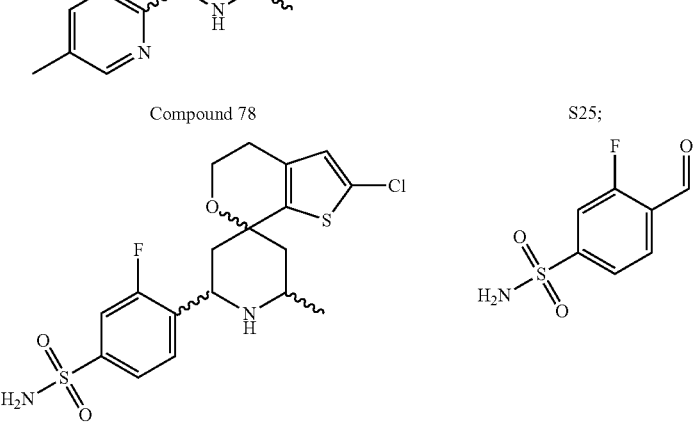 | S25; | Compound 21 | $^1$H NMR (400 MHz, DMSO-d$_6$) δ 9.37 (s, 1H), 8.92 (s, 1H), 7.91 (t, J = 7.6 Hz, 1H), 7.79 (d, J = 8.5 Hz, 1H), 7.69 (d, J = 9.4 Hz, 1H), 7.62 (s, 2H), 6.94 (s, 1H), 4.82 (t, J = 11.5 Hz, 1H), 3.98 (t, J = 5.5 Hz, 2H), 3.72 (s, 1H), 2.62 (t, J = 5.4 Hz, 2H), 2.42-2.18 (m, 3H), 1.93 (t, J = 13.3 Hz, 1H), 1.30 (d, J = 6.4 Hz, 3H). LCMS m/z 431.01 [M + H]$^+$. |
| Compound 79 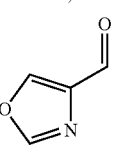 | S25; | Compound 21[11] | $^1$H NMR (400 MHz, DMSO-d$_6$) δ 9.28 (s, 1H), 8.85 (s, 1H), 8.57 (s, 1H), 8.31 (s, 1H), 6.95 (s, 1H), 4.60 (t, J = 11.1 Hz, 1H), 3.94 (t, J = 5.3 Hz, 2H), 3.58 (s, 1H), 2.60 (t, J = 5.5 Hz, 2H), 2.44-2.15 (m, 3H), 1.89-1.78 (m, 1H), 1.26 (d, J = 6.4 Hz, 3H). LCMS m/z 325.12 [M + H]$^+$. |
| Compound 80 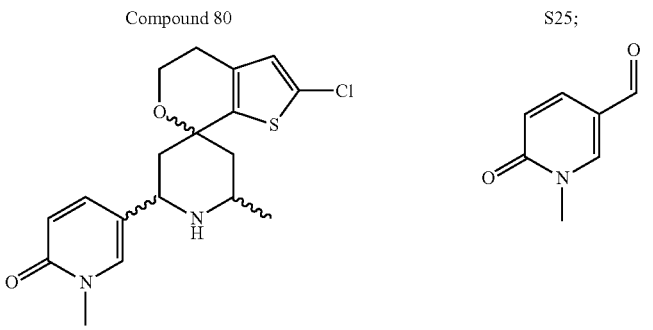 | S25; | Compound 21 | $^1$H NMR (400 MHz, DMSO-d$_6$) δ 8.94 (s, 1H), 8.56 (s, 1H), 7.96 (d, J = 2.6 Hz, 1H), 7.63 (dt, J = 9.5, 4.7 Hz, 1H), 6.94 (s, 1H), 6.46 (d, J = 9.4 Hz, 1H), 4.46-4.28 (m, 1H), 3.95-3.91 (m, 2H), 3.65-3.49 (m, 1H), 3.43 (s, 3H), 2.62-2.57 (m, 2H), 2.33-2.17 (m, 3H), 1.96-1.70 (m, 1H), 1.25 (d, J = 6.5 Hz, 3H). LCMS m/z 365.13 [M + H]$^+$. |
| Compound 81 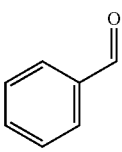 | S25; | Compound 19 | $^1$H NMR (400 MHz, DMSO-d$_6$) δ 9.11 (s, 1H), 8.59 (s, 1H), 7.63-7.54 (m, 2H), 7.52-7.41 (m, 3H), 6.94 (s, 1H), 4.54 (t, J = 11.3 Hz, 1H), 3.97 (t, J = 5.4 Hz, 2H), 3.65 (s, 1H), 2.64-2.58 (m, 2H), 2.27 (dt, J = 20.9, 13.8 Hz, 3H), 1.95-1.86 (m, 1H), 1.28 (d, J = 6.5 Hz, 3H). LCMS m/z 334.19 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 82 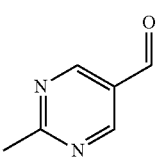 | S25; | Compound 19 | $^1$H NMR (400 MHz, DMSO-d$_6$) δ 9.07 (s, 1H), 8.88 (s, 2H), 8.78 (s, 1H), 6.95 (s, 1H), 4.71-4.61 (m, 1H), 3.96 (t, J = 5.5 Hz, 2H), 2.98-2.89 (m, 1H), 2.65 (s, 3H), 2.61 (dd, J = 8.5, 4.8 Hz, 2H), 2.38 (d, J = 8.1 Hz, 2H), 2.28 (d, J = 14.5 Hz, 1H), 1.93-1.83 (m, 1H), 1.28 (d, J = 6.6 Hz, 3H). LCMS m/z 350.22 [M + H]$^+$. |
| Compound 83 | S25; | Compound 19 | $^1$H NMR (400 MHz, DMSO-d$_6$) δ 9.37 (s, 1H), 8.92 (s, 1H), 8.69 (d, J = 4.9 Hz, 1H), 7.92 (td, J = 7.8, 1.9 Hz, 1H), 7.60 (d, J = 7.9 Hz, 1H), 7.48 (dd, J = 7.4, 4.8 Hz, 1H), 6.94 (s, 1H), 4.70 (s, 1H), 4.00 (dp, J = 11.6, 5.9, 5.5 Hz, 2H), 3.60 (s, 1H), 2.63 (t, J = 5.3 Hz, 2H), 2.46 (d, J = 14.3 Hz, 1H), 2.26 (d, J = 14.3 Hz, 1H), 2.09-1.99 (m, 1H), 1.97-1.89 (m, 1H), 1.32 (d, J = 6.5 Hz, 3H). LCMS m/z 335.19 [M + H]$^+$. |
| Compound 84 | S24; | Compound 20 | $^1$H NMR (400 MHz, DMSO-d$_6$) δ 11.42 (s, 1H), 9.29 (d J = 10.7 Hz, 1H), 8.93 (d, J = 11.3 Hz, 1H), 7.75 (dd, J = 8.8, 5.7 Hz, 1H), 6.96 (s, 1H), 6.65-6.57 (m, 2H), 4.74 (t, J = 11.3 Hz, 1H), 3.98 (t, J = 5.3 Hz, 2H), 3.84 (s, 3H), 2.67-2.58 (m, 2H), 2.39-2.26 (m, 2H), 1.94-1.80 (m, 1H), 1.30 (d, J = 6.5 Hz, 3H). Note: 1H appears to be hidden under DMSO and 1H hidden under water. LCMS m/z 404.14 [M + H]$^+$. |
| Compound 85 | S24; | Compound 20[1,6] | $^1$H NMR (400 MHz, DMSO-d$_6$) δ 7.56 (s, 1H), 6.94 (s, 1H), 6.88 (s, 1H), 4.13-4.05 (m, 1H), 3.89 (t, J = 5.4 Hz, 2H), 3.64-3.29 (m, under water, 1H), 3.22-3.11 (m, 1H), 2.57 (t, J = 5.2 Hz, 2H), 2.20 (d, J = 13.6 Hz, 1H), 2.02 (d, J = 13.6 Hz, 1H), 1.72 (t, J = 12.6 Hz, 1H), 1.37 (t, J = 12.5 Hz, 1H), 1.06 (d, J = 6.3 Hz, 3H). LCMS m/z: 324.17 [M + H]$^+$. |
| Compound 86 | S25; | Compound 20 | $^1$H NMR (400 MHz, DMSO-d$_6$) δ 13.37 (s, 1H), 9.36 (d, J = 8.7 Hz, 1H), 8.90-8.72 (m, 1H), 7.60 (d, J = 9.9 Hz, 1H), 7.03-6.96 (m, 1H), 6.95 (s, 1H), 4.58 (t, J = 11.1 Hz, 1H), 3.97 (tp, J = 11.8, 5.6 Hz, 2H), 3.55 (s, 1H), 2.61 (t, J = 5.4 Hz, 2H), 2.39-1.75 (m, 3H), 1.28 (d, J = 6.5 Hz, 3H). Note: 1H is hidden under DMSO peak. LCMS m/z 352.17 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 87 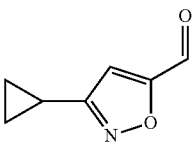 | S25; | Compound 21 | $^1$H NMR (400 MHz, DMSO-d$_6$) δ 9.51 (s, 1H), 9.11 (s, 1H), 6.95 (s, 1H), 6.52 (s, 1H), 4.78 (s, 1H), 3.94 (t, J = 5.4 Hz, 2H), 3.62 (s, 1H), 2.60 (t, 2H), 2.57-2.47 (m, hidden under DMSO, 1H), 2.24 (d, J = 14.1 Hz, 1H), 2.16 (t, J = 13.5 Hz, 1H), 2.05 (tt, 8.8, 4.1 Hz, 1H), 1.80 (t, J = 13.4 Hz, 1H), 1.26 (d, J = 6.5 Hz, 3H), 1.10-1.01 (m, 2H), 0.80-0.70 (m, 2H). LCMS m/z 365.13 [M + H]$^+$. |
| Compound 88 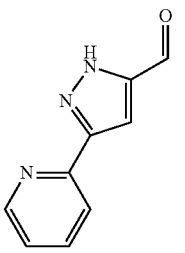 | S25; | Compound 21 | $^1$H NMR (400 MHz, DMSO-d$_6$) δ 13.86 (s, 1H), 9.38 (d, J = 10.4 Hz, 1H), 8.87 (d, J = 12.1 Hz, 1H), 8.64 (d, J = 4.9 Hz, 1H), 7.92 (t, J = 7.8 Hz, 1H), 7.83 (d, J = 7.9 Hz, 1H), 7.39 (t, J = 6.3 Hz, 1H), 7.07 (s, 1H), 6.95 (s, 1H), 4.60 (d, J = 10.2 Hz, 1H), 4.02-3.94 (m, 2H), 3.60 (s, 1H), 2.65-2.60 (m, 2H), 2.37-2.07 (m, 2H), 1.90-1.79 (m, 1H), 1.29 (d, J = 6.4 Hz, 3H), 1.25 (d, J = 6.2 Hz, 1H). LCMS m/z 380.16 [M + H]$^+$. |
| Compound 89 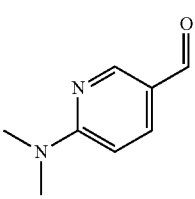 | S25; | Compound 21 | $^1$H NMR (400 MHz, DMSO-d$_6$) δ 8.97 (s, 1H), 8.55 (s, 1H), 8.20 (d, J = 2.4 Hz, 1H), 7.76 (d, J = 9.0 Hz, 1H), 6.94 (s, 1H), 6.79 (d, J = 8.9 Hz, 1H), 4.47 (t, J = 11.1 Hz, 1H), 3.95 (t, J = 5.4 Hz, 2H), 3.61 (s, 1H), 3.06 (s, 6H), 2.60 (t, J = 5.5 Hz, 2H), 2.35-2.17 (m, 3H), 1.90-1.81 (m, 1H), 1.26 (d, J = 6.6 Hz, 3H). LCMS m/z 378.17 [M + H]$^+$. |
| Compound 90 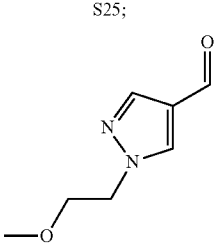 | S25; | Compound 21 | $^1$H NMR (400 MHz, DMSO-d$_6$) δ 8.96 (s, 1H), 8.54 (s, 1H), 7.89 (s, 1H), 7.62 (s, 1H), 6.94 (s, 1H), 4.50 (t, J = 11.0 Hz, 1H), 4.25 (t, J = 5.2 Hz, 2H), 3.93 (t, J = 5.4 Hz, 2H), 3.67 (t, J = 5.2 Hz, 2H), 3.55 (s, 1H), 3.22 (s, 3H), 2.59 (s, 2H), 2.36 (d, J = 14.3 Hz, 1H), 2.28-2.11 (m, 2H), 1.79 (t, J = 13.3 Hz, 1H), 1.25 (d, J = 6.6 Hz, 3H). LCMS m/z 382.15 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 91 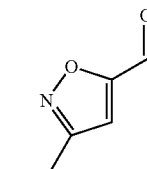 | S25; | Compound 21[12] | $^1$H NMR (400 MHz, DMSO-d$_6$) δ 9.55 (s, 1H), 9.14 (s, 1H), 6.95 (s, 1H), 6.70 (s, 1H), 4.83 (s, 1H), 3.95 (t, J = 5.5 Hz, 2H), 3.64 (s, 1H), 2.66 (q, J = 7.6 Hz, 3H), 2.61 (s, 2H), 2.31-2.13 (m, 2H), 1.82 (t, J = 13.2 Hz, 1H), 1.27 (d, J = 6.4 Hz, 3H), 1.19 (t, J = 7.5 Hz, 3H). LCMS m/z 353.16 [M + H]$^+$. |
| Compound 92 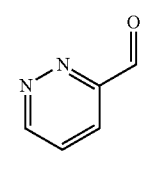 | S25; | Compound 19[13] | $^1$H NMR (400 MHz, DMSO-d$_6$) δ 9.56 (s, 1H), 9.33 (dd, J = 4.9, 1.6 Hz, 1H), 9.27 (d, J = 12.3 Hz, 1H), 7.94 (dd, J = 8.7, 1.6 Hz, 1H), 7.85 (dd, J = 8.5, 4.9 Hz, 1H), 6.96 (s, 1H), 4.94 (d, J = 11.6 Hz, 1H), 4.02 (tt, J = 11.9, 6.3 Hz, 2H), 3.63 (s, 1H), 2.64 (t, J = 5.4 Hz, 3H), 2.30 (d, J = 14.6 Hz, 1H), 2.07 (t, J = 13.4 Hz, 1H), 2.00-1.89 (m, 1H), 1.35 (d, J = 6.5 Hz, 3H). LCMS m/z 336.14 [M + H]$^+$. |
| Compound 93 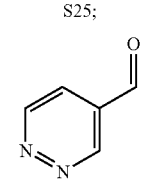 | S25; | Compound 19 | $^1$H NMR (400 MHz, DMSO-d$_6$) δ 9.43 (d, J = 2.3 Hz, 1H), 9.36 (d, J = 5.4 Hz, 1H), 9.13 (s, 1H), 8.79 (s, 1H), 7.88 (dd, J = 5.4, 2.4 Hz, 1H), 6.95 (s, 1H), 4.75-4.65 (m, 1H), 3.98 (t, J = 5.9 Hz, 2H), 3.68-3.65 (m, 1H), 2.63 (t, J = 4.7 Hz, 2H), 2.45 (d, J = 15.0 Hz, under DMSO, 1H), 2.29 (d, J = 15.0 Hz, 1H), 2.22 (t, J = 13.7 Hz, 1H), 1.87 (t, J = 13.4 Hz, 1H), 1.30 (d, J = 6.5 Hz, 3H). LCMS m/z 336.18 [M + H]$^+$. |
| Compound 94 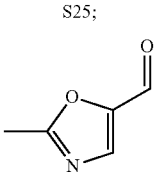 | S25; | Compound 21 | $^1$H NMR (400 MHz, DMSO-d$_6$) δ 9.29 (d, J = 35.4 Hz, 1H), 8.95 (s, 1H), 7.20 (s, 1H), 6.94 (s, 1H), 4.72 (t, J = 11.1 Hz, 1H), 3.93 (t, J = 5.5 Hz, 2H), 3.60 (s, 1H), 2.60 (q, J = 4.7 Hz, 2H), 2.46-2.38 (m, 4H), 2.28-2.16 (m, 2H), 1.82 (dd, J = 14.4, 12.3 Hz, 1H), 1.25 (d, J = 6.6 Hz, 3H). LCMS m/z 339.16 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 95 | S24; S22 | Compound 19[3,4,14] | ¹H NMR (300 MHz, Methanol-d$_4$) δ 8.40 (s, 2H), 8.23 (s, 3H), 6.75 (s, 1H), 4.57 (dd, J = 12.5, 3.1 Hz, 1H), 3.99 (t, J = 5.5 Hz, 2H), 3.80 (ddd, J = 12.2, 6.6, 2.8 Hz, 1H), 3.66 (s, 2H), 2.69-2.63 (m, 2H), 2.45-2.20 (m, 3H), 1.81 (dd, J = 14.7, 12.2 Hz, 1H), 1.36 (d, J = 6.6 Hz, 9H). LCMS m/z 423.19 [M + H]⁺. |
| Compound 96 | S25; | Compound 21 | ¹H NMR (400 MHz, DMSO-d$_6$) δ 9.64 (s, 1H), 9.17 (s, 1H), 9.06 (d, J = 1.7 Hz, 1H), 6.95 (s, 1H), 6.86 (d, J = 1.7 Hz, 1H), 4.81 (s, 1H), 3.98 (q, J = 5.4 Hz, 2H), 3.62 (s, 1H), 2.62 (t, J = 5.7 Hz, 2H), 2.61-2.53 (m, 1H), 2.28 (d, J = 14.4 Hz, 1H), 2.10 (t, J = 13.5 Hz, 1H), 1.90-1.79 (m, 1H), 1.30 (d, J = 6.5 Hz, 3H). LCMS m/z 325.12 [M + H]⁺. |
| Compound 97 | S25; | Compound 20 | ¹H NMR (300 MHz, Methanol-d$_4$) δ 7.97 (s, 1H), 7.73 (s, 1H), 6.76 (s, 1H), 5.27 (p, J = 7.2 Hz, 1H), 4.71 (dd, J = 12.5, 2.9 Hz, 1H), 3.99 (t, J = 5.5 Hz, 2H), 3.78 (s, 1H), 3.65 (dd, J = 13.8, 8.1 Hz, 1H), 3.56-3.39 (m, 2H), 3.23 (dd, J = 13.4, 7.7 Hz, 1H), 2.69 (dt, J = 15.4, 6.1 Hz, 4H), 2.58-2.44 (m, 1H), 2.38 (dt, J = 14.7 Hz, 1H), 2.19 (dd, J = 14.7, 12.7 Hz, 1H), 1.79 (dd, J = 14.7, 12.2 Hz, 1H), 1.37 (d, J = 6.6 Hz, 3H). LCMS m/z 442.11 [M + H]⁺. |
| Compound 98 | S25; | Compound 21 | ¹H NMR (300 MHz, Methanol-d$_4$) δ 7.97 (s, 1H), 7.73 (s, 1H), 6.76 (s, 1H), 5.27 (p, J = 7.2 Hz, 1H), 4.71 (dd, J = 12.5, 2.9 Hz, 1H), 3.99 (t, J = 5.5 Hz, 2H), 3.78 (s, 1H), 3.65 (dd, J = 13.8, 8.1 Hz, 1H), 3.56-3.39 (m, 2H), 3.23 (dd, J = 13, 4, 7.7 Hz, 1H), 2.69 (dt, J = 15.4, 6.1 Hz, 4H), 2.58-2.44 (m, 1H), 2.38 (dt, J = 14.7 Hz, 1H), 2.19 (dd, J = 14.7, 12.7 Hz, 1H), 1.79 (dd, J = 14.7, 12.2 Hz, 1H), 1.37 (d, J = 6.6 Hz, 3H). LCMS m/z 352.17 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 99 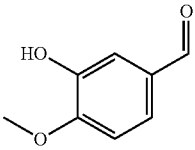 | S25; | Compound 21 | ¹H NMR (400 MHz, DMSO-$d_6$) δ 9.22 (s, 1H), 8.97 (d, J = 10.5 Hz, 1H), 8.41 (s, 1H), 7.01-6.90 (m, 4H), 4.38 (t, J = 10.7 Hz, 1H), 3.95 (t, J = 5.5 Hz, 2H), 3.78 (s, 3H), 3.60 (s, 1H), 2.60 (t, J = 5.4 Hz, 2H), 2.22 (t, J = 16.8 Hz, 3H), 1.86 (t, J = 13.4 Hz, 1H), 1.26 (d, J = 6.5 Hz, 3H). LCMS m/z 380.16 [M + H]⁺. |
| Compound 100 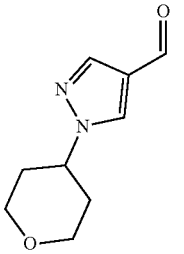 | S25; | Compound 21 | ¹H NMR (300 MHz, Methanol-$d_4$) δ 6.54 (s, 1H), 6.30 (s, 1H), 5.38 (s, 1H), 3.34 (dd, J = 12.7, 3.0 Hz, 1H), 3.13-2.99 (m, 1H), 2.73-2.62 (m, 2H), 2.62 (t, J = 5.5 Hz, 2H), 2.39 (d, J = 8.1 Hz, 1H), 2.19 (td, J = 11.6, 11.2, 4.4 Hz, 2H), 1.31-1.26 (m, 2H), 1.14 (dt, J = 14.7, 2.7 Hz, 1H), 0.99 (dt, J = 14.5, 2.7 Hz, 1H), 0.83 (dd, J = 14.7, 12.7 Hz, 1H), 0.67 (td, J = 9.7, 8.6, 3.9 Hz, 4H), 0.42 (dd, J = 14.7, 12.2 Hz, 1H), −0.01 (d, J = 6.6 Hz, 3H). LCMS m/z 408.11 [M + H]⁺. |
| Compound 101 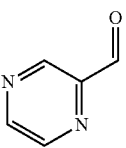 | S24; | Compound 20 | ¹H NMR (400 MHz, DMSO-$d_6$) δ 9.42 (s, 1H), 9.01 (d, J = 10.9 Hz, 1H), 8.89 (d, J = 1.5 Hz, 1H), 8.79-8.72 (m, 2H), 6.95 (s, 1H), 4.86 (t, J = 11.3 Hz, 1H), 4.00 (tt, J = 11.4, 5.7 Hz, 2H), 3.64 (s, 1H), 2.63 (t, J = 5.4 Hz, 2H), 2.58-2.51 (m, 1H), 2.27 (d, J = 14.6 Hz, 1H), 2.15-2.05 (m, 1H), 1.98-1.88 (m, 1H), 1.31 (d, J = 6.5 Hz, 3H). LCMS m/z 336.14 [M + H]⁺. |
| Compound 102 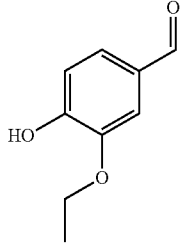 | S25; | Compound 21 | ¹H NMR (400 MHz, DMSO-$d_6$) δ 9.23 (s, 1H), 8.98 (d, J = 10.1 Hz, 1H), 8.46 (s, 1H), 7.15 (d, J = 2.1 Hz, 1H), 6.93 (q, J = 2.6, 2.2 Hz, 2H), 6.82 (d, J = 8.2 Hz, 1H), 4.49-4.33 (m, 1H), 4.04 (q, J = 7.0 Hz, 2H), 3.94 (t, J = 5.5 Hz, 2H), 3.59 (s, 1H), 2.60 (t, J = 5.4 Hz, 2H), 2.25 (t, 3H), 1.87 (t, J = 13.3 Hz, 1H), 1.34 (t, J = 7.0 Hz, 3H), 1.27 (d, J = 6.5 Hz, 3H). LCMS m/z 394.16 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 103 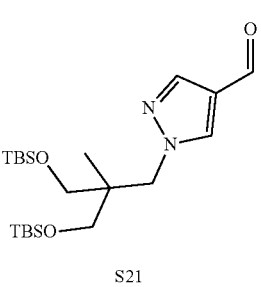 | S24; 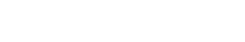 S21 | Compound 19[1,3,4,5] | ¹H NMR (300 MHz, Chloroform-d) δ 7.48 (s, 1H), 7.41 (s, 1H), 6.58 (s, 1H), 4.23-4.14 (m, 3H), 3.94 (t, J = 5.4 Hz, 2H), 3.49 (d, J = 11.3 Hz, 2H), 3.32 (d, J = 11.5 Hz, 2H), 3.31-3.18 (m, 1H), 2.61 (t, J = 5.4 Hz, 2H), 2.22 (dt, J = 13.7, 2.5 Hz, 1H), 2.07 (dd, J = 13.7, 2.6 Hz, 1H), 1.75-1.64 (m, 1H), 1.41 (dd, J = 13.8, 11.3 Hz, 1H), 1.13 (d, J = 6.4 Hz, 3H), 0.79 (s, 3H). LCMS m/z 426.13 [M + H]⁺. |
| Compound 104 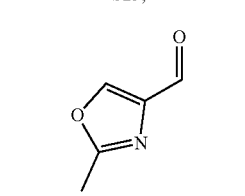 | S25; 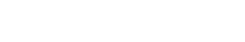 | Compound 20 | ¹H NMR (400 MHz, DMSO-d₆) δ 9.27-9.15 (m, 1H), 8.81 (d, J = 11.9 Hz, 1H), 8.14 (s, 1H), 6.94 (s, 1H), 4.51 (t, J = 11.1 Hz, 1H), 3.93 (t, J = 5.4 Hz, 2H), 3.60-3.51 (m, 1H), 2.60 (t, J = 5.4 Hz, 2H), 2.46 (s, 3H), 2.38-2.08 (m, 3H), 1.81 (dd, J = 14.5, 12.2 Hz, 1H), 1.25 (d, J = 6.5 Hz, 3H). LCMS m/z 339.16 [M + H]⁺. |
| Compound 105 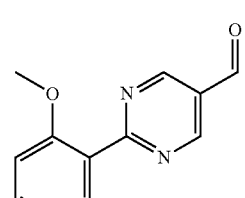 | S25;  | Compound 21 | ¹H NMR (300 MHz, Methanol-d₄) δ 9.03 (s, 2H), 7.67 (dd, J = 7.6, 1.8 Hz, 1H), 7.55-7.47 (m, 1H), 7.17 (d, J = 8.4 Hz, 1H), 7.08 (dd, J = 8.0, 7.0 Hz, 1H), 6.78 (s, 1H), 4.92 (dd, J = 12.8, 2.9 Hz, 1H), 4.05 (t, J = 5.5 Hz, 2H), 4.00-3.86 (m, 1H), 3.83 (s, 3H), 2.69 (t, J = 5.5 Hz, 2H), 2.61 (d, J = 14.5 Hz, 1H), 2.51-2.30 (m, 2H), 1.90 (dd, J = 14.8, 12.2 Hz, 1H), 1.43 (d,? 6.6 Hz, 3H). LCMS m/z 442.11 [M + H]⁺. |
| Compound 106 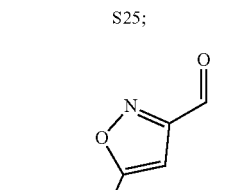 | S25;  | Compound 21 | ¹H NMR (400 MHz, DMSO-d₆) δ 9.60 (s, 1H), 9.14 (s, 1H), 6.95 (d, J = 1.2 Hz, 1H), 6.78 (s, 1H), 4.77 (t, ?= 11.2 Hz, 1H), 4.59 (s, 2H), 3.97 (hept, J = 6.1, 5.7 Hz, 2H), 3.62 (s, 1H), 3.32 (s, 3H), 2.62 (t, J = 5.6 Hz, 2H), 2.60-2.53 (m, 1H), 2.27 (d, J = 14.0 Hz, 1H), 2.09 (t, J = 13.5 Hz, 1H), 1.90-1.78 (m, 1H), 1.29 (d, J = 6.4 Hz, 3H). LCMS m/z 369.10 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 107 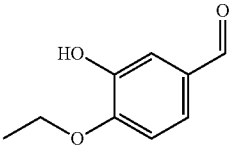 | S25; 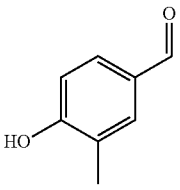 | Compound 21[1,6] | ¹H NMR (400 MHz, DMSO-d₆) δ 8.79 (s, 1H), 6.85 (s, 2H), 6.84-6.69 (m, 2H), 3.97 (q, J = 6.9 Hz, 2H), 3.90 (t, J = 5.4 Hz, 3H), 3.11 (s, 1H), 2.59-2.55 (m, 2H), 1.99 (d, J = 13.3 Hz, 2H), 1.56-1.19 (m, 2H), 1.30 (t, J = 6.9 Hz, 3H), 1.03 (d, J = 6.2 Hz, 3H). LCMS m/z 394.16 [M + H]⁺. |
| Compound 108 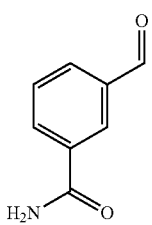 | S25; | Compound 20 | ¹H NMR (400 MHz, DMSO-d₆) δ 9.65 (s, 1H), 8.92 (d, J = 10.7 Hz, 1H), 8.40 (s, 1H), 7.27 (d, J = 2.3 Hz, 1H), 7.17 (d, J = 9.1 Hz, 1H), 6.93 (s, 1H), 6.81 (d, J = 8.2 Hz, 1H), 4.42-4.30 (m, 1H), 3.94 (t, J = 5.5 Hz, 2H), 3.65-3.55 (m, 1H), 2.59 (t, J = 5.9 Hz, 2H), 2.30-2.18 (m, 3H), 2.14 (s, 3H), 1.86 (t, J = 13.3 Hz, 1H), 1.25 (d, J = 6.5 Hz, 3H). LCMS m/z 364.18 [M + H]⁺. |
| Compound 109 | S25; | Compound 21 | ¹H NMR (400 MHz, DMSO-d₆) δ 9.12 (s, 1H), 8.62 (d, J = 12.3 Hz, 1H), 8.09 (d, J = 7.6 Hz, 2H), 7.93 (d, J = 7.6 Hz, 1H), 7.71 (d, J = 7.7 Hz, 1H), 7.54 (dd, J = 13.4, 5.7 Hz, 2H), 6.94 (s, 1H), 4.60 (t, J = 11.0 Hz, 1H), 3.97 (t, J = 5.4 Hz, 2H), 3.70-3.62 (m, 1H), 2.63-2.59 (m, 2H), 2.30 (dt, J = 26.0, 12.8 Hz, 3H), 1.91 (t, J = 13.3 Hz, 1H), 1.28 (d, J = 6.5 Hz, 3H). LCMS m/z 377.09 [M + H]⁺. |
| Compound 110 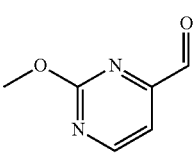 | S24; | Compound 20 | ¹H NMR (400 MHz, DMSO-d₆) δ 9.52 (d, J = 10.5 Hz, 1H), 8.96 (d, J = 11.3 Hz, 1H), 8.70 (d, J = 5.0 Hz, 1H), 7.36 (d, J = 5.2 Hz, 1H), 6.95 (s, 1H), 4.69 (t, J = 11.3 Hz, 1H), 4.11-3.92 (m, 5H), 3.63-3.54 (m, 1H), 2.63 (t, J = 5.4 Hz, 2H), 2.58-2.19 (m, 2H), 1.94 (dt, J = 27.4, 13.5 Hz, 2H), 1.33 (d, J = 6.5 Hz, 3H). LCMS m/z 366.16 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 111 | S25; | Compound 21 | $^1$H NMR (400 MHz, DMSO-d$_6$) δ 9.38 (s, 1H), 8.92 (d, J = 11.4 Hz, 1H), 8.21 (d, J = 1.8 Hz, 1H), 6.95 (s, 1H), 5.07 (s, 1H), 4.72 (t, J = 11.1 Hz, 1H), 4.42 (dd, J = 13.9, 3.9 Hz, 1H), 4.29 (dd, J = 13.8, 7.1 Hz, 1H), 3.96 (t, J = 5.2 Hz, 2H), 3.74 (s, 1H), 3.61 (s, 1H), 2.61 (s, 2H), 2.45 (s, 1H), 2.25 (t, J = 13.4 Hz, 2H), 1.92-1.76 (m, 1H), 1.44-1.30 (m, 2H), 1.27 (d, J = 6.5 Hz, 3H), 0.91 (t, J = 7.4 Hz, 3H). LCMS m/z 397.14 [M + H]$^+$. |
| Compound 112 | S25; | Compound 21 | $^1$H NMR (400 MHz, DMSO-d$_6$) δ 11.77 (s, 1H), 9.23 (s, 1H), 8.68 (s, 1H), 7.46 (d, J = 6.9 Hz, 1H), 6.93 (s, 1H), 6.50 (d, J = 1.8 Hz, 1H), 6.32 (d, J = 6.7 Hz, 1H), 4.36 (t, J = 11.5 Hz, 1H), 3.98-3.93 (m, 2H), 3.59 (s, 1H), 2.62-2.58 (m, 2H), 2.37-2.19 (m, 2H), 2.05 (t, J = 13.4 Hz, 1H), 1.86 (dd, J = 14.3, 12.3 Hz, 1H), 1.28 (d, J = 6.6 Hz, 3H). LCMS m/z 351.13 [M + H]$^+$. |
| Compound 113 | S25; | Compound 21 | $^1$H NMR (300 MHz, DMSO-d$_6$) δ 10.07 (s, 1H), 9.04 (s, 1H), 8.51 (s, 1H), 7.89 (s, 1H), 7.48 (d, J = 8.1 Hz, 1H), 7.39 (t, J = 7.8 Hz, 1H), 7.25 (d, J = 7.6 Hz, 1H), 6.94 (s, 1H), 4.47 (t, J = 11.0 Hz, 1H), 3.96 (t, J = 5.4 Hz, 2H), 3.88-3.50 (m, under water, 1H), 2.61 (t, J = 5.4 Hz, 2H), 2.22 (dd, J = 24.7, 11.8 Hz, 3H), 2.06 (s, 3H), 1.96-1.82 (m, 1H), 1.27 (d, J = 6.5 Hz, 3H). LCMS m/z 391.13 [M + H]$^+$. |
| Compound 114 | S25; | Compound 21 | $^1$H NMR (400 MHz, DMSO-d$_6$) δ 12.92 (s, 1H), 9.24 (s, 1H), 8.74 (s, 1H), 6.94 (s, 1H), 6.25 (s, 1H), 4.49 (t, J = 11.4 Hz, 1H), 3.95 (t, 2H), 3.90 (d, J = 9.1 Hz, 2H), 3.54 (s, 1H), 3.46-3.41 (m, 2H), 2.90 (d, J = 12.3 Hz, 1H), 2.61 (d, J = 5.6 Hz, 2H), 2.44 (d, J = 14.6 Hz, 1H), 2.23 (d, J = 14.5 Hz, 1H), 2.17-2.07 (m, 1H), 1.80 (d, J = 13.2 Hz, 3H), 1.60 (tt, J = 12.3, 6.2 Hz, 2H), 1.26 (d, J = 6.4 Hz, 3H). LCMS m/z 408.11 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 115 | S25; | Compound 21 | ¹H NMR (400 MHz, DMSO-$d_6$) δ 9.93 (s, 1H), 9.09 (d, J = 10.2 Hz, 1H), 8.59 (s, 1H), 7.44 (t, J = 7.8 Hz, 1H), 7.37-7.30 (m, 2H), 7.23 (d, J = 8.1 Hz, 1H), 6.94 (s, 1H), 4.51 (t, J = 11.1 Hz, 1H), 3.96 (t, J = 5.4 Hz, 2H), 3.66 (s, 1H), 3.03 (s, 3H), 2.61 (t, J = 5.5 Hz, 2H), 2.26 (dt, J = 28.3, 13.6 Hz, 3H), 1.90 (t, J = 13.3 Hz, 1H), 1.28 (d, J = 6.5 Hz, 3H). LCMS m/z 427.08 [M + H]⁺. |
| Compound 116 | S24; | Compound 20 | ¹H NMR (400 MHz, DMSO-$d_6$) δ 9.46 (s, 1H), 8.99 (d, J = 11.1 Hz, 1H), 8.79 (d, J = 5.2 Hz, 1H), 7.54 (d, J = 5.2 Hz, 1H), 6.95 (s, 1H), 4.69 (t, J = 11.2 Hz, 1H), 4.00 (dp, J = 17.5, 6.0 Hz, 2H), 3.58 (s, 1H), 2.71 (s, 3H), 2.63 (t, J = 5.3 Hz, 2H), 2.25 (d, J = 14.5 Hz, 1H), 2.42-2.11 (m, 1H), 1.95 (dt, J = 22.3, 13.5 Hz, 2H), 1.33 (d, J = 6.5 Hz, 3H). LCMS m/z 350.18 [M + H]⁺. |
| Compound 117 | S25; | Compound 19 | ¹H NMR (300 MHz, Methanol-$d_4$) δ 8.60 (d, J = 7.0 Hz, 1H), 8.19 (s, 1H), 7.88 (d, J = 9.0 Hz, 1H), 7.40 (t, J = 7.9 Hz, 1H), 7.02 (t, J = 6.8 Hz, 1H), 6.77 (s, 1H), 5.09-5.02 (m, 1H), 4.04 (t, J = 5.5 Hz, 2H), 3.93 (s, 1H), 2.68 (t, J = 5.5 Hz, 2H), 2.58-2.38 (m, 3H), 1.88 (dd, J = 14.7, 12.2 Hz, 1H), 1.39 (d, J = 6.5 Hz, 3H). LCMS m/z 374.16 [M + H]⁺. |
| Compound 118 | S25; | Compound 20 | ¹H NMR (400 MHz, DMSO-$d_6$) δ 9.27 (d, J = 12.1 Hz, 1H), 8.77 (d, J = 11.0 Hz, 1H), 7.77 (d, J = 2.3 Hz, 1H), 6.94 (s, 1H), 6.42 (dd, J = 10.9, 2.3 Hz, 1H), 4.52 (t, J = 11.1 Hz, 1H), 3.95 (t, J = 5.4 Hz, 2H), 3.86 (s, 3H), 3.56 (s, 1H), 2.60 (t, J = 5.3 Hz, 2H), 2.34 (dd, J = 75.5, 14.6 Hz, 2H), 2.17-2.06 (m, 1H), 1.81 (dd, J = 14.5, 12.2 Hz, 1H), 1.26 (d, J = 6.5 Hz, 3H). LCMS m/z 338.17 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
| --- | --- | --- | --- |
| Compound 119 | S25; | Compound 21 | $^1$H NMR (400 MHz, DMSO-d$_6$) δ 13.96 (s, 1H), 9.29 (s, 1H), 9.05 (s, 1H), 6.96 (s, 1H), 6.95 (s, 1H), 4.73 (s, 1H), 3.96 (t, J = 5.3 Hz, 2H), 3.60 (s, 1H), 2.60 (d, J = 5.9 Hz, 2H), 2.26 (d, J = 14.4 Hz, 2H), 1.83 (t, J = 13.2 Hz, 1H), 1.27 (d, J = 6.5 Hz, 3H). Note: 1H obscured under DMSO peak. LCMS m/z 392.08 [M + H]$^+$. |
| Compound 120 | S25; | Compound 21 | $^1$H NMR (400 MHz, DMSO-d$_6$) δ 12.87 (s, 1H), 9.23 (d, J = 10.3 Hz, 1H), 8.72 (s, 1H), 6.94 (s, 1H), 6.09 (s, 1H), 4.44 (t, J = 11.1 Hz, 1H), 4.08-3.82 (m, 2H), 3.52 (s, 1H), 2.63-2.57 (m, 2H), 2.44-2.36 (m, 1H), 2.23 (d, J = 14.4 Hz, 1H), 2.08 (t, J = 13.6 Hz, 1H), 1.92 (dt, J = 10.1, 5.2 Hz, 1H), 1.86-1.74 (m, 1H), 1.26 (d, J = 6.5 Hz, 3H), 1.02-0.88 (m, 2H), 0.77-0.58 (m, 2H). LCMS m/z 364.13 [M + H]$^+$. |
| Compound 121 | S25; | Compound 20 | $^1$H NMR (400 MHz, DMSO-d$_6$) δ 12.10 (s, 1H), 8.99 (d, J = 10.4 Hz, 1H), 8.49 (d, J = 11.0 Hz, 1H), 7.67 (dd, J = 7.0, 2.0 Hz, 1H), 7.49 (s, 1H), 6.93 (s, 1H), 6.32 (t, J = 6.7 Hz, 1H), 4.61 (t, J = 11.2 Hz, 1H), 3.95 (t, J = 5.6 Hz, 2H), 3.58 (s, 1H), 2.60 (t, J = 5.5 Hz, 2H), 2.24 (ddt, J = 43.3, 26.7, 14.5 Hz, 3H), 1.94-1.82 (m, 1H), 1.28 (d, J = 6.5 Hz, 3H). LCMS m/z 351.17 [M + H]$^+$. |
| Compound 122 | S25; | Compound 21 | LCMS m/z 379.12 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 123 | S25; | Compound 20 | $^1$H NMR (300 MHz, DMSO-d$_6$) δ 9.10 (s, 1H), 8.96 (d, J = 2.1 Hz, 1H), 8.77 (s, 1H), 8.32 (dd, J = 8.1, 2.2 Hz, 1H), 8.06 (d, J = 8.2 Hz, 1H), 6.95 (s, 1H), 4.80 (t, J = 10.9 Hz, 1H), 3.98 (t, J = 5.4 Hz, 2H), 3.69 (s, 1H), 2.62 (q, J = 4.8 Hz, 2H), 2.34 (dd, J = 27.2, 14.5 Hz, 3H), 1.91 (t, J = 13.3 Hz, 1H), 1.29 (d, J = 6.4 Hz, 3H). LCMS m/z 403.1 [M + H]$^+$. |
| Compound 124 | S25; | Compound 20 | $^1$H NMR (400 MHz, DMSO-d$_6$) δ 8.91 (d, J = 10.9 Hz, 1H), 8.48 (d, J = 11.6 Hz, 1H), 8.03 (s, 1H), 6.94 (s, 1H), 4.43 (t, J = 11.1 Hz, 1H), 3.91 (hept, J = 5.8, 5.4 Hz, 2H), 3.53 (s, 1H), 3.36 (s, 3H), 3.22 (s, 3H), 2.60 (t, J = 5.5 Hz, 2H), 2.40-2.12 (m, 3H), 1.87-1.75 (m, 1H), 1.26 (d, J = 6.5 Hz, 3H). LCMS m/z 396.15 [M + H]$^+$. |
| Compound 125 | S25; | Compound 21 | $^1$H NMR (400 MHz, DMSO-d$_6$) δ 11.77 (s, 1H), 9.01 (s, 1H), 8.48 (s, 1H), 7.60 (s, 1H), 6.93 (s, 1H), 6.23 (s, 1H), 4.38 (t, J = 11.4 Hz, 1H), 3.96 (t, J = 5.2 Hz, 2H), 3.64 (s, 1H), 2.63-2.57 (m, 2H), 2.27 (dd, J = 31.8, 14.9 Hz, 2H), 2.19 (s, 3H), 2.07 (t, J = 13.5 Hz, 1H), 1.84 (t, J = 13.3 Hz, 1H), 1.26 (d, J = 6.4 Hz, 3H). LCMS m/z 365.13 [M + H]$^+$. |
| Compound 126 | S24; | Compound 20 | $^1$H NMR (400 MHz, DMSO-d$_6$) δ 9.36-9.17 (m, 1H), 8.80 (s, 1H), 7.79 (t, J = 7.7 Hz, 1H), 7.35 (dd, J = 19.9, 7.7 Hz, 2H), 6.94 (s, 1H), 4.62 (d, J = 12.1 Hz, 1H), 4.07-3.92 (m, 2H), 3.57 (s, 1H), 2.62 (t, J = 5.3 Hz, 2H), 2.56 (s, 3H), 2.35 (dd, J = 79.8, 14.4 Hz, 2H), 1.98 (dt, J = 35.2, 13.8 Hz, 2H), 1.32 (d, J = 6.5 Hz, 3H). LCMS m/z 349.19 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 127 | S25; | Compound 21 | $^1$H NMR (400 MHz, DMSO-d$_6$) δ 9.45 (s, 1H), 8.69 (s, 1H), 8.38 (d, J = 5.1 Hz, 1H), 6.95 (s, 1H), 6.73 (d, J = 5.0 Hz, 1H), 4.50 (t, J = 11.4 Hz, 1H), 4.01 (dp, J = 18.3, 6.2, 5.4 Hz, 2H), 3.63-3.53 (m, 1H), 3.18 (s, 6H), 2.63 (t, J = 5.4 Hz, 2H), 2.55-2.48 (m, hidden under DMSO, 1H), 2.26 (d, J = 14.5 Hz, 1H), 1.95 (dt, J = 25.4, 13.5 Hz, 2H), 1.34 (d, J = 6.4 Hz, 3H). LCMS m/z 379.12 [M + H]$^+$. |
| Compound 128 | S25; | Compound 21[1] | $^1$H NMR (300 MHz, Methanol-d$_4$) δ 7.62 (s, 1H), 6.76 (s, 1H), 4.91 (dd, J = 12.8, 3.3 Hz, 1H), 4.01 (t, J = 5.5 Hz, 2H), 3.83 (dddt, J = 13.2, 9.6, 6.7, 3.0 Hz, 1H), 3.00 (q, J = 7.7 Hz, 2H), 2.67 (t, J = 5.6 Hz, 2H), 2.56 (dt, J = 14.4, 2.8 Hz, 1H), 2.46-2.33 (m, 2H), 1.90 (dd, J = 14.8, 12.3 Hz, 1H), 1.45-1.35 (m, 6H). LCMS m/z 352.17 [M + H]$^+$. |
| Compound 129 | S25; | Compound 21[15] | $^1$H NMR (400 MHz, DMSO-d$_6$) δ 10.20 (s, 1H), 9.15 (s, 1H), 8.86 (s, 1H), 8.61 (s, 2H), 6 94 (s, 1H), 4.72 (s, 2H), 4.53 (t, J = 11.5 Hz, 1H), 3.95 (t, J = 5.1 Hz, 2H), 3.61 (s, 1H), 3.56-3.18 (m, 4H), 3.12-3.02 (m, 2H), 2.84 (s, 3H), 2.61 (t, J = 5.0 Hz, 2H), 2.42 (t, J = 13.7 Hz, 1H), 2.32-2.22 (m, 2H), 1.87 (t, J = 13.4 Hz, 1H), 1.27 (d, J = 6.5 Hz, 3H). LCMS m/z 434.16 [M + H]$^+$. |
| Compound 130 | S25; | Compound 21[1] | $^1$H NMR (400 MHz, DMSO-d$_6$) δ 7.36 (s, 1H), 6.94 (s, 1H), 4.50 (d, J = 11.1 Hz, 1H), 3.93 (t, J = 5.5 Hz, 2H), 3.54 (s, 1H), 2.60 (s, 2H), 2.39 (d, J = 14.9 Hz, 1H), 2.23 (d, J = 13.9 Hz, 2H), 2.10 (s, 1H), 1.87-1.75 (m, 1H), 1.26 (d, J = 6.4 Hz, 3H), 1.07 (s, 2H), 0.96 (s, 2H). Exchangeables not observed. LCMS m/z 364.13 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 131 | S25; | Compound 21 | ¹H NMR (400 MHz, DMSO-d₆) δ 9.27 (d, J = 10.4 Hz, 1H), 8.76 (d, J = 10.9 Hz, 1H), 6.94 (s, 1H), 5.70 (s, 1H), 4.39 (t, J = 11.4 Hz, 1H), 4.29 (t, J = 5.3 Hz, 2H), 4.09 (t, J = 6.2 Hz, 2H), 3.94 (t, J = 5.6 Hz, 2H), 3.57-3.47 (m, 1H), 2.60 (t, J = 5.5 Hz, 2H), 2.39 (d, J = 15.1 Hz, 1H), 2.23 (d, J = 16.9 Hz, 1H), 2.17 (q, J = 5.7 Hz, 2H), 2.11-2.01 (m, 1H), 1.80 (t, J = 13.4 Hz, 1H), 1.26 (d, J = 6.5 Hz, 3H). LCMS m/z 380.12 [M + H]⁺. |
| Compound 132 | S25; | Compound 21 | ¹H NMR (400 MHz, DMSO-d₆) δ 9.08 (d, J = 9.6 Hz, 1H), 9.01 (s, 1H), 8.77 (s, 1H), 6.94 (s, 1H), 4.36 (t, J = 11.4 Hz, 1H), 3.95 (t, J = 5.3 Hz, 2H), 3.66 (s, 1H), 2.66-2.58 (m, 2H), 2.40 (d, J = 14.4 Hz, 1H), 2.32 (s, 3H), 2.22 (q, J = 14.1, 13.2 Hz, 2H), 1.82 (t, J = 13.4 Hz, 1H), 1.27 (d, J = 6.5 Hz, 3H). LCMS m/z 339.16 [M + H]⁺. |
| Compound 133 | S25; | Compound 21 | ¹H NMR (400 MHz, DMSO-d₆) δ 9.39 (s, 1H), 8.93 (d, J = 10.9 Hz, 1H), 8.24 (s, 1H), 7.80 (s, 1H), 7.45 (s, 1H), 6.95 (s, 1H), 5.14 (s, 2H), 4.74 (t, J = 11.0 Hz, 1H), 3.96 (t, J = 5.4 Hz, 2H), 3.61 (s, 1H), 2.62 (d, J = 5.5 Hz, 2H), 2.47-2.17 (m, 3H), 1.89-1.78 (m, 1H), 1.27 (d, J = 6.5 Hz, 3H). LCMS m/z 382.15 [M + H]⁺. |
| Compound 134 | S24; | Compound 20 | ¹H NMR (400 MHz, DMSO-d₆) δ 9.70 (s, 1H), 9.31-9.09 (m, 1H), 7.00 (d, J = 1.5 Hz, 1H), 6.95 (s, 1H), 4.75 (d, J = 11.5 Hz, 1H), 3.95 (t, J = 5.4 Hz, 2H), 3.61 (s, 1H), 2.61 (t, J = 5.4 Hz, 2H), 2.33 (d, J = 1.3 Hz, 3H), 2.60-2.08 (m, 3H), 1.82 (dd, J = 14.4, 12.2 Hz, 1H), 1.28 (d, J = 6.4 Hz, 3H). LCMS m/z 339.16 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 135 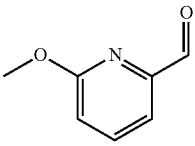 | S25; | Compound 20[7] | ¹H NMR (400 MHz, DMSO-d₆) δ 9.40 (s, 1H), 8.68 (s, 1H), 7.81 (t, J = 7.8 Hz, 1H), 7.17 (d, J = 8.0 Hz, 1H), 6.95 (s, 1H), 6.87 (d, J = 8.1 Hz, 1H), 4.61 (t, J = 11.3 Hz, 1H), 3.95 (s, 5H), 3.66-3.55 (m, 1H), 2.63 (t, J = 5.5 Hz, 2H), 2.49-2.44 (m, partly obstructed by DMSO, 1H), 2.28 (d, J = 14.4 Hz, 1H), 2.11 (t, J = 13.4 Hz, 1H), 1.95 (t, J = 13.3 Hz, 1H), 1.34 (d, J = 6.4 Hz, 3H). LCMS m/z 365.17 [M + H]⁺. |
| Compound 136 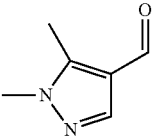 | S25; | Compound 19 | ¹H NMR (400 MHz, DMSO-d₆) δ 8.81 (s, 1H), 8.39 (d, J = 11.5 Hz, 1H), 7.54 (s, 1H), 6.93 (s, 1H), 4.34 (t, J = 11.2 Hz, 1H), 3.94 (t, J = 5.4 Hz, 2H), 3.73 (s, 3H), 3.64 (s, 1H), 2.59 (t, J = 5.4 Hz, 2H), 2.26 (s, 3H), 2.21 (dd, J = 23.1, 12.6 Hz, 3H), 1.88-1.77 (m, 1H), 1.24 (d, J = 6.6 Hz, 3H). LCMS/w/z 352.21 [M + H]⁺. |
| Compound 137 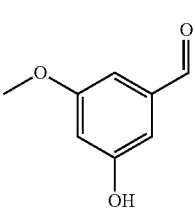 | S25; | Compound 21 | ¹H NMR (400 MHz, DMSO-d₆) δ 9.77 (s, 1H), 9.08 (d, J = 10.4 Hz, 1H), 8.47 (s, 1H), 6.94 (s, 1H), 6.61 (s, 1H), 6.52 (s, 1H), 6.38 (s, 1H), 4.38 (t, J = 11.4 Hz, 1H), 3.95 (t, J = 5.4 Hz, 2H), 3.73 (s, 3H), 3.60 (s, 1H), 2.60 (t, J = 5.4 Hz, 2H), 2.26 (d, J = 13.9 Hz, 2H), 2.16 (t, J = 13.4 Hz, 1H), 1.87 (t, J = 13.3 Hz, 1H), 1.27 (d, J = 6.4 Hz, 3H). LCMS m/z 380.16 [M + H]⁺. |
| Compound 138 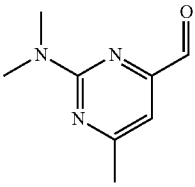 | S25; | Compound 21 | ¹H NMR (400 MHz, DMSO-d₆) δ 9.38 (d, J = 10.2 Hz, 1H), 8.63 (s, 1H), 6.95 (s, 1H), 6.64 (s, 1H), 4.43 (t, J = 11.2 Hz, 1H), 4.09-3.91 (m, 2H), 3.68-3.50 (m, 1H), 3.17 (s, 6H), 2.63 (t, J = 5.4 Hz, 2H), 2.28 (s, 3H), 2.24 (d, J = 12.6 Hz, 1H), 1.93 (dt, J = 21.5, 13.5 Hz, 2H), 1.33 (d, J = 6.4 Hz, 3H), 1.16 (q, J = 7.0 Hz, 1H). LCMS m/z 393.16 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 139 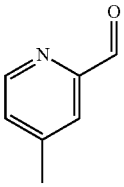 | S25; | Compound 19 | LCMS m/z 349.23 [M + H]⁺. |
| Compound 140 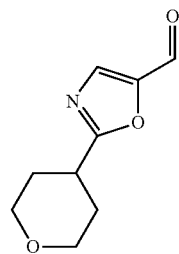 [SMILES: O=Cc1cnc(C2CCOCC2)o1] | S25; | Compound 21[14] | ¹H NMR (400 MHz, DMSO-$d_6$) δ 9.37 (s, 1H), 8.99 (s, 1H), 7.27 (s, 1H), 6.95 (s, 1H), 4.73 (t, J = 11.0 Hz, 1H), 3.93 (t, J = 5.5 Hz, 2H), 3.91-3.84 (m, 2H), 3.63 (s, 1H), 3.46 (td, J = 11.5, 2.4 Hz, 2H), 3.16-3.04 (m, 1H), 2.60 (dd, J = 8.4, 4.5 Hz, 2H), 2.47-2.42 (m, under DMSO, 1H), 2.23 (dt, J = 13.5, 6.2 Hz, 2H), 1.91 (d, J = 13.3 Hz, 2H), 1.83 (t, J = 13.3 Hz, 1H), 1.78-1.65 (m, 2H), 1.26 (d, J = 6.5 Hz, 3H). LCMS m/z 409.11 [M + H]⁺. |
| Compound 141 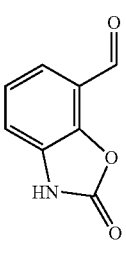 [SMILES: O=Cc1cccc2[nH]c(=O)oc12] | S25; | Compound 21 | ¹H NMR (400 MHz, DMSO-$d_6$) δ 11.93 (s, 1H), 9.31 (s, 1H), 8.85 (s, 1H), 7.34 (d, J = 8.1 Hz, 1H), 7.26 (t, J = 7.9 Hz, 1H), 7.20-7.12 (m, 1H), 6.94 (s, 1H), 4.78 (t, J = 10.8 Hz, 1H), 3.99 (t, J = 5.5 Hz, 2H), 3.71 (s, 1H), 2.62 (t, J = 5.2 Hz, 2H), 2.46-2.21 (m, 3H), 1.92 (t, J = 13.3 Hz, 1H), 1.29 (d, J = 6.5 Hz, 3H). LCMS m/z 391.09 [M + H]⁺. |
| Compound 142 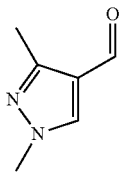 | S25; | Compound 19 | ¹H NMR (400 MHz, DMSO-$d_6$) δ 8.80 (s, 1H), 8.38 (d, J = 10.8 Hz, 1H), 7.79 (s, 1H), 6.94 (s, 1H), 4.31 (t, J = 11.1 Hz, 1H), 3.94 (t, J = 5.4 Hz, 2H), 3.76 (s, 3H), 3.62 (s, 1H), 2.60 (t, J = 5.5 Hz, 2H), 2.25 (d, J = 14.3 Hz, 2H), 2.19-2.10 (m, 4H), 1.83-1.74 (m, 1H), 1.25 (d, J = 6.7 Hz, 3H). LCMS m/z 352.21 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 143 | S24; | Compound 20[1,6] | ¹H NMR (400 MHz, DMSO-d$_6$) δ 8.42 (dd, J = 6.8, 1.2 Hz, 1H), 7.92 (d, J = 1.3 Hz, 1H), 7.53 (d, J = 1.2 Hz, 1H), 7.25 (d, J = 6.9 Hz, 1H), 6.89-6.81 (m, 2H), 4.61 (dd, J = 11.5, 2.5 Hz, 1H), 3.99 (hept, J = 6.0 Hz, 2H), 3.18 (d, J = 12.0 Hz, 1H), 2.59 (t, J = 5.5 Hz, 2H), 2.51-1.90 (m, 2H), 1.41 (ddd, J = 79.2, 13.2, 11.3 Hz, 2H), 1.07 (d, J = 6.3 Hz, 3H). LCMS m/z 374.16 [M + H]⁺. |
| Compound 144 | S25; | Compound 21 | ¹H NMR (400 MHz, DMSO-d$_6$) δ 9.70 (s, 1H), 9.17 (s, 1H), 6.95 (s, 1H), 4.70 (s, 1H), 3.94 (t, J = 5.5 Hz, 2H), 3.68-3.53 (m, 1H), 2.60 (t, J = 5.4 Hz, 2H), 2.31-2.08 (m, 6H), 2.08-2.04 (m, 3H), 1.86-1.75 (m, 1H), 1.27 (d, J = 6.6 Hz, 3H). LCMS m/z 353.16 [M + H]⁺. |
| Compound 145 | S25; | Compound 21[2] | ¹H NMR (400 MHz, DMSO-d$_6$) δ 9.59 (s, 1H), 8.99 (s, 1H), 8.63 (d, J = 6.3 Hz, 1H), 7.00 (s, 1H), 6.95 (s, 1H), 4.60 (t, J = 11.0 Hz, 1H), 4.03-3.93 (m, 2H), 3.97 (s, 3H), 3.58 (s, 1H), 2.74-2.56 (m, 3H), 2.31 (d, J = 14.7 Hz, 1H), 2.04-1.93 (m, 1H), 1.93-1.81 (m, 1H), 1.35 (d, J = 6.5 Hz, 3H). LCMS m/z 366.12 [M + H]⁺. |
| Compound 146 | S25; | Compound 21 | ¹H NMR (400 MHz, DMSO-d$_6$) δ 9.16 (s, 1H), 8.73 (s, 1H), 8.16 (s, 1H), 8.00 (d, J = 7.8 Hz, 1H), 7.93 (d, J = 7.8 Hz, 1H), 7.75 (t, J = 7.8 Hz, 1H), 6.95 (s, 1H), 4.73 (t, J = 11.2 Hz, 1H), 3.98 (t, J = 5.4 Hz, 2H), 3.68 (s, 1H), 3.25 (s, 3H), 2.61 (d, J = 4.5 Hz, 2H), 2.39 (d, J = 14.5 Hz, 1H), 2.30 (t, J = 13.5 Hz, 2H), 1.91 (t, J = 13.3 Hz, 1H), 1.29 (d, J = 6.5 Hz, 3H). LCMS m/z 412.09 [M + H]⁺. |
| Compound 147 | S25; | Compound 20 | ¹H NMR (300 MHz, DMSO-d$_6$) δ 9.12 (d, J = 10.8 Hz, 1H), 8.72-8.54 (m, 1H), 8.05 (d, J = 1.8 Hz, 1H), 7.92-7.87 (m, 1H), 7.79 (d, J = 7.8 Hz, 1H), 7.67 (t, J = 7.7 Hz, 1H), 7.44 (s, 2H), 6.94 (s, 1H), 4.67 (t, J = 10.5 Hz, 1H), 3.97 (t, J = 5.4 Hz, 2H), 3.68 (s, 1H), 2.65-2.58 (m, 2H), 2.35-2.24 (m, 3H), 1.90 (t, J = 13.3 Hz, 1H), 1.29 (d, J = 6.4 Hz, 3H). LCMS m/z 413.12 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 148 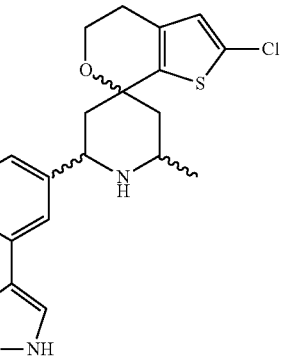 | S25; 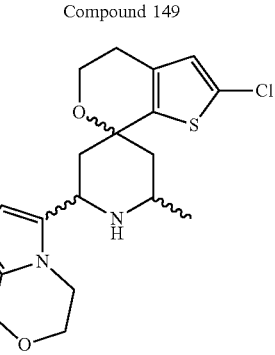 | Compound 21 | $^1$H NMR (400 MHz, DMSO-d$_6$) δ 9.16 (s, 1H), 8.73 (s, 1H), 8.11 (s, 2H), 7.82 (s, 1H), 7.67 (d, J = 7.5 Hz, 1H), 7.44 (t, J = 7.6 Hz, 1H), 7.38 (d, J = 7.7 Hz, 1H), 6.94 (s, 1H), 4.61-4.47 (m, 1H), 3.98 (t, J = 5.5 Hz, 2H), 3.69-3.59 (m, 2H), 2.62 (s, 2H), 2.39-2.24 (m, 3H), 1.94 (t, J = 13.3 Hz, 1H), 1.30 (d, J = 6.4 Hz, 3H). LCMS m/z 400.12 [M + H]$^+$. |
| Compound 149 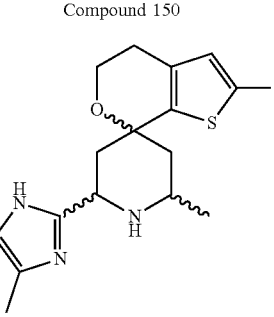 | S25; | Compound 21 | $^1$H NMR (300 MHz, Methanol-d$_6$) δ 7.77-7.54 (m, 1H), 6.77 (s, 1H), 4.96 (s, 3H), 4.18 (s, 4H), 4.03 (t, J = 5.4 Hz, 2H), 3.98-3.84 (m, 1H), 2.67 (t, J = 5.5 Hz, 2H), 2.58 (d, J = 14.8 Hz, 1H), 2.42 (d, J = 15.9 Hz, 1H), 2.37-2.23 (m, 1H), 1.88 (s, 1H), 1.41 (d, J = 6.5 Hz, 3H). LCMS m/z 380.12 [M + H]$^+$. |
| Compound 150 | S25; | Compound 21$^1$ | $^1$H NMR (400 MHz, DMSO-d$_6$) δ 6.95 (s, 1H), 4.58 (s, 1H), 3.95 (t, J = 5.5 Hz, 2H), 3.58-3.45 (m, 1H), 2.64-2.55 (m, 4H), 2.22 (d, J = 14.4 Hz, 1H), 2.13 (s, 6H), 1.77 (t, J = 13.3 Hz, 1H), 1.26 (d, J = 6.5 Hz, 3H). Exchangeables not observed. LCMS m/z 352.17 [M + H]$^+$. |
| Compound 151 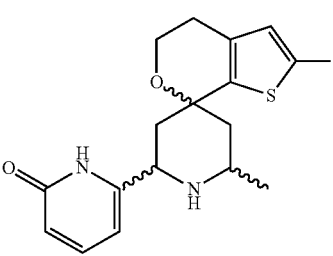 | S24; | Compound 20 | $^1$H NMR (300 MHz, Methanol-d$_6$) δ 7.69 (t, J = 7.9 Hz, 1H), 6.86 (d, J = 7.3 Hz, 1H), 6.75 (s, 1H), 6.68 (d, J = 8.4 Hz, 1H), 4.64 (dd, J = 12.4, 3.0 Hz, 1H), 4.03 (t, J = 5.5 Hz, 2H), 3.83-3.72 (m, 1H), 2.67 (t, J = 5.5 Hz, 2H), 2.57-2.45 (m, 1H), 2.38 (dt, J = 14.5, 2.6 Hz, 1H), 2.14 (dd, J = 14.1, 12.9 Hz, 1H), 1.86 (dd, 1H), 1.41 (d, J = 6.6 Hz, 3H). LCMS m/z 351.17 [M + H]$^+$. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 152 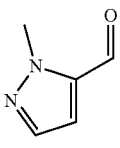 | S25; 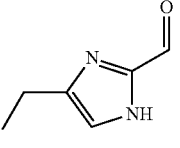 | Compound 19[17] | NMR not integrated due to a complex mixture of stereoisomers LCMS m/z 338.21 [M + H]$^+$. |
| Compound 153 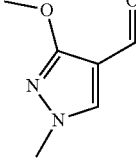 | S25; | Compound 21[1] | $^1$H NMR (400 MHz, DMSO-d$_6$) δ 6.99 (s, 1H), 6.95 (s, 1H), 4.60 (d, J = 12.2 Hz, 1H), 3.96 (t, J = 5.5 Hz, 2H), 3.6 (1H under water peak), 2.65-2.47 (m, 5H), 2.23 (d, J = 14.4 Hz, 1H), 2.11 (t, J = 13.3 Hz, 1H), 1.82 (t, J = 13.2 Hz, 1H), 1.28 (d, J = 6.5 Hz, 3H), 1.18 (t, J = 7.5 Hz, 3H). LCMS m/z 352.17 [M + H]$^+$. |
| Compound 154 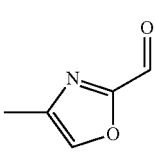 | S25; | Compound 21 | $^1$H NMR (400 MHz, DMSO-d$_6$) δ 8.94 (s, 1H), 8.51 (s, 1H), 7.70 (s, 1H), 6.93 (s, 1H), 4.32-4.22 (m, 1H), 3.92 (t, J = 5.5 Hz, 2H), 3.83 (s, 3H), 3.70 (s, 3H), 3.59-3.48 (m, 1H), 2.59 (t, J = 5.4 Hz, 2H), 2.27-2.18 (m, 3H), 1.82-1.71 (m, 1H), 1.23 (d, J = 6.4 Hz, 3H). LCMS m/z 368.15 [M + H]$^+$. |
| Compound 155 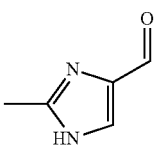 | S24; | Compound 20 | $^1$H NMR (400 MHz, DMSO-d$_6$) δ 9.92-9.60 (m, 1H), 9.35-9.09 (m, 1H), 8.01-7.95 (m, 1H), 6.95 (s, 1H), 4.78 (s, 1H), 3.95 (t, J = 5.4 Hz, 2H), 3.61 (s, 1H), 2.60 (q, J = 5.1 Hz, 3H), 2.25 (d, J = 14.3 Hz, 1H), 2.13 (d, J = 1.3 Hz, 3H), 2.18-2.06 (m, 1H), 1.87-1.75 (m, 1H), 1.28 (d, J = 6.4 Hz, 3H). LCMS m/z 339.16 [M + H]$^+$. |
| Compound 156 | S24; | Compound 20 | $^1$H NMR (400 MHz, DMSO-d$_6$) δ 9.17 (s, 1H), 9.01-8.60 (m, 1H), 8.32 (s, 1H), 6.94 (s, 1H), 4.56 (d, J = 12.2 Hz, 1H), 3.94 (t, J = 5.4 Hz, 2H), 3.69-3.61 (m, 1H), 2.60 (t, J = 5.4 Hz, 2H), 2.45-2.33 (m, 1H), 2.27 (s, 3H), 2.25 (s, 2H), 1.83 (dd, J = 14.4, 12.3 Hz, 1H), 1.25 (d, J = 6.5 Hz, 3H). LCMS m/z 338.17 [M + H]$^+$. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 157 | S25; | Compound 21 | ¹H NMR (400 MHz, DMSO-$d_6$) δ 9.22 (s, 1H), 8.92 (s, 1H), 8.44 (s, 1H), 6.94 (s, 1H), 4.75 (s, 1H), 3.94 (t, J = 5.6 Hz, 2H), 3.70 (s, 1H), 2.60 (t, J = 5.5 Hz, 2H), 2.36-2.22 (m, 3H), 2.17 (s, 3H), 1.84 (t, J = 13.4 Hz, 1H), 1.24 (d, J = 6.6 Hz, 3H). LCMS m/z 339.12 [M + H]⁺. |
| Compound 158 | S24; | Compound 20 | ¹H NMR (300 MHz, Methanol-$d_4$) δ 7.80 (s, 1H), 6.75 (s, 1H), 4.56 (dd, J = 12.6, 2.8 Hz, 1H), 4.16 (t, J = 5.2 Hz, 2H), 4.01 (t, J = 5.5 Hz, 2H), 3.84 (q, J = 5.5 Hz, 3H), 2.66 (t, J = 5.4 Hz, 2H), 2.45-2.34 (m, 2H), 2.29 (s, 3H), 2.15 (dd, J = 14.8, 12.6 Hz, 1H), 1.80 (dd, J = 14.9, 12.2 Hz, 1H), 1.37 (d, J = 6.6 Hz, 3H). LCMS m/z 382.15 [M + H]⁺. |
| Compound 159 | S24; | Compound 20[12] | ¹H NMR (300 MHz, Methanol-$d_4$) δ 7.79 (s, 1H), 6.76 (s, 1H), 4.94-4.89 (dd, under water, 1H), 4.06-3.90 (m, 3H), 3.83 (s, 3H), 2.70-2.64 (m, 5H), 2.55 (dt, J = 14.6, 2.7 Hz, 1H), 2.46-2.28 (m, 2H), 1.92 (dd, J = 14.8, 12.3 Hz, 1H), 1.42 (d, J = 6.6 Hz, 3H). LCMS m/z 352.17 [M + H]⁺. |
| Compound 160 | S25; | Compound 21 | ¹H NMR (400 MHz, DMSO-$d_6$) δ 11.99 (s, 1H), 9.00 (s, 1H), 8.52 (s, 1H), 7.95 (s, 1H), 7.78 (d, J = 7.4 Hz, 1H), 6.93 (s, 1H), 6.27 (d, J = 7.3 Hz, 1H), 4.64-4.54 (m, 1H), 3.94 (t, J = 5.5 Hz, 2H), 3.6 (1H under water peak), 2.60 (t, 2H), 2.23 (q, J = 12.2, 11.0 Hz, 3H), 1.93-1.83 (m, 1H), 1.28 (d, J = 6.4 Hz, 3H). LCMS m/z 351.13 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 161 | S24; | Compound 20 | ¹H NMR (400 MHz, DMSO-$d_6$) δ 9.12 (s, 1H), 8.95-8.65 (m, 1H), 8.30 (s, 1H), 6.94 (s, 1H), 4.56 (d, J = 12.2 Hz, 1H), 3.94 (t, J = 5.4 Hz, 2H), 3.65 (s, 1H), 2.63-2.57 (m, 2H), 2.44-2.34 (m, 1H), 2.27 (s, 3H), 2.23 (d, J = 13.0 Hz, 2H), 1.90-1.76 (m, 1H), 1.25 (d, J = 6.5 Hz, 3H). LCMS m/z 340.2 [M + H]⁺. |
| Compound 162 | S25; | Compound 21[1] | ¹H NMR (300 MHz, Methanol-$d_4$) δ 7.19 (s, 1H), 6.76 (s, 1H), 4.97-4.88 (m, under water, 1H), 4.01 (t, J = 5.5 Hz, 2H), 3.76 (s, 1H), 3.03 (dd, J = 13.4, 7.0 Hz, 1H), 2.66 (t, J = 5.5 Hz, 2H), 2.57 (s, 1H), 2.35 (d, J = 14.8 Hz, 2H), 1.87 (t, J = 13.3 Hz, 1H), 1.39 (d, J = 6.8 Hz, 3H), 1.30 (dd, J = 7.0, 1.6 Hz, 6H). LCMS m/z 366.16 [M + H]⁺. |
| Compound 163 | S25; | Compound 21 | ¹H NMR (400 MHz, DMSO-$d_6$) δ 8.93 (s, 1H), 8.50 (s, 1H), 7.45 (s, 1H), 6.93 (s, 1H), 4.34 (s, 2H), 4.26 (t, J = 11.4 Hz, 1H), 4.07 (t, J = 6.0 Hz, 2H), 3.91 (t, J = 5.4 Hz, 2H), 3.51 (s, 1H), 2.59 (t, J = 5.4 Hz, 2H), 2.22 (dd, J = 29.3, 12.9 Hz, 5H), 1.84-1.71 (m, 1H), 1.23 (d, J = 6.1 Hz, 3H). LCMS m/z 380.12 [M + H]⁺. |
| Compound 164 | S25; | Compound 21 | ¹H NMR (400 MHz, DMSO-$d_6$) δ 9.40 (s, 1H), 9.00 (d, J = 12.1 Hz, 1H), 8.61 (q, J = 2.7 Hz, 2H), 6.95 (s, 1H), 4.94 (t, J = 11.2 Hz, 1H), 4.04 (t, J = 5.4 Hz, 2H), 3.78-3.61 (m, 1H), 2.63 (d, J = 5.4 Hz, 2H), 2, 6 (1H under DMSO peak) 2.58 (s, 3H), 2.24 (dd, J = 14.0, 10.2 Hz, 1H), 2.08-1.79 (m, 2H), 1.32 (d, J = 6.6 Hz, 3H). LCMS m/z 350.14 [M + H]⁺. |
| Compound 165 | S25; | Compound 21 | ¹H NMR (400 MHz, DMSO-$d_6$) δ 13.16 (s, 1H), 9.61 (s, 1H), 9.16 (s, 1H), 7.94 (s, 1H), 6.96 (s, 1H), 4.70 (t, J = 10.9 Hz, 1H), 3.97 (t, J = 5.5 Hz, 2H), 3.56 (s, 1H), 2.62 (t, J = 5.8 Hz, 2H), 2.56 (s, 1H), 2.24 (d, J = 14.4 Hz, 1H), 2.06 (t, J = 13.4 Hz, 1H), 1.93-1.82 (m, 1H), 1.30 (d, J = 6.4 Hz, 3H). LCMS m/z 392.08 [M + H]⁺. |

TABLE 3-continued

Method of preparation, structure and physicochemical data for compounds 22-172

| Product | Starting Material and Aldehyde | Method | ¹H NMR; LCMS m/z [M + H]⁺ |
|---|---|---|---|
| Compound 166 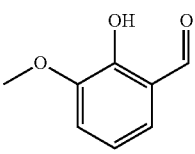 | S25; <br> | Compound 21 | ¹H NMR (300 MHz, Methanol-d₄) δ 7.12 (dd, J = 8.2, 1.6 Hz, 1H), 7.01 (t, J = 7.9 Hz, 1H), 6.94-6.89 (m, 2H), 4.90 (t, J = 2.9 Hz, 1H), 3.88 (s, 3H), 3.81 (td, J = 6.7, 1.5 Hz, 2H), 3.42-3.30 (m, 1H), 3.03-2.85 (m, 2H), 2.66 (td, J = 14.5, 3.3 Hz, 2H), 2.44 (dt, J = 14.2, 2.6 Hz, 1H), 2.18 (dd, J = 14.5, 12.3 Hz, 1H), 1.31 (d, J = 6.5 Hz, 3H). LCMS m/z 380.16 [M + H]⁺. |
| Compound 167 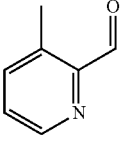 | S25; <br> | Compound 20 | ¹H NMR (400 MHz, DMSO-d₆) δ 9.26 (d, J = 9.9 Hz, 1H), 8.94 (d, J = 11.5 Hz, 1H), 8.56-8.50 (m, 1H), 7.76-7.70 (m, 1H), 7.40 (dd, J = 7.7, 4.8 Hz, 1H), 6.94 (s, 1H), 4.84 (t, J = 11.3 Hz, 1H), 4.02 (t, J = 5.4 Hz, 2H), 3.65 (dq, J = 20.5, 5.7, 5.0 Hz, 1H), 2.62 (dt, J = 5.5, 3.2 Hz, 2H), 2.34 (s, 3H), 2.47-2.19 (m, 2H), 1.93 (ddd, J = 66.7, 14.5, 12.1 Hz, 2H), 1.32 (d, J = 6.5 Hz, 3H). LCMS m/z 349.19 [M + H]⁺. |
| Compound 168 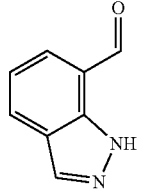 [SMILES: O=Cc1cccc2cn[nH]c12] | S25; <br> | Compound 21[2] | NMR not annotated due a complex mixture of stereoisomers. LCMS m/z 374.11 [M + H]⁺. |
| Compound 169 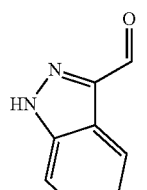 | S24; <br> | Compound 20 | ¹H NMR (300 MHz, Methanol-d₄) δ 7.79 (d, J = 8.2 Hz, 1H), 7.55 (d, J = 8.5 Hz, 1H), 7.42 (dd, J = 8.1, 6.9 Hz, 1H), 7.21 (t, J = 7.6 Hz, 1H), 6.76 (s, 1H), 5.21 (dd, J = 12.5, 3.0 Hz, 1H), 4.10 (t, J = 5.6 Hz, 2H), 3.89 (dtq, J = 12.6, 6.2, 3.1 Hz, 1H), 2.73-2.61 (m, 3H), 2.50-2.37 (m, 2H), 2.34 (dd, J = 14.6, 12.7 Hz, 1H), 1.93 (dd, J = 14.8, 12.3 Hz, 1H), 1.42 (d, J = 6.6 Hz, 3H). LCMS m/z 374.16 [M + H]⁺. |

TABLE 3-continued

Method of preparation, structure and physicochemical data for compounds 22-172

| Product | Starting Material and Aldehyde | Method | $^1$H NMR; LCMS m/z [M + H]$^+$ |
|---|---|---|---|
| Compound 170 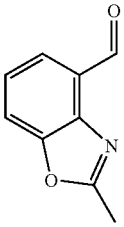 | S25; | Compound 20[10] | LCMS m/z 389.1 [M + H]$^+$. |
| Compound 171 | S24; | Compound 20[12] | $^1$H NMR (400 MHz, DMSO-d$_6$) δ 9.52 (s, 1H), 9.17 (s, 1H), 8.09 (s, 1H), 6.95 (s, 1H), 4.98 (s, 1H), 3.99 (t, J = 5.4 Hz, 2H), 3.90 (d, J = 5.2 Hz, 3H), 3.69 (d, J = 10.8 Hz, 1H), 2.71-2.56 (m, 3H), 2.32-2.05 (m, 2H), 1.97-1.86 (m, 1H), 1.28 (d, J = 6.5 Hz, 3H). LCMS m/z 339.16 [M + H]$^+$. |
| Compound 172 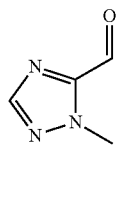 | S25; 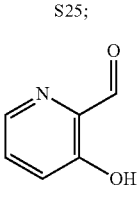 | Compound 20 | $^1$H NMR (300 MHz, DMSO-d$_6$) δ 10.67 (s, 1H), 9.17 (d, J = 8.6 Hz, 1H), 8.91 (d, J = 12.0 Hz, 1H), 8.16 (dd, J = 3.9, 2.1 Hz, 1H), 7.37-7.27 (m, 2H), 6.93 (s, 1H), 4.85 (d, J = 11.6 Hz, 1H), 3.99 (s, 2H), 3.59 (s, 1H), 2.63 (t, J = 5.5 Hz, 2H), 2.44 (s, 1H), 2.26 (d, J = 14.1 Hz, 1H), 2.02-1.91 (m, 1H), 1.90-1.80 (m, 1H), 1.32 (d, J = 6.4 Hz, 3H). LCMS m/z 351.17 [M + H]$^+$. |

[1]The product was afforded as the free-base.

[2]Product was isolated as a 3:2 mixture of diastereomers with unknown absolute stereochemistry.

[3]The mixture from step 1 was blown down with nitrogen at 40° C. .

[4]Purification by silica gel chromatography (Gradient: 0-100% of 20% MeOH/DCM in DCM) yielded the product.

[5]The TBS was deprotected during the reaction (step 2).

[6]The product was impure after the purification and was repurified by reversed-phase HPLC (Method: C18 Waters Sunfire column (30 x 150 mm, 5 micron). Gradient: MeCN in H$_2$O with 10 mM ammonium hydroxide).

[7]Product was isolated as a 4.5:1 mixture of diastereomers with unknown absolute stereochemistry.

[8]Step 1 was stirred at room temperature for one week.

[9]The pH was carefully adjusted to pH 7 with 2N NaOH prior to DCM extraction.

[10]Product was isolated as a 2:1 mixture of diastereomers with unknown absolute stereochemistry.

[11]Product was isolated as a 3:1 mixture of diastereomers with unknown absolute stereochemistry.

[12]Product was isolated as a 5:1 mixture of diastereomers with unknown absolute stereochemistry.

[13]Product was isolated as a 3.5:1 mixture of diastereomers with unknown absolute stereochemistry.

[14]The product was impure after the purification and was repurified by reversed-phase HPLC (Method: C18 Waters Sunfire column (30 x 150 mm, 5 micron). Gradient: MeCN in H2O with 0.2% formic acid). The product was afforded as the formic acid salt.

[15]The product was afforded as the di-TFA salt.

[16]Product was isolated as a 4:1 mixture of diastereomers with unknown absolute stereochemistry.

[17]Complex mixture of stereoisomers was afforded.

Compound 173

(2S)-2-chloro-2'-methyl-6'-(1-methyltriazol-4-yl)spiro[6,7-dihydrothieno[3,2-c]pyran-4,4'-piperidine] (173)

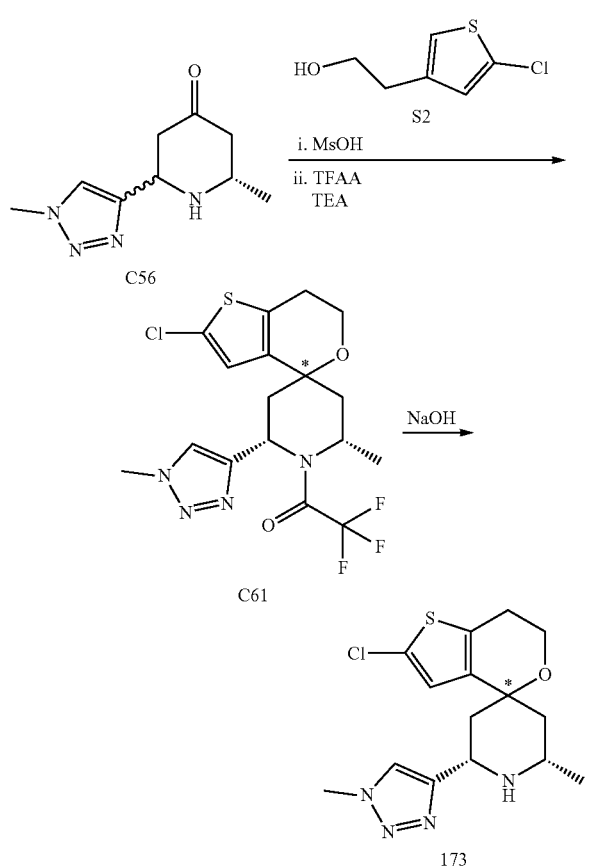

Step 1. Synthesis of 1-[(2S)-2-chloro-2'-methyl-6'-(1-methyltriazol-4-yl)spiro[6,7-dihydrothieno[3,2-c]pyran-4,4'-piperidine]-1'-yl]-2,2,2-trifluoro-ethanone (C61)

To a solution of 2-(5-chloro-2-thienyl)ethanol S2 (410 mg, 2.521 mmol) and (2S)-2-methyl-6-(1-methyltriazol-4-yl)piperidin-4-one C56 (420 mg, 2.141 mmol) in DCM (8 mL) was added methanesulfonic acid (800 µL, 12.33 mmol). The resulting mixture was heated to 40° C. for 40 minutes. More methanesulfonic acid (800 µL, 12.33 mmol) was added and the reaction was continued heating for another 30 minutes. The reaction was cooled to room temperature, diluted with water, and basified with 2 N NaOH solution. The mixture was extracted with DCM (3×20 mL) through a phase separator and the organic layers were concentrated in vacuo to afford crude (2S)-2-chloro-2'-methyl-6'-(1-methyltriazol-4-yl)spiro[6,7-dihydrothieno[3,2-c]pyran-4,4'-piperidine]

A solution of crude (2S)-2-chloro-2'-methyl-6'-(1-methyltriazol-4-yl)spiro[6,7-dihydrothieno[3,2-c]pyran-4,4'-piperidine] in DCM (9 mL) with DIPEA (600 µL, 3.445 mmol) was cooled to 0° C. TFAA (390 µL, 2.806 mmol) was added slowly over 2 minutes, and the reaction was stirred at 0° C. After 15 minutes, the reaction was quenched with saturated sodium bicarbonate solution and extracted with DCM (3×). The organics were dried over sodium sulfate and concentrated in vacuo. Purification by silica gel chromatography (Gradient: 0-50% EtOAc in Heptane) afforded a single major product 1-[(2S)-2-chloro-2'-methyl-6'-(1-methyltriazol-4-yl)spiro[6,7-dihydrothieno[3,2-c]pyran-4,4'-piperidine]-1'-yl]-2,2,2-trifluoro-ethanone C61 (450 mg, 43%). $^1$H NMR (300 MHz, Chloroform-d) δ 7.58 (s, 1H), 6.91 (s, 1H), 5.57 (s, 1H), 4.40 (d, J=7.4 Hz, 1H), 4.10 (s, 3H), 3.89 (t, J=5.4 Hz, 2H), 3.20 (dd, J=14.9, 6.4 Hz, 1H), 2.80-2.61 (m, 2H), 2.45 (dd, J=14.8, 8.4 Hz, 1H), 2.38-2.13 (m, 1H), 2.04 (s, 1H), 1.41-1.12 (m, 3H).

Step 2. Synthesis of (2S)-2-chloro-2'-methyl-6'-(1-methyltriazol-4-yl)spiro[6,7-dihydrothieno[3,2-c]pyran-4,4'-piperidine] (173)

To a solution of 1-[(2S)-2-chloro-2'-methyl-triazol-4-yl)spiro[6,7-dihydrothieno[3,2-c]pyran-4,4'-piperidine]-1'-yl]-2,2,2-trifluoro-ethanone C61 (20 mg, 0.04415 mmol) in MeOH (1 mL) was treated with NaOH (400 µL of 2 M, 0.8000 mmol). The solution was heated to 50° C. for 3 hours at which point it was cooled to room temperature and stirred overnight. The reaction was extracted with DCM (3×) through a phase separator and the organics concentrated in vacuo to afford (2S)-2-chloro-2'-methyl-6'-(1-methyltriazol-4-yl)spiro[6,7-dihydrothieno[3,2-c]pyran-4,4'-piperidine] 173 (14.0 mg, 91%) as an off-white film with an approximate e.r. of 85%. $^1$H NMR (300 MHz, Chloroform-d) δ 7.41 (s, 1H), 6.61 (s, 1H), 4.40 (dd, J=11.8, 2.7 Hz, 1H), 4.05 (s, 3H), 3.96 (td, J=5.7, 2.0 Hz, 2H), 3.28 (dtd, J=12.6, 6.3, 2.5 Hz, 1H), 2.85-2.60 (m, 2H), 2.18 (dt, J=13.5, 2.6 Hz, 1H), 1.89 (dt, J=13.7, 2.5 Hz, 1H), 1.80 (dd, J=13.6, 11.9 Hz, 1H), 1.44 (dd, J=13.7, 11.4 Hz, 1H), 1.11 (d, J=6.3 Hz, 3H). LCMS m/z 339.1 [M+H]$^+$

Preparation of S32

(2S,4S,6S)-2-methyl-6-(1-methyltriazol-4-yl)-1-(2,2,2-trifluoroacetyl)-2'-(trifluoromethyl)spiro[piperidine-4,7'-thieno[2,3-c]pyran]-4'-one (S32)

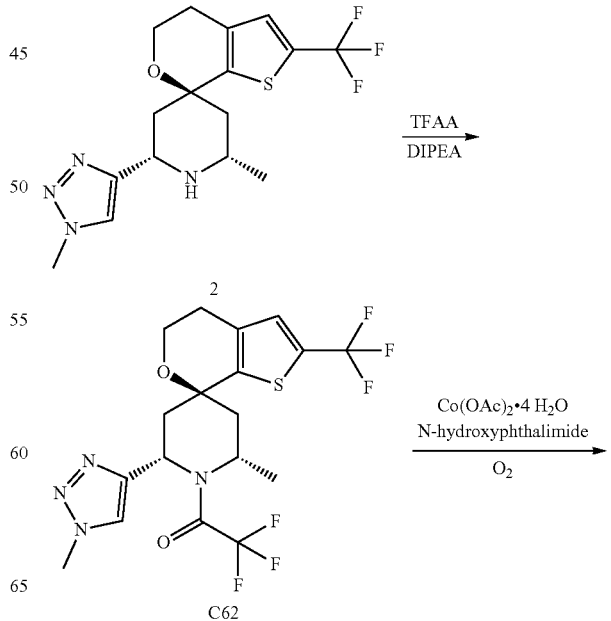

-continued

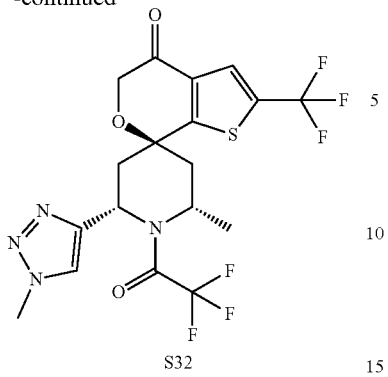

S32

Step 1. Synthesis of 2,2,2-trifluoro-1-[(2'S,6'S, 7S)-2'-methyl-6'-(1-methyltriazol-4-yl)-2-(trifluoromethyl)spiro[4,5-dihydrothieno[2,3-c]pyran-7,4'-piperidine]-1'-yl]ethanone (C62)

To a solution of (2'S,6'S,7S)-2'-methyl-6'-(1-methyltriazol-4-yl)-2-(trifluoromethyl)spiro[4,5-dihydrothieno[2,3-c]pyran-7,4'-piperidine] 2 (1260 mg, 3.352 mmol) dissolved in DCM (25 mL) cooled to −15° C. was added DIPEA (800 µL, 4.593 mmol) followed by TFAA (550 µL, 3.957 mmol). After 5 minutes, the mixture was quenched with 1 N HCl (25 mL) and the phases were separated. The organic layer was dried with MgSO$_4$, filtered, and concentrated. Purification by silica gel chromatography (Gradient: 0-50% EtOAc in Heptane) yielded 2,2,2-trifluoro-1-[(2'S,6'S,7S)-2'-methyl-6'-(1-methyltriazol-4-yl)-2-(trifluoromethyl)spiro[4,5-dihydrothieno[2,3-c]pyran-7,4'-piperidine]-1'-yl]ethanone C62 (1444 mg, 90%). $^1$H NMR (400 MHz, Methanol-d4) δ 7.93 (s, 1H), 7.27 (d, J=1.3 Hz, 1H), 5.63 (s, 1H), 4.46 (h, J=7.1 Hz, 1H), 4.11 (d, J=1.4 Hz, 3H), 3.96 (td, J=5.6, 1.7 Hz, 2H), 3.04 (s, 1H), 2.79-2.70 (m, 3H), 2.51 (s, 1H), 2.09 (dd, J=14.7, 7.3 Hz, 1H), 1.23 (q, J=9.6, 8.4 Hz, 3H). LCMS m/z 469.14 [M+H]$^+$.

Step 2. Synthesis of (2S,4S,6S)-2-methyl-6-(1-methyltriazol-4-yl)-1-(2,2,2-trifluoroacetyl)-2'-(trifluoromethyl)spiro[piperidine-4,7'-thieno[2,3-c]pyran]-4'-one (S32)

To a mixture of 2,2,2-trifluoro-1-[(2'S,6'S,7S)-2'-methyl-6'-(1-methyltriazol-4-yl)-2-(trifluoromethyl)spiro[4,5-dihydrothieno[2,3-c]pyran-7,4'-piperidine]-1'-yl]ethanone C62 (708 mg, 1.511 mmol) in acetonitrile (10 mL) was added N-hydroxyphthalimide (165 mg, 1.011 mmol) and cobaltous diacetate tetrahydrate (35 mg, 0.1405 mmol), and then the mixture was vacuum purged with an oxygen balloon three times. The mixture was heated to 60° C. and stirred. After an hour and a half the reaction was cooled to room temperature. The mixture was vacuum purged with nitrogen three times and then diluted with MTBE (25 mL) and saturated aqueous bicarbonate (25 mL). The layers were separated, and the organic layer was washed with aqueous NaHCO$_3$ (2×50 mL) and brine (50 mL). The organic layer was dried with Na$_2$SO$_4$, filtered, and concentrated. Purification by silica gel chromatography (Gradient: 0-50% EtOAc in heptane) afforded (2S,4S,6S)-2-methyl-6-(1-methyltriazol-4-yl)-1-(2,2,2-trifluoroacetyl)-2'-(trifluoromethyl)spiro[piperidine-4,7'-thieno[2,3-c]pyran]-4'-one S32 (207 mg, 26%), $^1$H NMR (300 MHz, Methanol-d4) δ 7.98 (s, 1H), 7.80 (d, J=1.4 Hz, 1H), 5.70 (s, 1H), 4.48 (s, 1H), 4.45 (s, 2H), 4.12 (s, 3H), 2.95 (dd, J=14.8, 9.8 Hz, 1H), 2.73 (s, 1H), 2.22 (dd, J=14.8, 8.4 Hz, 1H), 1.29 (s, 1H), 1.19 (d, J=14.9 Hz, 3H). LCMS m/z 483.45 [M+H]$^+$.

Preparation of Intermediates S33-S36

Intermediate ketones S33-S36 (see Table 4) were prepared in two steps from the relevant compounds using a TFAA protection and benzylic oxidation as described for intermediate S32. Any modifications to methods are noted in Table 4 and accompanying footnotes.

TABLE 4

Method of preparation, structure and physicochemical data for ketone intermediates S33-S36

| Product | Compound Starting Material | $^1$H NMR; LCMS m/z [M + H]$^+$ |
|---|---|---|
| S33 | Compound 1[2,3,4,9] | $^1$H NMR (300 MHz, Chloroform-d) δ 7.63 (s, 1H), 7.21 (s, 1H), 5.63 (s, 1H), 4.45 (q, J = 7.5 Hz, 1H), 4.33 (s, 2H), 4.14 (s, 3H), 3.36 (dd, J = 15.1, 6.3 Hz, 1H), 2.80 (dd, J = 15.5, 8.7 Hz, 1H), 2.05 (d, J = 11.0 Hz, 2H), 1.27 (s, 3H). LCMS m/z 449.04 [M + H]$^+$. |

TABLE 4-continued

Method of preparation, structure and physicochemical data for ketone intermediates S33-S36

| Product | Compound Starting Material | $^1$H NMR; LCMS m/z [M + H]$^+$ |
|---|---|---|
| 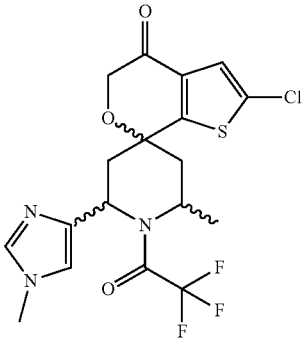<br>S34 | 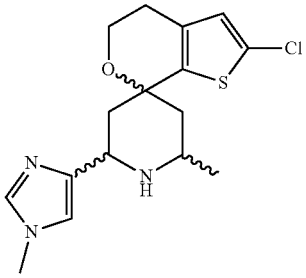<br>Compound 22[1,5,2,6,7,9,10] | LCMS m/z 448.0 [M + H]$^+$. |
| 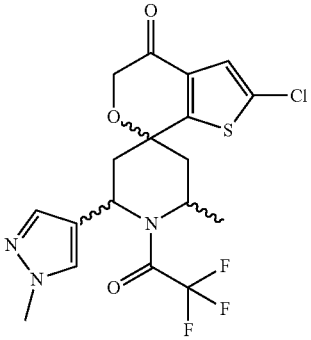<br>S35 | 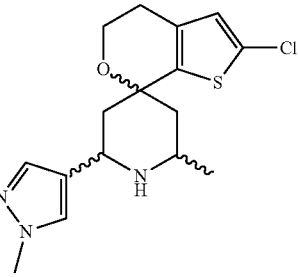<br>Compound 19[1,2,5,8,9,11] | LCMS m/z 448.05 [M + H]$^+$ |
| 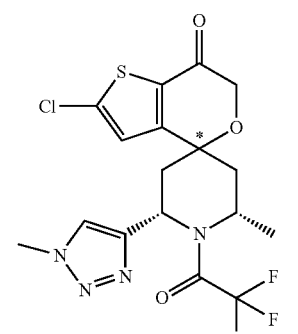<br>S36 | 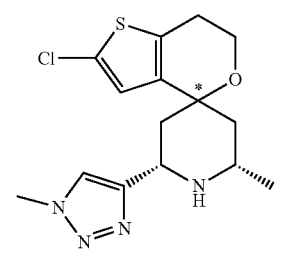<br>Compound 173[1,8,9,12,13,14] | $^1$H NMR (300 MHz, Chloroform-d) δ 5.80-5.44 (m, 1H), 7.47-6.97 (m, 1H), 7.53 (d, J = 42.1 Hz, 1H), 4.42 (q, J = 7.2 Hz, 1H), 4.33 (d, J = 2.6 Hz, 2H), 4.13 (s, 3H), 3.36 (dd, J = 14.9, 5.2 Hz, 1H), 2.64 (dd, J = 15.1, 8.6 Hz, 1H), 2.46 (s, 1H), 2.16 (s, 1H), 1.32 (d, J = 7.0 Hz, 3H). LCMS m/z 449.12 [M + H]$^+$ |

[1] TFAA was added at 0° C. (step 1)
[2] Reaction was stirred at 45° C. (step 2)
[3] The mixture was quenched with water (10 mL) and the layers were separated. The organic layer was washed with 1N HCl (10 mL), brine (10 mL), dried with magnesium sulfate, filtered, and concentrated, (step 1)
[4] Reaction stirred for 18 hours (step 2)
[5] Purification by silica gel chromatography (0-100% EtOAc:heptane) yielded the product (step 1)
[6] Quenched with water before 1N HCl (step 1)
[7] Reaction stirred for 45 minutes (step 1)
[8] Reaction was diluted with DCM, water, and saturated sodium bicarbonate. Extracted with DCM (3x) and collected through a phase separator (step 1)
[9] Reaction was diluted with DCM, water, and saturated sodium bicarbonate. Extracted with DCM (3x) and collected through a phase separator (step 2)
[10] Purification by silica gel chromatography (0-100% EtOAc in heptane) yielded the product (step 2)
[11] Purification by silica gel chromatography (0-80% EtOAc in heptane) yielded the product (step 2)
[12] Purification by silica gel chromatography (0-45% EtOAc in heptane) yielded the product (step 2)
[13] Reaction stirred overnight (step 2)
[14] S36 has an approximately 85% e.r.

Preparation of S33

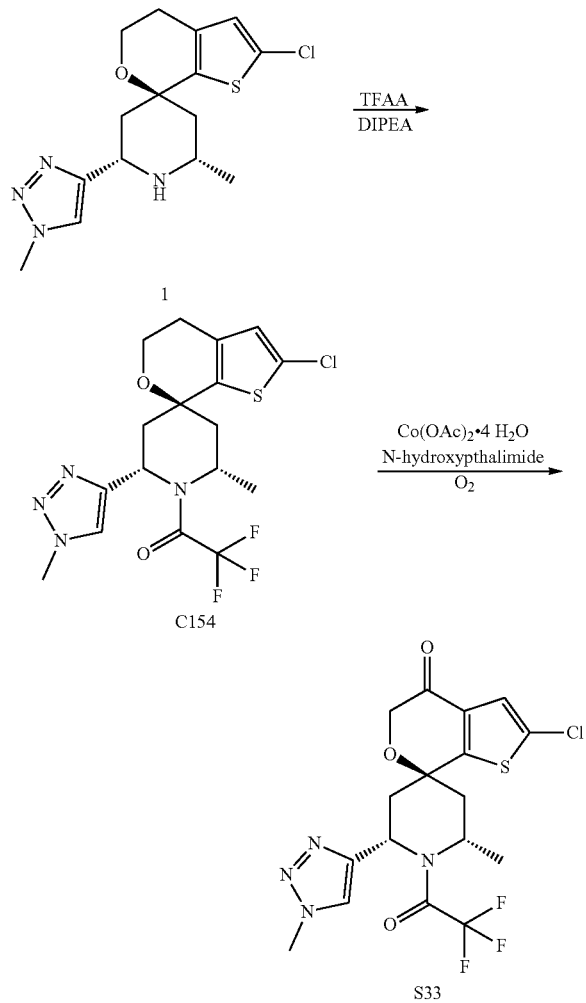

Step 1. Synthesis of 1-[(2'S,6'S, 7S)-2-chloro-2'-methyl-6'-(1-methyltriazol-4-yl)spiro[4,5-dihydrothieno[2,3-c]pyran-7,4'-piperidine]-1'-yl]-2,2,2-trifluoro-ethanone (C154)

To a mixture of (2'S,6'S,7S)-2-chloro-2'-methyl-6'-(1-methyltriazol-4-yl)spiro[4,5-dihydrothieno[2,3-c]pyran-7,4'-piperidine] 1 (15.0 g, 43.82 mmol) and DIPEA (10 mL, 57.41 mmol) in DCM (150 mL), cooled to 3° C., was added TFAA (6.4 mL, 46.04 mmol). After 5 minutes, the mixture was quenched with 1 N HCl (100 mL), and the phases were separated. The organic layer was washed with brine (100 mL), dried with magnesium sulfate, filtered, and concentrated. The solid was suspended in TBME (100 mL) and heated to reflux. After 30 minutes, the mixture was cooled to 0° C., and after 10 minutes, the material was filtered and rinsed with additional cold TBME. The product was dried to yield 1-[(2'S,6'S,7S)-2-chloro-2'-methyl-6'-(1-methyltriazol-4-yl)spiro[4,5-dihydrothieno[2,3-c]pyran-7,4'-piperidine]-1'-yl]-2,2,2-trifluoro-ethanone C154 (15.532 g, 81%). LCMS m/z calc. 435.18 [M+H]$^+$.

Step 2. Synthesis of 2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one (S33)

To a mixture of 1-[(2'S,6'S,7S)-2-chloro-2'-methyl-6'-(1-methyltriazol-4-yl)spiro[4,5-dihydrothieno[2,3-c]pyran-7,4'-piperidine]-1'-yl]-2,2,2-trifluoro-ethanone (C154) (4.5 g, 10.24 mmol) in acetonitrile (70 mL) was added N-hydroxyphthalimide (1.2 g, 7.36 mmol) and cobaltous diacetate tetrahydrate (550 mg, 0.216 mmol), and then the mixture was vacuum purged with an oxygen balloon three times. The mixture was heated to 45° C. and stirred for 18 hours before cooling to room temperature. The reaction was diluted with DCM, water, and saturated sodium bicarbonate, then extracted with DCM (3×150 mL) and collected through a phase separator. The organic layer was dried with Na$_2$SO$_4$, filtered, and concentrated. Purification by silica gel chromatography (Gradient: 0-50% EtOAc in heptane) afforded (2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one S33 (3.50 g, 68%). $^1$H NMR (300 MHz, Chloroform-d) δ 7.61 (s, 1H), 7.19 (s, 1H), 5.61 (s, 1H), 4.44 (q, J=7.1 Hz, 1H), 4.31 (s, 2H), 4.12 (s, 3H), 3.34 (dd, J=15.1, 6.2 Hz, 1H), 2.78 (dd, J=15.1, 8.3 Hz, 1H), 2.70-2.43 (m, 1H), 2.16 (s, 1H), 1.27 (d, J=7.3 Hz, 3H). LCMS m/z 449.12 [M+H]$^+$.

Compound 174

(2'S,4S,6'S, 7S)-2-chloro-2'-methyl-6'-(1-methyltriazol-4-yl)spiro[4,5-dihydrothieno[2,3-c]pyran-7,4'-piperidine]-4-ol (174)

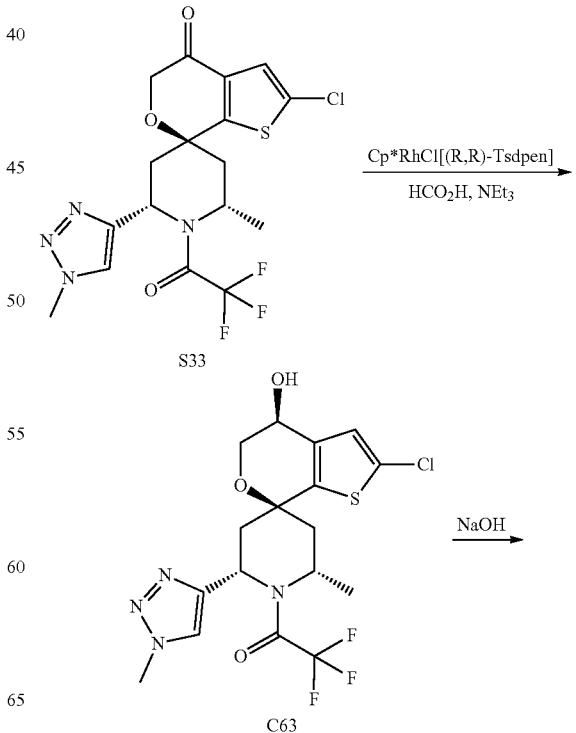

355

-continued

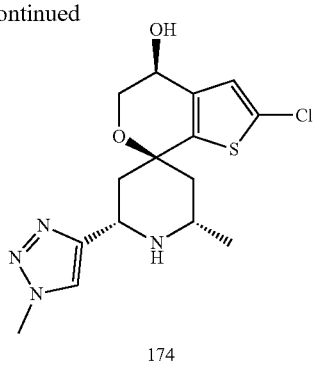

174

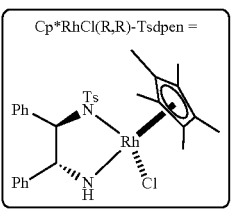

Step 1. Synthesis of 1-[(2'S,4S,6'S, 7S)-2-chloro-4-hydroxy-2'-methyl-6'-(1-methyltriazol-4-yl)spiro[4,5-dihydrothieno[2,3-c]pyran-7,4'-piperidine]-1'-yl]-2,2,2-trifluoro-ethanone (C63)

To (2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one S33 (3.5 g, 7.025 mmol) in DCM (60 mL) was added a solution of 1,2,3,4,5 pentamethylcyclopentane rhodium(2+) tetrachloride (24 mg, 0.03821 mmol) and N-[(1R,2R)-2-amino-1,2-diphenyl-ethyl]-4-methyl-benzenesulfonamide (27 mg, 0.074 mmol) in DCM (7 mL) followed by a solution of formic acid (1.4 mL, 37.11 mmol) and triethylamine (2.1 mL, 15.07 mmol). The flask was fitted with an empty balloon to capture the $CO_2$ off-gas byproduct. After two hours, the mixture was washed with saturated aqueous sodium bicarbonate (150 mL). The organic phase was separated, passed through a phase separator, and concentrated. Silica gel purification (Column: 120 g silica gel, Gradient: 0-45% EtOAc in Heptane) afforded 1-[(2'S,4S,6'S,7S)-2-chloro-4-hydroxy-2'-methyl-6'-(1-methyltriazol-4-yl)spiro[4,5-dihydrothieno[2,3-c]pyran-7,4'-piperidine]-1'-yl]-2,2,2-trifluoro-ethanone C63 (3.3 g, 86%) as a pale off-white foam. $^1$H NMR (300 MHz, Chloroform-d) δ 7.59 (s, 1H), 6.83 (s, 1H), 5.53 (s, 1H), 4.46 (dt, J=9.1, 3.1 Hz, 2H), 4.10 (s, 3H), 4.03-3.80 (m, 2H), 3.10 (dd, J=15.1, 7.3 Hz, 1H), 2.65 (ddd, J=15.1, 8.1, 2.2 Hz, 1H), 2.47 (s, 1H), 2.21-2.08 (m, 1H), 2.08 (d, J=9.2 Hz, 1H), 1.40-1.19 (m, 3H). LCMS m/z 451.05 [M+H]$^+$.

Note that stereochemistry of alcohol C63 was assigned using NMR NOE studies and literature understanding of reductions using this catalyst and ligand system. (Reference: New Chiral Rhodium and Iridium Complexes with Chiral Diamine Ligands for Asymmetric Transfer Hydrogenation of Aromatic Ketones. Kunihiko Murata, Takao Ikariya, and Ryoji Noyori. The Journal of Organic Chemistry 1999 64 (7), 2186-2187).

Step 2. Synthesis of (2'S,4S,6'S, 7S)-2-chloro-2'-methyl-6'-(1-methyltriazol-4-yl)spiro[4,5-dihydrothieno[2,3-c]pyran-7,4'-piperidine]-4-ol (174)

To a solution of 1-[(2'S,4S,6'S,7S)-2-chloro-4-hydroxy-2'-methyl-6'-(1-methyltriazol-4-yl)spiro[4,5-dihydrothieno

356

[2,3-c]pyran-7,4'-piperidine]-1'-yl]-2,2,2-trifluoro-ethanone C63 (3.33 g, 100%) in MeOH (50 mL) was added NaOH (40 mL of 2 M, 80.00 mmol) and the mixture was stirred at 60° C. After 40 minutes, the mixture was diluted with saturated aqueous ammonium chloride until pH 10 (about 50 mL) and extracted with MTBE (5×100 mL) and ethyl acetate (1×75 mL). The combined organic layers were washed with saturated aqueous NaCl, dried over $Na_2SO_4$, and concentrated. The residue was brought up in EtOH and stripped down (3×) to afford a white solid. The solid was transferred to a vial and dried under vacuum at 55° C. overnight to give amorphous (2'S,4S,6'S,7S)-2-chloro-2'-methyl-6'-(1-methyltriazol-4-yl)spiro[4,5-dihydrothieno[2,3-c]pyran-7,4'-piperidine]-4-ol 174 (2.1817 g, 87%). $^1$H NMR (400 MHz, Methanol-$d_4$) δ 7.82 (s, 1H), 6.88 (s, 1H), 4.46 (t, J=3.8 Hz, 1H), 4.34-4.28 (m, 1H), 4.08 (s, 3H), 4.04 (dd, J=12.2, 3.6 Hz, 1H), 3.81 (dd, J=12.2, 4.1 Hz, 1H), 3.36-3.25 (m, 1H), 2.39 (dt, J=13.8, 2.6 Hz, 1H), 2.17 (dt, J=13.7, 2.6 Hz, 1H), 1.71 (dd, J=13.9, 11.9 Hz, 1H), 1.45 (dd, J=13.7, 11.4 Hz, 1H), 1.16 (d, J=6.4 Hz, 3H). LCMS m/z 355.03 [M+H]$^+$.

Compounds 175 and 176

(2S)-2-chloro-2'-methyl-6'-(1-methylimidazol-4-yl)spiro[4,5-dihydrothieno[2,3-c]pyran-7,4'-piperidine]-4-ol (175)[DIASTERIOMER-1] and (176) [DIASTERIOMER-2]

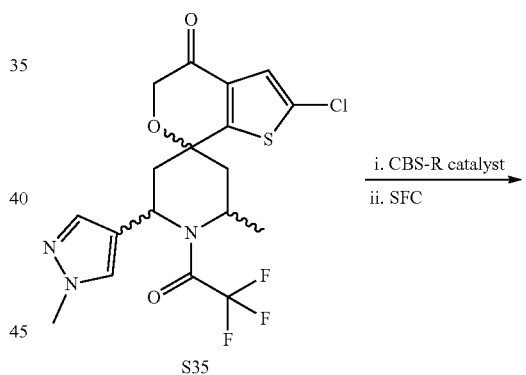

S35 i. CBS-R catalyst
ii. SFC

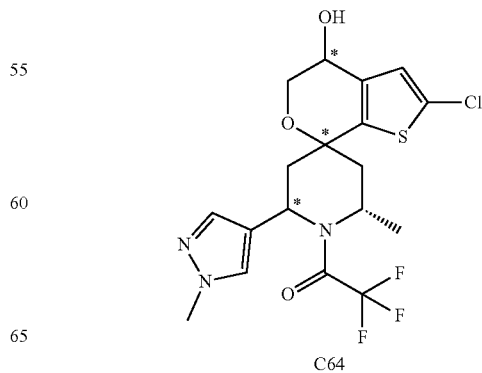

C64

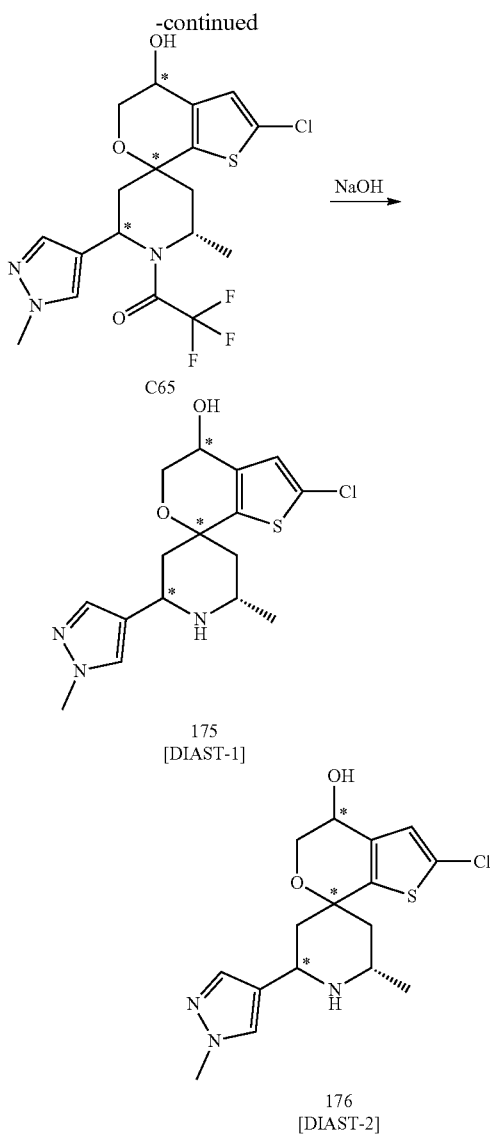

Step 1. Synthesis of 1-[(2S)-2-chloro-4-hydroxy-2'-methyl-6'-(1-methylpyrazol-4-yl)spiro[4,5-dihydrothieno[2,3-c]pyran-7,4'-piperidine]-1'-yl]-2,2,2-trifluoro-ethanone (C64)[DIAST-1] and (C65) [DIAST-2]

(R)-(+)-2-Methyl-CBS-oxazaborolidine solution (40 μL of 1 M, 0.04000 mmol) (1 M solution in THF) in THF (1 mL) was cooled to 0° C. and treated with borane; tetrahydrofuran (220 μL of 1 M, 0.2200 mmol). After 4 minutes, a solution of (2S,4S,6S)-2'-chloro-2-methyl-6-(1-methylpyrazol-4-yl)-1-(2,2,2-trifluoroacetyl)spiro[piperidine-4,7'-thieno[2,3-c]pyran]-4'-one S35 (50 mg, 0.1023 mmol) in THF (300 μL) was added slowly and the reaction was stirred at 0° C. After 15 minutes, another solution of (R)-(+)-2-Methyl-CBS-oxazaborolidine solution (40 μL of 1 M, 0.04000 mmol) and borane; tetrahydrofuran (220 μL of 1 M, 0.2200 mmol) was made and added to the reaction. After 30 minutes, the reaction was quenched with 2 N HCl, the ice bath was removed, and the mixture was stirred vigorously for 24 hours. The reaction was extracted with DCM (3×) through a phase separator. The organics were concentrated via rotovap. Purification by silica gel chromatography (0-60% EtOAc in Heptane) yielded racemic intermediate.

SFC separation (AD-H column with 10% MeOH w/5 mM ammonia) gave 1-[(2S) 2-chloro-4-hydroxy-2'-methyl-6'-(1-methylpyrazol-4-yl)spiro[4,5-dihydrothieno[2,3-c]pyran-7,4'-piperidine]-1'-yl]-2,2,2-trifluoro-ethanone (C64) [DIAST-1] (50 mg, 101%) $^1$H NMR (300 MHz, Chloroform-d) δ 7.40 (d, J=5.6 Hz, 2H), 6.88 (s, 1H), 5.52 (s, 1H), 4.52-4.37 (m, 2H), 4.00-3.76 (m, 5H), 2.74-2.48 (m, 2H), 2.27 (s, 1H), 1.81 (dd, J=14.9, 6.8 Hz, 1H), 1.28 (s, 3H). LCMS m/z 450.07 [M+H]$^+$; 1-[(2S)-2-chloro-4-hydroxy-2'-methyl-6'-(1-methylpyrazol-4-yl)spiro[4,5-dihydrothieno[2,3-c]pyran-7,4'-piperidine]-1'-yl]-2,2,2-trifluoro-ethanone (C65) [DIAST-2] (34 mg, 62%)$^1$H NMR (300 MHz, Chloroform-d) δ 7.43 (s, 1H), 7.35 (s, 1H), 6.85 (s, 1H), 5.43 (s, 1H), 4.56-4.40 (m, 2H), 4.02-3.79 (m, 5H), 2.71 (ddd, J=15.1, 8.1, 2.3 Hz, 1H), 2.37 (dd, J=15.1, 6.4 Hz, 1H), 2.08 (d, J=9.2 Hz, 1H), 1.95 (dd, J=14.6, 6.9 Hz, 1H), 1.27 (d, J=6.6 Hz, 3H). LCMS m/z 450.03 [M+H]$^+$.

Step 2. Synthesis of (2S)-2-chloro-2'-methyl-6'-(1-methylimidazol-4-yl)spiro[4,5-dihydrothieno[2,3-c]pyran-7,4'-piperidine]-4-ol (175)[DIAST-1] and (176) [DIAST-1]

1-[(2'S,4S,6'S,7S)-2-chloro-4-hydroxy-2'-methyl-6'-(1-methylpyrazol-4-yl)spiro[4,5-dihydrothieno[2,3-c]pyran-7,4'-piperidine]-1'-yl]-2,2,2-trifluoro-ethanone (C64) (50 mg, 0.094 mmol) in MeOH (2 mL) was treated with NaOH (1 mL of 1 M, 1.000 mmol) and heated to 40° C. for 30 minutes. Additional NaOH (1 mL of 1 M, 1.000 mmol) was added and the reaction was heated to 50° C. After two more hours the reaction was diluted with DCM. The organic phase was separated, passed through a phase separator, and concentrated. The material was brought up in MTBE (3 mL) and treated with hydrogen chloride (28 μL of 4 M, 0.1120 mmol) in dioxane dropwise. A white precipitate formed. The solution was concentrated and the residue brought up in water, frozen at −78° C., and lyophilized over the weekend to afford (2S)-2-chloro-2'-methyl-6'-(1-methylpyrazol-4-yl)spiro[4,5-dihydrothieno[2,3-c]pyran-7,4'-piperidine]-4-ol (Hydrochloride salt) (175) [DIAST-1] (37.9 mg, 98%). $^1$H NMR (400 MHz, Methanol-d$_4$) δ 7.72 (s, 1H), 7.58 (s, 1H), 6.92 (s, 1H), 4.52-4.45 (m, 2H), 4.03 (dd, J=12.2, 3.5 Hz, 1H), 3.88 (s, 3H), 3.83 (dd, J=12.2, 4.0 Hz, 1H), 3.69-3.58 (m, 1H), 2.47 (dt, J=14.5, 2.8 Hz, 1H), 2.33 (dt, J=14.4, 2.8 Hz, 1H), 1.98 (t, J=13.7 Hz, 1H), 1.71 (t, J=13.1 Hz, 1H), 1.30 (d, J=6.6 Hz, 3H). LCMS m/z 353.99 [M+H]$^+$.

1-[(2'S,4R,6'S,7S)-2-chloro-4-hydroxy-2'-methyl-6'-(1-methylpyrazol-4-yl)spiro[4,5-dihydrothieno[2,3-c]pyran-7,4'-piperidine]-1'-yl]-2,2,2-trifluoro-ethanone (C65) (34 mg, 0.07 mmol) in MeOH (1.5 mL) was treated with NaOH (800 μL of 1 M, 0.8 mmol) and heated to 40° C. for 30 minutes. More NaOH (800 μL of 1 M, 0.8 mmol) was added and the reaction was heated to 50° C. After two more hours the reaction was cooled to room temperature, diluted with DCM. The organic phase was separated, passed through a phase separator, and concentrated. The material was brought up in MTBE (1.5 mL) and treated with HCl (22 μL of 4 M, 0.08800 mmol) dropwise. A white precipitate formed. The solution was concentrated via rotovap and the residue brought up in water, frozen at −78° C., and lyophilized overnight to give (2S)-2-chloro-2'-methyl-6'-(1-methylpyrazol-4-yl)spiro[4,5-dihydrothieno[2,3-c]pyran-7,4'-piperidine]-4-ol (Hydrochloride salt) (176) [DIAST-2] (26.7 mg, 96%) was afforded as a white powder. $^1$H NMR (400 MHz, Methanol-d$_4$) δ 7.81 (s, 1H), 7.63 (s, 1H), 6.94 (s, 1H), 4.71

(dd, J=12.6, 2.9 Hz, 1H), 4.50 (t, J=3.6 Hz, 1H), 4.05 (dd, J=12.3, 3.4 Hz, 1H), 3.90 (s, 3H), 3.85 (dd, J=12.2, 3.9 Hz, 1H), 3.71 (dtq, J=13.4, 6.8, 2.9 Hz, 1H), 2.53 (dt, J=14.4, 2.8 Hz, 1H), 2.42 (dt, J=14.8, 2.8 Hz, 1H), 2.21 (dd, J=14.4, 12.6 Hz, 1H), 1.72 (dd, J=14.8, 12.2 Hz, 1H), 1.35 (d, J=6.6 Hz, 3H). LCMS m/z 354.04 [M+H]$^+$.

Compound 177

(2'S,4R,6'S, 7S)-2-chloro-2'-methyl-6'-(1-methyltriazol-4-yl)spiro[4,5-dihydrothieno[2,3-c]pyran-7,4'-piperidine]-4-ol] (177)

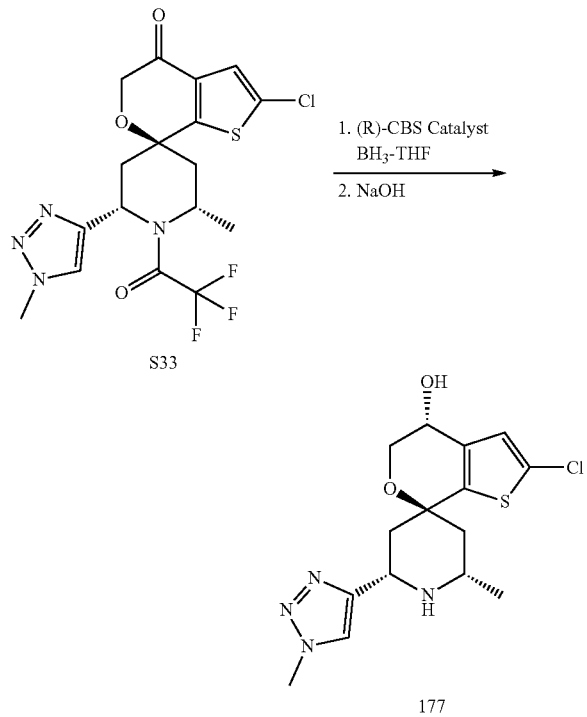

Step 1. Synthesis of (2'S,4R,6'S, 7S)-2-chloro-2'-methyl-6'-(1-methyltriazol-4-yl)spiro[4,5-dihydrothieno[2,3-c]pyran-7,4'-piperidine]-4-ol] (177)

To tetrahydrofuran (500 μL) cooled to 0° C. was added (3aR)-1-methyl-3,3-diphenyl-3a,4,5,6-tetrahydropyrrolo[1,2-c][1,3,2]oxazaborole ((R)—CBS catalyst) (25 μL of 1 M, 0.025 mmol) followed by borane tetrahydrofuran (250 μL of 1 M, 0.25 mmol). After stirring for 5 minutes, a solution of (2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one S33 (25 mg, 0.05570 mmol) in THF (1000 μL) was added, dropwise. The mixture stirred at 0° C. for 1 hour. The mixture was concentrated, diluted with MeOH (1.5 mL) and quenched with NaOH (100 μL of 6 M, 0.6000 mmol). The mixture was warmed to 50° C. and stirred overnight. Purification by reversed-phase HPLC (Method: C18 Waters Sunfire column (30×150 mm, 5 micron). Gradient: MeCN in H$_2$O with 5 mM HCl) afforded (2'S,4R,6'S, 7S)-2-chloro-2'-methyl-6'-(1-methyltriazol-4-yl)spiro[4,5-dihydrothieno[2,3-c]pyran-7,4'-piperidine]-4-ol (Hydrochloride salt) 177 (3.0 mg, 13%). $^1$H NMR (300 MHz, Methanol-d$_4$) δ 8.11 (d, J=2.4 Hz, 1H), 6.94 (s, 1H), 4.90 (d, J=3.1 Hz, 1H), 4.51 (t, J=3.6 Hz, 1H), 4.13 (d, J=2.2 Hz, 3H), 4.07 (dd, J=12.2, 3.5 Hz, 1H), 3.87 (dd, J=12.3, 3.9 Hz, 1H), 3.74 (ddt, J=13.0, 9.4, 6.4 Hz, 1H), 2.78-2.51 (m, 1H), 2.51-2.19 (m, 2H), 1.87 (ddd, J=30.8, 14.7, 12.2 Hz, 1H), 1.39 (dd, J=6.6, 3.1 Hz, 3H). LCMS m/z 355.03 [M+H]$^+$.

Compounds 178-182

Compounds 178-182 (see Table 5) were prepared in two or three steps from ketone intermediates in Table 5 using the reduction and deprotection methods as described for compounds 174-177. Final compounds were made through hydrolysis with NaOH. Any modifications to these methods are noted in Table 5 and accompanying footnotes.

TABLE 5

Method of preparation, structure and physicochemical data for compounds 178-182

| Product | Ketone intermediate | Reduction method | $^1$H NMR; LCMS m/z [M + H]$^+$ |
|---|---|---|---|
| Compound 178 | S34 | Compound 175 and 176[6,7] | $^1$H NMR (300 MHz, Chloroform-d) δ 7.31 (s, 1H), 6.82 (s, 1H), 6.73 (s, 1H), 4.45 (t, J = 3.2 Hz, 1H), 4.23 (dd, J = 11.6, 2.6 Hz, 1H), 4.01 (dd, J = 12.2, 3.1 Hz, 1H), 3.88 (dd, J = 12.2, 3.4 Hz, 1H), 3.62 (s, 3H), 3.22 (dtt, J = 12.5, 6.1, 3.2 Hz, 1H), 2.23 (dt, J = 13.4, 2.6 Hz, 1H), 2.10 (dt, J = 13.9, 2.6 Hz, 1H), 1.83 (dd, J = 13.4, 11.6 Hz, 1H), 1.30 (dd, J = 14.0, 11.4 Hz, 1H), 1.11 (d, J = 6.4 Hz, 3H). LCMS m/z 354.04 [M + H]$^+$ |

TABLE 5-continued

Method of preparation, structure and physicochemical data for compounds 178-182

| Product | Ketone intermediate | Reduction method | $^1$H NMR; LCMS m/z [M + H]$^+$ |
|---|---|---|---|
| 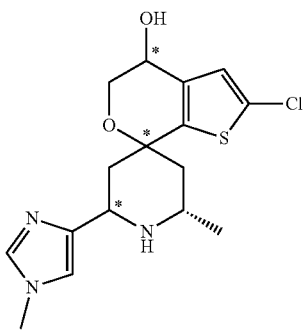 Compound 179 | 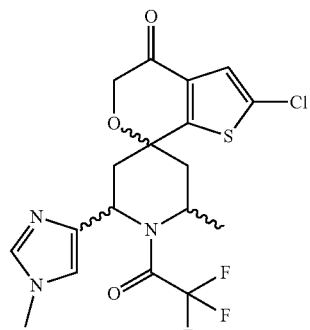 S34 | Compound 175 and 176[6,7] | $^1$H NMR (300 MHz, Chloroform-d) δ 7.34 (s, 1H), 6.81 (s, 1H), 6.75 (s, 1H), 4.42 (t, J = 2.7 Hz, 1H), 4.14 (dd, J = 11.8, 2.5 Hz, 1H), 4.03 (dd, J = 12.4, 2.8 Hz, 1H), 3.92 (dd, J = 12.4, 2.7 Hz, 1H), 3.62 (s, 3H), 3.44-3.26 (m, 1H), 2.39 (dd, J = 13.9, 2.8 Hz, 1H), 2.06-1.96 (m, 1H), 1.68 (dd, J = 13.9, 11.7 Hz, 1H), 1.49 (dd, J = 13.4, 11.3 Hz, 1H), 1.13 (d, J = 6.3 Hz, 3H). LCMS m/z 354.04 [M + H]$^+$ |
| 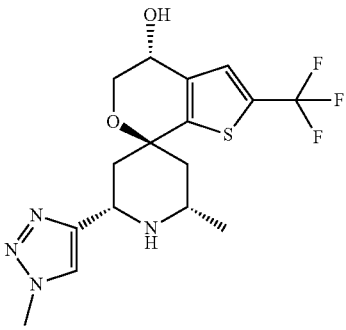 Compound 180 | 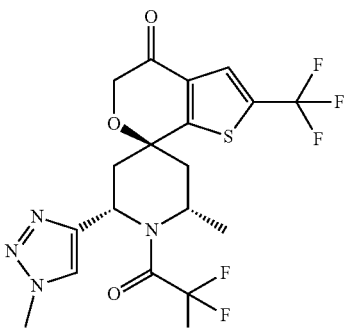 S32 | Compound 177[4,5] | $^1$H NMR (300 MHz, Methanol-d$_4$) δ 7.89 (d, J = 4.5 Hz, 1H), 7.47 (d, J = 1.3 Hz, 1H), 4.59 (t, J = 3.8 Hz, 1H), 4.45 (dd, J = 12.0, 2.7 Hz, 1H), 4.13-4.02 (m, 4H), 3.87 (dd, J = 12.3, 4.1 Hz, 1H), 3.51-3.34 (m, 1H), 2.47 (dt, J = 14.0, 2.7 Hz, 1H), 2.27 (dt, J = 13.8, 2.7 Hz, 1H), 1.95 (ddd, J = 34.7, 13.9, 12.0 Hz, 1H), 1.57 (ddd, J = 29.0, 14.0, 11.6 Hz, 1H), 1.21 (dd, J = 6.5, 4.0 Hz, 3H). LCMS m/z 388.87 [M + H]$^+$ |
| 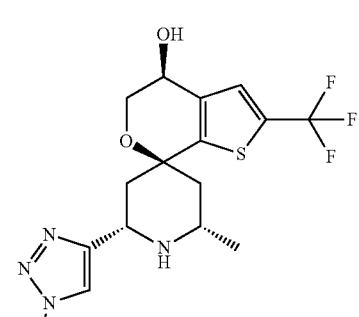 Compound 181 (Note: Amorphous form obtained) | 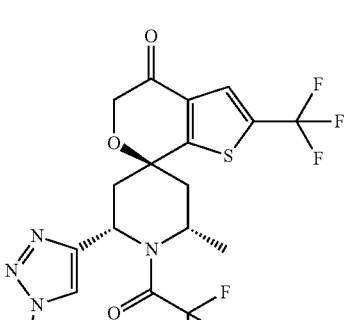 S32 | Compound 174[1,2,3] | $^1$H NMR (400 MHz, Methanol-d$_4$) δ 7.83 (s, 1H), 7.46 (d, J = 1.2 Hz, 1H), 4.58 (t, J = 3.8 Hz, 1H), 4.34 (dd, J = 11.8, 2.6 Hz, 1H), 4.11-4.03 (m, 5H), 3.86 (dd, J = 12.2, 4.2 Hz, 1H), 3.39-3.34 (m, 1H), 2.46-2.41 (m, 1H), 2.26-2.19 (m, 1H), 1.78 (dd, J = 13.8, 11.9 Hz, 1H), 1.53 (dd, J = 13.6, 11.5 Hz, 1H), 1.17 (d, J = 6.5 Hz, 3H). LCMS m/z 389.14 [M + H]$^+$. |

TABLE 5-continued

Method of preparation, structure and physicochemical data for compounds 178-182

| Product | Ketone intermediate | Reduction method | $^1$H NMR; LCMS m/z [M + H]$^+$ |
|---|---|---|---|
| 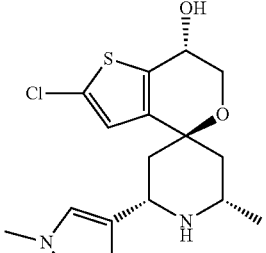<br>Compound 182 | 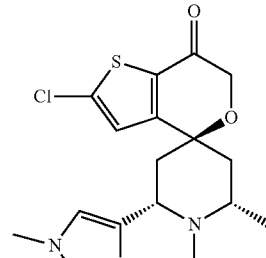<br>S36 | Compound 174[3,2,8,9,10] | $^1$H NMR (300 MHz, Chloroform-d) δ 7.43 (s, 1H), 6.63 (s, 1H), 4.53 (t, J = 2.9 Hz, 1H), 4.37 (dd, J = 11.8, 2.6 Hz, 1H), 4.05 (s, 3H), 3.99 (dd, J = 13.8, 2.8 Hz, 2H), 3.35 (ddt, J = 12.7, 6.4, 3.2 Hz, 1H), 2.25 (dt, J = 13.9, 2.6 Hz, 1H), 1.86 (dt, J = 13.5, 2.5 Hz, 1H), 1.69 (dd, J = 13.9, 11.8 Hz, 1H), 1.54 (dd, J = 13.5, 11.3 Hz, 1H), 1.12 (d, J = 6.4 Hz, 3H). LCMS m/z 355.08 [M + H]$^+$. |

[1]Formic acid and triethylamine were added before Ketone intermediate (step 1)
[2]Silica gel purification (0-60% EtOAc in Heptane) afforded product (step 1)
[3]Product was not washed with EtOH (step 2)
[4]Reaction was stirred for 15 minutes before quenching
[5]Stirred at 40° C. for four hours after quenching with NaOH and MeOH (step 2)
[6]Step 1 was run with both the CBS-(S) catalyst and the CBS-(R) catalysts in two separate reactions. However, both reactions proceeded with poor d.r. and so they were combined to make the racemic which was separated by SFC as in Step 2.
[7]After extracted with DCM, purification by silica gel chromatography (Gradient: 0-20% MeOH in DCM) yielded the product (step 3)
[8]Reaction was stirred overnight (step 1)
[9]Stirred at 50° C. for two hours after quenching with NaOH and MeOH (step 2)
[10]Compound 182 contained approximately 15% of a diastereomer created via differentiation from the enantiomer of S36 present in S36.

Compound 181

(2S,4S,4'S,6S)-2-methyl-6-(1-methyl-1H-1,2,3-triazol-4-yl)-2'-(trifluoromethyl)-4',5'-dihydrospiro[piperidine-4,7'-thieno[2,3-c]pyran]-4'-ol (181), Amorphous Form

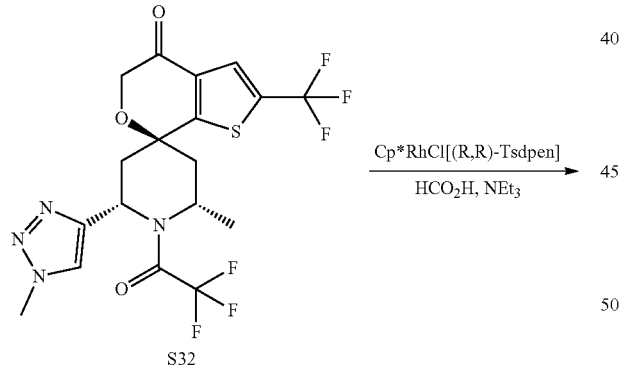

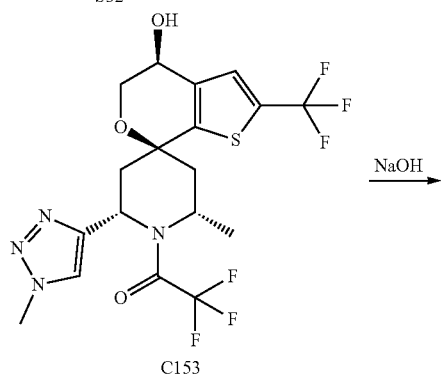

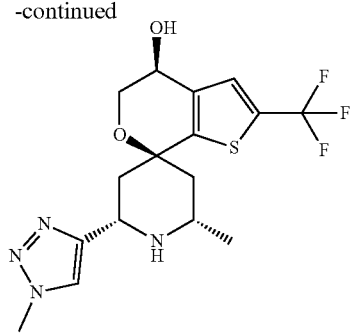
181

Step 1. Synthesis of 2,2,2-trifluoro-1-[(2'S,4S,6'S,7S)-4-hydroxy-2'-methyl-6'-(1-methyltriazol-4-yl)-2-(trifluoromethyl)spiro[4,5-dihydrothieno[2,3-c]pyran-7,4'-piperidine]-1'-yl]ethenone (C153)

To (2S,4S,6S)-2-methyl-6-(1-methyltriazol-4-yl)-1-(2,2,2-trifluoroacetyl)-2'-(trifluoromethyl)spiro[piperidine-4,7'-thieno[2,3-c]pyran]-4'-one S32 (2.23 g, 4.63 mmol) in DCM (20 mL) was added a solution of 1,2,3,4,5 pentamethylcyclopentane rhodium(2+) tetrachloride (7 mg, 0.002 mmol) and N-[(1R,2R)-2-amino-1,2-diphenyl-ethyl]-4-methylbenzenesulfonamide (8.5 mg, 0.005 mmol) in DCM (2 mL), followed by a solution of formic acid (0.9 mL, 5.15 mmol) and triethylamine (1.3 mL, 2.01 mmol). The flask was fitted with an empty balloon to capture the CO$_2$ off-gas byproduct. After three hours, the mixture was washed with saturated aqueous sodium bicarbonate (10 mL). The organic phase was separated, passed through a phase separator, and concentrated. Silica gel purification (Column: 40 g silica gel, Gradient: 0-50% EtOAc in Heptane) afforded 2,2,2-trifluoro-1-[(2'S,4S,6'S,7S)-4-hydroxy-2'-methyl-6'-(1-methyltriazol-4-yl)-2-(trifluoromethyl)spiro[4,5-dihydrothieno[2,3-c]pyran-7,4'-piperidine]-1'-yl]ethenone C153 (2.27 g, 100%) as a white solid. LCMS m/z 485.11 [M+H]⁺.

Step 2. Synthesis of (2'S,4S,6'S, 7S)-2'-methyl-6'-(1-methyltriazol-4-yl)-2-(trifluoromethyl)spiro[4,5-dihydrothieno[2,3-c]pyran-7,4'-piperidine]-4-ol (181)

To a solution of 2,2,2-trifluoro-1-[(2'S,4S,6'S,7S)-4-hydroxy-2'-methyl-6'-(1-methyltriazol-4-yl)-2-(trifluoromethyl)spiro[4,5-dihydrothieno[2,3-c]pyran-7,4'-piperidine]-1'-yl]ethenone C153 (2.27 g, 4.63 mmol) in MeOH (45 mL) was added NaOH (8 mL of 6 M, 48.00 mmol), and the mixture was stirred at 60° C. After 75 minutes, the mixture was diluted with saturated aqueous ammonium chloride until pH 10 (about 40 mL), water (40 mL), and extracted with MTBE (100 mL). The aqueous layer was extracted with additional MTBE (2×50 mL), and the combined organic layers were washed with saturated aqueous NaCl, dried over MgSO₄, and concentrated to give amorphous (2'S,4S,6'S, 7S)-2'-methyl-6'-(1-methyltriazol-4-yl)-2-(trifluoromethyl)spiro[4,5-dihydrothieno[2,3-c]pyran-7,4'-piperidine]-4-ol 181 (1.84 g, 88%). ¹H NMR (400 MHz, Chloroform-d) δ 7.48 (s, 1H), 7.39 (q, J=1.2 Hz, 1H), 4.58 (d, J=8.0 Hz, 1H), 4.44 (dd, J=11.7, 2.5 Hz, 1H), 4.09 (s, 4H), 4.01 (dd, J=12.5, 2.7 Hz, 1H), 3.43 (ddd, J=11.2, 6.4, 2.5 Hz, 1H), 2.48 (dt, J=13.8, 2.6 Hz, 1H), 2.16-2.07 (m, 2H), 1.77 (dd, J=13.9, 11.8 Hz, 1H), 1.63 (s, 1H), 1.28 (s, 1H), 1.18 (d, J=6.3 Hz, 3H). LCMS m/z 389.09 [M+H]⁺.

Compound 183

(2'S,6'S, 7S)-2-chloro-4,4-difluoro-2'-methyl-6'-(1-methyltriazol-4-yl)spiro[5H-thieno[2,3-c]pyran-7,4'-piperidine] (183)

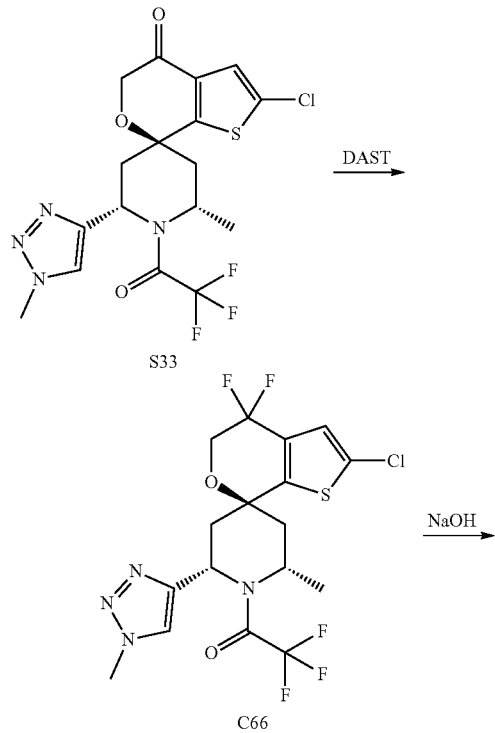

Step 1. Synthesis of 1-[(2'S,6'S, 7S)-2-chloro-4,4-difluoro-2'-methyl-6'-(1-methyltriazol-4-yl)spiro [5H-thieno[2,3-c]pyran-7,4'-piperidine]-1'-yl]-2,2,2-trifluoro-ethanone (C66)

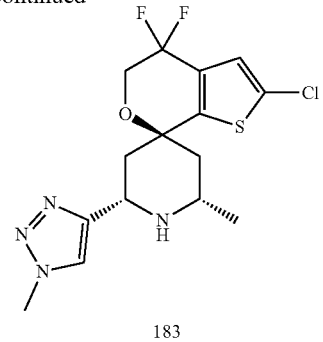

183

(2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one S33 (40 mg, 0.08912 mmol) was dissolved in DCM (100 μL) and DAST (35 μL, 0.2649 mmol) was added. The reaction was heated to 40° C. and stirred for 3 hours. Additional DAST (35 μL, 0.2649 mmol) was added and stirred over the weekend. The solution was diluted with DCM and poured into aqueous NaHCO₃ stirring at 0° C. The organic phase was separated, passed through a phase separator, and concentrated to give crude 1-[(2'S,6'S,7S)-2-chloro-4,4-difluoro-2'-methyl-6'-(1-methyltriazol-4-yl)spiro [5H-thieno[2,3-c]pyran-7,4'-piperidine]-1'-yl]-2,2,2-trifluoro-ethanone C66 (41 mg, 42%). LCMS m/z 468.71 [M+H]⁺.

Step 2. Synthesis of (2'S,6'S, 7S)-2-chloro-4,4-difluoro-2'-methyl-6'-(1-methyltriazol-4-yl)spiro[5H-thieno[2,3-c]pyran-7,4'-piperidine] (183)

(2'S,6'S,7S)-2-chloro-4,4-difluoro-2'-methyl-6'-(1-methyltriazol-4-yl)spiro[5H-thieno[2,3-c]pyran-7,4'-piperidine]-1'-yl]-2,2,2-trifluoro-ethanone C66 was stirred in 6M aqueous NaOH (10 eq) for five hours. Solvent was removed through rotary evaporation. Purification by reversed-phase HPLC (Method: C18 Waters Sunfire column (30×150 mm, 5 micron) with 10 mM Ammonium Hydroxide) to afford (2'S,6'S,7S)-2-chloro-4,4-difluoro-2'-methyl-6'-(1-methyltriazol-4-yl)spiro[5H-thieno[2,3-c]pyran-7,4'-piperidine] 183 (2 mg, 6%). LCMS m/z 375.11 [M+H]⁺.

Compounds 184 and 185

(2'S,6'S, 7S)-2-chloro-4-(difluoromethyl)-2'-methyl-6'-(1-methyltriazol-4-yl)spiro[5H-thieno[2,3-c]pyran-7,4'-piperidine]-4-ol (184) [DIAST-1] and (185) [DIAST-2]

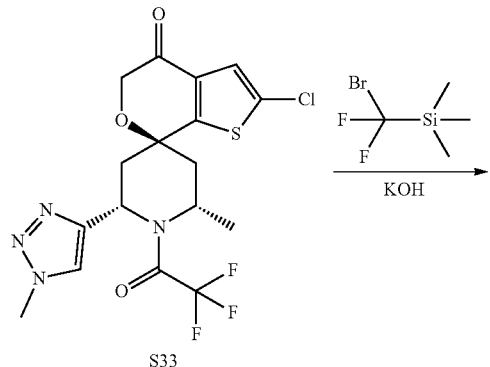

S33

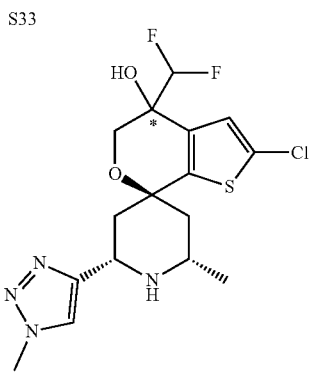

184
DIAST-1

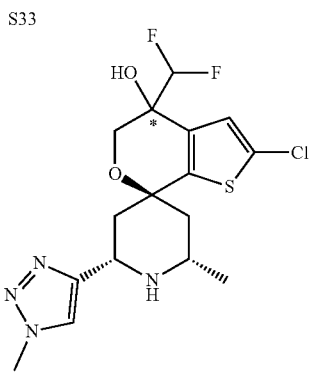

185
DIAST-2

To a solution of (2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one S33 (65 mg, 0.1448 mmol) in MeCN (2.4 mL) was added DMPU (34 μL, 0.2822 mmol) followed by [bromo(difluoro)methyl]-trimethyl-silane (35 mg, 0.1723 mmol) and PPh₃ (40 μL, 0.1726 mmol). The resulting solution was heated at 55° C. After four hours the reaction was cooled to room temperature. Aqueous KOH (720 μL of 1 M, 0.7200 mmol) was added and the reaction was stirred for 48 hours. The reaction was quenched with sodium bicarbonate and DCM. The organic phase was separated, passed through a phase separator. Purification by reversed-phase HPLC (Method: C18 Waters Sunfire column (30×150 mm, 5 micron). Gradient: MeCN in H₂O with 0.1% trifluoroacetic) was performed.

Some impurities still existed. Purification by silica gel chromatography (Gradient: 0-20% MeOH in DCM) yielded both separated diastereomers (2'S,6'S,7S)-2-chloro-4-(difluoromethyl)-2'-methyl-6'-(1-methyltriazol-4-yl)spiro[5H-thieno[2,3-c]pyran-7,4'-piperidine]-4-ol (Trifluoroacetate salt) 184[DIAST-1](4.3 mg, 6%). $^1$H NMR (400 MHz, Methanol-d₄) δ 7.94 (s, 1H), 7.01 (s, 1H), 5.97 (t, J=55.2 Hz, 1H), 4.57 (dd, J=12.3, 2.9 Hz, 1H), 4.10 (s, 4H), 3.81 (dt, J=12.6, 2.2 Hz, 1H), 3.60-3.42 (m, 1H), 2.60 (dt, J=14.4, 2.7 Hz, 1H), 2.18 (dt, J=14.1, 2.6 Hz, 1H), 2.08-1.95 (m, 1H), 1.69 (dd, J=14.2, 11.8 Hz, 1H), 1.26 (d, J=6.5 Hz, 3H). LCMS m/z 405.02 [M+H]⁺. (2'S,6'S,7S)-2-chloro-4-(difluoromethyl)-2'-methyl-6'-(1-methyltriazol-4-yl)spiro[5H-thieno[2,3-c]pyran-7,4'-piperidine]-4-ol (Trifluoroacetate salt) 185[DIAST-2](8.5 mg, 11%). $^1$H NMR (400 MHz, Methanol-d₄) δ 8.06 (s, 1H), 7.04 (d, J=0.9 Hz, 1H), 5.98 (t, J=55.1 Hz, 1H), 4.91-4.86 (m, 1H), 4.20-4.05 (m, 4H), 3.90-3.71 (m, 2H), 2.64-2.33 (m, 3H), 1.85 (dd, J=14.8, 12.2 Hz, 1H), 1.40 (d, J=6.6 Hz, 3H). LCMS m/z 405.02 [M+H]⁺.

Preparation of S37

4-aminohexan-2-one hydrochloride salt (S37)

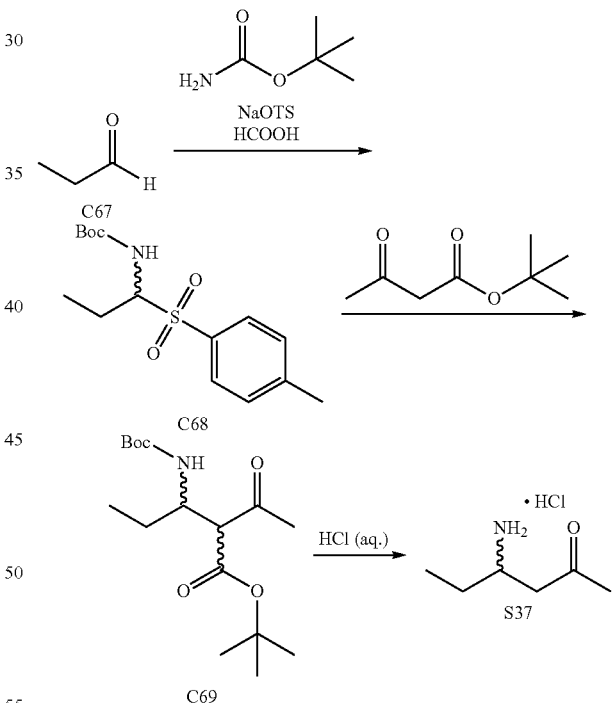

Step 1. Synthesis of tert-butyl N-[1-(p-tolylsulfonyl)propyl]carbamate (C68)

To a solution of tert-butyl carbamate C67 (20 g, 0.1639 mol) and 4-methylbenzenesulfinate (53 g, 0.3313 mol) in MeOH (120 mL) and H₂O (240 mL) was added propanal (15.082 g, 19 mL, 0.2545 mol) and formic acid (76.921 g, 65 mL, 1.6211 mol) dropwise at 0° C. The reaction mixture was stirred at room temperature for 24 hours. The reaction mixture was filtered, washed with water (100 mL), and dried to afford tert-butyl N-[1-(p-tolylsulfonyl)propyl]carbamate C68 (46 g, 85%). $^1$H NMR (300 MHz, DMSO-$d_6$) δ 7.82 (d, J=9.6 Hz, 1H), 7.65 (d, J=8.4 Hz, 2H), 7.48-7.40 (m, 2H), 4.63-4.56 (m, 1H), 2.39 (d, J=14.4 Hz, 3H), 2.01-1.95 (m, 1H), 1.69-1.61 (m, 1H), 1.17 (s, 9H), 0.91 (t, J=7.2 Hz, 3H) as an off white solid.

Step 2. Synthesis of tert-butyl 2-acetyl-3-(tert-butoxycarbonylamino) pentanoate (C69)

To a solution of NaH (2.5 g, 60% (w/w), 0.0625 mol) in THF (160 mL) was added tert-butyl N-[1-(p-tolylsulfonyl)propyl]carbamate C68 (10 g, 0.0303 mol) portion-wise at room temperature and stirred for 5 minutes and then tert-butyl 3-oxobutanoate (5.1001 g, 5.4 mL, 0.0319 mol) in THF (40 mL) was added dropwise and stirred at same temperature for 2 hours. The reaction mixture was quenched with NH$_4$Cl solution (150 mL) and extracted with DCM (2×300 mL). The organic layer was dried over anhydrous Na$_2$SO$_4$ concentrated under reduced pressure and dried to provide crude tert-butyl 2-acetyl-3-(tert-butoxycarbonylamino)pentanoate C69 (11 g, 98%) as a yellow gum. $^1$H NMR (300 MHz, DMSO-$d_6$) δ 6.72-6.56 (m, 1H), 3.97-3.89 (m, 1H), 3.58-3.44 (m, 1H), 2.16 (s, 3H), 1.48-1.15 (m, 20H), 0.85-0.76 (m, 3H). LCMS m/z 316.27 [M+H]$^+$.

Step 3. Synthesis of 4-aminohexan-2-one (S37)

A solution of tert-butyl 2-acetyl-3-(tert-butoxycarbonylamino)pentanoate C69 (11 g, 0.0296 mol) in 10% aqueous HCl (120 mL of 10% (w/v), 0.3291 mol) was heated to 110° C. and stirred for 2 hours. The reaction mixture was extracted with diethyl ether (4×50 mL). The aqueous part was evaporated under reduced pressure and dried to afford 4-aminohexan-2-one S37 (Hydrochloride Salt) (3.92 g, 85%) as a pale brown liquid. $^1$H NMR (400 MHz, DMSO-$d_6$) δ 8.00 (s, 3H), 3.38-3.30 (m, 1H), 2.89-2.73 (m, 2H), 2.14 (s, 3H), 1.63-1.49 (m, 2H), 0.91 (t, J=10.4 Hz, 3H). LCMS m/z 116.3 [M+H]$^+$.

Preparation of S38

4-amino-5-methyl-hexan-2-one hydrochloride salt (S38)

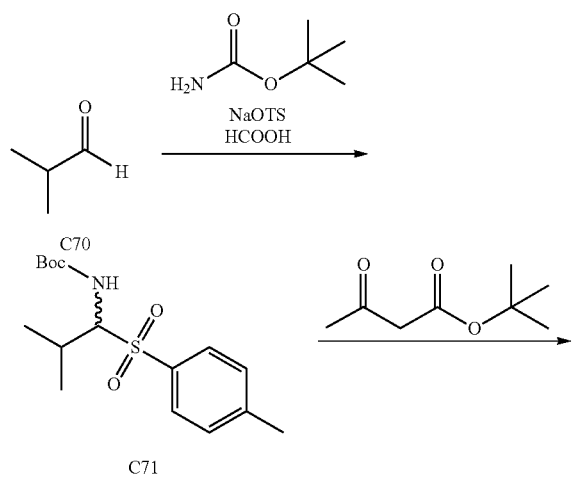

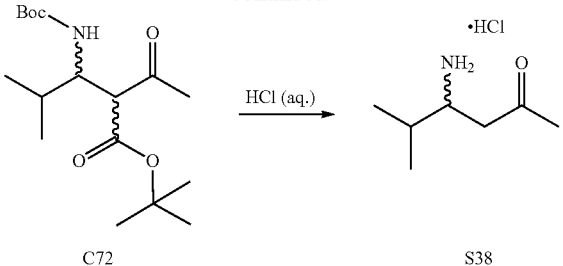

Step 1. Synthesis of tert-butyl N-[2-methyl-1-(p-tolylsulfonyl)propyl]carbamate (C71)

To a stirred solution of 2-methylpropanal (18.652 g, 23.610 mL, 0.2535 mol) and tert-butyl carbamate C70 (20 g, 0.1690 mol) in MeOH (200 mL) and Water (50 mL) at room temperature was added sodium p-toluenesulfinate (60.835 g, 0.3380 mol) followed by formic acid (79.370 g, 65.057 mL, 1.6900 mol) and then the reaction mixture was stirred at room temperature for 24 hours. The reaction mixture was filtered, washed with water (200 mL) and diethyl ether (50 mL), and dried under vacuum to afford crude tert-butyl N-[2-methyl-1-(p-tolylsulfonyl)propyl]carbamate C71 (45 g, 73%) as an off white solid. $^1$H NMR (300 MHz, DMSO-$d_6$) δ 7.81 (d, J=10.5 Hz, 1H), 7.67 (d, J=8.1 Hz, 2H), 7.39 (d, J=8.1 Hz, 2H), 4.58 (q, J=5.7 Hz, 1H), 2.46-2.36 (m, 4H), 1.14 (s, 9H), 1.00 (s, 6H).

Step 2. Synthesis of tert-butyl 2-acetyl-3-(tert-butoxycarbonylamino)-4-methyl-pentanoate (C72)

To a stirred solution of NaH (2.1998 g, 0.0550 mol) in THF (100.00 mL) was added tert-butyl N-[2-methyl-1-(p-tolylsulfonyl)propyl]carbamate C71 (10 g, 0.0275 mol) at room temperature and the reaction was stirred for 20 minutes. tert-Butyl 3-oxobutanoate (5.3270 g, 5.6074 mL, 0.0330 mol) in THF (30.000 mL) was added and stirred for 2 hours at room temperature. The reaction mixture was poured into saturated ammonium chloride (500 mL) at 10° C. and extracted with EtOAc (2×200 mL). The combined organic layers were dried over anhydrous Na$_2$SO$_4$ and filtered, concentrated under reduced pressure to get crude tert-butyl 2-acetyl-3-(tert-butoxycarbonylamino)-4-methyl-pentanoate C72 (11 g, 45%) as a brown liquid. LCMS m/z 330.2 [M+H]$^+$.

Step 3. Synthesis of 4-amino-5-methyl-hexan-2-one (S38)

A solution of tert-butyl 2-acetyl-3-(tert-butoxycarbonylamino)-4-methyl-pentanoate C72 (15 g, 0.0319 mol) in HCl (290 mL of 10% (w/v), 0.7954 mol) was heated to 110° C. for 3 hours. The reaction mixture was concentrated under reduced pressure to obtained crude compound (6.2 g). The reaction was titrated with n-pentane (2×100 mL) and dried under vacuum to afford 4-amino-5-methyl-hexan-2-one S38 (Hydrochloride Salt) (5.1 g, 96%), as a brown semi-solid. $^1$H NMR (400 MHz, DMSO-$d_6$) δ 7.96 (br s, 3H), 3.34-3.28 (m, 1H), 2.86-2.75 (m, 2H), 2.15 (s, 3H), 1.94-1.86 (m, 1H), 0.88 (s, 6H) LCMS m/z 130.2 [M+H]$^+$.

Preparation of S39

1-cyclobutyl-3-oxo-butyl)ammonium chloride (S39)

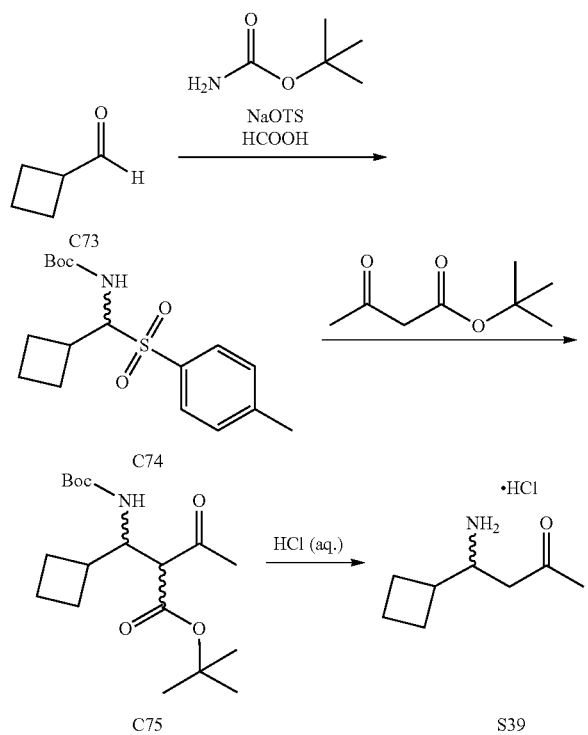

Step 1. Synthesis of tert-butyl N-[cyclobutyl(p-tolylsulfonyl)methyl]carbamate (C74)

To a mixture of sodium p-toluenesulfinate (27.843 g, 0.1547 mol) and tert-butyl carbamate C73 (Hydrochloride Salt) (12 g, 0.0773 mol) in MeOH (120.00 mL) and Water (240.00 mL) was added formic acid (12.20 g, 10.00 mL, 0.2598 mol) and cyclobutanecarbaldehyde C77 (10 g, 0.1177 mol) at 0° C. The mixture was stirred under nitrogen at room temperature for 48 hours. The white precipitate was filtered under vacuum, washed with water (3×50 mL), and dried to afford tert-butyl N-[cyclobutyl(p-tolylsulfonyl)methyl]carbamate C74 (25 g, 93%), as a white solid. $^1$H NMR (300 MHz, DMSO-$d_6$) δ 7.82 (d, J=9.9 Hz, 1H), 7.67 (d, J=8.4 Hz, 2H), 7.42 (d, J=8.1 Hz, 2H), 4.72 (t, J=9.3 Hz, 1H), 2.86-2.82 (m, 1H), 2.37 (s, 3H), 2.01-1.73 (m, 6H), 1.18 (s, 9H).

Step 2. Synthesis of tert-butyl 2-[(tert-butoxycarbonylamino)-cyclobutyl-methyl]-3-oxo-butanoate (C75)

A mixture of tert-butyl N-[cyclobutyl(p-tolylsulfonyl)methyl]carbamate C74 (25 g, 0.0722 mol) and tert-butyl 3-oxobutanoate (Hydrochloride Salt) (15.5 g, 0.0788 mol) in THF (550 mL) was added NaH (5.35 g, 60% (w/w), 0.133 mmol) at 0° C. The mixture was stirred under nitrogen at room temperature for 48 hours, and white precipitate was filtered under vacuum, washed with water (3×5 mL), and dried to afford tert-butyl 2-[(tert-butoxycarbonylamino)-cyclobutyl-methyl]-3-oxo-butanoate C75 (25 g, 99%), as pale yellow oil. $^1$H NMR (400 MHz, Chloroform-d): δ 4.30-4.11 (m, 1H), 3.46 (d, J=4.0 Hz, 1H), 2.49-2.42 (m, 1H), 2.25 (s, 3H), 1.94-1.74 (m, 6H), 1.48-1.44 (m, 18H). LCMS m/z 342.13 [M+1]$^+$.

Step 3. Synthesis of (1-cyclobutyl-3-oxo-butyl)ammonium chloride (S39)

To a mixture of tert-butyl 2-[(tert-butoxycarbonylamino)-cyclobutyl-methyl]-3-oxo-butanoate C75 (25 g, 0.0718 mol) in Water (100 mL) was added with HCl (100 mL of 5 M, 0.5000 mol) at room temperature. The mixture was stirred under nitrogen at 110° C. for 16 hours. The reaction mixture was diluted with water (100 mL) and washed with diethyl ether (3×100 mL). The aqueous layer was evaporated under vacuum and dried to afford (1-cyclobutyl-3-oxo-butyl)ammonium chloride S39 (12.81 g, 100%), as pale brown semisolid. $^1$H NMR (400 MHz, DMSO-$d_6$) δ 7.86 (brs, 3H), 3.40-3.36 (m, 1H), 2.69-2.67 (m, 2H), 2.51-2.43 (m, 1H), 2.14 (s, 3H), 1.97-1.68 (m, 6H). LCMS m/z 142.2 [M+H]$^+$.

Preparation of S40

4-amino-5-methoxy-pentan-2-one hydrochloride salt (S40)

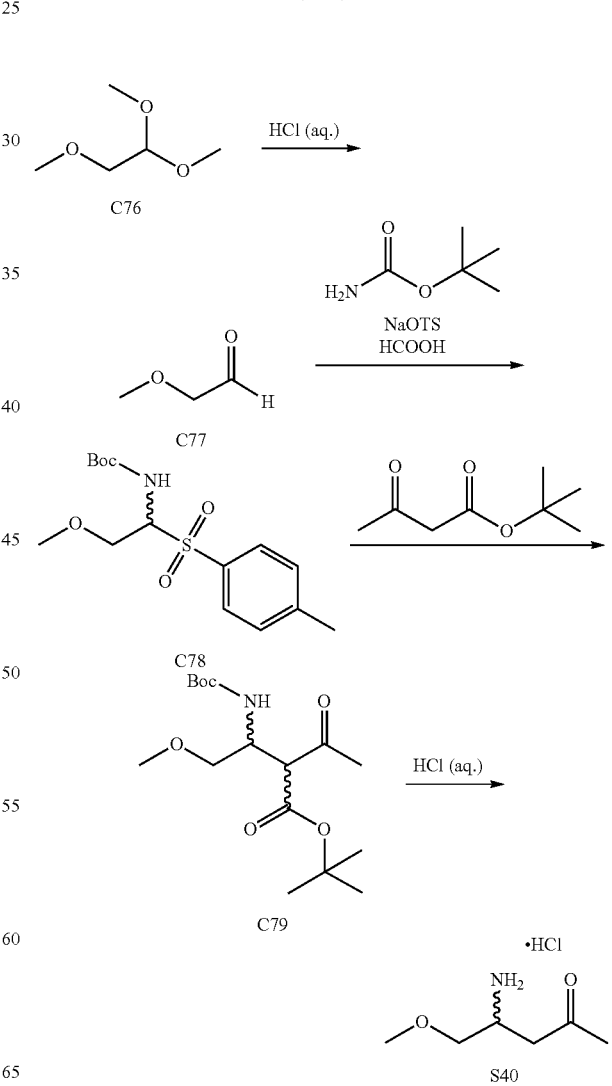

Step 1. Synthesis of 2-methoxyacetaldehyde (C77)

A stirred solution of 1,1,2-trimethoxyethane C76 (20 g, 0.1631 mol) in aqueous HCl (300 mL of 0.5 M, 0.1500 mol) was heated to 55° C. for 4 hours. The reaction mixture was cooled to room temperature and saturated with excess NaCl salt. The reaction was extracted with DCM (5×500 mL). The combined organic layer was dried over sodium sulfate, filtered, and evaporated under vacuum at below 25° C. to afford crude 2-methoxyacetaldehyde C77 (10 g, 66%) as a yellow liquid. $^1$H NMR (400 MHz, Chloroform-d) δ: 9.73 (s, 1H), 4.05 (s, 2H), 3.52 (s, 3H).

Step 2. Synthesis of tert-butyl N-[2-methoxy-1-(p-tolylsulfonyl)ethyl] carbamate (C78)

To a stirred solution of tert-butyl carbamate (2.2 g, 0.0186 mol) in MeOH (10 mL) and water (20 mL) were added sodium p-toluenesulfinate (6.7 g, 0.0368 mol), 2-methoxy-acetaldehyde C77 (2 g, 0.0243 mol) and formic acid (8.784 g, 7.20 mL, 0.1889 mol) at 0° C. The reaction mixture was stirred at room temperature for 16 hours. The reaction mixture was extracted with DCM (3×100 ml). The combined organic extracts were dried over Na$_2$SO$_4$, filtered and evaporated under vacuum. Purification by silica chromatography (Eluent: 20% EtOAc in pet. ether) afforded tert-butyl N-[2-methoxy-1-(p-tolylsulfonyl)ethyl]carbamate C78 (5 g, 68%) as a white solid. $^1$H NMR (400 MHz, Chloroform-d) δ: 7.78 (d, J=8 Hz, 2H), 7.32 (d, J=8 Hz, 2H), 4.99-4.94 (m, 1H), 4.13-4.09 (m, 1H), 3.83-3.79 (m, 1H), 3.42 (s, 3H), 2.42 (s, 3H), 1.26 (s, 9H). LCMS m/z 330.36 [M+H]$^+$.

Step 3. Synthesis of tert-butyl 2-acetyl-3-(tert-butoxycarbonylamino)-4-methoxy-butanoate (C79)

To a stirred solution of NaH (1 g, 57% (w/w), 0.0238 mol) in THF (35 mL) was added tert-butyl 3-oxobutanoate (2.35 g, 2.4737 mL, 0.0147 mol) at 0° C. The reaction was stirred at 0° C. for 30 minutes. A solution of tert-butyl N-[2-methoxy-1-(p-tolylsulfonyl)ethyl]carbamate C78 (5 g, 0.0126 mol) in THF (35 mL) was added to the reaction dropwise at 0° C. The reaction was allowed to stir for 3 hours at room temperature. The reaction mixture was quenched with ice cold water (100 mL) and extracted with EtOAc (2×150 mL). The combined organic extracts were dried over Na$_2$SO$_4$, filtered and evaporated under vacuum to afford tert-butyl 2-acetyl-3-(tert-butoxycarbonylamino)-4-methoxy-butanoate C79 (5 g, 72%) as a pale-yellow liquid. $^1$H NMR (400 MHz, DMSO-d$_6$) δ: 5.55-5.41 (m, 1H), 3.78 (dd, J=16.4 Hz, 1H), 3.49-3.45 (m, 1H), 3.37-3.30 (m, 4H), 2.25 (s, 3H), 1.49-1.41 (m, 18H).

Step 4. Synthesis of 4-amino-5-methoxy-pentan-2-one (S40)

A solution of tert-butyl 2-acetyl-3-(tert-butoxycarbonylamino)-4-methoxy-butanoate C79 (18 g, 0.0473 mol) in aqueous HCl (200 mL of 1 M, 0.2000 mol) was stirred at 55° C. for 3 hours. After cooling to room temperature, the mixture was washed with diethylether (2×100 mL). The aqueous layer was evaporated under vacuum to afford 4-amino-5-methoxy-pentan-2-one S40 (Hydrochloride Salt) (7.4 g, 93%). $^1$H NMR (400 MHz, DMSO-d$_6$) δ: 8.17 (brs, 3H), 3.64-3.54 (m, 1H), 3.47-3.40 (m, 2H), 3.28 (s, 3H), 2.83 (t, J=6.4 Hz, 2H), 2.13 (s, 3H). LCMS m/z 132.2 [M+H]$^+$.

Preparation of S41

2-ethyl-6-(1-methyltriazol-4-yl)piperidin-4-one (S41)

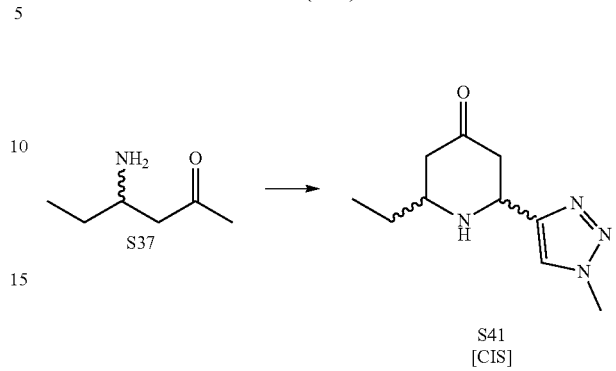

S41
[CIS]

4-aminohexan-2-one S37 (Hydrochloride salt) (298 mg, 1.965 mmol) was dissolved in EtOH (9 mL) and to it was added TEA (280 µL, 2.009 mmol), 1-methyltriazole-4-carbaldehyde S17 (225 mg, 2.025 mmol), L-proline (47 mg, 0.4082 mmol) and MgSO$_4$ (255 mg, 2.119 mmol). The reaction was stirred at room temperature for 16 hours. The mixture was filtered, concentrated, quenched with saturated aqueous NaHCO$_3$ (50 mL), and extracted with DCM (5×20 mL). The combined organic layers were dried with MgSO$_4$, filtered, and concentrated under reduced pressure. Purification by silica gel chromatography (Gradient: 0-10% MeOH in DCM) afforded 2-ethyl-6-(1-methyltriazol-4-yl)piperidin-4-one S41 (162 mg, 38%). $^1$H NMR (300 MHz, Chloroform-d) δ 7.46 (d, J=2.0 Hz, 1H), 4.22 (ddd, J=10.3, 5.0, 2.0 Hz, 1H), 4.09 (d, J=2.1 Hz, 3H), 2.93 (dtd, J=11.8, 6.3, 2.9 Hz, 1H), 2.77-2.56 (m, 2H), 2.48 (ddd, J=14.1, 2.9, 1.6 Hz, 1H), 2.16 (dd, J=14.1, 11.7 Hz, 1H), 1.74-1.50 (m, 2H), 0.98 (td, J=7.6, 2.0 Hz, 3H). LCMS m/z 209.08 [M+H]$^+$. Minor trans isomer purged during isolation.

Preparation of S42

2-isopropyl-6-(1-methyltriazol-4-yl)piperidin-4-one (S42)

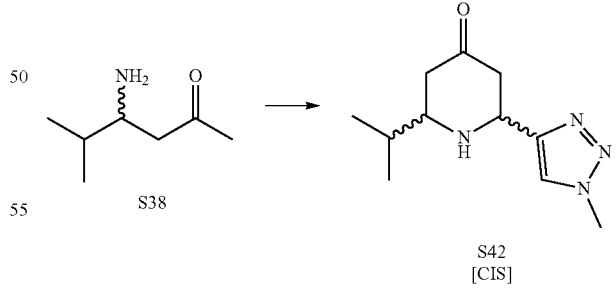

S42
[CIS]

4-amino-5-methyl-hexan-2-one S38 (Hydrochloride salt) (500 mg, 3.018 mmol) was dissolved in EtOH (15 mL) and to it was added TEA (430 µL, 3.085 mmol), 1-methyltriazole-4-carbaldehyde S17 (350 mg, 3.150 mmol), L-proline (72 mg, 0.6254 mmol) and MgSO$_4$ (392 mg, 3.257 mmol) The reaction was stirred at room temperature for 3 days. The mixture was filtered, concentrated, and quenched with saturated aqueous bicarbonate (50 mL) and extracted with DCM (5×20 mL). The combined organic layers were dried with MgSO₄, filtered, and concentrated. Crude ¹H NMR showed about 5.5:1 dr. Purification by silica gel chromatography (Gradient: 0-5% MeOH in DCM) afforded=2-isopropyl-6-(1-methyltriazol-4-yl)piperidin-4-one S42 (272 mg, 38%). ¹H NMR (300 MHz, Chloroform-d) δ 7.45 (s, 1H), 4.19 (dd, J=11.0, 4.2 Hz, 1H), 4.10 (s, 3H), 2.79 (ddd, J=11.8, 5.7, 2.9 Hz, 1H), 2.73-2.54 (m, 2H), 2.46 (ddd, J=13.9, 2.8, 1.7 Hz, 1H), 2.21 (dd, J=13.9, 11.8 Hz, 1H), 2.08 (s, 1H), 1.78 (dt, J=13.2, 6.6 Hz, 1H), 0.98 (t, J=6.5 Hz, 6H). The minor trans isomer was purged during isolation.

Preparation of S43

2-cyclobutyl-6-(1-methyltriazol-4-yl)piperidin-4-one (S43)

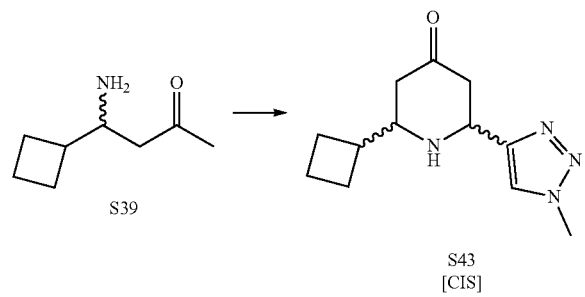

To a solution of 4-amino-4-cyclobutylbutan-2-one S39 (Hydrochloride salt) (1260 mg, 7.092 mmol) in EtOH (38 mL) was added TEA (1.0 mL, 7.175 mmol), 1-methyltriazole-4-carbaldehyde S17 (835 mg, 7.516 mmol), L-proline (168 mg, 1.459 mmol) and MgSO₄ (919 mg, 7.635 mmol). The reaction was stirred at room temperature for 24 hours. The mixture was filtered, concentrated, and quenched with saturated aqueous bicarbonate (50 mL) and extracted with DCM (5×20 mL). The combined organic layers were dried with MgSO₄, filtered, and concentrated. Purification by silica gel chromatography (Gradient: 0-3% MeOH in DCM) afforded, 2-cyclobutyl-6-(1-methyltriazol-4-yl)piperidin-4-one S43 (849 mg, 48%). ¹H NMR (300 MHz, Chloroform-d) δ 7.45 (s, 1H), 4.27-4.16 (m, 1H), 4.09 (s, 3H), 2.92 (ddd, J=11.5, 8.6, 2.8 Hz, 1H), 2.67-2.56 (m, 2H), 2.49-2.30 (m, 2H), 2.23-1.70 (m, 8H). The minor trans isomer was purged during isolation.

Preparation of S44

2-(methoxymethyl)-6-(1-methyltriazol-4-yl)piperidin-4-one (S40)

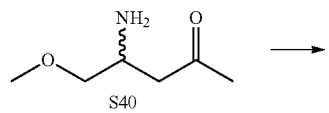

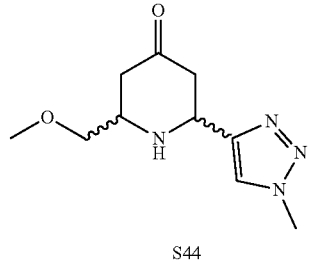

To a solution of 4-amino-5-methoxy-pentan-2-one S40 (Hydrochloride salt) (750 mg, 4.474 mmol) in EtOH (22 mL) was added TEA (650 μL, 4.664 mmol), 1-methyltriazole-4-carbaldehyde S17 (520 mg, 4.680 mmol), L-proline (107 mg, 0.9294 mmol) and MgSO₄ (590 mg, 4.902 mmol). The reaction was stirred at room temperature for 16 hours. The mixture was filtered, concentrated, and quenched with saturated aqueous bicarbonate (50 mL) and extracted with DCM (7×20 mL). The combined organic layers were dried with sodium sulfate, filtered, and concentrated. Purification by silica gel chromatography (Gradient: 0-12% MeOH in DCM) provided 2-(methoxymethyl)-6-(1-methyltriazol-4-yl)piperidin-4-one S44 (373 mg, 37%). ¹H NMR (300 MHz, Chloroform-d) δ 7.47 (s, 1H), 4.24 (dd, J=10.1, 5.0 Hz, 1H), 4.09 (s, 3H), 3.48 (dd, J=9.2, 3.3 Hz, 1H), 3.43-3.34 (m, 4H), 3.25 (ddt, J=10.9, 7.4, 3.8 Hz, 1H), 2.71-2.59 (m, 3H), 2.40-2.28 (m, 2H). LCMS m/z 225.06 [M+H]⁺. The product was isolated as a mixture of 5:1 dr.

Compound 186

2-chloro-2'-ethyl-6'-(1-methyltriazol-4-yl)spiro[4,5-dihydrothieno[2,3-c]pyran-7,4'-piperidine]

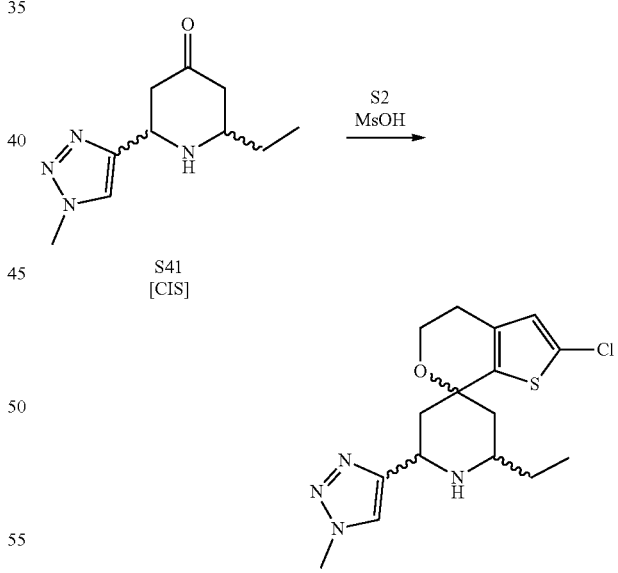

To a mixture of 2-ethyl-6-(1-methyltriazol-4-yl)piperidin-4-one S41 (31 mg, 0.1414 mmol) and 2-(5-chloro-3-thienyl)ethanol (26 mg, 0.1599 mmol) S2 in DCM (700 μL) was added MsOH (37 μL, 0.5702 mmol) and the mixture was heated to 40° C. for 4 hours and then stirred at room temperature for 72 hours. The reaction was quenched with saturated NaHCO₃ solution and extracted with DCM (6×). The combined organic layers were dried over anhydrous Na₂SO₄, filtered, and concentrated under reduced pressure. Purification by silica gel chromatography (Gradient: 0-10% MeOH in DCM). The final product was dissolved in MeCN and water and subjected to lyophilization to provide 2-chloro-2'-ethyl-6'-(1-methyltriazol-4-yl)spiro[4,5-dihydrothieno[2,3-c]pyran-7,4'-piperidine] 186 (42.2 mg, 75%). ¹H NMR (300 MHz, Chloroform-d) δ 7.43 (s, 1H), 6.58 (s, 1H), 4.40 (dd, J=11.8, 2.7 Hz, 1H), 4.06 (s, 3H), 4.00-3.89 (m, 2H), 3.15-2.99 (m, 1H), 2.74-2.49 (m, 2H), 2.36 (dt, J=13.5, 2.6 Hz, 1H), 2.10 (dt, J=13.7, 2.5 Hz, 1H), 1.96-1.74 (m, 2H), 1.42 (qt, J=11.1, 4.9 Hz, 3H), 0.94 (t, J=7.6 Hz, 3H). LCMS m/z 353.05 [M+H]⁺.

Compound 187

2'-ethyl-6'-(1-methyltriazol-4-yl)-2-(trifluoromethyl)spiro[4,5-dihydrothieno[2,3-c]pyran-7,4'-piperidine] (187)

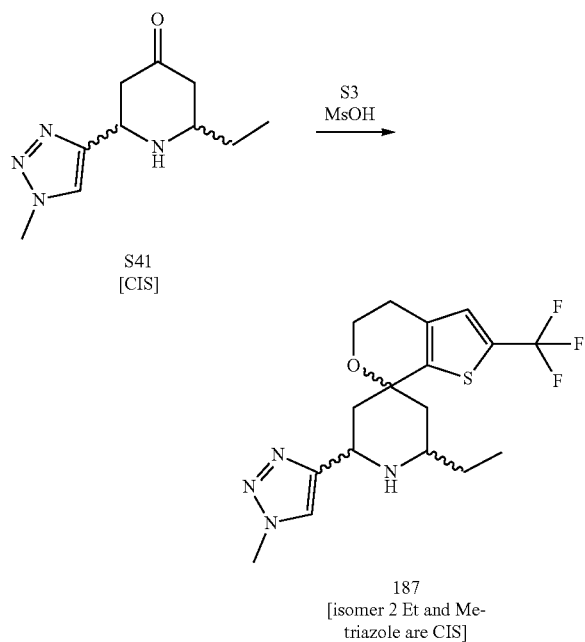

To a mixture of 2-ethyl-6-(1-methyltriazol-4-yl)piperidin-4-one S41 (31 mg, 0.1414 mmol) and 2-[5-(trifluoromethyl)-3-thienyl]ethanol (31 mg, 0.1580 mmol) S3 in DCM (700 μL) was added MeOH (37 μL, 0.5702 mmol) and the mixture was heated to 40° C. for 3 hours. To the solution was added MsOH (11 μL) and stirred at 40° C. for 1.5 hours and then stirred at 35° C. for 3.5 days. To the solution was added MsOH (11 μL) and stirred at 50° C. for 5 days during that time the solvent evaporated. The reaction was quenched with saturated NaHCO₃ solution and extracted with DCM (6×). The combined organic layers were dried over anhydrous Na₂SO₄, filtered, and concentrated. Purification by reversed-phase HPLC (Method: C18 Waters Sunfire column (30×150 mm, 5 micron). Gradient: MeCN in H₂O with 0.1% trifluoroacetic acid) to provide 2'-ethyl-6'-(1-methyltriazol-4-yl)-2-(trifluoromethyl)spiro[4,5-dihydrothieno[2,3-c]pyran-7,4'-piperidine] (Trifluoroacetate salt) 187 (33.5 mg, 46%). ¹H NMR (300 MHz, Chloroform-d) δ 7.89 (s, 1H), 7.16 (s, 1H), 4.94 (d, J=10.2 Hz, 1H), 4.09 (s, 3H), 3.98 (h, J=6.2 Hz, 2H), 3.67 (s, 1H), 2.93-2.64 (m, 3H), 2.49-2.34 (m, 2H), 2.19-2.04 (m, 2H), 1.94 (s, 1H), 1.67 (dt, J=14.5, 7.8 Hz, 1H), 1.00 (t, J=7.5 Hz, 3H). LCMS m/z 387.16 [M+H]⁺.

Compounds 188-193

Compounds 188-193 (see Table 6) were prepared in one step in an Oxa-Pictet Spengler reaction with thiophene ethanol intermediates S2 and S3 and piperidones (S42-S44). Any modifications to the methods are noted in Table 6 and accompanying footnotes.

TABLE 6

Method of preparation, structure, and physiochemical data for compounds 188-193

| Product | Piperidone | Method | ¹H NMR; LCMS m/z [M + H]⁺ |
|---|---|---|---|
| Compound 188 | S42 [CIS] | Compound 186[1,2,3] | ¹H NMR (300 MHz, Chloroform-d) δ 7.47 (s, 1H), 6.59 (s, 1H), 4.43 (dd, J = 11.9, 2.6 Hz, 1H), 4.06 (s, 3H), 3.95 (td, J = 5.4, 1.4 Hz, 2H), 2.95 (ddd, J = 11.6, 6.5, 2.4 Hz, 1H), 2.80-2.52 (m, 2H), 2.36 (dt, J = 13.6, 2.6 Hz, 1H), 2.16-2.05 (m, 1H), 1.84 (dd, J = 13.6, 11.8 Hz, 1H), 1.66 (dt, J = 13.4, 6.7 Hz, 1H), 1.47 (dd, J = 13.6, 11.6 Hz, 1H), 0.95 (dd, J = 9.1, 6.8 Hz, 6H). LCMS m/z 367.04 [M + H]⁺. |

TABLE 6-continued

Method of preparation, structure, and physiochemical data for compounds 188-193

| Product | Piperidone | Method | $^1$H NMR; LCMS m/z [M + H]$^+$ |
|---|---|---|---|
| 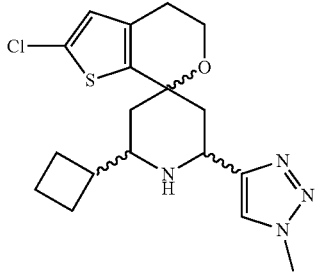<br>Compound 189 | 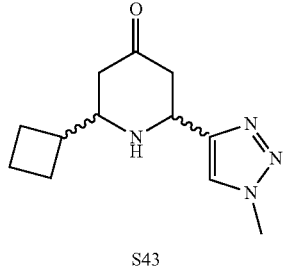<br>S43 | Compound 186[4,5] | $^1$H NMR (300 MHz, Chloroform-d) δ 7.86 (s, 1H), 6.62 (s, 1H), 4.91 (dd, J = 12.7, 3.0 Hz, 1H), 4.08 (s, 3H), 3.94 (q, J = 5.3 Hz, 2H), 3.63 (t, J = 10.9 Hz, 1H), 2.87-2.50 (m, 4H), 2.36 (d, J = 14.2 Hz, 1H), 2.17 (t, J = 16.2 Hz, 3H), 2.09-1.87 (m, 5H), 1.77 (d, J = 9.0 Hz, 2H). LCMS m/z 379.06 [M + H]$^+$. |
| 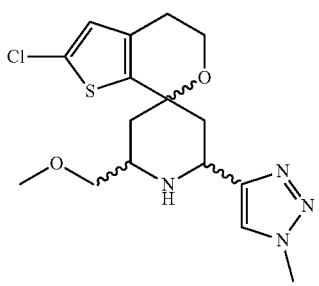<br>Compound 190 | 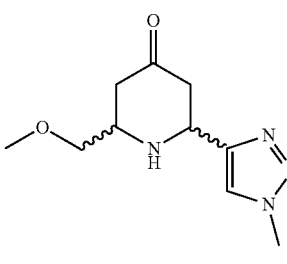<br>S44 | Compound 186[3,8] | $^1$H NMR (300 MHz, Chloroform-d) δ 7.52 (s, 1H), 6.58 (s, 1H), 4.49 (dd, J = 11.9, 2.7 Hz, 1H), 4.06 (s, 3H), 3.95 (t, J = 5.4 Hz, 2H), 3.60-3.38 (m, 3H), 3.34 (s, 3H), 2.61 (q, J = 5.1 Hz, 2H), 2.38 (dd, J = 13.7, 2.8 Hz, 1H), 2.02-1.91 (m, 2H), 1.61 (dd, J = 13.6, 11.7 Hz, 1H). LCMS m/z 369.07 [M + H]$^+$. |
| 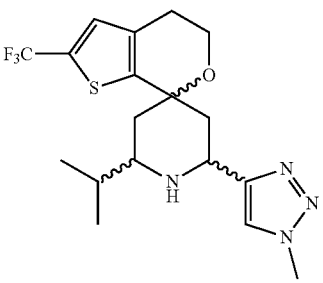<br>Compound 191 | 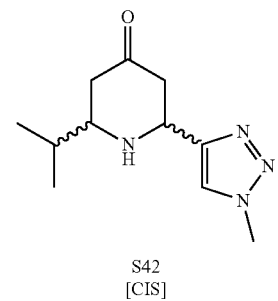<br>S42<br>[CIS] | Compound 187[3,6,7,8] | $^1$H NMR (300 MHz, Chloroform-d) δ 7.78 (s, 1H), 7.14 (s, 1H), 4.75 (t, J = 7.7 Hz, 1H), 4.08 (s, 3H), 3.97 (q, J = 5.1 Hz, 2H), 3.39-3.20 (m, 1H), 2.73 (q, J = 5.7, 5.2 Hz, 2H), 2.42 (d, J = 7.7 Hz, 2H), 2.23 (d, J = 14.2 Hz, 1H), 2.08-1.76 (m, 2H), 1.00 (dd, J = 11.8, 6.8 Hz, 6H). LCMS m/z 401.11 [M + H]$^+$. |
| 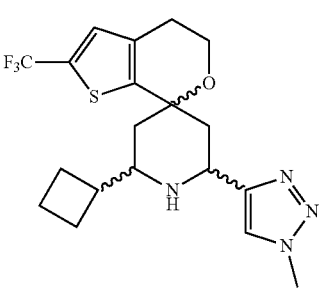<br>Compound 192 | 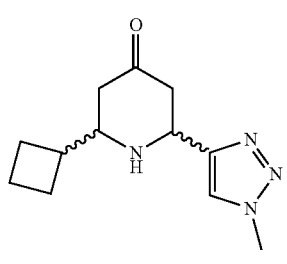<br>S43 | Compound 187[5,9] | $^1$H NMR (300 MHz, Chloroform-d) δ 7.91 (s, 1H), 7.16 (d, J = 1.3 Hz, 1H), 4.97 (dd, J = 12.8, 3.0 Hz, 1H), 4.10 (s, 3H), 3.99 (hept, J = 5.6 Hz, 2H), 3.79-3.53 (m, 1H), 2.92-2.68 (m, 3H), 2.61 (q, J = 8.1 Hz, 1H), 2.40 (d, J = 14.5 Hz, 1H), 2.26 (d, J = 14.7 Hz, 1H), 2.02 (td, J = 24.1, 21.4, 13.0 Hz, 6H), 1.80 (p, J = 9.3, 8.2 Hz, 2H). LCMS m/z 413.21 [M + H]$^+$. |

TABLE 6-continued

Method of preparation, structure, and physiochemical data for compounds 188-193

| Product | Piperidone | Method | ¹H NMR; LCMS m/z [M + H]⁺ |
|---|---|---|---|
| 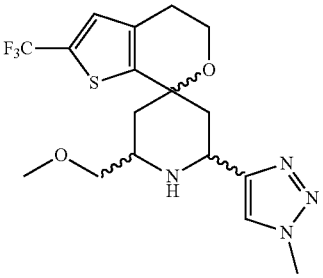<br>Compound 193 | 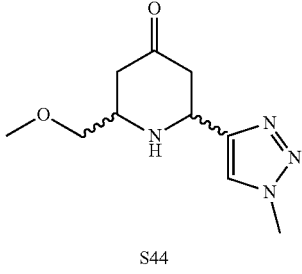<br>S44 | Compound 187[5,10] | ¹H NMR (300 MHz, Chloroform-d) δ 7.97 (s, 1H), 7.20-7.06 (m, 1H), 5.07 (dd, J = 12.7, 3.2 Hz, 1H), 4.10 (s, 3H), 3.98 (h, J = 6.1 Hz, 3H), 3.71 (dd, J = 10.2, 3.3 Hz, 1H), 3.57 (dd, J = 10.2, 5.6 Hz, 1H), 3.39 (s, 3H), 2.93-2.63 (m, 3H), 2.47 (d, J = 14.9 Hz, 1H), 2.44-2.25 (m, 1H), 2.20 (s, 1H) LCMS m/z 403.04 [M + H]⁺. |

[1]The reaction stirred at 40° C. for 22 hours
[2]Additional MsOH (31 μL, 4 equiv) was added and the reaction stirred at 40° C. for 4 hours then at room temperature overnight
[3]Purification by reversed-phase HPLC (Method: C18 Waters Sunfire column (30 × 150 mm, 5 micron). Gradient: MeCN in H₂O with 0.2% formic acid) yielded the product
[4]The reaction was stirred at 40° C. for 4 hours
[5]Purification by reversed-phase HPLC (Method: C18 Waters Sunfire column (30 × 150 mm, 5 micron). Gradient: MeCN in H₂O with 0.1% trifluoroacetic acid) yielded the product
[6]Additional MsOH (11 μL, 1.3 equiv) was added to the reaction and stirred at 80° C. for 24 hours
[7]The reaction stirred at 40° C. for 2.5 hours
[8]The reaction stirred at 65° C. for 4 days
[9]The reaction stirred at 60° C. for 5 days

Compound 194

2-chloro-2',6'-dimethyl-spiro[4,5-dihydrothieno[2,3-c]pyran-7,4'-piperidine] (194)

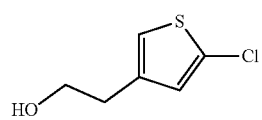

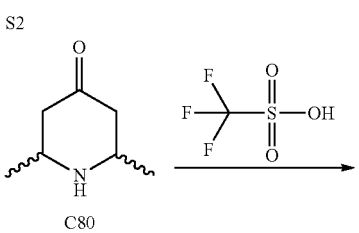

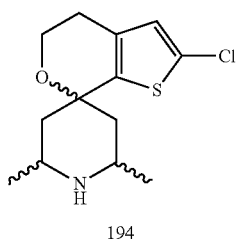

Step 1. Synthesis of 2-chloro-2',6'-dimethyl-spiro[4,5-dihydrothieno[2,3-c]pyran-7,4'-piperidine] (194)

To a solution of 2,6-dimethylpiperidin-4-one C80 (Hydrochloride salt) (40 mg, 0.2444 mmol) and 2-(5-chloro-3-thienyl)ethanol S2 (39.75 mg, 30.23 μL, 0.2444 mmol) in DCM (1 mL) was added Triflic Acid (91.70 mg, 54.07 μL, 0.6110 mmol). The reaction was stirred at room temperature overnight. The reaction was quenched with NaOH (2 M), and then extracted with DCM. Purification by reversed-phase HPLC (Method: C18 Waters Sunfire column (30×150 mm, 5 micron). Gradient: MeCN in H₂O with 5 mM HCl) afforded 2-chloro-2',6'-dimethyl-spiro[4,5-dihydrothieno[2,3-c]pyran-7,4'-piperidine] (Trifluoroacetate salt) 194. ¹H NMR (300 MHz, Chloroform-d) δ 9.87 (s, 1H), 8.98-8.36 (m, 1H), 6.62 (s, 1H), 3.90 (t, J=5.4 Hz, 2H), 3.61 (s, 2H), 2.64 (q, J=5.4 Hz, 2H), 2.35-1.79 (m, 4H), 1.35 (d, J=6.6 Hz, 6H). LCMS m/z 272.03 [M+H]⁺.

Compounds 195 and 196

Compounds 195 and 196 (see Table 7) were prepared from a single Oxa-Pictet Spengler step with relevant piperidone and thiophene ethanol as described for compound 194. Thiophene ethanols were prepared by methods described above or obtained from commercial sources. Piperdinones were obtained from commercial sources. Any modifications to methods are noted in Table 7 and accompanying footnotes.

TABLE 7

Method of preparation, structure and physicochemical data for compounds 195-196

| Product | Thiophene Ethanol And piperidone | Method | ¹H NMR; LCMS m/z [M + H]⁺ |
|---|---|---|---|
| Compound 195 | S6, C81 | Compound 194 | ¹H NMR (400 MHz, DMSO-$d_6$) δ 9.35 (s, 1H), 8.83 (s, 1H), 7.34 (s, 1H), 3.94 (hept, J = 5.9, 5.4 Hz, 2H), 3.75-3.64 (m, 1H), 3.57 (s, 1H), 2.87 (d, J = 5.6 Hz, 2H), 2.22 (dd, J = 15.2, 6.2 Hz, 1H), 2.12 (t, J = 13.3 Hz, 1H), 2.06-1.91 (m, 2H), 1.47 (d, J = 7.1 Hz, 3H), 1.29 (d, J = 6.4 Hz, 3H). LCMS m/z. 306.24 [M + H]⁺ |
| Compound 196 | S6, C82 | Compound 194 | LCMS m/z 306.24 [M + H]⁺ |

Preparation of S45

1-[(2R,6S)-2″,6′-dimethylspiro[4,5-dihydrothieno[2,3-c]pyran-7,4′-piperidine]-1′-yl]-2,2,2-trifluoro-ethanone (S45)

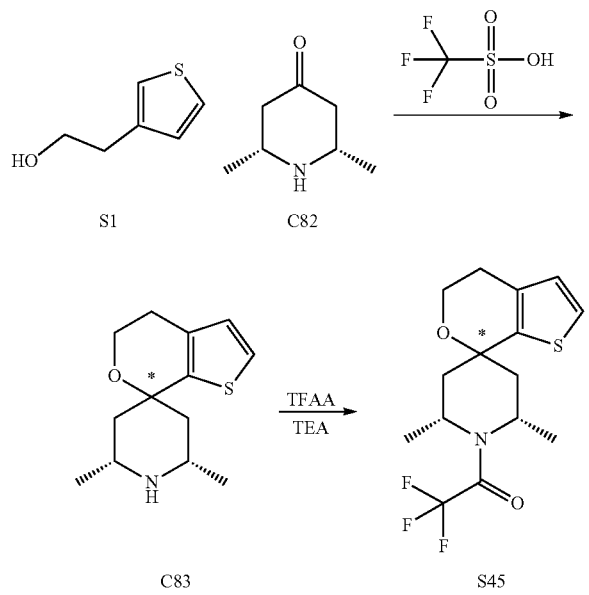

Step 1. Synthesis of (2R,6S)-2′,6′-dimethylspiro[4,5-dihydrothieno[2,3-c]pyran-7,4′-piperidine] (C83)

To a solution of (2S,6R)-2,6-dimethylpiperidin-4-one C82 (900 mg, 7.076 mmol) in dioxane (21 mL) at 0° C. was added 2-(3-thienyl)ethanol S1 (850 mg, 6.631 mmol) followed by Triflic Acid (2 g, 13.33 mmol). The reaction was warmed to room temperature. After stirring for 2 hours the reaction had gone to completion. The reaction was carefully quenched with saturated sodium bicarbonate solution. The reaction mixture was partitioned between DCM and aqueous saturated sodium bicarbonate solution. The organic phase was separated, passed through a phase separator, and concentrated via rotary evaporation to give crude (2R,6S)-2′,6′-dimethylspiro[4,5-dihydrothieno[2,3-c]pyran-7,4′-piperidine] C83 (1.059 g, quant.) LCMS m/z 238.11 [M+H]⁺.

Step 2. Synthesis of 1-[(2R,6S)-2′,6′-dimethylspiro[4,5-dihydrothieno[2,3-c]pyran-7,4′-piperidine]-1′-yl]-2,2,2-trifluoro-ethanone (S45)

(2R,6S)-2′,6′-dimethylspiro[4,5-dihydrothieno[2,3-c]pyran-7,4′-piperidine] C83 was dissolved in DCM (12.7 mL) and Boc₂O (1.4 g, 6.415 mmol) and DIPEA (1.7 g, 13.15 mmol) were added. The reaction was stirred for five hours but only small amounts of conversion were observed. The reaction mixture was concentrated to dryness and re-dissolved in DCM (12.7 mL). To this solution at 0° C. was added TEA (1.34 g, 13.24 mmol) and TFAA (1.8 g, 8.570 mmol). The reaction was warmed to room temperature and stirred for two hours until the reaction had gone to completion. The reaction was quenched with saturated sodium bicarbonate and extracted with EtOAc (2×). The organics were washed with brine, dried over Na$_2$SO$_4$, and concentrated in vacuo. Purification by silica gel chromatography (Column: 24 g silica gel, Gradient: 0-50% EtOAc in Heptane) afforded 1-[(2R,6S)-2',6'-dimethylspiro[4,5-dihydrothieno[2,3-c]pyran-7,4'-piperidine]-1'-yl]-2,2,2-trifluoro-ethanone S45 (1 g, 67%). $^1$H NMR (300 MHz, Chloroform-d) δ 7.19 (d, J=5.0 Hz, 1H), 6.78 (d, J=5.0 Hz, 1H), 4.47 (d, J=7.8 Hz, 2H), 3.85 (t, J=5.5 Hz, 2H), 2.68 (t, J=5.5 Hz, 2H), 2.50 (dd, J=14.4, 8.2 Hz, 2H), 1.97 (dd, J=14.7, 6.6 Hz, 2H), 1.49 (dd, J=20.4, 6.6 Hz, 6H). LCMS m/z 334.05 [M+H]$^+$.

400 mg of the boc protected compound was also isolated during purification. $^1$H NMR (300 MHz, Chloroform-d) δ 7.18 (dd, J=7.6, 5.0 Hz, 1H), 6.76 (d, J=5.0 Hz, 1H), 4.36 (h, J=7.1 Hz, 2H), 3.88 (t, J=5.5 Hz, 2H), 2.68 (t, J=5.5 Hz, 2H), 2.49-2.31 (m, 2H), 1.83 (dd, J=14.5, 7.0 Hz, 2H), 1.51 (d, J=25.0 Hz, 9H), 1.33 (d, J=6.8 Hz, 6H).

Compound 197

(2R,6S)-2-bromo-2',6'-dimethyl-spiro[4,5-dihydrothieno[2,3-c]pyran-7,4'-piperidine](197)

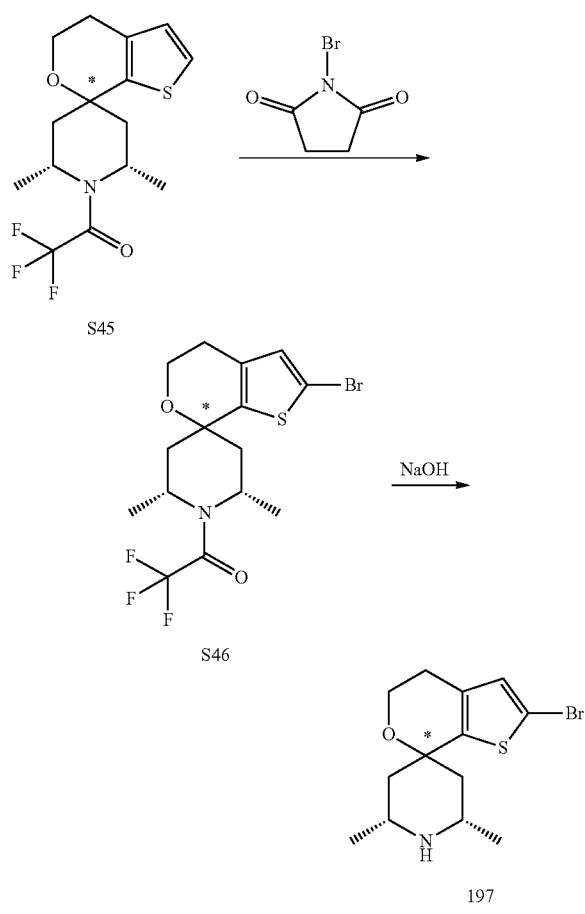

Step 1. Synthesis of 1-[(2R,6S)-2-bromo-2',6'-dimethyl-spiro[4,5-dihydrothieno[2,3-c]pyran-7,4'-piperidine]-1'-yl]-2,2,2-trifluoro-ethanone (S46)

To a solution of 1-[(2R,6S)-2',6'-dimethylspiro[4,5-dihydrothieno[2,3-c]pyran-7,4'-piperidine]-1'-yl]-2,2,2-trifluoro-ethanone S45 (1 g, 3.000 mmol) dissolved in MeCN (10.7 mL) was added NBS (610 mg, 3.427 mmol) and the reaction was stirred at 65° C. for one hour. The solution was concentrated and dissolved in DCM. The reaction was quenched with aqueous sodium thiosulfate and DCM. The organic phase was separated, passed through a phase separator, and concentrated in vacuo and the solid NBS was filtered off. Purification by silica gel chromatography (Gradient: 0-60% EtOAc in heptane) yielded the product 1-[(2R,6S)-2-bromo-2',6'-dimethyl-spiro[4,5-dihydrothieno[2,3-c]pyran-7,4'-piperidine]-1'-yl]-2,2,2-trifluoro-ethanone S46 (1.12 g, 76%). $^1$H NMR (300 MHz, Chloroform-d) δ 6.74 (s, 1H), 4.61-4.32 (m, 2H), 3.83 (t, J=5.5 Hz, 2H), 2.65-2.40 (m, 4H), 1.88 (dd, J=14.9, 6.5 Hz, 2H), 1.43 (d, J=6.9 Hz, 6H). LCMS m/z 412.05 [M+H]$^+$.

Step 2. Synthesis of (2R,6S)-2-bromo-2',6'-dimethyl-spiro[4,5-dihydrothieno[2,3-c]pyran-7,4'-piperidine] (197)

To a solution of 1-[(2R,6S)-2-bromo-2',6'-dimethyl-spiro[4,5-dihydrothieno[2,3-c]pyran-7,4'-piperidine]-1'-yl]-2,2,2-trifluoro-ethanone S46 (1.12 g, 2.716 mmol) in DCM (10 mL) was added aqueous NaOH (1.5 mL of 2 M, 3.000 mmol). The reaction was heated to 40° C. The reaction was stirred for 30 minutes. The organic phase was separated, passed through a phase separator, and concentrated in vacuo. Purification by reversed-phase HPLC (Method: C18 Waters Sunfire column (30×150 mm, 5 micron). Gradient: MeCN in H$_2$O with 0.1% trifluoroacetic acid) yielded (2R,6S)-2-bromo-2',6'-dimethyl-spiro[4,5-dihydrothieno[2,3-c]pyran-7,4'-piperidine] (trifluoroacetate salt) 197 (11.9 mg, 1%). $^1$H NMR (300 MHz, Chloroform-d) δ 9.43 (s, 1H), 8.79-8.07 (m, 1H), 6.76 (s, 1H), 3.90 (t, J=5.4 Hz, 2H), 3.64 (d, J=8.0 Hz, 2H), 2.66 (t, J=5.4 Hz, 2H), 2.17 (d, J=14.4 Hz, 2H), 1.93 (dd, J=14.5, 12.2 Hz, 2H), 1.35 (d, J=6.6 Hz, 6H). LCMS m/z 316.18 [M+H]$^+$.

Compound 198

(2R,6S)-2-(3,3-difluorocyclobutyl)-2',6'-dimethyl-spiro[4,5-dihydrothieno[2,3-c]pyran-7,4'-piperidine] (198)

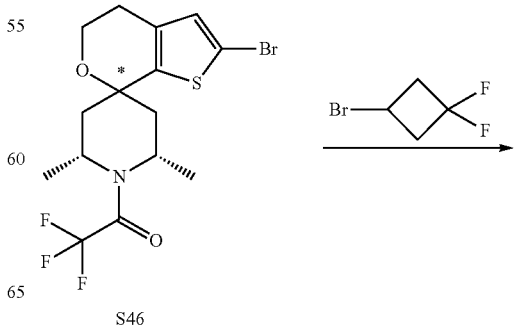

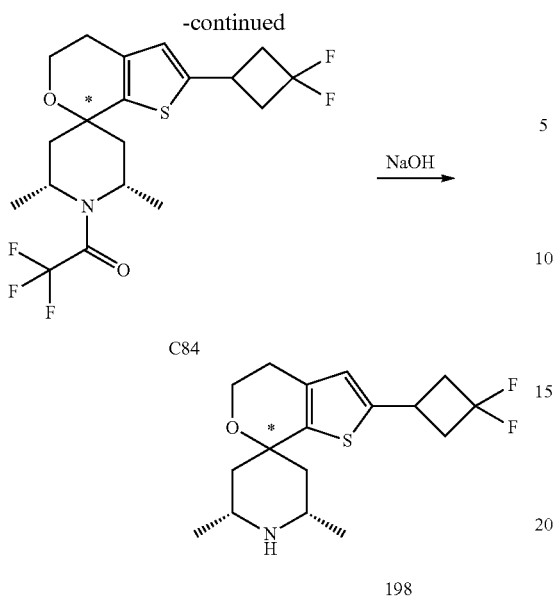

C84

198

Step 1. Synthesis of 1-[(2R,6S)-2-(3,3-difluorocyclobutyl)-2',6'-dimethyl-spiro[4,5-dihydrothieno[2,3-c]pyran-7,4'-piperidine]-1'-yl]-2,2,2-trifluoro-ethanone (C84)

To Ir[df(CF$_3$)ppy]$_2$(dtbbpy)PF$_6$ (Phosphorus Hexafluoride Ion) (3 mg, 0.002971 mmol), Dichloro(dimethoxyethane)nickel (4 mg, 0.01820 mmol), and 4-tert-butyl-2-(4-tert-butyl-2-pyridyl)pyridine (5 mg, 0.01863 mmol) under an inert atmosphere was added a solution of 1-[(2R,6S)-2-bromo-2',6'-dimethyl-spiro[4,5-dihydrothieno[2,3-c]pyran-7,4'-piperidine]-1'-yl]-2,2,2-trifluoro-ethanone S46 (65 mg, 0.1577 mmol), bis(trimethylsilyl)silyl-trimethyl-silane (61 μL, 0.1963 mmol), and 2,6-dimethylpyridine (41.64 mg, 45.01 μL, 0.3886 mmol) dissolved in DME (2 mL). 3-bromo-1,1-difluoro-cyclobutane (158 μL, 1.571 mmol) was added. The resulting mixture was sealed and irradiated in a Sigma SynLED photoreactor overnight with tumble stirring. The reaction vial was unsealed and evaporated under a stream of nitrogen. The resulting residues were diluted with 2 mL water and 2 mL DCM and stirred for several minutes. The biphasic mixtures were passed through a parallel hydrophobic filter plate. The DCM layers were concentrated in vacuo. Purification by reversed-phase HPLC (Method: C18 Waters Sunfire column (30×150 mm, 5 micron). Gradient: MeCN in H$_2$O with 0.1% trifluoroacetic acid) yielded TFA protected intermediate C84. LCMS m/z 424.18 [M+H]$^+$.

Step 2. Synthesis of (2R,6S)-2-(3,3-difluorocyclobutyl)-2',6'-dimethyl-spiro[4,5-dihydrothieno[2,3-c]pyran-7,4'-piperidine] (198)

To 1-[(2R,6S)-2-(3,3-difluorocyclobutyl)-2',6'-dimethyl-spiro[4,5-dihydrothieno[2,3-c]pyran-7,4'-piperidine]-1'-yl]-2,2,2-trifluoro-ethanone (15.5 mg, 0.037 mmol) C84 in DCM (2 mL) was added NaOH 6M (10 eq). The reaction was heated to 40° C. and stirred for 5 hours. The organic phase was separated, passed through a phase separator, and concentrated in vacuo. Purification by reversed-phase HPLC (Method: C18 Waters Sunfire column (30×150 mm, 5 micron). Gradient: MeCN in H$_2$O with 0.1% trifluoroacetic acid) yielded deprotected product (2R,6S)-2-(3,3-difluorocyclobutyl)-2',6'-dimethyl-spiro[4,5-dihydrothieno[2,3-c]pyran-7,4'-piperidine] (Trifluoroacetate salt) 198 (5.6 mg, 8%). $^1$H NMR (300 MHz, Chloroform-d) δ 6.50 (d, J=1.0 Hz, 1H), 3.84 (t, J=5.4 Hz, 2H), 3.73-3.28 (m, 3H), 2.97 (tdd, J=14.3, 7.3, 4.1 Hz, 2H), 2.79-2.35 (m, 5H), 2.10 (d, J=13.8 Hz, 2H), 2.02-1.74 (m, 2H), 1.28 (d, J=6.6 Hz, 7H).

Compounds 199-202

Compounds 199-202 (see Table 8) were prepared from intermediate S47 using the appropriate reagent and using the photo-redox method and deprotection method as described for compound 198. Alkyl bromides were obtained from commercial sources. Any modifications to methods are noted in Table 8.

TABLE 8

Method of preparation, structure and physicochemical data for compounds 199-202

| Product | Alkyl Bromide | Method | $^1$H NMR; LCMS m/z [M + H]$^+$ |
|---|---|---|---|
| Compound 199 | ⟍⟋Br | Compound 198 | $^1$H NMR (300 MHz, Chloroform-d) δ 9.55 (s, 1H), 8.55 (s, 1H), 6.48 (d, J = 1.1 Hz, 1H), 3.90 (t, J = 5.4 Hz, 2H), 3.65 (s, 2H), 2.93-2.45 (m, 4H), 2.27-1.76 (m, 4H), 1.49-1.17 (m, 9H). LCMS m/z 266.28 [M + H]$^+$. |

TABLE 8-continued

Method of preparation, structure and physicochemical data for compounds 199-202

| Product | Alkyl Bromide | Method | $^1$H NMR; LCMS m/z [M + H]$^+$ |
|---|---|---|---|
| Compound 200 | isopropyl bromide | Compound 198 | $^1$H NMR (300 MHz, Chloroform-d) δ 9.51 (s, 1H), 8.50 (s, 1H), 6.49 (d, J = 0.9 Hz, 1H), 3.90 (t, J = 5.4 Hz, 2H), 3.64 (s, 2H), 3.12 (hept, J = 6.9 Hz, 1H), 2.64 (t, J = 5.4 Hz, 2H), 2.27-1.82 (m, 4H), 1.34 (dd, J = 9.0, 6.7 Hz, 12H). LCMS m/z 280.32 [M + H]$^+$. |
| Compound 201 | isobutyl bromide | Compound 198 | $^1$H NMR (300 MHz, Chloroform-d) δ 6.44 (s, 1H), 3.90 (t, J = 5.4 Hz, 2H), 3.84-3.49 (m, 2H), 2.83-2.47 (m, 5H), 2.18 (d, J = 14.5 Hz, 2H), 2.02-1.78 (m, 3H), 1.35 (d, J = 6.6 Hz, 6H), 0.96 (d, J = 6.6 Hz, 6H). LCMS m/z 294.32 [M + H]$^+$. |
| Compound 202 | cyclohexyl bromide | Compound 198 | $^1$H NMR (300 MHz, Chloroform-d) δ 9.60 (s, 1H), 8.57 (d, J = 12.5 Hz, 1H), 6.47 (s, 1H), 3.64 (s, 2H), 3.35 (s, 2H), 2.74 (s, 1H), 2.64 (t, J = 5.3 Hz, 2H), 2.26-1.68 (m, 9H), 1.61-1.04 (m, 11H). LCMS m/z 320.5 [M + H]$^+$. |

Compound 203

(2R,6S)-2-(2,2-difluoroethyl)-2',6'-dimethyl-spiro[4,5-dihydrothieno[2,3-c]pyran-7,4'-piperidine] (203)

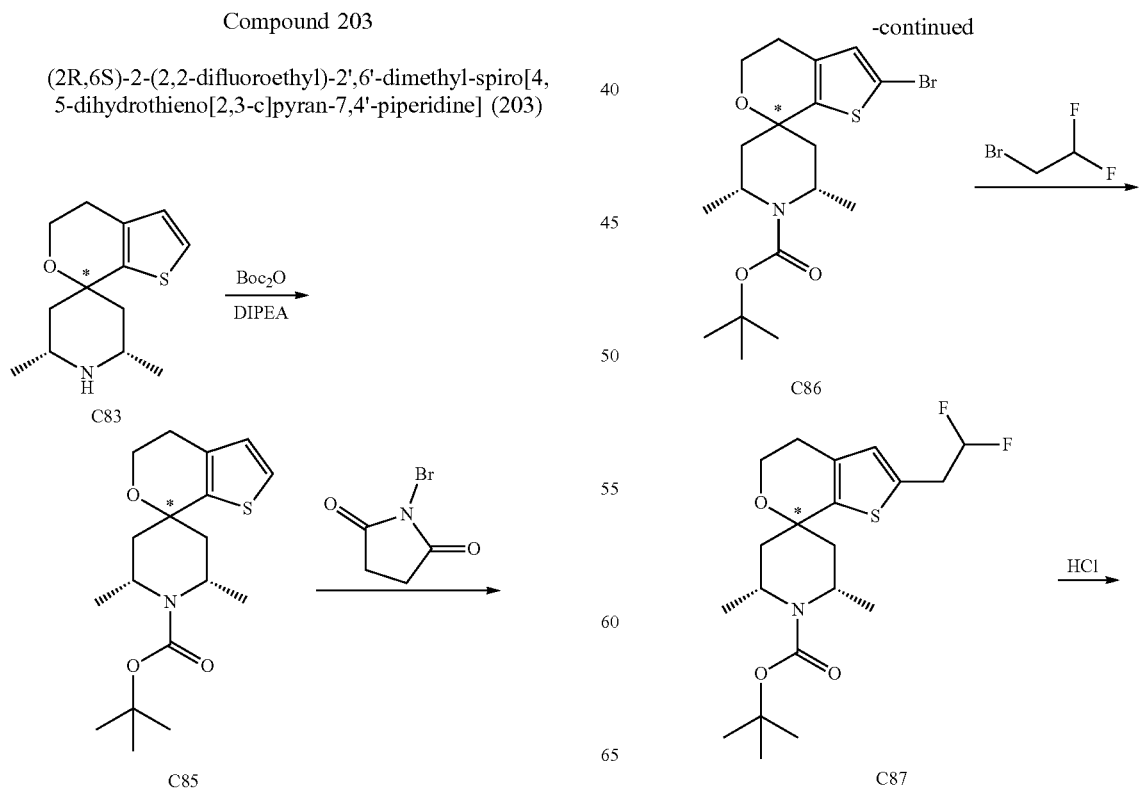

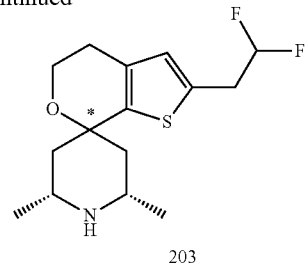

203

Step 1. Synthesis of tert-butyl (2R,6S)-2',6'-dimethylspiro[4,5-dihydrothieno[2,3-c]pyran-7,4'-piperidine]-1'-carboxylate (C85)

To a solution of (2R,6S)-2',6'-dimethylspiro[4,5-dihydrothieno[2,3-c]pyran-7,4'-piperidine] C83 in DCM (4 mL) was added Boc₂O (525 µL, 2.285 mmol) and DIPEA (597 µL, 3.427 mmol). The reaction was stirred overnight until the reaction had gone to completion. The reaction was quenched with saturated sodium bicarbonate and extracted with EtOAc (2×). The organics were washed with brine, dried over anhydrous Na₂SO₄, and concentrated in vacuo. Purification by silica gel chromatography (Column: 24 g silica gel, Gradient: 0-30% EtOAc in Heptane) afforded tert-butyl (2R,6S)-2',6'-dimethylspiro[4,5-dihydrothieno[2,3-c]pyran-7,4'-piperidine]-1'-carboxylate C85 (210 mg, 54%). LCMS m/z 338.1 [M+H]⁺;

Step 2. Synthesis of tert-butyl (2R,6S)-2-bromo-2',6'-dimethyl-spiro[4,5-dihydrothieno[2,3-c]pyran-7,4'-piperidine]-1'-carboxylate (C86)

To a solution of tert-butyl (2R,6S)-2',6'-dimethylspiro[4,5-dihydrothieno[2,3-c]pyran-7,4'-piperidine]-1'-carboxylate C85 (140 mg, 0.4148 mmol) in MeCN (1.5 mL) was added NBS (84 mg, 0.4720 mmol). The reaction was stirred at 65° C. for one hour. The reaction was quenched with a solution of sodium thiosulfate and DCM. The organic phase was separated, passed through a phase separator, and concentrated in vacuo. Purification by silica gel chromatography (Gradient: 0-30% EtOAc in heptane) yielded the product tert-butyl (2R,6S)-2-bromo-2',6'-dimethyl-spiro[4,5-dihydrothieno[2,3-c]pyran-7,4'-piperidine]-1'-carboxylate C86 (120 mg, 69%). LCMS m/z 416.14 [M+H]⁺.

Step 3. Synthesis of tert-butyl (2R,6S)-2-(2,2-difluoroethyl)-2',6'-dimethyl-spiro[4,5-dihydrothieno[2,3-c]pyran-7,4'-piperidine]-1'-carboxylate (C87)

To vial was added Ir[df(CF₃)ppy]₂(dtbbpy)PF₆ (Phosphorus Hexafluoride Ion) (3 mg, 0.002971 mmol), Dichloro(dimethoxyethane)nickel (4 mg, 0.01820 mmol), and 4-tert-butyl-2-(4-tert-butyl-2-pyridyl)pyridine (5 mg, 0.01863 mmol) as solids. The vial was purged and refilled with N2 (3×). To the vial was added sequentially tert-butyl (2R,6S)-2-bromo-2',6'-dimethyl-spiro[4,5-dihydrothieno[2,3-c]pyran-7,4'-piperidine]-1'-carboxylate C86 (70 mg, 0.1680 mmol), bis(trimethylsilyl)silyl-trimethyl-silane (51 mg, 0.2051 mmol), 2,6-dimethylpyridine (45 mg, 0.4200 mmol) and DME (2 mL). Purged with N2 (3×) and 2-bromo-1,1-difluoro-ethane (244 mg, 1.683 mmol) was added. The reaction was irradiated with Merck Integrated Photoreactor for 7 h, Royal Blue (450 nm) LED light. 100% LED light power was applied. The stir rate was 1000 rpm. The reaction was quenched with aqueous saturated sodium bicarbonate and DCM and the organic layer was collected through a phase separator. The solvent was concentrated in vacuo to give crude tert-butyl-(2R,6S)-2-(2,2-difluoroethyl)-2',6'-dimethyl-spiro[4,5-dihydrothieno[2,3-c]pyran-7,4'-piperidine]-1'-carboxylate C87 (8 mg, 12%). LCMS m/z 402.23 [M+H]⁺.

Step 4. Synthesis of (2R,6S)-2-(2,2-difluoroethyl)-2',6'-dimethyl-spiro[4,5-dihydrothieno[2,3-c]pyran-7,4'-piperidine] (203)

To a solution of tert-butyl-(2R,6S)-2-(2,2-difluoroethyl)-2',6'-dimethyl-spiro[4,5-dihydrothieno[2,3-c]pyran-7,4'-piperidine]-1'-carboxylate C87 (8 mg, 0.02 mmol) in Dioxane (350 µL) was added HCl (630 µL of 4 M, 2.520 mmol) in dioxane. The reaction was stirred for 3 hours. Solvent was removed in vacuo. Purification by reversed-phase HPLC (Method: C18 Waters Sunfire column (30×150 mm, 5 micron). Gradient: MeCN in H₂O with 0.1% trifluoroacetic acid) yielded (2R,6S)-2-(2,2-difluoroethyl)-2',6'-dimethyl-spiro[4,5-dihydrothieno[2,3-c]pyran-7,4'-piperidine] (Trifluoroacetate salt) 203 (6.1 mg, 78%). ¹H NMR (300 MHz, Chloroform-d) δ 9.81 (s, 1H), 8.80 (s, 1H), 6.65 (s, 1H), 5.93 (tt, J=56.4, 4.4 Hz, 1H), 3.90 (t, J=5.4 Hz, 2H), 3.30 (td, J=16.7, 4.5 Hz, 3H), 2.67 (t, J=5.5 Hz, 2H), 2.30-1.75 (m, 4H), 1.36 (d, J=6.5 Hz, 6H). LCMS m/z 302.22 [M+H]⁺.

Compounds 204 and 205

(2R,6S)-2-chloro-2',6'-dimethyl-spiro[4,5-dihydrothieno[2,3-c]pyran-7,4'-piperidine] (204) and (2R,6S)-2-chloro-2',6'-dimethyl-spiro[4,5-dihydrothieno[2,3-c]pyran-7,4'-piperidine]-4-ol

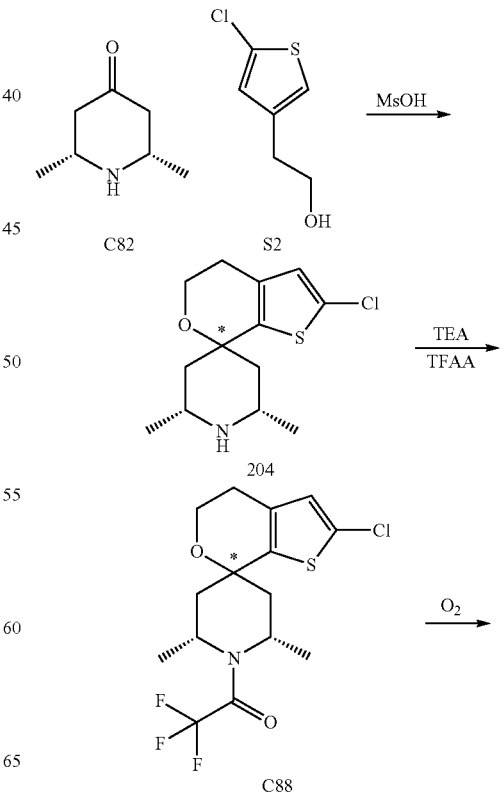

-continued

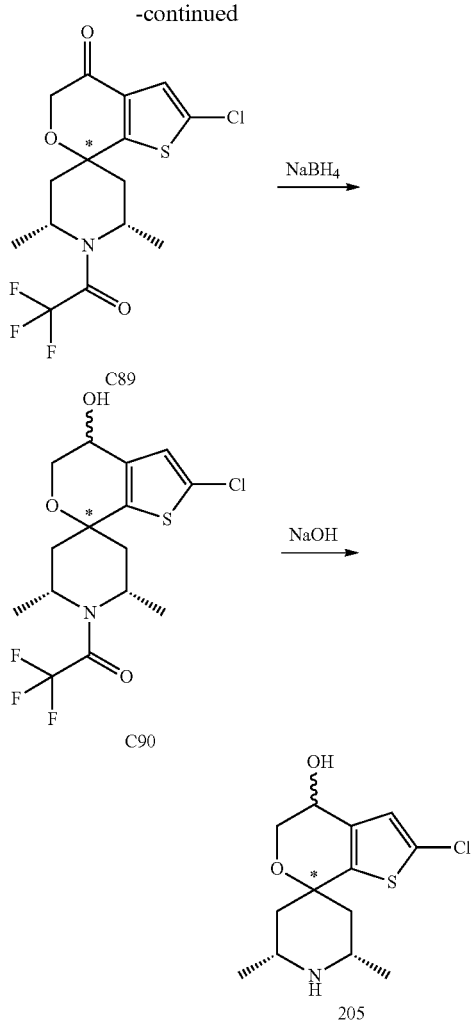

Step 1. Synthesis of (2R,6S)-2-chloro-2',6'-dimethyl-spiro[4,5-dihydrothieno[2,3-c]pyran-7,4'-piperidine] (204)

To a solution of (2S,6R)-2,6-dimethylpiperidin-4-one (Hydrochloride salt) C82 (98 mg, 0.5989 mmol) and 2-(5-chloro-3-thienyl)ethanol S2 (100 μL, 0.8184 mmol) in DCM (2 mL) was added MsOH (200 μL, 3.082 mmol) and the mixture was stirred at 40° C. for 1 hour. The mixture was cooled to room temperature, and the pH was adjusted to pH 14 with aqueous NaOH. The aqueous layer was extracted with additional DCM (2 mL). The combined organic layer was passed through a phase separator and concentrated in vacuo. Purification by silica gel chromatography (Gradient: 0-10% MeOH in DCM) yielded the product which was diluted in diethyl ether (4 mL). HCl (200 μL of 4 M, 0.8000 mmol) was added to salt the product, and the solid was filtered, rinsed with additional ether and dried to yield (2R,6S)-2-chloro-2',6'-dimethyl-spiro[4,5-dihydrothieno[2,3-c]pyran-7,4'-piperidine] (Hydrochloride salt) 204 (102 mg, 55%). $^1$H NMR (400 MHz, DMSO-d$_6$) δ 9.21 (d, J=10.4 Hz, 1H), 8.82 (d, J=10.2 Hz, 1H), 6.93 (s, 1H), 3.89 (t, J=5.4 Hz, 2H), 3.36 (d, J=8.5 Hz, 2H), 2.58 (t, J=5.4 Hz, 2H), 2.17 (d, J=14.1 Hz, 2H), 1.82 (dd, J=14.3, 12.2 Hz, 2H), 1.27 (d, J=6.5 Hz, 6H). LCMS m/z 272.09 [M+H]$^+$.

Step 2. Synthesis of 1-[(2R,6S)-2-chloro-2',6'-dimethyl-spiro[4,5-dihydrothieno[2,3-c]pyran-7,4'-piperidine]-1'-yl]-2,2,2-trifluoro-ethanone (C88)

To a solution of (2R,6S)-2-chloro-2',6'-dimethyl-spiro[4,5-dihydrothieno[2,3-c]pyran-7,4'-piperidine] (Hydrochloride salt) 204 (319 mg, 1.173 mmol) in DCM (6 mL) was added TFAA (750 mg, 3.571 mmol) and TEA (600 mg, 5.929 mmol). The reaction was stirred for 30 minutes at room temperature. The reaction was quenched with sodium bicarbonate and DCM. The organic phase was separated, passed through a phase separator, and concentrated in vacuo. Purification by silica gel chromatography (Gradient: 0-50% EtOAc in heptane) yielded the product 1-[(2R,6S)-2-chloro-2',6'-dimethyl-spiro[4,5-dihydrothieno[2,3-c]pyran-7,4'-piperidine]-1'-yl]-2,2,2-trifluoro-ethanone C88 (388 mg, 85%). LCMS m/z 368.08 [M+H]$^+$.

Step 3. Synthesis of (2R,6S)-2'-chloro-2,6-dimethyl-1-(2,2,2-trifluoroacetyl)spiro[piperidine-4,7'-thieno[2,3-c]pyran]-4'-one (C89)

To a solution of 1-[(2R,6S)-2-chloro-2',6'-dimethyl-spiro[4,5-dihydrothieno[2,3-c]pyran-7,4'-piperidine]-1'-yl]-2,2,2-trifluoro-ethanone C88 in MeCN (10 mL) was added cobaltous acetate tetrahydrate (128 mg, 0.5139 mmol) and N-hydroxyphthalimide (168 mg, 1.030 mmol). The reaction was purged and evacuated with oxygen (3×) and then heated to 45° C. under an oxygen balloon. The reaction was stirred for 7 hours. The reaction was diluted with water and DCM. The organic phase was separated, passed through a phase separator, and concentrated in vacuo. The material was brought up in a minimal amount of DCM and a solid began crashing out of solution. The liquid was decanted off. Purification by silica gel chromatography (Gradient: 0-60% EtOAc in Heptane) afforded (2R,6S)-2'-chloro-2,6-dimethyl-1-(2,2,2-trifluoroacetyl)spiro[piperidine-4,7'-thieno[2,3-c]pyran]-4'-one C89 (122 mg, 31%). $^1$H NMR (300 MHz, Chloroform-d) δ 7.21 (s, 1H), 4.63-4.39 (m, 2H), 4.29 (s, 2H), 2.69 (dd, J=14.4, 8.1 Hz, 2H), 2.07-1.80 (m, 2H), 1.48 (d, J=6.9 Hz, 6H). LCMS m/z 382.03 [M+H]$^+$.

Step 4. Synthesis of 1-[(2R,6S)-2-chloro-4-hydroxy-2',6'-dimethyl-spiro[4,5-dihydrothieno[2,3-c]pyran-7,4'-piperidine]-1'-yl]-2,2,2-trifluoro-ethanone (C90)

To a solution of (2R,6S)-2'-chloro-2,6-dimethyl-1-(2,2,2-trifluoroacetyl)spiro[piperidine-4,7'-thieno[2,3-c]pyran]-4'-one C89 (122 mg, 0.3195 mmol) in DCM (2.44 mL) and MeOH (620 μL) was added NaBH$_4$ (73 mg, 1.930 mmol). The reaction was stirred for 45 minutes. The reaction was quenched with aqueous HCl and DCM. The organic phase was separated, passed through a phase separator, and concentrated in vacuo to give 1-[(2R,6S)-2-chloro-4-hydroxy-2',6'-dimethyl-spiro[4,5-dihydrothieno[2,3-c]pyran-7,4'-piperidine]-1'-yl]-2,2,2-trifluoro-ethanone C90 (122 mg, 98%). LCMS m/z 384.28 [M+H]$^+$.

Step 5. Synthesis of (2R,6S)-2-chloro-2',6'-dimethyl-spiro[4,5-dihydrothieno[2,3-c]pyran-7,4'-piperidine]-4-ol (205)

To a solution of 1-[(2R,6S)-2-chloro-4-hydroxy-2',6'-dimethyl-spiro[4,5-dihydrothieno[2,3-c]pyran-7,4'-piperidine]-1'-yl]-2,2,2-trifluoro-ethanone C90 (122 mg, 0.3195 mmol) in MeOH (620 μL) was added NaOH 6M (10 eq).

Compound 206

(2R,6S)-2-chloro-2',6-dicyclopropyl-spiro[4,5-dihydrothieno[2,3-c]pyran-7,4'-piperidine] (206)

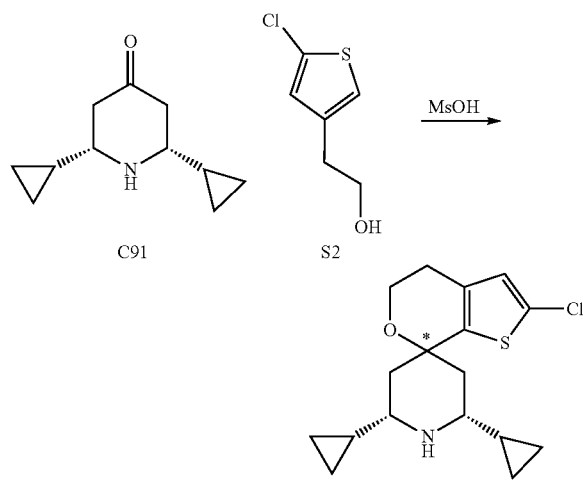

Step 1. Synthesis of (2R,6S)-2-chloro-2',6'-dicyclopropyl-spiro[4,5-dihydrothieno[2,3-c]pyran-7,4'-piperidine] (206)

To a solution of 2,6-dicyclopropylpiperidin-4-one C91 (30 mg, 0.1674 mmol) in DCM (1000 µL) was added 2-(5-chloro-3-thienyl)ethanol S2 (25 µL) followed by MsOH (44 µL, 0.6780 mmol) and the mixture was stirred at reflux. After 5 minutes, the mixture was cooled, pH adjusted with aqueous NaOH (150 µL of 6 M, 0.9000 mmol) to pH 14 and the organic layer was separated and concentrated. Silica gel purification (Gradient: 0-20% MeOH in DCM) yielded a mixture of cis and trans isomers. SFC purification yielded (2R,6S)-2-chloro-2',6'-dicyclopropyl-spiro[4,5-dihydrothieno[2,3-c]pyran-7,4'-piperidine] 206 (5.6 mg, 10%). $^1$H NMR (300 MHz, Methanol-d$_4$) δ 6.66 (s, 1H), 3.84 (t, J=5.5 Hz, 2H), 2.57 (t, J=5.5 Hz, 2H), 2.24-2.11 (m, 2H), 2.06 (ddd, J=11.5, 9.0, 2.4 Hz, 2H), 1.54 (dd, J=13.3, 11.5 Hz, 2H), 0.87-0.69 (m, 2H), 0.62-0.39 (m, 4H), 0.37-0.21 (m, 2H), 0.21-0.04 (m, 2H). LCMS m/z 324.02 [M+H]$^+$.

Compound 207

(2R,6S)-2',6'-dimethyl-2-(trifluoromethyl)spiro[4,5-dihydrothieno[2,3-c]pyran-7,4'-piperidine] (207)

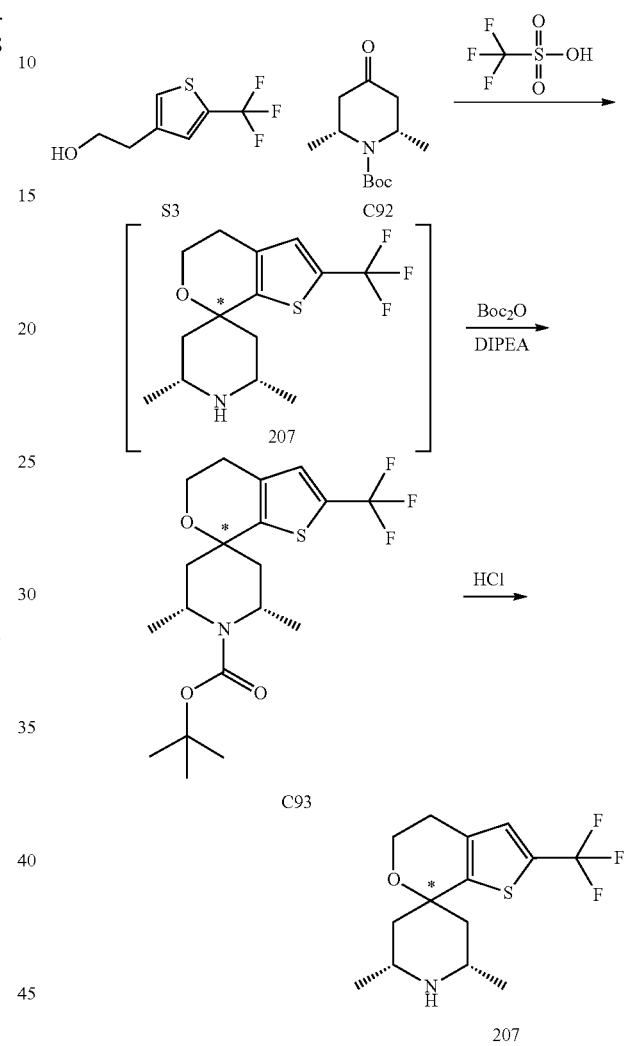

Step 1. Synthesis of (2R,6S)-2',6'-dimethyl-2-(trifluoromethyl)spiro[4,5-dihydrothieno[2,3-c]pyran-7,4'-piperidine] (207)

To a solution of tert-butyl (2S,6R)-2,6-dimethyl-4-oxo-piperidine-1-carboxylate C92 (300 mg, 1.320 mmol) and 2-[5-(trifluoromethyl)-3-thienyl]ethanol S3 (300 mg, 1.483 mmol) in dioxane (4.5 mL) cooled to 0° C. was added Triflic Acid (345 µL, 3.899 mmol). The reaction was warmed to room temperature. After 10 minutes ketal formation was observed. The solution was stirred for 6 hours. The solution was diluted with DCM and washed with 2 M Na$_2$CO$_3$. The reaction was extracted with DCM (3x), dried with Na$_2$SO$_4$, filtered, and the DCM was removed in vacuo to give crude (2R,6S)-2',6'-dimethyl-2-(trifluoromethyl)spiro[4,5-dihydrothieno[2,3-c]pyran-7,4'-piperidine] 207 (400 mg, 71%). LCMS m/z 306.06 [M+H]$^+$.

Step 2. Synthesis of tert-butyl (2R,6S)-2',6'-dimethyl-2-(trifluoromethyl)spiro[4,5-dihydrothieno[2,3-c]pyran-7,4'-piperidine]-1'-carboxylate (C93)

To a solution of (2R,6S)-2',6'-dimethyl-2-(trifluoromethyl)spiro[4,5-dihydrothieno[2,3-c]pyran-7,4'-piperidine] 207 (400 mg, 71%) in DCM (8 mL) was added boc anhydride (1.5 mL, 6.529 mmol) and DIPEA (670 µL, 3.847 mmol). The reaction was stirred for four days until full conversion was observed. The solvent was concentrated in vacuo. Purification by silica gel chromatography (Gradient: 0-30% EtOAc in heptane) yielded the product tert-butyl (2R,6S)-2',6'-dimethyl-2-(trifluoromethyl)spiro[4,5-dihydrothieno[2,3-c]pyran-7,4'-piperidine]-1'-carboxylate C93 (440 mg, 82%). $^1$H NMR (300 MHz, Chloroform-d) δ 7.11 (d, J=1.3 Hz, 1H), 4.47-4.25 (m, 2H), 3.89 (t, J=5.5 Hz, 2H), 2.67 (t, J=5.5 Hz, 2H), 2.43 (ddd, J=15.5, 8.5, 2.3 Hz, 2H), 1.79 (dd, J=14.5, 6.9 Hz, 2H), 1.50 (s, 9H), 1.33 (d, J=6.8 Hz, 6H).

Step 3. Synthesis of (2R,6S)-2',6'-dimethyl-2-(trifluoromethyl)spiro[4,5-dihydrothieno[2,3-c]pyran-7,4'-piperidine] (207)

To a solution of tert-butyl (2R,6S)-2',6'-dimethyl-2-(trifluoromethyl)spiro[4,5-dihydrothieno[2,3-c]pyran-7,4'-piperidine]-1'-carboxylate C93 (20 mg, 0.049 mmol) dissolved in dioxane (100 µL) was added HCl (100 µL of 4 M, 0.4000 mmol) in dioxane. The reaction was stirred at room temperature for 1 hour. The solvent was concentrated in vacuo. Purification by reversed-phase HPLC (Method: C18 Waters Sunfire column (30×150 mm, 5 micron). Gradient: MeCN in H$_2$O with 0.1% trifluoroacetic acid) afforded (2R,6S)-2',6'-dimethyl-2-(trifluoromethyl)spiro[4,5-dihydrothieno[2,3-c]pyran-7,4'-piperidine] (Trifluoroacetate salt) 207 (6.6 mg, 32%). $^1$H NMR (300 MHz, Chloroform-d) δ 9.55 (s, 1H), 8.67 (s, 1H), 7.16 (d, J=1.3 Hz, 1H), 3.94 (t, J=5.4 Hz, 2H), 3.67 (s, 2H), 2.74 (t, J=5.4 Hz, 2H), 2.38-1.84 (m, 4H), 1.37 (d, J=6.6 Hz, 6H). LCMS m/z 306.24 [M+H]$^+$.

Compound 208

[(2R,6S)-2',6'-dimethyl-2-(trifluoromethyl)spiro[4,5-dihydrothieno[2,3-c]pyran-7,4'-piperidine]-3-yl]methanol (208)

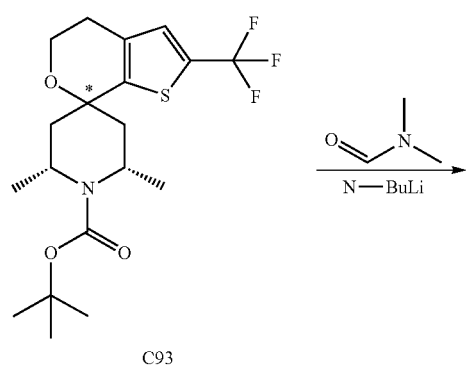

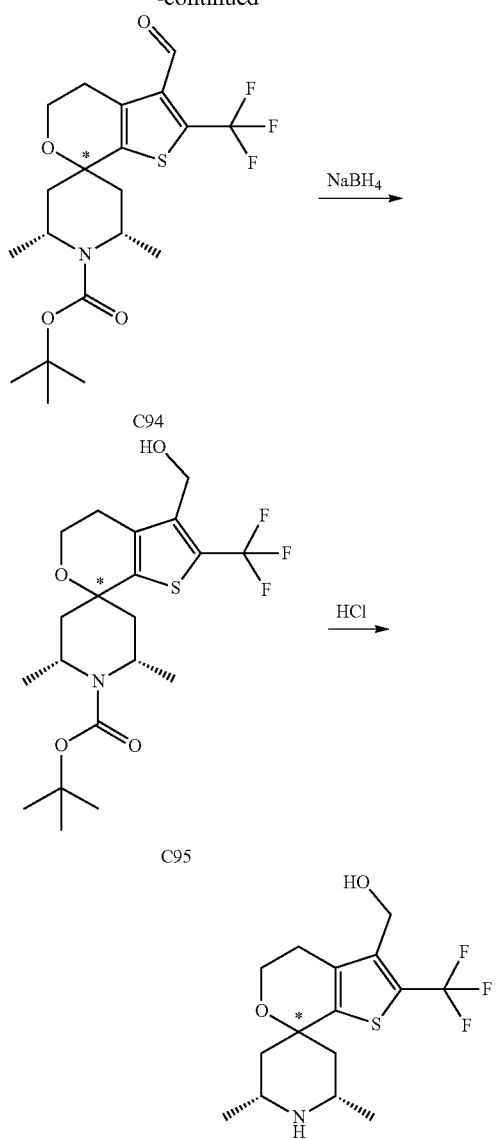

Step 1. Synthesis of tert-butyl (2R,6S)-3-formyl-2',6'-dimethyl-2-(trifluoromethyl)spiro[4,5-dihydrothieno[2,3-c]pyran-7,4'-piperidine]-1'-carboxylate (C94)

To a solution of tert-butyl (2R,6S)-2',6'-dimethyl-2-(trifluoromethyl)spiro[4,5-dihydrothieno[2,3-c]pyran-7,4'-piperidine]-1'-carboxylate C93 (420 mg, 1.036 mmol) in THF (6 mL) at −78° C. under N$_2$ was added s-BuLi (1 mL of 1.4 M, 1.400 mmol). The reaction was stirred for 30 minutes, followed by addition of DMF (160 µL, 2.066 mmol). The reaction was stirred for 30 minutes and warmed to room temperature. The reaction was quenched with NH$_4$Cl and DCM. The organic phase was separated, passed through a phase separator, and concentrated to give crude tert-butyl (2R,6S)-3-formyl-2',6'-dimethyl-2-(trifluoromethyl)spiro[4,5-dihydrothieno[2,3-c]pyran-7,4'-piperidine]-1'-carboxylate C94. LCMS m/z 434.32 [M+H]$^+$.

Step 2. Synthesis of tert-butyl (2R,6S)-3-(hydroxymethyl)-2',6'-dimethyl-2-(trifluoromethyl)spiro[4,5-dihydrothieno[2,3-c]pyran-7,4'-piperidine]-1'-carboxylate (C95)

The reaction was stirred for 30 minutes. The reaction was quenched with aqueous sodium bicarbonate and DCM. The organic phase was separated, passed through a phase separator, and concentrated in vacuo to give crude tert-butyl (2R,6S)-3-(hydroxymethyl)-2',6'-dimethyl-2-(trifluoromethyl)spiro[4,5-dihydrothieno[2,3-c]pyran-7,4'-piperidine]-1'-carboxylate C95 LCMS m/z 436.35 [M+H]$^+$.

Step 3. Synthesis of (2R,6S)-2',6'-dimethyl-2-(trifluoromethyl)spiro[4,5-dihydrothieno[2,3-c]pyran-7,4'-piperidine]-3-yl]methanol (208)

To a solution of crude C95 in dioxane (2 mL) was added HCl (2.5 mL of 4 M, 10.00 mmol) in dioxane. The reaction was stirred for 1 hour. Solvent was removed in vacuo. Purification by reversed-phase HPLC (Method: C18 Waters Sunfire column (30×150 mm, 5 micron)) afforded (2'S,6'R)-2',6'-dimethyl-2-(trifluoromethyl)spiro[4,5-dihydrothieno[2,3-c]pyran-7,4'-piperidine]-3-yl]methanol 208 (192 mg, 55%). $^1$H NMR (300 MHz, Chloroform-d) δ 4.66 (d, J=1.4 Hz, 2H), 3.98 (t, J=5.5 Hz, 2H), 3.17 (dtt, J=12.6, 6.3, 3.1 Hz, 2H), 2.75 (t, J=5.5 Hz, 2H), 2.19-1.97 (m, 2H), 1.35 (dd, J=13.5, 11.4 Hz, 2H), 1.10 (d, J=6.4 Hz, 6H). LCMS m/z 336.08 [M+H]$^+$.

Compound 209 methyl (2'S,6'R, 7S)-2-chloro-6'-methyl-spiro[4,5-dihydrothieno[2,3-c]pyran-7,4'-piperidine]-2'-carboxylate (209)

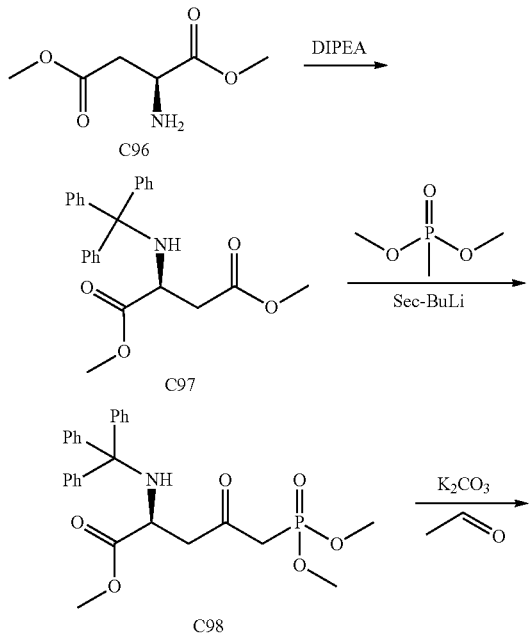

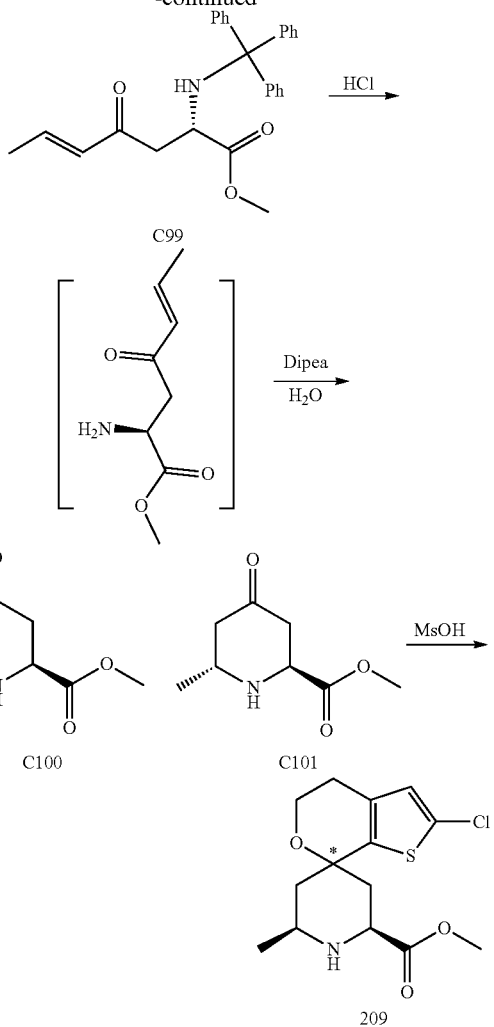

Step 1. Synthesis of dimethyl (2S)-2-(tritylamino)butanedioate (C97)

To a mixture of dimethyl (2S)-2-aminobutanedioate C96 (Hydrochloride salt) (2000 mg, 10.12 mmol) and DIPEA (3.7 mL, 21.24 mmol) in DCM (40 mL) was added [chloro(diphenyl)methyl]benzene (3 g, 10.76 mmol). The mixture was stirred at room temperature overnight. The mixture was quenched with water, phase separated, and the organic layer was dried with MgSO$_4$, filtered, and concentrated. Purification by silica gel chromatography (Gradient: 0-30% EtOAc in heptane) yielded dimethyl (2S)-2-(tritylamino)butanedioate (3.11 g, 75%) C97. $^1$H NMR (300 MHz, Chloroform-d) δ 7.59-7.43 (m, 6H), 7.35-7.24 (m, 6H), 7.24-7.13 (m, 3H), 3.70 (s, 4H), 3.28 (s, 3H), 2.95 (d, J=10.1 Hz, 1H), 2.67 (dd, J=14.7, 5.4 Hz, 1H), 2.53 (dd, J=14.7, 7.0 Hz, 1H). LCMS m/z 402.23 [M+H]$^+$.

Step 2. Synthesis of methyl (2S)-5-dimethoxyphosphoryl-4-oxo-2-(tritylamino)pentanoate (C98)

To a mixture of [methoxy(methyl)phosphoryl]oxymethane (2 mL, 18.46 mmol) in THF (90 mL) cooled to −78° C. was added a solution of sec-butyllithium (13.5 mL of 1.4 M, 18.90 mmol), dropwise. After 5 minutes at this temperature, a solution of dimethyl (2S)-2-(tritylamino)butanedioate C97 (3100 mg, 7.683 mmol) in THF (10 mL) was added, dropwise, and the mixture was stirred for 10 additional minutes and then quenched with AcOH (1.3 mL, 22.86 mmol). The mixture was diluted with water (100 mL) and ether (100 mL). The organic layer was removed, and subsequently washed with water (100 mL), brine (100 mL), dried with MgSO$_4$, filtered, and concentrated. Purification by silica gel chromatography (Gradient: 0-20% MeOH in DCM) yielded methyl (2S)-5-dimethoxyphosphoryl-4-oxo-2-(tritylamino)pentanoate C98 (1580 mg, 41%). $^1$H NMR (300 MHz, Chloroform-d) δ 7.56-7.42 (m, 6H), 7.30 (t, J=1.6 Hz, 3H), 7.28-7.16 (m, 6H), 3.81 (s, 3H), 3.78 (s, 3H), 3.72 (s, 1H), 3.31 (s, 3H), 3.07 (d, J=22.6 Hz, 2H), 2.91 (dd, J=16.7, 4.6 Hz, 2H), 2.79 (dd, J=16.7, 6.9 Hz, 1H). LCMS m/z 494.31 [M+H]$^+$.

Step 3. Synthesis of methyl (E,2S)-4-oxo-2-(tritylamino)hept-5-enoate (C99)

To a mixture of methyl (2S)-5-dimethoxyphosphoryl-4-oxo-2-(tritylamino)pentanoate C98 (553 mg, 1.108 mmol) in MeCN (30 mL) was added potassium carbonate (170 mg, 1.230 mmol) followed by acetaldehyde (200 μL, 3.564 mmol). The mixture was warmed to 50° C. and stirred overnight. The mixture was cooled to room temperature, concentrated, and re-diluted in ethyl acetate (50 mL) and water (30 mL). The organic layer was separated, washed with brine (30 mL), dried with MgSO$_4$, filtered, and concentrated. Purification by silica gel chromatography (Gradient: 0-40% EtOAc in Heptane) yielded methyl (E,2S)-4-oxo-2-(tritylamino)hept-5-enoate C99 (282 mg, 61%). LCMS m/z 412.27 [M+H]$^+$.

Step 4. Synthesis of methyl (2S,6S)-6-methyl-4-oxo-piperidine-2-carboxylate (C100) and methyl (2S,6R)-6-methyl-4-oxo-piperidine-2-carboxylate (C101)

To a mixture of methyl (E,2S)-4-oxo-2-(tritylamino)hept-5-enoate C99 (187 mg, 0.4203 mmol) in methanol (30 mL) at room temperature was added hydrochloric acid (7500 μL of 2 M, 15.00 mmol). The mixture was stirred for 10 minutes. Intermediate, methyl (E,2S)-2-amino-4-oxo-hept-5-enoate, was formed. To the mixture was added water (15 mL) and DIPEA (4500 μL, 25.84 mmol) and the reaction was stirred for 15 minutes. The mixture was diluted with EtOAc (60 mL), water (60 mL), and the layers were separated. The aqueous layer was extracted with EtOAc (2×50 mL), and the combined organic layer was dried with MgSO$_4$, filtered, and concentrated. Purification by silica gel chromatography (Gradient: 0-10% MeOH in DCM) yielded C100 and C101 as a 2:1 mixture of cis:trans isomers (28 mg, 39%).

C100 [DIAST-1] $^1$H NMR (300 MHz, Chloroform-d) δ 3.75 (s, 3H), 3.64 (dd, J=12.2, 3.5 Hz, 1H), 2.97 (dqd, J=12.3, 6.2, 2.9 Hz, 1H), 2.72-2.53 (m, 2H), 2.43-2.34 (m, 1H), 2.08 (ddd, J=14.2, 11.7, 1.0 Hz, 1H), 1.24 (d, J=6.2 Hz, 3H). LCMS m/z 172.0 [M+H]$^+$.

C101 [DIAST-2] $^1$H NMR (300 MHz, Chloroform-d) δ 4.06 (dd, J=6.6, 3.7 Hz, 1H), 3.73 (s, 3H)), 3.32-3.15 (m, 1H), 2.72-2.53 (m, 2H), 2.43-2.34 (m, 1H), 2.08 (ddd, J=14.2, 11.7, 1.0 Hz, 1H), 1.17 (d, J=6.2 Hz, 3H). LCMS m/z 172.0 [M+H]$^+$.

Step 5. Synthesis of methyl (2'S,6'S, 7S)-2-chloro-6'-methyl-spiro[4,5-dihydrothieno[2,3-c]pyran-7,4'-piperidine]-2'-carboxylate (209)

To a mixture C100 and C101 (28 mg, 0.1636 mmol) (2:1 cis to trans) in DCM (1000 μL) was added 2-(5-chloro-3-thienyl)ethanol S2 (25 μL, 0.2021 mmol) followed by MsOH (50 μL, 0.7705 mmol) and the mixture was refluxed for 5 minutes. The mixture was cooled, and the pH was adjusted with aqueous NaOH (150 μL of 6 M, 0.90 mmol) to a pH of 14 and the organic layer was separated and concentrated. Purification by silica gel chromatography (Gradient: 0-20% MeOH in DCM) yielded methyl (2'S,6'S, 7S)-2-chloro-6'-methyl-spiro[4,5-dihydrothieno[2,3-c]pyran-7,4'-piperidine]-2'-carboxylate 209 (24 mg, 68%). $^1$H NMR (300 MHz, Chloroform-d) δ 6.57 (s, 1H), 3.92 (t, J=5.5 Hz, 2H), 3.84 (dd, J=11.9, 2.8 Hz, 1H), 3.71 (s, 3H), 3.12 (dtd, J=12.7, 6.4, 2.6 Hz, 1H), 2.69-2.51 (m, 2H), 2.40 (dt, J=13.7, 2.7 Hz, 1H), 1.98 (dt, J=13.7, 2.6 Hz, 1H), 1.62 (dd, J=13.6, 11.9 Hz, 1H), 1.33 (dd, J=13.7, 11.3 Hz, 1H), 1.12 (d, J=6.3 Hz, 3H). LCMS m/z 316.01 [M+H]$^+$. Minor 2,6-trans isomer was purged during isolation.

Compound 210

(2-chloro-6'-methyl-spiro[4,5-dihydrothieno[2,3-c]pyran-7,4'-piperidine]-2'-yl)methanol (210)

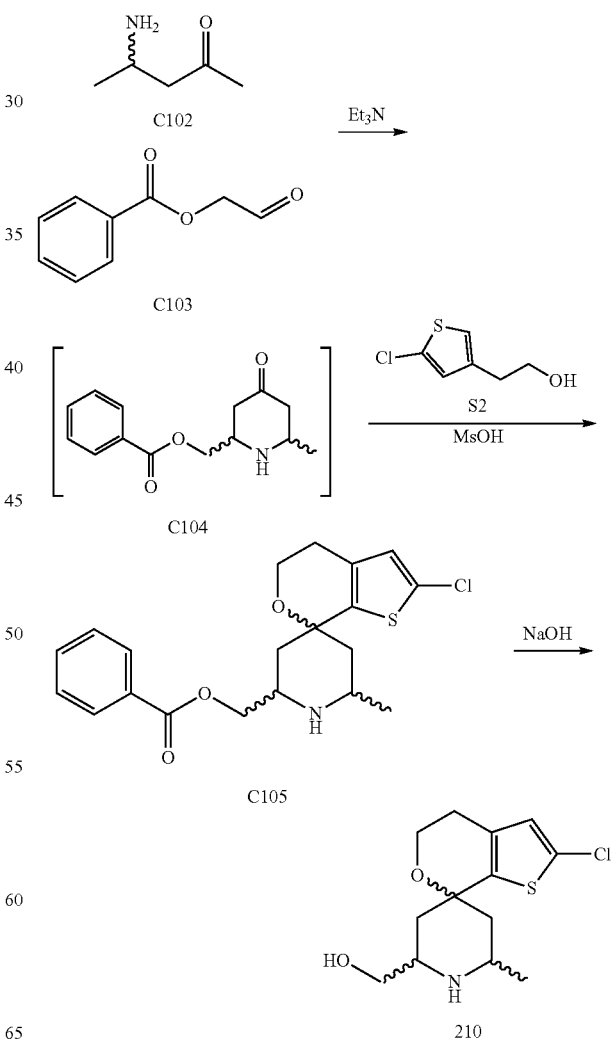

Step 1. Synthesis of [(2-chloro-6'-methyl-spiro[4,5-dihydrothieno[2,3-c]pyran-7,4'-piperidine]-2'-yl] methyl benzoate (C105)

To a solution of 4-aminopentan-2-one C102 (50 mg, 0.36 mmol) in EtOH (1.5 mL) was added Et₃N (51 µL, 0.3659 mmol) followed by 2-2-oxoethyl benzoate C103 (65 mg, 0.396 mmol), L-proline (9 mg, 0.07817 mmol), and MgSO₄ (45 mg, 0.3739 mmol). The mixture was stirred at room temperature overnight. The mixture was filtered, concentrated, and quenched with saturated sodium bicarbonate (50 mL) and extracted with DCM (75 mL). Additional DCM (4×50 mL) was used to wash the aqueous layer, and then the combined organic layer was dried with MgSO₄, filtered, and concentrated to yield crude intermediate ((6-methyl-4-oxopiperidin-2-yl)methyl benzoate) C104, which was used in the next step without further purification.

To the C104 mixture from the first step was added 2-(5-chloro-3-thienyl)ethanol S2 (50 µL, 0.4043 mmol), MsOH (100 µL, 1.541 mmol) and DCM (1 mL). The mixture was stirred at 40° C. overnight. The mixture was pH adjusted to around pH 10, and then the mixture was phase separated. Purification by silica gel chromatography (Gradient: 0-20% MeOH in DCM) yielded [(2'S,6'S,7S)-2-chloro-6'-methyl-spiro[4,5-dihydrothieno[2,3-c]pyran-7,4'-piperidine]-2'-yl] methyl benzoate C105 (12 mg, 7%). $^1$H NMR (300 MHz, Chloroform-d) δ 8.15-7.94 (m, 2H), 7.60 (t, J=7.4 Hz, 1H), 7.48 (t, J=7.6 Hz, 2H), 6.60 (s, 1H), 4.37 (dd, J=10.9, 4.2 Hz, 1H), 4.18 (dd, J=10.9, 8.0 Hz, 1H), 3.93 (t, J=5.5 Hz, 2H), 3.61-3.44 (m, 1H), 3.21 (ddd, J=11.4, 6.3, 2.4 Hz, 1H), 2.62 (t, J=5.5 Hz, 2H), 2.09 (td, J=13.3, 2.5 Hz, 2H), 1.57-1.34 (m, 2H), 1.14 (d, J=6.3 Hz, 3H). LCMS m/z 392.02 [M+H]⁺.

Step 2. Synthesis of (2-chloro-6'-methyl-spiro[4,5-dihydrothieno[2,3-c]pyran-7,4'-piperidine]-2'-yl) methanol (210)

To a mixture of C105 (10 mg, 0.02552 mmol) in methanol (1 mL) was added NaOH (100 µL of 2 M, 0.2000 mmol) and the mixture was stirred at room temperature for five minutes. Purification by reversed-phase HPLC (Method: C18 Waters Sunfire column (30×150 mm, 5 micron). Gradient: MeCN in H₂O with 5 mM HCl) yielded (2-chloro-6'-methyl-spiro[4,5-dihydrothieno[2,3-c]pyran-7,4'-piperidine]-2'-yl)methanol (Hydrochloride salt) 210 (5.5 mg, 66%). $^1$H NMR (300 MHz, DMSO-d₆) δ 8.83 (s, 1H), 8.33 (s, 1H), 6.93 (s, 1H), 3.90 (d, J=5.5 Hz, 2H), 3.66 (dd, J=11.8, 3.9 Hz, 1H), 3.53 (dd, J=11.6, 5.3 Hz, 1H), 3.34 (s, 2H), 2.58 (t, J=5.4 Hz, 2H), 2.15 (t, J=14.4 Hz, 3H), 1.78 (q, J=12.8 Hz, 2H), 1.27 (d, J=6.5 Hz, 3H). LCMS m/z 288.14 [M+H]⁺.

Preparation of S47

(2S,6S)-2-cyclopropyl-6-methyl-piperidin-4-one (S47)

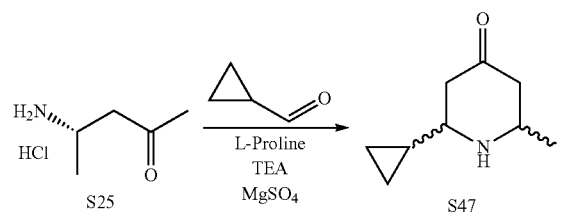

To a mixture of (4S)-4-aminopentan-2-one (Hydrochloride salt) S25 (150 mg, 1.090 mmol) in Et₃N (153 µL, 1.098 mmol) and EtOH (9 mL) was added cyclopropanecarbaldehyde (90 µL, 1.204 mmol), L-proline (25 mg, 0.2171 mmol), and MgSO₄ (130 mg, 1.080 mmol). The mixture was stirred at room temperature for 2 hours. The mixture was filtered, concentrated, and diluted in saturated aqueous bicarbonate (3 mL), diluted with water (7 mL) and extracted with DCM (2×10 mL). The combined organic layer was washed with brine (5 mL), dried with MgSO₄, filtered, and concentrated. Purification by silica gel chromatography (Gradient: 0-20% MeOH in DCM) afforded (2S,6S)-2-cyclopropyl-6-methyl-piperidin-4-one S47 (65 mg, 39%). $^1$H NMR (300 MHz, Chloroform-d) δ 2.79 (dqd, J=12.2, 6.1, 3.0 Hz, 1H), 2.35 (ddd, J=14.0, 3.1, 2.1 Hz, 1H), 2.27-2.13 (m, 2H), 2.02 (ddd, J=14.0, 11.6, 1.1 Hz, 1H), 1.96-1.85 (m, 1H), 1.80 (s, 1H), 1.12 (d, J=6.2 Hz, 3H), 0.78 (qt, J=8.2, 4.9 Hz, 1H), 0.59-0.27 (m, 2H), 0.23-0.03 (in, 2H). LCMS m/z 154.05 [M+1]⁺.

Preparation of Intermediates S48-S53

Intermediates S48-S53 were prepared in a single step from intermediate S25 or S24 using the appropriate aldehyde and the method described for intermediate S47. Aldehydes were prepared by methods described above or obtained from commercial sources. In this method, partial stereochemical erosion of the enantiomerically pure starting material (4S)-4-aminopentan-2-one (Hydrochloride salt) S25 was observed, leading to unseparated mixtures of stereoisomers where the cis-product was the major isomer. Any modifications to methods are noted in Table 9 and accompanying footnotes.

TABLE 9

Method of preparation, structure and physicochemical data for intermediates S48-S53

| Product | Aldehyde Reagent And Amine | Method | $^1$H NMR |
|---|---|---|---|
| ![S48] | ![S25] | Preparation of S47[1,2] | $^1$H NMR (300 MHz, Chloroform-d) δ 3.03-2.85 (m, 1H), 2.73-2.51 (m, 1H), 2.53-2.37 (m, 1H), 2.37-2.19 (m, 2H), 2.19-1.98 (m, 1H), 1.74 (s, 1H), 1.73-1.58 (m, 1H), 1.49 (ttd, J = 12.1, 8.0, 4.2 Hz, 1H), 1.22 (d, J = 6.2 Hz, 3H), 1.18-1.03 (m, 1H) LCMS m/z 190.09 [M + H]⁺. |

TABLE 9-continued

Method of preparation, structure and physicochemical data for intermediates S48-S53

| Product | Aldehyde Reagent And Amine | Method | ¹H NMR |
|---|---|---|---|
| 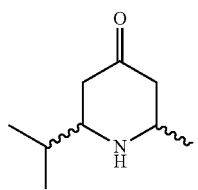 S49 |  S24 | Preparation of S47[1,2,3] | ¹H NMR (300 MHz, Chloroform-d) δ 2.92 (dqd, J = 12.3, 6.2, 2.9 Hz, 1H), 2.61 (ddd, J = 11.8, 6.0, 2.8 Hz, 1H), 2.41-2.25 (m, 2H), 2.12-1.98 (m, 2H), 1.69 (dq, J = 13.3, 6.7 Hz, 1H), 1.20 (d, J = 6.2 Hz, 3H), 0.94 (dd, J = 9.2, 6.8 Hz, 6H). |
| 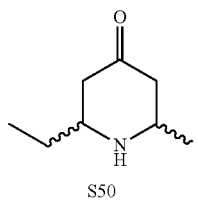 S50 |  S24 | Preparation of S47[1,2,3] | ¹H NMR (300 MHz, Chloroform-d) δ 2.98 (dqd, J = 12.2, 6.2, 2.9 Hz, 1H), 2.77 (ddt, J = 12.5, 6.4, 3.3 Hz, 1H), 2.36 (ddt, J = 14.4, 9.9, 2.4 Hz, 2H), 2.15-1.98 (m, 2H), 1.69-1.41 (m, 2H), 1.22 (d, J = 6.2 Hz, 3H), 0.95 (t, J = 7.5 Hz, 3H). |
| 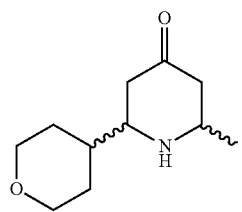 S51 | 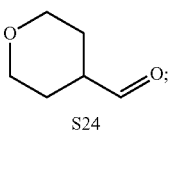 S24 | Preparation of S47[1,2,3] | ¹H NMR (300 MHz, Chloroform-d) δ 4.08-3.85 (m, 2H), 3.35 (td, J = 11.8, 2.2 Hz, 2H), 2.92 (dqd, J = 12.2, 6.2, 2.8 Hz, 1H), 2.65 (ddd, J = 11.9, 6.3, 2.8 Hz, 1H), 2.35 (ddt, J = 14.4, 11.6, 2.4 Hz, 2H), 2.12-1.97 (m, 2H), 1.73-1.63 (m, 1H), 1.63-1.52 (m, 2H), 1.46-1.30 (m, 2H), 1.19 (d, J = 6.2 Hz, 3H). |
| 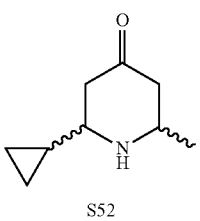 S52 |  S24 | Preparation of S47[1,2,3] | ¹H NMR (300 MHz, Chloroform-d) δ 2.89 (dqd, J = 12.2, 6.1, 3.0 Hz, 1H), 2.45 (ddd, J = 14.0, 3.1, 2.2 Hz, 1H), 2.36-2.23 (m, 2H), 2.13 (ddd, J = 13.9, 11.6, 1.0 Hz, 1H), 2.00-1.93 (m, 1H), 1.22 (d, J = 6.2 Hz, 3H), 0.89 (qt, J = 8.3, 5.0 Hz, 1H), 0.61-0.46 (m, 2H), 0.20 (qq, J = 8.0, 3.9, 3.4 Hz, 2H). |
| 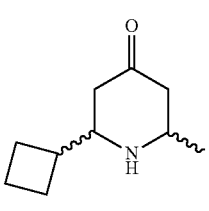 S53 |  S24 | Preparation of S47[4,5] | ¹H NMR (300 MHz, Chloroform-d) δ 2.94 (dqd, J = 12.3, 6.1, 2.7 Hz, 1H), 2.75 (ddd, J = 11.7, 8.8, 2.7 Hz, 1H), 2.69 (s, 1H), 2.37-2.23 (m, 3H), 2.07 (ddd, J = 13.8, 11.3, 7.9 Hz, 2H), 2.01-1.83 (m, 3H), 1.83-1.61 (m, 3H), 1.19 (d, J = 6.2 Hz, 3H). LCMS m/z 167.95 [M + H]⁺. |

[1] The reaction was stirred overnight.

[2] Purification by silica gel chromatography (Gradient: 0-10% MeOH in DCM) afforded the product.

[3] After completion the mixtures were concentrated, re-diluted in DCM and filtered.

[4] After completion the mixture was poured into saturated aqueous sodium bicarbonate (10 mL) and diluted with water (3 mL) and ethyl acetate (30 mL).

[5] The reaction was not purified, telescoped to the next step.

Compound 211

(2S,6S)-2-chloro-2'-cyclopropyl-6'-methyl-spiro[4,5-dihydrothieno[2,3-c]pyran-7,4'-piperidine]

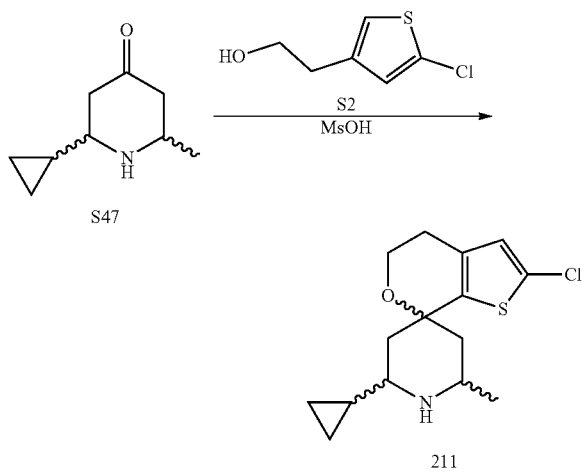

To a mixture of (2S,6S)-2-cyclopropyl-6-methyl-piperidin-4-one S47 (65 mg, 0.4242 mmol) in DCM (2 mL) was added 2-(5-chloro-3-thienyl)ethanol (75 µL) followed by MsOH (130 µL, 2.003 mmol) and the mixture was refluxed for 40 minutes. The mixture was cooled, pH adjusted with NaOH (500 µL of 6 M, 3.000 mmol) pH 14 and the organic layer was separated and concentrated. Purification by silica gel chromatography (Gradient: 0-20% MeOH in DCM) afforded the freebase. The freebase was re-diluted in diethyl ether and HCl (100 µL of 4 M in dioxane, 0.4000 mmol), at which point a white solid precipitated. The mixture was concentrated to yield (2S,6S)-2-chloro-2'-cyclopropyl-6'-methyl-spiro[4,5-dihydrothieno[2,3-c]pyran-7,4'-piperidine] 211 (hydrochloride salt) (15.2 mg, 11%). $^1$H NMR (300 MHz, Methanol-$d_4$) δ 6.74 (s, 1H), 3.92 (t, J=5.5 Hz, 2H), 3.65-3.51 (m, 1H), 2.75 (ddd, J=12.6, 9.8, 3.0 Hz, 1H), 2.63 (dd, J=6.1, 4.9 Hz, 2H), 2.35 (ddt, J=23.2, 14.7, 2.8 Hz, 2H), 1.85 (dd, J=14.6, 12.3 Hz, 1H), 1.70 (dd, J=14.6, 12.2 Hz, 1H), 1.36 (d, J=6.6 Hz, 3H), 0.93 (ddt, J=13.1, 9.5, 4.2 Hz, 1H), 0.81-0.64 (m, 2H), 0.64-0.53 (m, 1H), 0.44-0.26 (m, 1H). LCMS m/z 298.05 [M+H]$^+$.

Compounds 212-218

Compounds 212-218 (see Table 10) were prepared from a single Oxa-Pictet Spengler step with isolated piperidone (see Table 9) and S2 as described for compound 211. Thiophene ethanol and piperidones were prepared by methods described above or obtained from commercial sources. As previously described in the preparation of the piperidinone intermediates, partial stereochemical erosion of the enantiomerically pure starting material (4S)-4-aminopentan-2-one (Hydrochloride salt) S25 was observed, leading to unseparated mixtures of stereoisomers where the cis-product was the major isomer. Any modifications to methods are noted in Table 10 and accompanying footnotes.

TABLE 10

| | | | |
|---|---|---|---|
| Method of preparation, structure and physicochemical data for compounds 212-218. | | | |
| Product | Piperidone | Method | $^1$H NMR; LCMS m/z [M + H]$^+$ |
| Compound 212 | S48 | Compound 211[1,2,3] | $^1$H NMR (300 MHz, DMSO-$d_6$) δ 9.00 (d, J = 23.3 Hz, 2H), 3.90 (d, J = 4.6 Hz, 2H), 3.51 (s, 1H), 3.09 (s, 1H), 2.57 (d, J = 5.4 Hz, 2H), 2.24 (d, J = 15.6 Hz, 2H), 1.94 (d, J = 13.2 Hz, 2H), 1.75 (d, J = 13.3 Hz, 2H), 1.57 (s, 1H), 1.27 (d, J = 6.6 Hz, 3H). LCMS m/z 334.15 [M + H]$^+$. |
| Compound 213 | S48 | Compound 211[1,2,3] | $^1$H NMR (300 MHz, DMSO-$d_6$) δ 8.92 (s, 1H), 8.70 (s, 1H), 3.96-3.82 (m, 2H), 3.45 (s, 1H), 3.21 (s, 1H), 2.59 (s, 2H), 2.31-2.24 (m, 1H), 2.21 (s, 1H), 2.08 (d, J = 13.1 Hz, 2H), 1.76 (dd, J = 28.8, 15.3 Hz, 4H), 1.27 (d, J = 6.5 Hz, 3H). LCMS m/z 333.96 [M + H]$^+$. |

TABLE 10-continued

Method of preparation, structure and physicochemical data for compounds 212-218.

| Product | Piperidone | Method | ¹H NMR; LCMS m/z [M + H]⁺ |
|---|---|---|---|
| 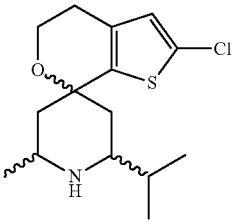<br>Compound 214 | 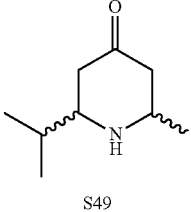<br>S49 | Compound 211[4] | ¹H NMR (300 MHz, Chloroform-d) δ 6.58 (s, 1H), 3.91 (t, J = 5.5 Hz, 2H), 3.10 (dddd, J = 12.6, 8.9, 6.4, 2.5 Hz, 1H), 2.71 (ddd, J = 11.5, 6.8, 2.4 Hz, 1H), 2.60 (t, J = 5.5 Hz, 2H), 2.10 (dt, J = 13.5, 2.5 Hz, 1H), 2.02 (dt, J = 13.6, 2.6 Hz, 1H), 1.58 (dt, J = 13.4, 6.7 Hz, 2H), 1.31 (ddd, J = 13.5, 11.4, 4.3 Hz, 2H), 1.10 (d, J = 6.4 Hz, 3H), 0.94 (dd, J = 12.7, 6.7 Hz, 6H). LCMS m/z 300.08 [M + H]⁺. |
| 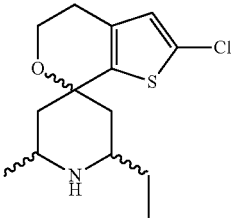<br>Compound 215 | 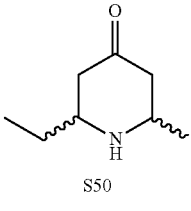<br>S50 | Compound 211[4] | ¹H NMR (300 MHz, Chloroform-d) δ 6.58 (s, 1H), 3.92 (t, J = 5.5 Hz, 2H), 3.16 (dt, J = 9.4, 3.6 Hz, 1H), 3.00-2.85 (m, 1H), 2.61 (t, J = 5.5 Hz, 2H), 2.14-1.96 (m, 2H), 1.49-1.42 (m, 2H), 1.41-1.26 (m, 3H), 1.13 (d, J = 6.4 Hz, 3H), 0.95 (t, J = 7.5 Hz, 3H). LCMS m/z 286.04 [M + H]⁺. |
| 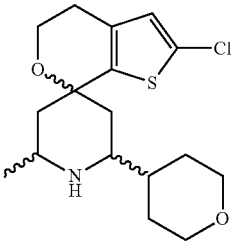<br>Compound 216 | 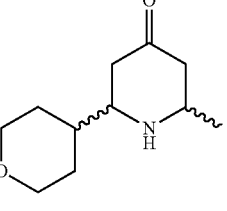<br>S51 | Compound 211[4] | ¹H NMR (300 MHz, Chloroform-d) δ 6.56 (s, 1H), 4.07-3.92 (m, 2H), 3.89 (t, J = 5.5 Hz, 2H), 3.35 (tt, J = 11.7, 2.6 Hz, 2H), 3.07 (dtd, J = 12.6, 6.3, 2.4 Hz, 1H), 2.76 (ddd, J = 11.5, 6.9, 2.4 Hz, 1H), 2.58 (td, J = 5.4, 1.3 Hz, 2H), 2.06 (ddt, J = 20.3, 13.5, 2.5 Hz, 2H), 1.69 (dt, J = 12.4, 2.6 Hz, 1H), 1.64-1.59 (m, 1H), 1.52-1.29 (m, 4H), 1.26 (dd, J = 10.2, 3.1 Hz, 1H), 1.08 (d, J = 6.3 Hz, 3H). LCMS m/z 342.06 [M + H]⁺. |
| 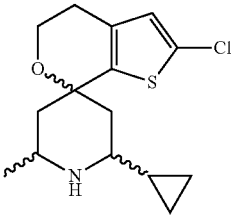<br>Compound 217 | 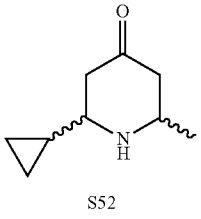<br>S52 | Compound 211[4] | ¹H NMR (300 MHz, Chloroform-d) δ 6.56 (s, 1H), 3.87 (t, J = 5.5 Hz, 2H), 3.03 (dtd, J = 12.5, 6.3, 2.5 Hz, 1H), 2.58 (t, J = 5.5 Hz, 2H), 2.22-2.02 (m, 2H), 1.98 (dt, J = 13.7, 2.5 Hz, 1H), 1.54 (dd, J = 13.3, 11.1 Hz, 1H), 1.37 (dd, J = 13.6, 11.3 Hz, 1H), 1.10 (d, J = 6.3 Hz, 3H), 0.77 (ddq, J = 13.2, 8.5, 4.8 Hz, 1H), 0.55-0.36 (m, 2H), 0.26-0.04 (m, 2H). LCMS m/z 298.1 [M + H]⁺. |
| 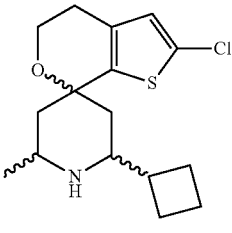<br>Compound 218 | 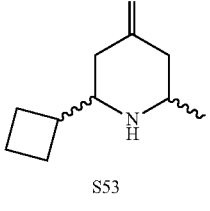<br>S53 | Compound 211[4,5] | ¹H NMR (300 MHz, Chloroform-d) δ 6.56 (s, 1H), 3.91 (t, J = 5.5 Hz, 2H), 3.08 (q, J = 4.9, 4.2 Hz, 1H), 2.96-2.75 (m, 1H), 2.59 (t, J = 5.5 Hz, 2H), 2.28-2.04 (m, 2H), 2.08-1.81 (m, 4H), 1.74 (dq, J = 16.8, 8.3, 7.8 Hz, 3H), 1.42-1.23 (m, 2H), 1.16 (d, J = 13.4 Hz, 1H), 1.08 (d, J = 6.4 Hz, 3H). LCMS m/z 312.05 [M + H]⁺. |

[1]The reaction was pH adjusted with saturated aqueous sodium bicarbonate, the organic layer was separated, and the solvent was removed in vacuo.
[2]Purification by reversed-phase HPLC (Method: C18 Waters Sunfire column (30 × 150 mm, 5 micron). Gradient: MeCN in H₂O with 5 mM HCl) afforded the product.
[3]Compounds 212 and 213 were separated during purification.
[4]The compound was not salted with HCl after column chromatography
[5]Reaction was run for 5 minutes

411

Compound 219

(2S,6R)-2-chloro-2'-methyl-6'-(tetrahydropyran-4-ylmethyl)spiro[4,5-dihydrothieno[2,3-c]pyran-7,4'-piperidine] (219)

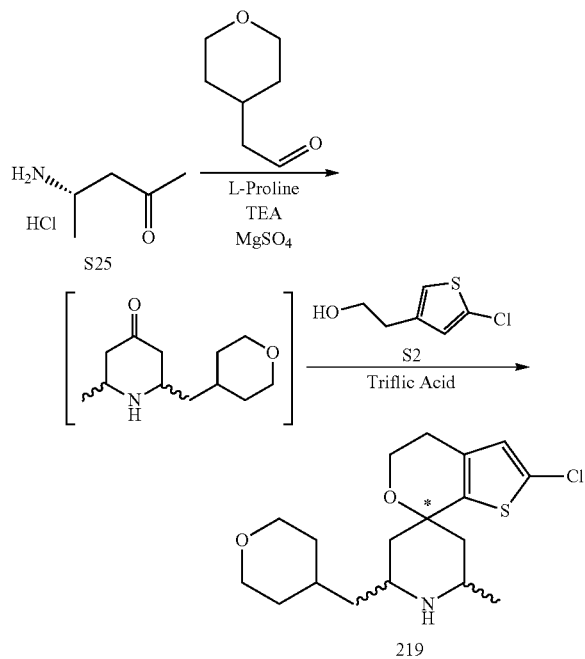

To a vial of 2-tetrahydropyran-4-ylacetaldehyde (23.99 mg, 0.1872 mmol), MgSO$_4$ (35 mg, 0.2908 mmol) and L-proline (5 mg, 0.04343 mmol) was added a solution of (4S)-4-aminopentan-2-one (Hydrochloride salt) S28 (28 mg, 0.1872 mmol)) in EtOH (1 mL). Triethylamine (30 µL, 0.2152 mmol) was added to each vial. The reaction was stirred at room temperature over the weekend. The reaction mixture was evaporated under a stream of nitrogen. A solution of 2-(5-chloro-3-thienyl)ethanol (25 µL, 0.2075 mmol) in dioxane (750 µL) was added. A solution of triflic acid (100 µL, 1.130 mmol) in dioxane (750 µL) was added. The resulting mixture was stirred at room temperature for 30 minutes. The reaction mixture was quenched with NaOH (2.0 mL of 2 M, 4.000 mmol) and DCM (1.5 mL), and the resulting biphasic mixtures were stirred for several minutes. The mixture was passed through a 25 µM polypropylene filter plate, and the resulting DCM layers were isolated and evaporated. Purification by reversed-phase HPLC (Method: C18 Waters Sunfire column (30×150 mm, 5 micron). Gradient: MeCN in H$_2$O with 0.1% trifluoroacetic acid) yielded (2S,6R)-2-chloro-2'-methyl-6'-(tetrahydropyran-4-ylmethyl)spiro[4,5-dihydrothieno[2,3-c]pyran-7,4'-piperidine] (Trifluoroacetate salt) 219 (22.8 mg, 32%). $^1$H NMR (400 MHz, DMSO-d$_6$) δ 8.56 (s, 1H), 8.23 (s, 1H), 6.93 (s, 1H), 3.90 (t, J=5.5 Hz, 2H), 3.81 (d, J=11.4 Hz, 2H), 3.55-3.20 (m, 4H), 2.62-2.55 (m, 2H), 2.24 (t, J=14.0 Hz, 2H), 1.76-1.38 (m, 7H), 1.23 (d, J=6.5 Hz, 3H), 1.28-1.03 (m, 2H). LCMS m/z 356.23 [M+H]$^+$.

412

Preparation of S54

(2S,6S)-2'-chloro-2-cyclopropyl-6-methyl-1-(2,2,2-trifluoroacetyl)spiro[piperidine-4,7'-thieno[2,3-c]pyran]-4'-one (S54)

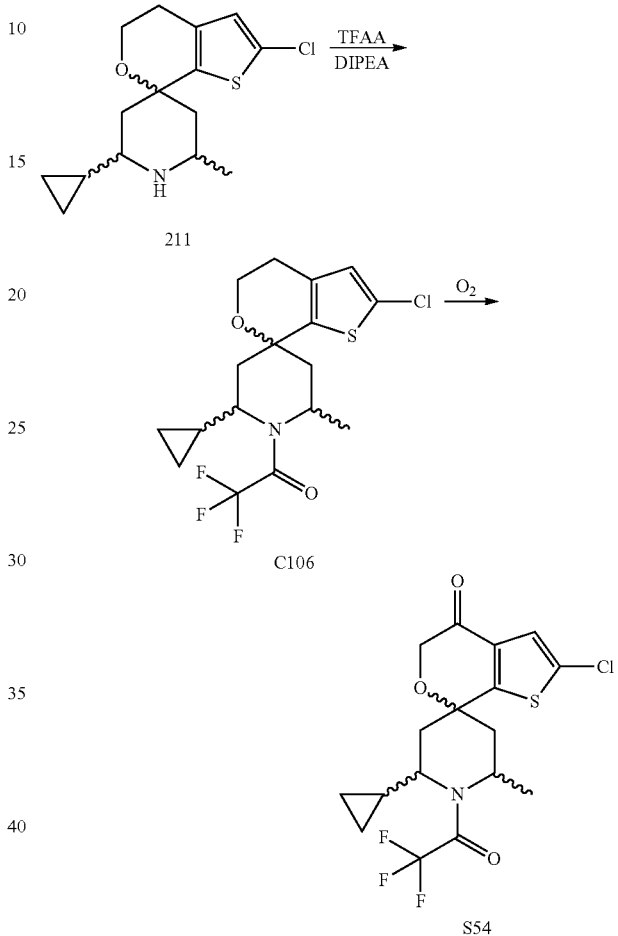

Step 1. Synthesis of 1-[(2S,6S)-2-chloro-2'-cyclopropyl-6'-methyl-spiro[4,5-dihydrothieno[2,3-c]pyran-7,4'-piperidine]-1'-yl]-2,2,2-trifluoro-ethanone (C106)

To a mixture of (2'S,6'S,7S)-2-chloro-2'-cyclopropyl-6'-methyl-spiro[4,5-dihydrothieno[2,3-c]pyran-7,4'-piperidine] 211 (Hydrochloride salt) (30 mg, 0.08974 mmol) in DCM (1 mL) was added DIPEA (50 µL, 0.2871 mmol) followed by trifluoroacetic anhydride (15 µL, 0.1079 mmol). The reaction was stirred for 2 hours. The mixture was quenched with 1 N HCl, separated, and concentrated. Purification by silica gel chromatography (Gradient: 0-30% EtOAc in Heptane) afforded 1-[(2S,6S)-2-chloro-2'-cyclopropyl-6'-methyl-spiro[4,5-dihydrothieno[2,3-c]pyran-7,4'-piperidine]-1'-yl]-2,2,2-trifluoro-ethanone C106 (31 mg, 87%). $^1$H NMR (300 MHz, Chloroform-d) δ 6.59 (s, 1H), 4.60-3.95 (m, 1H), 3.82 (t, J=5.5 Hz, 2H), 3.25 (s, 1H), 2.57 (t, J=5.5 Hz, 2H), 2.50 (dd, J=16.1, 8.1 Hz, 2H), 2.07 (d, J=15.1 Hz, 2H), 1.62-1.19 (m, 3H), 1.18-0.85 (m, 1H), 0.86-0.38 (m, 3H), 0.32 (dq, J=9.2, 4.7 Hz, 1H). LCMS m/z 394.04 [M+H]⁺. The product is a mixture of two rotamers based on NMR.

Step 2. Synthesis of (2S,6S)-2'-chloro-2-cyclopropyl-6-methyl-1-(2,2,2-trifluoroacetyl)spiro[piperidine-4,7'-thieno[2,3-c]pyran]-4'-one (S54)

To a mixture of 1-[(2S,6S)-2-chloro-2'-cyclopropyl-6'-methyl-spiro[4,5-dihydrothieno[2,3-c]pyran-7,4'-piperidine]-1'-yl]-2,2,2-trifluoro-ethanone C106 (30 mg, 0.07617 mmol) in acetonitrile (500 µL) was added N-hydroxyphthalimide (8 mg, 0.04904 mmol) and cobaltous diacetate tetrahydrate (2 mg, 0.008029 mmol). The mixture was vacuum purged with an oxygen balloon three times. The mixture was heated to 45° C. and stirred. After 6 hours, the reaction was cooled to room temperature. The mixture was vacuum purged with nitrogen three times and then diluted with MTBE (3 mL) and saturated sodium bicarbonate (3 mL). The layers were separated, and the organic layer was washed with water (2×2 mL) and brine (20 mL). The organic layer was dried with Na₂SO₄, filtered, and concentrated. Purification by silica gel chromatography (Gradient: 0-30% EtOAc in heptane) afforded (2S,6S)-2'-chloro-2-cyclopropyl-6-methyl-1-(2,2,2-trifluoroacetyl)spiro[piperidine-4,7'-thieno[2,3-c]pyran]-4'-one (13 mg, 41%) S54. LCMS m/z 408.0 [M+H]⁺.

Compound 220

(2'S,6'S, 7S)-2-chloro-2'-cyclopropyl-6'-methyl-spiro[4,5-dihydrothieno[2,3-c]pyran-7,4'-piperidine]1-4-ol)(226)

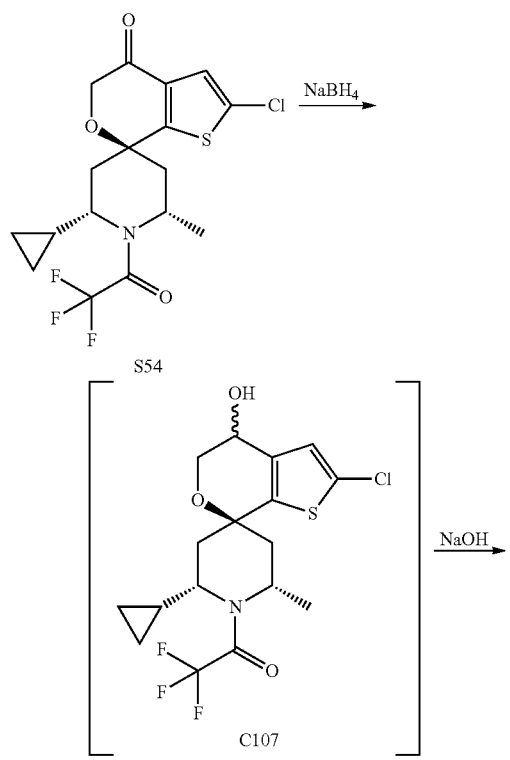

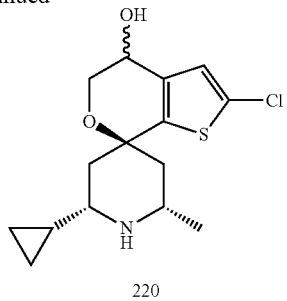

Step 1. Synthesis of I-[(2S,6S)-2-chloro-2'-cyclopropyl-4-hydroxy-6'-methyl-spiro[4,5-dihydrothieno[2,3-c]pyran-7,4'-piperidine]-1'-yl]-2,2,2-trifluoro-ethanone (C107)

To a solution of (2S,6S)-2'-chloro-2-cyclopropyl-6-methyl-1-(2,2,2-trifluoroacetyl)spiro[piperidine-4,7'-thieno[2,3-c]pyran]-4'-one S54 in MeOH (0.5 mL) was added NaBH₄ (1 mg, 0.02643 mmol). After 1 hour, the mixture was diluted with MTBE (5 mL), washed with saturated brine, and concentrated to give crude 1-[(2'S,6'S,7S)-2-chloro-2'-cyclopropyl-4-hydroxy-6'-methyl-spiro[4,5-dihydrothieno[2,3-c]pyran-7,4'-piperidine]-1'-yl]-2,2,2-trifluoro-ethanone C107.

Step 2. Synthesis of (2S,6S)-2'-chloro-2-cyclopropyl-6'-methyl-spiro[4,5-dihydrothieno[2,3-c]pyran-7,4'-piperidine]-4-ol (220)

Crude 1-[(2'S,6'S,7S)-2-chloro-2'-cyclopropyl-4-hydroxy-6'-methyl-spiro[4,5-dihydrothieno[2,3-c]pyran-7,4'-piperidine]-1'-yl]-2,2,2-trifluoro-ethanone C107 was diluted with NaOH (500 µL of 6 M, 3.000 mmol) followed by MeOH (0.5 mL) and the mixture was stirred at 50° C. After 40 minutes, the mixture was cooled to room temperature, diluted with DCM (5 mL) and pH adjusted to pH 10 with saturated aqueous ammonium chloride. The organic phase was separated, passed through a phase separator, and concentrated. Purification by silica gel chromatography (Gradient: 0-20% MeOH in DCM) afforded (2S,6S)-2'-chloro-2'-cyclopropyl-6'-methyl-spiro[4,5-dihydrothieno[2,3-c]pyran-7,4'-piperidine]-4-ol 220 (6 mg, 24%). ¹H NMR (300 MHz, Chloroform-d) δ 6.60 (s, 1H), 4.20 (q, J=3.1 Hz, 1H), 3.74 (dd, J=12.3, 2.9 Hz, 1H), 3.63 (dd, J=12.3, 2.8 Hz, 1H), 3.01-2.71 (m, 1H), 2.12-1.70 (m, 4H), 1.46 (t, J=12.2 Hz, 1H), 1.37-1.19 (m, 1H), 1.19-1.02 (m, 1H), 0.92 (dd, J=6.3, 3.4 Hz, 3H), 0.61 (t, J=10.9 Hz, 1H), 0.28 (dt, J=9.9, 6.2 Hz, 2H), −0.08 (dd, J=9.0, 4.4 Hz, 2H). LCMS m/z 314.07 [M+H]⁺.

Compound 221

(2S,4S,6S)-2'-chloro-2-ethynyl-6-methyl-4',5'-dihydrospiro[piperidine-4,7'-thieno[2,3-c]pyran]

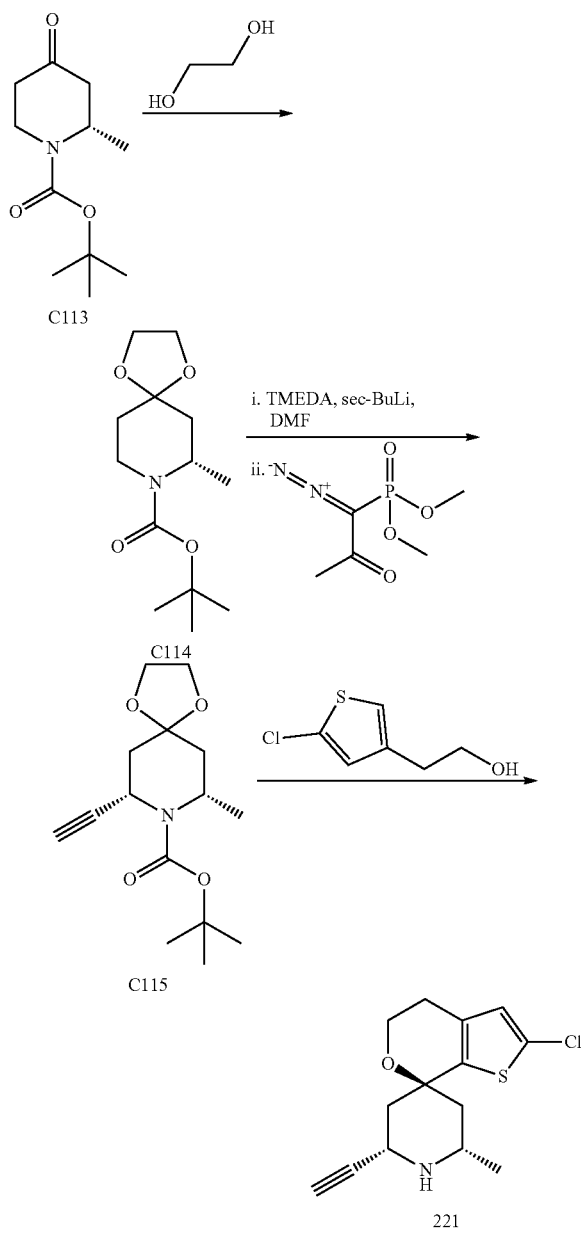

Step 1. Synthesis of tert-butyl (S)-7-methyl-1,4-dioxa-8-azaspiro[4.5]decane-8-carboxylate To a solution of tert-butyl (2S)-2-methyl-4-oxo-piperidine-1-carboxylate C113 (40 g, 183.80 mmol) in toluene (1000 mL) were added ethylene glycol (22.916 g, 21 mL, 361.82 mmol) and PPTS (7.5 g, 29.248 mmol). The mixture was refluxed for 72 hours under Dean-Stark conditions. The mixture was then cooled to room temperature, quenched with saturated sodium bicarbonate (300 mL), and extracted with EtOAc (2×500 mL). The combined organic layer was dried over $Na_2SO_4$ and concentrated. Purification by silica gel column chromatography (Gradient: 0-5% EtOAc:Heptane) afforded tert-butyl (7S)-7-methyl-1,4-dioxa-8-azaspiro[4.5]decane-8-carboxylate C114 (35 g, 67%) as a yellow liquid. $^1$H NMR (300 MHz, $CDCl_3$) δ 4.49-4.44 (m, 1H), 4.03-3.88 (m, 5H), 3.12-3.02 (m, 1H), 1.90-1.83 (m, 1H), 1.68-1.56 (m, 3H), 1.46 (s, 9H), 1.23 (d, J=6.9 Hz, 3H), LCMS m/z 258.31 [M+1]$^+$.

Step 2. Synthesis of tert-butyl (7S,9S)-7-ethynyl-9-methyl-1,4-dioxa-8-azaspiro[4.5]decane-8-carboxylate (C115)

i. To a solution of tert-butyl (S)-7-methyl-1,4-dioxa-8-azaspiro[4.5]decane-8-carboxylate C114 (14 g, 53.862 mmol) in diethyl ether (210 mL) was added TMEDA (7.5460 g, 10 mL, 63.638 mmol) at room temperature. The reaction was cooled to −78° C., and then sec-Butyllithium (60 mL of 1.4 M, 84.000 mmol) was added slowly. The reaction was stirred at −78° C. for 2 hours. DMF (7.8635 g, 8.5 mL, 105.43 mmol) was added slowly while maintaining temperature at −78° C. and stirred for 1 hour. The reaction was then warmed to room temperature and stirred for 1 hour. The mixture was quenched with saturated ammonium chloride solution (100 mL) and extracted with ethyl acetate (2×200 mL). The combined organic layer was concentrated. Purification by silica gel chromatography (Gradient: 0-50% EtOAc:Heptane) to yield crude tert-butyl (9S)-7-formyl-9-methyl-1,4-dioxa-8-azaspiro[4.5]decane-8-carboxylate (20 g, 65%) as a pale yellow liquid. The intermediate did not ionize by LCMS, and material was a mixture of diastereomers as observed by $^1$H NMR, so the crude product was carried forward to the next step.

ii. To the crude product from the previous step dissolved in MeOH (300 mL) was added 1-diazo-1-dimethoxyphosphoryl-propan-2-one (17 g, 75.217 mmol) and $K_2CO_3$ (15 g, 106.36 mmol) at room temperature. The reaction mixture was stirred for 16 hours at room temperature. The reaction mixture was filtered and washed with EtOAc (50 mL). The filtrates were concentrated. Purification by silica gel column chromatography (0-5% EtOAc:Heptane) provided the isolated single stereoisomer tert-butyl (7S,9S)-7-ethynyl-9-methyl-1,4-dioxa-8-azaspiro[4.5]decane-8-carboxylate C115 (9.4 g, 59%) as a colorless liquid. $^1$H NMR (400 MHz, DMSO-$d_6$) δ: 5.032-5.014 (m, 1H), 4.23-4.19 (m, 1H), 3.97-3.93 (m, 2H), 3.84-3.80 (m, 2H), 3.11-3.10 (m, 1H), 1.95-1.78 (m, 4H), 1.39 (s, 9H), 1.35 (d, J=6.8 Hz, 3H), LCMS m/z 282.35 [M+1]$^+$ Step 3. Synthesis of (2'S,6'S, 7S)-2-chloro-2'-ethynyl-6'-methyl-spiro[4,5-dihydrothieno[2,3-c]pyran-7,4'-piperidine] (221)

To a mixture of tert-butyl (7S,9S)-7-ethynyl-9-methyl-1,4-dioxa-8-azaspiro[4.5]decane-8-carboxylate C115 (25 mg, 0.08886 mmol) and 2-(5-chloro-3-thienyl)ethanol (20 μL, 0.1986 mmol) in DCM (0.5 mL) was added MsOH (40 μL, 0.6164 mmol). The mixture was heated to 40° C. for 2 hours. The mixture was allowed to cool to room temperature and then pH adjusted with saturated aqueous bicarbonate and aqueous 1 N NaOH to pH 11. Additional DCM (2 mL) was added, and the organic layer was separated and concentrated. Purification by silica gel chromatography (Gradient: 0-10% MeOH:DCM) yielded (2'S,6'S,7S)-2-chloro-2'-ethynyl-6'-methyl-spiro[4,5-dihydrothieno[2,3-c]pyran-7,4'-piperidine]221 (14 mg, 50%) as a yellow oil. $^1$H NMR (300 MHz, Methanol-$d_4$) δ 6.67 (s, 1H), 3.90 (t, J=5.5 Hz, 2H), 3.84 (dt, J=11.8, 2.6 Hz, 1H), 3.05 (dqd, J=13.0, 6.4, 2.6 Hz, 1H), 2.68 (d, J=2.3 Hz, 1H), 2.59 (t, J=5.5 Hz, 2H), 2.20 (dt, J=13.8, 2.7 Hz, 1H), 1.97 (dt, J=13.8, 2.6 Hz, 1H), 1.71 (dd, J=13.8, 11.8 Hz, 1H), 1.32 (dd, J=13.8, 11.5 Hz, 1H), 1.07 (d, J=6.4 Hz, 3H). LCMS m/z 282.09 [M+1]$^+$ NMR analysis by NOE confirmed the 2,4-trans 2,6-cis stereochemistry.

Preparation of S55

(2S,4S,6S)-2'-chloro-2-ethynyl-6-methyl-1-(2,2,2-trifluoroacetyl)spiro[piperidine-4,7'-thieno[2,3-c]pyran]-4'(5'H)-one

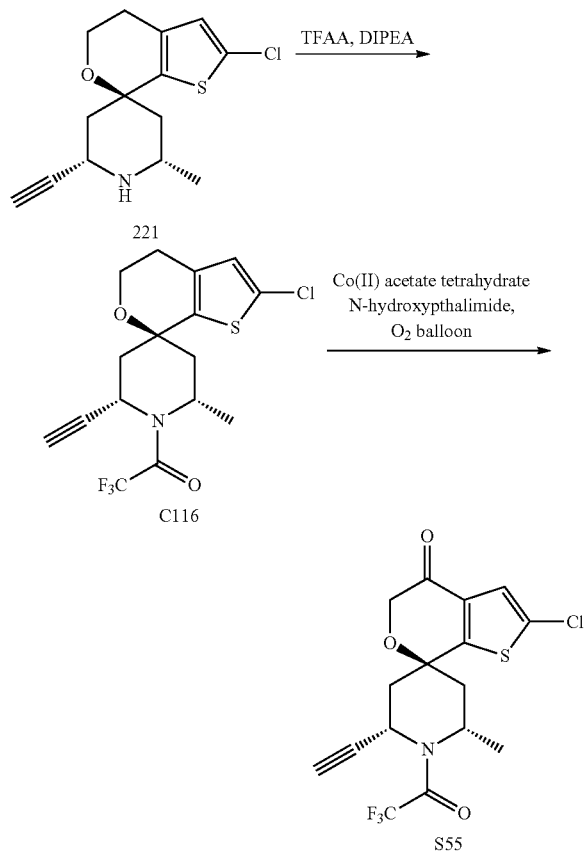

Step 1. Synthesis of I-[(2'S,6'S, 7S)-2-chloro-2'-ethynyl-6'-methyl-spiro[4,5-dihydrothieno[2,3-c]pyran-7,4'-piperidine]-1'-yl]-2,2,2-trifluoro-ethanone (C16)

A solution of (2'S,6'S,7S)-2-chloro-2'-ethynyl-6'-methyl-spiro[4,5-dihydrothieno[2,3-c]pyran-7,4'-piperidine] 221 (6.91 g, 24.5 mmol) in DCM (100 mL) was cooled to 0° C. DIPEA (8.5 mL, 48.80 mmol) was added, followed by TFAA (4.3 mL, 30.93 mmol), and the mixture was stirred for 1 minute. The mixture was quenched with 1 N HCl (50 mL), and the organic layer separated. The organic layer was washed with aqueous 1 N HCl (50 mL), dried with MgSO$_4$, filtered, and concentrated. Purification by silica gel chromatography (Gradient: 0-5% EtOAc:heptane) provided the crude product as a crystalline white-pink solid. This material was suspended in TBME (28 mL) and stirred at reflux, which fully dissolved the solid. The solution was cooled to 0° C. and stirred for 15 minutes. The resulting solid was filtered and rinsed with cold TBME. The resulting mother liquor was concentrated, and the recrystallization process was repeated twice to provide three crops of white solid. The combined crops were concentrated to yield 1-[(2'S,6'S,7S)-2-chloro-2'-ethynyl-6'-methyl-spiro[4,5-dihydrothieno[2,3-c]pyran-7,4'-piperidine]-1'-yl]-2,2,2-trifluoro-ethanone C116 (7.42 g, 80%). $^1$H NMR (300 MHz, Chloroform-d) δ 6.60 (s, 1H), 5.19 (s, 1H), 4.40 (p, J=7.4, 6.9 Hz, 1H), 3.83 (td, J=5.6, 2.2 Hz, 2H), 2.68-2.52 (m, 4H), 2.37 (dt, J=23.7, 14.2 Hz, 3H), 1.51 (d, J=6.6 Hz, 3H). LCMS m/z 378.07 [M+1]$^+$ Step 2. Synthesis of 1-[(2'S,6'S, 7S)-2-chloro-2'-ethynyl-6'-methyl-spiro[4,5-dihydrothieno[2,3-c]pyran-7,4'-piperidine]-1'-yl]-2,2,2-trifluoro-ethanone (S55)

To a solution of 1-[(2'S,6'S,7S)-2-chloro-2'-ethynyl-6'-methyl-spiro[4,5-dihydrothieno[2,3-c]pyran-7,4'-piperidine]-1'-yl]-2,2,2-trifluoro-ethanone C116 (5.0 g, 13.18 mmol) in MeCN (50 mL) was added N-hydroxyphthalimide (3.0 g, 18.39 mmol) and cobalt(II) acetate tetrahydrate (330 mg, 1.325 mmol). The mixture was vacuum purged with an oxygen balloon six times and oxygen balloon placed into septum to maintain oxygen atmosphere. The mixture was heated to 55° C. and stirred overnight. The mixture was cooled to room temperature, then vacuum purged with nitrogen three times and diluted with MTBE (200 mL) and saturated bicarbonate (100 mL). The layers were separated, and the organic layer was washed with saturated bicarbonate (4×100 mL). Brine (100 mL) was added and the layers were separated. The organic layer was dried with MgSO$_4$, filtered, and concentrated. Purification by silica gel chromatography (Gradient: 0-10% EtOAc:heptane) yielded (2S,4S,6S)-2'-chloro-2-ethynyl-6-methyl-1-(2,2,2-trifluoroacetyl)spiro[piperidine-4,7'-thieno[2,3-c]pyran]-4'-one S55 (2.67 g, 52%) as a white crystalline solid. $^1$H NMR (300 MHz, Chloroform-d) δ 7.19 (s, 1H), 5.26 (d, J=21.5 Hz, 1H), 4.38 (tt, J=11.1, 5.8 Hz, 1H), 4.26 (t, J=1.2 Hz, 2H), 2.77 (dd, J=15.2, 8.3 Hz, 1H), 2.65-2.45 (m, 3H), 2.43-2.27 (m, 1H), 1.53 (d, J=6.5 Hz, 3H).

Compound 222

(2'S,4S,6'S, 7S)-2-chloro-2'-ethynyl-6'-methyl-spiro[4,5-dihydrothieno[2,3-c]pyran-7,4'-piperidine]-4-ol (222)

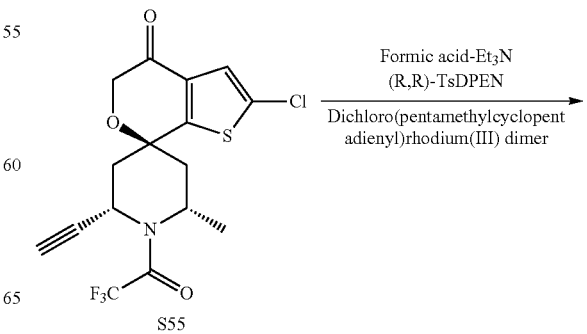

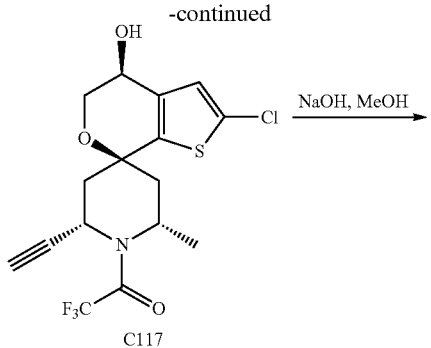

C117

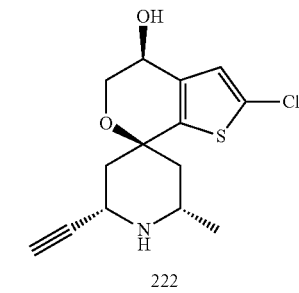

222

Step 1. Synthesis of 1-[(2'S,4S,6'S, 7S)-2-chloro-2'-ethynyl-4-hydroxy-6'-methyl-spiro[4,5-dihydrothieno[2,3-c]pyran-7,4'-piperidine]-1'-yl]-2,2,2-trifluoro-ethanone (C117)

To a solution of N-[(1R,2R)-2-amino-1,2-diphenyl-ethyl]-4-methyl-benzenesulfonamide (80 mg, 0.2183 mmol) in MeCN (15 mL) was added dichloro(pentamethylcyclopentadienyl) rhodium(III) dimer (65 mg, 0.1035 mmol). The mixture was stirred at room temperature for 5 minutes, then 5:2 formic acid-triethylamine complex (3 mL, 7.144 mmol) was added. After 5 minutes, the mixture was cooled to 0° C., and (2S,4S,6S)-2'-chloro-2-ethynyl-6-methyl-1-(2,2,2-trifluoroacetyl)spiro[piperidine-4,7'-thieno[2,3-c]pyran]-4'-one S55 (2670 mg, 6.809 mmol) in MeCN (70 mL) was added. The mixture was stirred at 0° C. for 2 hours and then allowed to warm to room temperature and stirred 72 hours. The mixture was diluted with ethyl acetate (20 mL) and then washed with 1 N HCl (20 mL), saturated sodium bicarbonate (20 mL), and brine (20 mL). The organic layer was dried with MgSO$_4$, filtered, and concentrated. Purification by silica gel chromatography (Gradient: 0-40% EtOAc:heptane) yielded 1-[(2'S,4S,6'S,7S)-2-chloro-2'-ethynyl-4-hydroxy-6'-methyl-spiro[4,5-dihydrothieno[2,3-c]pyran-7,4'-piperidine]-1'-yl]-2,2,2-trifluoro-ethanone C117 (2.27 g, 85%) as a white solid. $^1$H NMR (300 MHz, Chloroform-d) δ 6.85 (s, 1H), 5.19 (s, 1H), 4.48 (t, J=9.2 Hz, 2H), 3.86 (qd, J=12.5, 3.1 Hz, 2H), 2.75-2.46 (m, 3H), 2.37 (dd, J=14.6, 6.8 Hz, 1H), 2.20 (d, J=14.7 Hz, 1H), 2.01 (d, J=9.1 Hz, 1H), 1.53 (d, J=6.6 Hz, 3H). LCMS m/z 394.13 [M+1]$^+$ Step 2. Synthesis of (2'S,4S,6'S, 7S)-2-chloro-2'-ethynyl-6'-methyl-spiro[4,5-dihydrothieno[2,3-c]pyran-7,4'-piperidine]-4-ol (222)

To a solution of 1-[(2'S,4S,6'S,7S)-2-chloro-2'-ethynyl-4-hydroxy-6'-methyl-spiro[4,5-dihydrothieno[2,3-c]pyran-7,4'-piperidine]-1'-yl]-2,2,2-trifluoro-ethanone C117 (1.5 g, 3.809 mmol) in MeOH (7.5 mL) was added NaOH (4 mL of 6 M, 24.00 mmol). The mixture was stirred for 15 minutes at room temperature, then filtered and rinsed with additional water and concentrated to yield (2'S,4S,6'S,7S)-2-chloro-2'-ethynyl-6'-methyl-spiro[4,5-dihydrothieno[2,3-c]pyran-7,4'-piperidine]-4-ol 222 (1.07 g, 88%) as a white solid. $^1$H NMR (300 MHz, Chloroform-d) δ 6.84 (s, 1H), 4.44 (d, J=7.8 Hz, 1H), 4.04-3.80 (m, 3H), 3.51 (s, 2H), 3.21 (dd, J=11.4, 5.7 Hz, 1H), 2.35 (d, J=14.1 Hz, 1H), 2.05 (d, J=9.3 Hz, 1H), 2.00-1.85 (m, 1H), 1.74-1.63 (m, 1H), 1.45 (dd, J=13.4, 11.3 Hz, 1H), 1.13 (d, J=6.3 Hz, 3H). LCMS m/z 298.07 [M+1]$^+$.

Compound 223

(2'S,6'S, 7S)-2-chloro-2'-ethynyl-4,4-difluoro-6'-methyl-spiro[5H-thieno[2,3-c]pyran-7,4'-piperidine] (223)

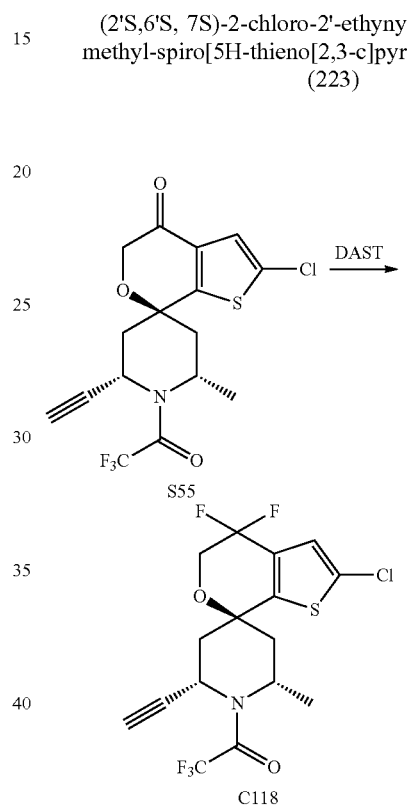

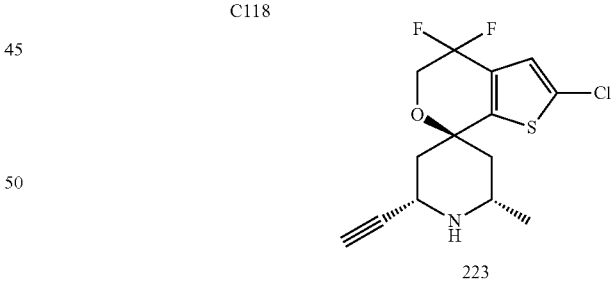

223

Step 1. Synthesis of 1-[(2'S,6'S, 7S)-2-chloro-2'-ethynyl-4,4-difluoro-6'-methyl-spiro[5H-thieno[2,3-c]pyran-7,4'-piperidine]-1'-yl]-2,2,2-trifluoro-ethanone (C118)

A mixture of (2S,4S,6S)-2'-chloro-2-ethynyl-6-methyl-1-(2,2,2-trifluoroacetyl)spiro[piperidine-4,7'-thieno[2,3-c]pyran]-4'-one S55 (1690 mg, 4.314 mmol) in DAST (5 mL, 37.84 mmol) was heated to 40° C. and stirred overnight. Another portion of DAST (5 mL, 37.84 mmol) was added, and the reaction was heated to 40° C. for 36 hours. The mixture was cooled to room temperature and added dropwise into a stirring solution of saturated sodium bicarbonate (25 mL) maintained at 0° C. The mixture was diluted with DCM (25 mL) and layers separated. The aqueous layer was extracted with additional DCM (25 mL), and the combined organic layer was dried with MgSO$_4$, filtered, and concentrated. Purification by silica gel chromatography (Gradient: 0-40% ETOAc:heptane) yielded 1-[(2'S,6'S,7S)-2-chloro-2'-ethynyl-4,4-difluoro-6'-methyl-spiro[5H-thieno[2,3-c]pyran-7,4'-piperidine]-1'-yl]-2,2,2-trifluoro-ethanone C118 (1.34 g, 73%) as an orange oil. $^1$H NMR (300 MHz, Chloroform-d) δ 6.99 (s, 1H), 5.29 (d, J=44.5 Hz, 1H), 4.41 (q, J=7.7 Hz, 1H), 3.99 (t, J=10.0 Hz, 2H), 2.70 (dd, J=15.2, 8.3 Hz, 1H), 2.60 (s, 1H), 2.50 (t, J=8.4 Hz, 2H), 2.32 (d, J=15.3 Hz, 1H), 1.53 (d, J=6.5 Hz, 3H). LCMS m/z 414.07 [M+1]$^+$ Step 2. Synthesis of (2'S,6'S, 7S)-2-chloro-2'-ethynyl-4,4-difluoro-6'-methyl-spiro[5H-thieno[2,3-c]pyran-7,4'-piperidine] (223)

To a mixture of 1-[(2'S,6'S,7S)-2-chloro-2'-ethynyl-4,4-difluoro-6'-methyl-spiro[5H-thieno[2,3-c]pyran-7,4'-piperidine]-1'-yl]-2,2,2-trifluoro-ethanone C118 (1.36 g, 3.287 mmol) in MeOH (25 mL) was added NaOH (2.5 mL of 6 M, 15.00 mmol). The reaction was heated to 50° C. for 1 hour. The mixture was cooled to room temperature and diluted with TBME (30 mL) and water (30 mL). The organic layer was washed with brine (50 mL) and dried with MgSO$_4$, filtered, and concentrated. Purification by silica gel chromatography (Gradient: 0-10% MeOH:DCM) yielded (2'S,6'S, 7S)-2-chloro-2'-ethynyl-4,4-difluoro-6'-methyl-spiro[5H-thieno[2,3-c]pyran-7,4'-piperidine] 223 (970 mg, 84%) as a brown oil. $^1$H NMR (300 MHz, Methanol-d4) δ 7.07 (s, 1H), 4.10 (t, J=10.4 Hz, 2H), 3.85 (dd, J=11.7, 3.0 Hz, 1H), 3.12-2.97 (m, 1H), 2.77-2.68 (m, 1H), 2.30 (dt, J=13.8, 2.9 Hz, 1H), 2.16-2.02 (m, 1H), 1.76 (dd, J=13.7, 11.8 Hz, 1H), 1.44-1.30 (m, 1H), 1.10 (d, J=6.4 Hz, 3H). LCMS m/z 317.99 [M+1]$^+$ Preparation of C120

N-diazosulfamoyl fluoride

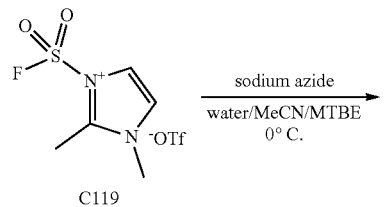

Synthesis of N-diazosulfamoyl fluoride (C120)

To a mixture of NaN$_3$ (1.95 g, 30.00 mmol) in water (60 mL) cooled to 0° C. was added MTBE (60 mL) followed by an MeCN (3 mL) solution of 2,3-dimethylimidazol-3-ium-1-sulfonyl fluoride (Trifluoromethanesulfonate) (11.8 g, 35.95 mmol) C119. After stirring vigorously for 10 minutes, the layers were allowed to separate for 30 minutes and the organic layer was removed, passed over a phase separator and placed in a conical flask, and aged overnight. At this time, the formed red solution at the bottom of the flask was removed with a pipet and the organic layer was diluted with DMSO (60 mL). A biphasic mixture was observed. Acetonitrile (about 25 mL) was added until a homogenous mixture was observed. The final total volume was about 150 mL. This reaction mixture was used in subsequent azide formations without purification or characterization. The yield was estimated to be about 90% of active reagent based on literature precedent[x]. Based on this, the concentration was estimated to be about 0.18 M.

Compound 224

(2'S,4S,6'S, 7S)-2-chloro-2'-[I-[[4-(hydroxymethyl)phenyl]methyl]triazol-4-yl]-6'-methyl-spiro[4,5-dihydrothieno[2,3-c]pyran-7,4'-piperidine]-4-ol (224)

Examples

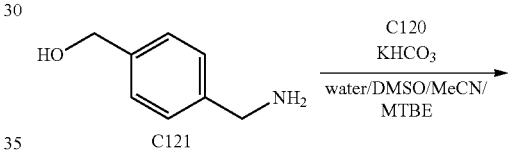

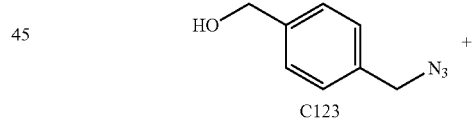

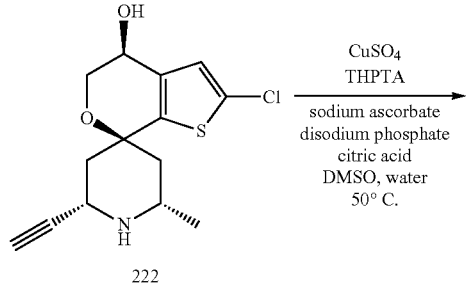

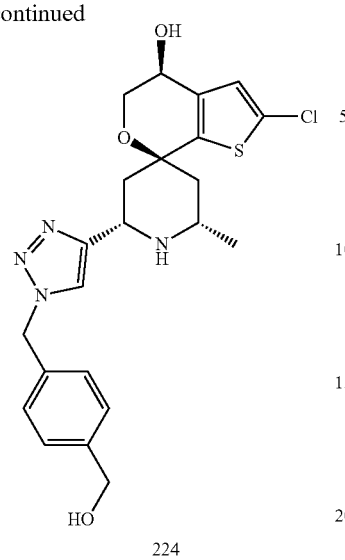

224

Step 1. Synthesis of [4-(azidomethyl)phenyl]methanol (C123)

To a mixture of [4-(aminomethyl)phenyl]methanol C121 and aqueous KHCO$_3$ (400 µL of 3 M) was added an MTBE/DMSO/MeCN solution of N-diazosulfamoyl fluoride C120 (1.7 mL of 0.18 M) and the reaction was stirred at room temperature for 2 hours. At this time, reactions were assumed to be complete based on literature precedent[x] and were not further characterized and [4-(azidomethyl)phenyl]methanol C123 was used directly in the next step.

Step 2. Synthesis of (2'S,4S,6'S, 7S)-2-chloro-2'-[i-[[4-(hydroxymethyl)phenyl]methyl]triazol-4-yl]-6'-methyl-spiro[4,5-dihydrothieno[2,3-c]pyran-7,4'-piperidine]-4-ol (224)

With continual rapid stirring, approximately a third of the formed biphasic suspension (700 µL) from Step 1 was added to a solution of (2'S,4S,6'S,7S)-2-chloro-2'-ethynyl-6'-methyl-spiro[4,5-dihydrothieno[2,3-c]pyran-7,4'-piperidine]-4-ol 222 in DMSO (0.1 mL), 350 µL of aqueous pH 5 buffer (sodium ascorbate (350 µL of 0.125 M):disodium phosphate:citric acid 1:4:2, 0.125 M based on sodium ascorbate) and 100 µL of an aqueous solution of CuSO$_4$ (100 µL of 0.035 M):3-[4-[[bis[[1-(3-hydroxypropyl)triazol-4-yl]methyl]amino]methyl]triazol-1-yl]propan-1-ol 1:1 was added and the mixture was stirred at 50° C. overnight. At this time, the reaction was cooled to room temperature and then dried in vacuo to remove highly volatile solvents. The resulting solution or suspension was then passed over a filter membrane for purification by reversed-phase HPLC. (Method: Waters XSelect CSH C18 OBD Prep Column; 19×100 mm, 5 micron. Gradient: Acetonitrile in Water with 10 mM Ammonium Hydroxide).) The product-containing fractions were pooled and concentrated to yield (2'S,4S,6'S, 7S)-2-chloro-2'-[1-[[4-(hydroxymethyl)phenyl]methyl]triazol-4-yl]-6'-methyl-spiro[4,5-dihydrothieno[2,3-c]pyran-7,4'-piperidine]-4-ol 224 (3.5 mg, 21%) as a yellow solid. $^1$H NMR (400 MHz, DMSO-d6) δ 7.97 (s, 1H), 7.30 (t, J=5.7 Hz, 4H), 6.96 (s, 1H), 5.50 (s, 2H), 5.39 (s, 1H), 5.20 (s, 1H), 4.47 (s, 2H), 4.38 (t, J=4.5 Hz, 1H), 4.10 (d, J=11.5 Hz, 1H), 3.92 (dd, J=11.9, 4.2 Hz, 1H), 3.63 (dd, J=11.7, 5.1 Hz, 1H), 3.07 (s, 1H), 2.27 (s, 1H), 2.17 (d, J=13.3 Hz, 1H), 2.03 (d, J=13.3 Hz, 1H), 1.54 (t, J=12.5 Hz, 1H), 1.23 (t, J=12.3 Hz, 1H), 1.00 (d, J=6.3 Hz, 3H). LCMS m/z 461.12 [M+1]$^+$

Compound 225

(4-((4-((2S,4S,6S)-2'-chloro-4',4'-difluoro-2-methyl-4',5'-dihydrospiro[piperidine-4,7'-thieno[2,3-c]pyran]-6-yl)-1-1, 2, 3-triazol-1-yl)methyl)phenyl)methanol (225)

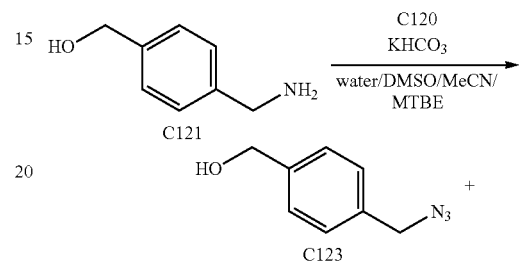

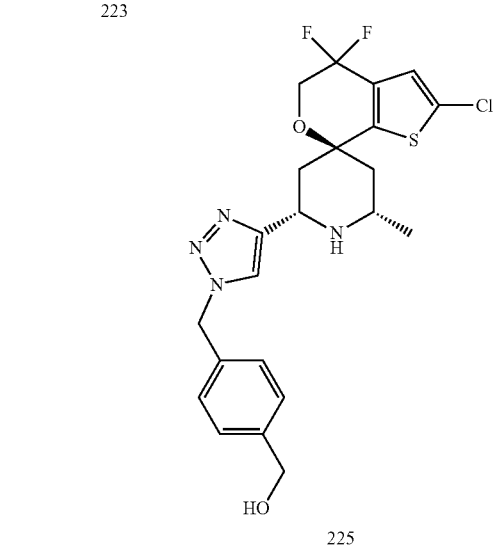

225

Step 1. Synthesis of [4-(azidomethyl)phenyl]methanol (C123)

To a mixture of [4-(aminomethyl)phenyl]methanol C121 and aqueous KHCO$_3$ (400 µL of 3 M) was added an MTBE/DMSO/MeCN solution of N-diazosulfamoyl fluoride C120 (1.7 mL of 0.18 M), and the reaction was stirred at room temperature for 2 hours. At this time, reactions were assumed to be complete based on literature precedent[x] and were not further characterized and [4-(azidomethyl)phenyl]methanol C123 was used directly in the next step.

Step 2. Synthesis of (4-((4-((2S,4S,6S)-2'-chloro-4',4'-difluoro-2-methyl-4',5'-dihydrospiro[piperidine-4,7'-thieno[2,3-c]pyran]-6-yl)-1H-1,2,3-triazol-1-yl)methyl)phenyl)methanol (225)

With continual rapid stirring, approximately a third of the formed biphasic suspension (700 µL) from Step 1 was added to a solution of (2'S,6'S,7S)-2-chloro-2'-ethynyl-4,4-difluoro-6'-methyl-spiro[5H-thieno[2,3-c]pyran-7,4'-piperidine] 223 in DMSO (0.1 mL), 350 µL of aqueous pH 5 buffer (sodium ascorbate (350 µL of 0.125 M):disodium phosphate:citric acid 1:4:2, 0.125 M based on sodium ascorbate) and 100 µL of an aqueous solution of CuSO$_4$ (100 µL of 0.035 M):3-[4-[[bis[[1-(3-hydroxypropyl)triazol-4-yl]methyl]amino]methyl]triazol-1-yl]propan-1-ol 1:1 was added and the mixture was stirred at 50° C. overnight. At this time, the reaction was cooled to room temperature and then dried in vacuo to remove highly volatile solvents. The resulting solution or suspension was then passed over a filter membrane for purification by reversed-phase HPLC. (Method: Waters XSelect CSH C18 OBD Prep Column; 19×100 mm, 5 micron. Gradient: Acetonitrile in Water with 10 mM Ammonium Hydroxide.) The product-containing fractions were pooled and concentrated to yield (4-((4-((2S,4S,6S)-2'-chloro-4',4'-difluoro-2-methyl-4',5'-dihydrospiro[piperidine-4,7'-thieno[2,3-c]pyran]-6-yl)-1H-1,2,3-triazol-1-yl)methyl)phenyl)methanol 225 (3.5 mg, 21%) as a yellow solid. $^1$H NMR (400 MHz, DMSO-d6) δ 8.00 (s, 1H), 7.34 (s, 1H), 7.29 (d, J=2.3 Hz, 4H), 5.52 (s, 2H), 5.20 (s, 1H), 4.47 (d, J=4.6 Hz, 2H), 4.21 (t, J=10.6 Hz, 2H), 4.11 (d, J=11.5 Hz, 1H), 3.02 (d, J=18.8 Hz, 1H), 2.33 (d, J=12.7 Hz, 2H), 2.10 (d, J=13.4 Hz, 1H), 1.66 (dd, J=13.5, 11.7 Hz, 1H), 1.30 (dd, J=13.6, 11.3 Hz, 1H), 1.01 (d, J=6.2 Hz, 3H). LCMS m/z 481.12 [M+1]$^+$ Compounds 226-371

Compounds 226-371 (see Table 11) were prepared as either parent or trifluoroacetate salts following the methods described for compounds 224 and 225. 222 or 223 and appropriate amine were used, where the amine is converted in situ to an azide for cycloaddition to the desired triazole.

TABLE 11

Method of preparation, structure, and physicochemical data for compounds 226-371

| Product | Starting Material and Amine | NMR, LCMS |
|---|---|---|
| Compound 226 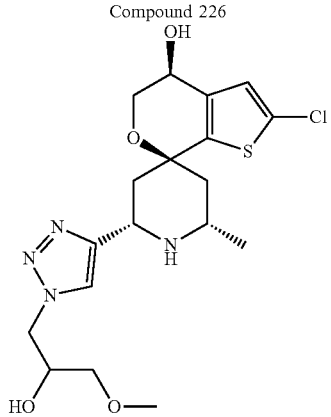 | 222; 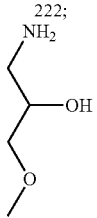 | $^1$H NMR (400 MHz, DMSO-d6) δ 7.87 (s, 1H), 6.96 (s, 1H), 5.40 (d, J = 6.3 Hz, 1H), 5.28 (d, J = 5.6 Hz, 1H), 4.43-4.34 (m, 2H), 4.27-4.17 (m, 1H), 4.12 (dd, J = 11.3, 2.5 Hz, 1H), 3.93 (dd, J = 11.8, 4.3 Hz, 2H), 3.64 (dd, J = 11.9, 5.2 Hz, 1H), 3.27 (s, 3H), 3.25 (d, J = 5.6 Hz, 1H), 3.10 (d, J = 8.5 Hz, 1H), 2.18 (d, J = 13.5 Hz, 1H), 2.05 (d, J = 13.3 Hz, 1H), 1.58 (t, J = 12.5 Hz, 1H), 1.31-1.20 (m, 1H), 1.03 (d, J = 6.3 Hz, 3H). LCMS m/z 429.15 (M + 1)$^+$ |
| Compound 227 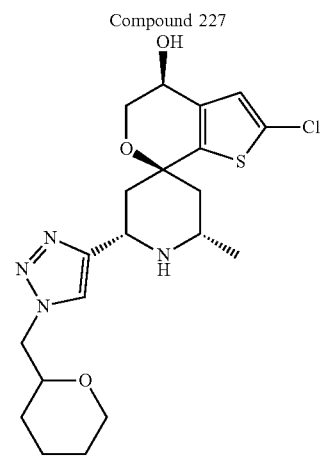 | 222; 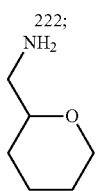 | $^1$H NMR (400 MHz, DMSO-d6) δ 7.86 (d, J = 1.6 Hz, 1H), 6.96 (s, 1H), 5.40 (s, 1H), 4.41-4.23 (m, 3H), 4.11 (d, J = 11.2 Hz, 1H), 3.93 (dd, J = 11.8, 4.2 Hz, 1H), 3.84 (d, J = 11.4 Hz, 1H), 3.64 (dd, J = 11.9, 5.2 Hz, 2H), 3.29 (s, 1H), 3.09 (s, 1H), 2.28 (s, 1H), 2.18 (d, J = 13.4 Hz, 1H), 2.05 (d, J = 13.3 Hz, 1H), 1.77 (s, 1H), 1.57 (t, J = 11.8 Hz, 2H), 1.43 (d, J = 10.2 Hz, 3H), 1.31-1.12 (m, 2H), 1.02 (d, J = 6.3 Hz, 3H). LCMS m/z 439.17 (M + 1)$^+$ |

TABLE 11-continued

Method of preparation, structure, and physicochemical data for compounds 226-371

| Product | Starting Material and Amine | NMR, LCMS |
|---|---|---|
| Compound 228 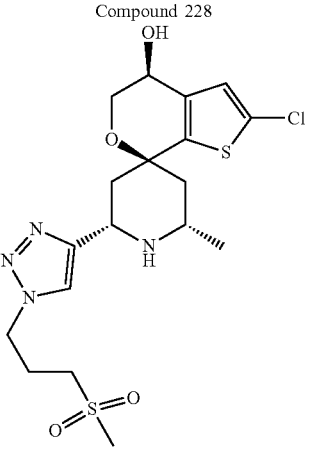 | 222; 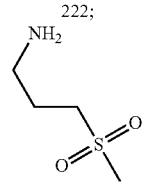 | $^1$H NMR (400 MHz, DMSO-d6) δ 8.01 (s, 1H), 6.97 (s, 1H), 5.41 (s, 1H), 4.44 (t, J = 7.0 Hz, 2H), 4.43-4.36 (m, 1H), 4.12 (d, J = 11.4 Hz, 1H), 3.93 (dd, J = 11.8, 4.3 Hz, 1H), 3.64 (dd, J = 11.8, 5.2 Hz, 1H), 3.15-3.06 (m, 3H), 2.99 (s, 3H), 2.28 (s, 1H), 2.22 (dt, J = 20.0, 9.8 Hz, 3H), 2.06 (d, J = 13.3 Hz, 1H), 1.58 (t, J = 12.5 Hz, 1H), 1.30-1.20 (m, 1H), 1.03 (d, J = 6.3 Hz, 3H). LCMS m/z 461.12 (M + 1)$^+$ |
| Compound 229 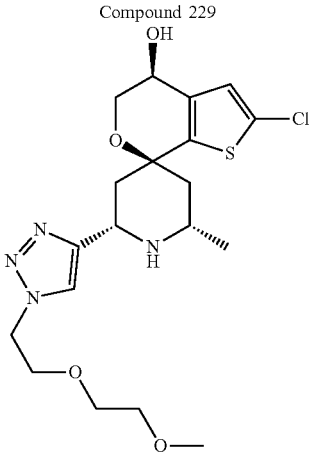 | 222; 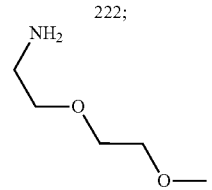 | $^1$H NMR (400 MHz, DMSO-d6) δ 7.94 (s, 1H), 6.96 (s, 1H), 5.42 (s, 1H), 4.46 (t, J = 5.3 Hz, 2H), 4.39 (t, J = 4.6 Hz, 1H), 4.12 (d, J = 11.4 Hz, 1H), 3.93 (dd, J = 11.8, 4.3 Hz, 1H), 3.79 (t, J = 5.2 Hz, 2H), 3.64 (dd, J = 11.8, 5.3 Hz, 1H), 3.51 (dd, J = 5.9, 3.5 Hz, 2H), 3.40 (dd, J = 5.7, 3.6 Hz, 2H), 3.21 (s, 3H), 3.10 (s, 1H), 2.24 (s, 1H), 2.17 (d, J = 13.4 Hz, 1H), 2.05 (d, J = 13.3 Hz, 1H), 1.56 (dd, J = 13.4, 11.6 Hz, 1H), 1.30-1.20 (m, 1H), 1.02 (d, J = 6.2 Hz, 3H). LCMS m/z 443.15 (M + 1)$^+$ |
| Compound 230 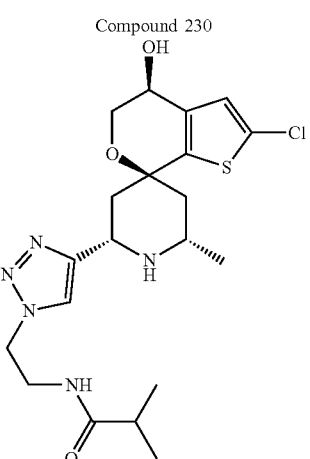 | 222; 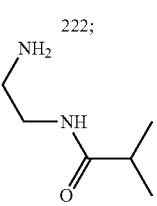 | $^1$H NMR (400 MHz, DMSO-d6) δ 7.88 (d, J = 7.5 Hz, 2H), 6.97 (s, 1H), 5.42 (s, 1H), 4.40 (t, J = 4.8 Hz, 1H), 4.36 (t, J = 6.1 Hz, 2H), 4.11 (d, J = 11.4 Hz, 1H), 3.92 (dd, J = 11.8, 4.3 Hz, 1H), 3.64 (dd, J = 11.7, 5.4 Hz, 1H), 3.44 (d, J = 6.1 Hz, 1H), 3.24 (t, J = 5.4 Hz, 1H), 3.21 (s, 0H), 3.10 (s, 1H), 2.28 (p, J = 7.0 Hz, 1H), 2.19 (s, 1H), 2.16 (d, J = 13.5 Hz, 1H), 2.06 (d, J = 13.4 Hz, 1H), 1.56 (t, J = 12.4 Hz, 1H), 1.29-1.16 (m, 1H), 1.02 (d, J = 6.3 Hz, 3H), 0.94 (dd, J = 6.9, 1.5 Hz, 6H). LCMS m/z 454.17 (M + 1)$^+$ |

TABLE 11-continued

Method of preparation, structure, and physicochemical data for compounds 226-371

| Product | Starting Material and Amine | NMR, LCMS |
|---|---|---|
| Compound 231 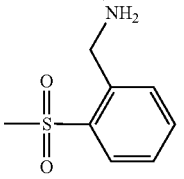 | 222; 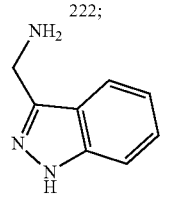 | $^1$H NMR (400 MHz, DMSO-d6) δ 8.06 (s, 1H), 8.01 (dd, J = 7.9, 1.4 Hz, 1H), 7.76-7.67 (m, 1H), 7.64 (t, J = 7.9 Hz, 1H), 7.10 (d, J = 7.6 Hz, 1H), 6.96 (s, 1H), 6.03 (s, 2H), 5.42 (s, 1H), 4.39 (t, J = 4.8 Hz, 1H), 4.14 (d, J = 11.5 Hz, 1H), 3.94 (dd, J = 11.9, 4.2 Hz, 1H), 3.64 (dd, J = 11.8, 5.2 Hz, 1H), 3.30 (s, 3H), 3.09 (s, 1H), 2.33 (s, 1H), 2.21 (d, J = 13.4 Hz, 1H), 2.05 (d, J = 13.3 Hz, 1H), 1.63-1.52 (m, 1H), 1.31-1.16 (m, 1H), 1.02 (d, J = 6.2 Hz, 3H). LCMS m/z 509.12 (M + 1)$^+$ |
| Compound 232 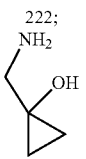 | 222; | $^1$H NMR (400 MHz, DMSO-d6) δ 7.95 (s, 1H), 7.69 (d, J = 8.1 Hz, 1H), 7.52 (d, J = 8.4 Hz, 1H), 7.34 (dd, J = 8.3, 6.9 Hz, 1H), 7.10 (t, J = 7.5 Hz, 1H), 6.95 (s, 1H), 5.90 (s, 2H), 4.37 (t, J = 4.7 Hz, 1H), 4.08 (d, J = 11.5 Hz, 1H), 3.91 (dd, J = 11.9, 4.2 Hz, 1H), 3.61 (dd, J = 11.9, 5.2 Hz, 1H), 3.05 (s, 1H), 2.24 (s, 1H), 2.15 (d, J = 13.3 Hz, 1H), 2.02 (d, J = 13.1 Hz, 1H), 1.58-1.47 (m, 1H), 1.22 (t, J = 12.2 Hz, 1H), 0.98 (d, J = 6.3 Hz, 3H). LCMS m/z 471.14 (M + 1)$^+$ |
| Compound 233 | 222; | $^1$H NMR (400 MHz, DMSO-d6) δ 7.93 (s, 1H), 6.97 (s, 1H), 5.49 (s, 2H), 4.40 (t, J = 4.7 Hz, 1H), 4.35 (s, 2H), 4.13 (d, J = 11.7 Hz, 1H), 3.94 (dd, J = 11.8, 4.2 Hz, 1H), 3.69-3.62 (m, 1H), 3.11 (s, 2H), 2.26 (s, 1H), 2.21 (d, J = 13.4 Hz, 1H), 2.05 (d, J = 13.3 Hz, 1H), 1.65-1.52 (m, 1H), 1.27 (dd, J = 13.5, 11.3 Hz, 1H), 1.03 (d, J = 6.3 Hz, 3H), 0.76-0.63 (m, 3H). LCMS m/z 411.14 (M + 1)$^+$ |

TABLE 11-continued

Method of preparation, structure, and physicochemical data for compounds 226-371

| Product | Starting Material and Amine | NMR, LCMS |
|---|---|---|
| Compound 234 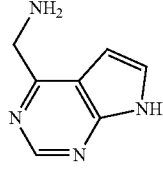 [SMILES: NCc1ncnc2[nH]ccc12] | 222; <br> H₂N-CH₂-(pyrrolopyrimidine) | $^1$H NMR (400 MHz, DMSO-d6) δ 8.69 (s, 1H), 8.06 (s, 1H), 7.55 (d, J = 3.5 Hz, 1H), 6.96 (s, 1H), 6.25 (d, J = 3.5 Hz, 1H), 5.94 (s, 2H), 5.41 (s, 1H), 4.39 (t, J = 4.5 Hz, 1H), 4.14 (d, J = 11.5 Hz, 1H), 3.94 (dd, J = 11.8, 4.3 Hz, 1H), 3.64 (dd, J = 11.9, 5.2 Hz, 1H), 3.10 (s, 1H), 2.29 (s, 1H), 2.20 (d, J = 13.4 Hz, 1H), 2.05 (d, J = 13.3 Hz, 1H), 1.64-1.53 (m, 1H), 1.25 (t, J = 12.2 Hz, 1H), 1.02 (d, J = 6.4 Hz, 3H). LCMS m/z 472.14 (M + 1)⁺ |
| Compound 235 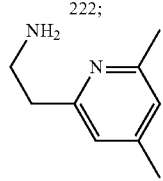 | 222; <br> H₂N-CH₂CH₂-(2,4-dimethylpyridine) | $^1$H NMR (400 MHz, DMSO-d6) δ 7.92 (s, 1H), 6.95 (d, J = 14.4 Hz, 2H), 6.84 (s, 1H), 5.42 (s, 1H), 4.65 (t, J = 7.4 Hz, 2H), 4.43-4.36 (m, 1H), 4.09 (d, J = 11.4 Hz, 1H), 3.92 (dd, J = 11.9, 4.2 Hz, 1H), 3.63 (dd, J = 11.8, 5.3 Hz, 1H), 3.18 (t, J = 7.4 Hz, 2H), 3.08 (s, 1H), 2.39 (s, 3H), 2.20 (s, 3H), 2.14 (d, J = 13.4 Hz, 1H), 2.05 (d, J = 13.2 Hz, 1H), 1.54 (t, J = 12.5 Hz, 1H), 1.24 (t, J = 12.3 Hz, 1H), 1.02 (d, J = 6.3 Hz, 3H). LCMS m/z 474.21 (M + 1)⁺ |
| Compound 236 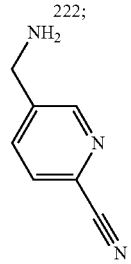 | 222; <br> H₂N-CH₂-(pyridine-CN) | $^1$H NMR (400 MHz, DMSO-d6) δ 8.74 (d, J = 2.1 Hz, 1H), 8.11 (s, 1H), 8.06 (d, J = 8.0 Hz, 1H), 7.91 (dd, J = 8.1, 2.2 Hz, 1H), 6.96 (s, 1H), 5.74 (s, 2H), 5.42 (s, 1H), 4.39 (t, J = 4.7 Hz, 1H), 4.12 (d, J = 11.5 Hz, 1H), 3.93 (dd, J = 11.8, 4.2 Hz, 1H), 3.63 (dd, J = 11.8, 5.3 Hz, 1H), 3.09 (s, 1H), 2.31 (s, 1H), 2.19 (d, J = 13.4 Hz, 1H), 2.04 (d, J = 13.1 Hz, 1H), 1.61-1.50 (m, 1H), 1.24 (dd, J = 13.3, 11.4 Hz, 1H), 1.01 (d, J = 6.3 Hz, 3H). LCMS m/z 457.15 (M + 1)⁺ |

TABLE 11-continued

Method of preparation, structure, and physicochemical data for compounds 226-371

| Product | Starting Material and Amine | NMR, LCMS |
|---|---|---|
| Compound 237 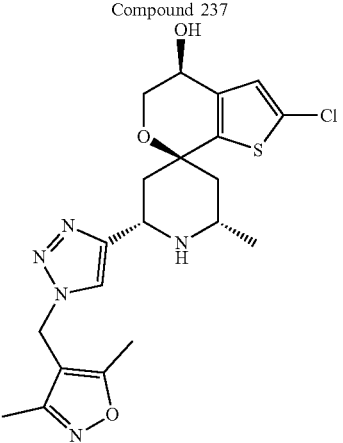 | 222; 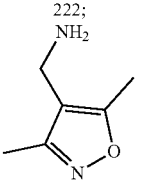 | ¹H NMR (400 MHz, DMSO-d6) δ 7.94 (s, 1H), 6.96 (s, 1H), 5.38 (s, 2H), 4.38 (t, J = 4.7 Hz, 1H), 4.10 (d, J = 11.5 Hz, 1H), 3.92 (dd, J = 11.7, 4.2 Hz, 1H), 3.63 (dd, J = 11.9, 5.2 Hz, 1H), 3.08 (s, 1H), 2.43 (s, 3H), 2.28 (s, 1H), 2.17 (d, J = 13.4 Hz, 1H), 2.14 (s, 3H), 2.04 (d, J = 13.3 Hz, 1H), 1.55 (t, J = 12.5 Hz, 1H), 1.22 (d, J = 12.6 Hz, 1H), 1.01 (d, J = 6.3 Hz, 3H). LCMS m/z 450.19 (M + 1)⁺ |
| Compound 238 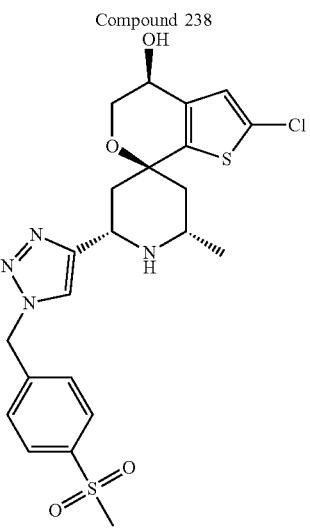 | 222; 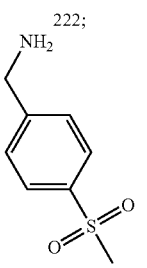 | ¹H NMR (400 MHz, DMSO-d6) δ 8.08 (s, 1H), 7.99-7.89 (m, 2H), 7.54 (d, J = 8.2 Hz, 2H), 6.96 (s, 1H), 5.69 (s, 2H), 5.42 (s, 1H), 4.39 (t, J = 4.7 Hz, 1H), 4.12 (d, J = 11.4 Hz, 1H), 3.93 (dd, J = 11.9, 4.2 Hz, 1H), 3.63 (dd, J = 11.8, 5.1 Hz, 1H), 3.20 (s, 3H), 3.09 (s, 1H), 2.30 (s, 1H), 2.19 (d, J = 13.3 Hz, 1H), 2.04 (d, J = 13.3 Hz, 1H), 1.61-1.50 (m, 1H), 1.29-1.16 (m, 1H), 1.01 (d, J = 6.3 Hz, 3H). LCMS m/z 509.12 (M + 1)⁺ |
| Compound 239 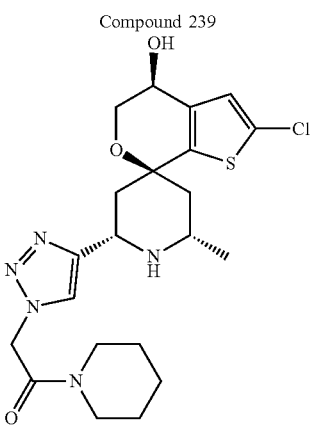 | 222; 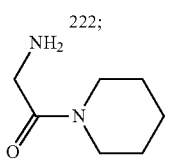 | ¹H NMR (400 MHz, DMSO-d6) δ 7.84 (s, 1H), 6.97 (s, 1H), 5.37 (s, 3H), 4.40 (t, J = 4.7 Hz, 1H), 4.13 (d, J = 11.7 Hz, 1H), 3.94 (dd, J = 11.9, 4.2 Hz, 1H), 3.64 (dd, J = 11.9, 5.3 Hz, 1H), 3.48-3.40 (m, 4H), 3.10 (s, 1H), 2.24 (s, 1H), 2.19 (d, J = 13.5 Hz, 1H), 2.06 (d, J = 13.3 Hz, 1H), 1.64-1.53 (m, 1H), 1.58 (s, 4H), 1.45 (s, 2H), 1.31-1.16 (m, 1H), 1.03 (d, J = 6.3 Hz, 3H). LCMS m/z 466.18 (M + 1)⁺ |

TABLE 11-continued

Method of preparation, structure, and physicochemical data for compounds 226-371

| Product | Starting Material and Amine | NMR, LCMS |
|---|---|---|
| Compound 240 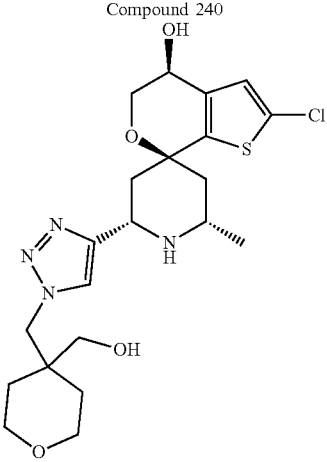 | 222; 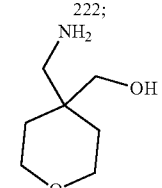 | $^1$H NMR (400 MHz, DMSO-d6) δ 7.85 (s, 1H), 6.96 (s, 1H), 5.38 (s, 1H), 4.93 (s, 1H), 4.39 (t, J = 4.6 Hz, 1H), 4.33 (s, 2H), 4.12 (d, J = 11.4 Hz, 1H), 3.93 (dd, J = 11.8, 4.2 Hz, 1H), 3.64 (dt, J = 12.2, 4.7 Hz, 3H), 3.54 (td, J = 7.9, 7.5, 3.6 Hz, 2H), 3.22 (s, 2H), 3.10 (s, 1H), 2.29 (s, 1H), 2.19 (d, J = 13.4 Hz, 1H), 2.05 (d, J = 13.2 Hz, 1H), 1.62-1.51 (m, 1H), 1.38-1.21 (m, 5H), 1.03 (d, J = 6.3 Hz, 3H). LCMS m/z 469.20 (M + 1)$^+$ |
| Compound 241 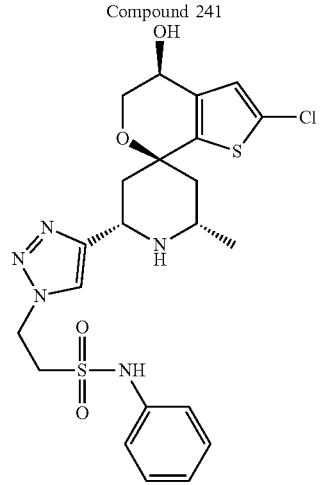 | 222; 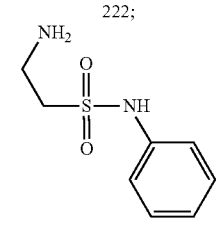 | $^1$H NMR (400 MHz, DMSO-d6) δ 8.00 (s, 1H), 7.26 (t, J = 7.7 Hz, 2H), 7.15-7.09 (m, 2H), 7.00 (t, J = 7.4 Hz, 1H), 6.96 (s, 1H), 5.40 (s, 1H), 4.67 (t, J = 7.1 Hz, 2H), 4.39 (s, 1H), 4.12-4.04 (m, 1H), 3.92 (dd, J = 11.9, 4.2 Hz, 1H), 3.68-3.61 (m, 1H), 3.61 (d, J = 7.2 Hz, 2H), 3.09 (d, J = 9.4 Hz, 1H), 2.13 (d, J = 13.4 Hz, 1H), 2.04 (d, J = 13.3 Hz, 1H), 1.52 (t, J = 12.5 Hz, 1H), 1.23 (t, J = 12.3 Hz, 1H), 1.02 (d, J = 6.2 Hz, 3H). LCMS m/z 424.20 (M + 1)$^+$ |
| Compound 242 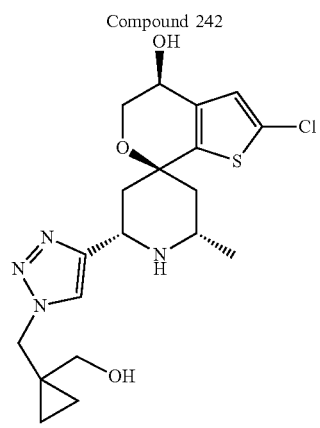 | 222; 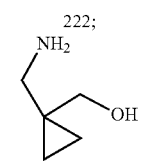 | $^1$H NMR (400 MHz, DMSO-d6) δ 7.93 (s, 1H), 6.97 (s, 1H), 5.41 (s, 1H), 4.74 (s, 1H), 4.39 (s, 1H), 4.28 (d, J = 1.4 Hz, 2H), 4.12 (d, J = 11.4 Hz, 1H), 3.94 (dd, J = 11.8, 4.2 Hz, 1H), 3.64 (dd, J = 11.8, 5.2 Hz, 1H), 3.11 (d, J = 4.6 Hz, 3H), 2.29 (s, 1H), 2.19 (d, J = 13.6 Hz, 1H), 2.05 (d, J = 13.3 Hz, 1H), 1.57 (dd, J = 13.3, 11.7 Hz, 1H), 1.31-1.16 (m, 1H), 1.03 (d, J = 6.3 Hz, 3H), 0.61 (q, J = 3.8 Hz, 2H), 0.48 (t, J = 2.9 Hz, 2H). LCMS m/z 425.18 (M + 1)$^+$ |

TABLE 11-continued

Method of preparation, structure, and physicochemical data for compounds 226-371

| Product | Starting Material and Amine | NMR, LCMS |
|---|---|---|
| Compound 243 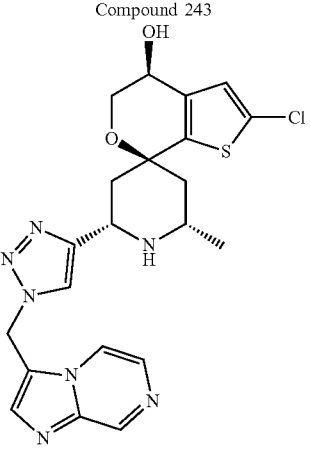 | 222; 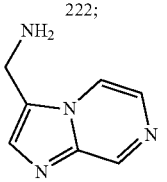 | $^1$H NMR (400 MHz, DMSO-d6) δ 9.11 (d, J = 1.5 Hz, 1H), 8.61 (dd, J = 4.6, 1.6 Hz, 1H), 8.07-7.95 (m, 3H), 6.95 (s, 1H), 6.07 (s, 2H), 5.40 (s, 1H), 4.37 (t, J = 4.7 Hz, 1H), 4.08 (d, J = 11.3 Hz, 1H), 3.90 (dd, J = 11.9, 4.2 Hz, 1H), 3.61 (dd, J = 11.9, 5.3 Hz, 1H), 3.06 (s, 1H), 2.27 (s, 1H), 2.15 (d, J = 13.5 Hz, 1H), 2.02 (d, J = 13.2 Hz, 1H), 1.57-1.46 (m, 1H), 1.27-1.16 (m, 1H), 0.99 (d, J = 6.2 Hz, 3H). LCMS m/z 472.18 (M + 1)$^+$ |
| Compound 244 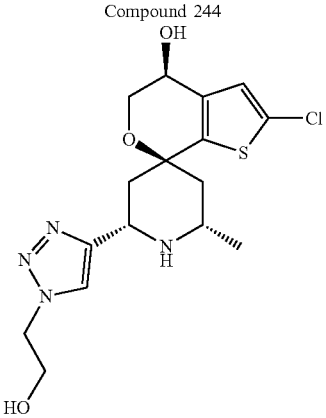 | 222; 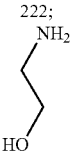 | $^1$H NMR (400 MHz, DMSO-d6) δ 7.92 (s, 1H), 6.96 (s, 1H), 5.40 (s, 1H), 5.05 (s, 1H), 4.39 (t, J = 4.8 Hz, 1H), 4.34 (t, J = 5.4 Hz, 2H), 4.12 (d, J = 11.4 Hz, 1H), 3.93 (dd, J = 11.9, 4.2 Hz, 1H), 3.75 (t, J = 5.5 Hz, 2H), 3.64 (dd, J = 11.9, 5.3 Hz, 1H), 3.10 (s, 1H), 2.23 (s, 1H), 2.18 (d, J = 13.5 Hz, 1H), 2.05 (d, J = 13.3 Hz, 1H), 1.63-1.50 (m, 1H), 1.30-1.20 (m, 1H), 1.02 (d, J = 6.2 Hz, 3H). LCMS m/z 385.17 (M + 1)$^+$ |
| Compound 245 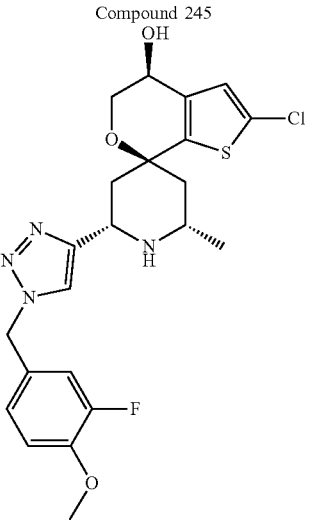 | 222; 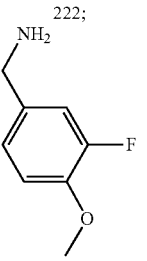 | $^1$H NMR (400 MHz, DMSO-d6) δ 7.99 (s, 1H), 7.28-7.20 (m, 1H), 7.20-7.10 (m, 2H), 6.96 (s, 1H), 5.46 (s, 2H), 5.41 (s, 1H), 4.38 (t, J = 4.7 Hz, 1H), 4.10 (d, J = 11.5 Hz, 1H), 3.92 (dd, J = 11.8, 4.2 Hz, 1H), 3.82 (s, 3H), 3.63 (dd, J = 11.8, 5.2 Hz, 1H), 3.08 (s, 1H), 2.28 (s, 1H), 2.17 (d, J = 13.5 Hz, 1H), 2.03 (d, J = 13.3 Hz, 1H), 1.54 (t, J = 12.5 Hz, 1H), 1.28-1.16 (m, 1H), 1.01 (d, J = 6.3 Hz, 3H). LCMS m/z 479.18 (M + 1)$^+$ |

TABLE 11-continued

*Method of preparation, structure, and physicochemical data for compounds 226-371*

| Product | Starting Material and Amine | NMR, LCMS |
|---|---|---|
| Compound 246 | 222; (S)-3-amino-propane-1,2-diol | $^1$H NMR (400 MHz, DMSO-d6) δ 7.87 (s, 1H), 6.96 (s, 1H), 5.21 (s, 2H), 4.90 (s, 1H), 4.48-4.36 (m, 1H), 4.39 (s, 1H), 4.23-4.08 (m, 2H), 3.93 (dd, J = 11.9, 4.3 Hz, 1H), 3.79 (s, 1H), 3.64 (dd, J = 11.8, 5.3 Hz, 1H), 3.29 (d, J = 6.4 Hz, 1H), 3.10 (s, 1H), 2.24 (s, 1H), 2.19 (d, J = 13.4 Hz, 1H), 2.05 (d, J = 13.2 Hz, 1H), 1.63-1.52 (m, 1H), 1.31-1.16 (m, 1H), 1.03 (d, J = 6.2 Hz, 3H). LCMS m/z 415.15 (M + 1)$^+$ |
| Compound 247 | 222; 1-amino-2-methyl-propan-2-ol | $^1$H NMR (400 MHz, DMSO-d6) δ 7.82 (s, 1H), 6.96 (s, 1H), 5.41 (s, 1H), 4.84 (s, 1H), 4.39 (t, J = 4.7 Hz, 1H), 4.21 (s, 2H), 4.12 (d, J = 11.7 Hz, 1H), 3.94 (dd, J = 11.9, 4.2 Hz, 1H), 3.64 (dd, J = 11.8, 5.2 Hz, 1H), 3.10 (s, 1H), 2.26 (s, 1H), 2.20 (d, J = 13.4 Hz, 1H), 2.05 (d, J = 13.3 Hz, 1H), 1.62-1.51 (m, 1H), 1.26 (dd, J = 13.3, 11.1 Hz, 1H), 1.08-1.00 (m, 8H). LCMS m/z 413.17 (M + 1)$^+$ |
| Compound 248 | 222; thiazol-5-ylmethanamine | $^1$H NMR (400 MHz, DMSO-d6) δ 9.08 (s, 1H), 8.03 (s, 1H), 7.98 (s, 1H), 6.96 (s, 1H), 5.87 (s, 2H), 5.41 (s, 1H), 4.38 (t, J = 4.6 Hz, 1H), 4.10 (d, J = 11.6 Hz, 1H), 3.92 (dd, J = 11.8, 4.3 Hz, 1H), 3.63 (dd, J = 11.9, 5.2 Hz, 1H), 3.08 (s, 1H), 2.29 (s, 1H), 2.17 (d, J = 13.4 Hz, 1H), 2.04 (d, J = 13.3 Hz, 1H), 1.54 (dd, J = 13.3, 11.6 Hz, 1H), 1.29-1.16 (m, 1H), 1.01 (d, J = 6.2 Hz, 3H). LCMS m/z 438.14 (M + 1)$^+$ |

TABLE 11-continued

Method of preparation, structure, and physicochemical data for compounds 226-371

| Product | Starting Material and Amine | NMR, LCMS |
| --- | --- | --- |
| Compound 249 | 222; benzimidazol-2-ol-5-methanamine | ¹H NMR (400 MHz, DMSO-d6) δ 7.94 (s, 1H), 6.98-6.85 (m, 4H), 5.47 (s, 2H), 4.38 (t, J = 4.7 Hz, 1H), 4.09 (d, J = 11.5 Hz, 1H), 3.92 (dd, J = 11.7, 4.2 Hz, 1H), 3.62 (dd, J = 11.9, 5.2 Hz, 1H), 3.07 (s, 1H), 2.25 (s, 1H), 2.17 (d, J = 13.4 Hz, 1H), 2.03 (d, J = 13.3 Hz, 1H), 1.58-1.48 (m, 1H), 1.22 (t, J = 12.4 Hz, 1H), 1.00 (d, J = 6.2 Hz, 3H). LCMS m/z 487.21 (M + 1)⁺ |
| Compound 250 | 222; cyclobutylmethanamine | ¹H NMR (400 MHz, DMSO-d6) δ 7.92 (s, 1H), 6.97 (s, 1H), 5.45 (d, J = 20.5 Hz, 1H), 4.39 (t, J = 4.7 Hz, 1H), 4.33 (d, J = 7.3 Hz, 2H), 4.11 (d, J = 11.3 Hz, 1H), 3.93 (dd, J = 11.9, 4.2 Hz, 1H), 3.64 (dd, J = 11.9, 5.2 Hz, 1H), 3.10 (s, 1H), 2.73 (h, J = 7.7 Hz, 1H), 2.27 (s, 1H), 2.22-2.14 (m, 1H), 2.05 (d, J = 13.3 Hz, 1H), 1.97 (qd, J = 7.3, 6.7, 4.4 Hz, 2H), 1.90-1.70 (m, 4H), 1.57 (dd, J = 14.3, 10.7 Hz, 1H), 1.26 (dd, J = 13.3, 11.1 Hz, 1H), 1.03 (d, J = 6.3 Hz, 3H). LCMS m/z 409.19 (M + 1)⁺ |
| Compound 251 | 222; 3-(2-methylimidazol-1-yl)propan-1-amine | 1H NMR (400 MHz, DMSO-d6) δ 8.00 (t, J = 9.2 Hz, 1H), 7.06 (s, 1H), 6.98 (d, J = 13.7 Hz, 1H), 6.73 (s, 1H), 5.59-5.45 (m, 1H), 4.35 (d, J = 34.4 Hz, 4H), 4.13 (d, J = 12.1 Hz, 1H), 2.51 (s, 7H), 2.23 (d, J = 12.7 Hz, 4H), 2.05 (d, J = 13.9 Hz, 1H), 1.58 (t, J = 12.8 Hz, 1H), 1.27 (t, J = 12.9 Hz, 1H), 1.03 (d, J = 6.3 Hz, 3H). LCMS m/z 463.19 (M + 1)⁺ |

TABLE 11-continued

*Method of preparation, structure, and physicochemical data for compounds 226-371*

| Product | Starting Material and Amine | NMR, LCMS |
|---|---|---|
| Compound 252 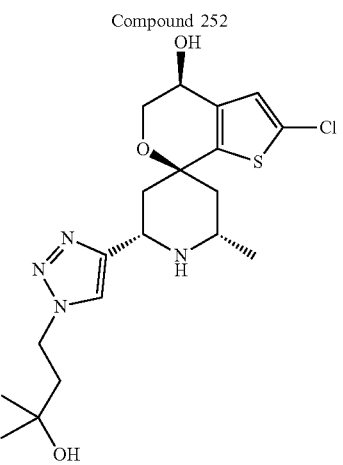 | 222;  | $^1$H NMR (400 MHz, DMSO-d6) δ 7.95 (s, 1H), 6.96 (s, 1H), 5.49 (s, 1H), 4.62 (s, 1H), 4.41-4.32 (m, 4H), 4.11 (d, J = 11.4 Hz, 1H), 3.92 (d, J = 4.0 Hz, 0H), 3.13-3.07 (m, 1H), 2.17 (d, J = 13.5 Hz, 1H), 2.04 (d, J = 13.3 Hz, 1H), 1.94-1.86 (m, 2H), 1.65-1.53 (m, 1H), 1.27 (t, J = 12.4 Hz, 1H), 1.12 (s, 6H), 1.02 (d, J = 6.3 Hz, 3H). LCMS m/z 427.21 (M + 1)$^+$ |
| Compound 253 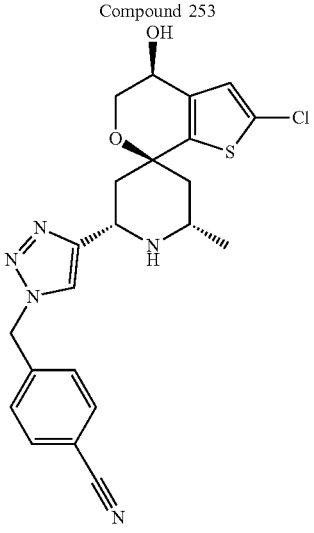 | 222; 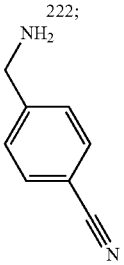 | $^1$H NMR (400 MHz, DMSO-d6) δ 8.05 (s, 1H), 7.84 (d, J = 8.0 Hz, 2H), 7.44 (d, J = 8.0 Hz, 2H), 6.95 (s, 1H), 5.67 (s, 2H), 5.50 (s, 1H), 4.39 (s, 1H), 4.12 (dd, J = 11.7, 2.5 Hz, 1H), 3.93 (dd, J = 11.9, 4.1 Hz, 1H), 3.09 (dt, J = 9.0, 4.0 Hz, 1H), 2.19 (dd, J = 13.2, 2.8 Hz, 1H), 2.03 (d, J = 13.6 Hz, 1H), 1.64-1.51 (m, 1H), 1.35-1.21 (m, 1H), 1.01 (d, J = 6.3 Hz, 3H). LCMS m/z 456.15 (M + 1)$^+$ |
| Compound 254 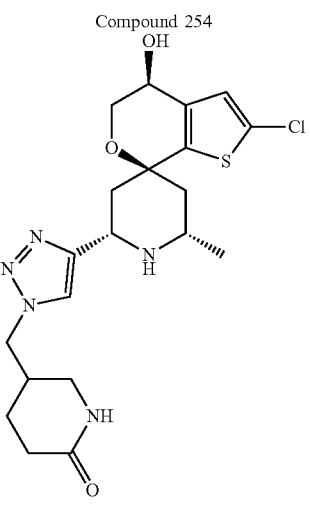 | 222; 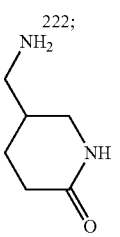 | $^1$H NMR (400 MHz, DMSO-d6) δ 7.95 (s, 1H), 7.47 (d, J = 3.3 Hz, 1H), 6.95 (s, 1H), 5.52 (d, J = 6.8 Hz, 1H), 4.39 (d, J = 4.9 Hz, 1H), 4.32 (d, J = 7.1 Hz, 2H), 4.12 (dd, J = 11.7, 2.6 Hz, 1H), 3.93 (dd, J = 12.0, 4.1 Hz, 1H), 3.10 (q, J = 5.7, 4.2 Hz, 1H), 3.00 (d, J = 10.2 Hz, 1H), 2.89 (t, J = 10.8 Hz, 1H), 2.32-2.10 (m, 4H), 2.03 (d, J = 13.4 Hz, 1H), 1.68 (s, 1H), 1.58 (t, J = 12.6 Hz, 1H), 1.42 (ddd, J = 10.5, 8.5, 4.1 Hz, 1H), 1.34-1.23 (m, 1H), 1.03 (d, J = 6.3 Hz, 3H). LCMS m/z 452.18 (M + 1)$^+$ |

TABLE 11-continued

*Method of preparation, structure, and physicochemical data for compounds 226-371*

| Product | Starting Material and Amine | NMR, LCMS |
|---|---|---|
| Compound 255 | 222; NH₂-CH₂-CN | ¹H NMR (400 MHz, DMSO-d6) δ 8.09 (s, 1H), 6.95 (s, 1H), 5.74 (s, 2H), 5.53 (s, 1H), 4.39 (d, J = 4.8 Hz, 1H), 4.14 (dd, J = 11.7, 2.5 Hz, 1H), 3.94 (dd, J = 11.9, 4.1 Hz, 1H), 3.09 (d, J = 10.6 Hz, 1H), 2.20 (d, J = 13.5 Hz, 1H), 2.04 (d, J = 13.3 Hz, 1H), 1.59 (t, J = 12.6 Hz, 1H), 1.29 (t, J = 12.4 Hz, 1H), 1.03 (d, J = 6.3 Hz, 4H). LCMS m/z 380.12 (M + 1)⁺ |
| Compound 256 | 222; NH₂-CH₂-CH(CH₃)-CH₂-OH | ¹H NMR (400 MHz, DMSO-d6) δ 7.90 (s, 1H), 6.95 (s, 1H), 5.50 (s, 1H), 4.83 (s, 1H), 4.39 (t, J = 4.6 Hz, 1H), 4.34 (dd, J = 13.6, 6.0 Hz, 1H), 4.12 (dd, J = 13.4, 7.8 Hz, 2H), 3.93 (dd, J = 11.9, 4.1 Hz, 1H), 3.26 (t, J = 6.3 Hz, 2H), 3.10 (s, 2H), 2.33 (s, 1H), 2.19 (dt, J = 13.6, 2.6 Hz, 1H), 2.10-1.99 (m, 2H), 1.58 (t, J = 12.6 Hz, 1H), 1.28 (dd, J = 13.4, 11.2 Hz, 1H), 1.03 (d, J = 6.3 Hz, 3H), 0.76 (d, J = 6.8 Hz, 3H). LCMS m/z 413.17 (M + 1)⁺ |
| Compound 257 | 222; NH₂-CH₂-CH₂-O-CH₂CH₃ | ¹H NMR (400 MHz, DMSO-d6) δ 7.92 (s, 1H), 6.96 (s, 1H), 5.42 (s, 1H), 4.46 (t, J = 5.3 Hz, 2H), 4.39 (t, J = 4.7 Hz, 1H), 4.12 (d, J = 11.4 Hz, 1H), 3.93 (dd, J = 11.9, 4.2 Hz, 1H), 3.74 (t, J = 5.3 Hz, 2H), 3.64 (dd, J = 11.9, 5.2 Hz, 1H), 3.47-3.39 (m, 2H), 3.09 (d, J = 9.9 Hz, 1H), 2.26 (s, 1H), 2.18 (d, J = 13.5 Hz, 1H), 2.05 (d, J = 13.4 Hz, 1H), 1.57 (t, J = 12.5 Hz, 1H), 1.26 (dd, J = 13.4, 11.3 Hz, 1H), 1.10-1.00 (m, 6H). LCMS m/z 413.17 (M + 1)⁺ |

TABLE 11-continued

Method of preparation, structure, and physicochemical data for compounds 226-371

| Product | Starting Material and Amine | NMR, LCMS |
|---|---|---|
| Compound 258 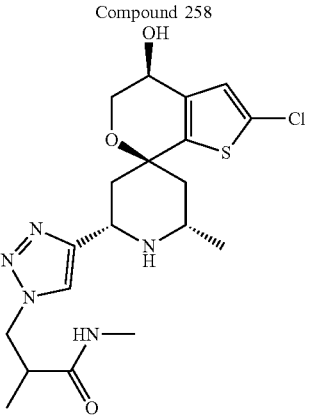 | 222; 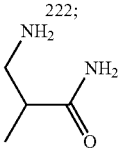 | ¹H NMR (400 MHz, DMSO-d6) δ 7.89 (d, J = 4.9 Hz, 1H), 7.82 (d, J = 2.3 Hz, 1H), 6.96 (s, 1H), 5.42 (s, 1H), 4.43 (dt, J = 12.7, 6.3 Hz, 1H), 4.39 (d, J = 4.9 Hz, 1H), 4.25 (ddd, J = 13.7, 6.8, 2.3 Hz, 1H), 4.10 (d, J = 11.4 Hz, 1H), 3.93 (dd, J = 11.9, 4.2 Hz, 1H), 3.63 (dd, J = 11.8, 5.3 Hz, 1H), 3.09 (s, 1H), 2.89-2.81 (m, 1H), 2.53 (d, J = 4.2 Hz, 3H), 2.24 (s, 1H), 2.16 (d, J = 13.4 Hz, 1H), 2.05 (d, J = 13.4 Hz, 1H), 1.54 (td, J = 13.0, 5.2 Hz, 1H), 1.23 (q, J = 12.3 Hz, 1H), 1.02 (d, J = 6.3 Hz, 3H), 0.98 (d, J = 6.9 Hz, 3H). LCMS m/z 440.21 (M + 1)⁺ |
| Compound 259 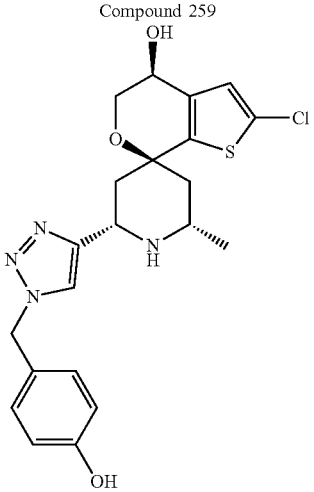 | 222; 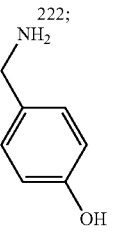 | ¹H NMR (400 MHz, DMSO-d6) δ 7.91 (s, 1H), 7.16 (d, J = 8.4 Hz, 2H), 6.95 (s, 1H), 6.76-6.70 (m, 2H), 5.38 (s, 3H), 4.38 (t, J = 4.7 Hz, 1H), 4.08 (d, J = 11.4 Hz, 1H), 3.92 (dd, J = 11.8, 4.2 Hz, 1H), 3.62 (dd, J = 11.9, 5.2 Hz, 1H), 3.07 (s, 1H), 2.26 (s, 1H), 2.17 (d, J = 13.4 Hz, 1H), 2.03 (d, J = 13.3 Hz, 1H), 1.60-1.48 (m, 1H), 1.23 (dd, J = 13.4, 11.2 Hz, 1H), 1.00 (d, J = 6.3 Hz, 3H). LCMS m/z 447.17 (M + 1)⁺ |
| Compound 260 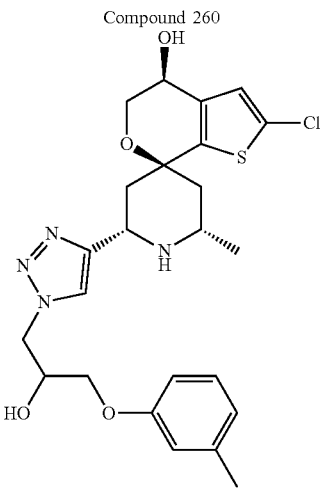 | 222; 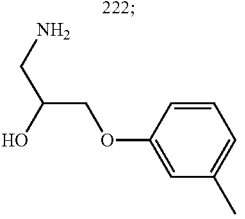 | ¹H NMR (400 MHz, DMSO-d6) δ 7.92 (s, 1H), 7.19-7.11 (m, 1H), 6.97 (s, 1H), 6.74 (s, 3H), 6.72 (d, J = 8.3 Hz, 1H), 5.54 (s, 1H), 5.45 (s, 1H), 4.52 (dd, J = 13.9, 4.1 Hz, 1H), 4.39 (s, 2H), 4.18 (s, 1H), 4.12 (d, J = 11.5 Hz, 1H), 3.97-3.84 (m, 2H), 3.64 (dd, J = 11.9, 5.2 Hz, 1H), 3.09 (s, 1H), 2.26 (s, 3H), 2.23 (s, 1H), 2.17 (d, J = 13.3 Hz, 1H), 2.05 (d, J = 13.2 Hz, 1H), 1.57 (s, 1H), 1.30-1.16 (m, 1H), 1.02 (d, J = 6.3 Hz, 3H). LCMS m/z 505.19 (M + 1)⁺ |

TABLE 11-continued

Method of preparation, structure, and physicochemical data for compounds 226-371

| Product | Starting Material and Amine | NMR, LCMS |
|---|---|---|
| Compound 261 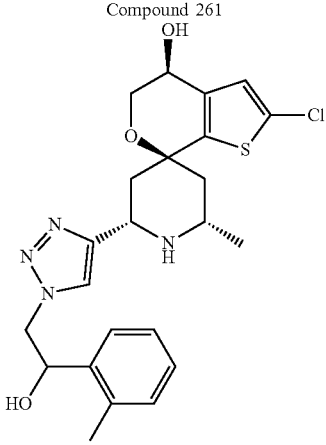 | 222; 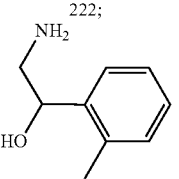 | ¹H NMR (400 MHz, DMSO-d6) δ 7.92 (d, J = 10.0 Hz, 1H), 7.47 (d, J = 7.3 Hz, 1H), 7.19 (ddt, J = 17.6, 10.0, 4.5 Hz, 3H), 6.97 (s, 1H), 5.65 (s, 1H), 5.44 (s, 1H), 5.11 (s, 1H), 4.47-4.37 (m, 2H), 4.37-4.27 (m, 1H), 4.13 (d, J = 11.7 Hz, 1H), 3.94 (dd, J = 11.9, 4.2 Hz, 1H), 3.64 (dd, J = 11.8, 5.3 Hz, 1H), 3.10 (s, 1H), 2.31 (d, J = 6.3 Hz, 3H), 2.24 (s, 1H), 2.18 (d, J = 15.4 Hz, 1H), 2.06 (d, J = 13.4 Hz, 1H), 1.57 (td, J = 12.4, 6.6 Hz, 1H), 1.31-1.16 (m, 1H), 1.03 (d, J = 6.3 Hz, 3H). LCMS m/z 475.20 (M + 1)⁺ |
| Compound 262 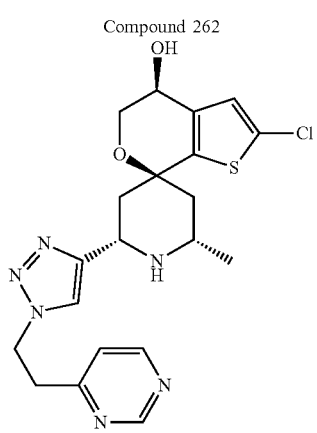 | 222; 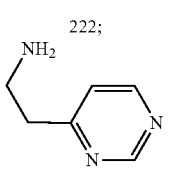 | ¹H NMR (400 MHz, DMSO-d6) δ 9.10 (d, J = 1.4 Hz, 1H), 8.68 (d, J = 5.1 Hz, 1H), 7.96 (s, 1H), 7.39 (dd, J = 5.2, 1.5 Hz, 1H), 6.96 (s, 1H), 5.41 (s, 1H), 4.75 (t, J = 7.1 Hz, 2H), 4.39 (s, 1H), 4.08 (d, J = 10.8 Hz, 1H), 3.92 (dd, J = 11.8, 4.3 Hz, 1H), 3.63 (dd, J = 11.8, 5.2 Hz, 1H), 3.34 (s, 2H), 3.08 (s, 1H), 2.23 (s, 1H), 2.14 (d, J = 13.4 Hz, 1H), 2.04 (d, J = 13.4 Hz, 1H), 1.58-1.48 (m, 1H), 1.29-1.19 (m, 1H), 1.01 (d, J = 6.2 Hz, 3H). LCMS m/z 447.17 (M + 1)⁺ |
| Compound 263 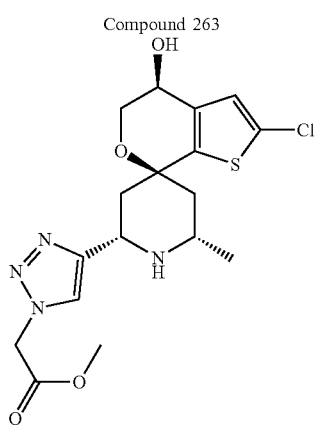 | 222; 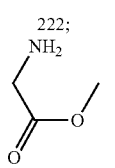 | ¹H NMR (400 MHz, DMSO-d6) δ 9.34 (s, 5H), 8.27 (s, 1H), 7.04 (s, 1H), 5.52 (d, J = 6.1 Hz, 1H), 5.50 (s, 2H), 4.73 (d, J = 12.3 Hz, 1H), 4.42 (q, J = 4.9 Hz, 1H), 4.00 (dd, J = 12.1, 4.0 Hz, 1H), 3.72 (s, 3H), 2.32 (d, J = 14.0 Hz, 1H), 2.19 (t, J = 13.8 Hz, 1H), 1.82 (t, J = 13.4 Hz, 1H), 1.28 (d, J = 6.5 Hz, 3H). LCMS m/z 413.12 (M + 1)⁺ |

TABLE 11-continued

Method of preparation, structure, and physicochemical data for compounds 226-371

| Product | Starting Material and Amine | NMR, LCMS |
|---|---|---|
| Compound 264 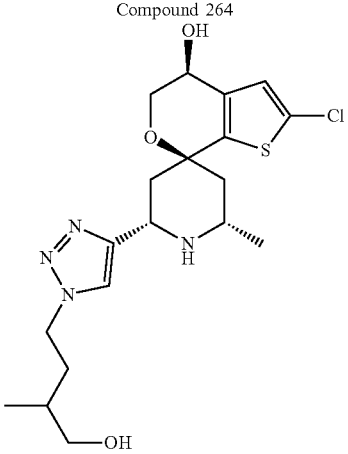 | 222; 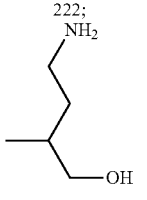 | $^1$H NMR (400 MHz, DMSO-d6) δ 9.36 (s, 1H), 8.91 (s, 1H), 8.28 (s, 1H), 7.04 (s, 1H), 5.53 (d, J = 6.1 Hz, 1H), 4.68 (s, 1H), 4.58 (s, 1H), 4.44 (td, J = 8.0, 7.3, 3.1 Hz, 3H), 3.99 (dd, J = 12.2, 4.0 Hz, 1H), 3.71 (dd, J = 12.1, 4.9 Hz, 1H), 3.64 (s, 1H), 3.26 (s, 2H), 2.45 (s, 1H), 2.33 (d, J = 14.0 Hz, 1H), 2.21 (t, J = 13.6 Hz, 1H), 1.94 (dt, J = 13.5, 6.8 Hz, 1H), 1.83 (dd, J = 14.3, 12.3 Hz, 1H), 1.58 (dq, J = 14.0, 7.4 Hz, 1H), 1.51-1.41 (m, 1H), 1.28 (d, J = 6.4 Hz, 3H), 0.87 (d, J = 6.6 Hz, 3H). LCMS m/z 427.16 (M + 1)$^+$ |
| Compound 265 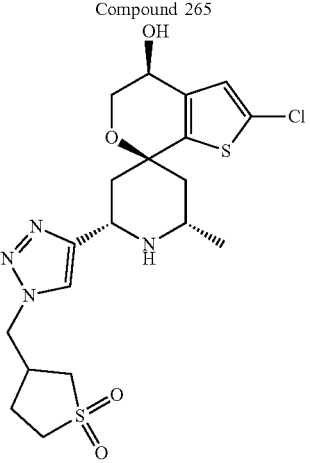 | 222; 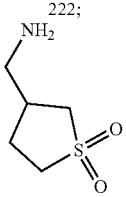 | $^1$H NMR (400 MHz, DMSO-d6) δ 9.32 (s, 1H), 8.92 (d, J = 11.3 Hz, 1H), 8.29 (s, 1H), 7.02 (d, J = 16.7 Hz, 1H), 5.53 (s, 1H), 4.70 (t, J = 11.2 Hz, 1H), 4.59 (d, J = 6.3 Hz, 2H), 4.42 (s, 1H), 3.99 (dd, J = 12.0, 4.0 Hz, 1H), 3.71 (dd, J = 12.1, 4.9 Hz, 1H), 3.64 (s, 1H), 3.28-3.20 (m, 1H), 3.18-3.03 (m, 2H), 3.02-2.85 (m, 2H), 2.46 (s, 1H), 2.33 (d, J = 14.2 Hz, 1H), 2.29-2.18 (m, 1H), 2.15 (s, 1H), 1.84 (t, J = 12.5 Hz, 2H), 1.28 (d, J = 6.4 Hz, 3H). LCMS m/z 473.13 (M + 1)$^+$ |
| Compound 266 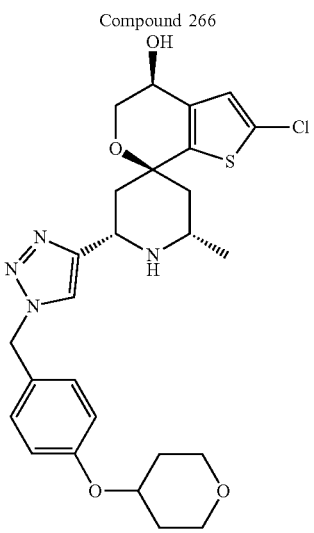 | 222; 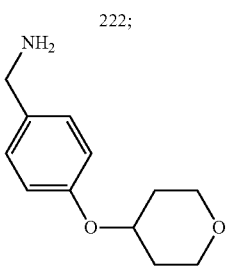 | 1H NMR (400 MHz, DMSO-d6) δ 9.30 (s, 1H), 8.88 (s, 1H), 8.26 (s, 1H), 7.33-7.27 (m, 2H), 7.03 (s, 1H), 6.98 (d, J = 8.3 Hz, 2H), 5.55 (s, 2H), 5.50 (d, J = 6.2 Hz, 1H), 4.66 (d, J = 12.5 Hz, 1H), 4.56 (dt, J = 8.8, 4.5 Hz, 1H), 4.40 (d, J = 5.4 Hz, 1H), 3.98 (dd, J = 12.0, 3.9 Hz, 1H), 3.88-3.78 (m, 1H), 3.83 (s, 1H), 3.69 (dd, J = 12.1, 4.8 Hz, 1H), 3.60 (s, 1H), 3.46 (td, J = 11.8, 10.7, 2.7 Hz, 2H), 2.30 (d, J = 14.4 Hz, 1H), 2.17 (t, J = 13.5 Hz, 1H), 1.93 (d, J = 12.4 Hz, 2H), 1.81 (t, J = 13.3 Hz, 1H), 1.54 (dtd, J = 13.2, 9.0, 4.0 Hz, 2H), 1.25 (d, J = 6.6 Hz, 3H). LCMS m/z 531.19 (M + 1)$^+$ |

TABLE 11-continued

Method of preparation, structure, and physicochemical data for compounds 226-371

| Product | Starting Material and Amine | NMR, LCMS |
|---|---|---|
| Compound 267 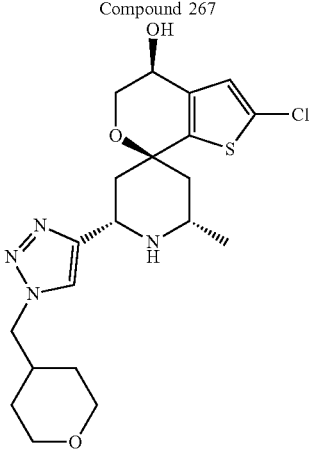 | 222; 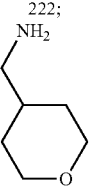 | $^1$H NMR (400 MHz, DMSO-d6) δ 9.35 (d, J = 10.2 Hz, 1H), 8.92 (d, J = 11.0 Hz, 1H), 8.24 (s, 1H), 7.03 (d, J = 14.3 Hz, 1H), 5.53 (s, 1H), 4.69 (t, J = 11.4 Hz, 1H), 4.42 (s, 1H), 4.33 (d, J = 7.0 Hz, 2H), 3.99 (dd, J = 12.0, 4.0 Hz, 1H), 3.83 (d, J = 11.6 Hz, 2H), 3.71 (dd, J = 12.0, 4.9 Hz, 1H), 3.64 (s, 1H), 3.24 (t, J = 11.8 Hz, 2H), 2.45 (s, 1H), 2.33 (d, J = 14.0 Hz, 1H), 2.28-2.17 (m, 1H), 1.84 (t, J = 13.3 Hz, 1H), 1.40 (d, J = 12.9 Hz, 2H), 1.28 (d, J = 6.6 Hz, 3H), 1.28-1.17 (m, 1H). LCMS m/z 439.22 (M + 1)$^+$ |
| Compound 268 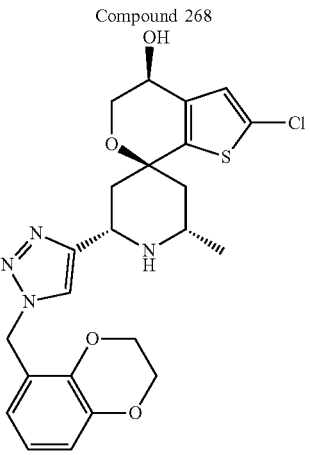 | 222; 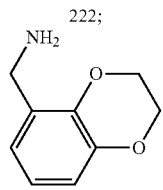 | $^1$H NMR (400 MHz, DMSO-d6) δ 9.31 (s, 1H), 8.91 (d, J = 11.5 Hz, 1H), 8.19 (s, 1H), 7.04 (s, 1H), 6.88 (dd, J = 8.1, 1.7 Hz, 1H), 6.82 (t, J = 7.8 Hz, 1H), 6.73 (dd, J = 7.6, 1.7 Hz, 1H), 5.55 (s, 2H), 5.52 (d, J = 5.9 Hz, 1H), 4.70 (t, J = 11.3 Hz, 1H), 4.41 (d, J = 4.5 Hz, 1H), 4.34-4.22 (m, 4H), 3.98 (dd, J = 12.1, 4.0 Hz, 1H), 3.70 (dd, J = 12.0, 4.9 Hz, 1H), 3.61 (s, 1H), 2.45 (s, 1H), 2.31 (d, J = 14.3 Hz, 1H), 2.25-2.14 (m, 1H), 1.83 (t, J = 13.3 Hz, 1H), 1.27 (d, J = 6.5 Hz, 3H). LCMS m/z 489.16 (M + 1)$^+$ |
| Compound 269 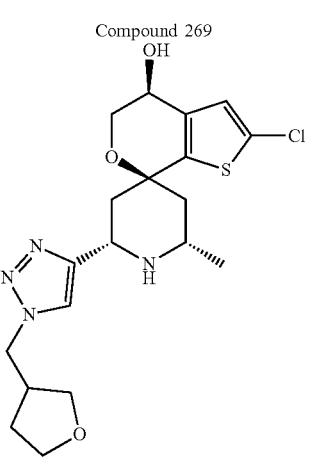 | 222; 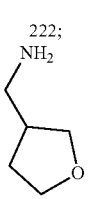 | $^1$H NMR (400 MHz, DMSO-d6) δ 9.36 (s, 1H), 8.93 (s, 1H), 8.30 (s, 1H), 7.04 (s, 1H), 5.53 (s, 1H), 4.69 (t, J = 10.9 Hz, 1H), 4.42 (d, J = 7.3 Hz, 3H), 3.99 (dd, J = 12.0, 4.0 Hz, 1H), 3.82-3.65 (m, 2H), 3.68-3.63 (m, 1H), 3.65-3.59 (m, 1H), 3.45 (dd, J = 8.8, 5.3 Hz, 1H), 2.72 (p, J = 6.4 Hz, 1H), 2.45 (s, 1H), 2.33 (d, J = 14.1 Hz, 1H), 2.28-2.16 (m, 1H), 1.99-1.78 (m, 2H), 1.61 (dt, J = 13.2, 6.6 Hz, 1H), 1.28 (d, J = 6.4 Hz, 3H). LCMS m/z 425.18 (M + 1)$^+$ |

TABLE 11-continued

Method of preparation, structure, and physicochemical data for compounds 226-371

| Product | Starting Material and Amine | NMR, LCMS |
|---|---|---|
| Compound 270 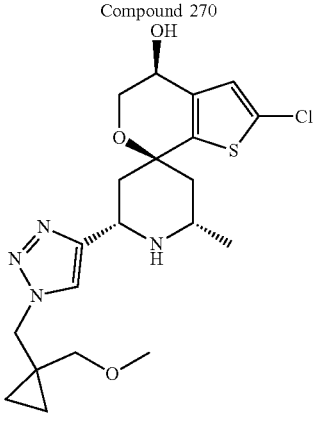 | 222; 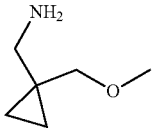 | $^1$H NMR (400 MHz, DMSO-d6) δ 9.40 (s, 1H), 8.95 (s, 1H), 8.23 (s, 1H), 7.04 (s, 1H), 5.53 (d, J = 6.2 Hz, 1H), 4.71 (s, 1H), 4.42 (d, J = 5.4 Hz, 1H), 4.36 (s, 2H), 4.00 (dd, J = 12.1, 4.0 Hz, 1H), 3.71 (dd, J = 12.0, 4.9 Hz, 1H), 3.65 (s, 1H), 3.22 (s, 3H), 3.03 (s, 2H), 2.47 (s, 1H), 2.33 (d, J = 14.1 Hz, 1H), 2.21 (t, J = 13.6 Hz, 1H), 1.84 (t, J = 13.3 Hz, 1H), 1.29 (d, J = 6.5 Hz, 3H), 0.73 (q, J = 4.3 Hz, 2H), 0.54 (t, J = 3.0 Hz, 2H). LCMS m/z 439.17 (M + 1)$^+$ |
| Compound 271 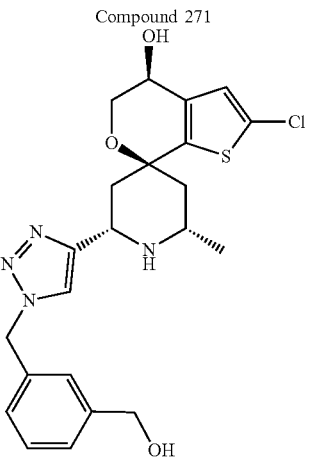 | 222; 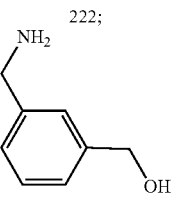 | $^1$H NMR (400 MHz, DMSO-d6) δ 9.30 (d, J = 10.4 Hz, 1H), 8.88 (d, J = 11.2 Hz, 1H), 8.31 (s, 1H), 7.38-7.24 (m, 3H), 7.21 (d, J = 7.5 Hz, 1H), 7.04 (s, 1H), 5.64 (s, 2H), 5.51 (s, 1H), 5.27 (s, 1H), 4.69 (t, J = 11.3 Hz, 1H), 4.48 (s, 2H), 4.41 (s, 1H), 3.98 (dd, J = 12.0, 3.9 Hz, 1H), 3.70 (dd, J = 12.0, 4.7 Hz, 1H), 3.62 (s, 1H), 2.45 (s, 1H), 2.31 (d, J = 14.4 Hz, 1H), 2.19 (t, J = 13.6 Hz, 1H), 1.82 (t, J = 13.3 Hz, 1H), 1.26 (d, J = 6.4 Hz, 3H). LCMS m/z 461.16 (M + 1)$^+$ |
| Compound 272 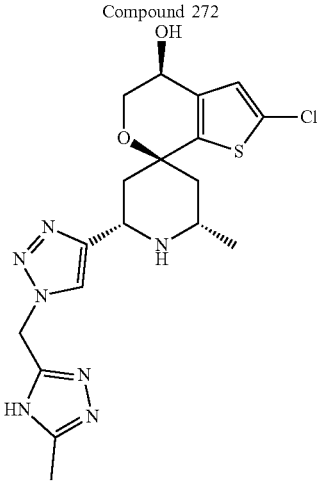 | 222; 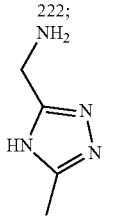 | $^1$H NMR (400 MHz, DMSO-d6) δ 9.33 (d, J = 10.6 Hz, 1H), 8.89 (d, J = 11.1 Hz, 1H), 8.28 (s, 1H), 7.02 (d, J = 15.6 Hz, 1H), 5.63 (s, 2H), 4.71 (t, J = 11.4 Hz, 1H), 4.41 (t, J = 4.4 Hz, 1H), 3.99 (dd, J = 12.0, 4.0 Hz, 1H), 3.70 (dd, J = 11.9, 4.8 Hz, 1H), 3.63 (s, 2H), 2.45 (s, 1H), 2.31 (s, 3H), 2.20 (t, J = 13.7 Hz, 1H), 1.83 (t, J = 13.3 Hz, 1H), 1.27 (d, J = 6.4 Hz, 3H). LCMS m/z 436.19 (M + 1)$^+$ |

TABLE 11-continued

Method of preparation, structure, and physicochemical data for compounds 226-371

| Product | Starting Material and Amine | NMR, LCMS |
|---|---|---|
| Compound 273 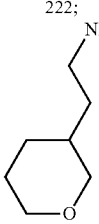 | 222; <br> structure with NH₂ and tetrahydropyran | 1H NMR (400 MHz, DMSO-d6) δ 9.36 (d, J = 10.2 Hz, 1H), 8.91 (d, J = 11.2 Hz, 1H), 8.29 (s, 1H), 7.04 (s, 1H), 5.52 (s, 1H), 4.69 (t, J = 11.2 Hz, 1H), 4.43 (t, J = 7.1 Hz, 3H), 3.99 (dd, J = 12.0, 4.0 Hz, 1H), 3.73 (d, J = 9.7 Hz, 3H), 3.65 (s, 1H), 3.27 (td, J = 11.0, 2.7 Hz, 1H), 3.07-2.97 (m, 1H), 2.45 (s, 1H), 2.33 (d, J = 14.2 Hz, 1H), 2.21 (t, J = 13.6 Hz, 1H), 1.85 (d, J = 14.0 Hz, 1H), 1.80 (s, 1H), 1.67 (ddq, J = 20.7, 13.9, 6.9 Hz, 2H), 1.53 (s, 1H), 1.41 (s, 2H), 1.28 (d, J = 6.4 Hz, 3H), 1.18 (d, J = 12.3 Hz, 1H). LCMS m/z 453.17 (M + 1)⁺ |
| Compound 274 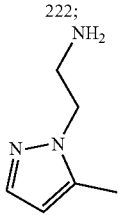 | 222; <br> structure with NH₂ and methylpyrazole | ¹H NMR (400 MHz, DMSO-d6) δ 9.36 (d, J = 10.8 Hz, 1H), 8.89 (d, J = 11.2 Hz, 1H), 8.04 (s, 1H), 7.38-7.30 (m, 1H), 7.05 (s, 1H), 5.95 (s, 1H), 4.82 (t, J = 5.9 Hz, 2H), 4.66 (t, J = 11.5 Hz, 1H), 4.46 (dt, J = 17.9, 5.3 Hz, 3H), 4.19 (t, J = 5.6 Hz, 1H), 3.98 (dd, J = 11.9, 4.2 Hz, 1H), 3.68 (td, J = 13.7, 13.0, 6.5 Hz, 1H), 2.34 (t, J = 12.8 Hz, 2H), 2.27 (s, 1H), 2.15 (t, J = 13.6 Hz, 1H), 1.98 (s, 3H), 1.82 (t, J = 13.3 Hz, 1H), 1.27 (d, J = 6.5 Hz, 3H). LCMS m/z 449.20 (M + 1)⁺ |
| Compound 275 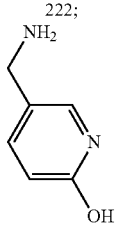 | 222; <br> structure with NH₂ and hydroxypyridine | ¹H NMR (400 MHz, DMSO-d6) δ 11.71 (s, 1H), 9.29 (d, J = 10.3 Hz, 1H), 8.87 (d, J = 10.9 Hz, 1H), 8.27 (s, 1H), 7.60 (d, J = 2.7 Hz, 1H), 7.41 (dd, J = 9.5, 2.7 Hz, 1H), 7.02 (d, J = 13.0 Hz, 1H), 6.34 (d, J = 9.4 Hz, 1H), 5.38 (s, 2H), 4.68 (t, J = 11.2 Hz, 1H), 4.41 (t, J = 4.3 Hz, 1H), 3.98 (dd, J = 12.0, 4.0 Hz, 1H), 3.74-3.62 (m, 1H), 2.45 (s, 1H), 2.31 (d, J = 14.6 Hz, 1H), 2.18 (t, J = 13.6 Hz, 1H), 1.82 (t, J = 13.3 Hz, 1H), 1.26 (d, J = 6.4 Hz, 3H). LCMS m/z 448.16 (M + 1)⁺ |

TABLE 11-continued

Method of preparation, structure, and physicochemical data for compounds 226-371

| Product | Starting Material and Amine | NMR, LCMS |
|---|---|---|
| Compound 276 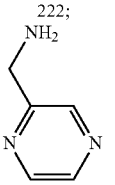 | 222; <br> pyrazin-2-ylmethanamine | $^1$H NMR (400 MHz, DMSO-d6) δ 9.34 (d, J = 10.3 Hz, 1H), 8.92 (d, J = 10.7 Hz, 1H), 8.72 (d, J = 1.4 Hz, 1H), 8.69-8.60 (m, 2H), 8.39 (s, 1H), 7.04 (s, 1H), 5.88 (s, 2H), 5.52 (s, 1H), 4.72 (t, J = 11.3 Hz, 1H), 4.42 (d, J = 4.5 Hz, 1H), 3.99 (dd, J = 12.0, 4.0 Hz, 1H), 3.71 (dd, J = 12.0, 4.8 Hz, 1H), 3.64 (s, 1H), 2.47 (s, 1H), 2.32 (d, J = 14.0 Hz, 1H), 2.27-2.16 (m, 1H), 1.89-1.78 (m, 1H), 1.28 (d, J = 6.4 Hz, 3H). LCMS m/z 433.17 (M + 1)$^+$ |
| Compound 277 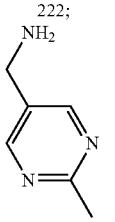 | 222; <br> (2-methylpyrimidin-5-yl)methanamine | 1H NMR (400 MHz, DMSO-d6) δ 9.27 (d, J = 10.3 Hz, 1H), 8.87 (d, J = 11.1 Hz, 1H), 8.72 (s, 2H), 8.38 (s, 1H), 7.02 (d, J 13.4 Hz, 1H), 5.72 (s, 2H), 5.50 (s, 1H), 4.69 (t, J = 11.2 Hz, 1H), 4.41 (t, J = 4.3 Hz, 1H), 3.98 (dd, J = 12.0, 4.0 Hz, 1H), 3.74-3.62 (m, 1H), 2.61 (s, 3H), 2.45 (s, 1H), 2.31 (d, J = 14.3 Hz, 1H), 2.26-2.15 (m, 1H), 1.82 (t, J = 13.3 Hz, 1H), 1.26 (d, J = 6.5 Hz, 3H). LCMS m/z 447.17 (M + 1)$^+$ |
| Compound 278 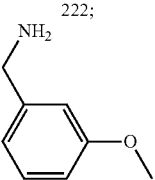 | 222; <br> (3-methoxyphenyl)methanamine | $^1$H NMR (400 MHz, DMSO-d6) δ 9.30 (s, 1H), 8.88 (d, J = 10.0 Hz, 1H), 8.32 (s, 1H), 7.29 (dt, J = 10.8, 8.3 Hz, 1H), 7.04 (s, 1H), 6.95-6.86 (m, 3H), 5.61 (s, 2H), 5.51 (d, J = 6.1 Hz, 1H), 4.69 (t, J = 10.9 Hz, 1H), 4.41 (s, 1H), 3.98 (dd, J = 12.0, 3.9 Hz, 1H), 3.74 (s, 3H), 3.70 (dd, J = 12.0, 4.8 Hz, 1H), 3.62 (s, 1H), 2.46 (s, 1H), 2.31 (d, J = 14.2 Hz, 1H), 2.20 (t, J = 13.6 Hz, 1H), 1.82 (t, J = 13.3 Hz, 1H), 1.26 (d, J = 6.5 Hz, 3H). LCMS m/z 461.16 (M + 1)$^+$ |

TABLE 11-continued

Method of preparation, structure, and physicochemical data for compounds 226-371

| Product | Starting Material and Amine | NMR, LCMS |
|---|---|---|
| Compound 279 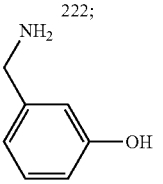 | 222; <br> 3-hydroxybenzylamine | $^1$H NMR (400 MHz, DMSO-d6) δ 9.61 (s, 1H), 9.30 (d, J = 10.3 Hz, 1H), 8.87 (d, J = 10.9 Hz, 1H), 8.29 (s, 1H), 7.21-7.11 (m, 1H), 7.04 (s, 1H), 6.78-6.70 (m, 3H), 5.55 (s, 2H), 4.69 (s, 1H), 4.41 (t, J = 4.3 Hz, 1H), 3.98 (dd, J = 12.0, 3.9 Hz, 1H), 3.70 (dd, J = 12.1, 4.8 Hz, 1H), 3.62 (s, 1H), 2.45 (s, 1H), 2.31 (d, J = 14.4 Hz, 1H), 2.25-2.14 (m, 1H), 1.88-1.76 (m, 1H), 1.26 (d, J = 6.4 Hz, 3H). LCMS m/z 447.17 (M + 1)$^+$ |
| Compound 280 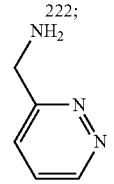 | 222; pyridazin-3-ylmethanamine | $^1$H NMR (400 MHz, DMSO-d6) δ 9.36 (d, J = 10.7 Hz, 1H), 9.23 (dd, J = 5.1, 1.7 Hz, 1H), 8.93 (d, J = 10.4 Hz, 1H), 8.43 (s, 1H), 7.77 (dd, J = 8.4, 4.9 Hz, 1H), 7.69 (dd, J = 8.4, 1.7 Hz, 1H), 7.02 (d, J = 14.2 Hz, 1H), 6.02 (s, 2H), 5.55 (s, 1H), 4.73 (t, J = 11.1 Hz, 1H), 4.42 (d, J = 4.6 Hz, 1H), 3.99 (dd, J = 12.1, 4.1 Hz, 1H), 3.71 (dd, J = 12.0, 4.9 Hz, 1H), 3.64 (s, 1H), 2.47 (s, 1H), 2.32 (d, J = 14.1 Hz, 1H), 2.22 (t, J = 13.6 Hz, 1H), 1.84 (t, J = 13.3 Hz, 1H), 1.28 (d, J = 6.4 Hz, 3H). LCMS m/z 433.13 (M + 1)$^+$ |
| Compound 281 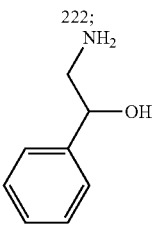 | 222; 2-amino-1-phenylethan-1-ol | $^1$H NMR (400 MHz, DMSO-d6) δ 9.40 (s, 1H), 8.92 (d, J = 11.4 Hz, 1H), 8.26 (d, J = 1.1 Hz, 1H), 7.43-7.24 (m, 5H), 7.05 (s, 1H), 5.86 (s, 1H), 5.52 (s, 1H), 4.99 (s, 1H), 4.71 (t, J = 11.2 Hz, 1H), 4.62-4.46 (m, 2H), 4.43 (s, 1H), 4.00 (dd, J = 12.1, 4.0 Hz, 1H), 3.72 (dd, J = 12.0, 4.9 Hz, 1H), 3.63 (s, 1H), 2.44 (s, 1H), 2.33 (d, J = 14.1 Hz, 1H), 2.21 (t, J = 13.2 Hz, 1H), 1.84 (t, J = 13.3 Hz, 1H), 1.29 (d, J = 6.4 Hz, 3H). LCMS m/z 461.16 (M + 1)$^+$ |

TABLE 11-continued

Method of preparation, structure, and physicochemical data for compounds 226-371

| Product | Starting Material and Amine | NMR, LCMS |
|---|---|---|
| Compound 282 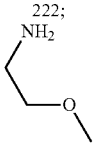 | 222; NH₂–CH₂–CH₂–O–CH₃ | ¹H NMR (400 MHz, DMSO-d6) δ 9.38 (s, 1H), 8.93 (d, J = 12.0 Hz, 1H), 8.25 (s, 1H), 7.03 (d, J = 14.3 Hz, 1H), 5.52 (s, 1H), 4.70 (t, J = 11.1 Hz, 1H), 4.58 (t, J = 5.0 Hz, 2H), 4.42 (s, 1H), 3.99 (dd, J = 12.1, 3.9 Hz, 1H), 3.77-3.67 (m, 3H), 3.63 (s, 1H), 3.24 (s, 3H), 2.45 (s, 1H), 2.32 (d, J = 14.2 Hz, 1H), 2.21 (t, J = 13.6 Hz, 1H), 1.84 (t, J = 13.3 Hz, 1H), 1.28 (d, J = 6.5 Hz, 3H). LCMS m/z 399.17 (M + 1)⁺ |
| Compound 283 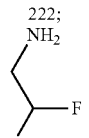 | 222; NH₂–CH₂–CHF₂ | ¹H NMR (400 MHz, DMSO-d6) δ 9.39 (s, 1H), 8.97 (d, J = 10.8 Hz, 1H), 8.33 (s, 1H), 7.04 (s, 1H), 6.66-6.32 (m, 1H), 5.52 (s, 1H), 5.04 (td, J = 16.1, 3.0 Hz, 2H), 4.75 (t, J = 10.9 Hz, 1H), 4.42 (s, 1H), 4.00 (dd, J = 12.1, 4.0 Hz, 1H), 3.71 (dd, J = 12.1, 4.8 Hz, 1H), 3.64 (s, 1H), 2.46 (s, 1H), 2.33 (d, J = 14.2 Hz, 1H), 2.23 (t, J = 13.6 Hz, 1H), 1.85 (t, J = 13.3 Hz, 1H), 1.29 (d, J = 6.5 Hz, 3H). LCMS m/z 405.13 (M + 1)⁺ |
| Compound 284 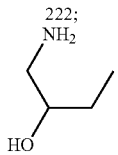 | 222; NH₂–CH₂–CH(OH)–CH₂–CH₃ | ¹H NMR (400 MHz, DMSO-d6) δ 9.37 (s, 1H), 8.91 (d, J = 10.3 Hz, 1H), 8.20 (d, J = 1.7 Hz, 1H), 7.03 (d, J = 13.2 Hz, 1H), 5.53 (s, 1H), 5.07 (s, 1H), 4.70 (t, J = 11.1 Hz, 1H), 4.46-4.37 (m, 2H), 4.29 (dd, J = 13.9, 7.1 Hz, 1H), 3.99 (dd, J = 12.1, 4.0 Hz, 1H), 3.77-3.68 (m, 2H), 3.64 (s, 1H), 2.45 (s, 1H), 2.33 (d, J = 14.2 Hz, 1H), 2.22 (td, J = 14.1, 13.5, 4.6 Hz, 1H), 1.84 (t, J = 13.3 Hz, 1H), 1.39-1.21 (m, 4H), 0.91 (t, J = 7.4 Hz, 3H). LCMS m/z 413.17 (M + 1)⁺ |

TABLE 11-continued

Method of preparation, structure, and physicochemical data for compounds 226-371

| Product | Starting Material and Amine | NMR, LCMS |
|---|---|---|
| Compound 285 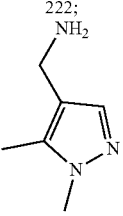 | 222; <br> amine | $^1$H NMR (400 MHz, DMSO-d6) δ 9.25 (d, J = 10.3 Hz, 1H), 8.83 (d, J = 11.1 Hz, 1H), 8.16 (s, 1H), 7.41 (s, 1H), 7.04 (s, 1H), 5.44 (s, 2H), 4.65 (t, J = 11.2 Hz, 1H), 4.40 (t, J = 4.2 Hz, 1H), 4.25 (s, 2H), 3.97 (dd, J = 11.9, 3.9 Hz, 1H), 3.70 (s, 3H), 2.44 (s, 1H), 2.30 (d, J = 14.7 Hz, 1H), 2.26 (s, 3H), 2.16 (t, J = 13.6 Hz, 1H), 1.81 (t, J = 13.2 Hz, 1H), 1.26 (d, J = 6.5 Hz, 4H). LCMS m/z 449.20 (M + 1)$^+$ |
| Compound 286 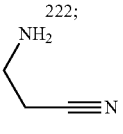 | 222; amine | $^1$H NMR (400 MHz, DMSO-d6) δ 9.41 (d, J = 10.3 Hz, 1H), 8.96 (d, J = 10.8 Hz, 1H), 8.35 (s, 1H), 7.05 (s, 1H), 5.52 (s, 1H), 4.73 (t, J = 6.3 Hz, 3H), 4.42 (t, J = 4.4 Hz, 1H), 4.00 (dd, J = 12.2, 4.0 Hz, 1H), 3.71 (dd, J = 11.9, 4.9 Hz, 1H), 3.65 (s, 1H), 3.19 (t, J = 6.3 Hz, 2H), 2.45 (s, 1H), 2.33 (d, J = 14.1 Hz, 1H), 2.22 (dd, J = 14.5, 12.7 Hz, 1H), 1.84 (dd, J = 14.4, 12.2 Hz, 1H), 1.29 (d, J = 6.5 Hz, 3H). LCMS m/z 394.16 (M + 1)$^+$ |
| Compound 287 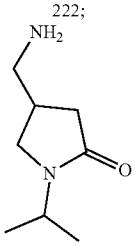 | 222; amine | $^1$H NMR (400 MHz, DMSO-d6) δ 9.36 (s, 1H), 8.93 (d, J = 11.0 Hz, 1H), 8.30 (s, 1H), 7.05 (s, 1H), 5.53 (s, 1H), 4.70 (t, J = 11.5 Hz, 1H), 4.52-4.39 (m, 3H), 4.11 (p, J = 6.7 Hz, 1H), 3.99 (dd, J = 12.0, 4.0 Hz, 1H), 3.71 (dd, J = 12.0, 5.0 Hz, 1H), 3.07 (dd, J = 10.1, 5.4 Hz, 1H), 2.87-2.77 (m, 1H), 2.44 (s, 1H), 2.35 (dd, J = 16.6, 9.3 Hz, 2H), 2.22 (td, J = 13.7, 5.0 Hz, 1H), 2.09 (dd, J = 16.6, 6.2 Hz, 1H), 1.84 (t, J = 13.3 Hz, 1H), 1.29 (d, J = 6.5 Hz, 3H), 1.03 (dd, J = 6.8, 4.7 Hz, 6H). LCMS m/z 480.22 (M + 1)$^+$ |

TABLE 11-continued

Method of preparation, structure, and physicochemical data for compounds 226-371

| Product | Starting Material and Amine | NMR, LCMS |
|---|---|---|
| Compound 288 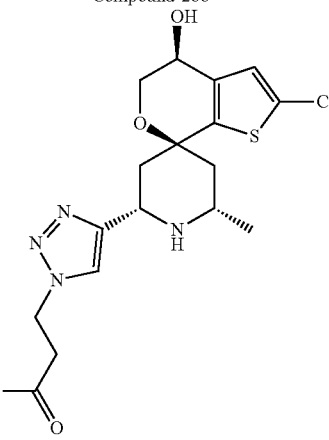 | 222; 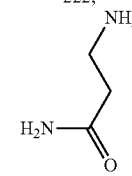 | ¹H NMR (400 MHz, DMSO-d6) δ 9.35 (d, J = 10.2 Hz, 1H), 8.90 (d, J = 11.0 Hz, 1H), 8.21 (s, 1H), 7.47 (s, 1H), 7.04 (s, 1H), 6.98 (s, 1H), 5.52 (s, 1H), 4.69 (t, J = 11.5 Hz, 1H), 4.58 (t, J = 6.6 Hz, 2H), 4.42 (d, J = 4.5 Hz, 1H), 3.99 (dd, J = 12.0, 4.0 Hz, 1H), 3.71 (dd, J = 12.1, 4.8 Hz, 1H), 3.09 (q, J = 6.8 Hz, 1H), 2.72 (t, J = 6.6 Hz, 2H), 2.49-2.35 (m, 1H), 2.32 (d, J = 13.9 Hz, 1H), 2.25-2.13 (m, 1H), 1.89-1.77 (m, 1H), 1.28 (d, J = 6.5 Hz, 3H). LCMS m/z 412.17 (M + 1)⁺ |
| Compound 289 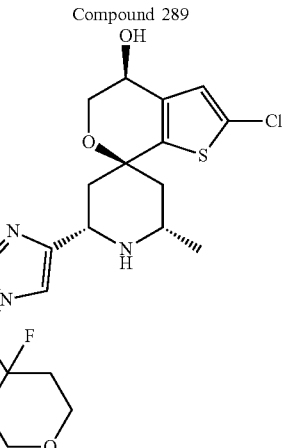 | 222; 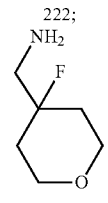 | ¹H NMR (400 MHz, DMSO-d6) δ 9.38 (d, J = 10.1 Hz, 1H), 8.95 (d, J = 10.9 Hz, 1H), 8.21 (s, 1H), 7.04 (s, 1H), 5.52 (s, 1H), 4.79 (s, 1H), 4.73 (s, 2H), 4.42 (t, J = 4.4 Hz, 1H), 4.00 (dd, J = 12.1, 4.0 Hz, 1H), 3.79-3.67 (m, 3H), 3.54-3.47 (m, 1H), 2.47 (s, 1H), 2.33 (d, J = 14.2 Hz, 1H), 2.29-2.18 (m, 1H), 1.85 (t, J = 13.2 Hz, 2H), 1.75 (d, J = 11.3 Hz, 2H), 1.50 (t, J = 12.3 Hz, 2H), 1.29 (d, J = 6.4 Hz, 3H). LCMS m/z 457.19 (M + 1)⁺ |
| Compound 290 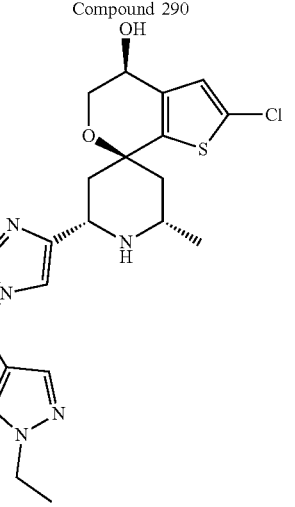 | 222; 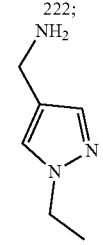 | ¹H NMR (400 MHz, DMSO-d6) δ 9.33 (s, 1H), 8.91 (s, 1H), 8.23 (s, 1H), 7.84 (s, 1H), 7.48 (s, 1H), 7.03 (s, 1H), 5.49 (s, 2H), 4.67 (t, J = 11.1 Hz, 1H), 4.41 (s, 1H), 4.09 (q, J = 7.3 Hz, 2H), 3.98 (dd, J = 11.9, 3.9 Hz, 1H), 3.70 (dd, J = 12.1, 4.8 Hz, 1H), 3.61 (s, 1H), 2.44 (s, 1H), 2.31 (d, J = 14.6 Hz, 1H), 2.20 (dd, J = 14.4, 12.7 Hz, 1H), 1.83 (t, J = 13.3 Hz, 1H), 1.33 (t, J = 7.2 Hz, 3H), 1.25 (t, J = 7.1 Hz, 3H). LCMS m/z 449.15 (M + 1)⁺ |

TABLE 11-continued

Method of preparation, structure, and physicochemical data for compounds 226-371

| Product | Starting Material and Amine | NMR, LCMS |
|---|---|---|
| Compound 291 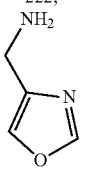 | 222; <br>oxazol-4-ylmethanamine | 1H NMR (400 MHz, DMSO-d6) δ 9.33 (d, J = 10.1 Hz, 1H), 8.90 (d, J = 10.7 Hz, 1H), 8.43 (s, 1H), 8.26 (d, J = 6.7 Hz, 2H), 7.04 (s, 1H), 5.61 (s, 2H), 5.50 (s, 1H), 4.70 (t, J = 11.3 Hz, 1H), 4.41 (s, 1H), 3.99 (dd, J = 12.1, 3.9 Hz, 1H), 3.70 (dd, J = 12.0, 4.8 Hz, 1H), 3.62 (s, 1H), 2.45 (s, 1H), 2.32 (d, J = 11.4 Hz, 1H), 2.20 (t, J = 13.6 Hz, 1H), 1.83 (t, J = 13.3 Hz, 1H), 1.27 (d, J = 6.5 Hz, 3H). LCMS m/z 422.11 (M + 1)$^+$ |
| Compound 292 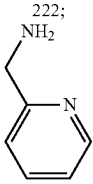 | 222; pyridin-2-ylmethanamine | $^1$H NMR (400 MHz, DMSO-d6) δ 9.35 (d, J = 10.5 Hz, 1H), 8.92 (d, J = 11.0 Hz, 1H), 8.54 (d, J = 4.6 Hz, 1H), 8.35 (s, 1H), 7.85 (td, J = 7.7, 1.9 Hz, 1H), 7.41-7.33 (m, 2H), 7.04 (s, 1H), 5.77 (s, 2H), 4.72 (t, J = 11.1 Hz, 1H), 4.42 (t, J = 4.2 Hz, 1H), 3.99 (dd, J = 12.1, 4.0 Hz, 1H), 3.71 (dd, J = 12.1, 4.8 Hz, 1H), 2.47 (s, 1H), 2.32 (d, J = 14.0 Hz, 1H), 2.27-2.16 (m, 1H), 1.83 (t, J = 13.3 Hz, 1H), 1.28 (d, J = 6.4 Hz, 3H). LCMS m/z 432.13 (M + 1)$^+$ |
| Compound 293 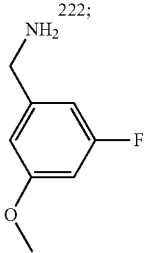 | 222; (3-fluoro-5-methoxyphenyl)methanamine | $^1$H NMR (400 MHz, DMSO-d6) δ 9.32 (d, J = 10.7 Hz, 1H), 8.91 (d, J = 11.0 Hz, 1H), 8.34 (s, 1H), 7.04 (s, 1H), 6.83 (dt, J = 11.2, 2.3 Hz, 1H), 6.78 (d, J = 2.5 Hz, 1H), 6.72 (dd, J = 9.0, 1.9 Hz, 1H), 5.63 (s, 2H), 5.51 (s, 1H), 4.70 (t, J = 11.2 Hz, 1H), 4.41 (s, 1H), 3.99 (dd, J = 12.1, 4.0 Hz, 1H), 3.76 (s, 3H), 3.70 (dd, J = 12.0, 4.8 Hz, 1H), 3.63 (s, 1H), 2.46 (s, 1H), 2.31 (d, J = 14.2 Hz, 1H), 2.27-2.16 (m, 1H), 1.83 (t, J = 13.3 Hz, 1H), 1.27 (d, J = 6.5 Hz, 3H). LCMS m/z 479.18 (M + 1)$^+$ |

TABLE 11-continued

Method of preparation, structure, and physicochemical data for compounds 226-371

| Product | Starting Material and Amine | NMR, LCMS |
|---|---|---|
| Compound 294 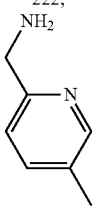 | 222; <br> pyridin-2-ylmethylamine (5-methyl) | $^1$H NMR (400 MHz, DMSO-d6) δ 9.34 (d, J = 10.4 Hz, 1H), 8.90 (d, J = 11.4 Hz, 1H), 8.38 (s, 1H), 8.32 (s, 1H), 7.66 (d, J = 8.2 Hz, 1H), 7.28 (d, J = 7.9 Hz, 1H), 7.04 (s, 1H), 5.71 (s, 2H), 4.71 (t, J = 11.3 Hz, 1H), 4.41 (t, J = 4.4 Hz, 1H), 3.99 (dd, J = 12.0, 4.0 Hz, 1H), 3.71 (dd, J = 12.1, 4.8 Hz, 1H), 2.46 (s, 1H), 2.29 (s, 3H), 2.20 (t, J = 13.6 Hz, 1H), 1.83 (t, J = 13.3 Hz, 1H), 1.27 (d, J = 6.5 Hz, 3H). LCMS m/z 446.17 (M + 1)$^+$ |
| Compound 295 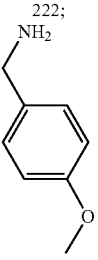 | 222; 4-methoxybenzylamine | $^1$H NMR (400 MHz, DMSO-d6) δ 9.30 (d, J = 10.5 Hz, 1H), 8.87 (d, J = 10.7 Hz, 1H), 8.26 (s, 1H), 7.36-7.29 (m, 2H), 7.04 (s, 1H), 6.98-6.90 (m, 2H), 5.56 (s, 2H), 4.68 (t, J = 11.2 Hz, 1H), 4.41 (d, J = 4.2 Hz, 1H), 3.98 (dd, J = 12.1, 3.9 Hz, 1H), 3.74 (s, 3H), 3.70 (dd, J = 12.0, 4.7 Hz, 1H), 2.44 (s, 1H), 2.30 (d, J = 14.6 Hz, 1H), 2.18 (t, J = 13.6 Hz, 1H), 1.82 (t, J = 13.3 Hz, 1H), 1.26 (d, J = 6.4 Hz, 3H). LCMS m/z 461.16 (M + 1)$^+$ |
| Compound 296 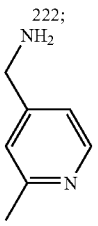 | 222; (2-methylpyridin-4-yl)methylamine | $^1$H NMR (400 MHz, DMSO-d6) δ 9.40 (d, J = 10.2 Hz, 1H), 8.98 (d, J = 11.1 Hz, 1H), 8.54 (d, J = 5.4 Hz, 1H), 8.39 (s, 1H), 7.26 (d, J = 3.9 Hz, 1H), 7.19 (d, J = 5.4 Hz, 1H), 7.04 (s, 1H), 5.79 (s, 2H), 4.73 (t, J = 11.3 Hz, 1H), 4.42 (t, J = 4.5 Hz, 1H), 3.99 (dd, J = 12.0, 4.0 Hz, 1H), 3.80-3.67 (m, 1H), 2.54 (s, 3H), 2.54-2.45 (m, 1H), 2.33 (d, J = 14.1 Hz, 1H), 2.23 (d, J = 13.8 Hz, 1H), 1.85 (t, J = 13.3 Hz, 1H), 1.28 (d, J = 6.4 Hz, 3H). LCMS m/z 446.17 (M + 1)$^+$ |

TABLE 11-continued

Method of preparation, structure, and physicochemical data for compounds 226-371

| Product | Starting Material and Amine | NMR, LCMS |
|---|---|---|
| Compound 297 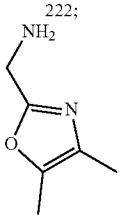 | 222; <br> 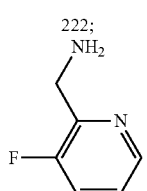 | $^1$H NMR (400 MHz, DMSO-d6) δ 9.38 (d, J = 10.6 Hz, 1H), 8.96 (d, J = 11.1 Hz, 1H), 8.36 (s, 1H), 5.79 (s, 2H), 4.73 (t, J = 11.4 Hz, 1H), 4.42 (t, J = 4.4 Hz, 1H), 3.99 (dd, J = 12.0, 4.1 Hz, 1H), 3.71 (dd, J = 12.1, 4.8 Hz, 1H), 3.64 (s, 2H), 2.46 (s, 1H), 2.32 (d, J = 13.8 Hz, 1H), 2.27-2.16 (m, 2H), 2.20 (s, 3H), 1.99 (s, 3H), 1.84 (t, J = 13.3 Hz, 1H), 1.28 (d, J = 6.4 Hz, 3H). LCMS m/z 450.19 (M + 1)$^+$ |
| Compound 298 | 222; | $^1$H NMR (400 MHz, DMSO-d6) δ 9.40 (s, 1H), 8.97 (s, 1H), 8.50 (d, J = 2.4 Hz, 1H), 8.33 (s, 1H), 8.13-8.04 (m, 1H), 7.04 (s, 1H), 5.84 (d, J = 2.0 Hz, 2H), 5.52 (s, 1H), 4.71 (s, 1H), 4.41 (s, 1H), 3.99 (dd, J = 12.0, 4.0 Hz, 1H), 3.70 (dd, J = 12.0, 4.8 Hz, 1H), 3.63 (s, 1H), 2.45 (s, 1H), 2.31 (d, J = 14.1 Hz, 1H), 2.20 (t, J = 13.6 Hz, 1H), 1.83 (t, J = 13.3 Hz, 1H), 1.28 (d, J = 6.5 Hz, 3H). LCMS m/z 468.16 (M + 1)$^+$ |
| Compound 299 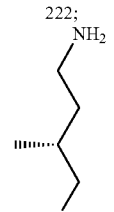 | 222; | $^1$H NMR (400 MHz, DMSO-d6) δ 9.36 (d, J = 10.3 Hz, 1H), 8.91 (d, J = 10.8 Hz, 1H), 8.28 (s, 1H), 7.02 (d, J = 15.6 Hz, 1H), 5.53 (s, 1H), 4.68 (t, J = 11.3 Hz, 1H), 4.59 (s, 1H), 4.44 (dd, J = 10.8, 7.0 Hz, 3H), 3.99 (dd, J = 12.0, 4.0 Hz, 1H), 3.71 (dd, J = 12.0, 4.9 Hz, 1H), 3.64 (s, 1H), 3.25 (q, J = 5.9, 5.4 Hz, 1H), 2.45 (s, 1H), 2.33 (d, J = 14.0 Hz, 1H), 2.27-2.15 (m, 1H), 1.93 (dq, J = 13.7, 7.4 Hz, 1H), 1.83 (dd, J = 14.5, 12.2 Hz, 1H), 1.58 (dq, J = 14.2, 7.4 Hz, 1H), 1.47 (dt, J = 13.1, 6.4 Hz, 1H), 1.28 (d, J = 6.5 Hz, 3H), 0.86 (dd, J = 11.0, 6.7 Hz, 3H). LCMS m/z 427.21 (M + 1)$^+$ |

TABLE 11-continued

Method of preparation, structure, and physicochemical data for compounds 226-371

| Product | Starting Material and Amine | NMR, LCMS |
|---|---|---|
| Compound 300 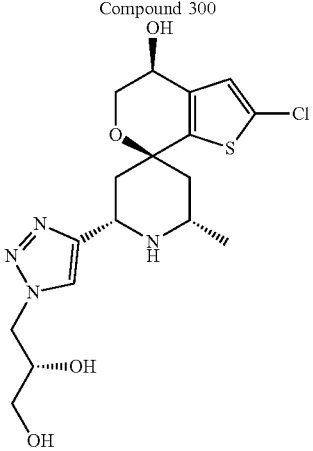 | 222; 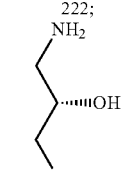 | 1H NMR (400 MHz, DMSO-d6) δ 7.87 (s, 1H), 6.96 (s, 1H), 5.40 (s, 1H), 5.13 (s, 1H), 4.86 (s, 1H), 4.44 (dd, J = 13.8, 3.5 Hz, 1H), 4.39 (s, 1H), 4.22-4.08 (m, 2H), 3.93 (dd, J = 11.8, 4.2 Hz, 1H), 3.78 (s, 1H), 3.64 (dd, J = 11.8, 5.3 Hz, 1H), 3.29 (s, 1H), 3.10 (s, 1H), 2.24 (s, 1H), 2.19 (d, J = 13.5 Hz, 1H), 2.05 (d, J = 13.3 Hz, 1H), 1.58 (dd, J = 13.3, 11.7 Hz, 1H), 1.30-1.16 (m, 1H), 1.03 (d, J = 6.2 Hz, 3H). LCMS m/z 415.15 (M + 1)+ |
| Compound 301 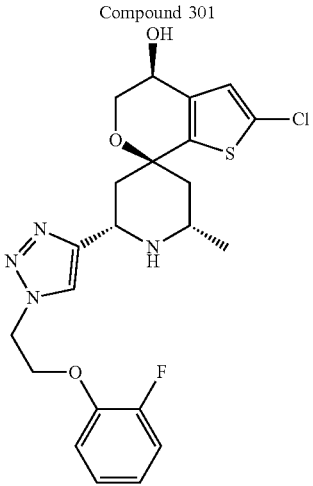 | 222; 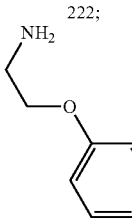 | 1H NMR (400 MHz, DMSO-d6) δ 8.02 (s, 1H), 7.24-7.07 (m, 3H), 6.96 (s, 1H), 6.95 (s, 1H), 5.41 (s, 1H), 4.74 (t, J = 5.1 Hz, 2H), 4.46 (t, J = 5.1 Hz, 2H), 4.39 (t, J = 4.6 Hz, 1H), 4.12 (d, J = 11.4 Hz, 1H), 3.93 (dd, J = 11.9, 4.2 Hz, 1H), 3.64 (dd, J = 11.8, 5.2 Hz, 1H), 3.10 (s, 1H), 2.26 (s, 1H), 2.17 (d, J = 13.5 Hz, 1H), 2.05 (d, J = 13.3 Hz, 1H), 1.56 (dd, J = 13.4, 11.7 Hz, 1H), 1.25 (dd, J = 13.3, 11.2 Hz, 1H), 1.02 (d, J = 6.2 Hz, 3H). LCMS m/z 479.18 (M + 1)+ |
| Compound 302 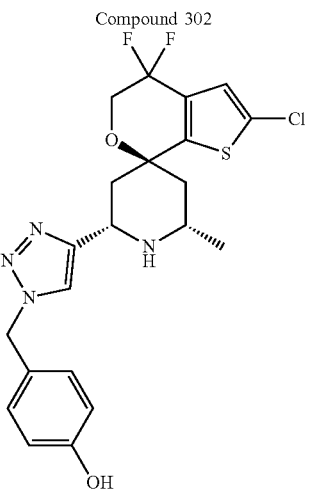 | 223; 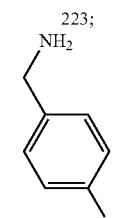 | 1H NMR (400 MHz, DMSO-d6) δ 9.55 (s, 1H), 7.94 (s, 1H), 7.34 (s, 1H), 7.21-7.13 (m, 2H), 6.77-6.70 (m, 2H), 5.39 (s, 2H), 4.21 (t, J = 10.6 Hz, 2H), 4.10 (dd, J = 11.6, 2.5 Hz, 1H), 3.04 (s, 1H), 2.32 (d, J = 13.5 Hz, 1H), 2.10 (d, J = 13.5 Hz, 1H), 1.66 (dd, J = 13.5, 11.7 Hz, 1H), 1.36-1.21 (m, 1H), 1.01 (d, J = 6.2 Hz, 3H). LCMS m/z 467.13 (M + 1)+ |

TABLE 11-continued

Method of preparation, structure, and physicochemical data for compounds 226-371

| Product | Starting Material and Amine | NMR, LCMS |
|---|---|---|
| Compound 303 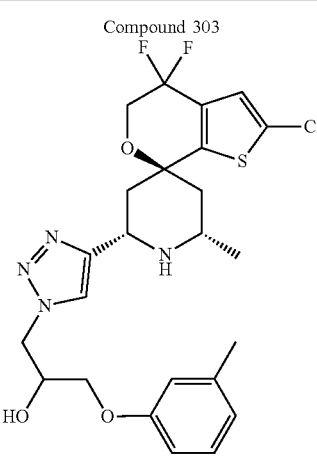 | 223; 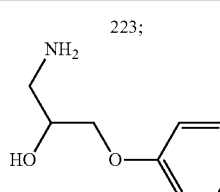 | $^1$H NMR (400 MHz, DMSO-d6) δ 7.95 (s, 1H), 7.35 (s, 1H), 7.15 (td, J = 8.0, 1.3 Hz, 1H), 6.74 (dd, J = 10.2, 6.3 Hz, 3H), 5.55 (d, J = 5.5 Hz, 1H), 4.53 (dd, J = 13.7, 3.9 Hz, 1H), 4.44-4.34 (m, 1H), 4.27-4.17 (m, 3H), 4.17-4.10 (m, 1H), 3.88 (d, J = 5.4 Hz, 2H), 3.07 (s, 1H), 2.30 (s, 1H), 2.26 (s, 3H), 2.13 (d, J = 13.6 Hz, 1H), 1.69 (t, J = 11.8 Hz, 1H), 1.32 (t, J = 12.4 Hz, 1H), 1.03 (d, J = 6.2 Hz, 3H). LCMS m/z 525.23 (M + 1)$^+$ |
| Compound 304 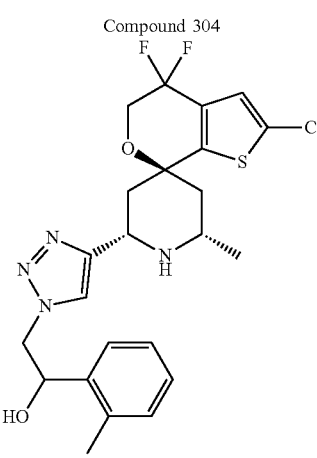 | 223; 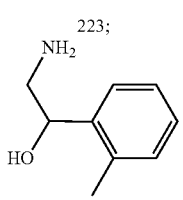 | 1H NMR (400 MHz, DMSO-d6) δ 7.96 (d, J = 7.3 Hz, 1H), 7.48 (d, J = 7.3 Hz, 1H), 7.36 (s, 1H), 7.26-7.13 (m, 3H), 5.65 (t, J = 3.8 Hz, 1H), 5.11 (s, 1H), 4.44 (d, J = 13.5 Hz, 1H), 4.38-4.11 (m, 4H), 3.08 (s, 1H), 2.32 (d, J = 4.9 Hz, 3H), 2.14 (d, J = 13.5 Hz, 1H), 1.76-1.64 (m, 1H), 1.33 (s, 1H), 1.04 (d, J = 6.3 Hz, 3H). LCMS m/z 495.16 (M + 1)$^+$ |
| Compound 305 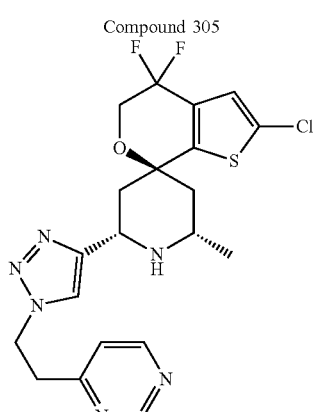 | 223; 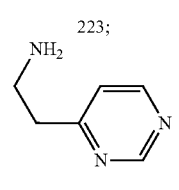 | 1H NMR (400 MHz, DMSO-d6) δ 9.11 (d, J = 1.5 Hz, 1H), 8.68 (d, J = 5.2 Hz, 1H), 7.99 (s, 1H), 7.40 (dd, J = 5.3, 1.5 Hz, 1H), 7.35 (s, 1H), 4.76 (t, J = 7.1 Hz, 2H), 4.21 (t, J = 10.7 Hz, 2H), 4.10 (dd, J = 11.7, 2.5 Hz, 1H), 3.34 (s, 2H), 3.09-2.98 (m, 1H), 2.33-2.25 (m, 1H), 2.12 (d, J = 13.7 Hz, 1H), 1.66 (dd, J = 13.6, 11.6 Hz, 1H), 1.32 (dd, J = 13.7, 11.2 Hz, 1H), 1.03 (d, J = 6.3 Hz, 3H). LCMS m/z 467.17 (M + 1)$^+$ |

TABLE 11-continued

Method of preparation, structure, and physicochemical data for compounds 226-371

| Product | Starting Material and Amine | NMR, LCMS |
|---|---|---|
| Compound 306 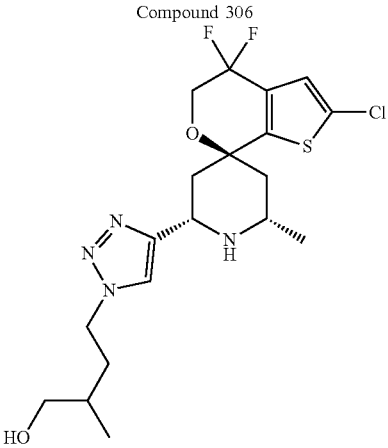 | 223; 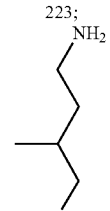 | $^1$H NMR (400 MHz, DMSO-d6) δ 8.01 (s, 1H), 7.36 (s, 1H), 4.53 (t, J = 5.3 Hz, 1H), 4.35 (td, J = 7.9, 7.3, 2.7 Hz, 2H), 4.23 (t, J = 10.6 Hz, 2H), 4.16 (d, J = 11.3 Hz, 1H), 3.25 (td, J = 5.6, 1.6 Hz, 2H), 3.09 (s, 1H), 2.35 (d, J = 14.0 Hz, 1H), 2.14 (d, J = 13.6 Hz, 1H), 1.91 (dq, J = 13.5, 7.5 Hz, 1H), 1.72 (t, J = 12.7 Hz, 1H), 1.62-1.30 (m, 3H), 1.05 (d, J = 6.2 Hz, 3H), 0.86 (d, J = 6.7 Hz, 3H). LCMS m/z 447.12 (M + 1)$^+$ |
| Compound 307 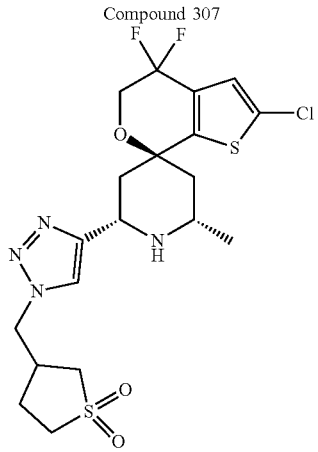 | 223;  | $^1$H NMR (400 MHz, DMSO-d6) δ 8.03 (s, 1H), 7.36 (s, 1H), 4.49 (d, J = 6.4 Hz, 2H), 4.23 (t, J = 10.7 Hz, 2H), 4.18-4.11 (m, 1H), 3.27-2.84 (m, 6H), 2.35 (d, J = 13.8 Hz, 1H), 2.14 (d, J = 13.5 Hz, 2H), 1.83 (q, J = 12.2, 10.7 Hz, 1H), 1.71 (t, J = 12.8 Hz, 1H), 1.39-1.28 (m, 1H), 1.04 (d, J = 6.2 Hz, 3H). LCMS m/z 493.13 (M + 1)$^+$ |
| Compound 308 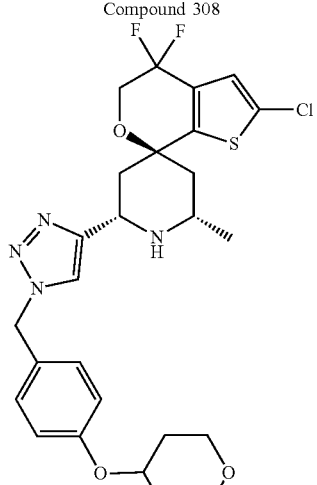 | 223; 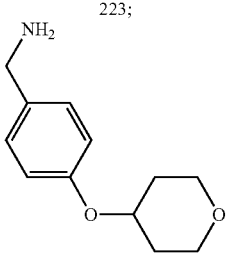 | $^1$H NMR (400 MHz, DMSO-d6) δ 7.98 (s, 1H), 7.34 (s, 1H), 7.31-7.19 (m, 2H), 7.05-6.91 (m, 2H), 5.45 (s, 2H), 4.56 (td, J = 8.5, 4.2 Hz, 1H), 4.21 (t, J = 10.6 Hz, 2H), 4.11 (dd, J = 11.6, 2.5 Hz, 1H), 3.83 (dt, J = 11.7, 4.4 Hz, 2H), 3.50-3.43 (m, 2H), 3.02 (d, J = 19.3 Hz, 1H), 2.32 (d, J = 13.5 Hz, 1H), 2.10 (d, J = 13.5 Hz, 1H), 1.94 (dd, J = 13.1, 3.8 Hz, 2H), 1.66 (dd, J = 13.5, 11.7 Hz, 1H), 1.54 (dtd, J = 12.9, 9.0, 4.0 Hz, 2H), 1.42-1.23 (m, 1H), 1.01 (d, J = 6.2 Hz, 3H). LCMS m/z 551.20 (M + 1)$^+$ |

TABLE 11-continued

Method of preparation, structure, and physicochemical data for compounds 226-371

| Product | Starting Material and Amine | NMR, LCMS |
|---|---|---|
| Compound 309 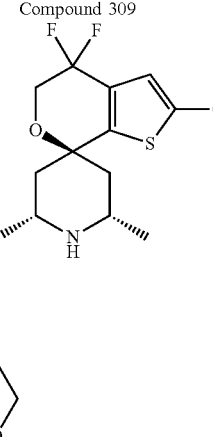 | 223; 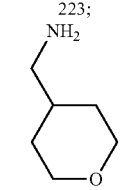 | $^1$H NMR (400 MHz, DMSO-d6) δ 7.97 (s, 1H), 7.35 (s, 1H), 4.27-4.18 (m, 4H), 4.18-4.10 (m, 1H), 3.87-3.78 (m, 2H), 3.24 (td, J = 11.7, 2.2 Hz, 2H), 3.08 (s, 1H), 2.34 (d, J = 13.4 Hz, 1H), 2.13 (d, J = 13.6 Hz, 1H), 2.04 (ddd, J = 11.5, 7.6, 4.0 Hz, 1H), 1.76-1.65 (m, 1H), 1.39 (d, J = 10.8 Hz, 2H), 1.36-1.25 (m, 1H), 1.24 (d, J = 4.6 Hz, 1H), 1.20 (dd, J = 12.1, 4.4 Hz, 1H), 1.04 (d, J = 6.2 Hz, 3H). LCMS m/z 459.18 (M + 1)$^+$ |
| Compound 310 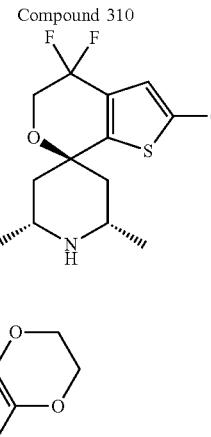 | 223; 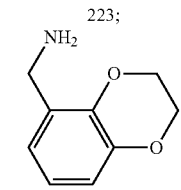 | $^1$H NMR (400 MHz, DMSO-d6) δ 7.89 (s, 1H), 7.34 (s, 1H), 6.86 (dd, J = 8.2, 1.7 Hz, 1H), 6.80 (t, J = 7.8 Hz, 1H), 6.65 (dd, J = 7.6, 1.7 Hz, 1H), 5.47 (s, 2H), 4.32 (dd, J = 5.8, 2.7 Hz, 2H), 4.26 (dd, J = 5.6, 2.9 Hz, 2H), 4.21 (t, J = 10.5 Hz, 2H), 4.13 (dd, J = 11.6, 2.5 Hz, 1H), 3.06 (d, J = 10.0 Hz, 1H), 2.33 (d, J = 13.6 Hz, 1H), 2.11 (d, J = 13.6 Hz, 1H), 1.70 (dd, J = 13.6, 11.6 Hz, 1H), 1.32 (dd, J = 13.6, 11.3 Hz, 1H), 1.02 (d, J = 6.3 Hz, 3H). LCMS m/z 509.16 (M + 1)$^+$ |
| Compound 311 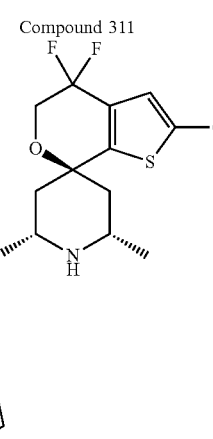 | 223; 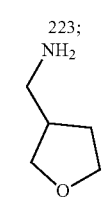 | $^1$H NMR (400 MHz, DMSO-d6) δ 8.02 (s, 1H), 7.35 (s, 1H), 4.32 (d, J = 7.5 Hz, 2H), 4.22 (t, J = 10.5 Hz, 2H), 4.13 (dd, J = 11.7, 2.5 Hz, 1H), 3.76 (td, J = 8.0, 5.5 Hz, 1H), 3.69-3.58 (m, 2H), 3.48-3.42 (m, 1H), 3.07 (t, J = 8.1 Hz, 1H), 2.71 (p, J = 6.7 Hz, 1H), 2.34 (dt, J = 13.9, 2.5 Hz, 1H), 2.13 (dd, J = 13.8, 2.7 Hz, 1H), 1.96-1.86 (m, 1H), 1.70 (dd, J = 13.6, 11.6 Hz, 1H), 1.59 (dt, J = 13.1, 6.6 Hz, 1H), 1.33 (dd, J = 13.6, 11.3 Hz, 1H), 1.04 (d, J = 6.3 Hz, 3H). LCMS m/z 445.18 (M + 1)$^+$ |

TABLE 11-continued

Method of preparation, structure, and physicochemical data for compounds 226-371

| Product | Starting Material and Amine | NMR, LCMS |
|---|---|---|
| Compound 312 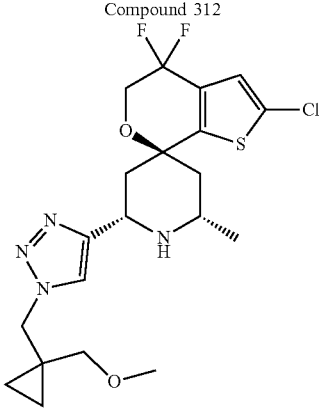 | 223; 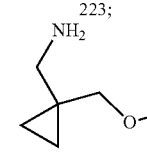 | $^1$H NMR (400 MHz, DMSO-d6) δ 7.94 (s, 1H), 7.35 (s, 1H), 4.27 (d, J = 2.5 Hz, 2H), 4.23 (t, J = 10.5 Hz, 2H), 4.14 (dd, J = 11.7, 2.6 Hz, 1H), 3.22 (s, 3H), 3.10-3.03 (m, 1H), 3.01 (s, 2H), 2.39-2.30 (m, 1H), 2.17-2.08 (m, 1H), 1.71 (dd, J = 13.5, 11.7 Hz, 1H), 1.34 (dd, J = 13.6, 11.2 Hz, 1H), 1.04 (d, J = 6.3 Hz, 3H), 0.70 (q, J = 4.0 Hz, 2H), 0.51 (q, J = 4.1 Hz, 2H). LCMS m/z 495.18 (M + 1)$^+$ |
| Compound 313 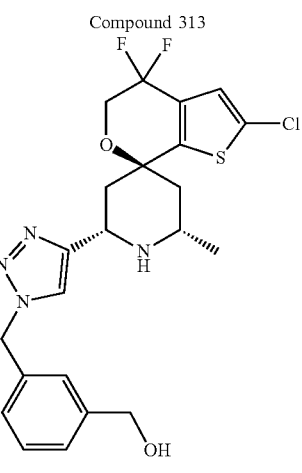 | 223; 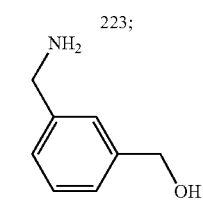 | $^1$H NMR (400 MHz, DMSO-d6) δ 8.01 (s, 1H), 7.36-7.28 (m, 3H), 7.26 (d, J = 7.6 Hz, 1H), 7.19 (d, J = 7.4 Hz, 1H), 5.53 (s, 2H), 5.23 (t, J = 5.7 Hz, 1H), 4.48 (d, J = 5.4 Hz, 2H), 4.21 (t, J = 10.6 Hz, 2H), 4.16-4.09 (m, 1H), 3.09-2.97 (m, 1H), 2.33 (d, J = 13.5 Hz, 1H), 2.11 (d, J = 13.5 Hz, 1H), 1.73-1.62 (m, 1H), 1.37-1.26 (m, 1H), 1.01 (d, J = 6.3 Hz, 3H). LCMS m/z 481.17 (M + 1)$^+$ |
| Compound 314 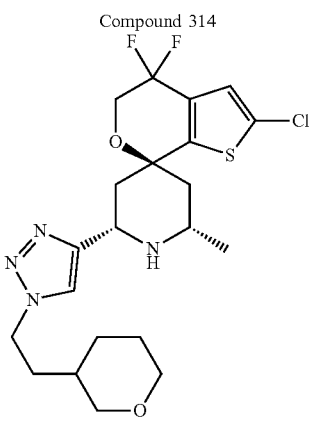 | 223; 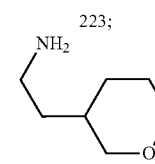 | $^1$H NMR (400 MHz, DMSO-d6) δ 8.00 (s, 1H), 7.35 (s, 1H), 4.33 (t, J = 7.3 Hz, 2H), 4.22 (t, J = 10.6 Hz, 2H), 4.13 (dd, J = 11.7, 2.6 Hz, 1H), 3.72 (dd, J = 11.4, 4.0 Hz, 2H), 3.26 (td, J = 11.1, 2.9 Hz, 2H), 3.08-2.95 (m, 2H), 2.33 (d, J = 13.5 Hz, 1H), 2.12 (dd, J = 13.7, 2.8 Hz, 1H), 1.81 (d, J = 12.8 Hz, 1H), 1.75-1.49 (m, 3H), 1.42 (s, 1H), 1.47-1.36 (m, 1H), 1.39-1.27 (m, 1H), 1.26-1.09 (m, 1H), 1.03 (d, J = 6.3 Hz, 3H). LCMS m/z 473.22 (M + 1)$^+$ |

TABLE 11-continued

Method of preparation, structure, and physicochemical data for compounds 226-371

| Product | Starting Material and Amine | NMR, LCMS |
|---|---|---|
| Compound 315 | 223 | $^1$H NMR (400 MHz, DMSO-d6) δ 7.71 (s, 1H), 7.38-7.31 (m, 2H), 5.94 (s, 1H), 4.71 (t, J = 6.0 Hz, 2H), 4.44 (t, J = 5.9 Hz, 2H), 4.22 (t, J = 10.7 Hz, 2H), 4.10 (dd, J = 11.7, 2.5 Hz, 1H), 3.09-2.97 (m, 1H), 2.25 (d, J = 14.0 Hz, 1H), 2.17-2.09 (m, 1H), 1.92 (s, 3H), 1.63 (dd, J = 13.5, 11.6 Hz, 1H), 1.36-1.21 (m, 1H), 1.02 (d, J = 6.2 Hz, 3H). LCMS m/z 469.20 (M + 1)$^+$ |
| Compound 316 | 223 | $^1$H NMR (400 MHz, DMSO-d6) δ 11.64 (s, 1H), 7.99 (s, 1H), 7.57-7.48 (m, 1H), 7.41 (dd, J = 9.5, 2.6 Hz, 1H), 7.34 (s, 1H), 6.32 (d, J = 9.4 Hz, 1H), 5.28 (s, 2H), 4.21 (t, J = 10.6 Hz, 2H), 4.11 (d, J = 10.9 Hz, 1H), 3.05 (s, 1H), 2.33 (d, J = 13.5 Hz, 1H), 2.11 (d, J = 13.9 Hz, 1H), 1.72-1.61 (m, 1H), 1.36-1.21 (m, 1H), 1.02 (d, J = 6.2 Hz, 3H). LCMS m/z 468.16 (M + 1)$^+$ |
| Compound 317 | 223 | $^1$H NMR (400 MHz, DMSO-d6) δ 8.70-8.61 (m, 3H), 8.10 (s, 1H), 7.35 (s, 1H), 5.77 (s, 2H), 4.22 (t, J = 10.6 Hz, 2H), 4.14 (dd, J = 11.6, 2.5 Hz, 1H), 3.06 (s, 1H), 2.39-2.31 (m, 1H), 2.12 (d, J = 13.6 Hz, 1H), 1.75-1.64 (m, 1H), 1.38-1.27 (m, 1H), 1.03 (d, J = 6.2 Hz, 3H). LCMS m/z 453.17 (M + 1)$^+$ |

TABLE 11-continued

Method of preparation, structure, and physicochemical data for compounds 226-371

| Product | Starting Material and Amine | NMR, LCMS |
|---|---|---|
| Compound 318 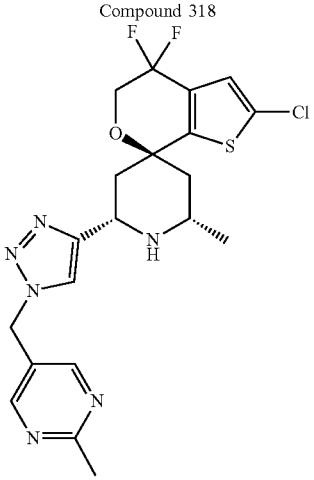 | 223; 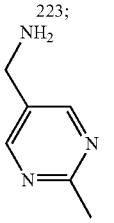 | $^1$H NMR (400 MHz, DMSO-d6) δ 8.71 (s, 2H), 8.11 (s, 1H), 7.35 (s, 1H), 5.61 (s, 2H), 4.21 (t, J = 10.6 Hz, 2H), 4.12 (dd, J = 11.7, 2.5 Hz, 1H), 3.10-2.98 2.33 (d, J = 13.5 Hz, 1H), 2.11 (d, J = 13.4 Hz, 1H), 1.67 (dd, J = 13.5, 11.6 Hz, 1H), 1.30 (dd, J = 13.6, 11.2 Hz, 1H), 1.02 (d, J = 6.2 Hz, 3H). LCMS m/z 467.17 (M + 1)$^+$ |
| Compound 319 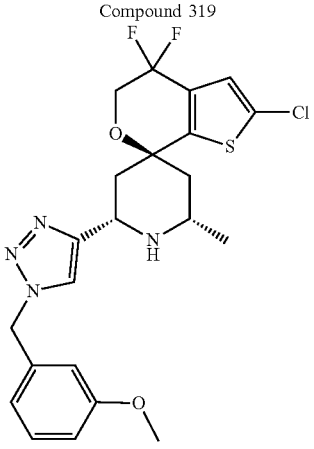 | 223; 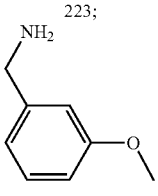 | $^1$H NMR (400 MHz, DMSO-d6) δ 8.02 (s, 1H), 7.34 (s, 1H), 7.29 (td, J = 7.3, 1.9 Hz, 1H), 6.94-6.83 (m, 3H), 5.51 (s, 2H), 4.21 (t, J = 10.6 Hz, 2H), 4.12 (dd, J = 11.6, 2.5 Hz, 1H), 3.74 (s, 3H), 3.10-2.98 (m, 1H), 2.38-2.29 (m, 1H), 2.15-2.06 (m, 1H), 1.68 (dd, J = 13.5, 11.6 Hz, 1H), 1.32 (dd, J = 13.6, 11.3 Hz, 1H), 1.02 (d, J = 6.3 Hz, 3H). LCMS m/z 481.21 (M + 1)$^+$ |
| Compound 320 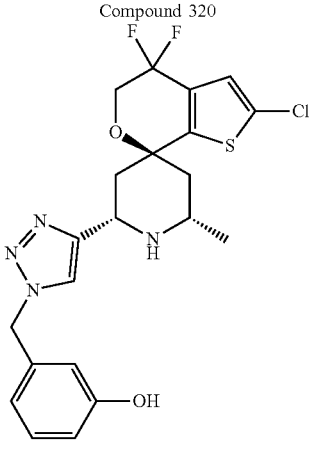 | 223; 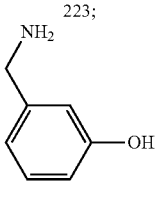 | $^1$H NMR (400 MHz, DMSO-d6) δ 9.60 (s, 1H), 7.99 (s, 1H), 7.34 (s, 1H), 7.15 (t, J = 7.8 Hz, 1H), 6.75-6.64 (m, 3H), 5.45 (s, 2H), 4.22 (t, J = 10.6 Hz, 2H), 4.12 (dd, J = 11.6, 2.5 Hz, 1H), 3.05 (s, 1H), 2.34 (d, J = 13.6 Hz, 1H), 2.15-2.07 (m, 1H), 1.68 (dd, J = 13.5, 11.6 Hz, 1H), 1.31 (dd, J = 13.5, 11.3 Hz, 1H), 1.02 (d, J = 6.2 Hz, 3H). LCMS m/z 467.17 (M + 1)$^+$ |

TABLE 11-continued

Method of preparation, structure, and physicochemical data for compounds 226-371

| Product | Starting Material and Amine | NMR, LCMS |
|---|---|---|
| Compound 321 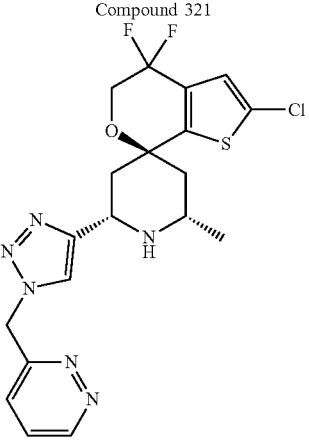 | 223; 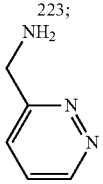 | $^1$H NMR (400 MHz, DMSO-d6) δ 9.22 (dd, J = 5.0, 1.7 Hz, 1H), 8.13 (s, 1H), 7.74 (dd, J = 8.5, 5.0 Hz, 1H), 7.59 (dd, J = 8.5, 1.7 Hz, 1H), 7.35 (s, 1H), 5.91 (s, 2H), 4.22 (t, J = 10.6 Hz, 2H), 4.15 (dd, J = 11.8, 2.6 Hz, 1H), 3.07 (s, 1H), 2.35 (d, J = 13.9 Hz, 1H), 2.12 (d, J = 13.5 Hz, 1H), 1.71 (dd, J = 13.6, 11.6 Hz, 1H), 1.33 (dd, J = 13.6, 11.2 Hz, 1H), 1.03 (d, J = 6.3 Hz, 3H). LCMS m/z 453.13 (M + 1)$^+$ |
| Compound 322 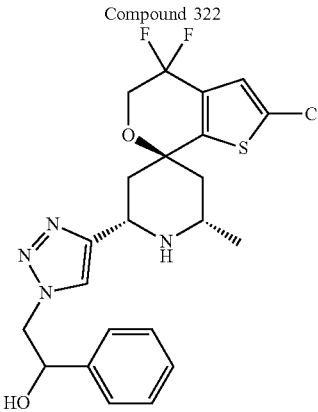 | 223; 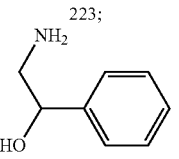 | $^1$H NMR (400 MHz, DMSO-d6) δ 7.95 (d, J = 4.9 Hz, 1H), 7.42-7.32 (m, 5H), 7.32-7.24 (m, 1H), 5.78 (d, J = 4.7 Hz, 1H), 4.97 (d, J = 8.1 Hz, 1H), 4.47 (dd, J = 13.9, 4.0 Hz, 1H), 4.40 (dd, J = 13.8, 8.5 Hz, 1H), 4.23 (t, J = 10.6 Hz, 2H), 4.14 (dd, J = 11.7, 2.5 Hz, 1H), 3.07 (t, J = 8.0 Hz, 1H), 2.54 (s, 1H), 2.36-2.27 (m, 1H), 2.14 (d, J = 13.6 Hz, 1H), 1.69 (ddd, J = 13.5, 11.6, 5.6 Hz, 1H), 1.33 (dd, J = 13.8, 11.0 Hz, 1H), 1.04 (d, J = 6.3 Hz, 3H). LCMS m/z 481.21 (M + 1)$^+$ |
| Compound 323 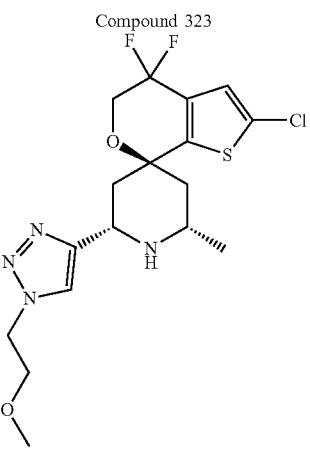 | 223; 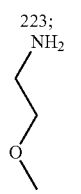 | $^1$H NMR (400 MHz, DMSO-d6) δ 7.95 (s, 1H), 7.35 (s, 1H), 4.48 (t, J = 5.2 Hz, 2H), 4.23 (t, J = 10.6 Hz, 2H), 4.13 (dd, J = 11.8, 2.5 Hz, 1H), 3.71 (t, J = 5.1 Hz, 2H), 3.24 (s, 3H), 3.07 (t, J = 5.3 Hz, 1H), 2.54 (s, 1H), 2.38-2.30 (m, 1H), 2.12 (d, J = 13.8 Hz, 1H), 1.70 (dd, J = 13.5, 11.6 Hz, 1H), 1.33 (dd, J = 13.6, 11.3 Hz, 1H), 1.03 (d, J = 6.3 Hz, 3H). LCMS m/z 419.17 (M + 1)$^+$ |

TABLE 11-continued

Method of preparation, structure, and physicochemical data for compounds 226-371

| Product | Starting Material and Amine | NMR, LCMS |
|---|---|---|
| Compound 324 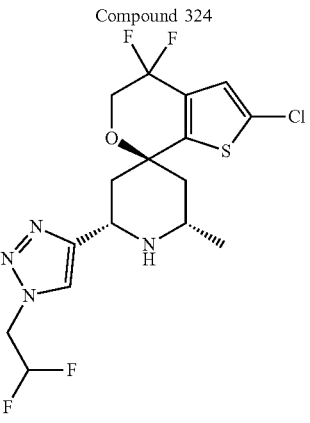 | 223; 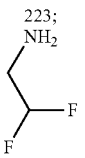 | ¹H NMR (400 MHz, DMSO-d6) δ 8.03 (s, 1H), 7.35 (s, 1H), 6.62-6.27 (m, 1H), 4.91 (td, J = 15.7, 3.3 Hz, 2H), 4.23 (t, J = 10.6 Hz, 2H), 4.16 (dd, J = 11.7, 2.6 Hz, 1H), 3.06 (d, J = 10.1 Hz, 1H), 2.54 (s, 1H), 2.35 (d, J = 13.9 Hz, 1H), 2.13 (d, J = 13.5 Hz, 1H), 1.70 (dd, J = 13.5, 11.6 Hz, 1H), 1.33 (dd, J = 13.5, 11.3 Hz, 1H), 1.04 (d, J = 6.2 Hz, 3H). LCMS m/z 425.13 (M + 1)⁺ |
| Compound 325 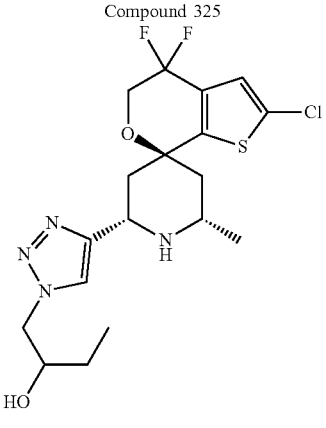 | 223; 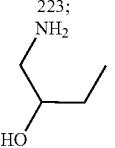 | ¹H NMR (400 MHz, DMSO-d6) δ 7.91 (s, 1H), 7.35 (s, 1H), 5.00 (dd, J = 5.7, 1.9 Hz, 1H), 4.31 (dd, J = 13.8, 4.2 Hz, 1H), 4.22 (t, J = 10.3 Hz, 3H), 4.18-4.08 (m, 1H), 3.72 (s, 1H), 3.07 (s, 1H), 2.40-2.25 (m, 2H), 2.13 (d, J = 13.5 Hz, 1H), 1.70 (t, J = 12.6 Hz, 1H), 1.32 (dtq, J = 26.5, 13.4, 6.3 Hz, 3H), 1.03 (d, J = 6.3 Hz, 3H), 0.89 (t, J = 7.4 Hz, 3H). LCMS m/z 433.17 (M + 1)⁺ |
| Compound 326 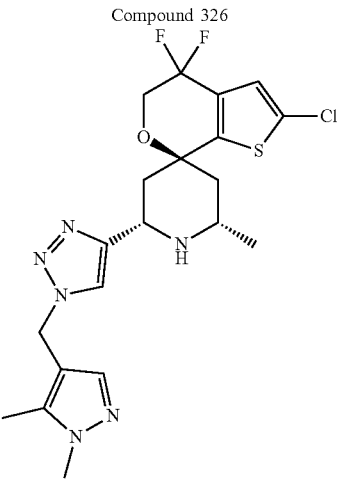 | 223; 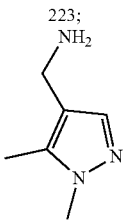 | ¹H NMR (400 MHz, DMSO-d6) δ 7.86 (s, 1H), 7.40 (s, 1H), 7.34 (s, 1H), 5.34 (s, 2H), 4.21 (t, J = 10.6 Hz, 2H), 4.09 (dd, J = 11.7, 2.5 Hz, 1H), 3.69 (s, 3H), 3.10-2.99 (m, 1H), 2.31 (d, J = 13.7 Hz, 2H), 2.25 (s, 3H), 2.10 (d, J = 13.4 Hz, 1H), 1.65 (dd, J = 13.6, 11.6 Hz, 1H), 1.30 (dd, J = 13.6, 11.2 Hz, 1H), 1.01 (d, J = 6.3 Hz, 3H). LCMS m/z 469.20 (M + 1)⁺ |

TABLE 11-continued

Method of preparation, structure, and physicochemical data for compounds 226-371

| Product | Starting Material and Amine | NMR, LCMS |
|---|---|---|
| Compound 327 | 223; isopropyl pyrrolidinone methylamine | $^1$H NMR (400 MHz, DMSO-d6) δ 8.03 (s, 1H), 7.35 (s, 1H), 4.37 (d, J = 7.3 Hz, 2H), 4.23 (t, J = 10.6 Hz, 2H), 4.12 (td, J = 13.5, 13.0, 4.7 Hz, 2H), 3.30 (s, 2H), 3.14-3.00 (m, 2H), 2.88-2.72 (m, 1H), 2.42-2.26 (m, 2H), 2.22-2.06 (m, 2H), 1.70 (t, J = 12.6 Hz, 1H), 1.33 (dd, J = 13.6, 11.3 Hz, 1H), 1.07-0.99 (m, 9H). LCMS m/z 500.22 (M + 1)$^+$ |
| Compound 328 | 223; 3-aminopropanamide | $^1$H NMR (400 MHz, DMSO-d6) δ 7.90 (s, 1H), 7.44 (s, 1H), 7.35 (s, 1H), 7.01-6.89 (m, 1H), 4.49 (t, J = 6.8 Hz, 2H), 4.22 (t, J = 10.6 Hz, 2H), 4.12 (dd, J = 11.6, 2.5 Hz, 1H), 3.05 (d, J = 13.6 Hz, 1H), 2.67 (t, J = 6.8 Hz, 2H), 2.32 (d, J = 13.7 Hz, 2H), 2.12 (d, J = 13.7 Hz, 1H), 1.68 (dd, J = 13.5, 11.7 Hz, 1H), 1.32 (dd, J = 13.6, 11.3 Hz, 1H), 1.03 (d, J = 6.3 Hz, 3H). LCMS m/z 432.13 (M + 1)$^+$ |
| Compound 329 | 223; 4-fluoro-4-(aminomethyl)tetrahydropyran | 1H NMR (400 MHz, DMSO-d6) δ 7.91 (s, 1H), 7.35 (s, 1H), 4.65 (d, J = 21.8 Hz, 2H), 4.23 (t, J = 10.6 Hz, 2H), 4.15 (dd, J = 11.6, 2.6 Hz, 1H), 3.74 (ddd, J = 11.5, 5.0, 2.5 Hz, 2H), 3.49 (t, J = 10.9 Hz, 3H), 3.07 (s, 1H), 2.40-2.30 (m, 1H), 2.12 (d, J = 13.6 Hz, 1H), 1.90-1.63 (m, 3H), 1.49 (t, J = 12.3 Hz, 2H), 1.34 (dd, J = 13.6, 11.3 Hz, 1H), 1.04 (d, J = 6.2 Hz, 3H). LCMS m/z 477.19 (M + 1)$^+$ |

TABLE 11-continued

*Method of preparation, structure, and physicochemical data for compounds 226-371*

| Product | Starting Material and Amine | NMR, LCMS |
|---|---|---|
| Compound 330 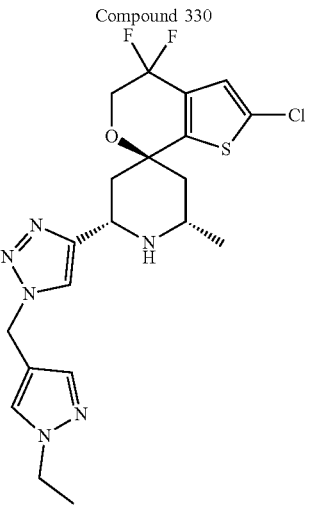 | 223; 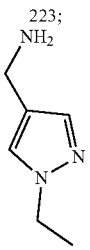 | ¹H NMR (400 MHz, DMSO-d6) δ 7.94 (s, 1H), 7.82 (s, 1H), 7.48 (s, 1H), 7.34 (s, 1H), 5.38 (s, 2H), 4.21 (t, J = 10.6 Hz, 2H), 4.09 (q, J = 7.4 Hz, 3H), 3.04 (d, J = 9.9 Hz, 1H), 2.32 (d, J = 13.7 Hz, 2H), 2.11 (d, J = 13.7 Hz, 1H), 1.67 (dd, J = 13.6, 11.6 Hz, 1H), 1.42-1.21 (m, 4H), 1.01 (d, J = 6.2 Hz, 3H). LCMS m/z 469.20 (M + 1)⁺ |
| Compound 331 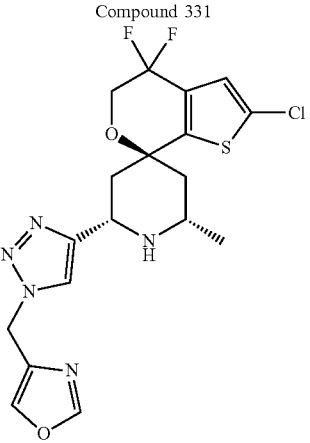 | 223; 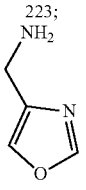 | ¹H NMR (400 MHz, DMSO-d6) δ 8.41 (s, 1H), 8.21 (s, 1H), 7.96 (s, 1H), 7.34 (s, 1H), 5.50 (s, 2H), 4.22 (t, J = 10.6 Hz, 2H), 4.12 (dd, J = 11.7, 2.5 Hz, 1H), 3.12-3.01 (m, 1H), 2.41-2.27 (m, 1H), 2.11 (d, J = 13.6 Hz, 1H), 1.68 (dd, J = 13.5, 11.6 Hz, 1H), 1.32 (dd, J = 13.6, 11.3 Hz, 1H), 1.02 (d, J = 6.2 Hz, 3H). LCMS m/z 442.16 (M + 1)⁺ |
| Compound 332 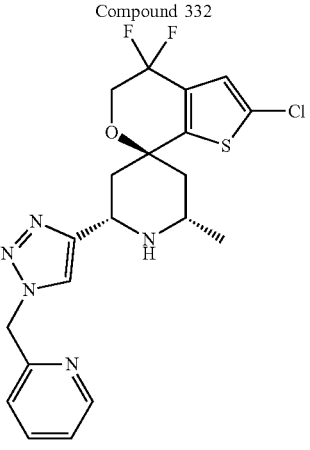 | 223; 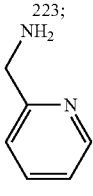 | ¹H NMR (400 MHz, DMSO-d6) δ 8.55 (d, J = 4.1 Hz, 1H), 8.05 (s, 1H), 7.82 (td, J = 7.7, 1.8 Hz, 1H), 7.35 (d, J = 4.7 Hz, 2H), 7.26 (d, J = 7.8 Hz, 1H), 5.66 (s, 2H), 4.22 (t, J = 10.6 Hz, 2H), 4.14 (dd, J = 11.6, 2.5 Hz, 1H), 3.12-3.04 (m, 1H), 2.35 (d, J = 13.9 Hz, 2H), 2.12 (d, J = 13.7 Hz, 1H), 1.70 (dd, J = 13.5, 11.7 Hz, 1H), 1.33 (dd, J = 13.6, 11.2 Hz, 1H), 1.03 (d, J = 6.3 Hz, 3H). LCMS m/z 452.18 (M + 1)⁺ |

TABLE 11-continued

Method of preparation, structure, and physicochemical data for compounds 226-371

| Product | Starting Material and Amine | NMR, LCMS |
|---|---|---|
| Compound 333 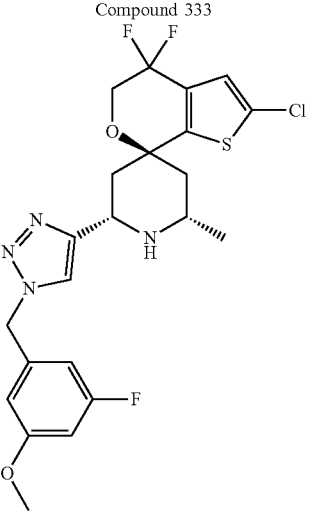 | 223; 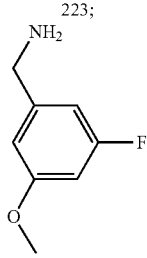 | ¹H NMR (400 MHz, DMSO-d6) δ 8.06 (s, 1H), 7.34 (s, 1H), 6.81 (dt, J = 11.1, 2.3 Hz, 1H), 6.76 (t, J = 1.9 Hz, 1H), 6.72-6.62 (m, 1H), 5.52 (s, 2H), 4.22 (t, J = 10.6 Hz, 2H), 4.16-4.07 (m, 1H), 3.76 (s, 3H), 3.05 (t, J = 9.1 Hz, 1H), 2.34 (d, J = 13.9 Hz, 2H), 2.11 (d, J = 13.6 Hz, 1H), 1.68 (dd, J = 13.6, 11.7 Hz, 1H), 1.32 (dd, J = 13.5, 11.3 Hz, 1H), 1.02 (d, J = 6.2 Hz, 3H). LCMS m/z 499.18 (M + 1)⁺ |
| Compound 334 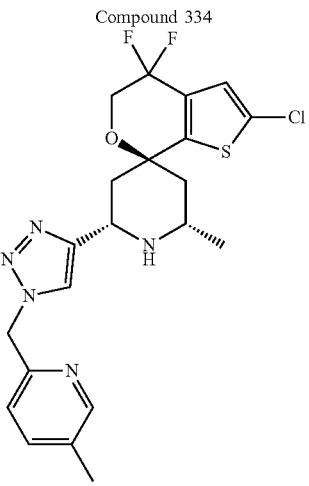 | 223; 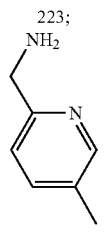 | ¹H NMR (400 MHz, DMSO-d6) δ 8.38 (d, J = 2.2 Hz, 1H), 8.01 (s, 1H), 7.63 (dd, J = 8.4, 2.3 Hz, 1H), 7.35 (s, 1H), 7.19 (d, J = 7.9 Hz, 1H), 5.60 (s, 2H), 4.22 (t, J = 10.6 Hz, 2H), 4.16-3.97 (m, 1H), 3.06 (s, 1H), 2.34 (d, J = 14.2 Hz, 2H), 2.28 (s, 3H), 2.11 (d, J = 13.5 Hz, 1H), 1.69 (dd, J = 13.5, 11.7 Hz, 1H), 1.44-1.29 (m, 1H), 1.02 (d, J = 6.3 Hz, 3H). LCMS m/z 466.22 (M + 1)⁺ |
| Compound 335 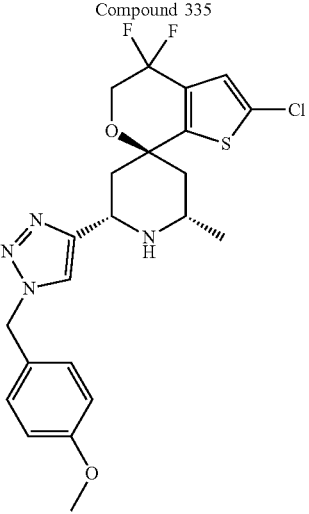 | 223; 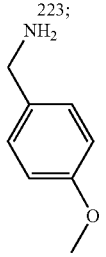 | 1H NMR (400 MHz, DMSO-d6) δ 7.97 (s, 1H), 7.34 (s, 1H), 7.33-7.24 (m, 2H), 7.03-6.87 (m, 2H), 5.46 (s, 2H), 4.21 (t, J = 10.6 Hz, 2H), 4.15-4.04 (m, 1H), 3.73 (s, 3H), 3.04 (s, 1H), 2.32 (d, J = 13.9 Hz, 2H), 2.10 (d, J = 13.5 Hz, 1H), 1.66 (dd, J = 13.6, 11.7 Hz, 1H), 1.30 (dd, J = 13.6, 11.3 Hz, 1H), 1.01 (d, J = 6.3 Hz, 3H). LCMS m/z 481.17 (M + 1)⁺ |

TABLE 11-continued

Method of preparation, structure, and physicochemical data for compounds 226-371

| Product | Starting Material and Amine | NMR, LCMS |
|---|---|---|
| Compound 336 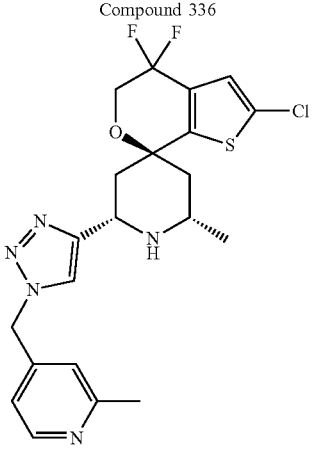 | 223; 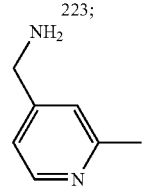 | $^1$H NMR (400 MHz, DMSO-d6) δ 8.42 (d, J = 5.1 Hz, 1H), 8.08 (s, 1H), 7.35 (s, 1H), 7.10 (s, 1H), 7.00 (d, J = 5.1 Hz, 1H), 5.58 (s, 2H), 4.22 (t, J = 10.6 Hz, 2H), 4.19-4.04 (m, 1H), 3.06 (s, 1H), 2.44 (s, 3H), 2.35 (d, J = 13.8 Hz, 2H), 2.12 (d, J = 13.5 Hz, 1H), 1.69 (dd, J = 13.5, 11.6 Hz, 1H), 1.32 (dd, J = 13.5, 11.3 Hz, 1H), 1.03 (d, J = 6.2 Hz, 3H). LCMS m/z 466.18 (M + 1)$^+$ |
| Compound 337 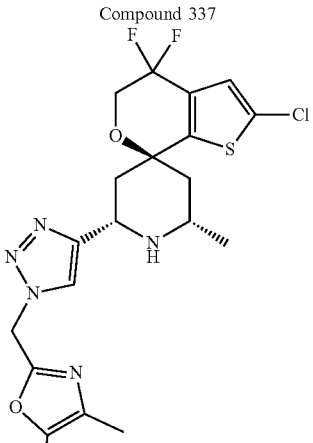 | 223; 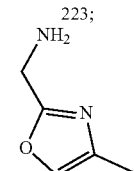 | $^1$H NMR (400 MHz, DMSO-d6) δ 8.04 (s, 1H), 7.35 (s, 1H), 5.67 (s, 2H), 4.22 (t, J = 10.6 Hz, 2H), 4.14 (dd, J = 11.7, 2.6 Hz, 1H), 3.06 (t, J = 8.5 Hz, 1H), 2.39-2.26 (m, 2H), 2.23-2.16 (m, 3H), 2.12 (d, J = 13.6 Hz, 1H), 2.04-1.95 (m, 3H), 1.70 (dd, J = 13.6, 11.7 Hz, 1H), 1.32 (dd, J = 13.5, 11.2 Hz, 1H), 1.03 (d, J = 6.2 Hz, 3H). LCMS m/z 470.15 (M + 1)$^+$ |
| Compound 338 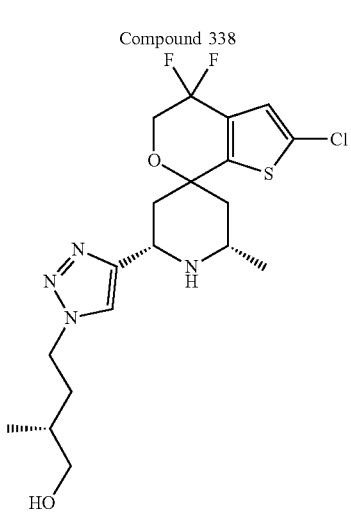 | 223; 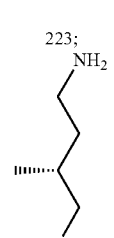 | $^1$H NMR (400 MHz, DMSO-d6) δ 8.00 (s, 1H), 7.35 (s, 1H), 4.53 (t, J = 5.3 Hz, 1H), 4.35 (td, J = 7.7, 7.2, 2.2 Hz, 2H), 4.22 (t, J = 10.6 Hz, 2H), 4.14 (d, J = 11.1 Hz, 1H), 3.25 (td, J = 5.8, 1.6 Hz, 2H), 3.08 (s, 1H), 2.34 (d, J = 13.4 Hz, 1H), 2.13 (d, J = 13.6 Hz, 1H), 1.91 (dt, J = 13.5, 6.9 Hz, 1H), 1.70 (t, J = 12.6 Hz, 1H), 1.62-1.49 (m, 1H), 1.45 (dt, J = 13.7, 6.6 Hz, 1H), 1.39-1.23 (m, 1H), 1.04 (d, J = 6.2 Hz, 3H), 0.86 (d, J = 6.6 Hz, 3H). LCMS m/z 447.21 (M + 1)$^+$ |

TABLE 11-continued

Method of preparation, structure, and physicochemical data for compounds 226-371

| Product | Starting Material and Amine | NMR, LCMS |
|---|---|---|
| Compound 339 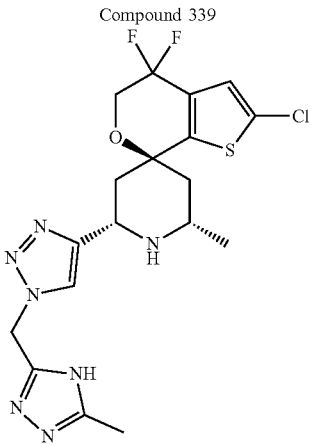 | 223; 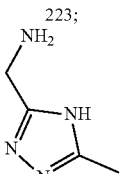 | 1H NMR (400 MHz, DMSO-d6) δ 7.89 (s, 1H), 7.34 (s, 1H), 5.47 (s, 2H), 4.21 (t, J = 10.6 Hz, 2H), 4.11 (d, J = 11.4 Hz, 1H), 3.05 (s, 1H), 2.32 (d, J = 13.1 Hz, 2H), 2.26 (s, 3H), 2.10 (d, J = 13.4 Hz, 1H), 1.76-1.60 (m, 1H), 1.40-1.24 (m, 1H), 1.02 (d, J = 6.2 Hz, 3H). LCMS m/z 456.15 (M + 1)+ |
| Compound 340 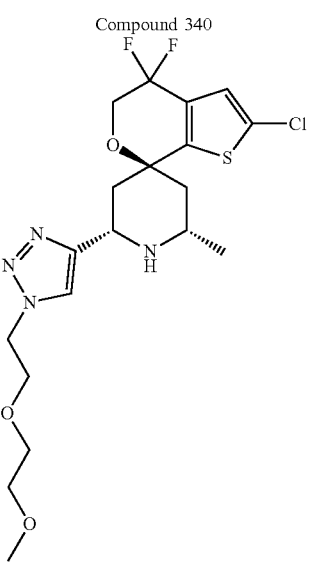 | 223; 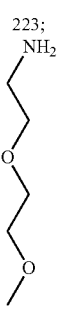 | $^1$H NMR (400 MHz, DMSO-d6) δ 7.97 (s, 1H), 7.35 (s, 1H), 4.48 (t, J = 5.3 Hz, 2H), 4.23 (t, J = 10.6 Hz, 2H), 4.14 (dd, J = 11.7, 2.5 Hz, 1H), 3.79 (t, J = 5.2 Hz, 2H), 3.52 (dd, J = 5.9, 3.5 Hz, 2H), 3.41 (dd, J = 5.7, 3.6 Hz, 2H), 3.21 (s, 3H), 3.14-2.97 (m, 1H), 2.54 (s, 1H), 2.33 (d, J = 13.6 Hz, 1H), 2.13 (d, J = 13.7 Hz, 1H), 1.70 (dd, J = 13.6, 11.6 Hz, 1H), 1.33 (dd, J = 13.6, 11.3 Hz, 1H), 1.04 (d, J = 6.3 Hz, 3H). LCMS m/z 463.15 (M + 1)+ |
| Compound 341 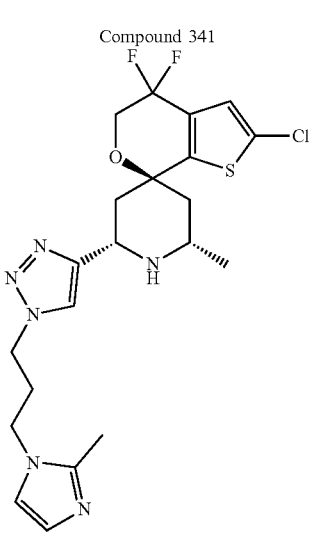 | 223; 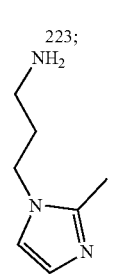 | $^1$H NMR (400 MHz, DMSO-d6) δ 8.03 (s, 1H), 7.35 (s, 1H), 7.06 (d, J = 1.4 Hz, 1H), 6.73 (d, J = 1.3 Hz, 1H), 4.31 (t, J = 7.1 Hz, 2H), 4.23 (t, J = 10.7 Hz, 2H), 4.14 (d, J = 11.6 Hz, 1H) 3.86 (t, J = 7.1 Hz, 2H), 3.07 (s, 1H), 2.33 (d, J = 13.6 Hz, 1H), 2.22 (s, 5H), 2.14 (d, J = 13.6 Hz, 1H), 1.80-1.62 (m, 1H), 1.35-1.16 (m, 1H), 1.03 (d, J = 6.3 Hz, 3H). LCMS m/z 483.24 (M + 1)+ |

TABLE 11-continued

Method of preparation, structure, and physicochemical data for compounds 226-371

| Product | Starting Material and Amine | NMR, LCMS |
|---|---|---|
| Compound 342 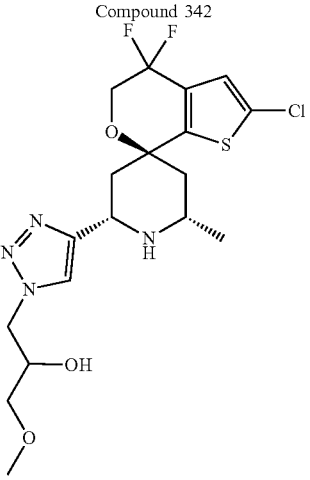 | 223; 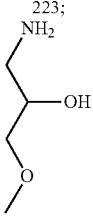 | $^1$H NMR (400 MHz, DMSO-d6) δ 7.90 (s, 1H), 7.35 (s, 1H), 5.28 (d, J = 5.5 Hz, 1H), 4.40 (dd, J = 13.7, 3.3 Hz, 1H), 4.29-4.18 (m, 3H), 4.14 (dd, J = 11.5, 2.6 Hz, 1H), 3.95 (s, 1H), 3.29-3.22 (m, 5H), 3.07 (s, 1H), 2.33 (d, J = 13.6 Hz, 1H), 2.13 (d, J = 13.6 Hz, 1H), 1.71 (t, J = 12.6 Hz, 1H), 1.33 (dd, J = 13.5, 11.3 Hz, 1H), 1.04 (d, J = 6.2 Hz, 3H). LCMS m/z 449.15 (M + 1)$^+$ |
| Compound 343 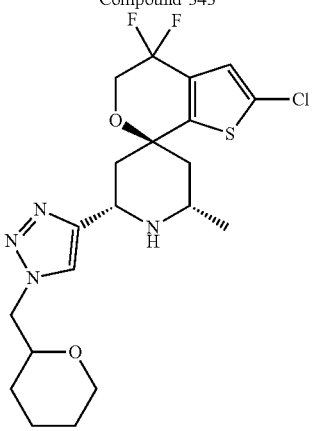 | 223; 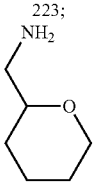 | $^1$H NMR (400 MHz, DMSO-d6) δ 7.89 (s, 1H), 7.35 (s, 1H), 4.46-4.28 (m, 2H), 4.28-4.18 (m, 2H), 4.12 (dd, J = 11.8, 2.6 Hz, 1H), 3.84 (d, J = 11.5 Hz, 1H), 3.65 (s, 1H), 3.28 (d, J = 10.7 Hz, 1H), 3.05 (d, J = 9.6 Hz, 1H), 2.34 (d, J = 13.4 Hz, 2H), 2.12 (d, J = 13.5 Hz, 1H), 1.72 (dd, J = 26.7, 14.3 Hz, 2H), 1.58 (d, J = 13.3 Hz, 1H), 1.51-1.27 (m, 4H), 1.19 (dd, J = 23.4, 11.5 Hz, 1H), 1.03 (d, J = 6.3 Hz, 3H). LCMS m/z 459.18 (M + 1)$^+$ |
| Compound 344 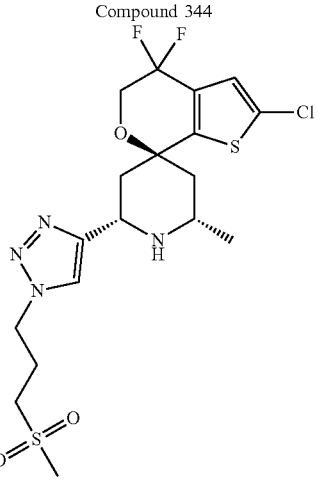 | 223; 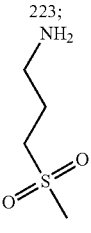 | 1H NMR (400 MHz, DMSO-d6) δ 8.04 (s, 1H), 7.35 (s, 1H), 4.46 (t, J = 7.0 Hz, 2H), 4.23 (t, J = 10.7 Hz, 2H), 4.14 (d, J = 11.2 Hz, 1H), 3.18-3.03 (m, 3H), 3.00 (s, 3H), 2.34 (d, J = 13.6 Hz, 2H), 2.23 (p, J = 7.1 Hz, 2H), 2.14 (d, J = 13.6 Hz, 1H), 1.70 (dd, J = 13.5, 11.6 Hz, 1H), 1.32 (dd, J = 13.6, 11.3 Hz, 1H), 1.04 (d, J = 6.3 Hz, 3H). LCMS m/z 481.08 (M + 1)$^+$ |

TABLE 11-continued

Method of preparation, structure, and physicochemical data for compounds 226-371

| Product | Starting Material and Amine | NMR, LCMS |
|---|---|---|
| Compound 345 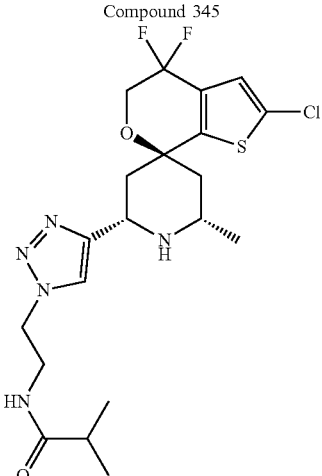 | 223; 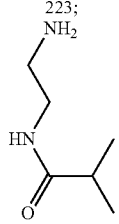 | $^1$H NMR (400 MHz, DMSO-d6) δ 7.92 (s, 1H), 7.88 (t, J = 5.6 Hz, 1H), 7.36 (s, 1H), 4.37 (t, J = 6.1 Hz, 2H), 4.29-4.18 (m, 2H), 4.13 (d, J = 11.5 Hz, 1H), 3.45 (q, J = 6.1 Hz, 2H), 3.07 (s, 1H), 2.35-2.23 (m, 3H), 2.14 (d, J = 13.6 Hz, 1H), 1.69 (dd, J = 13.6, 11.6 Hz, 1H), 1.38-1.25 (m, 1H), 1.03 (d, J = 6.2 Hz, 3H), 0.95 (dd, J = 6.9, 1.4 Hz, 6H). LCMS m/z 474.17 (M + 1)$^+$ |
| Compound 346 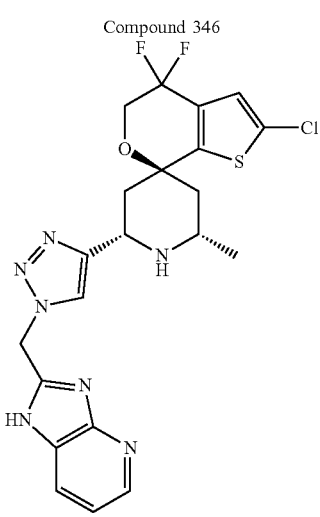 | 223; 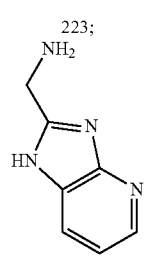 | $^1$H NMR (400 MHz, DMSO-d6) δ 8.19 (dd, J = 4.8, 1.6 Hz, 1H), 8.04 (s, 1H), 7.83 (dd, J = 7.9, 1.6 Hz, 1H), 7.34 (s, 1H), 7.05 (dd, J = 7.9, 4.7 Hz, 1H), 5.75 (s, 2H), 4.21 (t, J = 10.6 Hz, 2H), 4.14 (d, J = 11.3 Hz, 1H), 3.05 (s, 1H), 2.40-2.28 (m, 1H), 2.10 (d, J = 13.5 Hz, 1H), 1.74-1.60 (m, 1H), 1.32 (dd, J = 13.4, 11.4 Hz, 1H), 1.02 (d, J = 6.2 Hz, 3H). LCMS m/z 492.14 (M + 1)$^+$ |
| Compound 347 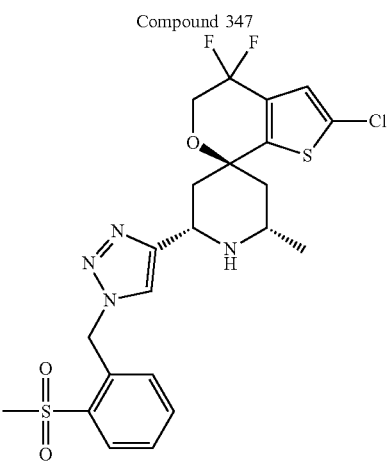 | 223; 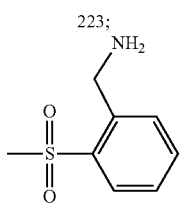 | $^1$H NMR (400 MHz, DMSO-d6) δ 8.08 (s, 1H), 8.01 (dd, J = 7.9, 1.5 Hz, 1H), 7.72 (td, J = 7.5, 1.5 Hz, 1H), 7.69-7.54 (m, 1H), 7.35 (s, 1H), 7.11 (d, J = 7.6 Hz, 1H), 6.04 (s, 2H), 4.22 (t, J = 10.6 Hz, 2H), 4.18-4.03 (m, 1H), 3.31 (s, 3H), 3.06 (s, 1H), 2.43-2.30 (m, 2H), 2.12 (d, J = 13.5 Hz, 1H), 1.70 (dd, J = 13.6, 11.6 Hz, 1H), 1.46-1.25 (m, 1H), 1.03 (d, J = 6.2 Hz, 3H). LCMS m/z 529.12 (M + 1)$^+$ |

TABLE 11-continued

*Method of preparation, structure, and physicochemical data for compounds 226-371*

| Product | Starting Material and Amine | NMR, LCMS |
|---|---|---|
| Compound 348 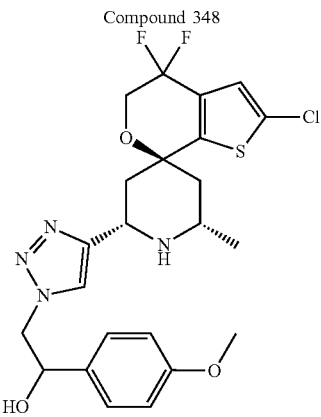 | 223; 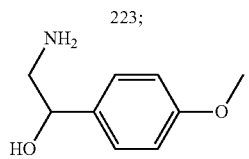 | $^1$H NMR (400 MHz, DMSO-d6) δ 7.90 (d, J = 7.1 Hz, 1H), 7.35 (s, 1H), 7.28 (dd, J = 8.8, 3.2 Hz, 2H), 6.95-6.84 (m, 2H), 5.71 (s, 1H), 4.90 (dd, J = 7.6, 4.9 Hz, 1H), 4.40 (dd, J = 6.2, 3.4 Hz, 2H), 4.23 (t, J = 10.6 Hz, 2H), 4.13 (d, J = 11.4 Hz, 1H), 3.73 (d, J = 1.8 Hz, 3H), 3.06 (s, 1H), 2.33 (d, J = 30.9 Hz, 2H), 2.13 (d, J = 13.5 Hz, 1H), 1.73-1.60 (m, 1H), 1.32 (t, J = 12.5 Hz, 1H), 1.04 (d, J = 6.2 Hz, 3H). LCMS m/z 511.19 (M + 1)$^+$ |
| Compound 349 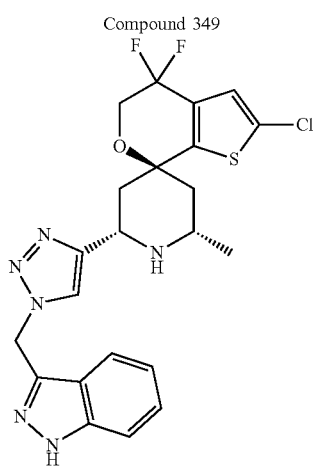 | 223; 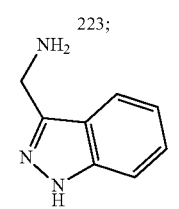 | 1H NMR (400 MHz, DMSO-d6) δ 7.97 (s, 1H), 7.70 (d, J = 8.1 Hz, 1H), 7.53 (d, Jr 8.4 Hz, 1H), 7.34 (d, J = 7.2 Hz, 2H), 7.10 (t, J = 7.5 Hz, 1H), 5.91 (s, 2H), 4.20 (t, J = 10.6 Hz, 2H), 4.09 (d, J = 11.6 Hz, 1H), 3.00 (s, 1H), 2.30 (d, J = 11.4 Hz, 2H), 2.08 (d, J = 13.6 Hz, 1H), 1.74-1.62 (m, 1H), 1.38-1.16 (m, 1H), 0.99 (d, J = 6.2 Hz, 3H). LCMS m/z 491.15 (M + 1)$^+$ |
| Compound 350 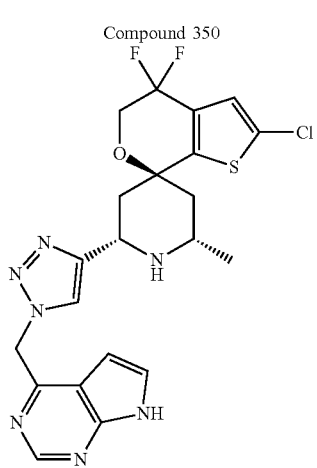 | 223; 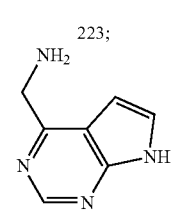 | $^1$H NMR (400 MHz, DMSO-d6) δ 12.29 (s, 1H), 8.70 (s, 1H), 8.09 (s, 1H), 7.56 (d, J = 3.6 Hz, 1H), 7.35 (s, 1H), 6.28 (d, J = 3.6 Hz, 1H), 5.96 (s, 2H), 4.22 (t, J = 10.6 Hz, 2H), 4.16 (d, J = 11.3 Hz, 1H), 3.06 (s, 1H), 2.35 (d, J = 13.2 Hz, 2H), 2.12 (d, J = 13.6 Hz, 1H), 1.82-1.64 (m, 1H), 1.33 (dd, J = 13.6, 11.2 Hz, 1H), 1.03 (d, J = 6.2 Hz, 3H). LCMS m/z 492.14 (M + 1)$^+$ |

TABLE 11-continued

Method of preparation, structure, and physicochemical data for compounds 226-371

| Product | Starting Material and Amine | NMR, LCMS |
|---|---|---|
| Compound 351 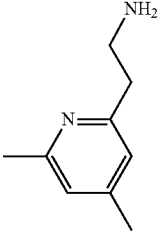 | 223; 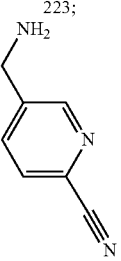 | $^1$H NMR (400 MHz, DMSO-d6) δ 7.95 (s, 1H), 7.35 (s, 1H), 6.93 (s, 1H), 6.85 (s, 1H), 4.66 (t, J = 7.4 Hz, 2H), 4.22 (t, J = 10.6 Hz, 2H), 4.11 (d, J = 11.4 Hz, 1H), 3.19 (t, J = 7.4 Hz, 2H), 3.05 (s, 1H), 2.40 (s, 3H), 2.29 (d, J = 11.4 Hz, 2H), 2.21 (s, 3H), 2.13 (d, J = 13.6 Hz, 1H), 1.67 (dd, J = 13.6, 11.6 Hz, 1H), 1.31 (dd, J = 13.5, 11.3 Hz, 1H), 1.03 (d, J = 6.2 Hz, 3H). LCMS m/z 494.21 (M + 1)$^+$ |
| Compound 352 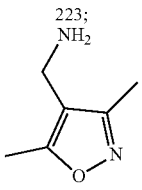 | 223; NH$_2$ | $^1$H NMR (400 MHz, DMSO-d6) δ 8.74 (d, J = 2.1 Hz, 1H), 8.13 (s, 1H), 8.07 (d, J = 8.0 Hz, 1H), 7.92 (dd, J = 8.0, 2.2 Hz, 1H), 7.34 (d, J = 5.9 Hz, 1H), 5.75 (s, 2H), 4.22 (t, J = 10.6 Hz, 2H), 4.14 (d, J = 11.2 Hz, 1H), 3.06 (s, 1H), 2.42-2.30 (m, 2H), 2.12 (d, J = 13.3 Hz, 1H), 1.68 (dd, J = 13.5, 11.6 Hz, 1H), 1.38-1.28 (m, 1H), 1.02 (d, J = 6.2 Hz, 3H). LCMS m/z 477.15 (M + 1)$^+$ |
| Compound 353 | 223; NH$_2$ | 1H NMR (400 MHz, DMSO-d6) δ 7.96 (s, 1H), 7.35 (s, 1H), 5.40 (s, 2H), 4.21 (t, J = 10.6 Hz, 2H), 4.11 (d, J = 11.5 Hz, 1H), 3.05 (s, 1H), 2.44 (s, 3H), 2.40-2.28 (m, 2H), 2.14 (s, 4H), 1.67 (dd, J = 13.6, 11.6 Hz, 1H), 1.30 (dd, J = 13.6, 11.3 Hz, 1H), 1.02 (d, J = 6.3 Hz, 3H). LCMS m/z 470.15 (M + 1)$^+$ |

TABLE 11-continued

Method of preparation, structure, and physicochemical data for compounds 226-371

| Product | Starting Material and Amine | NMR, LCMS |
|---|---|---|
| Compound 354 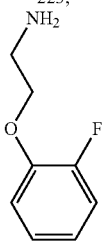 | 223; 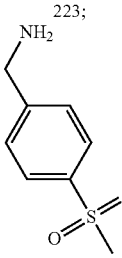 | $^1$H NMR (400 MHz, DMSO-d6) δ 8.05 (s, 1H), 7.35 (s, 1H), 7.16 (dddd, J = 19.9, 17.9, 11.2, 4.8 Hz, 3H), 7.02-6.90 (m, 1H), 4.75 (t, J = 5.1 Hz, 2H), 4.47 (t, J = 5.1 Hz, 2H), 4.22 (t, J = 10.6 Hz, 2H), 4.14 (d, J = 11.6 Hz, 1H), 3.06 (s, 1H), 2.32 (d, J = 10.6 Hz, 2H), 2.13 (d, J = 13.5 Hz, 1H), 1.69 (dd, J = 13.7, 11.6 Hz, 1H), 1.33 (dd, J = 13.6, 11.3 Hz, 1H), 1.03 (d, J = 6.2 Hz, 3H). LCMS m/z 499.18 (M + 1)$^+$ |
| Compound 355 | 223; | $^1$H NMR (400 MHz, DMSO-d6) δ 8.10 (s, 1H), 7.99-7.90 (m, 2H), 7.54 (d, J = 8.3 Hz, 2H), 7.35 (s, 1H), 5.70 (s, 2H), 4.22 (t, J = 10.6 Hz, 2H), 4.14 (d, J = 11.7 Hz, 1H), 3.21 (s, 3H), 3.06 (s, 1H), 2.35 (d, J = 15.3 Hz, 2H), 2.12 (d, J = 13.5 Hz, 1H), 1.74-1.63 (m, 1H), 1.31 (dd, J = 13.5, 11.3 Hz, 1H), 1.02 (d, J = 6.2 Hz, 3H). LCMS m/z 529.16 (M + 1)$^+$ |
| Compound 356 | 223; 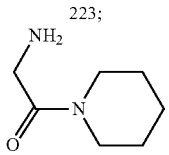 | $^1$H NMR (400 MHz, DMSO-d6) δ 7.86 (s, 1H), 7.35 (s, 1H), 5.38 (s, 2H), 4.23 (t, J = 10.6 Hz, 2H), 4.15 (d, J = 11.6 Hz, 1H), 3.45 (d, J = 8.8 Hz, 4H), 3.07 (s, 1H), 2.34 (d, J = 13.4 Hz, 2H), 2.13 (d, J = 13.6 Hz, 1H), 1.71 (dd, J = 13.5, 11.6 Hz, 1H), 1.59 (q, J = 6.5, 5.6 Hz, 4H), 1.45 (s, 2H), 1.41-1.26 (m, 1H), 1.04 (d, J = 6.3 Hz, 3H). LCMS m/z 429.15 (M + 1)$^+$ |

TABLE 11-continued

Method of preparation, structure, and physicochemical data for compounds 226-371

| Product | Starting Material and Amine | NMR, LCMS |
|---|---|---|
| Compound 357 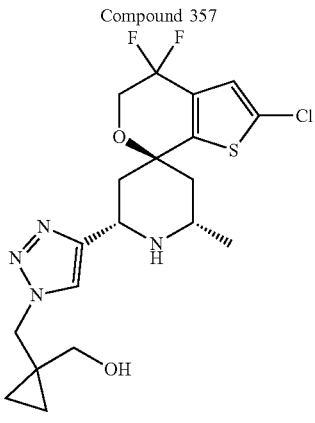 | 223; 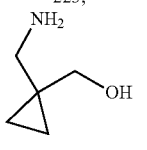 | $^1$H NMR (400 MHz, DMSO-d6) δ 7.95 (s, 1H), 7.35 (s, 1H), 4.75 (s, 1H), 4.29 (s, 2H), 4.23 (t, J = 10.6 Hz, 2H), 4.14 (d J = 11.5 Hz, 1H), 3.15-3.02 (m, 3H), 2.35 (d, J = 12.3 Hz, 2H), 2.12 (d, J = 13.5 Hz, 1H), 1.70 (dd, J = 13.7, 11.7 Hz, 1H), 1.34 (dd, J = 13.6, 11.3 Hz, 1H), 1.04 (d, J = 6.3 Hz, 3H), 0.62 (q, J = 4.0 Hz, 2H), 0.48 (q, J = 4.1 Hz, 2H). LCMS m/z 445.18 (M + 1)$^+$ |
| Compound 358 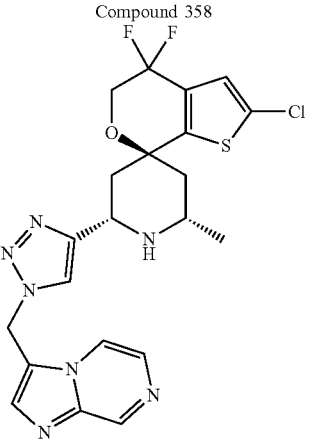 | 223; 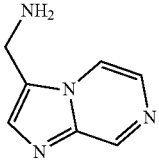 [SMILES: NCc1cnc2cnccn12] | 1H NMR (400 MHz, DMSO-d6) δ 9.12 (d, J = 1.5 Hz, 1H), 8.61 (dd, J = 4.7, 1.6 Hz, 1H), 8.07 (s, 1H), 8.02 (d, J = 4.7 Hz, 1H), 7.97 (s, 1H), 7.34 (s, 1H), 6.09 (s, 2H), 4.20 (t, J = 10.6 Hz, 2H), 4.09 (d, J = 11.3 Hz, 1H), 3.01 (d, J = 11.7 Hz, 1H), 2.30 (d, J = 15.4 Hz, 2H), 2.10 (d, J = 13.6 Hz, 1H), 1.64 (dd, J = 13.5, 11.7 Hz, 1H), 1.38-1.19 (m, 1H), 1.00 (d, J = 6.2 Hz, 3H). LCMS m/z 491.18 (M + 1)$^+$ |
| Compound 359 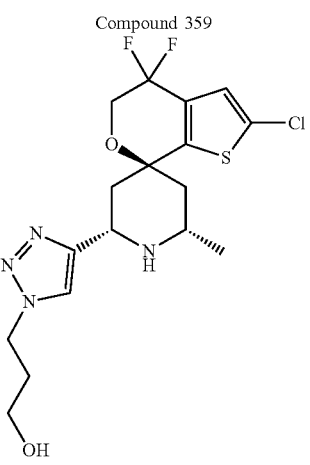 | 223;  | $^1$H NMR (400 MHz, DMSO-d6) δ 7.97 (s, 1H), 7.35 (s, 1H), 4.67 (s, 1H), 4.36 (t, J = 7.1 Hz, 2H), 4.22 (t, J = 10.6 Hz, 2H), 4.13 (d, J = 11.4 Hz, 1H), 3.39 (s, 2H), 3.07 (s, 1H), 2.34 (s, 2H), 2.13 (d, J = 13.8 Hz, 1H), 1.93 (p, J = 6.5 Hz, 2H), 1.70 (dd, J = 13.6, 11.6 Hz, 1H), 1.32 (dd, J = 13.6, 11.3 Hz, 1H), 1.03 (d, J = 6.3 Hz, 3H). LCMS m/z 419.13 (M + 1)$^+$ |

TABLE 11-continued

Method of preparation, structure, and physicochemical data for compounds 226-371

| Product | Starting Material and Amine | NMR, LCMS |
|---|---|---|
| Compound 360 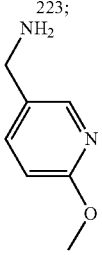 | 223; 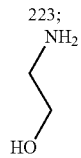 | $^1$H NMR (400 MHz, DMSO-d6) δ 8.23 (d, J = 2.5 Hz, 1H), 8.03 (s, 1H), 7.69 (dd, J = 8.6, 2.5 Hz, 1H), 7.34 (s, 1H), 6.83 (d, J = 8.5 Hz, 1H), 5.51 (s, 2H), 4.21 (t, J = 10.6 Hz, 2H), 4.11 (d, J = 11.4 Hz, 1H), 3.83 (s, 3H), 3.04 (s, 1H), 2.32 (d, J = 13.7 Hz, 2H), 2.11 (d, J = 13.6 Hz, 1H), 1.75-1.58 (m, 1H), 1.30 (dd, J = 13.5, 11.2 Hz, 1H), 1.01 (d, J = 6.2 Hz, 3H). LCMS m/z 482.16 (M + 1)$^+$ |
| Compound 361 | 223; | $^1$H NMR (400 MHz, DMSO-d6) δ 7.95 (s, 1H), 7.35 (s, 1H), 5.03 (s, 1H), 4.35 (t, J = 5.4 Hz, 2H), 4.22 (t, J = 10.6 Hz, 2H), 4.14(d, J = 11.6 Hz, 1H), 3.76 (t, J = 5.1 Hz, 2H), 3.07 (s, 1H), 2.33 (d, J = 14.0 Hz, 2H), 2.13 (d, J = 13.6 Hz, 1H), 1.70 (dd, J = 13.6, 11.6 Hz, 1H), 1.32 (dd, J = 13.6, 11.2 Hz, 1H), 1.03 (d, J = 6.2 Hz, 3H). LCMS m/z 405.13 (M + 1)$^+$ |
| Compound 362 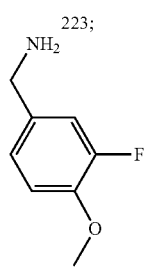 | 223; | $^1$H NMR (400 MHz, DMSO-d6) δ 8.01 (s, 1H), 7.34 (s, 1H), 7.28-7.21 (m, 1H), 7.20-7.10 (m, 2H), 5.47 (s, 2H), 4.21 (t, J = 10.6 Hz, 2H), 4.11 (d, J = 11.8 Hz, 1H), 3.82 (s, 3H), 3.02 (d, J = 19.8 Hz, 1H), 2.33 (d, J = 13.6 Hz, 2H), 2.11 (d, J = 13.5 Hz, 1H), 1.66 (dd, J = 13.6, 11.6 Hz, 1H), 1.31 (dd, J = 13.6, 11.3 Hz, 1H), 1.01 (d, J = 6.3 Hz, 3H). LCMS m/z 499.18 (M + 1)$^+$ |

TABLE 11-continued

*Method of preparation, structure, and physicochemical data for compounds 226-371*

| Product | Starting Material and Amine | NMR, LCMS |
|---|---|---|
| Compound 363 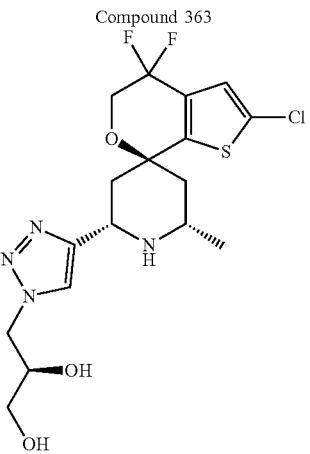 | 223; 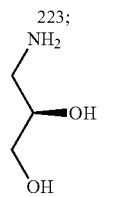 | $^1$H NMR (400 MHz, DMSO-d6) δ 7.90 (s, 1H), 7.35 (s, 1H), 5.14 (s, 1H), 4.86 (s, 1H), 4.45 (dd, J = 13.8, 3.6 Hz, 1H), 4.22 (dd, J = 13.3, 8.9 Hz, 3H), 4.14 (d, J = 14.4 Hz, 1H), 3.79 (s, 1H), 3.26 (s, 2H), 3.07 (s, 1H), 2.33 (d, J = 14.2 Hz, 2H), 2.13 (d, J = 13.6 Hz, 1H), 1.70 (dd, J = 13.5, 11.6 Hz, 1H), 1.38-1.27 (m, 1H), 1.04 (d, J = 6.3 Hz, 3H). LCMS m/z 435.16 (M + 1)$^+$ |
| Compound 364 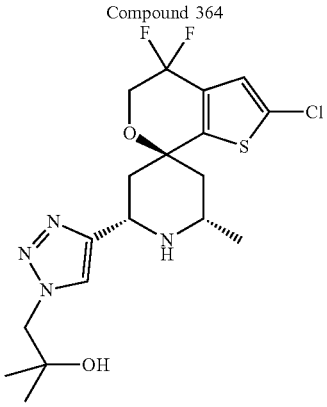 | 223; 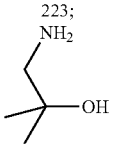 | $^1$H NMR (400 MHz, DMSO-d6) δ 7.85 (s, 1H), 7.35 (s, 1H), 4.83 (s, 1H), 4.24 (d, J = 12.4 Hz, 4H), 4.14 (d, J = 11.5 Hz, 1H), 3.07 (s, 1H), 2.35 (d, J = 13.8 Hz, 2H), 2.12 (d, J = 13.6 Hz, 1H), 1.70 (dd, J = 13.6, 11.6 Hz, 1H), 1.34 (dd, J = 13.6, 11.2 Hz, 1H), 1.08-1.01 (m, 9H). LCMS m/z 433.17 (M + 1)$^+$ |
| Compound 365 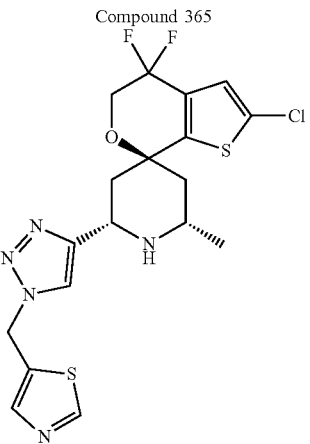 | 223; 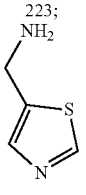 | $^1$H NMR (400 MHz, DMSO-d6) δ 9.09 (s, 1H), 8.05 (s, 1H), 7.99 (s, 1H), 7.34 (s, 1H), 5.88 (s, 2H), 4.21 (t, J = 10.6 Hz, 2H), 4.12 (d, J = 11.0 Hz, 1H), 3.05 (s, 1H), 2.33 (d, J = 13.6 Hz, 2H), 2.11 (d, J = 13.7 Hz, 1H), 1.67 (dd, J = 13.5, 11.6 Hz, 1H), 1.31 (dd, J = 13.5, 11.3 Hz, 1H), 1.02 (d, J = 6.3 Hz, 3H). LCMS m/z 458.10 (M + 1)$^+$ |

TABLE 11-continued

Method of preparation, structure, and physicochemical data for compounds 226-371

| Product | Starting Material and Amine | NMR, LCMS |
|---|---|---|
| Compound 366 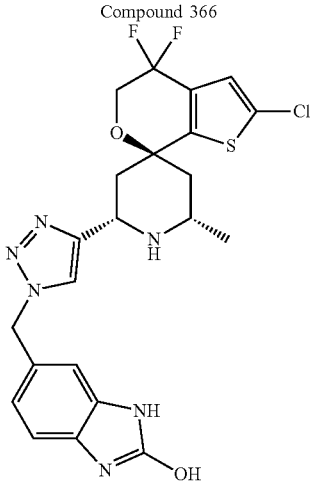 | 223; 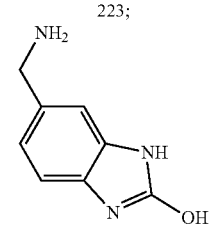 | $^1$H NMR (400 MHz, DMSO-d6) δ 10.68 (s, 2H), 7.96 (s, 1H), 7.34 (s, 1H), 6.95 (dd, J = 7.9, 1.6 Hz, 1H), 6.92 (d, J = 1.5 Hz, 1H), 6.89 (d, J = 7.9 Hz, 1H), 5.49 (s, 2H), 4.21 (t, J = 10.6 Hz, 2H), 4.10 (d, J = 11.5 Hz, 1H), 3.02 (d, J = 16.3 Hz, 1H), 2.33 (t, J = 13.7 Hz, 2H), 2.10 (d, J = 13.4 Hz, 1H), 1.66 (dd, J = 13.6, 11.6 Hz, 1H), 1.35-1.23 (m, 1H), 1.01 (d, J = 6.2 Hz, 3H). LCMS m/z 507.17 (M + 1)$^+$ |
| Compound 367 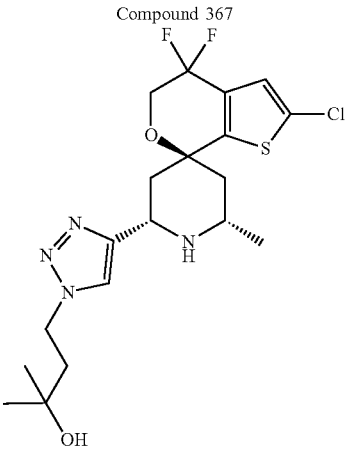 | 223; 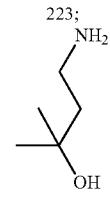 | $^1$H NMR (400 MHz, DMSO-d6) δ 7.99 (s, 1H), 7.35 (s, 1H), 4.52 (s, 1H), 4.38 (dd, J = 7.0, 4.2 Hz, 2H), 4.22 (t, J = 10.6 Hz, 2H), 4.12 (d, J = 11.2 Hz, 1H), 3.06 (s, 1H), 2.32 (d, J = 11.6 Hz, 2H), 2.13 (d, J = 13.5 Hz, 1H), 1.95-1.83 (m, 2H), 1.69 (dd, J = 13.6, 11.7 Hz, 1H), 1.32 (dd, J = 13.6, 11.2 Hz, 1H), 1.13 (s, 6H), 1.03 (d, J = 6.2 Hz, 3H). LCMS m/z 447.17 (M + 1)$^+$ |
| Compound 368 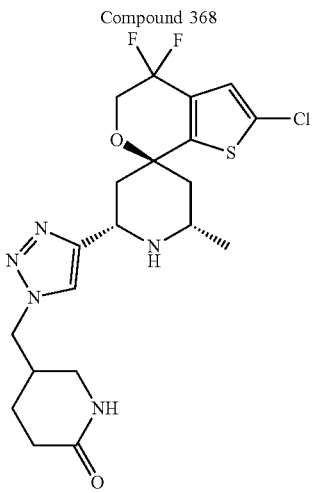 | 223; 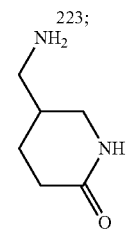 | $^1$H NMR (400 MHz, DMSO-d6) δ 8.00 (s, 1H), 7.44 (s, 1H), 7.35 (s, 1H), 4.33 (d, J = 7.2 Hz, 2H), 4.23 (t, J = 10.6 Hz, 2H), 4.13 (d, J = 11.4 Hz, 1H), 3.12-2.96 (m, 2H), 2.89 (t, J = 10.8 Hz, 1H), 2.34 (d, J = 13.0 Hz, 2H), 2.30-2.05 (m, 4H), 1.69 (t, J = 12.5 Hz, 2H), 1.43 (t, J = 9.9 Hz, 1H), 1.39-1.28 (m, 1H), 1.03 (d, J = 6.2 Hz, 3H). LCMS m/z 472.18 (M + 1)$^+$ |

TABLE 11-continued

Method of preparation, structure, and physicochemical data for compounds 226-371

| Product | Starting Material and Amine | NMR, LCMS |
|---|---|---|
| Compound 369 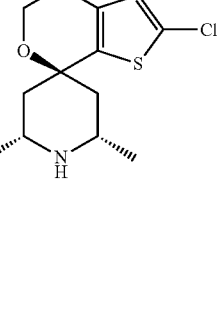 | 223;  | ¹H NMR (400 MHz, DMSO-d6) δ 8.03 (d, J = 90.8 Hz, 1H), 7.35 (s, 1H), 5.40 (d, J = 306.9 Hz, 2H), 4.19 (dt, J = 29.2, 9.8 Hz, 3H), 3.07 (s, 1H), 2.43 (s, 1H), 2.35 (d, J = 13.6 Hz, 1H), 2.13 (d, J = 13.5 Hz, 1H), 1.71 (t, J = 12.6 Hz, 1H), 1.40-1.29 (m, 1H), 1.04 (d, J = 6.2 Hz, 3H). LCMS m/z 400.12 (M + 1)⁺ |
| Compound 370 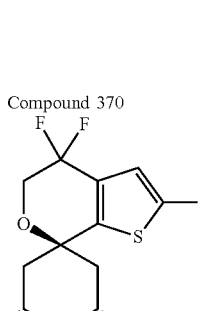 | 223;  | 1H NMR (400 MHz, DMSO-d6) δ 7.94 (s, 1H), 7.35 (s, 1H), 4.73 (t, J = 5.2 Hz, 1H), 4.35 (dd, J = 13.5, 5.9 Hz, 1H), 4.22 (t, J = 10.6 Hz, 2H), 4.17-4.07 (m, 2H), 3.30-3.19 (m, 2H), 3.08 (d, J = 9.7 Hz, 1H), 2.34 (d, J = 13.5 Hz, 2H), 2.17-1.99 (m, 2H), 1.70 (dd, J = 13.5, 11.6 Hz, 1H), 1.33 (dd, J = 13.6, 11.1 Hz, 1H), 1.03 (d, J = 6.2 Hz, 3H), 0.77 (d, J = 6.8 Hz, 3H). LCMS m/z 433.17 (M + 1)⁺ |
| Compound 371 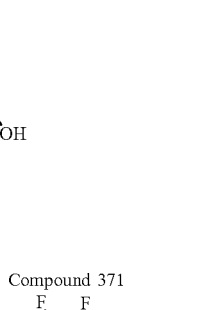 | 223;  | ¹H NMR (400 MHz, DMSO-d6) δ 7.90 (s, 1H), 7.35 (s, 1H), 5.12 (s, 1H), 4.84 (s, 1H), 4.45 (dd, J = 13.9, 3.5 Hz, 1H), 4.27-4.10 (m, 4H), 3.79 (s, 1H), 3.07 (t, J = 7.9 Hz, 1H), 2.34 (d, J = 13.4 Hz, 1H), 2.13 (d, J = 13.6 Hz, 1H), 1.71 (dd, J = 13.5, 11.7 Hz, 1H), 1.39-1.28 (m, 1H), 1.04 (d, J = 6.2 Hz, 3H). LCMS m/z 435.16 (M + 1)⁺ |

ˣSharpless, K. B. et al. *Nature*, 2019, 574, 86-89

Preparation of S56 methyl 1-[(2S,6S)-6-methyl-4-oxo-2-piperidyl]cyclopropanecarboxylate (S56)

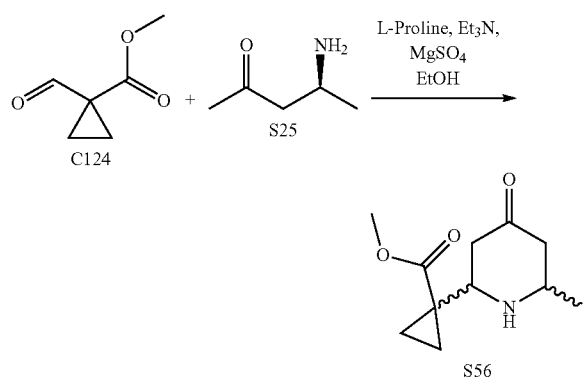

Standard Method C: Cyclization to Prepare Piperidone with Distillation Workup A stirred solution of (4S)-4-aminopentan-2-one (hydrochloric acid) S25 (1.25 g, 8.2 mmol) in EtOH (50 mL) was cooled to 0° C. Then Et$_3$N (2.28 g, 3.2 mL, 22.0 mmol), MgSO$_4$ (950 mg, 7.7 mmol), L-Proline (490 mg, 4.0 mmol) and methyl 1-formylcyclopropanecarboxylate C124 (1 g, 7.6 mmol) were added. After 30 minutes, the reaction mixture was slowly allowed to warm to room temperature and stirred for 24 hours. The reaction mixture was distilled under vacuum to give crude product as a brown color thick oil. The crude material was purified by silica gel flash column chromatography (eluted with 12% MeOH in DCM) to afford the product methyl 1-[(2S,6S)-6-methyl-4-oxo-2-piperidyl]cyclopropanecarboxylate S56 (600 mg, 37% yield) as a pale yellow oil. Partial stereochemical erosion of the enantiomerically pure starting material (4S)-4-aminopentan-2-one (Hydrochloride salt) S25 was observed under these conditions, leading to unseparated mixtures of stereoisomers where the cis-product was the major isomer. $^1$H NMR (400 MHz, DMSO-d$_6$) δ 3.58 (s, 3H), 2.90-2.86 (m, 1H), 2.81-2.72 (m, 1H), 2.30-2.13 (m, 3H), 2.06-1.97 (m, 1H), 1.10-0.94 (m, 8H). LCMS m/z 212.1 [M+H]$^+$.

Preparation of S57 tert-butyl N-[1-[(2S,6S)-6-methyl-4-oxo-2-piperidyl]cyclopropyl]carbamate (S57)

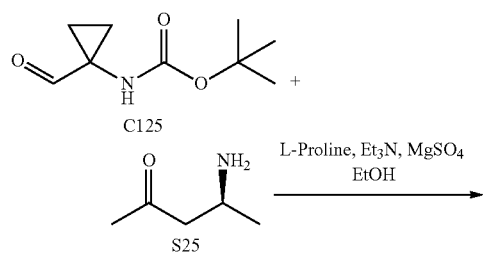

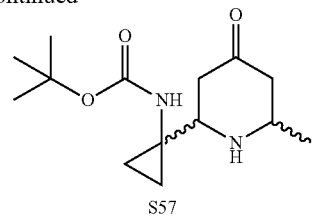

Standard Method D: Cyclization to Prepare Piperidone with Aqueous Quench Workup To a stirred solution of (4S)-4-aminopentan-2-one (hydrochloric acid) (1 g, 6.5 mmol) S25 in EtOH (20 mL) were added L-proline (150 mg, 1.3 mmol), MgSO$_4$ (783 mg, 6.4 mmol), Et$_3$N (718.74 mg, 1 mL, 7.0 mmol) and tert-butyl N-(1-formylcyclopropyl)carbamate C125 (1.2 g, 6.4 mmol) at room temperature. The reaction mass was allowed to stir for 16 hours at room temperature. The reaction mixture was diluted with saturated NaHCO$_3$ (50 mL) and extracted with EtOAc (3×100 mL). The combined organic layer was washed with 0.15 N aqueous HCl (3×50 mL), and then the aqueous layer pH was adjusted to 12 by using 1 N NaOH solution. The aqueous layer extracted with EtOAc (3×100 mL), and the combined organic layer was dried over Na$_2$SO$_4$, filtered, and evaporated under vacuum to provide the crude material. The crude material was purified by column chromatography using 100-200 mesh silica gel and eluted with 4% MeOH in DCM to provide tert-butyl N-[1-[(2S,6S)-6-methyl-4-oxo-2-piperidyl]cyclopropyl]carbamate S57 (800 mg, 46% yield). Partial stereochemical erosion of the enantiomerically pure starting material (4S)-4-aminopentan-2-one (Hydrochloride salt) S25 was observed under these conditions, leading to unseparated mixtures of stereoisomers where the cis-product was the major isomer. $^1$H NMR (400 MHz, DMSO-d$_6$) δ 7.11 (brs, 1H), 2.74 (brs, 1H), 2.49 (brs, 1H), 2.18-2.0 (m, 5H), 1.36 (s, 9H), 1.09 (d, J=6.0 Hz, 3H), 0.75-0.60 (m, 4H). LCMS m/z 269.2 [M+H]$^+$.

Preparation of S58 tert-butyl N-[1-[(2S,6S)-6-methyl-4-oxo-2-piperidyl]cyclopropyl]carbamate (S58)

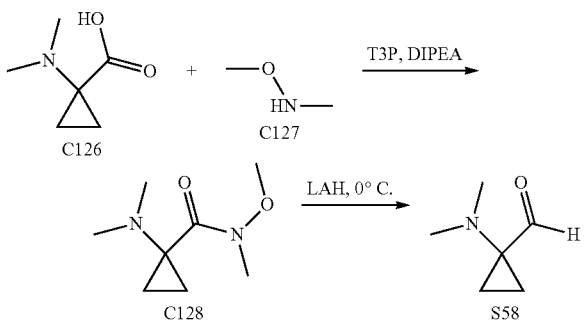

Step 1. 1-(dimethylamino)-N-methoxy-N-methylcyclopropanecarboxamide (C128)

To a stirred solution of 1-(dimethylamino)cyclopropanecarboxylic acid C126 (500 mg, 0.0038 mol) in DCM (10 mL) were added DIPEA (2.226 g, 3.00 mL, 0.0169 mol) and N-methoxymethanamine (hydrochloric acid) C127 (453 mg, 0.0046 mol) at 0° C. The reaction mixture was stirred for 10 minutes, and T3P (3.12 g, 2.92 mL of 50% w/w, 0.0049 mol) was slowly added at 0° C. The reaction mixture was stirred at room temperature for 16 hours. The reaction mixture was diluted with DCM (25 mL) and cooled to 0° C. 1 N NaOH solution (10 mL) was slowly added, and the organic layer was separated and washed with saturated NH₄Cl solution (10 mL). The organic layer was dried over anhydrous sodium sulfate, filtered, and concentrated under reduced pressure to obtained the crude material. The crude material was purified by column chromatography using 100-200 mesh silica gel and eluted with 70% EtOAc in petroleum ether to afford 1-(dimethylamino)-N-methoxy-N-methyl-cyclopropanecarboxamide C128 (300 mg, 44%) as a brown color liquid. ¹H NMR (400 MHz, DMSO-d₆) δ 3.62 (s, 3H), 3.19 (s, 3H), 2.23 (s, 6H), 0.82-0.80 (m, 4H). LCMS m/z 173.22 [M+H]⁺.

Step 2.
1-(dimethylamino)cyclopropanecarbaldehyde (S58)

To a stirred suspension of LAH (988 mg, 0.0255 mol) in diethyl ether (50 mL) was added 1-(dimethylamino)-N-methoxy-N-methyl-cyclopropanecarboxamide C128 (2 g, 0.0102 mol) dropwise at 0° C. The reaction mixture was allowed to stir for 4 hours at 0° C. The reaction was quenched with water (3.2 mL), 1 N NaOH solution (3.2 mL), and water (3.2 mL). The reaction mass was filtered through a Celite® pad and washed with diethyl ether (30 mL). The filtrate was evaporated under vacuum to afford crude 1-(dimethylamino)cyclopropanecarbaldehyde S58 (1.4 g, 97%) as a colorless oil. ¹H NMR (300 MHz, Chloroform-d) δ 9.01 (s, 1H), 2.63 (s, 6H), 1.28-1.14 (m, 4H).

Intermediates S59-S62

Intermediates S59-S62 (see Table 12) were prepared in a single step from intermediate S25 using standard Method C or D. Corresponding aldehydes were prepared by methods described above or obtained from commercial sources. Partial stereochemical erosion of the enantiomerically pure starting material (4S')-4-aminopentan-2-one (hydrochloride salt) S25 was observed in step 1 leading to unseparated mixtures of stereoisomers being generated in Step 1. In each case the cis-product was the major isomer. Any modifications to methods are noted in Table 12 and accompanying footnotes.

TABLE 12

Structure and physicochemical data for intermediates S59-S62

| Intermediate | Structure | Aldehyde Reagent | Method | ¹H NMR; LCMS m/z [M + H]⁺ |
|---|---|---|---|---|
| S59 | 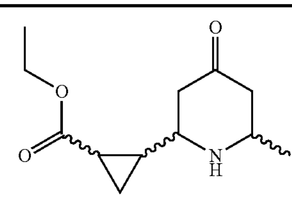 | | C | ¹H NMR (400 MHz, DMSO-d6) δ 4.09-4.01 (m, 2H), 2.78-2.65 (m, 1H), 2.39-2.31 (m, 1H), 2.25-1.97 (m, 4H), 1.68-1.60 (m, 1H), 1.43-1.32 (m, 1H), 1.20-1.18 (m, 6H), 1.11-0.87 (m, 3H) |
| S60 | 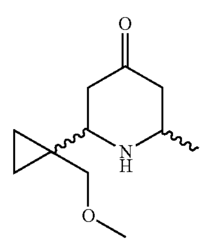 | | D | ¹H NMR (400 MHz, DMSO-d6) δ 4.09-4.01 (m, 2H), 2.78-2.65 (m, 1H), 2.39-2.31 (m, 1H), 2.25-1.97 (m, 4H), 1.68-1.60 (m, 1H), 1.43-1.32 (m, 1H), 1.20-1.18 (m, 6H), 1.11-0.87 (m, 3H); 198.1 |
| S61 | 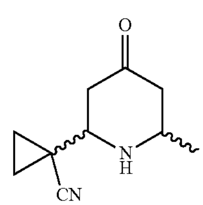 | | D | ¹H NMR (400 MHz, DMSO-d6) δ 2.80-2.75 (m, 2H), 2.33-2.22 (m, 3H), 2.13-2.11 (m, 2H), 1.23-1.00 (m, 7H); 179.2 |
| S62 | 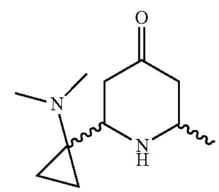 | | D¹ | ¹H NMR (400 MHz, DMSO-d6) δ 4.09-4.01 (m, 2H), 2.78-2.65 (m, 1H), 2.39-2.31 (m, 1H), 2.25-1.97 (m, 4H), 1.68-1.60 (m, 1H), 1.43-1.32 (m, 1H), 1.20-1.18 (m, 6H), 1.11-0.87 (m, 3H); 198.1 |

Note:
¹The workup procedure was modified as: the reaction mixture was diluted with saturated NaHCO₃ (50 mL) and extracted with EtOAc (4 × 300 mL). The combined organic layer was dried over sodium sulfate, filtered, and evaporated under vacuum to provide the crude material.

Compound 372 methyl 1-[(2'S, 6'S, 7S)-2-chloro-6'-methyl-spiro[4,5-dihydrothieno[2,3-c]pyran-7,4'-piperidine]-2'-yl] cyclopropanecarboxylate (372)

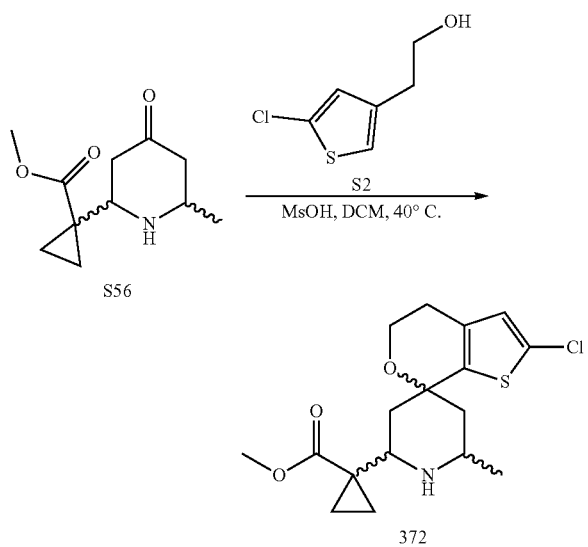

Standard Method E: To Prepare Spiropiperidine

To a mixture of methyl 1-[(2S,6S)-6-methyl-4-oxo-2-piperidyl]cyclopropanecarboxylate S56 (100 mg, 0.473 mmol) and 2-(5-chloro-3-thienyl)ethanol S2 (92 mg, 0.57 mmol, 1.2 equiv) in DCM (2.2 mL) was added MsOH (250 µL, 3.85 mmol, 8 equiv), and the mixture was heated to 40° C. After 5 hours, the reaction was quenched with saturated NaHCO$_3$ solution and extracted with DCM (6×). The combined organic layer was dried over Na$_2$SO$_4$, filtered, and concentrated. The crude material was purified with a silica gel column and eluted with 0 to 100% EtOAc in heptane to provide methyl 1-[(2'S,6'S,7S)-2-chloro-6'-methyl-spiro[4,5-dihydrothieno[2,3-c]pyran-7,4'-piperidine]-2'-yl]cyclopropanecarboxylate 372 (123 mg, 69%). Due to partial erosion of enantiomeric purity when preparing S56, 372 was also isolated as a mixture of enantiomers where the (2'S, 6'S,7S) configuration was the major enantiomer. $^1$H NMR (300 MHz, Chloroform-d) δ 6.56 (s, 1H), 3.88 (t, J=5.5 Hz, 2H), 3.63 (s, 3H), 3.04 (dtd, J=12.9, 6.5, 2.5 Hz, 1H), 2.73 (dd, J=11.8, 2.5 Hz, 1H), 2.58 (t, J=5.5 Hz, 2H), 2.00 (ddt, J=17.5, 13.4, 2.5 Hz, 2H), 1.70 (dd, J=13.3, 11.7 Hz, 2H), 1.40-1.16 (m, 3H), 1.11 (d, J=6.4 Hz, 3H), 1.04-0.92 (m, 1H), 0.77 (ddd, J=9.7, 5.4, 2.6 Hz, 1H). LCMS m/z 356.15 [M+H]$^+$.

Compound 373-378

Compounds 373-378 (see Table 13) were prepared in a single step from the corresponding piperidinone reagent using standard method E. Due to partial erosion of enantiomeric purity when preparing piperidone reagents, compounds were isolated as a mixture of enantiomers where the (2'S,6'S,7S) configuration was the major enantiomer. Any modifications to methods are noted in Table 13 and accompanying footnotes.

TABLE 13

Structure and physicochemical data for compounds 373-378

| Compound | Structures | Piperidone Reagent | $^1$H NMR; LCMS m/z [M + H]$^+$ |
|---|---|---|---|
| 373 | 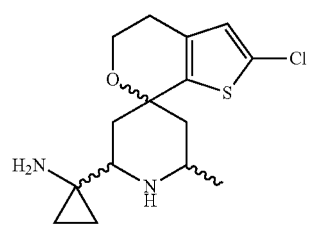 [SMILES: CC1CC2(CC(C3(N)CC3)N1)OCCc1cc(Cl)sc12] | | $^1$H NMR (300 MHz, Chloroform-d) δ 6.58 (s, 1H), 3.88 (t, J = 5.5 Hz, 2H), 3.17 (dd, J = 10.3, 5.1 Hz, 1H), 2.59 (t, J = 5.5 Hz, 2H), 2.34 (dd, J = 11.8, 2.3 Hz, 1H), 2.09-1.93 (m, 2H), 1.62 (d, J = 12.7 Hz, 1H), 1.45-1.28 (m, 1H), 1.14 (d, J = 6.3 Hz, 3H), 0.71-0.60 (m, 1H), 0.60-0.45 (m, 2H), 0.45-0.37 (m, 1H); 356.15 |
| 374[1] | 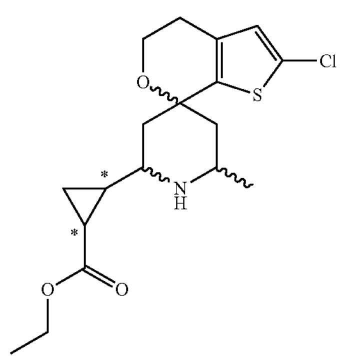 [SMILES: CCOC(=O)C1CC1C1CC2(CC(C)N1)OCCc1cc(Cl)sc12] | | $^1$H NMR (300 MHz, Chloroform-d) δ 8.40 (s, 1H), 6.59 (s, 1H), 4.10 (qd, J = 7.2, 2.7 Hz, 2H), 3.86 (t, J = 5.5 Hz, 2H), 3.29 (d, J = 12.3 Hz, 1H), 2.66-2.46 (m, 3H), 2.24-1.82 (m, 3H), 1.81-1.68 (m, 2H), 1.68-1.54 (m, 1H), 1.30-1.06 (m, 7H), 0.87-0.69 (m, 1H); 370.31 |

TABLE 13-continued

Structure and physicochemical data for compounds 373-378

| Compound | Structures | Piperidone Reagent | ¹H NMR; LCMS m/z [M + H]⁺ |
|---|---|---|---|
| 375[1] | 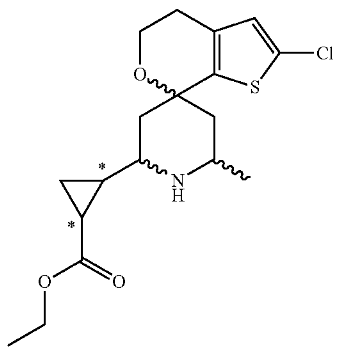 [SMILES: CCOC(=O)C1CC1C1CC2(CC(C)N1)OCCc1cc(Cl)sc12] | | ¹H NMR (300 MHz, Chloroform-d) δ 8.43 (s, 1H), 8.38 (s, 1H), 6.60 (s, 1H), 4.08 (qd, J = 7.1, 2.3 Hz, 2H), 3.87 (td, J = 5.6, 3.1 Hz, 2H), 3.70-3.28 (m, 2H), 2.78 (d, J = 10.8 Hz, 1H), 2.61 (q, J = 5.0, 4.4 Hz, 2H), 2.38-2.07 (m, 3H), 1.95 (t, J = 13.3 Hz, 1H), 1.70 (s, 1H), 1.53 (dt, J = 8.9, 4.4 Hz, 1H), 1.39 (dd, J = 6.5, 1.7 Hz, 3H), 1.33-0.97 (m, 5H); 370.31 |
| 376[2] | 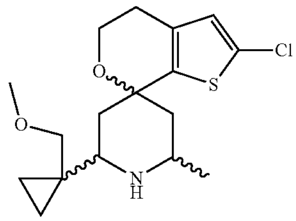 [SMILES: COCC1(C2CC3(CC(C)N2)OCCc2cc(Cl)sc23)CC1] | | ¹H NMR (300 MHz, Chloroform-d) δ 8.44 (d, J = 1.9 Hz, 2H), 6.61 (s, 1H), 3.87 (t, J = 5.4 Hz, 2H), 3.78-3.45 (m, 2H), 3.38 (d, J = 3.0 Hz, 3H), 3.15 (d, J = 12.2 Hz, 2H), 2.61 (t, J = 5.4 Hz, 2H), 2.16 (td, J = 10.4, 9.0, 2.8 Hz, 2H), 2.05 (d, J = 13.4 Hz, 1H), 1.82 (t, J = 13.2 Hz, 1H), 1.38 (d, J = 6.6 Hz, 3H), 1.02 (s, 1H), 0.65 (p, J = 5.6 Hz, 2H), 0.51 (t, J = 9.5 Hz, 1H); 342.32 |
| 377[2] | 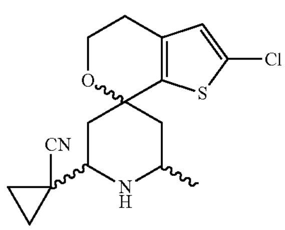 [SMILES: CC1CC2(CC(C3(C#N)CC3)N1)OCCc1cc(Cl)sc12] | | ¹H NMR (300 MHz, Chloroform-d) δ 8.26 (s, 2H), 6.60 (s, 1H), 4.13-3.60 (m, 2H), 3.44 (ddd, J = 12.0, 6.5, 2.8 Hz, 1H), 2.75 (dd, J = 12.0, 2.8 Hz, 1H), 2.61 (q, J = 5.2 Hz, 2H), 2.26 (dt, J = 14.2, 2.7 Hz, 1H), 2.19-2.01 (m, 2H), 1.76 (dd, J = 14.4, 11.9 Hz, 1H), 1.53-1.32 (m, 3H), 1.30 (d, J = 6.4 Hz, 3H), 1.06-0.82 (m, 1H); 323.26 |
| 378[3] | 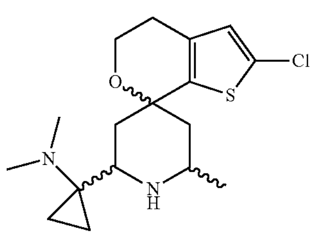 [SMILES: CC1CC2(CC(C3(N(C)C)CC3)N1)OCCc1cc(Cl)sc12] | | ¹H NMR (400 MHz, Methanol-d₄) δ 6.75 (s, 1H), 3.95 (t, J = 5.5 Hz, 2H), 3.70 (ddt, J = 13.3, 6.8, 3.4 Hz, 1H), 3.21 (d, J = 12.2 Hz, 1H), 2.64 (td, J = 5.4, 1.5 Hz, 2H), 2.42 (s, 6H), 2.30 (ddt, J = 14.4, 9.2, 2.7 Hz, 2H), 1.98 (dd, J = 14.5, 12.4 Hz, 1H), 1.80 (dd, J = 14.9, 12.2 Hz, 1H), 1.39 (d, J = 6.6 Hz, 3H), 1.27-1.04 (m, 2H), 0.93 (dd, J = 11.3, 4.8 Hz, 1H), 0.75 (dd, J = 11.0, 5.0 Hz, 1H); 341.37 |

Note:

[1]Compounds 374 and 375 were separated with silica gel chromatography and eluted with 0% to 70% EtOAc/EtOH (3:1) in heptane, followed by reversed-phase HPLC. Method: Waters XSelect CSH C18 OBD Prep Column; 30 × 150 mm, 5 micron. Gradient: acetonitrile in water with 0.2% formic acid.

[2]Purification by reversed-phase HPLC. Method: Waters XSelect CSH C18 OBD Prep Column; 30 × 150 mm, 5 micron. Gradient: acetonitrile in water with 0.2% formic acid.

[3]Purification by reversed-phase HPLC. Method: Waters XSelect CSH C18 OBD Prep Column; 30 × 150 mm, 5 micron. Gradient: acetonitrile in water with 0.1% trifluoroacetic acid.

Compound 379

N-[1-[(2'S,6'S, 7S)-2-chloro-6'-methyl-spiro[4,5-dihydrothieno[2,3-c]pyran-7,4'-piperidine]-2'-yl]cyclopropyl]acetamide (379)

Compound 380

[1-[(2'S,6'S, 7S)-2-chloro-6'-methyl-spiro[4,5-dihydrothieno[2,3-c]pyran-7,4'-piperidine]-2'-yl]cyclopropyl]methanol (380)

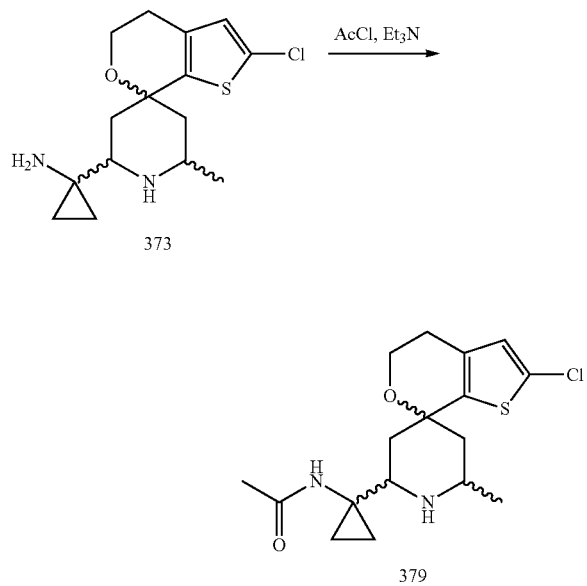

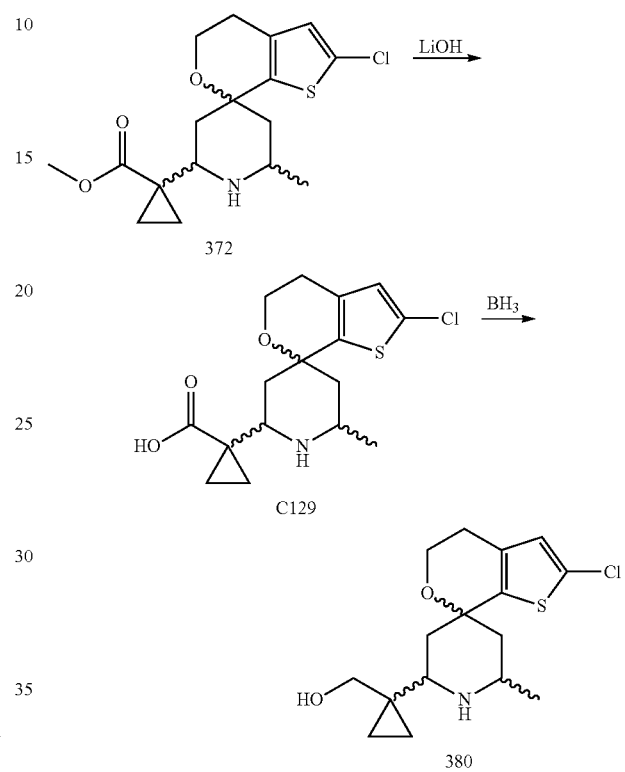

At 0° C., to a mixture of 1-[(2'S,6'S,7S)-2-chloro-6'-methyl-spiro[4,5-dihydrothieno[2,3-c]pyran-7,4'-piperidine]-2'-yl]cyclopropanamine 373 (14.5 mg, 0.044 mmol) in DCM (200 µL) was added N,N-diethylethanamine (20 µL, 0.13 mmol) and acetyl chloride (3 µL, 0.04 mmol). After 30 minutes, the reaction was quenched with saturated NaHCO$_3$ solution and extracted with EtOAc (4×). The combined organic layer was dried over Na$_2$SO$_4$, filtered, and concentrated. Purification by reversed-phase HPLC (Method: Waters XSelect CSH C18 OBD Prep Column; 30×150 mm, 5 micron. Gradient: acetonitrile in water with 5 mM hydrochloric acid) afforded the product N-[1-[(2'S,6'S,7S)-2-chloro-6'-methyl-spiro[4,5-dihydrothieno[2,3-c]pyran-7,4'-piperidine]-2'-yl]cyclopropyl]acetamide (hydrochloride salt) 379 (4.9 mg, 27% yield). Due to partial erosion of enantiomeric purity when preparing 373, 379 was isolated as a mixture of enantiomers where the (2'S,6'S,7S) configuration was the major enantiomer. $^1$H NMR (300 MHz, Chloroform-d) δ 9.40 (s, 1H), 9.07 (s, 1H), 7.48 (s, 1H), 6.60 (s, 1H), 3.87 (s, 2H), 3.69 (s, 1H), 3.36 (s, 1H), 2.61 (d, J=7.0 Hz, 2H), 2.29 (d, J=14.7 Hz, 1H), 2.20-1.97 (m, 5H), 1.86 (t, J=13.3 Hz, 1H), 1.64 (s, 3H), 1.18 (s, 1H), 1.08 (s, 1H), 0.96 (s, 1H). LCMS m/z 355.28 [M+H]$^+$. The site of N-acylation was tentatively assigned.

Step 1. 1-[(2'S,6'S, 7S)-2-chloro-6'-methyl-spiro[4,5-dihydrothieno[2,3-c]pyran-7,4'-piperidine]-2'-yl]cyclopropanecarboxylic acid (C129)

To a mixture of methyl 1-[(2'S,6'S,7S)-2-chloro-6'-methyl-spiro[4,5-dihydrothieno[2,3-c]pyran-7,4'-piperidine]-2'-yl]cyclopropanecarboxylate 372 (82 mg, 0.22 mmol) in THF (500 µL) was added an aqueous (500 µL) solution of LiOH (26 mg, 1.1 mmol). The reaction mixture was heated to 50° C. for 2 hours, and additional THF (1 mL) was added to help dissolve the starting material. After heating for almost 3 days, the reaction was cooled to room temperature. The reaction mixture was then concentrated to remove the solvent and redissolved in DMSO. Purification by reversed-phase HPLC (Method: Waters XSelect CSH C18 OBD Prep Column; 30×150 mm, 5 micron. Gradient: acetonitrile in water with 5 mM hydrochloric acid) was isolated as 1-[(2'S,6'S,7S)-2-chloro-6'-methyl-spiro[4,5-dihydrothieno[2,3-c]pyran-7,4'-piperidine]-2'-yl]cyclopropanecarboxylic acid C129 (58 mg, 77% yield). Due to partial erosion of enantiomeric purity when preparing 372, C129 was isolated as a mixture of enantiomers where the (2'S,6'S,7S) configuration was the major enantiomer. $^1$H NMR (300 MHz, DMSO-d6) δ 12.98 (s, 1H), 6.93 (s, 1H), 3.89 (t, J=5.4 Hz, 2H), 3.48 (s, 2H), 2.58 (s, 3H), 2.22-1.84 (m, 4H), 1.29 (d, J=6.3 Hz, 3H), 1.27-1.11 (m, 2H), 1.02 (s, 1H). LCMS m/z 342.27 [M+H]$^+$.

Step 2. [1-[(2'S,6'S, 7S)-2-chloro-6'-methyl-spiro[4,5-dihydrothieno[2,3-c]pyran-7,4'-piperidine]-2'-yl]cyclopropyl]methanol (380)

1-[(2'S,6'S,7S)-2-chloro-6'-methyl-spiro[4,5-dihydrothieno[2,3-c]pyran-7,4'-piperidine]-2'-yl]cyclopropanecarboxylic acid C129 (15 mg, 0.044 mmol) was dissolved in THF (200 μL) in a vial. The vial was cooled to 0° C. under nitrogen. Borane tetrahydrofuran complex (175 μL of 1 M, 0.1750 mmol) was slowly added, and significant bubbling was observed. The mixture was allowed to slowly warm to room temperature. After 4 hours, the reaction was quenched with saturated NaHCO₃ solution and extracted with DCM (5×). The combined organic layer was dried over Na₂SO₄, filtered, and concentrated in vacuo. Purification by reversed-phase HPLC (Method: Waters XSelect CSH C18 OBD Prep Column; 30×150 mm, 5 micron. Gradient: acetonitrile in water with 0.2% formic acid) afforded the product [1-[(2'S,6'S,7S)-2-chloro-6'-methyl-spiro[4,5-dihydrothieno[2,3-c]pyran-7,4'-piperidine]-2'-yl]cyclopropyl]methanol (formic acid salt) 380 (6.9 mg, 42% yield). Due to partial erosion of enantiomeric purity when preparing C129, 380 was isolated as a mixture of enantiomers where the (2'S,6'S,7S) configuration was the major enantiomer. ¹H NMR (400 MHz, Methanol-d₄) δ 6.74 (s, 1H), 3.93 (t, J=5.5 Hz, 2H), 3.86 (dd, J=11.7, 1.5 Hz, 1H), 3.66-3.47 (m, 1H), 3.24 (d, J=11.7 Hz, 1H), 3.06 (dd, J=12.4, 2.6 Hz, 1H), 2.63 (t, J=5.5 Hz, 2H), 2.27 (ddt, J=16.7, 14.2, 2.8 Hz, 2H), 2.10 (dd, J=14.6, 12.5 Hz, 1H), 1.85 (dd, J=14.7, 12.2 Hz, 1H), 1.36 (d, J=6.6 Hz, 3H), 0.93-0.79 (m, 1H), 0.79-0.67 (m, 1H), 0.56 (ddt, J=17.2, 9.5, 5.4 Hz, 2H). LCMS m/z 328.28 [M+H]⁺.

Compound 381

(2'R,6'S, 7S)-2-chloro-2'-cyclopropyl-6'-(1-methyl-triazol-4-yl)spiro[4,5-dihydrothieno[2,3-c]pyran-7,4'-piperidine] (381)

Step 1. tert-butyl (2S,3R,6R)-6-cyclopropyl-2-(1-methyltriazol-4-yl)-4-oxo-piperidine-3-carboxylate (C131)

To a solution of (3R)-3-(tert-butoxycarbonylamino)-3-cyclopropyl-propanoic acid C130 (500 mg, 2.181 mmol) in THF (4.5 mL) was added CDI (390 mg, 2.405 mmol), and the mixture was stirred at room temperature for 3 hours. Bis[(3-tert-butoxy-3-oxo-propanoyl)oxy]magnesium C109 (449 mg, 1.310 mmol) was added. After 20 hours, the reaction was diluted with MBTE (10 mL) and 1 N HCl (3 mL). The organic layer was separated and washed with saturated aqueous sodium bicarbonate (3 mL) and brine (3 mL), dried with magnesium sulfate, filtered, and concentrated to yield tert-butyl (5R)-5-(tert-butoxycarbonylamino)-5-cyclopropyl-3-oxo-pentanoate.

The crude material was dissolved in DCM (4 mL) and TFA (1 mL, 13 mmol) was added. After 1 h 30 min, the solution was azeotroped three times with DCM (4 mL).

The crude material from the second step was dissolved in DCM (4 mL) and 1-methyltriazole-4-carbaldehyde (250 mg, 2.250 mmol) was added. After stirring over 2 days, the mixture was directly loaded onto a silica gel column for purification (Gradient: 0-10% MeOH in DCM). The product-containing fractions were pooled and concentrated to yield tert-butyl (2S,3R,6R)-6-cyclopropyl-2-(1-methyltriazol-4-yl)-4-oxo-piperidine-3-carboxylate C131 (432 mg, 62% yield). ¹H NMR (400 MHz, Chloroform-d) δ 10.17 (s, 1H), 8.11 (s, 1H), 7.50 (s, 1H), 4.22 (s, 3H), 4.09-4.04 (m, 1H), 2.67-2.64 (m, 1H), 2.49-2.39 (m, 2H), 1.39 (s, 9H), 0.95 (dq, J=8.1, 2.7 Hz, 1H), 0.57 (dd, J=8.2, 1.5 Hz, 2H), 0.32-0.24 (m, 2H).

Step 2. (2'R,6'S, 7S)-2-chloro-2'-cyclopropyl-6'-(1-methyltriazol-4-yl)spiro[4,5-dihydrothieno[2,3-c]pyran-7,4'-piperidine] (381)

To a mixture of tert-butyl (2S,3R,6R)-6-cyclopropyl-2-(1-methyltriazol-4-yl)-4-oxo-piperidine-3-carboxylate C131 (25 mg, 0.078 mmol) in DCM (0.5 mL) was added

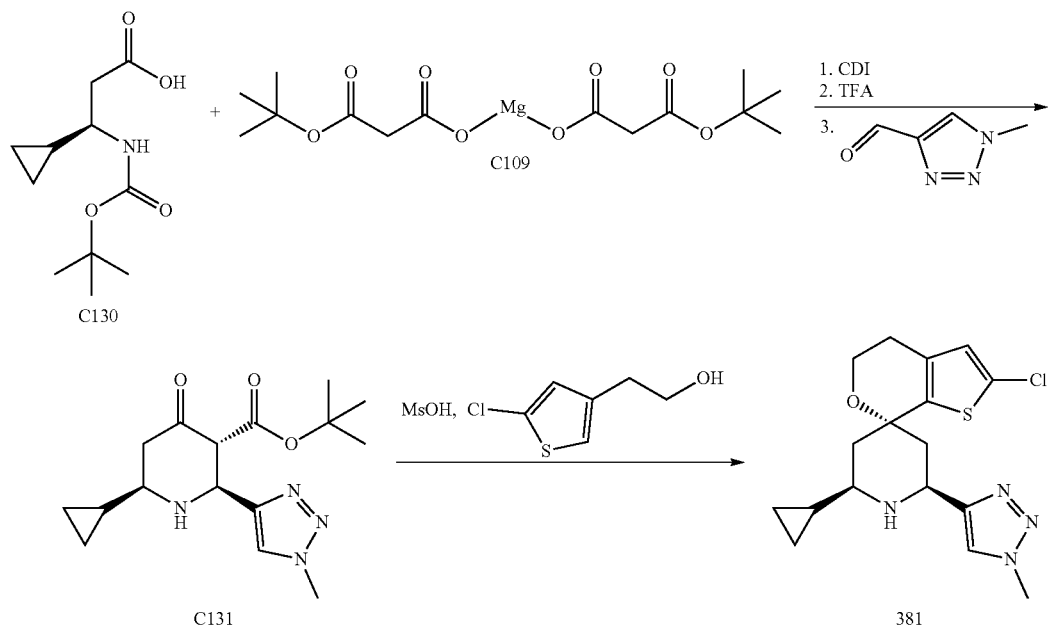

MsOH (20 μL, 0.3082 mmol) and the reaction was refluxed. After 1 hour, 2-(5-chloro-3-thienyl)ethanol S2 (20 mg, 0.1230 mmol) was added. The reaction was stirred overnight. The mixture was cooled to room temperature and diluted with additional DCM (2 mL) and saturated aqueous sodium bicarbonate (2 mL). The organic layer was separated and loaded onto a silica gel column for purification (Gradient: 0-10% MeOH in DCM). The product-containing fractions were found to be still under the purity threshold desired, so the combined fractions were concentrated and rediluted in DMSO. Purification by reversed-phase HPLC. Method: Waters XSelect CSH C18 OBD Prep Column; 30×150 mm, 5 micron. Gradient: acetonitrile in water with 0.1% trifluoroacetic acid. The product-containing fractions were diluted with DCM (1 mL) and saturated aqueous sodium bicarbonate (1 mL). The organic layer was dried to yield (2'R,6'S,7S)-2-chloro-2'-cyclopropyl-6'-(1-methyltriazol-4-yl)spiro[4,5-dihydrothieno[2,3-c]pyran-7,4'-piperidine] 381 (5.3 mg, 18% yield). $^1$H NMR (400 MHz, Chloroform-d) δ 7.45 (s, 1H), 6.58 (s, 1H), 4.35 (dd, J=11.7, 2.6 Hz, 1H), 4.06 (s, 3H), 3.99-3.85 (m, 2H), 2.68-2.50 (m, 2H), 2.38-2.25 (m, 2H), 2.20 (dt, J=13.6, 2.6 Hz, 1H), 1.80 (dd, J=13.5, 11.7 Hz, 2H), 1.65 (dd, J=13.6, 11.4 Hz, 1H), 0.79 (qt, J=8.5, 4.9 Hz, 1H), 0.46 (tdd, J=10.3, 8.3, 5.4 Hz, 2H), 0.23-0.12 (m, 2H). LCMS m/z 365.3 [M+H]$^+$.

Compound 382

(2'R,4S,6'S, 7S)-2-chloro-2'-cyclopropyl-6'-(1-methyltriazol-4-yl)spiro[4,5-dihydrothieno[2,3-c]pyran-7, 4'-piperidine]-4-ol (382)

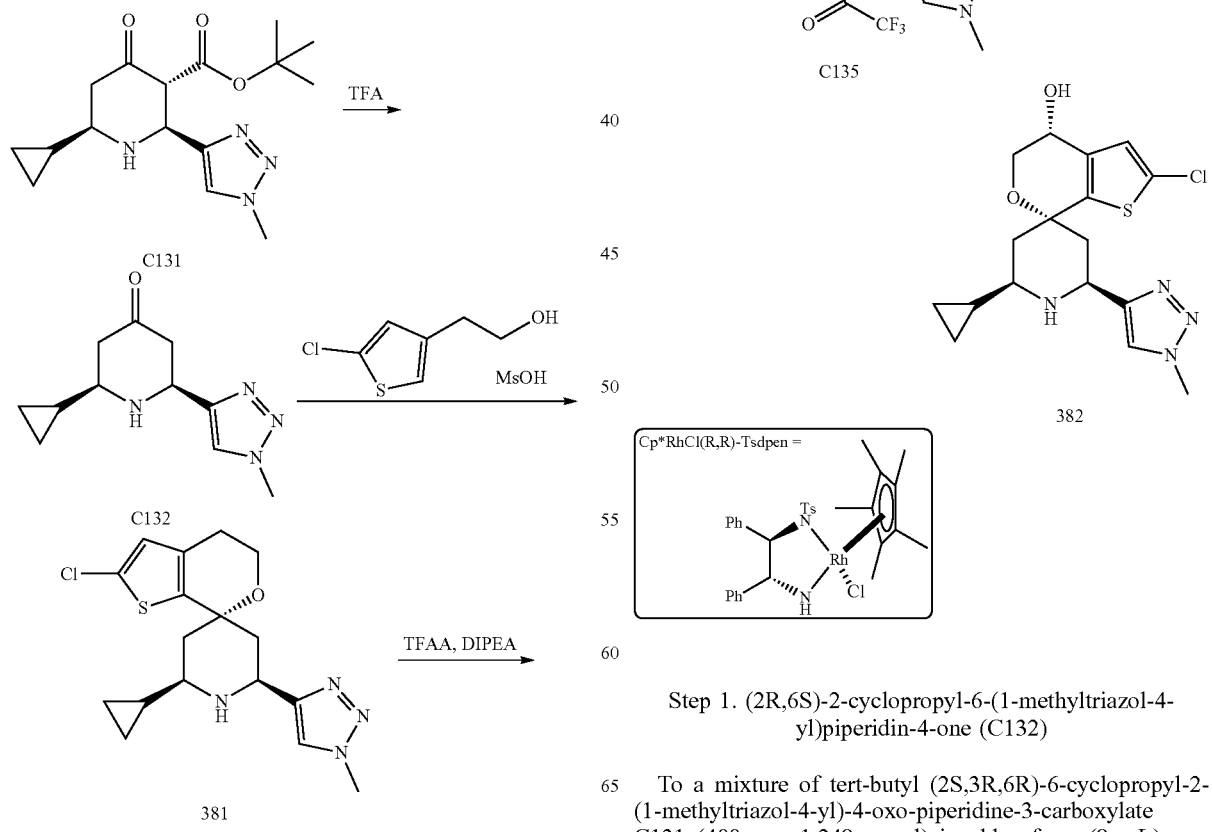

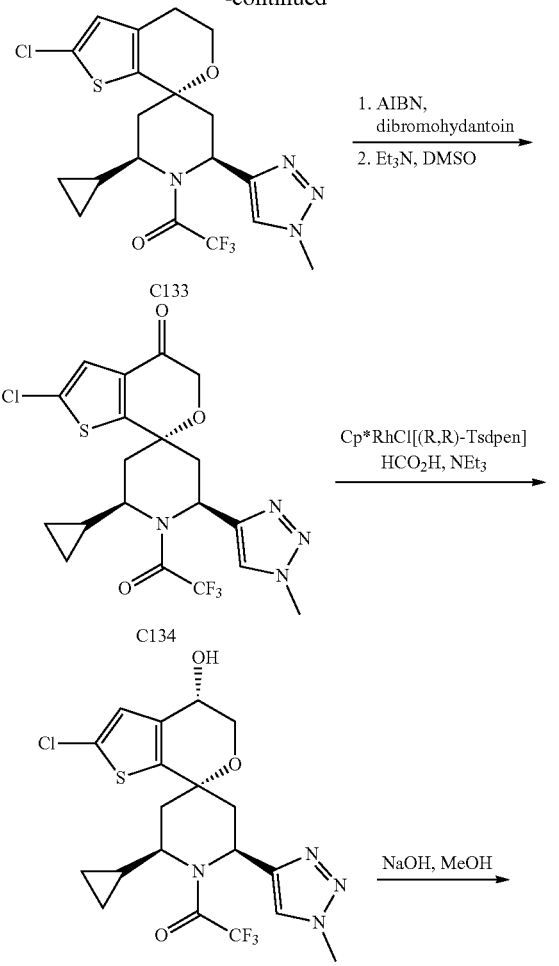

Step 1. (2R,6S)-2-cyclopropyl-6-(1-methyltriazol-4-yl)piperidin-4-one (C132)

To a mixture of tert-butyl (2S,3R,6R)-6-cyclopropyl-2-(1-methyltriazol-4-yl)-4-oxo-piperidine-3-carboxylate C131 (400 mg, 1.248 mmol) in chloroform (8 mL) was added 2,2,2-trifluoroacetic acid (500 µL, 6.490 mmol) and the reaction was refluxed. After stirring overnight, the mixture was cooled to room temperature, diluted with DCM (10 mL), and washed with saturated aqueous sodium bicarbonate (10 mL). The organic layer was dried with magnesium sulfate, filtered, and concentrated and then minimally diluted in DCM and loaded onto a silica gel column for purification (Gradient: 0-10% MeOH in DCM). The product-containing fractions were pooled and concentrated to yield (2R,6S)-2-cyclopropyl-6-(1-methyltriazol-4-yl)piperidin-4-one C132 (90 mg, 33% yield). $^1$H NMR (400 MHz, Chloroform-d) δ 7.50 (s, 1H), 4.22-4.15 (m, 1H), 4.12 (s, 3H), 2.67-2.64 (m, 2H), 2.61-2.56 (m, 1H), 2.47-2.40 (m, 1H), 2.19 (ddd, J=11.6, 8.7, 3.0 Hz, 1H), 0.95 (ddt, J=13.2, 8.4, 4.1 Hz, 1H), 0.59-0.52 (m, 2H), 0.33-0.21 (m, 2H).

Step 2. (2'R,6'S, 7S)-2-chloro-2'-cyclopropyl-6'-(1-methyltriazol-4-yl)spiro[4,5-dihydrothieno[2,3-c]pyran-7,4'-piperidine] (381)

To a mixture of (2R,6S)-2-cyclopropyl-6-(1-methyltriazol-4-yl)piperidin-4-one C132 (45 mg, 0.20 mmol) and 2-(5-chloro-3-thienyl)ethanol (43 mg, 0.26 mmol) in DCM (1000 µL) was added MsOH (90 µL, 1.4 mmol) and the mixture was refluxed. After stirring overnight, the mixture was cooled to room temperature and quenched with saturated aqueous sodium bicarbonate (1 mL). The layers were separated, and the organic layer was directly loaded onto a silica gel column for purification (Gradient: 0-10% MeOH in DCM). The product-containing fractions were pooled and concentrated to yield (2'R,6'S,7S)-2-chloro-2'-cyclopropyl-6'-(1-methyltriazol-4-yl)spiro[4,5-dihydrothieno[2,3-c]pyran-7,4'-piperidine] 381 (74 mg, 90% yield) as a yellow oil. LCMS m/z 365.15 [M+H]$^+$.

Step 3. 1-[(2'R,6'S, 7S)-2-chloro-2'-cyclopropyl-6'-(1-methyltriazol-4-yl)spiro[4,5-dihydrothieno[2,3-c]pyran-7,4'-piperidine]-1'-yl]-2,2,2-trifluoro-ethanone (C133)

To (2'R,6'S,7S)-2-chloro-2'-cyclopropyl-6'-(1-methyltriazol-4-yl)spiro[4,5-dihydrothieno[2,3-c]pyran-7,4'-piperidine] 381 (74 mg, 0.203 mmol) in DCM (1 mL) cooled to 0° C. was added DIPEA (50 µL, 0.2871 mmol), followed by TFAA (30 µL, 0.2158 mmol). After 35 minutes, the mixture was quenched with 1 N HCl (1 mL). The organic layer was separated and passed over a phase separator. The organic layer was loaded onto a silica gel column for purification (Gradient: 0-50% EtOAc in heptane). The product-containing fractions were pooled and concentrated to yield 1-[(2'R, 6'S,7S)-2-chloro-2'-cyclopropyl-6'-(1-methyltriazol-4-yl)spiro[4,5-dihydrothieno[2,3-c]pyran-7,4'-piperidine]-1'-yl]-2,2,2-trifluoro-ethanone C133 (51 mg, 50% yield) as a white solid. LCMS m/z 461.31 [M+H]$^+$.

Step 4. (2R,4S,6S)-2'-chloro-2-cyclopropyl-6-(1-methyltriazol-4-yl)-1-(2,2,2-trifluoroacetyl)spiro[piperidine-4,7'-thieno[2,3-c]pyran]-4'-one (C134)

A mixture of 1-[(2'R,6'S,7S)-2-chloro-2'-cyclopropyl-6'-(1-methyltriazol-4-yl)spiro[4,5-dihydrothieno[2,3-c]pyran-7,4'-piperidine]-1'-yl]-2,2,2-trifluoro-ethanone C133 (51 mg, 0.102 mmol) in chlorobenzene (1 mL) was vacuum purged with nitrogen 5 times. At this time, 5,5-dimethyl-1,3-dibromohydantoin (20 mg, 0.07 mmol) and 2-[(E)-(1-cyano-1-methyl-ethyl)azo]-2-methyl-propanenitrile (1.5 mg, 0.009 mmol) were added, and the mixture was once again vacuum purged 5 times. The mixture was heated to 75° C. After 15 minutes, the mixture was cooled to room temperature and mixed with saturated aqueous sodium bicarbonate (1 mL). The organic layer was separated, the aqueous layer was washed with ethyl acetate (1 mL), and the combined organic layer was dried with magnesium sulfate, filtered, and concentrated. The material was dried overnight to remove residual solvent.

The crude foam was diluted with DMSO (1 mL) in a flame-dried flask and vacuum purged with nitrogen 5 times. The mixture was heated to 60° C., triethylamine (75 µL, 0.54 mmol) was added, and the dark brown solution was heated further to 65° C. (internal temperature). After 75 minutes, the mixture was cooled to room temperature and diluted with water (5 mL) and ethyl acetate (5 mL). The aqueous layer was washed with ethyl acetate (2×5 mL), and then the combined organic layer was dried with sodium sulfate, filtered, and concentrated. The crude material was diluted with minimal DCM and loaded onto a silica gel column for purification (Gradient: 0-50% EtOAc in heptane). The product-containing fractions were pooled and concentrated to yield (2R,4S,6S)-2'-chloro-2-cyclopropyl-6-(1-methyltriazol-4-yl)-1-(2,2,2-trifluoroacetyl)spiro[piperidine-4,7'-thieno[2,3-c]pyran]-4'-one C134 (16 mg, 32%) as a white solid. LCMS m/z 475.21 [M+H]$^+$.

Step 5. 1-[(2'R,4S,6'S, 7S)-2-chloro-2'-cyclopropyl-4-hydroxy-6'-(1-methyltriazol-4-yl)spiro[4,5-dihydrothieno[2,3-c]pyran-7,4'-piperidine]-1'-yl]-2,2,2-trifluoro-ethanone (C135)

To a mixture of 5:2 diethylethanamine/formic acid (20 µL, 0.04763 mmol) in ACN (500 µL) was added a solution of N-[(1R,2R)-2-amino-1,2-diphenyl-ethyl]-4-methyl-benzenesulfonamide (0.12 mg, 3.274E-4 mmol) and 1,2,3,4,5-pentamethylcyclopentane rhodium(2+) tetrachloride (0.1 mg, 1.592E-4 mmol) in ACN (50 µL). After 5 minutes, the solution was added to (2R,4S,6S)-2'-chloro-2-cyclopropyl-6-(1-methyltriazol-4-yl)-1-(2,2,2-trifluoroacetyl)spiro[piperidine-4,7'-thieno[2,3-c]pyran]-4'-one C134 (16 mg, 0.03203 mmol), and the reaction was stirred at −10° C. and warmed slowly overnight. At this time, the mixture was concentrated and directly loaded onto a silica gel column for purification (Gradient: 0-50% EtOAc in heptane). The product-containing fractions were pooled and concentrated to yield 1-[(2'R,4S,6'S,7S)-2-chloro-2'-cyclopropyl-4-hydroxy-6'-(1-methyltriazol-4-yl)spiro[4,5-dihydrothieno[2,3-c]pyran-7,4'-piperidine]-1'-yl]-2,2,2-trifluoro-ethanone C135 (15 mg, 100%). LCMS m/z 477.24 [M+H]$^+$.

Step 6. (2'R,4S,6'S, 7S)-2-chloro-2'-cyclopropyl-6'-(1-methyltriazol-4-yl)spiro[4,5-dihydrothieno[2,3-c]pyran-7,4'-piperidine]-4-ol (382)

1-[(2'R,4S,6'S,7S)-2-chloro-2'-cyclopropyl-4-hydroxy-6'-(1-methyltriazol-4-yl)spiro[4,5-dihydrothieno[2,3-c]pyran-7,4'-piperidine]-1'-yl]-2,2,2-trifluoro-ethanone C135 (15 mg, 0.03 mmol) was dissolved in MeOH (0.2 mL) and heated to 60° C., at which point NaOH (50 µL of 6 M, 0.30 mmol) was added. After stirring for 7 hours, near full conversion was observed. The mixture was diluted with water (1 mL). Purification by reversed-phase HPLC (Method: Waters XSelect CSH C18 OBD Prep Column; 30×150 mm, 5 micron. Gradient: acetonitrile in water with 0.1% trifluoroacetic acid) afforded (2'R,4S,6'S,7S)-2-chloro-2'-cyclopropyl-6'-(1-methyltriazol-4-yl)spiro[4,5-dihydrothieno[2,3-c]pyran-7,4'-piperidine]-4-ol (trifluoroacetate salt) 382 (11.7 mg, 74% yield over 2 steps) as a white solid. ¹H NMR (400 MHz, Methanol-d₄) δ 8.03 (s, 1H), 6.95 (s, 1H), 4.49 (t, J=3.4 Hz, 1H), 4.13 (s, 3H), 4.04 (dd, J=12.2, 3.3 Hz, 1H), 3.86 (dd, J=12.2, 3.7 Hz, 1H), 3.32 (d, J=1.8 Hz, 1H), 2.99 (s, 1H), 2.64-2.50 (m, 2H), 2.28 (dd, J=14.8, 12.6 Hz, 1H), 2.12-2.01 (m, 1H), 1.02 (dd, J=8.7, 4.8 Hz, 1H), 0.74 (d, J=8.1 Hz, 2H), 0.65-0.59 (m, 1H), 0.42 (s, 1H). LCMS m/z 381.28 [M+H]⁺.

Compound 383

(2'R,4S,6'S, 7S)-2-chloro-2'-cyclopropyl-6'-(1-methyltriazol-4-yl)spiro[4,5-dihydrothieno[2,3-c]pyran-7,4'-piperidine]-4-ol (383)

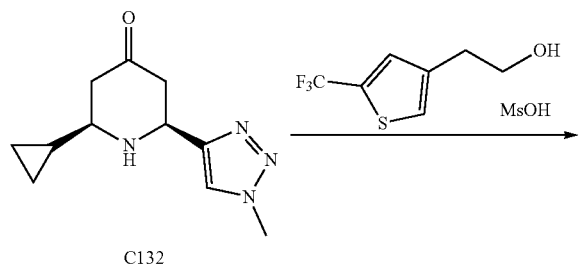

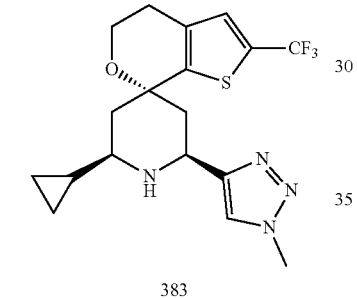

To a mixture of (2R,6S)-2-cyclopropyl-6-(1-methyltriazol-4-yl)piperidin-4-one C132 (45 mg, 0.20 mmol) and 2-[5-(trifluoromethyl)-3-thienyl]ethanol S3 (52 mg, 0.27 mmol) in DCM (1000 µL) was added MsOH (90 µL, 1.387 mmol) and the mixture was refluxed. After stirring overnight, the mixture was cooled to room temperature and quenched with saturated aqueous sodium bicarbonate (1 mL). The layers were separated, and the organic layer was directly loaded onto a silica gel column for purification (Gradient: 0-10% MeOH in DCM). The product-containing fractions were pooled and concentrated; however, UPLC analysis indicated presence of the intermediate. The product was dissolved in DMSO. Purification by reversed-phase HPLC (Method: Waters XSelect CSH C18 OBD Prep Column; 30×150 mm, 5 micron. Gradient: acetonitrile in water with 5 mM hydrochloric acid) afforded (2'R,6'S,7S)-2'-cyclopropyl-6'-(1-methyltriazol-4-yl)-2-(trifluoromethyl) spiro[4,5-dihydrothieno[2,3-c]pyran-7,4'-piperidine] (hydrochloride salt) 383 (18.7 mg, 21% yield) as a white solid. ¹H NMR (400 MHz, Methanol-d₄) δ 8.05 (s, 1H), 7.35 (s, 1H), 4.90-4.87 (m, 1H), 4.13 (s, 3H), 4.03 (t, J=5.4 Hz, 2H), 2.99 (s, 1H), 2.78 (d, J=2.4 Hz, 2H), 2.54 (d, J=17.3 Hz, 2H), 2.46-2.37 (m, 1H), 2.15-2.05 (m, 1H), 1.03 (s, 1H), 0.74 (d, J=8.2 Hz, 2H), 0.66-0.61 (m, 1H), 0.40 (s, 1H). LCMS m/z 399.3 [M+H]⁺.

Compound 384

(2'S,6'S, 7S)-2',4-dimethyl-6'-(1-methyltriazol-4-yl)-2-(trifluoromethyl)spiro[5H-thieno[2,3-c]pyran-7,4'-piperidine]-4-ol (384)

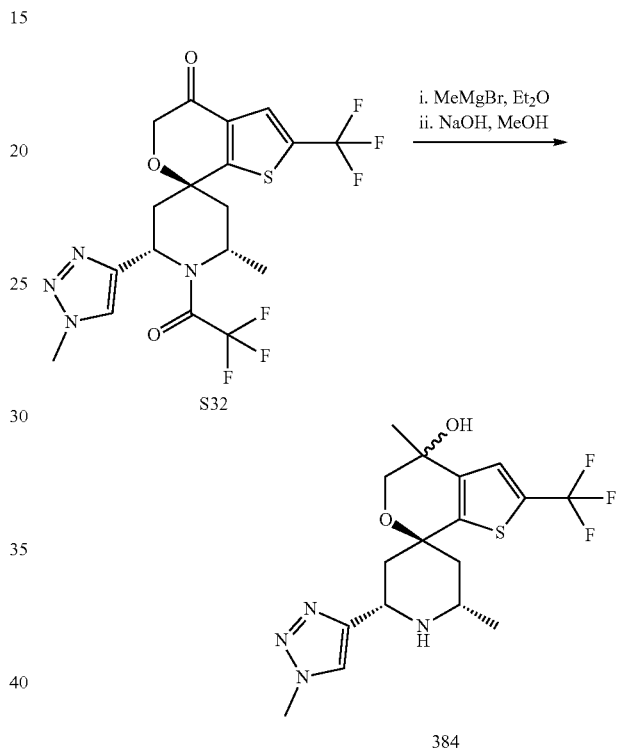

To a mixture of (2S,4S,6S)-2-methyl-6-(1-methyltriazol-4-yl)-1-(2,2,2-trifluoroacetyl)-2'-(trifluoromethyl)spiro[piperidine-4,7'-thieno[2,3-c]pyran]-4'-one S32 (53 mg, 0.1036 mmol) in diethyl ether (1 mL) cooled to 0° C. was added bromo(methyl)magnesium (35 µL of 3.4 M, 0.1190 mmol). The mixture was stirred at 0° C. for 5 minutes, then quenched with saturated ammonium chloride (2 mL) and diluted with TBME (3 mL). The organic layer was washed with brine and dried over MgSO₄, filtered, and concentrated to a crude residue.

To the crude residue diluted in MeOH (1 mL) was added NaOH (50 µL of 6 M, 0.3000 mmol). The mixture was stirred at 60° C. for 2 hours. The reaction mixture was directly purified by reversed-phase HPLC (Method: C18 Waters Sunfire column (30×150 mm, 5 micron). Gradient: MeCN in H₂O with 0.1% trifluoroacetic acid) to provide the product (2'S,6'S,7S)-2',4-dimethyl-6'-(1-methyltriazol-4-yl)-2-(trifluoromethyl)spiro[5H-thieno[2,3-c]pyran-7,4'-piperidine]-4-ol (Trifluoroacetate salt) 384 (10.6 mg, 20%) as a clear glassy solid. LCMS m/z 403.27 [M+1]⁺.

Compound 385

(2S,4S,4'S,6S)-2'-chloro-4, 5'5'-dideuterio-2-methyl-6-(1-methyltriazol-4-yl)spiro[piperidine-4,7'-thieno[2,3-c]pyran]-4'-ol (385)

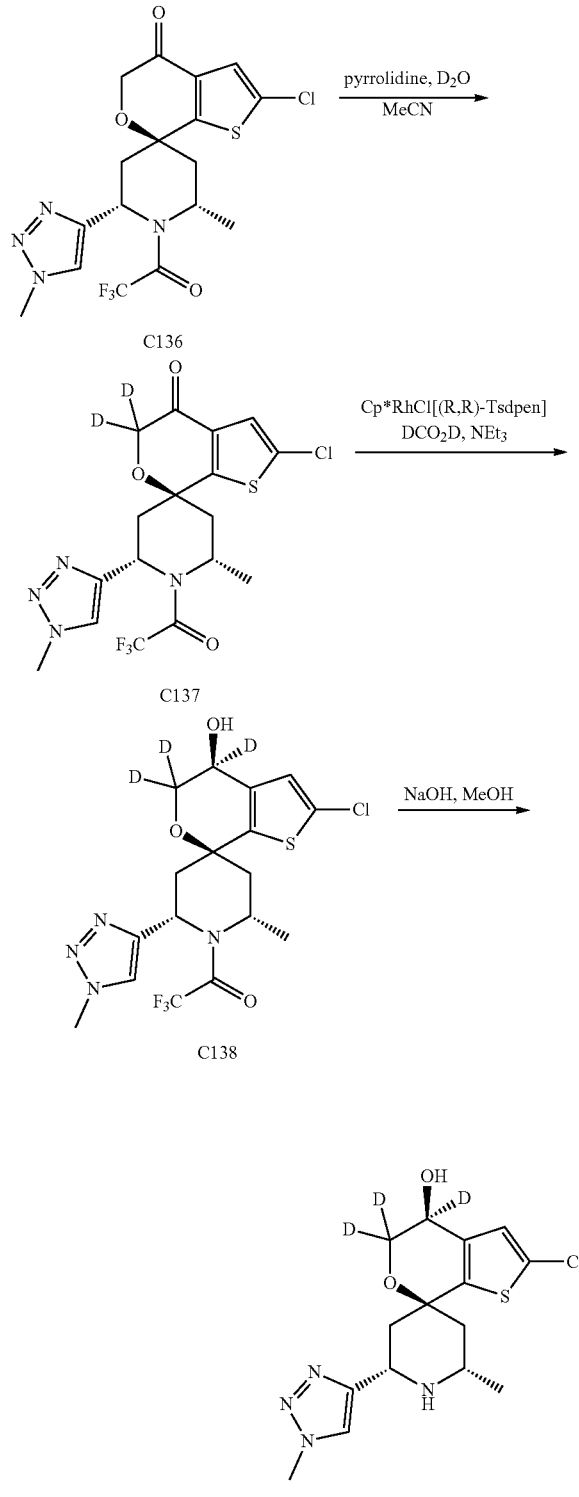

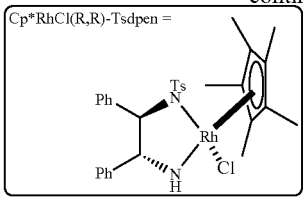

Step 1. (2S,4S,6S)-2'-chloro-5',5'-dideuterio-2-methyl-6-(1-methyltriazol-4-yl)-1-(2,2,2-trifluoro-acetyl)spiro[piperidine-4,7'-thieno[2,3-c]pyran]-4'-one (C137)

To a 40 mL vial was added (2S,4S,6S)-2'-chloro-2-methyl-6-(1-methyltriazol-4-yl)-1-(2,2,2-trifluoroacetyl)spiro[piperidine-4,7'-thieno[2,3-c]pyran]-4'-one C136 (404 mg, 0.817 mmol), followed by D2O (1.9 mL) and MeCN (5.6 mL). Then pyrrolidine (7 µL, 0.08 mmol) was added. Additional MeCN (1 mL) and dioxane (2 mL) were added, and the reaction mixture was heated to 75° C. After 18 hours, the reaction mixed was washed with water and extracted with EtOAc (3×). The combined organic layer was washed with brine, dried over Na2SO4, filtered, and concentrated in vacuo. Purification by silica gel chromatography (Gradient: 0 to 50% EtOAc in heptane) afforded (2S,4S,6S)-2'-chloro-5',5'-dideuterio-2-methyl-6-(1-methyltriazol-4-yl)-1-(2,2,2-trifluoroacetyl)spiro[piperidine-4,7'-thieno[2,3-c]pyran]-4'-one C137 (366 mg, 97%). LCMS m/z 451.15 [M+H]$^+$. 97.5% D based on $^1$H NMR.

Step 2. 1-[(2S,4S,4'S,6S)-2'-chloro-4',5',5'-trideuterio-4'-hydroxy-2-methyl-6-(1-methyltriazol-4-yl)spiro[piperidine-4,7'-thieno[2,3-c]pyran]-1-yl]-2,2,2-trifluoro-ethanone (C138)

To a mixture of HCOOH-d4 (23 µL, 0.6095 mmol) and triethylamine (32 µL, 0.23 mmol) in DCM (500 µL) was added a solution of 1,2,3,4,5-pentamethylcyclopentane rhodium(2+) tetrachloride (0.195 mg, 3.104E-4 mmol) and N-[(1R,2R)-2-amino-1,2-diphenyl-ethyl]-4-methyl-benzenesulfonamide (0.222 mg, 6.058E-4 mmol) in DCM (60 µL). After 5 minutes, (2S,4S,6S)-2'-chloro-5',5'-dideuterio-2-methyl-6-(1-methyltriazol-4-yl)-1-(2,2,2-trifluoroacetyl)spiro[piperidine-4,7'-thieno[2,3-c]pyran]-4'-one C137 (50 mg, 0.11 mmol) in DCM (500 µL) was added. The resulting orange reaction mixture was stirred at room temperature overnight. The reaction was washed with saturated aqueous sodium bicarbonate, 1 N HCl, and brine, and the aqueous layers were extracted with EtOAc separately. The combined organic layer was dried over Na2SO4, filtered, and concentrated in vacuo. Purification by silica gel chromatography (Gradient: 0-50% EtOAc in heptane) afforded the product 1-[(2S,4S,4'S,6S)-2'-chloro-4',5',5'-trideuterio-4'-hydroxy-2-methyl-6-(1-methyltriazol-4-yl)spiro[piperidine-4,7'-thieno[2,3-c]pyran]-1-yl]-2,2,2-trifluoro-ethanone C138 (45.8 mg, 93%). $^1$H NMR (300 MHz, Chloroform-d) δ 7.59 (s, 1H), 6.84 (s, 1H), 5.53 (s, 1H), 4.68-4.39 (m, 1H), 4.13-4.03 (m, 3H), 3.10 (dd, J=15.1, 7.4 Hz, 1H), 2.64 (ddd, J=15.1, 8.1, 2.2 Hz, 2H), 2.12 (s, 1H), 2.08 (s, 1H), 1.44-1.25 (m, 3H). LCMS m/z 454.17 [M+H]$^+$.

Step 3. (2S,4S,4'S,6S)-2'-chloro-4',5',5'-trideuterio-2-methyl-6-(1-methyltriazol-4-yl)spiro[piperidine-4,7'-thieno[2,3-c]pyran]-4'-ol (385)

To a solution of 1-[(2S,4S,4'S,6S)-2'-chloro-4',5',5'-trideuterio-4'-hydroxy-2-methyl-6-(1-methyltriazol-4-yl)spiro

[piperidine-4,7'-thieno[2,3-c]pyran]-1-yl]-2,2,2-trifluoroethanone C138 (45.8 mg, 0.1008 mmol) in MeOH (800 μL) was treated with an aqueous solution of NaOH (170 μL of 6 M, 1.020 mmol) and heated to 60° C. After 1 hour, the reaction vial was cooled to and quenched with saturated aqueous NaHCO₃ solution and extracted with EtOAc (4×). The combined organic layer was dried over sodium sulfate and concentrated in vacuo. Purification by silica gel chromatography (Gradient: 0-12% MeOH in DCM) afforded the product (2S,4S,4'S,6S)-2'-chloro-4',5',5'-trideuterio-2-methyl-6-(1-methyltriazol-4-yl)spiro[piperidine-4,7'-thieno[2,3-c]pyran]-4'-ol 385 (24.3 mg, 61% yield). $^1$H NMR (400 MHz, Chloroform-d) δ 7.45 (s, 1H), 6.82 (s, 1H), 4.38 (dd, J=11.7, 2.6 Hz, 1H), 4.05 (s, 3H), 3.47 (s, 1H), 3.37 (dqd, J=12.7, 6.4, 2.5 Hz, 1H), 2.40 (dt, J=13.9, 2.6 Hz, 1H), 2.03 (dt, J=13.5, 2.6 Hz, 1H), 1.69 (dd, J=13.9, 11.8 Hz, 1H), 1.50 (dd, J=13.5, 11.3 Hz, 1H), 1.13 (d, J=6.3 Hz, 3H). LCMS m/z 358.13 [M+H]$^+$.

Preparation of Compound 4761

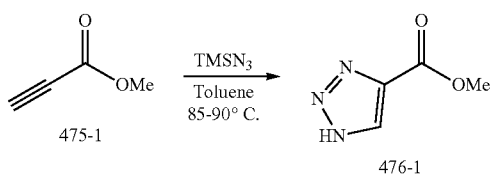

To a 500 mL three-necked RBF was added toluene (125 mL) and methyl propiolate (10.09 g, 1.0 eq.). TMSN₃ (27.65 g, 2.0 eq.) was slowly added at room temperature. The mixture was heated to 85-90° C. for 24 hours. The solution was cooled to 0° C. and diluted with THF (200 mL). Solid NaNO₂ (10.76 g, 1.3 eq.) was added to the mixture. To this was added 2.4 M HCl (aqueous) (63 mL, 1.3 eq.) dropwise while keeping the internal temperature at 0~10° C. After addition, the mixture was stirred for 1 hour at 0-10° C. The layers separated, and the aqueous layer was extracted with THF (2×200 mL). The combined organic extracts were washed with 3% NaHCO₃ (aqueous) (100 mL). The aqueous layer was extracted with THF (2×100 mL). The combined organic extracts were dried over Na₂SO₄, filtered, and concentrated under reduced pressure. The crude residue was washed with hexane (200 mL) and stirred for 1 hour at room temperature. The mixture was filtered, and the solid was washed with hexane (2×100 mL) to give a white powder (12.3 g, 81% yield). $^1$H NMR (400 MHz, DMSO): δ 8.53 (s, 1H), 3.83 (s, 3H).

Preparation of Compound 477-1a

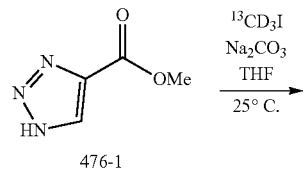

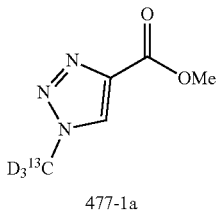

To a 500 mL three-necked round bottom flask was added THF (200 mL), 476-1 (14.8 g, 1.0 eq), and Na₂CO₃ (18.6 g, 1.5 eq) followed by slow, portionwise addition of $^{13}$CD₃I (20.0 g, 1.2 eq.). The mixture was stirred for 48 hours at 25° C. After reaction completion (TLC 1:1 Ethyl acetate: Hexane), the mixture was filtered through a Na₂SO₄ pad. The cake was rinsed with DCM and THF. The filtrate was concentrated under vacuum followed by dissolution in DCM (145 mL) and washed with 5% Na₂SO₃ (aqueous) (80 mL). The aqueous phase was extracted with DCM (4×80 mL). The combined organic extracts were concentrated and washed with hexane (6×300 mL). The solid was collected by filtration and dried to give 477-1a as a white powder (8.4 g, 50.6% yield). H NMR (400 MHz, DMSO): δ 8.70 (d, J=0.8 Hz, 1H), 3.82 (s, 3H), 3.32 (s, 3H).

Preparation of Compound 497a

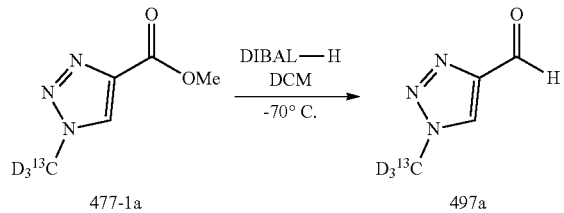

To a round bottom flask was added 477-1a (10.0 g, 68.9 mmol) and 240 mL of anhydrous DCM. The reaction mixture was cooled to −70° C. DIBAL (137 mL, 1M in DCM, 137.8 mmol) was added by addition funnel. The reaction mixture was stirred at −70° C. for 2 hours. Methanol (35 mL) was added at −70° C. by addition funnel and stirred for 1 hour. Sodium tartrate (40%, 170 mL) was added slowly. The mixture was stirred at room temperature overnight. The DCM layer was separated and the aqueous layer was extracted with DCM (4×150 mL). The combined organic extracts were concentrated, and hexanes (150 mL) was added to produce a white slurry, which was filtered and dried to give 497a (7.5 g, 94% yield) as a white solid. $^1$H NMR (400 MHz, CDCl₃) δ 10.14 (s, 1H) 8.09 (s, 1H).

Preparation of Compound 495a

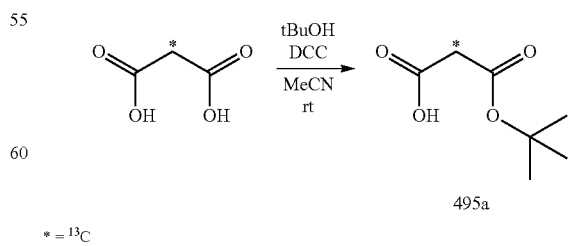

\* = $^{13}$C

To a round bottom flask was added tBuOH (28.2 g, 380.7 mmol), [2-$^{13}$C]malonic acid (20.0 g, 190.4 mmol) and MeCN (300 mL). DCC (43.2 g, 209.4 mmol) in MeCN (300 mL) was added at 5° C. in an ice-water bath. The white slurry was stirred at room temperature overnight. The reaction mixture was filtered and washed with MeCN (2×30 mL). The filtrate was concentrated to give a yellow oil, which was purified by silica gel flash chromatography (100% DCM to 4% MeOH in DCM) to provide 495a (20.7 g, 67% yield) as a colorless oil. $^1$H NMR (400 MHz, CDCl$_3$) δ 3.35 (d, J=132 Hz, 2H), 1.49 (s, 9H).

Preparation of Compound 496a

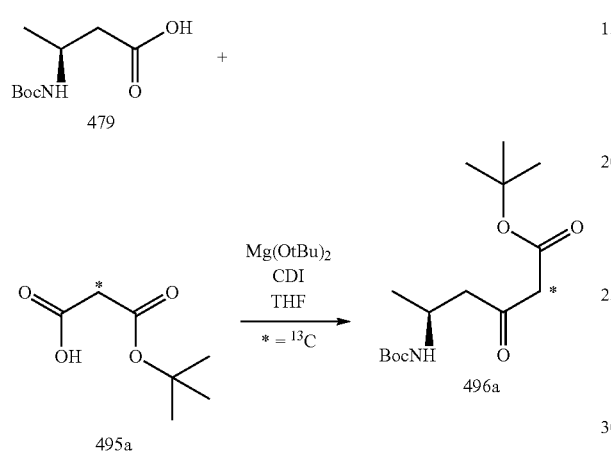

To a solution of compound 495a (19.50 g, 121.0 mmol) in THF (150 mL) was added Mg(OtBu)$_2$ (11.46 g, 60.50 mmol) in portions. After each addition, a minor exothermic was observed, with the round bottom flask being warm to the touch (~30° C.). The mixture was stirred at room temperature overnight. After 3 hours, the reaction was a clear, pale yellow solution. The mixture was concentrated via rotovap, and the residue was taken up in ether (50 mL) and concentrated again. This was repeated 3 times. The resulting solid was dried under vacuum to afford an off-white solid (21.20 g, 102% yield). In a separate flask, compound 479 (22.13 g, 108.9 mmol) in THF (230 mL) was treated with CDI (19.04 g, 117.4 mmol) in three portions. The reaction was stirred at room temperature under nitrogen and gas evolution was observed. After 3 hours, the previously prepared solid magnesium salt (21.20 g) was added and the reaction was stirred at room temperature overnight. The reaction mixture was poured into 1 N HCl (270 mL) and extracted with EtOAc (2×200 mL). The combined organic extracts were washed with saturated sodium bicarbonate (200 mL) and brine (200 mL), dried over sodium sulfate, and concentrated via rotovap to afford a brown oil (crude, 35.5 g). This material was taken up in THF (100 mL) and treated with 1 N NaOH (100 mL) and stirred at room temperature for 0.5 hour. This solution was diluted with water (300 mL) and extracted with EtOAc (3×300 mL). The combined organic extracts were washed with 0.5 HCl (100 mL) and brine (200 mL), dried over sodium sulfate, and concentrated via rotovap to give compound 496a (28.0 g, 85% yield) as a light yellow oil. $^1$H NMR (400 MHz, DMSO-d$_6$): δ 6.75 (d, J=7.2 Hz, 1H), 3.83 (p, J=7.2 Hz, 1H), 3.43 (d, J=132 Hz, 2H), 2.66-2.53 (m, 2H), 1.39 (s, 9H), 1.35 (s, 9H), 1.00 (d, J=6.8 Hz, 3H).

Preparation of Compound 498a

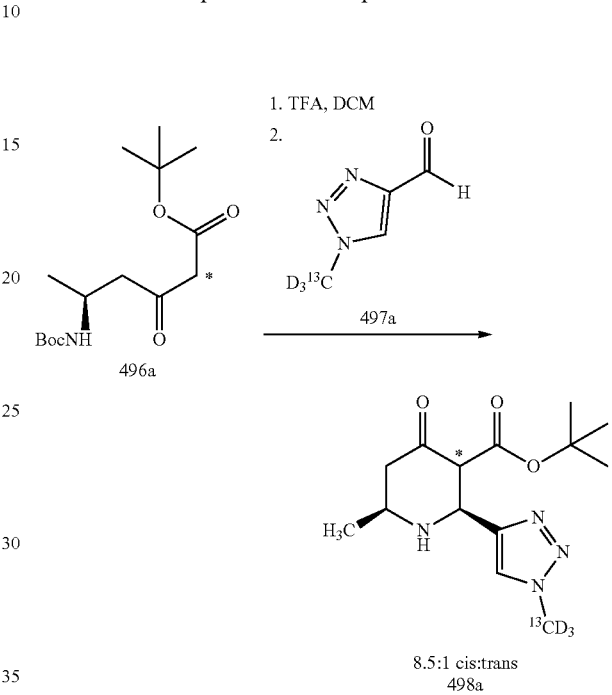

To a solution of compound 496a (28.0 g, 92.6 mmol) in DCM (110 mL) was added TFA (28.4 mL, 370.4 mmol) at room temperature. After 20 hours, TLC showed the reaction was completed. The mixture was concentrated via rotovap, and the residue brought up in DCM (100 mL) and concentrated again. This was repeated 3 times. The resulting solid was dried under vacuum to afford a pink solid (35.0 g). The solid was immediately dissolved in DCM (220 mL (sonicated to dissolve all solids)) and treated with compound 497a (10.13 g, 88.0 mmol). The reaction was stirred at room temperature overnight. TLC showed complete consumption of 497a and formation of the product. The reaction was quenched with saturated sodium bicarbonate (270 mL) and extracted with DCM (3×300 mL). The organic extracts were washed with brine (200 mL) and concentrated via rotovap to give crude solid (23.0 g). The crude solid was triturated in MTBE (70 mL) at room temperature for 1 hour. The white solid was collected via vacuum filtration, washed with cold MTBE (2×20 mL), and dried under high vacuum to afford compound 498a (14.1 g, 53% yield) as a white solid. $^1$H NMR (400 MHz, CDCl$_3$): δ 7.46 (s, 1H), 4.50 (d, J=10.8 Hz, 1H), 3.59 (dd, J=11.2, 132 Hz, 1H), 3.21-3.16 (m, 1H) 2.55-2.50 (m, 1H), 2.22-2.16 (m, 1H), 2.00-1.90 (br, 1H), 1.37 (s, 9H), 1.27 (d, J=6.4 Hz, 3H).

Preparations of Compounds 499a and 500a

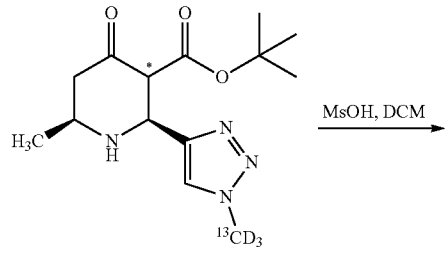

8:5:1 cis:trans

498a

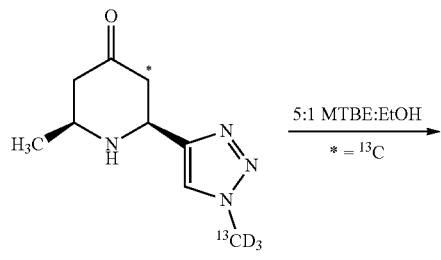

8:5:1 cis:trans

499a

* = ¹³C

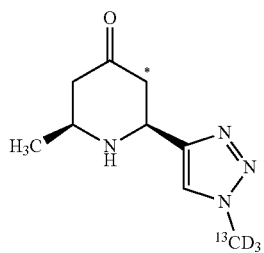

>20:1 cis:trans

500a

To a solution of compound 498a (14.1, 47.1 mmol) in DCM (180 mL) was added MsOH (15.3 mL, 235.5 mmol). The reaction was heated to 40° C. overnight and was monitored by TLC until the reaction was completed to give compound 499a. The reaction mixture was cooled to room temperature and quenched with saturated sodium bicarbonate solution, layers were separated, and the aqueous layer was extracted with DCM (5×120 mL). The combined organic extracts were concentrated via rotovap to afford compound 499a (crude, 9.15 g) as a pale yellow solid. The crude solid was triturated in MTBE (60 mL) for 3 hours, then filtered to give a white solid (8.30 g), which was further purified by silica gel flash chromatography (2-3% MeOH in DCM) to give pure compound 500a (6.80 g 72% yield). $^1$H NMR (400 MHz, CDCl$_3$): δ 7.45 (s, 1H), 4.23 (m, 1H), 3.18-3.10 (m, 1H), 2.84-2.72 (m, 1H), 2.49-2.41 (m, 1H+2× 0.5H), 2.21-2.14 (m, 2×0.5H), 2.06-1.90 (br s 1H), 1.25 (d, J=6.0 Hz, 3H).

Compound 386

(2S,4S,4'S,6S)-2-methyl-6-(1-(1$^{13}$C)methyltriazol-4-yl)-2'-(trifluoromethyl)spiro[(5$^{13}$C)azinane-4,7'-4,5-dihydrothieno[2,3-c]pyran]-4'-ol (386)

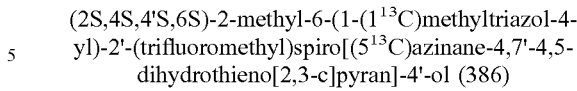

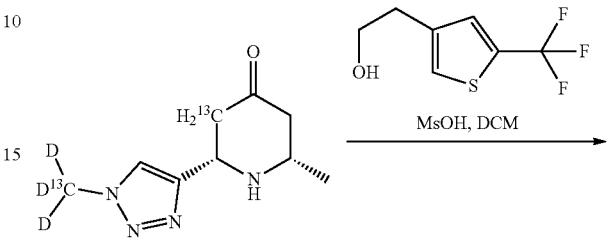

C139

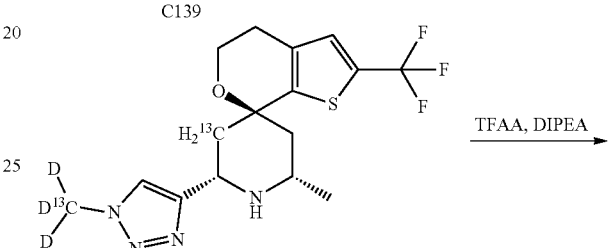

C140

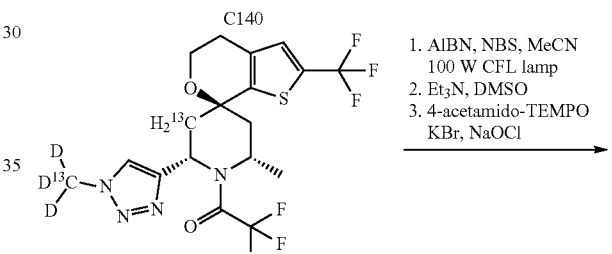

C141

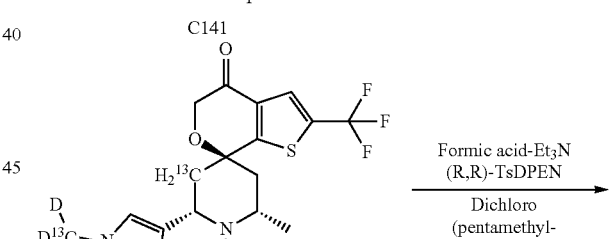

C142

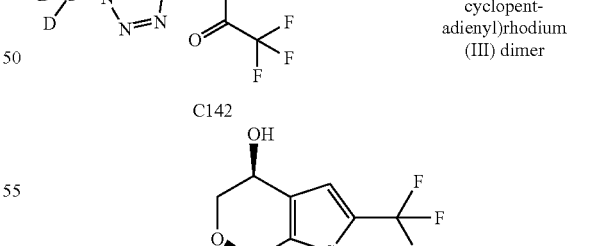

1. AIBN, NBS, MeCN 100 W CFL lamp
2. Et$_3$N, DMSO
3. 4-acetamido-TEMPO KBr, NaOCl Formic acid-Et$_3$N (R,R)-TsDPEN Dichloro (pentamethyl-cyclopent-adienyl)rhodium (III) dimer

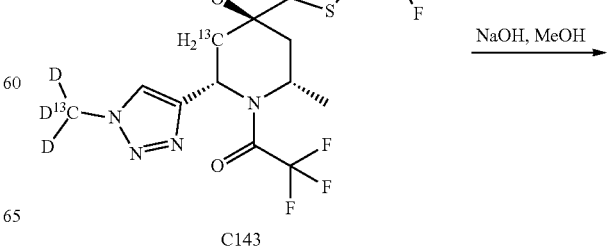

C143

NaOH, MeOH

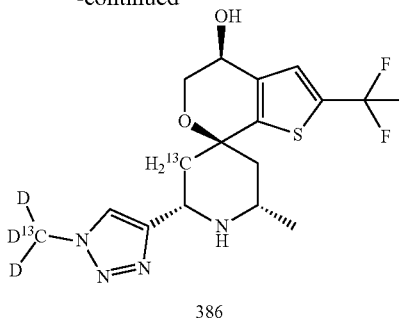

386

Step 1. Synthesis of (2S,4S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-5-$^{13}$C (C140)

A 500 mL 3-neck flask fitted with a magnetic stirrer, a heating mantle, a temperature probe, a water cooled reflux condenser, and a nitrogen inlet/outlet was charged with (2S,6S)-2-methyl-6-(1-(methyl-$^{13}$C-d$_3$)-1H-1,2,3-triazol-4-yl)piperidin-4-one-5-$^{13}$C C139 (10.4 g, 52.20 mmol) and dichloromethane (180 mL), and stirred for 5 minutes. 2-[5-(trifluoromethyl)-3-thienyl]ethanol (12.5 g, 63.71 mmol) was added to the mixture, followed by methanesulfonic acid (24 mL, 369.8 mmol). The resulting reaction mixture was warmed to 40° C., and stirred at this temperature for 5 days. The reaction mixture was cooled to 0° C. with an ice/water bath, and basified with 6 N NaOH solution until pH=11.5. The reaction mixture was extracted with DCM (2×100 mL). The combined organic fraction was dried over MgSO$_4$, filtered, and concentrated under reduced pressure. The crude residue was treated with MTBE (200 mL), aged for 1 hour, and then filtered through medium fritted funnel, washed with MTBE (50 mL), and dried under vacuum to afford one crop of the desired product in 12 g as a white solid. The mother liquor was concentrated under reduced pressure. Purification by silica gel chromatography (Gradient: 0-20% MeOH:DCM) afforded a second crop of the desired product in 5.7 g as a white solid. The two isolated crops of product were combined to give (2S,4S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-5-$^{13}$C (17.7 g, 90%) C140 as a white solid. $^1$H NMR (400 MHz, Chloroform-d) δ 7.44 (t, J=0.7 Hz, 1H), 7.12 (q, J=1.2 Hz, 1H), 4.44 (dt, J=11.8, 2.8 Hz, 1H), 4.04-3.89 (m, 2H), 3.33 (dtd, J=12.7, 6.4, 2.5 Hz, 1H), 2.79-2.61 (m, 2H), 2.38 (ddt, J=131.3, 13.5, 2.6 Hz, 1H), 2.14-2.04 (m, 1H), 2.05-1.57 (m, 1H), 1.49 (dd, J=13.7, 11.3 Hz, 1H), 1.13 (d, J=6.3 Hz, 3H). $^{19}$F NMR (376 MHz, Chloroform-d) δ −55.30. LCMS m/z 378.07 [M+1]$^+$.

Step 2. Synthesis of 2,2,2-trifluoro-((2S,4S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one (C141)

A 500 mL 3-neck flask fitted with a magnetic stirrer, a temperature probe, and a nitrogen inlet/outlet was charged with (2S,4S,6S)-2-methyl-6-(1-(1$^{13}$C)methyltriazol-4-yl)-2'-(trifluoromethyl)spiro[(5$^{13}$C)azinane-4,7'-4,5-dihydrothieno[2,3-c]pyran] (17.5 g, 46.37 mmol) and DCM (200 mL), stirred for 5 minutes, and then cooled to 0° C. with an ice/water bath. To the mixture, N-ethyl-N-isopropyl-propan-2-amine (13 mL, 74.63 mmol) was added, followed by (2,2,2-trifluoroacetyl) 2,2,2-trifluoroacetate (7.5 mL, 53.96 mmol). The resulting reaction mixture was stirred at this temperature for 1 hour. The reaction mixture was quenched with a saturated NaHCO$_3$ solution (100 mL). The layers were separated, and organic layer was washed with 2 M aqueous HCl (2×60 mL), water (100 mL), brine (100 mL), then dried over MgSO$_4$, filtered and concentrated. Purification by silica gel chromatography (0-100% EtOAc:Heptane) provided 2,2,2-trifluoro-1-((2S,4S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one C141 (21 g, 96%) as a white foam. $^1$H NMR (400 MHz, Chloroform-d) δ 7.59 (s, 1H), 7.12 (d, J=1.3 Hz, 1H), 5.60 (s, 1H), 4.52-4.32 (m, 1H), 3.91 (t, J=5.5 Hz, 2H), 3.24 (ddd, J=130.5, 14.8, 7.4 Hz, 1H), 2.88-2.59 (m, 2H), 2.55-2.38 (m, 1H), 2.07 (d, J=21.9 Hz, 1H), 1.49-1.00 (m, 3H). $^{19}$F NMR (376 MHz, Chloroform-d) δ −55.41, −68.97. LCMS m/z 474.02 [M+1]$^+$.

Step 3. Synthesis of (2S,4S,6S)-2-methyl-6-(1-(methyl-$^{13}$C-d$_3$)-1H-1,2,3-triazol-4-yl)-1-(2,2,2-trifluoroacetyl)-2'-(trifluoromethyl)spiro[piperidine-4,7'-thieno[2,3-c]pyran]-4'(5'H)-one-5-$^{13}$C (C142)

First Step—Photochemical Bromination: A 1 L flask fitted with a magnetic stirrer, a 100 W CFL light source, and a nitrogen inlet/outlet was charged with 2,2,2-trifluoro-1-((2S,4S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one C141 (21 g, 44.36 mmol) and acetonitrile (400 mL). The resulting reaction mixture was degassed with a stream of nitrogen via gas dispersion tube for 15 minutes. To the mixture, N-bromosuccinimide (10.2 g, 57.31 mmol) was added, followed by AIBN (200 mg, 1.218 mmol). The resulting reaction mixture was stirred under 100 W CFL irradiation for 4 hours. The reaction mixture was quenched with aqueous 10 wt % sodium bisulfite (200 mL), stirred for 10 minutes, and then MTBE (300 mL) was added. The organic phase was separated, washed with saturated aqueous sodium bicarbonate (200 mL) and brine (200 mL), dried over MgSO$_4$, filtered, and concentrated to afford 1-((2S,4S,6S)-4'-bromo-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)-2,2,2-trifluoroethan-1-one (25 g, 102%) as a tan foam. This crude material was taken into the next step without further purification. LCMS m/z 553.94 [M+1]$^+$ Second Step—Kornblum Oxidation: A mixture of 1-((2S,4S,6S)-4'-bromo-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)-2,2,2-trifluoroethan-1-one (25 g, 102%) and dimethylsulfoxide (200 mL) was stirred for 5 minutes. To the reaction mixture, Et$_3$N (45 mL, 322.9 mmol) was added. The resulting reaction mixture was warmed to 75° C. and stirred for 3 hours. The reaction mixture was cooled to room temperature, partitioned between MTBE (~400 mL), saturated aqueous NaHCO$_3$ solution (~200 mL) and water (~400 mL), and stirred for 10 minutes. The organic phase was separated, and the aqueous layer was extracted with MTBE (2×200 mL). The combined organic phase was washed with saturated NaHCO$_3$ solution (~200 mL), dried over MgSO$_4$, filtered, and concentrated to yield a product consisting of a mixture of the ketone (2S,4S,6S)-2-methyl-6-(1-(methyl-$^{13}$C-d$_3$)-1H-1,2,3-triazol-4-yl)-1-(2,2,2-trifluoroacetyl)-2'-(trifluoromethyl)spiro[piperidine-4,7'-thieno[2,3-c]pyran]-4'(5'H)-one-5-$^{13}$C C142 and alcohol 2,2,2-trifluoro-1-((2S,4S,6S)-4'-hydroxy-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one (21 g, 97%) in a 5:1 ratio as a tan color foam. This crude material of ketone and alcohol (5:1) was taken to the following step without further purification. LCMS m/z 487.95 [M+1]$^+$.

Third Step—Oxidation: A solution of the crude material from the second step (21 g, 42.91 mmol) (mixture of ketone and alcohol, ~5:1 ratio) and DCM (200 mL) was stirred for 5 minutes and then cooled to 0° C. To the reaction mixture, solid NaHCO$_3$ (2.4 g, 28.57 mmol) was added, followed by KBr (1.5 g, 12.60 mmol) in water (25 mL). To the reaction mixture, 4-acetamido-TEMPO (480 mg, 2.250 mmol) was added, followed by NaOCl (30 mL of 12% (w/w), 58.32 mmol) very slowly over 30 minutes while maintaining an internal temperature below 7° C. The resulting reaction mixture was stirred for 1 hour. The reaction mixture was quenched with aqueous 1 M Na$_2$S2O3 (100 mL). The organic phase was separated, washed with saturated aqueous NaHCO$_3$ solution (100 mL) and brine (100 mL), dried over MgSO$_4$, and then filtered and concentrated. Purification by silica gel chromatography (Gradient: 0-100% EtOAc:Heptane) yielded (2S,4S,6S)-2-methyl-6-(1-(methyl-$^{13}$C-d$_3$)-1H-1,2,3-triazol-4-yl)-1-(2,2,2-trifluoroacetyl)-2'-(trifluoromethyl)spiro[piperidine-4,7'-thieno[2,3-c]pyran]-4'(5'H)-one-5-$^{13}$C C142 (14 g, 66%) as a white solid. $^1$H NMR (400 MHz, Chloroform-d) δ 7.73 (q, J=1.2 Hz, 1H), 7.62 (s, 1H), 5.65 (s, 1H), 4.47 (p, J=7.1 Hz, 1H), 4.36 (d, J=4.4 Hz, 2H), 3.40 (ddd, J=131.1, 15.0, 5.8 Hz, 1H), 2.99 (dd, J=15.0, 8.5 Hz, 1H), 2.65 (dd, J=15.1, 8.5 Hz, 1H), 2.23 (d, J=23.2 Hz, 1H), 1.26 (s, 3H). $^{19}$F NMR (376 MHz, Chloroform-d) δ −55.96, −68.87. LCMS m/z 488.01 [M+1]$^+$ Step 4. Synthesis of 2,2,2-trifluoro-1-((2S,4S,4'S,6S)-4'-hydroxy-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one (C143)

A solution of dichloro(pentamethylcyclopentadienyl)rhodium(III) dimer (72 mg, 0.1146 mmol) and (R,R)-TsDPEN (90 mg, 0.2456 mmol) was prepared in MeCN (120 mL) and then stirred for 1 hour at room temperature. Formic acid-Et$_3$N (15.8 mL, 237.0 mmol, a 5:2 commercial solution) was added in one portion, and the reaction was then cooled to −15° C.

In as separate flask, (2S,4S,6S)-2-methyl-6-(1-(methyl-$^{13}$C-d$_3$)-1H-1,2,3-triazol-4-yl)-1-(2,2,2-trifluoroacetyl)-2'-(trifluoromethyl)spiro[piperidine-4,7'-thieno[2,3-c]pyran]-4'(5'H)-one-5-$^{13}$C C142 (14 g, 28.44 mmol) in ACN (120 mL) was cooled to −15° C., and then added to the previously prepared solution, while carefully maintaining the internal temperature between −17° C. and −20° C.

The resulting reaction mixture was warmed to −10° C. and stirred at this temperature for 6 hours. The reaction mixture was quenched with a saturated NaHCO$_3$ solution (200 mL) and stirred at room temperature for 6 hours. The reaction mixture was then extracted with MTBE (2×200 mL). The combined organic phase was washed with 1 N HCl (200 mL) and brine (200 mL), dried over sodium sulfate, filtered, and concentrated. The residue was dissolved in DCM (~200 mL), treated with 3-mercaptopropyl ethyl sulfide silica (SPM32f metal scavenging resin) (6 g), stirred for 2 hours at room temperature, and then filtered and washed with DCM (60 mL). The combined filtrate was concentrated. Purification by silica gel chromatography (Gradient: 0-100% EtOAc:Heptane) yielded 2,2,2-trifluoro-1-((2S,4S,4'S,6S)-4'-hydroxy-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one C143 (13 g, 93%) as a white foam. $^1$H NMR (400 MHz, Chloroform-d) δ 7.60 (s, 1H), 7.38 (q, J=1.2 Hz, 1H), 5.57 (s, 1H), 4.58 (dt, J=9.1, 3.3 Hz, 1H), 4.50 (s, 1H), 3.99 (dd, J=12.4, 3.2 Hz, 1H), 3.89 (dd, J=12.4, 3.4 Hz, 1H), 3.17 (ddd, J=131.1, 15.2, 7.0 Hz, 1H), 2.68 (ddd, J=132.9, 15.2, 8.3 Hz, 2H), 2.20 (s, 1H), 2.10 (d, J=9.1 Hz, 1H), 1.33 (s, 3H). $^{19}$F NMR (376 MHz, Chloroform-d) δ −55.56, −68.96. LCMS m/z 490.05 [M+1]$^+$.

Step 5. Synthesis of (2S,4S,4'S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-5-$^{13}$C-4'-ol (386)

A solution of 2,2,2-trifluoro-1-((2S,4S,4'S,6S)-4'-hydroxy-2-methyl-6-(1-(methyl-$^{13}$C-d 3)-1H-1,2,3-triazol-4-yl)-2'-(trifluoromethyl)-4',5'-dihydrospiro[piperidine-4,7'-thieno[2,3-c]pyran]-1-yl-5-$^{13}$C)ethan-1-one C143 (13 g, 26.56 mmol) and MeOH (120 mL) was stirred for 5 minutes. To the reaction mixture, aqueous NaOH (45 mL of 6 M, 270.0 mmol) was added in one portion. The resulting reaction mixture was warmed to 60° C. and stirred at this temperature for 1 hour. The reaction mixture was cooled to room temperature, then partitioned between cold water (100 mL) and MTBE (200 mL) and stirred for 20 minutes. The organic phase was then separated. The aqueous phase was extracted with MTBE (2×100 mL). The combined organic phases were washed with cold water (60 mL), brine (100 mL), dried over MgSO$_4$, filtered, and concentrated. The residue was dried under vacuum oven at 80° C. for 14 hours to afford (2S,4S,4'S,6S)-2-methyl-6-(1-(methyl-$^{13}$C-d$_3$)-1H-1,2,3-triazol-4-yl)-2'-(trifluoromethyl)-4',5'-dihydrospiro[piperidine-4,7'-thieno[2,3-c]pyran]-5-$^{13}$C-4'-ol 386 (9.5 g, 90%) as a white solid. $^1$H NMR (400 MHz, Methanol-d4) δ 7.83 (t, J=0.7 Hz, 1H), 7.46 (q, J=1.2 Hz, 1H), 4.58 (t, J=3.9 Hz, 1H), 4.35 (dt, J=11.8, 2.9 Hz, 1H), 4.08 (dd, J=12.2, 3.6 Hz, 1H), 3.86 (dd, J=12.2, 4.2 Hz, 1H), 3.35 (ddd, J=11.5, 6.3, 3.2 Hz, 1H), 2.64-2.17 (m, 2H), 1.78 (ddd, J=127.7, 13.8, 11.8 Hz, 1H), 1.53 (dd, J=13.6, 11.4 Hz, 1H), 1.17 (d, J=6.4 Hz, 3H). $^{19}$F NMR (376 MHz, Methanol-d4) δ −56.94. LCMS m/z 394.1 [M+1]$^+$.

Preparation of S63 tert-butyl (2S,3R,6R)-2-(1-methyl-1H-1,2,3-triazol-4-yl)-4-oxo-6-phenylpiperidine-3-carboxylate

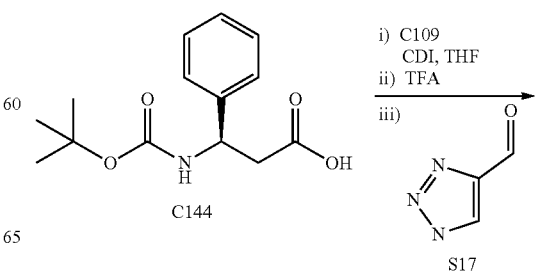

553

-continued

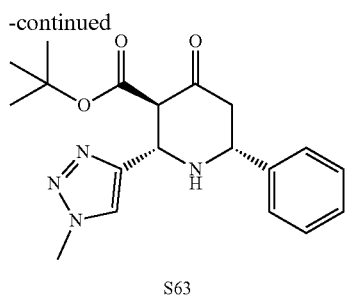

S63

Step 1. To a solution of (3R)-3-(tert-butoxycarbonylamino)-3-phenyl-propanoic acid C144 (500 mg, 1.885 mmol) in THF (4.5 mL) was added CDI (340 mg, 2.097 mmol), and the mixture was stirred at room temperature for 2.5 hours. Bis[(3-tert-butoxy-3-oxo-propanoyl)oxy]magnesium C109 (390 mg, 1.138 mmol) was then added, and stirring continued at room temperature for 20 hours. The reaction was diluted with TBME (10 mL) and 1 N HCl (3 mL). The organic layer was separated and washed with saturated sodium bicarbonate (3 mL), brine (3 mL). The organic layer was dried with magnesium sulfate, filtered, and concentrated to yield tert-butyl (2S,3R,6R)-2-(1-methyl-1H-1,2,3-triazol-4-yl)-4-oxo-6-phenylpiperidine-3-carboxylate S63 as a white crystalline solid, which was immediately carried forward to Step 2.

Step 2. To the white crystalline solid from the first step dissolved in DCM (4 mL) was added TFA (900 µL, 11.68 mmol) The mixture was stirred for 1 hour, and then the mixture was concentrated and azeotroped by DCM (3×4 mL) to provide a crude mixture of tert-butyl (5R)-5-amino-3-oxo-5-phenyl-pentanoate that was directly carried forward to Step 3.

Step 3. To the crude mixture from step 2 dissolved in DCM (4 mL) was added 1-methyltriazole-4-carbaldehyde S17 (225 mg, 2.025 mmol) and the mixture was stirred at room temperature for 2 hours. The mixture was quenched with saturated sodium bicarbonate (2 mL). 6 N NaOH was added to adjust the pH to >9. The organic layer was separated and concentrated. Purification by silica gel chromatography (Gradient: 0-10% MeOH:DCM) yielded tert-butyl (2S,3R,6R)-2-(1-methyltriazol-4-yl)-4-oxo-6-phenylpiperidine-3-carboxylate S63 (347 mg, 52%). This was observed as a mixture of keto and enol tautomers. LCMS m/z 357.23 $[M+H]^+$ Preparation of S64

1-[(2'S,6'R, 7S)-2-chloro-2'-(1-methyltriazol-4-yl)-6'-phenyl-spiro[4,5-dihydrothieno[2,3-c]pyran-7,4'-piperidine]-1'-yl]-2,2,2-trifluoro-ethanone (S64)

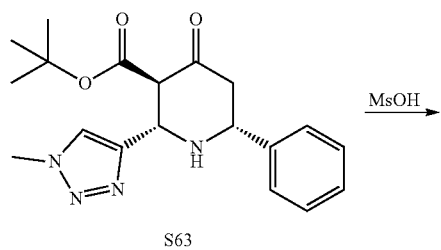

S63

554

-continued

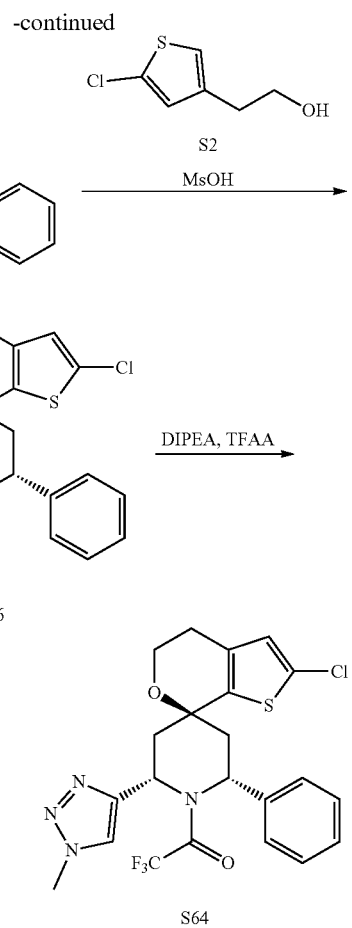

Step 1. Synthesis of (2S,6R)-2-(1-methyltriazol-4-yl)-6-phenyl-piperidin-4-one (C145)

To a mixture of tert-butyl (2S,3R,6R)-2-(1-methyltriazol-4-yl)-4-oxo-6-phenyl-piperidine-3-carboxylate S63 (320 mg, 0.8978 mmol) dissolved in DCM (5 mL) was added MsOH (300 µL, 4.623 mmol). The mixture was refluxed for 1 hour, then cooled to room temperature and quenched with saturated sodium bicarbonate (5 mL). The organic layer was separated, and the aqueous layer was extracted with additional DCM (3×5 mL). The combined organic layer was dried with MgSO₄, filtered, and concentrated. Purification by silica gel chromatography (0-10% MeOH:DCM) yielded (2S,6R)-2-(1-methyltriazol-4-yl)-6-phenyl-piperidin-4-one C145 (98 mg, 43%), as a yellow oil. $^1$H NMR (400 MHz, Chloroform-d) δ 7.53 (s, 1H), 7.46-7.42 (m, 2H), 7.40-7.30 (m, 3H), 4.41 (dd, J=9.8, 5.2 Hz, 1H), 4.18-4.14 (m, 1H), 4.13 (s, 3H), 2.84-2.72 (m, 2H), 2.65 (d, J=7.6 Hz, 2H).

Step 2. Synthesis of (2'S,6'R, 7S)-2-chloro-2'-(1-methyltriazol-4-yl)-6'-phenyl-spiro[4,5-dihydrothieno[2,3-c]pyran-7,4'-piperidine] (C146)

To a mixture of (2S,6R)-2-(1-methyltriazol-4-yl)-6-phenyl-piperidin-4-one C145 (49 mg, 0.1912 mmol) and 2-(5-chloro-3-thienyl)ethanol S2 (40 mg, 0.2459 mmol) dissolved in DCM (1000 µL) was added MsOH (90 µL, 1.387 mmol). The mixture was refluxed overnight and then cooled to room temperature and quenched with saturated sodium bicarbonate (1 mL). The organic layer was directly purified by silica gel chromatography (Gradient: 0-10% MeOH:DCM) to yield (2'S,6'R,7S)-2-chloro-2'-(1-methyltriazol-4-yl)-6'-phenyl-spiro[4,5-dihydrothieno[2,3-c]pyran-7,4'-piperidine] C146 (46 mg, 57%) as a white crystalline solid. $^1$H NMR (400 MHz, Chloroform-d) δ 7.48 (s, 1H), 7.45-7.38 (m, 2H), 7.36-7.29 (m, 2H), 7.24 (td, J=5.3, 4.8, 2.4 Hz, 1H), 6.58 (s, 1H), 4.58 (dd, J=11.7, 2.6 Hz, 1H), 4.32 (dd, J=11.6, 2.5 Hz, 1H), 4.06 (s, 3H), 4.02 (t, J=5.5 Hz, 2H), 2.72-2.54 (m, 2H), 2.44 (dt, J=13.6, 2.6 Hz, 1H), 2.22 (dt, J=13.6, 2.6 Hz, 1H), 1.86 (ddd, J=21.7, 13.6, 11.7 Hz, 3H). LCMS m/z 401.15 [M+1]$^+$

Step 3. Synthesis of 1-[(2'S,6'R, 7S)-2-chloro-2'-(1-methyltriazol-4-yl)-6'-phenyl-spiro[4,5-dihydrothieno[2,3-c]pyran-7,4'-piperidine]-1'-yl]-2,2,2-trifluoro-ethanone (S64)

A solution of (2'S,6'R,7S)-2-chloro-2'-(1-methyltriazol-4-yl)-6'-phenyl-spiro[4,5-dihydrothieno[2,3-c]pyran-7,4'-piperidine] C146 dissolved in DCM (1 mL) was cooled to 0° C. DIPEA (25 µL, 0.1435 mmol) was added, followed by TFAA (20 µL, 0.1439 mmol). The mixture was stirred for 20 min, and then quenched with 1 N HCl (1 mL). The organic layer was passed through a phase separator. Purification by silica gel chromatography (0-50% EtOAc:Heptane) yielded 1-[(2'S,6'R,7S)-2-chloro-2'-(1-methyltriazol-4-yl)-6'-phenyl-spiro[4,5-dihydrothieno[2,3-c]pyran-7,4'-piperidine]-1'-yl]-2,2,2-trifluoro-ethanone S64 (52 mg, 52%) as a clear oil. LCMS m/z 497.26 [M+1]$^+$

Compound 387

(2'S,4S,6'R, 7S)-2-chloro-2'-(1-methyltriazol-4-yl)-6'-phenyl-spiro[4,5-dihydrothieno[2,3-c]pyran-7,4'-piperidine]-4-ol (387)

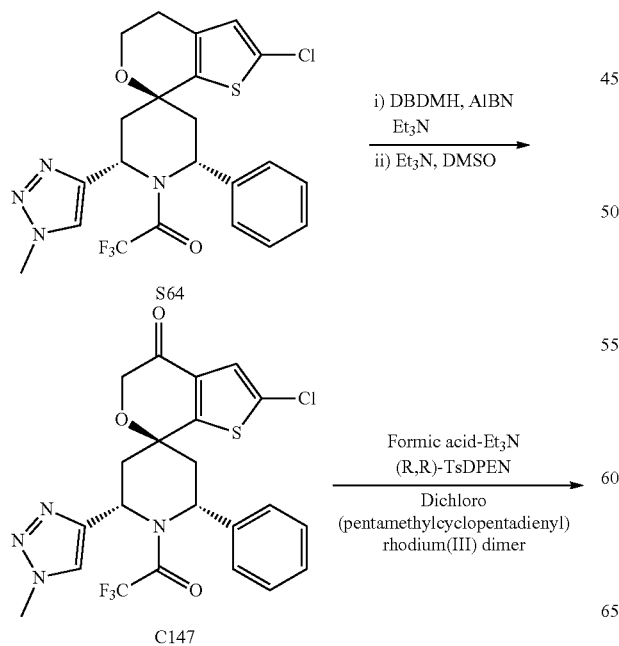

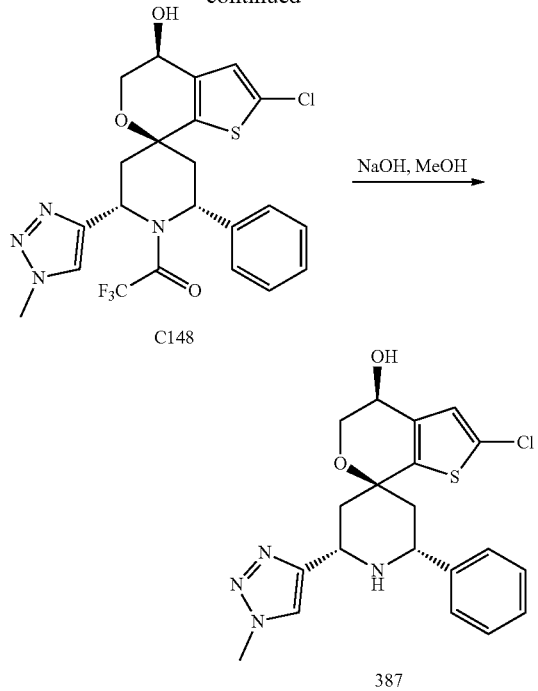

Step 1. Synthesis of (2S,4S,6R)-2'-chloro-2-(1-methyltriazol-4-yl)-6-phenyl-1-(2,2,2-trifluoro-acetyl)spiro[piperidine-4,7'-thieno[2,3-c]pyran]-4'-one (C147)

To a solution of 1-[(2'S,6'R,7S)-2-chloro-2'-(1-methyltriazol-4-yl)-6'-phenyl-spiro[4,5-dihydrothieno[2,3-c]pyran-7,4'-piperidine]-1'-yl]-2,2,2-trifluoro-ethanone S64 (52 mg, 0.09901 mmol) in chlorobenzene (1 mL) under nitrogen atmosphere was added 5,5-dimethyl-1,3-dibromohydantoin (20 mg, 0.06995 mmol) and 2-[(E)-(1-cyano-1-methyl-ethyl)azo]-2-methyl-propanenitrile (1.5 mg, 0.009135 mmol). The mixture was heated to 75° C. for 15 minutes. The mixture was cooled to room temperature and quenched with saturated sodium bicarbonate (1 mL). The organic layer was separated, dried with MgSO$_4$, filtered, and concentrated to provide a crude foam.

The crude foam was dissolved in DMSO (1 mL) under nitrogen atmosphere. The mixture was heated to 60° C. and triethylamine (75 µL, 0.5381 mmol) was added. The dark brown solution was heated to 65° C. and stirred for 75 minutes. The mixture was cooled to room temperature, and diluted with ethyl acetate (5 mL) and water (5 mL). The aqueous layer was washed with additional ethyl acetate (2×5 mL). The combined organic layers were dried with Na$_2$SO$_4$, filtered, and concentrated. Purification by silica gel chromatography (Gradient: 0-50% EtOAc:Heptane) yielded (2S,4S,6R)-2'-chloro-2-(1-methyltriazol-4-yl)-6-phenyl-1-(2,2,2-trifluoroacetyl)spiro[piperidine-4,7'-thieno[2,3-c]pyran]-4'-one C147 (21 mg, 39%) as a pale yellow solid. LCMS m/z 511.21 [M+1]$^+$

Step 2. Synthesis of 1-[(2'S,4S,6'R, 7S)-2-chloro-4-hydroxy-2'-(1-methyltriazol-4-yl)-6'-phenyl-spiro[4,5-dihydrothieno[2,3-c]pyran-7,4'-piperidine]-1'-yl]-2,2,2-trifluoro-ethanone (C148)

To a mixture of 5:2 formic acid-triethylamine complex (20 µL, 0.04763 mmol) in MeCN (500 µL) was added a solution of N-[(1R,2R)-2-amino-1,2-diphenyl-ethyl]-4-methyl-benzenesulfonamide (0.12 mg, $3.274E^{-4}$ mmol) and Dichloro(pentamethylcyclopentadienyl)rhodium(III) dimer (0.1 mg, $1.592E^{-4}$ mmol) dissolved in MeCN (50 μL). After 5 minutes, the resulting solution was added to a cooled solution at −10° C. of (2S,4S,6R)-2'-chloro-2-(1-methyltriazol-4-yl)-6-phenyl-1-(2,2,2-trifluoroacetyl)spiro[piperidine-4,7'-thieno[2,3-c]pyran]-4'-one C147 (21 mg, 0.03908 mmol) in MeCN (500 μL). The reaction mixture was warmed slowly to room temperature and stirred overnight. The mixture was concentrated and purified by silica gel chromatography (Gradient: 0-50% EtOAc:heptane) to yield 1-[(2'S,4S,6'R,7S)-2-chloro-4-hydroxy-2'-(1-methyltriazol-4-yl)-6'-phenyl-spiro[4,5-dihydrothieno[2,3-c]pyran-7,4'-piperidine]-1'-yl]-2,2,2-trifluoro-ethanone C148 as a white solid. LCMS m/z 514.94 [M+1]$^+$ Step 3. Synthesis of (2'S,4S,6'R, 7S)-2-chloro-2'-(1-methyltriazol-4-yl)-6'-phenyl-spiro[4,5-dihydrothieno[2,3-c]pyran-7,4'-piperidine]-4-ol (387)

A solution of 1-[(2'S,4S,6'R,7S)-2-chloro-4-hydroxy-2'-(1-methyltriazol-4-yl)-6'-phenyl-spiro[4,5-dihydrothieno[2,3-c]pyran-7,4'-piperidine]-1'-yl]-2,2,2-trifluoro-ethanone C148 dissolved in MeOH (250 μL) was heated to 60° C. NaOH (75 μL of 6 M, 0.4500 mmol) was then added, and reflux continued for 3 hours. The mixture was diluted with MTBE (3 mL) and saturated ammonium chloride (3 mL). The organic layer was separated, and the aqueous layer was extracted with additional MTBE (2×3 mL). The combined organic layer was passed over a phase separator and concentrated to yield (2'S,4S,6'R,7S)-2-chloro-2'-(1-methyltriazol-4-yl)-6'-phenyl-spiro[4,5-dihydrothieno[2,3-c]pyran-7,4'-piperidine]-4-ol 387 (13.8 mg, 82%) as a white solid. $^1$H NMR (400 MHz, Methanol-d$_4$) δ 7.88 (d, J=3.2 Hz, 1H), 7.48-7.41 (m, 2H), 7.37-7.30 (m, 2H), 7.30-7.21 (m, 1H), 6.88 (s, 1H), 4.60-4.47 (m, 2H), 4.37 (dd, J=11.8, 2.6 Hz, 1H), 4.12 (dt, J=11.5, 3.4 Hz, 1H), 4.07 (s, 3H), 3.93-3.84 (m, 1H), 2.49 (dt, J=13.9, 2.6 Hz, 1H), 2.35-2.22 (m, 1H), 1.89 (ddd, J=13.8, 11.8, 1.5 Hz, 2H). LCMS m/z 417.26 [M+1]$^+$ Preparation of S65

2-(difluoromethyl)-6-(1-methyltriazol-4-yl)piperidin-4-one (S65)

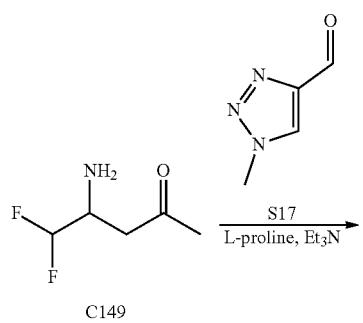

C149

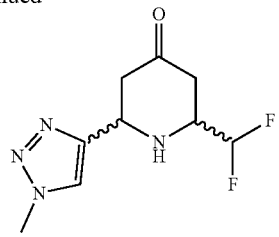

S65
[CIS]

To a solution of 4-amino-5,5-difluoro-pentan-2-one (Hydrochloride salt) C149 (250 mg, 1.440 mmol) in ethanol (15 mL) cooled to 0° C. was added 1-methyltriazole-4-carbaldehyde S17 (175 mg, 1.512 mmol), L-proline (35 mg, 0.3040 mmol), and Et$_3$N (210 μL, 1.507 mmol). The mixture was warmed to room temperature and 72 hours. The mixture was concentrated, and dissolved in DCM (10 mL) and saturated sodium bicarbonate (5 mL). The aqueous layer was extracted with additional DCM (2×10 mL), and the combined organic layer was concentrated. Purification by silica gel chromatography (Gradient: 0-10% MeOH:DCM) yielded 2-(difluoromethyl)-6-(1-methyltriazol-4-yl)piperidin-4-one S65 (303 mg, 91%) as a yellow oil. $^1$H NMR (400 MHz, Chloroform-d) δ 7.51 (s, 1H), 5.78 (tdd, J=56.0, 16.1, 4.3 Hz, 1H), 4.30 (dt, J=9.8, 4.7 Hz, 1H), 4.13 (s, 3H), 3.51 (d, J=5.0 Hz, 1H), 3.41 (d, J=18.7 Hz, 1H), 2.79-2.69 (m, 1H), 2.60 (s, 1H), 2.43 (dd, J=14.4, 11.9 Hz, 1H), 2.30 (s, 1H). LCMS m/z 231.18 [M+H]$^+$. The product was isolated as a mixture of 4:1 dr.

Compound 388

2-chloro-2'-(difluoromethyl)-6'-(1-methyltriazol-4-yl)spiro[4,5-dihydrothieno[2,3-c]pyran-7,4'-piperidine] (388)

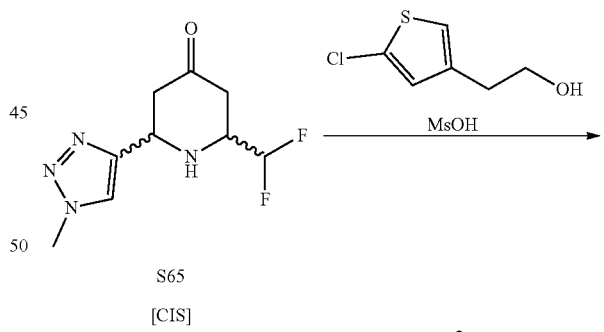

S65
[CIS]

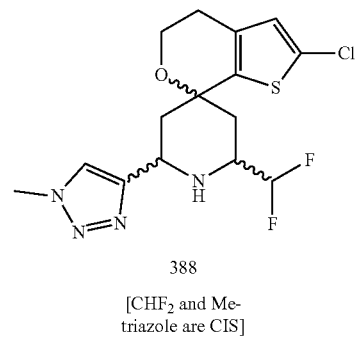

388
[CHF$_2$ and Me-triazole are CIS]

To a solution of 2-(difluoromethyl)-6-(1-methyltriazol-4-yl)piperidin-4-one S65 (140 mg, 0.6081 mmol) in DCM (3 mL) was added 2-(5-chloro-3-thienyl)ethanol S2 (100 µL, 0.8085 mmol) followed by MsOH (200 µL, 3.082 mmol). The mixture was refluxed overnight. The mixture was cooled to room temperature and quenched with saturated sodium bicarbonate. The organic layer was separated and concentrated. Purification by silica gel chromatography (Gradient: 0-10% MeOH:DCM) yielded 2-chloro-2'-(difluoromethyl)-6'-(1-methyltriazol-4-yl)spiro[4,5-dihydrothieno[2,3-c]pyran-7,4'-piperidine] 388 (139 mg, 53%) as a yellow oil. $^1$H NMR (400 MHz, Chloroform-d) δ 7.47 (s, 1H), 6.62 (s, 1H), 5.66 (td, J=56.5, 5.2 Hz, 1H), 4.48 (dd, J=11.8, 2.7 Hz, 1H), 4.10 (d, J=1.5 Hz, 3H), 3.98 (t, J=5.5 Hz, 2H), 3.64-3.51 (m, 1H), 2.65 (td, J=5.5, 3.1 Hz, 2H), 2.41-2.36 (m, 1H), 2.24-2.16 (m, 1H), 2.13 (dd, J=14.8, 6.6 Hz, 1H), 1.84 (dd, J=13.6, 11.8 Hz, 1H). LCMS m/z 375.14 [M+1]$^+$.

Compound 389

2'-(difluoromethyl)-6'-(1-methyltriazol-4-yl)-2-(trifluoromethyl)spiro[4,5-dihydrothieno[2,3-c]pyran-7,4'-piperidine] (389)

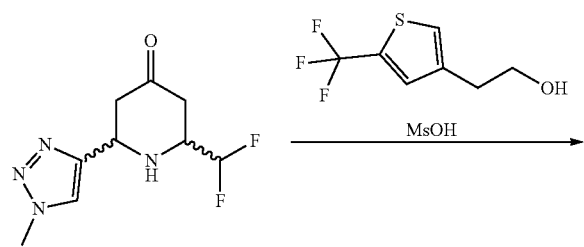

To a solution of 2-(difluoromethyl)-6-(1-methyltriazol-4-yl)piperidin-4-one S65 (140 mg, 0.6081 mmol) in DCM (3 mL) was added 2-[5-(trifluoromethyl)-3-thienyl]ethanol S3 (160 mg, 0.8155 mmol), followed by MsOH (200 µL, 3.082 mmol). The mixture was refluxed for 48 hours. The mixture was cooled to room temperature and quenched with saturated sodium bicarbonate. The organic layer was separated and concentrated. Purification by reversed-phase HPLC (Method: C18 Waters Sunfire column (30×150 mm, 5 micron). Gradient: MeCN in H$_2$O with 0.1% trifluoroacetic acid) provided the product that was neutralized by dilution with DCM followed by saturated sodium bicarbonate wash. The solution was passed over a phase separator, and the organic layer dried to yield 2'-(difluoromethyl)-6'-(1-methyltriazol-4-yl)-2-(trifluoromethyl)spiro[4,5-dihydrothieno[2,3-c]pyran-7,4'-piperidine] 389 (12 mg, 5%) as a clear oil. $^1$H NMR (400 MHz, Chloroform-d) δ 7.49 (s, 1H), 7.16 (q, J=1.1 Hz, 1H), 5.68 (td, J=56.4, 5.1 Hz, 1H), 4.51 (dd, J=11.7, 2.7 Hz, 1H), 4.10 (s, 3H), 4.02 (t, J=5.5 Hz, 2H), 3.64-3.54 (m, 1H), 2.75 (td, J=5.4, 2.8 Hz, 2H), 2.43 (dt, J=13.7, 2.7 Hz, 1H), 2.25 (dd, J=13.4, 2.7 Hz, 1H), 1.91 (dd, J=13.6, 11.7 Hz, 1H), 1.72-1.66 (m, 1H). LCMS m/z 409.21 [M+1]$^+$ Compound 390 (2'S,4S,6'S, 7R)-2'-methyl-6'-(1-methyltriazol-4-yl)-2-(trifluoromethyl)spiro[6,7-dihydrothieno[3,2-c]pyran-4,4'-piperidine]-7-ol (390)

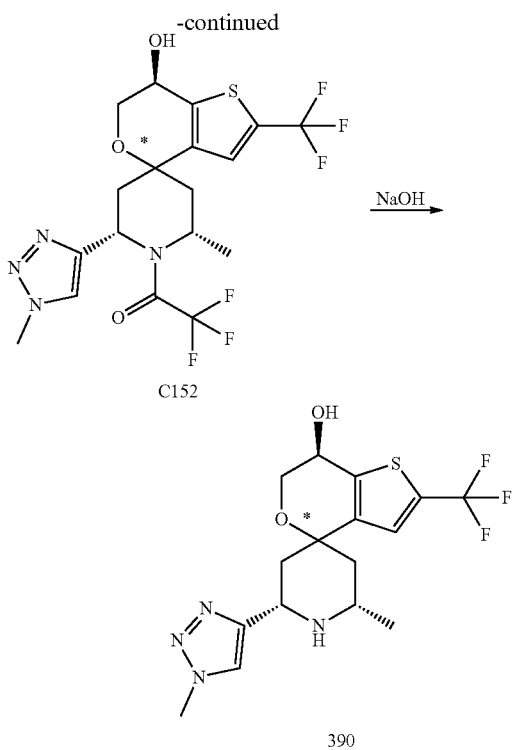

Step 1. Synthesis of 2,2,2-trifluoro-1-[(2'S,4S,6'S)-2'-methyl-6'-(1-methyltriazol-4-yl)-2-(trifluoromethyl)spiro[6,7-dihydrothieno[3,2-c]pyran-4,4'-piperidine]-1'-yl]ethanone (C150)

To a solution of (2'S,4S,6'S)-2'-methyl-6'-(1-methyltriazol-4-yl)-2-(trifluoromethyl)spiro[6,7-dihydrothieno[3,2-c]pyran-4,4'-piperidine] 8 (900 mg, 2.365 mmol) (Prepared via S26 intermediate using "Method B") and DIPEA (550 µL, 3.158 mmol in DCM (15 mL) at 0° C. was added TFAA (400 µL, 2.878 mmol) dropwise. After thirty minutes, the reaction was diluted with saturated sodium bicarbonate solution (10 mL), and the mixture passed over a phase separator, extracting with DCM (2×10 mL). The organics were concentrated in vacuo. Purification by silica gel chromatography (Gradient: 0-50% EtOAc in Heptane) yielded 2,2,2-trifluoro-1-[(2'S,4S,6'S)-2'-methyl-6'-(1-methyltriazol-4-yl)-2-(trifluoromethyl)spiro[6,7-dihydrothieno[3,2-c]pyran-4,4'-piperidine]-1'-yl]ethanone C150 (1.03 g, 91%) as a white foam. $^1$H NMR (300 MHz, Chloroform-d) δ 7.59 (s, 1H), 7.39 (s, 1H), 5.59 (s, 1H), 4.42 (q, J=7.0 Hz, 1H), 4.11 (s, 3H), 3.92 (t, J=5.5 Hz, 2H), 3.24 (dd, J=14.8, 6.5 Hz, 1H), 2.96-2.73 (m, 2H), 2.48 (dd, J=14.9, 8.4 Hz, 1H), 2.40-1.93 (m, 2H), 1.52-0.94 (m, 3H). LCMS m/z 469.07 [M+H]$^+$.

Step 2. Synthesis of (2S,4S,6S)-2-methyl-6-(1-methyltriazol-4-yl)-1-(2,2,2-trifluoroacetyl)-2'-(trifluoromethyl)spiro[piperidine-4,4'-thieno[3,2-c]pyran]-7'-one (C151)

To a mixture of 2,2,2-trifluoro-1-[(2'S,4S,6'S)-2'-methyl-6'-(1-methyltriazol-4-yl)-2-(trifluoromethyl)spiro[6,7-dihydrothieno[3,2-c]pyran-4,4'-piperidine]-1'-yl]ethanone C150 (1.03 g, 2.153 mmol) in acetonitrile (18 mL) was added N-hydroxyphthalimide (260 mg, 1.594 mmol) and cobaltous diacetate tetrahydrate (120 mg, 0.4818 mmol), and then the mixture was vacuum purged with an oxygen balloon three times. The reaction was heated to 45° C. and stirred under an oxygen balloon atmosphere overnight. The mixture was cooled to room temperature, vacuum purged with nitrogen three times, and then diluted with water (10 mL) and saturated aqueous bicarbonate (20 mL). The mixture was extracted with DCM (3×20 mL), and the organics were dried over sodium sulfate and concentrated in vacuo. Purification by silica gel chromatography (Gradient: 0-40% EtOAc in Heptane) afforded (2S,4S,6S)-2-methyl-6-(1-methyltriazol-4-yl)-1-(2,2,2-trifluoroacetyl)-2'-(trifluoromethyl)spiro[piperidine-4,4'-thieno[3,2-c]pyran]-7'-one C151 (440 mg, 42%) as a white foam. $^1$H NMR (300 MHz, Chloroform-d) δ 8.03-7.38 (m, 2H), 5.64 (s, 1H), 4.51-4.30 (m, 3H), 4.13 (s, 3H), 3.48-3.35 (m, 1H), 2.67 (dd, J=15.2, 8.5 Hz, 1H), 2.24 (s, 2H), 1.47-0.91 (m, 3H). LCMS m/z 483.11 [M+H]$^+$.

Step 3. Synthesis of 2,2,2-trifluoro-1-[(2'S,4S,6'S,7R)-7-hydroxy-2'-methyl-6'-(1-methyltriazol-4-yl)-2-(trifluoromethyl)spiro[6,7-dihydrothieno[3,2-c]pyran-4,4'-piperidine]-1'-yl]ethenone (C152)

To a pre-mixed solution of N-[(1R,2R)-2-amino-1,2-diphenyl-ethyl]-4-methyl-benzenesulfonamide (1.5 mg, 0.004093 mmol) and 1,2,3,4,5-pentamethylcyclopentane; rhodium(2+) tetrachloride (1 mg, 0.001592 mmol) in ACN (200 µL) was added a solution of formic acid (40 µL, 1.060 mmol) and TEA (50 µL, 0.3587 mmol). After 10 minutes, the mixture was cooled to 0° C. and a solution of (2S,4S,6S)-2-methyl-6-(1-methyltriazol-4-yl)-1-(2,2,2-trifluoroacetyl)-2'-(trifluoromethyl)spiro[piperidine-4,4'-thieno[3,2-c]pyran]-7'-one C151 (80 mg, 0.1653 mmol) in ACN (1.5 mL) was added. The reaction was stirred at 0° C., and after one hour, it was quenched with saturated aqueous bicarbonate and extracted with DCM (2×3 mL) through a phase separator. The organics were concentrated in vacuo. Purification by silica gel chromatography (Gradient: 0-30% EtOAc in DCM) afforded 2,2,2-trifluoro-1-[(2'S,4S,6'S,7R)-7-hydroxy-2'-methyl-6'-(1-methyltriazol-4-yl)-2-(trifluoromethyl)spiro[6,7-dihydrothieno[3,2-c]pyran-4,4'-piperidine]-1'-yl]ethanone C152 (65 mg, 81%) as a colorless film. $^1$H NMR (300 MHz, Chloroform-d) δ 7.77-7.26 (m, 2H), 5.57 (s, 1H), 4.78-4.67 (m, 1H), 4.48 (d, J=7.9 Hz, 1H), 4.11 (s, 3H), 3.94 (ddd, J=41.9, 12.2, 3.7 Hz, 2H), 3.16 (dd, J=15.0, 6.1 Hz, 1H), 2.52 (dd, J=15.1, 8.5 Hz, 1H), 2.44-1.98 (m, 3H), 1.55-0.83 (m, 3H). LCMS m/z 485.09 [M+H]$^+$.

Step 4. Synthesis of (2'S,4S,6'S, 7R)-2'-methyl-6'-(1-methyltriazol-4-yl)-2-(trifluoromethyl)spiro[6,7-dihydrothieno[3,2-c]pyran-4,4'-piperidine]-7-ol (390)

To a solution of 2,2,2-trifluoro-1-[(2'S,4S,6'S,7R)-7-hydroxy-2'-methyl-6'-(1-methyltriazol-4-yl)-2-(trifluoromethyl)spiro[6,7-dihydrothieno[3,2-c]pyran-4,4'-piperidine]-1'-yl]ethenone C152 (65 mg, 0.1331 mmol) in MeOH (1.3 mL) was added NaOH (900 µL of 2 M, 1.800 mmol) and the mixture was heated to 50° C. After 50 minutes, the mixture was cooled to room temperature, diluted with water (2 mL), and extracted with DCM (2×3 mL) through a phase separator. The organics were concentrated in vacuo to afford a clear film. The residue was brought up in DCM and heptane and stripped down to afford (2'S,4S,6'S,7R)-2'-methyl-6'-(1-methyltriazol-4-yl)-2-(trifluoromethyl)spiro[6,7-dihydrothieno[3,2-c]pyran-4,4'-piperidine]-7-ol 390 (48.3 mg, 91%)

as a white foam. $^1$H NMR (300 MHz, Chloroform-d) δ 7.45 (s, 1H), 7.15 (s, 1H), 4.69 (s, 1H), 4.40 (dt, J=11.8, 1.9 Hz, 1H), 4.10-3.93 (m, 6H), 3.45-3.33 (m, 1H), 2.25 (d, J=13.9 Hz, 1H), 1.91 (d, J=13.6 Hz, 1H), 1.81-1.70 (m, 1H), 1.58 (dd, J=13.3, 11.5 Hz, 1H), 1.14 (d, J=6.3 Hz, 3H). LCMS m/z 389.1 [M+H]+.
Compound 391
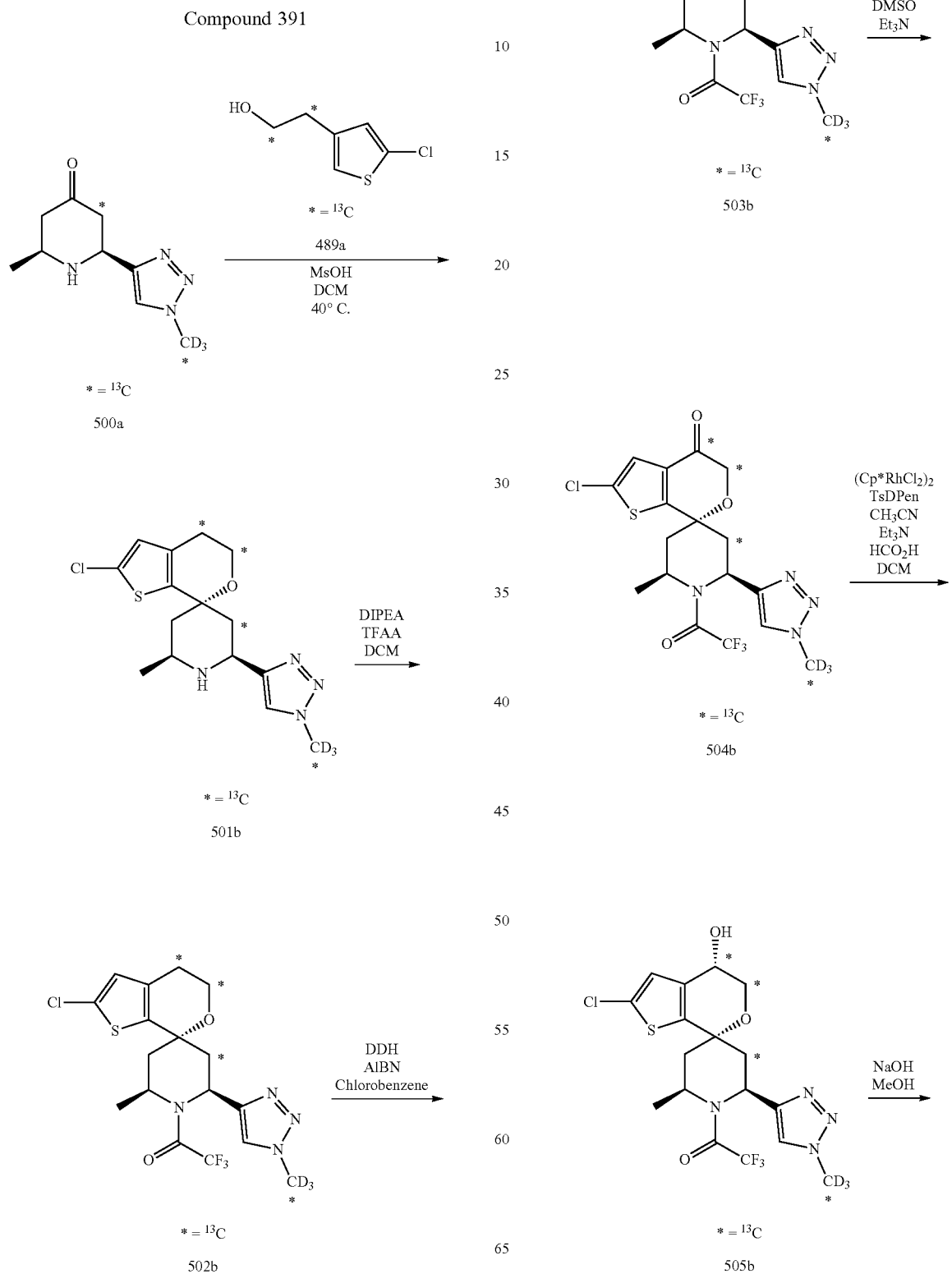

-continued

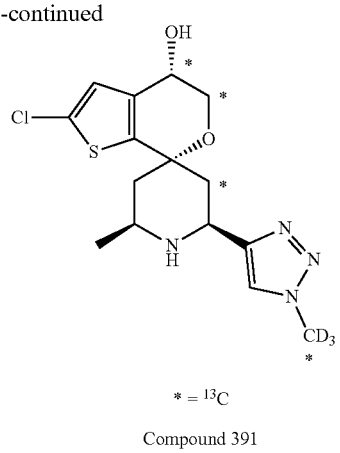

\* = $^{13}C$

Compound 391

Step 1. To a mixture of compound 500a (8.84 g, 44.4 mmol) and 489a (9.50 g, 57.7 mmol) in DCM (250 mL) was added MsOH (34.6 mL, 532.8 mmol). The mixture was heated to 40° C. and stirred overnight. TLC showed reaction completed. The mixture was cooled to 0° C., diluted with water (200 mL) and quenched with aqueous NaOH (6 N, 100 mL). The mixture was separated, and the aqueous layer was extracted with DCM (3×300 mL). The combined organic layers were washed with brine (300 mL), dried over sodium sulfate, and concentrated via rotovap to afford a brown oil (crude, 20.0 g), which was further purified by flash column chromatography (DCM/acetone (1:2), then 5% MeOH/DCM and 0.5% NH$_4$OH) to give pure compound 501b (14.50 g, 94% yield). HPLC: 99.5% at 254 nm. LCMS: 346.20 (M+1). $^1$H NMR (500 MHz, CDCl$_3$) δ 7.42 (s, 1H), 6.58 (s, 1H), 4.43-4.39 (m, 1H), 4.09 (m, 1H), 3.81-3.79 (m, 1H), 3.33-3.28 (m, 1H), 2.76-2.70 (m, 1H), 2.50-2.46 (m, 0.5H) 2.22-2.19 (m, 0.5H), 2.07-2.03 (m, 1H), 1.93-1.89 (m, 1H), 1.84 (br s, 1H), 1.68-1.63 (m, 1H), 1.44-1.40 (m, 1H), 1.11 (d, J=6.5 Hz, 3H).

Step 2. To a mixture of compound 501b (11.4 g, 33.0 mmol) and DIPEA (17.2 mL, 99.0 mmol) in DCM (170 mL) in an ice-water bath was added TFAA (7.80 mL, 56.1 mmol) dropwise. After addition completed, the mixture was warmed to room temperature and stirred for 2 hours. TLC showed reaction completed. The reaction mixture was quenched with water (100 mL) in an ice-water bath. The biphasic mixture was stirred for 15 minutes, separated, and then the aqueous layer was extracted with additional DCM (50 mL). The combined organic layers were washed with 0.5 M aqueous HCl (50 mL), saturated NaHCO$_3$ (50 mL), dried over sodium sulfate, filtered, and concentrated to give a brown solid (crude 16.3 g). The solid was treated with MTBE (40 mL) and stirred at 0° C. to break up chunks for 1 hour. The white solid was collected via vacuum filtration, washed with cold MTBE (2×10 mL) and dried under high vacuum to afford compound 502b (12.6 g, 86% yield) as a white solid. HPLC: 99.0% at 230 nm. LCMS: 442.20 (M+1). $^1$H NMR (500 MHz, CDCl$_3$) δ 7.59 (s, 1H), 6.58 (s, 1H), 5.57 (m, 1H), 4.41 (m, 1H), 3.88 (dt, J=144 Hz and 5.5 Hz, 2H), 3.17 (d, J=144 Hz, 2H), 2.59 (d, J=125 Hz, 2H), 2.47 (m, 1H), 2.02 (m, 1H), 1.35 (m, 3H).

Step 3. In a 250 mL three-neck round-bottom flask, compound 502b (10.70 g, 24.21 mmol) was dissolved in chlorobenzene (160 mL). The solution was sparged with nitrogen via a gas dispersion tube for 10 minutes at room temperature. DDH (4.85 g, 16.95 mmol) and AIBN (0.32 g, 1.94 mmol) were added. The resulting suspension was sparged with N$_2$ for an additional 5 minutes, then heated to 75-80° C. for 4 hours. HPLC showed residual starting material (~2%), which was minor compared to the desired bromide isomers. The mixture was cooled to 20° C., then treated with saturated NaHCO$_3$ (160 mL) and stirred for 25 minutes. The layers were separated. The aqueous layer was extracted with DCM (2×150 mL). The combined organic extracts were dried over sodium sulfate and concentrated via rotovap to afford a brown oil 503b (crude, 14.5 g), which was used directly in the next step.

Step 4. Crude compound 503b (14.5 g) was dissolved in DMSO (120 mL), then treated with triethylamine (15.2 mL, 109 mmol). The solution was stirred and heated to 75° C. After 2 hours, TLC showed conversion was completed. The mixture was cooled to 20° C., then partitioned between water (200 mL) and EtOAc (200 mL). The layers were separated. The aqueous layer was extracted with EtOAc (2×200 mL). The combined organic extracts were washed successively with 0.5 N aqueous HCl (150 mL), brine (150 mL), dried over sodium sulfate, filtered, and concentrated to give 11.0 g of crude solid. The solid was treated with EtOAc/MTBE (20 mL/20 mL) and stirred at room temperature for 1 hour to break up the chunks. The light-yellow solid was collected via vacuum filtration, washed with cold MTBE (2×10 mL) and dried under high vacuum to afford compound 504b (6.40 g, 58% yield). HPLC: 95.4% at 230 nm. $^1$H NMR (500 MHz, DMSO-d$_6$): δ 8.14 (s, 1H), 7.36 (s, 1H), 5.54 (m, 1H), 4.61 (m, 1H), 4.26 (m, 2H), 3.04 (m, 1H), 2.88 (m, 1H), 2.66 (m, 1H), 1.95 (m, 1H), 1.02 (m, 3H).

Step 5. To a 250 mL round-bottom flask was added (Cp\*RhCl$_2$)$_2$ (130 mg, 0.21 mmol) and TsDPEN (116 mg, 0.32 mmol) in CH$_3$CN (50 mL). The mixture was degassed with N$_2$ for 5 minutes. Then Et$_3$N (4.2 mL, 30 mmol) and HCO$_2$H (2.8 mL, 74.8 mmol) were added. The resulting mixture was cooled in an ice-saltwater bath. To another flask, compound 504b (3.10 g, 6.80 mmol) was dissolved in dry CH$_3$CN/dry DCM (20 mL/20 mL), and the solution was degassed with N$_2$ for 5 minutes. The resulting solution was added dropwise via dropping funnel to the above catalyst solution, keeping the internal temperature around 0° C. during the addition of compound 504b. After addition of compound 504b, the reaction mixture was stirred at 0° C. to 2° C. (internal temp) for 4 hours. TLC showed the reaction was almost completed. A saturated NaHCO$_3$ solution (50 mL) was added, and the cooling bath was removed. The mixture was stirred for 2 hours and extracted with EtOAc (3×50 mL). The combined organic extracts were washed with brine (100 mL), dried over Na$_2$SO$_4$, filtered, and concentrated to dryness. The product was purified by flash column chromatography on silica gel eluting with EtOAc/DCM (1/10 to 1/3). The product fractions were combined and concentrated in vacuo to give the product, 505b, as a white foam (2.90 g, 93% yield). HPLC: 98.3%. LCMS: 458.21 (M+1). $^1$H NMR (400 MHz, CDCl$_3$): δ 7.59 (s, 1H), 6.83 (s, 1H), 5.53 (br s, 1H), 4.64 (d, J=8.4 Hz, 0.5H), 4.47 (m, 1H), 4.25 (d, J=8.0 Hz 0.5H), 4.16-4.00 (m, 2H), 3.80 (m, 0.5H), 3.65 (m, 0.5H), 3.26 (m, 0.5H), 2.93 (m, 0.5H), 2.81 (m, 0.5H), 2.51-2.45 (m, 1H), 2.16-2.03 (m, 1.5H), 1.29 (br s, 3H).

Step 6. To a 250 mL flask was charged compound 505b (6.44 g, 14.07 mmol) dissolved in MeOH (100 mL) and water (25 mL). Solid NaOH (6.5 g, 162.5 mmol) was added, and the stirred reaction mixture was warmed to 60° C. (oil bath temperature) for 3 hours. TLC showed the reaction went to completion. The reaction mixture was cooled to room temperature and then concentrated to dryness. The residue was purified by flash column chromatography on silica gel with MeOH/DCM/NH₄OH (7/93/0.5) to give Compound 391 (4.35 g, 86% yield) as off-white solid. HPLC: 99.4%. LCMS: 362.21 (M+1). $^1$H NMR (400 MHz, DMSO-d$_6$): δ 7.88 (s, 1H), 6.95 (s, 1H), 5.37 (t, J=3.2 Hz, 1H), 4.57 (d, J=5.2 Hz, 0.5H), 4.20 (d, J=5.2 Hz, 0.5H), 4.12-4.05 (m, 2H), 3.82-3.71 (m, 1H), 3.47-3.41 (m, 0.5H), 3.15 (d, J=4.8 Hz, 1H), 3.11-3.06 (m, 1H), 2.33-1.97 (m, 1.5H), 1.75-1.68 (m, 0.5H), 1.43-1.36 (m, 0.5H), 1.27-1.21 (m, 1H), 1.01 (d, J=6.4 Hz, 3H).

Solid State NMR Experimental (Compounds 174 and 181 Forms)

A Bruker-Biospin 400 MHz wide-bore spectrometer equipped with Bruker-Biospin 4 mm HFX probe was used. Samples were packed into 4-mm ZrO₂ rotors and spun under Magic Angle Spinning (MAS) condition with spinning speed typically set to 12.5 kHz. The proton relaxation time was measured using $^1$H MAS T$_1$ saturation recovery relaxation experiment in order to set up proper recycle delay of the $^{13}$C and $^{31}$P cross-polarization (CP) MAS experiments. The fluorine relaxation time was measured using $^{19}$F MAS T$_1$ saturation recovery relaxation experiment in order to set up proper recycle delay of the $^{19}$F MAS experiment. The CP contact time of carbon as well as phosphorus CPMAS experiments was set to 2 ms. A CP proton pulse with linear ramp (from 50% to 100%) was employed. The carbon Hartmann-Hahn match was optimized on external reference sample (glycine), while phosphorus Hartmann-Hahn match was optimized on the actual samples. All carbon, phosphorus, and fluorine spectra were recorded with proton decoupling using TPPM15 decoupling sequence with the field strength of approximately 100 kHz.

Preparation of K2

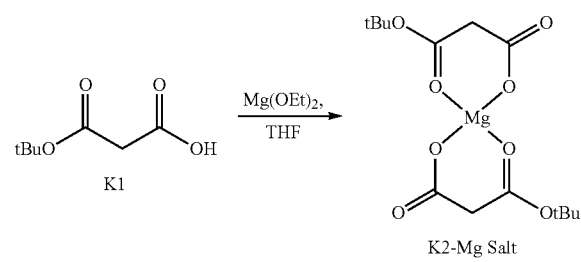

K2-Mg Salt

THF (3720 mL, 6.2 vol) was charged to a 5 L glass flask, then K1 (600 g, 3.47 mol, 576.92 mL, 92.6% purity by Q-NMR, 1 equiv) was added at 20° C. The mixture was cooled to 0° C. and Mg(OEt)₂ (198.46 g, 1.73 mol, 0.5 equiv) was charged to the reactor. The resulting mixture was stirred at 0-5° C. for 10 minutes, then warmed to 20° C. and stirred for 18 hours to give a milky white suspension. The hazy solution was distilled at 40° C. under reduced pressure to remove THF (3.1 L). n-Hexane (3.1 L) was added, and the mixture was stirred for 2 hours to give a thick slurry. The slurry was filtered, and the filter cake was washed with n-hexane (1×300 mL). The solid was dried under vacuum at 40° C. for 16 hours to provide 533.6 g of K2-Mg salt (89.8% yield).

Preparation of K7

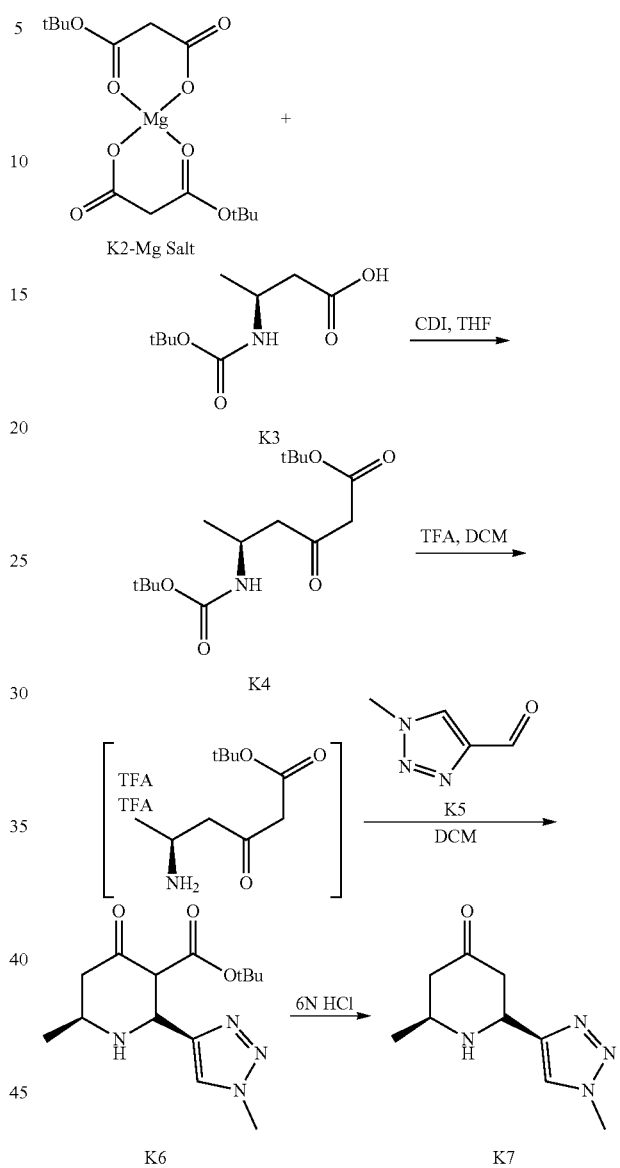

Step 1. K3 (600 g, 2.85 mol, 1 equiv, 96.5% purity by Q-NMR) was dissolved in anhydrous THF (3660 mL) in a 5000 mL glass flask. CDI (508.15 g, 3.13 mol, 1.1 equiv) was charged to the flask in 5 portions over 15 minutes to give a solution. The resulting reaction mixture was stirred at 18° C. for 2.5 hours. K2-Mg salt (755.77 g, 2.02 mol, 91.7% purity, 0.71 eq) was charged to the reactor in 5 portions over 8 minutes. The resulting suspension was stirred for 18 hours at 18° C. The reaction mixture was diluted with methyl tert-butyl ether (1.8 L, 3 vol) and treated with 2 N HCl (7.1 L) to adjust the pH to 2.0-3.0. The organic layer was separated. The organic layer was combined and washed with saturated sodium bicarbonate (3.3 L). The organic layer was dried over anhydrous sodium sulfate and filtered, and the filtrate was evaporated at 40° C. under reduced pressure to give 862.3 g of K4 (96.9% yield).

Steps 2 and 3. A solution of K4 (570.0 g, 1.83 mol, 96.7% purity by Q-NMR, 1 equiv) in dichloromethane (2850 mL, 5 vol) was cooled to 5° C. At 0-5° C., trifluoroacetic acid (859.15 g, 7.54 mol, 557.89 mL, 4.12 equiv=4 eq/0.97) was added over 80 minutes. The resulting solution was stirred at 5° C. for 1 hour, then warmed to 20° C. and stirred for 18 hours. K5 (180.76 g, 1.59 mol, 97.8% purity, 0.87 equiv) was charged as a solid in one portion, and the resulting solution was stirred for 18 hours at 20° C. The reaction mixture was diluted with saturated brine (1.14 L, 2 vol), cooled to 5 to 10° C., and then adjusted to pH 10 with 6 N sodium hydroxide (950 mL). The organic layer was separated and dried over sodium sulfate (400 g). The resulting solution was distilled at 30° C. under reduced pressure to remove DCM (1 L). MTBE (1.14 L) was charged, and the mixture was evaporated to dryness under reduced pressure to give an off-white solid 533.5 g. The residue was diluted with methyl tert-butyl ether (3.2 L, 6 vol) and stirred at 10-20° C. for 24 hours. The mixture was filtered, and the filter cake was washed with fresh methyl tert-butyl ether (453 mL, 0.85 vol) and dried under vacuum at 45° C. for 1 hour to provide 290.4 g of K6 (62.0% yield).

Step 4. To an aqueous solution of HCl (6 M, 1.52 L, 8.83 eq) was added K6 (303 g, 1.03 mol, 1 eq) in nine portions at 30-35° C. in a 3000 mL three-necked, round-bottomed flask. The mixture was stirred at 35° C. for 1 hour. A light yellow solution was obtained. TLC and LCMS analysis indicated K6 was reacted completely. HPLC (External standard method) indicated about 0.03% of K6 remained. When the reaction was completed, the mixture was cooled to 5° C. and charged with 3 g of solid $K_3PO_4$. 1.11 g of 45% KOH solution was charged portion-wise at a rate to keep the temperature less than 30° C. 156 g of 45% KOH was charged resulting in a pH of 11-12. The mixture was extracted with DCM (6×900 mL). The combined organic layers were dried over sodium sulfate (300 g) and concentrated at 25° C. under vacuum until a heavy slurry of product was obtained. n-Heptane (200 mL) was added, and the mixture was further concentrated at 25° C. to remove solvents (200 mL). This process was repeated three times. The resulting solution was filtered, and the filter cake was washed with n-heptane (200 mL). The solid was dried under vacuum for 10 hours at 40° C. to give 186 g of K7 (92.9% yield).

Preparation of K8

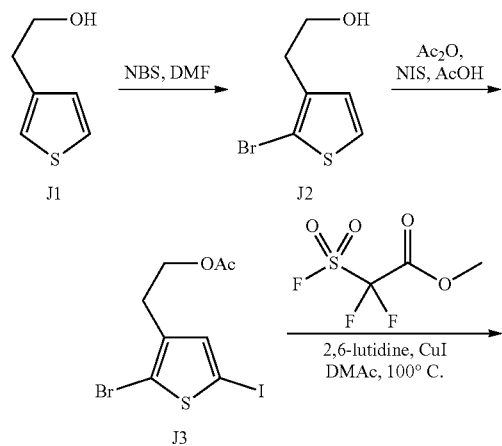

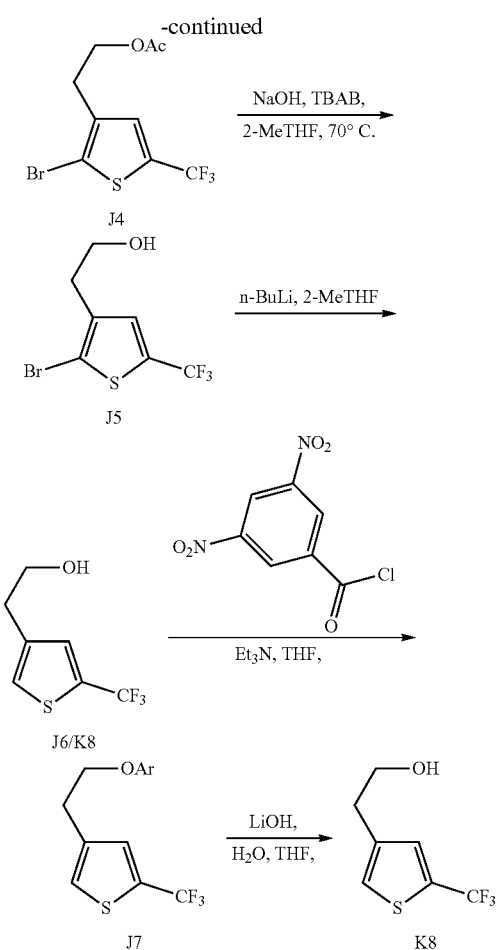

Step 1 (J2): J1 (85.0 kg, 663.1 mol, 1.0 equiv) was dissolved in DMF (162.3 kg) in a 1000 L reactor with stirring under nitrogen and then cooled to −10-0° C. NBS (122.7 kg, 689.6 mol, 1.04 eq) was dissolved in DMF (241.0 kg) in a separate, 500 L reactor with stirring under nitrogen. The solution of NBS was added slowly to the 1000 L reactor over 5 hours while maintaining the temperature between −10-0° C. After the addition, the reaction mixture was held at −10-0° C. for 1-2 hours. A saturated aqueous solution of NaCl (480 kg) was added to the reaction mixture followed by EtOAc (460.7 kg), and the reaction mixture was stirred for 30 minutes. The organic layer was separated and the aqueous layer was extracted with EtOAc (230.4 kg). The organic layers were combined and washed with 0.5 N HCl (420.0 kg). After separation, a saturated solution of NaCl (300 kg) was added, and the mixture was stirred for 30 minutes. The phases were separated and the organic layer was concentrated at 40-50° C. to afford J2 (147.95 kg, 92.3% purity, 75% QNMR, 80.78% yield) as a brown liquid.

Step 2 (J3): J2 (147.95 kg, QNMR 75%, 535.8 mol, 1.0 equiv) was treated with AcOH (349.65 kg) and Ac2O (82.05 kg, 803.7 mol, 1.5 eq) in a 1000 L reactor with stirring under nitrogen. The mixture was heated to 90-100° C. for 5-10 hours and until less than 0.5% J2 remained by GC. The mixture was cooled to 35-40° C. NIS (138.6 kg, 616.2 mol, 1.15 eq) was added to the 1000 L reactor, and the mixture was stirred at 35-40° C. for 6-10 hours. When less than 0.5% of the intermediate remained, the mixture was cooled to 20-30° C. and transferred to a 3000 L reactor. A mixture of MTBE/heptane (250 kg/226.4 kg) and water (333 kg) were added. The mixture was stirred for 30 minutes and then separated. The aqueous layer was extracted with a mixture of MTBE/heptane (250 kg/226.4 kg). The organic layers were combined, and a 13% solution of aqueous $NaHSO_3$ (510.6 kg) was added. After stirring the mixture for 30 minutes, the layers were separated, and the organic layer was washed with 1 M NaOH (461.8 kg) and water (333 kg). The organic layer was concentrated at 40-60° C. to afford J3 (220.75 kg, 92.3% purity, 85.57% QNMR, 94% yield) as a brown liquid.

Step 3 (J4): J3 (111 kg, 85.57% QNMR, 252.2 mol, 1.0 equiv), CuI (12.06 kg, 63.3 mol, 0.25 equiv), and 2,6-lutidine (6.78 kg, 63.3 mol, 0.25 equiv) were dissolved in DMAc (356.25 kg) in a 3000 L reactor with stirring under nitrogen and then heated to 85-100° C. Methyl fluorosulfonyldifluoroacetate (MFSDA, 194.65 kg, 1013.2 mol, 4.0 equiv) was added to the 3000 L reactor while maintaining the temperature between 85-100° C. After the reaction mixture was held at 90-95° C. for 1-4 hours, less than 5.0% J3 remained and the reaction mixture was cooled to 5-15° C. In another 3000 L reactor, water (1140 kg) and n-heptane (439.3 kg) were charged, and the mixture was cooled to 10-20° C. The reaction was quenched to this reactor at 10-20° C., and the resulting mixture was stirred for 30 minutes. The layers were filtered and then separated. The aqueous phase was extracted with n-heptane (220 kg), and the combined organics were washed with 20% NaCl (570 kg) and dried with $MgSO_4$ (9.5 kg, 10% w/w). The mixture was filtered and concentrated at 35-45° C. to give crude J4. This same procedure was repeated on three additional batches of J4 (109.8 kg, QNMR 85.57%)+(110.2 kg, QNMR 85.1%)+(108.15 kg, QNMR 85.1%). The four total batches of crude J4 were combined and distilled to afford J4 (246.5 kg, 89.6% purity, 87% QNMR, 67.7% yield) as a yellow liquid.

Step 4 (J5): NaOH (61.63 kg, 1540.8 mol, 2.28 equiv) was dissolved in water (493 kg) in a 3000 L reactor with stirring. J4 (246.5 kg, 87% QNMR, 676.2 mol, 1.0 equiv) and tetrabutylammonium bromide (TBAB, 12.33 kg, 38.25 mol, 0.057 eq) were charged, followed by 2-MeTHF (1059.95 kg). The reaction mixture was heated to 65-75° C. and held at that temperature for 1-4 hours, at which time less than 1.0% J4 remained by HPLC analysis. The reaction mixture was cooled to 30° C., and the phases were separated. The organic layer was washed twice with water (739.5 kg) and dried over $MgSO_4$ (36.98 kg). The mixture was filtered and concentrated to dryness at 40-50° C. n-Heptane (167.6 kg) was added, and the mixture was again concentrated to remove residual water. This process was repeated one time to afford J5 (203.2 kg, 89.46% QNMR, 94.57% plurity, 97.72% yield) as a yellow liquid.

Step 5 (J6/K8): J5 (203.2 kg, 89.46% QNMR, 660.8 mol, 1.0 equiv) was dissolved in THE (817.2 kg) in a 2000 L reactor with stirring under nitrogen. The solution was cooled to −50 to −30° C. and charged with n-BuLi (377.5 kg, 1387.7 mol, 2.1 equiv) while maintaining the temperature between −50 to −30° C. After the reaction mixture was held at −50 to −30° C. for 1-2 hours, less than 1.0% J5 remained. The mixture was quenched into 20% aqueous $NH_4Cl$ (671.9 kg) at 15° C., and the resulting mixture was stirred for 30 minutes and separated. The aqueous phase was extracted with EtOAc (817 kg). The combined organic phases were washed twice with 20% aqueous $NH_4Cl$ (671.9 kg), followed by 20% aqueous NaCl (408.6 kg) and then concentrated to dryness at 40-55° C. THE (100 kg) was added, and the mixture was concentrated to remove residual water. This process was repeated one time to afford J6/K8 (147.8 kg, 89.71% purity, 83.62% QNMR, 95.41% yield) as a yellow liquid.

Step 6 (J7): J6/K8 (147.8 kg, 83.62% QNMR, 627.0 mol, 1.0 equiv) and triethylamine (95.2 kg, 940.5 mol, 1.5 equiv) were dissolved in THE (587.0 kg) in a 3000 L reactor with stirring under nitrogen. The mixture was cooled to −10-0° C. 3,5-dinitrobenzoyl chloride (173.5 kg, 752.4 mol, 1.2 equiv) was dissolved in THF (587.0 kg) in a separate 1000 L reactor, and the resulting solution was transferred into the 3000 L reactor at −10-5° C. After the reaction mixture was warmed to 10-20° C. and stirred for 1.5-2 hours, less than 1.0% J6/K8 remained. 8% aqueous $NaHCO_3$ (667.4 kg) and EtOAc (500 kg) were added to the 3000 L reactor. The mixture was stirred for 30 minutes and then separated. The organic layer was washed with an 8% aqueous solution of $NaHCO_3$ (667.4 kg), followed by 10% aqueous NaCl (680 kg), and then concentrated at 40-55° C. n-Heptane (168 kg) was added, and the mixture was concentrated at 40-55° C. EtOAc (300 kg) and n-heptane (420 kg) were added, and the mixture was heated to 65-75° C. with stirring for 1-2 hours. The slurry was cooled to 15-25° C., was stirred for 1-2 hours, and then was filtered. The solid was treated with a combination of EtOAc (450 kg) and EtOH (352 kg), and the resulting mixture was heated to 65-75° C. with stirring for 1-2 hours. The mixture was cooled to 5-10° C., stirred for 1-2 hours, and filtered. The filter cake was washed with EtOH (50 kg) and dried at 40-50° C. to afford J7 (206.4 kg, 99.04% purity, 83.59% yield) as a light yellow solid.

Step 7 (K8): $LiOH \cdot H_2O$ (66.57 kg, 1586.5 mol, 3.0 equiv) was dissolved in water (619.2 kg) in a 3000 L reactor with stirring. J7 (206.4 kg, 528.8 mol, 1.0 equiv) and THE (928.8 kg) were charged. After stirring the mixture at 30-40° C. for 3 hours, less than 1% J7 remained. The layers were separated, and the THF layer was concentrated at 40-55° C. MTBE (1548 kg) was added, and the resulting mixture was washed twice with 8% aqueous $NaHCO_3$ (668.7 kg) and then washed with 20% aqueous NaCl (743 kg). The mixture was dried over $MgSO_4$ (20.64 kg, 10% w/w) for 1-2 hours and filtered. The organic phase was concentrated at 40-50° C. n-Heptane (138 kg) was added, and the mixture was concentrated to remove residual MTBE. This process was repeated one time, and the resulting solution was concentrated to yield K8 (89.9 kg, 98.61% QNMR, 99.24% purity, 86.72% yield) as a light yellow, brown liquid.

Compound 181 Phosphate Salt Hydrate

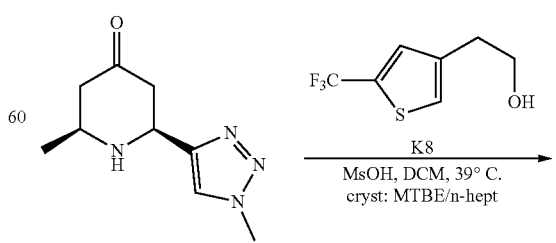

K7

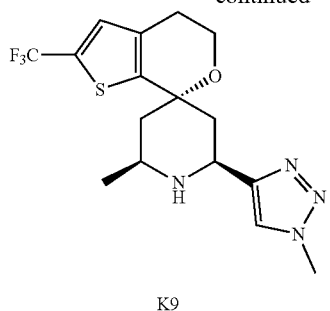

K9

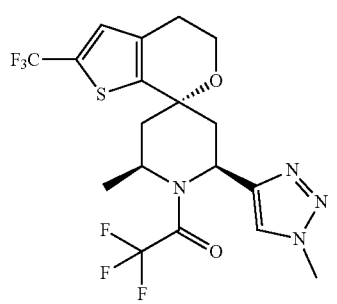

K10

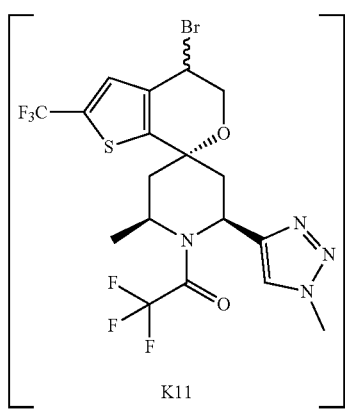

K11

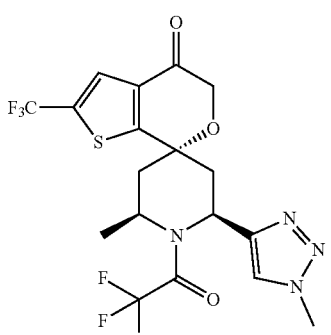

K12

TFAA, Et₃N,
DCM
cryst: MTBE,
n-hept
→

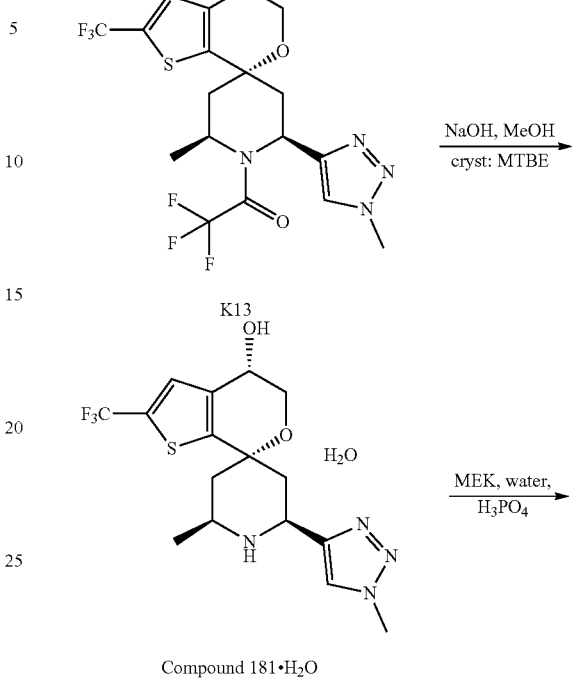

K13

Compound 181•H₂O

Compound 181•H₃PO₄

NaOH, MeOH
cryst: MTBE
→

MEK, water,
H₃PO₄
→

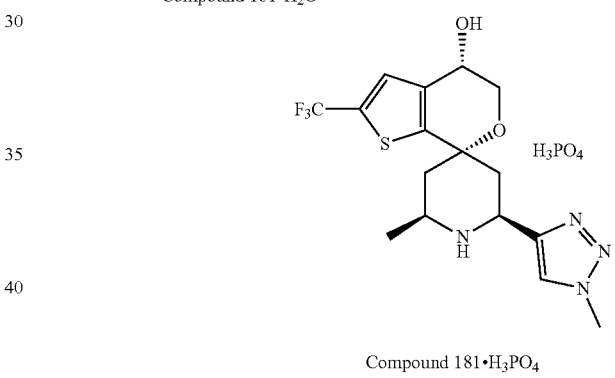

Et₃N, DMSO,
75° C.
cryst: IPA/n-hept
recryst: IPA
→

(RhCl₂Cp*)₂
(R,R)-TsDPEN,
HCO₂H, Et₃N,
ACN. -15° C.
cryst: MTBE/n-hept
→

Step 1. A solution of K7 (70 g, 0.360 mol, 1.0 equiv) and 2-[5-trifluoromethyl)-3-thienyl]ethanol K8 (74.2 g, 0.378 mol, 1.05 equiv) in dichloromethane (210 mL, 3 vol) was cooled to 5° C. Methanesulfonic acid (210.6 mL, 3.24 mol, 9 equiv) was charged to the reactor while maintaining an internal temperature of less than 30° C. The resulting reaction mixture was heated to 39° C. After 18 hours, HPLC analysis indicated greater than 99% conversion to K9. The reaction mixture was cooled to 30° C., charged with dichloromethane (280 mL, 4 vol), and further cooled to 0° C. The pH was adjusted to pH 10 with 4 N sodium hydroxide (830 mL). The organic layer was separated, and the aqueous phase was back-extracted with DCM (350 mL, 5 vol). The combined organics were washed with water (350 mL, 5 vol) and concentrated at reduced pressure to 3.5 total volumes. The batch was charged with MTBE (5 vol) and concentrated under reduced pressure to 3.5 total volumes. This put/take cycle was repeated three additional times, and the resulting 3.5 vol. mixture was diluted with MTBE (6.5 vol) to provide a 10 vol. mixture. The slurry was heated to 50° C. and stirred for 5 hours, then charged with n-heptane (700 mL, 10 vol) over 2 hours. The resulting suspension was cooled to 20° C.

over 5 hours and stirred for 18 hours. The suspension was filtered, washed with 1:2 MTBE/n-heptane (2×140 mL, 2×2 vol), and dried under vacuum while flushing with nitrogen at 50° C. for 18 hours to give 103 g of K9 (77% yield).

Step 2. A solution of K9 (50 g, 0.134 mol, 1.0 equiv) and triethylamine (22.5 mL, 0.161 mol, 1.2 equiv) in dichloromethane (380 mL, 7.6 vol) was cooled to 5° C. At 5° C., trifluoroacetic acid anhydride (20.5 mL, 0.148 mol, 1.1 equiv) was charged to the reactor while keeping the internal temperature below 15° C. The resulting reaction mixture was stirred at 5° C. for 1 hour, at which time HPLC showed 99.8% conversion to K10. The reaction mixture was charged at 5° C. with water (200 mL, 4 vol). The organic layer was separated and sequentially washed with 5% $NaHCO_3$ (200 mL, 4 vol), 2 N HCl (2×200 mL, 2×4 vol), and water (2×200 mL, 2×4 vol). The organic layer was concentrated under reduced pressure to 3.5 total volumes. MTBE (400 mL, 8 vol) was charged, and the batch was concentrated under reduced pressure to 3.5 vol. This put/take cycle was repeated two additional times, and the mixture was concentrated to 3 volumes after the final cycle. The solution was heated to 40° C. and charged with n-heptane (190 mL, 2 vol) over 1 hour. The batch was cooled to 20° C. over 2 hours to yield a suspension. n-Heptane (500 mL, 10 vol) was charged over 2 hours, and the resulting suspension was stirred for 18 hours. The suspension was filtered, washed with 5% MTBE/n-heptane (2×125 mL, 2×2.5 vol), and dried under vacuum while flushing with nitrogen at 50° C. for 18 hours to give 53 g of K10 (84% yield).

Step 3. A suspension of K10 (70 g, 149.4 mmol, 1.0 equiv), and 1,3-dibromo-5,5'-dimethylhydantoin (29.9 g, 104.6 mmol, 0.7 equiv) in anhydrous chlorobenzene (280 L, 4 vol) was sparged with sub-surface nitrogen bubble for 60 minutes. The mixture was heated to 75° C. and charged at that temperature with a prepared solution of azobisisobutyronitrile (0.49 g, 3 mmol, 0.02 equiv) in anhydrous chlorobenzene (70 mL, 1 vol) over 60 minutes. After stirring for 2 hours at 75° C., HPLC analysis showed conversion to K11. The reaction mixture was cooled to 60° C. and charged with anhydrous, degassed DMSO (350 mL, 5 vol) over 30 minutes, followed by anhydrous, degassed triethylamine (104 mL, 747 mmol, 5 equiv) over 30 minutes. The reactor headspace was well purged with nitrogen, and the batch was heated to 75° C. After 15 hours, HPLC analysis showed >99% conversion of K11 to K12. The batch was cooled to 20° C. and diluted with dichloromethane (210 mL, 3 vol). The batch was further cooled to 5° C. and charged with water (350 mL, 5 vol) while keeping the solution temperature below 30° C. The organic layer was separated, and the aqueous layer was back-extracted with dichloromethane (210 mL, 3 vol). The organic phases were combined and washed sequentially with 2 N HCl (350 mL, 5 vol) and water (2×350 mL, 2×5 vol). The organic phase was concentrated under reduced pressure to 3 total volumes. The solution was charged with IPA (560 mL, 8 vol) and concentrated under reduced pressure to 3 volumes. This put/take cycle was repeated two additional times, giving a 3-volume solution that was further diluted with IPA (70 mL, 1 vol). The resulting 4 vol mixture was heated to 75° C. to provide a homogenous solution and then cooled to 50° C. The solution was seeded (0.1 wt %) at 50° C., stirred for 1 hour, and further cooled to 20° C. over 2 hours. After stirring an additional 18 hours at 20° C., the slurry was charged with n-heptane (70 mL, 1 vol) over 1 hour. The slurry was stirred for 4 hours at 20° C., filtered, washed with 1:1 IPA/n-heptane (2×70 mL, 2×2 vol), and dried under vacuum while flushing with nitrogen at 50° C. for 18 hours to give 31.2 g of K12 (43% yield from K10). The dried K12 was suspended in IPA (93 mL, 3 vol), heated to 80° C., and stirred at that temperature for 2 hours. The solution was cooled to 70° C. over 1 hour and stirred for 1 hour. The suspension was cooled to 20° C. over 5 hours and stirred at that temperature for 18 hours. The suspension was filtered, washed with 1:1 IPA/n-heptane (2×35 mL, 2×0.5 vol), and dried under vacuum while flushing with nitrogen at 50° C. for 18 hours to give 28.8 g of K12 (40% yield from K10).

Step 5. The pentamethylcyclopentadienylrhodium(III) chloride dimer (154 mg, 0.002 eq) and (R,R)-TsDPEN (182 mg, 0.004 eq) were combined in acetonitrile (240 mL, 4 vol), and the mixture was sparged with nitrogen while stirring at 20° C. for 1 hour. The mixture was cooled to −15° C. and a prepared mixture of formic acid (27.0 mL, 5.5 equiv) and triethylamine (38.1 mL, 2.2 eq) was added over 30 minutes and the resultant red/orange solution was stirred for 15 minutes at −15° C. A solution of K12 (60 g, 1.0 equiv) in acetonitrile (240 mL, 4 vol) was separately prepared and added to the cold catalyst solution over 45 minutes. The mixture was sparged with subsurface nitrogen bubble for 15 minutes, stirred at −15° C. for 20 hours, warmed to 0° C., and stirred for an additional 20 hours. The temperature was adjusted to 20° C. and the mixture was charged with MTBE (360 mL, 6 vol) and 18% NaCl (aq) (360 mL, 6 vol). The phases were mixed, and the phases separated. The organic phase was washed sequentially with 18% NaCl (aq) (2×360 mL, 6 vol), 4% $NaHCO_3$ (aq) (360 mL, 6 vol), and 18% NaCl (aq.) (180 mL, 3 vol). The reaction solution was concentrated to 3 total volumes under reduced pressure, then solvent swapped to MTBE by adding MTBE (360 mL, 6 vol) and concentrating to 3 volumes under reduced pressure. This put/take cycle was repeated 3 additional times. The resulting solution was diluted to 4 total volumes with MTBE and charged with DCM (240 mL, 4 vol) and MTBE-prewashed SiliaMetS DMT resin (30 g, 50 wt %). The mixture was stirred vigorously at 20° C. for 2 hours. The resin slurry was filtered under vacuum. The reaction flask was rinsed with a solution of 2:1 DCM:MTBE (120 mL, 2 vol) and the rinse was transferred to the resin. The resulting slurry was mixed, then filtered under vacuum. The resin was rinsed once more with a solution of 2:1 DCM:MTBE (120 mL, 2 vol) by adding it to the resin, mixing, then filtering under vacuum. The rinses and original filtrate were combined and transferred back to the reaction flask using 2:1 DCM:MTBE (30 mL, 0.5 vol) as a final rinse after the transfer. The filtrate was combined with MTBE-pre-washed SiliaMetS DMT resin (30 g, 50 wt %) and stirred vigorously for 2 hours at 20° C. The resin slurry was under vacuum. A solution of 2:1 DCM:MTBE (120 mL, 2 vol) was used to rinse the reaction flask, and the rinse was transferred to the resin in the frit. The slurry was mixed and filtered under vacuum. A solution of 2:1 DCM:MTBE (120 mL, 2 vol) was charged to the resin in the frit and the slurry was mixed, then filtered under vacuum. The combined filtrates were transferred back to the reaction flask using 2:1 DCM:MTBE (30 mL, 0.5 vol) as a rinse. The filtrate was combined with MTBE-pre-washed SiliaMetS DMT resin (30 g, 50 wt % loading) and stirred vigorously for 18 hours. The resultant resin slurry was filtered under vacuum. The reaction flask was rinsed with a solution of 2:1 DCM:MTBE (120 mL, 2 vol). The rinse was added to the resin in the frit, and the slurry was mixed then filtered under vacuum. A solution of 2:1 DCM:MTBE (120 mL, 2 vol) was added to the resin in the frit, and the slurry was mixed then filtered under vacuum. The combined filtrate was transferred to a flask, then concentrated to 3 total volumes (180 mL) of solution. MTBE (480 mL, 8 vol) was added, and the solution was concentrated to 3 total volumes (180 mL). This put/take cycle was repeated two additional times. The resulting solution was diluted to 5 vol (300 mL) with MTBE, heated to 50° C. and stirred for 3 hours. n-Heptane (240 mL, 4 vol) was added over 60 minutes, and the slurry was maintained at 50° C. for an additional 1 hour. The slurry was cooled to 20° C. over 3 hours and stirred overnight. The slurry was filtered under vacuum. The cake was rinsed with 1:1 MTBE:heptane (2×60 mL, 2×1 vol), and the solids were dried under vacuum at 50° C. for 18 hours to yield 58.5 g of K13 (83% yield).

Step 6. K13 (43.5 g, 89 mmol, 1 equiv) and methanol (150.0 mL, 3 vol) were combined and agitated until full dissolution was observed. 6 N NaOH (89 mL, 6 eq) was added drop-wise over 30 minutes, and the mixture was heated to 60° C. and stirred for 1 hour at which time complete conversion to Compound 181 was achieved. The reaction solution was cooled to 15° C. and treated with isopropyl acetate (250 mL, 5.75 vol). Water (100 mL, 2.3 vol) was then added, and the mixture was agitated for 30 minutes. The phases were separated, and the aqueous phase was back-extracted with isopropyl acetate (250 mL, 5.75 vol). The organics were combined and washed with 10% NaCl (aq.) (2×250 mL, 2×5.75 vol) and water (250 mL, 5.75 vol). The organics were concentrated to 4.0 total volumes (174 mL). The solution was charged with MTBE (11.5 vol, 500 mL) and concentrated again to 4.0 vol. This put/take cycle was repeated three additional times. MTBE (75 mL, 1.75 vol) was added to give a 5.75 vol, 250 mL, solution. While stirring at 20° C., water (3.2 mL, 180 mmol, 2 eq) was added over 2 hours, inducing crystallization. The slurry was stirred at 20° C. for 1 hour, then heated to 50° C. and stirred at that temperature for 3 hours. The suspension was cooled to 20° C. and stirred for 18 hours. The slurry was filtered under vacuum, and the cake was washed with MTBE (100 mL, 2.3 vol). The solids were dried at 50° C. under vacuum for 18 hours to provide 29 g of Compound 181 Free Form Monohydrate (Compound 181. $H_2O$) (81% yield).

Step 7. Method A. 1 eq. of Compound 181 free form monohydrate was charged to a reactor followed by 6 vol. of MEK. Agitation was started at 20° C. Once a clear solution was obtained, the solution was polish filtered and charged back to the reactor. Water (0.2 vol.) was added to the clear solution and agitation continued. 1 wt % of Compound 181 Phosphate Salt was added as seeds. In a separate container, 1.02 eq. of 85 wt % phosphoric acid was diluted with 3.8 vol. of MEK. This phosphoric acid solution was then added to the reactor slowly over 3 hours. The final slurry was agitated at 20° C. for 2 hours, then filtered under vacuum. The resulting wet cake was washed with 3 vol. of MEK. The wet cake was dried under vacuum with a nitrogen bleed at 80° C. to yield Compound 181 Phosphate Salt Hydrate (Compound 181. $H_3PO_4$) (about 90% yield).

Method B. 1 eq. of Compound 181 free form monohydrate was charged to a reactor, followed by 6 vol. of MEK. Agitation was commenced at 20° C., and once a clear solution was obtained, the solution was polish filtered and charged back to the reactor. Water (0.2 vol.) was added to the clear solution and agitation continued. In a separate container, 1.02 eq. of 85 wt % phosphoric acid was diluted with 3.8 vol. of MEK. This phosphoric acid solution was then added to the reactor slowly over 3 hours. The final slurry was agitated at 20° C. for 2 hours then filtered under vacuum. The resulting wet cake was washed with 3 vol. of MEK. The wet cake was dried under vacuum with a nitrogen bleed at 80° C. to yield Compound 181 Phosphate Salt Hydrate (Compound 181. $H_3PO_4$) (about 90% yield).

Not: Compound 181 Phosphate Salt Hydrate is a crystalline hydrate.

XRPD and VH-XRPD

The powder, X-ray powder diffraction (XRPD), diffractogram of Compound 181 Phosphate Salt Hydrate (FIG. 1) was acquired at room temperature (25±2° C.) in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder was placed in sample stage AP CHC stage and CHC chamber. The CHC chamber was attached to a water pump which collected the relative humidity. The relative humidity in the chamber was stepwise changed in increments, starting at 5% for 1 hour, then increased to 10% and held for an hour followed by 10% relative humidity (RH) stepwise increased to 60% and held for an hour at each, with a jump at 60% to 90% and held for 1 hour. The CHC Chamber was then held at 90% for an additional hour, then decreased from 90% to 80% and held for 3 hours, then from 80% to 70% and held for 3 hours, then from 70% to 60% and held for 3 hours, then from 60% to 10% decreased stepwise by 10% RH and held for an hour at each step and last decreased from 10% to 5% and held for an hour. At the hour time point, XRPD collection was run over the range of about 3° to about 40°2θ with a step size of 0.0131303° and 49 s per step.

Figure 2:
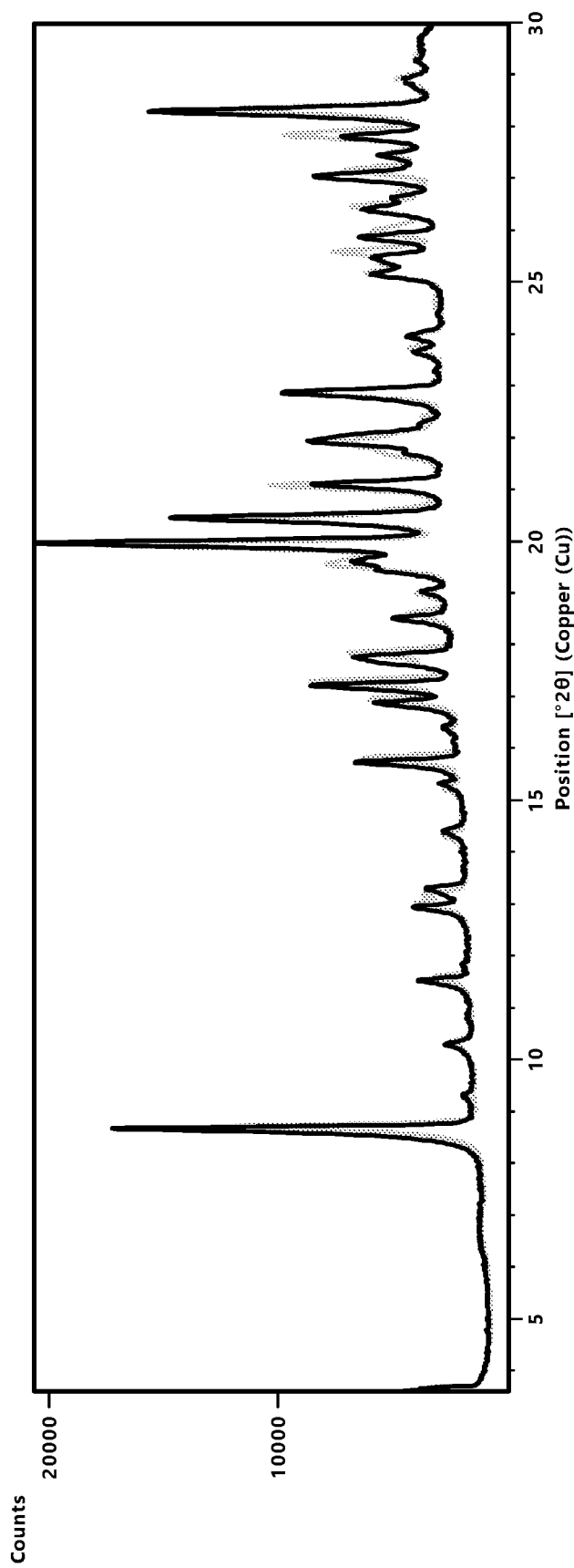
FIG. 2 depicts an XRPD diffractogram of Compound 181 Phosphate Salt Hydrate at 25±2° C. and 5% RH (black trace) or 90% (gray trace).

Variable Humidity XRPD (VH-XRPD): Compound 181 Phosphate Salt Hydrate was observed to have continuous peak shift which are all (within ±0.2°2θ) from 5-90% relative humidity (FIG. 2, Table 14).

TABLE 14

Peak List from XRPD Diffractogram of Compound 181 Phosphate Salt Hydrate

| XRD Peaks | Relative Humidity 40% | | Relative Humidity 5% | | Relative Humidity 90% | |
|---|---|---|---|---|---|---|
| | Angle (°2θ ± 0.2) | Intensity % | Angle (°2θ ± 0.2) | Intensity % | Angle (°2θ ± 0.2) | Intensity % |
| 1 | 19.9 | 100.0 | 19.9 | 100.0 | 19.9 | 100.0 |
| 2 | 8.6 | 76.2 | 8.6 | 79.2 | 8.6 | 65.3 |
| 3 | 28.3 | 64.3 | 28.3 | 69.4 | 28.3 | 60.9 |
| 4 | 20.4 | 56.7 | 20.4 | 61.9 | 20.4 | 55.2 |
| 5 | 21.0 | 43.0 | 22.8 | 37.1 | 21.0 | 48.7 |
| 6 | 22.8 | 41.4 | 17.2 | 31.9 | 27.8 | 44.9 |
| 7 | 17.2 | 38.3 | 21.9 | 30.1 | 22.8 | 40.9 |
| 8 | 27.8 | 37.2 | 21.1 | 29.7 | 17.2 | 40.5 |
| 9 | 26.4 | 28.4 | 27.0 | 29.3 | 19.5 | 30.9 |
| 10 | 17.8 | 27.2 | 15.7 | 23.7 | 25.5 | 30.6 |

TABLE 14-continued

Peak List from XRPD Diffractogram of Compound 181 Phosphate Salt Hydrate

| XRD Peaks | Relative Humidity 40% | | Relative Humidity 5% | | Relative Humidity 90% | |
|---|---|---|---|---|---|---|
| | Angle (°2θ ± 0.2) | Intensity % | Angle (°2θ ± 0.2) | Intensity % | Angle (°2θ ± 0.2) | Intensity % |
| 11 | 15.7 | 26.8 | 27.8 | 22.9 | 17.8 | 29.2 |
| 12 | 25.5 | 26.2 | 25.8 | 18.2 | 15.8 | 26.6 |
| 13 | 19.5 | 25.8 | 16.9 | 17.6 | 21.9 | 25.8 |
| 14 | 21.9 | 25.5 | 17.8 | 17.1 | 16.9 | 24.1 |
| 15 | 27.1 | 23.3 | 19.6 | 16.7 | 27.1 | 23.2 |
| 16 | 16.9 | 22.7 | 26.4 | 15.9 | 26.4 | 22.5 |
| 17 | 21.7 | 20.1 | 25.1 | 15.2 | 25.1 | 20.0 |
| 18 | 25.1 | 19.4 | 25.4 | 15.1 | 25.9 | 16.1 |
| 19 | 25.9 | 16.6 | 22.1 | 14.3 | 25.3 | 15.1 |
| 20 | 19.7 | 14.7 | 17.7 | 14.2 | 13.0 | 13.7 |
| 21 | 22.0 | 13.6 | 12.9 | 12.6 | 20.6 | 13.4 |
| 22 | 13.0 | 13.1 | 18.5 | 12.2 | 18.5 | 12.1 |
| 23 | 25.3 | 12.7 | 27.4 | 11.6 | 11.5 | 10.4 |
| 24 | 18.5 | 12.3 | 11.5 | 11.5 | 17.6 | 10.4 |
| 25 | 17.6 | 11.9 | | | 27.4 | 10.4 |
| 26 | 11.5 | 11.5 | | | 13.1 | 10.2 |
| 27 | 27.4 | 11.0 | | | | |
| 28 | 13.2 | 10.1 | | | | |

TGA

Figure 3:
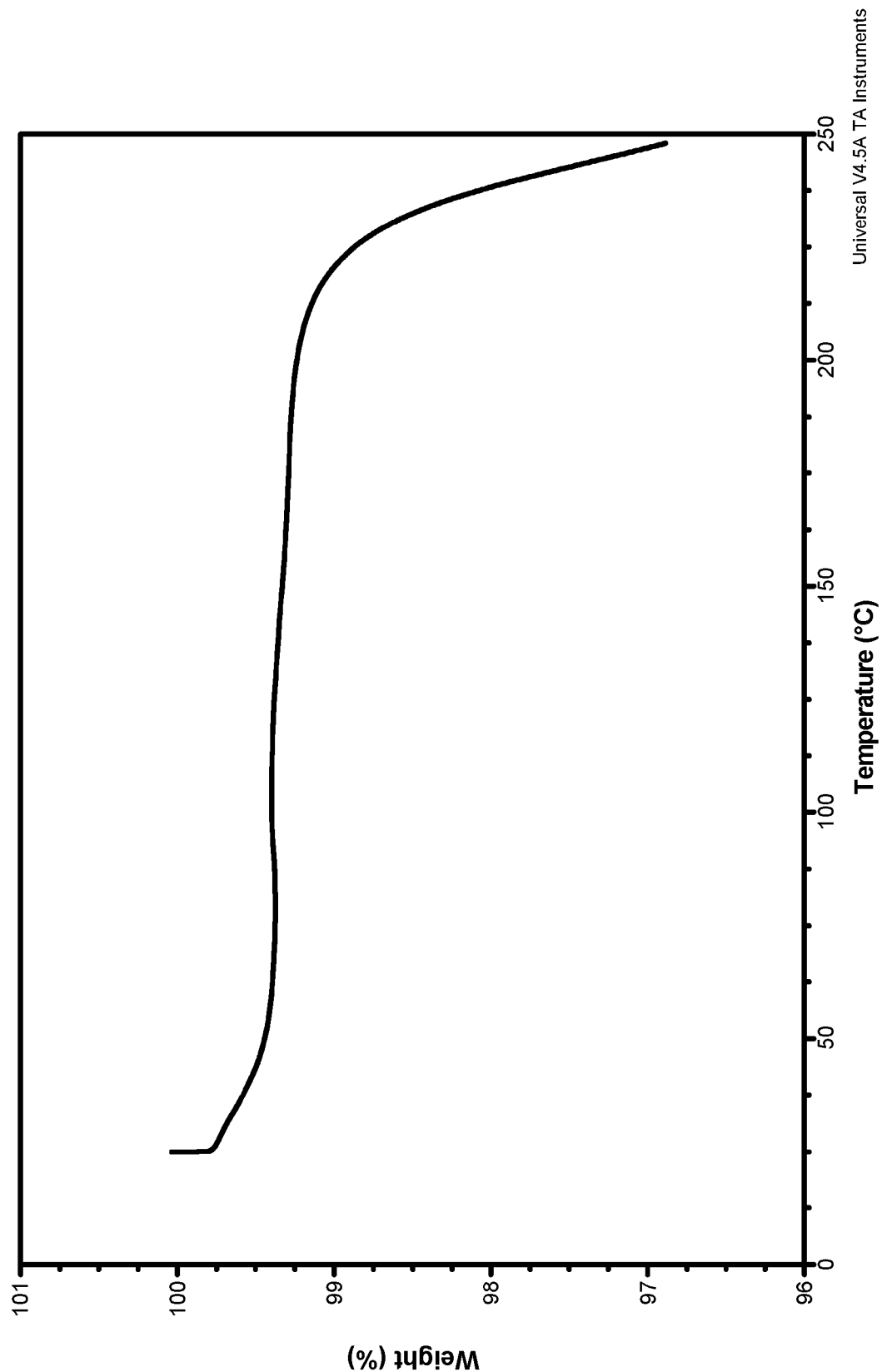
FIG. 3 depicts a TGA thermogram of Compound 181 Phosphate Salt Hydrate.

Thermal gravimetric analysis of Compound 181 Phosphate Salt Hydrate was performed using the TA Instruments Q5000 TGA. A sample with a weight of approximately 1-10 mg was scanned from ambient to 250° C. at a heating rate of 10° C./min with nitrogen purge. The TGA thermogram shows around 0.5% weight loss from ambient temperature up until 150° C. (FIG. 3).

DSC

Figure 4:
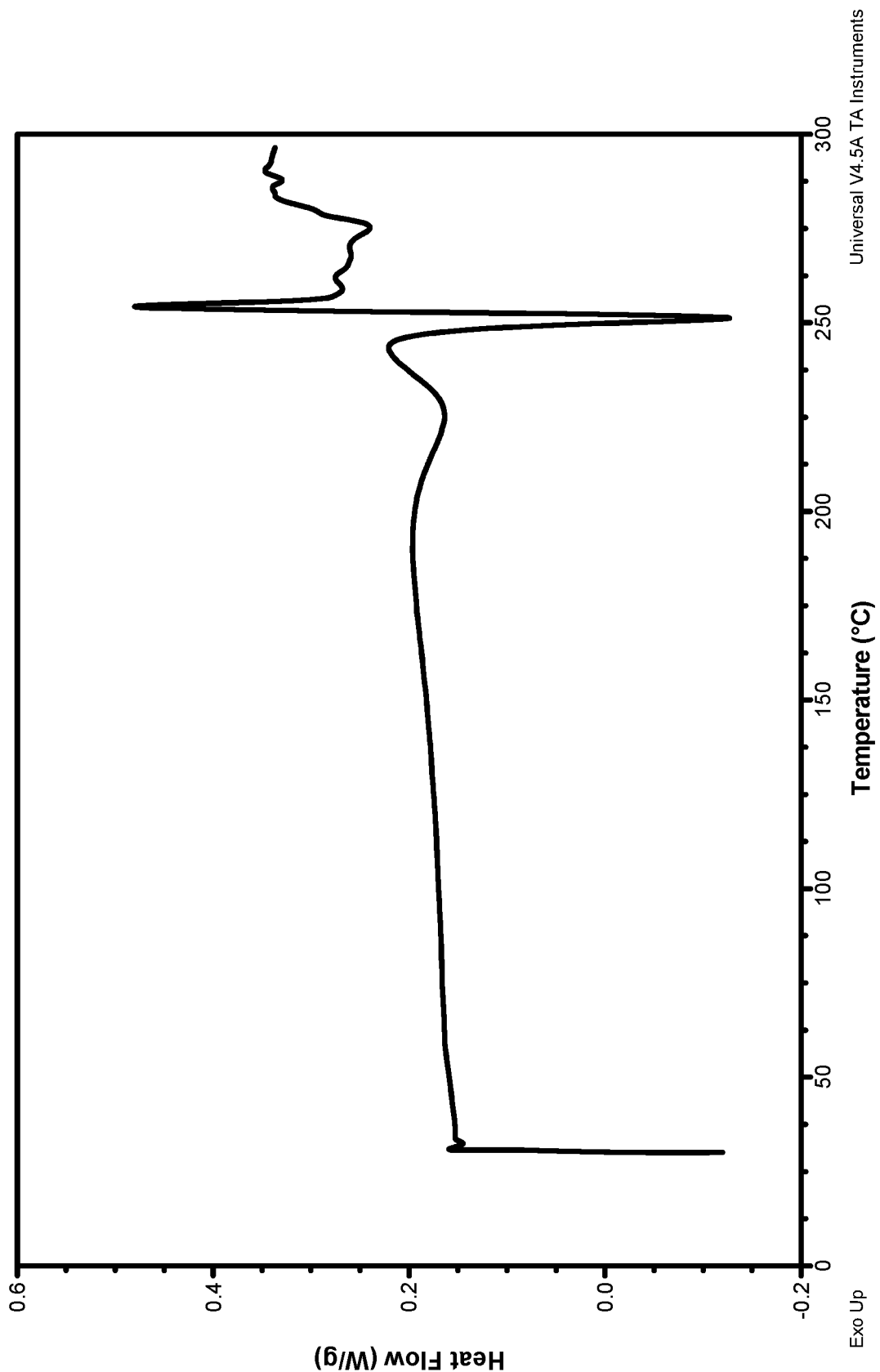
FIG. 4 depicts a DSC curve of Compound 181 Phosphate Salt Hydrate.

Differential Scanning Calorimetry (DSC) analysis of Compound 181 Phosphate Salt Hydrate was performed using the TA Instruments Q2000 DSC. A sample with a weight between 1-10 mg was weighed into an aluminum crimp sealed pan with a pinhole. This pan was placed in the sample position in the calorimeter cell. An empty pan was placed in the reference position. The calorimeter cell was closed, and a flow of nitrogen was passed through the cell. The program was set to modulate 0.320 per 60 seconds, then heat rate at of 2° C. per min to a temperature to 300° C. The thermogram shows two endotherm peaks around 226° C. and 251° C. (FIG. 4).

SSNMR

Figure 5:
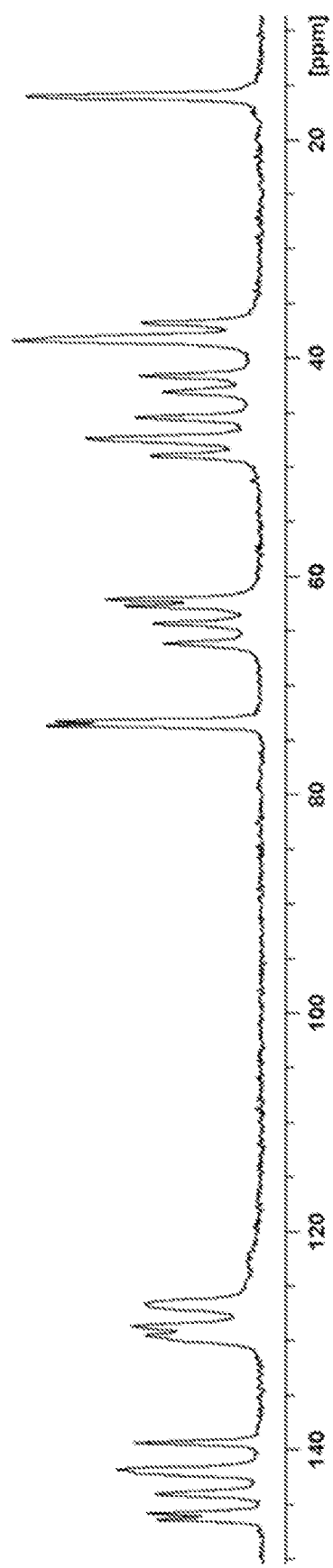
FIG. 5 depicts a solid state $^{13}$C NMR spectrum of Compound 181 Phosphate Salt Hydrate.

The $^{13}$C CPMAS of Compound 181 Phosphate Salt Hydrate (FIG. 5, Table 15) was acquired at 275K and 43% relative humidity (RH) with 12.5 kHz spinning and using adamantane as a reference.

TABLE 15

Peak List from $^{13}$C CPMAS of Compound 181 Phosphate Salt Hydrate

| Peak # | Chem Shift [ppm] | Intensity [rel] |
|---|---|---|
| 1 | 146.3 | 42.1 |
| 2 | 145.8 | 45.6 |
| 3 | 144.0 | 42.5 |
| 4 | 141.7 | 58.3 |
| 5 | 139.3 | 51.8 |
| 6 | 129.4 | 46.4 |
| 7 | 128.6 | 52.3 |
| 8 | 126.6 | 46.8 |
| 9 | 73.6 | 87.5 |
| 10 | 73.2 | 83.2 |
| 11 | 66.1 | 38.9 |

TABLE 15-continued

Peak List from $^{13}$C CPMAS of Compound 181 Phosphate Salt Hydrate

| Peak # | Chem Shift [ppm] | Intensity [rel] |
|---|---|---|
| 12 | 64.3 | 43.7 |
| 13 | 62.7 | 55.1 |
| 14 | 62.1 | 62.3 |
| 15 | 48.9 | 44.6 |
| 16 | 47.3 | 70.8 |
| 17 | 45.4 | 50.6 |
| 18 | 43.0 | 39.6 |
| 19 | 41.6 | 48.8 |
| 20 | 38.4 | 100.0 |
| 21 | 36.7 | 48.3 |
| 22 | 16.0 | 94.4 |

Figure 6:
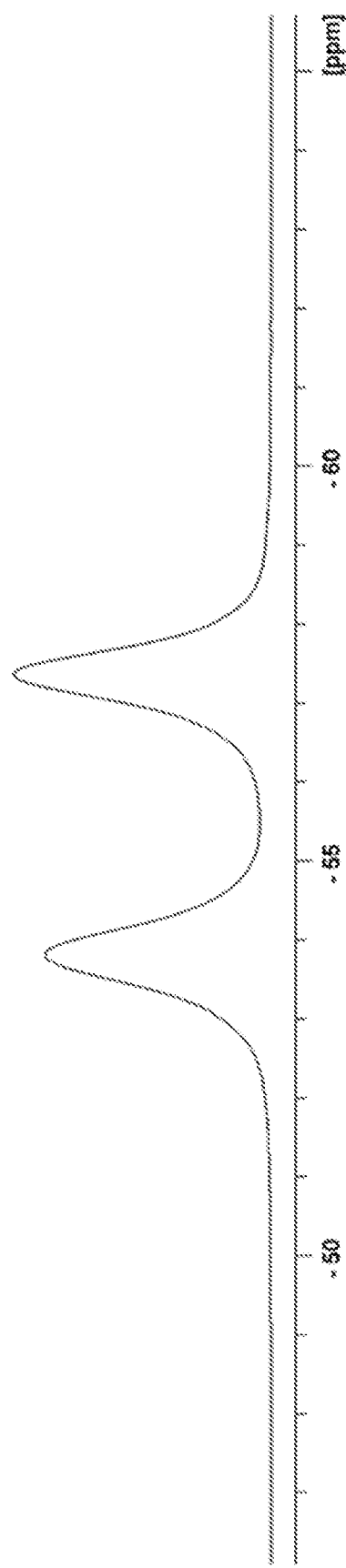
FIG. 6 depicts a solid state $^{19}$F NMR spectrum of Compound 181 Phosphate Salt Hydrate at 43% RH.
Figure 7:
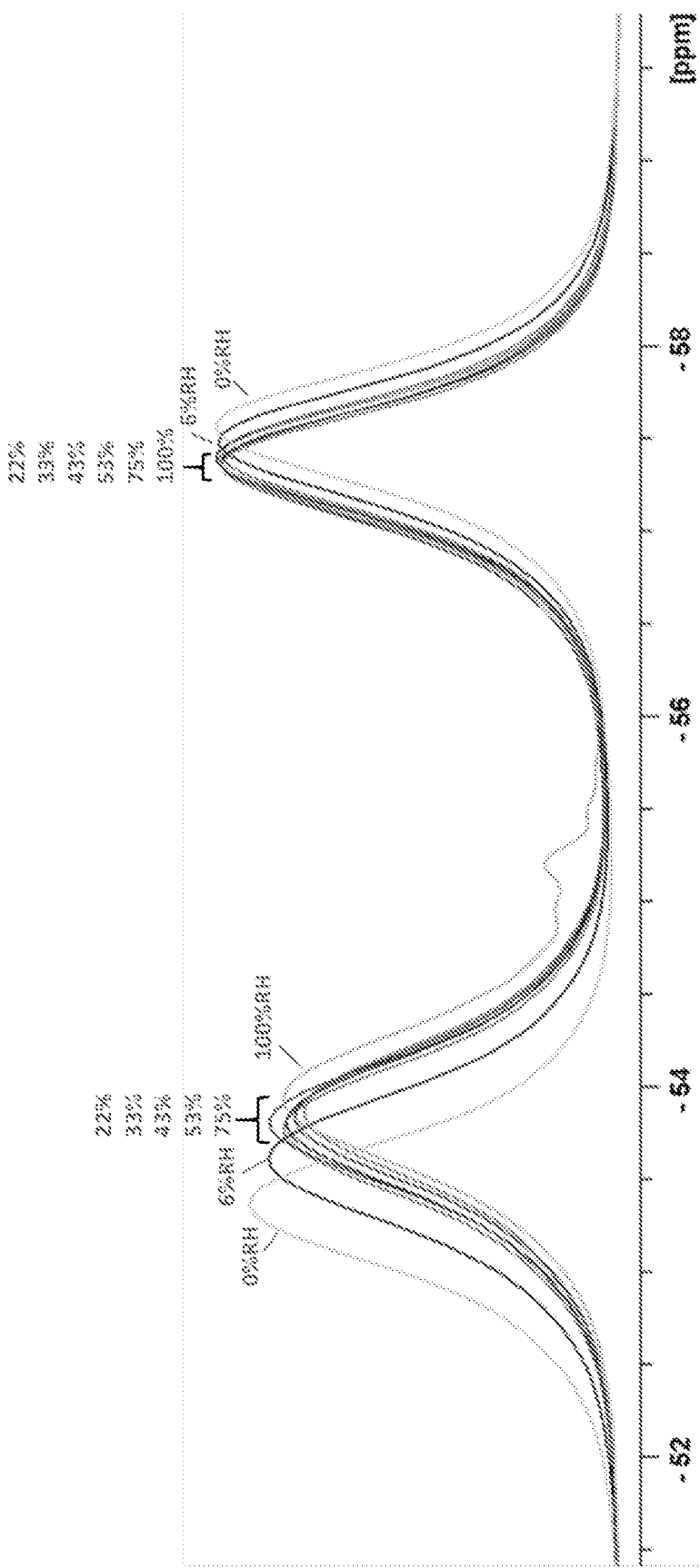
FIG. 7 depicts the effects of relative humidity on solid state $^{19}$F NMR spectrum of Compound 181 Phosphate Salt Hydrate.

The $^{19}$F MAS of Compound 181 Phosphate Salt Hydrate (FIGS. 6, 7; Tables 16, 17) was acquired at 275K and 0%, 6%, 22%, 43%, 53%, 75%, and 100% relative humidity (RH) with 12.5 kHz spinning and using adamantane as a reference.

TABLE 16

Peak List from $^{19}$F MAS of Compound 181 Phosphate Salt Hydrate at 43% RH

| Peak # | Chem Shift [ppm] | Intensity [rel] |
|---|---|---|
| 1 | −53.8 | 11.0 |
| 2 | −57.4 | 12.5 |

TABLE 17

Effect of Relative Humidity on $^{19}$F MAS of Compound 181 Phosphate Salt Hydrate

| RH [%] | Peak 1 [ppm] | Peak 2 [ppm] |
|---|---|---|
| 0 | −53.4 | −57.6 |
| 6 | −53.6 | −57.5 |
| 22 | −53.8 | −57.5 |
| 33 | −53.8 | −57.4 |
| 43 | −53.8 | −57.4 |

TABLE 17-continued

Effect of Relative Humidity on $^{19}$F MAS
of Compound 181 Phosphate Salt Hydrate

| RH [%] | Peak 1 [ppm] | Peak 2 [ppm] |
|---|---|---|
| 53 | −53.8 | −57.4 |
| 75 | −53.9 | −57.4 |
| 100 | −53.9 | −57.4 |

Figure 8:
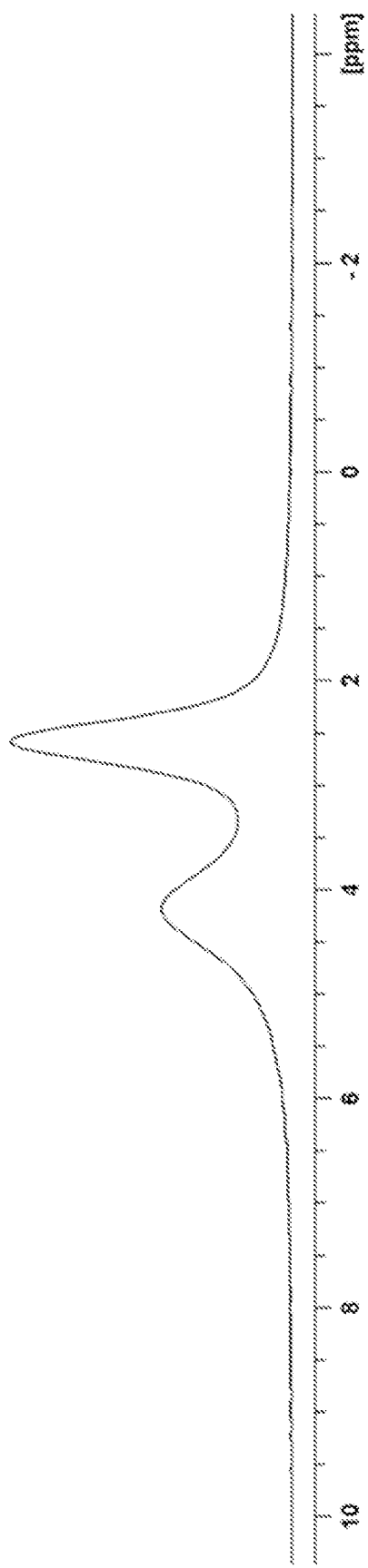
FIG. 8 depicts a solid state $^{31}$P NMR spectrum of Compound 181 Phosphate Salt Hydrate at 43% RH.
Figure 9:
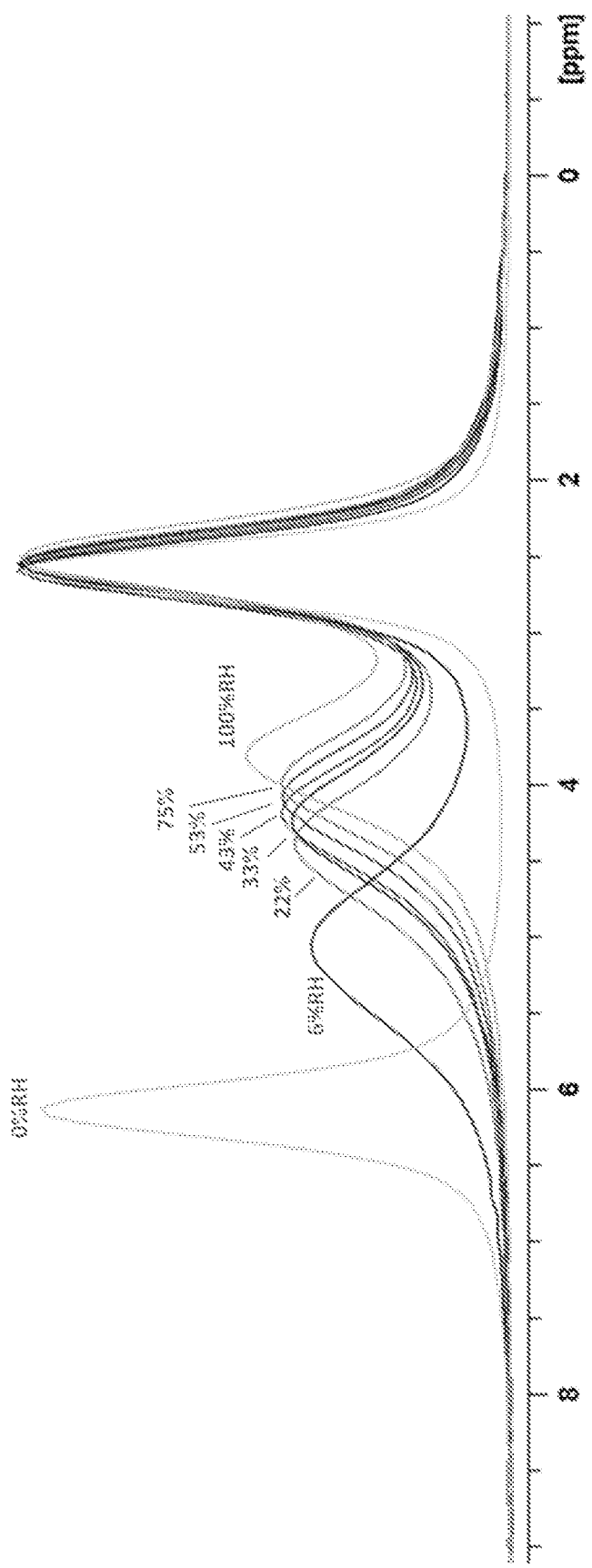
FIG. 9 depicts the effects of relative humidity on solid state $^{31}$P NMR spectrum of Compound 181 Phosphate Salt Hydrate.

The $^{31}$P CPMAS of Compound 181 Phosphate Salt Hydrate (FIGS. 8, 9; Tables 18, 19) was acquired at 275K and 0%, 6%, 22%, 43%, 53%, 75%, and 100% relative humidity (RH) with 12.5 kHz spinning and using adamantane as a reference.

TABLE 18

Peak List from $^{31}$P CPMAS of Compound 181
Phosphate Salt Hydrate at 43% RH

| Peak # | Chem Shift [ppm] | Intensity [rel] |
|---|---|---|
| 1 | 4.2 | 46.4 |
| 2 | 2.6 | 100.0 |

TABLE 19

Effect of Relative Humidity on $^{31}$P CPMAS of
Compound 181 Phosphate Salt Hydrate

| RH [%] | Peak 1 [ppm] | Peak 2 [ppm] |
|---|---|---|
| 0 | 6.1 | 2.6 |
| 6 | 5.1 | 2.6 |
| 22 | 4.4 | 2.6 |
| 33 | 4.2 | 2.6 |
| 43 | 4.2 | 2.6 |
| 53 | 4.1 | 2.5 |
| 75 | 4.0 | 2.5 |
| 100 | 3.8 | 2.5 |

Alternative Preparation of Compound 181 Free Form Monohydrate

Amorphous Compound 181 (30 mg) was added to saline (1 mL). After mild vortexing to see if the material would dissolve, a white milky precipitate formed. The sample was left overnight at ambient temperature. The solid material was filtered using a 0.22 m PVDF Eppendorf filter tube, rinsing with ice cold water. The sample was dried in a vacuum oven at 45° C. overnight. Both the wet cake and dried materials were crystalline Compound 181 Free Form Monohydrate.

XRPD

Figure 10:
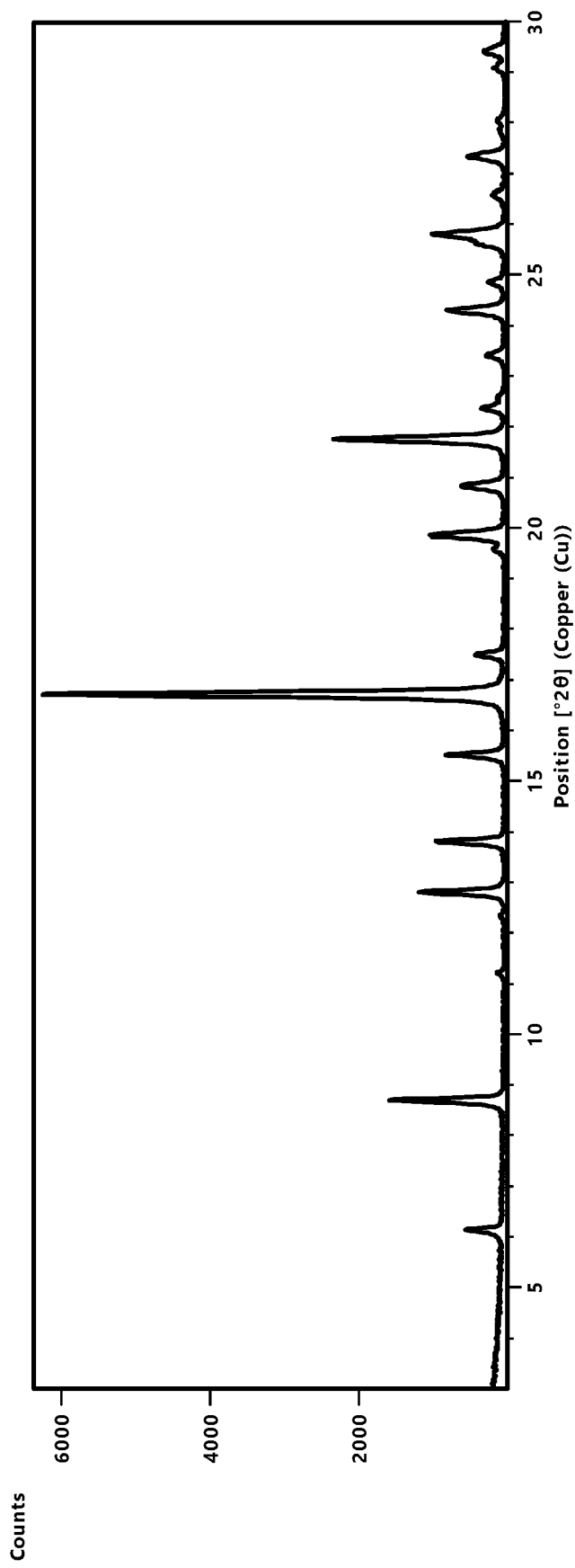
FIG. 10 depicts an XRPD diffractogram of Compound 181 Free Form Monohydrate.

The powder, X-ray powder diffraction (XRPD), diffractogram of Compound 181 Free Form Monohydrate was acquired at room temperature in transmission mode using a PANalytical Empyrean system equipped with a sealed tube source and a PIXcel 1D Medipix-3 detector (Malvern PANalytical Inc, Westborough, Massachusetts) (FIG. 10, Table 20). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303 and 49 s per step.

TABLE 20

Peak List from XRPD Diffractogram of
Compound 181 Free Form Monohydrate

| XRD Peaks | Angle (°2θ ± 0.2) | Intensity % |
|---|---|---|
| 1 | 16.7 | 100.0 |
| 2 | 21.7 | 37.0 |
| 3 | 8.7 | 23.3 |
| 4 | 12.8 | 18.4 |
| 5 | 19.8 | 15.9 |
| 6 | 25.8 | 15.8 |
| 7 | 13.8 | 15.1 |
| 8 | 15.5 | 12.7 |
| 9 | 24.3 | 12.7 |

TGA

Figure 11:
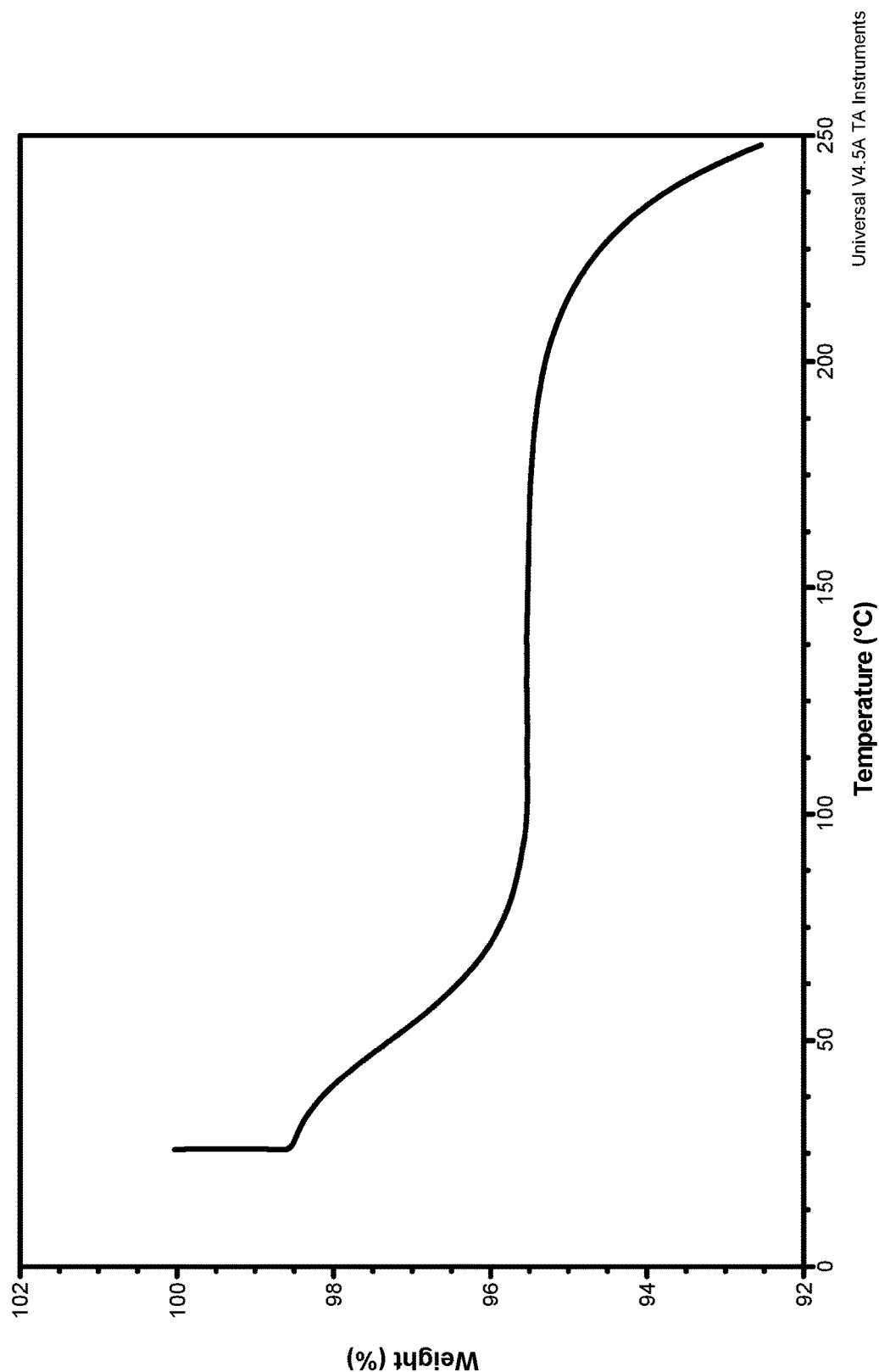
FIG. 11 depicts a TGA thermogram of Compound 181 Free Form Monohydrate.

Thermal gravimetric analysis of Compound 181 Free Form Monohydrate was performed using the TA5500 Discovery TGA. A sample with a weight of approximately 1-10 mg was scanned from ambient temperature to 250° C. at a heating rate of 10° C./min with nitrogen purge. The TGA thermogram showed around −4% weight loss from ambient temperature up until 100° C. (FIG. 11).

DSC

Figure 12:
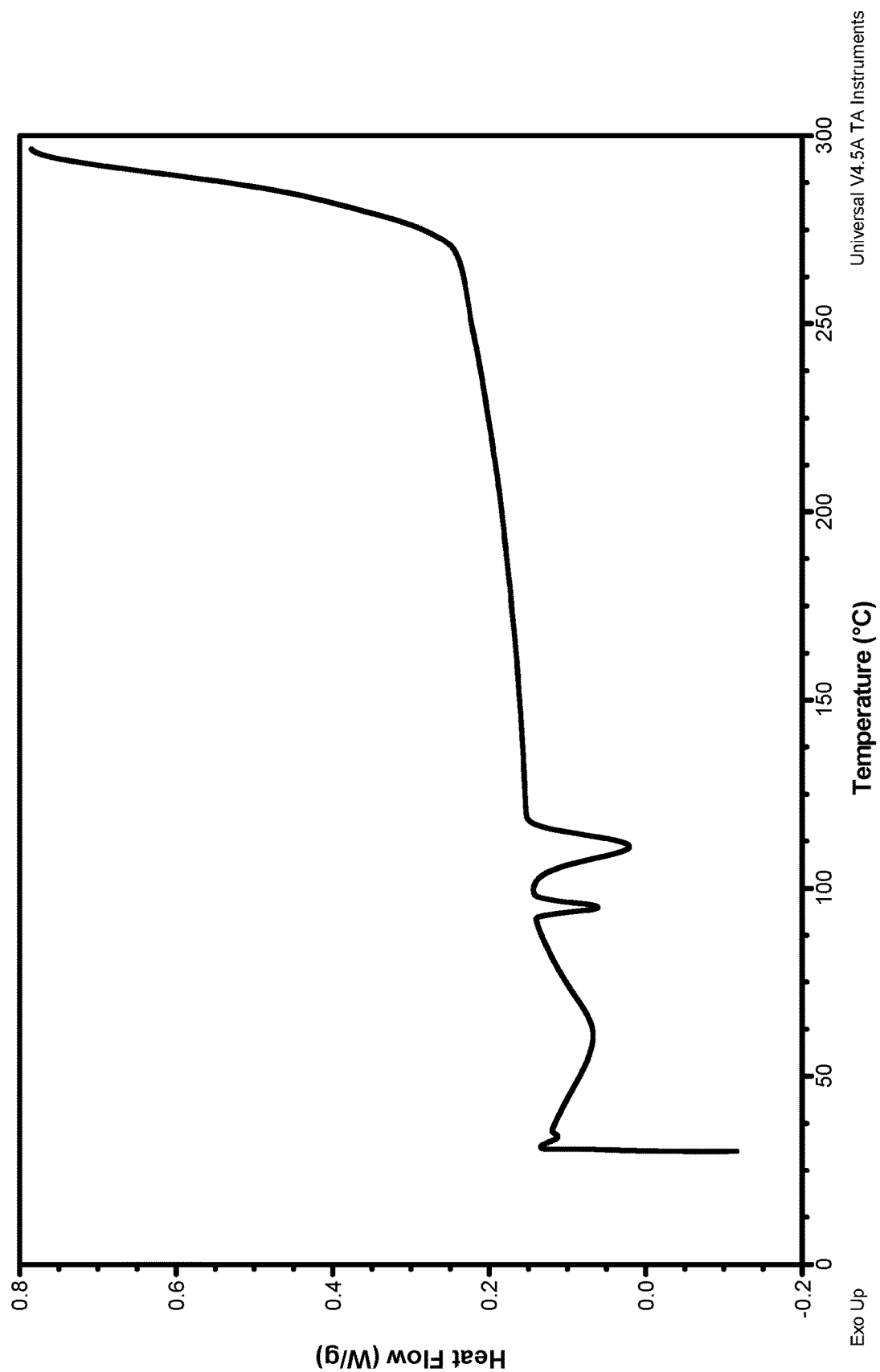
FIG. 12 depicts a DSC curve of Compound 181 Free Form Monohydrate.

The Differential Scanning Calorimetric analysis of Compound 181 Free Form Monohydrate was performed using the TA Instruments Q2000 DSC. A sample with a weight between 1-10 mg was weighed into an aluminum crimp sealed pan with a pinhole. This pan was placed in the sample position in the calorimeter cell. An empty pan was placed in the reference position. The calorimeter cell was closed, and a flow of nitrogen was passed through the cell. The program was set to modulate 0.320 per 60 seconds, then heated at a rate of 2° C. per min to a temperature to 300° C. The thermogram showed three endotherm peaks around 61° C., 94° C., and 111° C. (FIG. 12).

SSNMR

Figure 13:
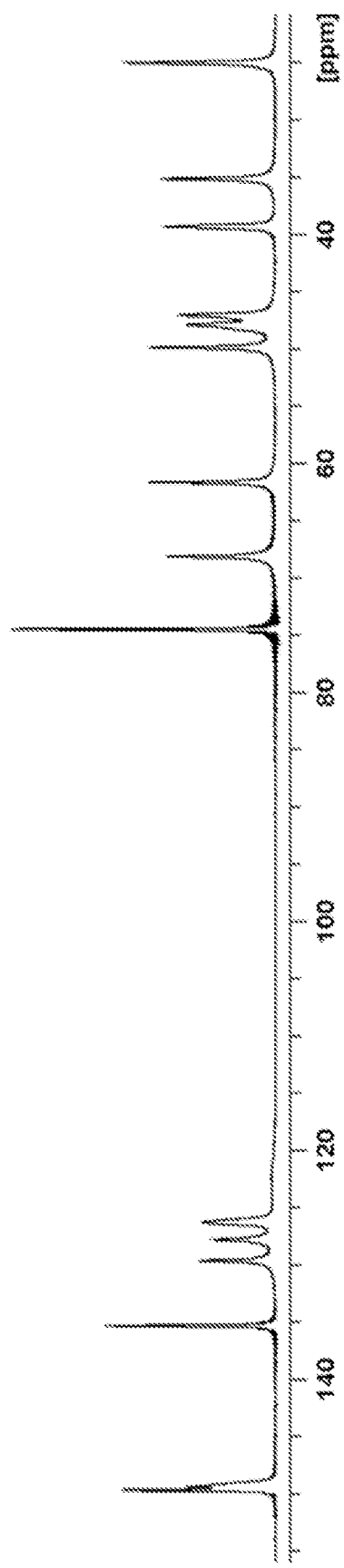
FIG. 13 depicts a solid state $^{13}$C NMR spectrum of Compound 181 Free Form Monohydrate.
Figure 14:
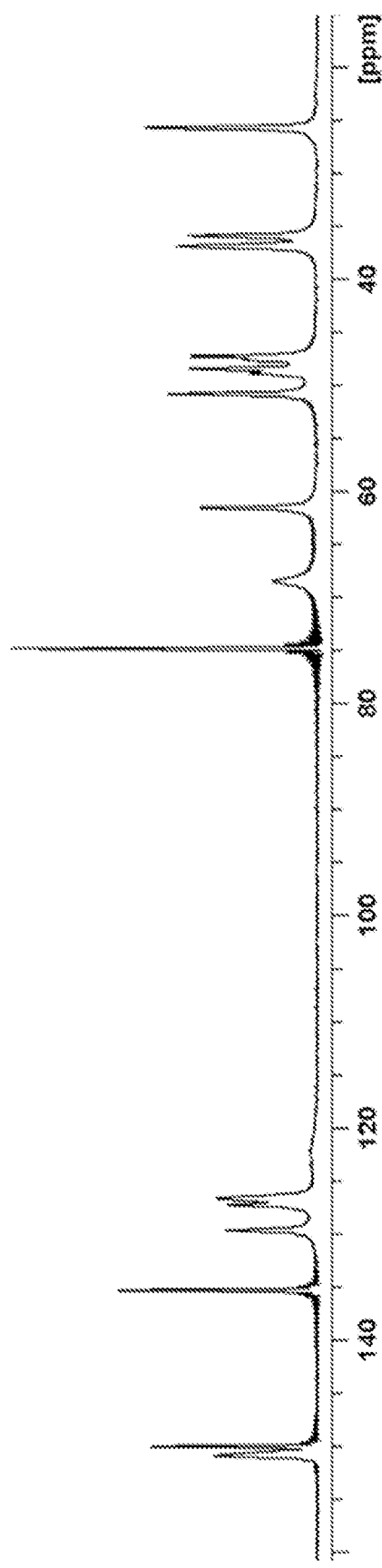
FIG. 14 depicts a solid state $^{13}$C NMR spectrum of dehydrated Compound 181 Free Form Monohydrate.

The $^{13}$C CPMAS of Compound 181 Free Form Monohydrate (FIG. 13, Table 21) was acquired at 275K and 43% relative humidity (RH) with 12.5 kHz spinning and using adamantane as a reference. Additionally, the $^{13}$C CPMAS of Compound 181 Free Form Monohydrate following dehydration (80° C. in rotor overnight (2×), 80° C. weekend incubation with $P_2O_5$) (FIG. 14, Table 22) was acquired at 275K with 12.5 kHz spinning and using adamantane as a reference.

TABLE 21

Peak List from $^{13}$C CPMAS of
Compound 181 Free Form Monohydrate

| Peak # | Chem Shift [ppm] | Intensity [rel] |
|---|---|---|
| 1 | 149.6 | 57.4 |
| 2 | 149.4 | 33.3 |
| 3 | 135.5 | 63.4 |
| 4 | 129.6 | 28.0 |
| 5 | 127.7 | 23.3 |
| 6 | 126.2 | 26.9 |
| 7 | 74.4 | 100.0 |
| 8 | 68.1 | 40.7 |
| 9 | 61.6 | 47.1 |
| 10 | 49.8 | 47.2 |
| 11 | 47.8 | 33.0 |
| 12 | 47.0 | 36.0 |
| 13 | 39.3 | 41.7 |
| 14 | 35.1 | 43.2 |
| 15 | 24.9 | 55.8 |

TABLE 22

Peak List from $^{13}$C CPMAS of Dehydrated Compound 181 Free Form Monohydrate

| Peak # | Chem Shift [ppm] | Intensity [rel] |
|---|---|---|
| 1 | 150.9 | 33.4 |
| 2 | 150.0 | 53.9 |
| 3 | 135.3 | 64.6 |
| 4 | 129.6 | 30.1 |
| 5 | 127.2 | 29.2 |
| 6 | 126.6 | 32.6 |
| 7 | 74.7 | 100.0 |
| 8 | 68.4 | 14.9 |
| 9 | 61.5 | 38.6 |
| 10 | 50.7 | 48.5 |
| 11 | 48.8 | 22.2 |
| 12 | 48.3 | 41.7 |
| 13 | 47.5 | 23.4 |
| 14 | 47.2 | 41.7 |
| 15 | 36.8 | 45.2 |
| 16 | 35.8 | 42.5 |
| 17 | 25.6 | 56.2 |

Figure 15:
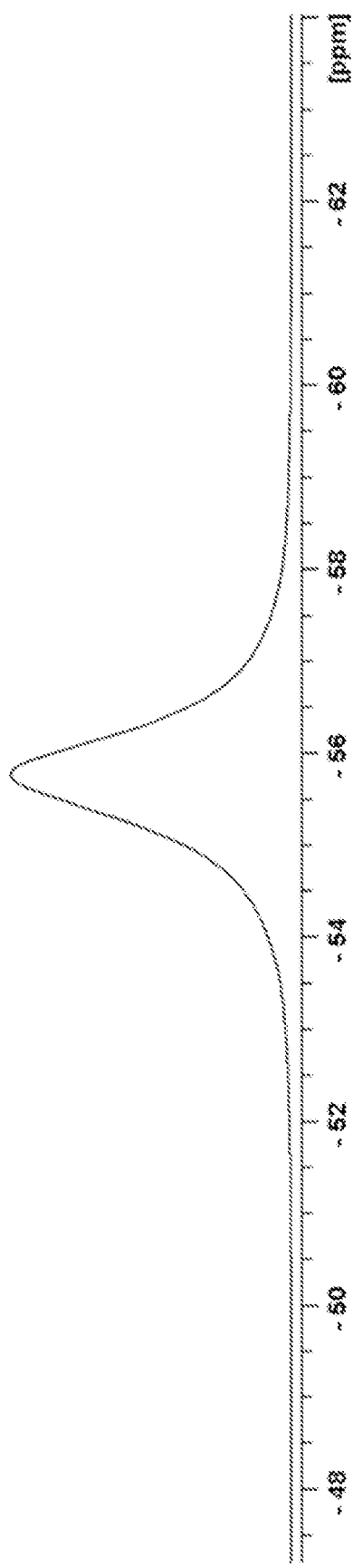
FIG. 15 depicts a solid state $^{19}$F NMR spectrum of Compound 181 Free Form Monohydrate.
Figure 16:
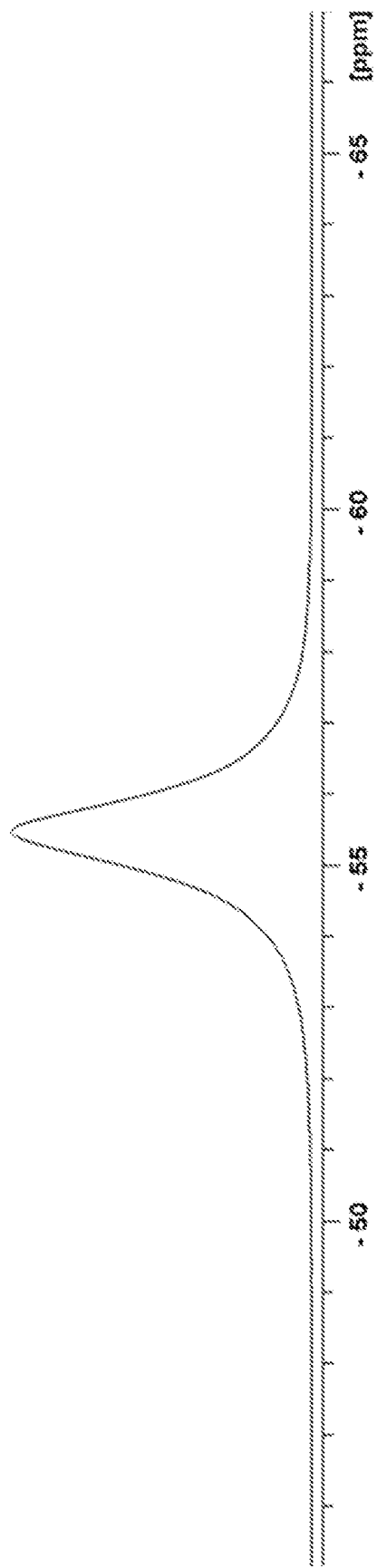
FIG. 16 depicts a solid state $^{19}$F NMR spectrum of dehydrated Compound 181 Free Form Monohydrate.

The $^{19}$F MAS of Compound 181 Free Form Monohydrate (FIG. 15, Table 23) was acquired at 275K and 43% relative humidity (RH) with 12.5 kHz spinning and using adamantane as a reference, with $^{19}$F background subtracted. Additionally, the $^{19}$F MAS of Compound 181 Free Form Monohydrate following dehydration (80° C. in rotor overnight (2×), 80° C. weekend incubation with $P_2O_5$) (FIG. 16, Table 24) was acquired at 275K with 12.5 kHz spinning and using adamantane as a reference, with $^{19}$F background subtracted.

TABLE 23

Peak List from $^{19}$F MAS of Compound 181 Free Form Monohydrate

| Peak # | Chem Shift [ppm] | Intensity [rel] |
|---|---|---|
| 1 | −55.8 | 12.5 |

TABLE 24

Peak List from $^{19}$F MAS of Dehydrated Compound 181 Free Form Monohydrate

| Peak # | Chem Shift [ppm] | Intensity [rel] |
|---|---|---|
| 1 | −55.5 | 12.5 |

Compound 181 Phosphate Salt Methanol Solvate

Amorphous Compound 181 (50 mg) was added to MEK (0.3 mL). To this was added 0.27 mL of a 0.5 M stock solution of $H_3PO_4$ in MeOH. The sample was left at ambient temperature overnight. The solids were filtered using a 0.22 m PVDF Eppendorf filter tube and washed with 4:1 n-Heptane/MEK (v/v) that was chilled over ice. Subsequent washes were performed with n-Heptane, resulting in a solid white powder. XRPD of the wet material showed the product was Compound 181 Phosphate Salt Methanol Solvate.

XRPD

Figure 17:
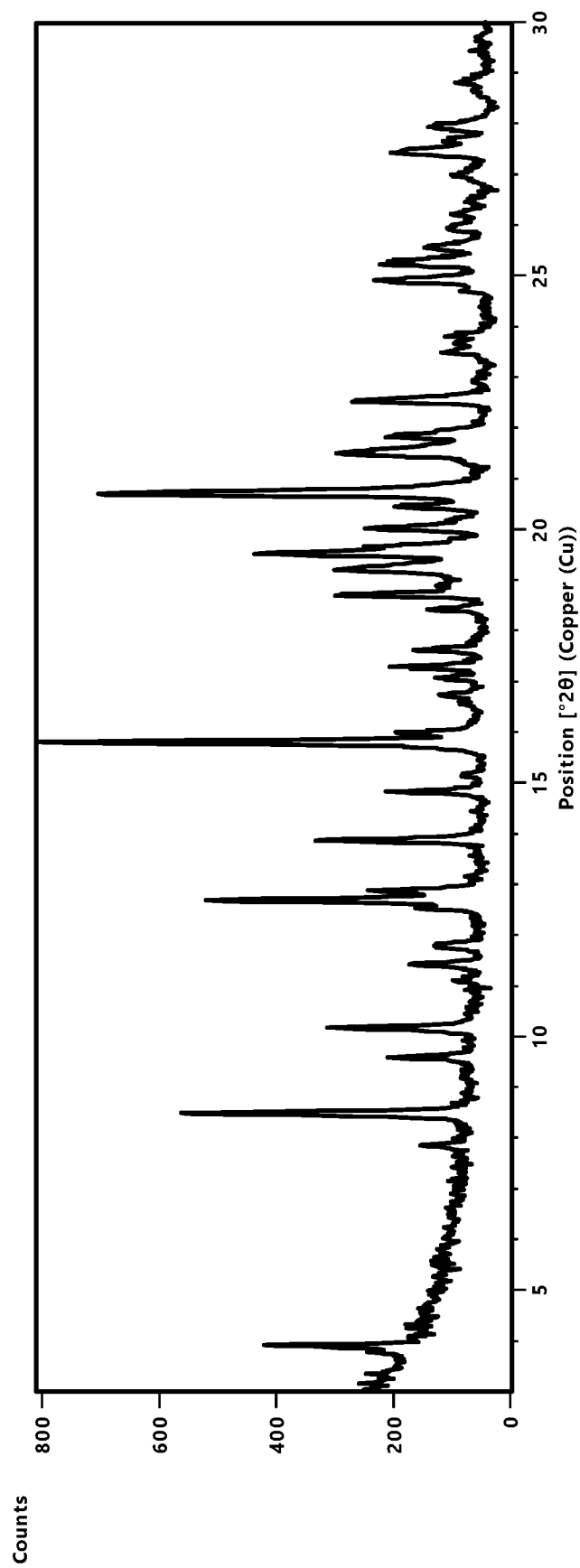
FIG. 17 depicts an XRPD diffractogram of Compound 181 Phosphate Salt Methanol Solvate.

The powder, X-ray powder diffraction (XRPD), diffractogram of Compound 181 Phosphate Salt Methanol Solvate (FIG. 17, Table 25) was acquired at room temperature in transmission mode using a PANalytical Empyrean system equipped with a sealed tube source and a PIXcel 3D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step.

TABLE 25

Peak List from XRPD Diffractogram of Compound 181 Phosphate Salt Methanol Solvate

| XRD Peaks | Angle (°2θ ± 0.2) | Intensity % |
|---|---|---|
| 1 | 15.8 | 100.0 |
| 2 | 20.7 | 89.2 |
| 3 | 12.7 | 59.5 |
| 4 | 8.5 | 54.2 |
| 5 | 19.5 | 45.5 |
| 6 | 18.7 | 36.8 |
| 7 | 13.9 | 35.6 |
| 8 | 10.2 | 30.3 |
| 9 | 22.5 | 29.5 |
| 10 | 21.5 | 27.4 |
| 11 | 3.9 | 26.4 |
| 12 | 20.0 | 24.9 |
| 13 | 19.2 | 24.5 |
| 14 | 24.9 | 24.0 |
| 15 | 19.6 | 23.3 |
| 16 | 21.8 | 21.5 |
| 17 | 27.4 | 21.3 |
| 18 | 12.9 | 21.0 |
| 19 | 25.2 | 20.8 |
| 20 | 14.8 | 20.7 |
| 21 | 17.3 | 18.0 |
| 22 | 9.6 | 17.8 |
| 23 | 20.4 | 17.0 |
| 24 | 17.6 | 15.9 |
| 25 | 16.0 | 15.5 |
| 26 | 11.4 | 13.9 |
| 27 | 18.4 | 13.7 |
| 28 | 25.5 | 12.5 |
| 29 | 27.9 | 12.2 |
| 30 | 27.6 | 11.1 |
| 31 | 12.5 | 10.8 |
| 32 | 23.5 | 10.7 |

SSNMR

Figure 18:
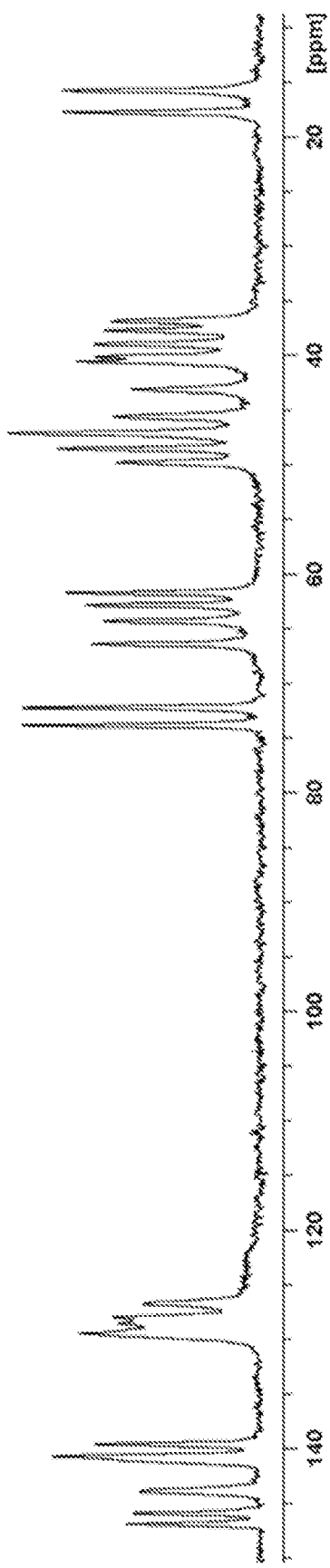
FIG. 18 depicts a solid state $^{13}$C NMR spectrum of Compound 181 Phosphate Salt Methanol Solvate.

The $^{13}$C CPMAS of Compound 181 Phosphate Salt Methanol Solvate (FIG. 18, Table 26) was acquired at 275K with 12.5 kHz spinning and using adamantane as a reference.

TABLE 26

Peak List from $^{13}$C CPMAS of Compound 181 Phosphate Salt Methanol Solvate

| Peak # | Chem Shift [ppm] | Intensity [rel] |
|---|---|---|
| 1 | 146.8 | 54.0 |
| 2 | 145.8 | 50.8 |
| 3 | 143.9 | 47.8 |
| 4 | 140.6 | 82.3 |
| 5 | 139.5 | 66.0 |
| 6 | 129.4 | 71.6 |
| 7 | 128.5 | 56.2 |
| 8 | 127.9 | 58.2 |

TABLE 26-continued

Peak List from $^{13}$C CPMAS of Compound
181 Phosphate Salt Methanol Solvate

| Peak # | Chem Shift [ppm] | Intensity [rel] |
|---|---|---|
| 9 | 126.7 | 46.5 |
| 10 | 73.8 | 94.9 |
| 11 | 72.2 | 95.2 |
| 12 | 66.3 | 66.8 |
| 13 | 64.2 | 61.7 |
| 14 | 62.8 | 69.1 |
| 15 | 61.6 | 77.9 |
| 16 | 49.7 | 56.9 |
| 17 | 48.5 | 80.3 |
| 18 | 47.1 | 100.0 |
| 19 | 45.5 | 57.9 |
| 20 | 43.0 | 51.0 |
| 21 | 40.5 | 73.1 |
| 22 | 40.1 | 65.6 |
| 23 | 38.9 | 66.2 |
| 24 | 37.7 | 62.1 |
| 25 | 36.8 | 58.6 |
| 26 | 17.7 | 78.3 |
| 27 | 15.7 | 78.5 |

Figure 19:
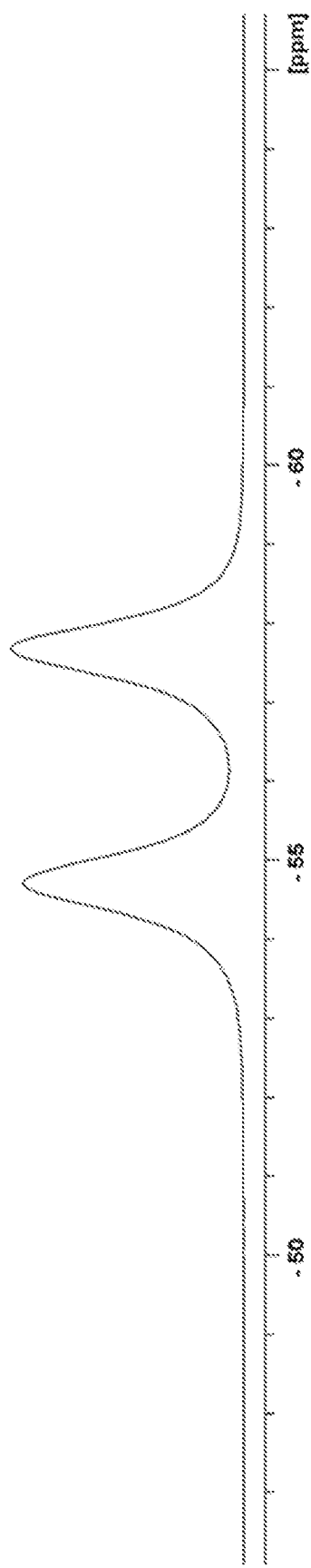
FIG. 19 depicts a solid state $^{19}$F NMR spectrum of Compound 181 Phosphate Salt Methanol Solvate.

The $^{19}$F MAS of Compound 181 Phosphate Salt Methanol Solvate (FIG. 19, Table 27) was acquired at 275K with 12.5 kHz spinning and using adamantane as a reference, with $^{19}$F background subtracted.

TABLE 27

Peak List from $^{19}$F MAS of Compound 181
Phosphate Salt Methanol Solvate

| Peak # | Chem Shift [ppm] | Intensity [rel] |
|---|---|---|
| 1 | −54.7 | 11.8 |
| 2 | −57.7 | 12.5 |

Figure 20:
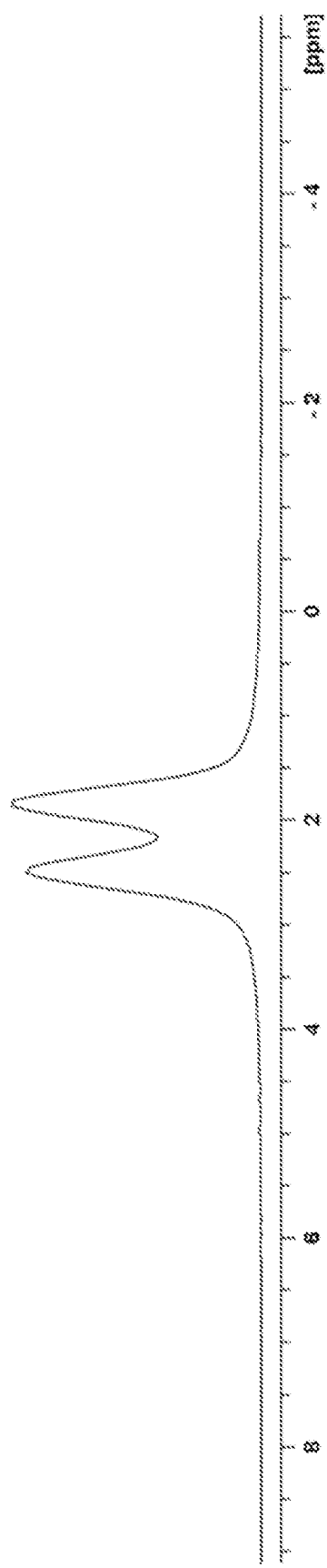
FIG. 20 depicts a solid state $^{31}$P NMR spectrum of Compound 181 Phosphate Salt Methanol Solvate.

The $^{31}$P CPMAS of Compound 181 Phosphate Salt Methanol Solvate (FIG. 20, Table 28) was acquired at 275K with 12.5 kHz spinning and using adamantane as a reference.

TABLE 28

Peak List from $^{31}$P CPMAS of Compound 181
Phosphate Salt Methanol Solvate

| Peak # | Chem Shift [ppm] | Intensity [rel] |
|---|---|---|
| 1 | 2.5 | 93.9 |
| 2 | 1.8 | 100.0 |

Compound 181 Phosphate Salt MEK Solvate

Compound 181 Phosphate Salt Hydrate (25 mg) was added to 2-butanone (MEK) (1 mL) in an HPLC vial. The sample was mixed and formed a slurry. The slurry was placed in a cold room at 5° C. with a small stir bar for 11 days. The solid material was centrifuged and filtered using a 0.22 m PVDF Eppendorf filter tube at room temperature. The XRD of the wet cake sample showed that it was Compound 181 Phosphate Salt MEK Solvate.

XRPD

Figure 21:
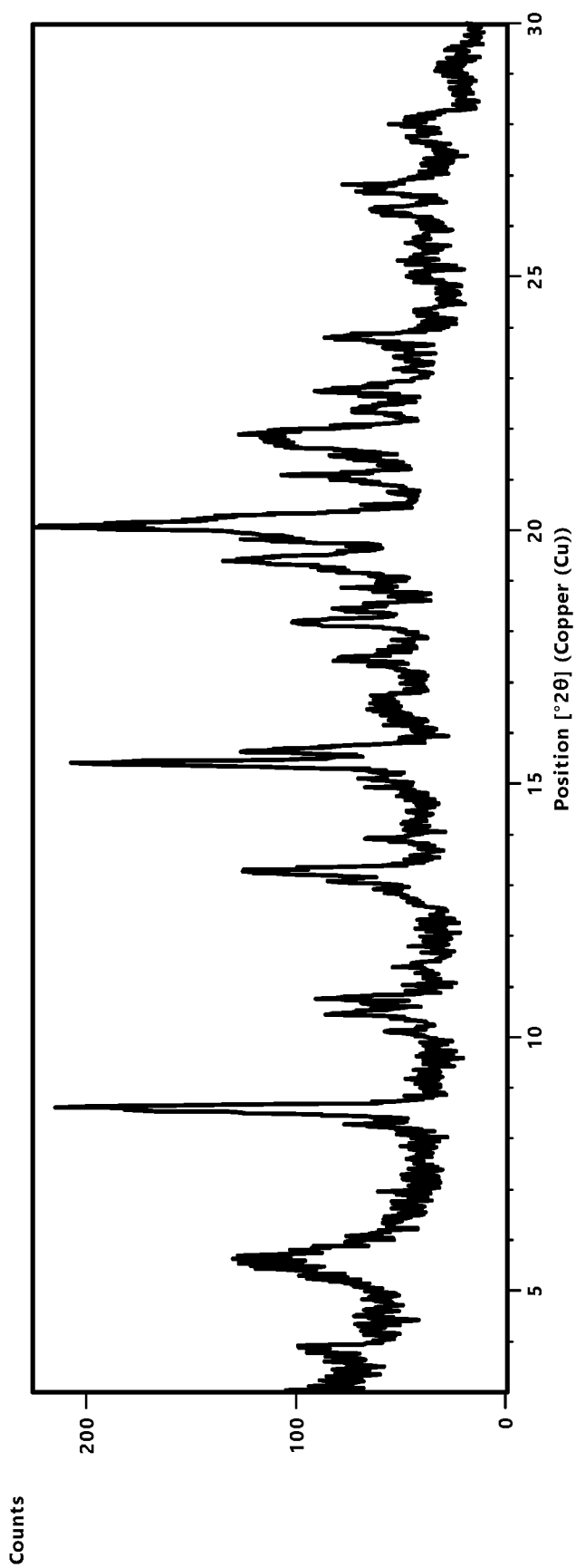
FIG. 21 depicts an XRPD diffractogram of Compound 181 Phosphate Salt MEK Solvate.

The powder, X-ray powder diffraction (XRPD), diffractogram of Compound 181 Phosphate Salt MEK Solvate was acquired at room temperature (25±2° C.) in transmission mode using a PANalytical Empyrean system equipped with a sealed tube source and a PIXcel 1D Medipix-3 detector (Malvern PANalytical Inc, Westborough, Massachusetts) (FIG. 21, Table 29). The X-Ray generator operated at a voltage of 45 kV and a current of 40 mA with copper radiation (1.54060 Å). The powder sample was placed on a 96 well sample holder with mylar film as well Kapton tape over the sample and loaded into the instrument. The sample was scanned over the range of about 3° to about 40°2θ with a step size of 0.0131303° and 49 s per step.

TABLE 29

Peak List from XRPD Diffractogram of
Compound 181 Phosphate Salt MEK Solvate

| XRD Peaks | Angle (°2θ ± 0.2) | Intensity % |
|---|---|---|
| 1 | 20.1 | 100.0 |
| 2 | 15.4 | 85.7 |
| 3 | 8.6 | 80.8 |
| 4 | 15.7 | 36.5 |
| 5 | 19.4 | 32.1 |
| 6 | 18.2 | 32.0 |
| 7 | 21.7 | 30.8 |
| 8 | 21.9 | 29.0 |
| 9 | 13.2 | 28.6 |
| 10 | 23.8 | 25.9 |
| 11 | 10.8 | 25.1 |
| 12 | 10.5 | 24.1 |
| 13 | 21.0 | 23.0 |
| 14 | 22.8 | 21.7 |
| 15 | 17.5 | 18.8 |
| 16 | 18.4 | 18.2 |
| 17 | 26.7 | 16.8 |
| 18 | 22.4 | 14.4 |
| 19 | 3.8 | 12.4 |
| 20 | 8.3 | 11.0 |
| 21 | 16.5 | 10.6 |

SSNMR

Figure 22:
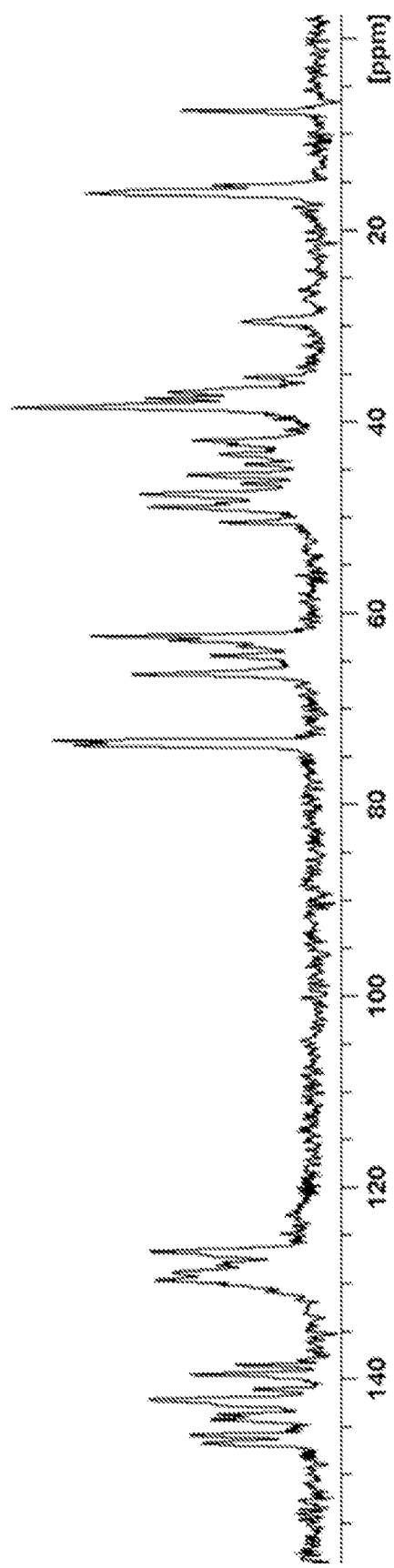
FIG. 22 depicts a solid state $^{13}$C NMR spectrum of Compound 181 Phosphate Salt MEK Solvate.

The $^{13}$C CPMAS of Compound 181 Phosphate Salt MEK Solvate (FIG. 22, Table 30) was acquired at 275K with 12.5 kHz spinning and using adamantane as a reference.

TABLE 30

Peak List from $^{13}$C CPMAS of Compound 181
Phosphate Salt MEK Solvate

| Peak # | Chem Shift [ppm] | Intensity [rel] |
|---|---|---|
| 1 | 146.6 | 36.9 |
| 2 | 145.8 | 41.2 |
| 3 | 144.1 | 34.3 |
| 4 | 143.6 | 32.3 |
| 5 | 142.0 | 55.2 |
| 6 | 140.9 | 20.2 |
| 7 | 139.4 | 41.6 |
| 8 | 138.4 | 26.0 |
| 9 | 130.7 | 16.3 |
| 10 | 129.6 | 52.8 |
| 11 | 128.7 | 46.9 |
| 12 | 128.0 | 32.6 |
| 13 | 126.5 | 54.5 |
| 14 | 73.7 | 79.9 |
| 15 | 73.2 | 86.8 |
| 16 | 66.3 | 60.6 |
| 17 | 64.3 | 35.0 |
| 18 | 63.3 | 25.6 |

TABLE 30-continued

Peak List from $^{13}$C CPMAS of Compound 181 Phosphate Salt MEK Solvate

| Peak # | Chem Shift [ppm] | Intensity [rel] |
|---|---|---|
| 19 | 62.7 | 48.2 |
| 20 | 62.3 | 73.8 |
| 21 | 50.4 | 31.2 |
| 22 | 48.8 | 54.4 |
| 23 | 48.4 | 32.8 |
| 24 | 47.4 | 57.8 |
| 25 | 46.3 | 24.0 |
| 26 | 45.5 | 42.2 |
| 27 | 44.3 | 23.2 |
| 28 | 43.3 | 31.7 |
| 29 | 42.3 | 28.9 |
| 30 | 41.9 | 40.4 |
| 31 | 38.4 | 100.0 |
| 32 | 37.5 | 56.0 |
| 33 | 36.8 | 48.4 |
| 34 | 35.3 | 23.6 |
| 35 | 29.5 | 24.2 |
| 36 | 16.0 | 74.8 |
| 37 | 15.2 | 33.7 |
| 38 | 7.4 | 44.5 |

Figure 23:
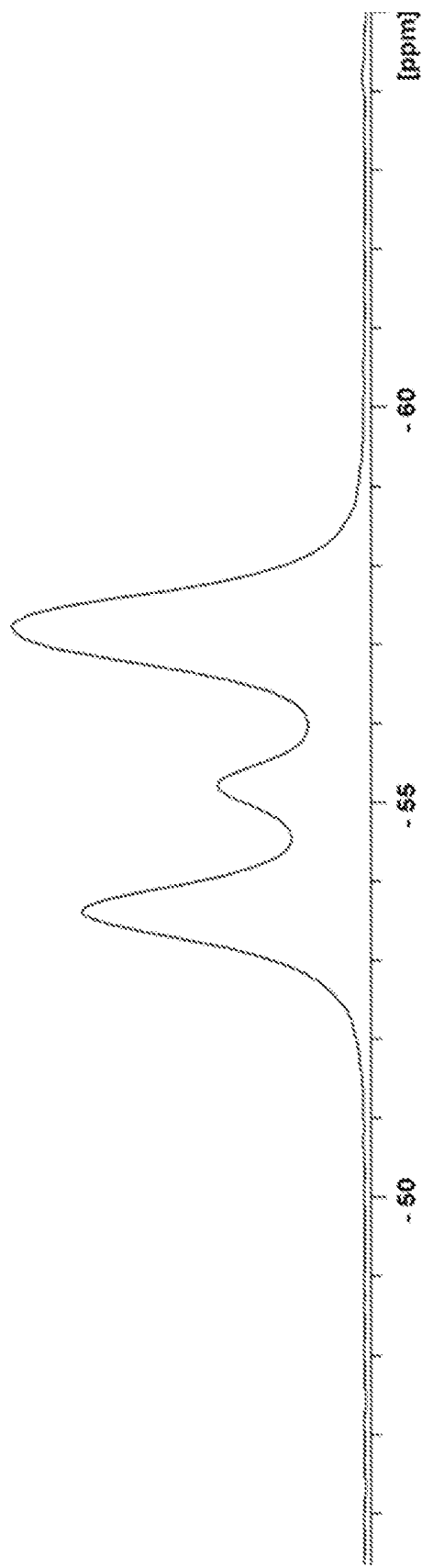
FIG. 23 depicts a solid state $^{19}$F NMR spectrum of Compound 181 Phosphate Salt MEK Solvate.

The $^{19}$F MAS of Compound 181 Phosphate Salt MEK Solvate (FIG. 23, Table 31) was acquired at 275K with 12.5 kHz spinning and using adamantane as a reference, with $^{19}$F background subtracted.

TABLE 31

Peak List from $^{19}$F MAS of Compound 181 Phosphate Salt MEK Solvate

| Peak # | Chem Shift [ppm] | Intensity [rel] |
|---|---|---|
| 1 | −53.6 | 10.0 |
| 2 | −55.2 | 5.2 |
| 3 | −57.2 | 12.5 |

The $^{31}$P CPMAS of Compound 181 Phosphate Salt MEK Solvate (FIG. 24, Table 32) was acquired at 275K with 12.5 kHz spinning and using adamantane as a reference.

TABLE 32

Peak List from $^{31}$P CPMAS of Compound 181 Phosphate Salt MEK Solvate

| Peak # | Chem Shift [ppm] | Intensity [rel] |
|---|---|---|
| 1 | 4.8 | 94.7 |
| 2 | 2.7 | 15.7 |
| 3 | 0.1 | 100.0 |

Alternative Preparation of Compound 181 Phosphate Salt Hydrate 2.05 g Compound 181 Phosphate Salt Methanol Solvate was dried at 50° C. for 21 hours with N$_2$ purge. The resultant solid was Compound 181 Phosphate Salt Hydrate.

Compound 174 Hemihydrate

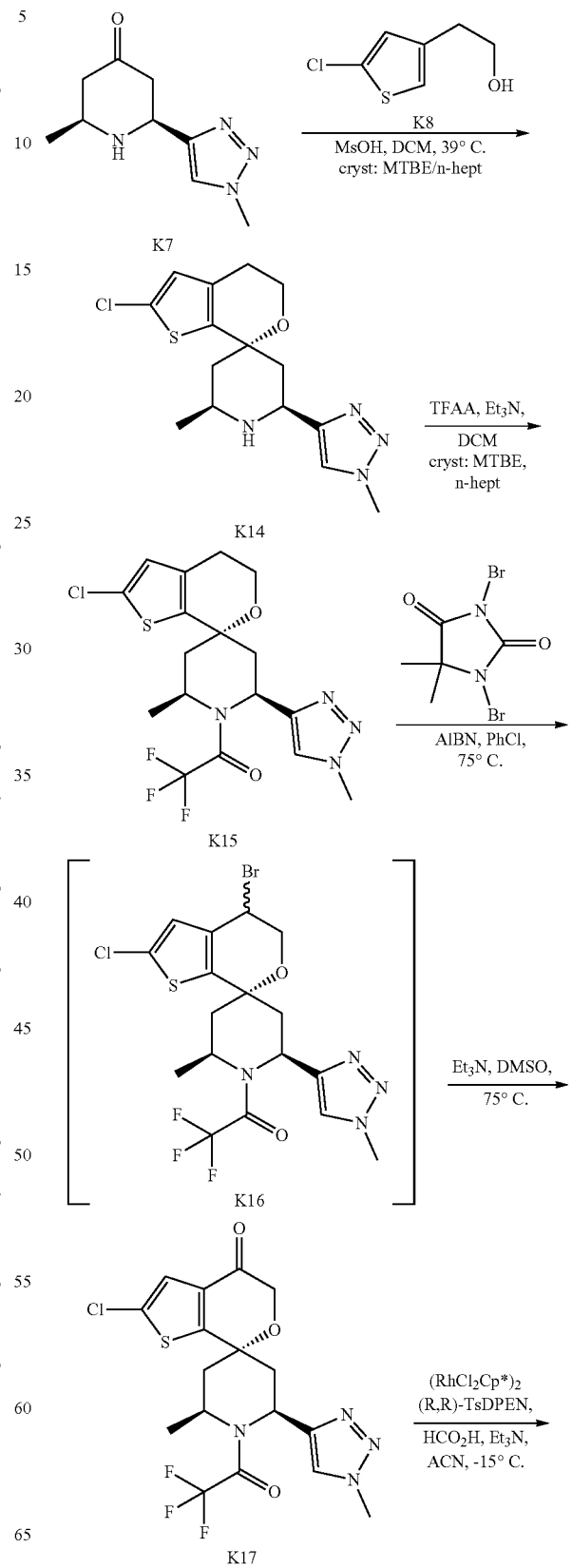

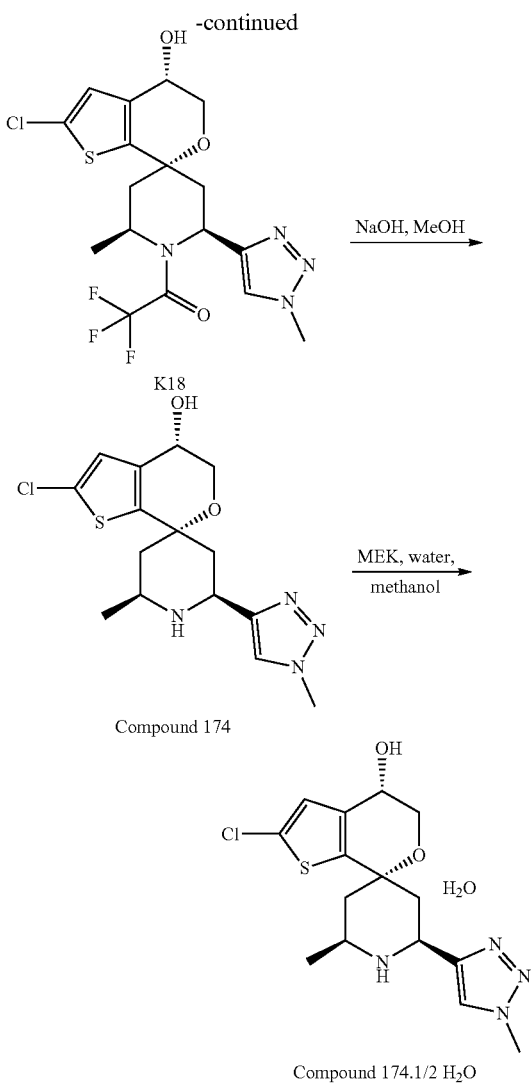

Compound 174

Compound 174.1/2 H₂O

Step 1. A solution of K7 (4153 g, 1 equiv, 81.11% purity by Q-NMR, 21.53 mmol, 1 equiv) and K8 (3651 g, 22.45 mmol, 1.05 equiv) in dichloromethane (33.2 L, 8 vol) was treated with methanesulfonic acid (14384 g, 149.7 mol, 7 equiv) at 0° C. over 1 hour. The resulting mixture was heated at 40° C. After 14 hours, analysis showed >99% consumption of K7. The reaction mixture was cooled to 10° C. and adjusted to pH 10 with 4 N sodium hydroxide (40 L). The organic layer was separated, dried over sodium sulfate (1.5 kg), and evaporated under reduced pressure at 25° C. to give crude K14 as an off-white solid (8.1 kg). This solid was suspended in methyl tert-butyl ether (22 L), stirred at 10° C. for 2.5 hours, and then filtered. The filter cake was washed with methyl tert-butyl ether (4 L) and dried under vacuum while flushing with nitrogen at 20° C. for 18 hours to give purified 5950 g K14 (96.8% yield).

Step 2. A solution of K14 (5937 g, 17.52 mol, 1 equiv) and N,N-diisopropylethylamine (3967 mL, 22.78 mol, 1.3 equiv) in dichloromethane (59 L, 10 vol) was cooled to 0-5° C. and treated with trifluoroacetic acid anhydride (2680 mL, 19.27 mol, 1.1 equiv) over 40 minutes while keeping the reaction temperature below 14° C. The resulting reaction mixture was stirred at 0-10° C. After 2 hours, HPLC analysis indicated >99.5% conversion. The reaction mixture was cooled to 5° C. and diluted with saturated brine (27 L). The resulting mixture was adjusted to pH 10 with 6 N sodium hydroxide solution (5 L) while keeping the temperature below 12° C. The resulting mixture was stirred for 20 minutes, then the layers were separated. The organic layer was sequentially washed with 2 N HCl (3×22 L), water (3×22 L), and brine (22 L), then dried over sodium sulfate (1 kg) and evaporated under reduced pressure at 30° C. to give crude K15 (7519 g). The crude material was suspended in a mixture of methyl tert-butyl ether (16 L) and n-heptane (8 L) at 50° C. for 5 hours, then cooled to 20° C. over 5 hours. After 18 hours of stirring at 20° C., the suspension was filtered. The filter cake was washed with a mixture of methyl tert-butyl ether (8 L) and n-heptane (4 L), then dried under vacuum while flushing with nitrogen at 20° C. for 18 hours to give 6824 g of K15 (94.1% yield).

Steps 3 and 4. A suspension of K15 (5879 g, 13.52 mol, 1 equiv), azobisisobutyronitrile (178 g, 1.082 mol, 0.08 equiv), and 1,3-dibromo-5,5-dimethylhydantoin (2900 g, 10.14 mol, 0.75 equiv) in chlorobenzene (41.2 L, 7 vol) was sparged with nitrogen for 20 minutes in a 100 L jacketed glass reactor. The reaction mixture was then heated to 70° C. After 30 minutes, HPLC analysis indicated >99% conversion to K16. The reaction was cooled to 45° C., treated with anhydrous dimethylsulfoxide (41.2 L, 7 vol) and triethylamine (9.42 L, 67.55 mol, 5 equiv), and heated at 65° C. After 12 hours, HPLC analysis indicated complete consumption of K16. The reaction mixture was cooled to 0° C. and divided into two equal halves. Each half was treated with ice cold water (22 L), keeping the temperature below 15° C., then extracted with ethyl acetate (2×20 L). The aqueous layers were extracted with ethyl acetate (18 L). The combined organic layers were washed with water (2×24 L), brine (24 L), dried over anhydrous sodium sulfate (2 kg) then evaporated under reduced pressure at 50° C. to give a semi-solid residue which was co-evaporated with methanol (2×4 L) at 50° C. to give the crude product (6.65 kg) as a dark brown solid. The residue was triturated with methanol (32 L) at 65° C. for 5 hours, cooled to 15° C. over 5 hours, then filtered to give 3643 g of K17. This solid was triturated with a 1:2 mixture of acetone and methanol (18 L) at 65° C. for 5 hours, cooled to 20° C. over 5 hours, then filtered. The filter cake was rinsed with a 1:2 mixture of acetone and methanol (2×3 L), followed by methanol (3 L) at 20° C. The product was dried under nitrogen convection at 20° C. for 18 hours to give 2780 g of K17 (45.8% yield).

Step 5. A solution of N-[(1R,2R)-2-amino-1,2-diphenylethyl]-4-methyl-benzenesulfonamide (22.1 g, 0.06 mol, 0.01 equiv) and dichloro-(1,2,3,4,5-pentamethylcyclopenta-2,4-dien-1-yl)rhodium dimer (18.26 g, 0.03 mol, 0.005 equiv) in acetonitrile (12 L) was stirred for 30 minutes at 20° C., then cooled to −5° C. This solution was added to a suspension of K17 (2704 g, 6.024 mol, 1 equiv) in acetonitrile (16 L) and a mixture of formic acid (1.25 L, 33.13 mol, 5.5 equiv) and triethylamine (1.85 L, 13.25 mol, 2.2 equiv) (premixed and precooled to 0° C.) at 0° C. The resulting mixture was stirred at 0° C. and the progress of the reaction was monitored by HPLC. After 31 hours, HPLC analysis indicated >99.9% conversion to K18. The reaction mixture was diluted with a solution of sodium bicarbonate (2.1 kg) in water (30 L). The resulting mixture was stirred for 15 minutes at 10° C., then warmed to 15° C. and diluted with methyl tert-butyl ether (12 L). The resulting mixture was stirred for 15 minutes at 15° C. The layers were separated and the aqueous layer was extracted with methyl tert-butyl ether (12 L). The combined organic layers were sequentially washed with 1N HCl (2×11 L) and brine (2×11 L). During the second brine wash, the pH of the brine layer was adjusted to ~8 using solid sodium bicarbonate (288 g). The organic layer was dried over anhydrous sodium sulfate (2 kg) and evaporated under reduced pressure to give 3.4 kg of crude K18. A solution of crude K18 in methyl tert-butyl ether (35 L) was treated with SiliaMetS DMT (1.7 kg) at 20° C. for 18 hours, then filtered. The filter cake was rinsed with methyl tert-butyl ether (5 L). The combined filtrates were treated with SiliaMetS DMT (1.7 kg, 0.5 vol) in 3 consecutive runs at 50° C. for 5 hours. The mixture was cooled to 20° C. in between treatments and filtered. The filtrate after final trituration was evaporated at 45° C. under reduced pressure to give 2.4 kg of K18 (68.9% yield).

Step 6. A solution of K18 (1785.8 g (corrected for NMR purity), 3.96 mol) in methanol (12.5 L, 7 vol) at 20° C. was treated with 6 N sodium hydroxide (5.0 L, 29.71 mol, 7.5 equiv, precooled to 5° C.) added in 4 equal portions over 20 minutes in a 100 L jacketed glass reactor. The resulting solution was stirred at 40° C. After 1.5 hours, LC-MS analysis indicated >99.9% conversion. The reaction mixture was cooled to 5-10° C. and adjusted to pH 10 to 11 with 6 N HCl (4 L). The reaction mixture was partially evaporated under reduced pressure at 37° C. to remove methanol. The mixture was diluted with isopropyl acetate (18 L) and water (2 L). The resulting suspension was heated to 46° C. to give clear phases. After stirring for 15 minutes at 46° C., the layers were separated. The aqueous layer was extracted with isopropyl acetate (10 L) at 40° C. The combined organic layers were washed with half saturated brine (10 L), followed by water (5 L) at 40° C. The organic layer was evaporated under reduced pressure at 40° C. to dryness to give 1298 g of crude Compound 174 (Compound 174) (~92% yield).

Step 7. Compound 174 (1207 g, 3.4 mol (corrected for ~90% $^1$H NMR purity), 1 equiv) was co-evaporated with methyl ethyl ketone (4 L) at 40° C. under reduced pressure. The residue was dissolved in methyl ethyl ketone (6 L) and filtered (~8 μm porosity). The filtrate was charged to the reactor along with water (40 mL, 2.2 mol, 0.65 equiv). The resulting solution was heated to 60-62° C. n-Heptane (6 L, 5 vol) was charged to the hot solution over an hour, maintaining the temperature at 60-62° C. The resulting mixture was seeded (1 g, ~0.1% wt) and heated at 62° C. for an hour. The resulting solution was cooled to 20° C. over 5 hours. After stirring at 20° C. for 18 hours, the suspension was filtered through Whatman #113 filter paper at 20° C. The filter cake was washed with a 4:1 mixture of n-heptane and methyl ethyl ketone (3 L) in 2 equal portions. The product was dried under nitrogen convection at 20° C. for 3 hours to give 1091.5 g of Compound 174 Hemihydrate (Compound 174.0.5 H$_2$O) as a white powder (86.1% yield).

Preparation 1 of Compound 174 Phosphate Hemihydrate 628 mg Compound 174 Hemihydrate was weighed in a 10 mL vial, followed by adding about 7.6 mL 2-MeTHF. About 3.7 mL 0.5 M H$_3$PO$_4$, pre-formulated via mixing with about 0.42 mL 6 M H$_3$PO$_4$ (aq.) and about 4.6 mL MeOH was added to the vial dropwise. The mixture was stirred with a magnetic stirring bar at ambient temperature for two days. Then the solids were collected via centrifugation and dried in 40° C. vacuum oven overnight. Total solids recovered were 670 mg.

Preparation 2 of Compound 174 Phosphate Hemihydrate 1 eq. of Compound 174 Hemihydrate was charged to a reactor followed by 8 vol. of 2-MeTHF. The mixture was agitated at 40° C. The clear solution at 40° C. was seeded with 1 wt % of Compound 174 Phosphate Hemihydrate. In a separate container, 1.02 eq. of 85 wt % phosphoric acid was diluted with 0.35 vol. of water, 3 vol. of 2-MeTHF, and 0.6 vol. of acetone. This phosphoric acid solution was then added to the reactor slowly over 2 hours. The resulting slurry was then cooled to 20° C. over 5 hours. The final slurry was agitated at 20° C. for not less than 2 hours then filtered under vacuum. The resulting wet cake was washed with 3 vol. of 2-MeTHF. The wet cake was dried under vacuum with a nitrogen bleed at 50° C. to yield about 94% of Compound 174 Phosphate Hemihydrate.

XRPD

Figure 24:
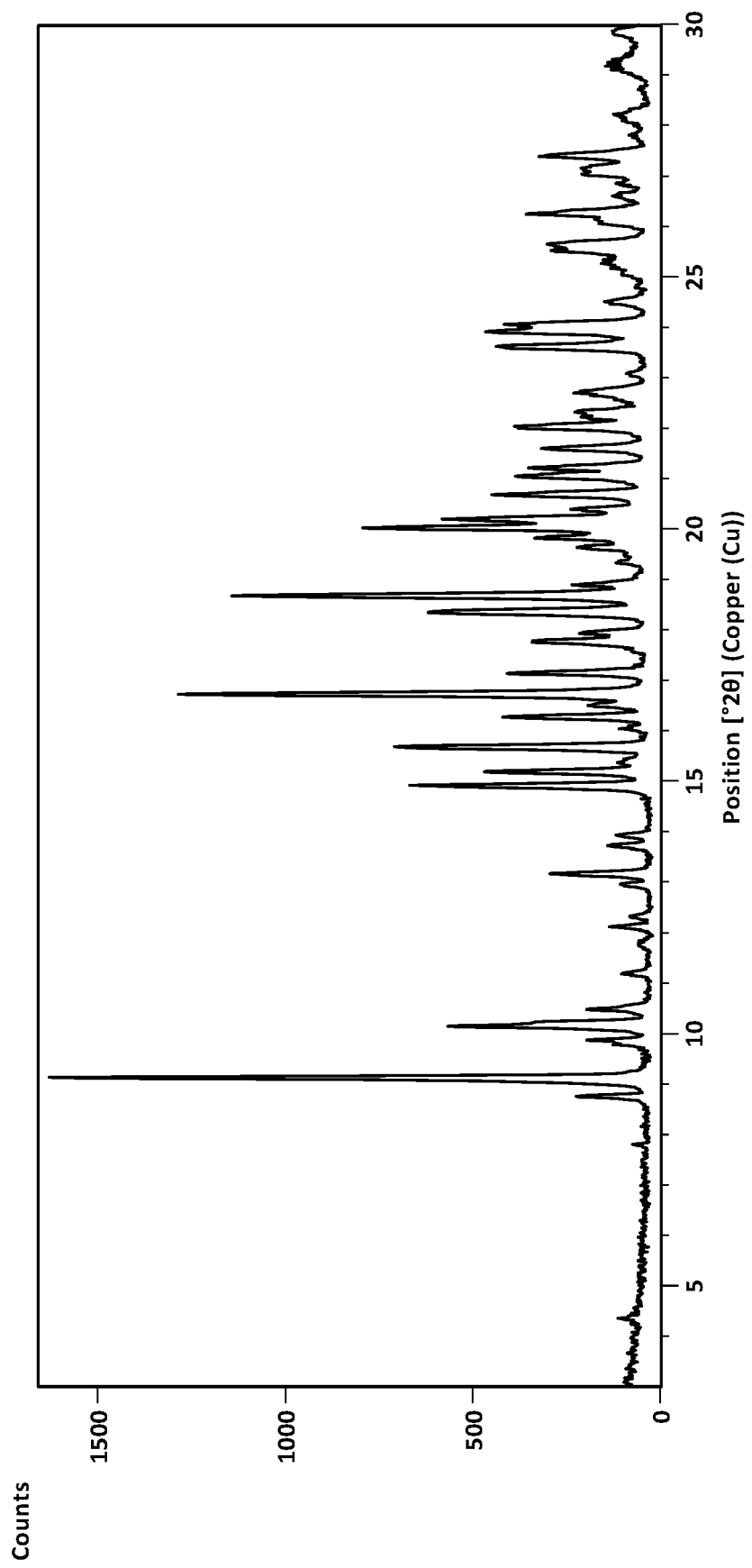
FIG. 24 depicts an XRPD diffractogram of Compound 174 Phosphate Hemihydrate.

X-ray powder diffraction (XRPD) spectra were recorded at room temperature (25±2° C.) in transmission mode using a PANalytical Empyrean system equipped with a sealed tube source and a PIXcel 3D Medipix-3 detector (Malvern PANalytical Inc, Westborough, Massachusetts) (FIG. 24, Table 33). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step.

TABLE 33

Peak List from XRPD Diffractogram of Compound 174 Phosphate Hemihydrate

| No. | Pos. [±0.2, °2θ] | Rel. Int. [%] |
|---|---|---|
| 1 | 9.1 | 100.0 |
| 2 | 16.7 | 77.4 |
| 3 | 18.7 | 68.1 |
| 4 | 20.0 | 43.3 |
| 5 | 15.7 | 41.9 |
| 6 | 14.9 | 39.0 |
| 7 | 18.4 | 36.1 |
| 8 | 10.1 | 32.8 |
| 9 | 20.2 | 32.4 |
| 10 | 15.2 | 27.0 |
| 11 | 23.9 | 25.7 |
| 12 | 20.7 | 25.6 |
| 13 | 23.6 | 24.6 |
| 14 | 16.3 | 23.9 |
| 15 | 17.1 | 23.4 |
| 16 | 21.0 | 21.4 |
| 17 | 26.2 | 20.5 |
| 18 | 22.0 | 20.4 |
| 19 | 21.2 | 19.8 |
| 20 | 19.8 | 19.0 |
| 21 | 27.4 | 18.1 |
| 22 | 17.8 | 18.0 |
| 23 | 10.2 | 17.1 |
| 24 | 21.6 | 16.6 |
| 25 | 24.1 | 15.8 |
| 26 | 13.2 | 15.3 |
| 27 | 25.5 | 14.9 |
| 28 | 25.7 | 14.8 |
| 29 | 18.9 | 12.5 |
| 30 | 20.4 | 12.0 |
| 31 | 22.7 | 11.8 |
| 32 | 22.3 | 11.7 |
| 33 | 17.9 | 11.1 |
| 34 | 8.8 | 11.0 |
| 35 | 19.6 | 10.6 |
| 36 | 27.0 | 10.5 |
| 37 | 10.5 | 10.3 |
| 38 | 27.2 | 10.1 |

TGA

Figure 25:
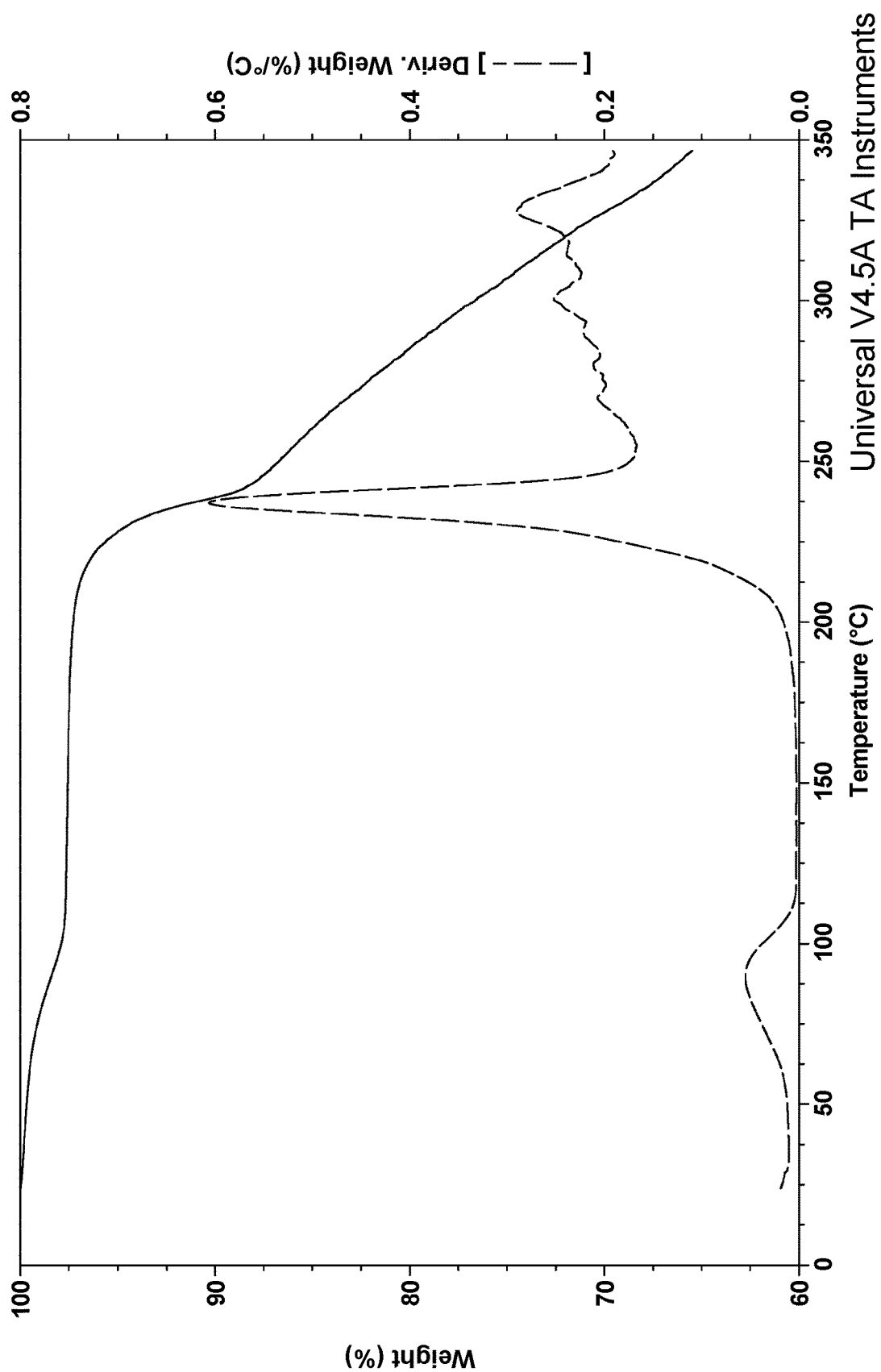
FIG. 25 depicts a TGA thermogram of Compound 174 Phosphate Hemihydrate.

Thermal gravimetric analysis of Compound 174 Phosphate Hemihydrate was conducted using a TA Discovery 550 TGA from TA Instrument. A sample with a weight of 1-10 mg was scanned from 25° C. to 350° C. at a heating rate of 10° C./min with nitrogen purge. Data were collected by Thermal Advantage Q Series™ software and analyzed by Trios and/or Universal Analysis software (TA Instruments, New Castle, DE). The thermogram showed 2.4% weight loss from ambient temperature up to 150° C. (FIG. 25).

DSC

Figure 26:
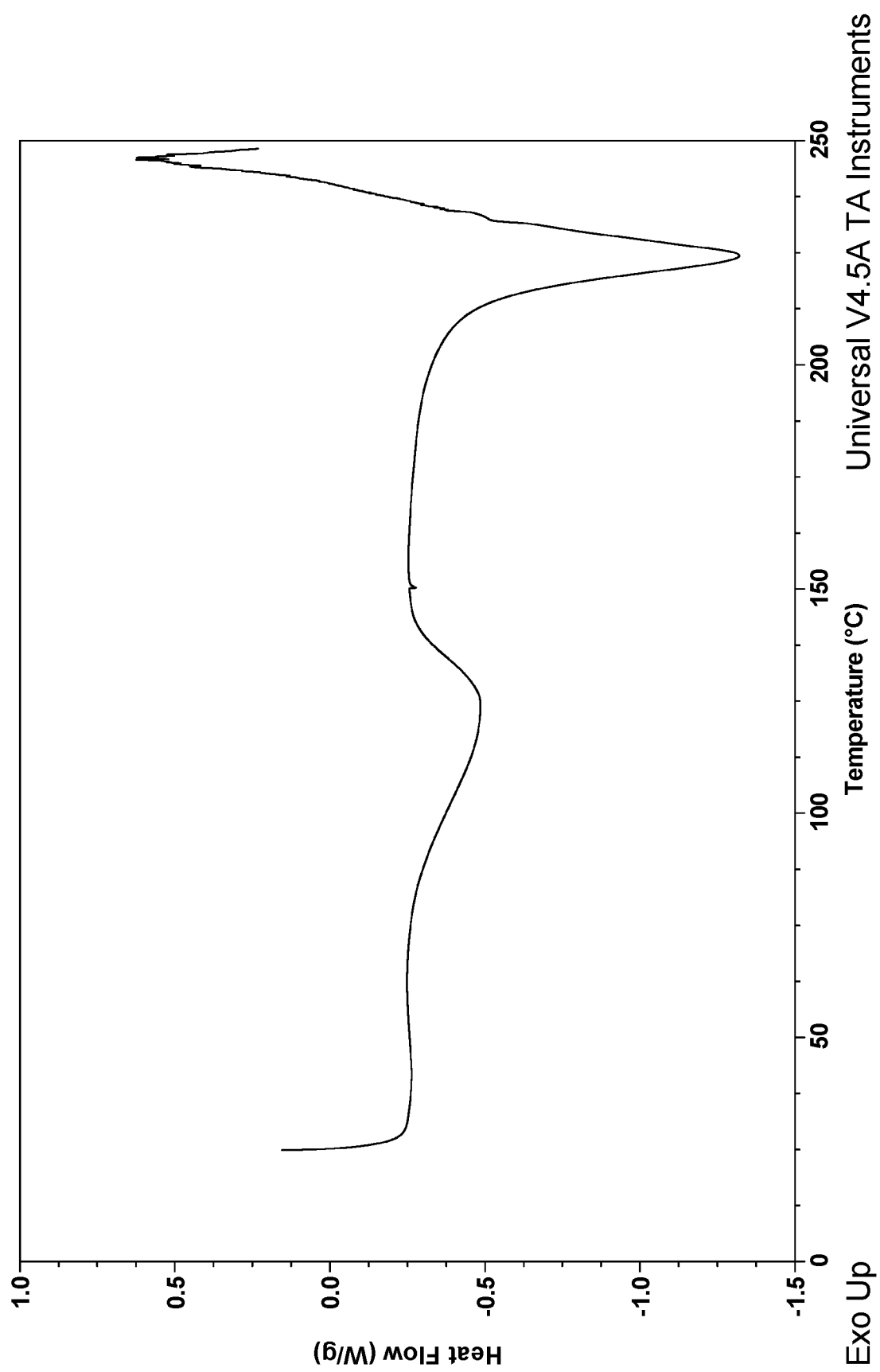
FIG. 26 depicts a DSC curve of Compound 174 Phosphate Hemihydrate.

DSC of Compound 174 Phosphate Hemihydrate was conducted using a TA Discovery 550 DSC. A sample with a weight between 1-10 mg was weighed into an aluminum crimp sealed pan with a pinhole. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 250° C. When the run was completed, the data were analyzed by Trios and/or Universal Analysis software (TA Instruments, New Castle, DE). The thermogram showed two endothermic peaks around 123° C. and 224° C. (FIG. 26).

SSNMR

Figure 27:
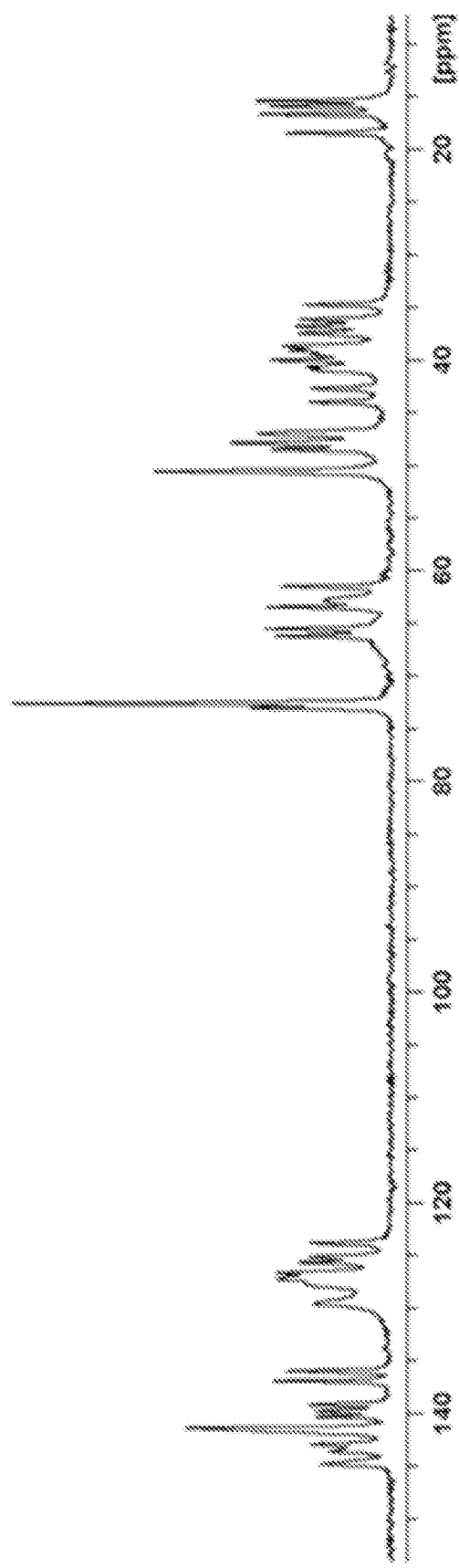
FIG. 27 depicts a solid state $^{13}$C NMR spectrum of Compound 174 Phosphate Hemihydrate.
Figure 28:
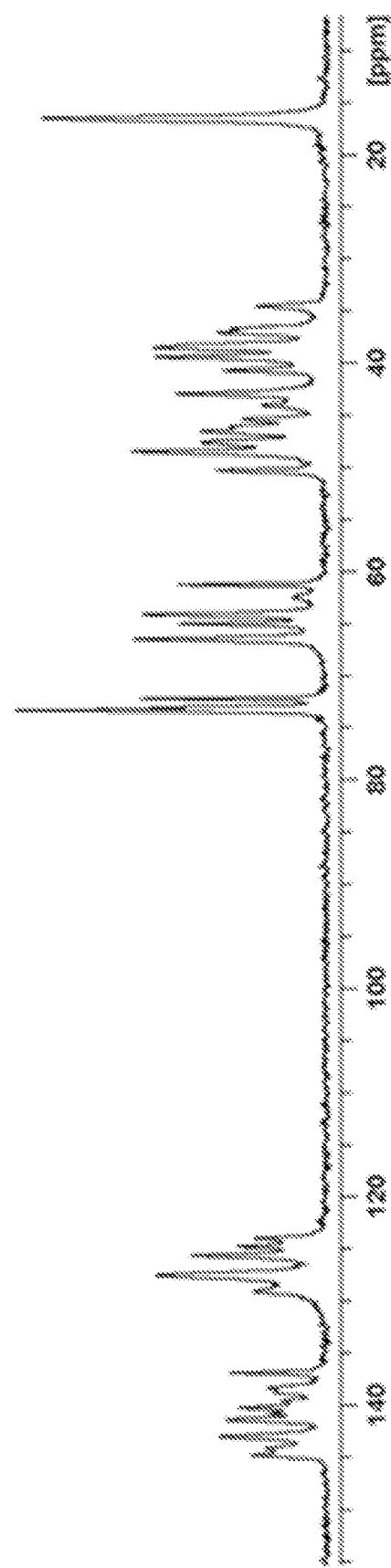
FIG. 28 depicts a solid state $^{13}$C NMR spectrum of dehydrated Compound 174 Phosphate Hemihydrate.

The $^{13}$C CPMAS of Compound 174 Phosphate Hemihydrate (FIG. 27, Table 34) was acquired at 275K with 12.5 kHz spinning and using adamantane as a reference. Additionally, the $^{13}$C CPMAS of Compound 174 Phosphate Hemihydrate following dehydration (FIG. 28, Table 35) was acquired at 275K with 12.5 kHz spinning and using adamantane as a reference.

TABLE 34

Peak List from $^{13}$C CPMAS of Compound 174 Phosphate Hemihydrate

| Peak # | Chem Shift [ppm] | Intensity [rel] |
|---|---|---|
| 1 | 144.7 | 17.8 |
| 2 | 143.5 | 16.3 |
| 3 | 142.9 | 20.7 |
| 4 | 141.3 | 53.4 |
| 5 | 140.6 | 4.3 |
| 6 | 140.2 | 19.6 |
| 7 | 139.7 | 20.0 |
| 8 | 139.1 | 21.1 |
| 9 | 136.8 | 30.3 |
| 10 | 135.9 | 27.0 |
| 11 | 129.5 | 20.2 |
| 12 | 127.6 | 22.6 |
| 13 | 127.1 | 29.4 |
| 14 | 126.6 | 30.0 |
| 15 | 125.6 | 24.1 |
| 16 | 125.1 | 21.1 |
| 17 | 123.7 | 20.8 |
| 18 | 73.0 | 36.2 |
| 19 | 72.5 | 100.0 |
| 20 | 66.1 | 29.9 |
| 21 | 65.4 | 32.8 |
| 22 | 63.4 | 32.1 |
| 23 | 62.8 | 17.5 |
| 24 | 61.4 | 28.2 |
| 25 | 50.5 | 62.2 |
| 26 | 48.4 | 30.7 |
| 27 | 47.7 | 41.4 |
| 28 | 46.9 | 34.6 |
| 29 | 43.9 | 21.2 |
| 30 | 42.6 | 21.0 |
| 31 | 40.8 | 20.6 |
| 32 | 40.5 | 21.9 |
| 33 | 39.9 | 31.2 |
| 34 | 39.4 | 20.8 |
| 35 | 39.0 | 26.3 |
| 36 | 38.6 | 28.0 |
| 37 | 37.4 | 23.9 |
| 38 | 36.7 | 24.6 |
| 39 | 36.1 | 23.7 |
| 40 | 34.6 | 22.34 |
| 41 | 18.4 | 27.3 |
| 42 | 16.6 | 34.58 |
| 43 | 15.8 | 31.5 |
| 44 | 15.3 | 35.4 |

TABLE 35

Peak List from $^{13}$C CPMAS of Dehydrated Compound 174 Phosphate Hemihydrate

| Peak # | Chem Shift [ppm] | Intensity [rel] |
|---|---|---|
| 1 | 144.7 | 23.3 |
| 2 | 144.1 | 18.6 |
| 3 | 143.0 | 33.0 |
| 4 | 141.3 | 31.2 |
| 5 | 140.7 | 17.7 |
| 6 | 140.2 | 27.1 |
| 7 | 139.5 | 14.1 |
| 8 | 138.6 | 16.1 |
| 9 | 138.3 | 18.2 |
| 10 | 136.8 | 29.8 |
| 11 | 129.0 | 22.5 |
| 12 | 127.5 | 53.1 |
| 13 | 125.6 | 42.3 |
| 14 | 124.7 | 27.6 |
| 15 | 123.9 | 22.3 |
| 16 | 73.3 | 100.0 |
| 17 | 73.0 | 55.6 |
| 18 | 72.2 | 58.5 |
| 19 | 66.5 | 60.3 |
| 20 | 65.0 | 46.4 |
| 21 | 64.1 | 57.4 |
| 22 | 62.4 | 10.5 |
| 23 | 61.2 | 46.6 |
| 24 | 50.2 | 34.2 |
| 25 | 48.5 | 60.9 |
| 26 | 47.6 | 39.0 |
| 27 | 46.5 | 39.4 |
| 28 | 46.1 | 29.9 |
| 29 | 45.3 | 26.1 |
| 30 | 44.0 | 20.1 |
| 31 | 42.9 | 46.8 |
| 32 | 40.6 | 32.6 |
| 33 | 39.3 | 53.4 |
| 34 | 38.5 | 54.1 |
| 35 | 37.0 | 33.9 |
| 36 | 36.6 | 29.5 |
| 37 | 34.5 | 21.6 |
| 38 | 16.5 | 89.0 |

Figure 29A:
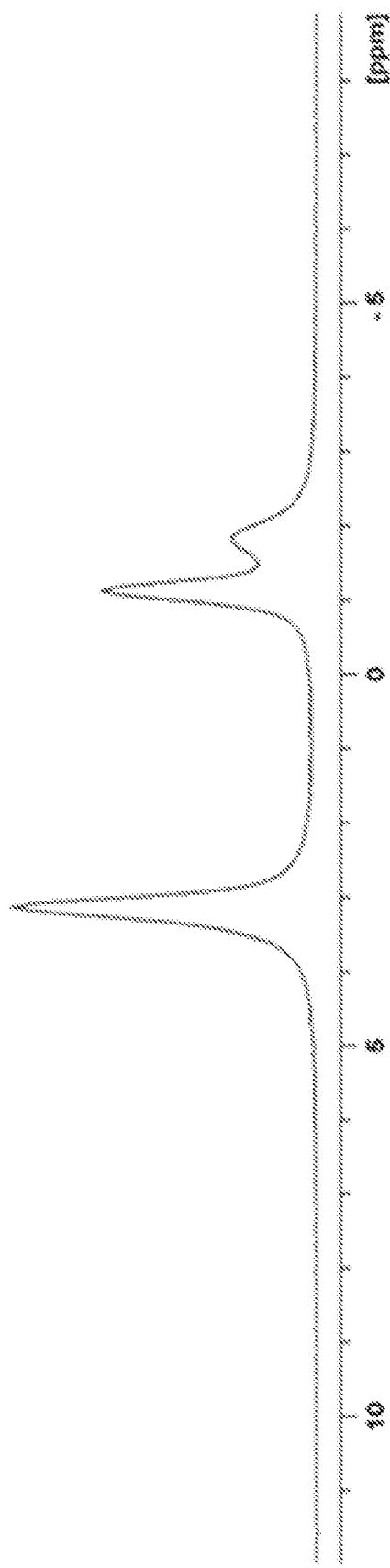
FIG. 29A depicts a solid state $^{31}$P NMR spectrum of Compound 174 Phosphate Hemihydrate.
Figure 29B:
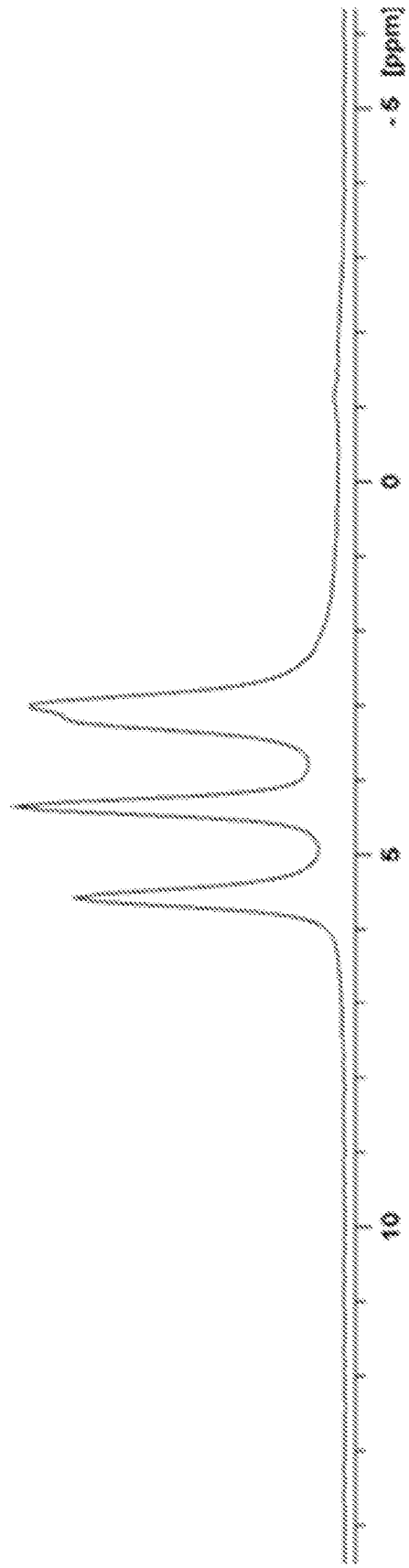
FIG. 29B depicts a solid state $^{31}$P NMR spectrum of dehydrated Compound 174 Phosphate Hemihydrate.

The $^{13}$C CPMAS of Compound 174 Phosphate Hemihydrate (FIG. 29A, Table 36A) was acquired at 275K with 12.5 kHz spinning and using adamantane as a reference. Additionally, the $^{31}$P CPMAS of Compound 174 Phosphate Hemihydrate following dehydration (FIG. 29B, Table 36B) was acquired at 275K with 12.5 kHz spinning and using adamantane as a reference.

TABLE 36A

Peak List from $^{31}$P CPMAS of Compound 174 Phosphate Hemihydrate

| Peak # | Chem Shift [ppm] | Intensity [rel] |
|---|---|---|
| 1 | 3.1 | 100.0 |
| 2 | −1.1 | 70.6 |
| 3 | −1.8 | 28.0 |

TABLE 36B

Peak List from $^{31}$P CPMAS of Dehydrated Compound 174 Phosphate Hemihydrate

| Peak # | Chem Shift [ppm] | Intensity [rel] |
|---|---|---|
| 1 | 5.6 | 81.9 |
| 2 | 4.4 | 100.0 |
| 3 | 3.2 | 85.0 |
| 4 | 3.0 | 96.7 |

Alternative Preparation of Compound 174 Hemihydrate 100 mg of amorphous Compound 174 was added to a glass vial. To this was added 0.4 mL MEK, and all solids dissolved. 3 µL water was then added to aid the hemihydrate formation. To this mixture was added 0.25 mL of n-Heptane directly. After stirring for 18 hours at ambient temperature, the solids were filtered, rinsing with 1:4 MEK/n-Heptane (v/v), followed by 100% n-Heptane. The solids were collected, dried in a vacuum oven (60° C.) overnight, and characterized.

XRPD

Figure 30:
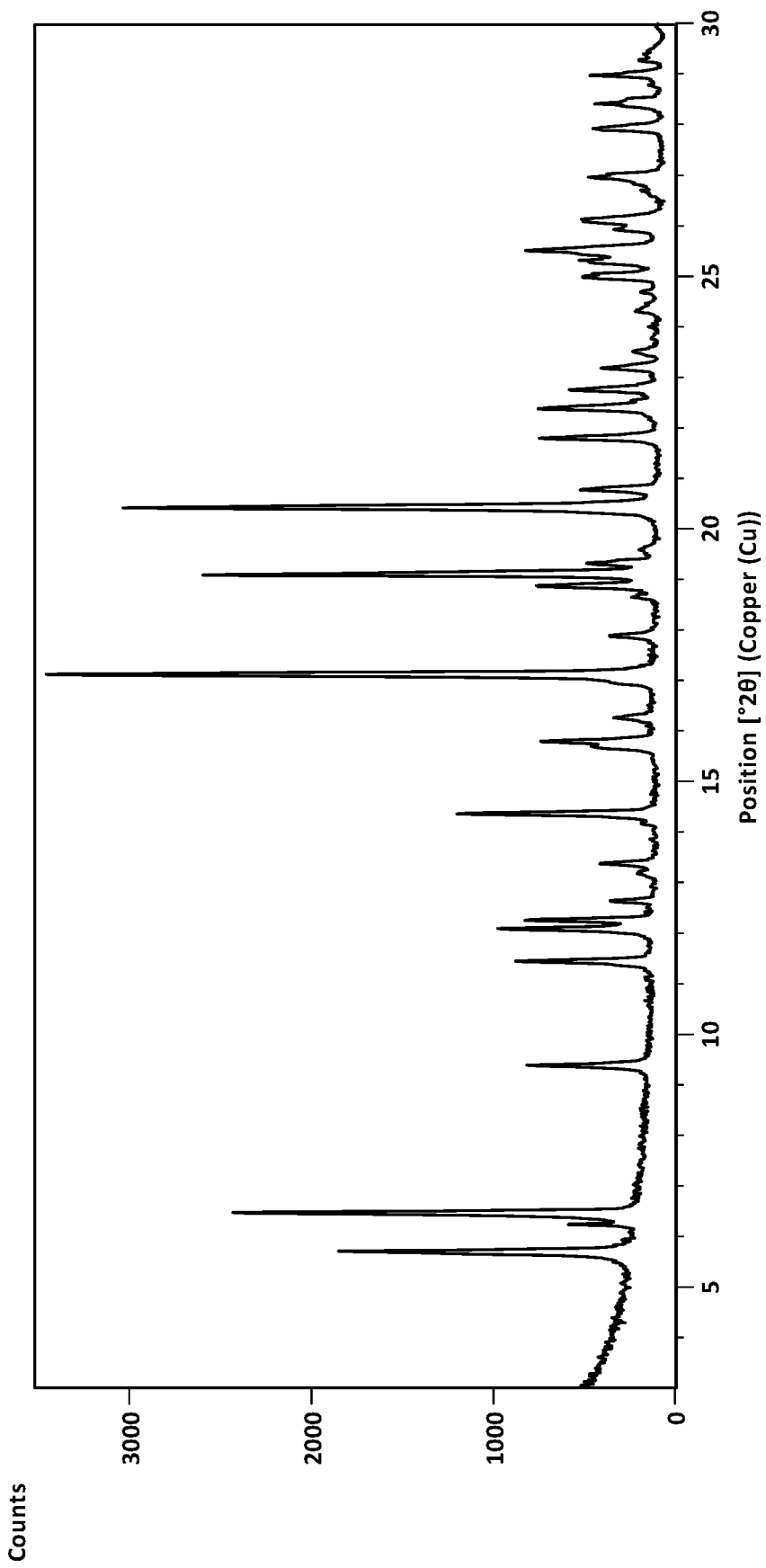
FIG. 30 depicts an XRPD diffractogram of Compound 174 Hemihydrate.

X-ray powder diffraction (XRPD) spectra were recorded at room temperature (25±2° C.) in transmission mode using a PANalytical Empyrean system equipped with a sealed tube source and a PIXcel 1D Medipix-3 detector (Malvern PANalytical Inc, Westborough, Massachusetts) (FIG. 30, Table 37). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 40°2θ with a step size of 0.0131303° and 49 s per step.

TABLE 37

Peak List from XRPD Diffractogram of Compound 174 Hemihydrate (Room Temperature)

| No. | Pos. [±0.2, °2θ] | Rel. Int. [%] |
|---|---|---|
| 1 | 17.1 | 100.0 |
| 2 | 20.4 | 87.3 |
| 3 | 19.1 | 74.1 |
| 4 | 6.5 | 66.2 |
| 5 | 5.7 | 46.8 |
| 6 | 14.4 | 32.6 |
| 7 | 12.1 | 25.6 |
| 8 | 11.4 | 22.3 |
| 9 | 25.5 | 22.0 |
| 10 | 12.3 | 20.5 |
| 11 | 18.9 | 19.9 |
| 12 | 9.4 | 19.9 |
| 13 | 22.4 | 19.7 |
| 14 | 21.8 | 18.8 |
| 15 | 15.8 | 17.7 |
| 16 | 22.7 | 14.5 |
| 17 | 22.4 | 14.2 |
| 18 | 20.8 | 12.9 |
| 19 | 25.0 | 12.4 |
| 20 | 26.1 | 12.1 |
| 21 | 29.0 | 12.0 |
| 22 | 26.1 | 11.8 |
| 23 | 27.0 | 11.8 |
| 24 | 19.3 | 11.5 |
| 25 | 25.1 | 11.2 |
| 26 | 25.3 | 11.1 |
| 27 | 6.2 | 10.9 |
| 28 | 27.9 | 10.9 |
| 29 | 28.4 | 10.7 |
| 30 | 15.7 | 10.0 |

Additionally, in one test of in situ variable temperature XRPD (VT-XRPD), Compound 174 Hemihydrate was observed to show peak shifts at elevated temperature. Variable temperature X-ray powder diffraction (VT-XRPD) spectra were recorded in 30-90° C. in reflection mode using a PANalytical Empyrean system equipped with a sealed tube source and a PIXcel 1D Medipix-2 detector (Malvern PANalytical Inc, Westborough, Massachusetts). The step-wise temperature change in increments of 10° C. from 30° C. to 90° C. with a hold at each temperature for 1 hour, followed by XRD collection. The sample chamber was purged with house nitrogen. The X-Ray generator operated at a voltage of 45 kV and a current of 40 mA with copper radiation (1.54060 Å). The sample was scanned over the range of about 3° to about 40°2θ with a step size of 0.0131303° and 49.725 s per step.

Three distinct XRPD patterns were found, respectively, at: (1) ambient temperature to 30° C.; (2) 40-50° C.; and (3) 60-90° C. The sample returned to its initial form after re-equilibration at ambient temperature and humidity. The XRPD spectrum from ambient temperature to 30° C. was the same (within ±0.2°2θ) as the XRPD spectrum collected at room temperature (25±2° C.). Table 38 lists the peaks observed between 40-50° C., and Table 39 lists the peaks observed between 60-90° C.

TABLE 38

Peak List from XRPD Diffractogram of Compound 174 Hemihydrate (40-50° C.)

| No. | Pos. [±0.2, °2θ] | Rel. Int. [%] |
|---|---|---|
| 1 | 20.1 | 100.0 |
| 2 | 19.0 | 85.2 |
| 3 | 11.3 | 58.1 |
| 4 | 5.6 | 56.8 |
| 5 | 22.3 | 56.2 |
| 6 | 25.1 | 45.7 |
| 7 | 24.8 | 43.1 |
| 8 | 27.8 | 42.5 |
| 9 | 22.1 | 40.3 |
| 10 | 17.2 | 32.5 |
| 11 | 9.5 | 30.8 |
| 12 | 11.9 | 29.1 |
| 13 | 18.7 | 28.0 |
| 14 | 15.6 | 23.2 |
| 15 | 20.9 | 22.6 |
| 16 | 6.6 | 22.5 |
| 17 | 21.9 | 21.6 |

TABLE 38-continued

Peak List from XRPD Diffractogram of
Compound 174 Hemihydrate (40-50° C.)

| No. | Pos. [±0.2, °2θ] | Rel. Int. [%] |
|---|---|---|
| 18 | 23.9 | 21.4 |
| 19 | 22.6 | 21.2 |
| 20 | 29.9 | 20.6 |
| 21 | 19.6 | 20.1 |
| 22 | 30.0 | 19.8 |
| 23 | 26.6 | 19.7 |
| 24 | 25.9 | 19.5 |
| 25 | 28.9 | 18.4 |
| 26 | 26.2 | 17.1 |
| 27 | 26.9 | 16.3 |
| 28 | 27.0 | 16.2 |
| 29 | 28.7 | 15.6 |
| 30 | 19.3 | 15.3 |
| 31 | 28.3 | 14.5 |
| 32 | 14.4 | 12.4 |
| 33 | 17.8 | 12.3 |
| 34 | 25.5 | 11.6 |
| 35 | 23.4 | 11.0 |
| 36 | 23.1 | 11.0 |
| 37 | 29.4 | 10.9 |
| 38 | 24.2 | 10.6 |

TABLE 39

Peak List from XRPD Diffractogram
of Compound 174 Hemihydrate
(60-90° C.)

| No. | Pos. [±0.2, °2θ] | Rel. Int. [%] |
|---|---|---|
| 1 | 19.8 | 100.0 |
| 2 | 19.2 | 72.1 |
| 3 | 5.5 | 62.0 |
| 4 | 21.8 | 60.5 |
| 5 | 11.0 | 50.3 |
| 6 | 27.2 | 48.3 |
| 7 | 24.7 | 46.0 |
| 8 | 19.0 | 44.5 |
| 9 | 22.0 | 40.6 |
| 10 | 24.3 | 40.4 |
| 11 | 17.3 | 35.5 |
| 12 | 11.7 | 28.8 |
| 13 | 9.6 | 28.7 |
| 14 | 29.3 | 24.2 |
| 15 | 29.3 | 23.4 |
| 16 | 21.0 | 21.8 |
| 17 | 26.8 | 20.7 |
| 18 | 23.5 | 20.5 |
| 19 | 15.5 | 20.0 |
| 20 | 6.7 | 19.9 |
| 21 | 27.4 | 18.0 |
| 22 | 25.1 | 17.7 |
| 23 | 25.8 | 16.4 |
| 24 | 23.0 | 15.8 |
| 25 | 29.9 | 15.1 |
| 26 | 14.4 | 14.8 |
| 27 | 25.9 | 14.4 |
| 28 | 28.3 | 14.3 |
| 29 | 17.8 | 13.2 |
| 30 | 15.6 | 13.0 |
| 31 | 25.6 | 12.3 |
| 32 | 20.3 | 12.3 |
| 33 | 22.6 | 12.2 |

TGA

Figure 31:
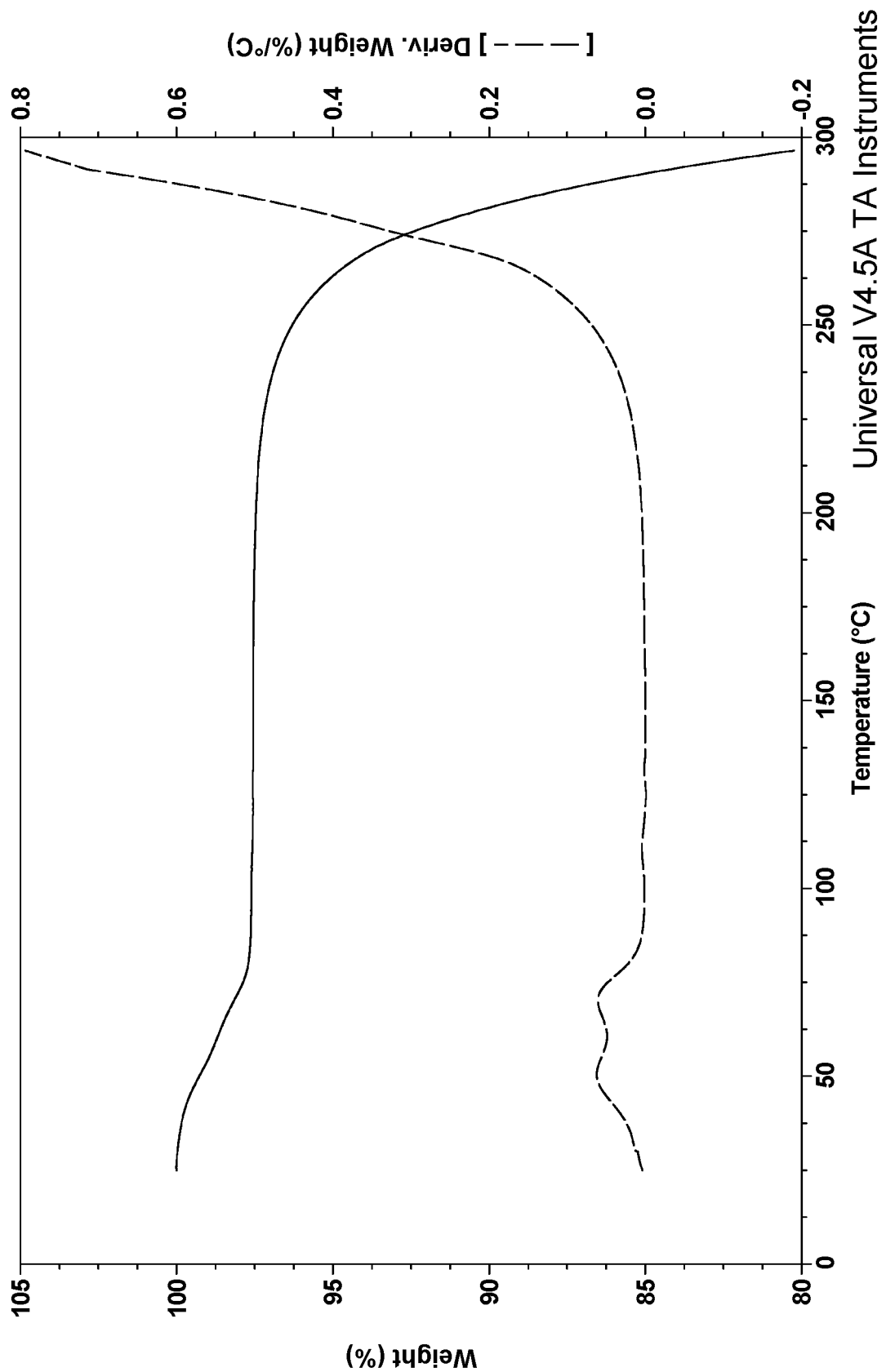
FIG. 31 depicts a TGA thermogram of Compound 174 Hemihydrate.

Thermal gravimetric analysis of Compound 174 Hemihydrate was conducted using a TA Discovery 550 TGA from TA Instrument. A sample with a weight of approximately 1-10 mg was scanned from 25° C. to 300° C. at a heating rate of 10° C./min with nitrogen purge. Data were collected by Thermal Advantage Q Series™ software and analyzed by Trios and/or Universal Analysis software (TA Instruments, New Castle, DE). The thermogram showed 2.4% weight loss from ambient temperature up to 150° C. (FIG. 31).

DSC

Figure 32:
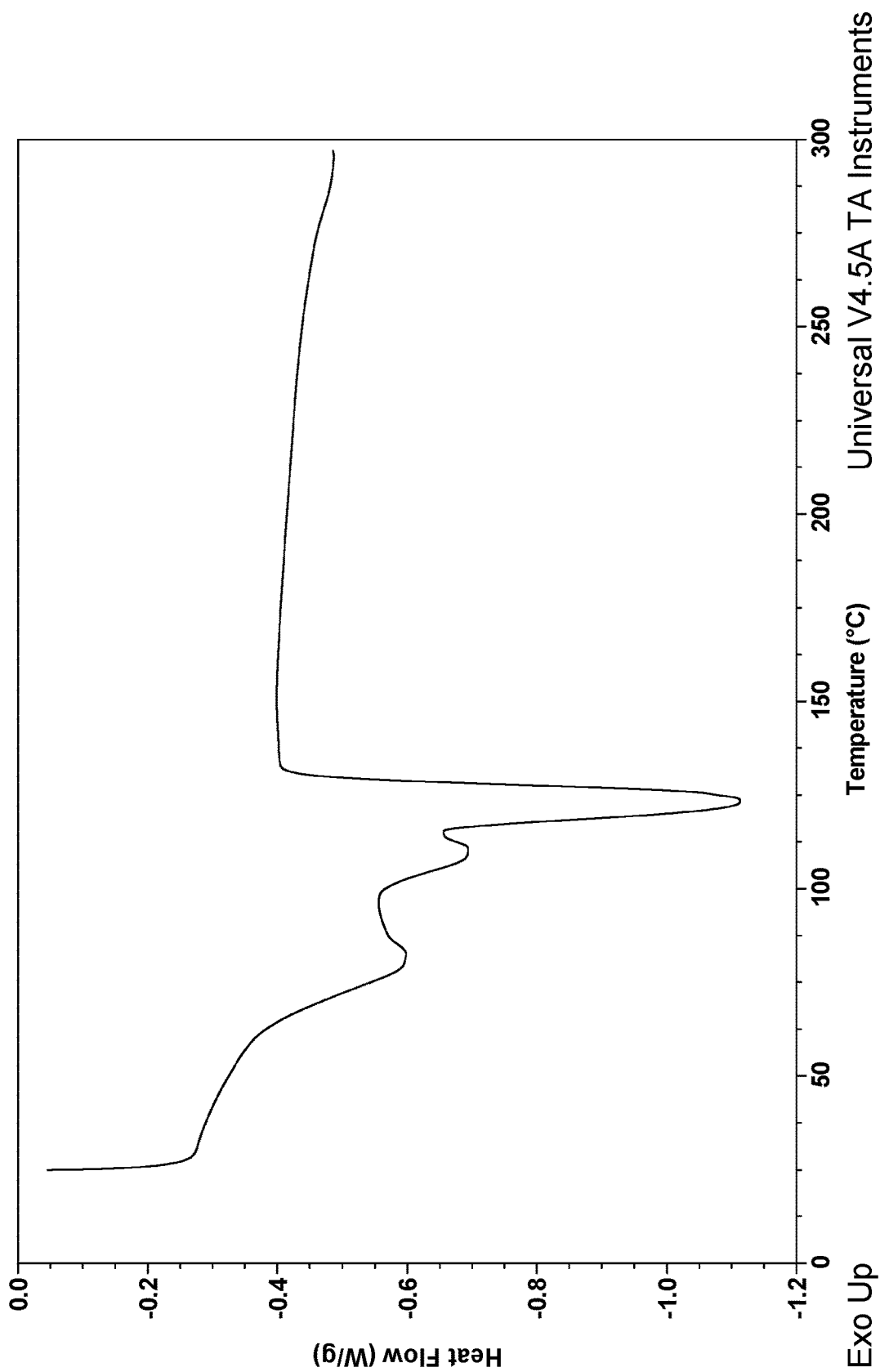
FIG. 32 depicts a DSC curve of Compound 174 Hemihydrate.

DSC of Compound 174 Hemihydrate was conducted using the TA Instruments Q2000 DSC. A sample with a weight between 1-10 mg was weighed into an aluminum crimp sealed pan with a pinhole. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 300° C. When the run was completed, the data were analyzed by Trios and/or Universal Analysis software (TA Instruments, New Castle, DE). The thermogram showed endothermic peaks around 77° C., 107° C., and 125° C. (FIG. 32).

SSNMR

Figure 33:
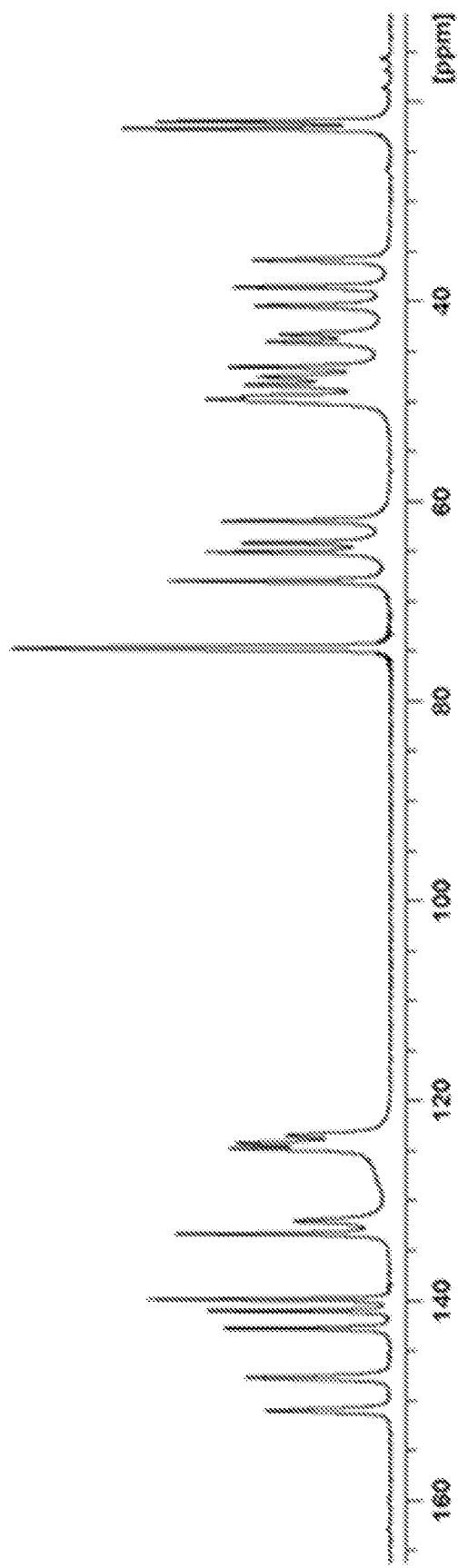
FIG. 33 depicts a solid state $^{13}$C NMR spectrum of Compound 174 Hemihydrate.
Figure 34:
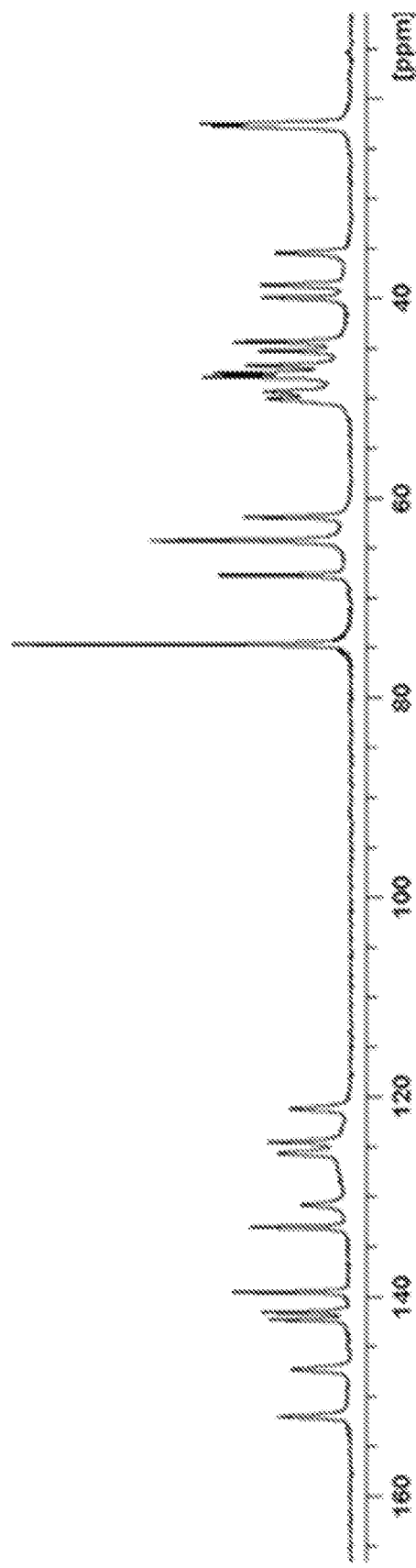
FIG. 34 depicts a solid state $^{13}$C NMR spectrum of dehydrated Compound 174 Hemihydrate.

The $^{13}$C CPMAS of Compound 174 Hemihydrate (FIG. 33, Table 40) was acquired at 275K with 12.5 kHz spinning and using adamantane as a reference. Additionally, the $^{13}$C CPMAS of Compound 174 Hemihydrate following dehydration (weekend at ambient temperature and overnight at 80° C. in rotor) (FIG. 34, Table 41) was acquired at 275K with 12.5 kHz spinning and using adamantane as a reference.

TABLE 40

Peak List from $^{13}$C CPMAS
of Compound 174 Hemihydrate

| Peak # | Chem Shift [ppm] | Intensity [rel] |
|---|---|---|
| 1 | 150.9 | 32.6 |
| 2 | 147.6 | 38.4 |
| 3 | 142.7 | 44.5 |
| 4 | 140.9 | 47.7 |
| 5 | 139.8 | 65.2 |
| 6 | 133.2 | 56.1 |
| 7 | 131.9 | 25.5 |
| 8 | 124.7 | 42.9 |
| 9 | 124.2 | 40.7 |
| 10 | 123.4 | 27.4 |
| 11 | 74.6 | 100.0 |
| 12 | 67.9 | 58.3 |
| 13 | 65.0 | 48.6 |
| 14 | 64.0 | 39.3 |
| 15 | 61.9 | 44.1 |
| 16 | 49.7 | 48.6 |
| 17 | 49.4 | 39.6 |
| 18 | 48.2 | 38.3 |
| 19 | 47.4 | 34.0 |
| 20 | 46.4 | 42.4 |
| 21 | 43.9 | 33.0 |
| 22 | 43.2 | 28.9 |
| 23 | 40.3 | 35.4 |
| 24 | 38.4 | 41.0 |
| 25 | 35.8 | 36.3 |
| 26 | 22.6 | 70.0 |
| 27 | 21.9 | 61.5 |

TABLE 41

Peak List from $^{13}$C CPMAS of Dehydrated
Compound 174 Hemihydrate

| Peak # | Chem Shift [ppm] | Intensity [rel] |
|---|---|---|
| 1 | 151.9 | 20.5 |
| 2 | 147.2 | 17.3 |
| 3 | 142.2 | 23.6 |
| 4 | 141.5 | 25.6 |

TABLE 41-continued

Peak List from $^{13}$C CPMAS of Dehydrated Compound 174 Hemihydrate

| Peak # | Chem Shift [ppm] | Intensity [rel] |
|---|---|---|
| 5 | 139.4 | 34.1 |
| 6 | 132.9 | 29.6 |
| 7 | 130.7 | 14.4 |
| 8 | 125.5 | 21.1 |
| 9 | 124.4 | 24.0 |
| 10 | 121.1 | 17.5 |
| 11 | 74.6 | 100.0 |
| 12 | 67.6 | 39.4 |
| 13 | 64.1 | 58.3 |
| 14 | 61.8 | 30.9 |
| 15 | 49.9 | 24.8 |
| 16 | 49.2 | 25.8 |
| 17 | 47.7 | 42.9 |
| 18 | 47.3 | 39.9 |
| 19 | 46.6 | 30.3 |
| 20 | 45.2 | 26.8 |
| 21 | 44.3 | 33.9 |
| 22 | 39.8 | 26.2 |
| 23 | 38.5 | 26.3 |
| 24 | 35.3 | 22.2 |
| 25 | 22.6 | 41.1 |
| 26 | 22.4 | 43.6 |

Example 3. Assays for Detecting and Measuring APOL1 Inhibitor Properties of Compounds MultiTox-Fluor Multiplex Cytotoxicity Assay The MultiTox-Fluor Multiplex Cytotoxicity Assay is a single-reagent-addition, homogeneous, fluorescence assay that measures the number of live and dead cells simultaneously in culture wells. The assay measures cell viability and cytotoxicity by detecting two distinct protease activities. The live-cell protease activity is restricted to intact viable cells and is measured using a fluorogenic, cell-permeant peptide glycyl-phenylalanylamino fluorocoumarin (GF-AFC) substrate. The substrate enters intact cells, where it is cleaved to generate a fluorescent signal proportional to the number of living cells. This live-cell protease activity marker becomes inactive upon loss of membrane integrity and leakage into the surrounding culture medium. A second, cell-impermeant, fluorogenic peptide substrate (bis-AAF-R110 Substrate) is used to measure dead-cell protease that has been released from cells that have lost membrane integrity. A ratio of dead to live cells is used to normalize data.

Briefly, the tet-inducible transgenic APOL1 T-REx-HEK293 cell lines were incubated with 50 ng/mL tet to induce APOL1 in the presence of 3-(2-(4-fluorophenyl)-1H-indol-3-yl)-N-((3S,4R)-4-hydroxy-2-oxopyrrolidin-3-yl) propenamide at 10.03, 3.24, 1.13, 0.356, 0.129, 0.042, 0.129, 0.0045, 0.0015, 0.0005 µM in duplicate for 24 hours in a humidified 37° C. incubator. The MultiTox reagent was added to each well and placed back in the incubator for an additional 30 minutes. The plate was read on the EnVision plate reader. A ratio of dead to live cells was used to normalize, and data was imported, analyzed and fit using Genedata Screener (Basel, Switzerland) software. Data was normalized using percent of control, no tet (100% viability), and 50 ng/mL tet treated (0% viability), and fit using Smart Fit. The reagents, methods, and complete protocol for the MultiTox assay are described below.

TABLE 42

Reagents Used in the Multi-Tox Assay

| Reagent | Catalog Number | Vendor |
|---|---|---|
| 384 well, transparent, flat bottom tissue culture treated, Poly-D lysine coated | 356663 | Corning (Corning, NY) |
| 384 well round bottom polypropylene plates | 3656 | CoStar (Corning, NY) |
| Universal plate lids | 250002 | Thermo Fisher (Waltham) |
| Axygen 30 µL tips for Bravo 384 well | VT-384-31UL-R-S | Corning (Corning, NY) |
| MultiTox-Fluor Multiplex Cytotoxicity Assay | G9202 | Promega (Madison, WI) |
| 225 cm$^2$ flask, angled neck, treated, vented cap | 431082 | Corning (Corning, NY) |
| Dulbecco's Phosphate-Buffered Saline (DPBS), calcium and magnesium-free | 14190-136 | Thermo Fisher (Waltham) |
| Dulbecco's Modified Eagle Medium (DMEM), high glucose, no glutamine, no sodium pyruvate | 11960-077 | Thermo Fisher (Waltham) |
| Fetal Bovine Serum (FBS), tetracycline-free, US-Sourced | 631368 | Takara (Kusatsu, Japan) |
| L-Glutamine, 200 mM | 25030-081 | Thermo Fisher (Waltham) |
| Penicillin-Streptomycin, 10,000 Units/mL | 15140-122 | Thermo Fisher (Waltham) |
| Blasticidin S HCl, 10 mg/mL | A11139-03 | Thermo Fisher (Waltham) |
| Tetracycline hydrochloride | T7660-5G | Sigma (St. Louis, MO) |
| Puromycin dihydrochloride, 10 mg/mL | A11138-03 | Thermo Fisher (Waltham) |
| Trypsin-EDTA | 25300-054 | Thermo Fisher (Waltham) |

TABLE 43

Equipment Used in the Multi-Tox Assay

| Instrument | Model | Supplier | Location |
|---|---|---|---|
| Bravo | 16050-101 | Agilent Technologies | Santa Clara, CA |
| Multidrop Combi | N/A | Thermo Scientific | Waltham, MA |
| EnVision | N/A | PerkinElmer | Waltham, MA |

Multi-Tox Assay Protocol

Human embryonic kidney (HEK293) cell lines containing a tet-inducible expression system (T-REx™; Invitrogen, Carlsbad, CA) and Adeno-associated virus site 1 pAAVS1-Puro-APOL1 G0 or pAAVS1-Puro-APOL1 G1 or pAAVS1-Puro-APOL1 G2 Clones G0 DC2.13, G1 DC3.25, and G2 DC4.44 were grown in a T-225 flask at ~90% confluency in cell growth media (DMEM, 10% Tet-free FBS, 2 mM L-glutamine, 100 Units/mL penicillin-streptomycin, 5 µg/mL blasticidin S HCl, 1 µg/mL puromycin dihydrochloride). Cells were washed with DPBS and then trypsinized to dissociate from the flask. Media was used to quench the trypsin, cells were then pelleted at 200 g and resuspended in fresh cell assay media (DMEM, 2% Tet-free FBS, 2 mM L-glutamine, 100 Units/mL penicillin-streptomycin). Cells were counted and diluted to 1.17×10$^6$ cells/mL. 20 µL of cells (23,400/well) were dispensed to every well of a 384-well Poly-D-Lysine coated plate using the Multidrop dispenser. The plates were then incubated at room temperature for one hour.

Tetracycline is needed to induce APOL1 expression. 1 mg/mL tet stock in water was diluted to 250 ng/mL (5×) in cell assay media. 60 µL of cell assay media (no tet control) was dispensed in columns 1 and 24, and 60 µL of 5× tet was dispensed in 384-PP-round bottom plate in columns 2 to 23 with the Multidrop dispenser.

Assay ready plates from the Global Compound Archive were ordered using template 384_APOL1Cell_DR10n2_50 µM_v3. Compounds were dispensed at 200 nL in DMSO. The final top concentration was 10 µM with a 10 point 3-fold dilution in duplicate in the MultiTox assay.

20 µL were transferred from the 5× tet plate to the ARP and mixed, then 5 µL of 5× tet and the compounds were transferred to the cell plate and mixed using the Bravo. The cell plate was placed in the humidified 37° C. 5% $CO_2$ incubator for 24 hours.

The MultiTox-Fluor Multiplex Cytotoxicity Assay was performed in accordance with the manufacturer's protocol. After cells were incubated with tet and compound for 24 hours, 25 µL of 1× MultiTox reagent was added to each well using the Multidrop dispenser; the plates were placed on a plate shaker (600 rpm) for 2 minutes, then centrifuged briefly and placed back in the 37° C. incubator for 30 minutes. The cell viability (excitation: 400 nm, emission: 486 nm) and cytotoxicity (excitation: 485 nm, emission: 535 nm) were read using the EnVision plate reader. A ratio of dead (cytotoxicity) to live (viability) cells was reported. Data was exported and analyzed in Genedata. Data was normalized using percent of control, no tet (100% viability), and 50 ng/mL tet treated (0% viability), and fit using Smart Fit settings in Genedata.

*Trypanosoma brucei brucei* Lysis Assay Using APOL1 Recombinant Protein

*Trypanosoma brucei brucei* is a blood stream parasite to which human, gorillas, and baboons are immune due to the presence of the APOL1 protein in their HDL particles. The protein is uptaken by the parasite via the TbHpHb receptor located in its flagellar pocket and is bonded by the Hpr protein contained in the HDL particles which triggers the receptor endocytosis by the parasite.

Following endocytosis, the formed vesicle containing the HDL particle matures from early to late endosome, and subsequently to lysosome. The concomitant pH change in the lumen of the vesicle triggers the insertion of the APOL1 protein into the membrane of the late endosome/lysosome and hereby triggers lysosomal membrane permeabilization and as a further downstream event, trypanosome lysis. *Trypanosoma brucei brucei* is sensitive to lysis by all three APOL1 variants (G0, G1, and G2).

The *Trypanosoma brucei brucei* lysis assay is a lysis assay of the parasite using recombinant APOL1 protein variant followed by a fluorescent detection method of viability by the addition of AlamarBlue reagent to the assay well, a general metabolic redox indicator (AlamarBlue assay).

Briefly, the AlamarBlue active compound, resazurin, a blue, water soluble, non-toxic and cell permeable molecule, which can be followed by absorbance, is reduced by various metabolic pathways into resorufin, a red compound which can be followed by either absorbance or fluorescence. The assay allows the calculation of the percent viability (percent of living Trypanosomes remaining in each well) at the end of a lysis relative to the untreated condition by interpolation of fluorescent values (FLU) on a standard curve with a known amount of seeded trypanosome/well.

Reagents and Materials

*Trypanosoma brucei brucei* (ATCC, Cat. No. PRA-382)
  Lister 427 VSG 221 bloodstream form.

| Thaw/Expansion Media (ATCC Medium 2834 Modified HMI-9 Medium) | | |
|---|---|---|
| IMDM | 250 mL | 76.3% |
| FBS | 25 mL | 7.63% |
| Serum Plus | 25 mL | 7.63% |
| HMI-9 | 25 mL | 7.63% |
| Hypoxanthine | 2.5 mL | 0.763% |
| 327.5 mL total | | |
| Assay Media (No Phenol Red/No FBS): Make on Day of Use | | |
| IMDM No Phenol Red | 250 mL | 82.6% |
| Serum Plus | 25 mL | 8.26% |
| HMI-9 | 25 mL | 8.26% |
| Hypoxanthine | 2.5 mL | 0.826% |
| 302.5 mL total | | |
| HMI-9 (10X) | | |
| Bathocuproine disulfonic acid | 280 mg | |
| Cysteine | 1820 mg | |
| Sodium pyruvate (100x) | 100 mL | |
| Uracil | 100 mg | |
| Cytosine | 100 mg | |
| 2-mercaptoethanol | 140 µL | |
| Water | 900 mL | |
| 1000 mL total | | |
| Hypoxanthine Stock (100x)-9 (10X) | | |
| Sodium Hydroxide | 0.8 g | |
| Hypoxanthine | 2.72 g | |
| Water | 200 mL | |
| 200 mL total | | |

TABLE 44

Media Reagents in *Trypanosoma brucei brucei* used in Lysis Assay

| | | |
|---|---|---|
| IMDM | Phenol Red sodium pyruvate L-glutamine 25 mM HEPES | Life Technologies, Cat. No. 12440 |
| IMDM | NO Phenol Red sodium pyruvate L-glutamine 25 mM HEPES | Life Technologies, Cat. No. 21056 |
| FBS | Heat inactivated | Sigma-Aldrich, Cat. No. F8317-500 mL |
| Serum Plus | medium supplement | Sigma-Aldrich, Cat. No. 14008C |
| Bathocuproine disulfonic acid | | Sigma-Aldrich, Cat. No. B1125-1G |
| Cysteine | | Sigma-Aldrich, Cat. No. C7352-25G |
| Sodium Pyruvate Solution | 100× | Sigma-Aldrich, Cat. No. S8636-100 ml |
| Uracil | | Sigma-Aldrich, Cat. No. U1128-25G |
| Cytosine | | Sigma-Aldrich, Cat. No. C3506-1G |
| 2-mercaptoethanol | | Sigma-Aldrich, Cat. No. M3148-25 ml |
| Hypoxanthine | | Sigma, Cat. No. H9636 |
| Sodium hydroxide | | Sigma-Aldrich, Cat. No. S8045-500G |

TABLE 45

*Materials used in Trypanosoma brucei brucei Lysis Assay*

| | | |
|---|---|---|
| T75/T175 | Nunc ™ Non-Treated flask Non-TC treated Vented/White lids with filter | T75 Thermo-Fisher Cat. No. 156800 T175 Thermo-Fisher Cat. No. 159926 |
| Assay Plates | 384 well black clear bottom Non-sterile Non-TC treated | Corning ® Cat. No. 3762 |
| Polypropylene storage plates | | Corning ® Cat. No. 3656 |
| Plate Lids | Clear universal sterile lids | Thermo-Fisher Cat. No. 250002 |
| Bravo Tips | 30 µL tips for 384 well | Axygen Cat. No. VT-384-31UL-R-S |
| E1-Clip Tip pipette 12 channel adjustable 2-125 µL | | Thermo-Fisher Cat. No. 4672070BT |
| Tips | 125 µL E1-Clip sterile filter | Thermo-Fisher Cat. No. 94420153 |
| Tips | 125 uL E1-Clip sterile (non-filter) | Thermo-Fisher Cat. No. 94410153 |

Equipment
  E1-Clip Tip pipette 12 channel adjustable 2-125 µL, Cat. No. 4672070BT
  ThermoFisher MultiDrop 384, Cat. No. 5840300
  Multidrop
  Agilent Bravo, Cat. No. G5409A
  Bravo
  SpectraMax M5
Assay Ready Plates (ARPs)
  ARPs comes in two formats:
    10 mM final top concentration with a 2.5 fold dilution down.
    5 mM final top concentration with a 3 fold dilution down.
      Both have a 10 point Dose response.
      0.1% DMSO final in the Black Assay Plate.
      Compounds are diluted 1000 fold in the Black Assay Plate.
      Each plate is designed for 14 compounds in duplicate.
  In the final Black Assay Plate:
    Column 1: Media only (no APOL1) (100% viable)
    Column 2-23: 0.05 µg/mL APOL1 (~$EC_{90}$) (10% viable with APOL1)
    Column 24: 0.1 µg/mL APOL1 ($EC_{100}$) (Approx. 0% viable)
Assay Procedures
*Trypanosoma brucei brucei* Culture
Protocol A
Step 1, Day 1
  Thaw the cells at 35° C. for no more than 2 minutes.
  Resuspend one vial gently in 20 mL pre-warmed media and incubate in a T75 flask at 37° C. and 5% $CO_2$.
  Do not remove the cryoprotective agent.
Step 2, Day 4
  Centrifuge at 800×g for 5 minutes at room temperature.
  Resuspend in 1 mL media.
  Make a 1:25 fold dilution (10 µL/240 µL media).
  Count on a hemocytometer (after adding parasites).
    Let sit for 1-2 minutes for the parasites to settle.
    Count should be approximately 100 viable motile parasites/16 grid or approximately $25 \times 10^6$ parasites/flask.
  Passage the parasites by adding $1 \times 10^6$ parasites/T75 flask in 20 mL media.
  Passage the parasites by adding $2.33 \times 10^6$ parasites/T175 flask in 46.6 mL media.
    For every T75 flask should make enough for approximately 1.5×384 well assay plates.
    For every T175 flask should make enough for approximately 3.8×384 well assay plates.
Step 3, Day 6
  Centrifuge at 800×g for 5 minutes.
    Resuspend in 3 mL assay media (No phenol red, no FBS) per 75 starting flask.
    Resuspend in 7 mL assay media (No phenol red, no FBS) per 175 flask
  Make a 1:25 fold dilution.
  Count by hemocytometer.
    Every T75 flask set up should have approximately $75 \times 10^6$ parasites/flask (verify doubling time=8.7 hours±1 hour).
    Every T175 flask set up should have approximately $175 \times 10^6$ parasites/flask (verify doubling time=8.7 hours±1 hour).
    Require $46 \times 10^6$ parasites per 384 well plate (at 120,000 parasites per well).
Protocol B
Step 1, Day 1
  Thaw the cells at 35° C. for not more than 2 minutes.
  Resuspend one vial gently in 20 mL of pre-warmed mediate and incubate in a T75 flask at 37° C. and 5% $CO_2$.
  Do not remove the cryoprotective agent.
Step 2, Day 2
  Centrifuge at 800×g for 5 minutes at room temperature.
  Resuspend in 1 mL media.
  Make a 1:25 fold dilution (10 µL/240 µL media).
    Let sit for 1-2 minutes for the parasites to settle.
    Count should be approximately 100 viable motile parasites/16 grid or approximately $8 \times 10^6$ parasites per flask.
  Passage the parasites by adding $1.25 \times 10^6$ parasites per T75 flask in 20 mL media.
    For every T75 flask set up should have approximately 1.5×384 well assay plates.
    For every T175 flask set up should have approximately 3.8×384 well assay plates.
Step 3, Day 5
  Centrifuge at 800×g for 5 minutes.
    Resuspend in 3 mL assay media (no phenol red, no FBS) per T75 starting flask.
    Resuspend in 7 mL assay media (no phenol red, no FBS) per T175 starting flask.
  Make a 1:25 fold dilution.
  Count by hemocytometer.
    Every T75 flask should have approximately $75 \times 10^6$ parasites per flask (verify doubling time: 7.7 hours±1 hour).
    Every T175 flask should have approximately $175 \times 10^6$ parasites per flask (verify doubling time: 7.7 hours±1 hour).
Lysis Assay Setup
APOL1 G1 Protein
  Remove an aliquot of the 1.2 mg/mL APOL1 protein stock from −70° C.
  Determine amount required for the experiment:
    Need 11.5 mL of 0.1 µg/mL APOL1 per 384 well plate.
    Need 0.5 mL of 0.2 µg/mL APOL1 per 384 well plate for control.
  Make initial 1:10 dilution (10 µL/90 µL) into Assay media (now at 120 µg/mL).

Using APOL1 at a final concentration of 0.05 μg/mL for an ~EC$_{50}$. Need to determine this value for each new lot of protein used.

Adding 30 mL/well of 2×APOL1 concentration of 0.1 μg/mL.

Solution A: Measure 8.33 μL (120 μg/mL) in 10 mL for a 0.1 μg/mL 2× stock.

Solution B: Measure 16.67 μL (120 μg/mL) in 10 mL for a 0.2 μg/mL 2× stock control.

Multidrop

Black Assay Plate (384 well black well clear bottom, Cat. No. 3762).

Column 1: Dispense 30 μL/well of Assay media (no APOL1).

Column 2-23: Dispense 30 μL/well of Solution A (0.1 μg/mL APOL1).

Column 24: Dispense 30 μL/well of Solution B (0.2 μg/mL APOL1).

Storage Plate (Polypropylene storage plate, Corning® Cat. No. 3656).

Column 1-24: Dispense 80 μL Assay media (no APOL1) per well (30 mL media/plate).

Bravo: Compound Transfer

Place the storage plate, the Assay Ready Plate (ARP), and Black Assay Plate on the deck.

Transfer 20 μL from the storage plate to the ARP and mix.

Transfer 6 μL from the ARP to the Black Assay Plate and mix.

Black Assay Plates are now ready for Trypanosome addition.

Trypanosome Addition:

Once the Black Assay Plates have compounds added, begin harvesting the Trypanosomes as described in Step 3 of the *Trypanosoma brucei brucei* Culture section.

Count the Trypanosomes and prepare at 5×10$^6$/mL in Assay media (no Phenol red and no FBS).

Requires 9.2 mL of 5×10$^6$ trypanosomes/mL for each 384 well plate (46×10$^6$/p late).

Add 24 μL of 5×10$^6$ trypanosomes mix to each well of a 384 well plate using the E1-Clip multichannel 12 channel 2-125 μL adjustable pipette.

Once addition is complete, tap plate on the surface to ensure liquid is within each well.

Place plates on the plate shaker for approximately 10 seconds and shake to ensure even distribution and that no drops are left on any edges.

Place in incubator overnight (16 hours) at 37° C. and 5% CO$_2$.

Each well should include 60 μL:

30 μL 2×APOL1 media, 6 μL of 10× compounds, and 24 μL of trypanosome solution.

AlamarBlue Addition

After 16 hours overnight in incubator, remove required amount of AlamarBlue (2.3 mL/plate) from the bottle stored in refrigerator, and warm up briefly in a 37° C. water bath.

Add 6 μL/well using the E1-Clip Multichannel 12 channel 2-125 μL adjustable pipette.

Protect from light and incubate the plate at 37° C. and 5% CO$_2$ for 2.5 hours.

Read on SpectraMax (Softmax Pro 6.4 software, excitation: 555 nm, emission: 585 nm)

Potency Data for Compounds 1 to 390

The compounds of Formula I are useful as inhibitors of APOL1 activity. Table 46 below illustrates the IC$_{50}$ of Compounds 1 to 390 using procedures described above. In Table 46 below, the following meanings apply. For IP$_{50}$ (i.e., IC$_{50}$ for cell proliferation) and IC$_{90}$: "+++" means≤50 nM; "C++" means between 50 nM and 500 nM; "+" means≥500 nM. N.D.=Not determined.

TABLE 46

Potency data for Compounds 1 to 390

| Compound No. | Multi-Tox Assay | | | Trypanosome Assay | |
|---|---|---|---|---|---|
| | IC$_{90}$ (nM) | IP$_{50}$ (nM) | Max Activity (%) | IP$_{50}$ (nM) | Max Activity (%) |
| 1 | +++ | +++ | 99.3 | +++ | 124.1 |
| 2 | +++ | +++ | 100.0 | +++ | 117.3 |
| 3 | +++ | +++ | 99.7 | +++ | 107.0 |
| 4 | +++ | +++ | 99.3 | +++ | 117.5 |
| 5 | ++ | ++ | 100.0 | ++ | 111.0 |
| 6 | +++ | +++ | 99.7 | +++ | 102.5 |
| 7 | ++ | ++ | 96.0 | + | 92.0 |
| 8 | +++ | +++ | 100.0 | ++ | 105.5 |
| 9 | ++ | +++ | 100.0 | ++ | 108.0 |
| 10 | +++ | +++ | 99.7 | ++ | 101.0 |
| 11 | +++ | +++ | 99.3 | +++ | 101.5 |
| 12 | +++ | +++ | 99.3 | +++ | 102.0 |
| 13 | +++ | +++ | 99.0 | +++ | 100.0 |
| 14 | ++ | +++ | 99.3 | +++ | 102.5 |
| 15 | +++ | +++ | 99.0 | +++ | 101.0 |
| 16 | ++ | +++ | 100.0 | ++ | 99.5 |
| 17 | +++ | +++ | 100.0 | ++ | 102.0 |
| 18 | +++ | +++ | 99.5 | ++ | 103.0 |
| 19 | +++ | +++ | 99.3 | +++ | 106.7 |
| 20 | +++ | +++ | 99.4 | +++ | 115.7 |
| 21 | +++ | +++ | 99.7 | +++ | 108.0 |
| 22 | +++ | +++ | 99.7 | +++ | 128.7 |
| 23 | +++ | +++ | 99.7 | +++ | 115.7 |
| 24 | +++ | +++ | 100.0 | +++ | 107.0 |
| 25 | +++ | +++ | 100.0 | +++ | 109.0 |
| 26 | +++ | +++ | 100.0 | +++ | 110.0 |
| 27 | +++ | +++ | 100.3 | +++ | 112.0 |
| 28 | +++ | +++ | 100.0 | +++ | 104.0 |
| 29 | +++ | +++ | 100.0 | +++ | 109.0 |
| 30 | +++ | +++ | 99.0 | +++ | 124.3 |
| 31 | +++ | +++ | 100.0 | +++ | 123.0 |
| 32 | +++ | +++ | 99.6 | +++ | 116.3 |
| 33 | +++ | +++ | 98.7 | +++ | 111.0 |
| 34 | +++ | +++ | 99.0 | +++ | 115.0 |
| 35 | +++ | +++ | 99.3 | +++ | 111.0 |
| 36 | +++ | +++ | 100.0 | +++ | 117.5 |
| 37 | +++ | +++ | 99.7 | +++ | 113.5 |
| 38 | +++ | +++ | 100.0 | +++ | 112.0 |
| 39 | +++ | +++ | 99.7 | +++ | 116.0 |
| 40 | +++ | +++ | 100.0 | +++ | 118.5 |
| 41 | +++ | +++ | 99.7 | +++ | 111.5 |
| 42 | +++ | +++ | 99.7 | +++ | 110.5 |
| 43 | +++ | +++ | 100.0 | +++ | 103.0 |
| 44 | +++ | +++ | 99.5 | +++ | 105.5 |
| 45 | +++ | +++ | 100.0 | +++ | 103.3 |
| 46 | +++ | +++ | 99.0 | +++ | 107.7 |
| 47 | +++ | +++ | 99.3 | +++ | 100.5 |
| 48 | +++ | +++ | 99.0 | +++ | 101.5 |
| 49 | +++ | +++ | 99.7 | +++ | 103.5 |
| 50 | +++ | +++ | 99.7 | +++ | 103.0 |
| 51 | +++ | +++ | 99.7 | +++ | 102.5 |
| 52 | +++ | +++ | 99.7 | +++ | 103.5 |
| 53 | +++ | +++ | 99.3 | ++ | 106.0 |
| 54 | +++ | +++ | 100.0 | +++ | 102.5 |
| 55 | +++ | +++ | 99.7 | +++ | 111.5 |
| 56 | +++ | +++ | 99.8 | +++ | 115.7 |
| 57 | +++ | +++ | 99.7 | +++ | 105.0 |
| 58 | +++ | +++ | 99.7 | +++ | 100.5 |
| 59 | +++ | +++ | 99.3 | +++ | 116.5 |
| 60 | +++ | +++ | 99.7 | +++ | 102.5 |
| 61 | +++ | +++ | 99.7 | +++ | 105.0 |
| 62 | +++ | +++ | 99.3 | +++ | 95.0 |
| 63 | +++ | +++ | 99.8 | +++ | 104.0 |
| 64 | +++ | +++ | 100.0 | +++ | 101.0 |
| 65 | +++ | +++ | 99.5 | +++ | 105.3 |
| 66 | +++ | +++ | 99.8 | +++ | 102.7 |
| 67 | +++ | +++ | 99.7 | +++ | 105.0 |

TABLE 46-continued

Potency data for Compounds 1 to 390

| Compound No. | Multi-Tox Assay IC$_{90}$ (nM) | IP$_{50}$ (nM) | Max Activity (%) | Trypanosome Assay IP$_{50}$ (nM) | Max Activity (%) |
|---|---|---|---|---|---|
| 68 | +++ | +++ | 99.7 | +++ | 105.5 |
| 69 | +++ | +++ | 99.7 | +++ | 110.0 |
| 70 | +++ | +++ | 99.3 | +++ | 104.0 |
| 71 | +++ | +++ | 100.0 | +++ | 103.5 |
| 72 | +++ | +++ | 99.7 | +++ | 118.3 |
| 73 | +++ | +++ | 99.8 | +++ | 110.3 |
| 74 | +++ | +++ | 99.2 | ++ | 109.7 |
| 75 | +++ | +++ | 100.0 | +++ | 105.0 |
| 76 | +++ | +++ | 99.3 | +++ | 105.5 |
| 77 | +++ | +++ | 99.0 | +++ | 110.0 |
| 78 | +++ | +++ | 99.7 | +++ | 102.5 |
| 79 | ++ | +++ | 99.7 | +++ | 97.5 |
| 80 | +++ | +++ | 99.7 | +++ | 100.5 |
| 81 | +++ | +++ | 99.7 | +++ | 100.7 |
| 82 | +++ | +++ | 99.7 | +++ | 106.3 |
| 83 | +++ | +++ | 99.0 | +++ | 111.0 |
| 84 | +++ | +++ | 99.8 | +++ | 112.3 |
| 85 | +++ | +++ | 99.3 | +++ | 99.5 |
| 86 | +++ | +++ | 99.5 | +++ | 112.0 |
| 87 | +++ | +++ | 99.3 | +++ | 100.0 |
| 88 | +++ | +++ | 99.3 | +++ | 98.0 |
| 89 | +++ | +++ | 99.3 | +++ | 101.0 |
| 90 | +++ | +++ | 100.0 | +++ | 104.5 |
| 91 | +++ | +++ | 100.0 | +++ | 109.5 |
| 92 | +++ | +++ | 100.0 | +++ | 103.0 |
| 93 | +++ | +++ | 99.3 | ++ | 112.0 |
| 94 | +++ | +++ | 100.0 | +++ | 104.0 |
| 95 | +++ | +++ | 99.8 | ++ | 106.3 |
| 96 | +++ | +++ | 99.8 | +++ | 104.0 |
| 97 | +++ | +++ | 99.0 | +++ | 104.5 |
| 98 | +++ | +++ | 99.0 | +++ | 110.5 |
| 99 | +++ | +++ | 99.0 | +++ | 102.0 |
| 100 | +++ | +++ | 99.3 | +++ | 99.0 |
| 101 | +++ | +++ | 100.0 | ++ | 114.3 |
| 102 | +++ | +++ | 99.8 | +++ | 112.0 |
| 103 | +++ | +++ | 99.6 | ++ | 117.7 |
| 104 | ++ | +++ | 99.3 | ++ | 100.5 |
| 105 | ++ | +++ | 99.3 | +++ | 72.0 |
| 106 | +++ | +++ | 99.7 | +++ | 107.0 |
| 107 | +++ | +++ | 99.7 | +++ | 92.5 |
| 108 | ++ | +++ | 99.0 | +++ | 94.5 |
| 109 | ++ | +++ | 100.0 | ++ | 100.0 |
| 110 | ++ | +++ | 99.2 | ++ | 115.0 |
| 111 | ++ | +++ | 99.3 | ++ | 98.5 |
| 112 | +++ | +++ | 100.0 | ++ | 112.0 |
| 113 | ++ | +++ | 100.0 | ++ | 97.0 |
| 114 | ++ | +++ | 99.7 | ++ | 95.0 |
| 115 | ++ | +++ | 99.3 | ++ | 100.0 |
| 116 | ++ | +++ | 99.4 | ++ | 100.7 |
| 117 | ++ | +++ | 99.0 | +++ | 100.7 |
| 118 | ++ | +++ | 99.3 | ++ | 98.0 |
| 119 | ++ | +++ | 99.7 | ++ | 97.5 |
| 120 | ++ | +++ | 99.0 | ++ | 91.5 |
| 121 | ++ | +++ | 99.0 | ++ | 97.5 |
| 122 | ++ | +++ | 99.7 | ++ | 105.5 |
| 123 | ++ | +++ | 100.0 | +++ | 103.5 |
| 124 | ++ | ++ | 99.3 | ++ | 103.5 |
| 125 | ++ | +++ | 99.7 | ++ | 103.0 |
| 126 | ++ | ++ | 99.4 | ++ | 114.7 |
| 127 | ++ | ++ | 99.3 | ++ | 107.0 |
| 128 | ++ | ++ | 99.3 | ++ | 107.0 |
| 129 | ++ | ++ | 100.0 | +++ | 88.0 |
| 130 | ++ | ++ | 99.0 | ++ | 101.5 |
| 131 | ++ | ++ | 99.3 | ++ | 111.0 |
| 132 | ++ | ++ | 99.3 | ++ | 91.5 |
| 133 | ++ | ++ | 99.7 | ++ | 111.0 |
| 134 | ++ | ++ | 99.2 | ++ | 96.7 |
| 135 | ++ | ++ | 98.0 | ++ | 94.0 |
| 136 | ++ | ++ | 98.7 | ++ | 100.3 |
| 137 | ++ | ++ | 98.7 | ++ | 84.5 |
| 138 | ++ | ++ | 98.0 | ++ | 104.5 |
| 139 | ++ | ++ | 98.0 | + | 98.3 |
| 140 | ++ | ++ | 99.7 | ++ | 101.5 |
| 141 | ++ | ++ | 96.3 | ++ | 90.0 |
| 142 | ++ | ++ | 99.0 | ++ | 83.7 |
| 143 | ++ | ++ | 98.0 | ++ | 101.0 |
| 144 | + | ++ | 98.0 | ++ | 101.5 |
| 145 | + | ++ | 97.7 | ++ | 88.0 |
| 146 | ++ | ++ | 97.0 | ++ | 88.0 |
| 147 | + | ++ | 92.3 | ++ | 93.5 |
| 148 | ++ | ++ | 97.0 | ++ | 92.5 |
| 149 | + | ++ | 95.7 | + | 95.0 |
| 150 | + | ++ | 96.3 | + | 87.0 |
| 151 | + | ++ | 96.2 | + | 85.7 |
| 152 | + | ++ | 98.0 | + | 92.7 |
| 153 | + | ++ | 96.0 | + | 89.5 |
| 154 | + | + | 94.0 | + | 96.5 |
| 155 | + | ++ | 95.2 | + | 97.0 |
| 156 | + | + | 93.0 | + | 85.0 |
| 157 | + | ++ | 96.3 | + | 95.0 |
| 158 | + | + | 90.4 | + | 75.5 |
| 159 | + | + | 92.2 | + | 63.5 |
| 160 | + | + | 94.3 | + | 97.5 |
| 161 | + | + | 92.4 | + | 73.0 |
| 162 | + | + | 92.0 | + | 81.0 |
| 163 | + | + | 92.7 | + | 79.5 |
| 164 | + | + | 91.7 | + | 85.0 |
| 165 | + | + | 92.0 | + | 61.0 |
| 166 | + | + | 96.7 | + | 57.5 |
| 167 | + | + | 89.7 | + | 73.0 |
| 168 | + | + | 89.0 | + | 54.5 |
| 169 | + | + | 86.8 | + | 61.0 |
| 170 | + | + | 89.7 | + | 71.5 |
| 171 | + | + | 71.8 | + | 14.0 |
| 172 | + | + | 52.0 | + | 64.5 |
| 173 | +++ | +++ | 99.5 | +++ | 116.0 |
| 174 | +++ | +++ | 99.8 | +++ | 104.2 |
| 175 | +++ | +++ | 100.0 | +++ | 105.5 |
| 176 | +++ | +++ | 100.0 | +++ | 115.5 |
| 177 | +++ | +++ | 100.0 | ++ | 107.3 |
| 178 | +++ | +++ | 99.7 | +++ | 101.0 |
| 179 | +++ | +++ | 99.0 | +++ | 119.5 |
| 180 | +++ | +++ | 99.8 | +++ | 102.5 |
| 181 | +++ | +++ | 99.8 | +++ | 101.9 |
| 182 | +++ | +++ | 100.0 | +++ | 113.0 |
| 183 | +++ | +++ | 99.5 | ++ | 105.5 |
| 184 | ++ | +++ | 99.3 | ++ | 100.5 |
| 185 | +++ | +++ | 99.5 | ++ | 99.0 |
| 186 | ++ | +++ | 99.3 | ++ | 104.0 |
| 187 | +++ | +++ | 100.0 | ++ | 106.5 |
| 188 | ++ | ++ | 99.0 | ++ | 108.0 |
| 189 | + | ++ | 97.0 | + | 87.5 |
| 190 | ++ | ++ | 99.0 | + | 92.5 |
| 191 | ++ | ++ | 99.7 | ++ | 108.0 |
| 192 | ++ | ++ | 99.0 | ++ | 100.5 |
| 193 | ++ | ++ | 99.0 | ++ | 100.5 |
| 194 | ++ | ++ | 98.7 | ++ | 117.3 |
| 195 | + | + | 76.0 | + | 50.7 |
| 196 | ++ | ++ | 99.0 | ++ | 111.0 |
| 197 | ++ | ++ | 99.0 | ++ | 106.5 |
| 198 | ++ | ++ | 98.7 | ++ | 99.3 |
| 199 | ++ | +++ | 99.3 | ++ | 110.3 |
| 200 | + | ++ | 97.0 | ++ | 98.7 |
| 201 | + | ++ | 95.0 | + | 76.7 |
| 202 | + | + | 94.7 | + | 19.0 |
| 203 | +++ | +++ | 99.3 | +++ | 102.3 |
| 204 | ++ | ++ | 99.0 | ++ | 112.0 |
| 205 | ++ | +++ | 99.3 | ++ | 105.7 |
| 206 | ++ | +++ | 99.3 | ++ | 104.0 |
| 207 | ++ | +++ | 100.0 | +++ | 108.0 |
| 208 | ++ | +++ | 99.5 | ++ | 103.5 |
| 209 | + | + | 76.7 | ++ | 100.3 |
| 210 | + | + | 92.2 | + | 103.5 |
| 211 | ++ | +++ | 99.6 | ++ | 113.3 |
| 212 | +++ | +++ | 99.0 | +++ | 101.3 |
| 213 | ++ | ++ | 99.5 | ++ | 98.7 |

TABLE 46-continued

Potency data for Compounds 1 to 390

| Compound No. | Multi-Tox Assay | | | Trypanosome Assay | |
|---|---|---|---|---|---|
| | $IC_{90}$ (nM) | $IP_{50}$ (nM) | Max Activity (%) | $IP_{50}$ (nM) | Max Activity (%) |
| 214 | ++ | +++ | 99.3 | ++ | 108.7 |
| 215 | ++ | +++ | 99.3 | ++ | 112.5 |
| 216 | + | ++ | 97.7 | ++ | 103.7 |
| 217 | +++ | +++ | 99.2 | +++ | 110.4 |
| 218 | ++ | +++ | 99.3 | ++ | 111.0 |
| 219 | + | + | 88.7 | + | 71.0 |
| 220 | +++ | +++ | 99.3 | +++ | 110.0 |
| 221 | ++ | +++ | 99.0 | | |
| 222 | ++ | ++ | 100.0 | | |
| 223 | + | + | 93.0 | | |
| 224 | ++ | ++ | 99.0 | | |
| 225 | ++ | ++ | 97.0 | | |
| 226 | ++ | ++ | 100.0 | | |
| 227 | ++ | ++ | 100.0 | | |
| 228 | ++ | ++ | 100.0 | | |
| 229 | ++ | ++ | 98.0 | | |
| 230 | + | ++ | 98.0 | | |
| 231 | ++ | ++ | 95.0 | | |
| 232 | ++ | +++ | 100.0 | | |
| 233 | ++ | ++ | 100.0 | | |
| 234 | ++ | +++ | 100.0 | | |
| 235 | ++ | +++ | 100.0 | | |
| 236 | ++ | +++ | 100.0 | | |
| 237 | ++ | +++ | 99.0 | | |
| 238 | ++ | ++ | 100 | | |
| 239 | ++ | ++ | 97.0 | | |
| 240 | + | ++ | 95.0 | | |
| 241 | ++ | +++ | 97.0 | | |
| 242 | ++ | ++ | 97.0 | | |
| 243 | ++ | ++ | 98.0 | | |
| 244 | ++ | ++ | 100.0 | | |
| 245 | ++ | +++ | 99.0 | | |
| 246 | ++ | ++ | 97.0 | | |
| 247 | + | ++ | 91.0 | | |
| 248 | ++ | +++ | 101.0 | | |
| 249 | + | ++ | 92.0 | | |
| 250 | ++ | +++ | 95.0 | | |
| 251 | ++ | ++ | 99.0 | | |
| 252 | ++ | +++ | 100.0 | | |
| 253 | ++ | +++ | 100.0 | | |
| 254 | + | + | 92.0 | | |
| 255 | ++ | ++ | 100.0 | | |
| 256 | ++ | ++ | 96.0 | | |
| 257 | ++ | +++ | 101.0 | | |
| 258 | + | ++ | 98.0 | | |
| 259 | ++ | ++ | 100.0 | | |
| 260 | ++ | +++ | 99.0 | | |
| 261 | ++ | ++ | 100.0 | | |
| 262 | ++ | ++ | 99.0 | | |
| 263 | + | + | 86.0 | | |
| 264 | ++ | +++ | 100.0 | | |
| 265 | ++ | ++ | 99.0 | | |
| 266 | ++ | +++ | 100.0 | | |
| 267 | ++ | ++ | 99.0 | | |
| 268 | ++ | ++ | 99.0 | | |
| 269 | ++ | ++ | 99.0 | | |
| 270 | + | ++ | 93.0 | | |
| 271 | ++ | +++ | 97.0 | | |
| 272 | + | ++ | 95.0 | | |
| 273 | ++ | +++ | 101.0 | | |
| 274 | ++ | ++ | 97.0 | | |
| 275 | + | ++ | 94.0 | | |
| 276 | ++ | ++ | 100.0 | | |
| 277 | ++ | +++ | 100.0 | | |
| 278 | ++ | +++ | 100.0 | | |
| 279 | ++ | ++ | 97.0 | | |
| 280 | ++ | ++ | 99.0 | | |
| 281 | ++ | ++ | 99.0 | | |
| 282 | ++ | +++ | 99.0 | | |
| 283 | ++ | ++ | 101.0 | | |
| 284 | ++ | ++ | 101.0 | | |
| 285 | ++ | ++ | 98.0 | | |
| 286 | ++ | +++ | 98.0 | | |
| 287 | ++ | ++ | 96.0 | | |
| 288 | ++ | ++ | 97.0 | | |
| 289 | + | + | 83.0 | | |
| 290 | ++ | ++ | 99.0 | | |
| 291 | ++ | ++ | 100.0 | | |
| 292 | ++ | ++ | 99.0 | | |
| 293 | +++ | +++ | 100.0 | | |
| 294 | ++ | ++ | 100.0 | | |
| 295 | ++ | +++ | 99.0 | | |
| 296 | ++ | ++ | 99.0 | | |
| 297 | ++ | +++ | 99.0 | | |
| 298 | + | ++ | 95.0 | | |
| 299 | ++ | +++ | 99.0 | | |
| 300 | ++ | ++ | 100.0 | | |
| 301 | +++ | +++ | 99.0 | | |
| 302 | ++ | ++ | 94.0 | | |
| 303 | ++ | ++ | 99.0 | | |
| 304 | ++ | ++ | 99.0 | | |
| 305 | ++ | +++ | 100.0 | | |
| 306 | + | + | 99.0 | | |
| 307 | ++ | +++ | 99.0 | | |
| 308 | + | ++ | 95.0 | | |
| 309 | ++ | ++ | 97.0 | | |
| 310 | + | ++ | 94.0 | | |
| 311 | ++ | +++ | 99.0 | | |
| 312 | + | + | 91.0 | | |
| 313 | ++ | ++ | 98.0 | | |
| 314 | +++ | +++ | 99.0 | | |
| 315 | ++ | ++ | 98.0 | | |
| 316 | + | ++ | 95.0 | | |
| 317 | ++ | ++ | 98.0 | | |
| 318 | +++ | +++ | 99.0 | | |
| 319 | ++ | ++ | 95.0 | | |
| 320 | + | ++ | 95.0 | | |
| 321 | ++ | +++ | 99.0 | | |
| 322 | ++ | ++ | 97.0 | | |
| 323 | ++ | +++ | 100.0 | | |
| 324 | + | ++ | 96.0 | | |
| 325 | ++ | +++ | 98.0 | | |
| 326 | ++ | ++ | 97.0 | | |
| 327 | ++ | +++ | 98.0 | | |
| 328 | ++ | +++ | 100.0 | | |
| 329 | + | + | 90.0 | | |
| 330 | ++ | +++ | 99.0 | | |
| 331 | ++ | +++ | 98.0 | | |
| 332 | ++ | ++ | 96.0 | | |
| 333 | ++ | ++ | 97.0 | | |
| 334 | + | ++ | 96.0 | | |
| 335 | + | ++ | 96.0 | | |
| 336 | ++ | +++ | 99.0 | | |
| 337 | ++ | +++ | 99.0 | | |
| 338 | +++ | +++ | 99.0 | | |
| 339 | ++ | ++ | 97.0 | | |
| 340 | ++ | ++ | 98.0 | | |
| 341 | + | ++ | 98.0 | | |
| 342 | ++ | ++ | 98.0 | | |
| 343 | ++ | ++ | 97.0 | | |
| 344 | ++ | +++ | 99.0 | | |
| 345 | ++ | +++ | 99.0 | | |
| 346 | ++ | ++ | 99.0 | | |
| 347 | ++ | ++ | 96.0 | | |
| 348 | + | ++ | 97.0 | | |
| 349 | + | ++ | 91.0 | | |
| 350 | ++ | +++ | 99.0 | | |
| 351 | ++ | +++ | 98.0 | | |
| 352 | ++ | +++ | 99.0 | | |
| 353 | +++ | +++ | 100.0 | | |
| 354 | ++ | ++ | 99.0 | | |
| 355 | ++ | ++ | 98.0 | | |
| 356 | ++ | ++ | 99.0 | | |
| 357 | ++ | ++ | 99.0 | | |
| 358 | +++ | +++ | 98.0 | | |
| 359 | +++ | +++ | 98.0 | | |

TABLE 46-continued

Potency data for Compounds 1 to 390

| Compound No. | Multi-Tox Assay | | | Trypanosome Assay | |
|---|---|---|---|---|---|
| | IC$_{90}$ (nM) | IP$_{50}$ (nM) | Max Activity (%) | IP$_{50}$ (nM) | Max Activity (%) |
| 360 | ++ | ++ | 99.0 | | |
| 361 | ++ | +++ | 98.0 | | |
| 362 | ++ | ++ | 98.0 | | |
| 363 | ++ | +++ | 99.0 | | |
| 364 | + | ++ | 95.0 | | |
| 365 | ++ | +++ | 99.0 | | |
| 366 | + | ++ | 95.0 | | |
| 367 | +++ | +++ | 99.0 | | |
| 368 | + | ++ | 96.0 | | |
| 369 | + | ++ | 98.0 | | |
| 370 | ++ | ++ | 99.0 | | |
| 371 | ++ | +++ | 99.0 | | |
| 372 | + | + | 92.0 | | |
| 373 | ++ | +++ | 99.0 | | |
| 374 | ++ | +++ | 99.0 | | |
| 375 | ++ | +++ | 99.0 | | |
| 376 | ++ | ++ | 99.0 | | |
| 377 | + | ++ | 98.0 | | |
| 378 | ++ | +++ | 99.0 | | |
| 379 | + | + | 94.0 | | |
| 380 | ++ | +++ | 99.0 | | |
| 381 | +++ | +++ | 100.0 | | |
| 382 | ++ | +++ | 100.0 | | |
| 383 | +++ | +++ | 100.0 | | |
| 384 | +++ | +++ | 100.0 | | |
| 385 | +++ | +++ | 100.0 | +++ | 103.5 |
| 386 | +++ | +++ | 100.0 | | |
| 387 | + | + | 94.0 | | |
| 388 | + | + | 90.0 | | |
| 389 | + | ++ | 99.0 | | |
| 390 | +++ | +++ | 99.0 | | |

Other Embodiments

This disclosure provides merely exemplary embodiments of the disclosed subject matter. One skilled in the art will readily recognize from the disclosure and claims, that various changes, modifications and variations can be made therein without departing from the spirit and scope of the disclosure as defined in the following claims.

The invention claimed is:

1. A compound represented by:

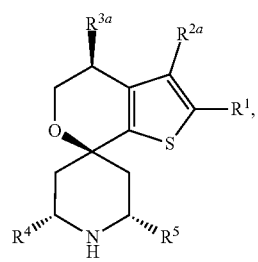

(Formula IIa″)

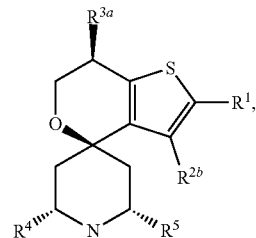

(Formula IIb″)

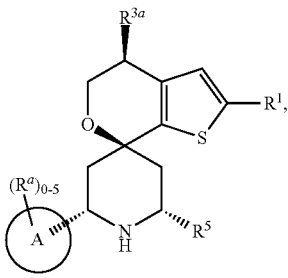

(Formula IIIa″)

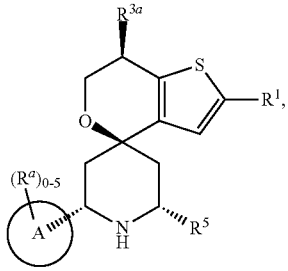

(Formula IIIb″)

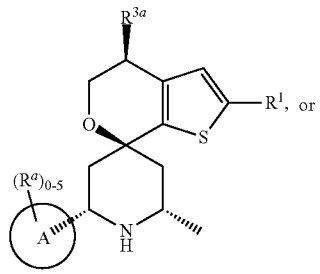

(Formula IVa″)

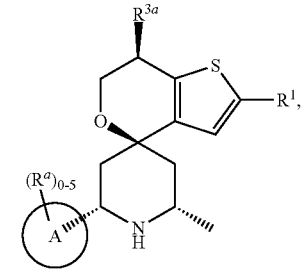

(Formula IVb″)

a tautomer thereof, a deuterated derivative of that compound or tautomer, or a pharmaceutically acceptable salt of any of the foregoing, wherein:

$R^1$ is selected from hydrogen, halogen, cyano, —OH, $C_1$-$C_6$ alkyl, $C_1$-$C_6$ alkoxy, $C_3$-$C_6$ cycloalkyl, and phenyl, wherein:

the $C_1$-$C_6$ alkyl of $R^1$ is optionally substituted with 1 to 3 groups independently selected from halogen, cyano, —OH, —NH$_2$, —NH($C_1$-$C_4$ alkyl), —N($C_1$-$C_4$ alkyl)$_2$, and $C_1$-$C_4$ alkoxy;

the $C_1$-$C_6$ alkoxy of $R^1$ is optionally substituted with 1 to 3 groups independently selected from halogen;

the $C_3$-$C_6$ cycloalkyl of $R^1$ is optionally substituted with 1 to 3 groups independently selected from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$; and the phenyl of $R^1$ is optionally substituted with 1 to 3 groups independently selected from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$;

$R^{2a}$ is selected from hydrogen, halogen, cyano, —OH, =O, and $C_1$-$C_6$ alkyl, wherein:
the $C_1$-$C_6$ alkyl of $R^{2a}$ is optionally substituted with 1 to 3 groups independently selected from halogen, cyano, —OH, and $C_1$-$C_4$ alkoxy;

$R^{2b}$ is selected from hydrogen, halogen, cyano, —OH, =O, and $C_1$-$C_6$ alkyl;

$R^{3a}$ is selected from halogen, cyano, —OH, $C_1$-$C_6$ alkyl, and =O; wherein:
the $C_1$-$C_6$ alkyl of $R^{3a}$ is optionally substituted with 1 to 3 groups independently selected from halogen, cyano, and —OH;

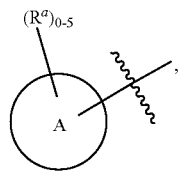

$R^4$ is selected from $C_1$-$C_6$ alkyl, —C(=O)O($C_1$-$C_4$ alkyl), $C_2$-$C_6$ alkynyl, and wherein:
the $C_1$-$C_6$ alkyl of $R^4$ is optionally substituted with 1 to 3 groups independently selected from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), —C(=O)N($C_1$-$C_4$ alkyl)$_2$, $C_3$-$C_6$ cycloalkyl, 5 to 10-membered heterocyclyl, phenyl, and 5 to 10-membered heteroaryl;

Ring A is selected from $C_3$-$C_{12}$ carbocyclyl, 3 to 12-membered heterocyclyl, $C_6$ and $C_{10}$ aryl, and 5 to 10-membered heteroaryl, wherein Ring A is optionally substituted with 1, 2, 3, 4, or 5 $R^a$ groups; wherein:
$R^a$, for each occurrence, is independently selected from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —[O(CH$_2$)$_q$]$_r$O($C_1$-$C_6$ alkyl), —S(=O)$_p$R$^k$, —S(=O)$_p$NR$^h$R$^i$, —C(=O)OR$^k$, $C_3$-$C_{12}$ carbocyclyl, 3- to 12-membered heterocyclyl, $C_6$ and $C_{10}$ aryl, and 5- to 10-membered heteroaryl; wherein:
the $C_1$-$C_6$ alkyl, $C_1$-$C_6$ alkoxy, and the $C_2$-$C_6$ alkenyl of $R^a$ are each optionally substituted with 1 to 3 groups independently selected from $C_6$ to $C_{10}$ aryl (optionally substituted with 1 to 3 $R^m$ groups), 5- to 10-membered heterocyclyl (optionally substituted with 1 to 3 $R^m$ groups), 5- to 10-membered heteroaryl (optionally substituted with 1 to 3 $R^m$ groups), cyano, —C(=O)R$^k$, —C(=O)OR$^k$, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —S(=O)$_p$R$^k$, —S(=O)$_p$NR$^h$R$^i$, and $C_3$-$C_6$ carbocyclyl (optionally substituted with 1 to 3 $R^m$ groups);

the $C_3$-$C_{12}$ carbocyclyl, the 3 to 12-membered heterocyclyl, the $C_6$ and $C_{10}$ aryl, and the 5 to 10-membered heteroaryl of $R^a$ are each optionally substituted with 1 to 3 groups independently selected from halogen, cyano, $C_1$-$C_4$ alkyl, —NR$^h$R$^i$, and —OR$^k$; wherein:
R$^h$, R$^i$, and R$^j$, for each occurrence, are each independently selected from hydrogen, $C_1$-$C_4$ alkyl, $C_6$-$C_{10}$ aryl, and $C_3$-$C_6$ cycloalkyl; wherein:
the $C_1$-$C_4$ alkyl of any one of R$^h$, R$^i$, and R$^j$ is optionally substituted with 1 to 3 groups independently selected from halogen, cyano, and —OH;

R$^k$, for each occurrence, are each independently selected from hydrogen, $C_1$-$C_4$ alkyl, 5- to 10-membered heterocyclyl, and $C_3$-$C_6$ carbocyclyl; wherein:
the $C_1$-$C_4$ alkyl of any one of R$^k$ is optionally substituted with 1 to 3 groups independently selected from halogen, cyano, and —OH;

R$^m$, for each occurrence, is independently selected from halogen, cyano, oxo, $C_1$-$C_6$ alkyl, $C_1$-$C_6$ alkoxy, —S(=O)$_p$R$^k$, and —OR$^k$; wherein:
the $C_1$-$C_6$ alkyl of R$^m$ is optionally substituted with 1 to 3 groups independently selected from halogen, cyano, and —OH;

$R^5$ is selected from $C_1$-$C_6$ alkyl, —C(=O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl; wherein:
the $C_1$-$C_6$ alkyl of $R^5$ is optionally substituted with 1 to 3 groups independently selected from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), and —C(=O)N($C_1$-$C_4$ alkyl)$_2$;

the $C_3$-$C_{12}$ carbocyclyl, the 3 to 12-membered heterocyclyl, the $C_6$ and $C_{10}$ aryl, and the 5 to 10-membered heteroaryl of $R^5$ are each optionally substituted with 1 to 3 groups independently selected from halogen, cyano, —OH, —NH$_2$, —NH($C_1$-$C_4$ alkyl) (optionally substituted with —OH), —N($C_1$-$C_4$ alkyl)$_2$, $C_1$-$C_5$ alkyl (optionally substituted with —OH), $C_1$-$C_4$ alkoxy, —C(=O)NH$_2$, —C(=O)NH($C_1$-$C_4$ alkyl), —NHC(=O)($C_1$-$C_4$ alkyl), —C(=O)($C_1$-$C_4$ alkoxy), and —C(=O)N($C_1$-$C_4$ alkyl)$_2$;

p is an integer selected from 1 and 2; and q and r are each an integer selected from 1, 2, 3, and 4.

2. The compound, tautomer, deuterated derivative, or pharmaceutically acceptable salt according to claim 1, wherein Ring A is selected from

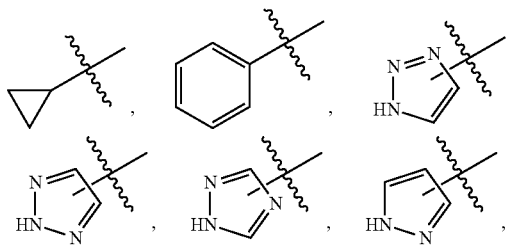

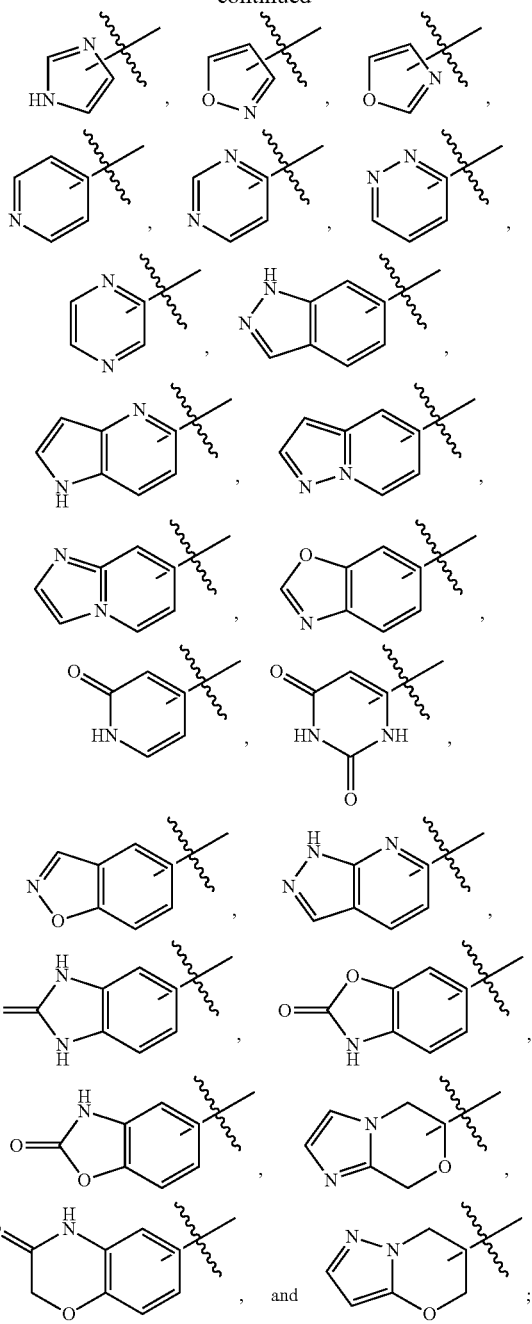

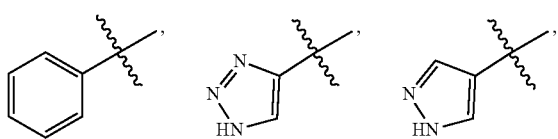

each of which is optionally substituted with 1, 2, 3, 4, or 5 $R^a$ groups.

3. The compound, tautomer, deuterated derivative, or pharmaceutically acceptable salt according to claim 1, wherein $R^4$ is selected from —$CH_3$ and Ring A; wherein Ring A is selected from

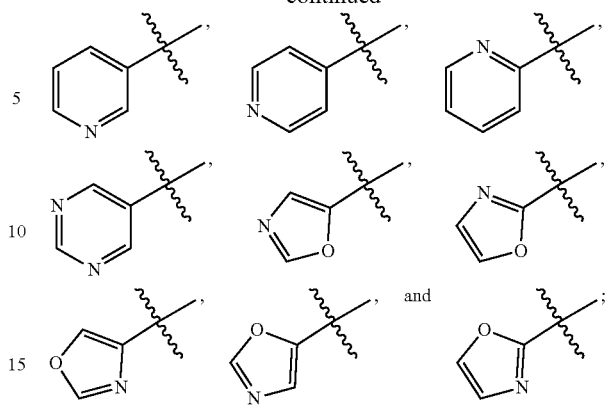

each of which is optionally substituted with 1, 2, 3, 4, or 5 $R^a$ groups.

4. The compound, tautomer, deuterated derivative, or pharmaceutically acceptable salt according to claim 1, wherein Ring A is selected from

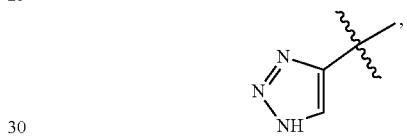

which is optionally substituted with 1 or 2 $R^a$ groups.

5. The compound, tautomer, deuterated derivative, or pharmaceutically acceptable salt according to claim 1, wherein $R^a$, for each occurrence, is independently selected from F, cyano, —OH, —$CH_3$, —$CF_3$, —$CH(CH_3)_2$, —$(CH_2)_2OH$, —$(CH_2)_2OCH_3$, —$CH_2CH(OH)C_2H_5$, —$CH_2C(CH_3)(CH_2OH)_2$, —$OCH_3$, —$OCH_2CH_3$, [O$(CH_2)_2]_2OCH_3$, —$CH_2C(=O)NHCH_3$, —$(CH_2)_2SO_2CH_3$, —$CH_2C(=O)N(CH_3)_2$, —$CH_2$(cyclopropyl), —C(=O)$NH_2$, —C(=O)NH(cyclopropyl), —$NH_2$, —$NHCH_3$, —$N(CH_3)_2$, —$NHC(CH_3)_2CH_2OH$, —NHC(=O)$CH_3$, —$SO_2CH_3$, —$SO_2NH_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide.

6. The compound, tautomer, deuterated derivative, or pharmaceutically acceptable salt according to claim 1, wherein $R^a$, for each occurrence, is $C_1$-$C_6$ alkyl.

7. The compound, tautomer, deuterated derivative, or pharmaceutically acceptable salt according to claim 1, wherein $R^1$ is selected from Cl, Br, —$CH_3$, —$CF_3$, —$CH_2CH_3$, —$CH(CH_3)_2$, —$CH_2CHF_2$, —$CH_2CH(CH_3)_2$, difluorocyclobutyl, and cyclohexyl.

8. The compound, tautomer, deuterated derivative, or pharmaceutically acceptable salt according to claim 1, wherein $R^1$ is Cl or $CF_3$.

9. The compound, tautomer, deuterated derivative, or pharmaceutically acceptable salt according to claim 1, wherein $R^{3a}$ is selected from F, —OH, —$CH_3$, —$CHF_2$, and $CH_2OH$.

10. The compound, tautomer, deuterated derivative, or pharmaceutically acceptable salt according to claim 1, wherein $R^{3a}$ is —OH.

11. The compound, tautomer, deuterated derivative, or pharmaceutically acceptable salt according to claim 1, wherein $R^5$ is selected from —$CH_3$, —$CH_2CH_3$, —$CH_2OH$, —C(=O)OCH₃, —CH₂OCH₃, —CH(CH₃)₂, cyclopropyl, difluorocyclopropyl, and tetrahydro-2H-pyranyl.
12. The compound, tautomer, deuterated derivative, or pharmaceutically acceptable salt according to claim 1, wherein the compound is selected from:
1
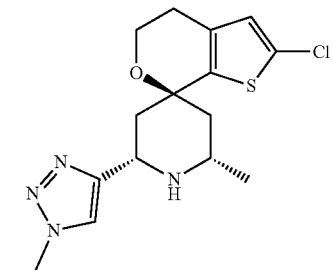
2
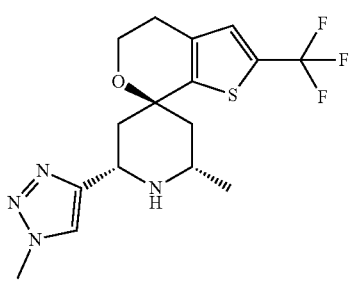
3
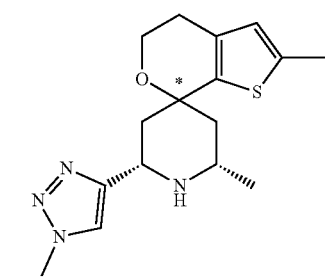
4
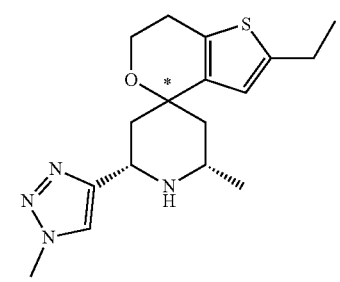
6
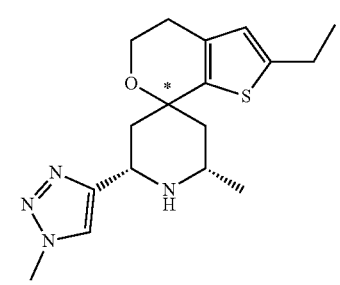
8
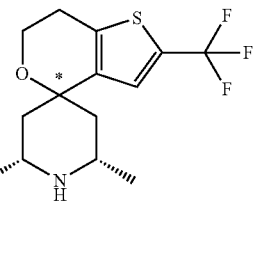
10
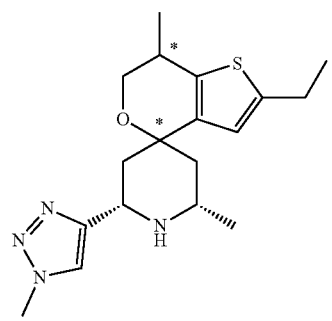
11
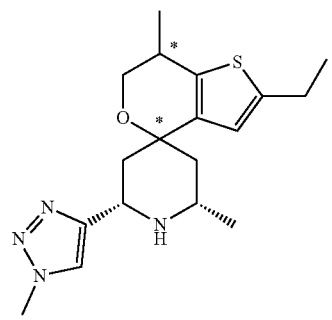
12
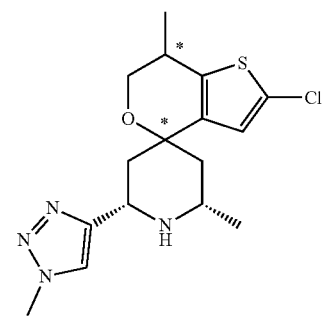
13
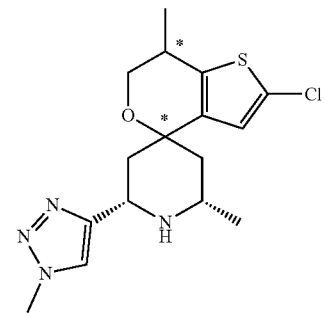

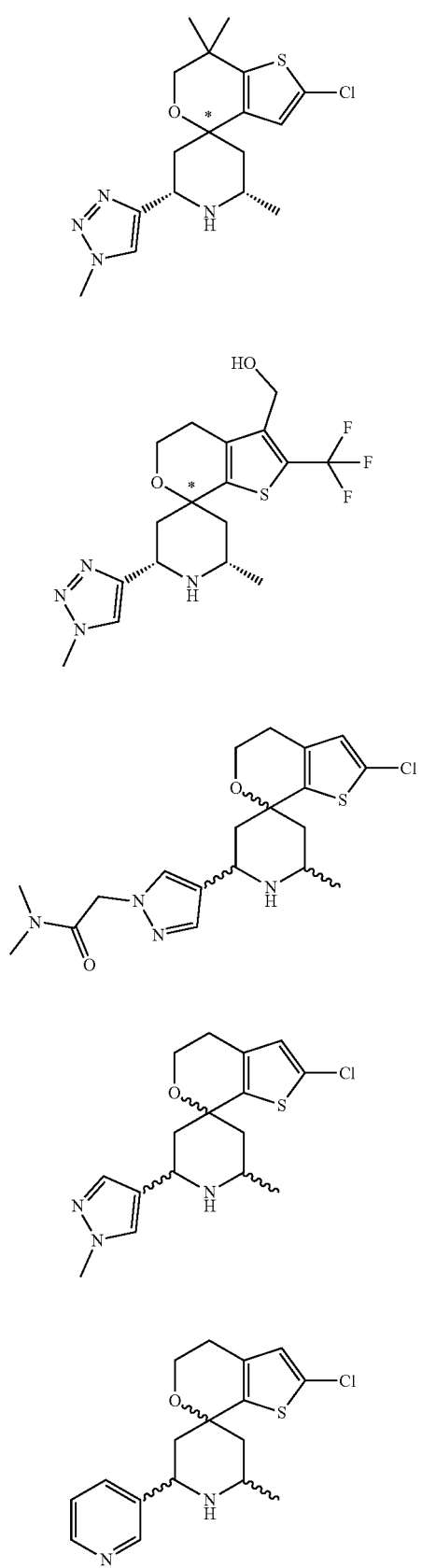
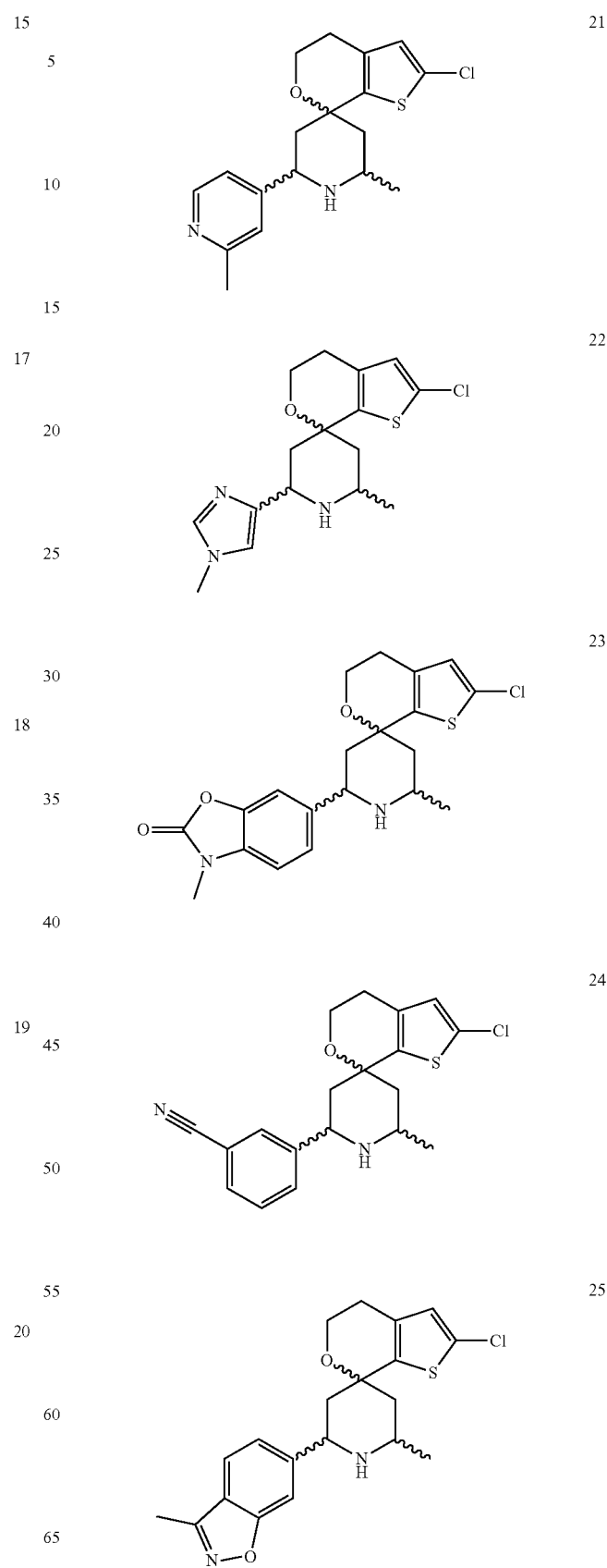

-continued
26
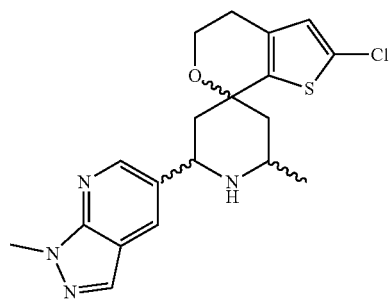
27
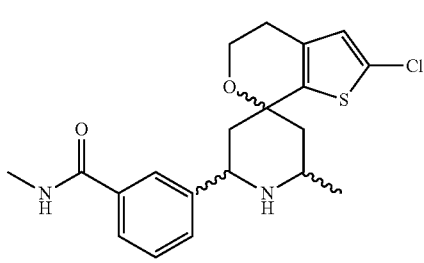
28
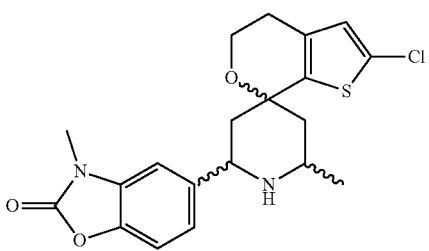
29
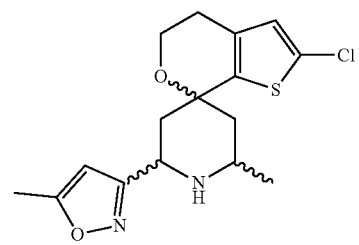
30
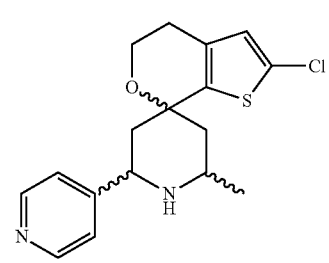
-continued
31
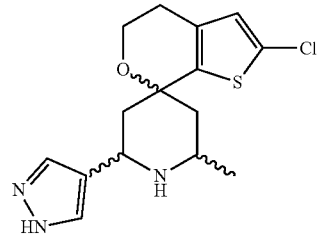
32
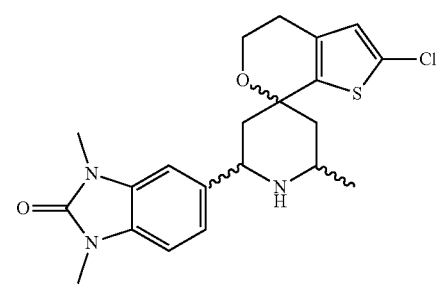
33
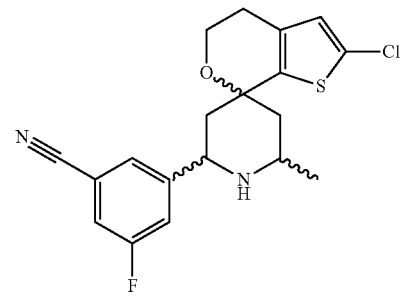
34
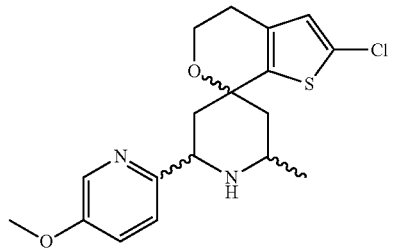
35
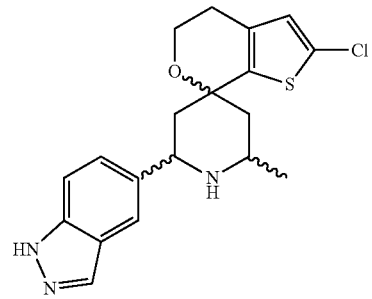

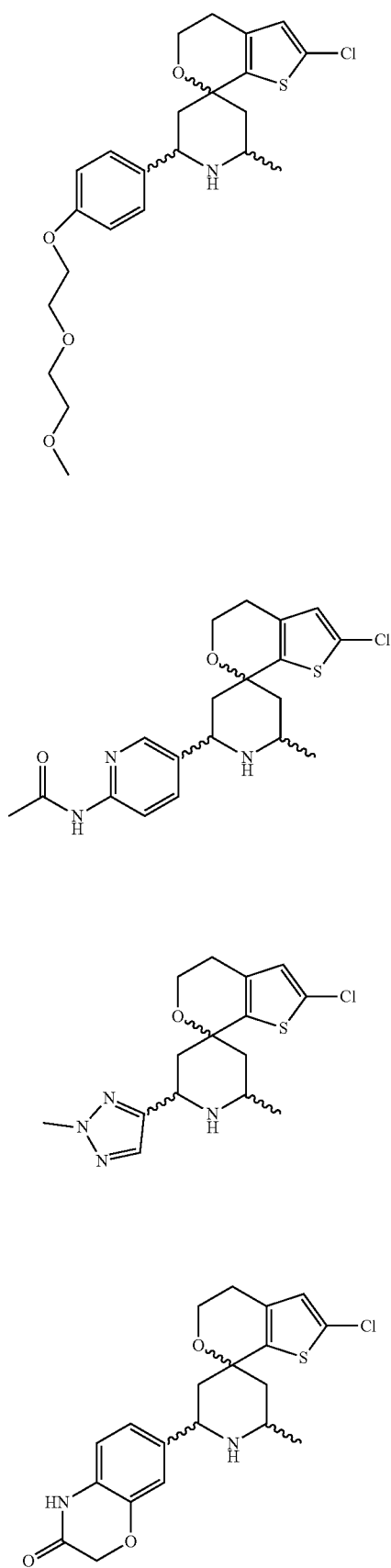
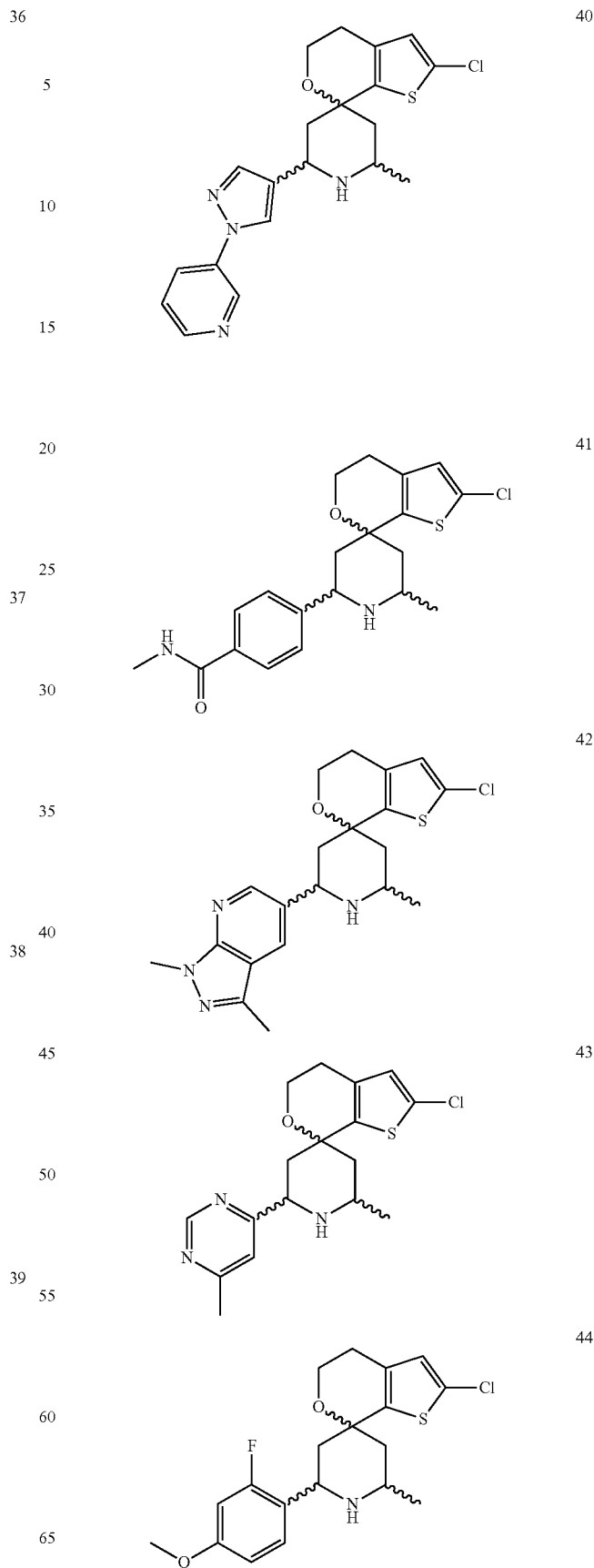

-continued
45
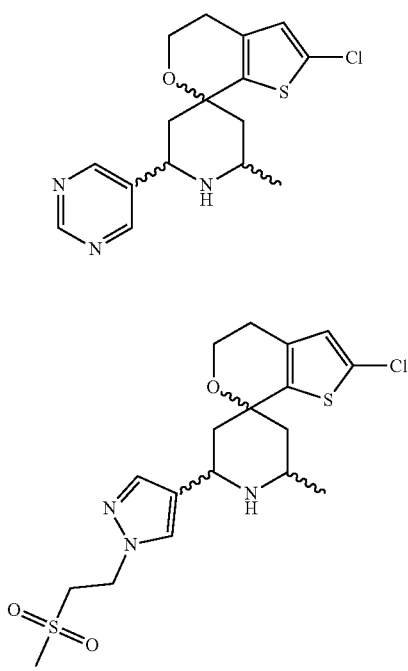
46
47
48
49
-continued
50
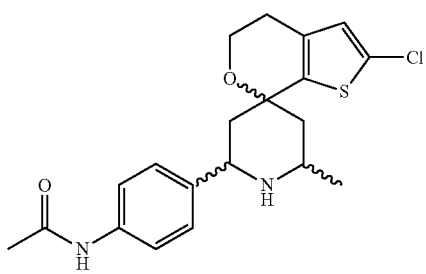
51
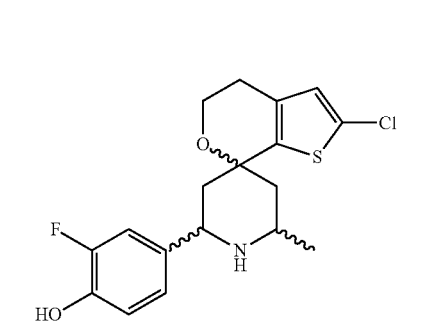
52
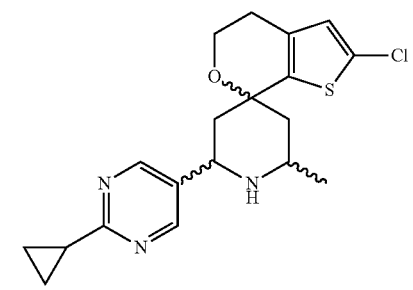
53
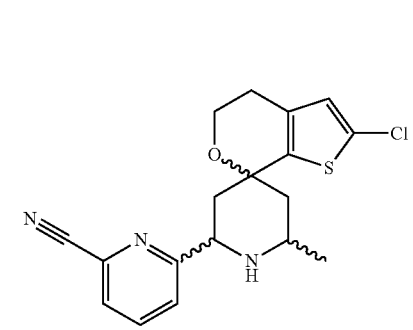
54
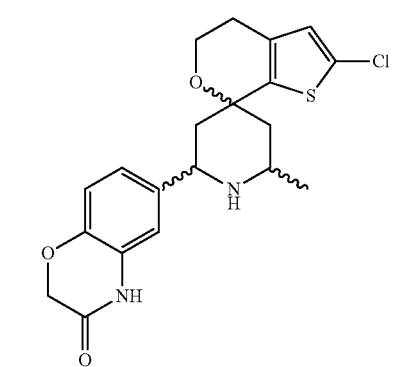

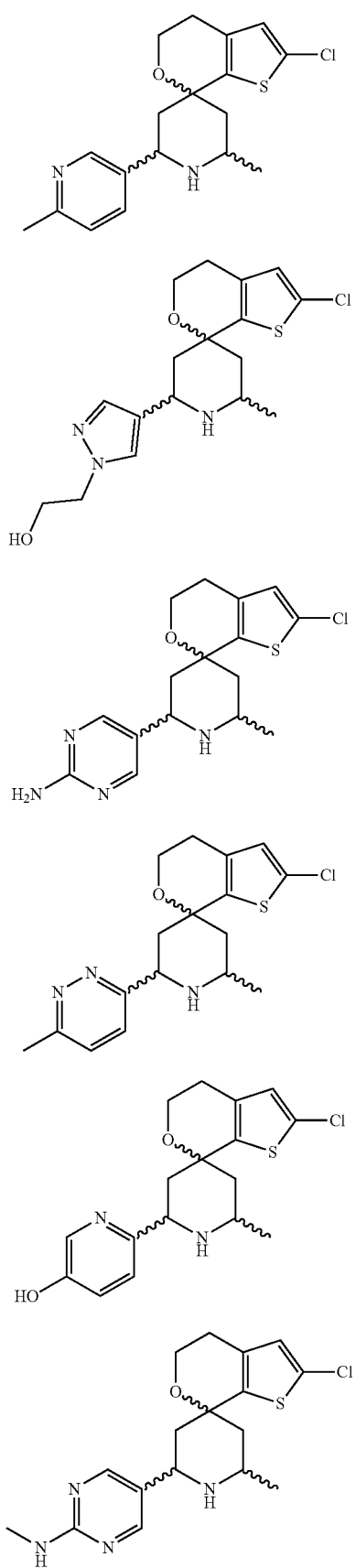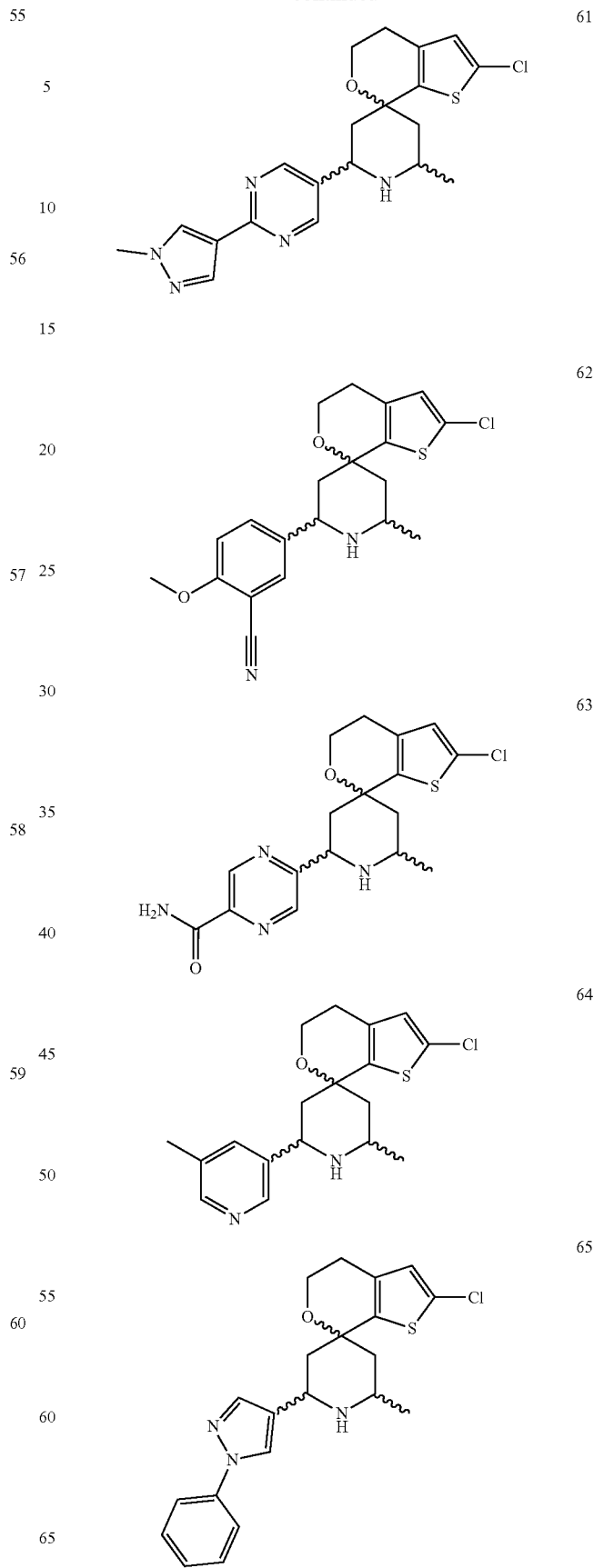

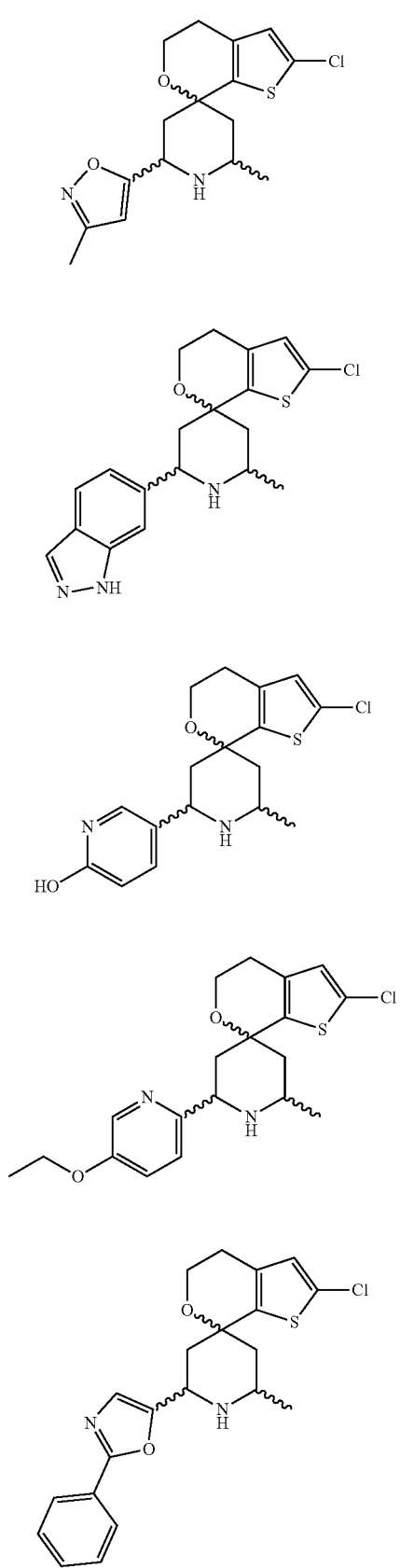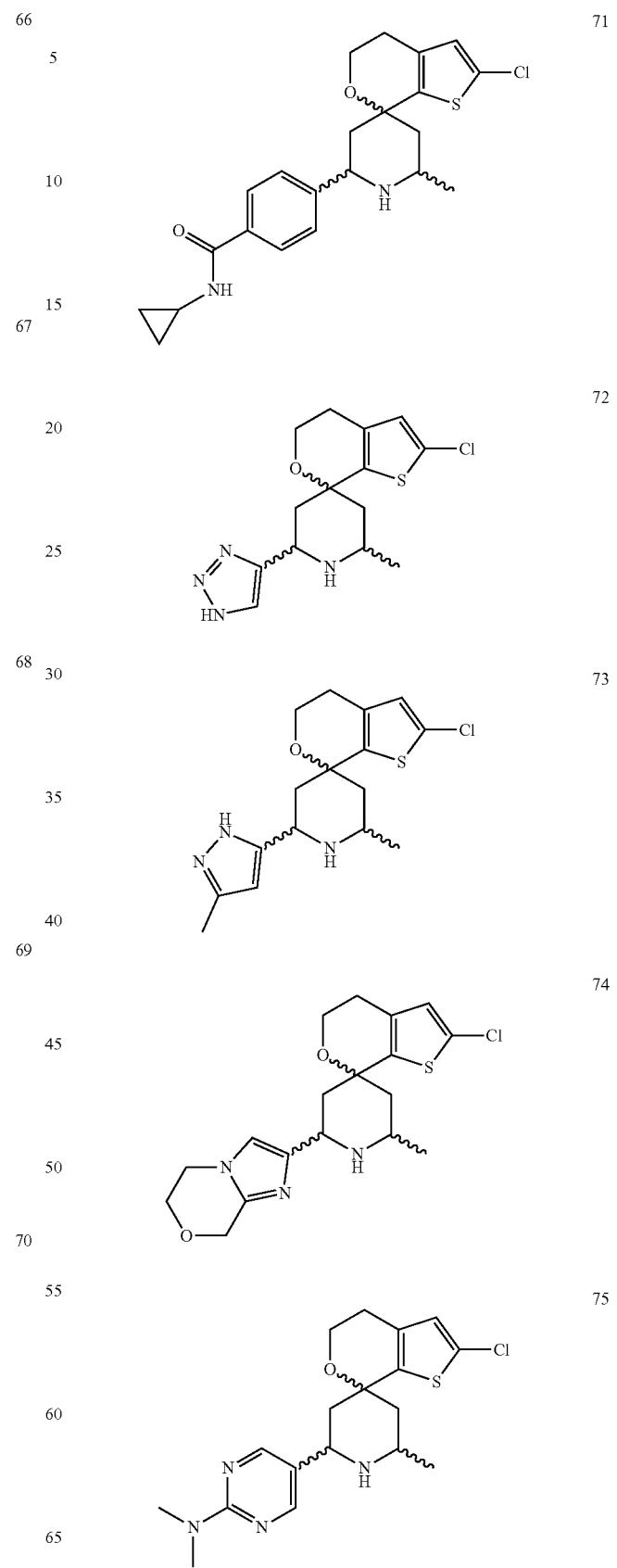

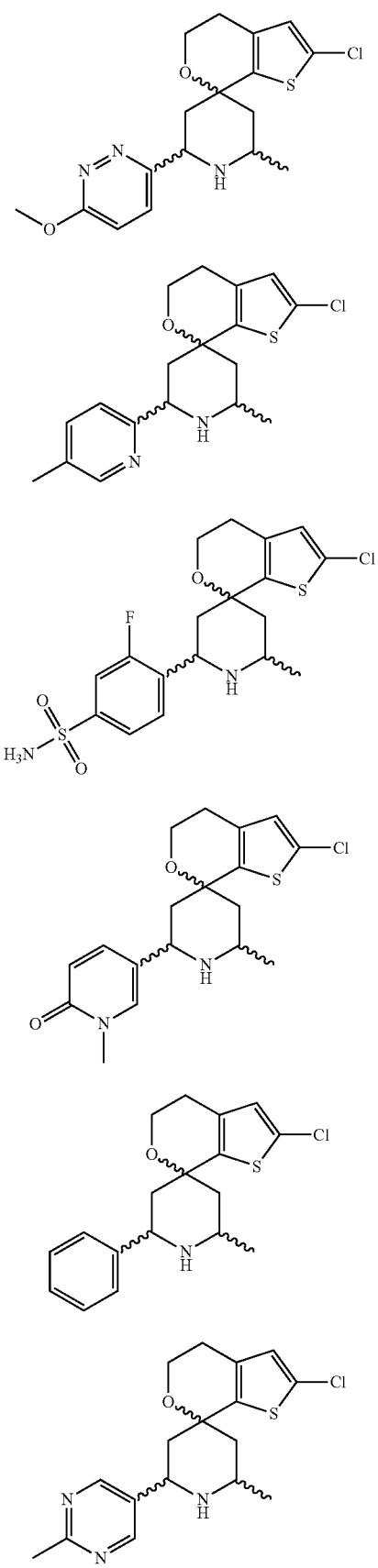
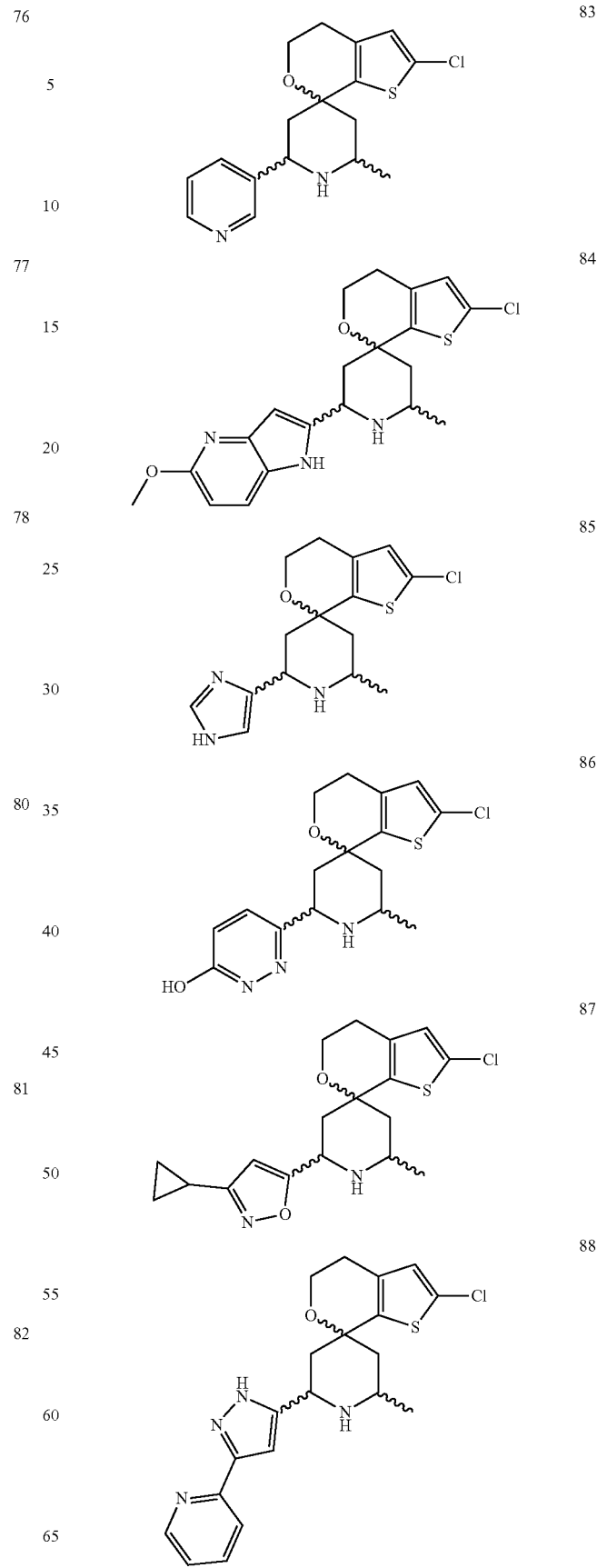

89
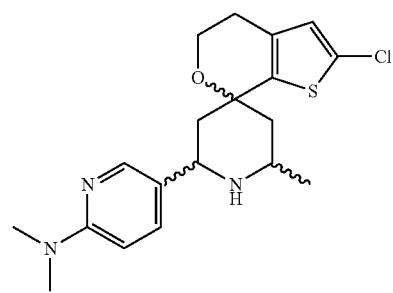
90
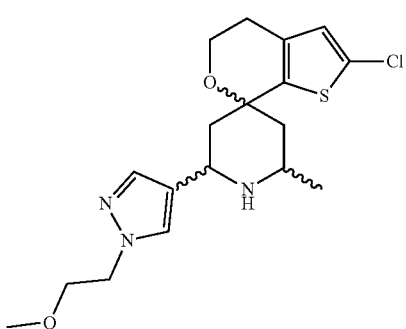
91
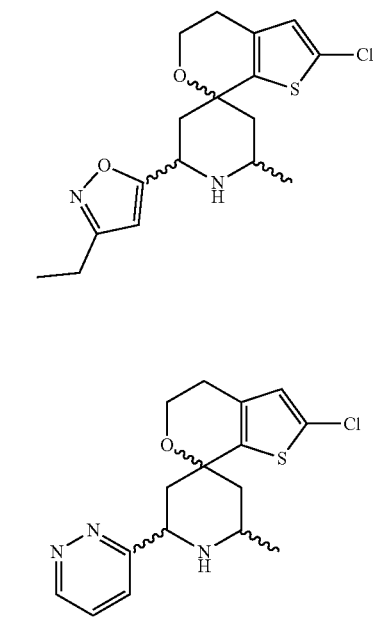
92
93
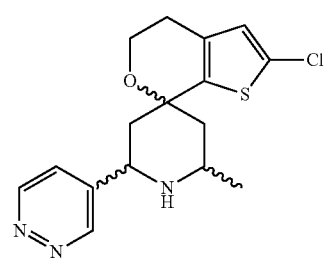
94
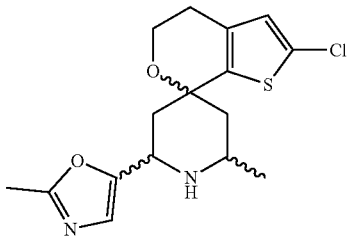
95
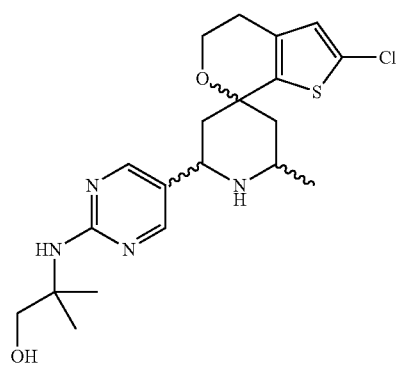
96
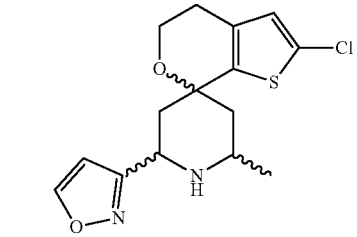
97
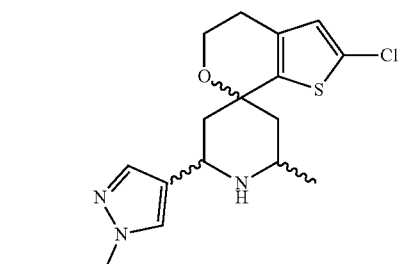
98
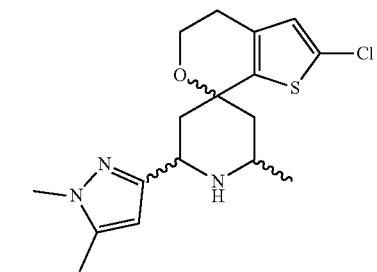

99
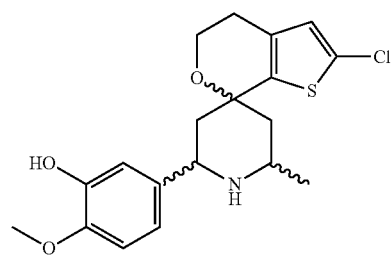
100
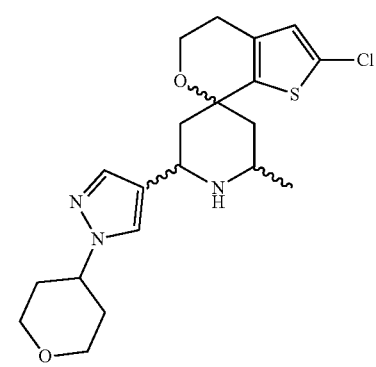
101
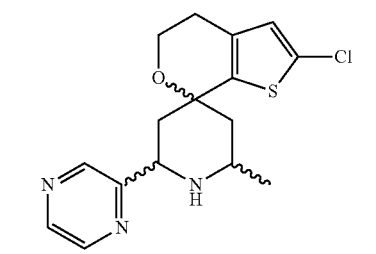
102
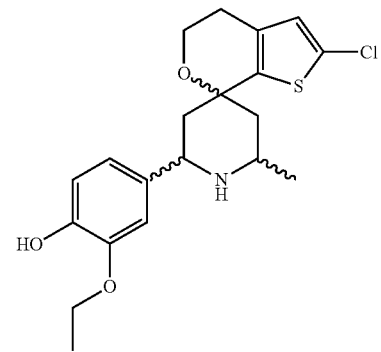
103
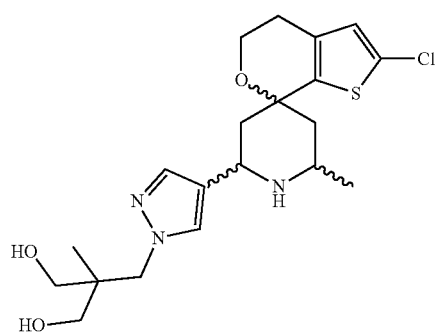
106
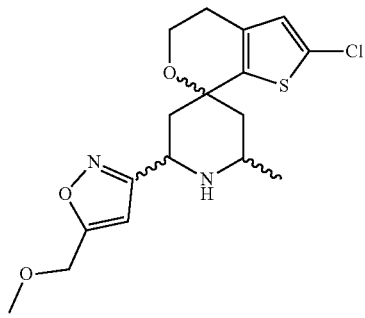
107
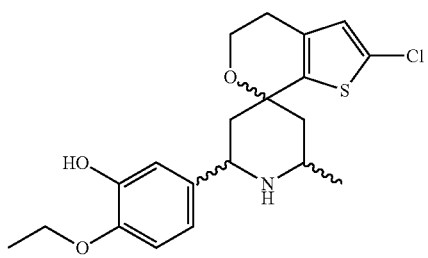
112
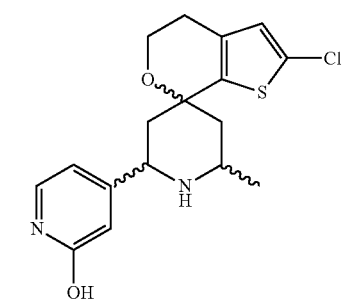
172
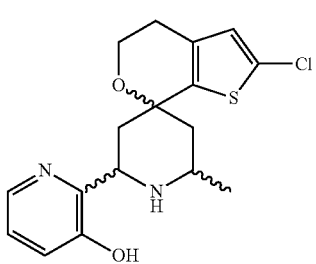
173
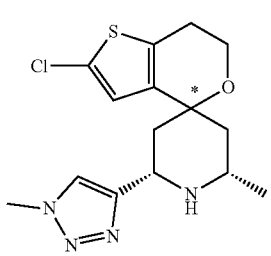

-continued
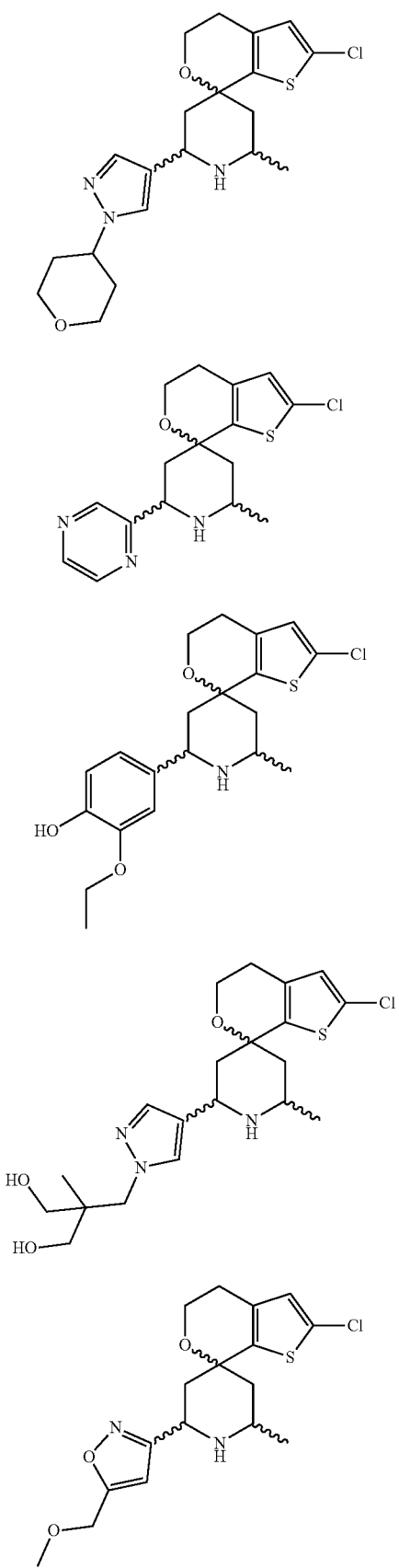
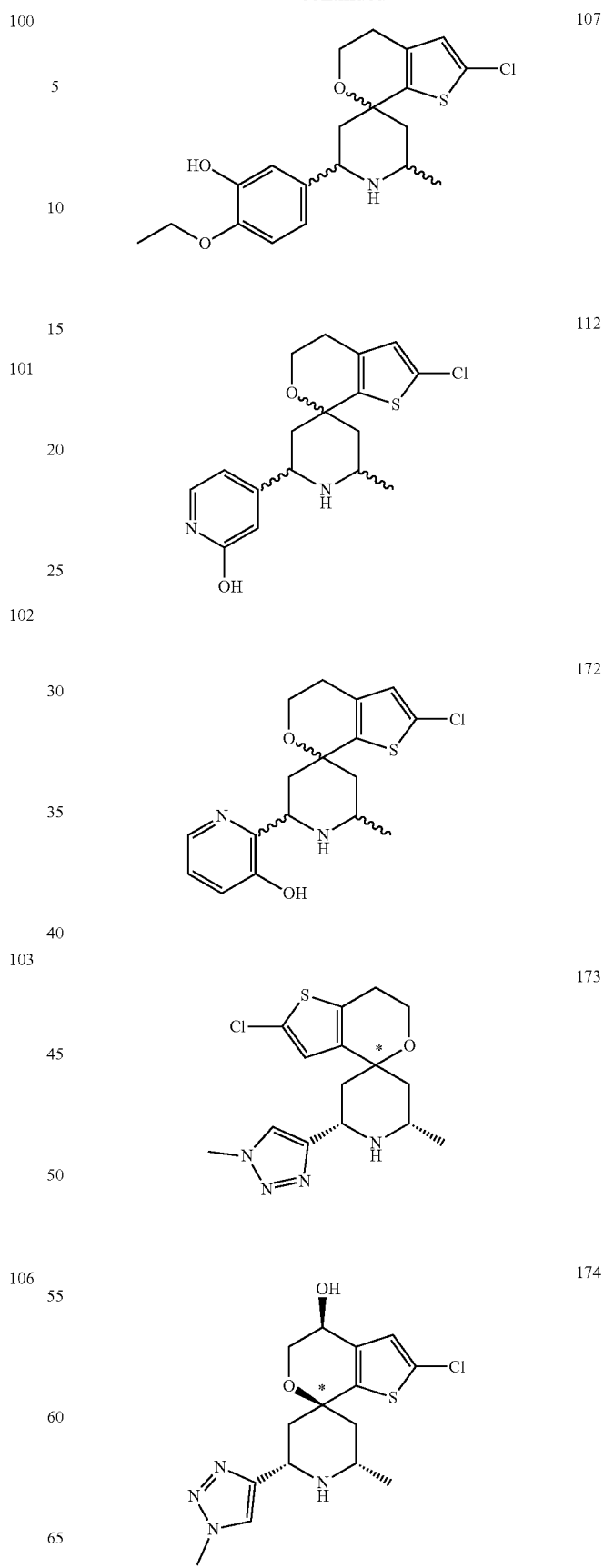

175 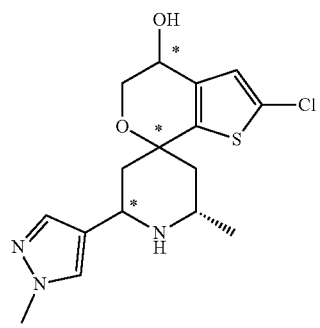
176 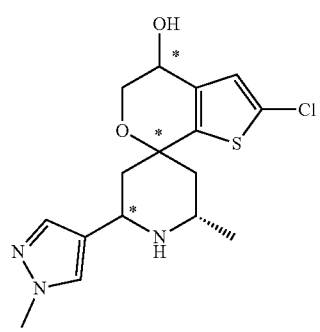
177 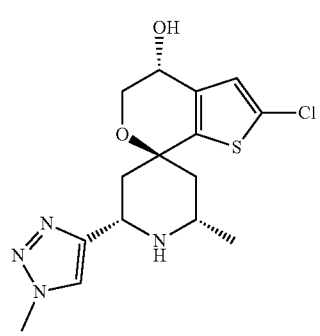
178 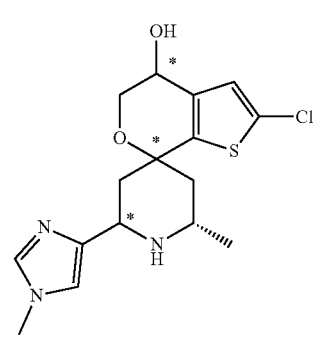
179 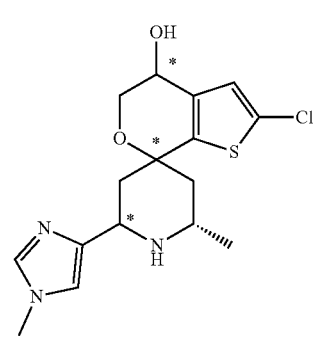
180 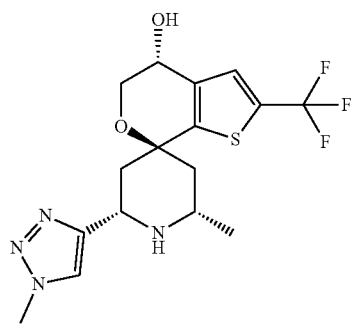
181 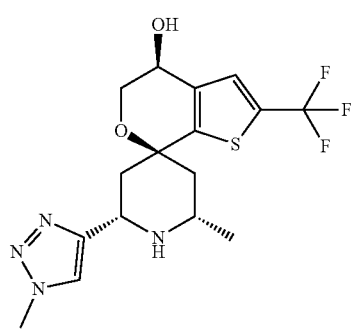
182 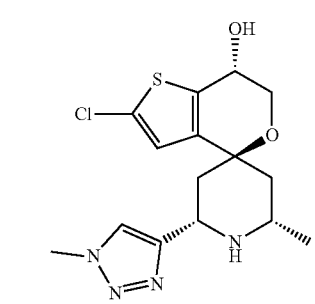
183 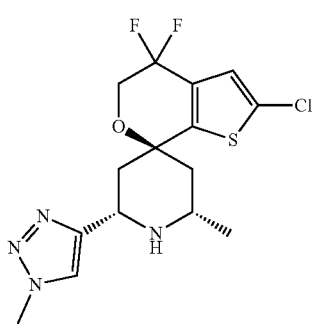
185 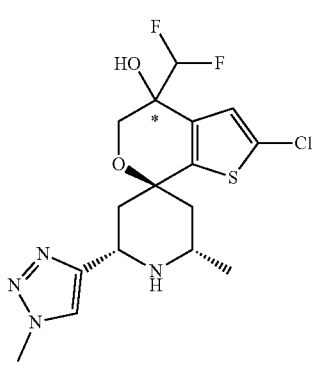

| | |
|---|---|
| 187 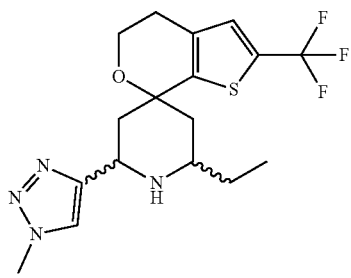 | 293 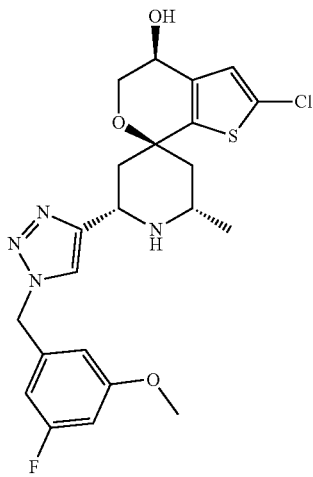 |
| 203 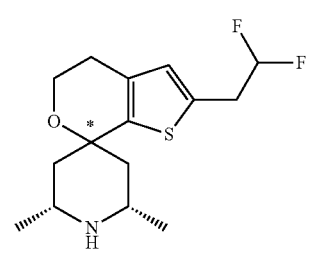 | |
| 212 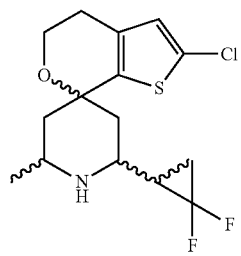 | 301 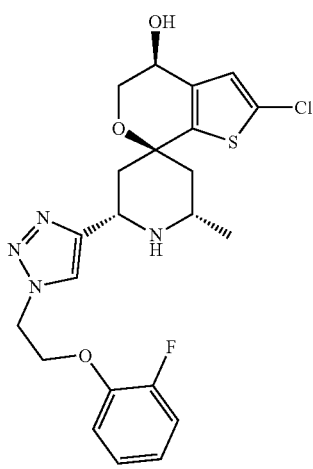 |
| 217 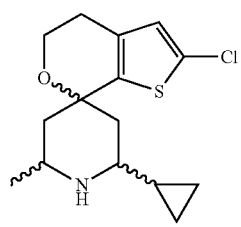 | |
| 220 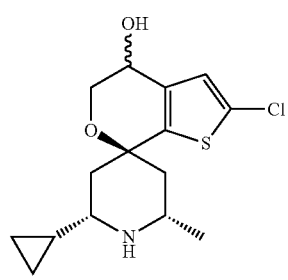 | 314 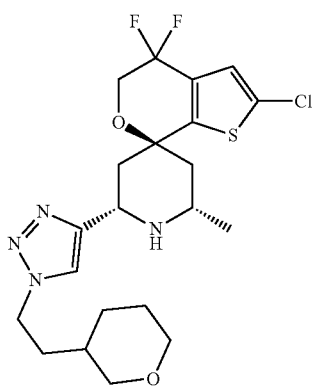 |

| | |
|---|---|
| 318 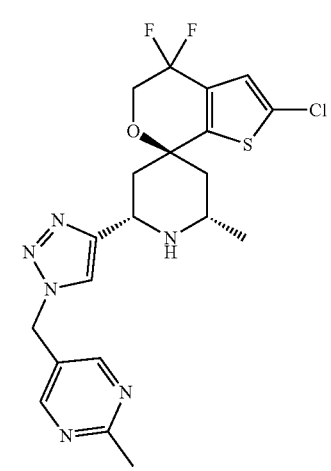 | 358 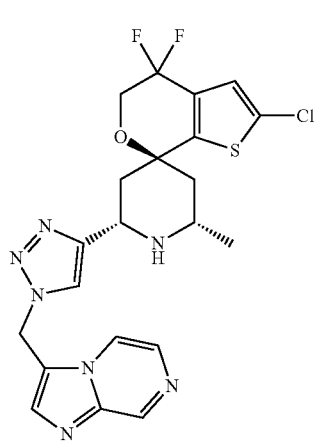 |
| 338 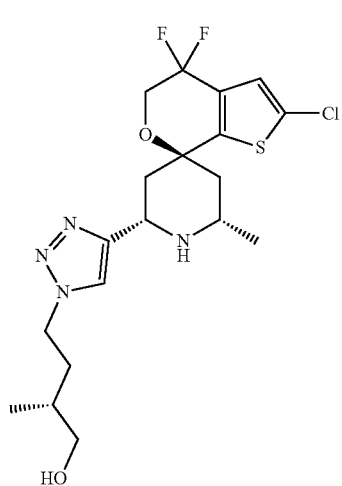 | 359 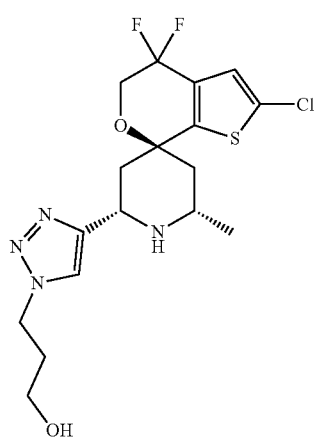 |
| | 367 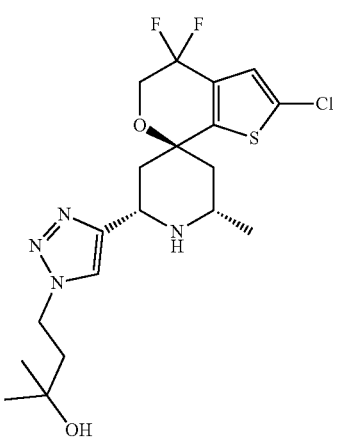 |
| 353 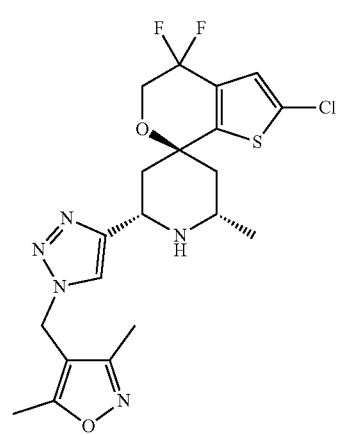 | 381 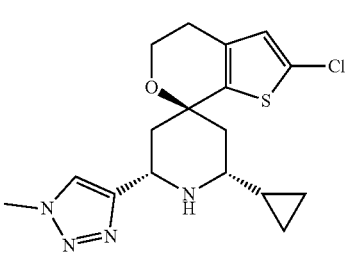 |

-continued

383

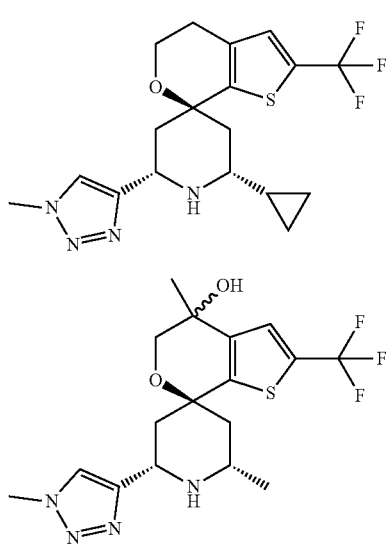

384 tautomers thereof, deuterated derivatives of those compounds and tautomers, and pharmaceutically acceptable salts of any of the foregoing.

13. A compound selected from Compound 174:

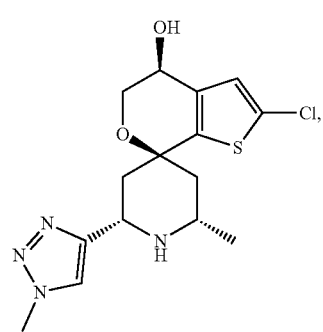

174 and a pharmaceutically acceptable salt thereof.

14. A compound selected from Compound 181:

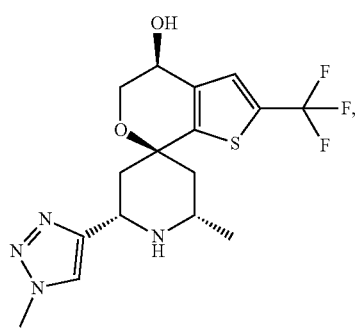

181 and a pharmaceutically acceptable salt thereof.

15. A pharmaceutical composition comprising the compound, tautomer, deuterated derivative, or pharmaceutically acceptable salt according to claim 1 and a pharmaceutically acceptable carrier.

16. A method of treating focal segmental glomerulosclerosis and/or non-diabetic kidney disease comprising administering to a patient in need thereof the compound, tautomer, deuterated derivative, or pharmaceutically acceptable salt according to claim 1.

17. A method of treating an APOL1-mediated disease comprising administering to a patient in need thereof the compound, tautomer, deuterated derivative, or pharmaceutically acceptable salt according to claim 1.

18. The method according to claim 17, wherein the APOL1-mediated disease is cancer.

19. The method according to claim 17, wherein the APOL1-mediated disease is pancreatic cancer.

20. The method according to claim 17, wherein the APOL1-mediated disease is an APOL1-mediated kidney disease.

21. A compound that is Compound 174:

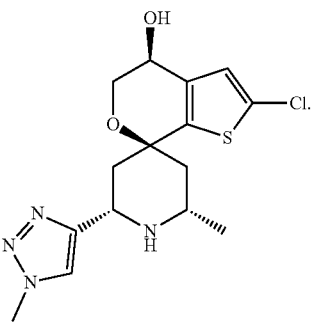

174

22. A compound that is Compound 181:

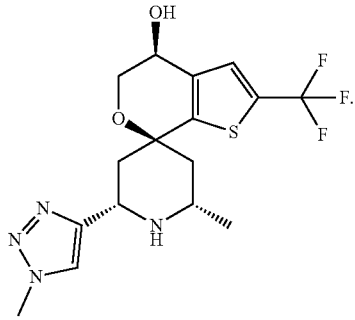

181

23. A compound selected from:

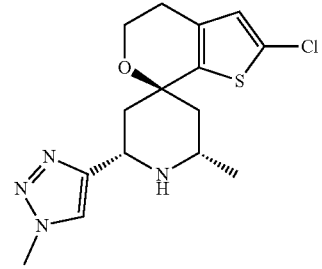

1

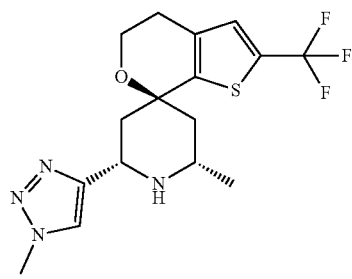
2
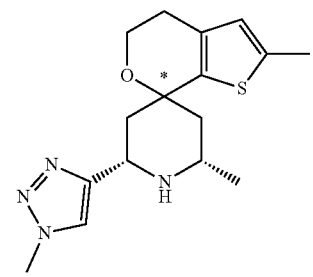
3
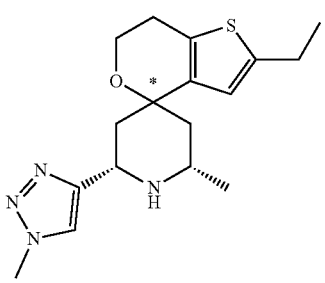
4
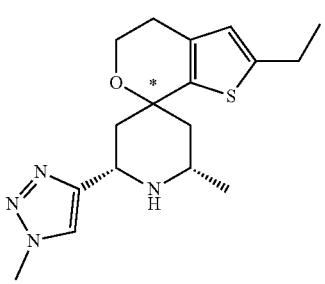
6
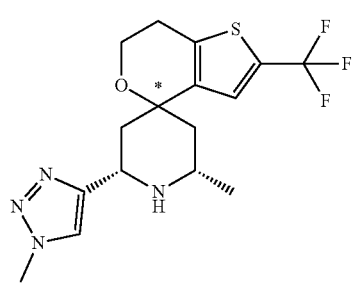
8
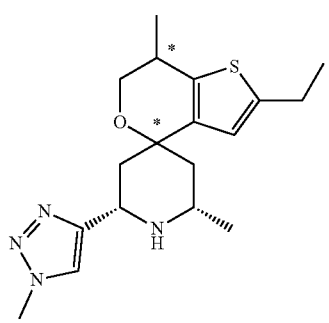
10
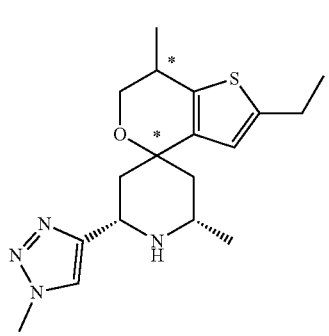
11
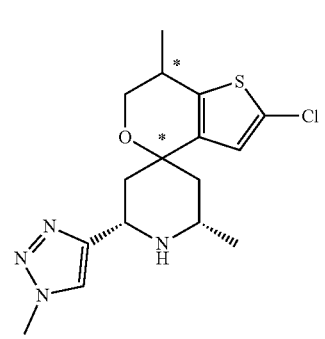
12
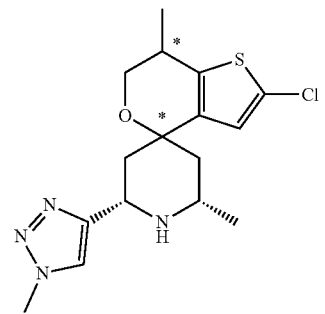
13
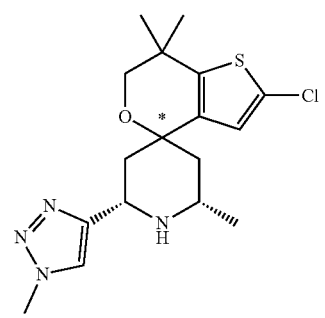
15

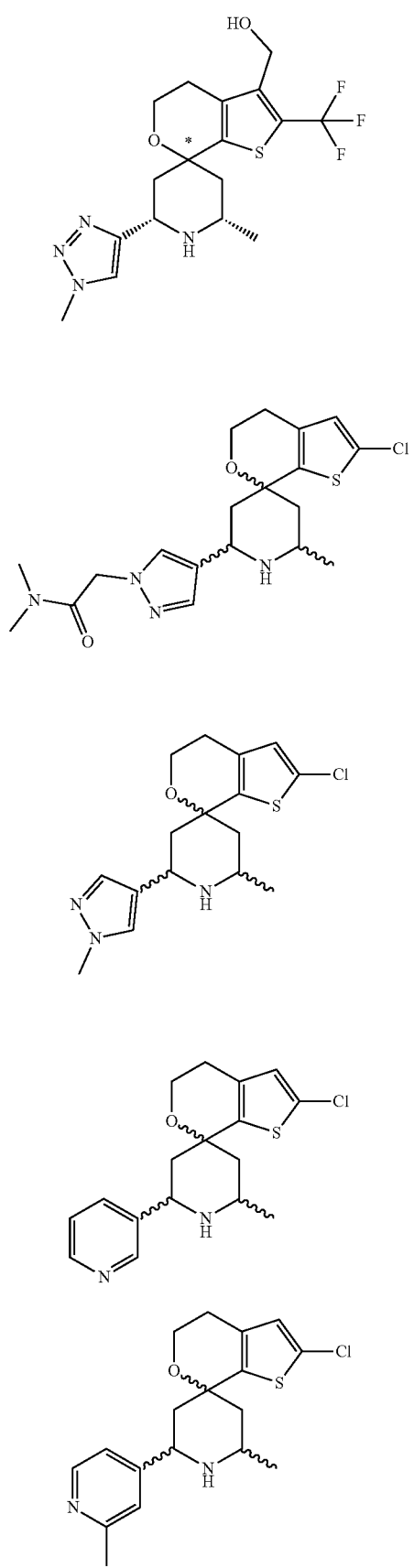
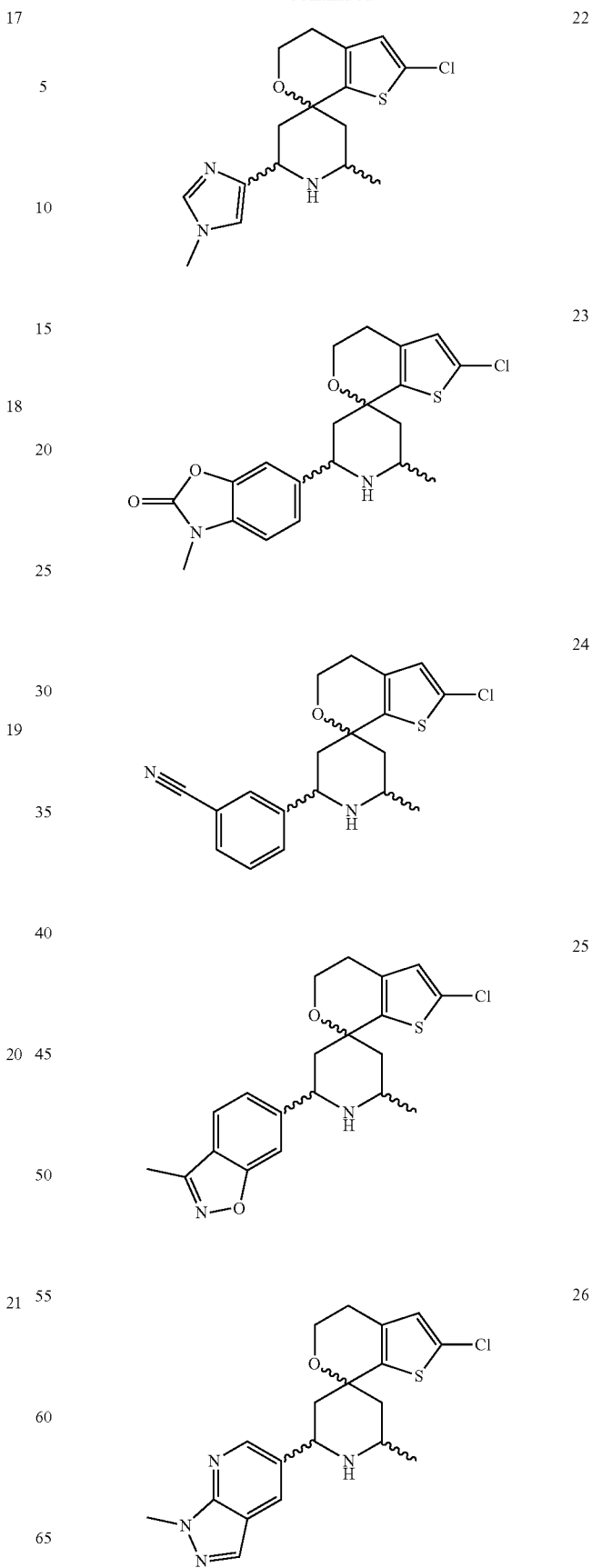

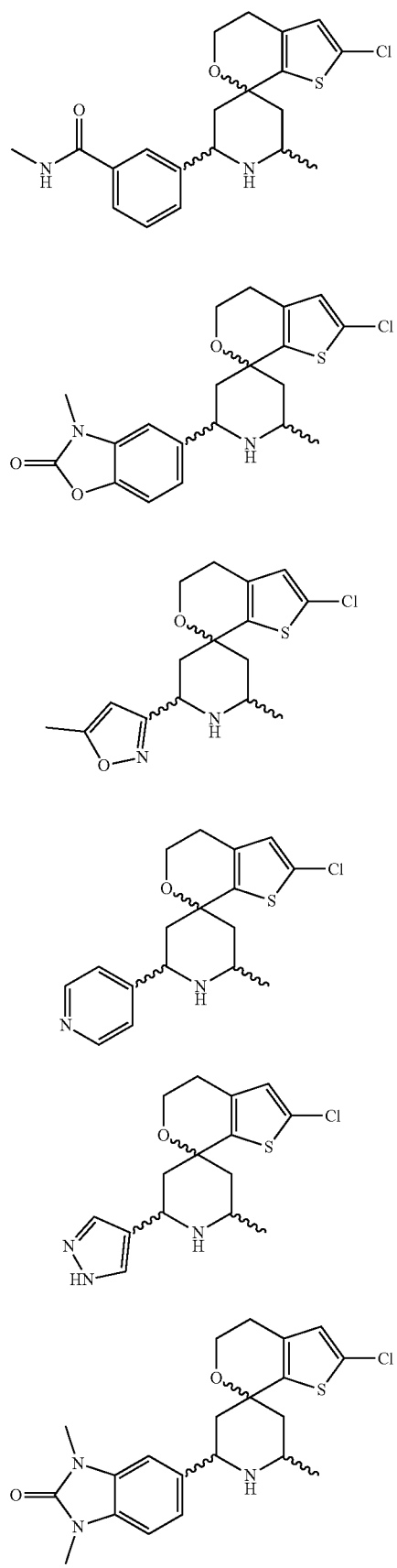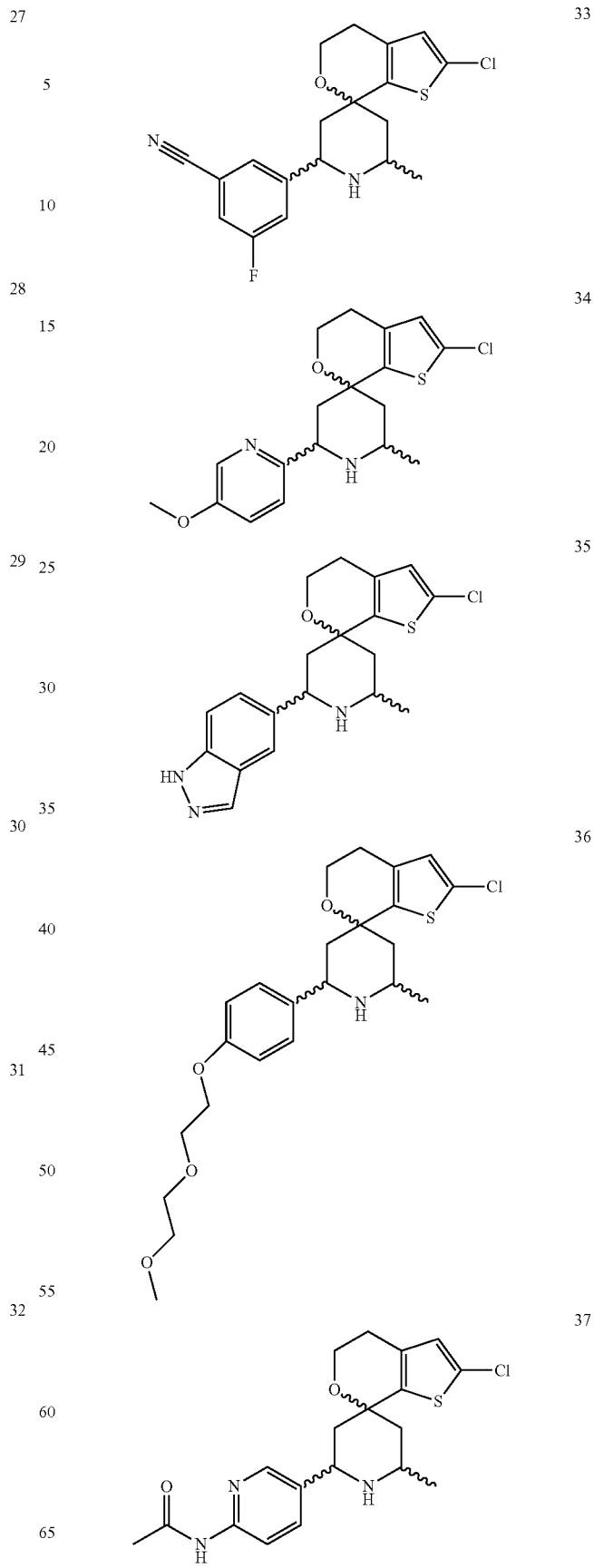

| 38 | 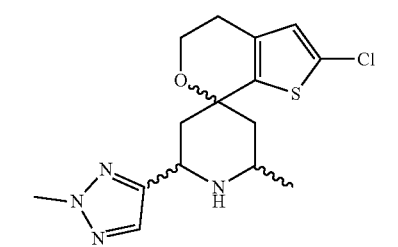 | 43 | 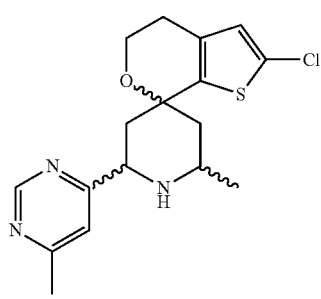 |
| 39 | 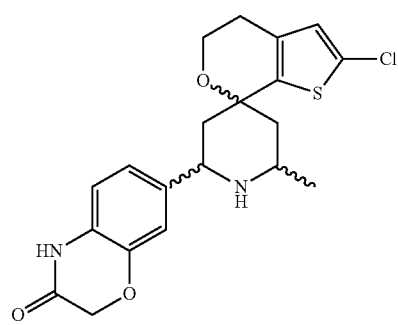 | 44 | 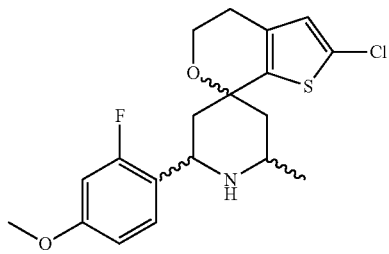 |
| 40 | 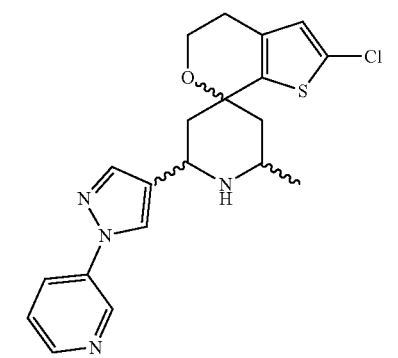 | 45 | 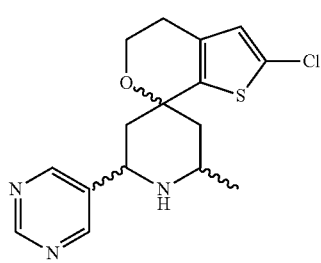 |
| 41 | 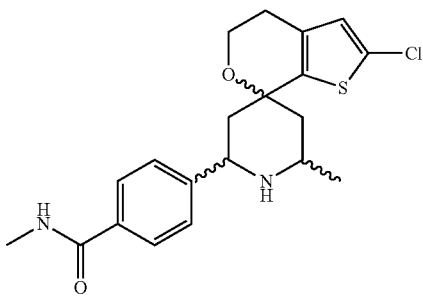 | 46 | 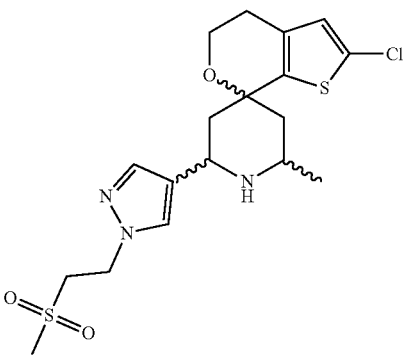 |
| 42 | 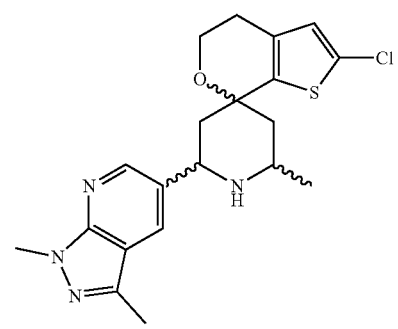 | 47 | 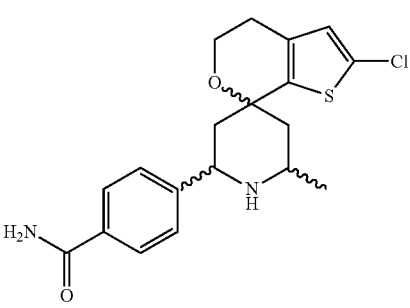 |

48
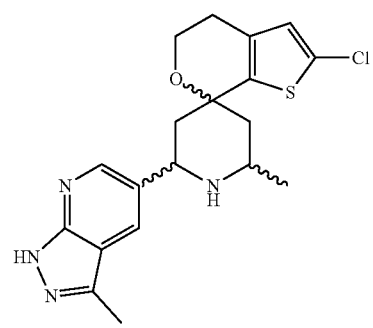
49
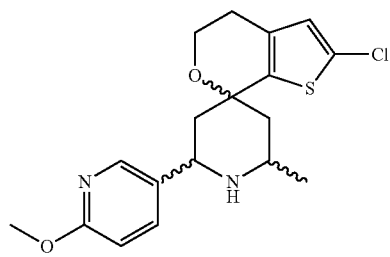
50
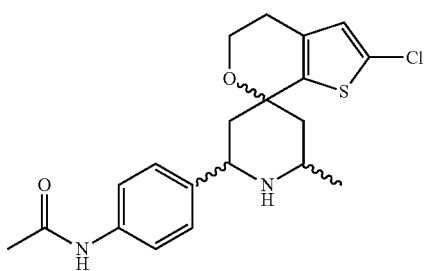
51
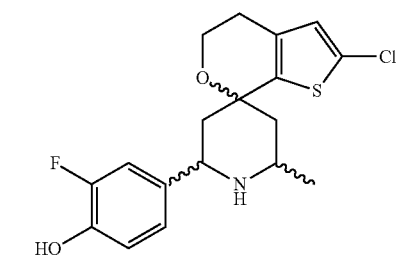
52
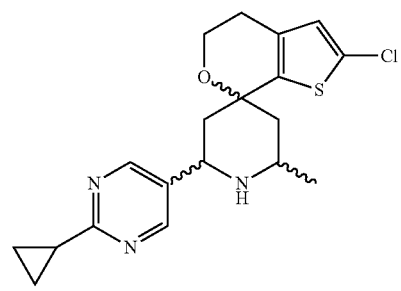
53
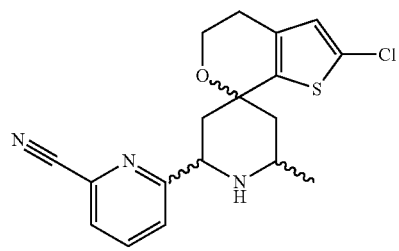
54
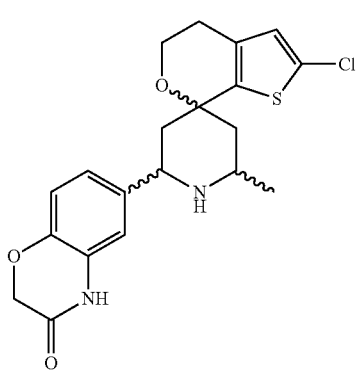
55
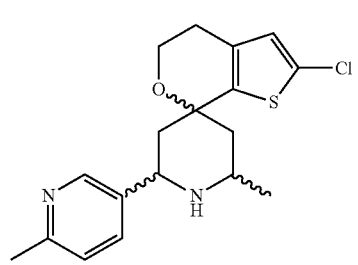
56
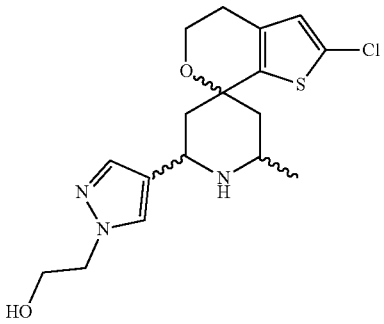
57
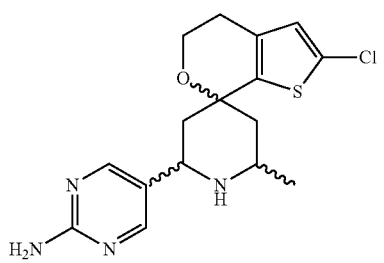

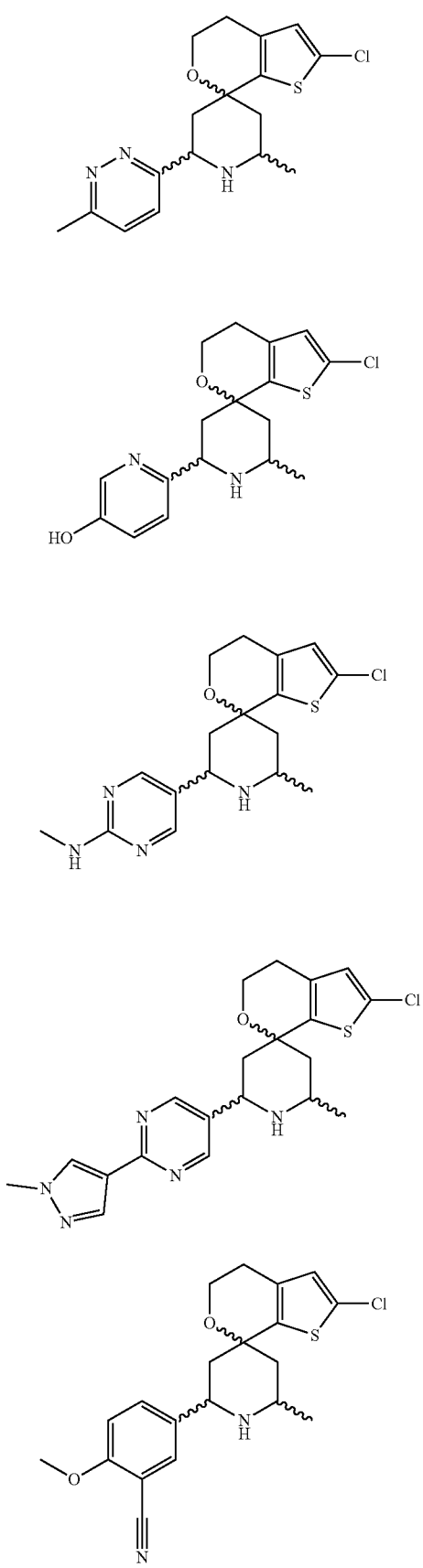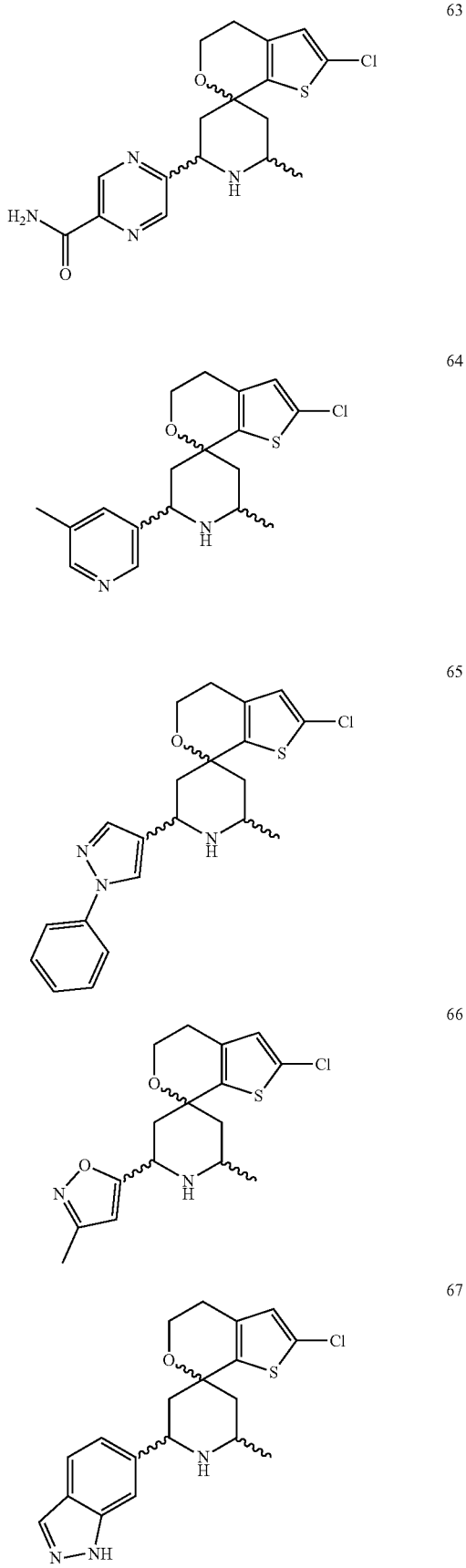

| | |
|---|---|
| 68 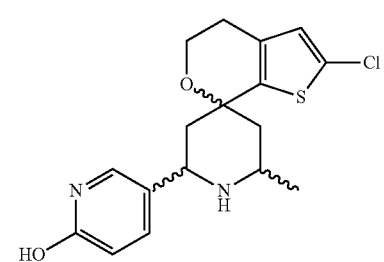 | 73 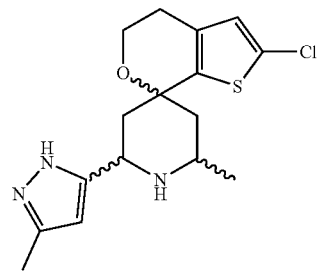 |
| 69 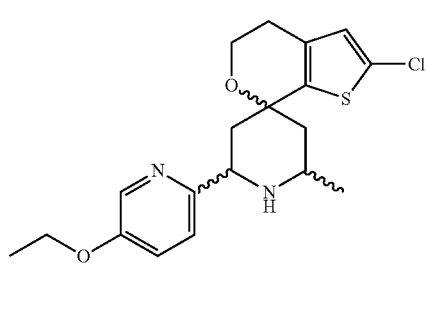 | 74 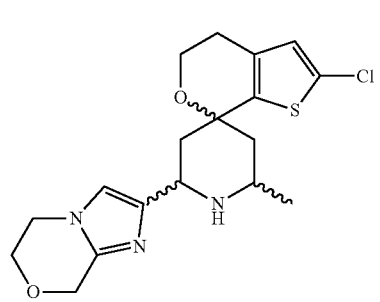 |
| 70 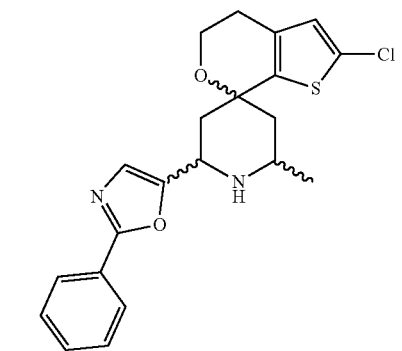 | 75 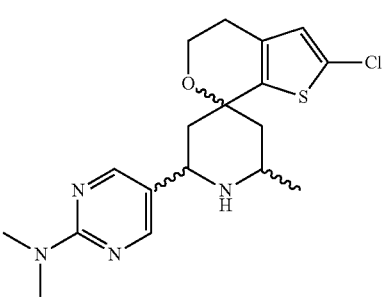 |
| 71 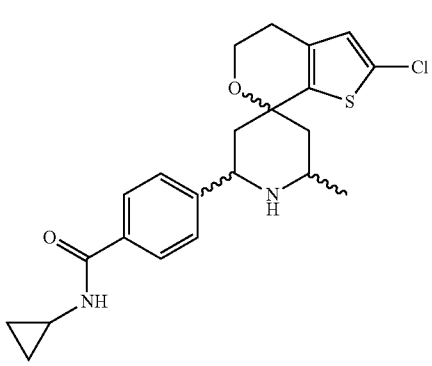 | 76 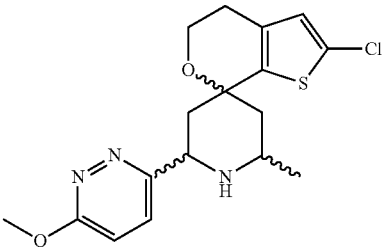 |
| 72 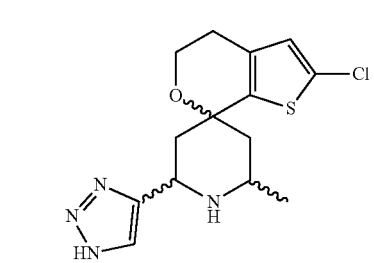 | 77 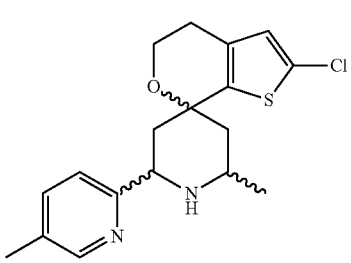 |

-continued
78 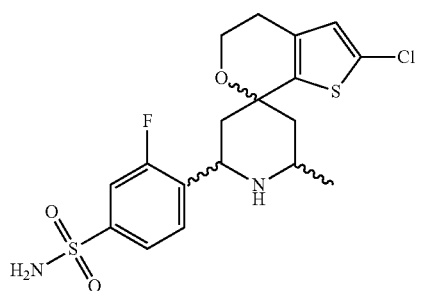
80 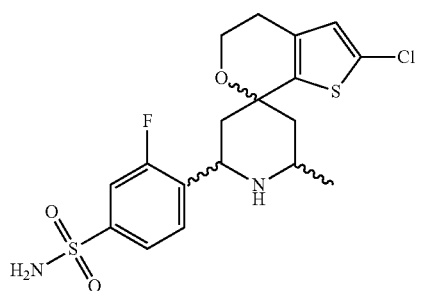
81 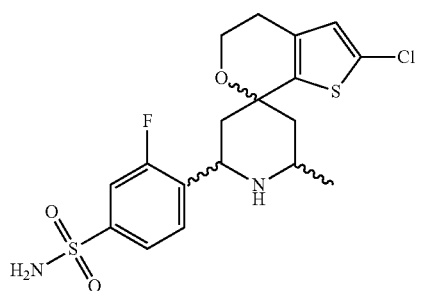
82 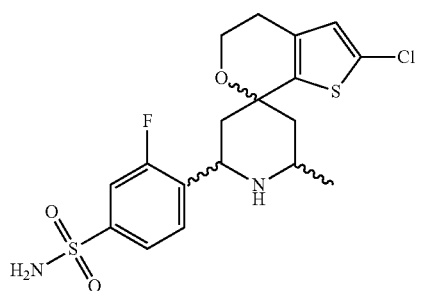
83 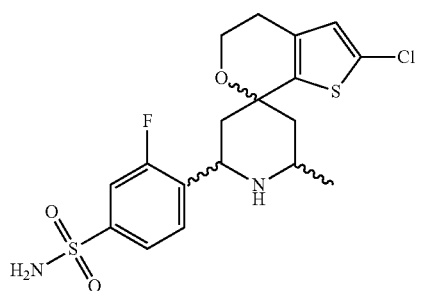
84 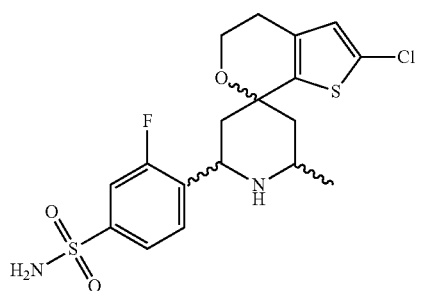
-continued
85 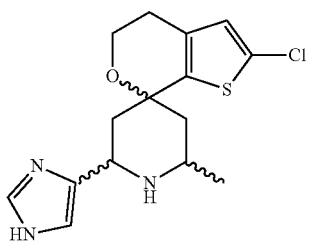
86 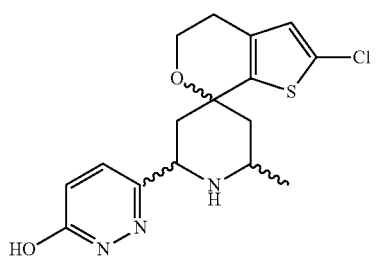
87 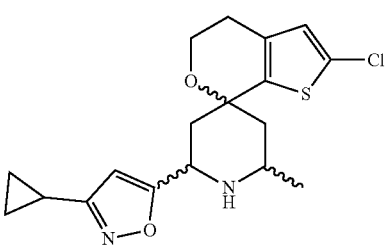
88 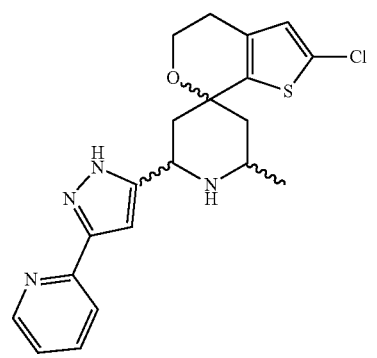
89 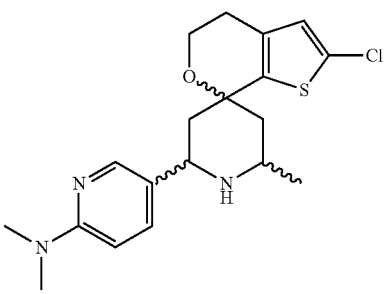

663
-continued
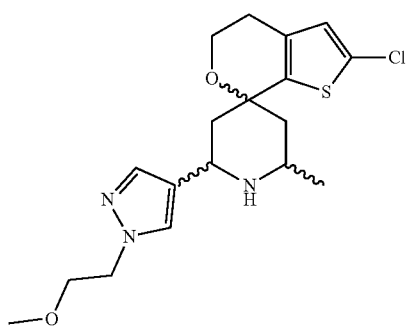
90
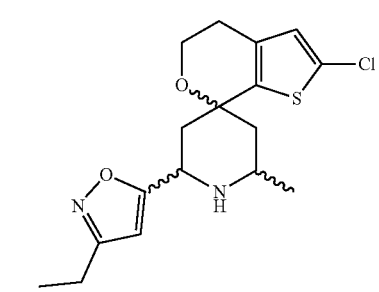
91
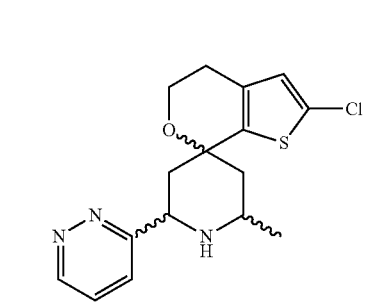
92
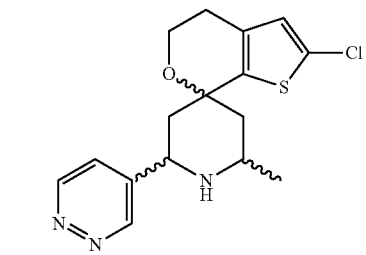
93
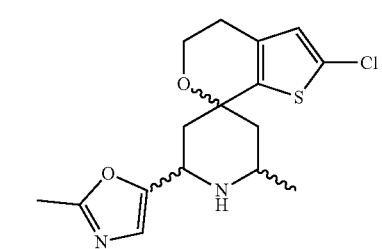
94
664
-continued
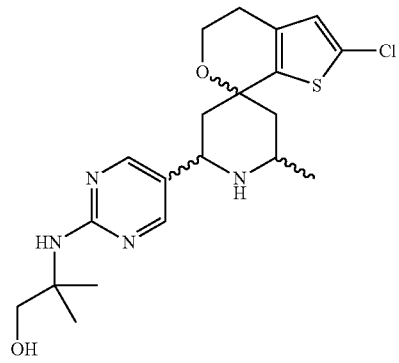
95
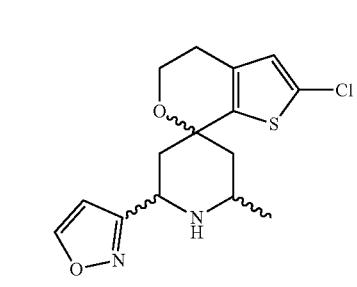
96
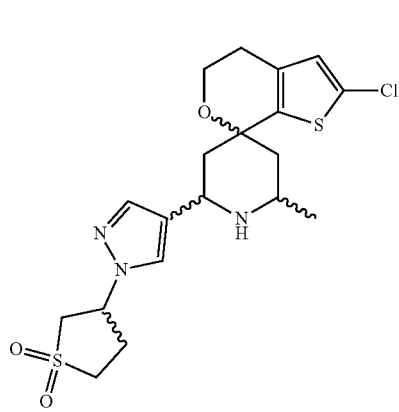
97
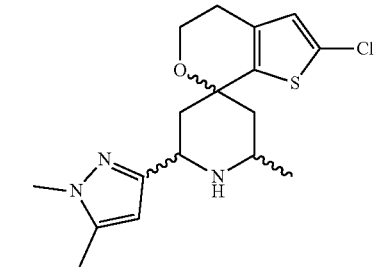
98
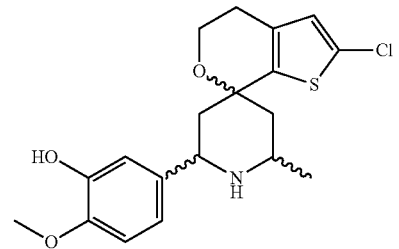
99

| | |
|---|---|
| 100 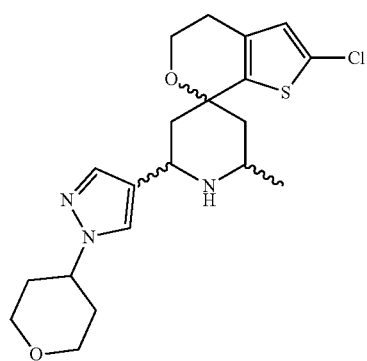 | 106 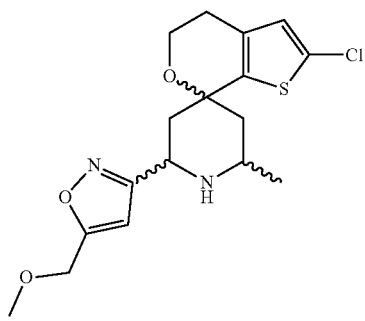 |
| 101 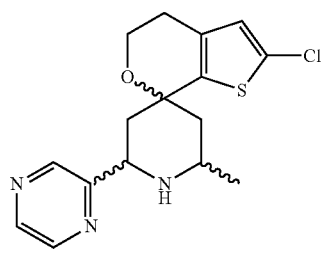 | 107 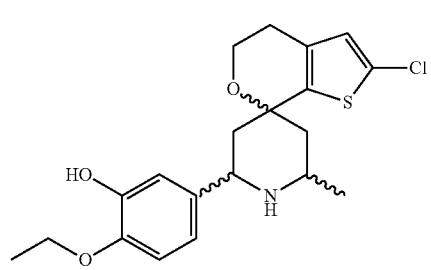 |
| 102 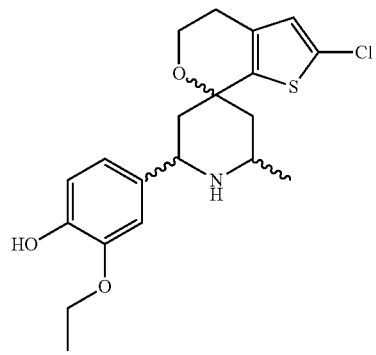 | 112 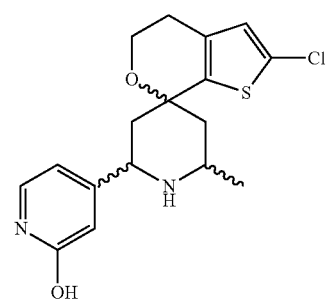 |
| 103 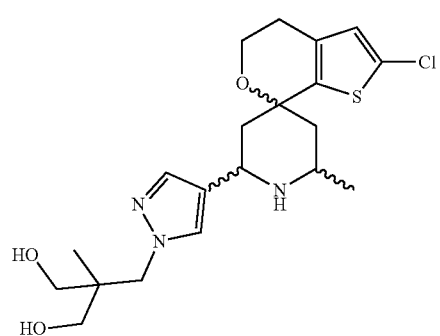 | 172 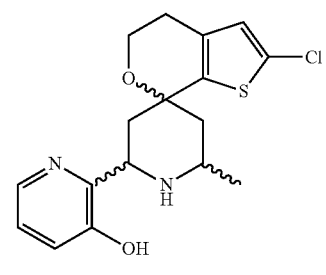 |
| | 173 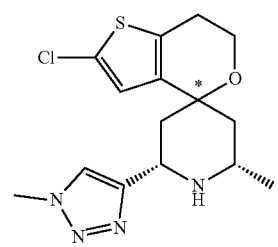 |

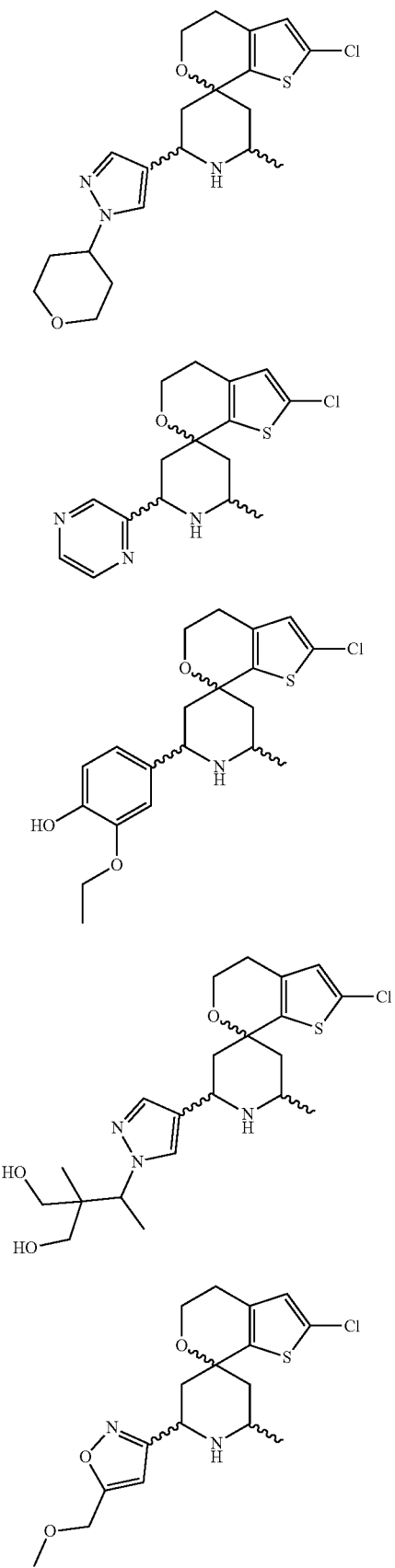
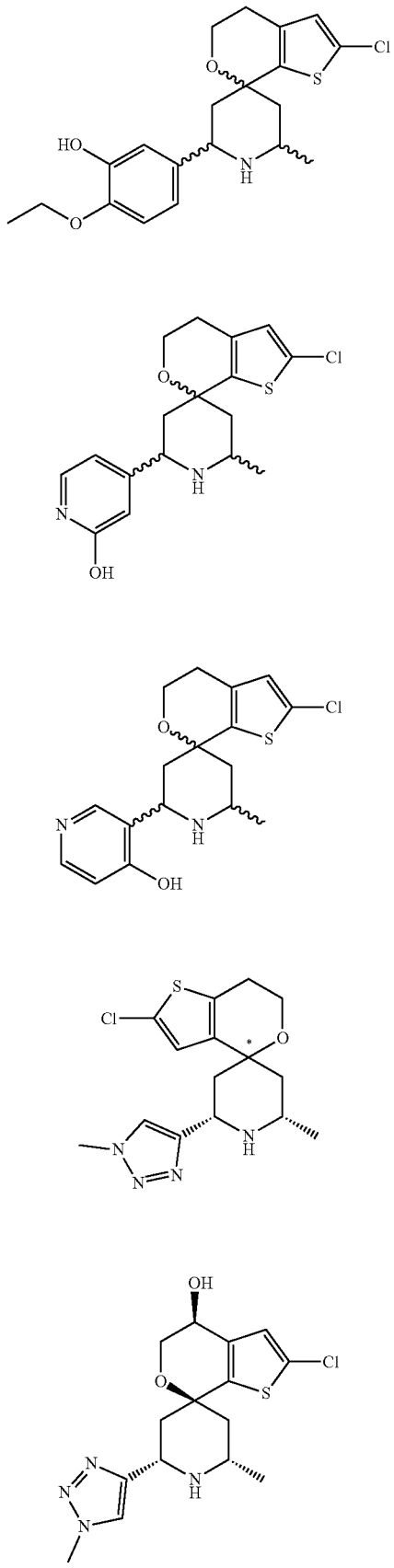

175 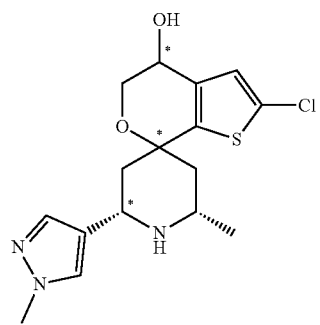
176 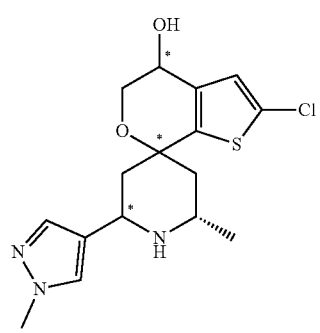
177 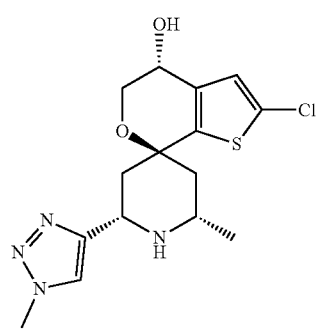
178 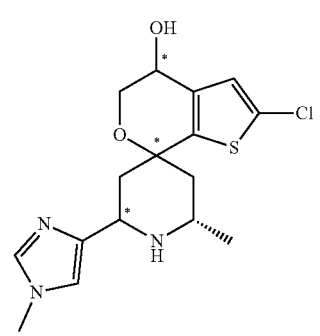
179 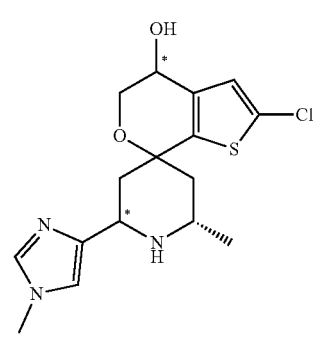
180 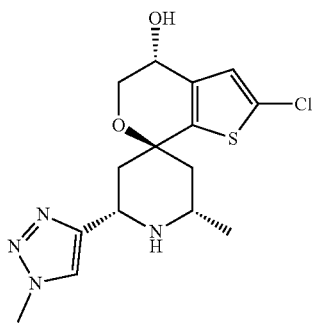
181 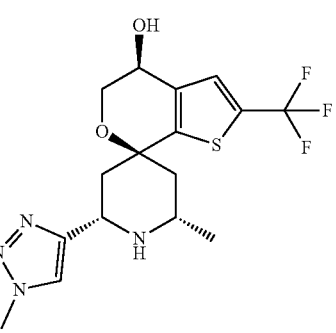
182 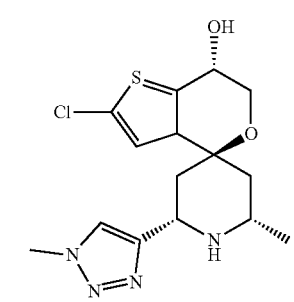
183 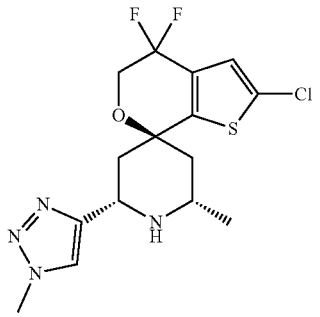
185 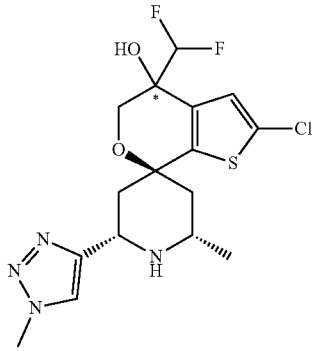

187 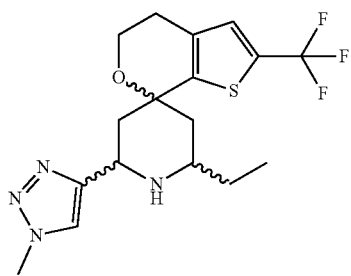
181 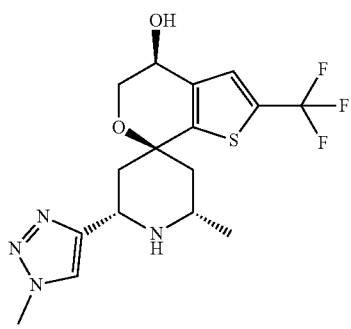
182 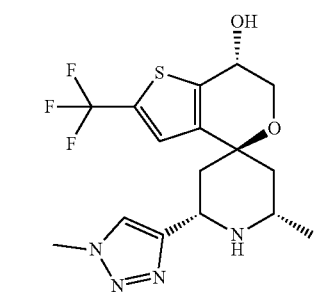
183 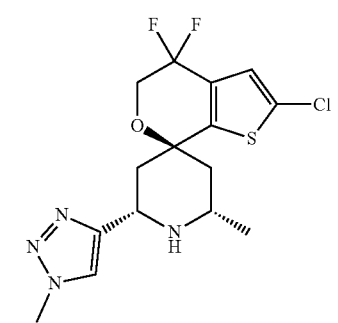
185 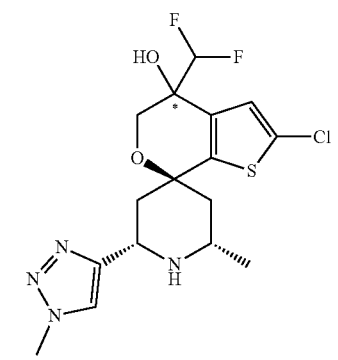
187 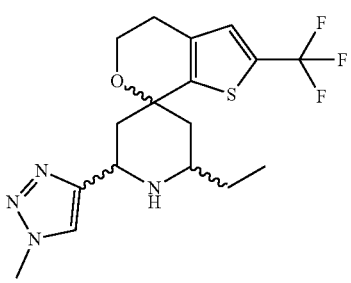
203 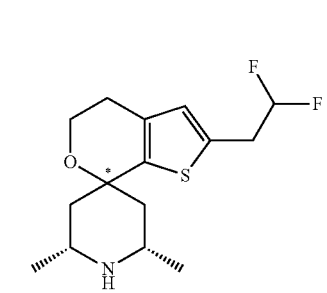
212 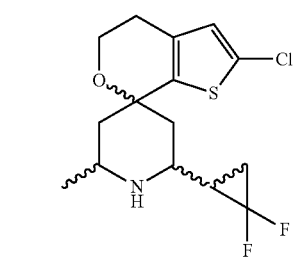
217 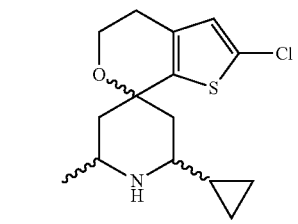
220 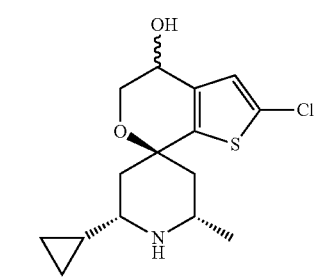

| 293 | 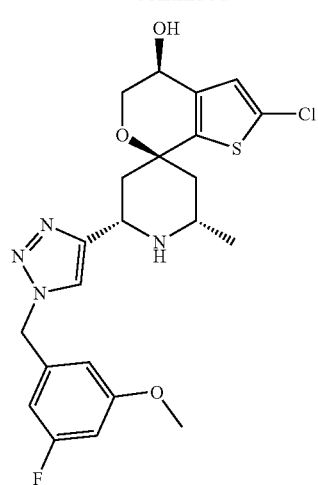 | 338 | 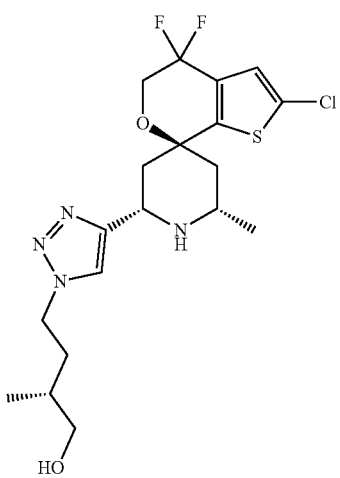 |
| 314 | 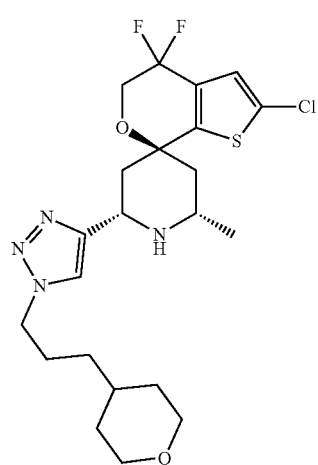 | 353 | 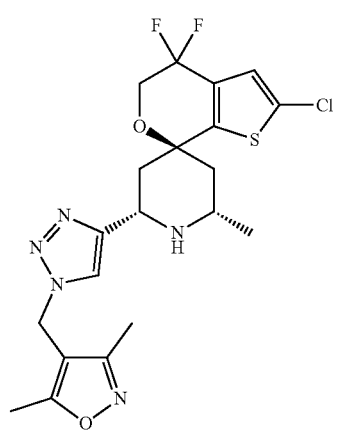 |
| 318 | 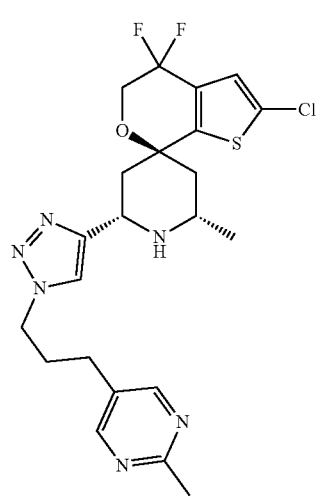 | 358 | 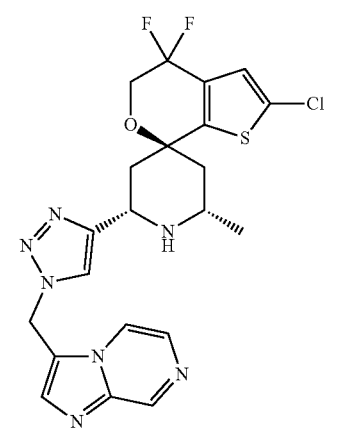 |

675 -continued
359 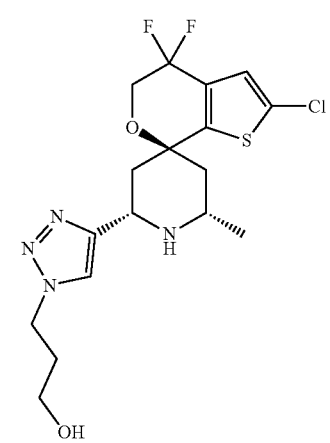
367 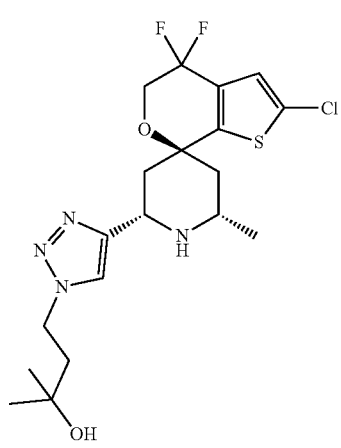
676 -continued
381 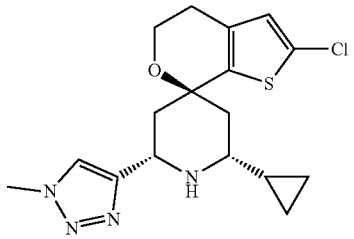
383 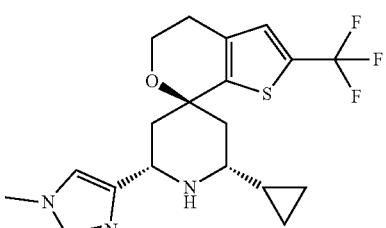
384 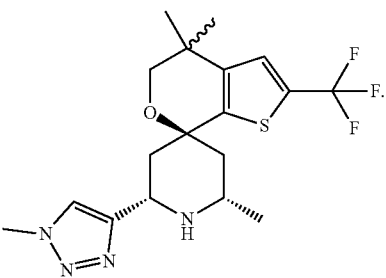
* * * * *